US012116380B2

(12) United States Patent
Chun et al.

(10) Patent No.: US 12,116,380 B2
(45) Date of Patent: Oct. 15, 2024

(54) PHOSPHOLIPID COMPOUNDS AND METHODS OF MAKING AND USING THE SAME

(71) Applicant: Gilead Sciences, Inc., Foster City, CA (US)

(72) Inventors: Byoung-Kwon Chun, Pleasanton, CA (US); Michael O. Clarke, Redwood City, CA (US); Deeba Ensan, Foster City, CA (US); Rao V. Kalla, Foster City, CA (US); Richard L Mackman, Millbrae, CA (US); Jagadeesh N. Manda, Santa Clara, CA (US); Devan Naduthambi, San Bruno, CA (US); Dustin S. Siegel, Half Moon Bay, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/820,183

(22) Filed: Aug. 16, 2022

(65) Prior Publication Data
US 2023/0212199 A1 Jul. 6, 2023

Related U.S. Application Data

(60) Provisional application No. 63/313,633, filed on Feb. 24, 2022, provisional application No. 63/234,515, filed on Aug. 18, 2021.

(51) Int. Cl.
*C07F 9/09* (2006.01)
*A61K 31/706* (2006.01)
*A61P 31/14* (2006.01)

(52) U.S. Cl.
CPC .............. *C07F 9/095* (2013.01); *A61P 31/14* (2018.01)

(58) Field of Classification Search
CPC ......... C07F 9/095; A61P 31/14; A61K 31/706
See application file for complete search history.

(56) References Cited

U.S. PATENT DOCUMENTS

| | | | |
|---|---|---|---|
| 4,707,540 A | 11/1987 | Manser et al. | |
| 5,446,137 A | 8/1995 | Maag et al. | |
| 6,699,994 B1 | 3/2004 | Babu et al. | |
| 8,101,745 B2 | 1/2012 | Hostetler et al. | |
| 8,119,607 B2 | 2/2012 | Francom et al. | |
| 8,242,085 B2 | 8/2012 | Babu et al. | |
| 8,318,700 B2 | 11/2012 | Hostetler et al. | |
| 8,440,813 B2 | 5/2013 | Babu et al. | |
| 9,370,528 B2 | 6/2016 | Schentag et al. | |
| 9,388,208 B2 | 7/2016 | Clarke et al. | |
| 9,701,682 B2 | 7/2017 | Clarke et al. | |
| 9,724,360 B2 | 8/2017 | Chun et al. | |
| 9,777,035 B2 | 10/2017 | Girijavallabhan et al. | |
| 9,815,864 B2 | 11/2017 | Beigelman et al. | |
| 10,004,719 B1 | 6/2018 | Hsu et al. | |
| 10,059,716 B2 | 8/2018 | Clarke et al. | |
| 10,251,904 B2 | 4/2019 | Clarke et al. | |
| 10,377,761 B2 | 8/2019 | Clarke et al. | |
| 10,682,368 B2 | 6/2020 | Perron et al. | |
| 11,773,122 B2 | 10/2023 | Lazerwith et al. | |
| 2002/0035082 A1 | 3/2002 | Grinstaff et al. | |
| 2002/0188137 A1 | 12/2002 | Dershem et al. | |
| 2003/0170891 A1 | 9/2003 | McSwiggen | |
| 2003/0175950 A1 | 9/2003 | McSwiggen | |
| 2003/0199516 A1 | 10/2003 | Moser et al. | |
| 2004/0009959 A1 | 1/2004 | Potter et al. | |
| 2004/0157838 A1 | 8/2004 | Griffith | |
| 2004/0157839 A1 | 8/2004 | Griffith | |
| 2004/0214837 A1 | 10/2004 | Griffith et al. | |
| 2004/0229839 A1 | 11/2004 | Babu et al. | |
| 2004/0229840 A1 | 11/2004 | Bhat et al. | |
| 2006/0121312 A1 | 6/2006 | Yamada et al. | |
| 2006/0194144 A1 | 8/2006 | Sooriyakumaran et al. | |
| 2006/0281922 A1 | 12/2006 | Gao et al. | |
| 2007/0232635 A1 | 10/2007 | Chelliah et al. | |
| 2009/0318380 A1 | 12/2009 | Sofia et al. | |
| 2009/0323011 A1 | 12/2009 | He et al. | |
| 2009/0323012 A1 | 12/2009 | He et al. | |
| 2010/0035836 A1 | 2/2010 | Francom et al. | |
| 2010/0040804 A1 | 2/2010 | Zhang | |
| 2010/0096603 A1 | 4/2010 | Wang et al. | |
| 2010/0184942 A1 | 7/2010 | Chen et al. | |
| 2010/0186626 A1 | 7/2010 | Shin et al. | |
| 2011/0212994 A1 | 9/2011 | Clem et al. | |
| 2011/0216273 A1 | 9/2011 | He et al. | |
| 2011/0287927 A1 | 11/2011 | Grasset et al. | |

(Continued)

FOREIGN PATENT DOCUMENTS

| | | |
|---|---|---|
| CN | 102000103 A | 4/2011 |
| CN | 102286047 A | 12/2011 |

(Continued)

OTHER PUBLICATIONS

Kaler et al. "Respiratory Syncytial virus: a comprehensive review of transmission, pathophysiology, and manifestation," Cureus, 2023, 15(3): e36342. DOI 10.7759/cureus.36342 (Year: 2023).*
Coultas et al. "Experimental antiviral therapeutics studies for human rhinovirus infections," J. Experimental Pharmacology, 2021:13 645-659, DOI: 10.2147/JEP.S255211 (Year: 2021).*
Brachwitz et al. (1999) "Synthesis and Antiproliferative Potency of 9-Beta-D-Arabiofuranosyl-2-Fluoroadenine Phospholipid Adducts", Bioorganic & Medicinal Chemistry, Eslevier, Astermdam, NL, vol. 7, No. 6, pp. 1195-1200, XP001031156.
Cockerill et al. (2019) "State of the Art in Respiratory Syncytial Virus Drug Discovery and Development", Journal of Medicinal Chemistry, 62(7):3206-3227.

(Continued)

*Primary Examiner* — Yong S. Chong

(57) ABSTRACT

Phospholipid compounds and methods of using the same, singly or in combination with additional agents, and pharmaceutical formulations of said compounds for the treatment of viral infections are disclosed.

18 Claims, No Drawings

Specification includes a Sequence Listing.

(56) References Cited

U.S. PATENT DOCUMENTS

| | | |
|---|---|---|
| 2011/0319459 A1 | 12/2011 | Gupta et al. |
| 2012/0009147 A1 | 1/2012 | Cho et al. |
| 2012/0020921 A1 | 1/2012 | Cho et al. |
| 2012/0035115 A1 | 2/2012 | Manoharan et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0214735 A1 | 8/2012 | Bhuniya et al. |
| 2012/0214762 A1 | 8/2012 | Staben et al. |
| 2012/0219568 A1 | 8/2012 | Liu et al. |
| 2012/0264649 A1 | 10/2012 | Bazan et al. |
| 2013/0303669 A1 | 11/2013 | Morimoto et al. |
| 2014/0038991 A1 | 2/2014 | Yu et al. |
| 2014/0200215 A1 | 7/2014 | Buckman et al. |
| 2014/0309413 A1 | 10/2014 | Rose et al. |
| 2015/0011497 A1 | 1/2015 | Beigelman et al. |
| 2015/0051167 A1 | 2/2015 | Wang et al. |
| 2015/0105341 A1 | 4/2015 | Beigelman et al. |
| 2015/0252265 A1 | 9/2015 | Archetti et al. |
| 2015/0274767 A1 | 10/2015 | Girijavallabhan et al. |
| 2015/0366887 A1 | 12/2015 | Blatt et al. |
| 2015/0366888 A1 | 12/2015 | Blatt et al. |
| 2016/0024107 A1 | 1/2016 | Clarke et al. |
| 2016/0053175 A1 | 2/2016 | Song et al. |
| 2016/0122374 A1 | 5/2016 | Chun et al. |
| 2016/0244668 A1 | 8/2016 | Saito et al. |
| 2016/0257657 A1 | 9/2016 | Wipf et al. |
| 2017/0071964 A1 | 3/2017 | Clarke et al. |
| 2017/0186964 A1 | 6/2017 | Cho et al. |
| 2018/0002366 A1 | 1/2018 | Girijavallabhan et al. |
| 2018/0044369 A1 | 2/2018 | Beigelman et al. |
| 2018/0079774 A1 | 3/2018 | Beigelman et al. |
| 2018/0226580 A1 | 8/2018 | Fitzgerald et al. |
| 2019/0185748 A1 | 6/2019 | Liao |
| 2019/0185754 A1 | 6/2019 | Archetti et al. |
| 2019/0241807 A1 | 8/2019 | Mizusaki et al. |
| 2021/0060051 A1 | 3/2021 | Schinazi et al. |
| 2021/0284669 A1 | 9/2021 | Chun et al. |
| 2021/0284670 A1 | 9/2021 | Chin et al. |
| 2021/0292348 A1 | 9/2021 | Byun et al. |
| 2022/0143052 A1 | 5/2022 | Lazerwith et al. |
| 2023/0248753 A1 | 8/2023 | Lazerwith et al. |
| 2023/0250117 A1 | 8/2023 | Lazerwith et al. |
| 2024/0025932 A1 | 1/2024 | Lazerwith et al. |

FOREIGN PATENT DOCUMENTS

| | | |
|---|---|---|
| CN | 102603836 A | 7/2012 |
| CN | 103709220 A | 4/2014 |
| CN | 104086612 A | 10/2014 |
| CN | 105646629 A | 6/2016 |
| CN | 105777580 A | 7/2016 |
| CN | 106518766 A | 3/2017 |
| CN | 106518767 A | 3/2017 |
| CN | 106892920 A | 6/2017 |
| CN | 107286190 A | 10/2017 |
| CN | 108276352 A | 7/2018 |
| CN | 109748921 A | 5/2019 |
| CN | 109748943 A | 5/2019 |
| CN | 109748944 A | 5/2019 |
| CN | 110215456 A | 9/2019 |
| CN | 110330540 A | 10/2019 |
| CN | 110724174 A | 1/2020 |
| CN | 110776512 A | 2/2020 |
| CN | 111620909 A | 9/2020 |
| DE | 2626792 A1 | 12/1977 |
| DE | 3528753 A1 | 2/1987 |
| DE | 4232852 A1 | 3/1994 |
| DE | 19934799 A1 | 2/2001 |
| DE | 10064823 A1 | 6/2002 |
| EP | 0284952 A2 | 10/1988 |
| EP | 0419944 A2 | 4/1991 |
| EP | 0458214 A1 | 11/1991 |
| EP | 0682098 A2 | 11/1995 |
| EP | 0924265 A2 | 6/1999 |
| EP | 1046631 A1 | 10/2000 |
| EP | 1170353 A2 | 1/2002 |
| EP | 1593713 A1 | 11/2005 |
| EP | 1975718 A2 | 10/2008 |
| EP | 1978077 A1 | 10/2008 |
| EP | 2098226 A1 | 9/2009 |
| EP | 2388069 A1 | 11/2011 |
| EP | 2778169 A1 | 9/2014 |
| EP | 2896678 A1 | 7/2015 |
| EP | 2980182 A1 | 2/2016 |
| FR | 2354774 A1 | 1/1978 |
| FR | 2669639 A1 | 5/1992 |
| JP | S6286363 A | 4/1987 |
| JP | H0931092 A | 2/1997 |
| JP | H09328497 A | 12/1997 |
| JP | 2002326995 A | 11/2002 |
| JP | 2002326996 A | 11/2002 |
| JP | 2003246770 A | 9/2003 |
| JP | 2004315613 A | 11/2004 |
| JP | 2005120172 A | 5/2005 |
| JP | 2006232875 A | 9/2006 |
| JP | 2008007634 A | 1/2008 |
| JP | 2012216832 A | 11/2012 |
| JP | 5295692 B2 | 9/2013 |
| JP | 2014145852 A | 8/2014 |
| JP | 2016132779 A | 7/2016 |
| JP | 2018044028 A | 3/2018 |
| JP | 2018203945 A | 12/2018 |
| KR | 20120135501 A | 12/2012 |
| KR | 20160098975 A | 8/2016 |
| KR | 20160110899 A | 9/2016 |
| KR | 20160110900 A | 9/2016 |
| KR | 20190041918 A | 4/2019 |
| KR | 20190076339 A | 7/2019 |
| NL | 7606413 A | 12/1977 |
| WO | WO-8807043 A1 | 9/1988 |
| WO | WO-9110671 A1 | 7/1991 |
| WO | WO-9201695 A1 | 2/1992 |
| WO | WO-9201696 A1 | 2/1992 |
| WO | WO-9214805 A1 | 9/1992 |
| WO | WO-9316075 A1 | 8/1993 |
| WO | WO-9614329 A1 | 5/1996 |
| WO | WO-9640705 A1 | 12/1996 |
| WO | WO-9816184 A2 | 4/1998 |
| WO | WO-9900399 A1 | 1/1999 |
| WO | WO-9914226 A2 | 3/1999 |
| WO | WO-9926933 A1 | 6/1999 |
| WO | WO-9926941 A1 | 6/1999 |
| WO | WO-9951565 A1 | 10/1999 |
| WO | WO-9961583 A2 | 12/1999 |
| WO | WO-0001381 A1 | 1/2000 |
| WO | WO-0032152 A2 | 6/2000 |
| WO | WO-0034276 A1 | 6/2000 |
| WO | WO-0063154 A1 | 10/2000 |
| WO | WO-0066604 A2 | 11/2000 |
| WO | WO-0100197 A2 | 1/2001 |
| WO | WO-0110842 A2 | 2/2001 |
| WO | WO-0114320 A1 | 3/2001 |
| WO | WO-0119841 A1 | 3/2001 |
| WO | WO-0121577 A2 | 3/2001 |
| WO | WO-0123357 A2 | 4/2001 |
| WO | WO-0147862 A1 | 7/2001 |
| WO | WO-0164642 A2 | 9/2001 |
| WO | WO-0177091 A2 | 10/2001 |
| WO | WO-0207516 A2 | 1/2002 |
| WO | WO-0234711 A1 | 5/2002 |
| WO | WO-0234736 A1 | 5/2002 |
| WO | WO-0239987 A2 | 5/2002 |
| WO | WO-02062766 A2 | 8/2002 |
| WO | WO-02094185 A2 | 11/2002 |
| WO | WO-02100415 A2 | 12/2002 |
| WO | WO-03039523 A2 | 5/2003 |
| WO | WO-03041649 A2 | 5/2003 |
| WO | WO-03049772 A2 | 6/2003 |
| WO | WO-03088908 A2 | 10/2003 |
| WO | WO-03090748 A1 | 11/2003 |
| WO | WO-03091262 A1 | 11/2003 |
| WO | WO-2004002999 A2 | 1/2004 |
| WO | WO-2004007472 A1 | 1/2004 |

(56) References Cited

FOREIGN PATENT DOCUMENTS

| | | |
|---|---|---|
| WO | WO-2004014312 A2 | 2/2004 |
| WO | WO-2004037159 A2 | 5/2004 |
| WO | WO-2004041752 A2 | 5/2004 |
| WO | WO-2004080966 A1 | 9/2004 |
| WO | WO-2004083177 A2 | 9/2004 |
| WO | WO-2004083263 A1 | 9/2004 |
| WO | WO-2004087153 A2 | 10/2004 |
| WO | WO-2004091499 A2 | 10/2004 |
| WO | WO-2004106356 A1 | 12/2004 |
| WO | WO-2004110350 A2 | 12/2004 |
| WO | WO-2005020885 A2 | 3/2005 |
| WO | WO-2005021568 A2 | 3/2005 |
| WO | WO-2005023771 A1 | 3/2005 |
| WO | WO-2005025515 A2 | 3/2005 |
| WO | WO-2005040135 A1 | 5/2005 |
| WO | WO-2005058832 A1 | 6/2005 |
| WO | WO-2005093476 A1 | 10/2005 |
| WO | WO-2005095544 A1 | 10/2005 |
| WO | WO-2005097052 A1 | 10/2005 |
| WO | WO-2005111099 A1 | 11/2005 |
| WO | WO-2006001463 A1 | 1/2006 |
| WO | WO-2006006490 A1 | 1/2006 |
| WO | WO-2006008438 A1 | 1/2006 |
| WO | WO-2006016101 A1 | 2/2006 |
| WO | WO-2006030193 A1 | 3/2006 |
| WO | WO-2006038594 A1 | 4/2006 |
| WO | WO-2006048634 A1 | 5/2006 |
| WO | WO-2006061094 A1 | 6/2006 |
| WO | WO-2006063717 A2 | 6/2006 |
| WO | WO-2006066074 A2 | 6/2006 |
| WO | WO-2006094347 A1 | 9/2006 |
| WO | WO-2006098380 A1 | 9/2006 |
| WO | WO-2006105440 A2 | 10/2006 |
| WO | WO-2006110656 A2 | 10/2006 |
| WO | WO-2006119800 A1 | 11/2006 |
| WO | WO-2006130217 A2 | 12/2006 |
| WO | WO-2007007588 A1 | 1/2007 |
| WO | WO-2007011759 A2 | 1/2007 |
| WO | WO-2007024021 A1 | 3/2007 |
| WO | WO-2007031185 A1 | 3/2007 |
| WO | WO-2007056143 A2 | 5/2007 |
| WO | WO-2007056170 A2 | 5/2007 |
| WO | WO-2007076034 A2 | 7/2007 |
| WO | WO-2007084667 A2 | 7/2007 |
| WO | WO-2007095188 A2 | 8/2007 |
| WO | WO-2007125320 A1 | 11/2007 |
| WO | WO-2007130783 A2 | 11/2007 |
| WO | WO-2008001195 A2 | 1/2008 |
| WO | WO-2008011557 A2 | 1/2008 |
| WO | WO-2008012555 A2 | 1/2008 |
| WO | WO-2008021388 A1 | 2/2008 |
| WO | WO-2008024364 A2 | 2/2008 |
| WO | WO-2008082601 A2 | 7/2008 |
| WO | WO-2008092006 A2 | 7/2008 |
| WO | WO-2008095040 A2 | 8/2008 |
| WO | WO-2008109177 A2 | 9/2008 |
| WO | WO-2008109180 A2 | 9/2008 |
| WO | WO-2008109181 A2 | 9/2008 |
| WO | WO-2008117047 A1 | 10/2008 |
| WO | WO-2008121360 A1 | 10/2008 |
| WO | WO-2008133966 A1 | 11/2008 |
| WO | WO-2008151437 A1 | 12/2008 |
| WO | WO-2009001097 A2 | 12/2008 |
| WO | WO-2009009951 A1 | 1/2009 |
| WO | WO-2009011228 A1 | 1/2009 |
| WO | WO-2009011229 A1 | 1/2009 |
| WO | WO-2009067409 A1 | 5/2009 |
| WO | WO-2009069095 A2 | 6/2009 |
| WO | WO-2009076593 A1 | 6/2009 |
| WO | WO-2009076618 A2 | 6/2009 |
| WO | WO-2009086192 A1 | 7/2009 |
| WO | WO-2009086201 A1 | 7/2009 |
| WO | WO-2009111653 A2 | 9/2009 |
| WO | WO-2009132123 A1 | 10/2009 |
| WO | WO-2009132135 A1 | 10/2009 |
| WO | WO-2009151921 A1 | 12/2009 |
| WO | WO-2009152095 A2 | 12/2009 |
| WO | WO-2010001174 A1 | 1/2010 |
| WO | WO-2010007116 A2 | 1/2010 |
| WO | WO-2010026153 A1 | 3/2010 |
| WO | WO-2010036407 A2 | 4/2010 |
| WO | WO-2010060952 A1 | 6/2010 |
| WO | WO-2010073126 A2 | 7/2010 |
| WO | WO-2010084115 A2 | 7/2010 |
| WO | WO-2010108135 A1 | 9/2010 |
| WO | WO-2010108140 A1 | 9/2010 |
| WO | WO-2010145778 A1 | 12/2010 |
| WO | WO-2011005860 A2 | 1/2011 |
| WO | WO-2011015037 A1 | 2/2011 |
| WO | WO-2011016430 A1 | 2/2011 |
| WO | WO-2011031896 A2 | 3/2011 |
| WO | WO-2011032169 A2 | 3/2011 |
| WO | WO-2011035231 A1 | 3/2011 |
| WO | WO-2011035250 A1 | 3/2011 |
| WO | WO-2011035842 A1 | 3/2011 |
| WO | WO-2011036557 A1 | 3/2011 |
| WO | WO-2011038207 A1 | 3/2011 |
| WO | WO-2011057214 A2 | 5/2011 |
| WO | WO-2011086075 A1 | 7/2011 |
| WO | WO-2011097300 A1 | 8/2011 |
| WO | WO-2011100131 A2 | 8/2011 |
| WO | WO-2011109799 A1 | 9/2011 |
| WO | WO-2011119869 A1 | 9/2011 |
| WO | WO-2011146401 A1 | 11/2011 |
| WO | WO-2011150288 A1 | 12/2011 |
| WO | WO-2011156632 A2 | 12/2011 |
| WO | WO-2012012465 A1 | 1/2012 |
| WO | WO-2012012776 A1 | 1/2012 |
| WO | WO-2012031539 A1 | 3/2012 |
| WO | WO-2012034626 A1 | 3/2012 |
| WO | WO-2012037038 A1 | 3/2012 |
| WO | WO-2012040124 A1 | 3/2012 |
| WO | WO-2012040126 A1 | 3/2012 |
| WO | WO-2012040127 A1 | 3/2012 |
| WO | WO-2012068340 A2 | 5/2012 |
| WO | WO-2012083048 A2 | 6/2012 |
| WO | WO-2012087596 A1 | 6/2012 |
| WO | WO-2012088155 A1 | 6/2012 |
| WO | WO-2012088438 A1 | 6/2012 |
| WO | WO-2012092471 A2 | 7/2012 |
| WO | WO-2012121973 A1 | 9/2012 |
| WO | WO-2012128944 A1 | 9/2012 |
| WO | WO-2012139028 A2 | 10/2012 |
| WO | WO-2012142075 A1 | 10/2012 |
| WO | WO-2012142085 A1 | 10/2012 |
| WO | WO-2012142523 A2 | 10/2012 |
| WO | WO-2012160392 A1 | 11/2012 |
| WO | WO-2013000855 A1 | 1/2013 |
| WO | WO-2013007586 A1 | 1/2013 |
| WO | WO-2013030288 A1 | 3/2013 |
| WO | WO-2013033270 A2 | 3/2013 |
| WO | WO-2013040492 A2 | 3/2013 |
| WO | WO-2013040568 A1 | 3/2013 |
| WO | WO-2013044030 A1 | 3/2013 |
| WO | WO-2013056132 A2 | 4/2013 |
| WO | WO-2013072466 A1 | 5/2013 |
| WO | WO-2013087765 A1 | 6/2013 |
| WO | WO-2013090420 A2 | 6/2013 |
| WO | WO-2013096679 A1 | 6/2013 |
| WO | WO-2013096680 A1 | 6/2013 |
| WO | WO-2013101552 A1 | 7/2013 |
| WO | WO-2013135339 A1 | 9/2013 |
| WO | WO-2013138236 A1 | 9/2013 |
| WO | WO-2013142124 A1 | 9/2013 |
| WO | WO-2013142157 A1 | 9/2013 |
| WO | WO-2013142159 A1 | 9/2013 |
| WO | WO-2013142525 A1 | 9/2013 |
| WO | WO-2013147795 A1 | 10/2013 |
| WO | WO-2013151975 A1 | 10/2013 |
| WO | WO-2013182262 A1 | 12/2013 |
| WO | WO-2014005125 A2 | 1/2014 |
| WO | WO-2014008236 A1 | 1/2014 |
| WO | WO-2014015936 A1 | 1/2014 |
| WO | WO-2014026198 A1 | 2/2014 |

(56) References Cited

FOREIGN PATENT DOCUMENTS

| | | |
|---|---|---|
| WO | WO-2014031872 A2 | 2/2014 |
| WO | WO-2014035140 A2 | 3/2014 |
| WO | WO-2014048998 A1 | 4/2014 |
| WO | WO-2014057095 A1 | 4/2014 |
| WO | WO-2014058801 A1 | 4/2014 |
| WO | WO-2014059901 A1 | 4/2014 |
| WO | WO-2014059902 A1 | 4/2014 |
| WO | WO-2014090369 A1 | 6/2014 |
| WO | WO-2014100498 A1 | 6/2014 |
| WO | WO-2014100505 A1 | 6/2014 |
| WO | WO-2014102077 A1 | 7/2014 |
| WO | WO-2014124458 A1 | 8/2014 |
| WO | WO-2014134127 A1 | 9/2014 |
| WO | WO-2014134251 A1 | 9/2014 |
| WO | WO-2014149164 A1 | 9/2014 |
| WO | WO-2014160012 A2 | 10/2014 |
| WO | WO-2014209979 A1 | 12/2014 |
| WO | WO-2015003146 A1 | 1/2015 |
| WO | WO-2015006280 A1 | 1/2015 |
| WO | WO-2015016187 A1 | 2/2015 |
| WO | WO-2015024120 A1 | 2/2015 |
| WO | WO-2015031710 A1 | 3/2015 |
| WO | WO-2015038596 A1 | 3/2015 |
| WO | WO-2015046827 A1 | 4/2015 |
| WO | WO-2015051169 A2 | 4/2015 |
| WO | WO-2015061742 A2 | 4/2015 |
| WO | WO-2015069939 A1 | 5/2015 |
| WO | WO-2015089511 A2 | 6/2015 |
| WO | WO-2015118898 A1 | 8/2015 |
| WO | WO-2015120237 A2 | 8/2015 |
| WO | WO-2015129672 A1 | 9/2015 |
| WO | WO-2015143712 A1 | 10/2015 |
| WO | WO-2015148746 A1 | 10/2015 |
| WO | WO-2015148869 A1 | 10/2015 |
| WO | WO-2015160251 A1 | 10/2015 |
| WO | WO-2015196118 A1 | 12/2015 |
| WO | WO-2015196128 A2 | 12/2015 |
| WO | WO-2015196130 A2 | 12/2015 |
| WO | WO-2015198915 A1 | 12/2015 |
| WO | WO-2015200205 A1 | 12/2015 |
| WO | WO-2015200219 A1 | 12/2015 |
| WO | WO-2016010026 A1 | 1/2016 |
| WO | WO-2016018697 A1 | 2/2016 |
| WO | WO-2016029186 A1 | 2/2016 |
| WO | WO-2016031406 A1 | 3/2016 |
| WO | WO-2016041877 A1 | 3/2016 |
| WO | WO-2016066582 A1 | 5/2016 |
| WO | WO-2016069827 A1 | 5/2016 |
| WO | WO-2016069975 A1 | 5/2016 |
| WO | WO-2016070952 A1 | 5/2016 |
| WO | WO-2016074762 A1 | 5/2016 |
| WO | WO-2016096076 A1 | 6/2016 |
| WO | WO-2016100441 A1 | 6/2016 |
| WO | WO-2016100569 A1 | 6/2016 |
| WO | WO-2016107664 A1 | 7/2016 |
| WO | WO-2016115222 A1 | 7/2016 |
| WO | WO-2016116124 A1 | 7/2016 |
| WO | WO-2016116254 A1 | 7/2016 |
| WO | WO-2016116508 A1 | 7/2016 |
| WO | WO-2016117271 A1 | 7/2016 |
| WO | WO-2016145142 A1 | 9/2016 |
| WO | WO-2016148170 A1 | 9/2016 |
| WO | WO-2016152340 A1 | 9/2016 |
| WO | WO-2016161176 A1 | 10/2016 |
| WO | WO-2016162644 A1 | 10/2016 |
| WO | WO-2016170948 A1 | 10/2016 |
| WO | WO-2016172631 A2 | 10/2016 |
| WO | WO-2016178876 A2 | 11/2016 |
| WO | WO-2016184361 A1 | 11/2016 |
| WO | WO-2016192902 A1 | 12/2016 |
| WO | WO-2017005673 A1 | 1/2017 |
| WO | WO-2017019817 A1 | 2/2017 |
| WO | WO-2017019822 A1 | 2/2017 |
| WO | WO-2017019830 A1 | 2/2017 |
| WO | WO-2017023894 A1 | 2/2017 |
| WO | WO-2017024310 A1 | 2/2017 |
| WO | WO-2017027646 A1 | 2/2017 |
| WO | WO-2017032840 A1 | 3/2017 |
| WO | WO-2017041893 A1 | 3/2017 |
| WO | WO-2017045612 A1 | 3/2017 |
| WO | WO-2017045615 A1 | 3/2017 |
| WO | WO-2017045616 A1 | 3/2017 |
| WO | WO-2017045740 A1 | 3/2017 |
| WO | WO-2017049060 A1 | 3/2017 |
| WO | WO-2017058807 A1 | 4/2017 |
| WO | WO-2017059357 A1 | 4/2017 |
| WO | WO-2017066781 A1 | 4/2017 |
| WO | WO-2017066782 A1 | 4/2017 |
| WO | WO-2017066791 A1 | 4/2017 |
| WO | WO-2017066793 A1 | 4/2017 |
| WO | WO-2017066797 A1 | 4/2017 |
| WO | WO-2017068875 A1 | 4/2017 |
| WO | WO-2017073931 A1 | 5/2017 |
| WO | WO-2017073932 A1 | 5/2017 |
| WO | WO-2017073933 A1 | 5/2017 |
| WO | WO-2017091767 A2 | 6/2017 |
| WO | WO-2017093214 A1 | 6/2017 |
| WO | WO-2017097401 A1 | 6/2017 |
| WO | WO-2017153186 A1 | 9/2017 |
| WO | WO-2017156262 A1 | 9/2017 |
| WO | WO-2017161028 A1 | 9/2017 |
| WO | WO-2017165489 A1 | 9/2017 |
| WO | WO-2017184668 A1 | 10/2017 |
| WO | WO-2017205980 A1 | 12/2017 |
| WO | WO-2017207993 A1 | 12/2017 |
| WO | WO-2018015323 A2 | 1/2018 |
| WO | WO-2018031818 A2 | 2/2018 |
| WO | WO-2018065356 A1 | 4/2018 |
| WO | WO-2018067615 A1 | 4/2018 |
| WO | WO-2018098206 A1 | 5/2018 |
| WO | WO-2018106818 A1 | 6/2018 |
| WO | WO-2018106820 A1 | 6/2018 |
| WO | WO-2018110529 A1 | 6/2018 |
| WO | WO-2018116901 A1 | 6/2018 |
| WO | WO-2018119263 A1 | 6/2018 |
| WO | WO-2018138685 A2 | 8/2018 |
| WO | WO-2018169946 A1 | 9/2018 |
| WO | WO-2018175746 A1 | 9/2018 |
| WO | WO-2018183635 A1 | 10/2018 |
| WO | WO-2018184590 A1 | 10/2018 |
| WO | WO-2018189134 A1 | 10/2018 |
| WO | WO-2018204198 A1 | 11/2018 |
| WO | WO-2018208667 A1 | 11/2018 |
| WO | WO-2018213185 A1 | 11/2018 |
| WO | WO-2018218171 A1 | 11/2018 |
| WO | WO-2018218281 A1 | 12/2018 |
| WO | WO-2018222172 A1 | 12/2018 |
| WO | WO-2018226976 A1 | 12/2018 |
| WO | WO-2018237194 A1 | 12/2018 |
| WO | WO-2019014247 A1 | 1/2019 |
| WO | WO-2019018185 A1 | 1/2019 |
| WO | WO-2019051269 A1 | 3/2019 |
| WO | WO-2019052935 A1 | 3/2019 |
| WO | WO-2019053696 A1 | 3/2019 |
| WO | WO-2019084271 A1 | 5/2019 |
| WO | WO-2019086400 A1 | 5/2019 |
| WO | WO-2019092171 A1 | 5/2019 |
| WO | WO-2019098109 A1 | 5/2019 |
| WO | WO-2019125974 A1 | 6/2019 |
| WO | WO-2019129059 A1 | 7/2019 |
| WO | WO-2019133712 A1 | 7/2019 |
| WO | WO-2019154953 A1 | 8/2019 |
| WO | WO-2019154956 A1 | 8/2019 |
| WO | WO-2019173682 A1 | 9/2019 |
| WO | WO-2019195056 A1 | 10/2019 |
| WO | WO-2019215076 A1 | 11/2019 |
| WO | WO-2019218797 A1 | 11/2019 |
| WO | WO-2020032152 A1 | 2/2020 |
| WO | WO-2020033413 A2 | 2/2020 |
| WO | WO-2021167882 A1 | 8/2021 |
| WO | WO-2021168004 A1 | 8/2021 |
| WO | WO-2021168008 A1 | 8/2021 |
| WO | WO-2021168038 A1 | 8/2021 |

(56) References Cited

FOREIGN PATENT DOCUMENTS

| WO | WO-2021213288 A1 | | 10/2021 |
|---|---|---|---|
| WO | WO-2022020793 A1 | * | 1/2022 |
| WO | WO-2022046631 A1 | | 3/2022 |

OTHER PUBLICATIONS

Colombo et al. (1985) "Asymetric Dihydroxylations via Chiral Oxazolidines", Tetrahedron Letters, 26(44):5459-5462.
Feng et al. (2014) "Inhibition of Hepatitis C Virus Replication by GS-6620, a Potent C-Nucleoside Monophosphate Prodrug", Antimicrobial Agents and Chemotherapy, 58(4):1930-1942.
Griffon et al. (2001) "Synthesis And Antiproliferative Activity of Some 4'-C-Hydroxymethyl-α- and -β-D-Arabino-Pentofuranosyl Pyrimidine Nucleosides", Nucleosides, Nucleotides & Nucleic Acids, 20(4-7):649-652.
Griffon et al. (2006) "Synthesis and Biological Evaluation of Some 4'-C-(Hydroxymethyl)-α- and -β-D-Arabinofuranosyl Pyrimidine and Adenine Nucleosides", Collection of Czechoslovak Chemical Communications, 71(7):1063-1087.
International Preliminary Report on Patentability dated Dec. 15, 2021 for International Application No. PCT/US2021/018169 (20 pages).
International Preliminary Report on Patentability dated Sep. 1, 2022 for International Application No. PCT/US2021/018458 (12 pages).
International Search Report-Written Opinion dated Apr. 26, 2021 for International Application No. PCT/US2021/018169 (19 pages).
International Search Report-Written Opinion dated May 18, 2021 for International Application No. PCT/US2021/018458 (17 pages).
International Search Report-Written Opinion dated Dec. 13, 2022 for International Application No. PCT/US2022/075036 (17 pages).
Koshkin et al. (1998) "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, 54(14):3607-3630.
Leisvuori Anna (2015) "Prodrug Strategies of Antiviral Nucleotides: Studies on Enzymatically and Thermally Removable Phosphate Protecting Groups", University of Turku, Turku, Finland, 86 pages.
Milani et al. (2007) "Nucleolipoplexes:A New Paradigm for Phospholipid Bilayer-Nucleic Acid Interactions", Journal of the American Chemical Society, Sep. 26;129(38):11664-5.
Musich et al. (1978) "Synthesis of Anthopleurine, The Alarm Pheromone from Anthopleura Elegantissima", Journal of the American Chemical Society, 100(15):4865-4872.
Overend et al. (1970) "Branched Chain Sugars Part 12 Branched Sugars Derived from Methyl 2, 3-O-Isopropylidene-β-L-erythro-Pentopyranosid-4-Ulose and a Synthesis of L-Apiose", Carbohydrate Research, 15(2):185-195.
Patil et al. (1994) "4-Aza-7,9-Dideazaadenosine, a New Cytotoxic Synthetic C-Nucleoside Analogue of Adenosine", Tetrahedron Letters, 35(30):5339-5342.
Patil et al. (1994) "Synthesis of Pyrrolo[2,1-f][1,2,4]triazine Congeners of Nucleic Acid Purines via the N-Amination of 2-Substituted Pyrroles", Journal of Heterocyclic Chemistry, 31(4):781-786.
Schooley et al. (2021) "Rethinking Remdesivir: Synthesis, Antiviral Activity, and Pharmacokinetics of Oral Lipid Prodrugs" Antimicrobal Agents and Chemotherapy, Sep. 17;65(10):e0115521.
Shrestha et al. (2011) "Synthesis and Properties of a Bridged Nucleic Acid with a Perhydro-1,2-oxazin-3-one Ring", Journal of Organic Chemistry, 76(24):9891-9899.
Timpe et al. (1975) "3-desoxyhex-2-enono-1,4-lactone aus D-hexofuran(osid)-urono-6,3-lactonen", Carbohydrate Research, 39(1):53-60.
Waga et al. (1993) "Synthesis of 4'-C-Methylnucleosides", Bioscience, Biotechnology, Biochemistry, 57(9):1433-1438.
Wenska et al. (2007) "Synthesis of Conformationally Constrained 2'-N,4'-C-Ethylene-Bridged Adenosine (aza-ENA-A)", Heterocycles, 73(1):303-324.
Youssefyeh et al. (1977) "Synthetic Routes to 4'-hydroxymethylnucleosides" Tetrahedron Letters 18(5):435-438.
U.S. Appl. No. 18/301,179, filed Apr. 14, 2023, Lazerwith et al.
U.S. Appl. No. 18/332,587, filed Jun. 9, 2023, Lazerwith et al.
U.S. Appl. No. 17/502,559, filed Oct. 15, 2021, Lazerwith et al.
U.S. Appl. No. 18/304,270, filed Apr. 20, 2023, Lazerwith et al.

* cited by examiner

PHOSPHOLIPID COMPOUNDS AND METHODS OF MAKING AND USING THE SAME

CROSS-REFERENCE TO RELATED APPLICATIONS

This application claims priority to U.S. Provisional Application No. 63/234,515, filed Aug. 18, 2021, and U.S. Provisional Application No. 63/313,633, filed Feb. 24, 2022, both of which are incorporated herein in their entireties for all purposes.

SEQUENCE LISTING

The instant application contains a Sequence Listing which has been submitted electronically and is hereby incorporated by reference in its entirety.

BACKGROUND

There is a need for compounds, pharmaceutical formulations, and methods for treating viral infections, for example, Paramyxoviridae, Pneumoviridae, Picornaviridae, Flaviviridae, Filoviridae, and Orthomyxovirus infections. Embodiments of the present disclosure can address these and other needs.

SUMMARY

Disclosed herein are compounds of Formula I:

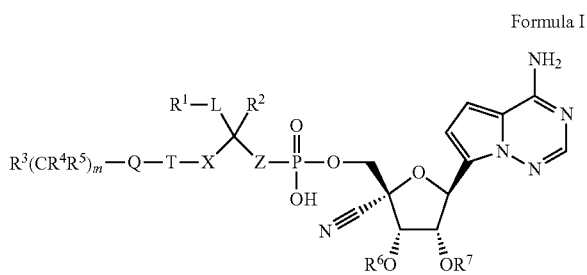

Formula I or a pharmaceutically acceptable salt thereof, wherein:
$R^1$ is $C_3$-$C_{10}$ cycloalkyl, $C_6$-$C_{10}$ aryl, or 5-10 membered heteroaryl containing one, two, or three N; wherein $R^1$ is optionally substituted with one, two, or three groups independently selected from $R^{1A}$ and $-NR^{13A}R^{14A}$;
 wherein each $R^{1A}$ is independently halo, cyano, $C_1$-$C_3$ alkyl, $C_1$-$C_3$ haloalkyl, $C_1$-$C_3$ alkoxy, $C_1$-$C_3$ haloalkoxy, or 5-10 membered heteroaryl containing one, two, or three heteroatoms selected from N and O;
 wherein each $R^{13A}$ is independently H or $C_1$-$C_3$ alkyl; and
 wherein each $R^{14A}$ is independently H or $C_1$-$C_3$ alkyl;
$R^2$ is H or $C_1$-$C_3$ alkyl;
$R^3$ is $C_1$-$C_3$ alkyl;
each $R^4$ is independently a bond, H, halo, $C_1$-$C_3$ alkyl, $C_1$-$C_3$ haloalkyl, or $C_3$-$C_6$ cycloalkyl,
each $R^5$ is independently a bond or H,
 wherein two or more adjacent ($CR^4R^5$) groups are optionally connected through a double bond;
$R^6$ is H or $-C(O)C_1$-$C_6$ alkyl;
$R^7$ is H or $-C(O)C_1$-$C_6$ alkyl;
m is 10, 11, 12, 13, 14, 15, 16, 17, 18, 19, 20, or 21;
L is $-O-$, $-(CR^{12A}R^{12B})_n-$, $-O-(CR^{12A}R^{12B})_n-O-$, or $-(CR^{12A}R^{12B})_n-O-(CR^{12A}R^{12B})_n-$;
 wherein
  each $R^{12A}$ is independently H or $C_1$-$C_6$ alkyl;
  each $R^{12B}$ is independently H or $C_1$-$C_6$ alkyl; and
  n is 1 or 2;
Q is a bond or phenylene;
T is a bond or $-O-$;
X is a bond or $C_1$-$C_3$ alkylene; and
Z is $-O-$, $-O-(C_1$-$C_6)$-alkylene or $NR^{15}-(C_1$-$C_6)$-alkylene;
 wherein $R^{15}$ is H or $C_1$-$C_3$ alkyl.

Also disclosed herein are compounds of sub-formulas of Formula I, such as Formulas Ia, Ib, II, III, IV, V, VI, VII, VIII, IX, X, XI, XIa, XIb, XII, XIIa, XIIb, XIII, XIIIa, and XIIIb Disclosed herein are pharmaceutical formulations comprising a pharmaceutically effective amount of a compound disclosed herein, or a pharmaceutically acceptable salt thereof, and a pharmaceutically acceptable carrier or excipient.

Also disclosed herein are methods of treating or preventing a viral infection in a subject in need thereof, wherein the method comprises administering to the subject a compound disclosed herein, or a pharmaceutically acceptable salt thereof.

Also disclosed herein are methods of treating or preventing a viral infection in a human in need thereof, wherein the method comprises administering to the human a compound disclosed herein, or a pharmaceutically acceptable salt thereof.

The present disclosure provides a method for manufacturing a medicament for treating or preventing a viral infection in a subject in need thereof, characterized in that a compound disclosed herein, or a pharmaceutically acceptable salt thereof, is used.

The present disclosure provides a method for manufacturing a medicament for treating or preventing a viral infection in a human in need thereof, characterized in that a compound disclosed herein, or a pharmaceutically acceptable salt thereof, is used.

The present disclosure provides use of a compound disclosed herein, or a pharmaceutically acceptable salt thereof, for the manufacture of a medicament for the treatment or prevention of a viral infection in a human in need thereof.

DETAILED DESCRIPTION

I. General

The disclosure relates generally to methods and compounds for treating or preventing viral infections, for example Paramyxoviridae, Pneumoviridae, Picornaviridae, Flaviviridae, Filoviridae, and Orthomyxovirus infections. The following description sets forth exemplary methods, parameters and the like. It should be recognized, however, that such description is not intended as a limitation on the scope of the present disclosure but is instead provided as a description of exemplary embodiments.

II. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups can be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

As used herein, "a compound of the disclosure" can mean a compound of any of the Formulas I-XIIIb or a pharmaceutically acceptable salt, thereof. Similarly, the phrase "a compound of Formula (number)" means a compound of that formula and pharmaceutically acceptable salts thereof.

The prefix "$C_u$-$C_v$" indicates that the following group has from u to v carbon atoms. For example, "$C_1$-$C_8$ alkyl" indicates that the alkyl group has from 1 to 8 carbon atoms.

"Alkyl" refers to an unbranched or branched saturated hydrocarbon chain. For example, an alkyl group can have 1 to 20 carbon atoms (i.e., $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 3 carbon atoms (i.e., $C_1$-$C_3$ alkyl). Examples of suitable alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$). Other alkyl groups include, but are not limited to, heptyl, octyl, nonyl, decyl, undecyl, dodecyl, pentadcyl, hexadecyl, heptadecyl and octadecyl.

"Alkylene" refers to an unbranched and branched divalent saturated hydrocarbon chain. As used herein, alkylene has 1 to 20 carbon atoms (i.e., $C_{1-20}$ alkylene), 1 to 12 carbon atoms (i.e., $C_{1-12}$ alkylene), 1 to 8 carbon atoms (i.e., $C_{1-8}$ alkylene), 1 to 6 carbon atoms (i.e., $C_{1-6}$ alkylene), 1 to 4 carbon atoms (i.e., $C_{1-4}$ alkylene), 1 to 3 carbon atoms (i.e., $C_{1-3}$ alkylene), or 1 to 2 carbon atoms (i.e., $C_{1-2}$ alkylene). Examples of alkyl groups include, but are not limited to, methyl, ethyl, propyl, isopropyl, n-butyl, sec-butyl, isobutyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons can be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkenyl" refers to an unbranched or branched hydrocarbon chain containing at least two carbon atoms and at least one carbon-carbon double bond. As used herein, alkenyl can have from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Alkenyl can include any number of carbons, such as $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, or any range therein. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), 1 to 8 carbon atoms (i.e., $C_1$-$C_8$ alkoxy), 1 to 6 carbon atoms (i.e., $C_1$-$C_6$ alkoxy) or 1 to 3 carbon atoms (i.e., $C_1$-$C_3$ alkoxy). Examples of suitable alkoxy groups include, but are not limited to, methoxy (—O—CH$_3$ or —OMe), ethoxy (—OCH$_2$CH$_3$ or -OEt), isopropoxy (—O—CH(CH$_3$)$_2$), t-butoxy (—O—C(CH$_3$)$_3$ or -OtBu) and the like. Other examples of suitable alkoxy groups include, but are not limited to, sec-butoxy, tert-butoxy, pentoxy, hexoxy, and the like. Alkoxy groups can be substituted or unsubstituted.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), 1 to 8 carbon atoms (i.e., $C_1$-$C_8$ haloalkyl), 1 to 6 carbon atoms (i.e., $C_1$-$C_6$ alkyl) or 1 to 3 carbon atoms (i.e., $C_1$-$C_3$ alkyl). Examples of suitable haloalkyl groups include, but are not limited to, —CF$_3$, —CHF$_2$, —CFH$_2$, —CH$_2$CF$_3$, fluorochloromethyl, difluorochloromethyl, 1,1,1-trifluoroethyl and pentafluoroethyl.

"Halo" or "halogen" as used herein refers to fluoro (—F), chloro (—Cl), bromo (—Br) and iodo (—I).

"Haloalkoxy" is an alkoxy group, as defined above, in which one or more hydrogen atoms of the alkoxy group is replaced with a halogen atom. The alkoxy portion of a haloalkoxy group can have 1 to 20 carbon atoms (i.e., $C_1$-$C_{20}$ haloalkoxy), 1 to 12 carbon atoms (i.e., $C_1$-$C_{12}$ haloalkoxy), 1 to 8 carbon atoms (i.e., $C_1$-$C_8$ haloalkoxy), 1 to 6 carbon atoms (i.e., $C_1$-$C_6$ alkoxy) or 1 to 3 carbon atoms (i.e., $C_1$-$C_3$ alkoxy). Examples of suitable haloalkoxy groups include, but are not limited to, —OCF$_3$, —OCHF$_2$, —OCFH$_2$, —OCH$_2$CF$_3$, and the like.

"Hydroxy" refers to —OH.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Exemplary aryl groups include, but are not limited to, radicals derived from benzene (e.g., phenyl), naphthalene, anthracene, biphenyl, and the like.

"Cycloalkyl" refers to a saturated or partially saturated cyclic alkyl group having a single ring or multiple rings including fused, bridged, and spiro ring systems. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include, but are not limited to, cyclopropyl, cyclobutyl, cyclopentyl, cyclohexyl, cycloheptyl, and cyclooctyl. Cycloalkyl groups also include partially unsaturated ring systems containing one or more double bonds, including fused ring systems with one aromatic ring and one non-aromatic ring, but not fully aromatic ring systems.

"Heteroaryl" refers to an aromatic group, including groups having an aromatic tautomer or resonance structure, having a single ring, multiple rings, or multiple fused rings, with at least one heteroatom in the ring, i.e., one or more ring heteroatoms independently selected from nitrogen, oxygen, and sulfur, wherein the nitrogen or sulfur can be oxidized. Thus, the term includes rings having one or more annular O, N, S, S(O), S(O)$_2$, and N-oxide groups. The term includes rings having one or more annular C(O) groups. As used herein, heteroaryl include 5 to 20 ring atoms (i.e., 5- to 20-membered heteroaryl), 5 to 12 ring atoms (i.e., 5- to 12-membered heteroaryl), or 5 to 10 ring atoms (i.e., 5- to 10-membered heteroaryl), and 1 to 5 heteroatoms independently selected from nitrogen, oxygen, and sulfur, and oxidized forms of the heteroatoms. Examples of heteroaryl groups include, but are not limited to, pyridin-2(1H)-one, pyridazin-3(2H)-one, pyrimidin-4(3H)-one, quinolin-2(1H)-one, pyrimidinyl, purinyl, pyridyl, pyridazinyl, benzothiazolyl, and pyrazolyl. Heteroaryl does not encompass or overlap with aryl as defined above.

"Heterocycle" or "heterocyclyl" refer to a saturated or unsaturated cyclic alkyl group, with one or more ring heteroatoms independently selected from nitrogen, oxygen and sulfur. A heterocyclyl can be a single ring or multiple rings wherein the multiple rings can be fused, bridged, or spiro. As used herein, heterocyclyl has 3 to 20 ring atoms (i.e., 3 to 20 membered heterocyclyl), 3 to 12 ring atoms (i.e., 3 to 12 membered heterocyclyl), 3 to 10 ring atoms (i.e., 3 to 10 membered heterocyclyl), 3 to 8 ring atoms (i.e., 3 to 8 membered heterocyclyl), 4 to 12 ring carbon atoms (i.e., 4 to 12 membered heterocyclyl), 4 to 8 ring atoms (i.e., 4 to 8 membered heterocyclyl), or 4 to 6 ring atoms (i.e., 4 to 6 membered heterocyclyl). Examples of heterocyclyl groups include pyrrolidinyl, piperidinyl, piperazinyl, oxetanyl, dioxolanyl, azetidinyl, and morpholinyl.

The term "optionally substituted" in reference to a particular moiety of the compound disclosed herein (e.g., an optionally substituted aryl group) refers to a moiety wherein all substituents are hydrogen or wherein one or more of the hydrogens of the moiety can be replaced by the listed substituents.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, formulations, dosage forms and other materials which are useful in preparing a pharmaceutical formulation that is suitable for veterinary or human pharmaceutical use.

The compounds described herein can be prepared and/or formulated as pharmaceutically acceptable salts or when appropriate as a free base. Pharmaceutically acceptable salts are non-toxic salts of a free base form of a compound that possess the desired pharmacological activity of the free base. These salts can be derived from inorganic or organic acids or bases. For example, a compound that contains a basic nitrogen can be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in REMINGTON: THE SCIENCE AND PRACTICE OF PHARMACY, 21$^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and NX$_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom can be replaced by a deuterium atom or D, in which n is the number of hydrogen atoms in the molecule. As known in the art, the deuterium atom is a non-radioactive isotope of the hydrogen atom. Such compounds can increase resistance to metabolism, and thus can be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism," TRENDS PHARMACOL. SCI., 5(12):524-527 (1984). Such compounds are synthesized by means well known in the art, for example by employing starting materials in which one or more hydrogen atoms have been replaced by deuterium. The compounds disclosed herein can be deuterated at various positions, including (but not limited to), the following positions:

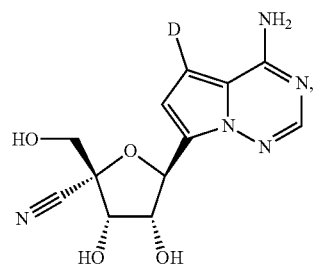

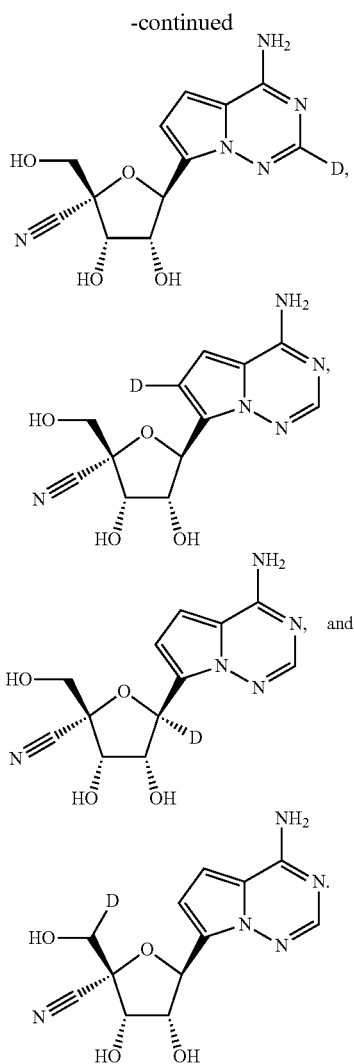

Examples of isotopes that can be incorporated into the disclosed compounds also include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula I-XIIIb, can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereometically or enantiomerically enriched form; or a racemic or scalemic mixture of such compound(s). As used herein, "scalemic mixture" is a mixture of stereoisomers at a ratio other than 1:1.

The terms "prevention" or "preventing" means any treatment of a disease or condition that causes the clinical symptoms of the disease or condition not to develop. The term "prevention" or "preventing" also encompasses the administration of a compound or composition according to the embodiments disclosed herein post-exposure of the subject to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the embodiments disclosed herein to prevent perinatal transmission of viral infection from mother to baby, by administration to the mother before giving birth and to the child within the first days of life.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds can exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of ADVANCED ORGANIC CHEMISTRY, 4th ed., J. March, John Wiley & Sons, New York, 1992).

A "subject" "patient" is meant to describe a human or vertebrate animal including a dog, cat, pocket pet, marmoset, horse, cow, pig, sheep, goat, elephant, giraffe, chicken, lion, monkey, owl, rat, squirrel, slender loris, and mouse. A "pocket pet" refers to a group of vertebrate animals capable of fitting into a commodious coat pocket such as, for example, hamsters, chinchillas, ferrets, rats, guinea pigs, gerbils, rabbits and sugar gliders.

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring =N— such as pyrazoles, imidazoles, benzimidazoles, triazoles, and tetrazoles.

Unless defined otherwise, all technical and scientific terms used herein have the same meaning as commonly understood by one of ordinary skill in the art. A dash at the front or end of a chemical group is a matter of convenience; chemical groups can be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "—SO$_2$CH$_2$—" is equivalent to "—CH$_2$SO$_2$—" and both can be connected in either direction. Similarly, an "arylalkyl" group, for example, can be attached to the remainder of the molecule at either an aryl or an alkyl portion of the group. A prefix such as "$C_{u-v}$" or ($C_u$-$C_v$) indicates that the following group has from u to v carbon atoms. For example, "$C_{1-6}$alkyl" and "$C_1$-$C_6$ alkyl" both indicate that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g., 3-12), of which up to 80% may be heteroatoms, such as N, O, S, and the remaining atoms are carbon.

Unless otherwise specified, the carbon atoms of the compounds of Formulas I-XIIIb are intended to have a valence of four. If in some chemical structure representations, carbon atoms do not have a sufficient number of variables attached to produce a valence of four, the remaining carbon substituents needed to provide a valence of four should be assumed to be hydrogen.

The terms "treating" and "treatment" as used herein are intended to mean the administration of a compound or composition according to the embodiments disclosed herein to alleviate or eliminate symptoms of a viral infection and/or to reduce viral load in a subject.

The term "therapeutically effective amount," as used herein, is the amount of compound disclosed herein present in a formulation described herein that is needed to provide a desired level of drug in the secretions and tissues of the airways and lungs, or alternatively, in the bloodstream of a subject to be treated to give an anticipated physiological response or desired biological effect when such a formulation is administered by the chosen route of administration. The precise amount will depend upon numerous factors, for example the particular compound disclosed herein, the specific activity of the formulation, the delivery device employed, the physical characteristics of the formulation, its intended use, as well as subject considerations such as severity of the disease state, subject cooperation, etc., and can readily be determined by one skilled in the art based upon the information provided herein. The term "therapeutically effective amount" or "effective amount" also means amounts that eliminate or reduce the subject's viral burden and/or viral reservoir.

The term "adjacent carbons" as used herein refers to consecutive carbons atoms that are directly attached to each other. For example, in

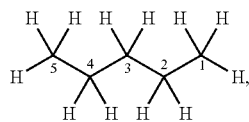

$C_1$ and $C_2$ are adjacent carbons, $C_2$ and $C_3$ are adjacent carbons, $C_3$ and $C_4$ are adjacent carbons, and $C_4$ and $C_5$ are adjacent carbons. Similarly, in

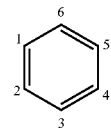

$C_1$ and $C_2$ are adjacent carbons, $C_2$ and $C_3$ are adjacent carbons, $C_3$ and $C_4$ are adjacent carbons, and $C_4$ and $C_5$ are adjacent carbons, $C_5$ and $C_6$ are adjacent carbons and $C_6$ and $C_1$ are adjacent carbons.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the parent drug according to some chemical or enzymatic pathway.

As used herein, "pharmaceutically acceptable carrier" or "pharmaceutically acceptable excipient" includes, but is not limited to, any and all solvents, dispersion media, coatings, antibacterial and antifungal agents, isotonic and absorption delaying agents, and combinations thereof. The use of pharmaceutically acceptable carriers and pharmaceutically acceptable excipients for pharmaceutically active substances is well known in the art. Except insofar as any conventional media or agent is incompatible with the active ingredient, its use in the therapeutic formulations is contemplated. Supplementary active ingredients can also be incorporated into the formulations. The carrier(s) must be "acceptable" in the sense of being compatible with the other ingredients of the formulation and physiologically innocuous to the recipient thereof.

III. Compounds

Provided herein are compounds of Formula I:

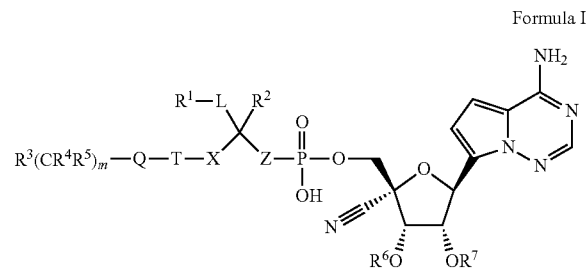

Formula I or a pharmaceutically acceptable salt thereof, wherein:
$R^1$ is $C_3$-$C_{10}$ cycloalkyl, $C_6$-$C_{10}$ aryl, or 5-10 membered heteroaryl containing one, two, or three N; wherein $R^1$ is optionally substituted with one, two, or three groups independently selected from $R^{14}$ and —$NR^{13A}R^{14A}$; wherein each $R^{14}$ is independently halo, cyano, $C_1$-$C_3$ alkyl, $C_1$-$C_3$ haloalkyl, $C_1$-$C_3$ alkoxy, $C_1$-$C_3$ haloalkoxy, or 5-10 membered heteroaryl containing one, two, or three heteroatoms selected from N and O;

wherein each $R^{13A}$ is independently H or $C_1$-$C_3$ alkyl; and wherein each $R^{14A}$ is independently H or $C_1$-$C_3$ alkyl;

$R^2$ is H or $C_1$-$C_3$ alkyl;

$R^3$ is $C_1$-$C_3$ alkyl;

each $R^4$ is independently a bond, H, halo, $C_1$-$C_3$ alkyl, $C_1$-$C_3$ haloalkyl, or $C_3$-$C_6$ cycloalkyl, each $R^5$ is independently a bond or H, wherein two or more adjacent $(CR^4R^5)$ groups are optionally connected through a double bond;

$R^6$ is H or —C(O)$C_1$-$C_6$ alkyl;

$R^7$ is H or —C(O)$C_1$-$C_6$ alkyl;

m is 10, 11, 12, 13, 14, 15, 16, 17, 18, 19, 20, or 21;

L is —O—, —(CR$^{12A}$R$^{12B}$)$_n$—, —O(CR$^{12A}$R$^{12B}$)$_n$—, —(CR$^{12A}$R$^{12B}$)$_n$—O—, or —(CR$^{12A}$R$^{12B}$)$_n$—O—(CR$^{12A}$R$^{12B}$)$_n$—;

wherein each $R^{12A}$ is independently H or $C_1$-$C_6$ alkyl;

each $R^{12B}$ is independently H or $C_1$-$C_6$ alkyl; and n is 1 or 2;

Q is a bond or phenylene;

T is a bond or —O—;

X is a bond or $C_1$-$C_3$ alkylene; and

Z is —O—, —O—($C_1$-$C_6$)-alkylene or NR$^{15}$—($C_1$-$C_6$)-alkylene;

wherein $R^{15}$ is H or $C_1$-$C_3$ alkyl.

In some embodiments, when $R^1$ is $C_6$-$C_{10}$ aryl, $R^2$ is H, $R^3$ is methyl, each $R^4$ is H, each $R^5$ is H, L is —O— or —O(CR$^{12A}$R$^{12B}$)$_n$—, X is —CH$_2$—, T is —O—, and Q is a bond, then $R^1$ is substituted with one to three $R^{1A}$ groups. In some embodiments, the compounds disclosed herein, and pharmaceutically acceptable salts thereof, do not include the following compound and its pharmaceutically acceptable salts:

$R^1$ can be $C_3$-$C_{10}$ cycloalkyl, $C_6$-$C_{10}$ aryl, or 5-10 membered heteroaryl containing one or two N. $R^1$ is optionally substituted with one, two, or three groups independently selected from $R^{1A}$ and —NR$^{13A}$R$^{14A}$. In some embodiments, $R^1$ is not substituted. In some embodiments, $R^1$ is substituted with one group selected from $R^{1A}$ and —NR$^{13A}$R$^{14A}$. In some embodiments, $R^1$ is substituted with one $R^{1A}$. In some embodiments, $R^1$ is substituted with one —NR$^{13A}$R$^{14A}$. In some embodiments, $R^1$ is substituted with two groups independently selected from $R^{1A}$ and —NR$^{13A}$R$^{14A}$. In some embodiments, $R^1$ is substituted with two groups independently selected from $R^{1A}$. In some embodiments, $R^1$ is substituted with two groups independently selected from —NR$^{13A}$R$^{14A}$. In some embodiments, $R^1$ is substituted with three groups independently selected from $R^{1A}$ and —NR$^{13A}$R$^{14A}$. In some embodiments, $R^1$ is substituted with three groups independently selected from $R^{1A}$. In some embodiments, $R^1$ is substituted with three groups independently selected from —NR$^{13A}$R$^{14A}$. In some embodiments, $R^1$ is substituted with one $R^{1A}$ and one —NR$^{13A}$R$^{14A}$. In some embodiments, $R^1$ is substituted with one $R^{1A}$ and two —NR$^{13A}$R$^{14A}$. In some embodiments, $R^1$ is substituted with two $R^{1A}$ and one —NR$^{13A}$R$^{14A}$. In some embodiments, $R^1$ is substituted with one, two, or three $R^{1A}$, wherein each $R^{1A}$ is independently selected from halo, cyano, $C_1$-$C_3$ alkyl, $C_1$-$C_3$ haloalkyl, $C_1$-$C_3$ alkoxy, $C_1$-$C_3$ haloalkoxy, and 5-10 membered heteroaryl containing one, two, or three heteroatoms selected from N and O. In some embodiments, $R^1$ is substituted with one, two, or three $R^{1A}$, wherein each $R^{1A}$ is independently selected from halo, cyano, $C_1$-$C_3$ alkoxy, $C_1$-$C_3$ haloalkoxy, and 5-10 (e.g., 5, 6, 7, 8, 9, or 10) membered heteroaryl containing one, two, or three heteroatoms selected from N and O. In some embodiments, $R^1$ is substituted with one, two, or three $R^{1A}$, wherein each $R^{1A}$ is independently selected from halo, cyano, $C_1$-$C_3$ alkoxy, $C_1$-$C_3$ haloalkoxy, and 5-6 membered heteroaryl containing one, two, or three heteroatoms selected from N and O. In some embodiments, $R^1$ is substituted with one, two, or three $R^{1A}$, wherein each $R^{1A}$ is independently selected from halo, cyano, methoxy, isopropoxy, triazolyl, and oxadiazolyl. In some embodiments, $R^1$ is substituted with one $R^{1A}$ selected from halo, cyano, methoxy, isopropoxy, triazolyl, and oxadiazolyl. In some embodiments, $R^1$ is substituted with two $R^{1A}$, wherein each $R^{1A}$ is independently selected from halo, cyano, methoxy, isopropoxy, triazolyl, and oxadiazolyl. In some embodiments, $R^1$ is substituted with three $R^{1A}$, wherein each $R^{1A}$ is independently selected from halo, cyano, methoxy, isopropoxy, triazolyl, and oxadiazolyl. In some embodiments, the cycloalkyl, aryl, or heteroaryl of $R^1$ is substituted with two $R^{1A}$ selected from halo and cyano. In some embodiments, the cycloalkyl, aryl, or heteroaryl of $R^1$ is substituted with two $R^{1A}$ selected from chloro and cyano. In some embodiments, the cycloalkyl, aryl, or heteroaryl of $R^1$ is substituted with two $R^{1A}$ selected from fluoro and cyano.

In some embodiments, $R^1$ is $C_3$-$C_{10}$ (e.g., $C_3$-$C_4$, $C_3$-$C_5$, $C_3$-$C_6$, $C_3$-$C_8$, $C_3$-$C_9$, $C_4$-$C_5$, $C_4$-$C_6$, $C_4$-$C_7$, $C_4$-$C_8$, $C_4$-$C_9$, $C_4$-$C_{10}$, $C_5$-$C_6$, $C_5$-$C_7$, $C_5$-$C_8$, $C_5$-$C_9$, $C_5$-$C_{10}$, $C_6$-$C_7$, $C_6$-$C_8$, $C_6$-$C_9$, $C_6$-$C_{10}$, $C_7$-$C_8$, $C_7$-$C_9$, $C_7$-$C_{10}$, $C_8$-$C_9$, $C_8$-$C_{10}$, or $C_9$-$C_{10}$) cycloalkyl. In some embodiments, $R^1$ is a $C_3$ cycloalkyl, $C_4$ cycloalkyl, $C_5$ cycloalkyl, $C_6$ cycloalkyl, $C_7$ cycloalkyl, $C_8$ cycloalkyl, $C_9$ cycloalkyl, or $C_{10}$ cycloalkyl. In some embodiments, the $C_3$-$C_{10}$ cycloalkyl is saturated. In some embodiments, the $C_3$-$C_{10}$ cycloalkyl is partially saturated. In some embodiments, the $C_3$-$C_{10}$ cycloalkyl has a single ring (i.e., the cycloalkyl is a monocyclic cycloalkyl). In some embodiments, the $C_3$-$C_{10}$ cycloalkyl has multiple rings (e.g., two rings, three rings, four rings, five rings, or six rings). In some embodiments, the $C_3$-$C_{10}$ cycloalkyl has multiple rings including fused, bridged, spiro, or a combination thereof of ring systems. In some embodiments, the $C_3$-$C_{10}$ cycloalkyl has two fused rings. In some embodiments, the $C_3$-$C_{10}$ cycloalkyl includes partially unsaturated ring systems containing one or more (e.g., one, two, three, or four) double bonds. In some embodiments, the $C_3$-$C_{10}$ cycloalkyl includes fused ring systems with one aromatic ring and one non-aromatic ring. The $C_3$-$C_{10}$ cycloalkyl does not include fully aromatic ring systems. In some embodiments, $R^1$ is cyclopropyl, cyclobutyl, cyclopentyl, cyclohexyl, cycloheptyl, or cyclooctyl.

The $C_3$-$C_{10}$ cycloalkyl is optionally substituted with one, two, or three groups independently selected from $R^{1A}$ and —NR$^{13A}$R$^{14A}$. In some embodiments, $C_3$-$C_{10}$ cycloalkyl is not substituted. In some embodiments, $C_3$-$C_{10}$ cycloalkyl is substituted with one group selected from $R^{1A}$ and —$NR^{13A}R^{14A}$. In some embodiments, $C_3$-$C_{10}$ cycloalkyl is substituted with one $R^{1A}$. In some embodiments, $C_3$-$C_{10}$ cycloalkyl is substituted with one —$NR^{13A}R^{14A}$. In some embodiments, $C_3$-$C_{10}$ cycloalkyl is substituted with two groups independently selected from $R^{1A}$ and —$NR^{13A}R^{14A}$. In some embodiments, $C_3$-$C_{10}$ cycloalkyl is substituted with two groups independently selected from $R^{1A}$. In some embodiments, $C_3$-$C_{10}$ cycloalkyl is substituted with two groups independently selected from —$NR^{13A}R^{14A}$. In some embodiments, $C_3$-$C_{10}$ cycloalkyl is substituted with three groups independently selected from $R^{1A}$ and —$NR^{13A}R^{14A}$. In some embodiments, $C_3$-$C_{10}$ cycloalkyl is substituted with three groups independently selected from $R^{1A}$. In some embodiments, $C_3$-$C_{10}$ cycloalkyl is substituted with three groups independently selected from —$NR^{13A}R^{14A}$. In some embodiments, $C_3$-$C_{10}$ cycloalkyl is an unsubstituted cyclopropyl, an unsubstituted cyclobutyl, an unsubstituted cyclopentyl, an unsubstituted cyclohexyl, an unsubstituted cycloheptyl, or an unsubstituted cyclooctyl. In some embodiments, $C_3$-$C_{10}$ cycloalkyl is cyclopropyl, cyclobutyl, cyclopentyl, cyclohexyl, cycloheptyl, or cyclooctyl substituted with one, two, or three groups independently selected from $R^{1A}$ and —$NR^{13A}R^{14A}$. In some embodiments, $C_3$-$C_{10}$ cycloalkyl is cyclopropyl, cyclobutyl, cyclopentyl, cyclohexyl, cycloheptyl, or cyclooctyl substituted with one, two, or three groups independently selected from $R^{1A}$.

In some embodiments, $R^1$ is $C_3$-$C_{10}$ (e.g., $C_3$, $C_4$, $C_5$, $C_6$, $C_7$, $C_8$, $C_9$, $C_{10}$) cycloalkyl substituted with one, two, or three $R^{1A}$, wherein each $R^{1A}$ is independently selected from halo, cyano, $C_1$-$C_3$ alkyl, $C_1$-$C_3$ haloalkyl, $C_1$-$C_3$ alkoxy, $C_1$-$C_3$ haloalkoxy, and 5-10 membered heteroaryl containing one, two, or three heteroatoms selected from N and O. In some embodiments, $R^1$ is $C_3$-$C_{10}$ (e.g., $C_3$, $C_4$, $C_5$, $C_6$, $C_7$, $C_8$, $C_9$, $C_{10}$) cycloalkyl substituted with one, two, or three $R^{1A}$, wherein each $R^{1A}$ is independently selected from halo, cyano, $C_1$-$C_3$ alkoxy, $C_1$-$C_3$ haloalkoxy, and 5-10 (e.g., 5, 6, 7, 8, 9, or 10) membered heteroaryl containing one, two, or three heteroatoms selected from N and O. In some embodiments, $R^1$ is $C_3$-$C_{10}$ (e.g., $C_3$, $C_4$, $C_5$, $C_6$, $C_7$, $C_8$, $C_9$, $C_{10}$) cycloalkyl substituted with one, two, or three $R^{1A}$, wherein each $R^{1A}$ is independently selected from halo, cyano, $C_1$-$C_3$ alkoxy, $C_1$-$C_3$ haloalkoxy, and 5-6 membered heteroaryl containing one, two, or three heteroatoms selected from N and O. In some embodiments, $R^1$ is $C_3$-$C_{10}$ (e.g., $C_3$, $C_4$, $C_5$, $C_6$, $C_7$, $C_8$, $C_9$, $C_{10}$) cycloalkyl substituted with one, two, or three $R^{1A}$, wherein each $R^{1A}$ is independently selected from halo, cyano, methoxy, isopropoxy, triazolyl, and oxadiazolyl. In some embodiments, $R^1$ is $C_3$-$C_{10}$ (e.g., $C_3$, $C_4$, $C_5$, $C_6$, $C_7$, $C_8$, $C_9$, $C_{10}$) cycloalkyl substituted with one $R^{1A}$ selected from halo, cyano, methoxy, isopropoxy, triazolyl, and oxadiazolyl. In some embodiments, $R^1$ is $C_3$-$C_{10}$ (e.g., $C_3$, $C_4$, $C_5$, $C_6$, $C_7$, $C_8$, $C_9$, $C_{10}$) cycloalkyl substituted with two $R^{1A}$, wherein each $R^{1A}$ is independently selected from halo, cyano, methoxy, isopropoxy, triazolyl, and oxadiazolyl. In some embodiments, $R^1$ is $C_3$-$C_{10}$ (e.g., $C_3$, $C_4$, $C_5$, $C_6$, $C_7$, $C_8$, $C_9$, $C_{10}$) cycloalkyl substituted with three $R^{1A}$, wherein each $R^{1A}$ is independently selected from halo, cyano, methoxy, isopropoxy, triazolyl, and oxadiazolyl.

In some embodiments, $R^1$ is a $C_6$-$C_{10}$ aryl. In some embodiments, $R^1$ is $C_6$ aryl (e.g., phenyl), or $C_{10}$ aryl (e.g., naphthyl). In some embodiments, $R^1$ is phenyl. In some embodiments, the $C_6$-$C_{10}$ aryl is phenyl. In some embodiments, the $C_6$-$C_{10}$ aryl is naphthyl.

$C_6$-$C_{10}$ aryl of $R^1$ is optionally substituted with one, two, or three groups independently selected from $R^{1A}$ and —$NR^{13A}R^{14A}$. In some embodiments, $C_6$-$C_{10}$ aryl is not substituted. In some embodiments, $C_6$-$C_{10}$ aryl is substituted with one group selected from $R^{1A}$ and —$NR^{13A}R^{14A}$. In some embodiments, $C_6$-$C_{10}$ aryl is substituted with one $R^{1A}$. In some embodiments, $C_6$-$C_{10}$ aryl is substituted with one —$NR^{13A}R^{14A}$. In some embodiments, $C_6$-$C_{10}$ aryl is substituted with two groups independently selected from $R^{1A}$ and —$NR^{13A}R^{14A}$. In some embodiments, $C_6$-$C_{10}$ aryl is substituted with two groups independently selected from $R^{1A}$. In some embodiments, $C_6$-$C_{10}$ aryl is substituted with two groups independently selected from —$NR^{13A}R^{14A}$. In some embodiments, $C_6$-$C_{10}$ aryl is substituted with three groups independently selected from $R^{1A}$ and —$NR^{13A}R^{14A}$. In some embodiments, $C_6$-$C_{10}$ aryl is substituted with three groups independently selected from $R^{1A}$. In some embodiments, $C_6$-$C_{10}$ aryl is substituted with three groups independently selected from —$NR^{13A}R^{14A}$. In some embodiments, $R^1$ is an unsubstituted $C_6$ aryl (e.g., phenyl), or an unsubstituted $C_{10}$ aryl (e.g., naphthyl). In some embodiments, $R^1$ is $C_6$ aryl (e.g., phenyl), or $C_{10}$ aryl (e.g., naphthyl) substituted with one, two, or three groups independently selected from $R^{1A}$ and —$NR^{13A}R^{14A}$. In some embodiments, the $C_6$-$C_{10}$ aryl is unsubstituted phenyl. In some embodiments, the $C_6$-$C_{10}$ aryl is phenyl substituted with one or two groups independently selected from $R^{1A}$ and —$NR^{13A}R^{14A}$. In some embodiments, the $C_6$-$C_{10}$ aryl is phenyl substituted with one or two groups independently selected from $R^{1A}$. In some embodiments, the $C_6$-$C_{10}$ aryl is phenyl substituted with one $R^{1A}$ and one —$NR^{13A}R^{14A}$. In some embodiments, the $C_6$-$C_{10}$ aryl is phenyl substituted with one $R^{1A}$ and two —$NR^{13A}R^{14A}$. In some embodiments, the $C_6$-$C_{10}$ aryl is phenyl substituted with two $R^{1A}$ and one —$NR^{13A}R^{14A}$.

In some embodiments, $R^1$ is $C_6$-$C_{10}$ aryl substituted with one, two, or three $R^{1A}$, wherein each $R^{1A}$ is independently selected from halo, cyano, $C_1$-$C_3$ alkyl, $C_1$-$C_3$ haloalkyl, $C_1$-$C_3$ alkoxy, $C_1$-$C_3$ haloalkoxy, and 5-10 membered heteroaryl containing one, two, or three heteroatoms selected from N and O. In some embodiments, $R^1$ is $C_6$-$C_{10}$ aryl substituted with one, two, or three $R^{1A}$, wherein each $R^{1A}$ is independently selected from halo, cyano, $C_1$-$C_3$ alkoxy, $C_1$-$C_3$ haloalkoxy, and 5-10 membered heteroaryl containing one, two, or three heteroatoms selected from N and O. In some embodiments, $R^1$ is $C_6$-$C_{10}$ aryl substituted with one, two, or three $R^{1A}$, wherein each $R^{1A}$ is independently selected from halo, cyano, $C_1$-$C_3$ alkoxy, $C_1$-$C_3$ haloalkoxy, and 5-6 membered heteroaryl containing one, two, or three heteroatoms selected from N and O. In some embodiments, $R^1$ is $C_6$-$C_{10}$ aryl substituted with one, two, or three $R^{1A}$, wherein each $R^{1A}$ is independently selected from halo, cyano, methoxy, isopropoxy, triazolyl, and oxadiazolyl. In some embodiments, $R^1$ is $C_6$-$C_{10}$ aryl substituted with one $R^{1A}$ selected from halo, cyano, methoxy, isopropoxy, triazolyl, and oxadiazolyl. In some embodiments, $R^1$ is $C_6$-$C_{10}$ aryl substituted with two $R^{1A}$, wherein each $R^{1A}$ is independently selected from halo, cyano, methoxy, isopropoxy, triazolyl, and oxadiazolyl. In some embodiments, $R^1$ $C_6$-$C_{10}$ aryl substituted with three $R^{1A}$, wherein each $R^{1A}$ is independently selected from halo, cyano, methoxy, isopropoxy, triazolyl, and oxadiazolyl.

In some embodiments, $R^1$ is 5-10 membered heteroaryl containing one or two N. In some embodiments, the 5-10 membered heteroaryl contains one N. In some embodiments, the 5-10 membered heteroaryl contains two N. In some embodiments, the 5-10 membered heteroaryl has one ring (i.e., the 5-10 membered heteroaryl is a monocyclic heteroaryl). In some embodiments, the 5-10 membered heteroaryl has more than one ring (e.g., two rings, three rings, or four rings). In some embodiments, the 5-10 membered heteroaryl comprises two fused rings. In some embodiments, the 5-10 membered heteroaryl is pyridinyl. In some embodiments, the 5-10 membered heteroaryl is pyrimidinyl.

$R^1$ can be a 5-10 membered heteroaryl containing one or two N is optionally substituted with one, two, or three groups independently selected from $R^{1A}$ and $—NR^{13A}R^{14A}$. In some embodiments, 5-10 membered heteroaryl containing one or two N is not substituted. In some embodiments, 5-10 membered heteroaryl containing one or two N is substituted with one group selected from $R^{1A}$ and $—NR^{13A}R^{14A}$. In some embodiments, 5-10 (e.g., 5, 6, 7, 8, 9, 10) membered heteroaryl containing one or two N is substituted with one $R^{1A}$. In some embodiments, 5-10 membered heteroaryl containing one or two N is substituted with one $—NR^{13A}R^{14A}$. In some embodiments, 5-10 membered heteroaryl containing one or two N is substituted with two groups independently selected from $R^{1A}$ and $—NR^{13A}R^{14A}$. In some embodiments, 5-10 membered heteroaryl containing one or two N is substituted with two groups independently selected from $R^{1A}$. In some embodiments, 5-10 membered heteroaryl containing one or two N is substituted with two groups independently selected from $—NR^{13A}R^{14A}$. In some embodiments, 5-10 membered heteroaryl containing one or two N is substituted with three groups independently selected from $R^{1A}$ and $—NR^{13A}R^{14A}$. In some embodiments, 5-10 membered heteroaryl containing one or two N is substituted with three groups independently selected from $R^{1A}$. In some embodiments, 5-10 membered heteroaryl containing one or two N is substituted with three groups independently selected from $—NR^{13A}R^{14A}$. In some embodiments, 5-10 membered heteroaryl containing one or two N is substituted with one or two groups independently selected from $R^{1A}$. In some embodiments, 5-10 membered heteroaryl containing one or two N is substituted with one $R^{1A}$ and one $—NR^{13A}R^{14A}$. In some embodiments, 5-10 membered heteroaryl containing one or two N is substituted with one $R^{1A}$ and two $—NR^{13A}R^{14A}$. In some embodiments, 5-10 membered heteroaryl containing one or two N is substituted with two $R^{1A}$ and one $—NR^{13A}R^{14A}$.

In some embodiments, $R^1$ is 5-10 membered heteroaryl containing one or two N is substituted with one, two, or three $R^{1A}$, wherein each $R^{1A}$ is independently selected from halo, cyano, $C_1$-$C_3$ alkyl, $C_1$-$C_3$ haloalkyl, $C_1$-$C_3$ alkoxy, $C_1$-$C_3$ haloalkoxy, and 5-10 membered heteroaryl containing one, two, or three heteroatoms selected from N and O. In some embodiments, $R^1$ is 5-10 membered heteroaryl containing one or two N is substituted with one, two, or three $R^{1A}$, wherein each $R^{1A}$ is independently selected from halo, cyano, $C_1$-$C_3$ alkoxy, $C_1$-$C_3$ haloalkoxy, and 5-10 (e.g., 5, 6, 7, 8, 9, or 10) membered heteroaryl containing one, two, or three heteroatoms selected from N and O. In some embodiments, $R^1$ is 5-10 membered heteroaryl containing one or two N is substituted with one, two, or three $R^{1A}$, wherein each $R^{1A}$ is independently selected from halo, cyano, $C_1$-$C_3$ alkoxy, $C_1$-$C_3$ haloalkoxy, and 5-6 membered heteroaryl containing one, two, or three heteroatoms selected from N and O. In some embodiments, $R^1$ is 5-10 membered heteroaryl containing one or two N is substituted with one, two, or three $R^{1A}$, wherein each $R^{1A}$ is independently selected from halo, cyano, methoxy, isopropoxy, triazolyl, and oxadiazolyl. In some embodiments, $R^1$ is 5-10 membered heteroaryl containing one or two N is substituted with one $R^{1A}$ selected from halo, cyano, methoxy, isopropoxy, triazolyl, and oxadiazolyl. In some embodiments, $R^1$ is 5-10 membered heteroaryl containing one or two N is substituted with two $R^{1A}$, wherein each $R^{1A}$ is independently selected from halo, cyano, methoxy, isopropoxy, triazolyl, and oxadiazolyl. In some embodiments, $R^1$ is 5-10 membered heteroaryl containing one or two N is substituted with three $R^{1A}$, wherein each $R^{1A}$ is independently selected from halo, cyano, methoxy, isopropoxy, triazolyl, and oxadiazolyl.

$R^1$ can be 5-10 membered heteroaryl containing one N is optionally substituted with one, two, or three groups independently selected from $R^{1A}$ and $—NR^{13A}R^{14A}$. In some embodiments, 5-10 membered heteroaryl containing one N is not substituted. In some embodiments, 5-10 membered heteroaryl containing one N is substituted with one group selected from $R^{1A}$ and $—NR^{13A}R^{14A}$. In some embodiments, 5-10 membered heteroaryl containing one N is substituted with one $R^{1A}$. In some embodiments, 5-10 membered heteroaryl containing one N is substituted with one $—NR^{13A}R^{14A}$. In some embodiments, 5-10 membered heteroaryl containing one N is substituted with two groups independently selected from $R^{1A}$ and $—NR^{13A}R^{14A}$. In some embodiments, 5-10 membered heteroaryl containing one N is substituted with two groups independently selected from $R^{1A}$. In some embodiments, 5-10 membered heteroaryl containing one N is substituted with two groups independently selected from $—NR^{13A}R^{14A}$. In some embodiments, 5-10 membered heteroaryl containing one N is substituted with three groups independently selected from $R^{1A}$ and $—NR^{13A}R^{14A}$. In some embodiments, 5-10 membered heteroaryl containing one N is substituted with three groups independently selected from $R^{1A}$. In some embodiments, 5-10 membered heteroaryl containing one N is substituted with three groups independently selected from $—NR^{13A}R^{14A}$.

$R^1$ can be 5-10 membered heteroaryl containing two N is optionally substituted with one, two, or three groups independently selected from $R^{1A}$ and $—NR^{13A}R^{14A}$. In some embodiments, 5-10 membered heteroaryl containing one N is not substituted. In some embodiments, 5-10 membered heteroaryl containing two N is substituted with one group selected from $R^{1A}$ and $—NR^{13A}R^{14A}$. In some embodiments, 5-10 membered heteroaryl containing two N is substituted with one $R^{1A}$. In some embodiments, 5-10 membered heteroaryl containing two N is substituted with one $—NR^{13A}R^{14A}$. In some embodiments, 5-10 membered heteroaryl containing two N is substituted with two groups independently selected from $R^{1A}$ and $—NR^{13A}R^{14A}$. In some embodiments, 5-10 membered heteroaryl containing two N is substituted with two groups independently selected from $R^{1A}$. In some embodiments, 5-10 membered heteroaryl containing two N is substituted with two groups independently selected from $—NR^{13A}R^{14A}$. In some embodiments, 5-10 membered heteroaryl containing two N is substituted with three groups independently selected from $R^{1A}$ and $—NR^{13A}R^{14A}$. In some embodiments, 5-10 membered heteroaryl containing two N is substituted with three groups independently selected from $R^{1A}$. In some embodiments, 5-10 membered heteroaryl containing two N is substituted with three groups independently selected from $—NR^{13A}R^{14A}$.

In some embodiments, the 5-10 membered heteroaryl is pyridinyl. The pyridinyl is optionally substituted with one, two, or three groups independently selected from $R^{1A}$ and $—NR^{13A}R^{14A}$. In some embodiments, pyridinyl is not substituted. In some embodiments, pyridinyl is substituted with one group selected from $R^{1A}$ and $—NR^{13A}R^{14A}$. In some embodiments, pyridinyl is substituted with one $R^{1A}$. In some embodiments, pyridinyl is substituted with one $—NR^{13A}R^{14A}$. In some embodiments, pyridinyl is substituted with two groups independently selected from $R^{1A}$ and $—NR^{13A}R'$ In some embodiments, pyridinyl is substituted with two groups independently selected from $R^{1A}$. In some embodiments, pyridinyl is substituted with two groups independently selected from $-NR^{13A}R^{14A}$. In some embodiments, pyridinyl is substituted with three groups independently selected from $R^{1A}$ and $-NR^{13A}R^{14A}$. In some embodiments, pyridinyl is substituted with three groups independently selected from $R^{1A}$ In some embodiments, pyridinyl is substituted with three groups independently selected from $-NR^{13A}R^{14A}$. In some embodiments, pyridinyl is substituted with one $R^{1A}$ and one $-NR^{13A}R^{14A}$. In some embodiments, pyridinyl is substituted with one $R^{1A}$ and two $-NR^{13A}R^{14A}$. In some embodiments, pyridinyl is substituted with two $R^{1A}$ and one $-NR^{13A}R^{14A}$.

In some embodiments, $R^1$ is pyridinyl substituted with one, two, or three $R^{1A}$, wherein each $R^{1A}$ is independently selected from halo, cyano, $C_1$-$C_3$ alkyl, $C_1$-$C_3$ haloalkyl, $C_1$-$C_3$ alkoxy, $C_1$-$C_3$ haloalkoxy, and 5-10 membered heteroaryl containing one, two, or three heteroatoms selected from N and O. In some embodiments, pyridinyl is substituted with one, two, or three $R^{1A}$, wherein each $R^{1A}$ is independently selected from halo, cyano, $C_1$-$C_3$ alkoxy, $C_1$-$C_3$ haloalkoxy, and 5-10 (e.g., 5, 6, 7, 8, 9, or 10) membered heteroaryl containing one, two, or three heteroatoms selected from N and O. In some embodiments, pyridinyl is substituted with one, two, or three $R^{1A}$, wherein each $R^{1A}$ is independently selected from halo, cyano, $C_1$-$C_3$ alkoxy, $C_1$-$C_3$ haloalkoxy, and 5-6 membered heteroaryl containing one, two, or three heteroatoms selected from N and O. In some embodiments, pyridinyl is substituted with one, two, or three $R^{1A}$, wherein each $R^{1A}$ is independently selected from halo, cyano, methoxy, isopropoxy, triazolyl, and oxadiazolyl. In some embodiments, pyridinyl is substituted with one $R^{1A}$ selected from halo, cyano, methoxy, isopropoxy, triazolyl, and oxadiazolyl. In some embodiments, pyridinyl is substituted with two $R^{1A}$, wherein each $R^{1A}$ is independently selected from halo, cyano, methoxy, isopropoxy, triazolyl, and oxadiazolyl. In some embodiments, pyridinyl is substituted with three $R^{1A}$, wherein each $R^{1A}$ is independently selected from halo, cyano, methoxy, isopropoxy, triazolyl, and oxadiazolyl.

In some embodiments, the 5-10 membered heteroaryl is pyridin-2-yl. The pyridin-2-yl is optionally substituted with one, two, or three groups independently selected from $R^{1A}$ and $-NR^{13A}R^{14A}$. In some embodiments, pyridin-2-yl is not substituted. In some embodiments, pyridin-2-yl is substituted with one group selected from $R^{1A}$ and $-NR^{13A}R^{14A}$. In some embodiments, pyridin-2-yl is substituted with one $R^{1A}$. In some embodiments, pyridin-2-yl is substituted with one $-NR^{13A}R^{14A}$. In some embodiments, pyridin-2-yl is substituted with two groups independently selected from $R^{1A}$ and $-NR^{13A}R^{14A}$. In some embodiments, pyridin-2-yl is substituted with two groups independently selected from $R^{1A}$. In some embodiments, pyridin-2-yl is substituted with two groups independently selected from $-NR^{13A}R^{14A}$. In some embodiments, pyridin-2-yl is substituted with three groups independently selected from $R^{1A}$ and $-NR^{13A}R^{14A}$. In some embodiments, pyridin-2-yl is substituted with three groups independently selected from $R^{1A}$. In some embodiments, pyridin-2-yl is substituted with three groups independently selected from $-NR^{13A}R^{14A}$. In some embodiments, pyridin-2-yl is substituted with one $R^{1A}$ and one $-NR^{13A}R^{14A}$. In some embodiments, pyridin-2-yl is substituted with one $R^{1A}$ and two $-NR^{13A}R^{14A}$. In some embodiments, pyridin-2-yl is substituted with two $R^{1A}$ and one $-NR^{13A}R^{14A}$.

In some embodiments, $R^1$ is pyridin-2-yl substituted with one, two, or three $R^{1A}$, wherein each $R^{1A}$ is independently selected from halo, cyano, $C_1$-$C_3$ alkyl, $C_1$-$C_3$ haloalkyl, $C_1$-$C_3$ alkoxy, $C_1$-$C_3$ haloalkoxy, and 5-10 membered heteroaryl containing one, two, or three heteroatoms selected from N and O. In some embodiments, pyridin-2-yl is substituted with one, two, or three $R^{1A}$, wherein each $R^{1A}$ is independently selected from halo, cyano, $C_1$-$C_3$ alkoxy, $C_1$-$C_3$ haloalkoxy, and 5-10 (e.g., 5, 6, 7, 8, 9, or 10) membered heteroaryl containing one, two, or three heteroatoms selected from N and O. In some embodiments, pyridin-2-yl is substituted with one, two, or three $R^{1A}$, wherein each $R^{1A}$ is independently selected from halo, cyano, $C_1$-$C_3$ alkoxy, $C_1$-$C_3$ haloalkoxy, and 5-6 membered heteroaryl containing one, two, or three heteroatoms selected from N and O. In some embodiments, pyridin-2-yl is substituted with one, two, or three $R^{1A}$, wherein each $R^{1A}$ is independently selected from halo, cyano, methoxy, isopropoxy, triazolyl, and oxadiazolyl. In some embodiments, pyridin-2-yl is substituted with one $R^{1A}$ selected from halo, cyano, methoxy, isopropoxy, triazolyl, and oxadiazolyl. In some embodiments, pyridin-2-yl is substituted with two $R^{1A}$, wherein each $R^{1A}$ is independently selected from halo, cyano, methoxy, isopropoxy, triazolyl, and oxadiazolyl. In some embodiments, pyridin-2-yl is substituted with three $R^{1A}$, wherein each $R^{1A}$ is independently selected from halo, cyano, methoxy, isopropoxy, triazolyl, and oxadiazolyl.

In some embodiments, the 5-10 membered heteroaryl is pyridin-3-yl. The pyridin-3-yl is optionally substituted with one, two, or three groups independently selected from $R^{1A}$ and $-NR^{13A}R^{14A}$. In some embodiments, pyridin-3-yl is not substituted. In some embodiments, pyridin-3-yl is substituted with one group selected from $R^{1A}$ and $-NR^{13A}R^{14A}$. In some embodiments, pyridin-3-yl is substituted with one $R^{1A}$. In some embodiments, pyridinyl is substituted with one $-NR^{13A}R^{14A}$. In some embodiments, pyridin-3-yl is substituted with two groups independently selected from $R^{1A}$ and $-NR^{13A}R^{14A}$. In some embodiments, pyridin-3-yl is substituted with two groups independently selected from $R^{1A}$. In some embodiments, pyridin-3-yl is substituted with two groups independently selected from $-NR^{13A}R^{14A}$. In some embodiments, pyridin-3-yl is substituted with three groups independently selected from $R^{1A}$ and $-NR^{13A}R^{14A}$. In some embodiments, pyridin-3-yl is substituted with three groups independently selected from $R^{1A}$. In some embodiments, pyridin-3-yl is substituted with three groups independently selected from $-NR^{13A}R^{14A}$. In some embodiments, pyridin-3-yl is substituted with one $R^{1A}$ and one $-NR^{13A}R^{14A}$. In some embodiments, pyridin-3-yl is substituted with one $R^{1A}$ and two $-NR^{13A}R^{14A}$. In some embodiments, pyridin-3-yl is substituted with two $R^{1A}$ and one $-NR^{13A}R^{14A}$.

In some embodiments, the 5-10 membered heteroaryl is pyrimidinyl. The pyrimidinyl is optionally substituted with one, two, or three groups independently selected from $R^{1A}$ and $-NR^{13A}R^{14A}$. In some embodiments, pyrimidinyl is not substituted. In some embodiments, pyrimidinyl is substituted with one group selected from $R^{1A}$ and $-NR^{13A}R'$ In some embodiments, pyrimidinyl is substituted with one $R^{1A}$. In some embodiments, pyrimidinyl is substituted with one $-NR^{13A}R^{14A}$. In some embodiments, pyrimidinyl is substituted with two groups independently selected from $R^{1A}$ and $-NR^{13A}R^{14A}$. In some embodiments, pyrimidinyl is substituted with two groups independently selected from $R^{1A}$. In some embodiments, pyrimidinyl is substituted with two groups independently selected from $-NR^{13A}R^{14A}$. In some embodiments, pyrimidinyl is substituted with three groups independently selected from $R^{1A}$ and $-NR^{13A}R^{14A}$. In some embodiments, pyrimidinyl is substituted with three groups independently selected from $R^{1A}$. In some embodiments, pyrimidinyl is substituted with three groups independently selected from —$NR^{13A}R^{14A}$. In some embodiments, pyrimidinyl is substituted with one $R^{1A}$ and one —$NR^{13A}R^{14A}$. In some embodiments, pyrimidinyl is substituted with one $R^{1A}$ and two —$NR^{13A}R^{14A}$. In some embodiments, pyrimidinyl is substituted with two $R^{1A}$ and one —$NR^{13A}R^{14A}$.

In some embodiments, $R^1$ is pyrimidinyl substituted with one, two, or three $R^{1A}$, wherein each $R^{1A}$ is independently selected from halo, cyano, $C_1$-$C_3$ alkyl, $C_1$-$C_3$ haloalkyl, $C_1$-$C_3$ alkoxy, $C_1$-$C_3$ haloalkoxy, and 5-10 membered heteroaryl containing one, two, or three heteroatoms selected from N and O. In some embodiments, $R^1$ is pyrimidinyl substituted with one, two, or three $R^{1A}$, wherein each $R^{1A}$ is independently selected from halo, cyano, $C_1$-$C_3$ alkoxy, $C_1$-$C_3$ haloalkoxy, and 5-10 (e.g., 5, 6, 7, 8, 9, or 10) membered heteroaryl containing one, two, or three heteroatoms selected from N and O. In some embodiments, $R^1$ is pyrimidinyl substituted with one, two, or three $R^{1A}$, wherein each $R^{1A}$ is independently selected from halo, cyano, $C_1$-$C_3$ alkoxy, $C_1$-$C_3$ haloalkoxy, and 5-6 membered heteroaryl containing one, two, or three heteroatoms selected from N and O. In some embodiments, $R^1$ is pyrimidinyl substituted with one, two, or three $R^{1A}$, wherein each $R^{1A}$ is independently selected from halo, cyano, methoxy, isopropoxy, triazolyl, and oxadiazolyl. In some embodiments, $R^1$ is pyrimidinyl substituted with one $R^{1A}$ selected from halo, cyano, methoxy, isopropoxy, triazolyl, and oxadiazolyl. In some embodiments, $R^1$ is pyrimidinyl substituted with two $R^{1A}$, wherein each $R^{1A}$ is independently selected from halo, cyano, methoxy, isopropoxy, triazolyl, and oxadiazolyl. In some embodiments, $R^1$ is pyrimidinyl substituted with three $R^{1A}$, wherein each $R^{1A}$ is independently selected from halo, cyano, methoxy, isopropoxy, triazolyl, and oxadiazolyl.

$R^1$ is optionally substituted with one, two, or three groups independently selected from $R^{1A}$ and —$NR^{13A}R^{14A}$. In some embodiments, at least one $R^{1A}$ is halo. In some embodiments, at least one $R^{1A}$ is fluoro. In some embodiments, at least one $R^{1A}$ is chloro. In some embodiments, at least one $R^{1A}$ is bromo. In some embodiments, the halo is iodo. In some embodiments, at least one $R^{1A}$ is cyano.

In some embodiments, at least one $R^{1A}$ is $C_1$-$C_3$ alkyl (e.g., methyl, ethyl, n-propyl, isopropyl).

In some embodiments, at least one $R^{1A}$ is $C_1$-$C_3$ alkoxy (e.g., methoxy, ethoxy, n-propoxy, isopropoxy).

In some embodiments, at least one $R^{1A}$ is $C_1$-$C_3$ haloalkoxy. In some embodiments, at least one $R^{1A}$ is $C_1$-$C_3$ fluoroalkoxy (e.g., fluoromethoxy, difluoromethoxy, trifluoromethoxy, fluoroethoxy, difluoroethoxy, trifluoroethoxy, tetrafluoroethoxy, pentafluoroethoxy, fluoro-n-propoxy, difluoro-n-propoxy, trifluoro-n-propoxy, tetrafluoro-n-propoxy, pentafluoro-n-propoxy, hexafluoro-n-propoxy, heptafluoro-n-propoxy, fluoroisopropoxy, difluoroisopropoxy, trifluoroisopropoxy, tetrafluoroisopropoxy, heptafluoroisopropoxy, hexafluoroisopropoxy, or heptafluoroisopropoxy). In some embodiments, at least one $R^{1A}$ is $C_1$-$C_3$ chloroalkoxy (e.g., chloromethoxy, dichloromethoxy, trichloromethoxy, chloroethoxy, dichloroethoxy, trichloroethoxy, tetrachloroethoxy, pentachloroethoxy, chloro-n-propoxy, dichloro-n-propoxy, trichloro-n-propoxy, tetrachloro-n-propoxy, pentachloro-n-propoxy, hexachloro-n-propoxy, heptachloro-n-propoxy, chloroisopropoxy, dichloroisopropoxy, trichloroisopropoxy, tetrachloroisopropoxy, heptachloroisopropoxy, hexachloroisopropoxy, or heptachloroisopropoxy). In some embodiments, at least one $R^{1A}$ is $C_1$-$C_3$ bromoalkoxy (e.g., bromomethoxy, dibromomethoxy, tribromomethoxy, bromoethoxy, dibromoethoxy, tribromoethoxy, tetrabromoethoxy, pentabromoethoxy, bromo-n-propoxy, dibromo-n-propoxy, tribromo-n-propoxy, tetrabromo-n-propoxy, pentabromo-n-propoxy, hexabromo-n-propoxy, heptabromo-n-propoxy, bromoisopropoxy, dibromoisopropoxy, tribromoisopropoxy, tetrabromoisopropoxy, heptabromoisopropoxy, hexabromoisopropoxy, or heptabromoisopropoxy). In some embodiments, at least one $R^{1A}$ is $C_1$-$C_3$ iodoalkoxy (e.g., iodomethoxy, diiodomethoxy, triiodomethoxy, iodoethoxy, diiodoethoxy, triiodoethoxy, tetraiodoethoxy, pentaiodoethoxy, iodo-n-propoxy, diiodo-n-propoxy, triiodo-n-propoxy, tetraiodo-n-propoxy, pentaiodo-n-propoxy, hexaiodo-n-propoxy, heptaiodo-n-propoxy, iodoisopropoxy, diiodoisopropoxy, triiodoisopropoxy, tetraiodoisopropoxy, heptaiodoisopropoxy, hexaiodoisopropoxy, or heptaiodoisopropoxy).

In some embodiments, at least one $R^{1A}$ is 5-10 membered heteroaryl containing one, two, or three heteroatoms selected from N and O. In some embodiments, at least one $R^{1A}$ is 5-10 membered heteroaryl containing one, two, or three heteroatoms selected from N and O. In some embodiments, at least one $R^{1A}$ is 5-10 membered heteroaryl containing one N. In some embodiments, at least one $R^{1A}$ is 5-10 membered heteroaryl containing two N. In some embodiments, at least one $R^{1A}$ is 5-10 membered heteroaryl containing three N. In some embodiments, at least one $R^{1A}$ is 5-10 membered heteroaryl containing one O. In some embodiments, at least one $R^{1A}$ is 5-10 membered heteroaryl containing two O. In some embodiments, at least one $R^{1A}$ is 5-10 membered heteroaryl containing three O. In some embodiments, at least one $R^{1A}$ is 5-10 membered heteroaryl containing one N and one O. In some embodiments, at least one $R^{1A}$ is 5-6 membered heteroaryl containing one N. In some embodiments, at least one $R^{1A}$ is 5-6 membered heteroaryl containing two N. In some embodiments, at least one $R^{1A}$ is 5-6 membered heteroaryl containing three N. In some embodiments, at least one $R^{1A}$ is 5-6 membered heteroaryl containing one O. In some embodiments, at least one $R^{1A}$ is 5-6 membered heteroaryl containing one N and one O. In some embodiments, at least one $R^{1A}$ is 5-6 membered heteroaryl containing two N and one O. In some embodiments, at least one $R^{1A}$ is 5-6 membered heteroaryl having one ring (i.e., the 5-10 membered heteroaryl is a monocyclic heteroaryl). In some embodiments, at least one $R^{1A}$ is 5-10 membered heteroaryl having more than one ring (e.g., two rings, three rings, or four rings). In some embodiments, at least one $R^{1A}$ is 5-10 membered heteroaryl comprising two fused rings. In some embodiments, the 5-10 membered heteroaryl is triazolyl. In some embodiments, the 5-10 membered heteroaryl is oxadiazolyl.

$R^1$ can be substituted with one, two, or three $NR^{13A}R^{14A}$, wherein each $R^{13A}$ is independently H or $C_1$-$C_3$ alkyl, and each $R^{14A}$ is independently H or $C_1$-$C_3$ alkyl. In some embodiments, at least one $R^{13A}$ is H. In some embodiments, at least one $R^{13A}$ is $C_1$-$C_3$ alkyl (e.g., methyl, ethyl, n-propyl, isopropyl). In some embodiments, at least two $R^{13A}$ is H. In some embodiments, at least two $R^{13A}$ is $C_1$-$C_3$ alkyl (e.g., methyl, ethyl, n-propyl, isopropyl). In some embodiments, three $R^{13A}$ is H. In some embodiments, three $R^{13A}$ is $C_1$-$C_3$ alkyl (e.g., methyl, ethyl, n-propyl, isopropyl). In some embodiments, at least one $R^{14A}$ is H. In some embodiments, at least one $R^{14A}$ is $C_1$-$C_3$ alkyl (e.g., methyl, ethyl, n-propyl, isopropyl). In some embodiments, at least two $R^{14A}$ is H. In some embodiments, at least two $R^{14A}$ is $C_1$-$C_3$ alkyl (e.g., methyl, ethyl, n-propyl, isopropyl). In some embodiments, three $R^{14A}$ is H. In some embodiments, three $R^{14A}$ is $C_1$-$C_3$ alkyl (e.g., methyl, ethyl, n-propyl, isopropyl). In some embodiments, at least one $NR^{13A}R^{14A}$ has $R^{13A}$ is H and $R^{14A}$ is $C_1$-$C_3$ alkyl (e.g., methyl, ethyl, n-propyl, isopropyl). In some embodiments, at least two $NR^{13A}R^{14A}$ have $R^{13A}$ is H and $R^{14A}$ is $C_1$-$C_3$ alkyl (e.g., methyl, ethyl, n-propyl, isopropyl). In some embodiments, three $NR^{13A}R^{14A}$ have $R^{13A}$ is H and $R^{14A}$ is $C_1$-$C_3$ alkyl (e.g., methyl, ethyl, n-propyl, isopropyl). In some embodiments, at least one $NR^{13A}R^{14A}$ has $R^{13A}$ is H and $R^{14A}$ is $C_1$-$C_3$ alkyl (e.g., methyl, ethyl, n-propyl, isopropyl) and at least one $NR^{13A}R^{14A}$ is $NH_2$. In some embodiments, one $NR^{13A}R^{14A}$ has $R^{13A}$ is H and $R^{14A}$ is $C_1$-$C_3$ alkyl (e.g., methyl, ethyl, n-propyl, isopropyl) and two $NR^{13A}R^{14A}$ are $NH_2$. In some embodiments, two $NR^{13A}R^{14A}$ have $R^{13A}$ is H and $R^{14A}$ is $C_1$-$C_3$ alkyl (e.g., methyl, ethyl, n-propyl, isopropyl) and one $NR^{13A}R^{14A}$ is $NH_2$. In some embodiments, at least one $NR^{13A}R^{14A}$ is $NH_2$. In some embodiments, at least two $NR^{13A}R^{14A}$ is $NH_2$. In some embodiments, three $NR^{13A}R^{14A}$ is $NH_2$.

In some embodiments, $R^1$ is $C_3$-$C_{10}$ cycloalkyl, $C_6$-$C_{10}$ aryl, or 5-10 membered heteroaryl containing one, two, or three N; wherein the cycloalkyl and heteroaryl of $R^1$ is optionally substituted with one, two, or three groups independently selected from $R^{1A}$ and —$NR^{13A}R^{14A}$, and the aryl is substituted with one, two, or three groups independently selected from $R^{1A}$ and —$NR^{13A}R^{14A}$. In some embodiments, $R^1$ is phenyl substituted with one, two, or three groups independently selected from $R^{1A}$ and —$NR^{13A}R^{14A}$. In some embodiments, $R^1$ is phenyl substituted with one $R^{1A}$. In some embodiments, $R^1$ is phenyl substituted with two $R^{1A}$. In some embodiments, $R^{1A}$ is halo or cyano. In some embodiments, $R^{1A}$ is chloro or cyano. In some embodiments, $R^{1A}$ is fluoro or cyano.

In some embodiments, $R^1$ is unsubstituted cyclohexyl; unsubstituted phenyl; phenyl substituted with one, two, or three substituents independently selected from cyano, halo, methoxy, isopropoxy, trifluoromethoxy, triazolyl, and oxadiazolyl; pyridinyl substituted with one, two, or three substituents independently selected from cyano and halo; or pyrimidinyl substituted with cyano. In some embodiments, $R^1$ is cyclohexyl, phenyl, phenyl substituted with cyano, phenyl substituted with cyano and fluoro, phenyl substituted with cyano and chloro, phenyl substituted with cyano and methoxy, phenyl substituted with cyano and isopropoxy, phenyl substituted with cyano and trifluoromethoxy, phenyl substituted with cyano and two methoxy, phenyl substituted with cyano and triazolyl, phenyl substituted with fluoro and oxadiazolyl, pyridinyl substituted with cyano, pyridinyl substituted with chloro, or pyrimidinyl substituted with cyano. In some embodiments, $R^1$ is

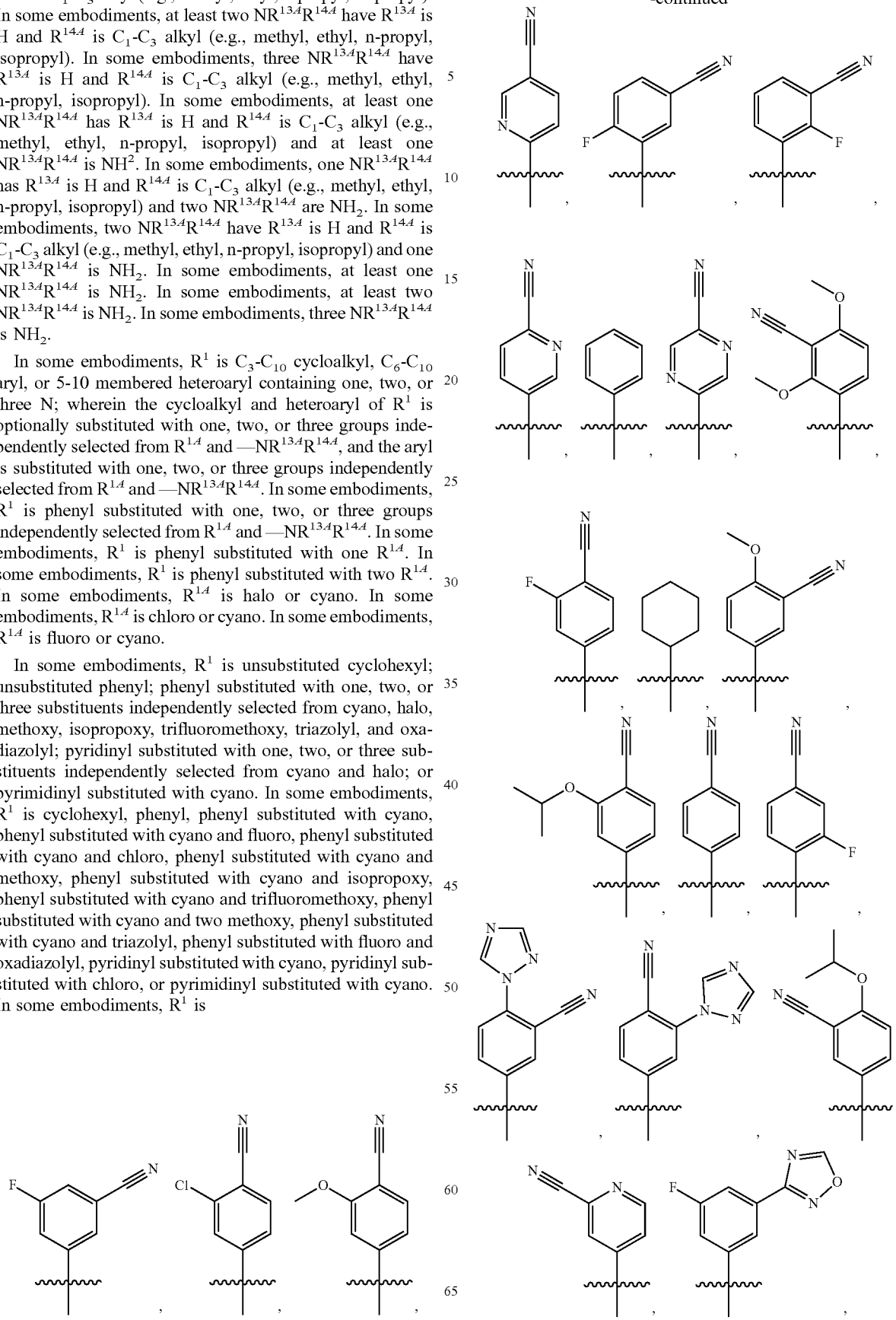

-continued

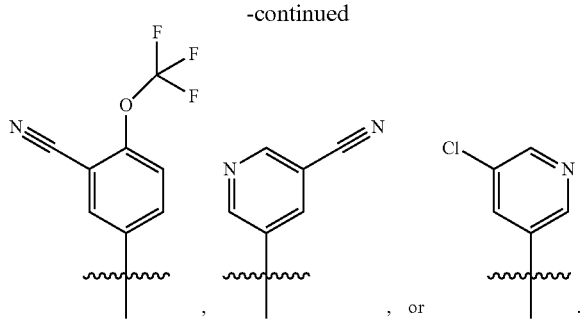

In some embodiments, $R^1$ is

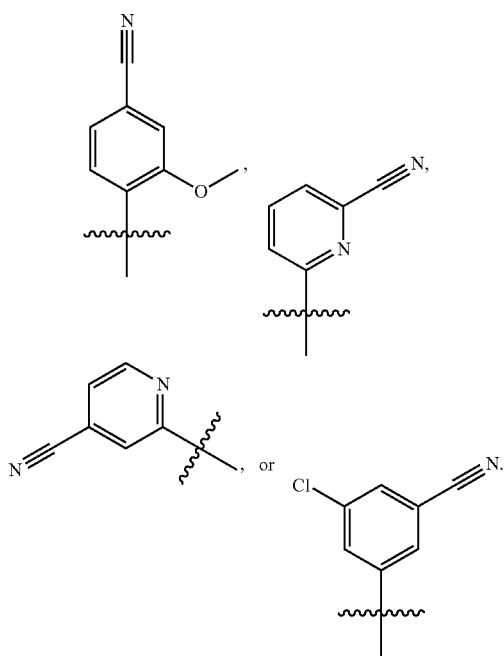

In some embodiments, $R^1$ is

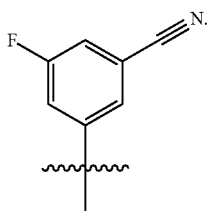

$R^2$ can be H or $C_1$-$C_3$ alkyl. In some embodiments, $R^2$ is H. In some embodiments, $R^2$ is $C_1$-$C_3$ alkyl (e.g., methyl, ethyl, n-propyl, isopropyl).

$R^3$ can be $C_1$-$C_3$ alkyl (e.g., methyl, ethyl, n-propyl, isopropyl).

In $(CR^4R^5)_m$, m is 10, 11, 12, 13, 14, 15, 16, 17, 18, 19, 20, or 21. In some embodiments, m is 16. In some embodiments, m is 17. In some embodiments, m is 18. In some embodiments, m is 19, in some embodiments, m is 20. In some embodiments, m is 21. In some embodiments, $(CR^4R^5)_m$ is a $C_{10}$-$C_{21}$ alkylenyl. In some embodiments, $(CR^4R^5)_m$ is an unsubstituted $C_{10}$-$C_{21}$ alkylenyl. In some embodiments, $(CR^4R^5)_m$ is a straight-chain $C_{10}$-$C_{21}$ alkylenyl. In some embodiments, $(CR^4R^5)_m$ is an unsubstituted, straight-chain $C_{10}$-$C_{21}$ alkylenyl. In some embodiments, $(CR^4R^5)_m$ is a branched $C_{10}$-$C_{21}$ alkylenyl. In some embodiments, $(CR^4R^5)_m$ is a $C_{10}$-$C_{21}$ alkenylenyl. In some embodiments, $(CR^4R^5)_m$ is an unsubstituted $C_{10}$-$C_{21}$ alkenylenyl. In some embodiments, $(CR^4R^5)_m$ is a straight-chain $C_{10}$-$C_{21}$ alkenylenyl. In some embodiments, $(CR^4R^5)_m$ is an unsubstituted, straight-chain $C_{10}$-$C_{21}$ alkenylenyl. In some embodiments, $(CR^4R^5)_m$ is a branched $C_{10}$-$C_{21}$ alkenylenyl. In some embodiments, $R^3(CR^4R^5)_m$ is a $C_{11}$-$C_{24}$ alkyl. In some embodiments, $R^3(CR^4R^5)_m$ is an unsubstituted $C_{11}$-$C_{24}$ alkyl. In some embodiments, $R^3(CR^4R^5)_m$ is a substituted $C_{11}$-$C_{24}$ alkyl. In some embodiments, $R^3(CR^4R^5)_m$ is a branched $C_{11}$-$C_{24}$ alkyl. In some embodiments, $R^3(CR^4R^5)_m$ is a straight-chain $C_{11}$-$C_{24}$ alkyl. In some embodiments, $R^3(CR^4R^5)_m$ is an unsubstituted, straight-chain $C_{11}$-$C_{24}$ alkyl. In some embodiments, $R^3(CR^4R^5)_m$ is octadecanyl. In some embodiments, $R^3(CR^4R^5)_m$ is nonadecanyl. In some embodiments, $R^3(CR^4R^5)_m$ is eicosanyl. In some embodiments, $R^3(CR^4R^5)_m$ is heneicosanyl.

Each $R^4$ can be independently a bond, H, halo, $C_1$-$C_3$ alkyl, $C_1$-$C_3$ haloalkyl, or $C_3$-$C_6$ cycloalkyl. In some embodiments, at least one $R^4$ is a bond. In some embodiments, from 10 to 21 (e.g., 10, 11, 12, 13, 14, 15, 16, 17, 18, 19, 20, or 21) of $R^4$ is H. In some embodiments, at least one $R^4$ is halo (e.g., chloro, bromo, fluoro, or iodo). In some embodiments, at least one $R^4$ is $C_1$-$C_3$ alkyl (e.g., methyl, ethyl, n-propyl, isopropyl). In some embodiments, from 10 to 21 (e.g., 10, 11, 12, 13, 14, 15, 16, 17, 18, 19, 20, or 21) of $R^4$ is $C_1$-$C_3$ alkyl (e.g., methyl, ethyl, n-propyl, isopropyl). In some embodiments, at least one $R^4$ is $C_1$-$C_3$ haloalkyl (e.g., halomethyl, haloethyl, halo-n-propyl, haloisopropyl). In some embodiments, from 10 to 21 (e.g., 10, 11, 12, 13, 14, 15, 16, 17, 18, 19, 20, or 21) of $R^4$ is $C_1$-$C_3$ haloalkyl (e.g., methyl, ethyl, n-propyl, isopropyl). Exemplary $C_1$-$C_3$ haloalkyl include fluoromethyl, fluoroethyl, fluoro-n-propyl, fluoroisopropyl, chloromethyl, chloroethyl, chloro-n-propyl, chloroisopropyl, bromomethyl, bromoethyl, bromo-n-propyl, bromoisopropyl, iodomethyl, iodoethyl, iodo-n-propyl, or iodoisopropyl.

Each $R^5$ can be independently a bond or H. In some embodiments, at least one $R^5$ is a bond. In some embodiments, only one $R^5$ is a bond. In some embodiments, from 10 to 21 (e.g., 10, 11, 12, 13, 14, 15, 16, 17, 18, 19, 20, or 21) of $R^5$ is H. In some embodiments, every $R^5$ is H.

In some embodiments, each $R^4$ and each $R^5$ are H. In some embodiments, two or more adjacent $(CR^4R^5)$ groups are optionally connected through a double bond. In some embodiments, $(CR^4R^5)_m$ has one double bond. In some embodiments, $(CR^4R^5)_m$ has at least one double bond (e.g., 2, 3, 4, or 5 double bonds).

$R^6$ can be H or —C(O)$C_1$-$C_6$ alkyl. In some embodiments, $R^6$ is H. In some embodiments, $R^6$ is —C(O)$C_1$-$C_6$ (e.g., —C(O)$C_1$, —C(O)$C_2$, —C(O)$C_3$, —C(O)$C_4$, —C(O)$C_5$, —C(O)$C_6$) alkyl, —C(O)methyl, —C(O)ethyl, —C(O)-n-propyl, —C(O)isopropyl, —C(O)-n-butyl, —C(O)isobutyl, —C(O)-s-butyl, —C(O)-t-butyl, —C(O)-n-pentyl, —C(O)-2-pentyl, —C(O)-3-pentyl, —C(O)-2-methyl-2-butyl, —C(O)-3-methyl-2-butyl, —C(O)-3-methyl-1-butyl, —C(O)-2-methyl-1-butyl, —C(O)-1-hexyl, —C(O)-2-hexyl, —C(O)-3-hexyl, —C(O)-2-methyl-2-pentyl, —C(O)-3-methyl-2-pentyl, —C(O)-4-methyl-2-pentyl, —C(O)-3-methyl-3-pentyl, —C(O)-2-methyl-3-pentyl, —C(O)-2,3-dimethyl-2-butyl, or —C(O)-3,3-dimethyl-2-butyl.

$R^7$ can be H or —C(O)$C_1$-$C_6$ alkyl. In some embodiments, $R^7$ is H. In some embodiments, $R^7$ is —C(O)$C_1$-$C_6$ (e.g., —C(O)$C_1$, —C(O)$C_2$, —C(O)$C_3$, —C(O)$C_4$, —C(O)$C_5$, —C(O)$C_6$) alkyl, —C(O)methyl, —C(O)ethyl, —C(O)-n-propyl, —C(O)isopropyl, —C(O)-n-butyl, —C(O)isobutyl, —C(O)-s-butyl, —C(O)-t-butyl, —C(O)-n-pentyl, —C(O)-2-pentyl, —C(O)-3-pentyl, —C(O)-2-methyl-2-butyl, —C(O)-3-methyl-2-butyl, —C(O)-3-methyl-1-butyl, —C(O)-2-methyl-1-butyl, —C(O)-1-hexyl, —C(O)-2-hexyl, —C(O)-3-hexyl, —C(O)-2-methyl-2-pentyl, —C(O)-3-methyl-2-pentyl, —C(O)-4-methyl-2-pentyl, —C(O)-3-methyl-3-pentyl, —C(O)-2-methyl-3-pentyl, —C(O)-2,3-dimethyl-2-butyl, or —C(O)-3,3-dimethyl-2-butyl.

In some embodiments, $R^6$ and $R^7$ are both H. In some embodiments, $R^6$ is H and $R^7$ is —C(O)$C_1$-$C_6$ alkyl. In some embodiments, $R^6$ is H and $R^7$ is —C(O)methyl, —C(O)ethyl, —C(O)-n-propyl, —C(O)isopropyl, —C(O)-n-butyl, —C(O)isobutyl, —C(O)-s-butyl, or —C(O)-t-butyl. In some embodiments, $R^6$ is —C(O)$C_1$-$C_6$ alkyl and $R^7$ is H. In some embodiments, $R^6$ is —C(O)methyl, —C(O)ethyl, —C(O)-n-propyl, —C(O)isopropyl, —C(O)-n-butyl, —C(O)isobutyl, —C(O)-s-butyl, or —C(O)-t-butyl and $R^7$ is H. In some embodiments, $R^6$ and $R^7$ are each independently selected from —C(O)methyl, —C(O)ethyl, —C(O)-n-propyl, —C(O)isopropyl, —C(O)-n-butyl, —C(O)isobutyl, —C(O)-s-butyl, and —C(O)-t-butyl. In some embodiments, $R^6$=$R^7$. In some embodiments, $R^6$ and $R^7$ are both —C(O)isopropyl.

L can be —O—, —(C$R^{12A}$$R^{12B}$)$_n$—, —O—(C$R^{12A}$$R^{12B}$)$_n$—, —(C$R^{12A}$$R^{12B}$)$_n$—O—, or —(C$R^{12A}$$R^{12B}$)$_n$—O—(C$R^{12A}$$R^{12B}$)$_n$—, wherein n is 1 or 2. In some embodiments, L is —O—. In some embodiments, L is —(C$R^{12A}$$R^{12B}$)— or —(C$R^{12A}$$R^{12B}$)—(C$R^{12A}$$R^{12B}$)—. In some embodiments, L is —O—(C$R^{12A}$$R^{12B}$)— or —O—(C$R^{12A}$$R^{12B}$)(C$R^{12A}$$R^{12B}$)—. In some embodiments, L is —(C$R^{12A}$$R^{12B}$)—O— or —(C$R^{12A}$$R^{12B}$(C$R^{12A}$$R^{12B}$)—. In some embodiments, L is —(C$R^{12A}$$R^{12B}$)—O—(C$R^{12A}$$R^{12B}$)— or —(C$R^{12A}$$R^{12B}$)(C$R^{12A}$$R^{12B}$)—O—C$R^{12A}$$R^{12B}$)(C$R^{12A}$$R^{12B}$)—.

Each $R^{12A}$ can be independently selected from H and $C_1$-$C_6$ alkyl. In some embodiments, at least one $R^{12A}$ is H. In some embodiments, at least one $R^{12A}$ is $C_1$-$C_6$ (e.g., $C_1$, $C_2$, $C_3$, $C_4$, $C_5$, or $C_6$) alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl.

Each $R^{12B}$ can be independently selected from H and $C_1$-$C_6$ alkyl. In some embodiments, at least one $R^{12B}$ is H. In some embodiments, at least one $R^{14A}$ is $C_1$-$C_6$ (e.g., $C_1$, $C_2$, $C_3$, $C_4$, $C_5$, or $C_6$) alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl.

In some embodiments, $R^{12A}$=$R^{12B}$. In some embodiments, each $R^{12A}$ and each $R^{12B}$ are H. In some embodiments, $R^{12A}$ and $R^{12B}$ are each independently selected from $C_1$-$C_6$ alkyl. In some embodiments, L is —O—, —O—$CH_2$—, —$CH_2$—O—, —$CH_2$—O—$CH_2$—, —O—$CH_2$—$CH_2$—, —$CH_2$—$CH_2$—O—, or —$CH_2$—$CH_2$—. In some embodiments, L is O. In some embodiments, L is —O—$CH_2$— or —$CH_2$—O—.

Q can be a bond or phenylene. In some embodiments, Q is a bond. In some embodiments, Q is phenylene. In some embodiments, Q is

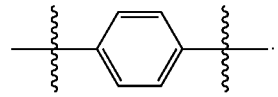 [SMILES: *c1ccc(*)cc1]

T can be a bond or —O—. In some embodiments, T is a bond. In some embodiments, T is —O—.

X can be a bond or $C_1$-$C_3$ alkylene. In some embodiments, X is a bond. In some embodiments, X is methylene, ethylene, n-propylene, or isopropylene.

In some embodiments, $R^3$(C$R^4$$R^5$)$_m$-Q-T-X— is

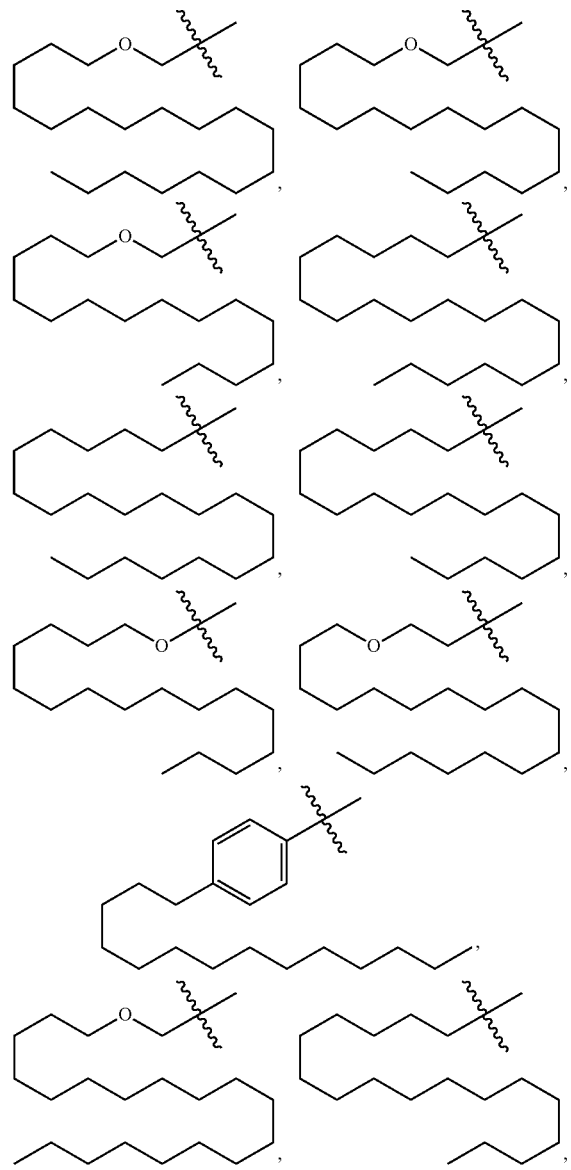

-continued

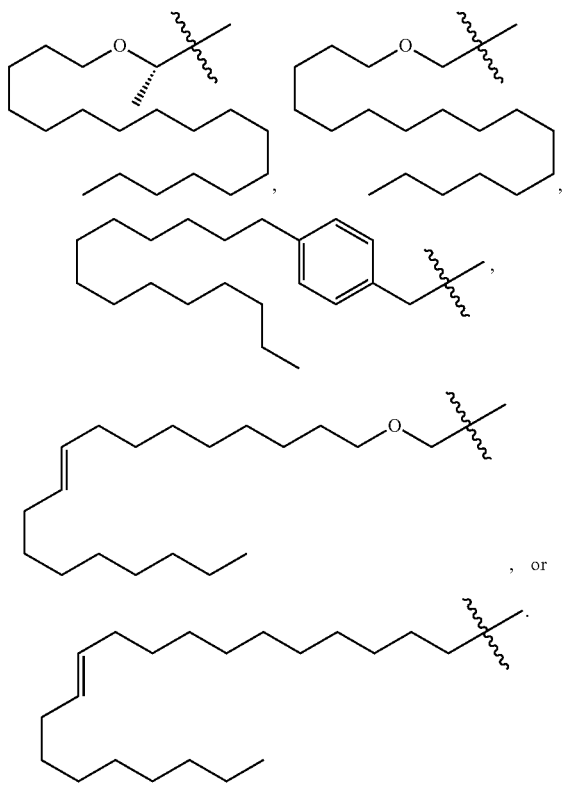

In some embodiments, $R^3(CR^4R^5)_m$-Q-T-X— is

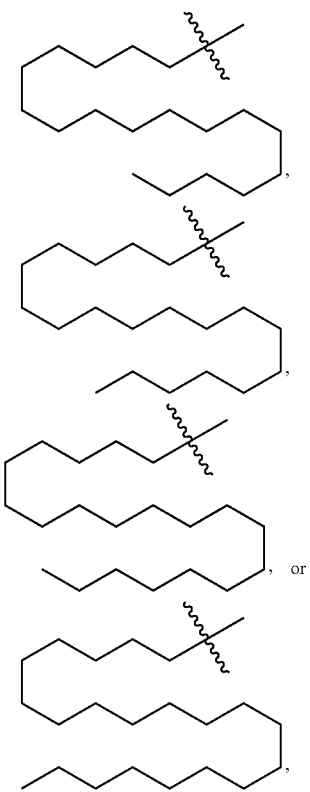

In some embodiments, $R^3(CR^4R^5)_m$-Q-T-X— is

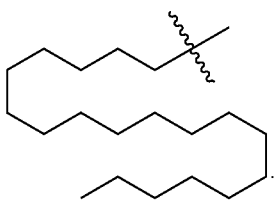 [SMILES: *CCCCCCCCCCCCCCCCCCC]

In some embodiments, $R^3(CR^4R^5)_m$-Q-T-X— is

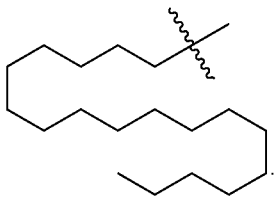 [SMILES: *CCCCCCCCCCCCCCCCCC]

In some embodiments, $R^3(CR^4R^5)_m$-Q-T-X— is

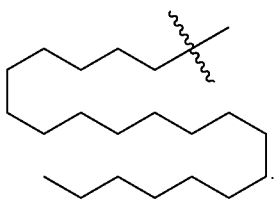 [SMILES: *CCCCCCCCCCCCCCCCCCCC]

In some embodiments, $R^3(CR^4R^5)_m$-Q-T-X— is

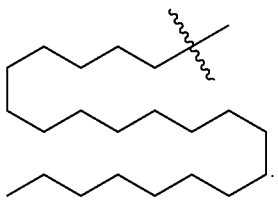 [SMILES: *CCCCCCCCCCCCCCCCCCCCC]

In some embodiments, $R^3(CR^4R^5)_m$-Q-T-X— is

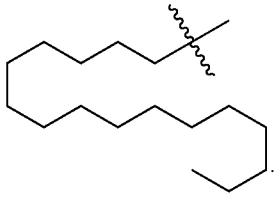 [SMILES: *CCCCCCCCCCCCCCCC]

Z can be —O—, —O—$(C_1$-$C_6)$-alkylene, or $NR^{15}$—$(C_1$-$C_6)$-alkylene, wherein $R^{15}$ is H or $C_1$-$C_3$ alkyl. In some embodiments, Z is —O—. In some embodiments, Z is —O—$(C_1$-$C_6)$-alkylene, wherein the $(C_1$-$C_6)$-alkylene is methylene, ethylene, -n-propylene, isopropyenlene, -n-butylene, isobutylene, -s-butylene, -t-butylene, -n-pentylene, -2-pentylene, -3-pentylene, -2-methyl-2-butylene, -3-methyl-2-butylene, -3-methyl-1-butylene, -2-methyl-1-butylene, -1-hexylene, -2-hexylene, -3-hexylene, -2-methyl-2-pentylene, -3-methyl-2-pentylene, -4-methyl-2-pentylene, -3-methyl-3-pentylene, -2-methyl-3-pentyenlene, -2,3-dimethyl-2-butylene, or -3,3-dimethyl-2-butylene.

In some embodiments, Z is NH—$(C_1-C_6)$-alkylene, N-methyl-$(C_1-C_6)$-alkylene, N-ethyl-$(C_1-C_6)$-alkylene, N-n-propyl-$(C_1-C_6)$-alkylene, or N-isopropyl-$(C_1-C_6)$-alkylene, wherein the $(C_1-C_6)$-alkylene is methylene, ethylene, n-propylene, isopropyenlene, -n-butylene, isobutylene, -s-butylene, -t-butylene, -n-pentylene, -2-pentylene, -3-pentylene, -2-methyl-2-butylene, -3-methyl-2-butylene, -3-methyl-1-butylene, -2-methyl-1-butylene, -1-hexylene, -2-hexylene, -3-hexylene, -2-methyl-2-pentylene, -3-methyl-2-pentylene, -4-methyl-2-pentylene, -3-methyl-3-pentylene, -2-methyl-3-pentyenlene, -2,3-dimethyl-2-butylene, or -3,3-dimethyl-2-butylene. In some embodiments, Z is —O—$CH_2$—, —NH—$CH_2$—, or —N($CH_3$)—$CH_2$—.

In some embodiments, $R^1$ is cyclohexyl, phenyl, phenyl substituted with cyano, phenyl substituted with cyano and fluoro, phenyl substituted with cyano and chloro, phenyl substituted with cyano and methoxy, phenyl substituted with cyano and isopropoxy, phenyl substituted with cyano and trifluoromethoxy, phenyl substituted with cyano and two methoxy, phenyl substituted with cyano and triazolyl, phenyl substituted with fluoro and oxadiazolyl, pyridinyl substituted with cyano, pyridinyl substituted with chloro, or pyrimidinyl substituted with cyano; $R^2$ is H or methyl; $R^3$ is methyl, ethyl, or n-propyl; each $R^4$ and $R^5$ is independently H or a bond; $R^6$ is H; $R^7$ is H; m is 11, 12, 13, 14, 15, 16, 17, or 18; L is —O—, —O—$CH_2$—, —$CH_2$—O—, —$CH_2$—O—$CH_2$—, —O—$CH_2$—$CH_2$—, —$CH_2$—$CH_2$—O—, or —$CH_2$—$CH_2$—; Q is a bond or phenylene; T is a bond or —O—; X is a bond, —$CH_2$—, —$CH_2$—$CH_2$—, or —CH($CH_3$)—; and Z is —O—$CH_2$—, —NH—$CH_2$—, or —N($CH_3$)—$CH_2$—.

In some embodiments, $R^1$ is unsubstituted cyclohexyl; unsubstituted phenyl; phenyl substituted with one, two, or three substituents independently selected from cyano, halo, methoxy, isopropoxy, trifluoromethoxy, triazolyl, and oxadiazolyl; pyridinyl substituted with one, two, or three substituents independently selected from cyano and halo; or pyrimidinyl substituted with cyano; $R^2$ is H or methyl; $R^3$ is methyl, ethyl, or n-propyl; each $R^4$ and $R^5$ is independently H or a bond; $R^6$ is H; $R^7$ is H; m is 11, 12, 13, 14, 15, 16, 17, or 18; L is —O—, —O—$CH_2$—, —$CH_2$—O—, —$CH_2$—O—$CH_2$—, —O—$CH_2$—$CH_2$—, —$CH_2$—$CH_2$—O—, or —$CH_2$—$CH_2$—; Q is a bond or phenylene; T is a bond or —O—; X is a bond, —$CH_2$—, —$CH_2$—$CH_2$—, or —CH($CH_3$)—; and Z is —O—$CH_2$—, —NH—$CH_2$—, or —N($CH_3$)—$CH_2$—. In some embodiment, $R^1$-L is

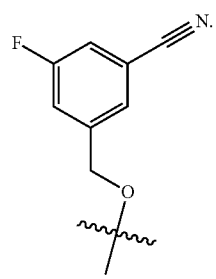 [SMILES: *OCc1cc(F)cc(C#N)c1]

One of skill in the art is aware that each and every embodiment of a group (e.g., $R^1$) disclosed herein may be combined with any other embodiment of each of the remaining groups (e.g., $R^2$, $R^3$, $R^4$, $R^5$, $R^6$, etc.) to generate a complete compound of Formula (I), or any Formula described herein or a pharmaceutically acceptable salt, stereoisomer, mixture of stereoisomers, or tautomer thereof, each of which is deemed within the ambit of the present disclosure.

In some embodiments, the compounds and pharmaceutically acceptable salts of Formula I include the compounds in Table 1 and the pharmaceutically acceptable salts thereof. In some embodiments, the compounds and pharmaceutically acceptable salts of Formula I include the compounds in Table 1A and the pharmaceutically acceptable salts thereof. Tables 1 and 1A provide some compounds disclosed herein with compound number and the corresponding structure.

TABLE 1

Some compounds of Formula I

| # | Structure |
|---|-----------|
| 1 | 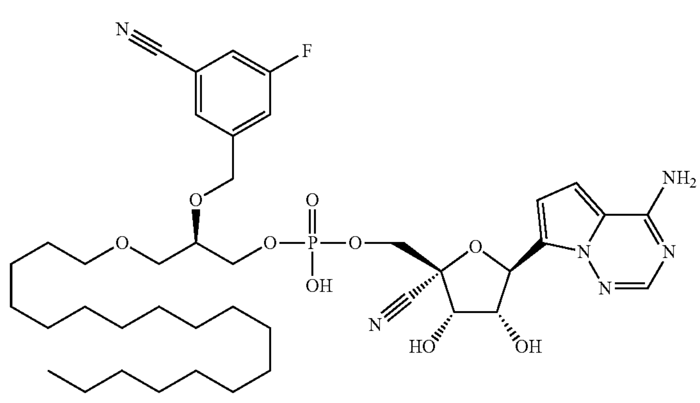 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1] |

TABLE 1-continued
Some compounds of Formula I
| # | Structure |
|---|---|
| 3 | 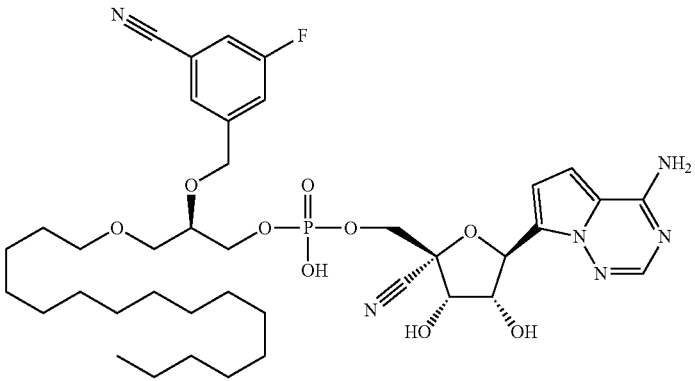 [SMILES: CCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1] |
| 5 | 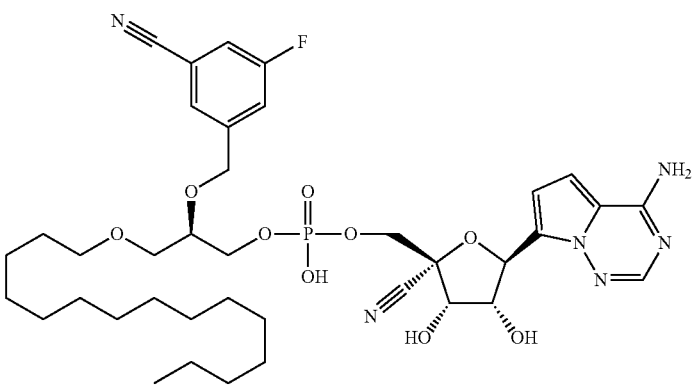 |
| 6 | 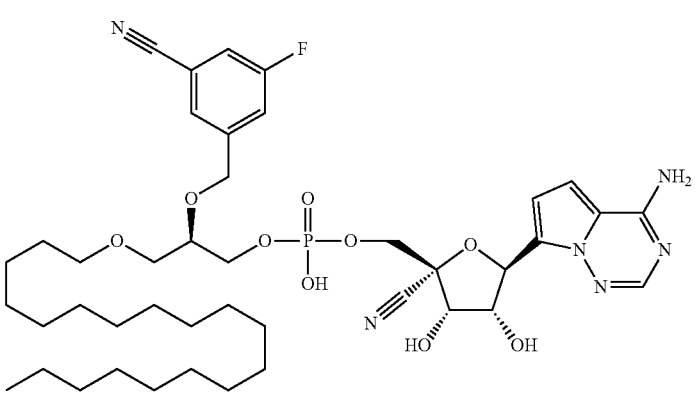 [SMILES: CCCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1] |

TABLE 1-continued
Some compounds of Formula I
| # | Structure |
|---|-----------|
| 7 | 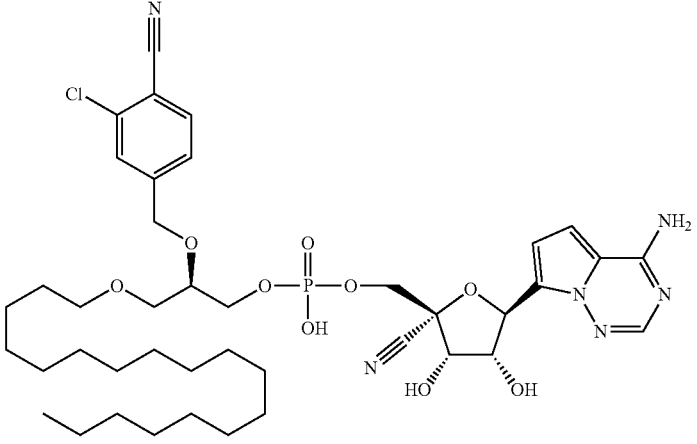 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(Cl)c1] |
| 8 | 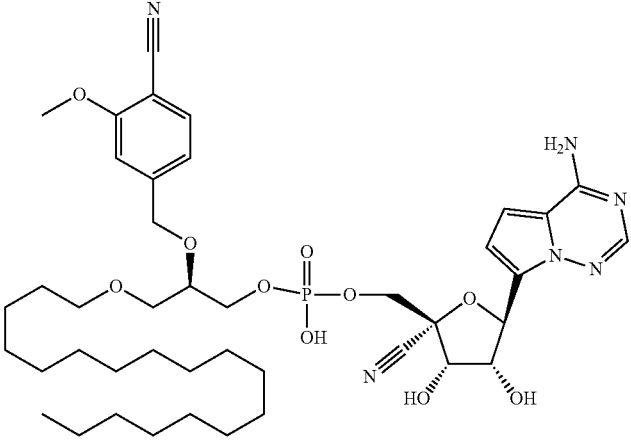 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1] |
| 9 | 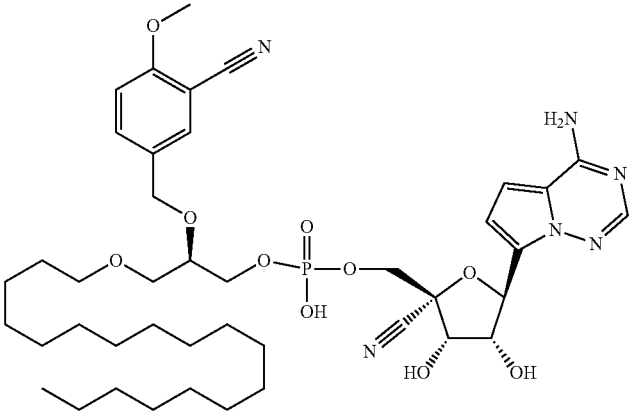 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1] |

TABLE 1-continued
Some compounds of Formula I
| # | Structure |
|---|---|
| 10 | 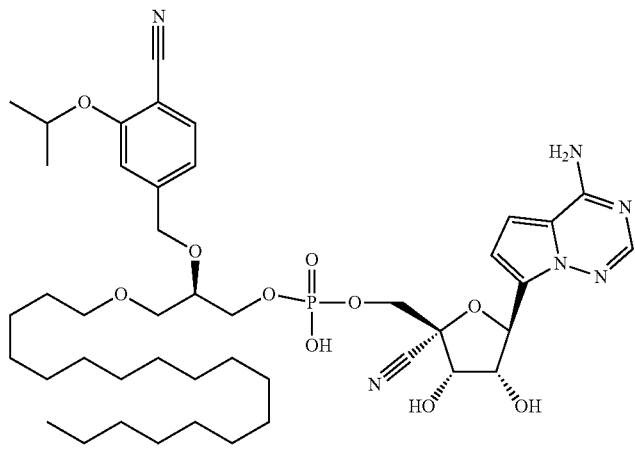 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1] |
| 11 | 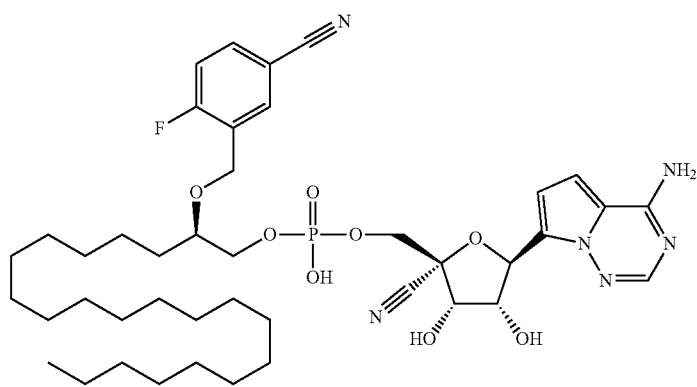 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(C#N)ccc1F] |
| 12 | 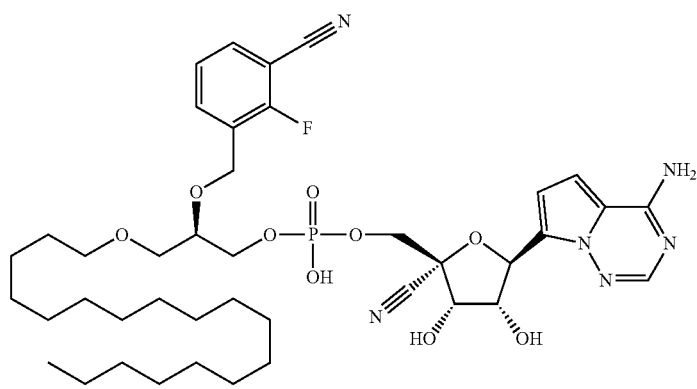 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F] |

TABLE 1-continued
Some compounds of Formula I
| # | Structure |
|---|---|
| 13 | 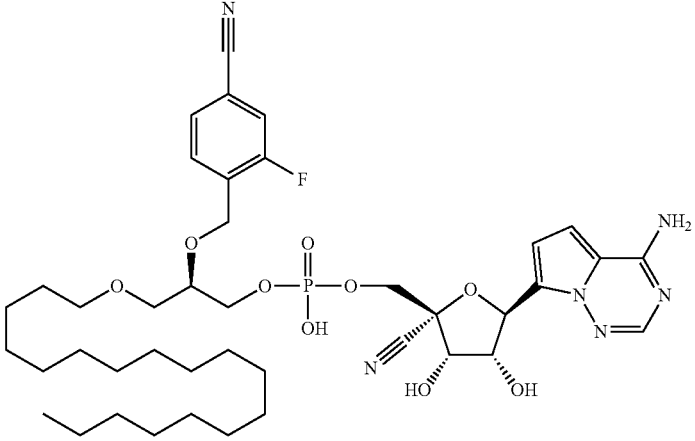 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F] |
| 14 | 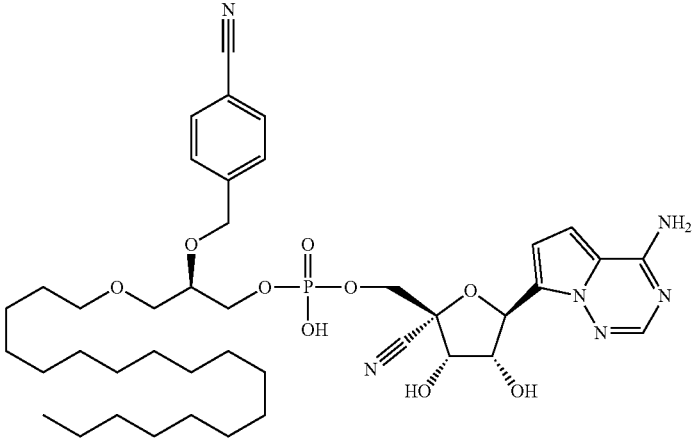 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1] |
| 15 | 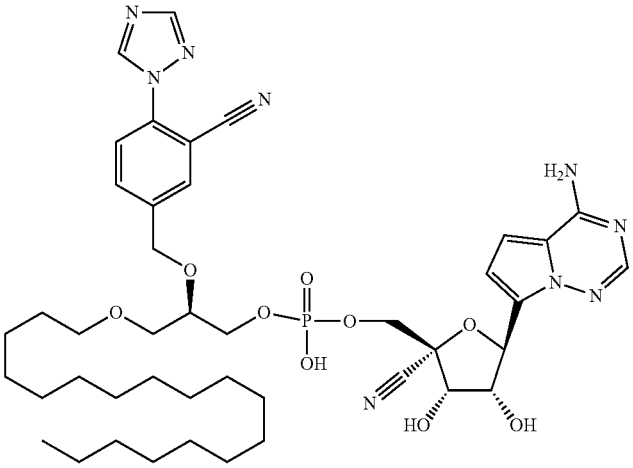 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1] |

TABLE 1-continued
Some compounds of Formula I
| # | Structure |
|---|---|
| 16 | 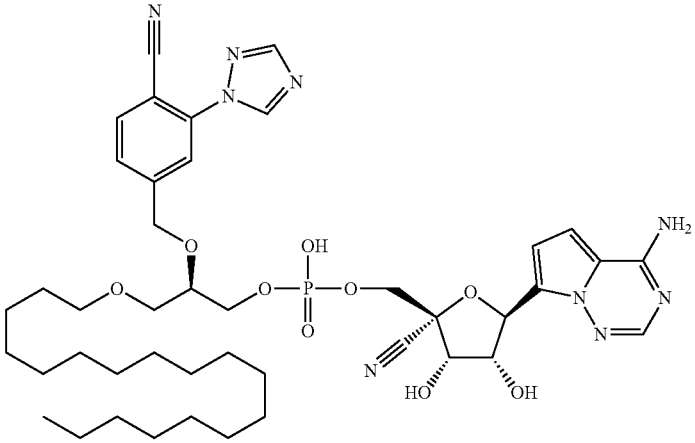 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1] |
| 17 | 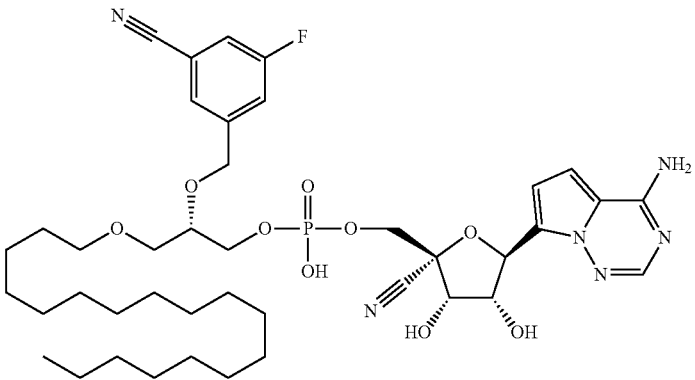 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1] |
| 18 | 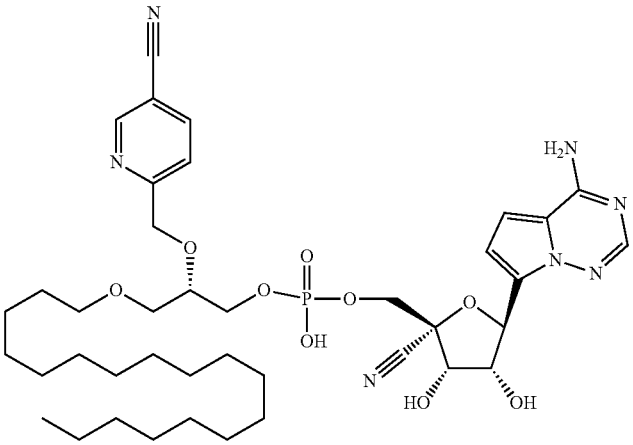 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1] |

TABLE 1-continued

Some compounds of Formula I

| # | Structure |
|---|---|
| 19 | 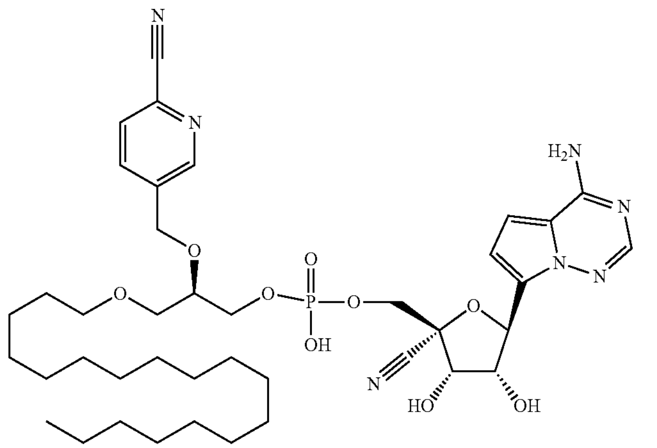 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)nc1] |
| 20 | 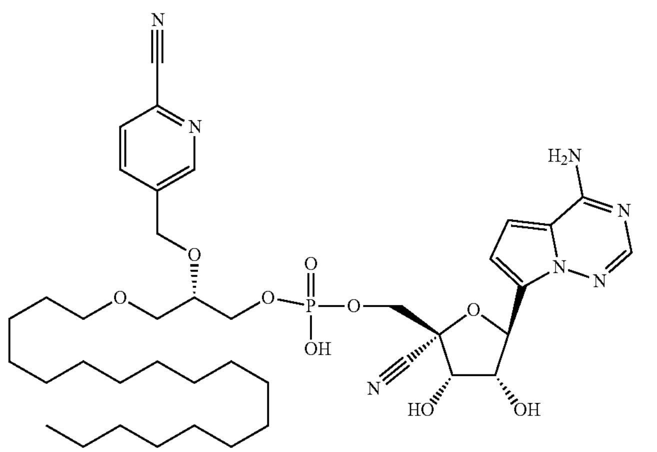 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)nc1] |
| 21 | 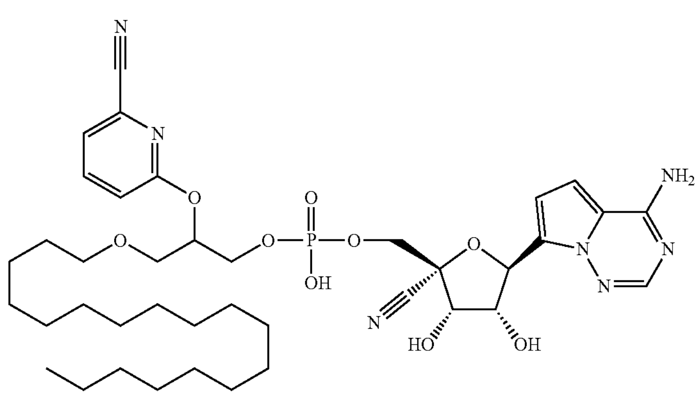 [SMILES: CCCCCCCCCCCCCCCCCCOCC(COP(=O)(O)OC[C@@]1(C#N)O[C@@H](c2ccc3c(N)ncnn23)[C@H](O)[C@@H]1O)Oc1cccc(C#N)n1] |

TABLE 1-continued
Some compounds of Formula I
| # | Structure |
|---|-----------|
| 22 | 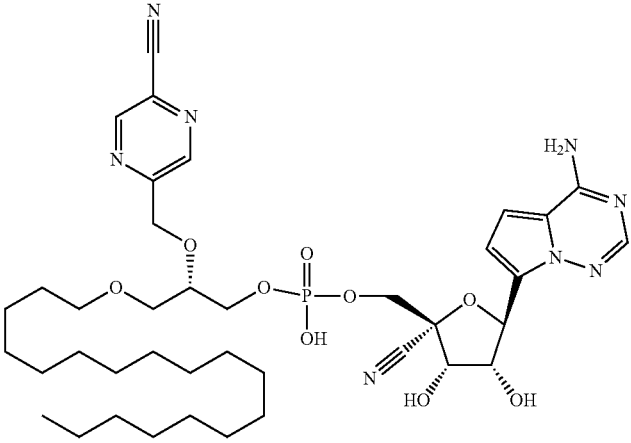 |
| 23 | 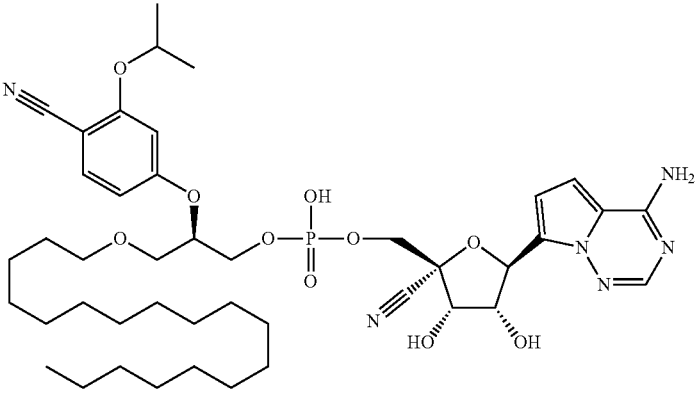 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(OC(C)C)c1] |
| 24 | 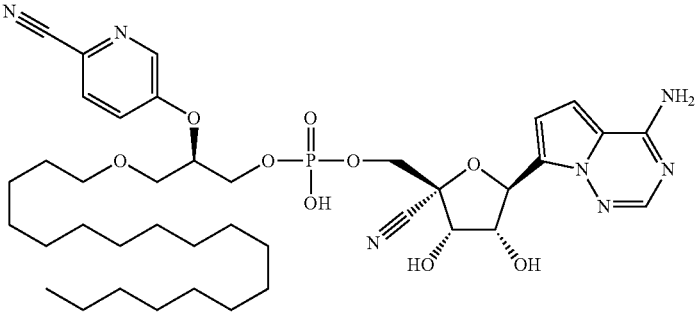 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)nc1] |
| 25 | 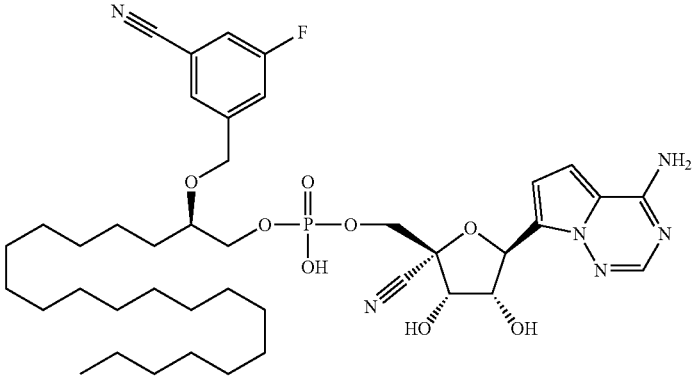 |

TABLE 1-continued
Some compounds of Formula I
| # | Structure |
|---|---|
| 26 | 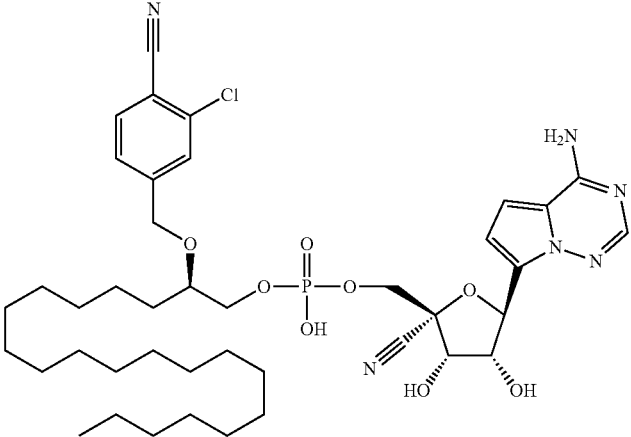 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(Cl)c1] |
| 27 | 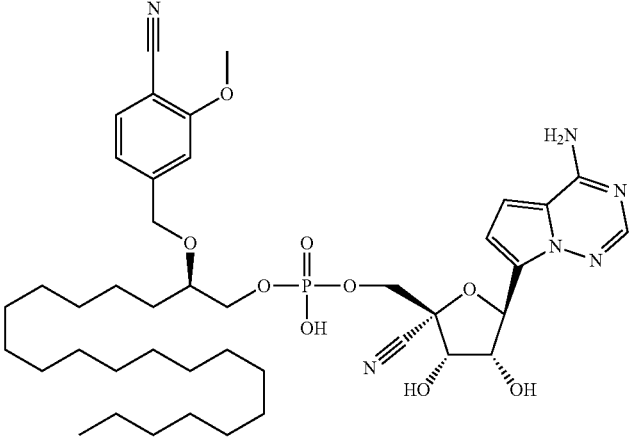 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC)c1] |
| 28 | 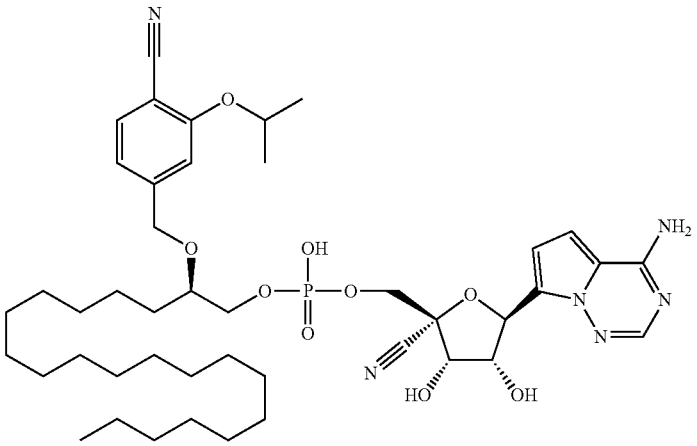 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1] |

TABLE 1-continued
Some compounds of Formula I
| # | Structure |
|---|---|
| 29 | 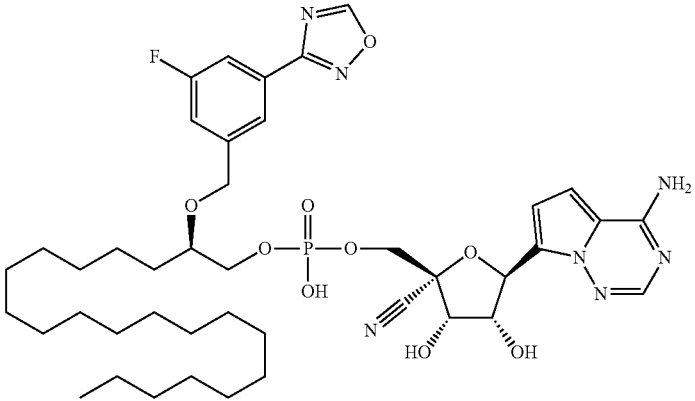 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(-c2ncon2)c1] |
| 30 | 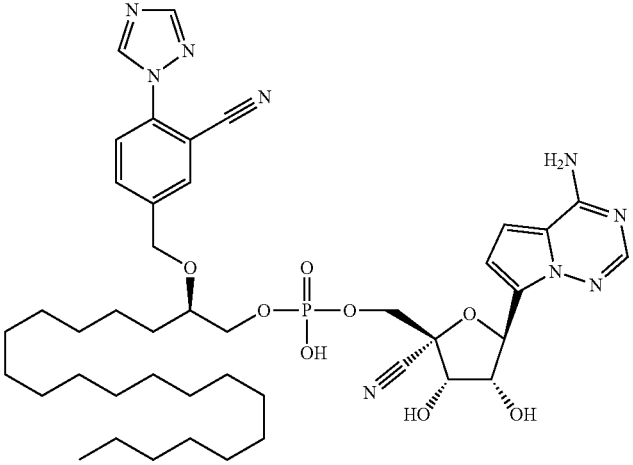 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1] |
| 31 | 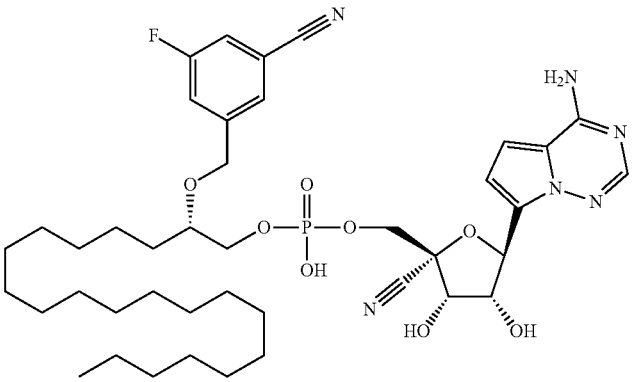 [SMILES: CCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1] |

TABLE 1-continued

Some compounds of Formula I

| # | Structure |
|---|---|
| 32 | 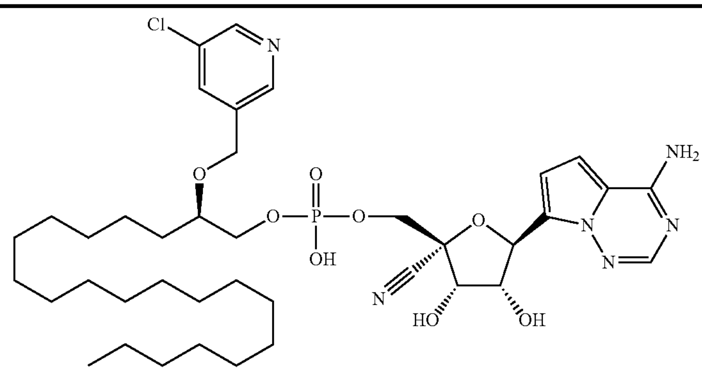 |
| 33 | 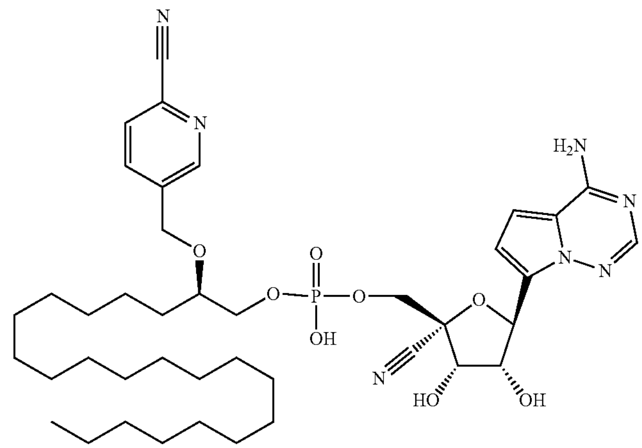 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)nc1] |
| 34 | 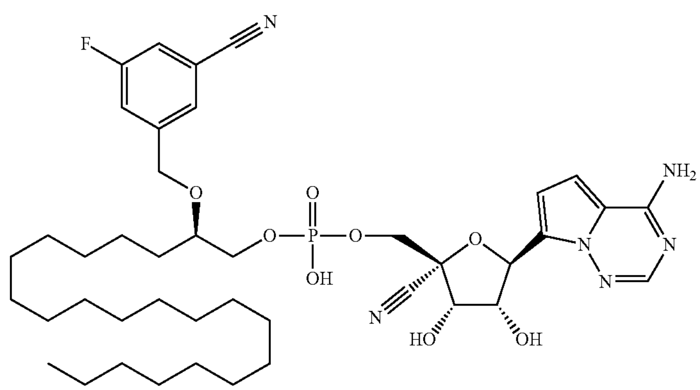 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1] |
| 35 | 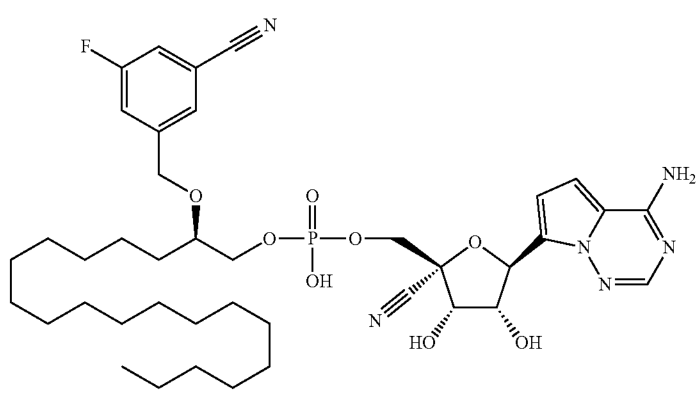 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1] |

TABLE 1-continued

Some compounds of Formula I

| # | Structure |
|---|---|
| 36 | 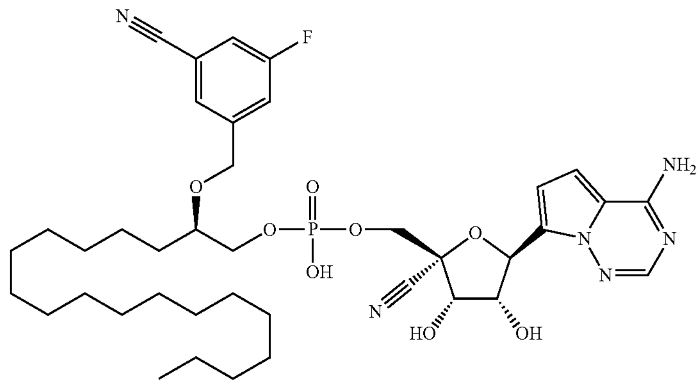 [SMILES: CCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1] |
| 37 | 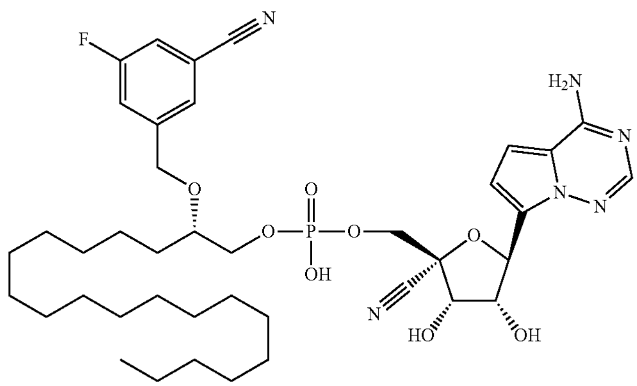 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1] |
| 38 | 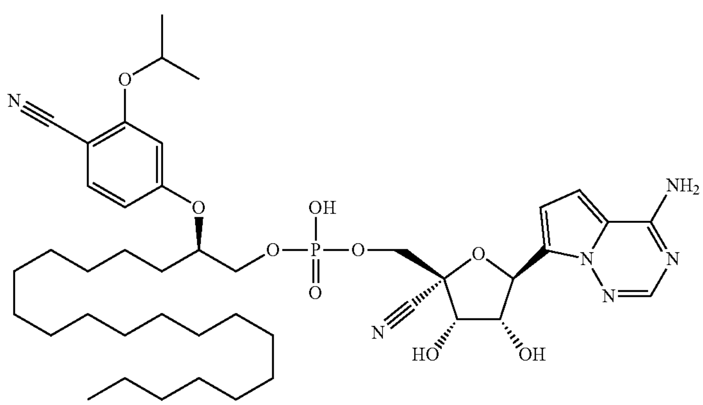 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(OC(C)C)c1] |
| 39 | 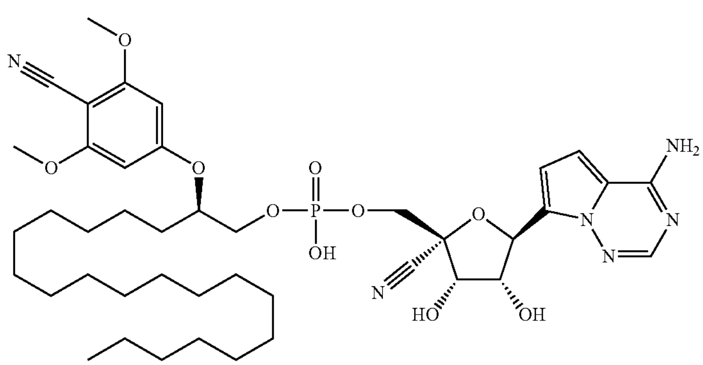 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1cc(OC)c(C#N)c(OC)c1] |

TABLE 1-continued
Some compounds of Formula I
| # | Structure |
|---|---|
| 40 | 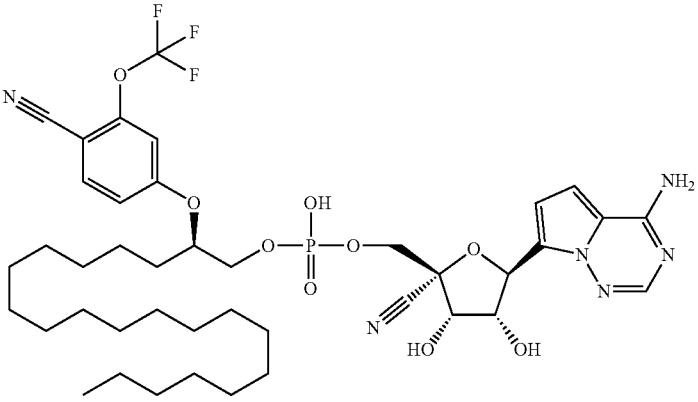 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(OC(F)(F)F)c1] |
| 41 | 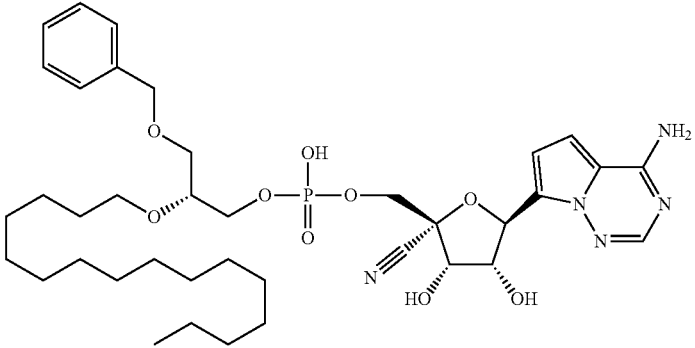 [SMILES: CCCCCCCCCCCCCCCCO[C@H](COCc1ccccc1)COP(=O)(O)OC[C@@]1(C#N)O[C@@H](c2ccc3c(N)ncnn23)[C@H](O)[C@@H]1O] |
| 42 | 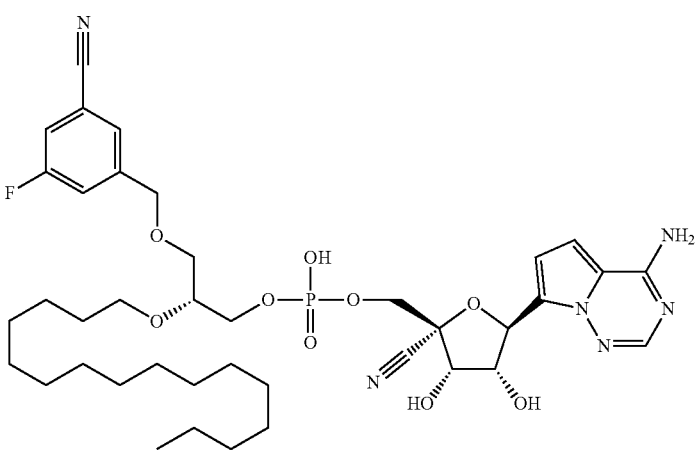 [SMILES: CCCCCCCCCCCCCCCCO[C@H](COCc1cc(F)cc(C#N)c1)COP(=O)(O)OC[C@@]1(C#N)O[C@@H](c2ccc3c(N)ncnn23)[C@H](O)[C@@H]1O] |

TABLE 1-continued

Some compounds of Formula I

| # | Structure |
|---|---|
| 43 | 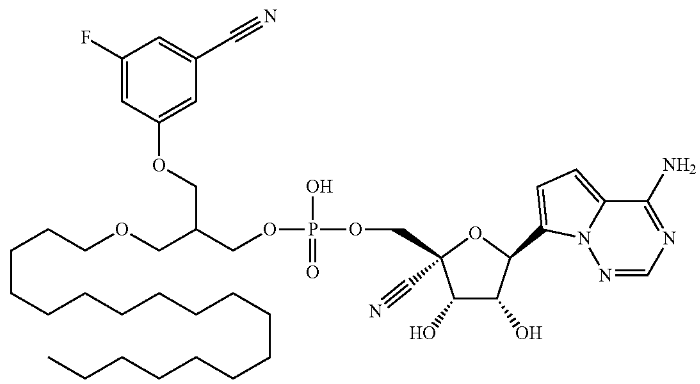 [SMILES: CCCCCCCCCCCCCCCCCCOCC(COc1cc(F)cc(C#N)c1)COP(=O)(O)OC[C@@]1(C#N)O[C@@H](c2ccc3c(N)ncnn23)[C@H](O)[C@@H]1O] |
| 44 | 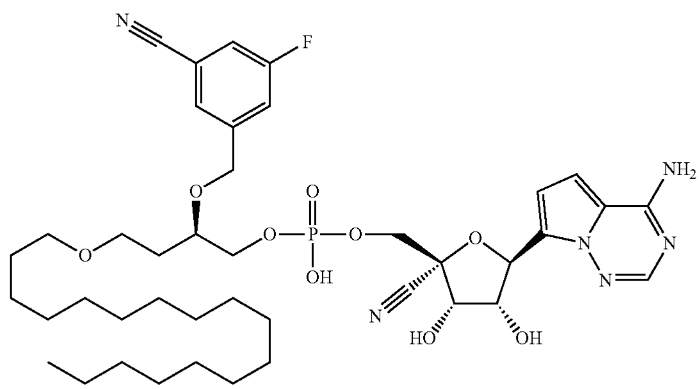 [SMILES: CCCCCCCCCCCCCCCCCOCC[C@H](COP(=O)(O)OC[C@@]1(C#N)O[C@@H](c2ccc3c(N)ncnn23)[C@H](O)[C@@H]1O)OCc1cc(F)cc(C#N)c1] |
| 45 | 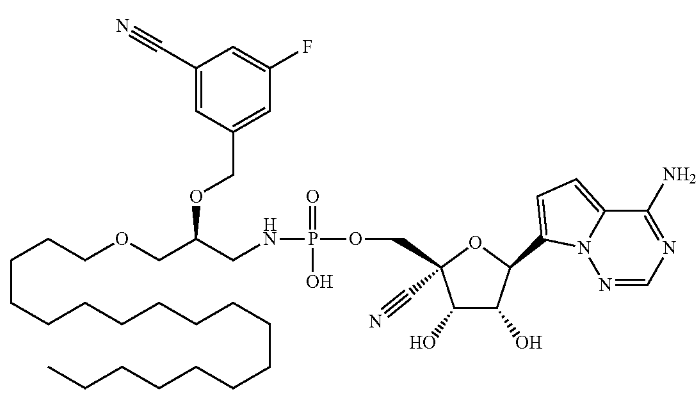 |
| 46 | 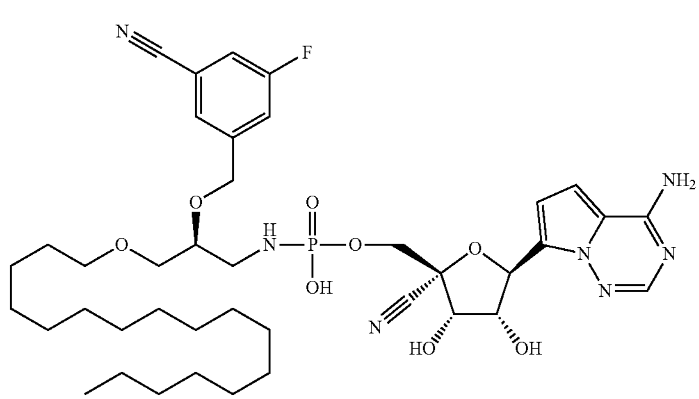 [SMILES: CCCCCCCCCCCCCCCCCOC[C@H](CNP(=O)(O)OC[C@@]1(C#N)O[C@@H](c2ccc3c(N)ncnn23)[C@H](O)[C@@H]1O)OCc1cc(F)cc(C#N)c1] |

TABLE 1-continued
Some compounds of Formula I
| # | Structure |
|---|---|
| 47 | 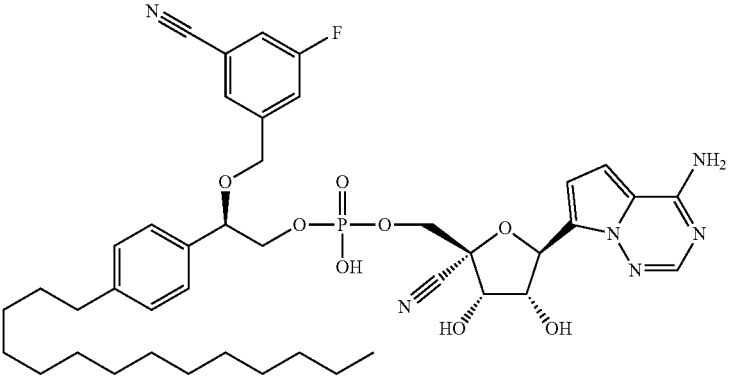 [SMILES: CCCCCCCCCCCCCCc1ccc([C@H](COP(=O)(O)OC[C@@]2(C#N)O[C@@H](c3ccc4c(N)ncnn34)[C@H](O)[C@@H]2O)OCc2cc(F)cc(C#N)c2)cc1] |
| 48 | 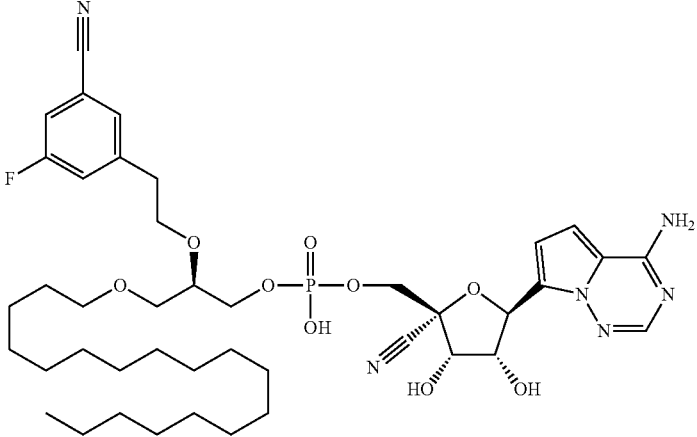 |
| 49 | 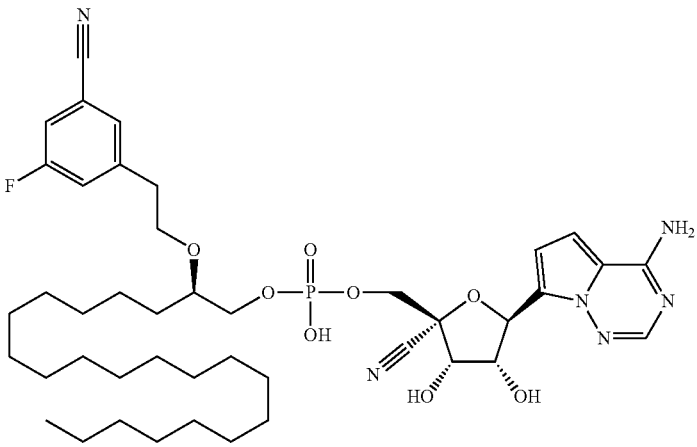 |

TABLE 1-continued
Some compounds of Formula I
| # | Structure |
|---|---|
| 50 | 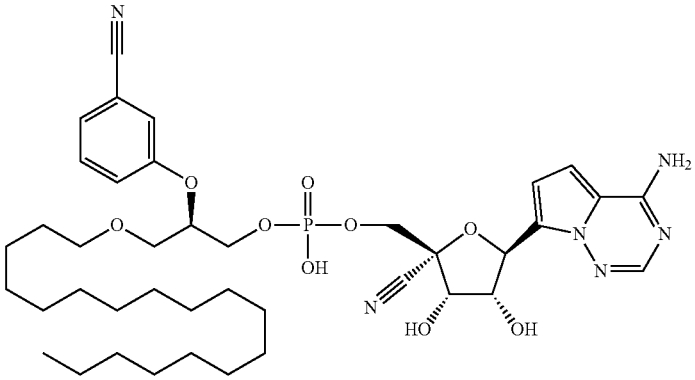 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1cccc(C#N)c1] |
| 51 | 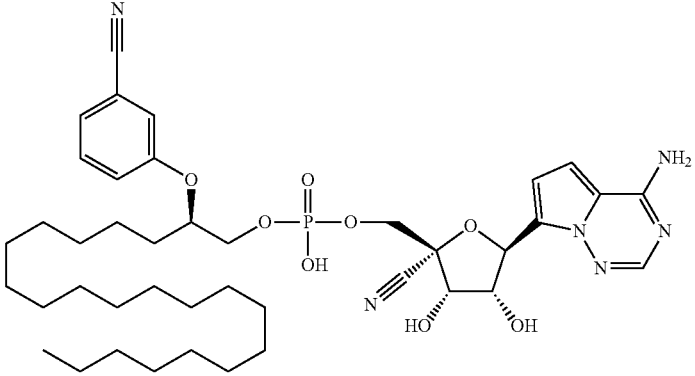 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)Oc1cccc(C#N)c1] |
| 52 | 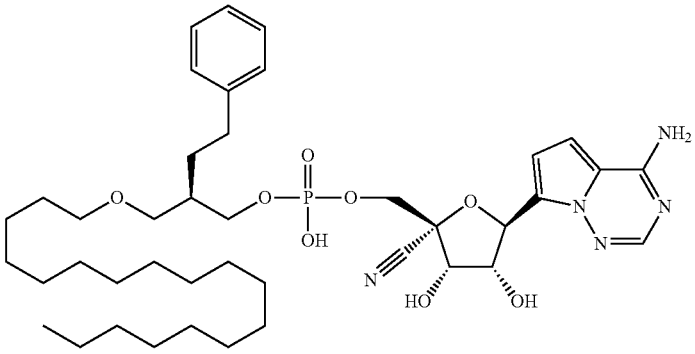 [SMILES: CCCCCCCCCCCCCCCCCCOC[C@@H](CCc1ccccc1)COP(=O)(O)OC[C@@]1(C#N)O[C@@H](c2ccc3c(N)ncnn23)[C@H](O)[C@@H]1O] |
| 53 | 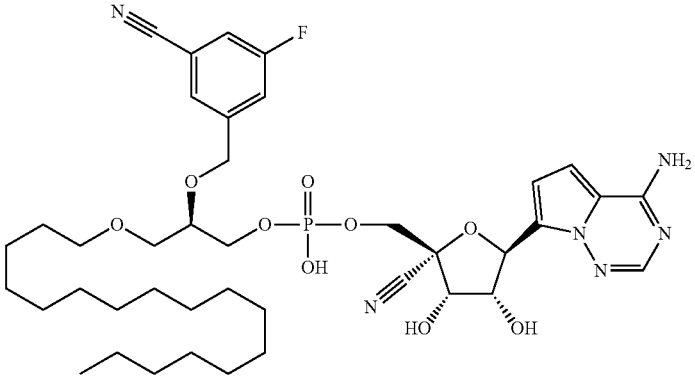 |

TABLE 1-continued
Some compounds of Formula I
| # | Structure |
|---|---|
| 54 | 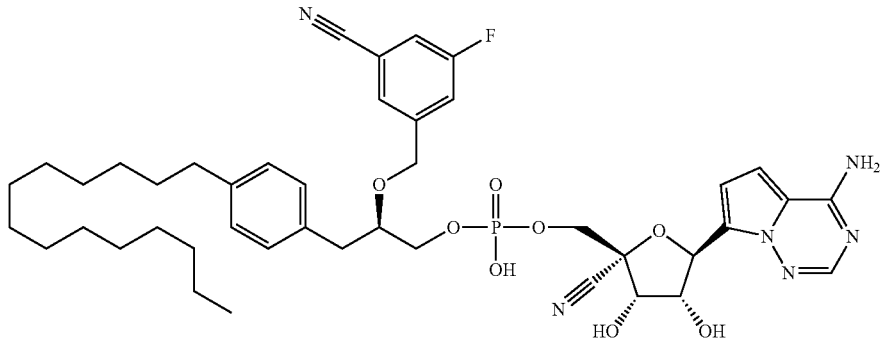 [SMILES: CCCCCCCCCCCCCCc1ccc(C[C@H](COP(=O)(O)OC[C@@]2(C#N)O[C@@H](c3ccc4c(N)ncnn34)[C@H](O)[C@@H]2O)OCc2cc(F)cc(C#N)c2)cc1] |
| 55 | 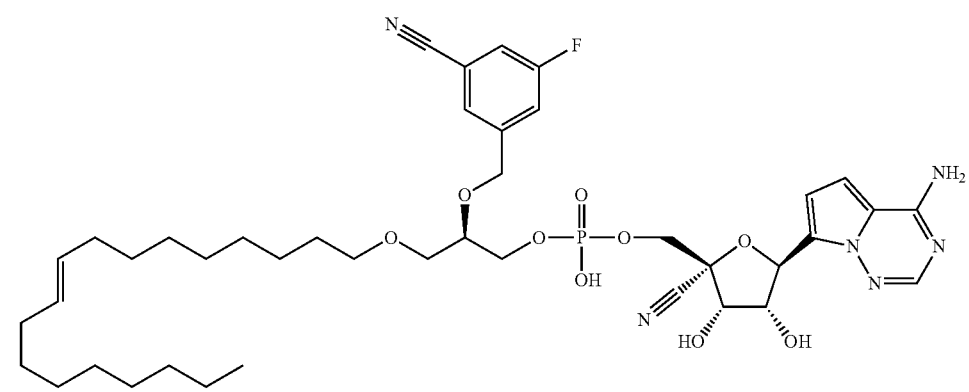 |
| 56 | 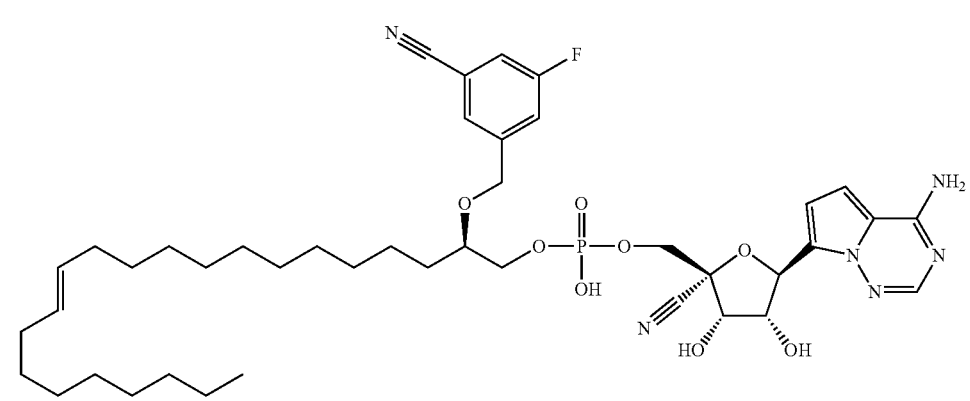 |
| 57 | 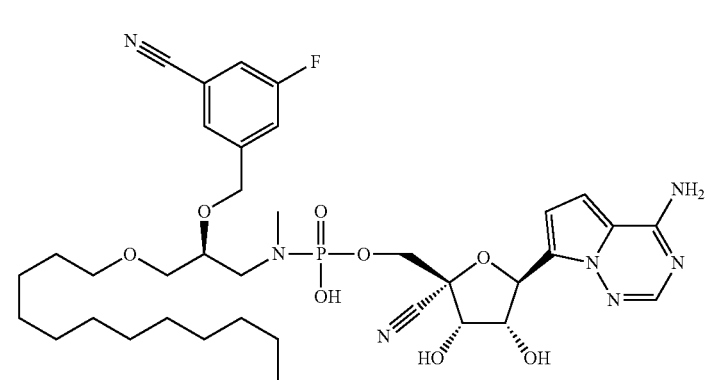 |

TABLE 1-continued
Some compounds of Formula I
| # | Structure |
|---|---|
| 58 | 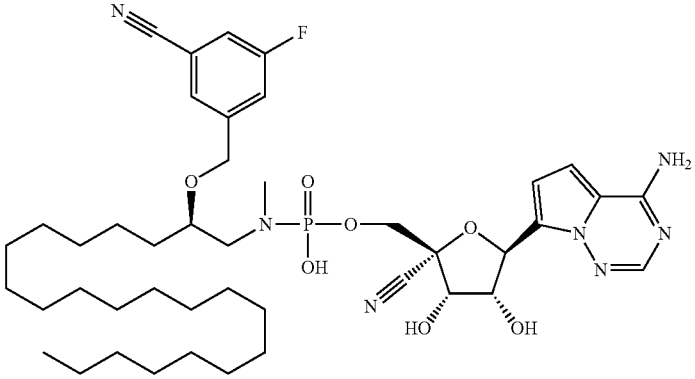 [SMILES: CCCCCCCCCCCCCCCCCCCC[C@H](CN(C)P(=O)(O)OC[C@@]1(C#N)O[C@@H](c2ccc3c(N)ncnn23)[C@H](O)[C@@H]1O)OCc1cc(F)cc(C#N)c1] |
| 59 | 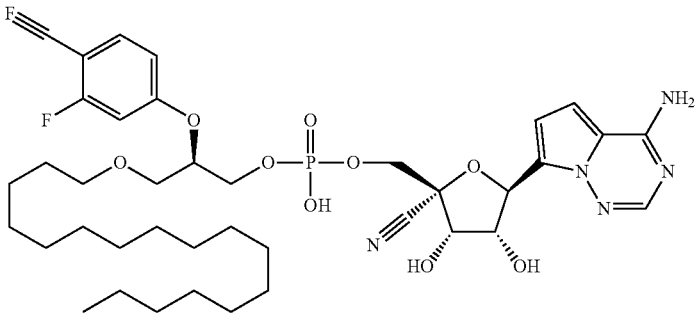 |
| 60 | 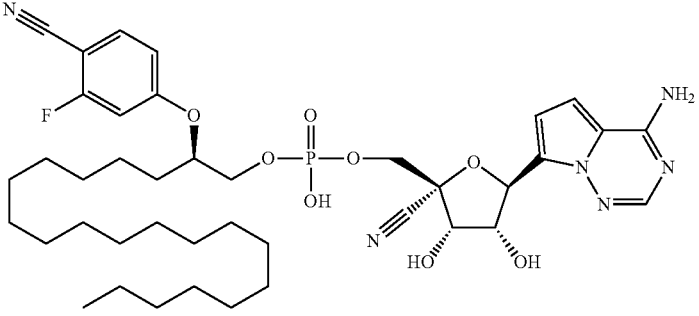 |
| 61 | 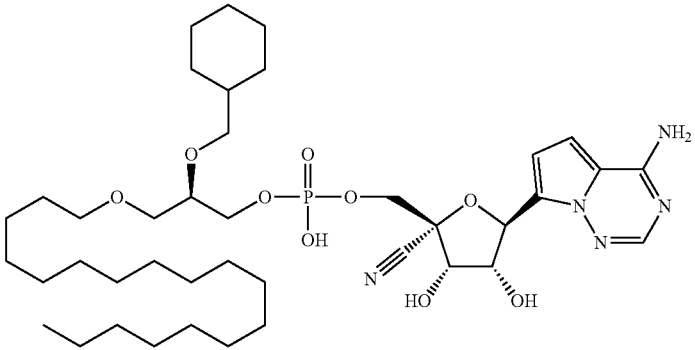 |

TABLE 1-continued
Some compounds of Formula I
| # | Structure |
|---|---|
| 62 | 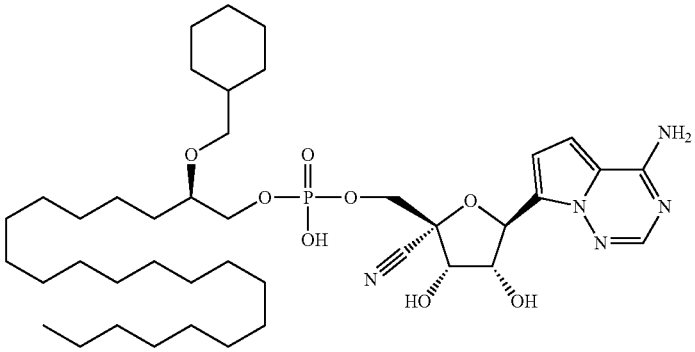 |
| 63 | 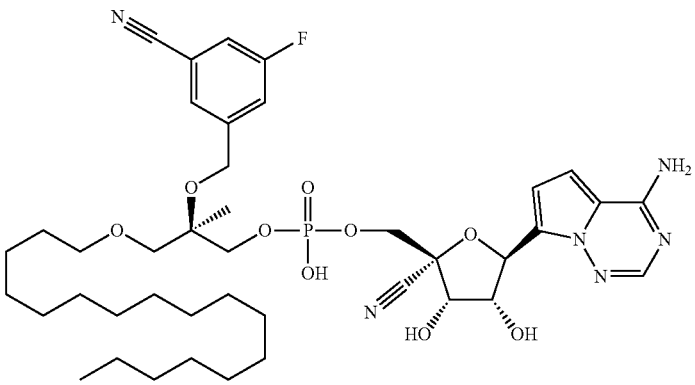 [SMILES: CCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1] |
| 64 | 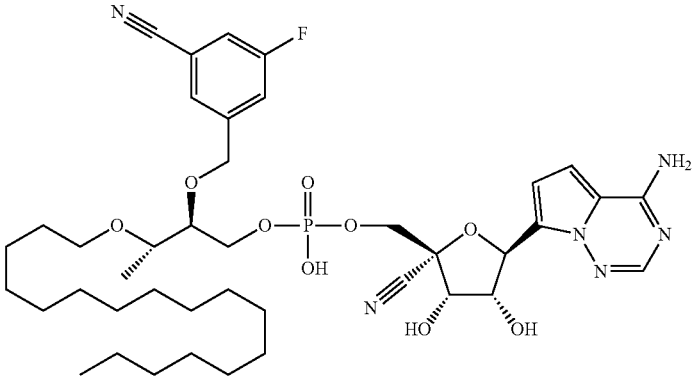 [SMILES: CCCCCCCCCCCCCCCCCO[C@@H](C)[C@H](COP(=O)(O)OC[C@@]1(C#N)O[C@@H](c2ccc3c(N)ncnn23)[C@H](O)[C@@H]1O)OCc1cc(F)cc(C#N)c1] |
| 65 | 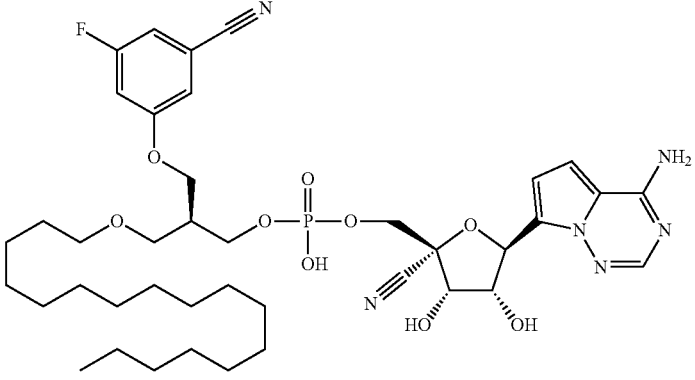 [SMILES: CCCCCCCCCCCCCCCCCOC[C@@H](COc1cc(F)cc(C#N)c1)COP(=O)(O)OC[C@@]1(C#N)O[C@@H](c2ccc3c(N)ncnn23)[C@H](O)[C@@H]1O] |

TABLE 1-continued

Some compounds of Formula I

| # | Structure |
|---|-----------|
| 66 | 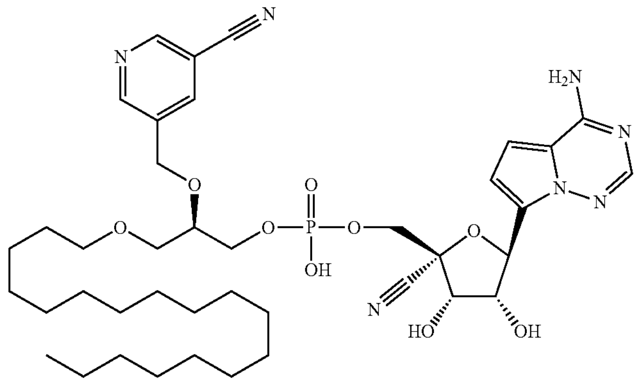 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cncc(C#N)c1] |
| 67 | 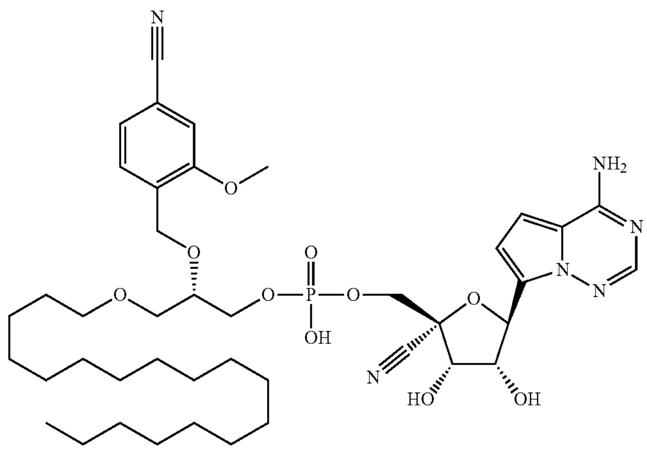 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cc1OC] |
| 68 | 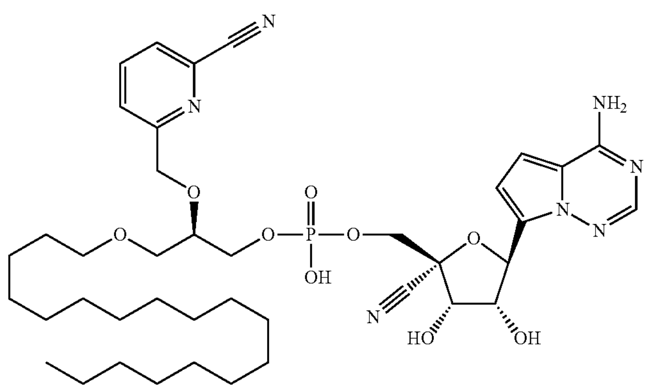 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)n1] |
| 69 | 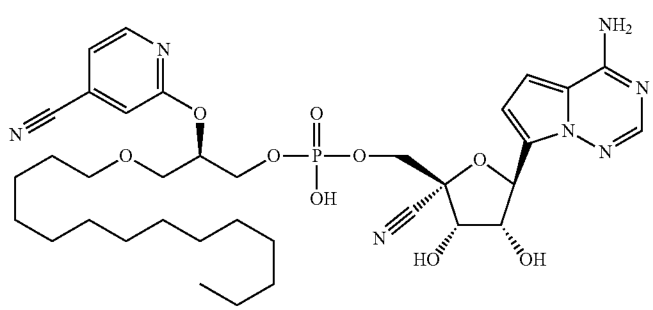 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1cc(C#N)ccn1] |

TABLE 1-continued
Some compounds of Formula I
| # | Structure |
|---|---|
| 70 | 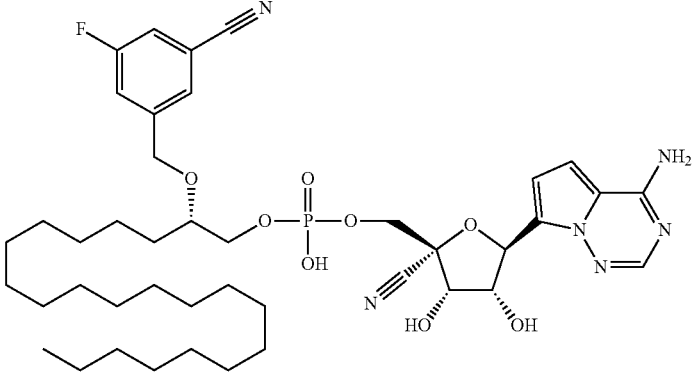 [SMILES: CCCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1] |
| 71 | 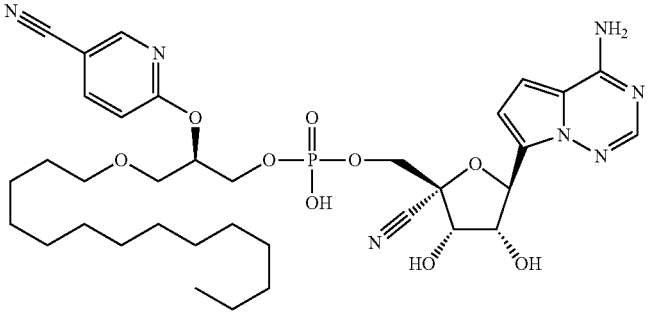 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)cn1] |
| 72 | 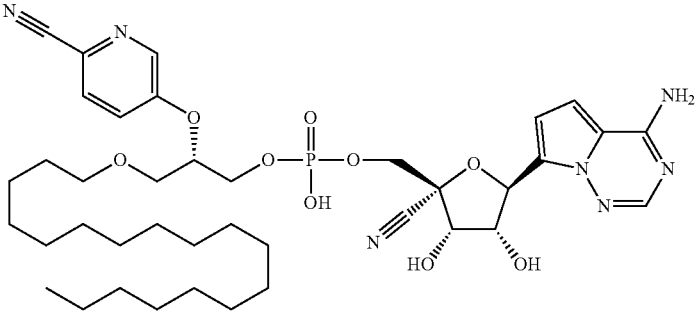 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)Oc1ccc(C#N)nc1] |
| 73 | 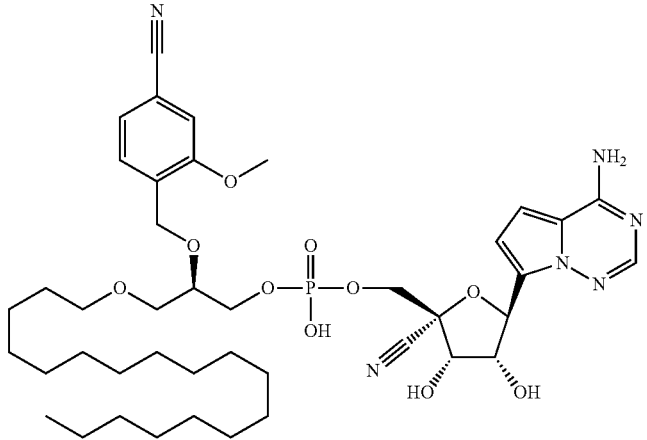 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1OC] |

TABLE 1-continued

Some compounds of Formula I

| # | Structure |
|---|---|
| 74 | 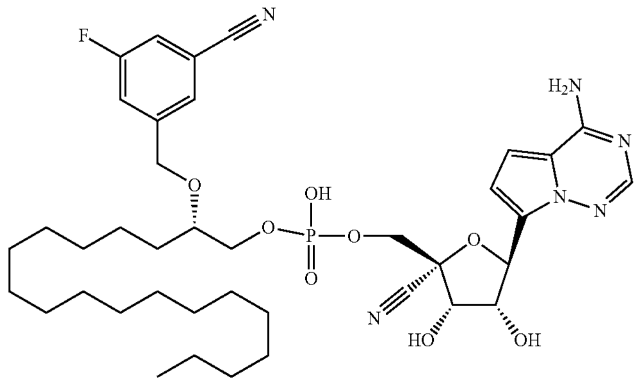 [SMILES: CCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1] |
| 75 | 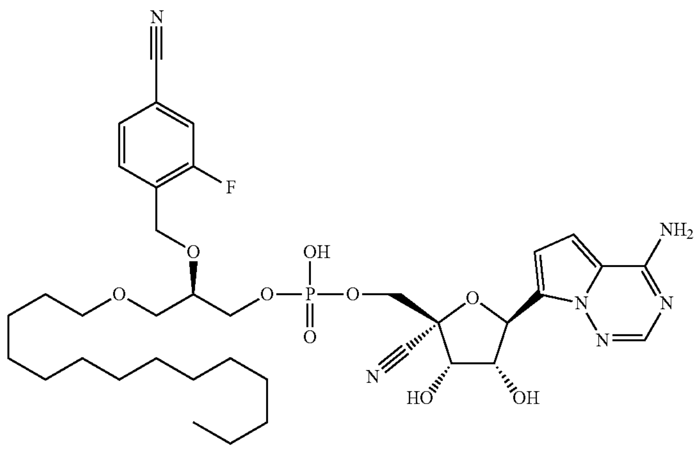 [SMILES: CCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F] |
| 76 | 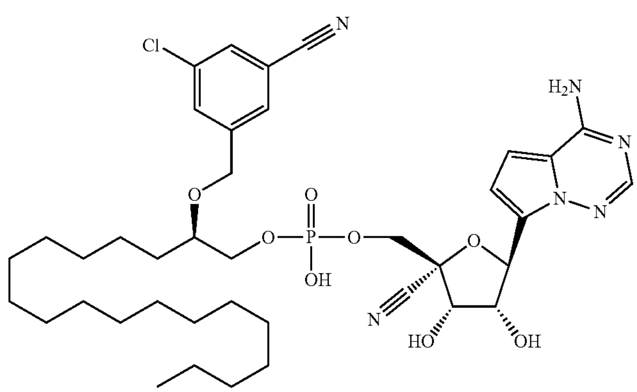 [SMILES: CCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1] |
| 77 | 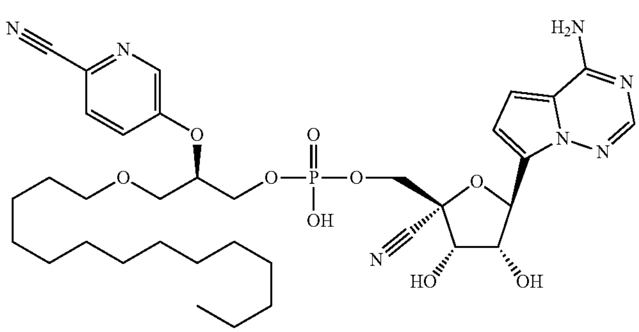 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)nc1] |

TABLE 1A
Some compounds of Formula I (Compound # and structure)
| # | Structure |
|---|---|
| 78 | 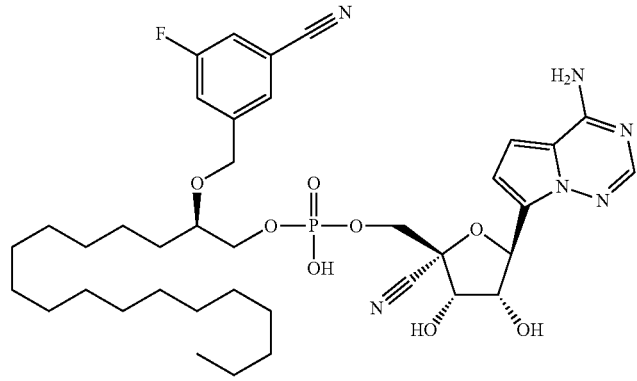 [SMILES: CCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1] |
| 79 | 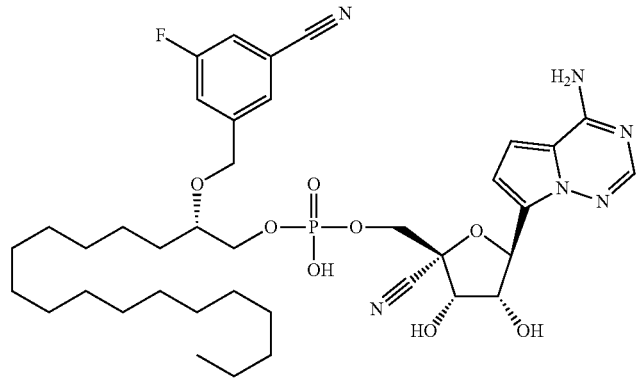 [SMILES: CCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1] |
| 80 | 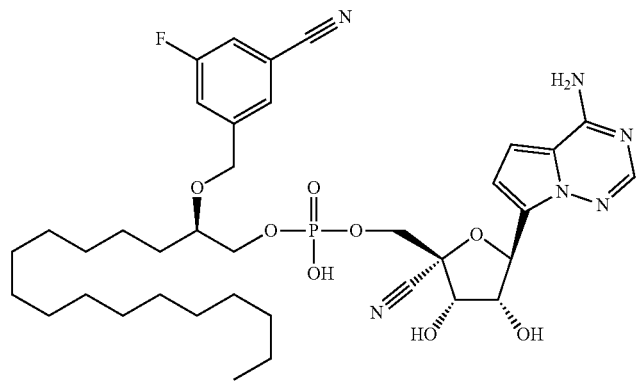 [SMILES: CCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1] |
| 81 | 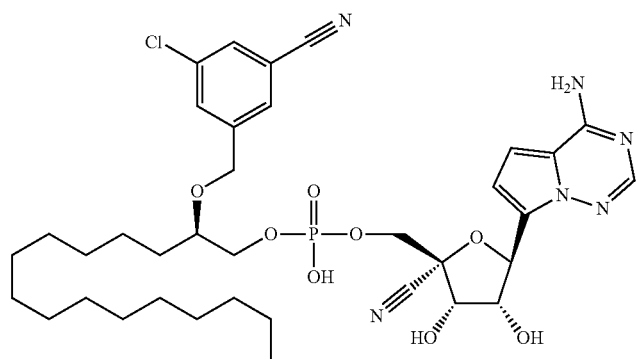 |

TABLE 1A-continued
Some compounds of Formula I (Compound # and structure)
| # | Structure |
|---|---|
| 82 | 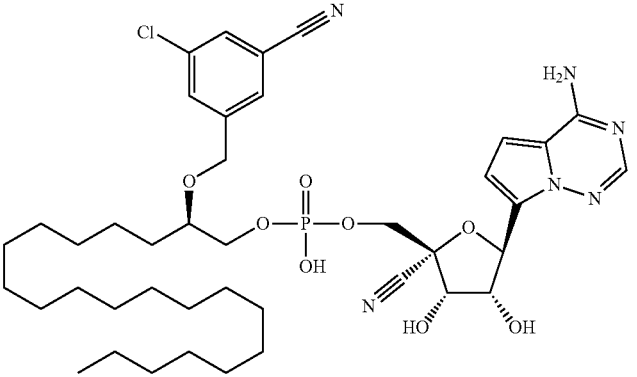 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1] |
| 84 | 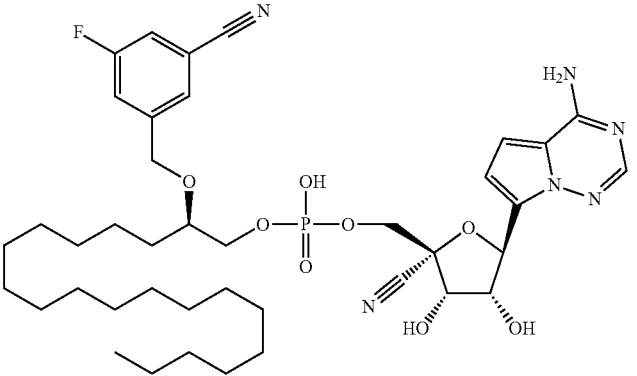 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1] |
| 85 | 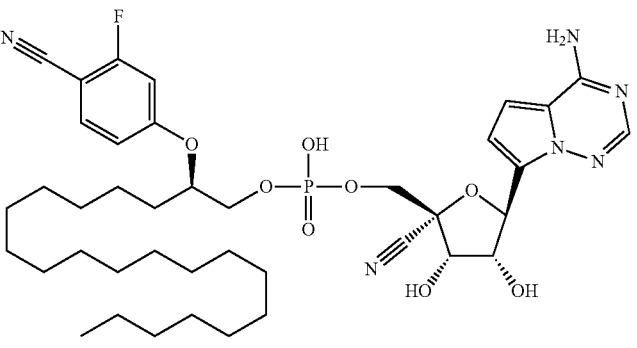 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1] |
| 86 | 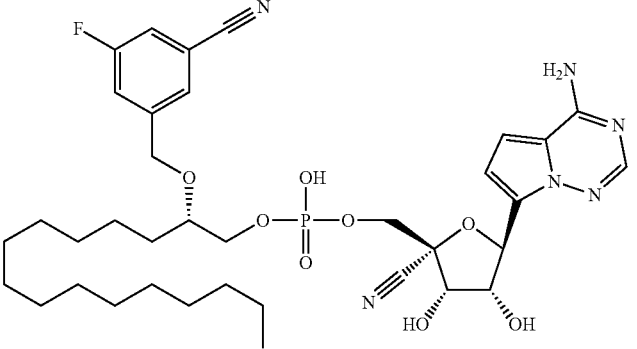 [SMILES: CCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1] |

TABLE 1A-continued

Some compounds of Formula I (Compound # and structure)

| # | Structure |
|---|---|
| 87 | 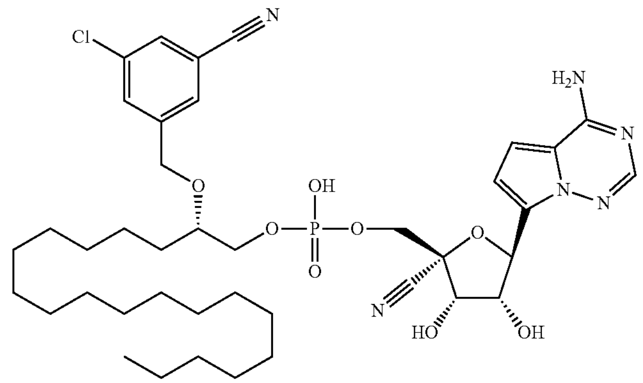 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(Cl)cc(C#N)c1] |
| 88 | 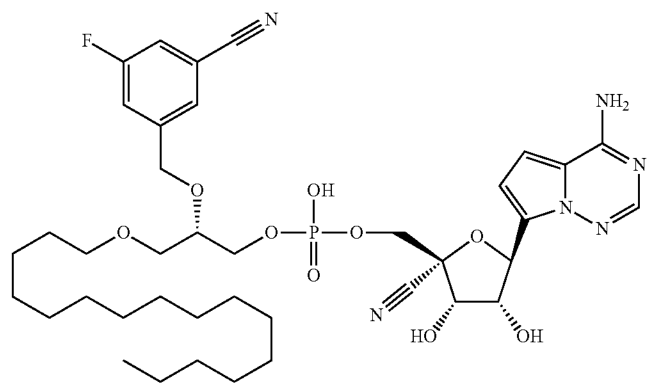 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1] |
| 92 | 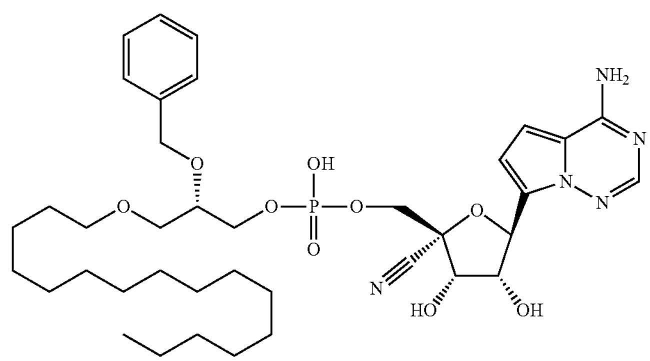 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccccc1] |
| 93 | 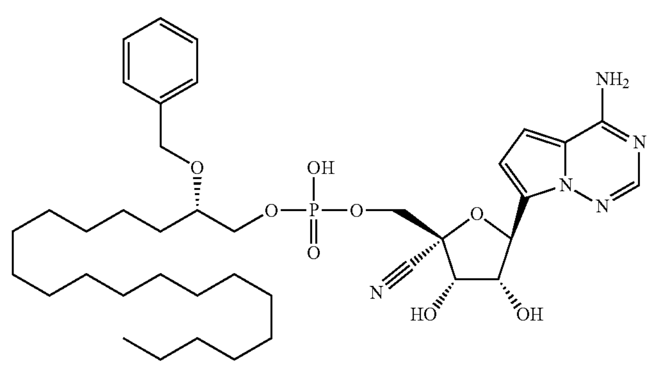 |

TABLE 1A-continued
Some compounds of Formula I (Compound # and structure)
| # | Structure |
|---|---|
| 94 | 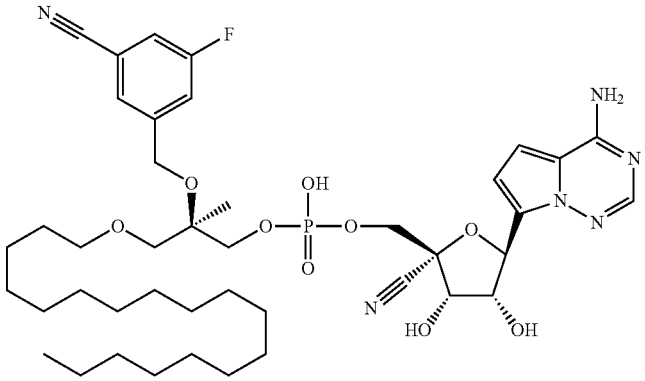 [SMILES: CCCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1] |
| 96 | 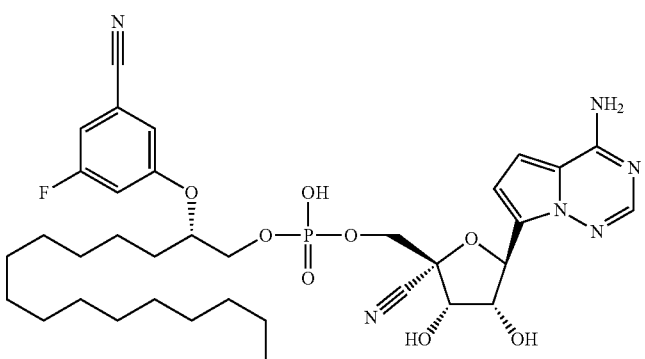 |
| 97 | 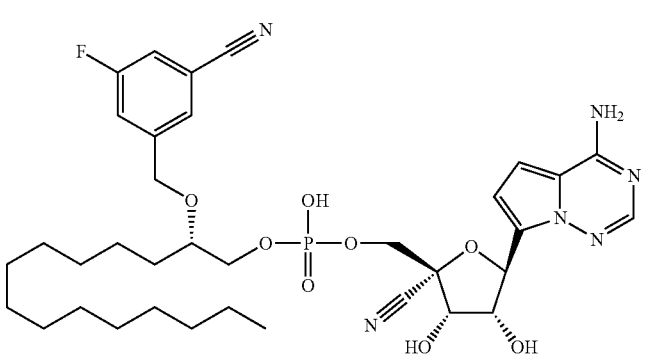 [SMILES: CCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1] |
| 98 | 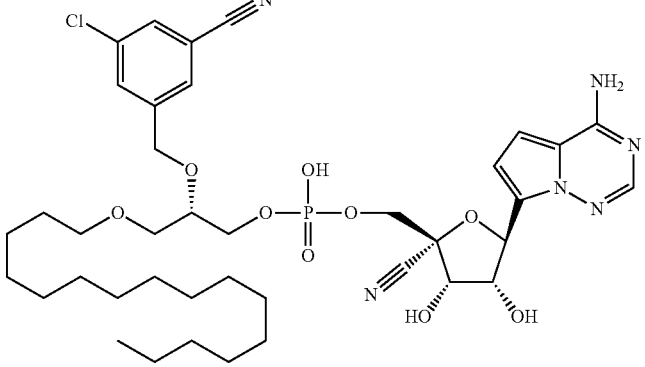 |

TABLE 1A-continued

Some compounds of Formula I (Compound # and structure)

| # | Structure |
|---|---|
| 99 | (structure shown) |

In some embodiments, the compound of Formula I has a Formula Ia:

Formula Ia

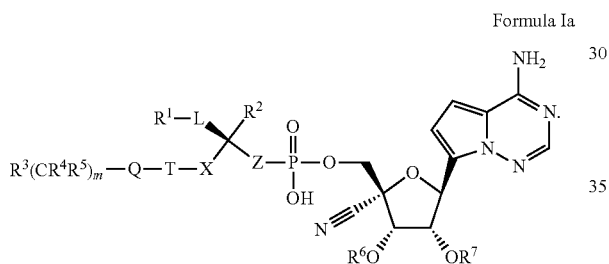

The description of substituents of Formula I (e.g., $R^1$, $R^2$, $R^3$, $R^4$, $R^5$, $R^6$, $R^7$, Q, T, X, Z, L, and m) applies to Formula Ia.

In some embodiments, the compounds and pharmaceutically acceptable salts of Formula Ia include the compounds in Table 2 and the pharmaceutically acceptable salts thereof.

TABLE 2

Some Compounds of Formula Ia
Structure (structure shown)

TABLE 2-continued
Some Compounds of Formula Ia
Structure
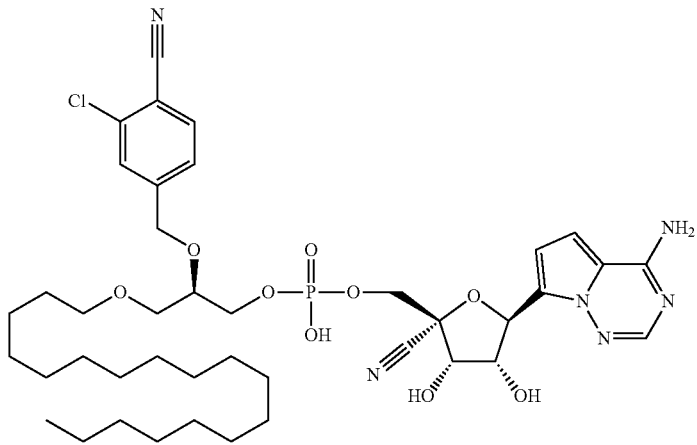 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(Cl)c1]
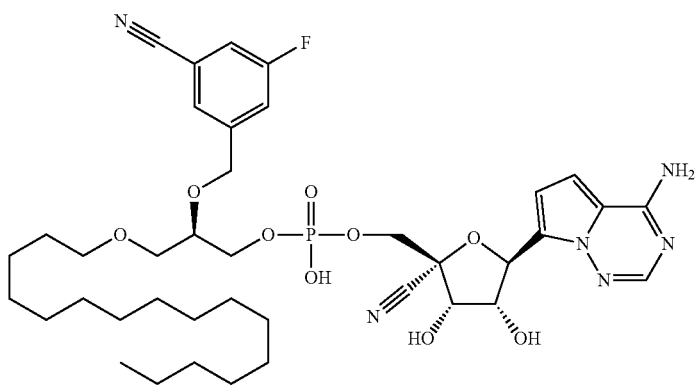 [SMILES: CCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
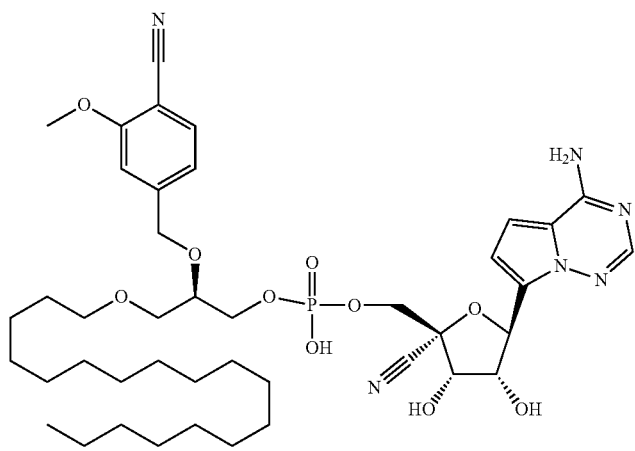 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]

TABLE 2-continued
Some Compounds of Formula Ia
Structure
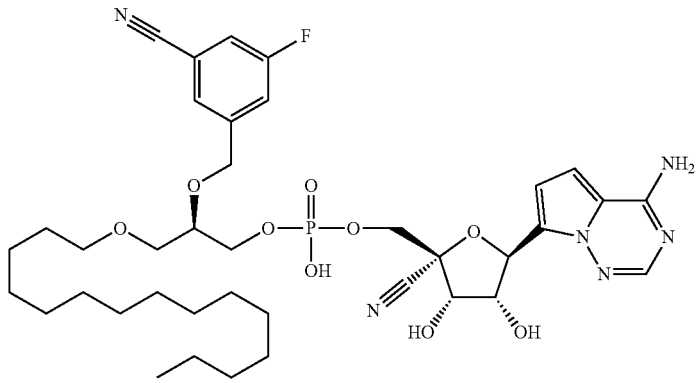
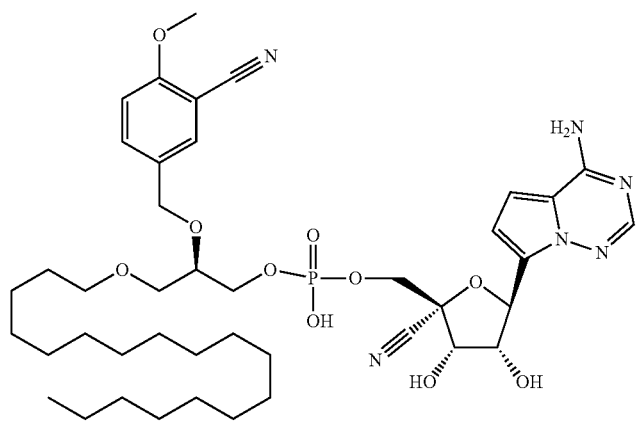 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]
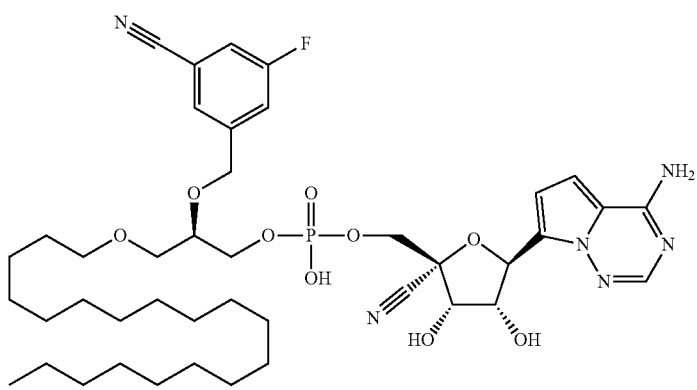 [SMILES: CCCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 2-continued
Some Compounds of Formula Ia
Structure
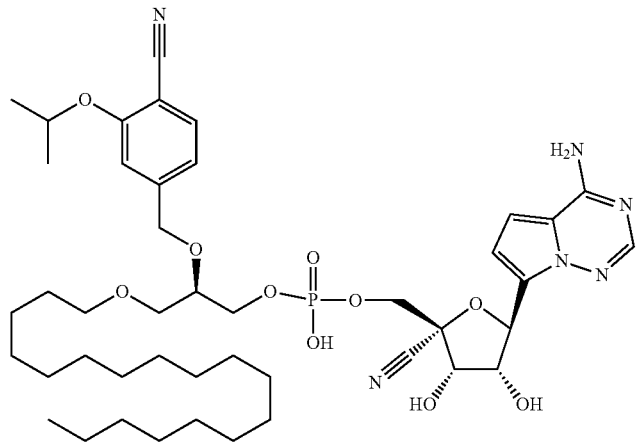 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
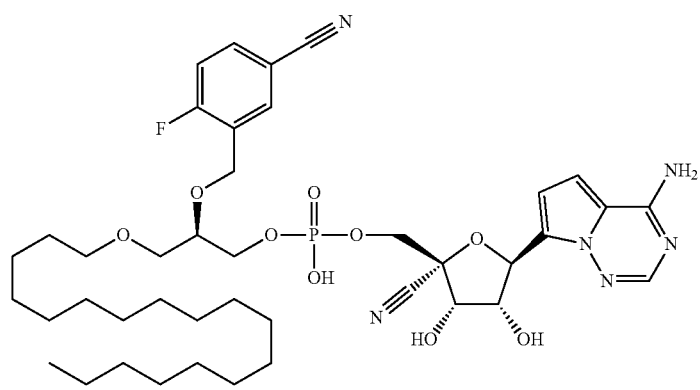
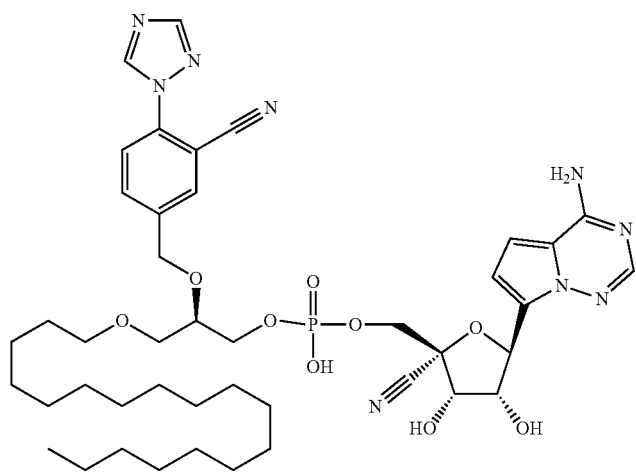 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]

TABLE 2-continued
Some Compounds of Formula Ia
Structure
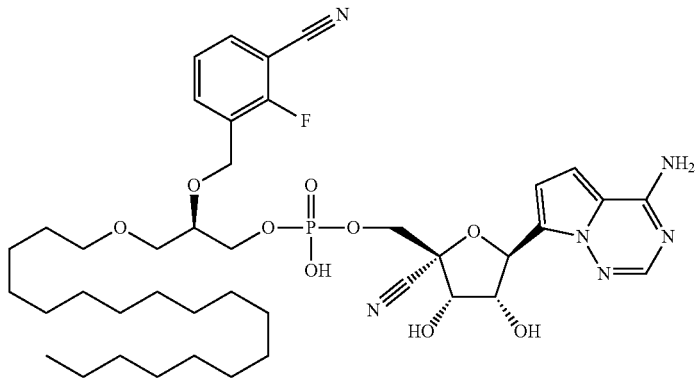 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
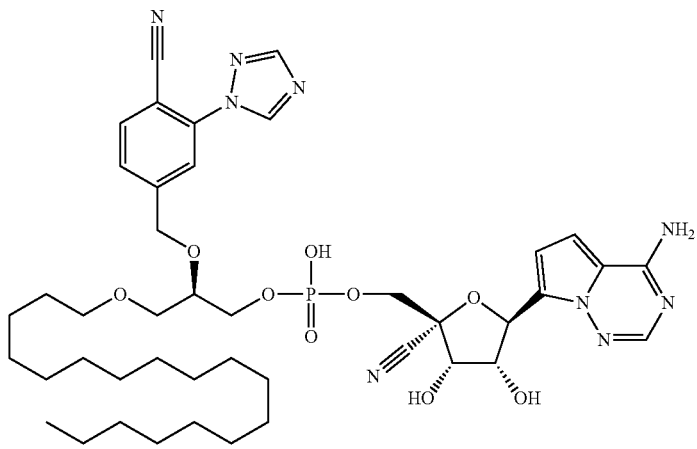 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]
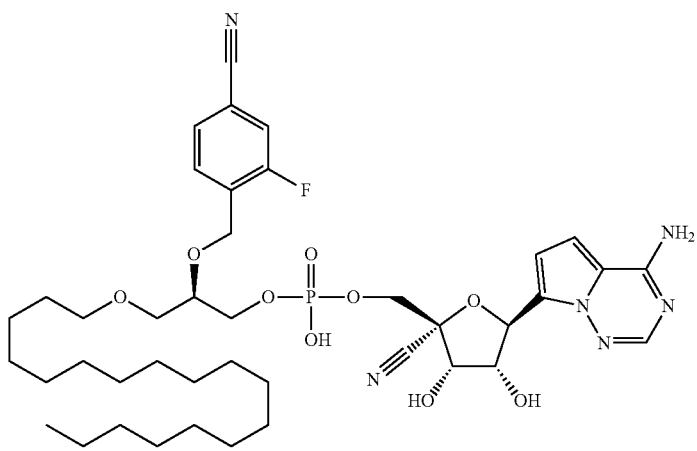 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]

TABLE 2-continued
Some Compounds of Formula Ia
Structure
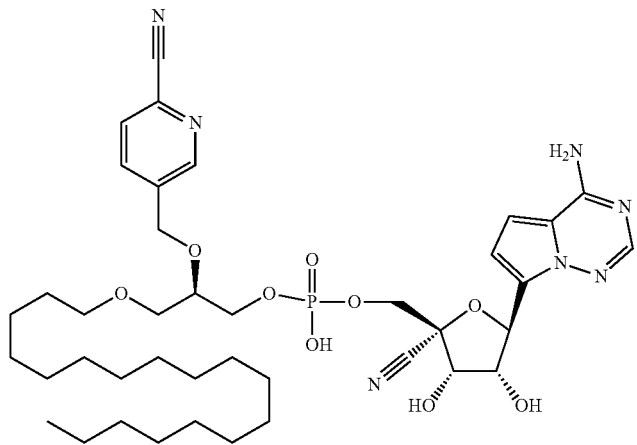
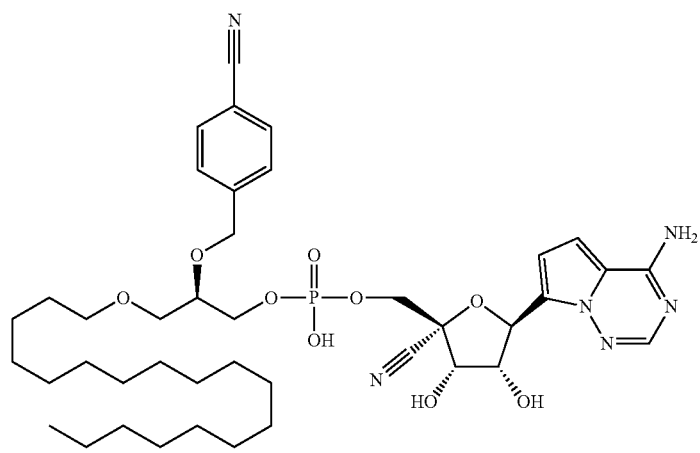 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]
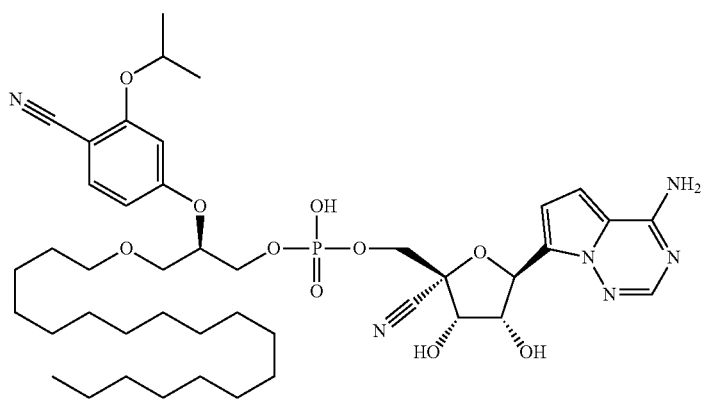 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(OC(C)C)c1]

TABLE 2-continued
Some Compounds of Formula Ia
Structure
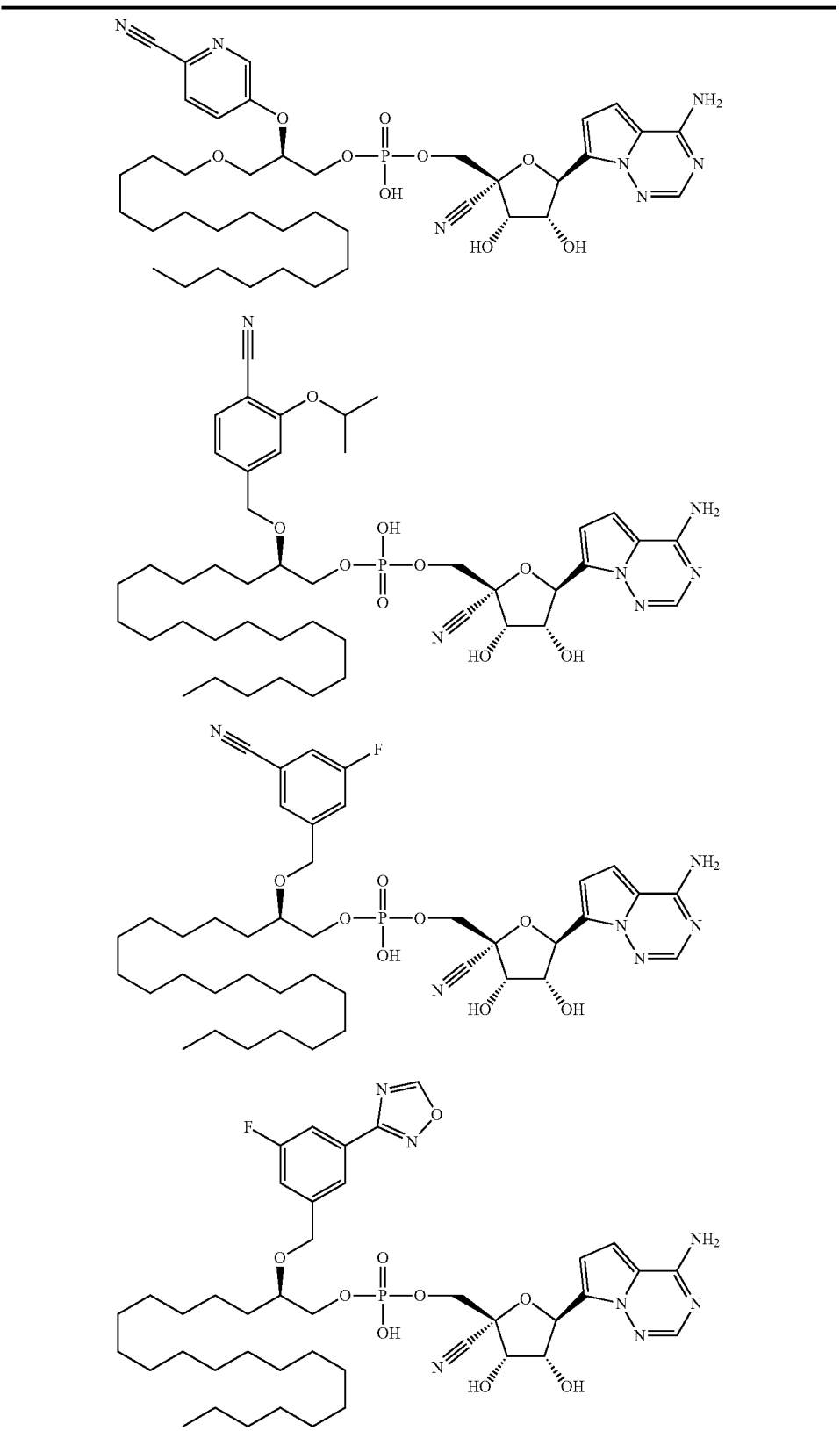

TABLE 2-continued
Some Compounds of Formula Ia
Structure
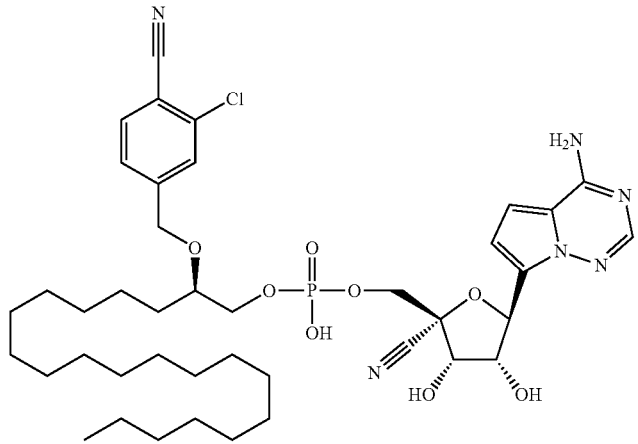 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(Cl)c1]
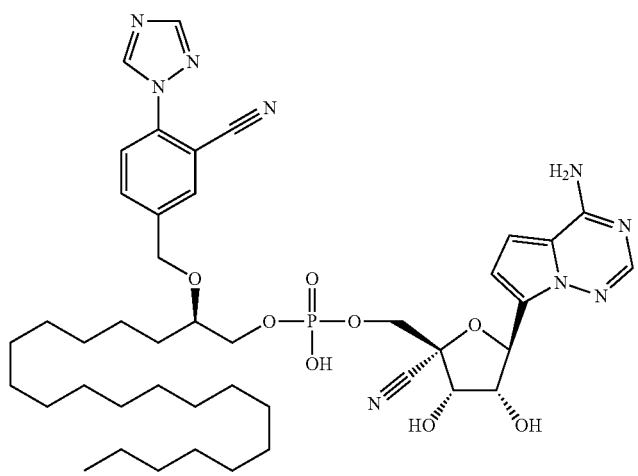 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
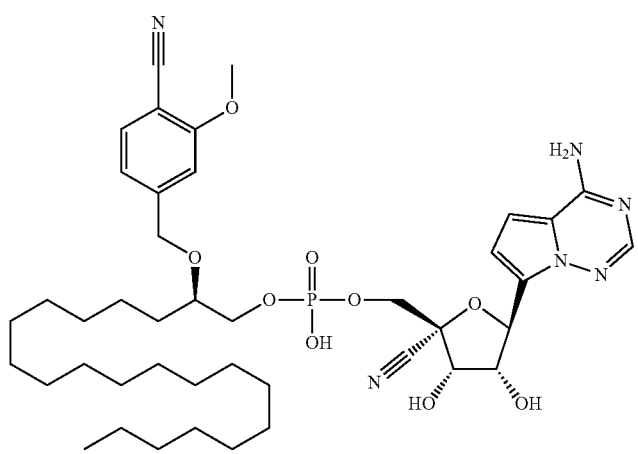 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC)c1]

TABLE 2-continued
Some Compounds of Formula Ia
Structure
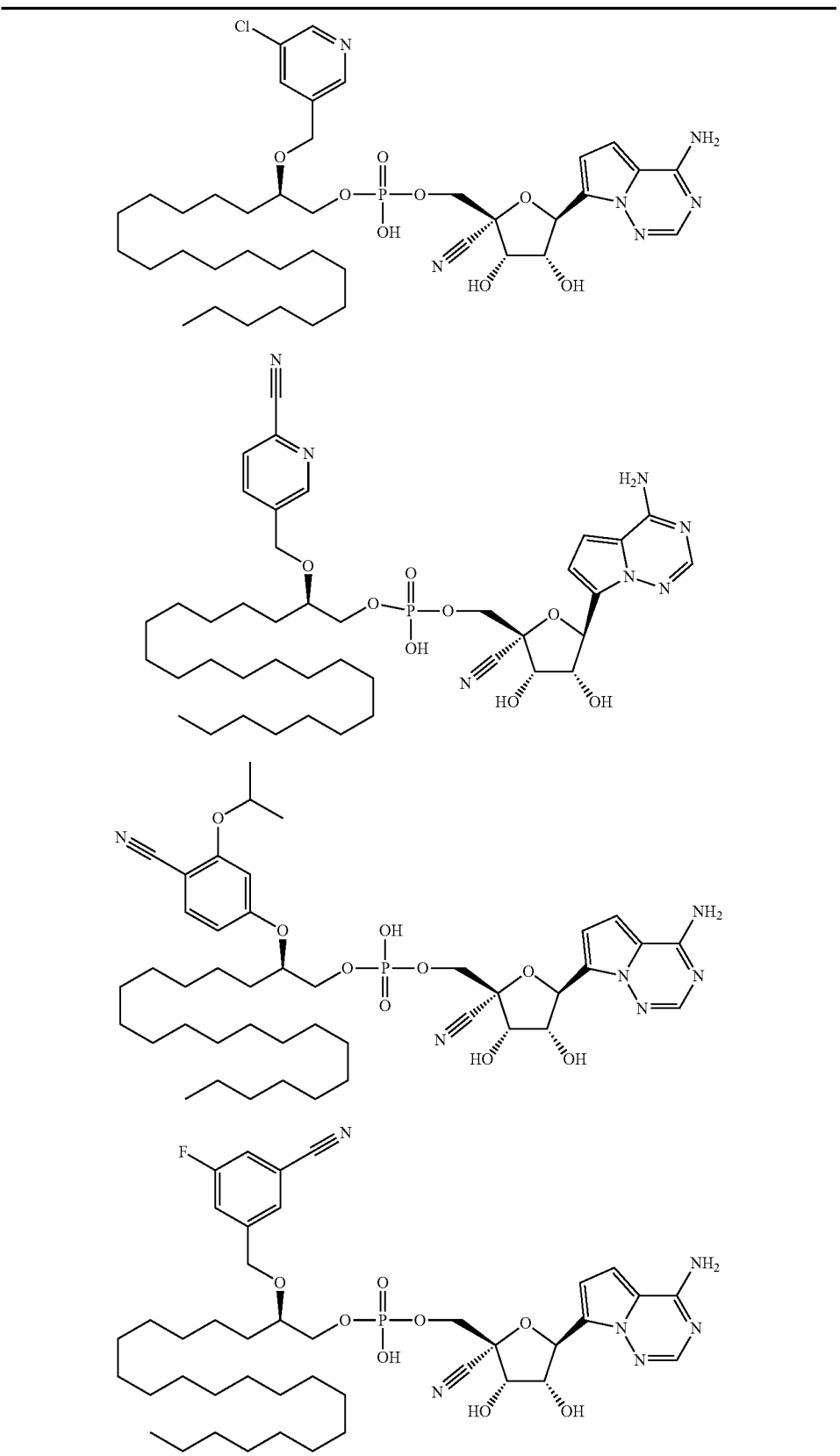

TABLE 2-continued
Some Compounds of Formula Ia
Structure
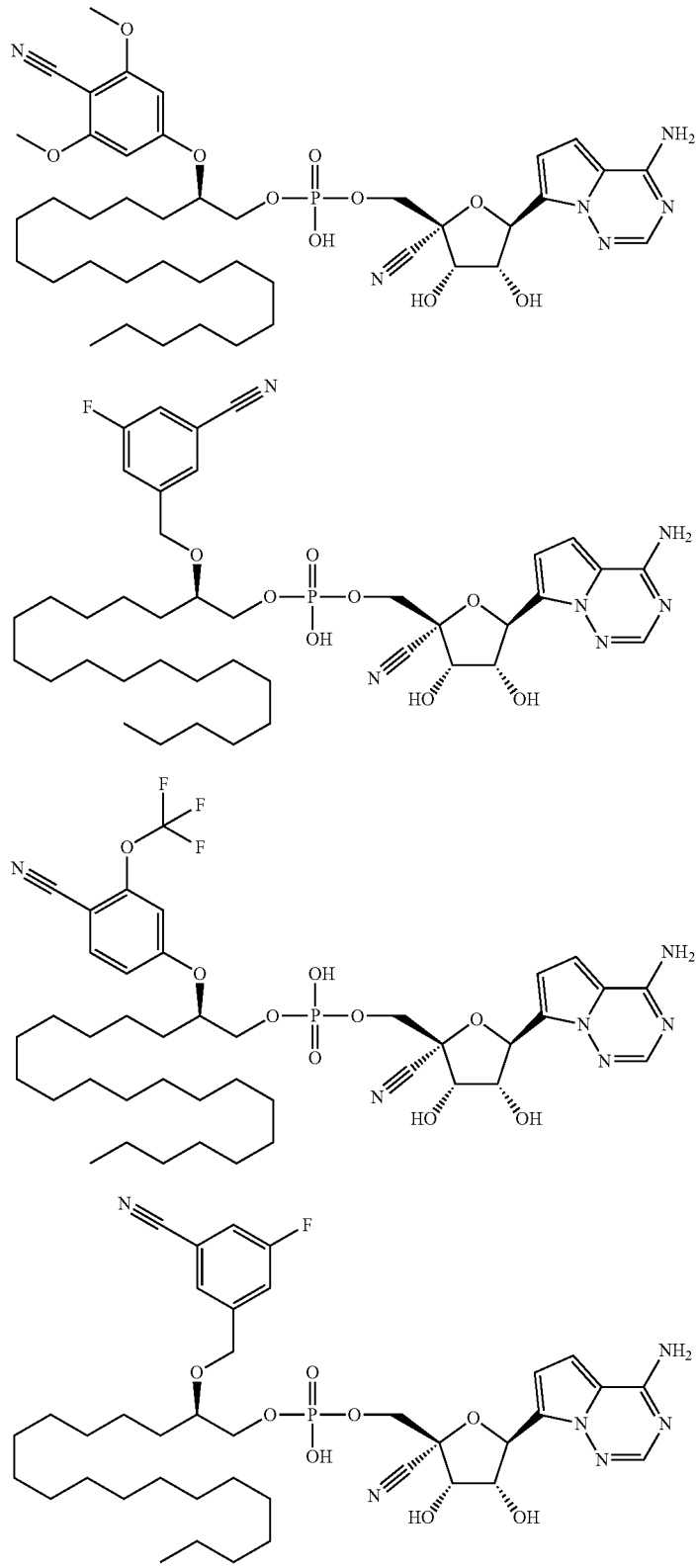

TABLE 2-continued
Some Compounds of Formula Ia
Structure
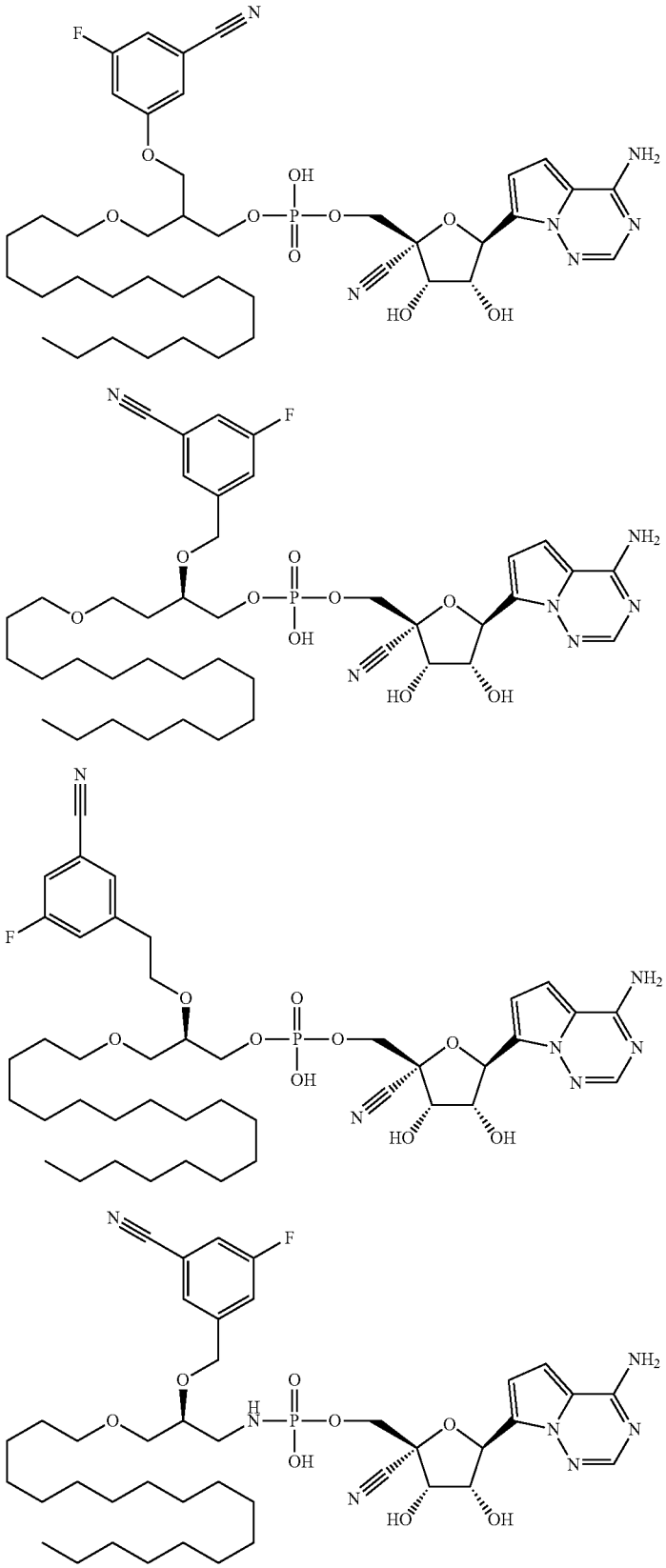

TABLE 2-continued
Some Compounds of Formula Ia
Structure
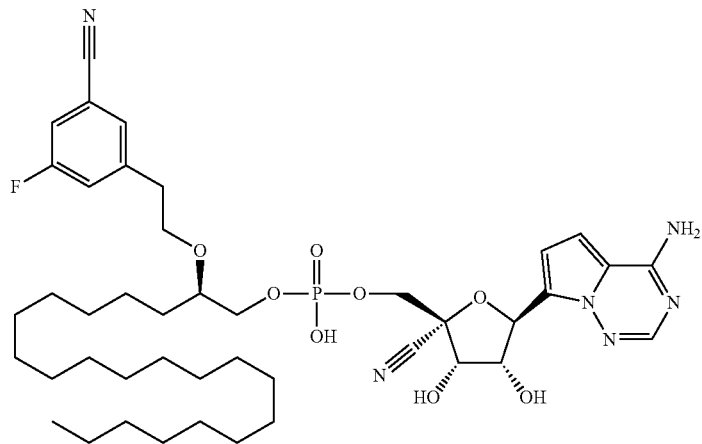
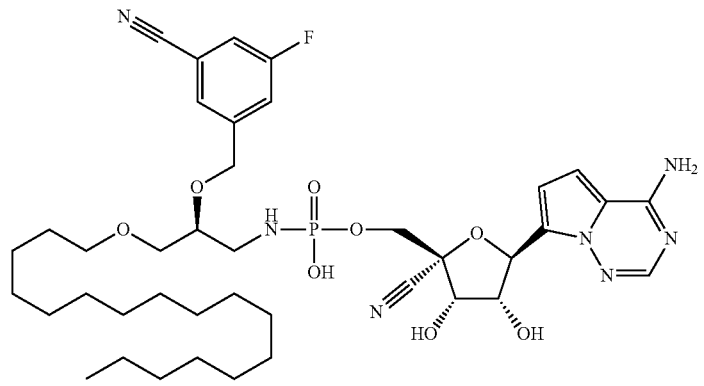
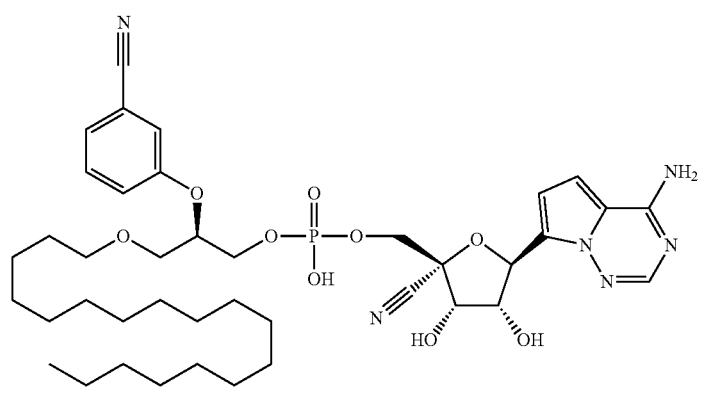

TABLE 2-continued
Some Compounds of Formula Ia
Structure
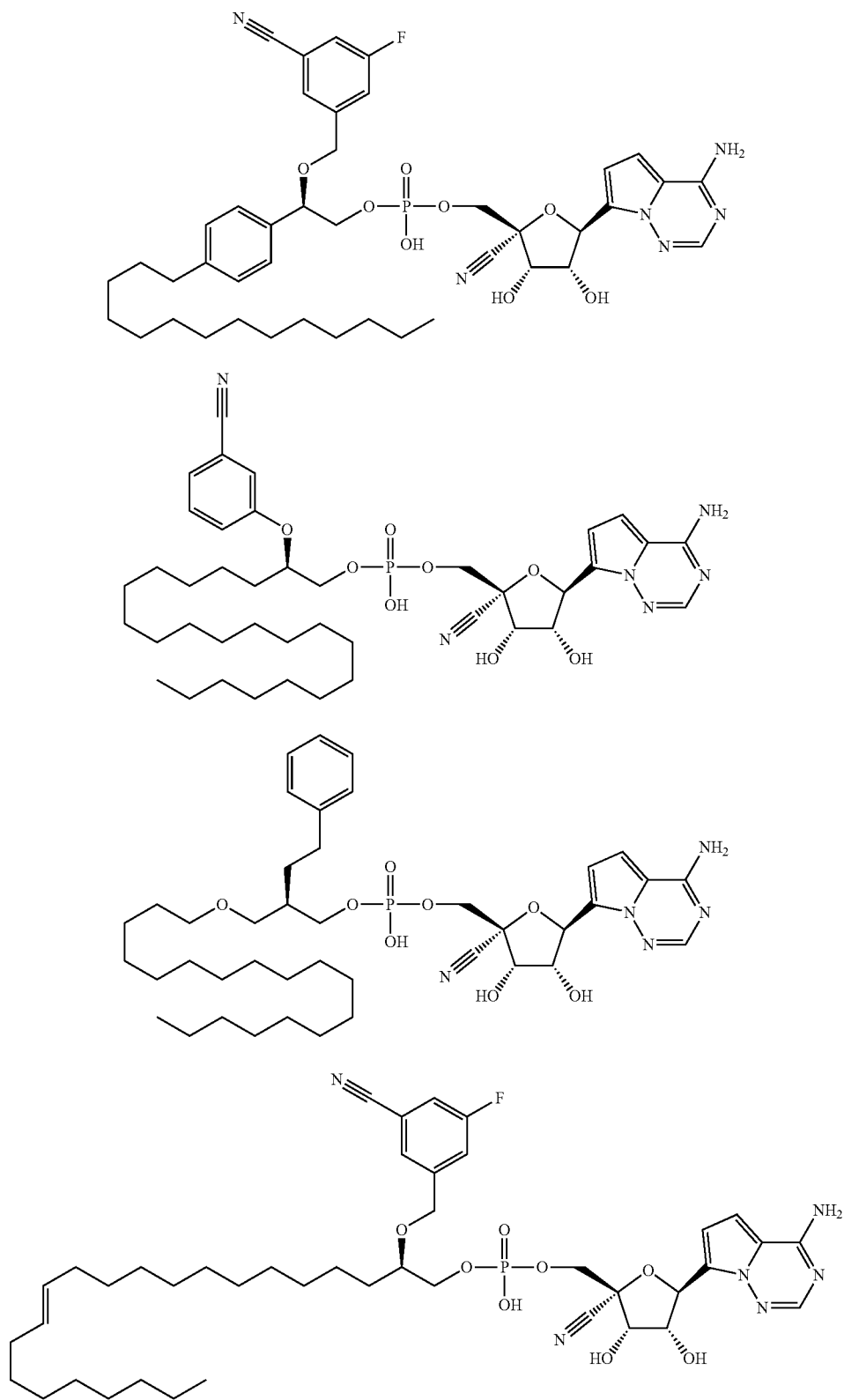

TABLE 2-continued
Some Compounds of Formula Ia
Structure
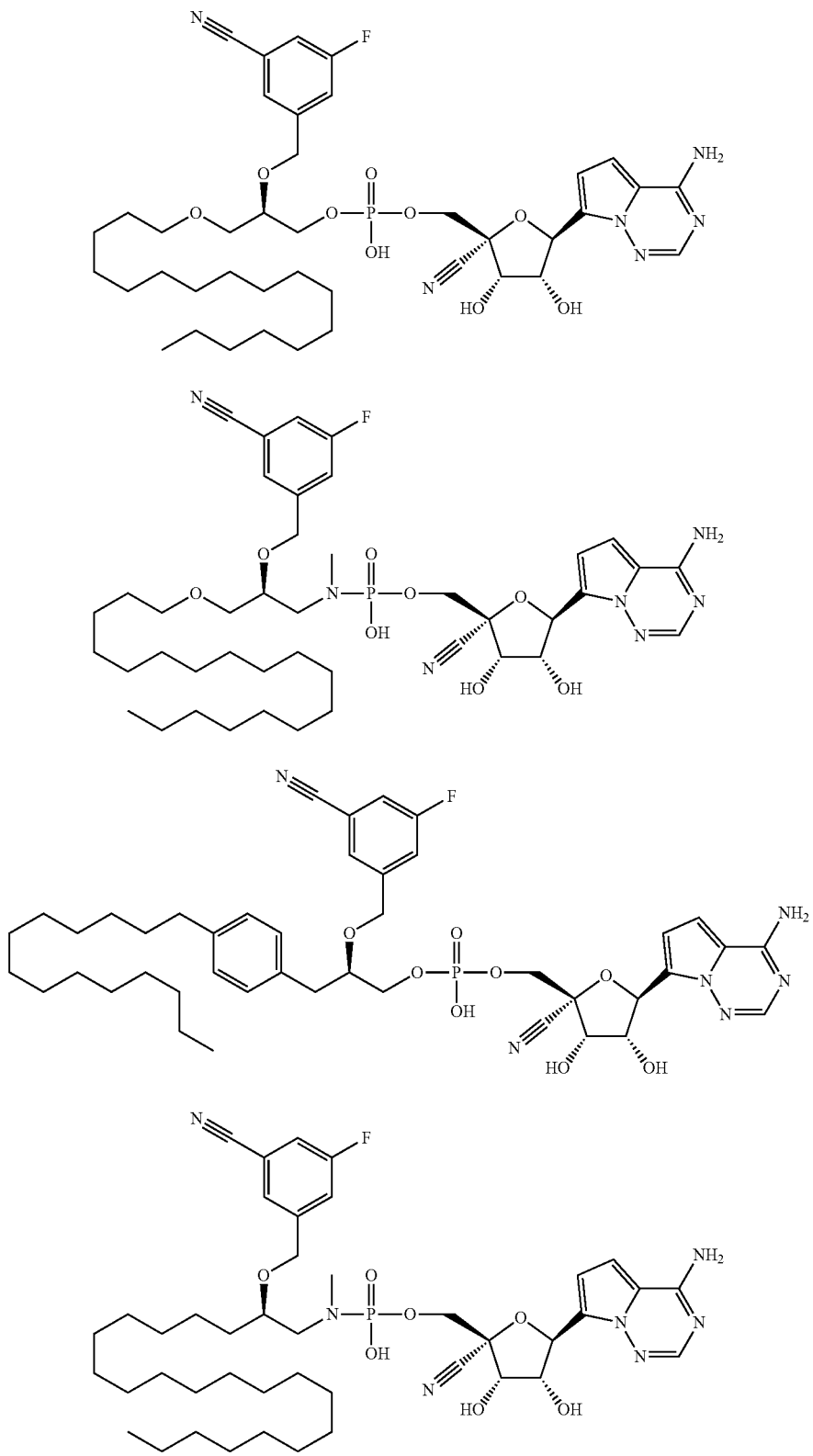

TABLE 2-continued
Some Compounds of Formula Ia
Structure
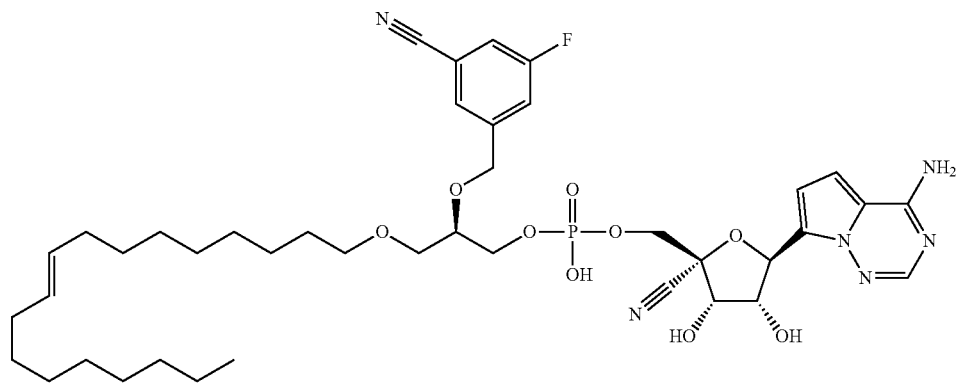
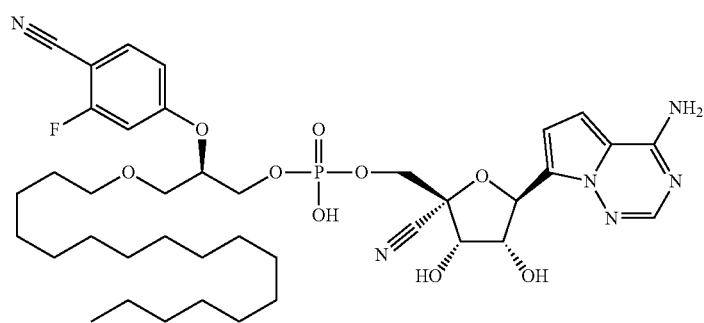
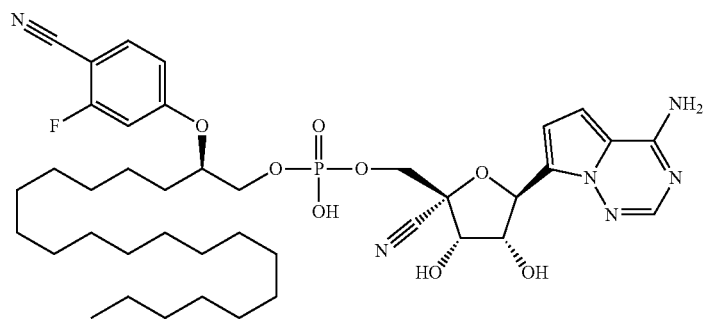 [SMILES: CCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(F)c1]
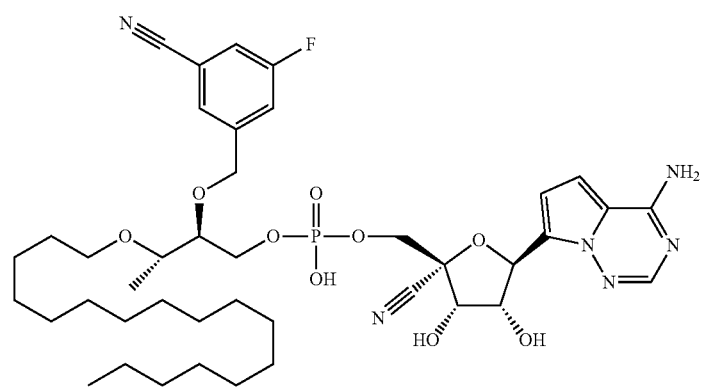 [SMILES: CCCCCCCCCCCCCCCCCO[C@@H](C)[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 2-continued
Some Compounds of Formula Ia
Structure
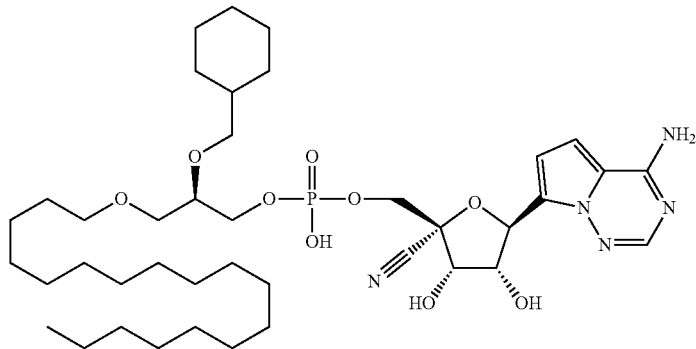
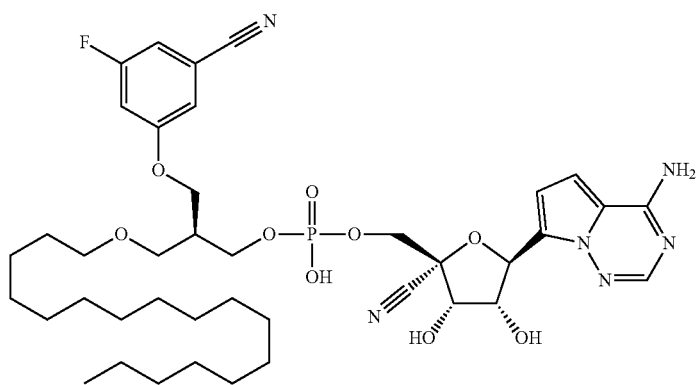 [SMILES: CCCCCCCCCCCCCCCCCOC[C@@H](COc1cc(F)cc(C#N)c1)COP(=O)(O)OC[C@@]1(C#N)O[C@@H](c2ccc3c(N)ncnn23)[C@H](O)[C@@H]1O]
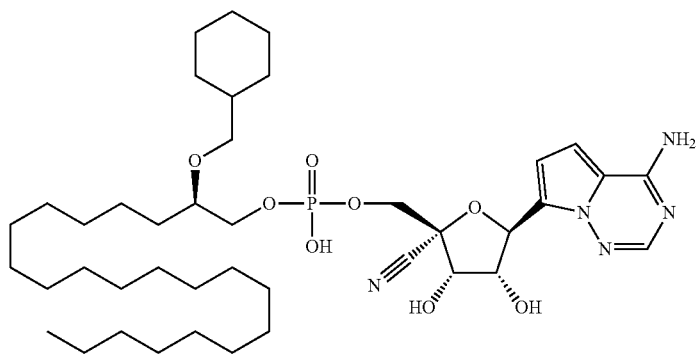 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCC1CCCCC1]
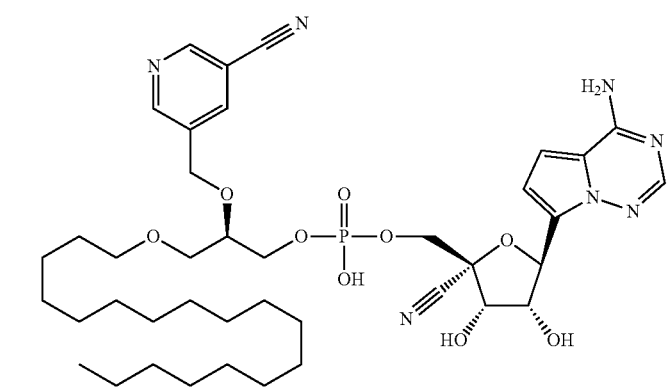 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cncc(C#N)c1]

TABLE 2-continued
Some Compounds of Formula Ia
Structure
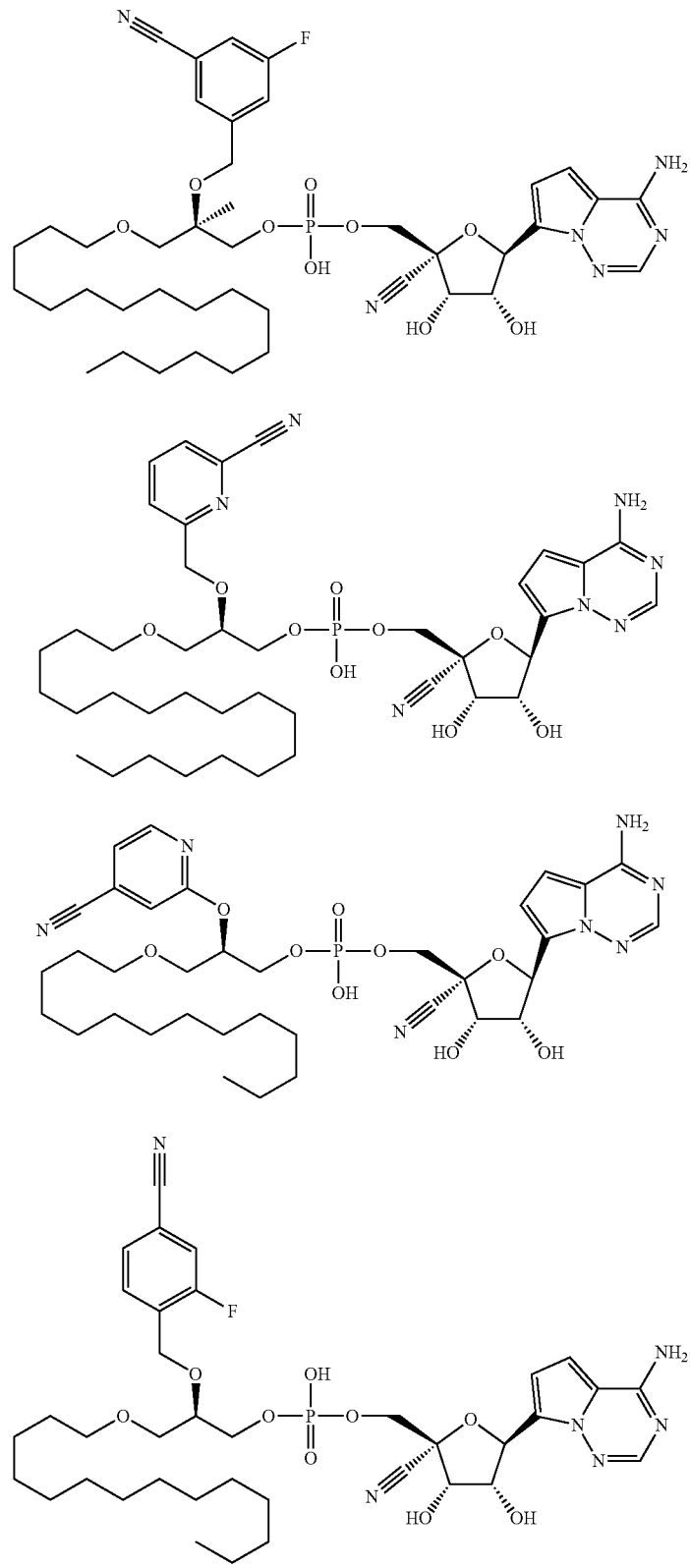

TABLE 2-continued
Some Compounds of Formula Ia
Structure
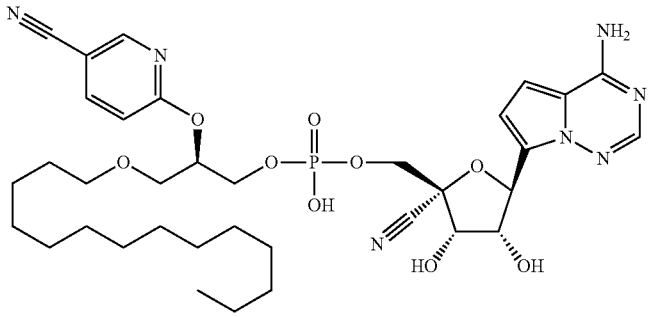 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)cn1]
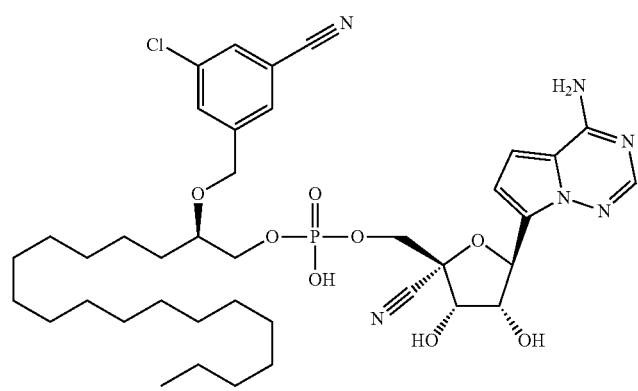 [SMILES: CCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
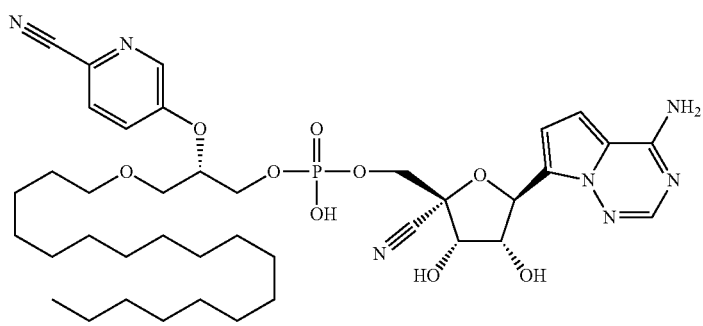 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)Oc1ccc(C#N)nc1]
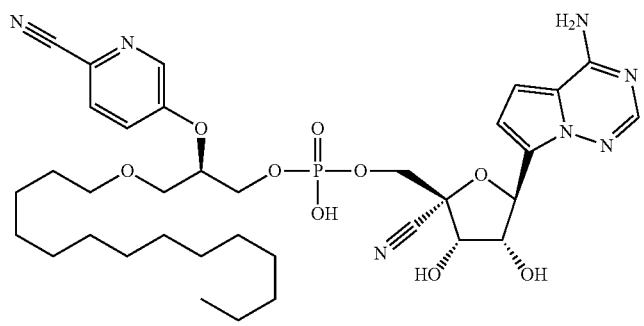 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)nc1]

TABLE 2-continued
Some Compounds of Formula Ia
Structure
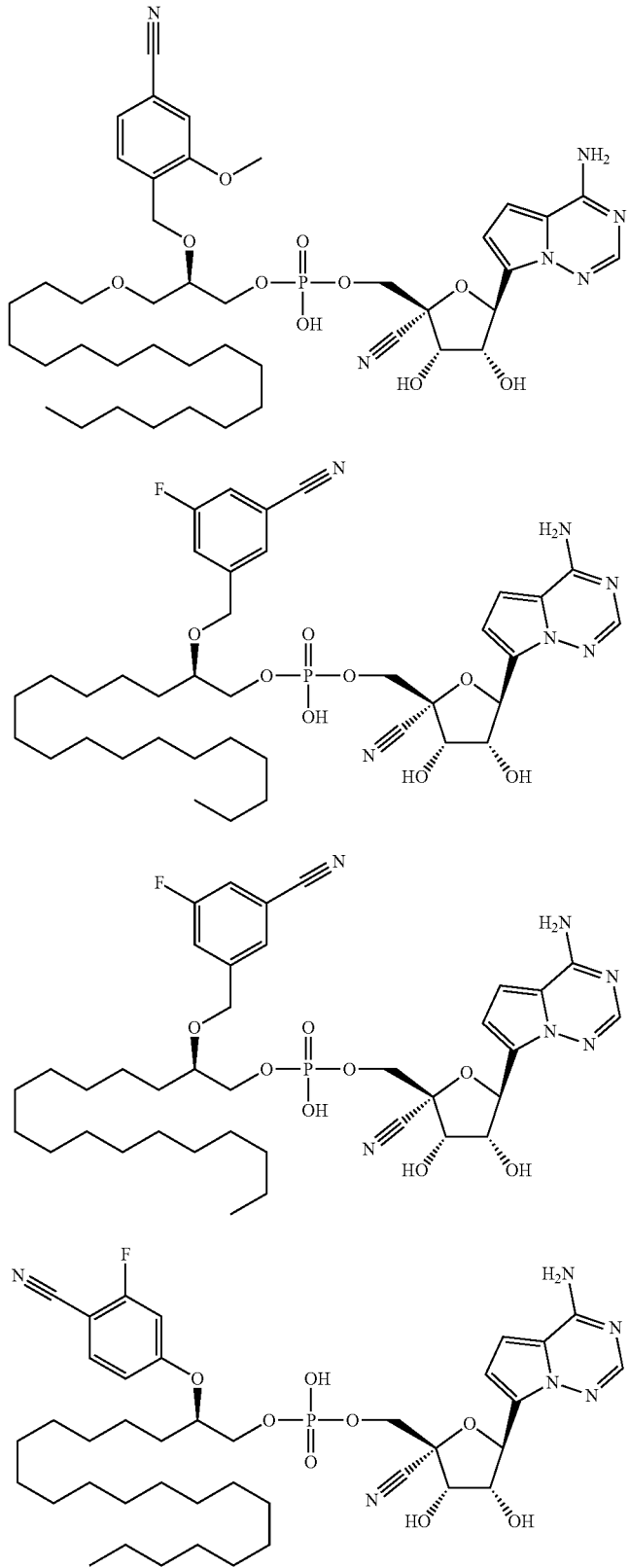

TABLE 2-continued
Some Compounds of Formula Ia
Structure
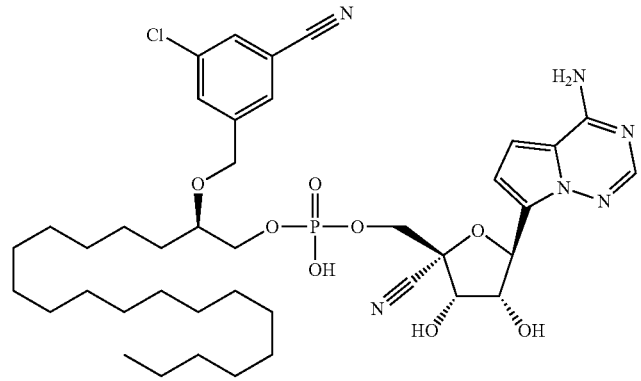 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
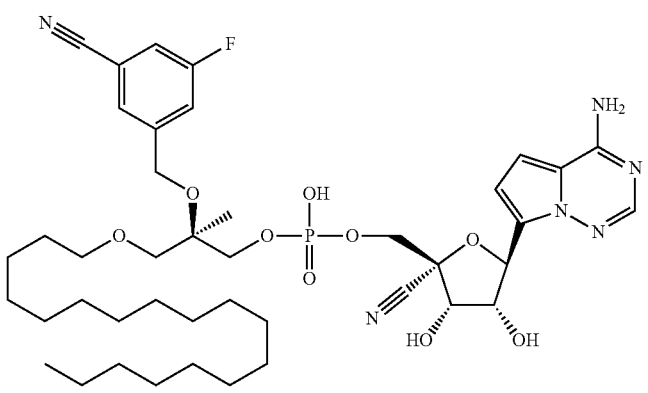 [SMILES: CCCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]
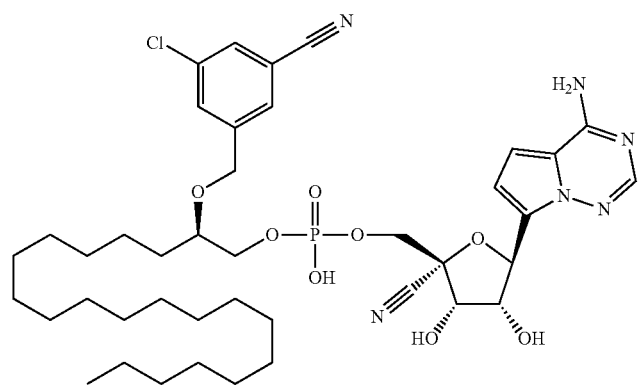 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
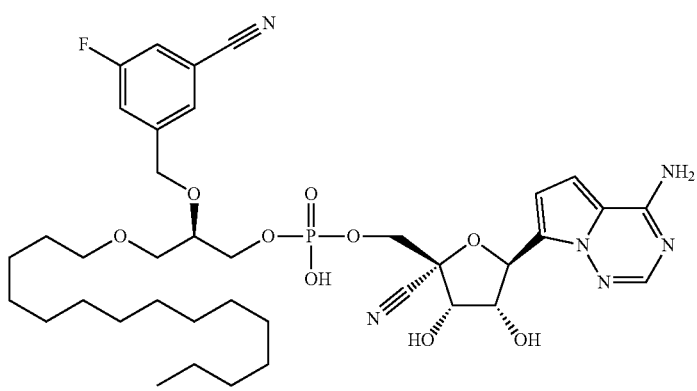

TABLE 2-continued

Some Compounds of Formula Ia
Structure

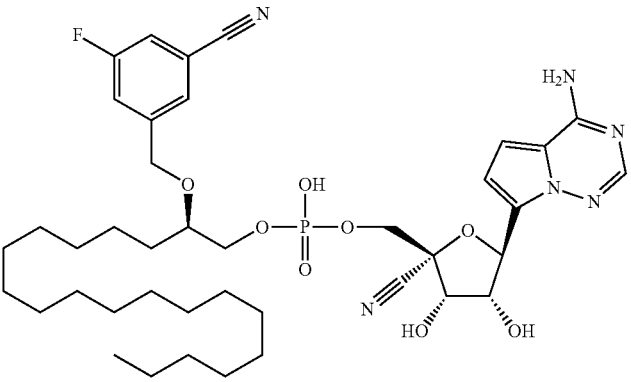 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]

In some embodiments, the compound of Formula I has a Formula Ib:

Formula Ib

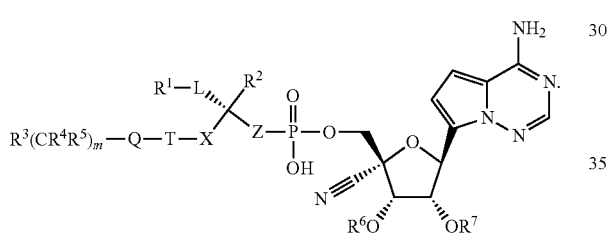

The description of substituents of Formula I (e.g., $R^1$, $R^2$, $R^3$, $R^4$, $R^5$, $R^6$, $R^7$, Q, T, X, Z, L, and m) applies to Formula Ib. In some embodiments, the compounds and pharmaceutically acceptable salts of Formula Ib include the compounds in Table 3 and the pharmaceutically acceptable salts thereof.

TABLE 3

Some Compounds of Formula Ib
Structure

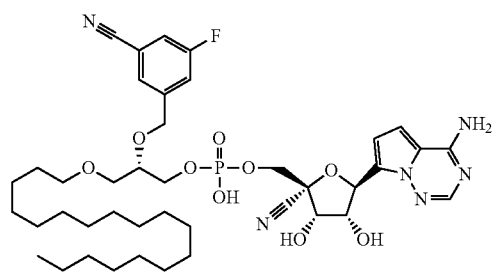 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 3-continued

Some Compounds of Formula Ib
Structure

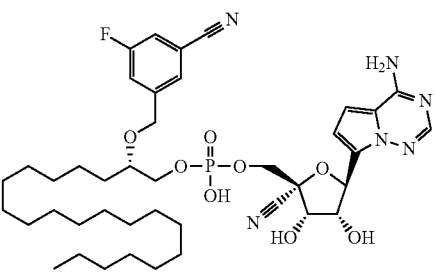 [SMILES: CCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

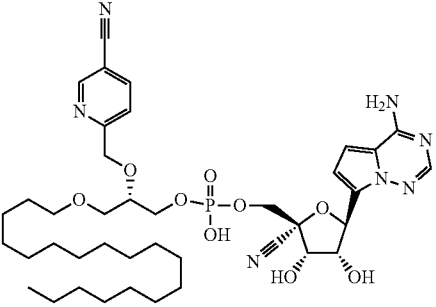 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1]

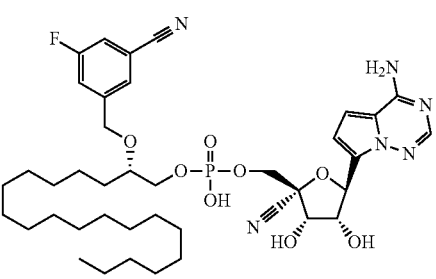 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 3-continued
Some Compounds of Formula Ib
Structure
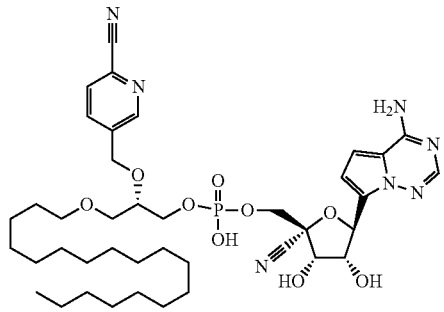
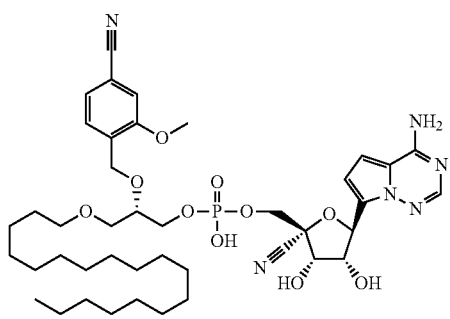 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cc1OC]
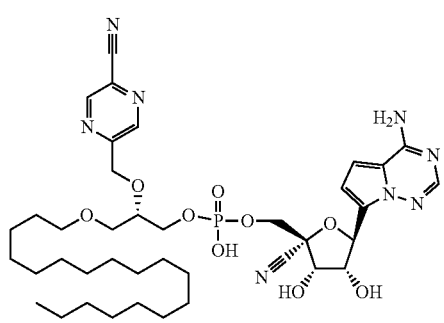
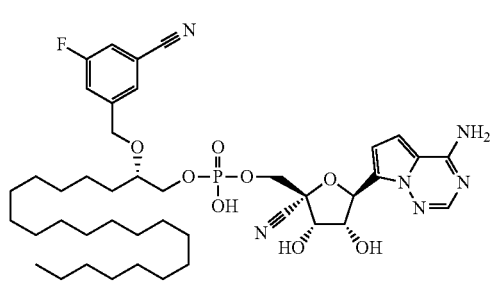 [SMILES: CCCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
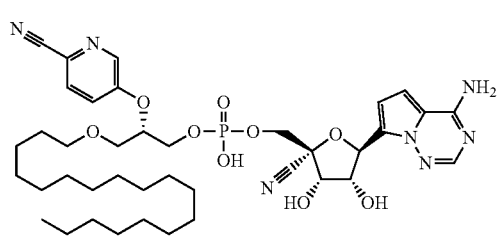 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)Oc1ccc(C#N)nc1]
TABLE 3-continued
Some Compounds of Formula Ib
Structure
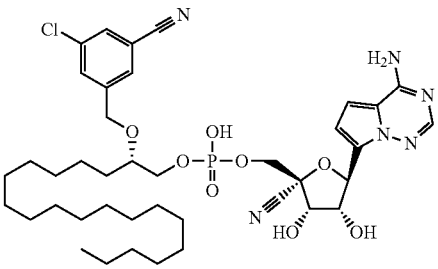 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(Cl)cc(C#N)c1]
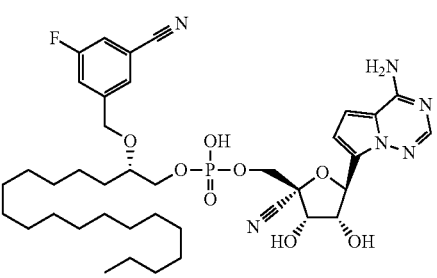 [SMILES: CCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
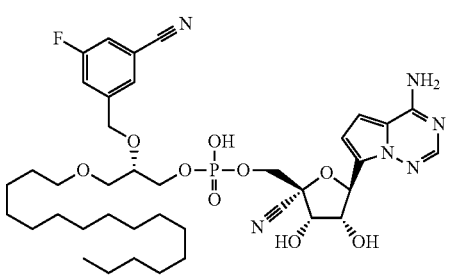 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]
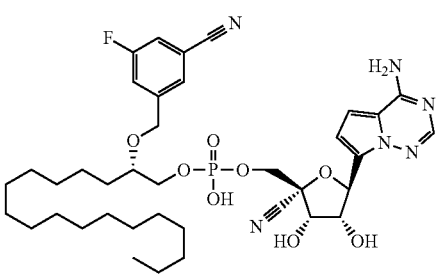 [SMILES: CCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
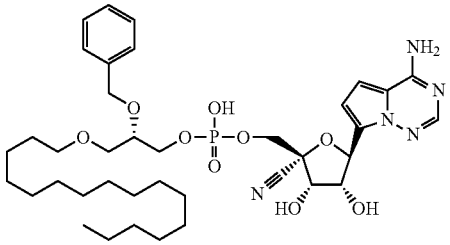 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccccc1]

TABLE 3-continued

Some Compounds of Formula Ib
Structure

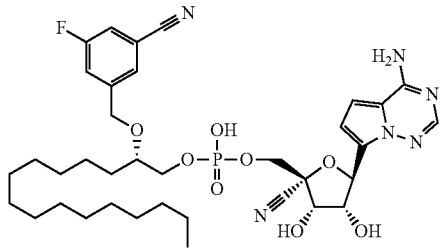 [SMILES: CCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

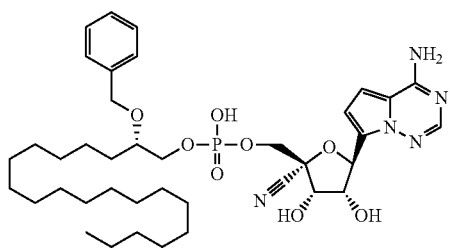

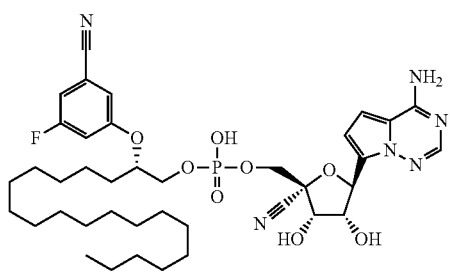 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)Oc1cc(F)cc(C#N)c1]

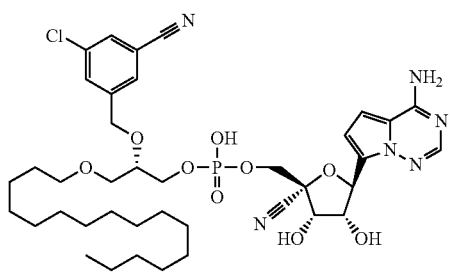 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(Cl)cc(C#N)c1]

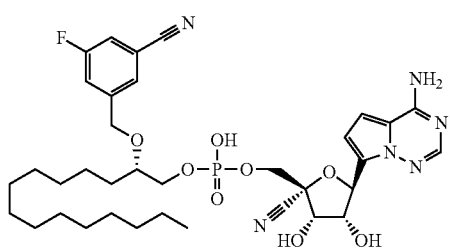 [SMILES: CCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

In some embodiments, the compound of Formula I has a Formula II:

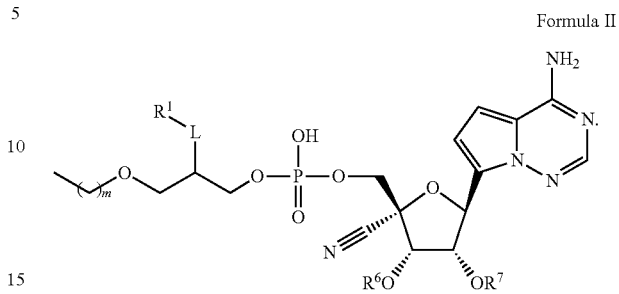

Formula II

The description of substituents of Formula I (e.g., $R^1$, $R^6$, $R^7$, L, and m) applies to Formula II. In some embodiments, the compounds and pharmaceutically acceptable salts of Formula II include the compounds in Table 4 and the pharmaceutically acceptable salts thereof.

TABLE 4

Some Compounds of Formula II
Structure

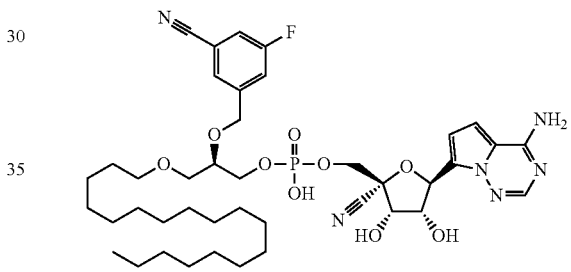

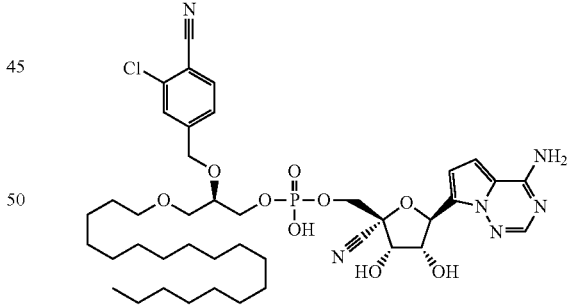

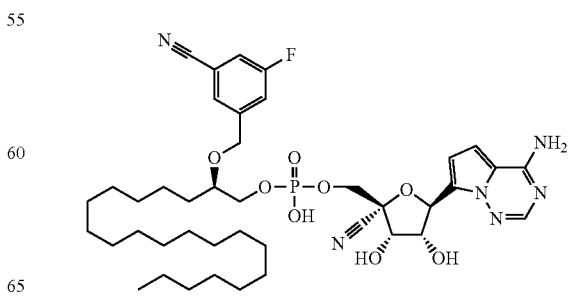

127
TABLE 4-continued
Some Compounds of Formula II
Structure
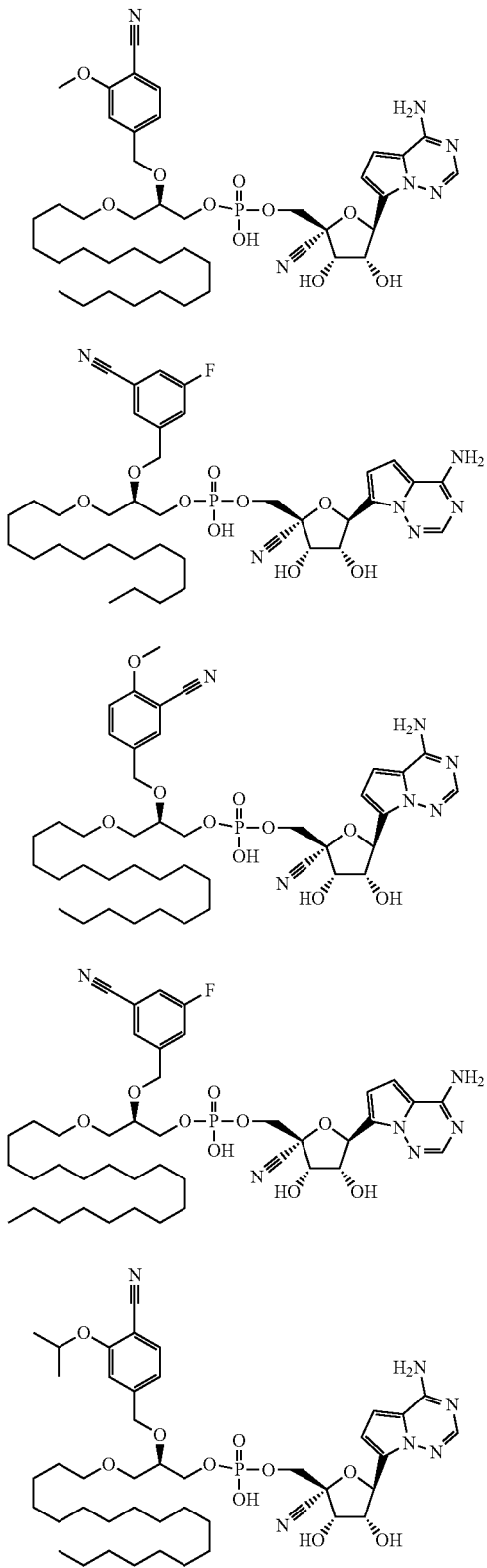
128
TABLE 4-continued
Some Compounds of Formula II
Structure
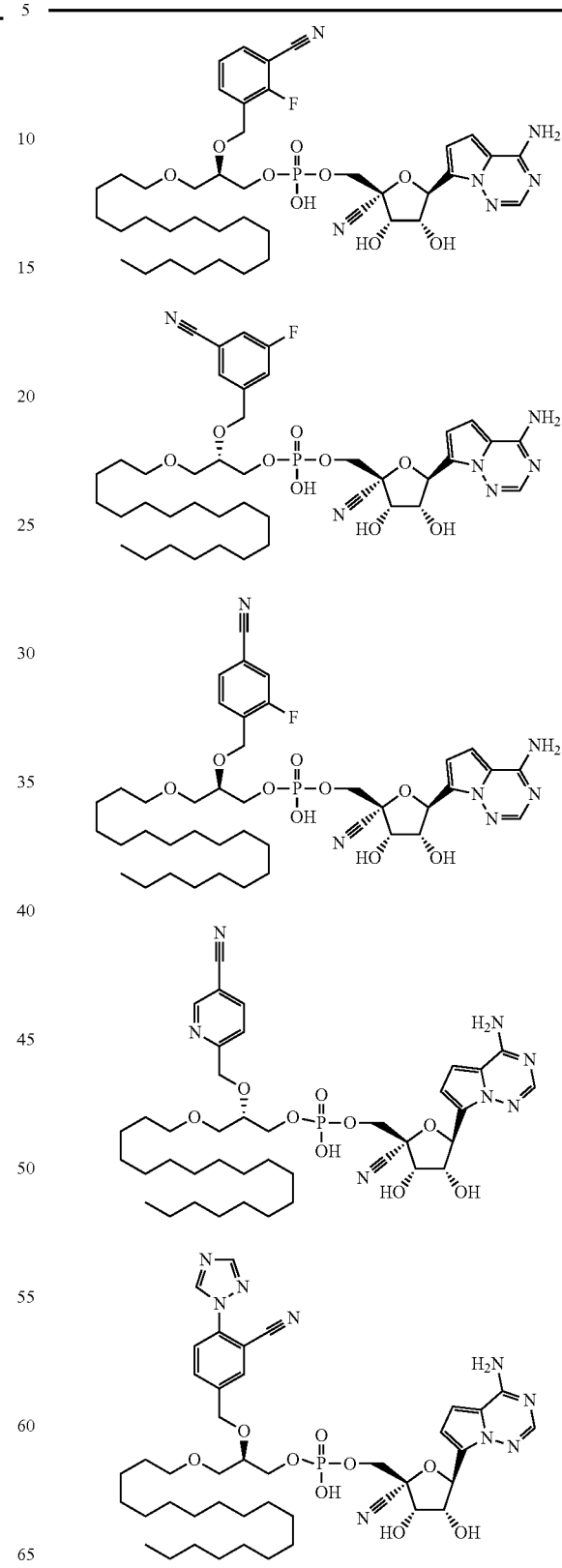

TABLE 4-continued
Some Compounds of Formula II
Structure
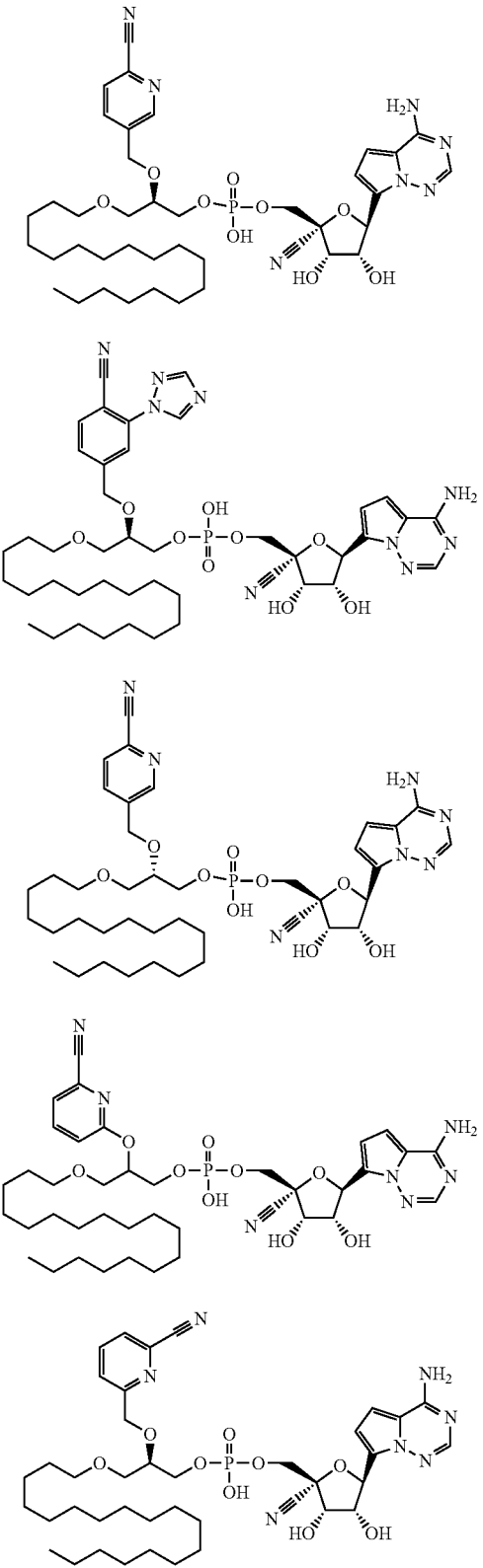

TABLE 4-continued

Some Compounds of Formula II
Structure

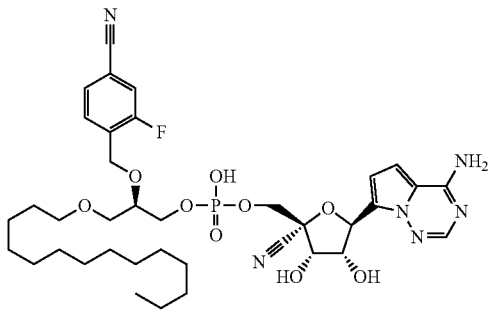 [SMILES: CCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]

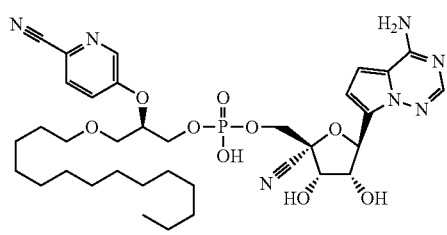 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)nc1]

In some embodiments, the compound of Formula I has a Formula IIa:

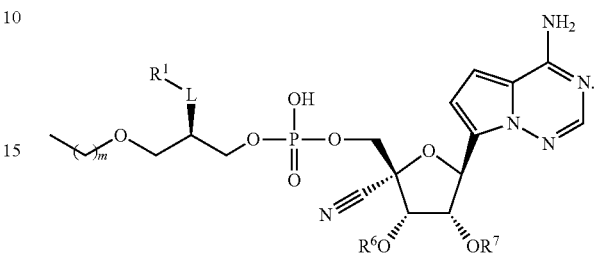

Formula IIa

The description of substituents of Formula I (e.g., $R^1$, $R^6$, $R^7$, L, and m) applies to Formula IIa.

In some embodiments, the compounds and pharmaceutically acceptable salts of Formula IIa include the compounds in Table 5 and the pharmaceutically acceptable salts thereof.

TABLE 5

Some Compounds of Formula IIa
Structure

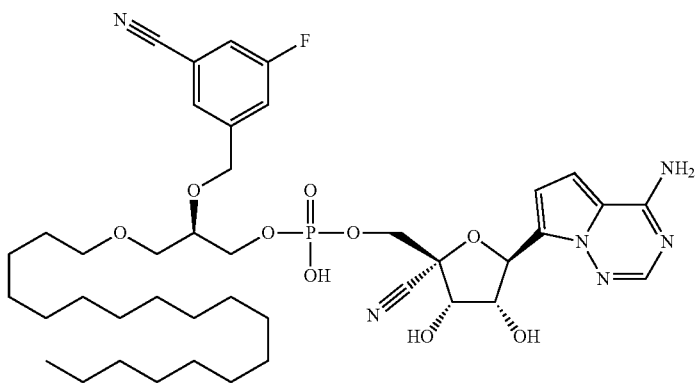 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

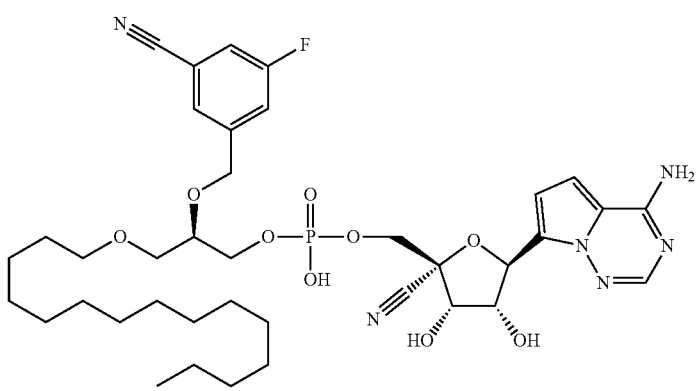

TABLE 5-continued
Some Compounds of Formula IIa
Structure
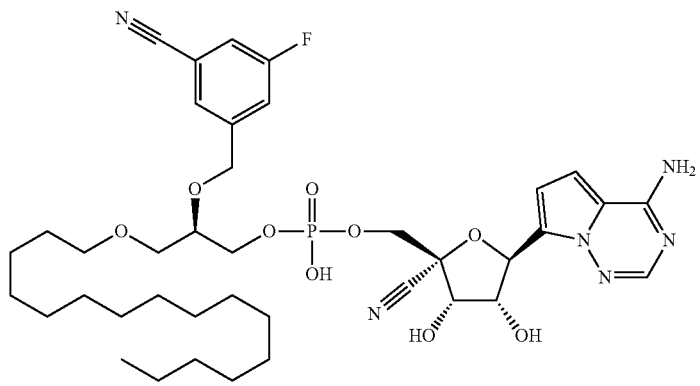 [SMILES: CCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
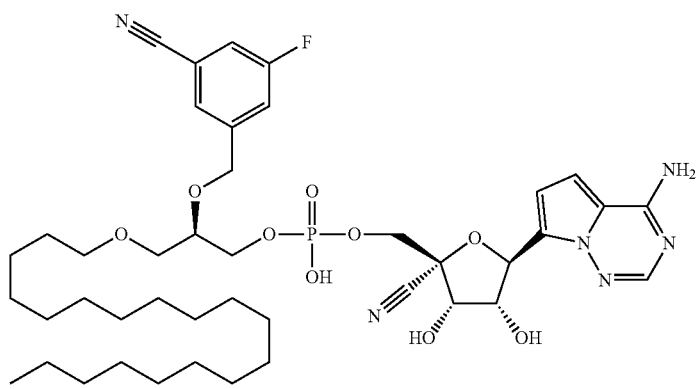 [SMILES: CCCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
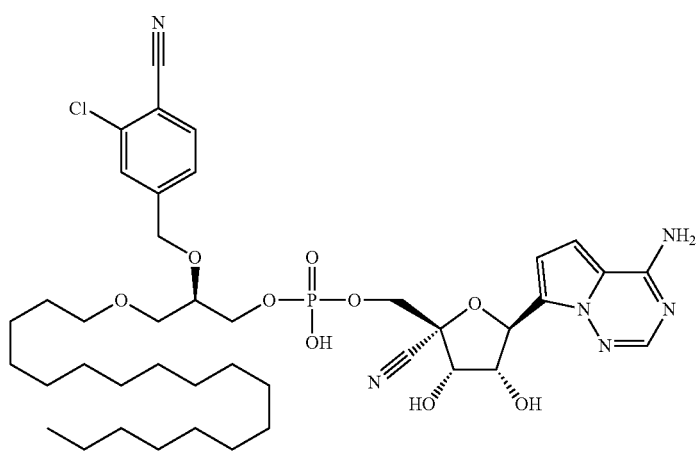 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(Cl)c1]

TABLE 5-continued
Some Compounds of Formula IIa
Structure
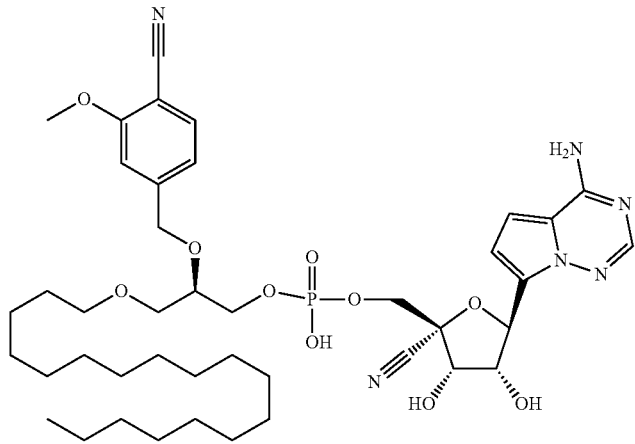 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]
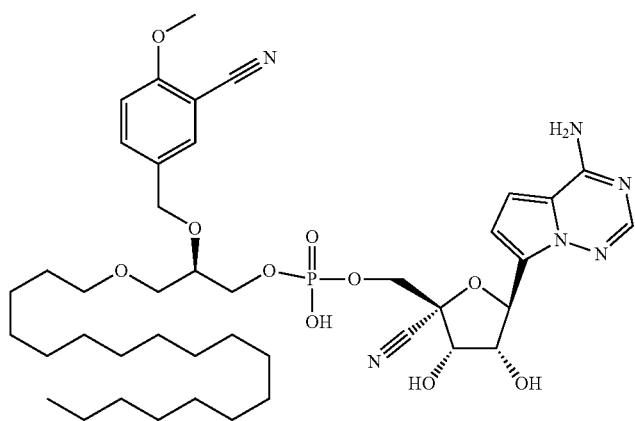 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]
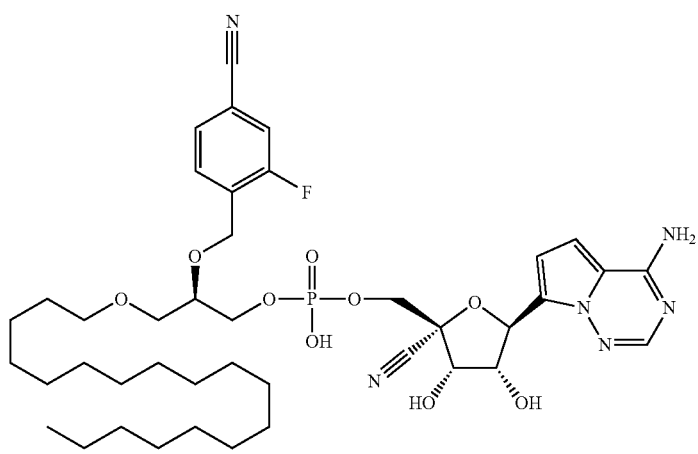

TABLE 5-continued
Some Compounds of Formula IIa
Structure
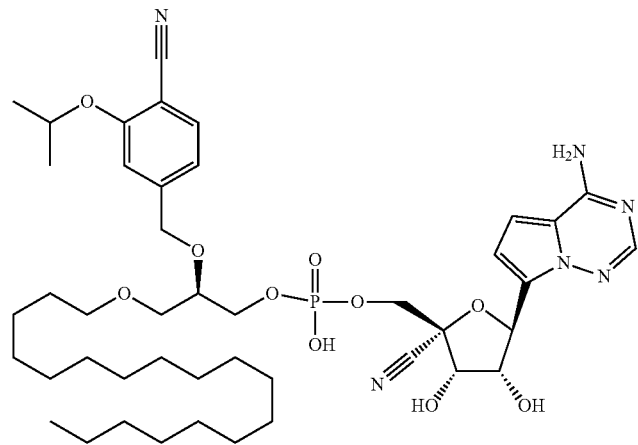 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
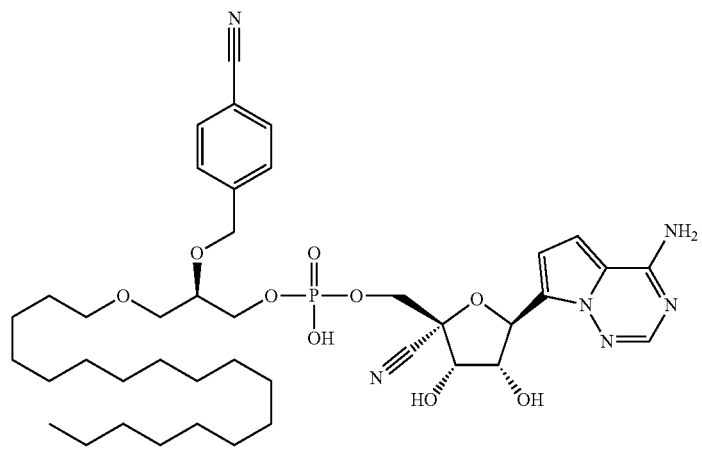 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]
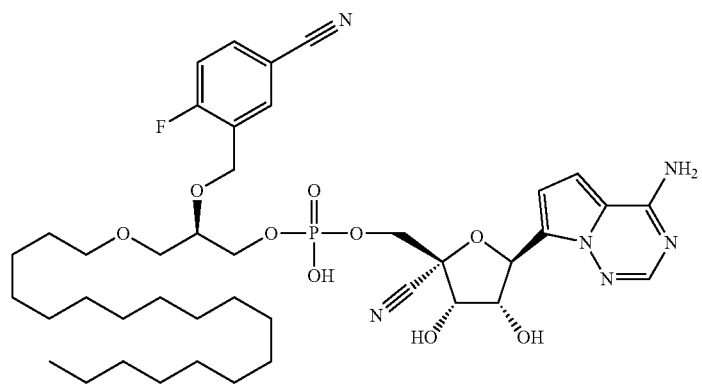 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(C#N)ccc1F]

139 140
TABLE 5-continued
Some Compounds of Formula IIa
Structure
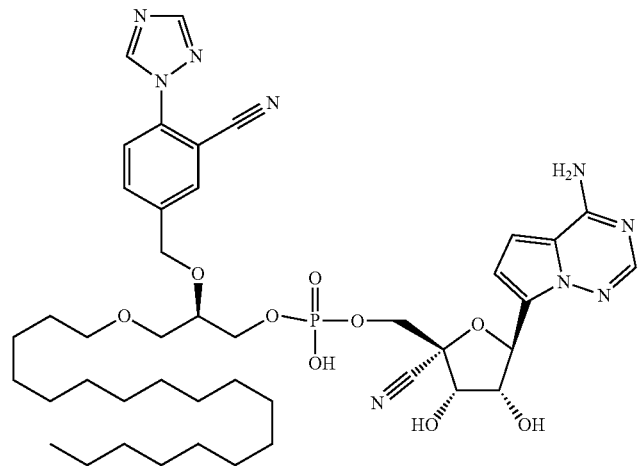 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
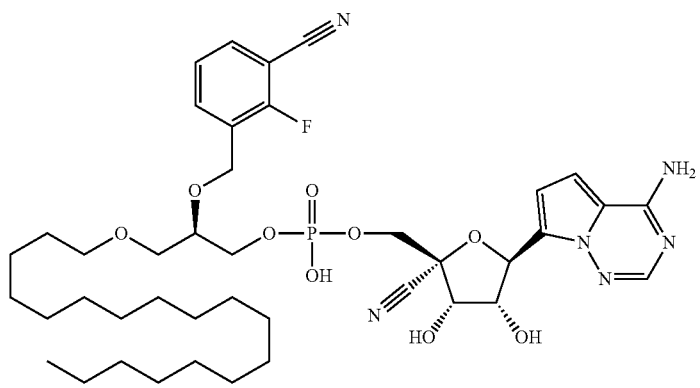 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
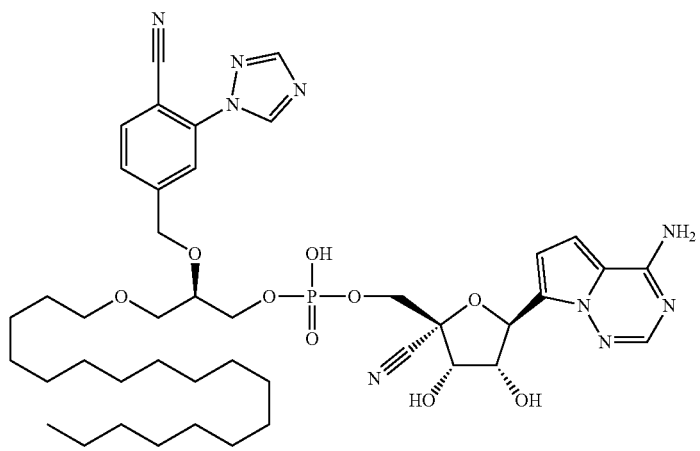 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]

TABLE 5-continued
Some Compounds of Formula IIa
Structure
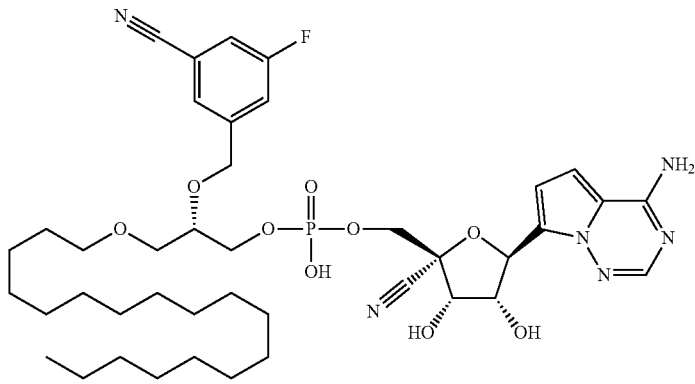 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]
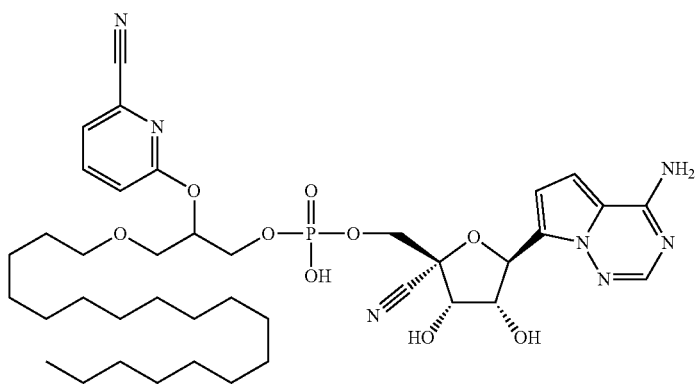 [SMILES: CCCCCCCCCCCCCCCCCCOCC(COP(=O)(O)OC[C@@]1(C#N)O[C@@H](c2ccc3c(N)ncnn23)[C@H](O)[C@@H]1O)Oc1cccc(C#N)n1]
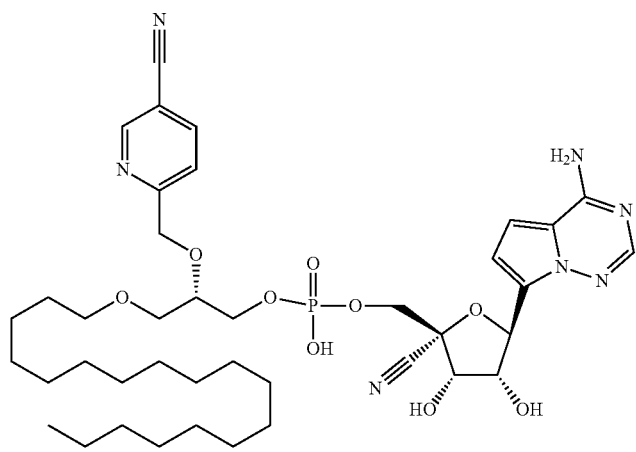 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1]

TABLE 5-continued
Some Compounds of Formula IIa
Structure
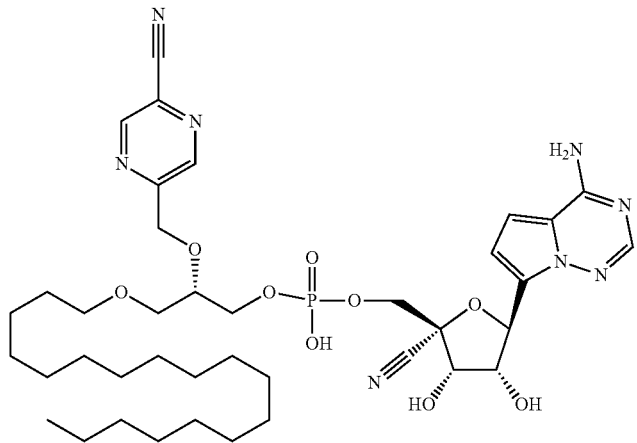
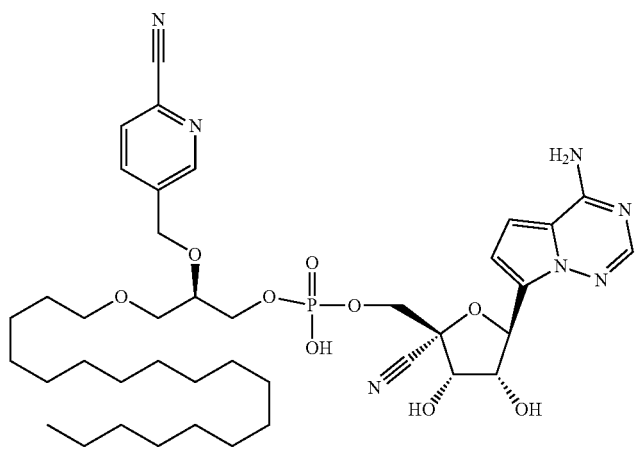 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)nc1]
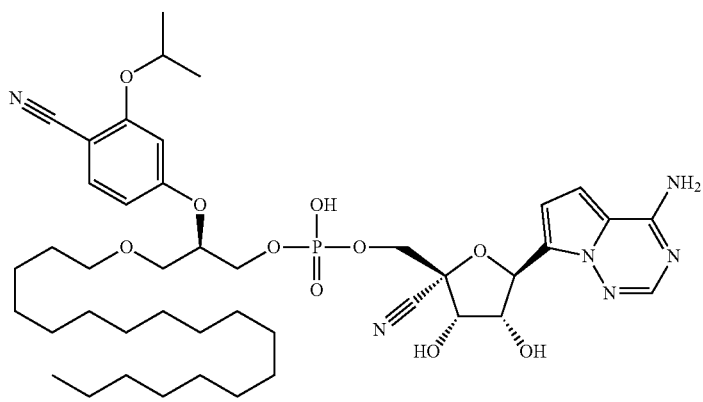 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(OC(C)C)c1]

TABLE 5-continued
Some Compounds of Formula IIa
Structure
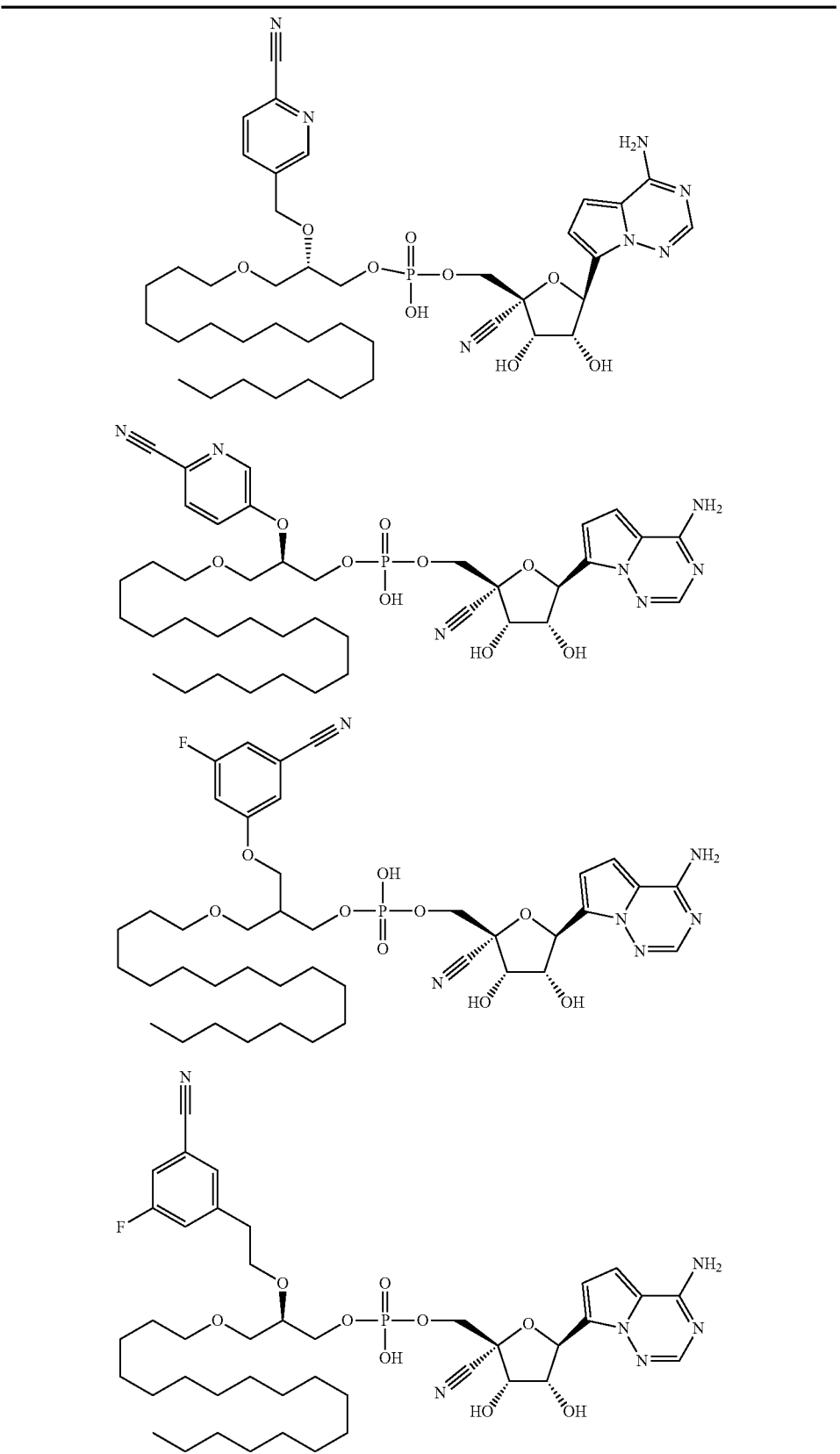

TABLE 5-continued
Some Compounds of Formula IIa
Structure
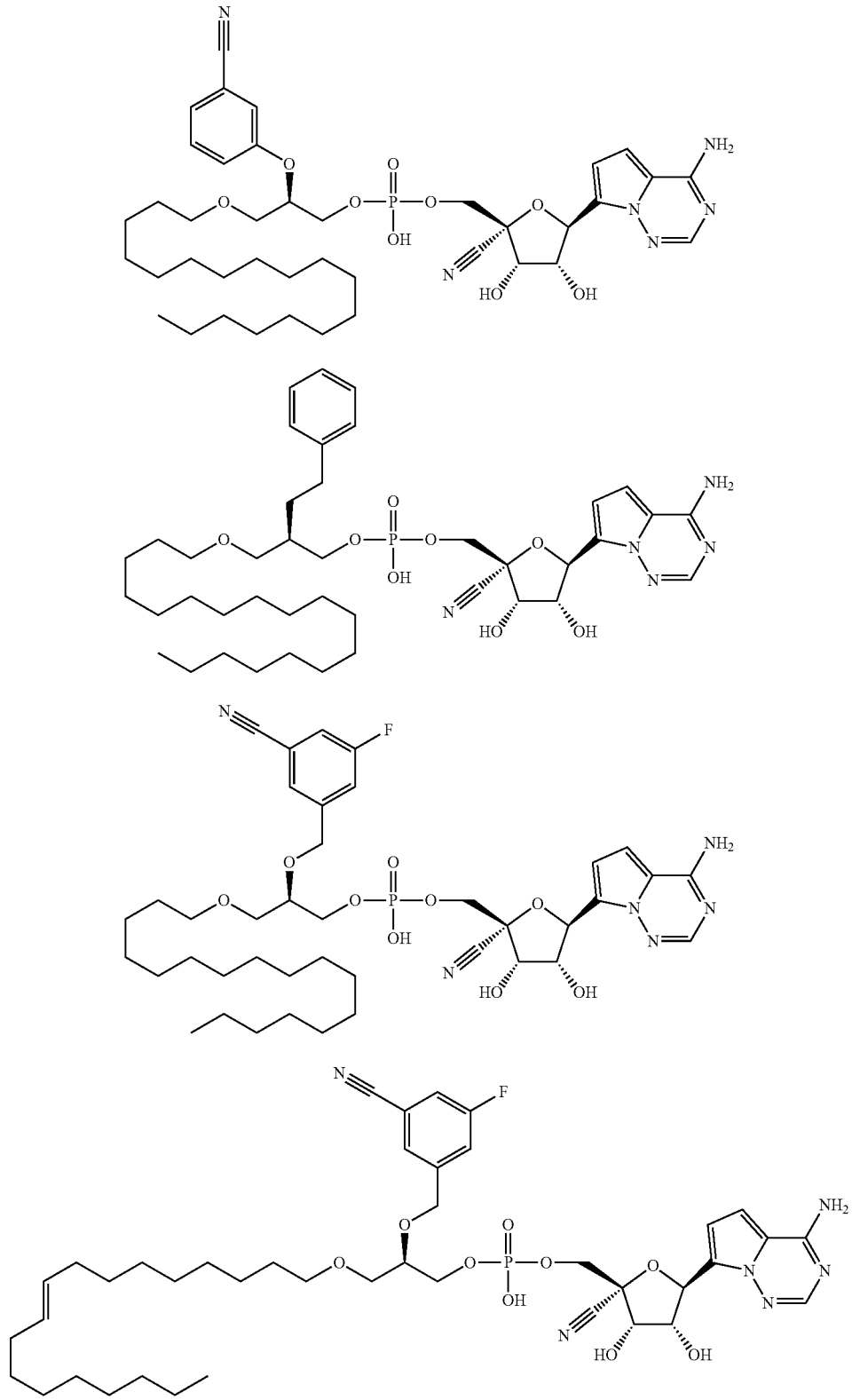

TABLE 5-continued
Some Compounds of Formula IIa
Structure
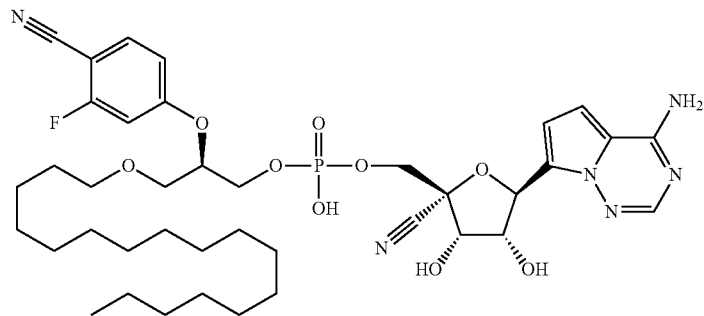
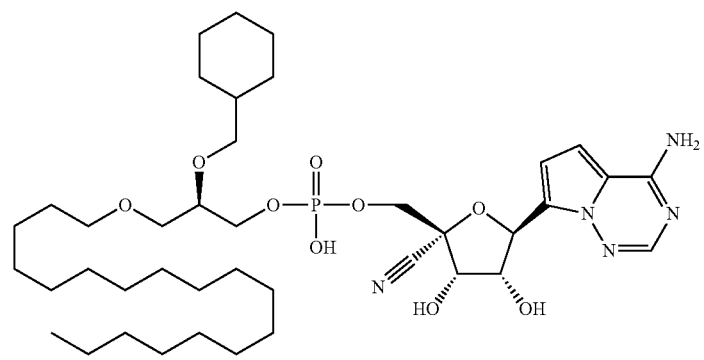
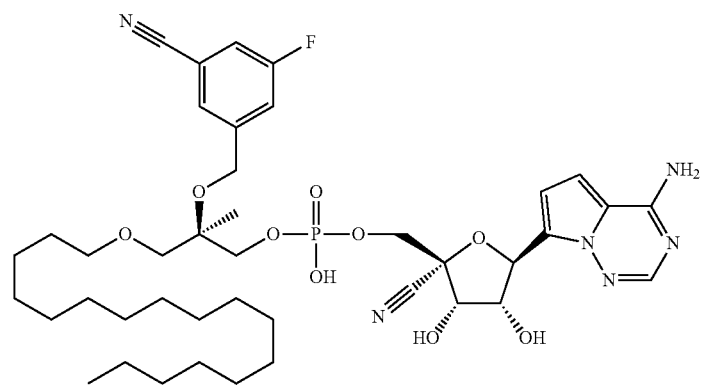 [SMILES: CCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]
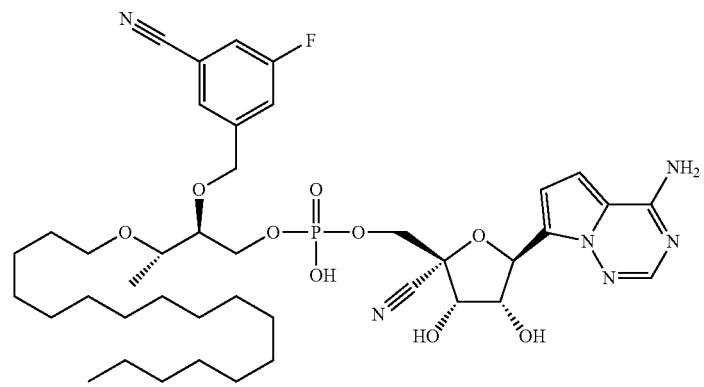 [SMILES: CCCCCCCCCCCCCCCCCO[C@@H](C)[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 5-continued
Some Compounds of Formula IIa
Structure
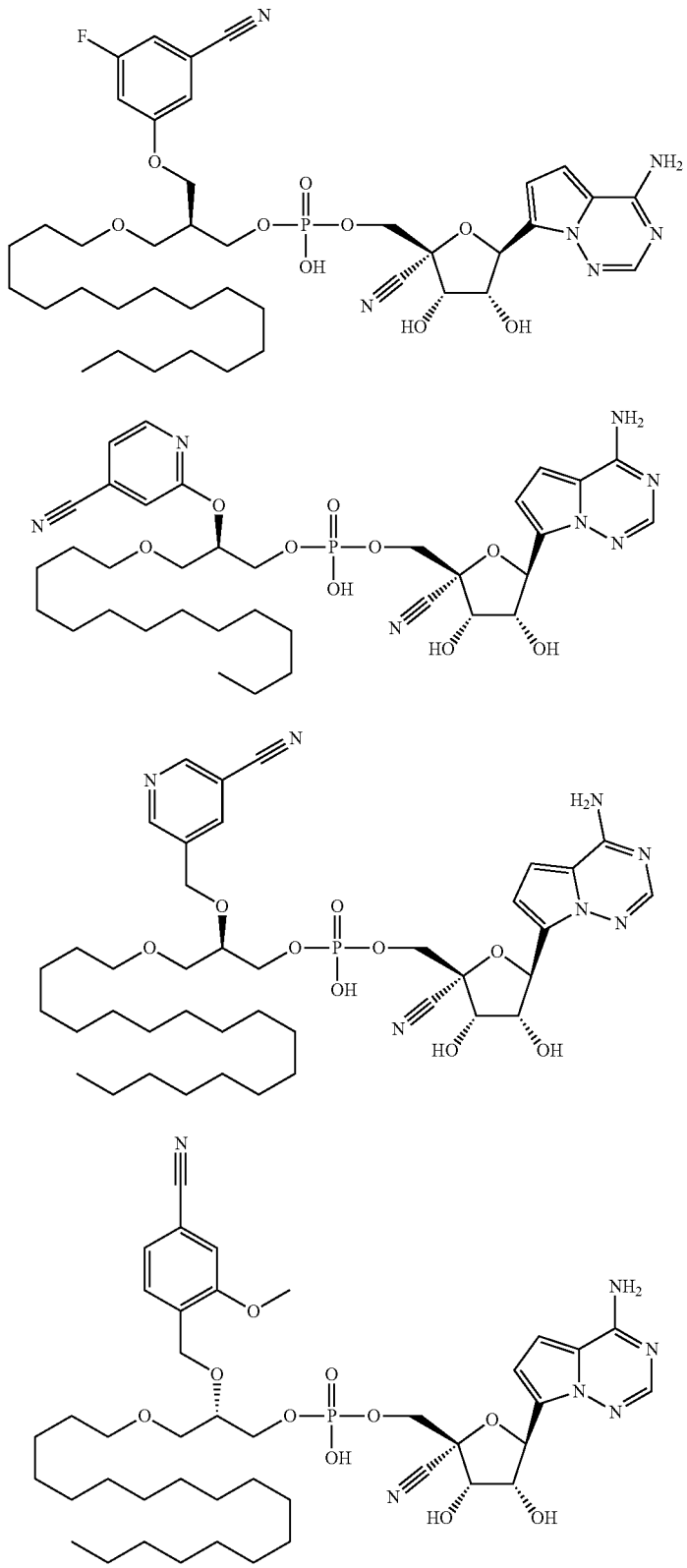

TABLE 5-continued
Some Compounds of Formula IIa
Structure
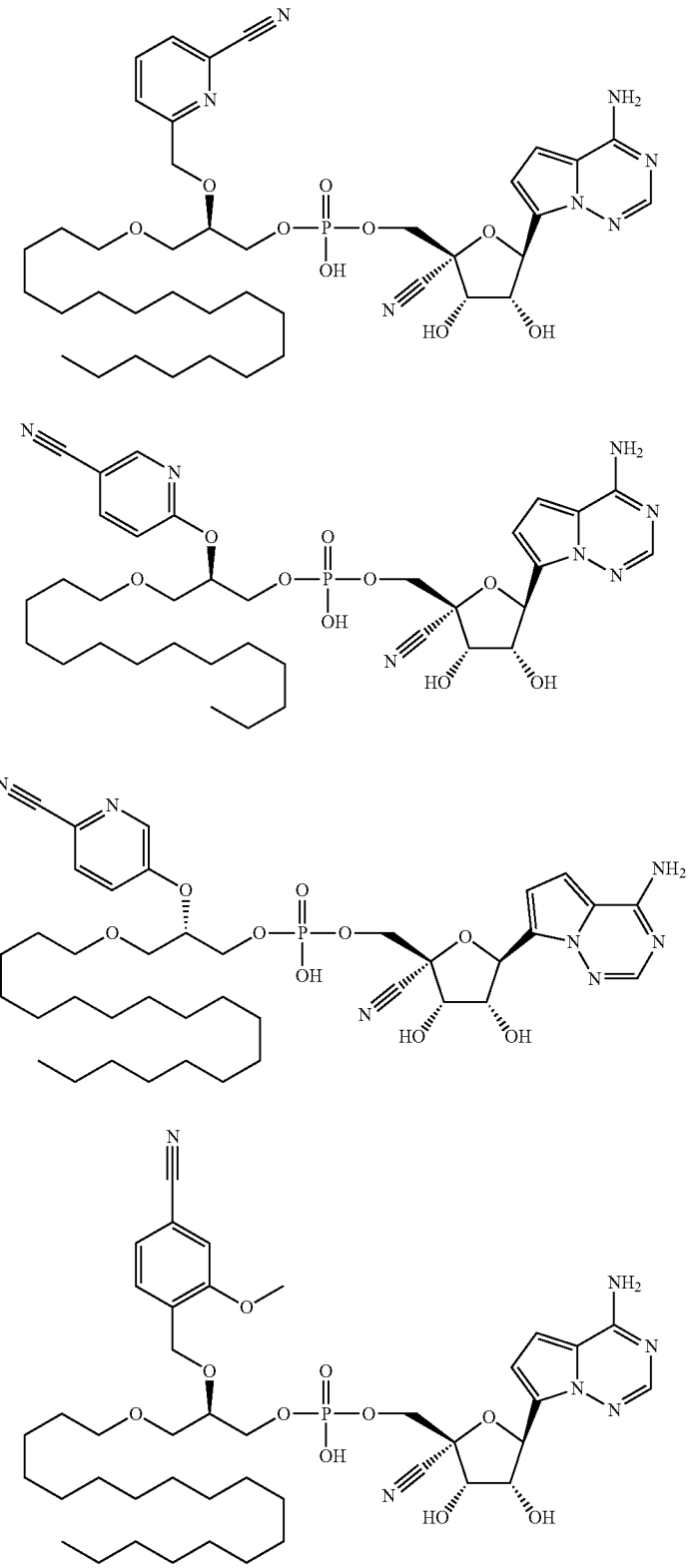

TABLE 5-continued
Some Compounds of Formula IIa
Structure
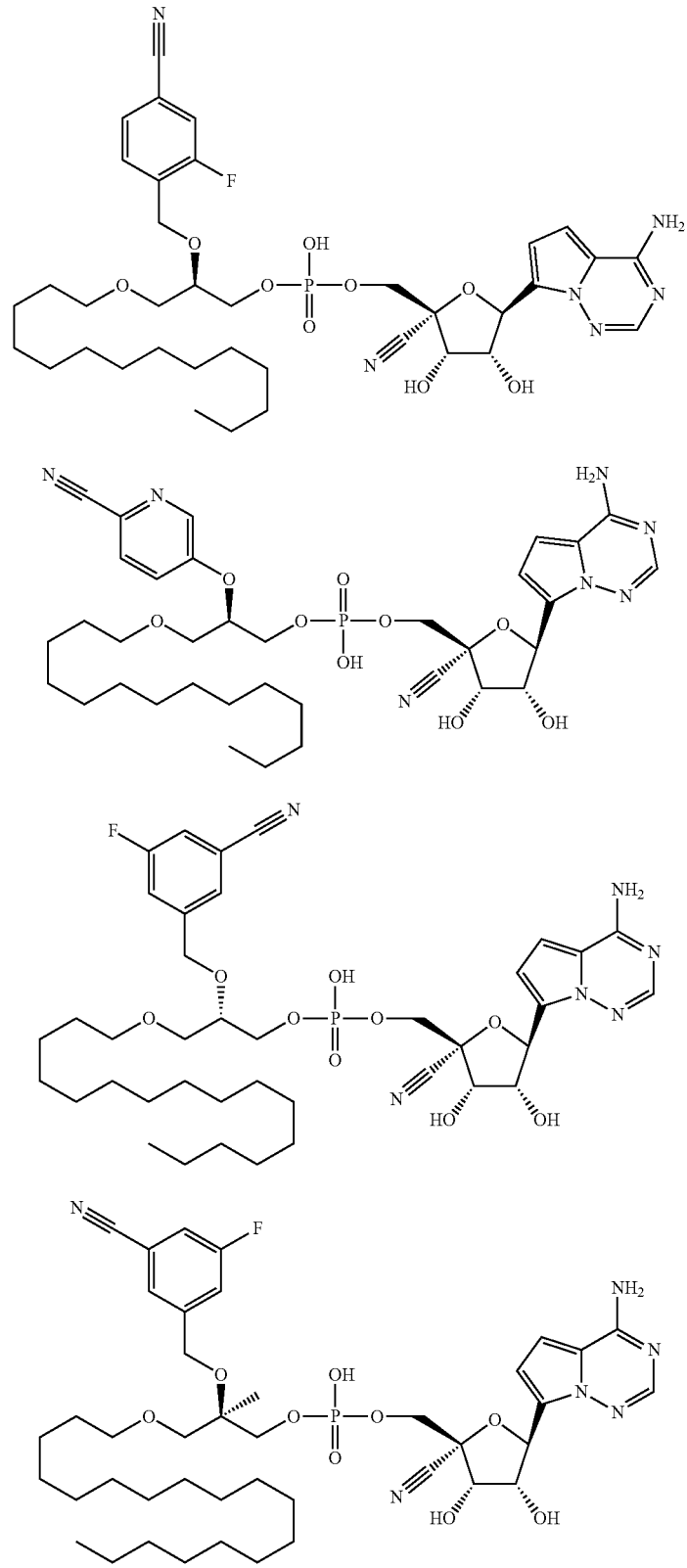

TABLE 5-continued
Some Compounds of Formula IIa
Structure
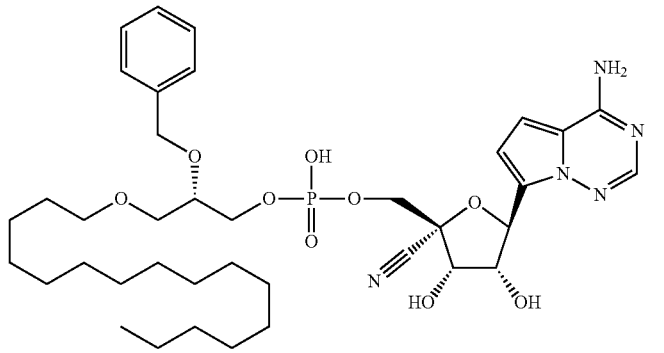
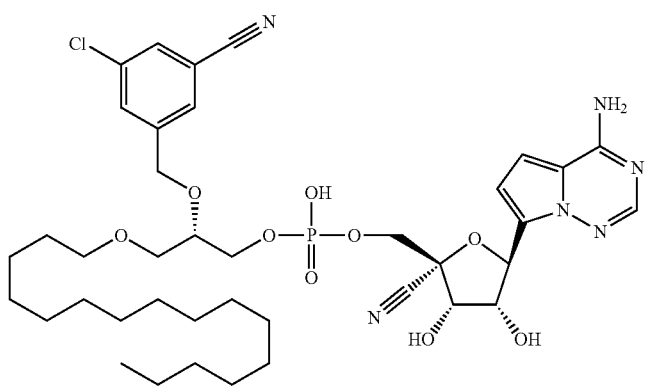
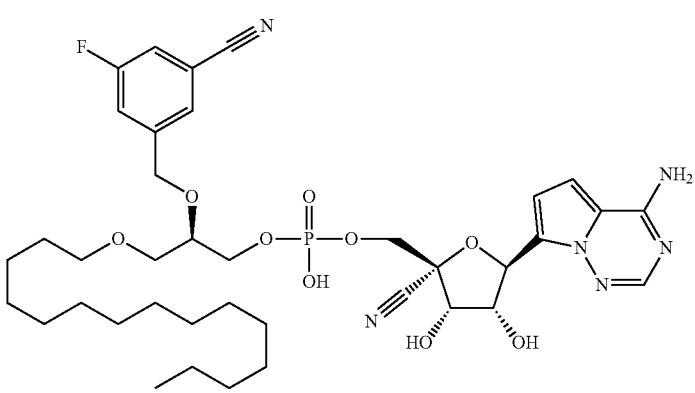 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
In some embodiments, the compound of Formula I has a Formula IIb:
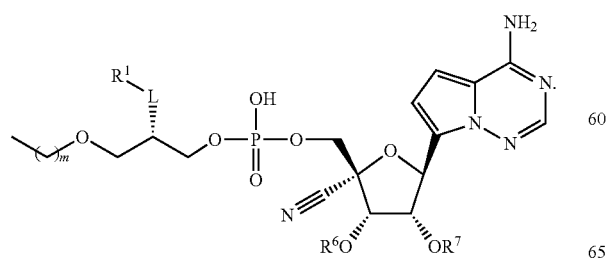
Formula IIb The description of substituents of Formula I (e.g., $R^1$, $R^6$, $R^7$, L, and m) applies to Formula IIb. In some embodiments, the compounds and pharmaceutically acceptable salts of Formula IIb include the compounds in Table 6 and the pharmaceutically acceptable salts thereof.

TABLE 6

Some Compounds of Formula IIb

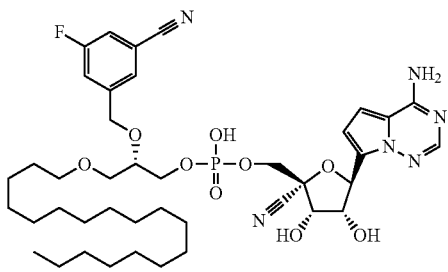 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]

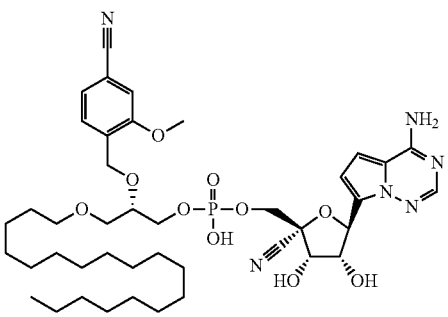

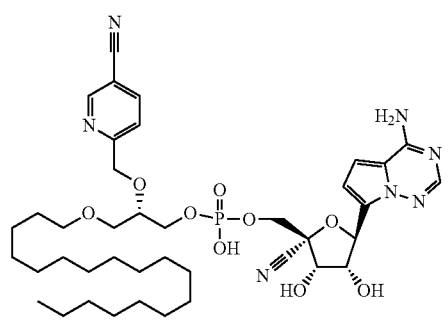 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1]

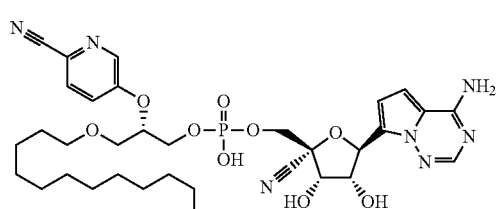

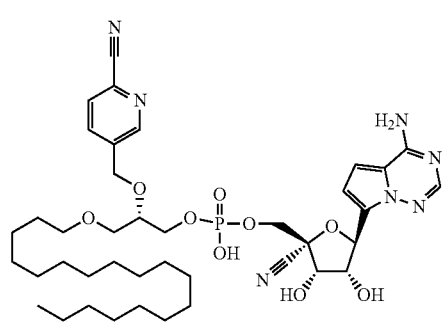 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)nc1]

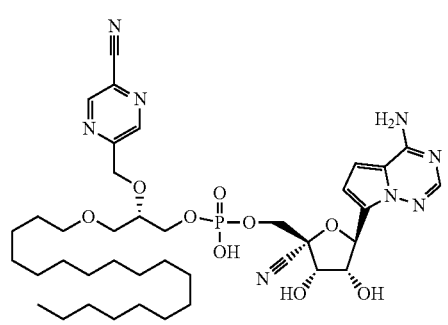 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cnc(C#N)cn1]

TABLE 6-continued

Some Compounds of Formula IIb

In some embodiments, the compound of Formula I has a Formula III:

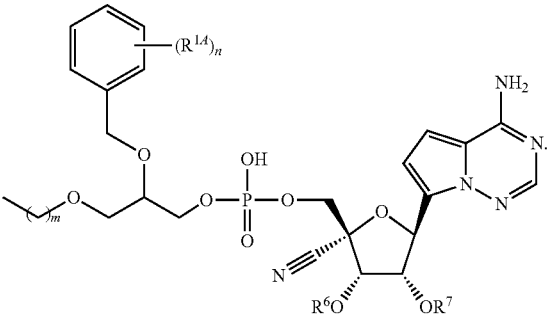

Formula III

The description of substituents of Formula I (e.g., $R^{14}$, $R^6$, $R^7$, m, and n) applies to Formula III.

In some embodiments, the compounds and pharmaceutically acceptable salts of Formula III include the compounds in Table 7 and the pharmaceutically acceptable salts thereof.

TABLE 7
Some Compounds of Formula III
Structure
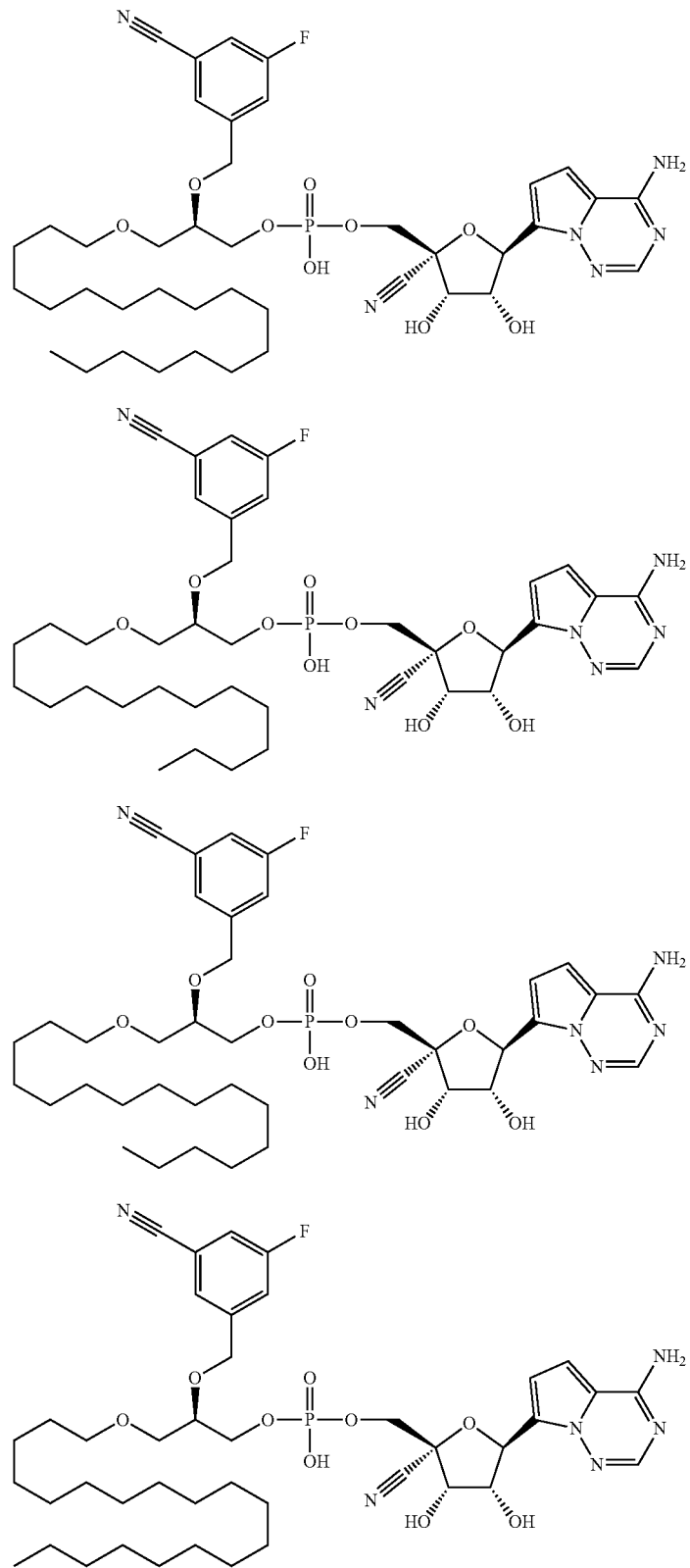

TABLE 7-continued
Some Compounds of Formula III
Structure
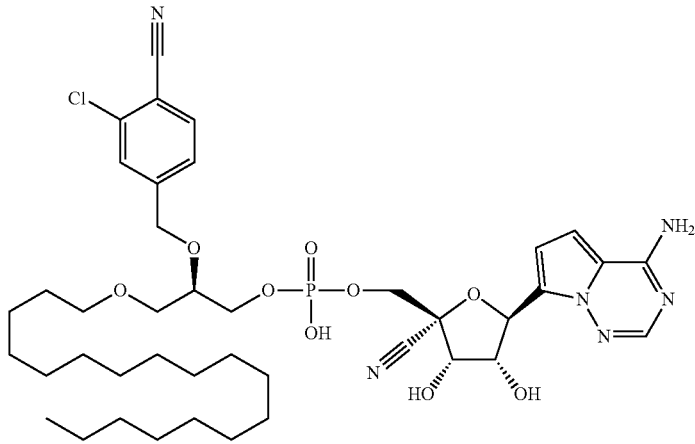 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(Cl)c1]
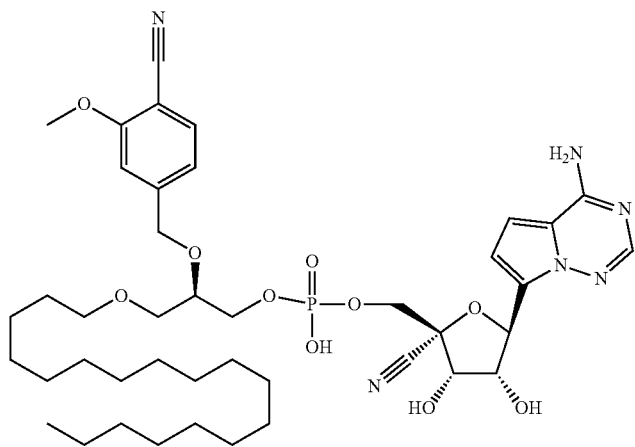 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]
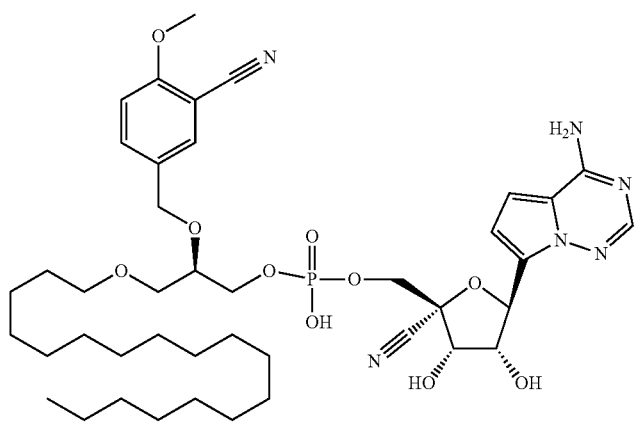 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]

TABLE 7-continued
Some Compounds of Formula III
Structure
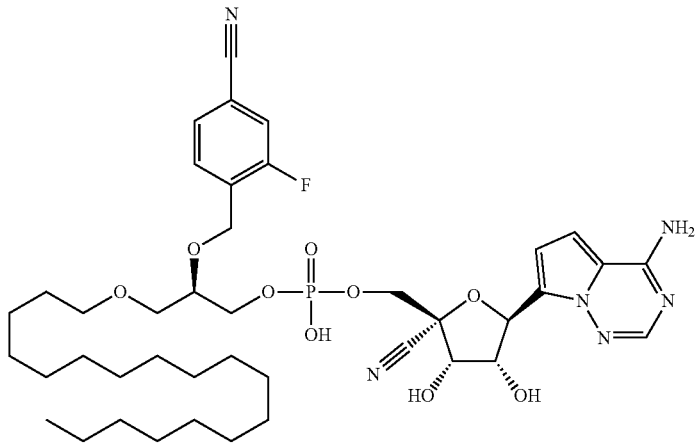 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]
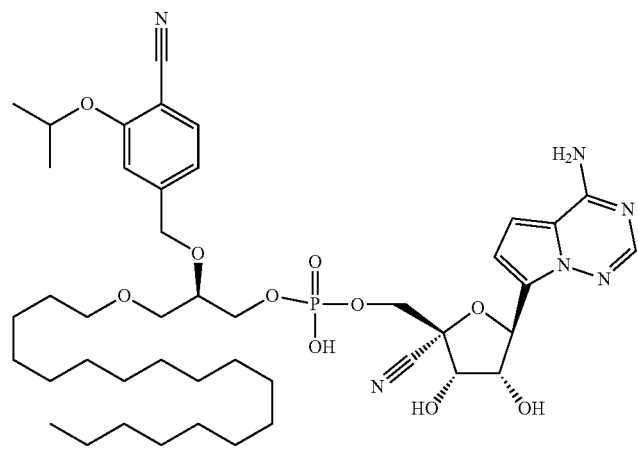 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
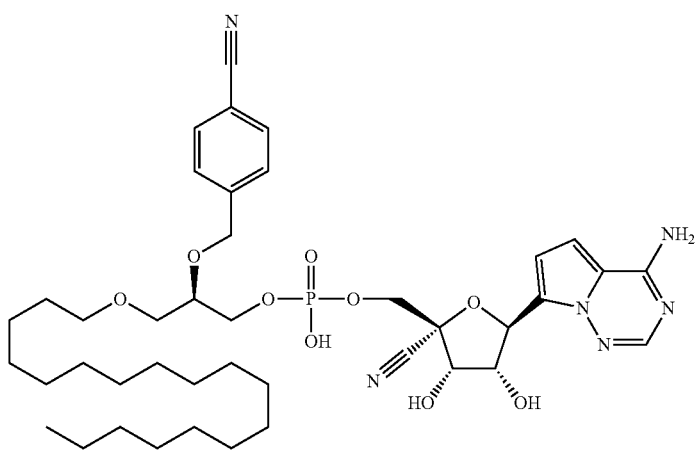 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]

TABLE 7-continued
Some Compounds of Formula III
Structure
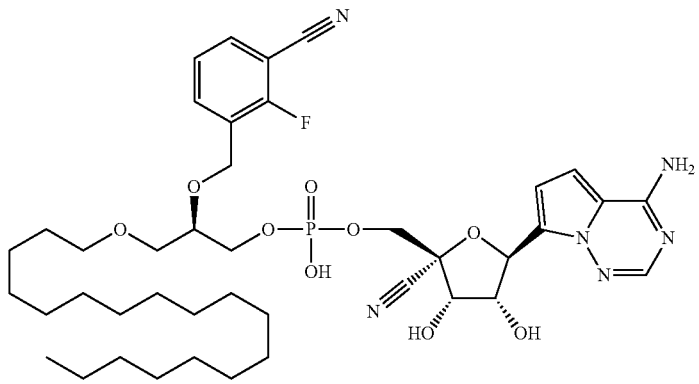 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
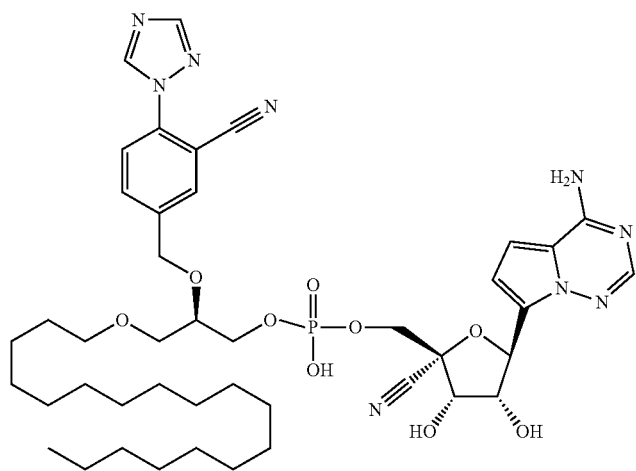 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
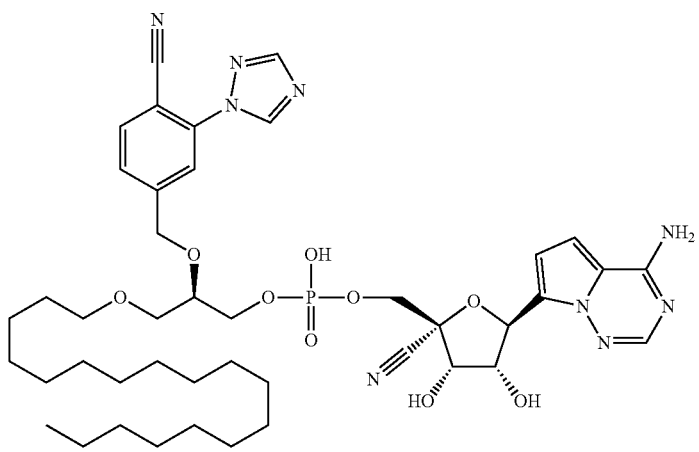 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]

TABLE 7-continued
Some Compounds of Formula III
Structure
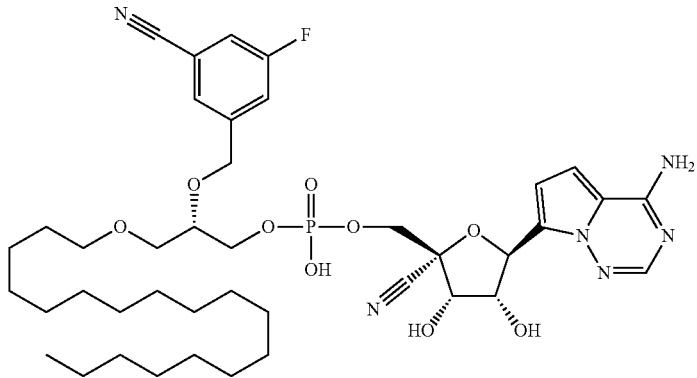 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]
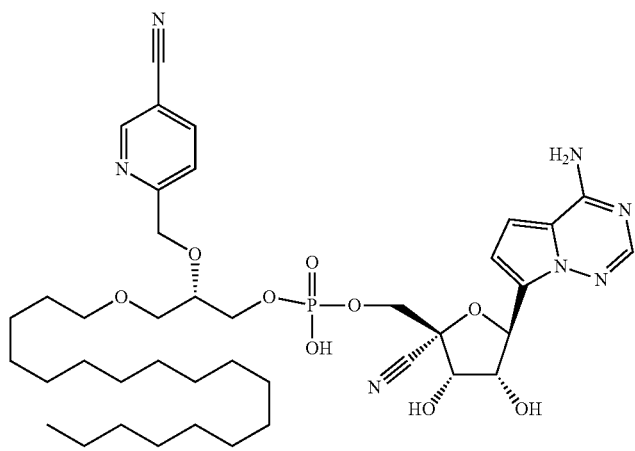 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1]
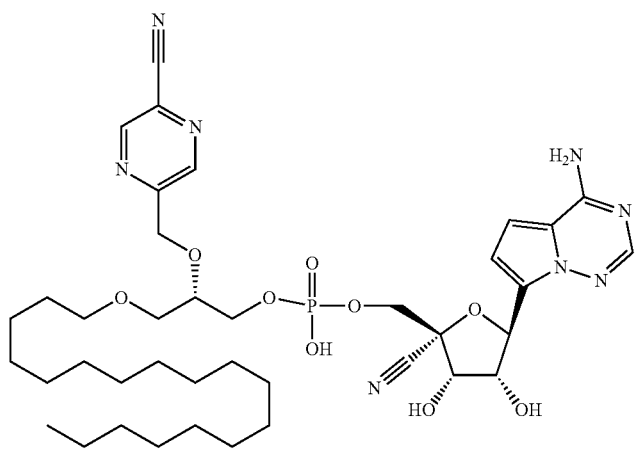 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cnc(C#N)cn1]

TABLE 7-continued
Some Compounds of Formula III
Structure
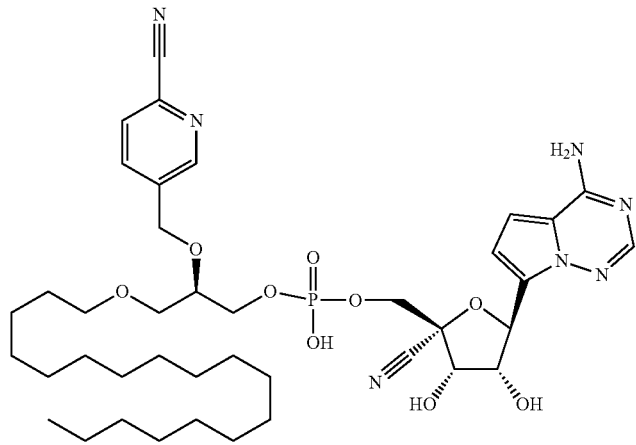 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)nc1]
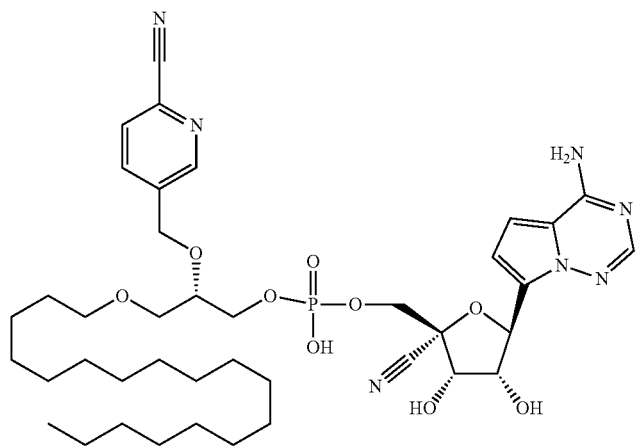 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)nc1]
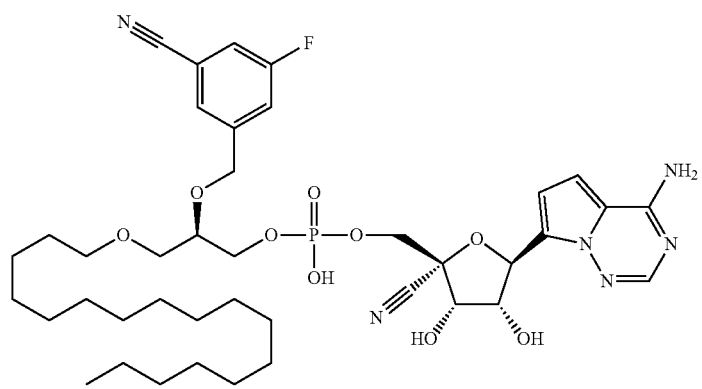

TABLE 7-continued
Some Compounds of Formula III
Structure
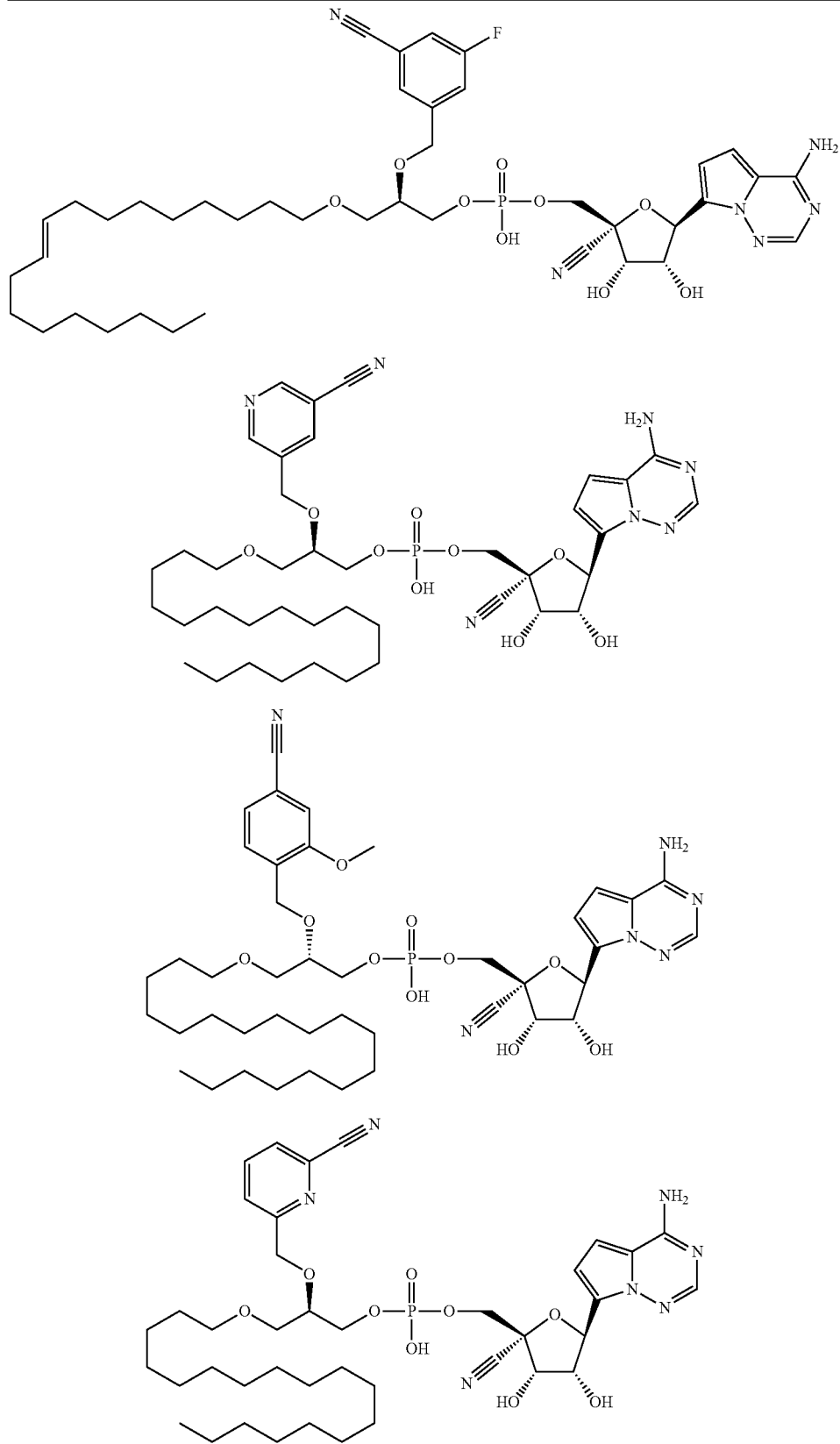

TABLE 7-continued
Some Compounds of Formula III
Structure
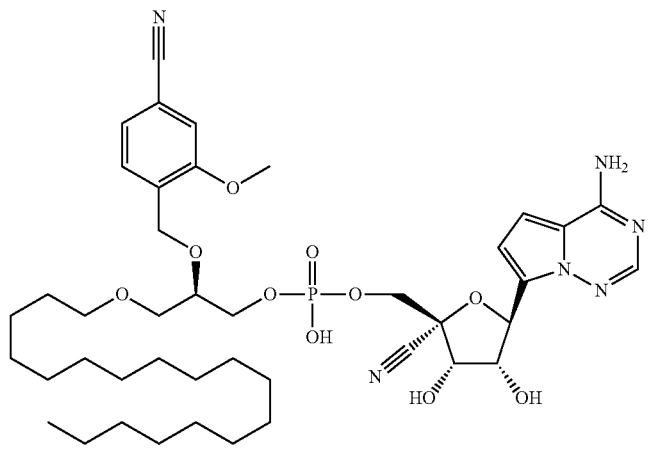 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1OC]
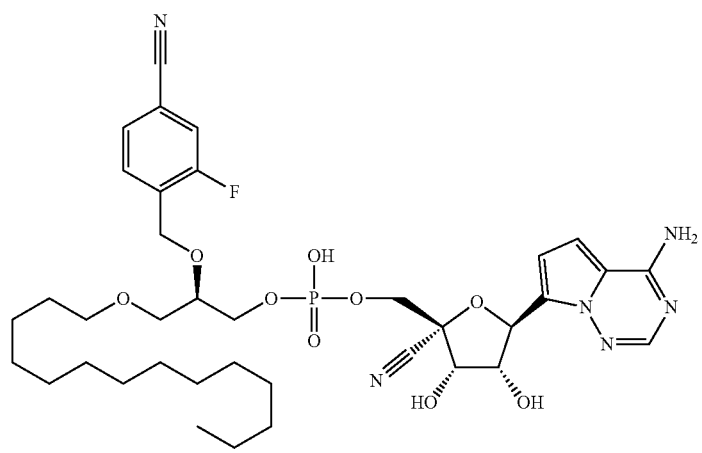 [SMILES: CCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]
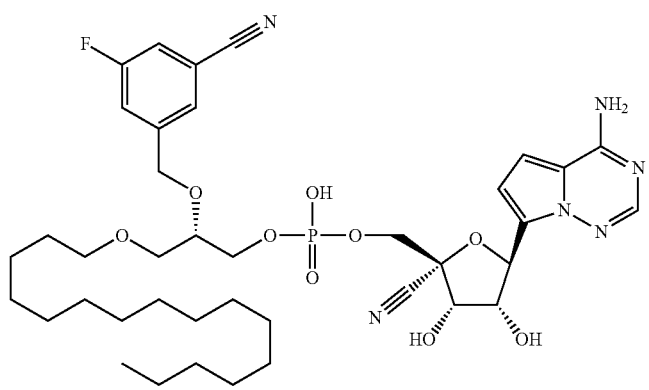 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 7-continued
Some Compounds of Formula III
Structure
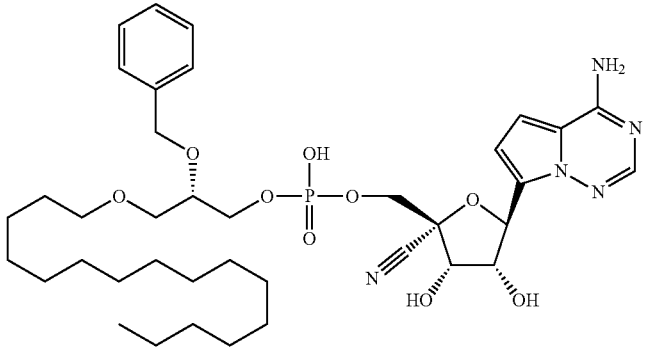 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccccc1]
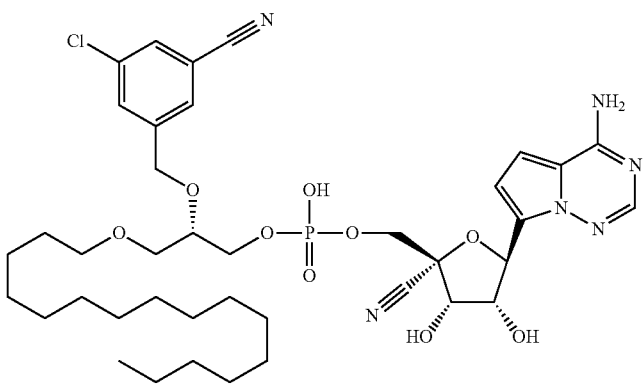 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(Cl)cc(C#N)c1]
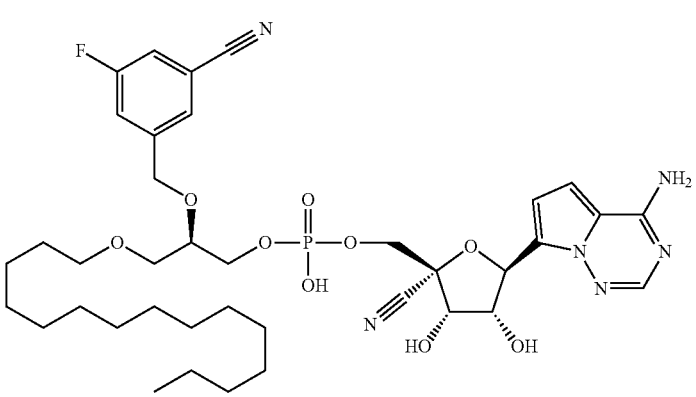 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
In some embodiments, the compound of Formula I has a Formula IIIa:
Formula IIIa
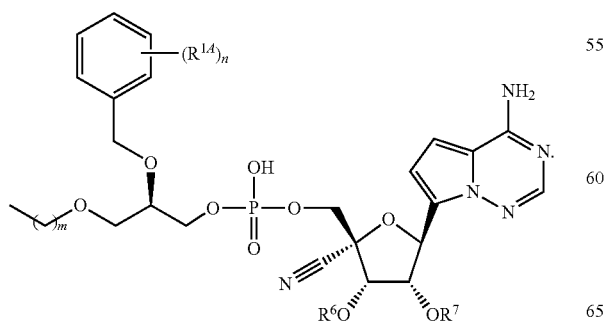

The description of substituents of Formula I (e.g., $R^{14}$, $R^6$, $R^7$, m, and n) applies to Formula IIIa. In some embodiments, the compounds and pharmaceutically acceptable salts of Formula IIIa include the compounds in Table 8 and the pharmaceutically acceptable salts thereof.

TABLE 8

Some Compounds of Formula IIIa
Structure

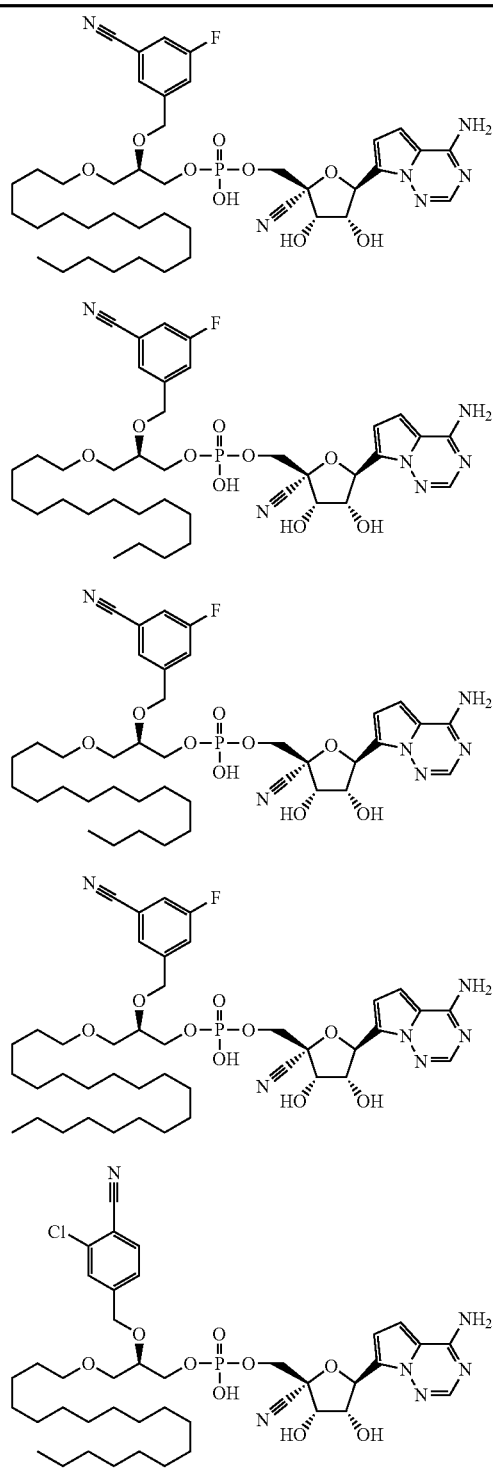

TABLE 8-continued

Some Compounds of Formula IIIa
Structure

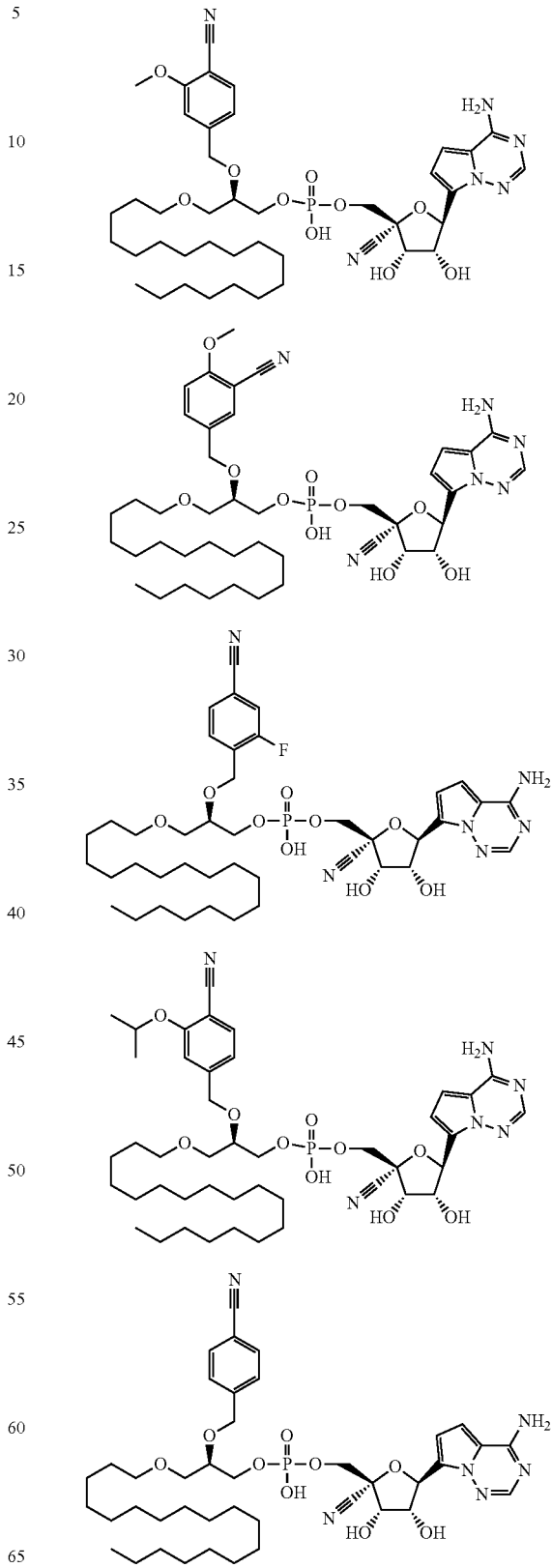

TABLE 8-continued

Some Compounds of Formula IIIa
Structure

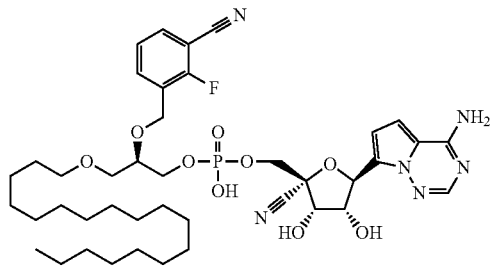 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]

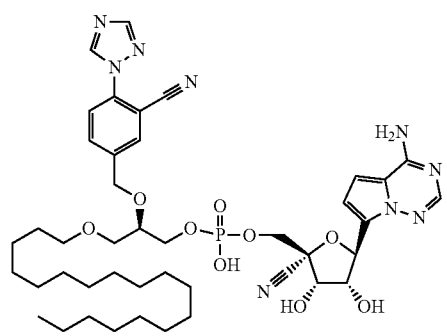 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]

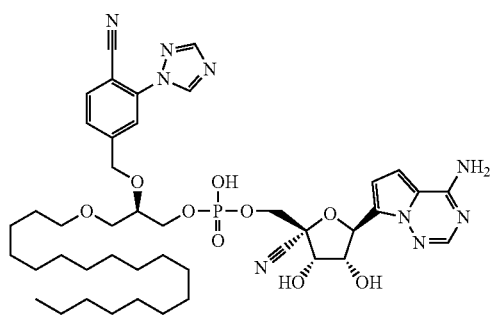 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]

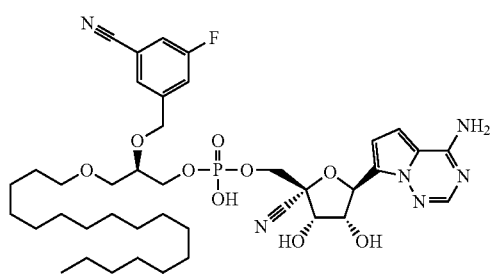 [SMILES: CCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

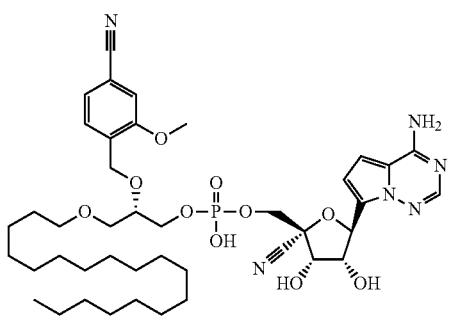 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cc1OC]

TABLE 8-continued

Some Compounds of Formula IIIa
Structure

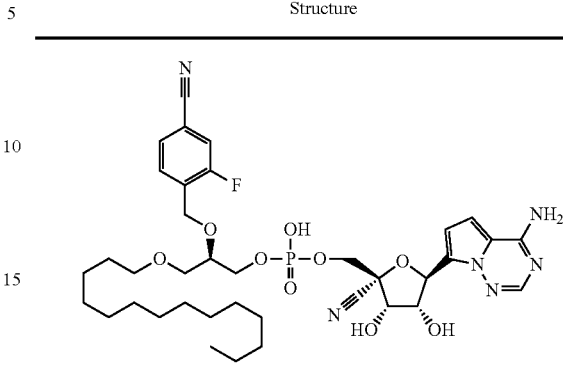

In some embodiments, the compound of Formula I has a Formula IIIb:

Formula IIIb

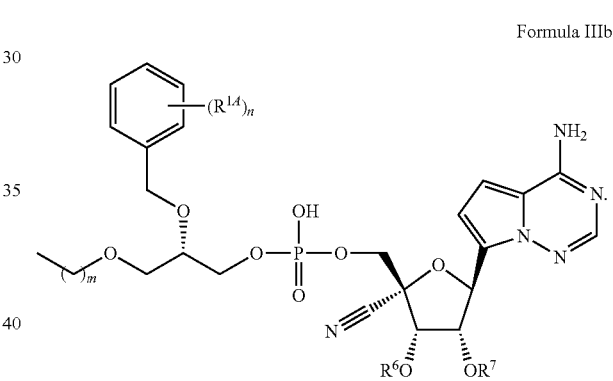

The description of substituents of Formula I (e.g., $R^{1A}$, $R^6$, $R^7$, m, and n) applies to Formula IIIb. In some embodiments, the compounds and pharmaceutically acceptable salts of Formula IIIb include the compounds in Table 9 and the pharmaceutically acceptable salts thereof.

TABLE 9

Some Compounds of Formula IIIb
Structure

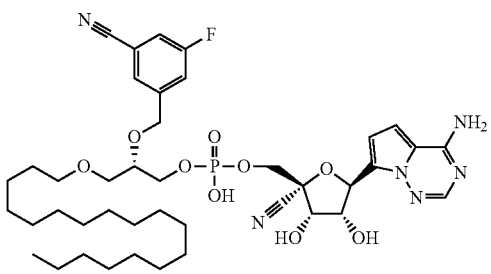 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 9-continued

Some Compounds of Formula IIIb
Structure

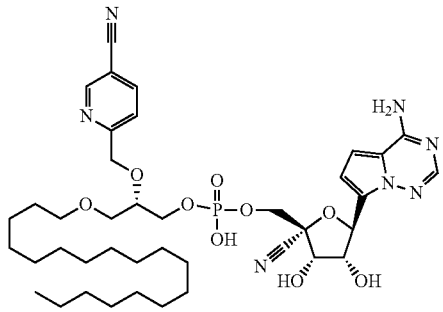

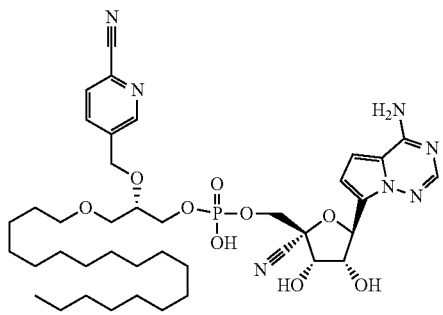 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)nc1]

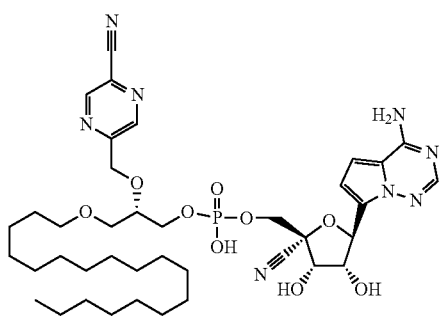 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cnc(C#N)cn1]

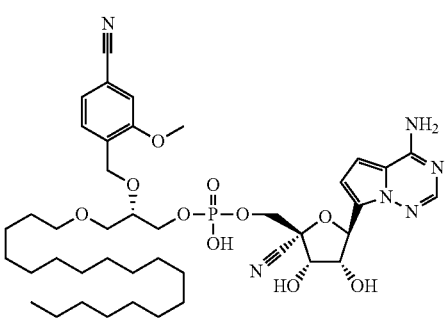 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cc1OC]

TABLE 9-continued

Some Compounds of Formula IIIb
Structure

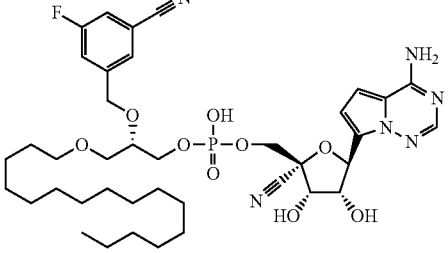

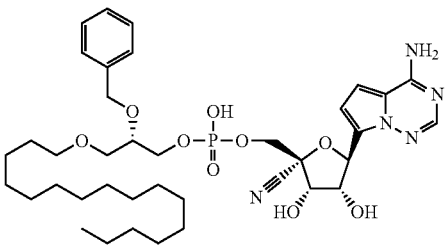

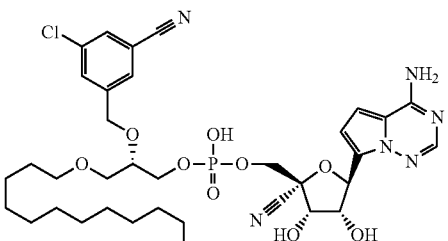

In some embodiments, the compound of Formula I has a Formula IV:

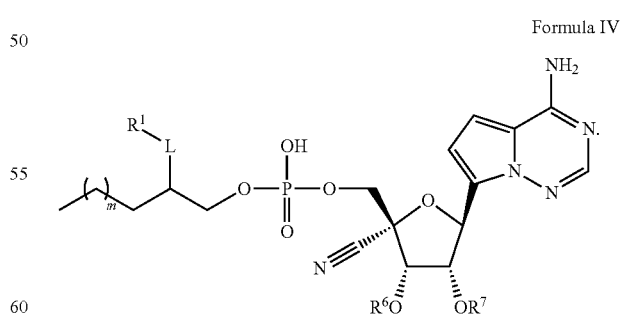

Formula IV

The description of substituents of Formula I (e.g., $R^1$, $R^6$, $R^7$, L, and m) applies to Formula IV. In some embodiments, the compounds and pharmaceutically acceptable salts of Formula IV include the compounds in Table 10 and the pharmaceutically acceptable salts thereof.

TABLE 10
Some Compounds of Formula IV
Structure
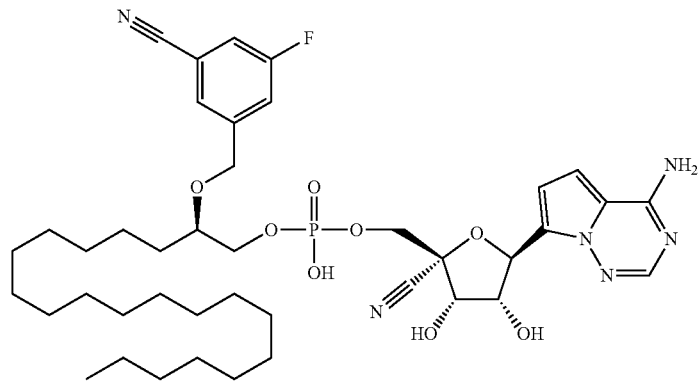
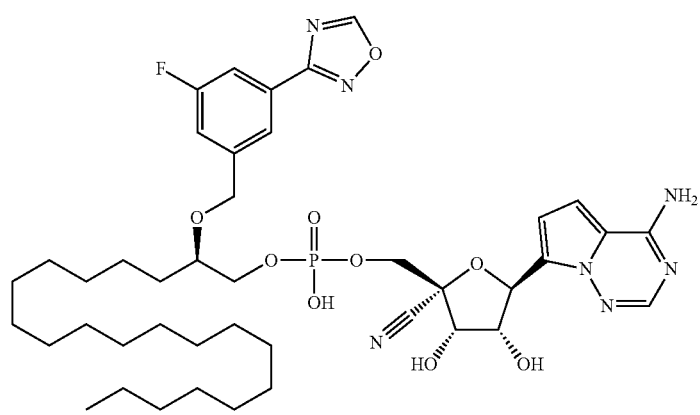 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(-c2ncon2)c1]
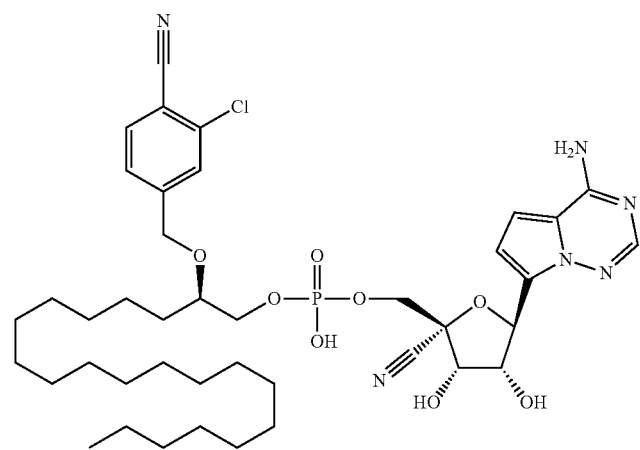 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(Cl)c1]

TABLE 10-continued
Some Compounds of Formula IV
Structure
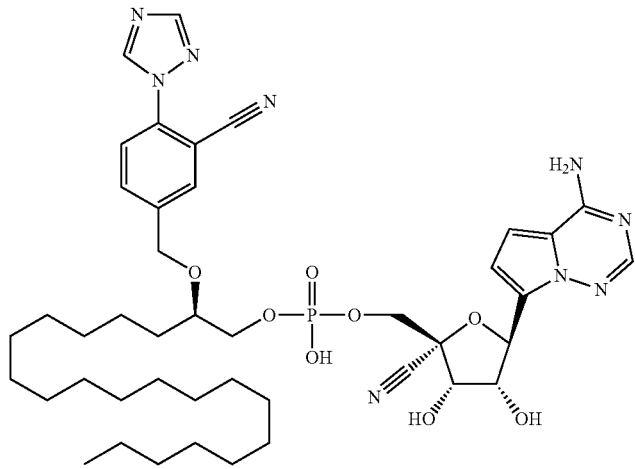 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
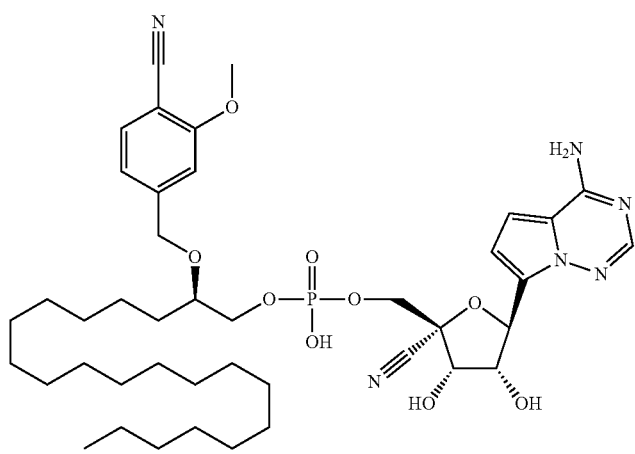 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC)c1]
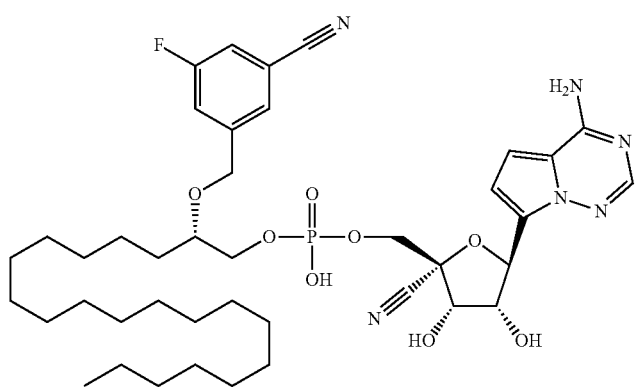 [SMILES: CCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 10-continued
Some Compounds of Formula IV
Structure
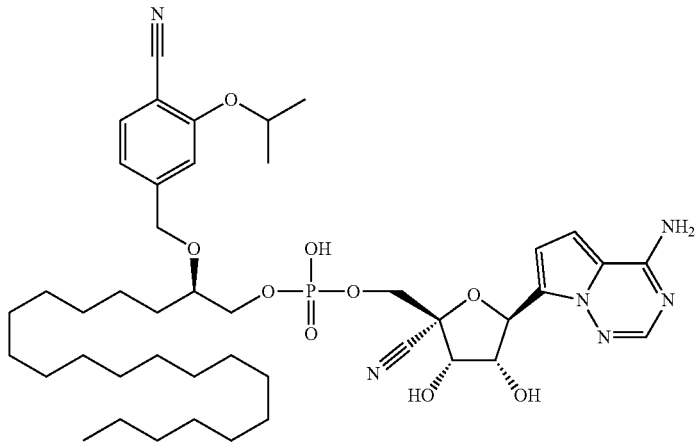 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
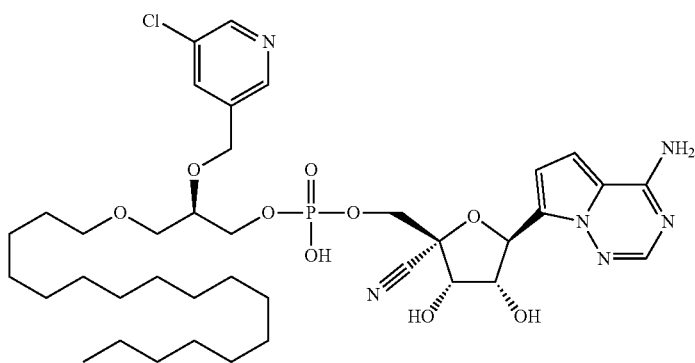
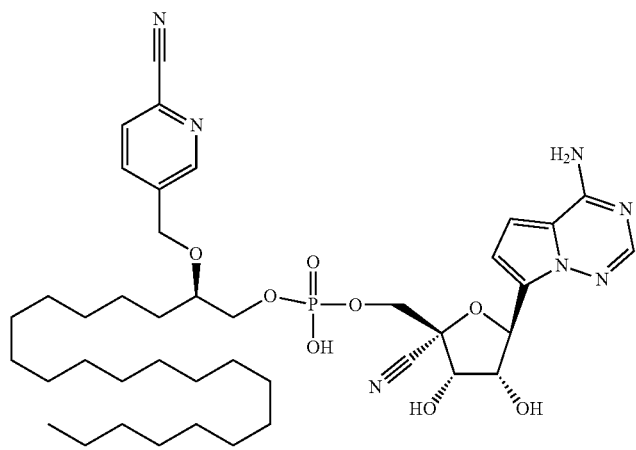

TABLE 10-continued
Some Compounds of Formula IV
Structure
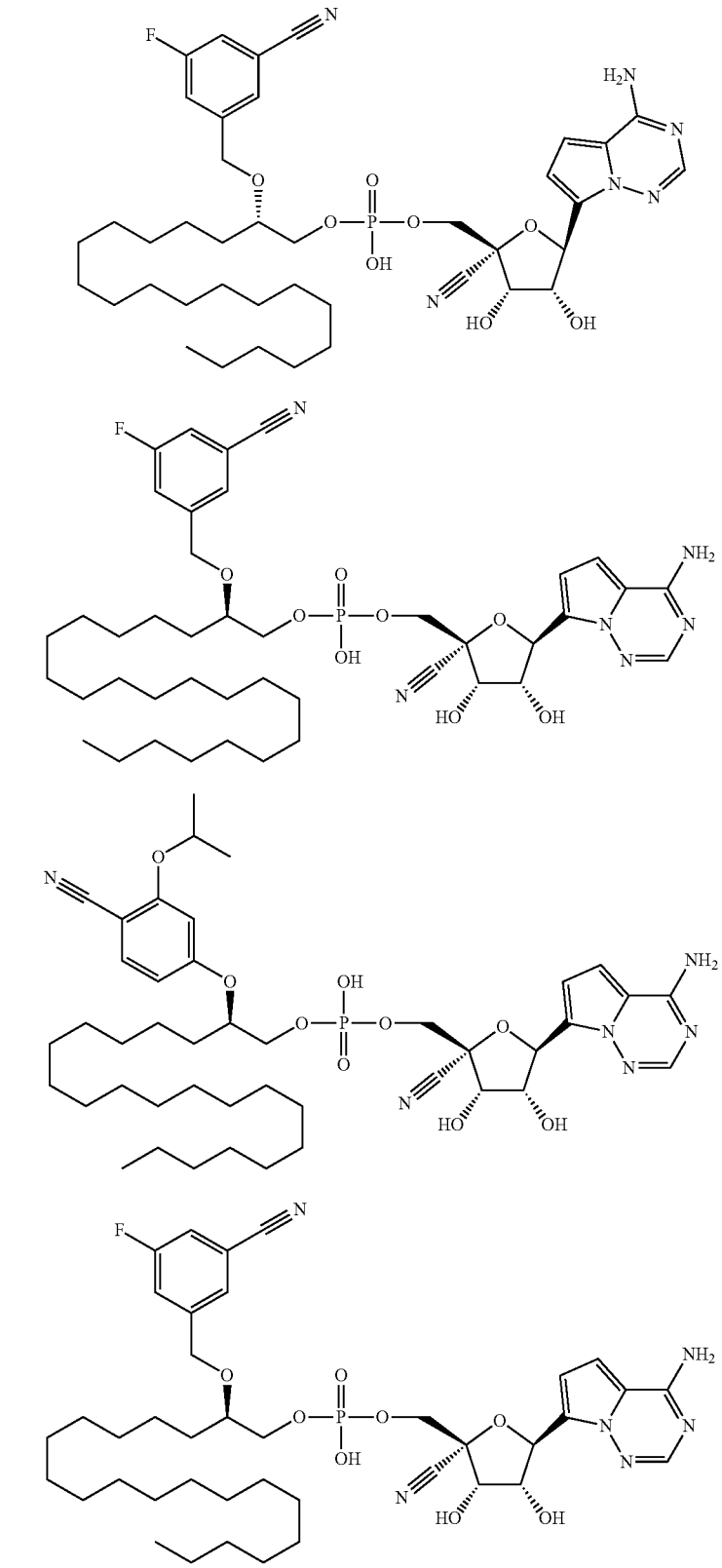

TABLE 10-continued
Some Compounds of Formula IV
Structure
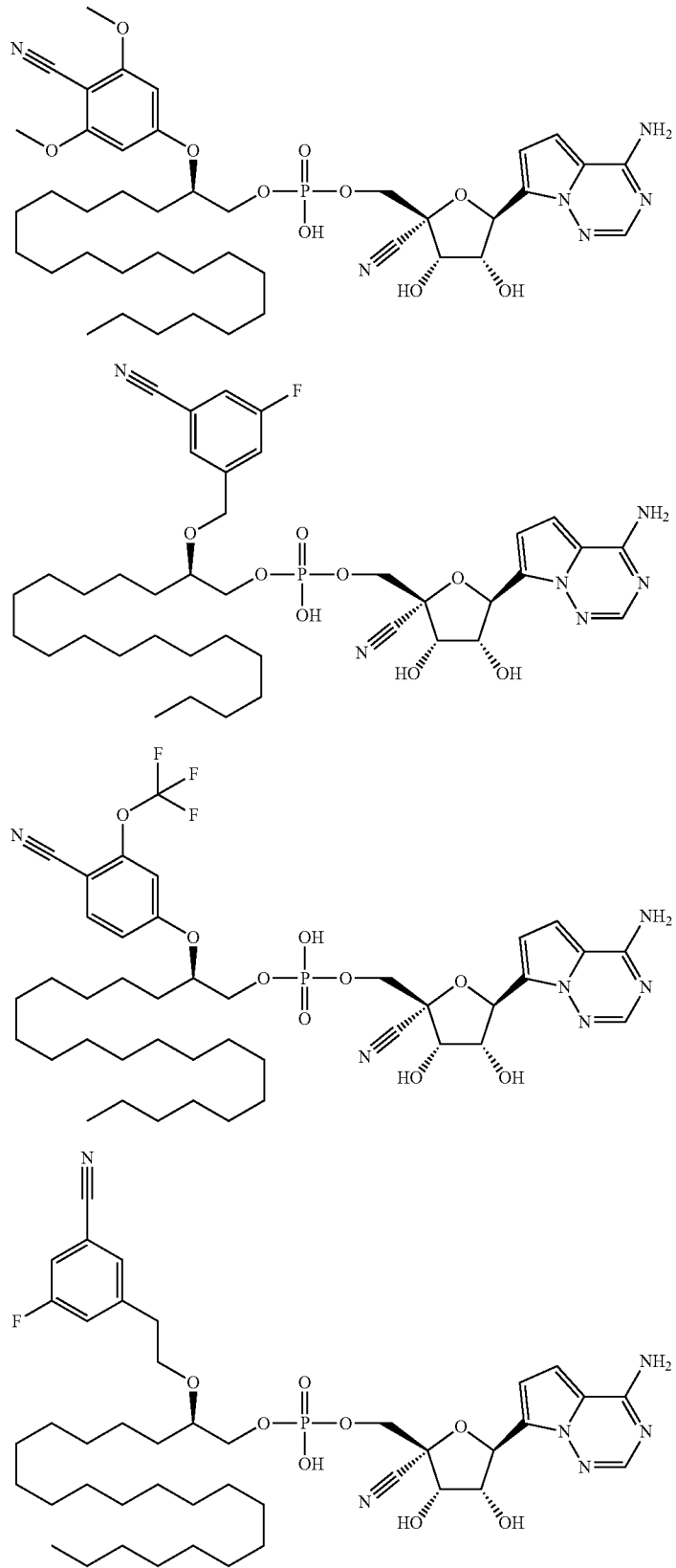

TABLE 10-continued
Some Compounds of Formula IV
Structure
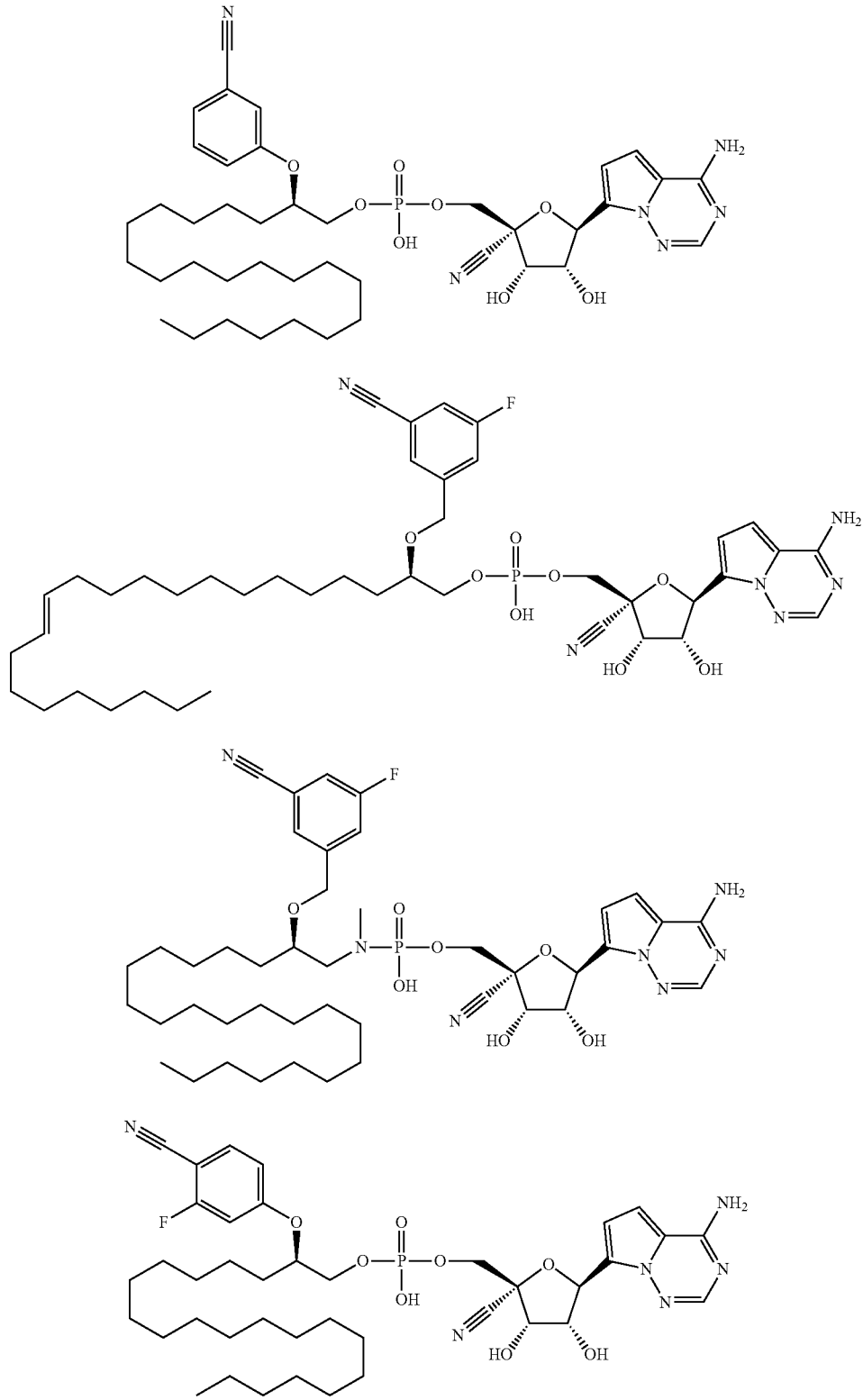

TABLE 10-continued
Some Compounds of Formula IV
Structure
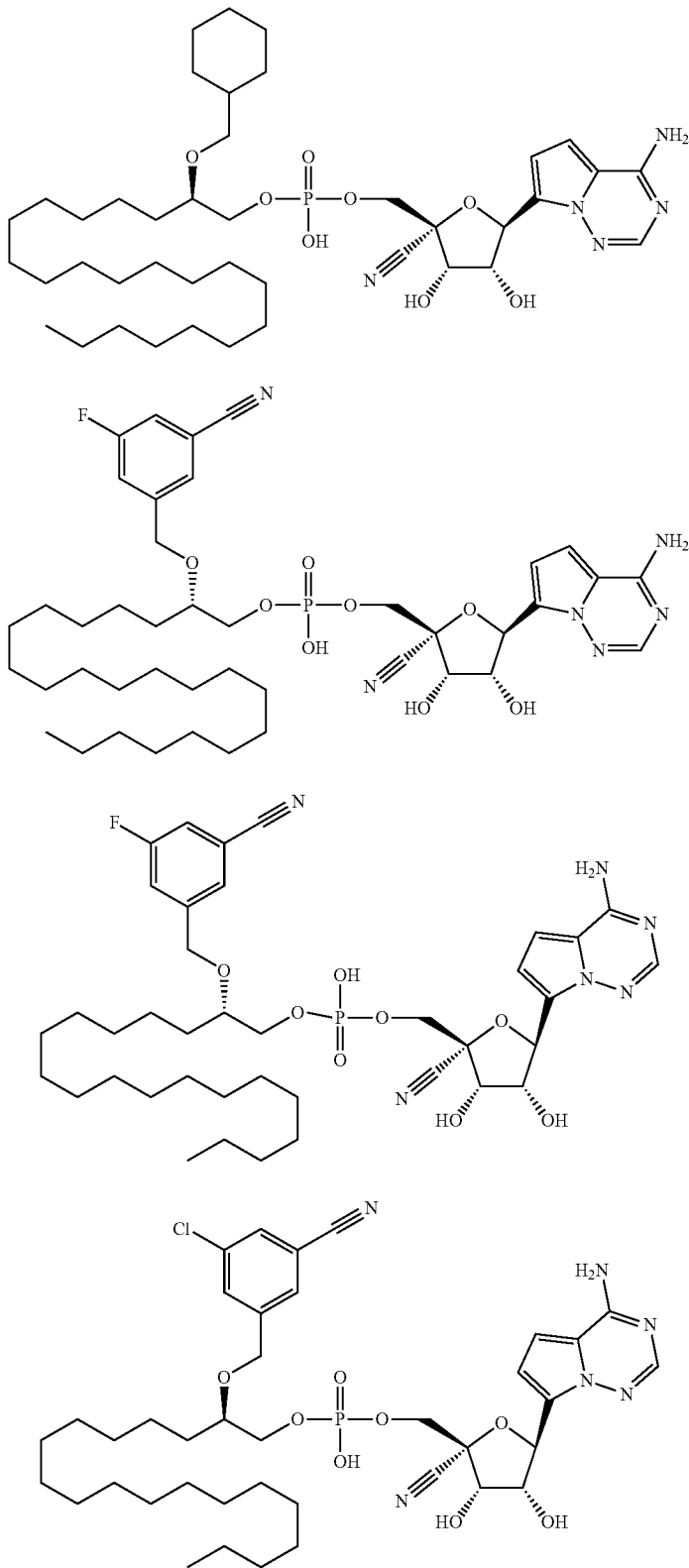

TABLE 10-continued
Some Compounds of Formula IV
Structure
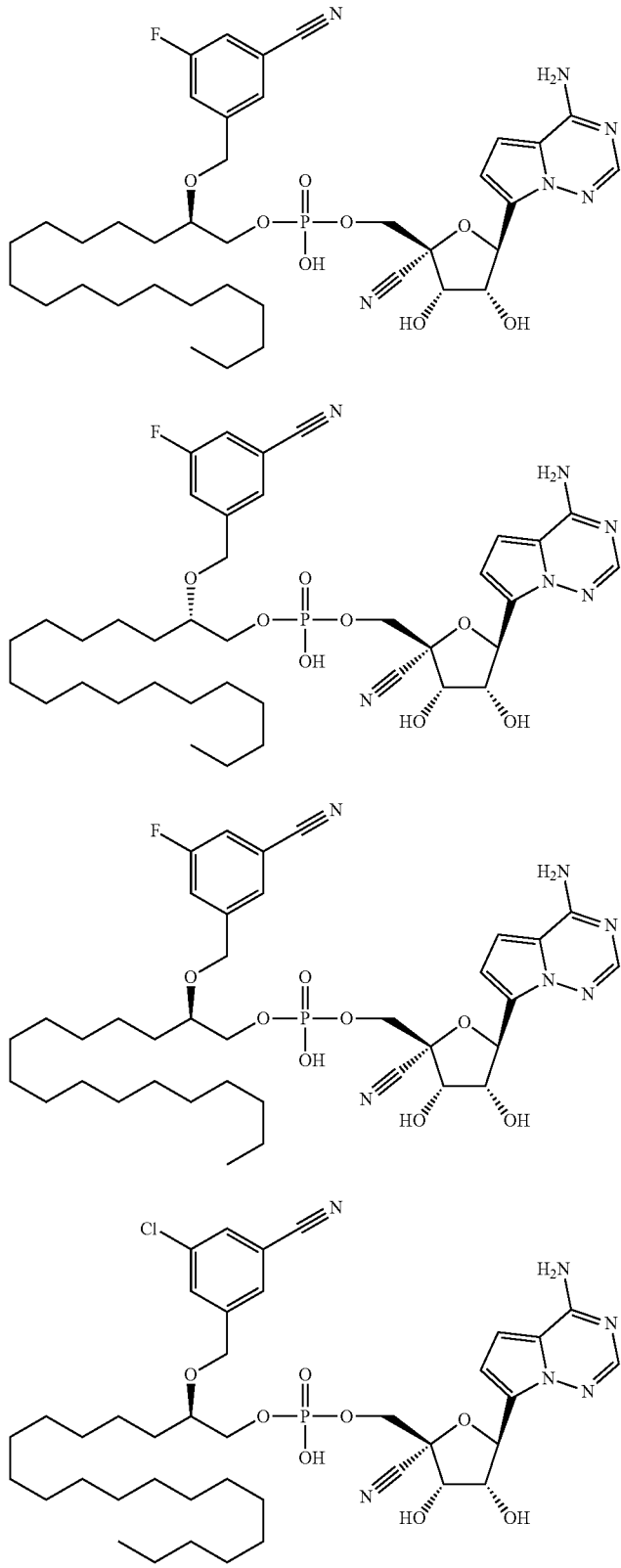

TABLE 10-continued
Some Compounds of Formula IV
Structure
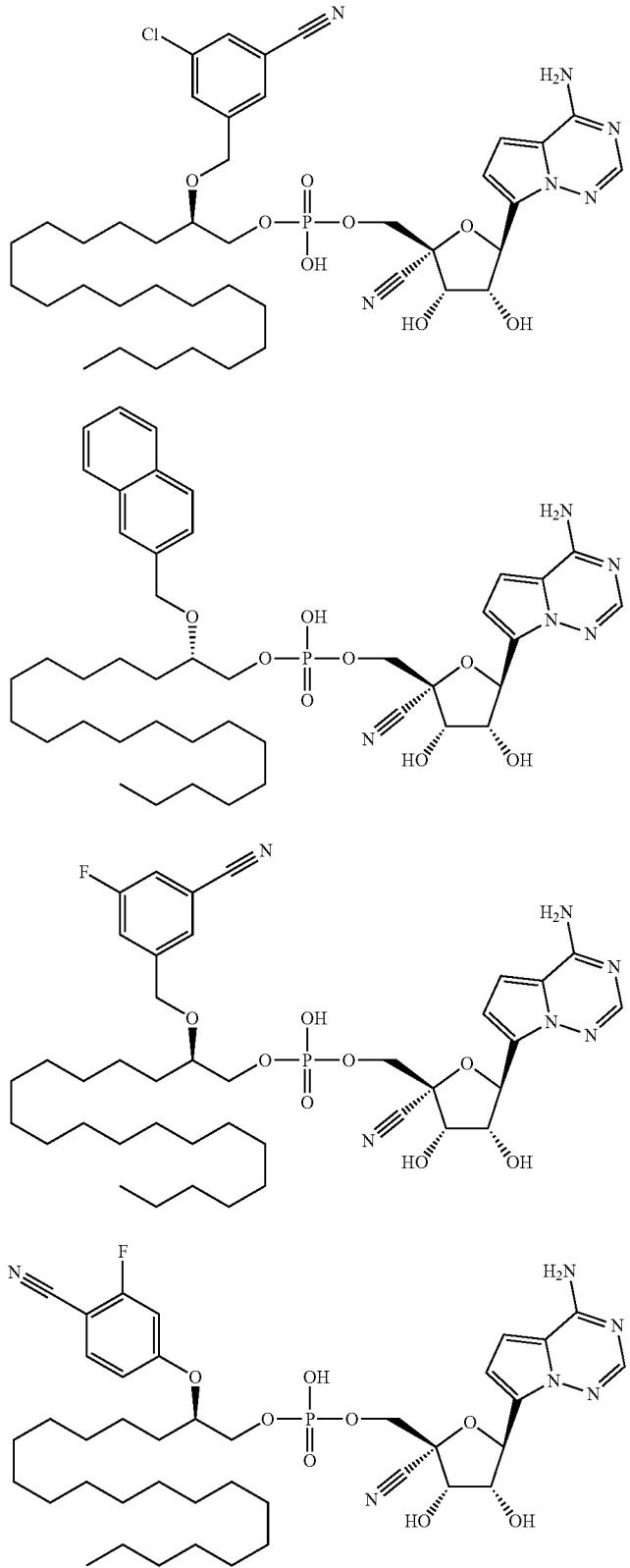

TABLE 10-continued
Some Compounds of Formula IV
Structure
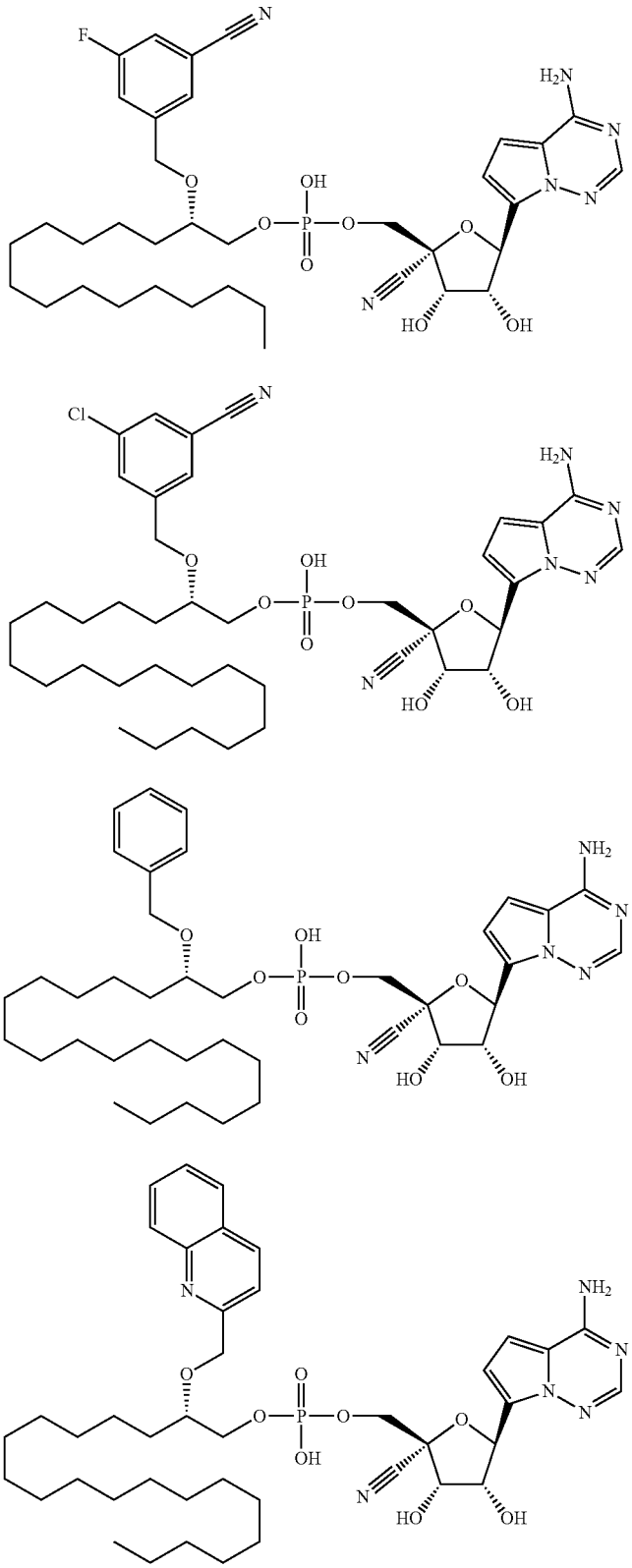

TABLE 10-continued

Some Compounds of Formula IV
Structure

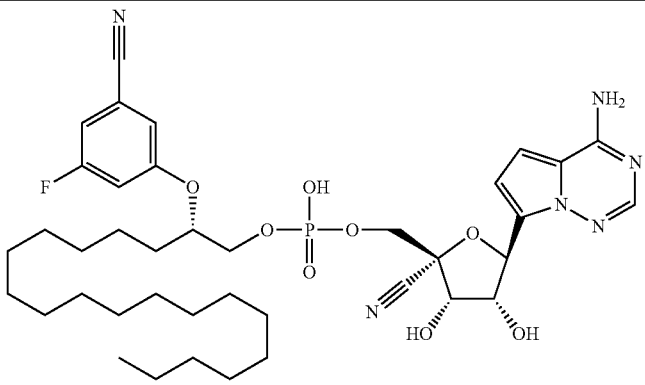

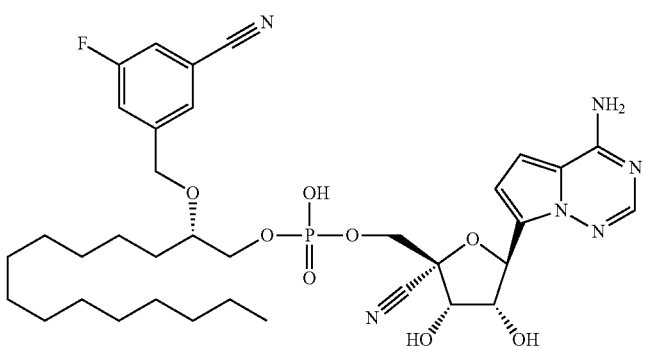 [SMILES: CCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

In some embodiments, the compound of Formula I has a Formula IVa:

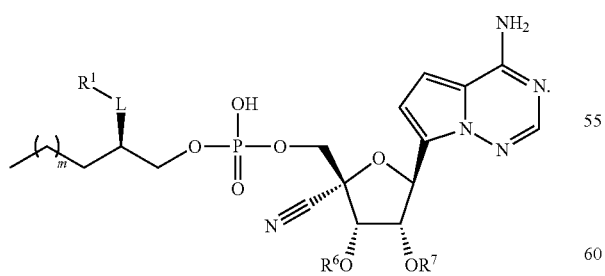

Formula IVa

The description of substituents of Formula I (e.g., $R^1$, $R^6$, $R^7$, L, and m) applies to Formula IVa. In some embodiments, the compounds and pharmaceutically acceptable salts of Formula IVa include the compounds in Table 11 and the pharmaceutically acceptable salts thereof.

TABLE 11
Some Compounds of Formula IVa
Structure
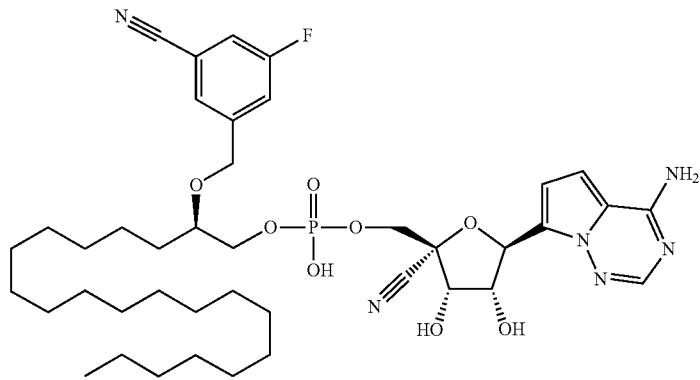
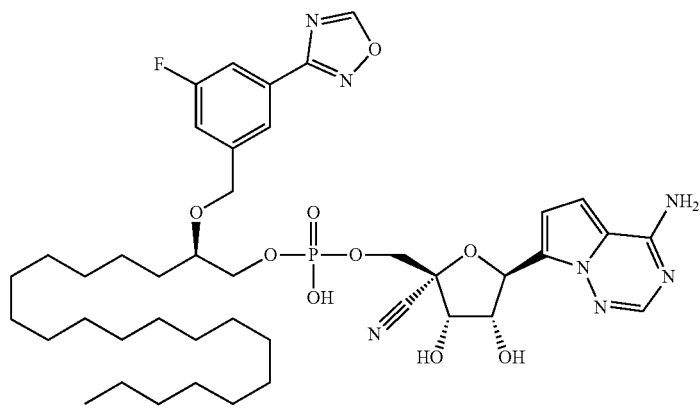 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(-c2ncon2)c1]
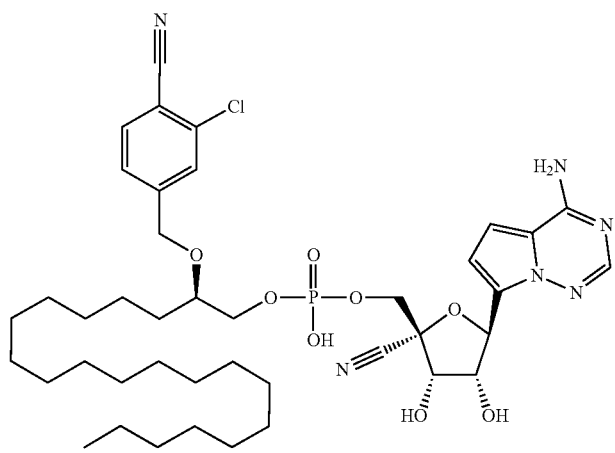 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(Cl)c1]

TABLE 11-continued
Some Compounds of Formula IVa
Structure
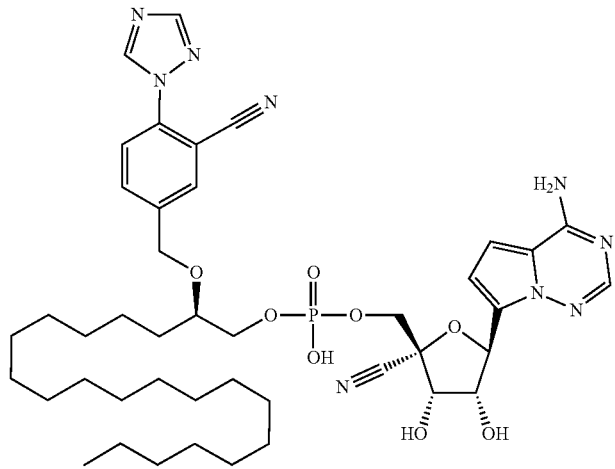 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
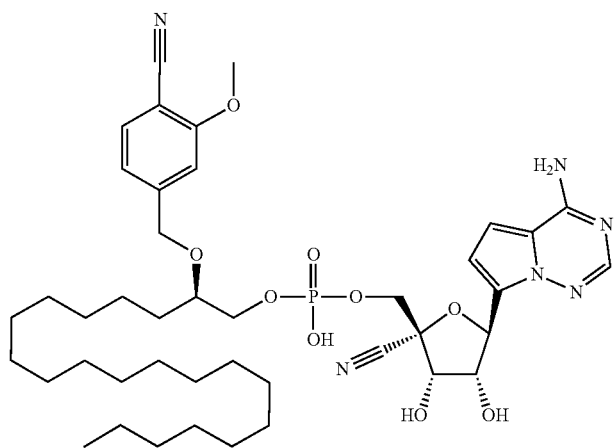 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC)c1]
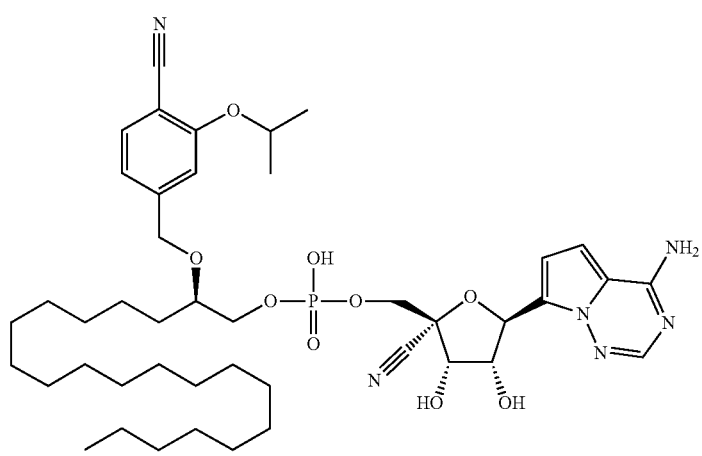 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]

TABLE 11-continued
Some Compounds of Formula IVa
Structure
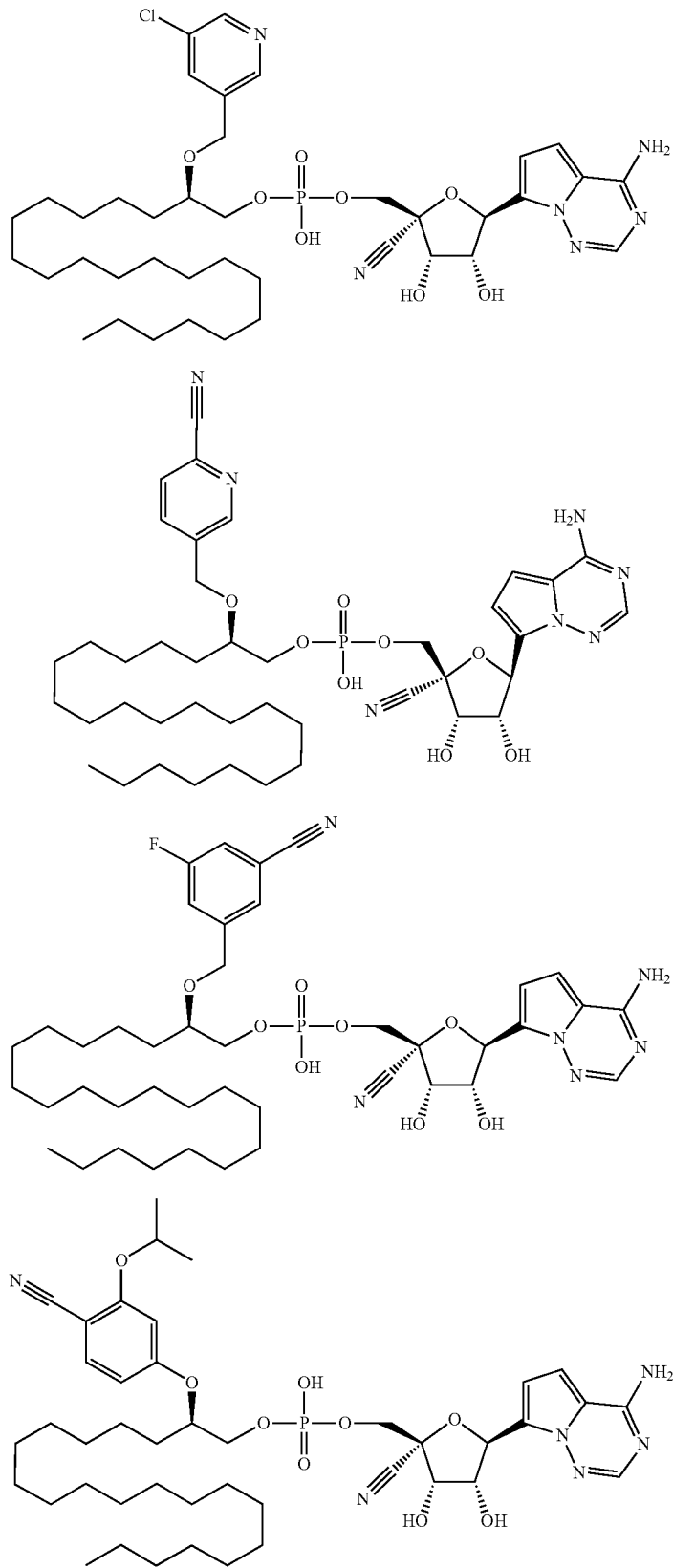

TABLE 11-continued
Some Compounds of Formula IVa
Structure
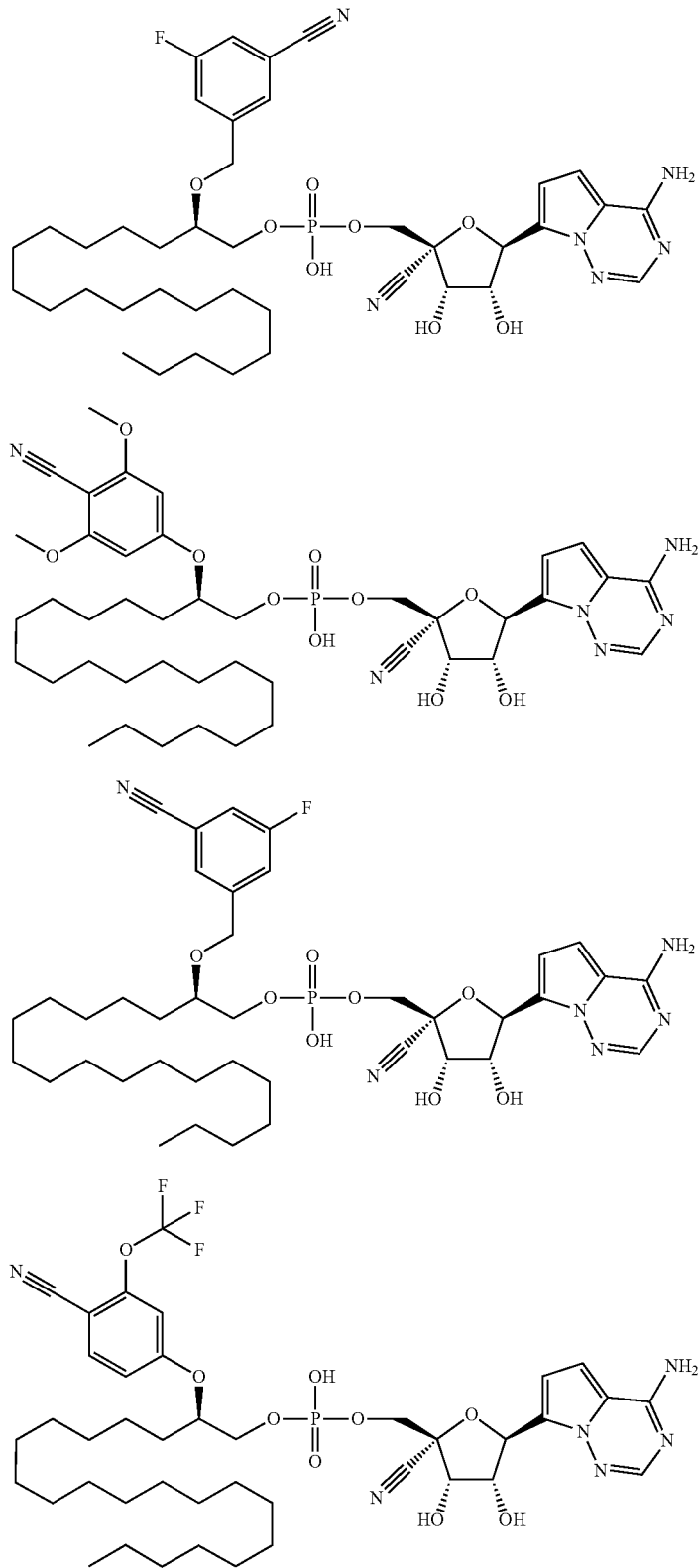

TABLE 11-continued
Some Compounds of Formula IVa
Structure
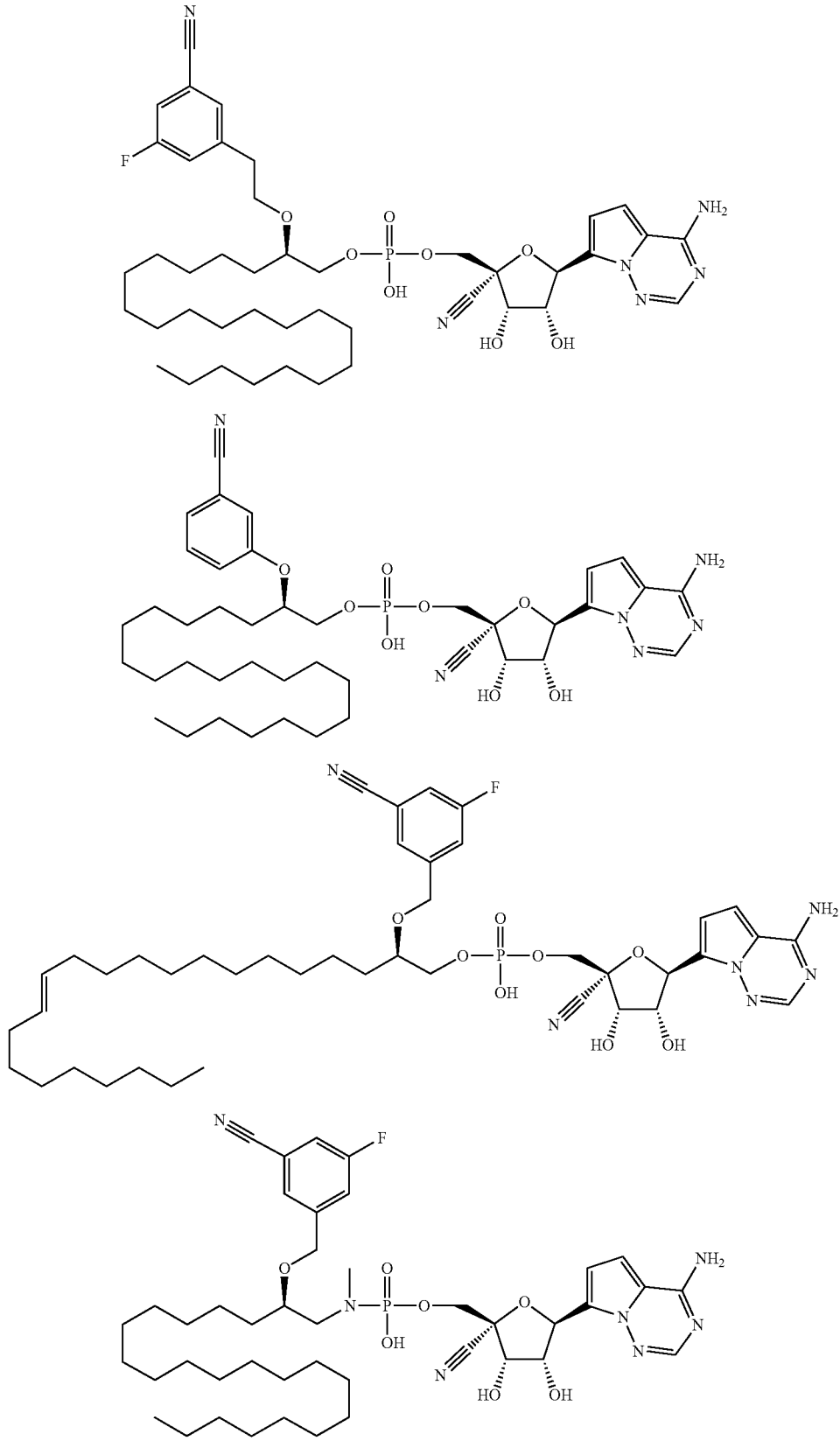

TABLE 11-continued
Some Compounds of Formula IVa
Structure
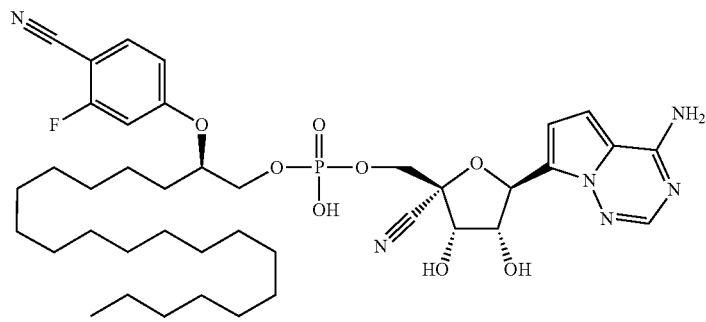 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1]
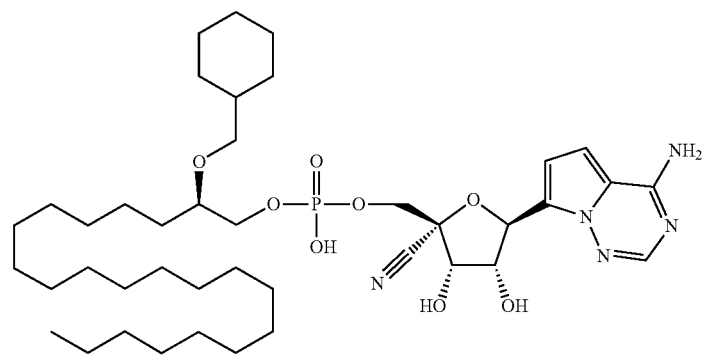 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCC1CCCCC1]
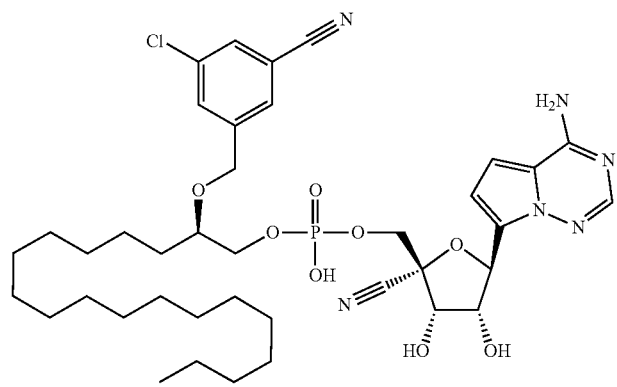 [SMILES: CCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
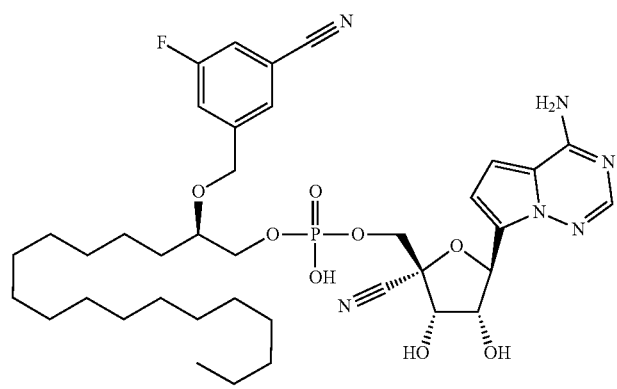 [SMILES: CCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 11-continued
Some Compounds of Formula IVa
Structure
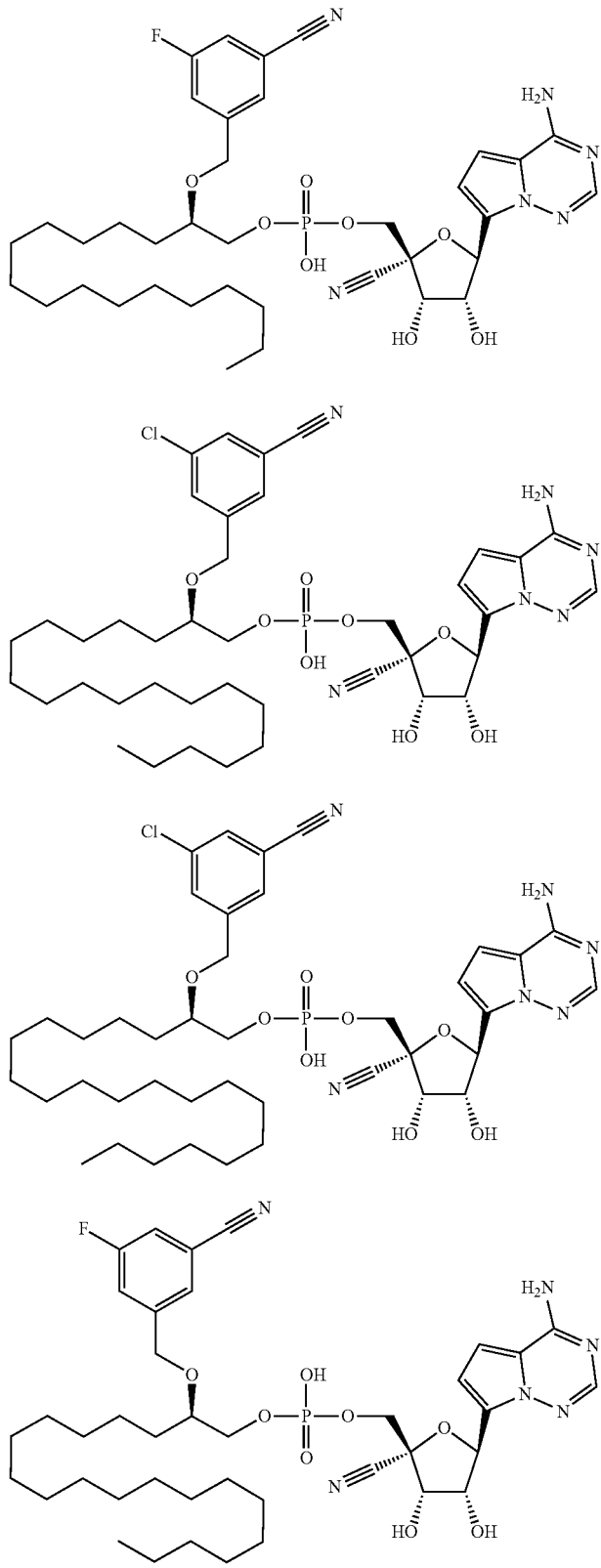

TABLE 11-continued

Some Compounds of Formula IVa
Structure

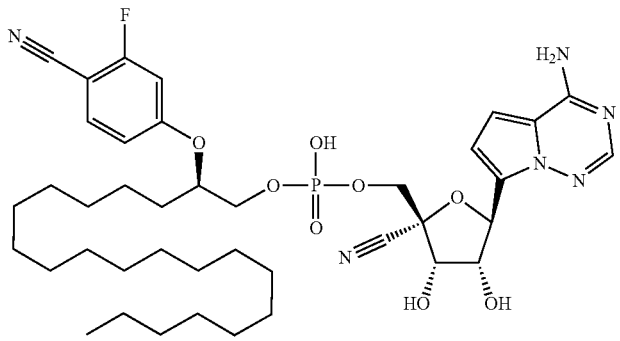 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1]

In some embodiments, the compound of Formula I has a Formula IVb:

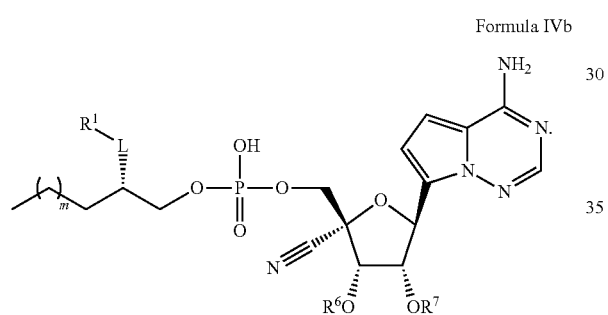

Formula IVb

The description of substituents of Formula I (e.g., $R^1$, $R^6$, $R^7$, L, and m) applies to Formula IVb. In some embodiments, the compounds and pharmaceutically acceptable salts of Formula IVb include the compounds in Table 12 and the pharmaceutically acceptable salts thereof.

TABLE 12

Compounds of Formula IVb
Structure

TABLE 12-continued

Compounds of Formula IVb
Structure

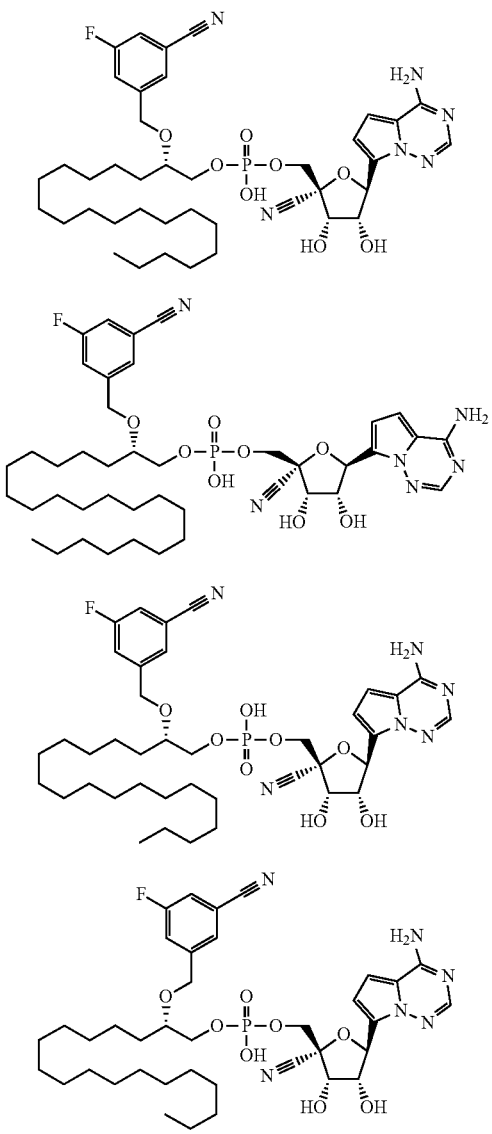

TABLE 12-continued

Compounds of Formula IVb
Structure

In some embodiments, the compound of Formula I has a Formula V:

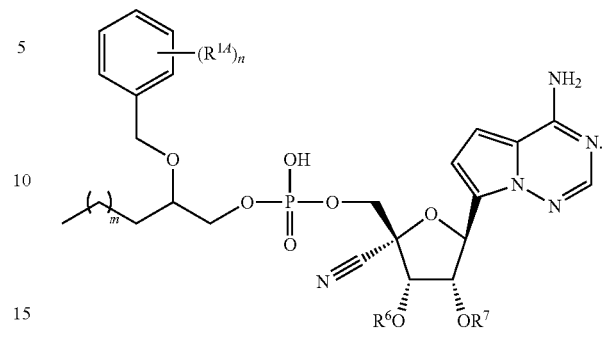

Formula V

The description of substituents of Formula I (e.g., $R^{1A}$, $R^6$, $R^7$, m, and n) applies to Formula V. In some embodiments, the compounds and pharmaceutically acceptable salts of Formula V include the compounds in Table 13 and the pharmaceutically acceptable salts thereof.

TABLE 13

Compounds of Formula V
Structure

TABLE 13-continued

Compounds of Formula V
Structure

TABLE 13-continued
Compounds of Formula V
Structure
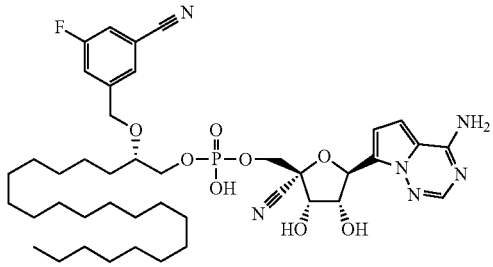 [SMILES: CCCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
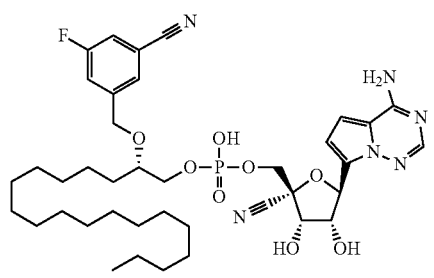 [SMILES: CCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
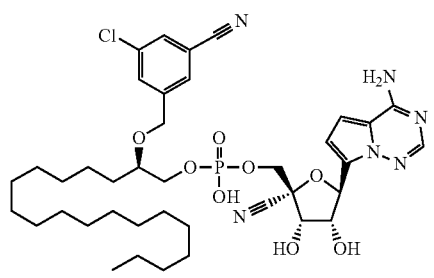 [SMILES: CCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
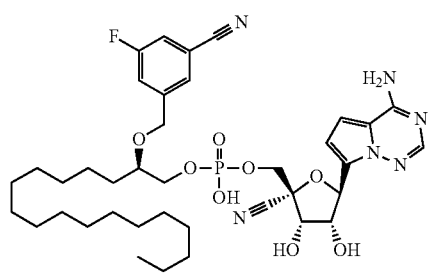 [SMILES: CCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
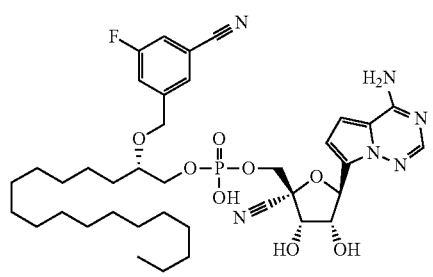 [SMILES: CCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
TABLE 13-continued
Compounds of Formula V
Structure
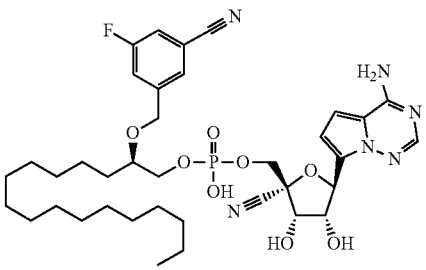 [SMILES: CCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
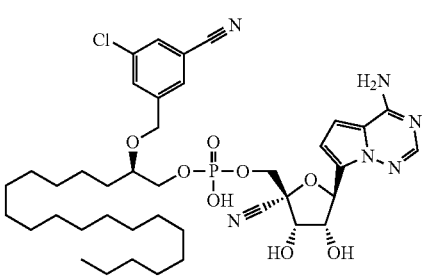 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
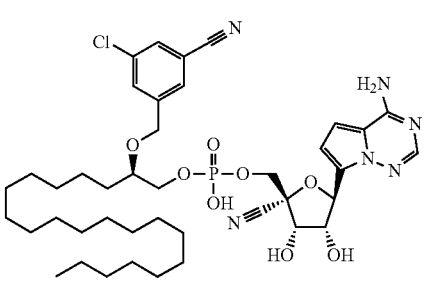 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
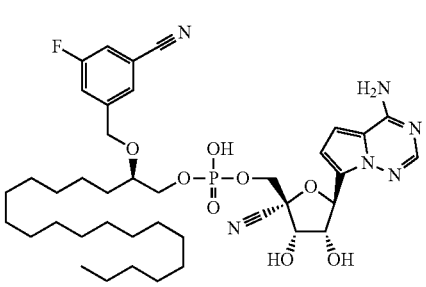 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
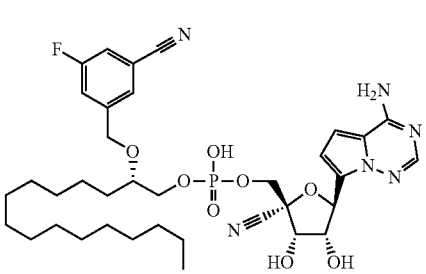 [SMILES: CCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 13-continued

Compounds of Formula V
Structure

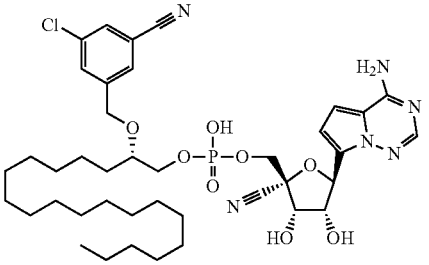 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(Cl)cc(C#N)c1]

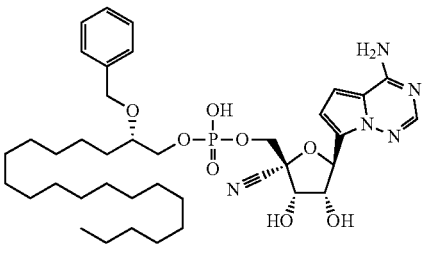 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1ccccc1]

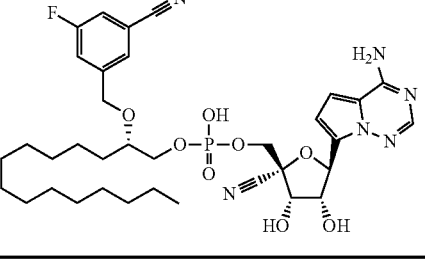

In some embodiments, the compound of Formula I has a Formula Va:

Formula Va

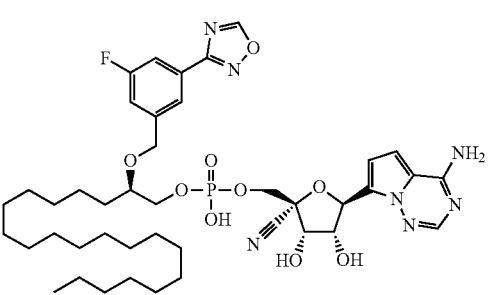 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(-c2ncon2)c1]

The description of substituents of Formula I (e.g., $R^{14}$, $R^6$, $R^7$, m, and n) applies to Formula Va. In some embodiments, the compounds and pharmaceutically acceptable salts of Formula Va include the compounds in Table 14 and the pharmaceutically acceptable salts thereof.

TABLE 14

Compounds of Formula Va
Structure

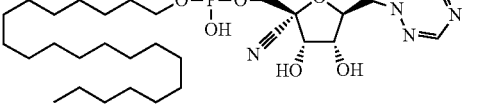

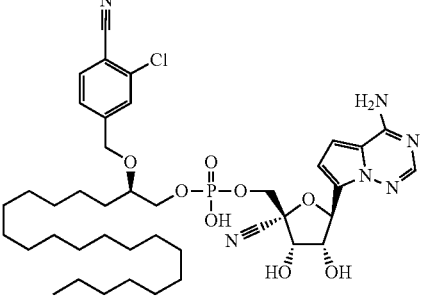

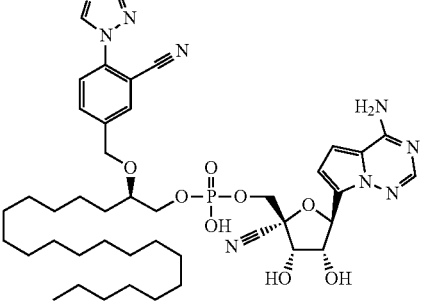

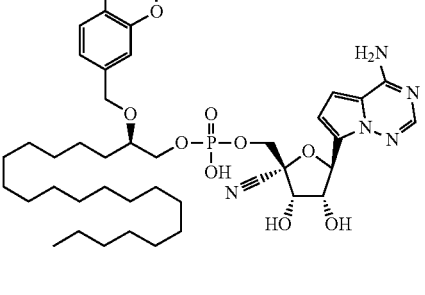

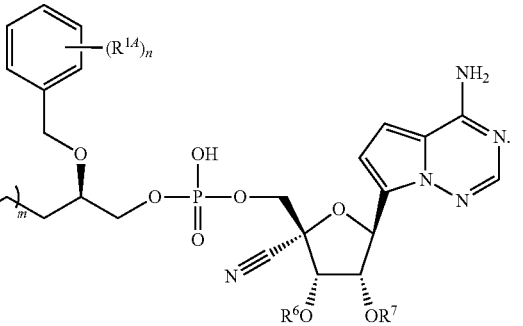

TABLE 14-continued
Compounds of Formula Va
Structure
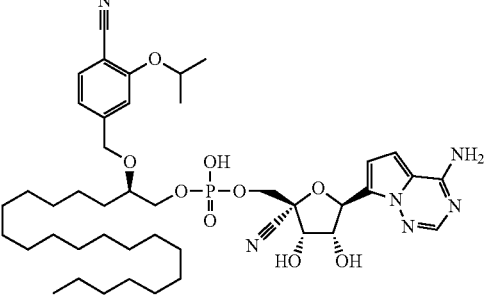
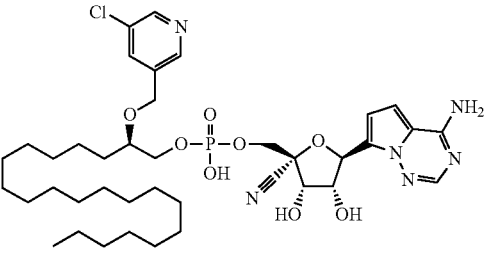 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cncc(Cl)c1]
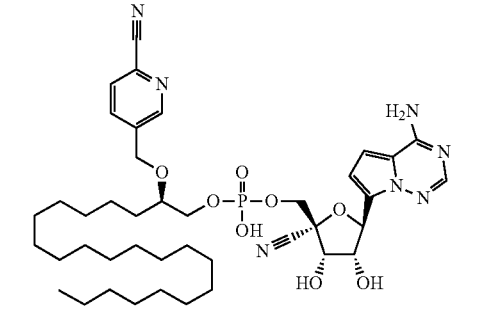 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)nc1]
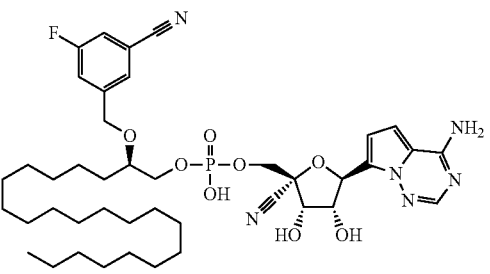 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
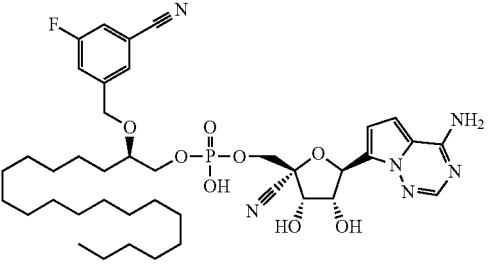 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
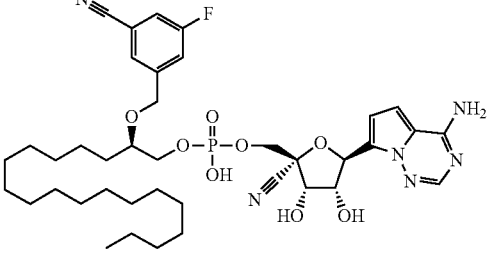
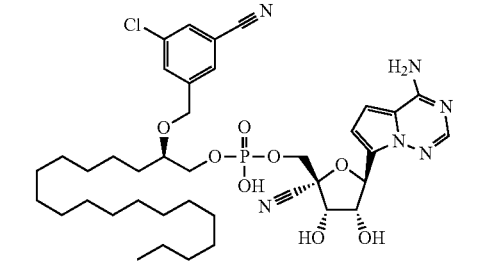 [SMILES: CCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
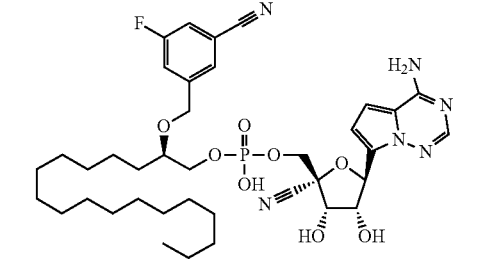 [SMILES: CCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
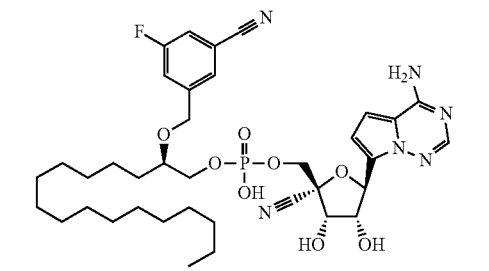
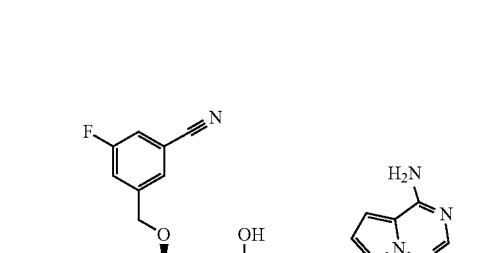

In some embodiments, the compound of Formula I has a Formula Vb:

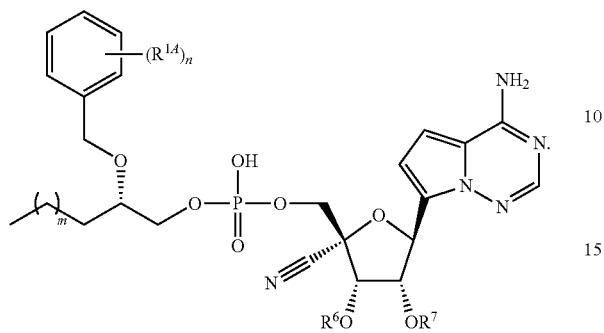

Formula Vb

The description of substituents of Formula I (e.g., $R^{14}$, $R^6$, $R^7$, m, and n) applies to Formula Vb. In some embodiments, the compounds and pharmaceutically acceptable salts of Formula Vb include the compounds in Table 15 and the pharmaceutically acceptable salts thereof.

TABLE 15

Compounds of Formula Vb
Structure

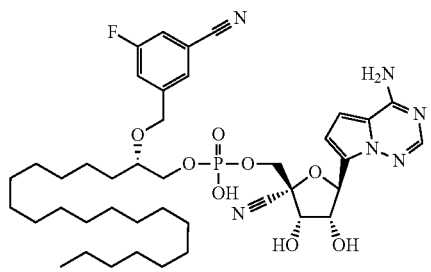 [SMILES: CCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

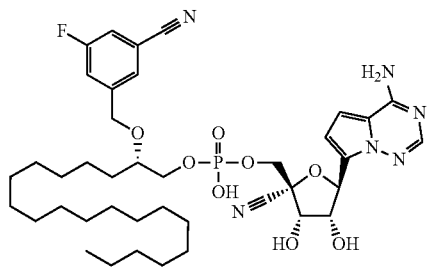 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

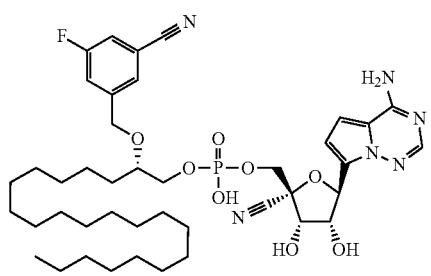 [SMILES: CCCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 15-continued
Compounds of Formula Vb
Structure
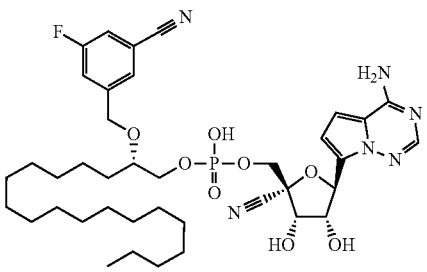 [SMILES: CCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
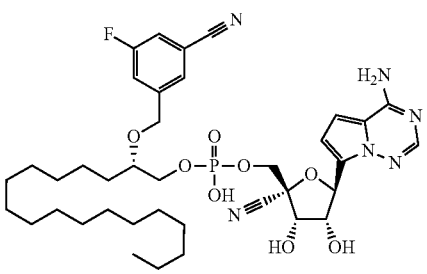 [SMILES: CCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
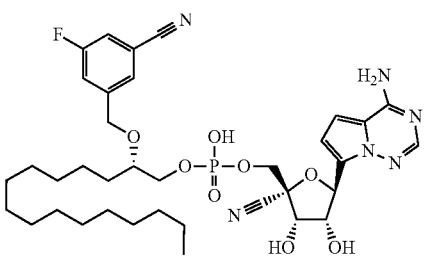 [SMILES: CCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
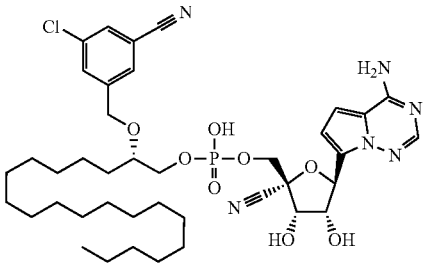 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(Cl)cc(C#N)c1]
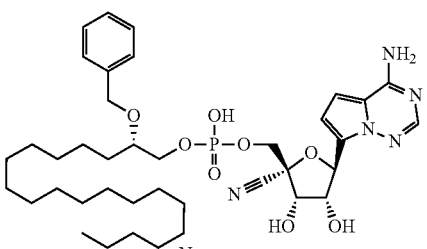 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1ccccc1]
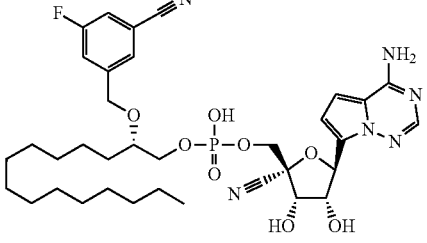

In some embodiments, the compound of Formula I has a Formula VI:

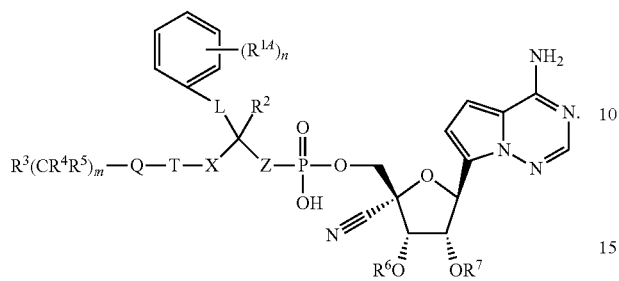

Formula VI

The description of substituents of Formula I (e.g., $R^{14}$, $R^2$, $R^3$, $R^4$, $R^5$, $R^6$, $R^7$, Q, T, X, Z, L, m and n) applies to Formula VI. In some embodiments, the compounds and pharmaceutically acceptable salts of Formula VI include the compounds in Table 16 and the pharmaceutically acceptable salts thereof.

TABLE 16

Some Compounds of Formula VI
Structure

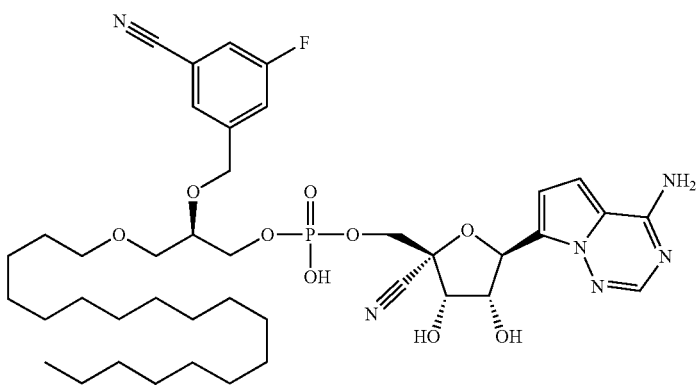 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

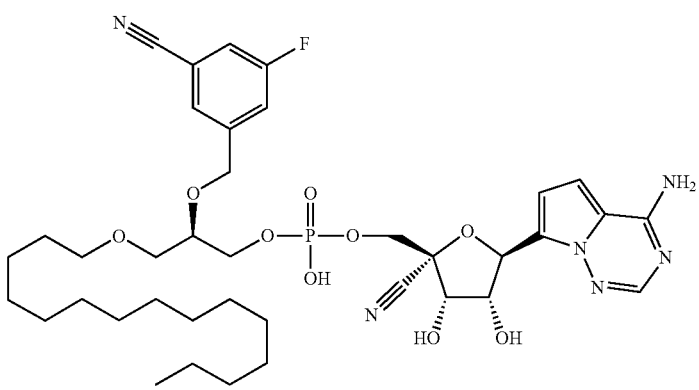 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 16-continued
Some Compounds of Formula VI
Structure
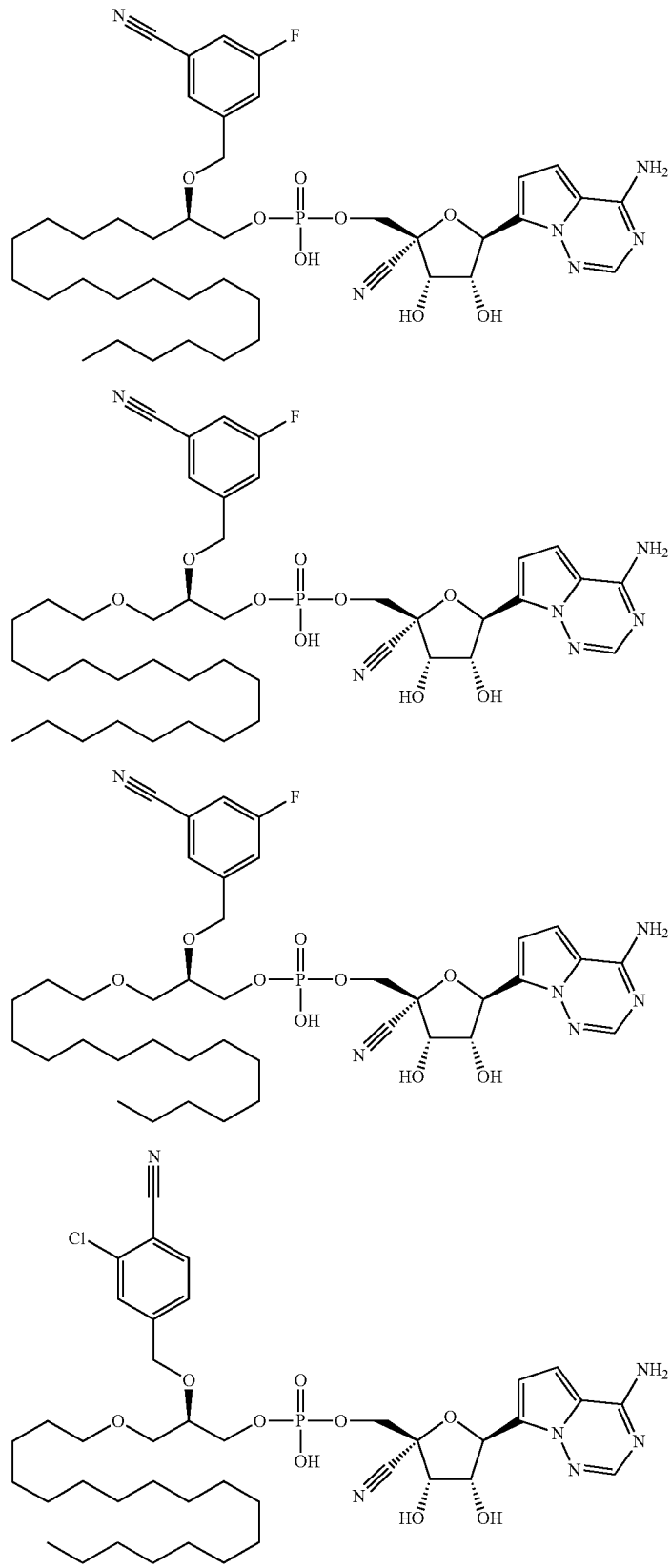

TABLE 16-continued
Some Compounds of Formula VI
Structure
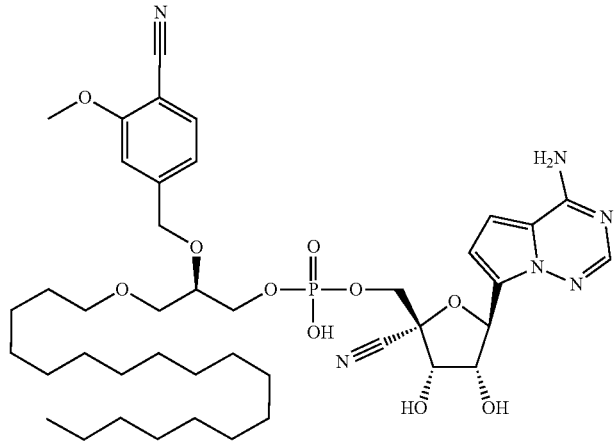 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]
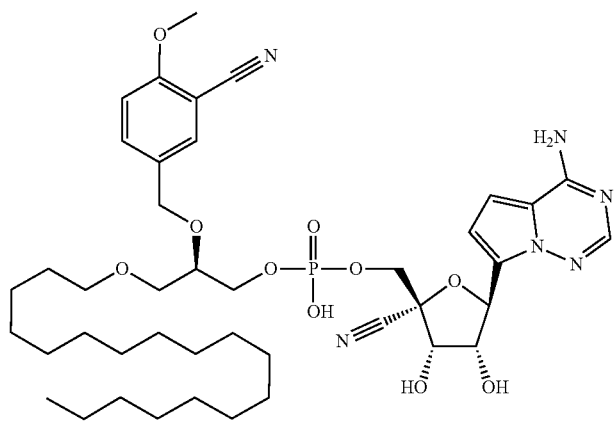 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]
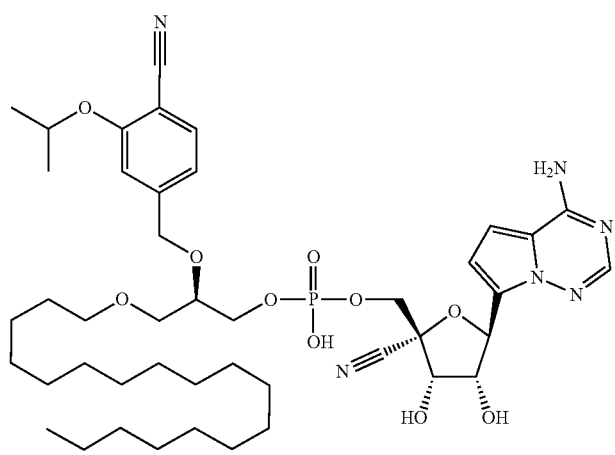 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]

TABLE 16-continued
Some Compounds of Formula VI
Structure
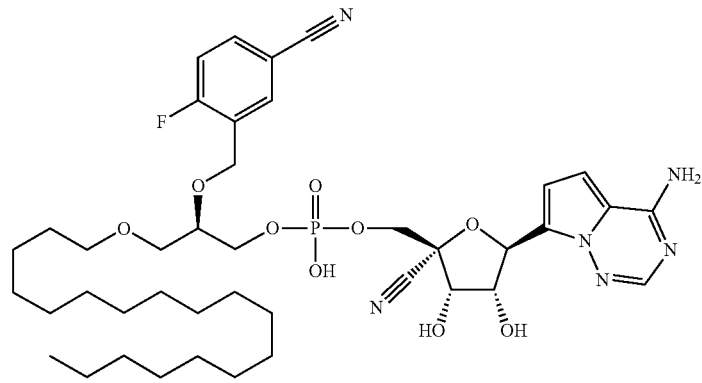 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(C#N)ccc1F]
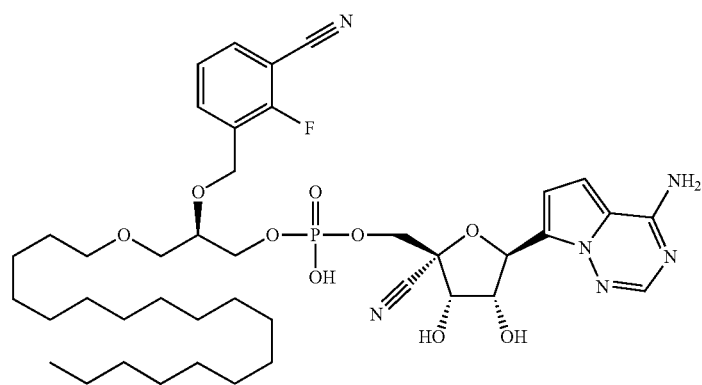 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
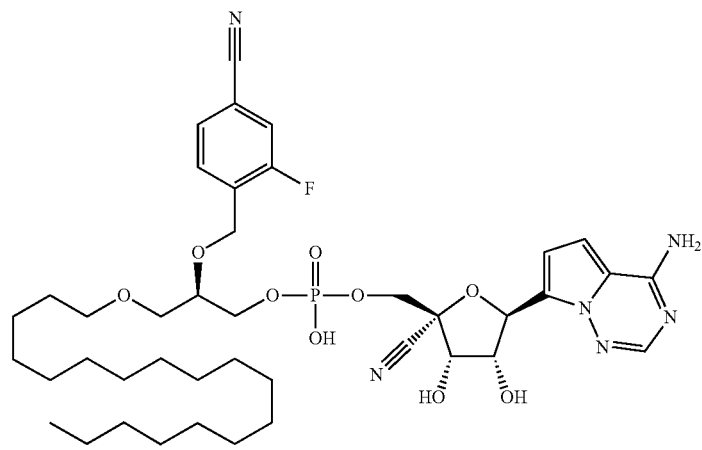 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]

TABLE 16-continued
Some Compounds of Formula VI
Structure
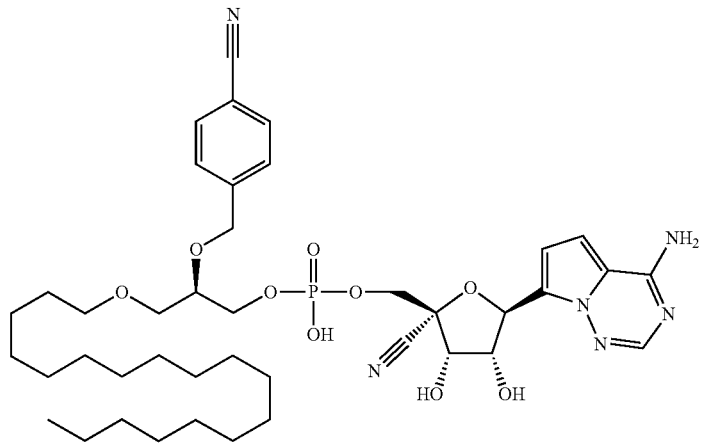 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]
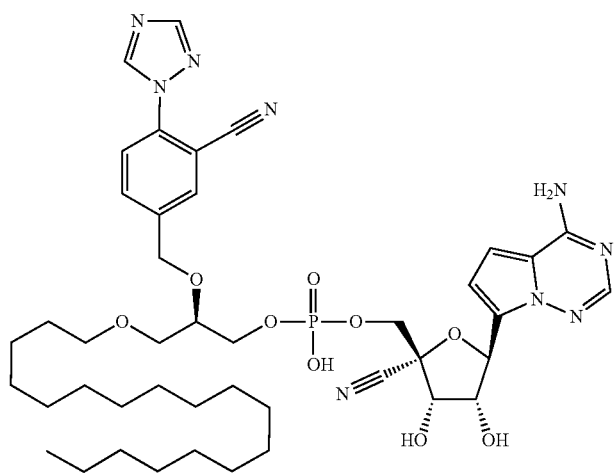 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
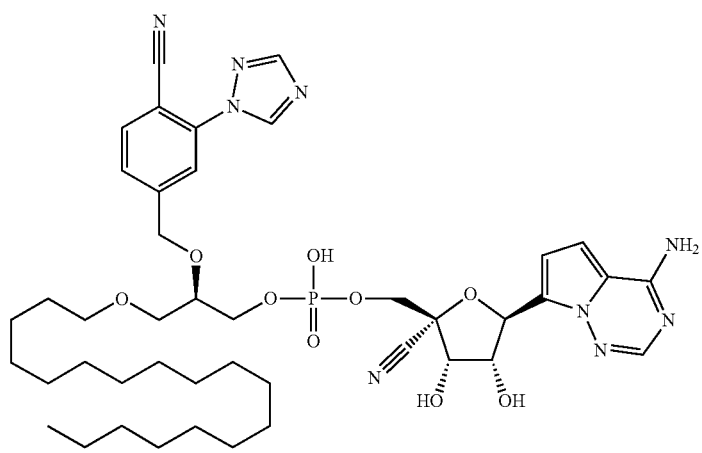 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]

247 248
TABLE 16-continued
Some Compounds of Formula VI
Structure
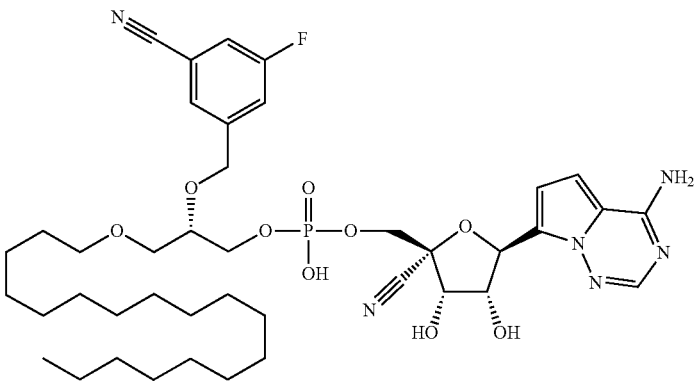 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]
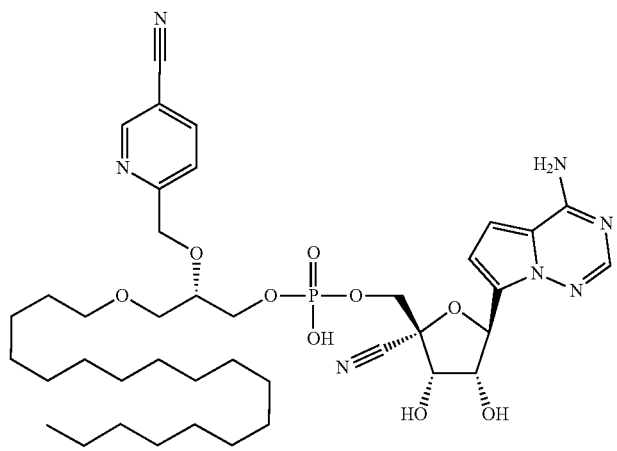 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1]
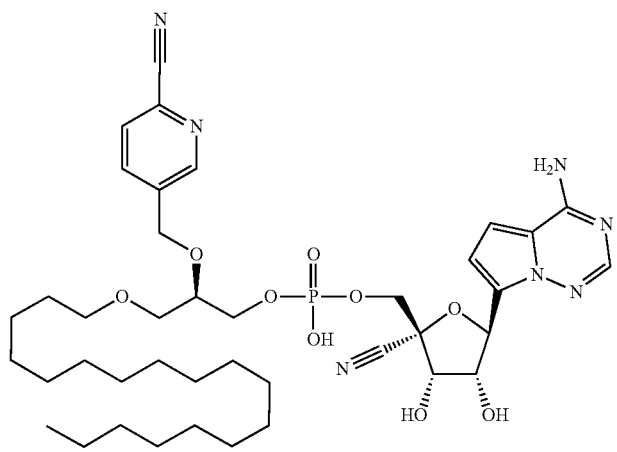

TABLE 16-continued
Some Compounds of Formula VI
Structure
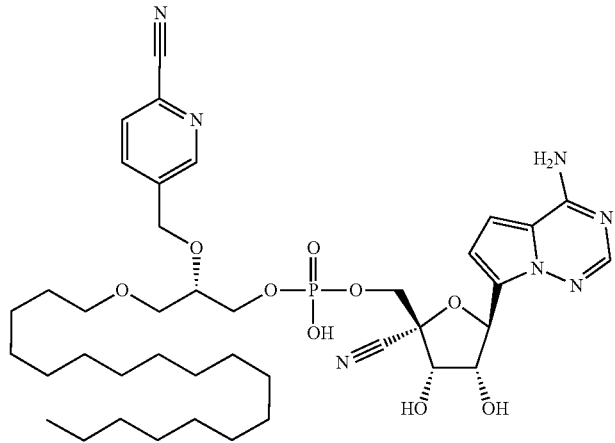 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)nc1]
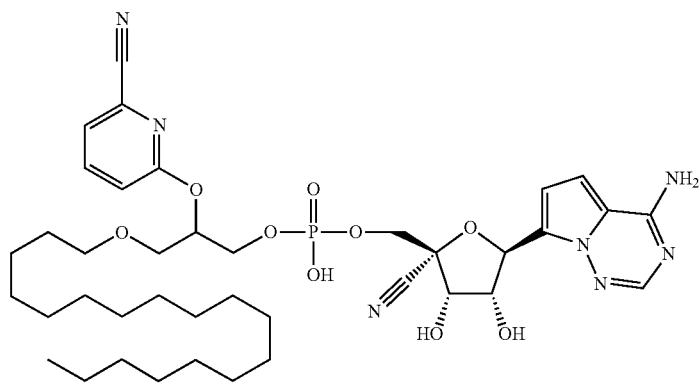 [SMILES: CCCCCCCCCCCCCCCCCCOCC(COP(=O)(O)OC[C@@]1(C#N)O[C@@H](c2ccc3c(N)ncnn23)[C@H](O)[C@@H]1O)Oc1cccc(C#N)n1]
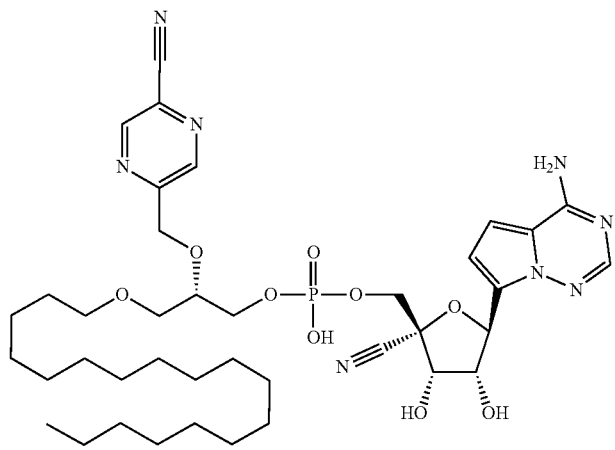 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cnc(C#N)cn1]

TABLE 16-continued
Some Compounds of Formula VI
Structure
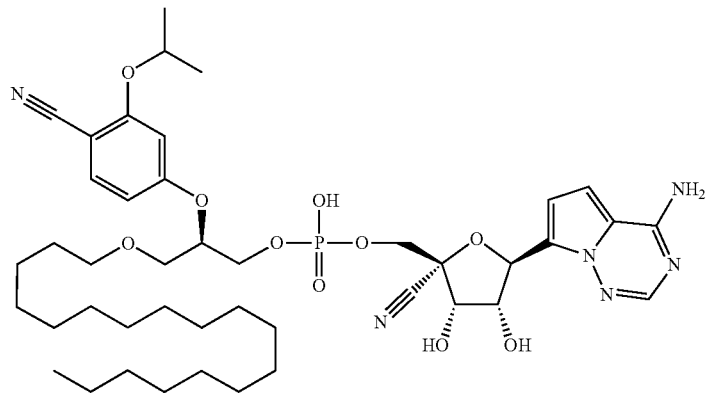 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(OC(C)C)c1]
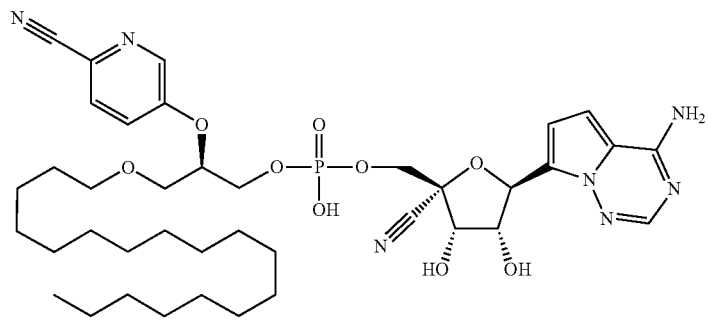 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)nc1]
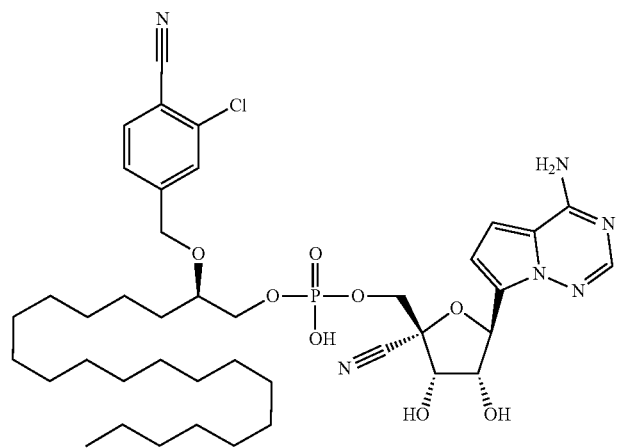 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(Cl)c1]

TABLE 16-continued
Some Compounds of Formula VI
Structure
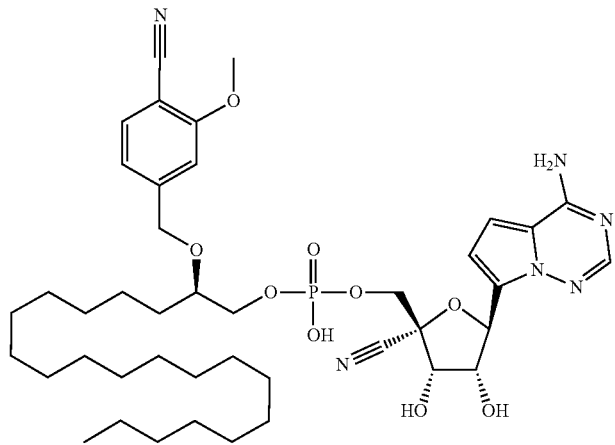 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC)c1]
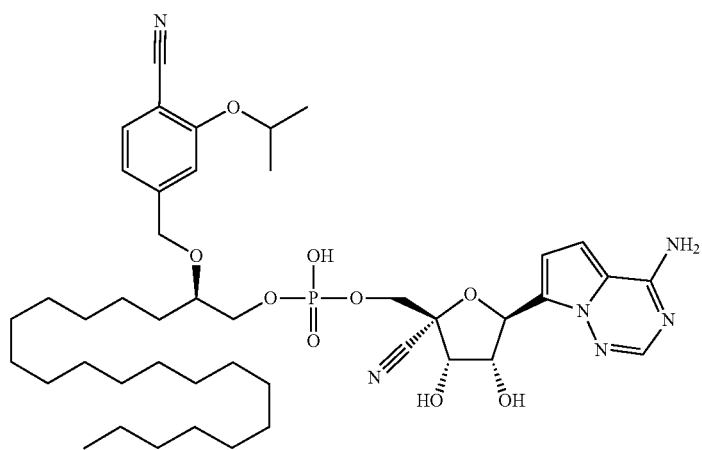 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
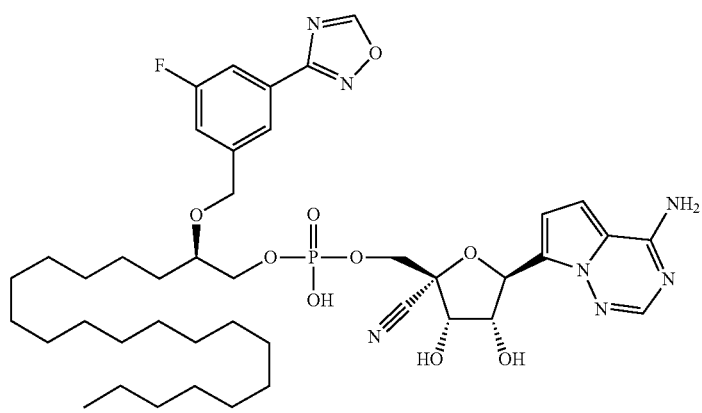 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(-c2ncon2)c1]

TABLE 16-continued
Some Compounds of Formula VI
Structure
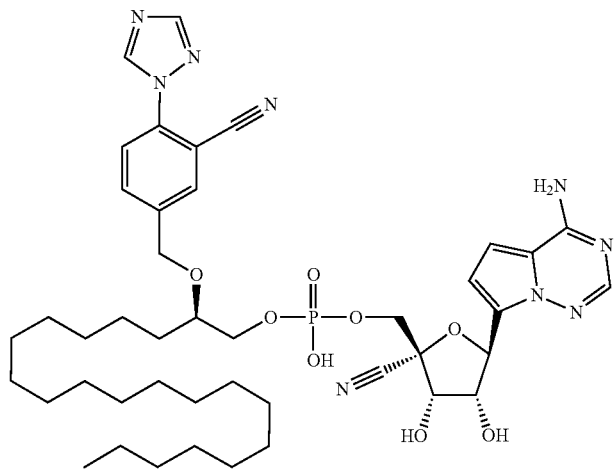 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
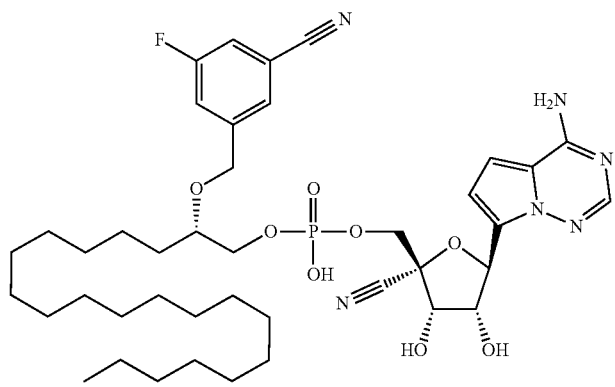 [SMILES: CCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
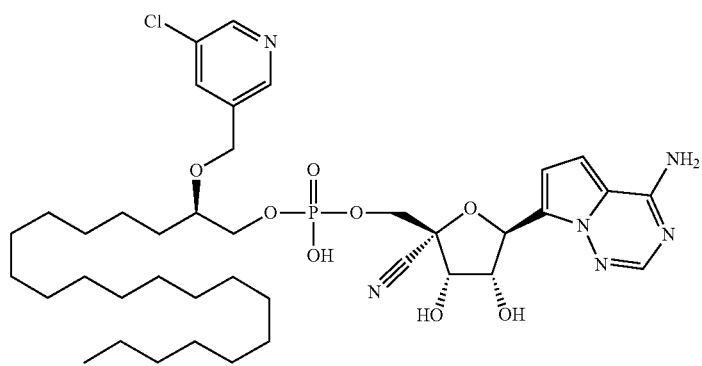 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cncc(Cl)c1]

TABLE 16-continued
Some Compounds of Formula VI
Structure
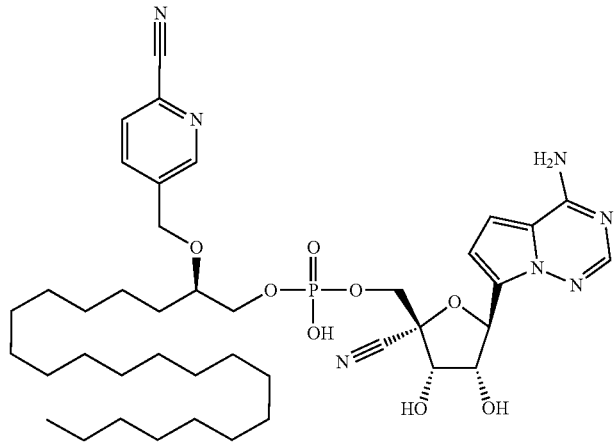 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)nc1]
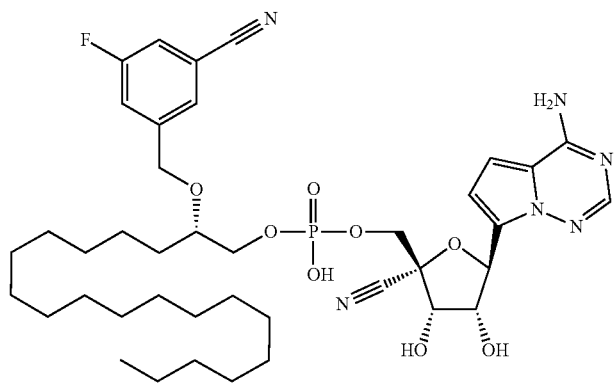 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
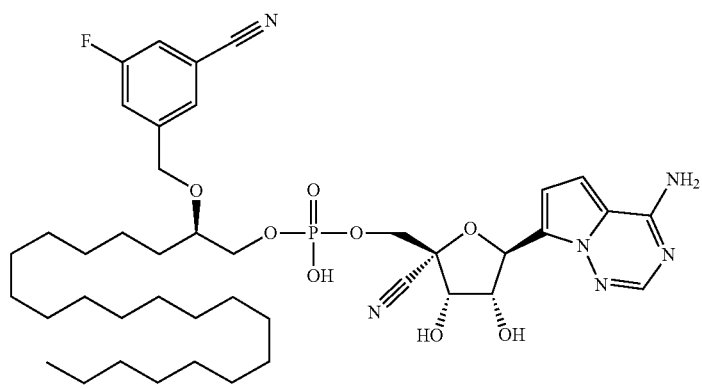 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 16-continued
Some Compounds of Formula VI
Structure
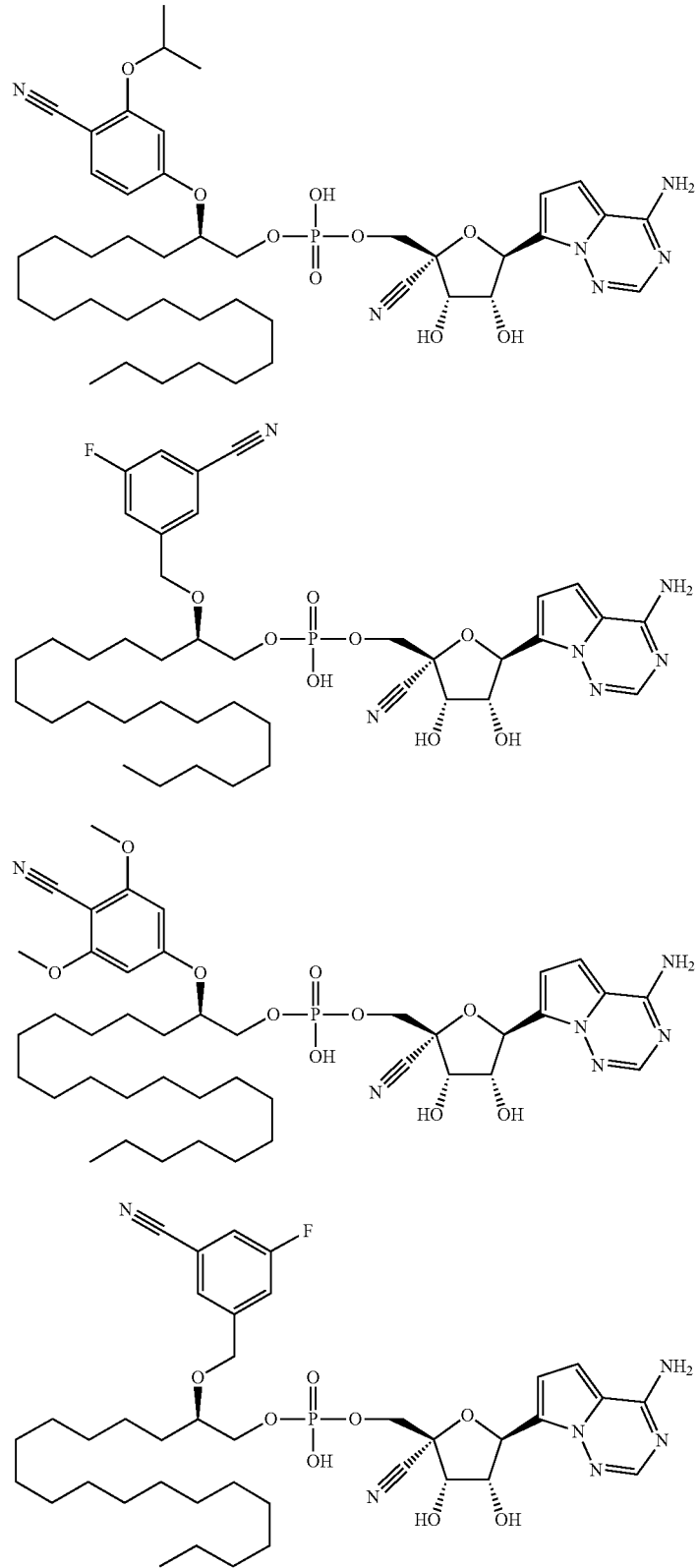

TABLE 16-continued
Some Compounds of Formula VI
Structure
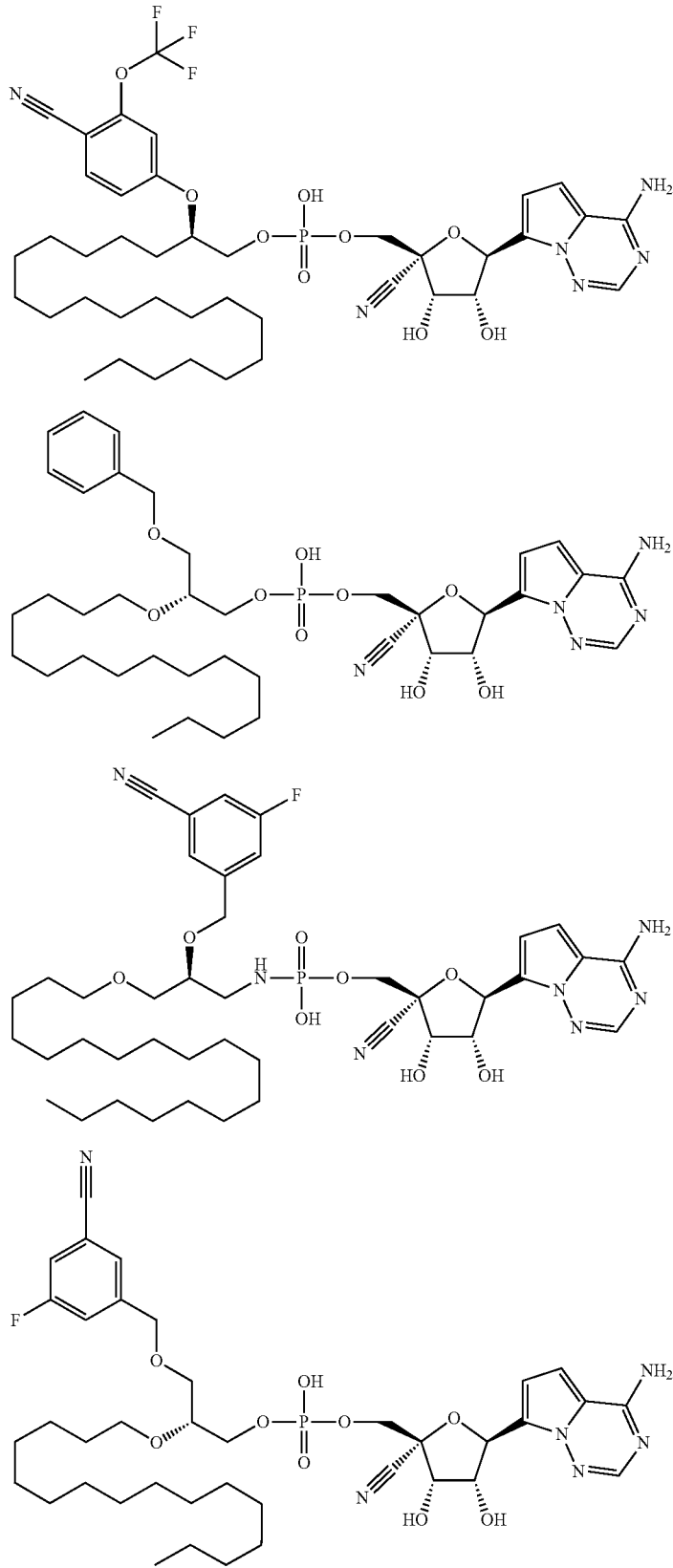

TABLE 16-continued
Some Compounds of Formula VI
Structure
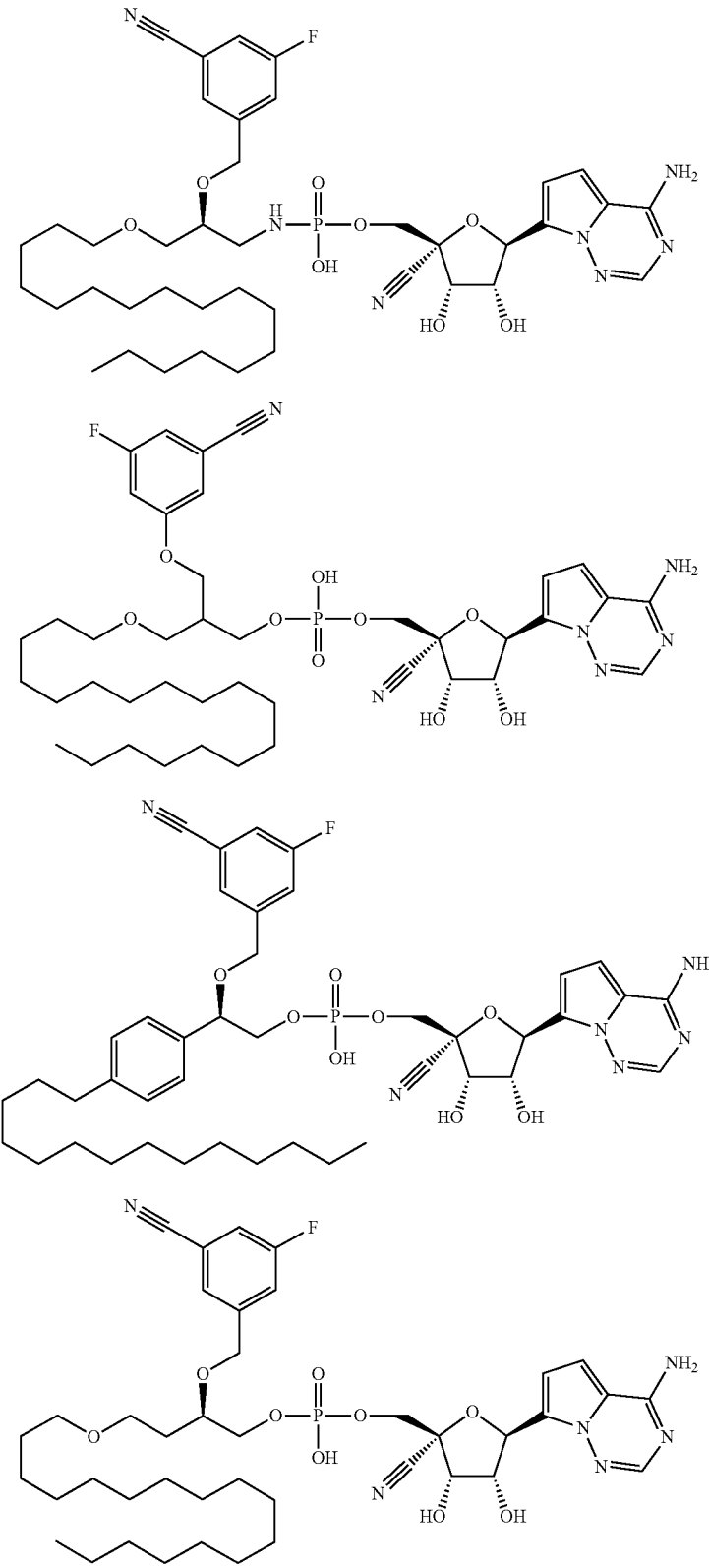

TABLE 16-continued
Some Compounds of Formula VI
Structure
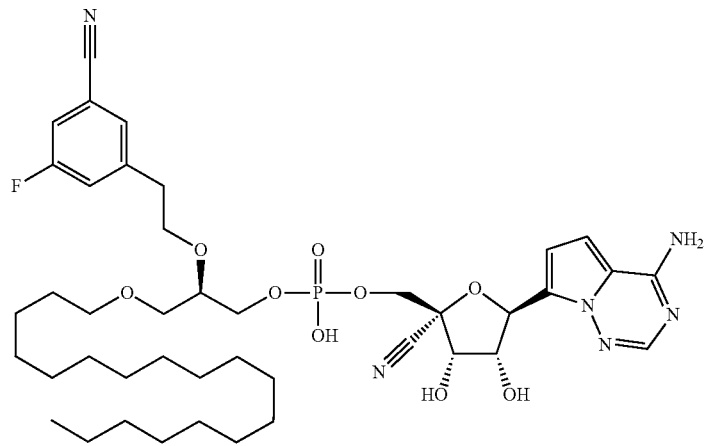 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCCc1cc(F)cc(C#N)c1]
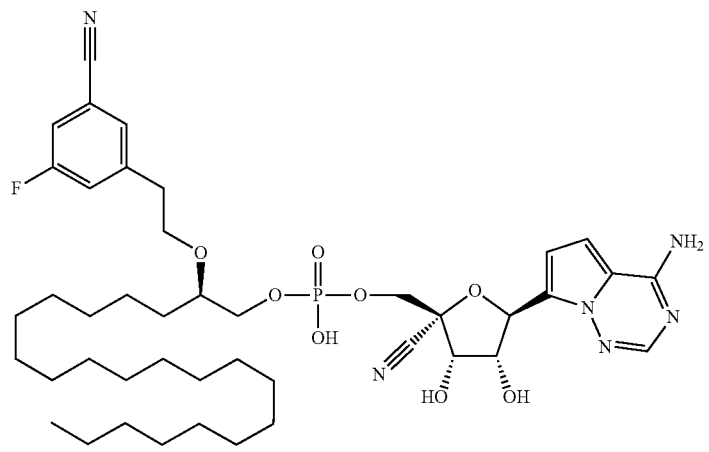 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCCc1cc(F)cc(C#N)c1]
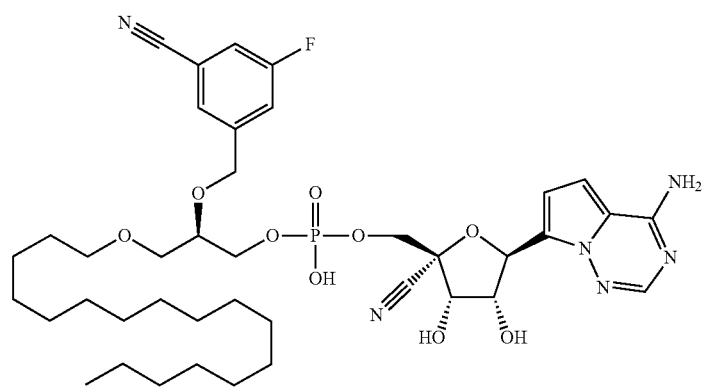 [SMILES: CCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 16-continued
Some Compounds of Formula VI
Structure
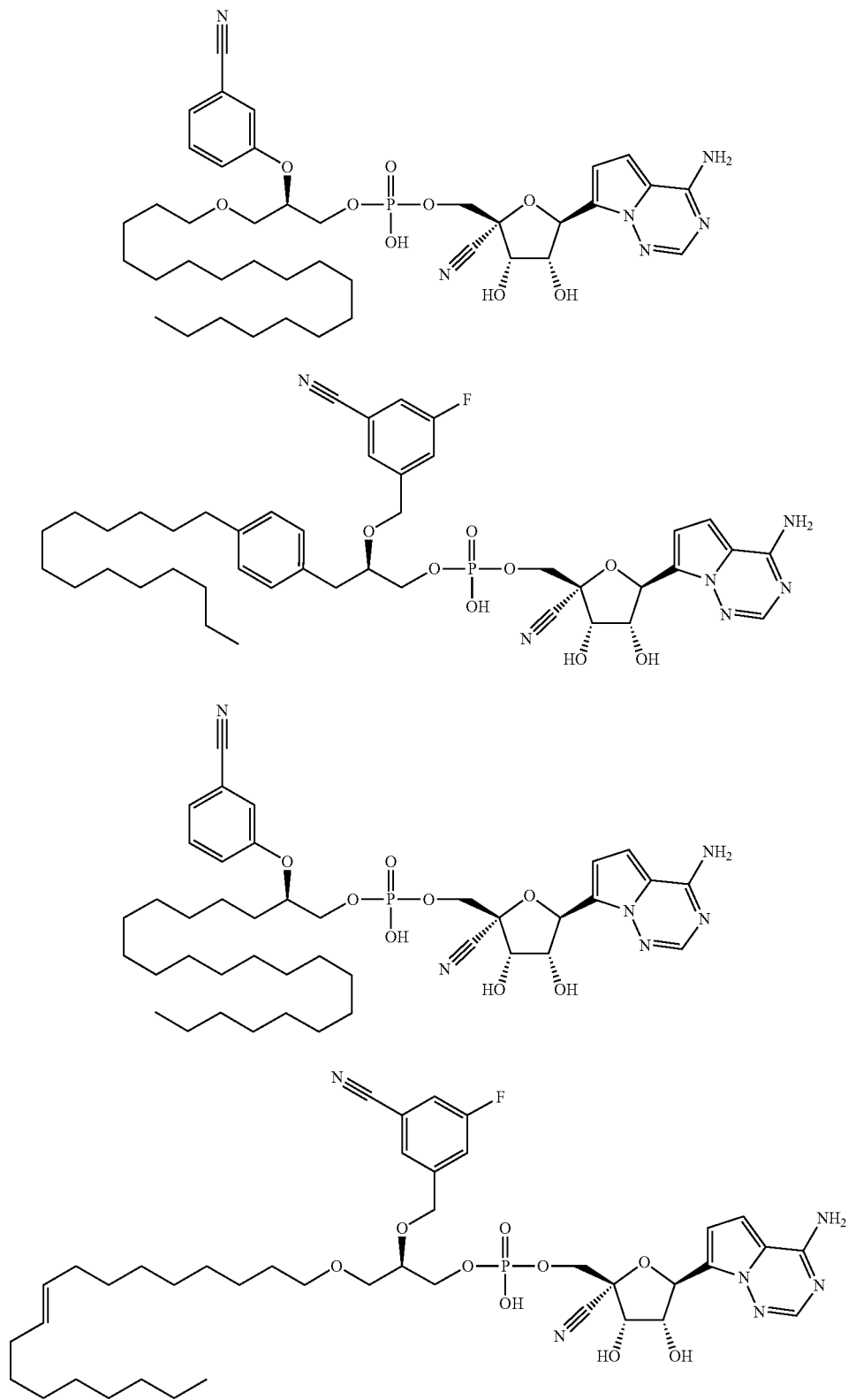

TABLE 16-continued
Some Compounds of Formula VI
Structure
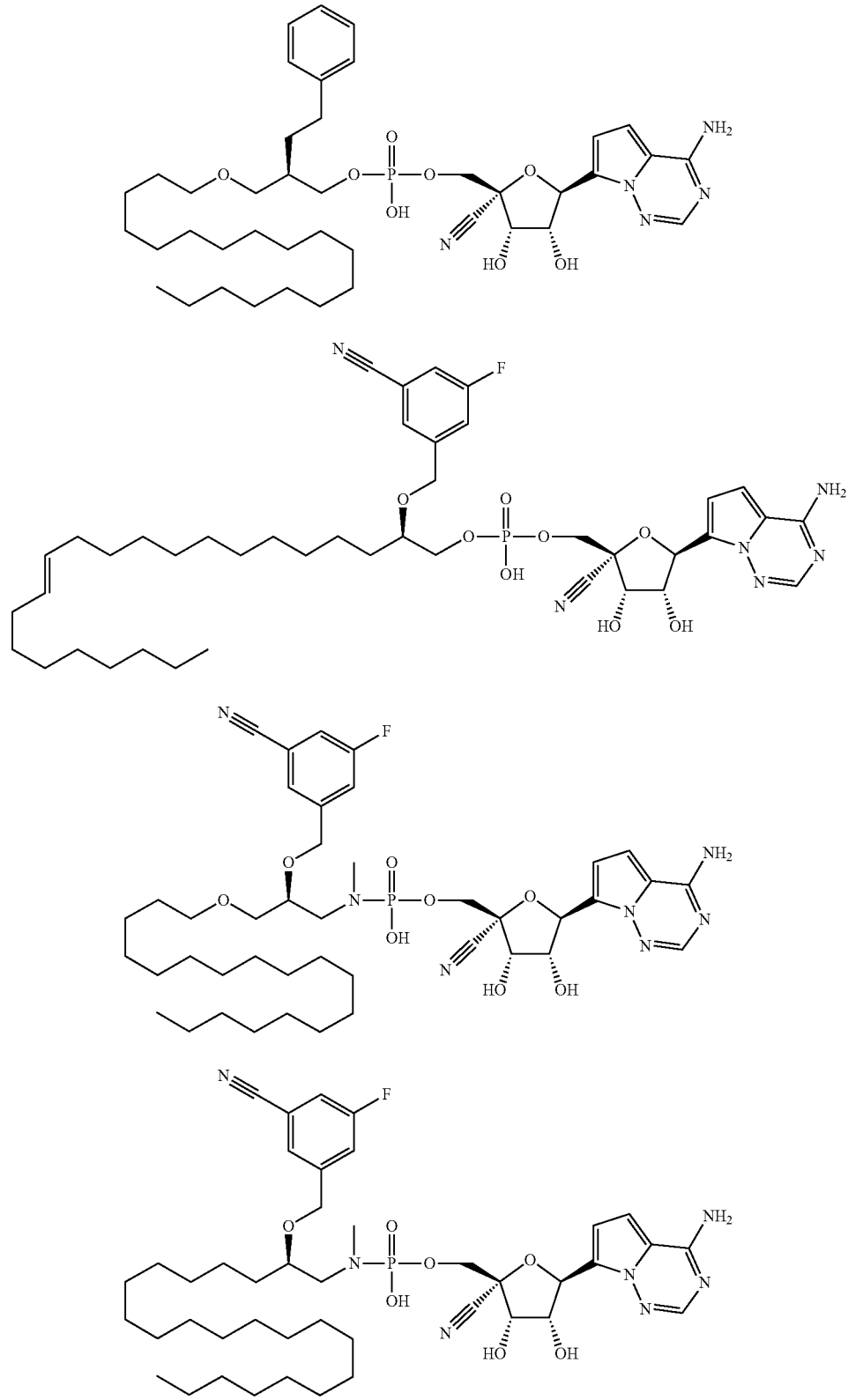

TABLE 16-continued
Some Compounds of Formula VI
Structure
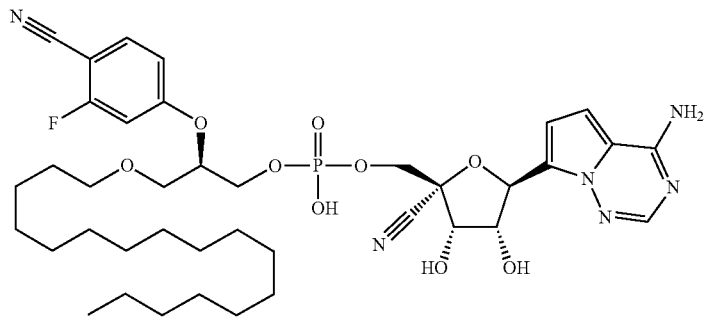 [SMILES: CCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(F)c1]
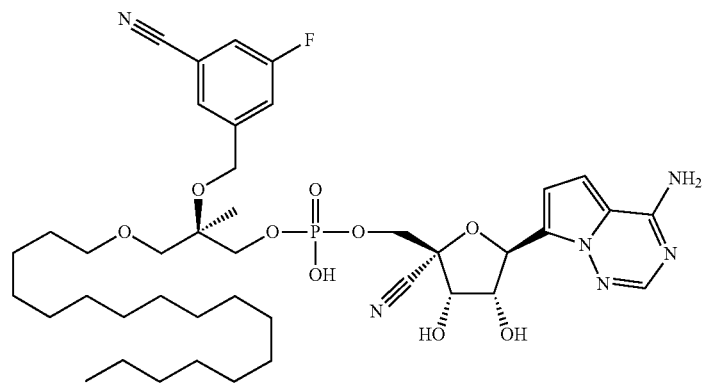 [SMILES: CCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]
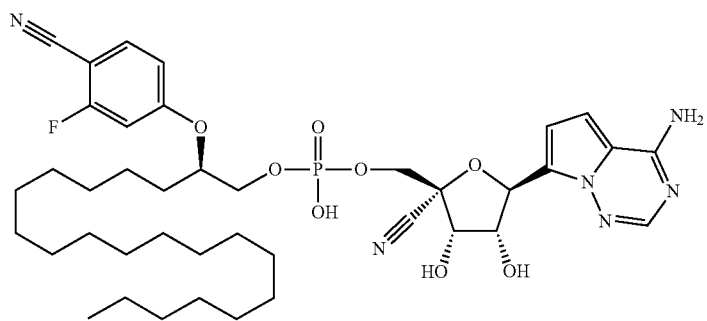 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1]
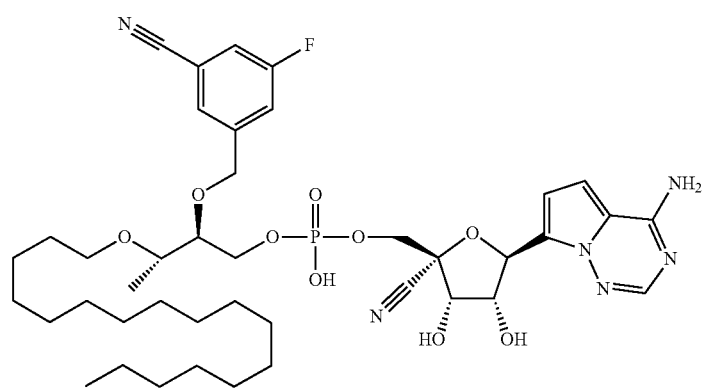 [SMILES: CCCCCCCCCCCCCCCCCO[C@@H](C)[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 16-continued
Some Compounds of Formula VI
Structure
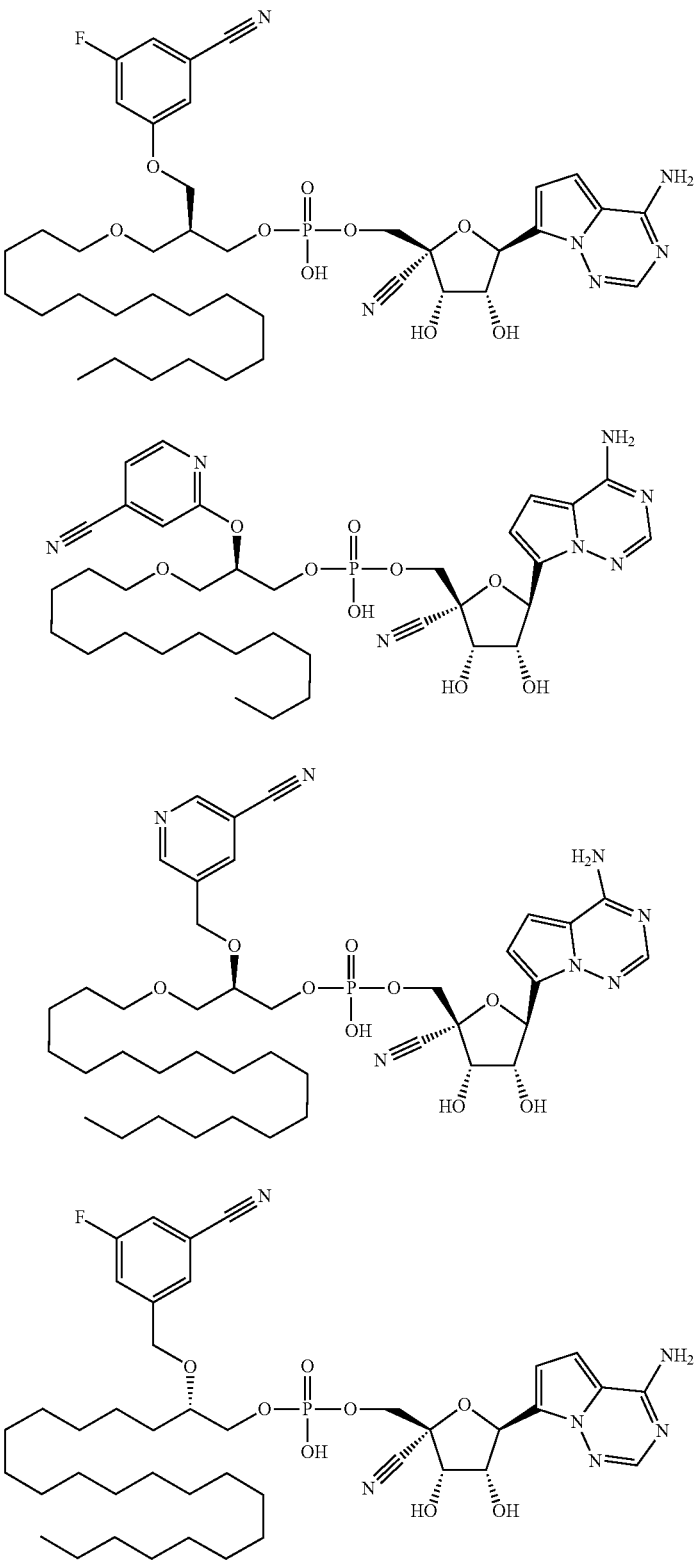

TABLE 16-continued
Some Compounds of Formula VI
Structure
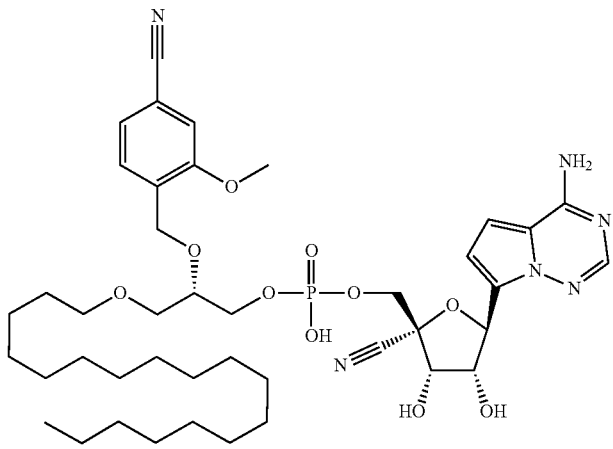 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cc1OC]
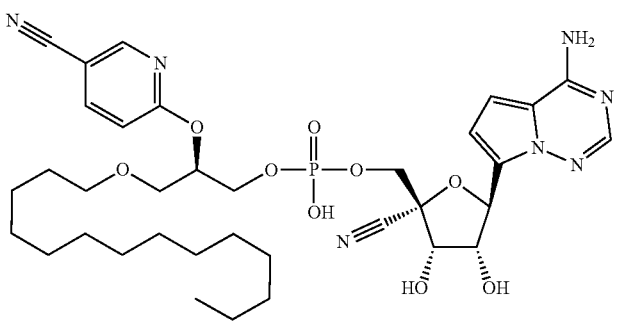 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)cn1]
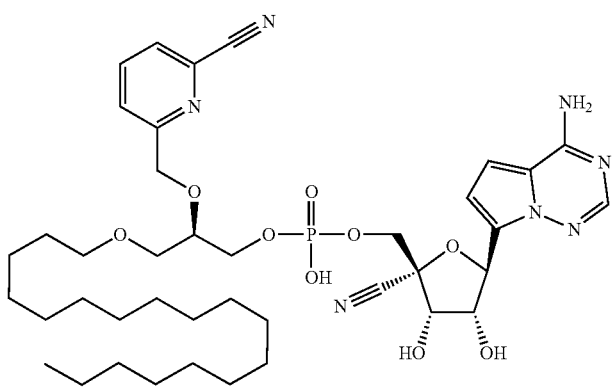 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)n1]
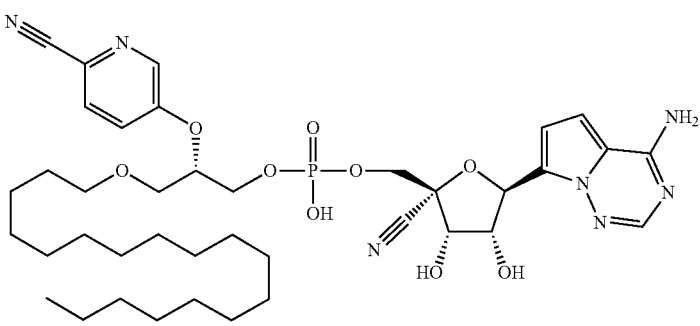 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)Oc1ccc(C#N)nc1]

TABLE 16-continued
Some Compounds of Formula VI
Structure
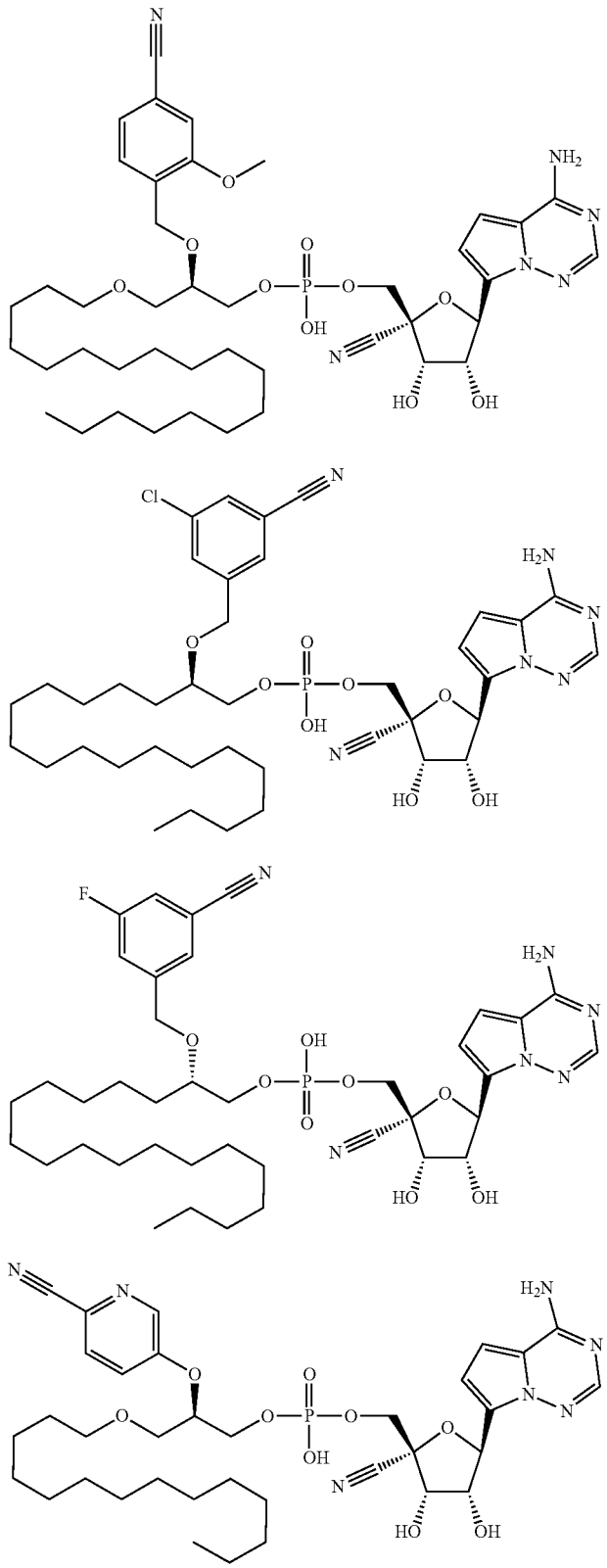

TABLE 16-continued
Some Compounds of Formula VI
Structure
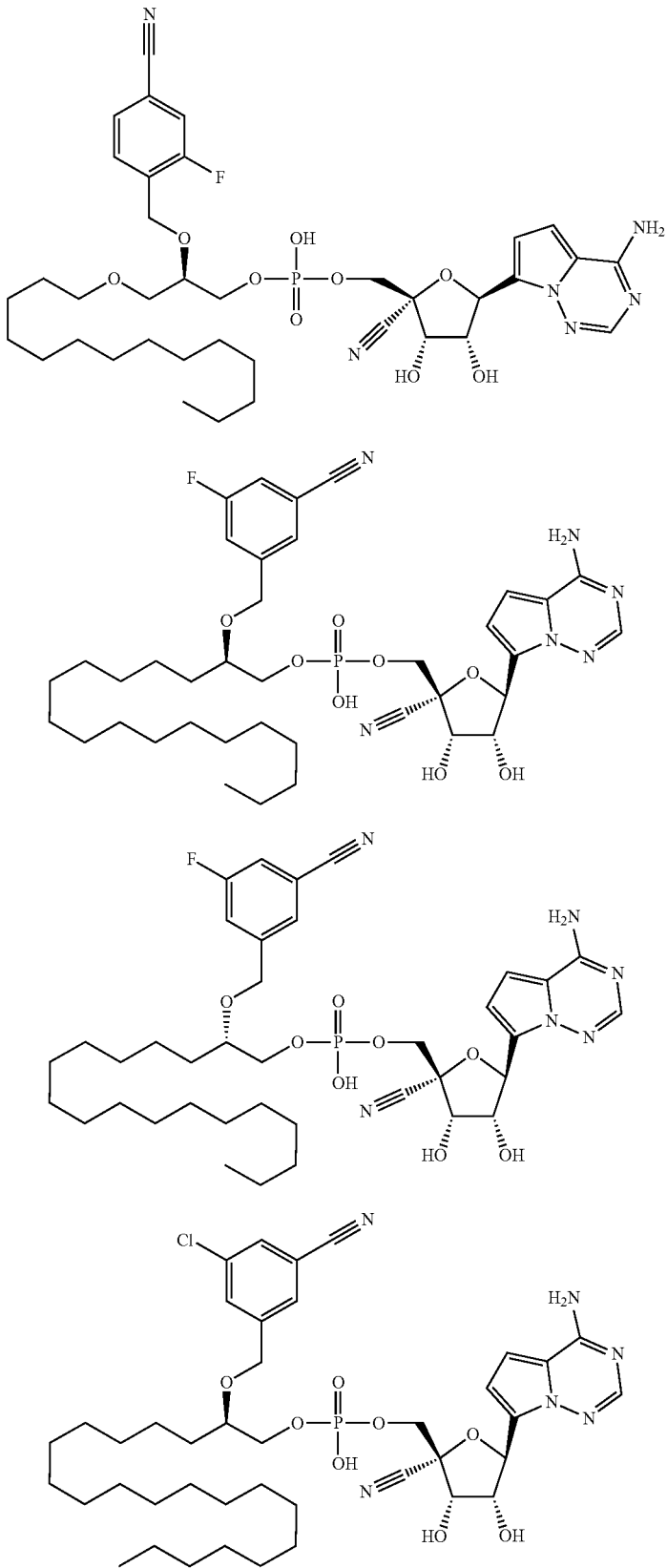

TABLE 16-continued
Some Compounds of Formula VI
Structure
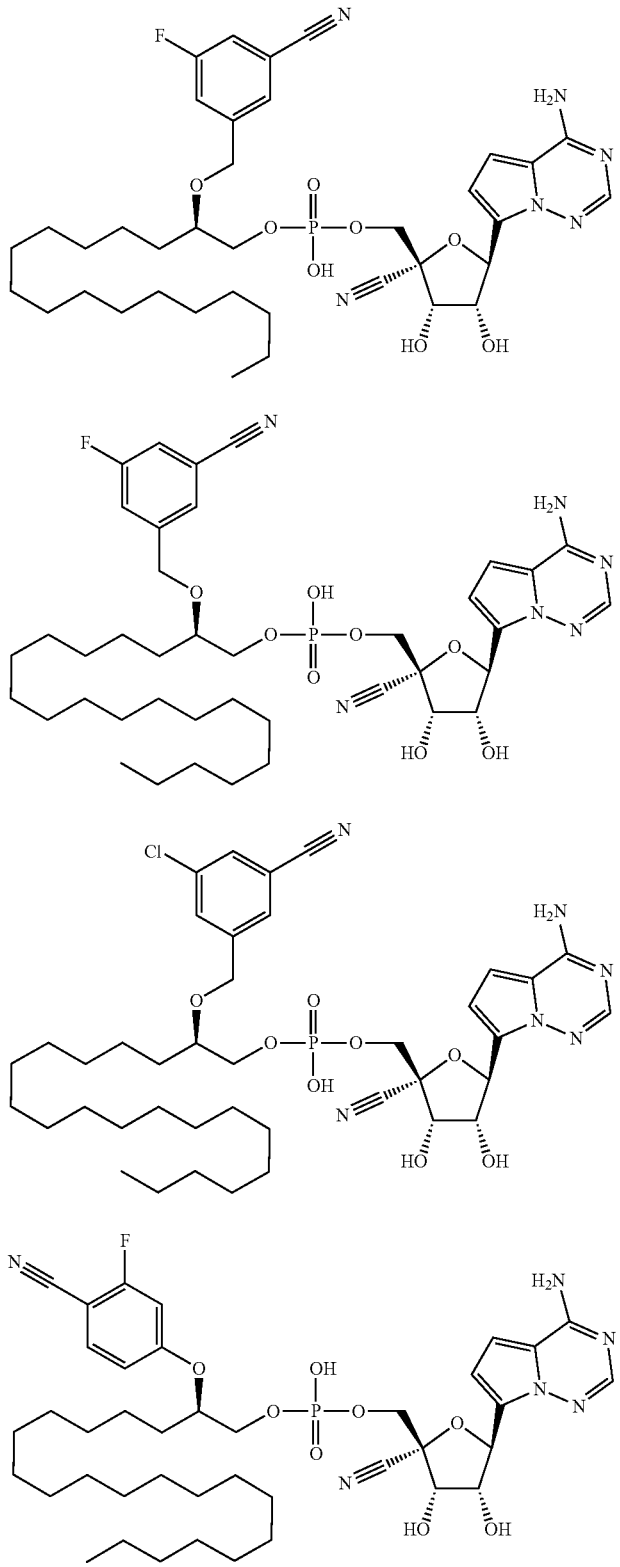

TABLE 16-continued
Some Compounds of Formula VI
Structure
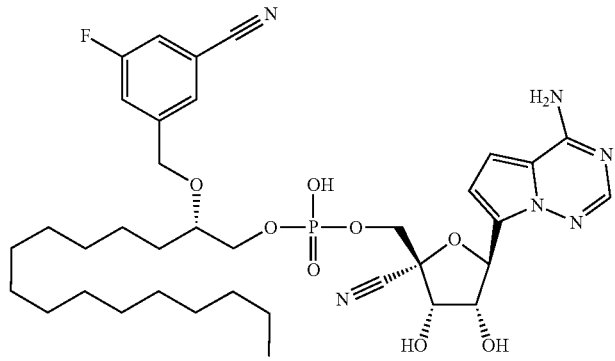 [SMILES: CCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
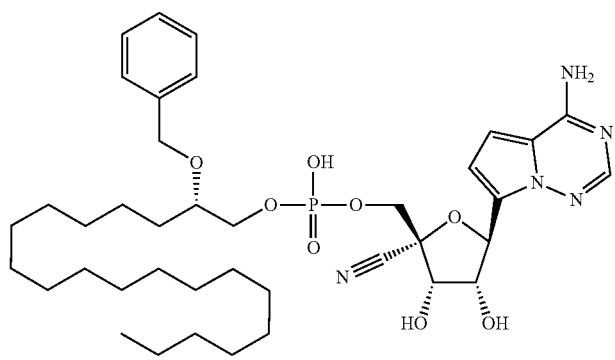 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1ccccc1]
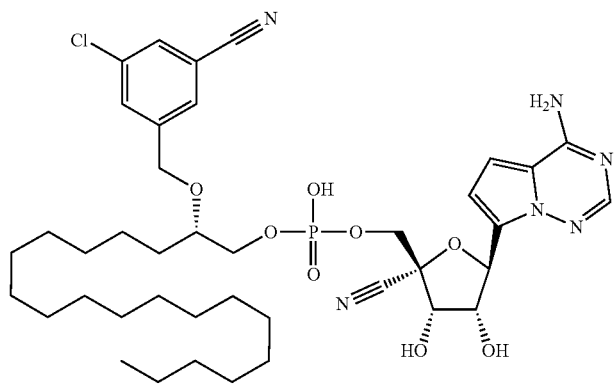 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(Cl)cc(C#N)c1]
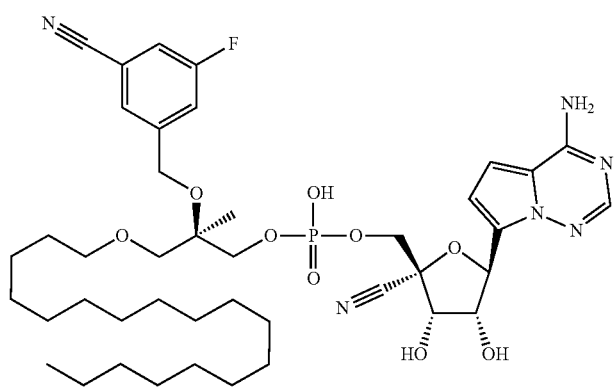 [SMILES: CCCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]

281
TABLE 16-continued
Some Compounds of Formula VI
Structure
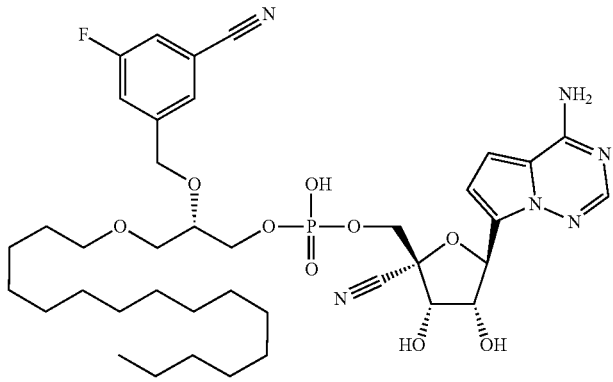 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]
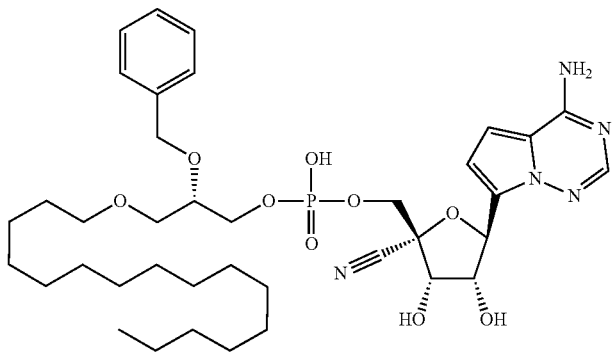 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccccc1]
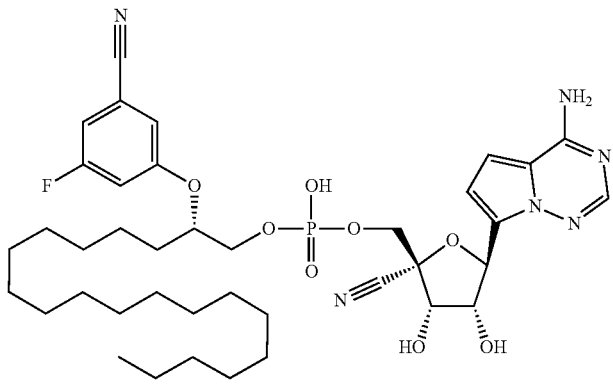 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)Oc1cc(F)cc(C#N)c1]
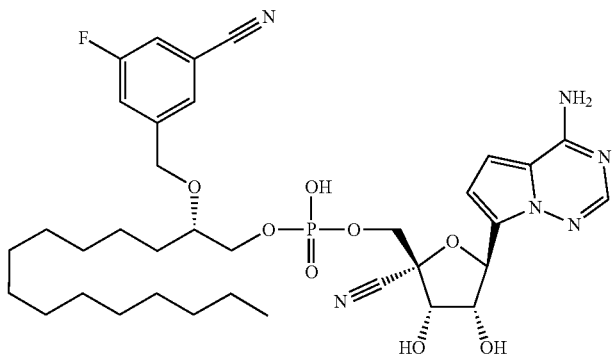 [SMILES: CCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
282

TABLE 16-continued

Some Compounds of Formula VI
Structure

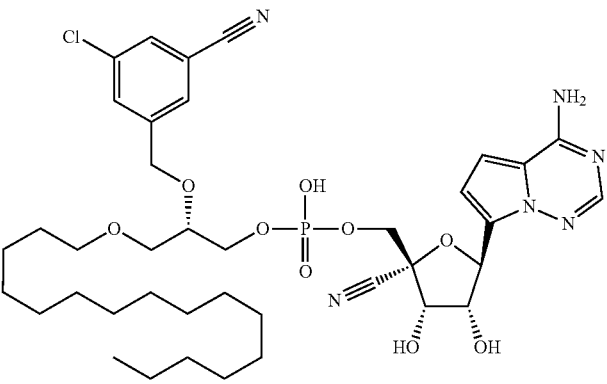 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(Cl)cc(C#N)c1]

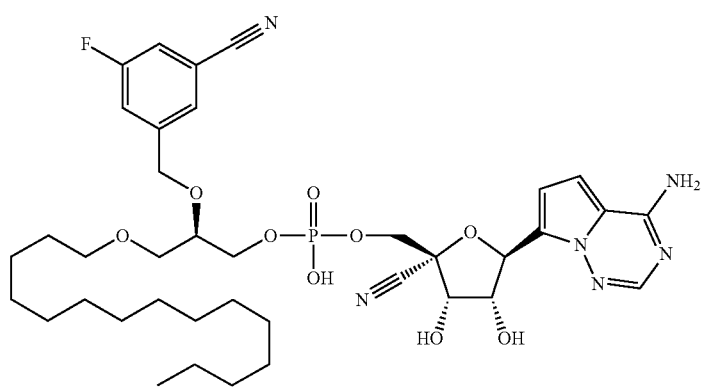

In some embodiments, the compound of Formula I has a Formula VIa:

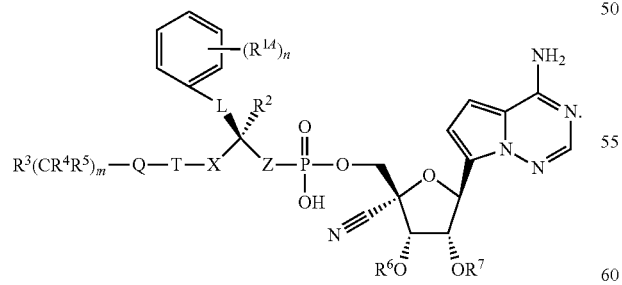

Formula VIa

The description of substituents of Formula I (e.g., $R^{14}$, $R^2$, $R^3$, $R^4$, $R^5$, $R^6$, $R^7$, Q, T, X, Z, L, m and n) applies to Formula VIa. In some embodiments, the compounds and pharmaceutically acceptable salts of Formula VIa include the compounds in Table 17 and the pharmaceutically acceptable salts thereof.

TABLE 17
Some Compounds of Formula VIa
Structure
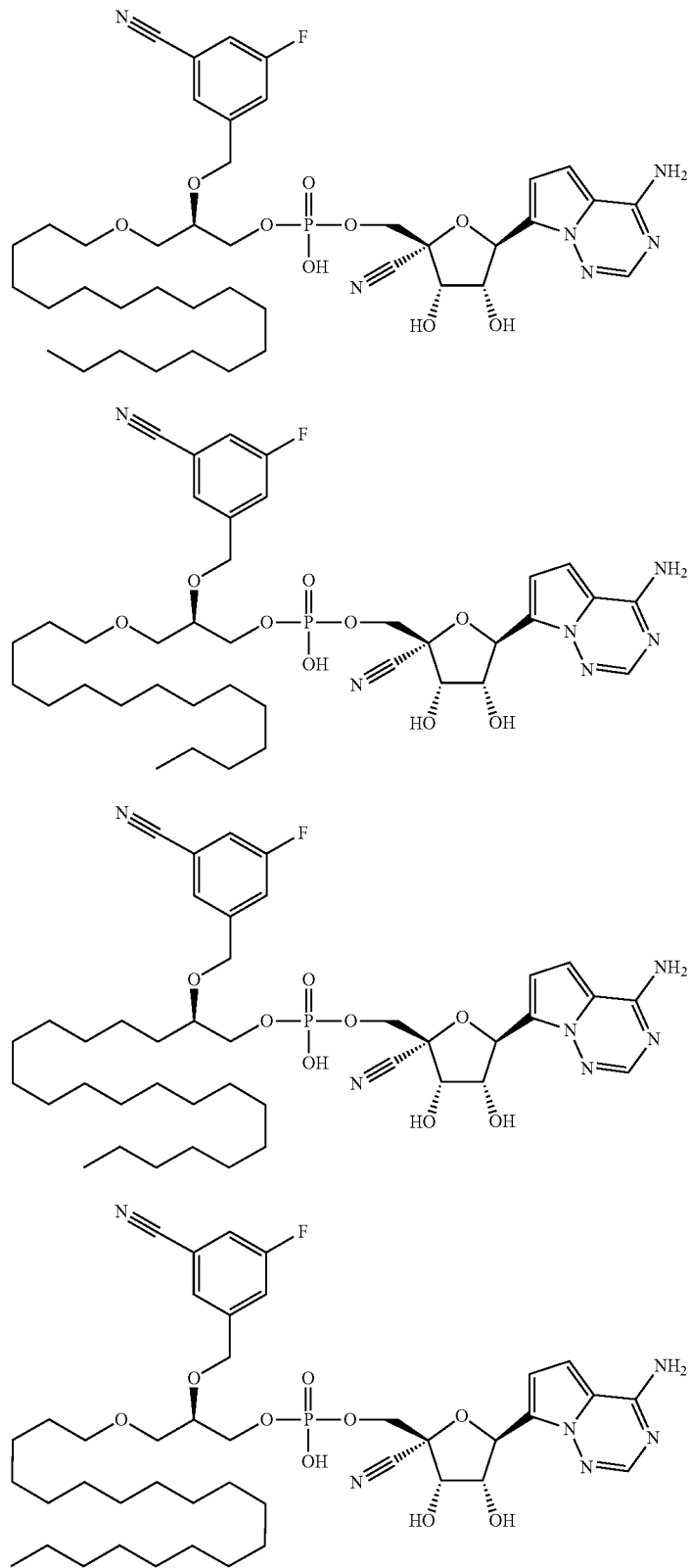

TABLE 17-continued
Some Compounds of Formula VIa
Structure
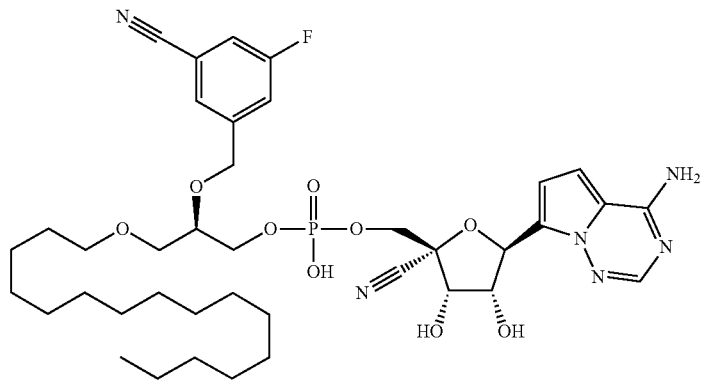 [SMILES: CCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
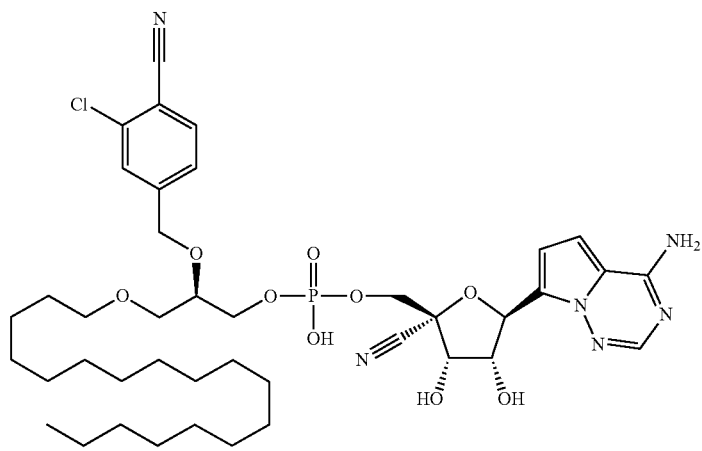 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(Cl)c1]
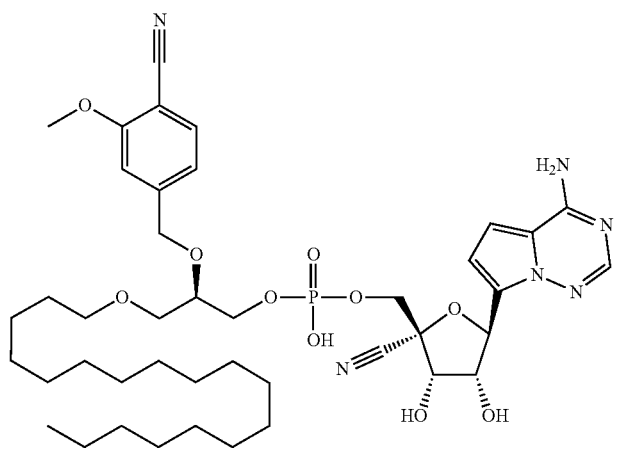 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]

TABLE 17-continued
Some Compounds of Formula VIa
Structure
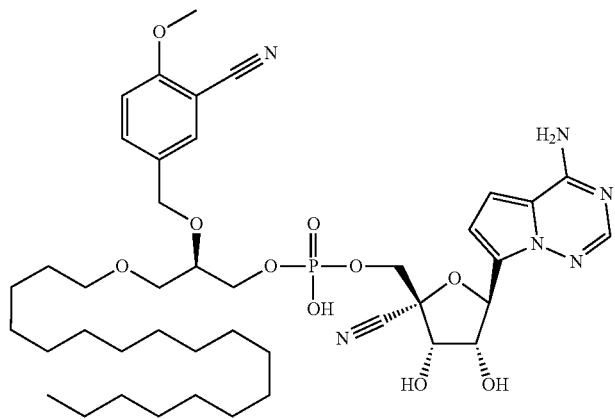 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]
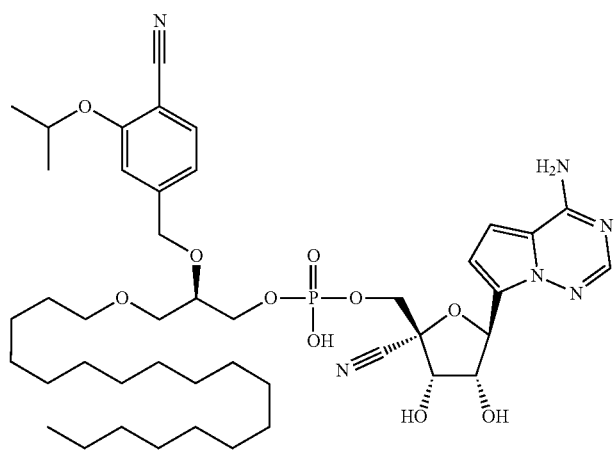 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
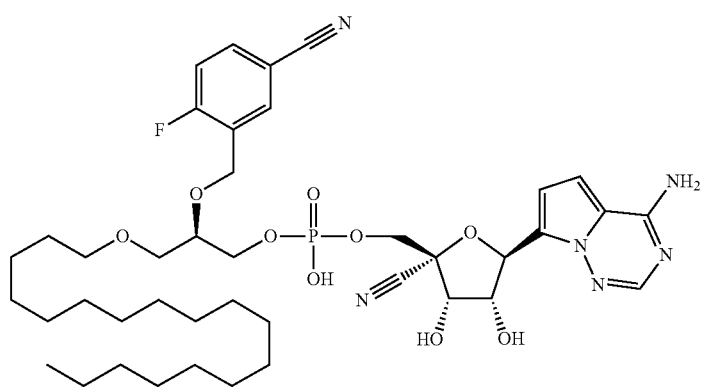 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(C#N)ccc1F]

TABLE 17-continued
Some Compounds of Formula VIa
Structure
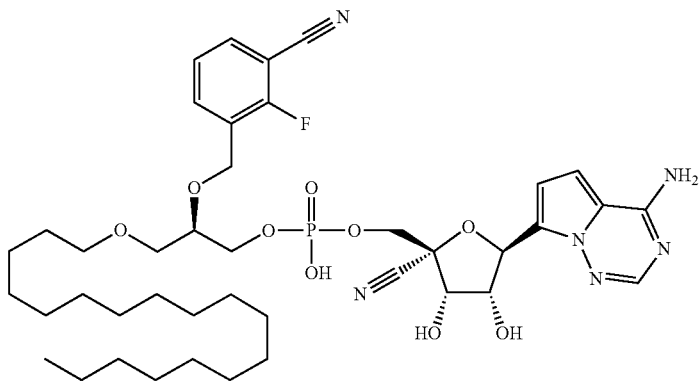 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
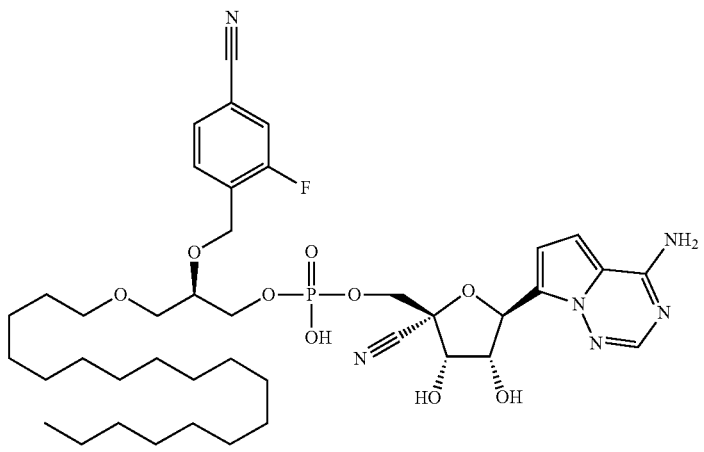 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]
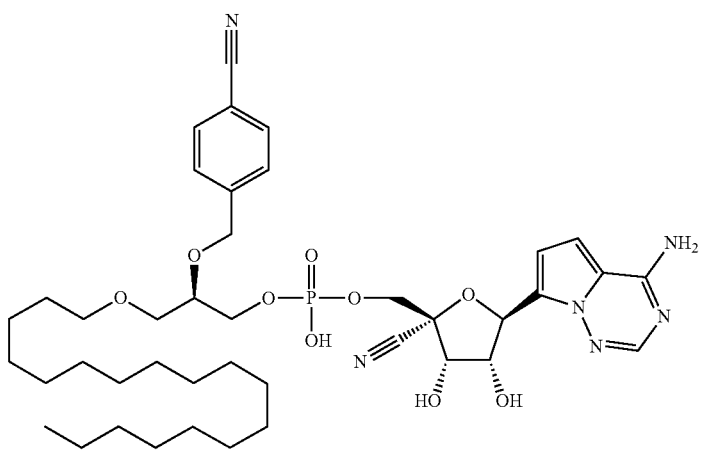 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]

TABLE 17-continued
Some Compounds of Formula VIa
Structure
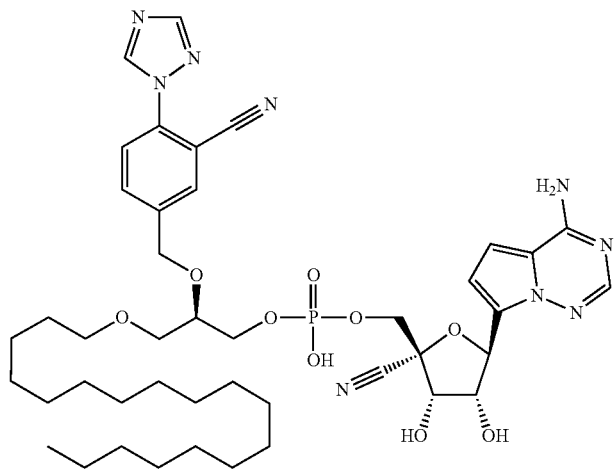 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
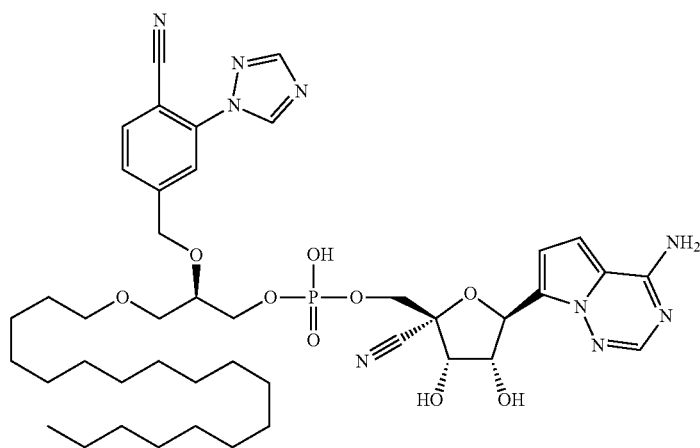 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]
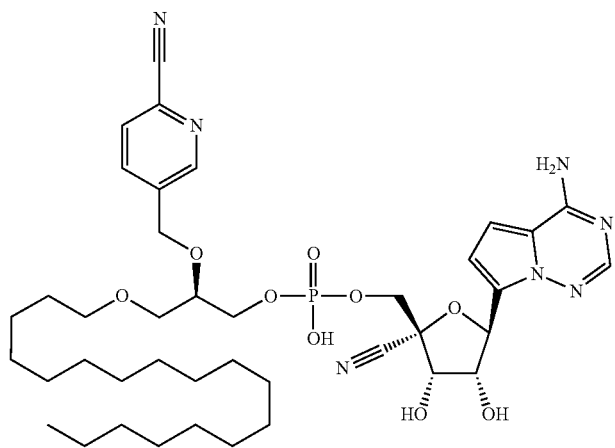 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)nc1]

TABLE 17-continued
Some Compounds of Formula VIa
Structure
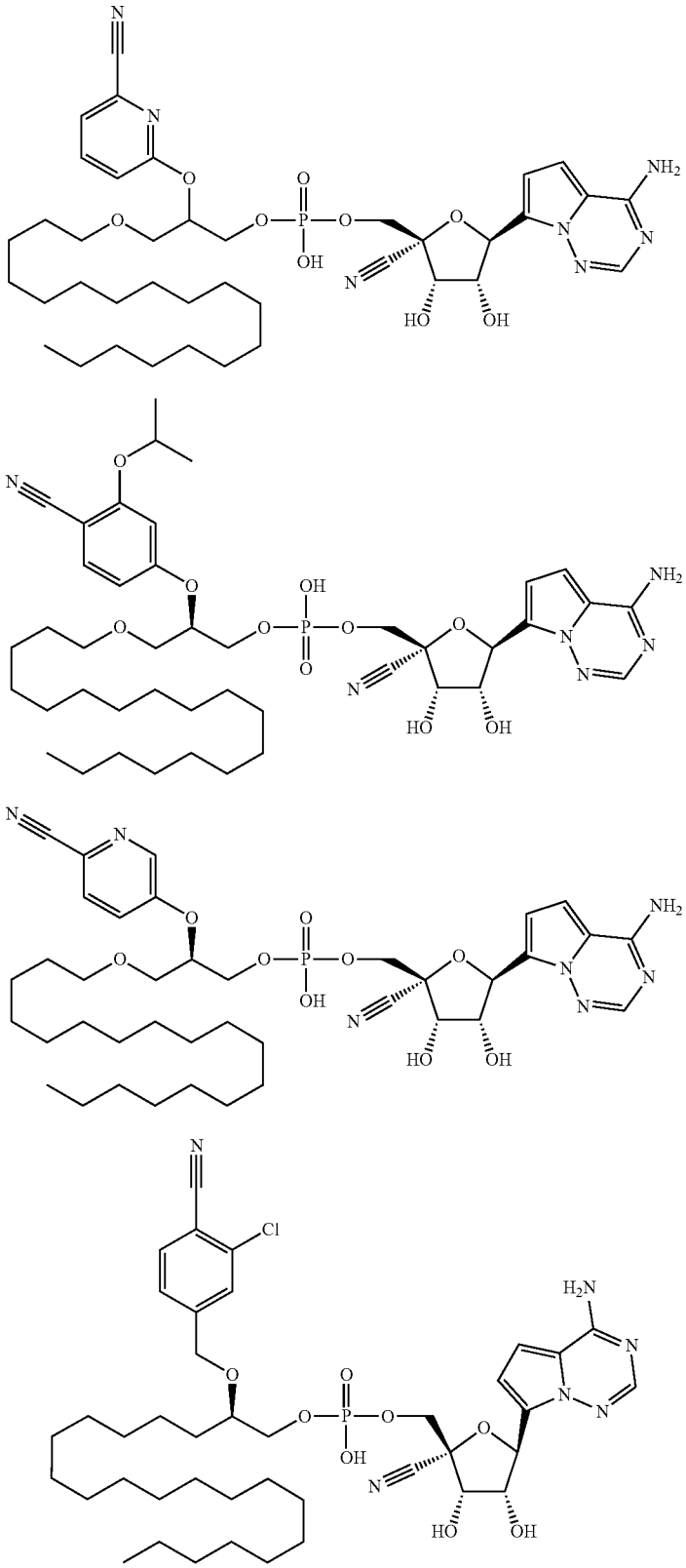

TABLE 17-continued
Some Compounds of Formula VIa
Structure
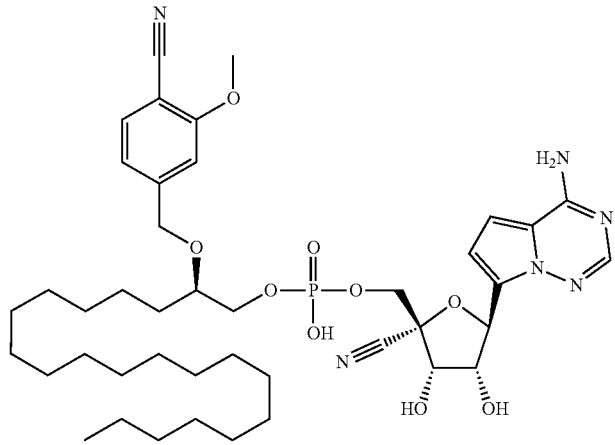 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC)c1]
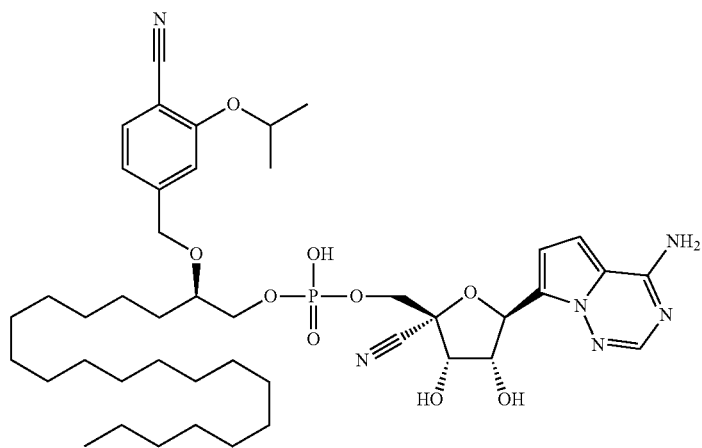 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
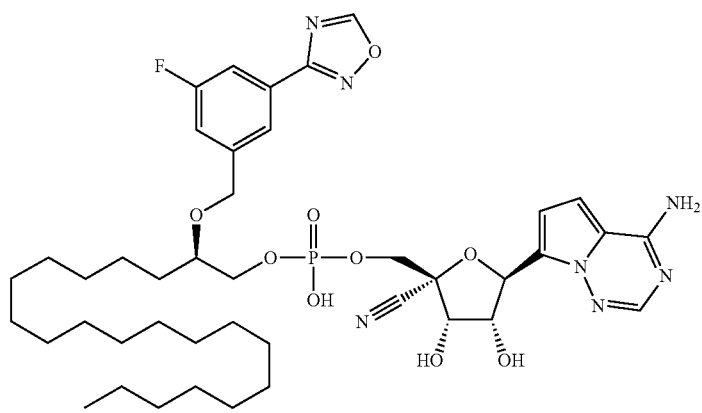 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(-c2ncon2)c1]

TABLE 17-continued
Some Compounds of Formula VIa
Structure
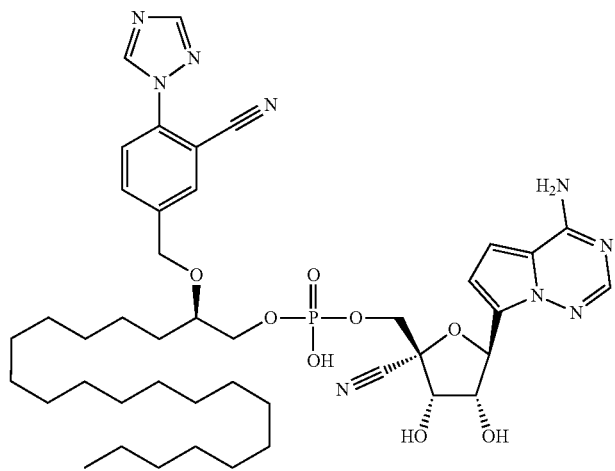 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
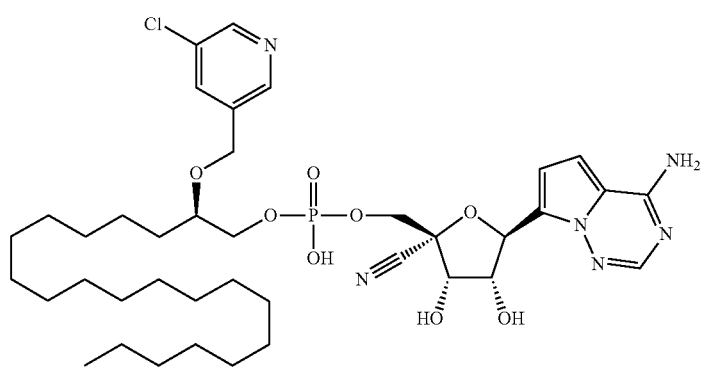 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cncc(Cl)c1]
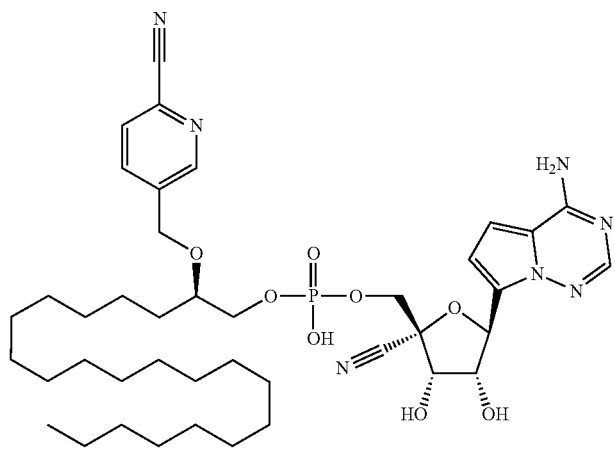 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)nc1]

TABLE 17-continued
Some Compounds of Formula VIa
Structure
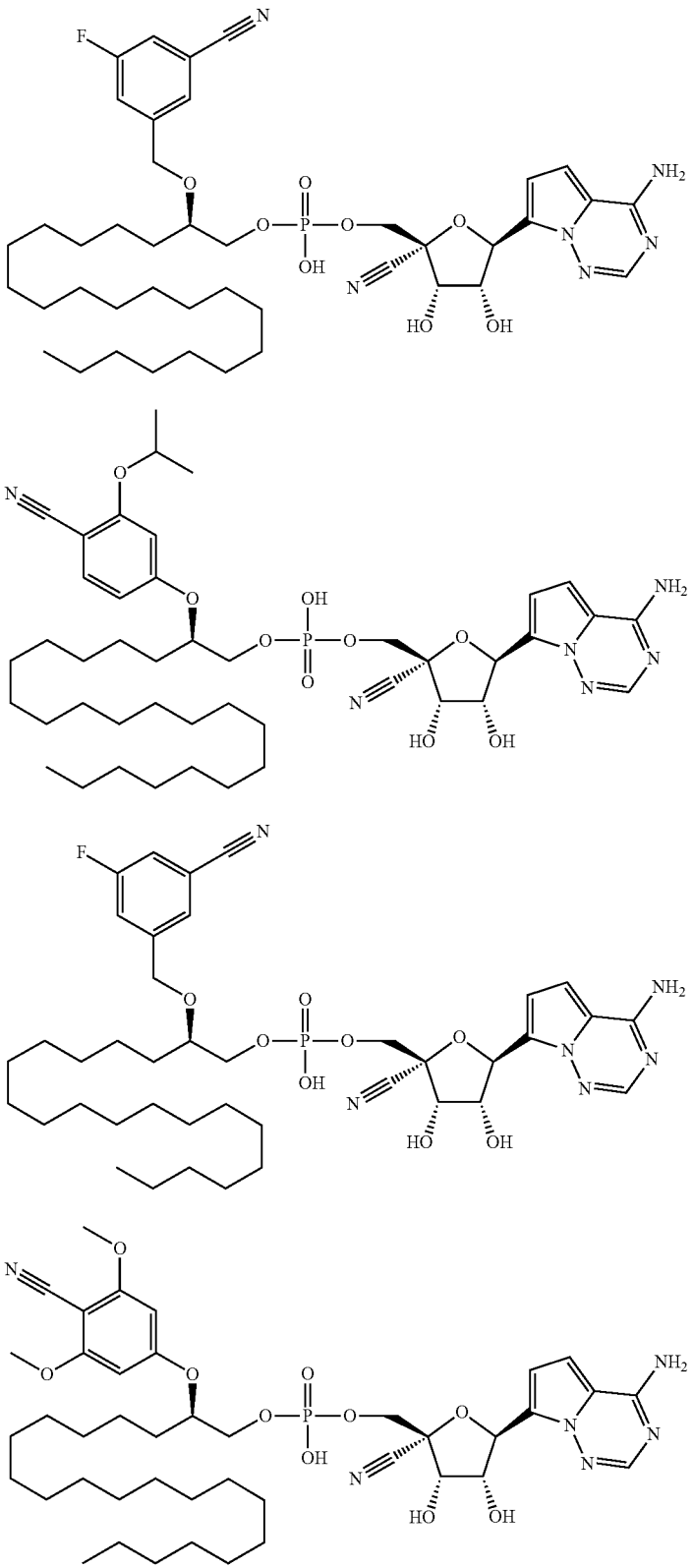

TABLE 17-continued
Some Compounds of Formula VIa
Structure
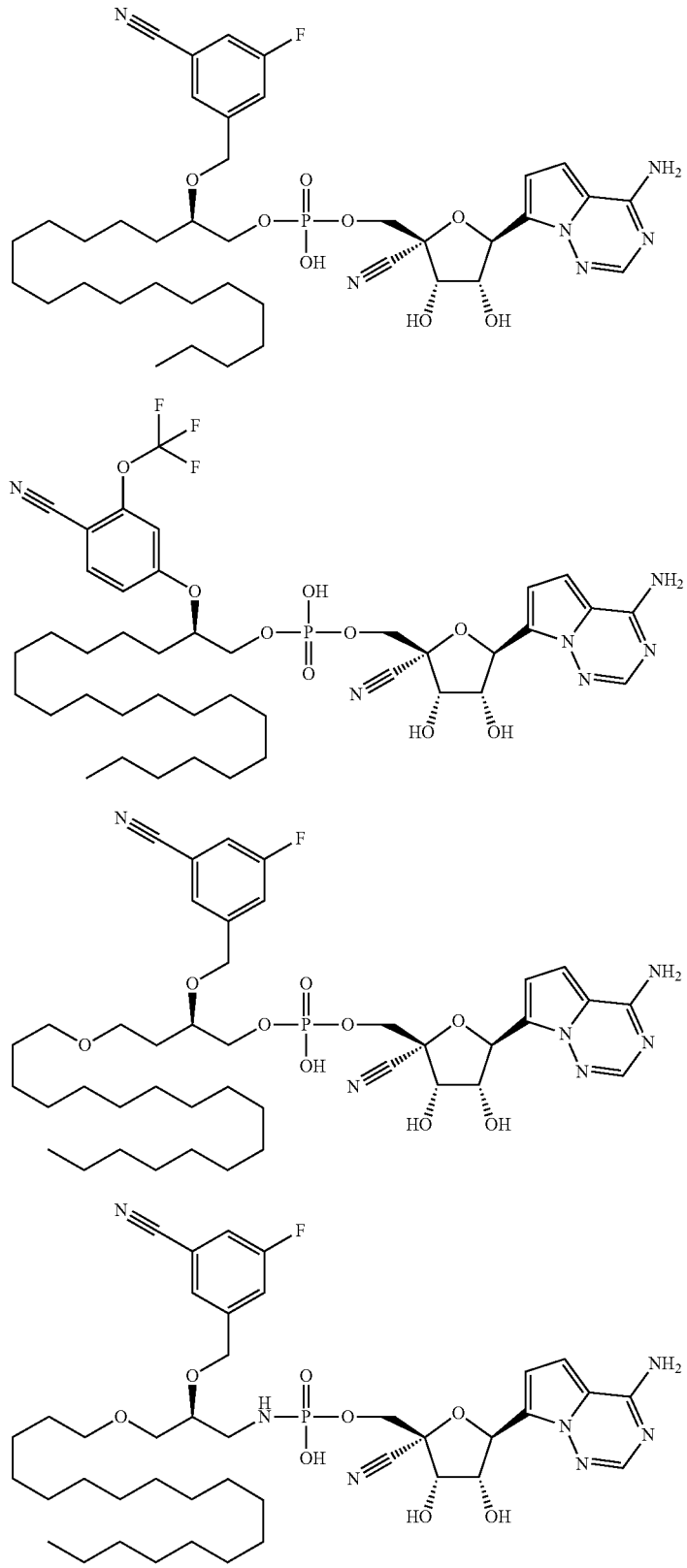

TABLE 17-continued
Some Compounds of Formula VIa
Structure
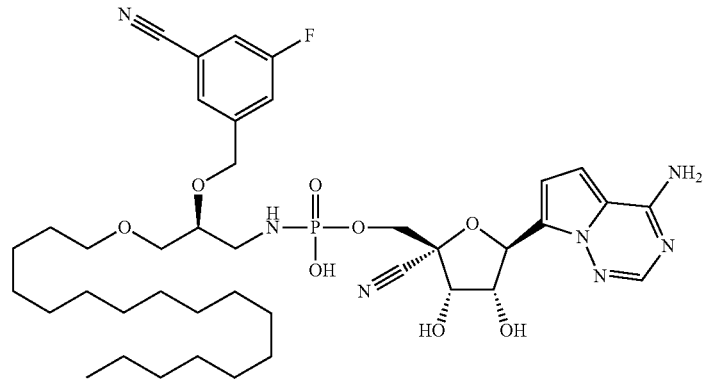 [SMILES: CCCCCCCCCCCCCCCCCOC[C@H](CNP(=O)(O)OC[C@@]1(C#N)O[C@@H](c2ccc3c(N)ncnn23)[C@H](O)[C@@H]1O)OCc1cc(F)cc(C#N)c1]
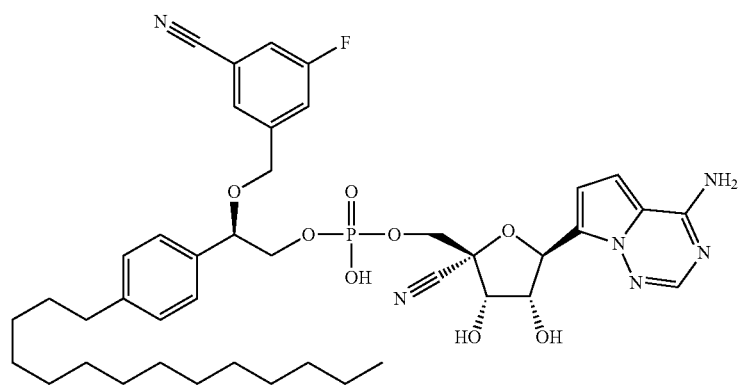 [SMILES: CCCCCCCCCCCCCCc1ccc([C@H](COP(=O)(O)OC[C@@]2(C#N)O[C@@H](c3ccc4c(N)ncnn34)[C@H](O)[C@@H]2O)OCc2cc(F)cc(C#N)c2)cc1]
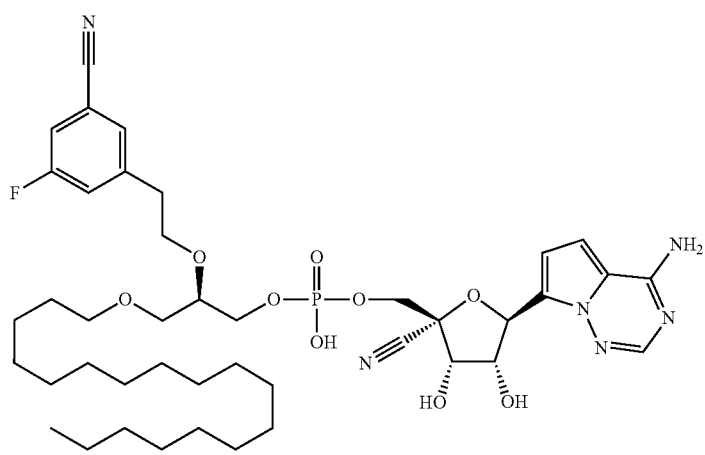 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCCc1cc(F)cc(C#N)c1]

TABLE 17-continued
Some Compounds of Formula VIa
Structure
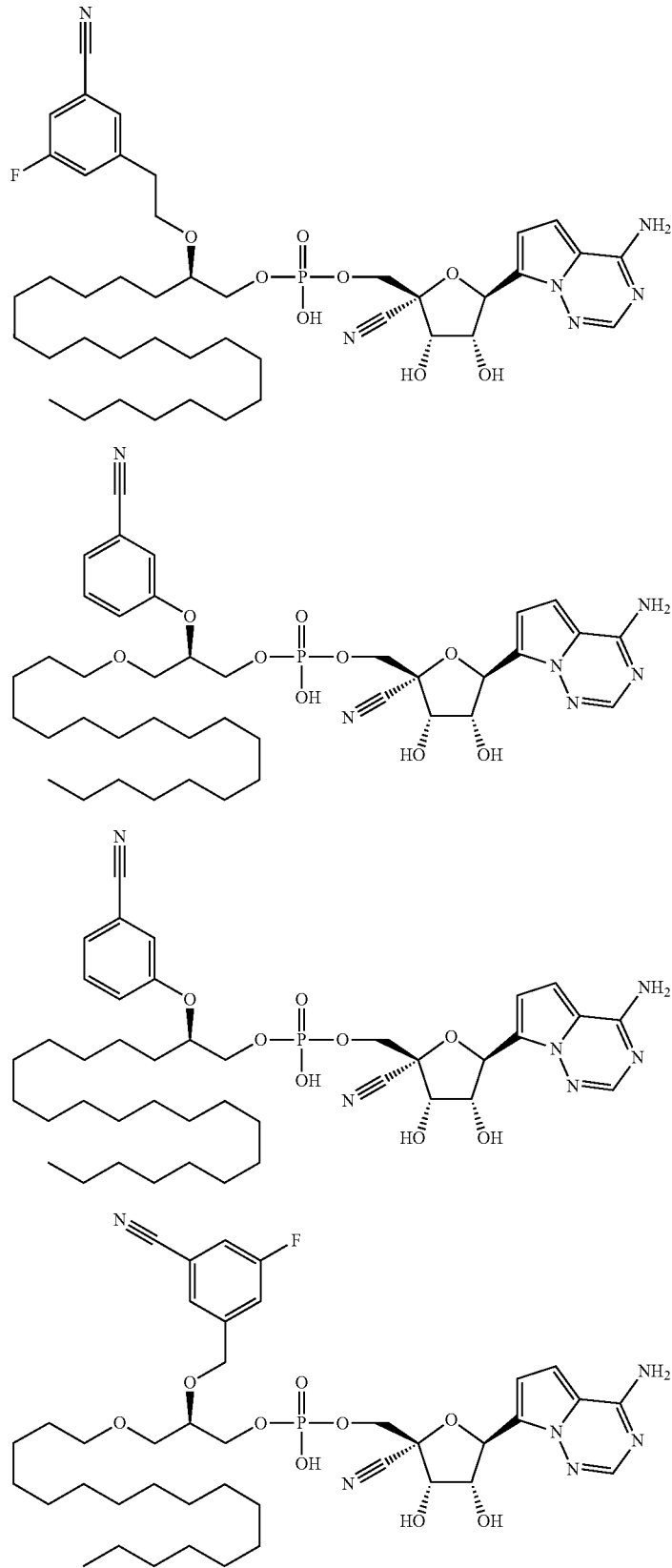

TABLE 17-continued
Some Compounds of Formula VIa
Structure
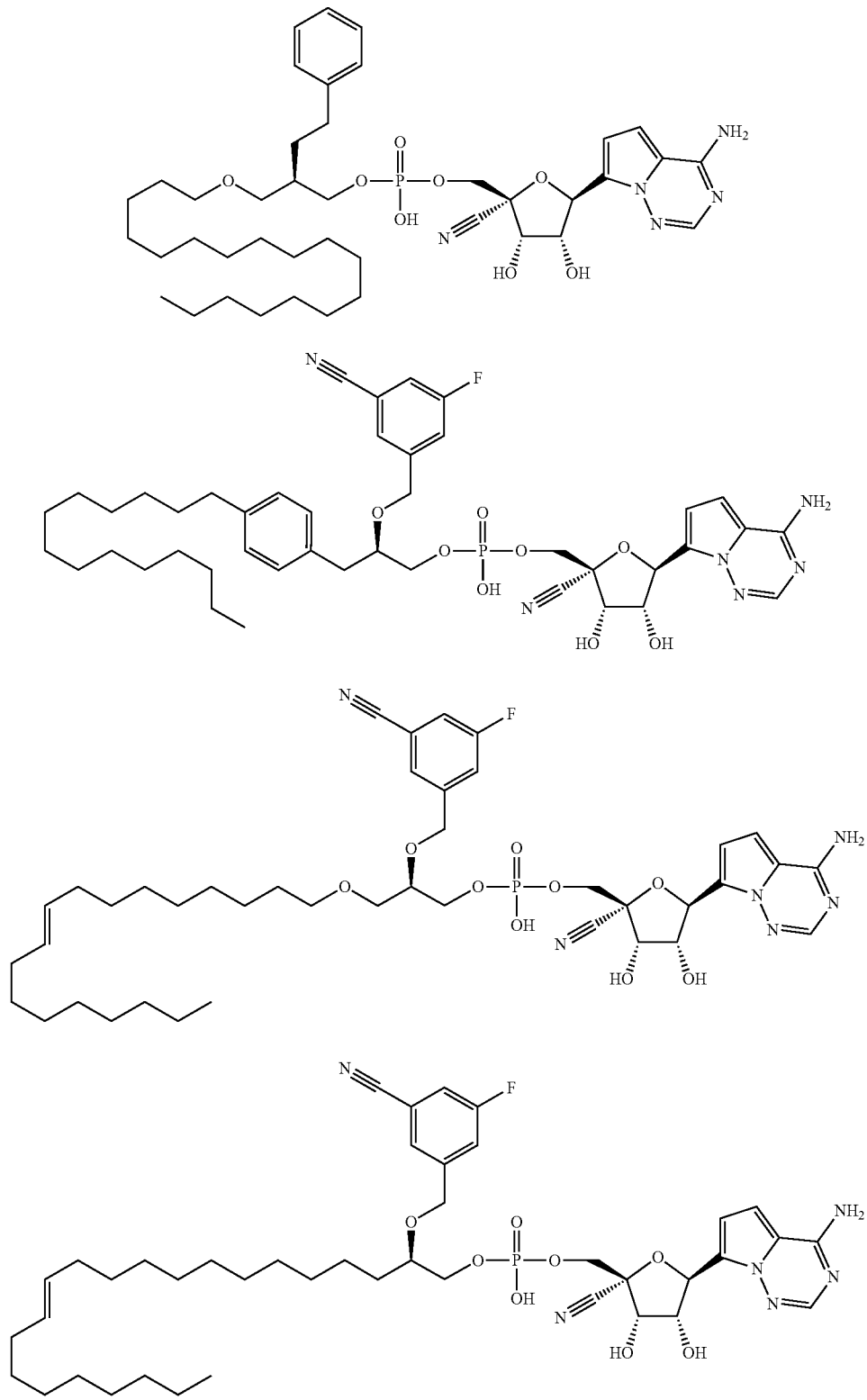

TABLE 17-continued
Some Compounds of Formula VIa
Structure
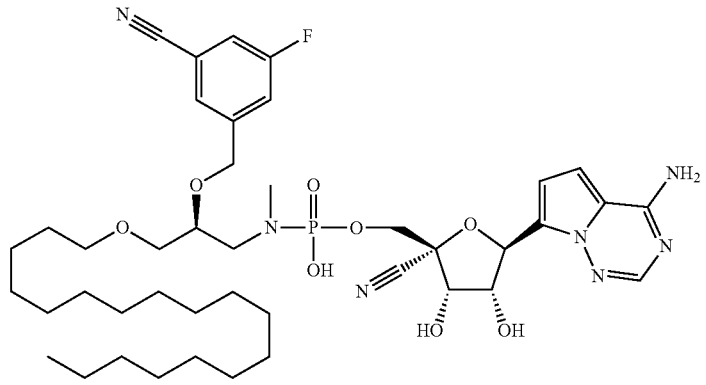 [SMILES: CCCCCCCCCCCCCCCCCCOC[C@H](CN(C)P(=O)(O)OC[C@@]1(C#N)O[C@@H](c2ccc3c(N)ncnn23)[C@H](O)[C@@H]1O)OCc1cc(F)cc(C#N)c1]
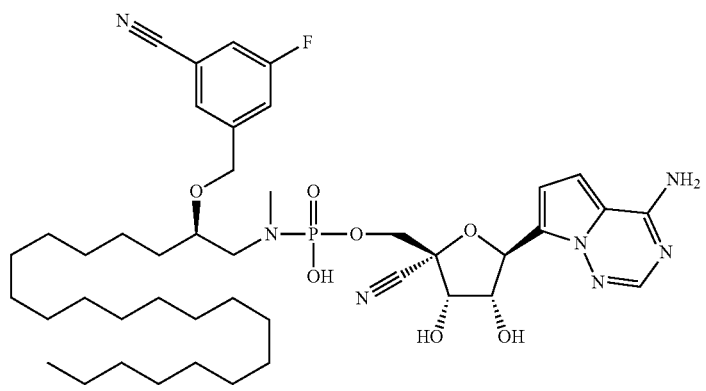 [SMILES: CCCCCCCCCCCCCCCCCCCC[C@H](CN(C)P(=O)(O)OC[C@@]1(C#N)O[C@@H](c2ccc3c(N)ncnn23)[C@H](O)[C@@H]1O)OCc1cc(F)cc(C#N)c1]
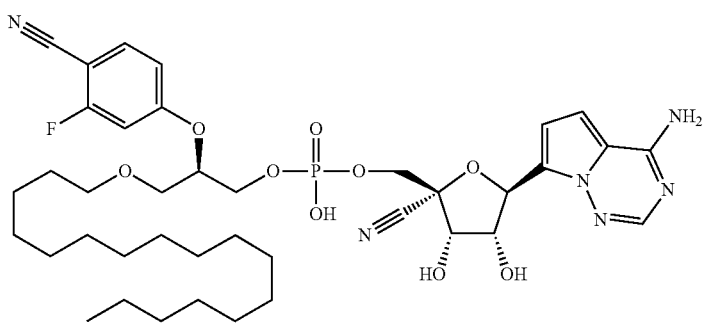 [SMILES: CCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(F)c1]
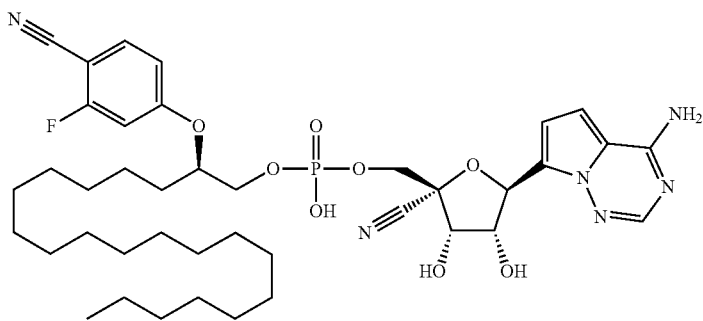 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1]

TABLE 17-continued
Some Compounds of Formula VIa
Structure
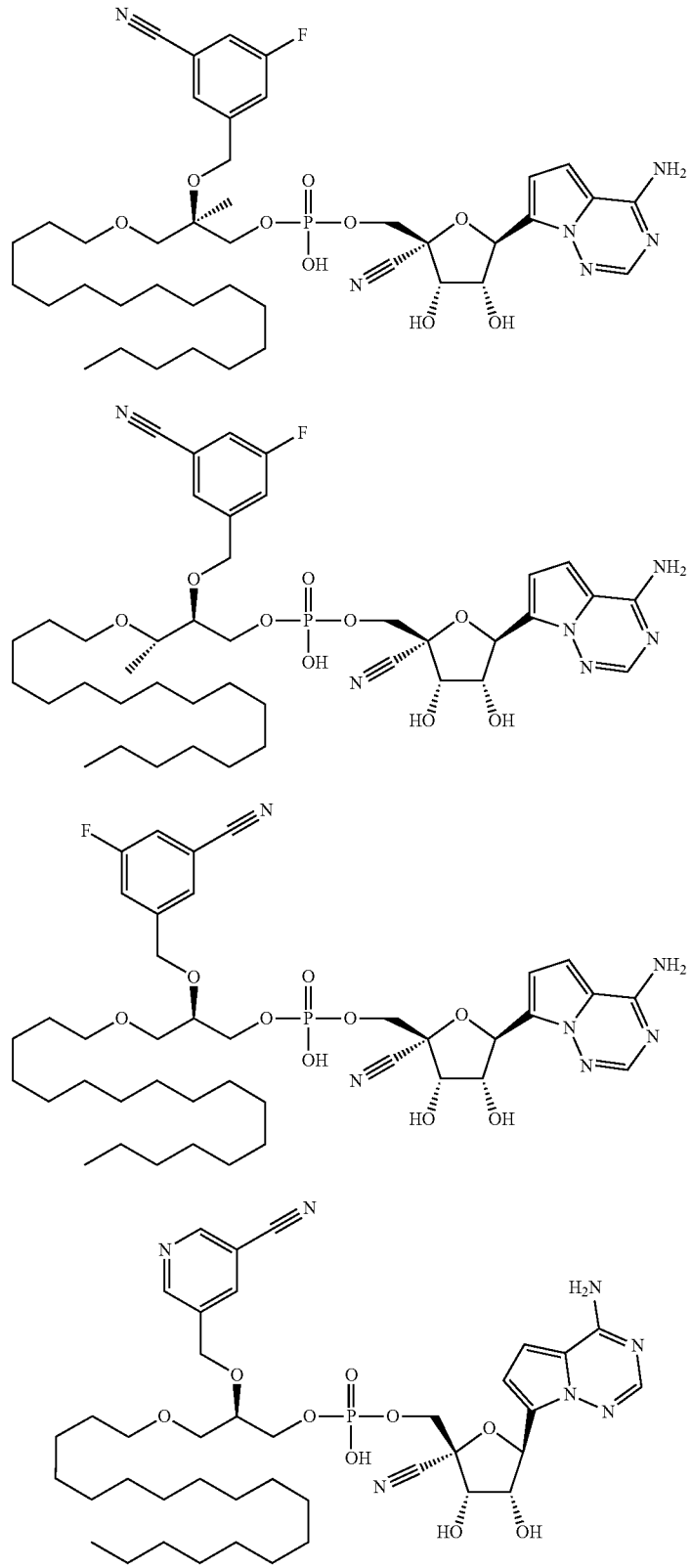

TABLE 17-continued
Some Compounds of Formula VIa
Structure
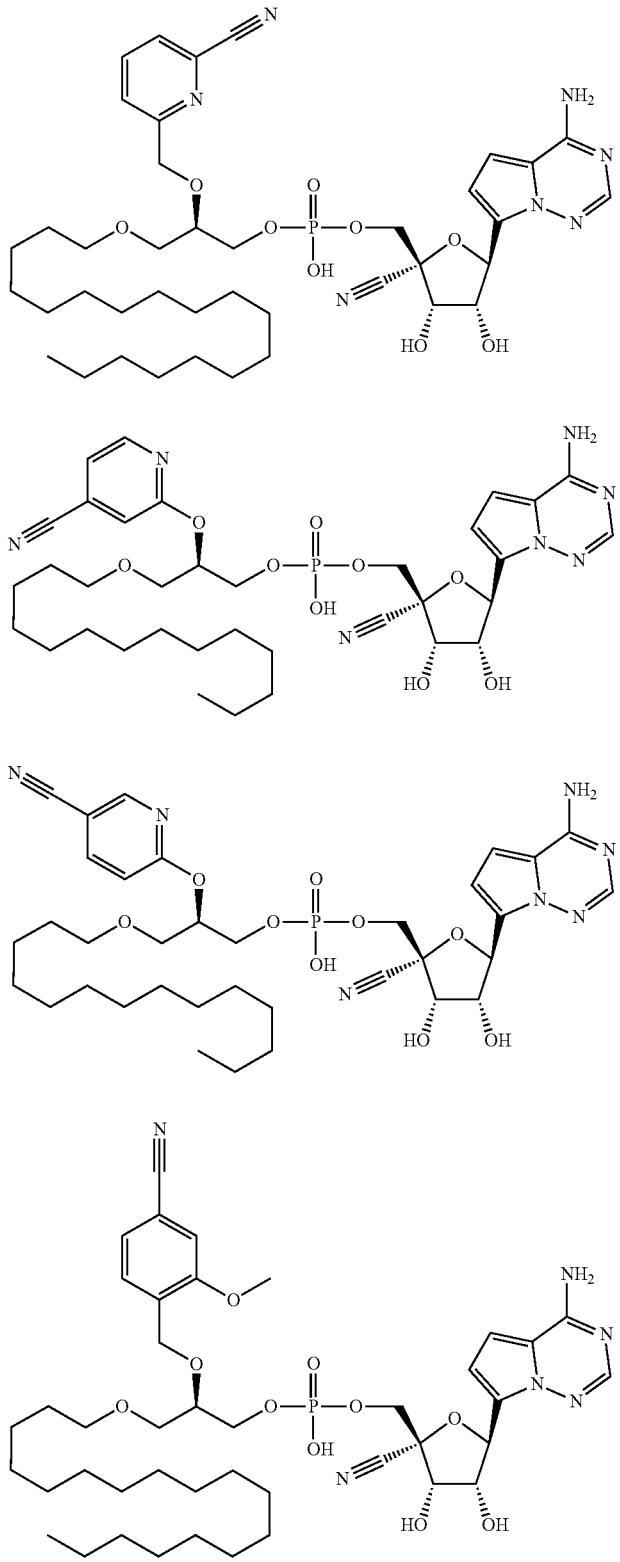

TABLE 17-continued
Some Compounds of Formula VIa
Structure
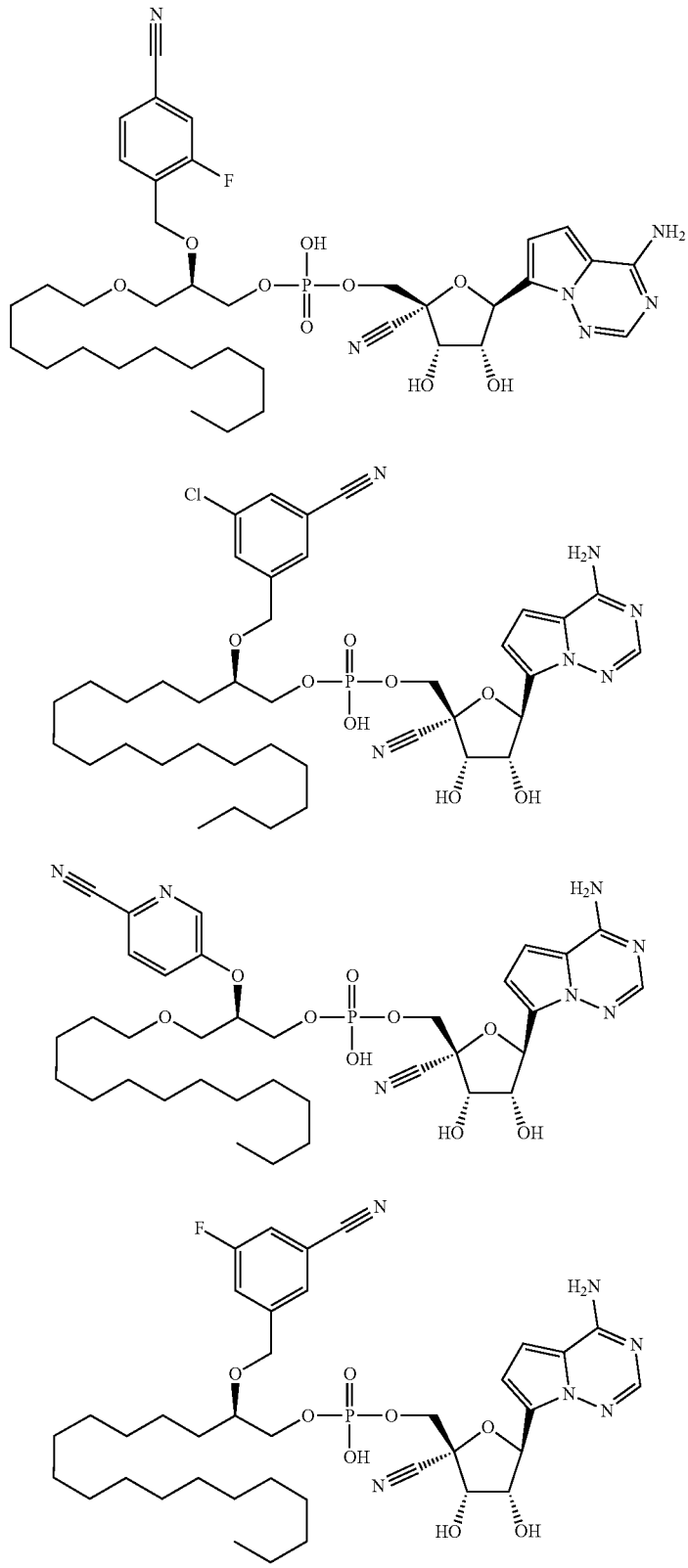

TABLE 17-continued
Some Compounds of Formula VIa
Structure
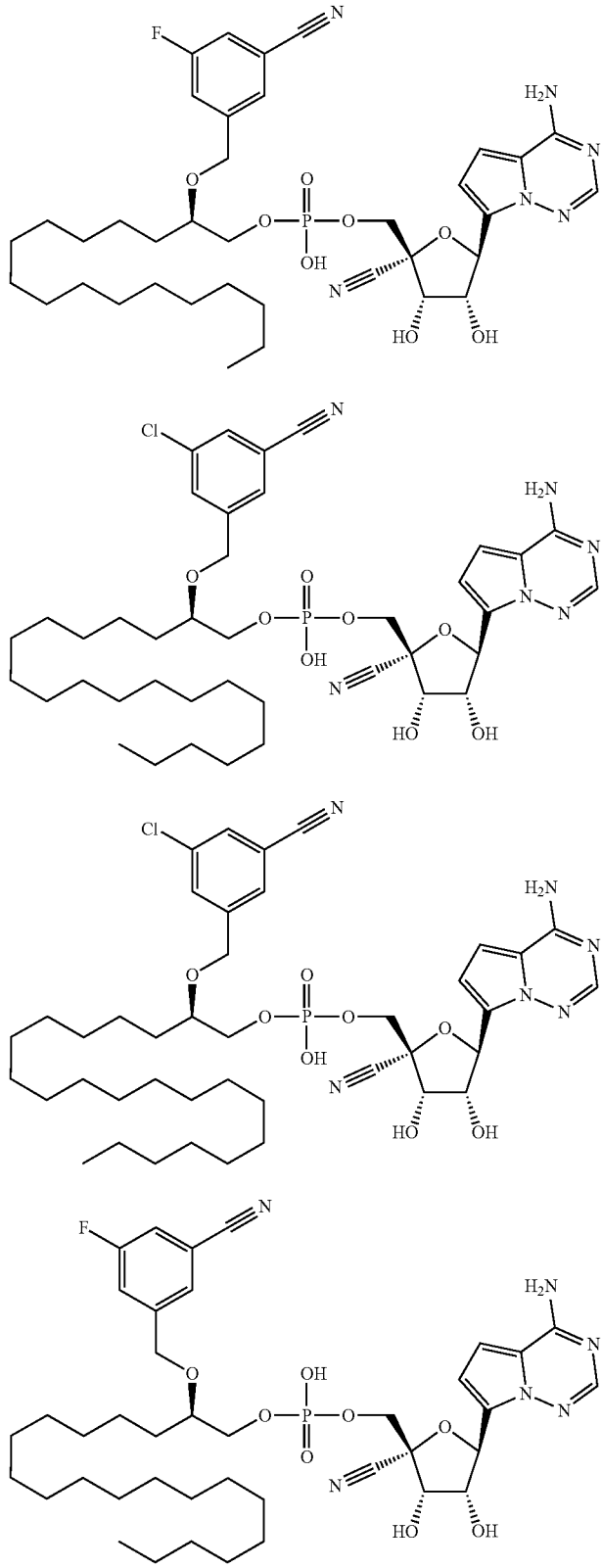

TABLE 17-continued
Some Compounds of Formula VIa
Structure
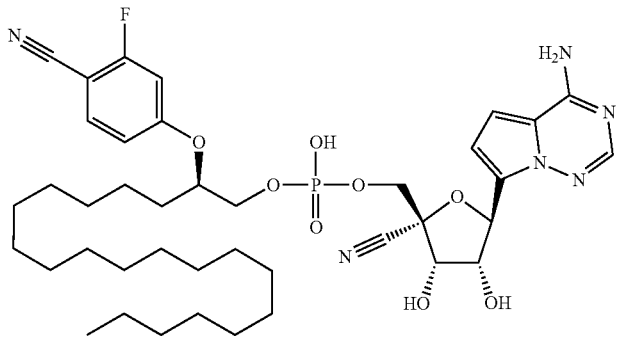 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1]
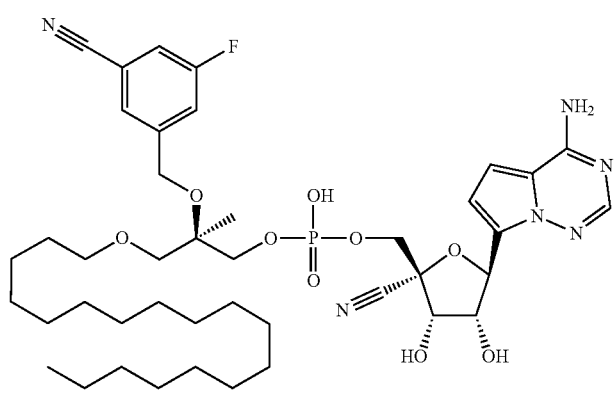 [SMILES: CCCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]
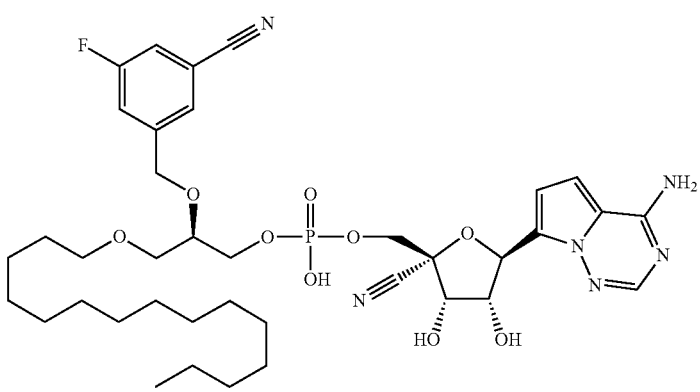 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
In some embodiments, the compound of Formula I has a Formula VIb:
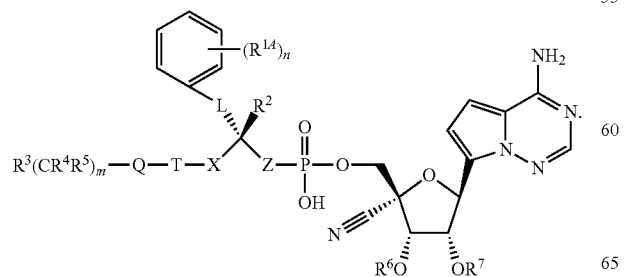
Formula VIb

323

The description of substituents of Formula I (e.g., $R^{1A}$, $R^2$, $R^3$, $R^4$, $R^5$, $R^6$, $R^7$, Q, T, X, Z, L, m and n) applies to Formula VIb.

In some embodiments, the compounds and pharmaceutically acceptable salts of Formula VIb include the compounds in Table 18 and the pharmaceutically acceptable salts thereof.

TABLE 18

Some Compounds of Formula VIb
Structure

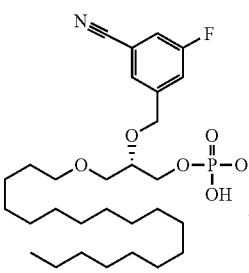

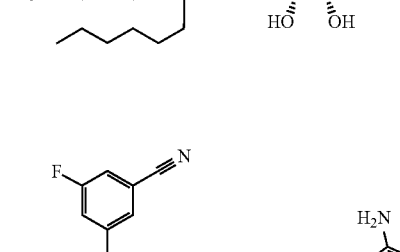

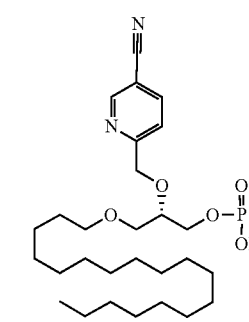

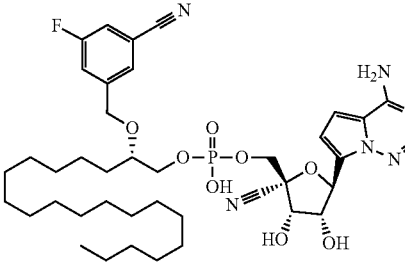

324

TABLE 18-continued

Some Compounds of Formula VIb
Structure

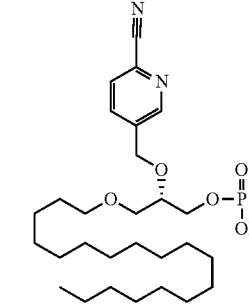

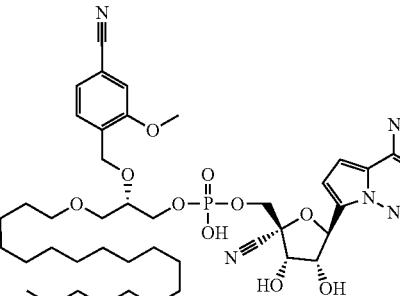

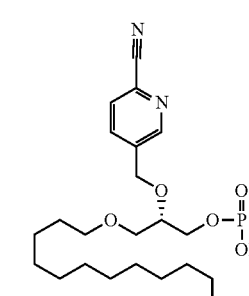

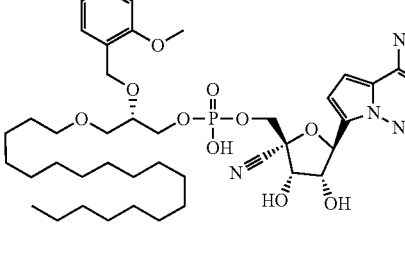

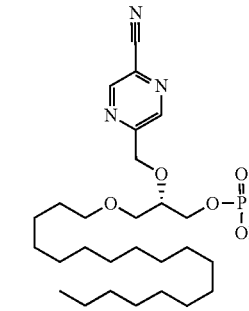

TABLE 18-continued
Some Compounds of Formula VIb
Structure
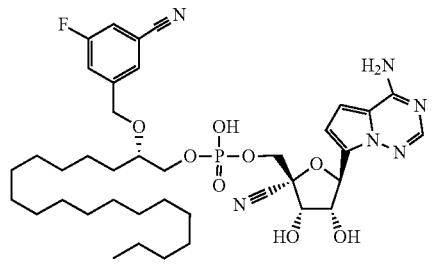 [SMILES: CCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
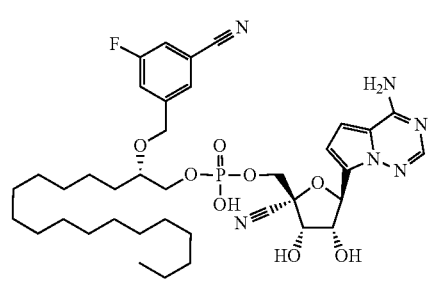 [SMILES: CCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
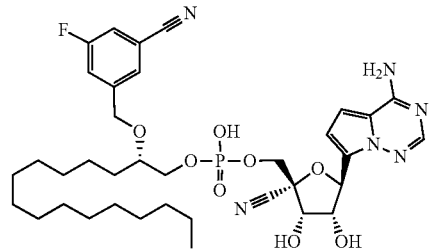 [SMILES: CCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
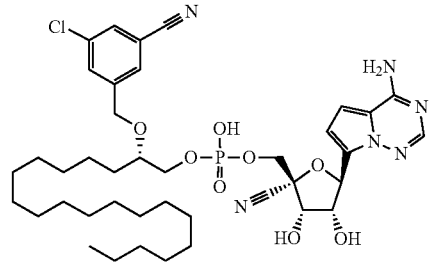 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(Cl)cc(C#N)c1]
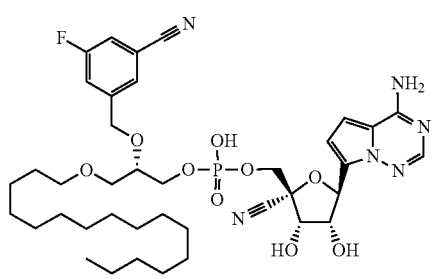 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]
TABLE 18-continued
Some Compounds of Formula VIb
Structure
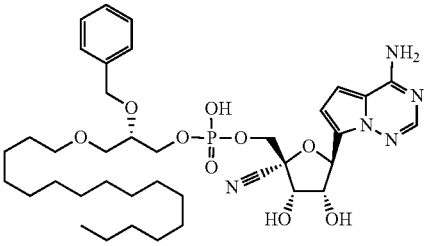 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccccc1]
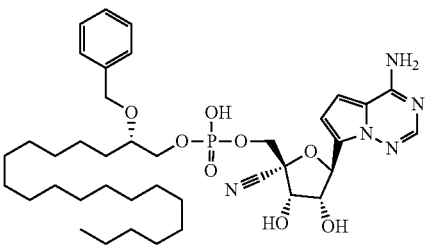 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1ccccc1]
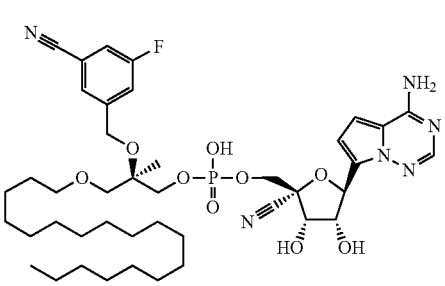 [SMILES: CCCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]
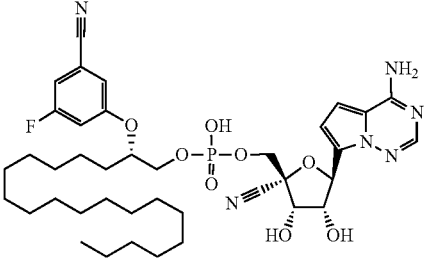 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)Oc1cc(F)cc(C#N)c1]
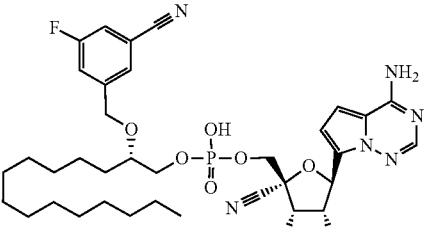
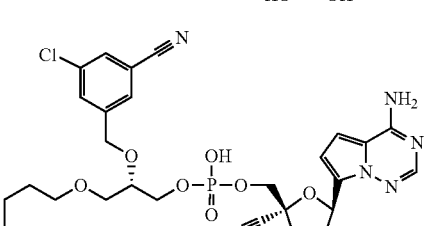

In some embodiments, the compound of Formula I has a Formula VII:

Formula VII

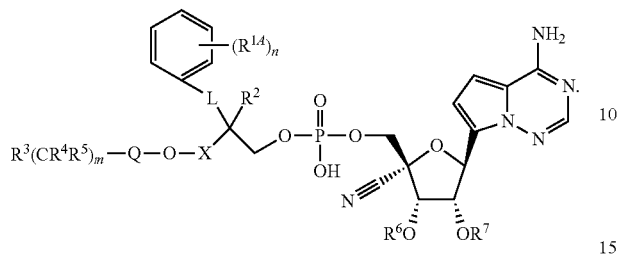

The description of substituents of Formula I (e.g., $R^{14}$, $R^2$, $R^3$, $R^4$, $R^5$, $R^6$, $R^7$, Q, X, L, m and n) applies to Formula VII.

In some embodiments, the compounds and pharmaceutically acceptable salts of Formula VII include the compounds in Table 19 and the pharmaceutically acceptable salts thereof.

TABLE 19

Some Compounds of Formula VII
Structure

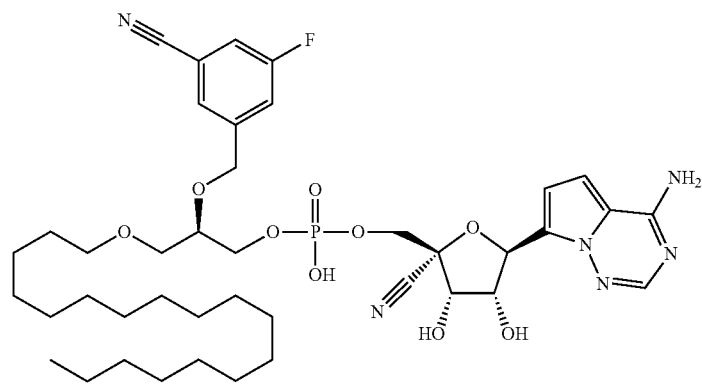

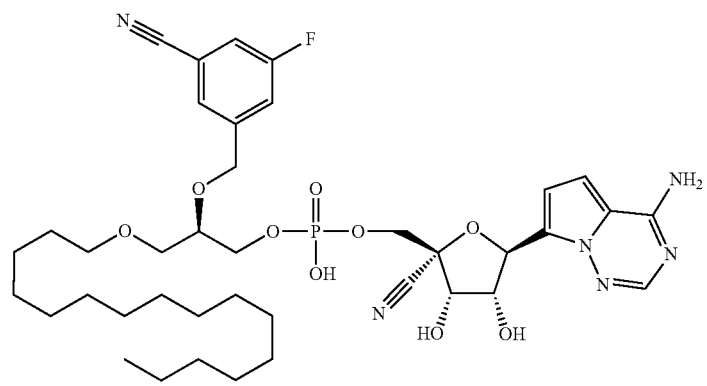 [SMILES: CCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 19-continued
Some Compounds of Formula VII
Structure
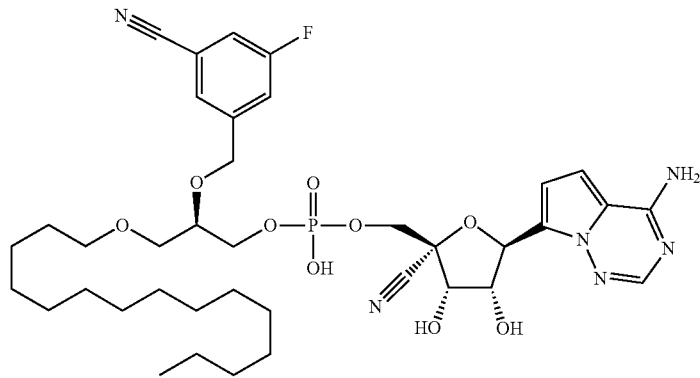 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
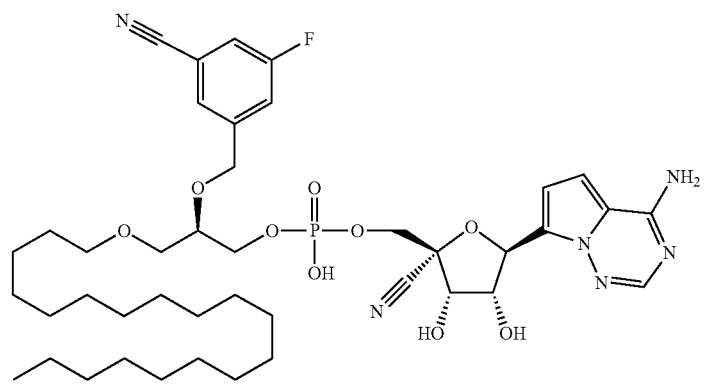 [SMILES: CCCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
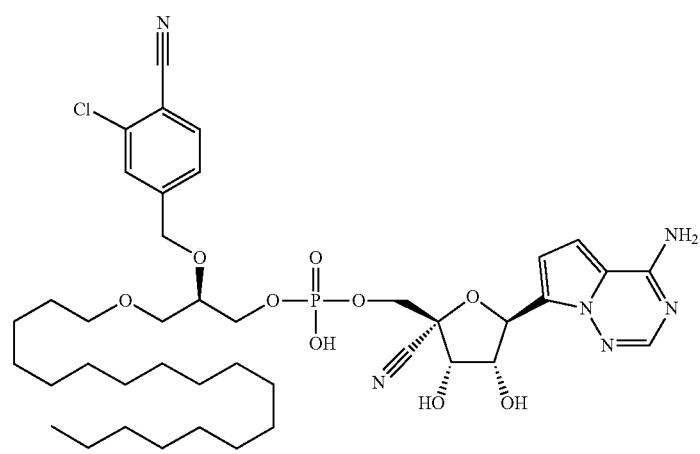 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(Cl)c1]

TABLE 19-continued
Some Compounds of Formula VII
Structure
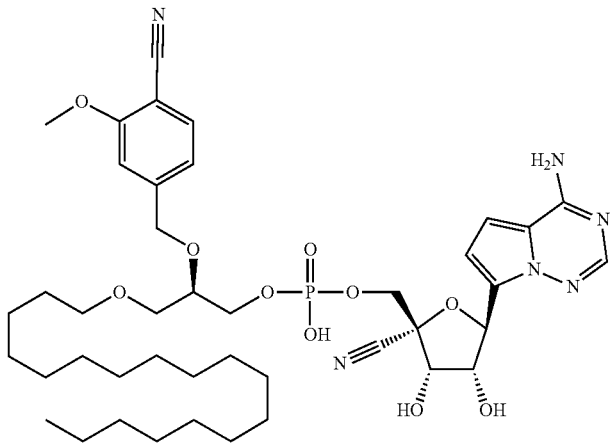 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]
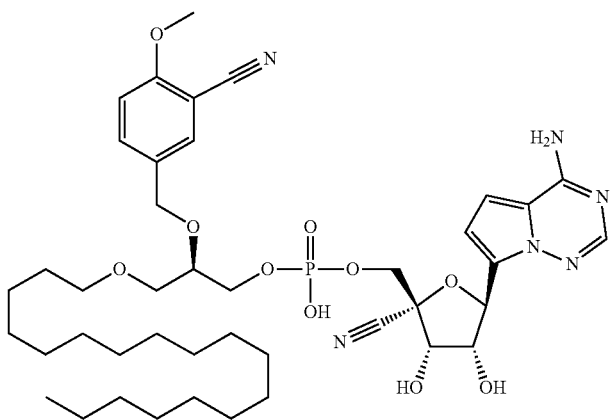 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]
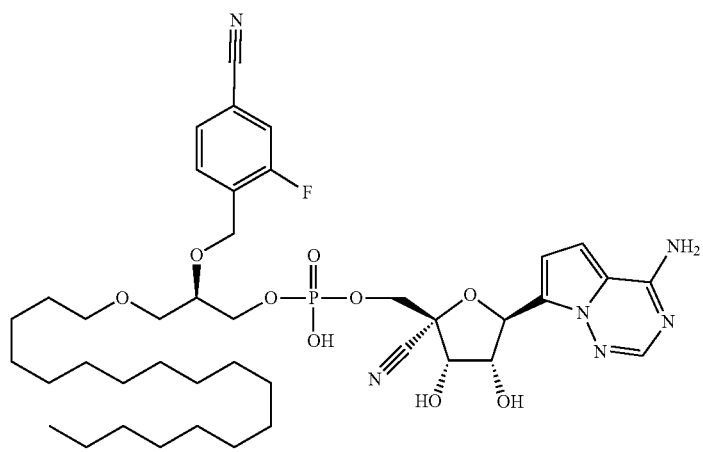 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]

TABLE 19-continued
Some Compounds of Formula VII
Structure
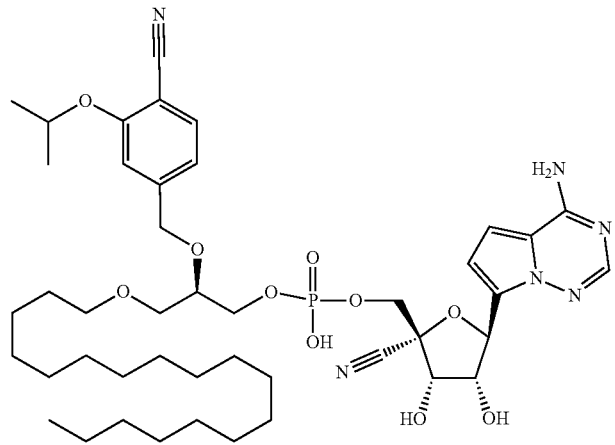 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
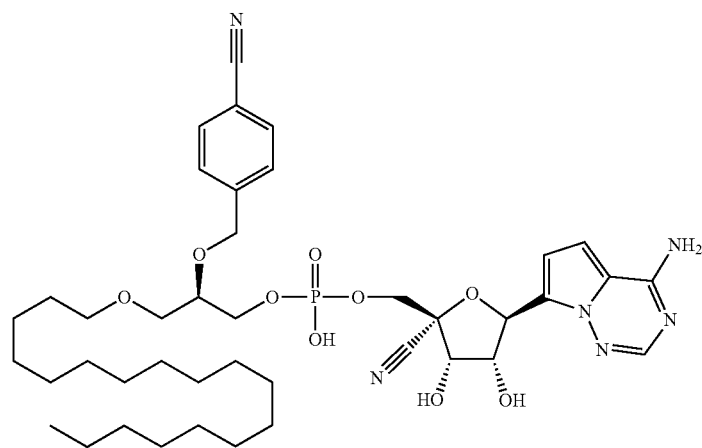 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]
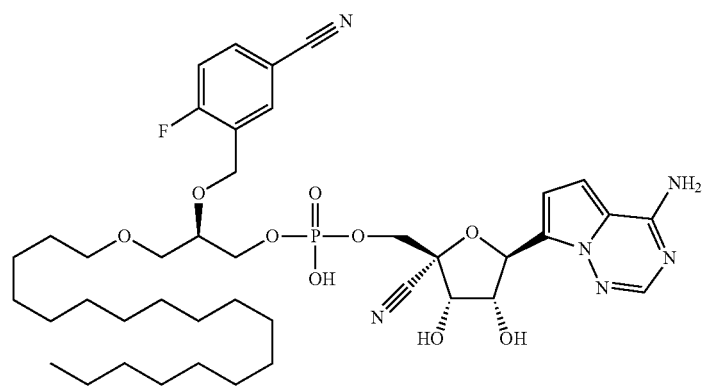 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(C#N)ccc1F]

TABLE 19-continued
Some Compounds of Formula VII
Structure
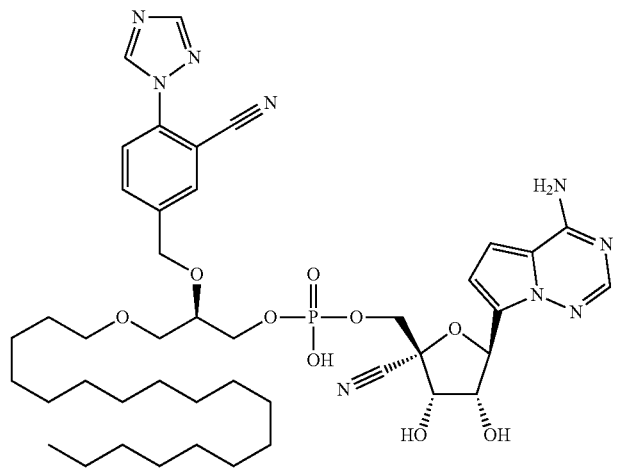 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
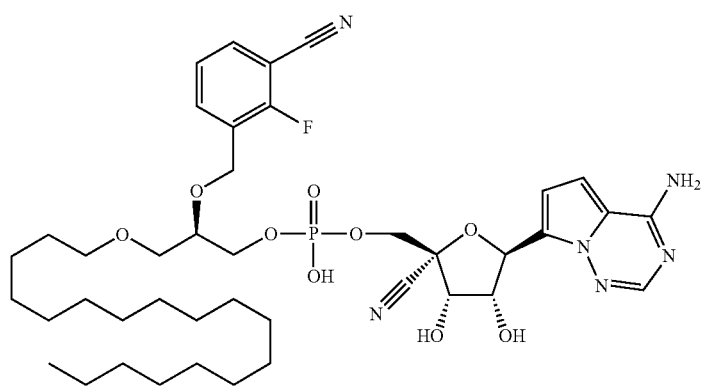 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
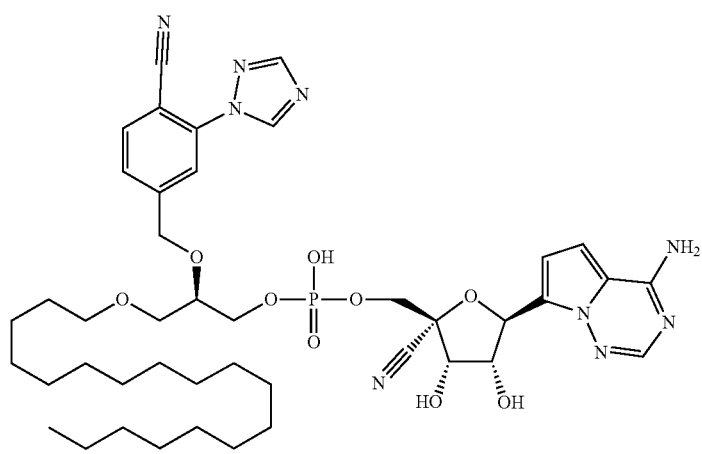 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]

TABLE 19-continued
Some Compounds of Formula VII
Structure
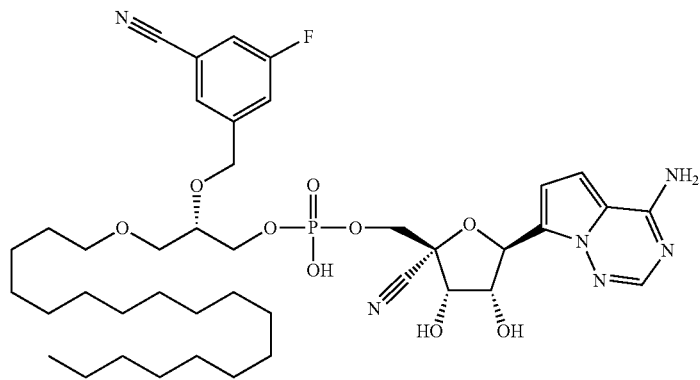 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]
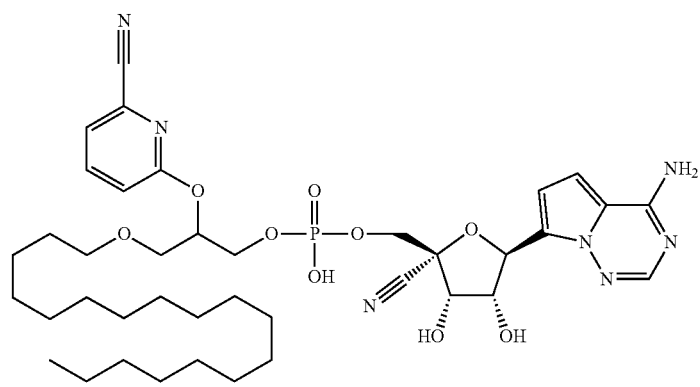 [SMILES: CCCCCCCCCCCCCCCCCCOCC(COP(=O)(O)OC[C@@]1(C#N)O[C@@H](c2ccc3c(N)ncnn23)[C@H](O)[C@@H]1O)Oc1cccc(C#N)n1]
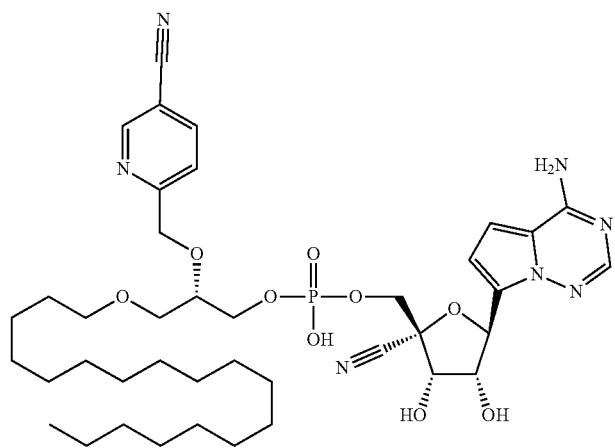 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1]

TABLE 19-continued
Some Compounds of Formula VII
Structure
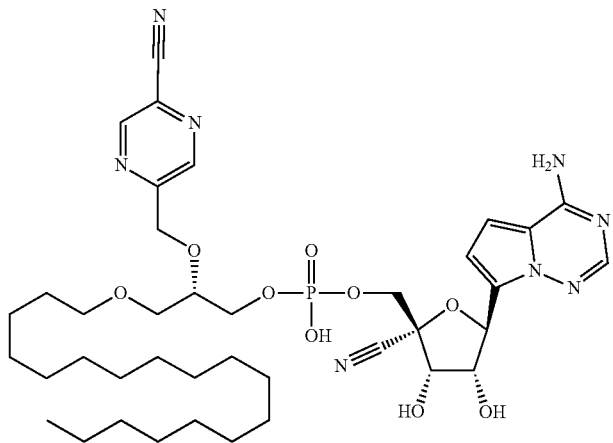
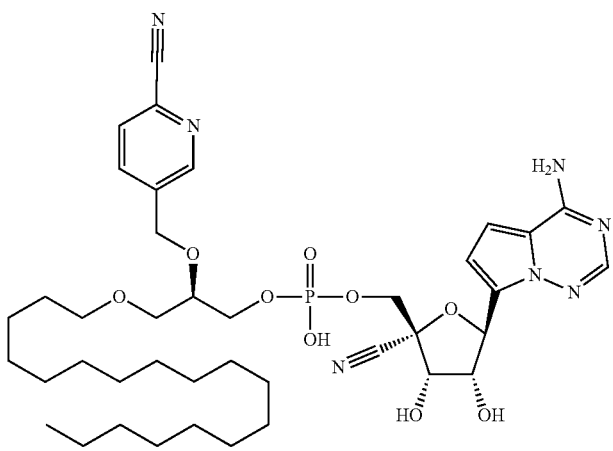
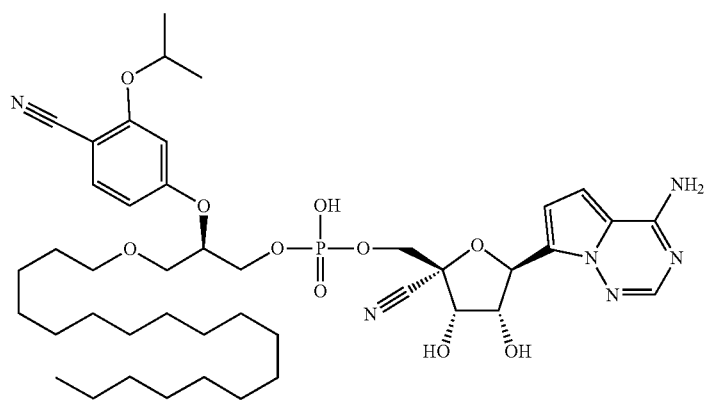 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(OC(C)C)c1]

TABLE 19-continued
Some Compounds of Formula VII
Structure
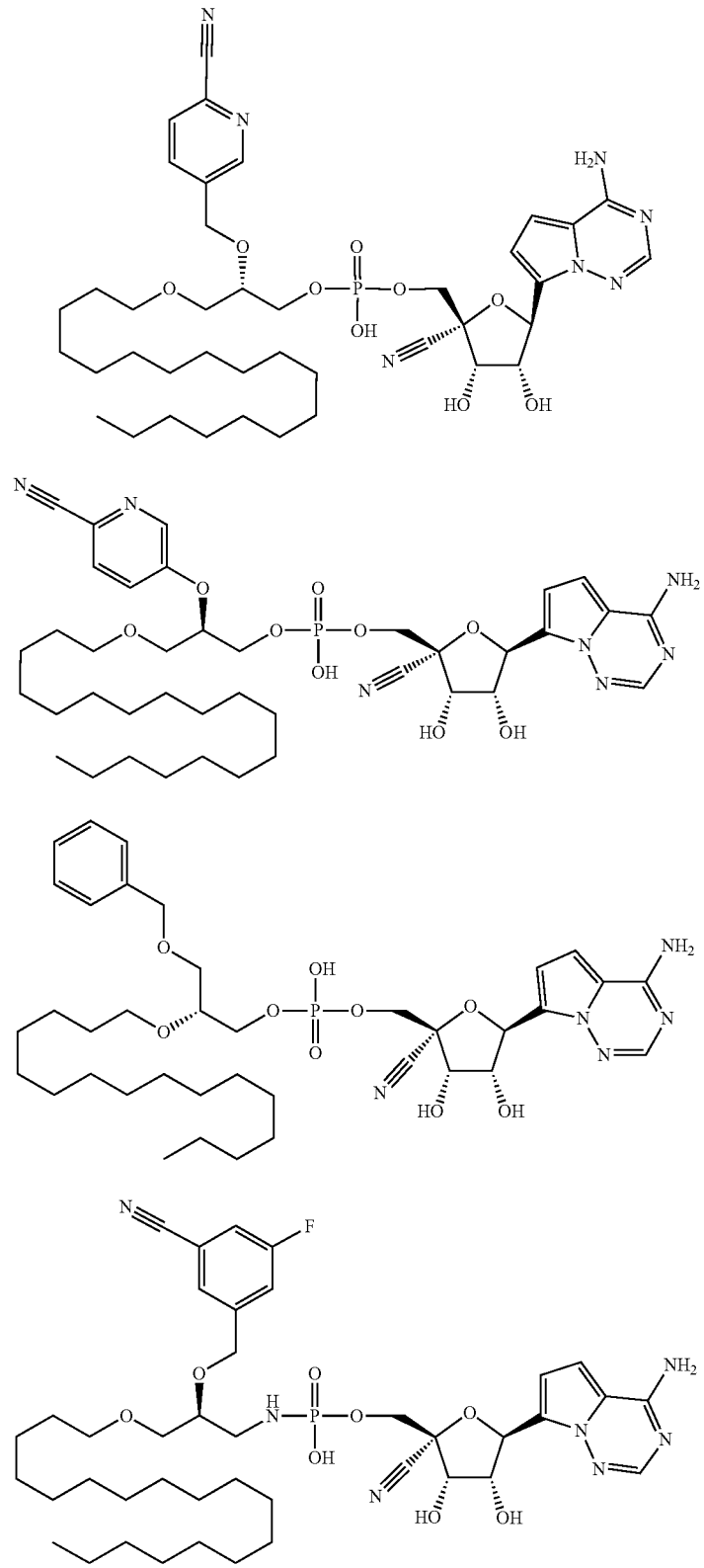

TABLE 19-continued
Some Compounds of Formula VII
Structure
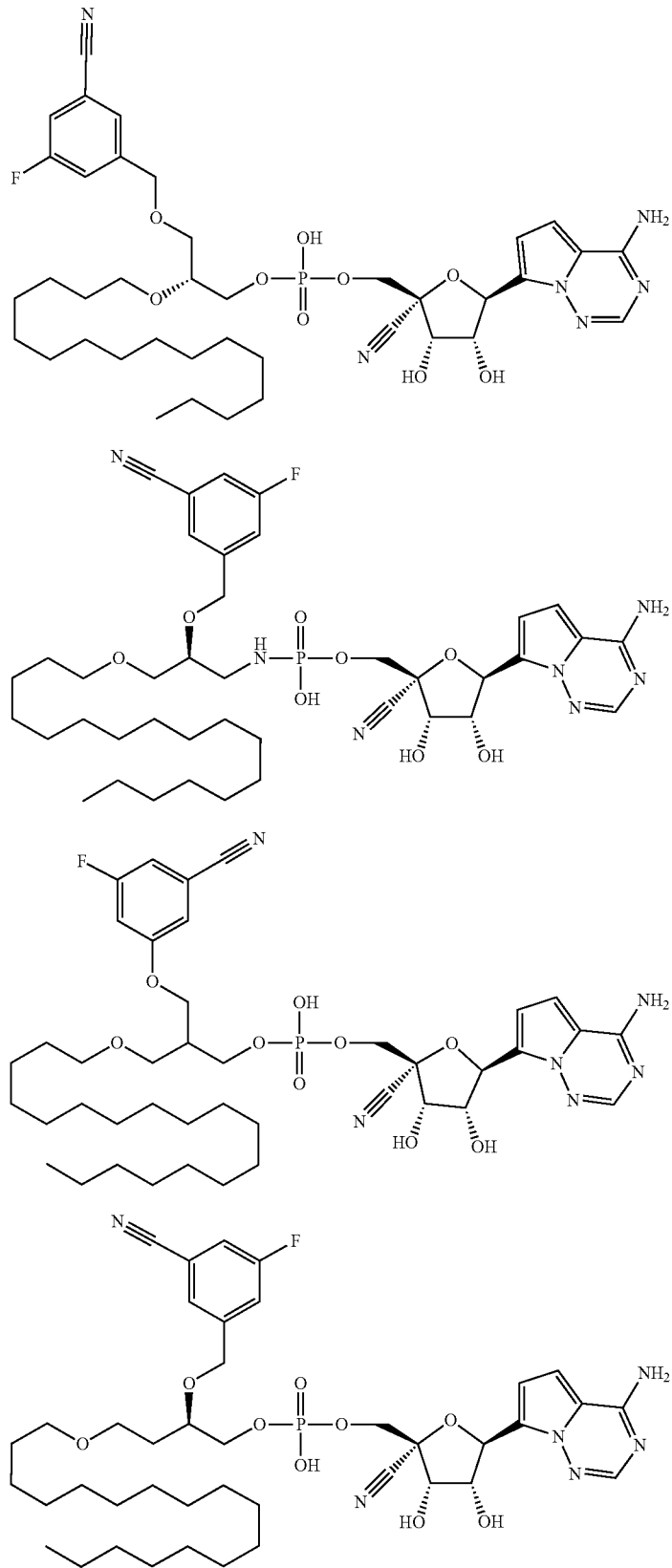

TABLE 19-continued
Some Compounds of Formula VII
Structure
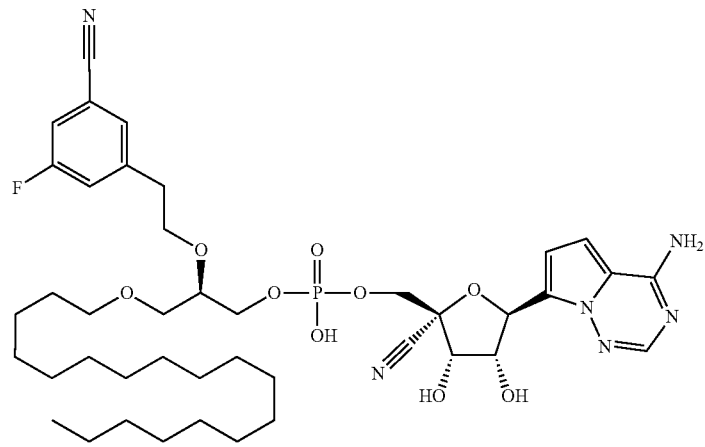 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCCc1cc(F)cc(C#N)c1]
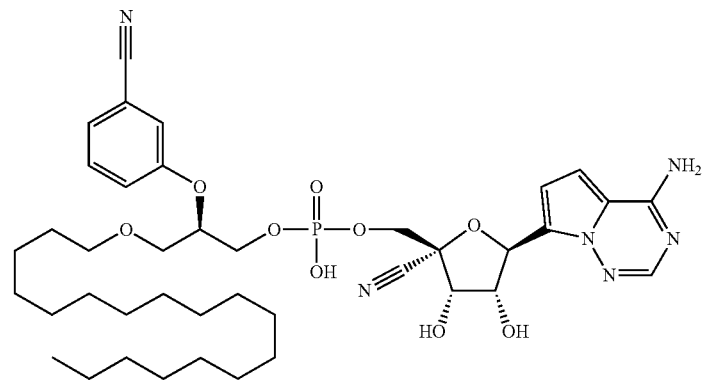 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1cccc(C#N)c1]
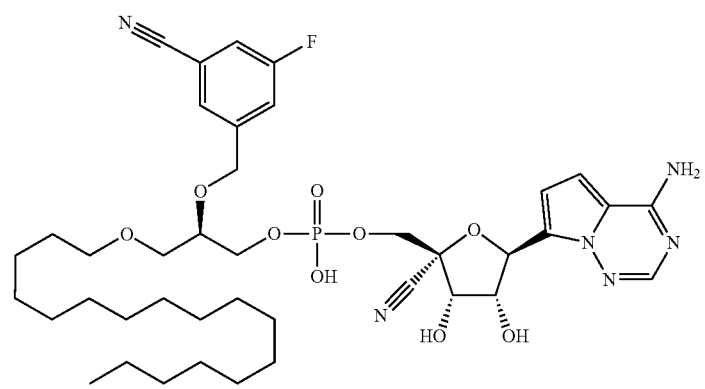 [SMILES: CCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 19-continued
Some Compounds of Formula VII
Structure
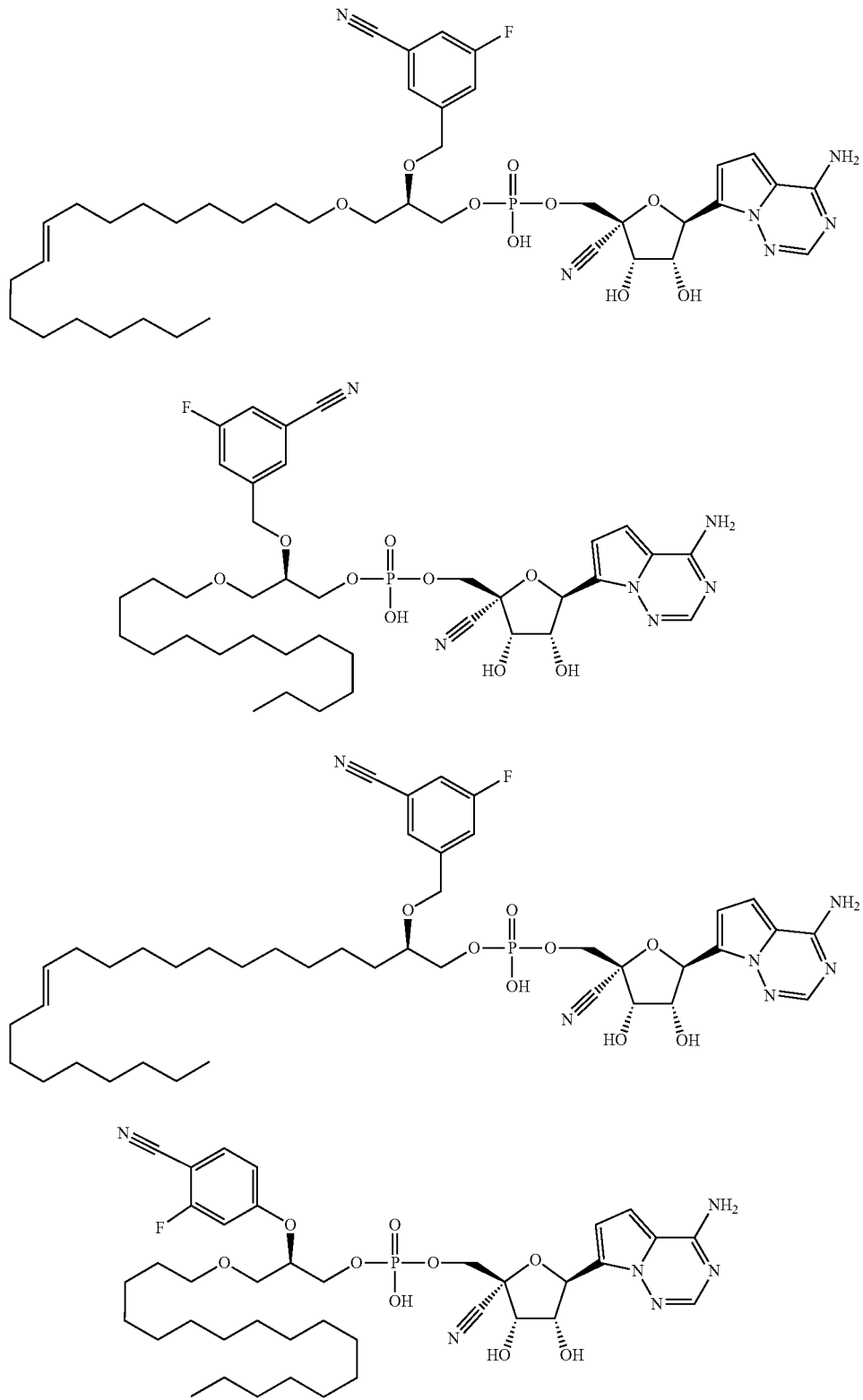

TABLE 19-continued
Some Compounds of Formula VII
Structure
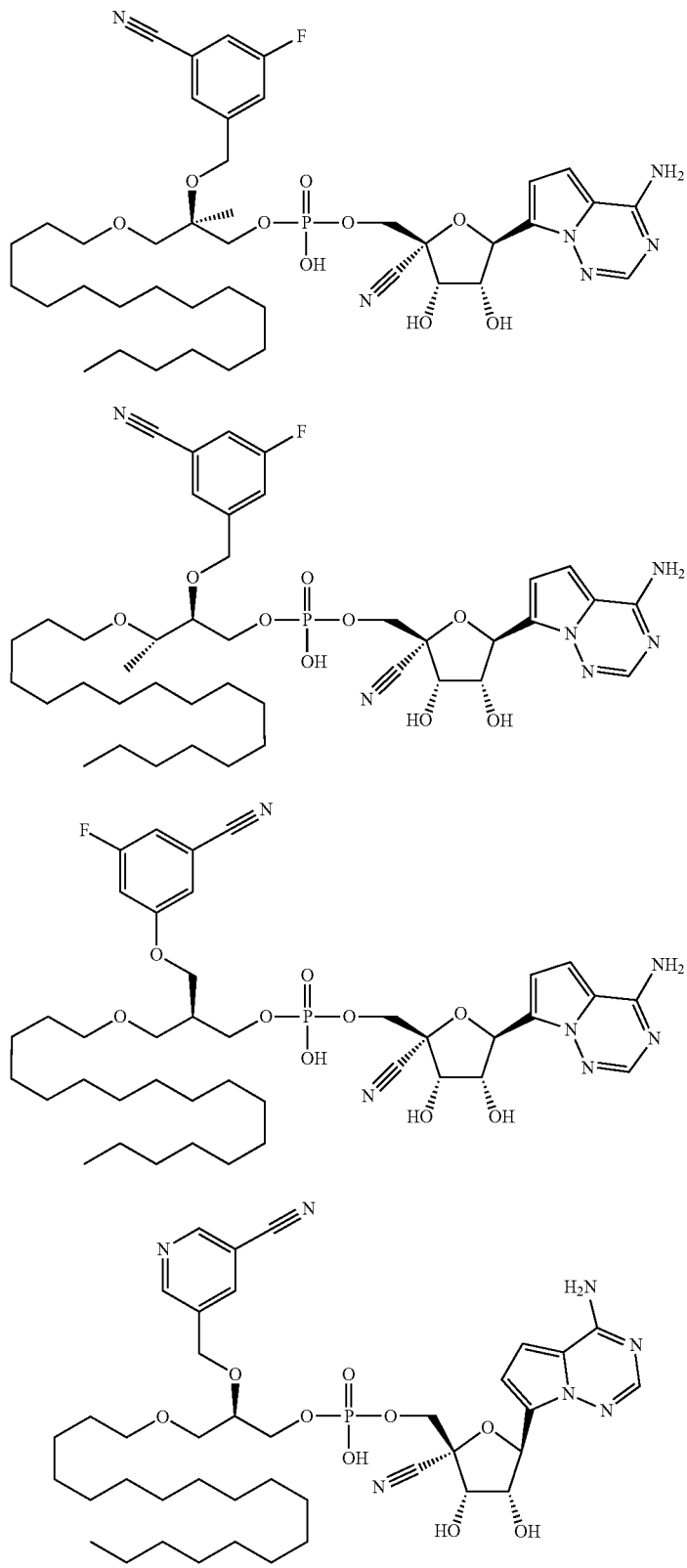

TABLE 19-continued
Some Compounds of Formula VII
Structure
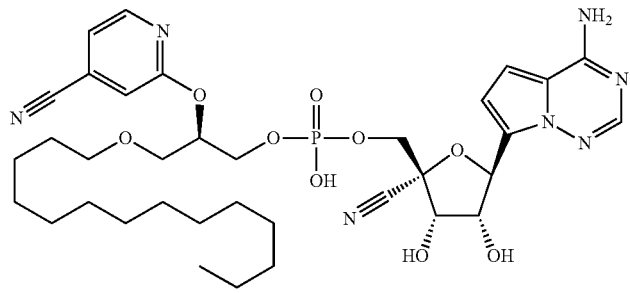 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1cc(C#N)ccn1]
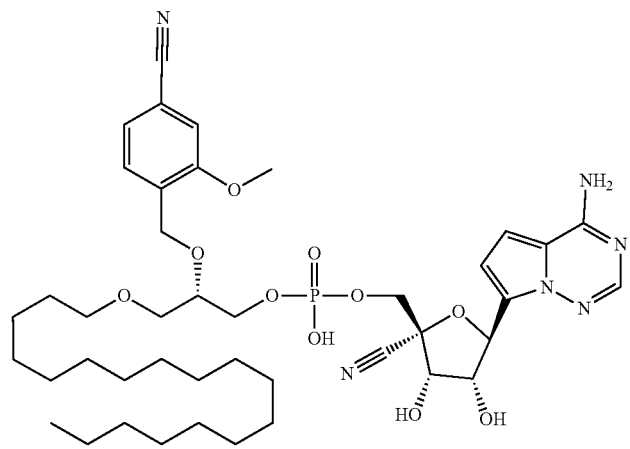 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cc1OC]
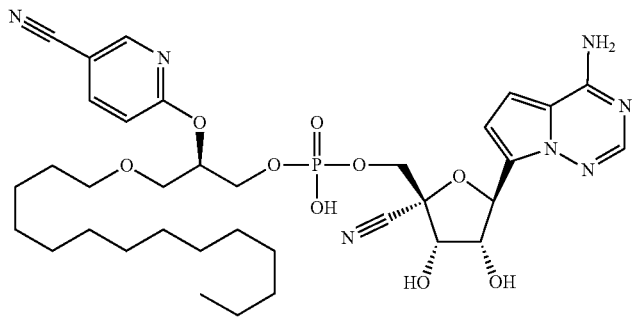 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)cn1]
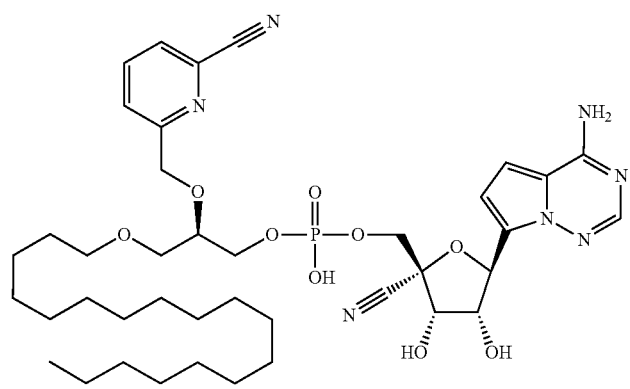 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)n1]

TABLE 19-continued
Some Compounds of Formula VII
Structure
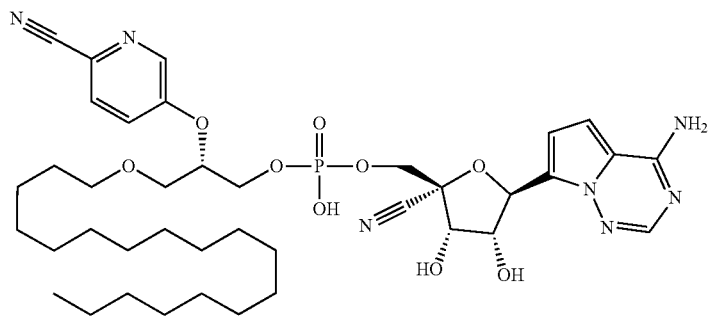 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)Oc1ccc(C#N)nc1]
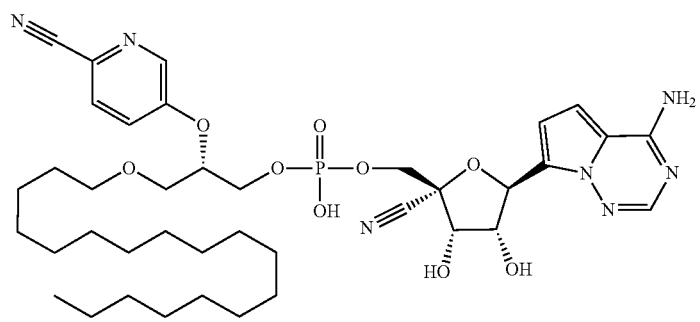 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)Oc1ccc(C#N)nc1]
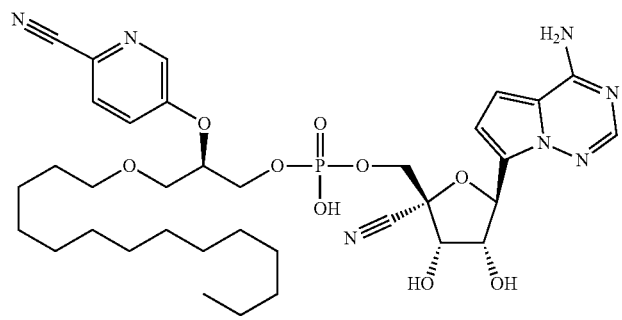 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)nc1]
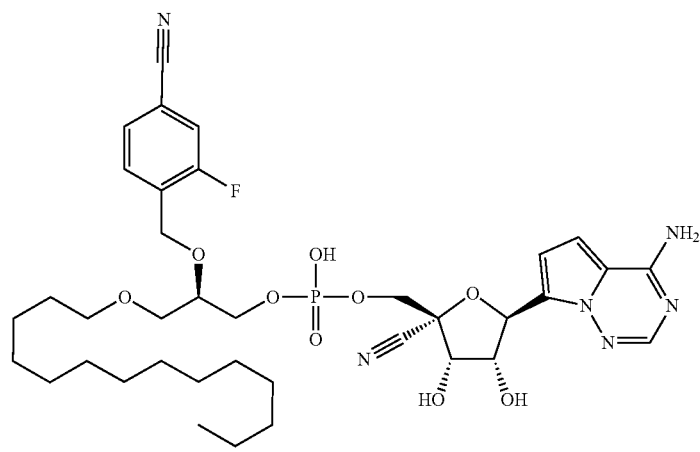 [SMILES: CCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]

TABLE 19-continued
Some Compounds of Formula VII
Structure
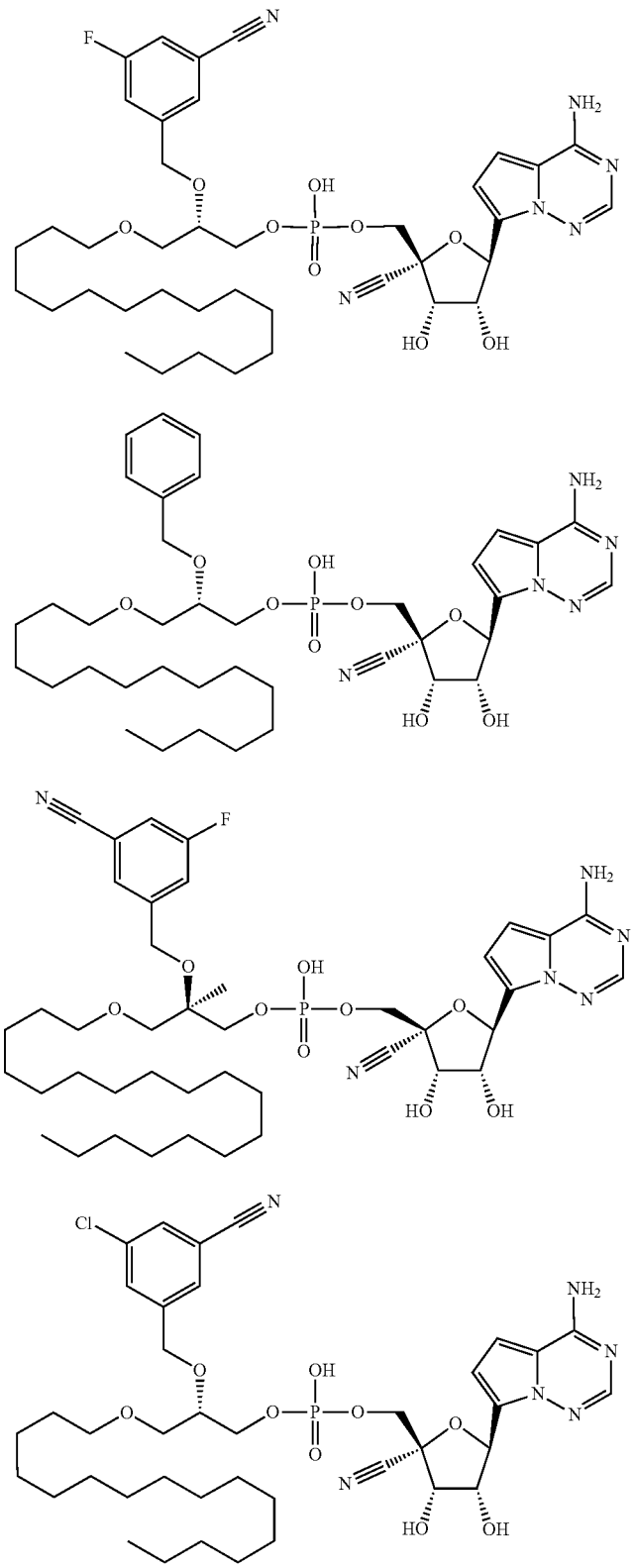

In some embodiments, the compound of Formula I has a Formula VIIa:

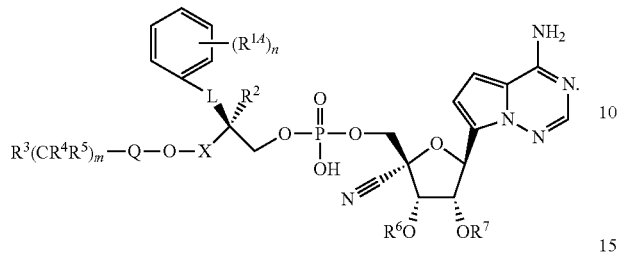

Formula VIIa

The description of substituents of Formula I (e.g., $R^{14}$, $R^2$, $R^3$, $R^4$, $R^5$, $R^6$, $R^7$, Q, X, L, m and n) applies to Formula VIIa. In some embodiments, the compounds and pharmaceutically acceptable salts of Formula VIIa include the compounds in Table 20 and the pharmaceutically acceptable salts thereof.

TABLE 20

Some Compounds of Formula VIIa

Structure

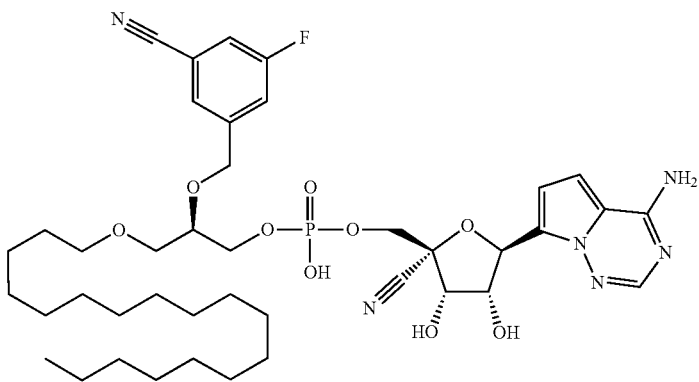 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

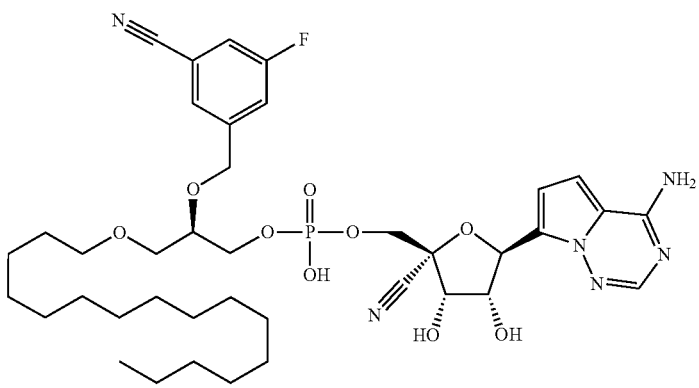 [SMILES: CCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 20-continued
Some Compounds of Formula VIIa
Structure
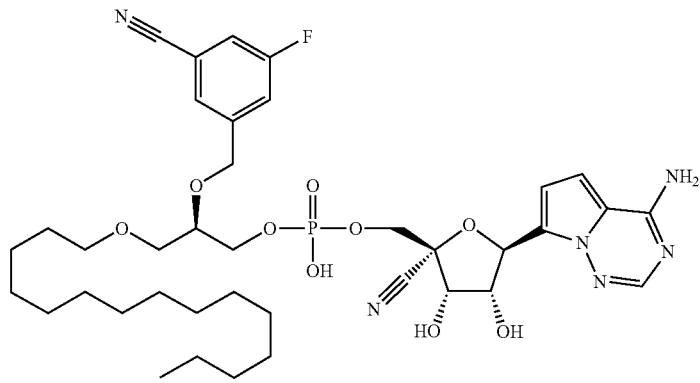 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
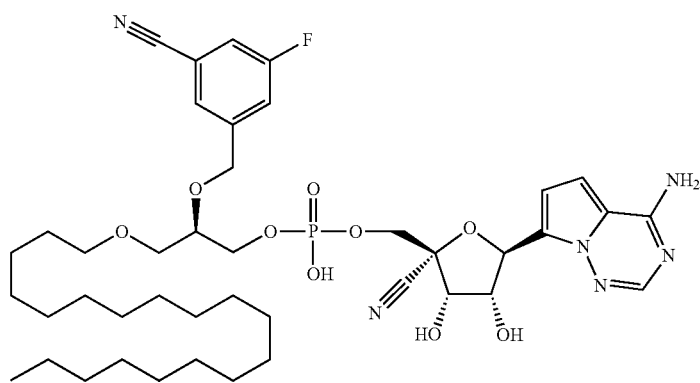 [SMILES: CCCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
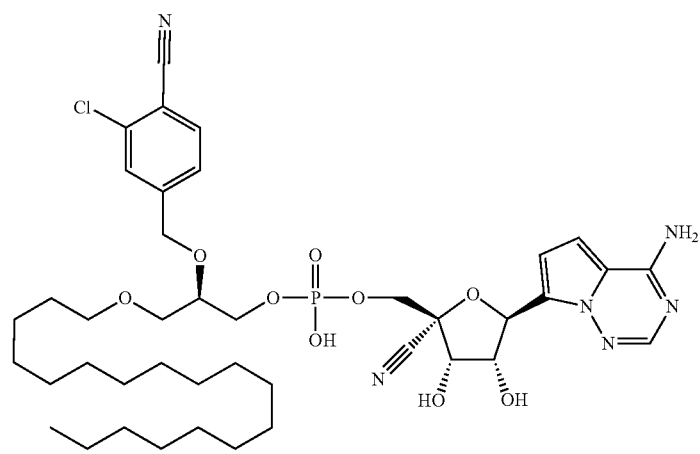 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(Cl)c1]

TABLE 20-continued
Some Compounds of Formula VIIa
Structure
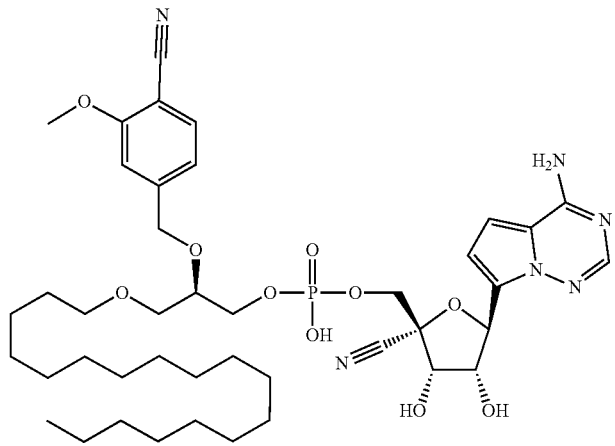 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]
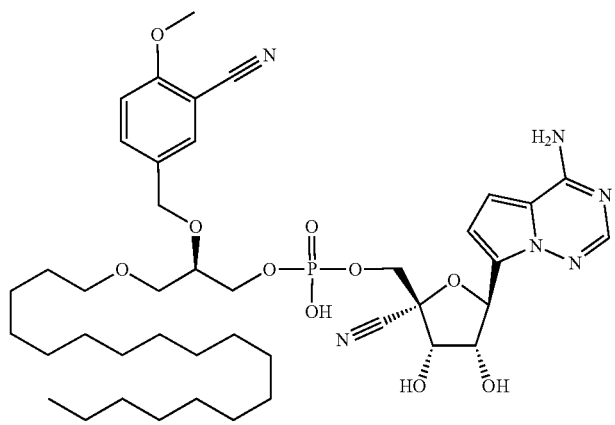 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]
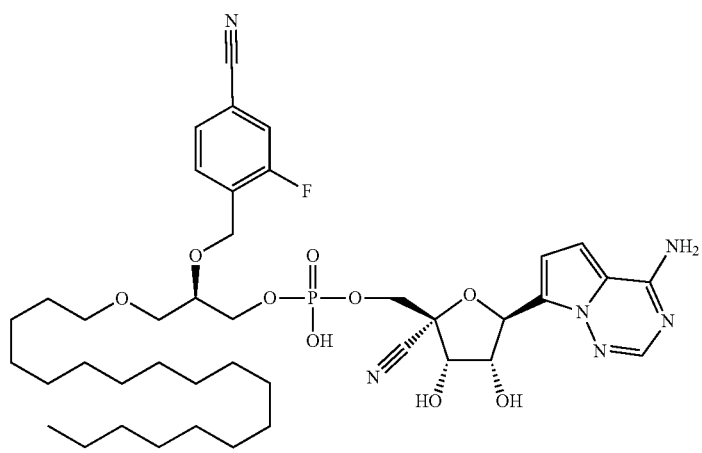 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]

TABLE 20-continued
Some Compounds of Formula VIIa
Structure
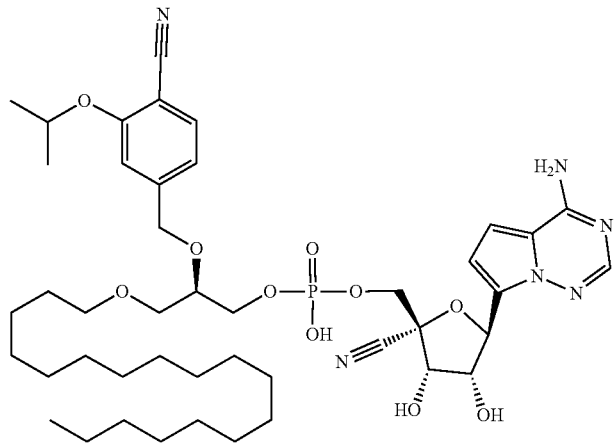 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
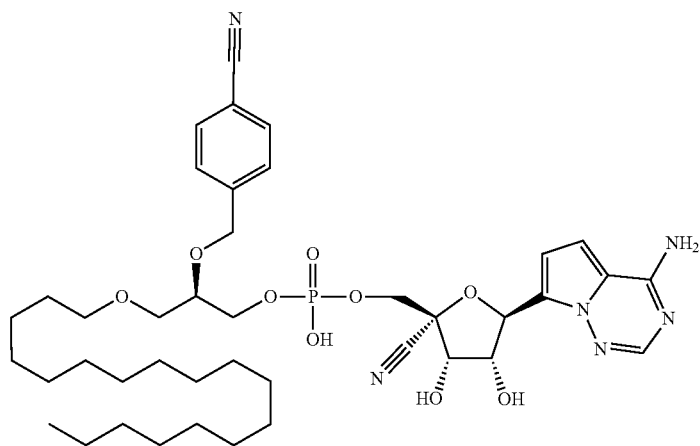 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]
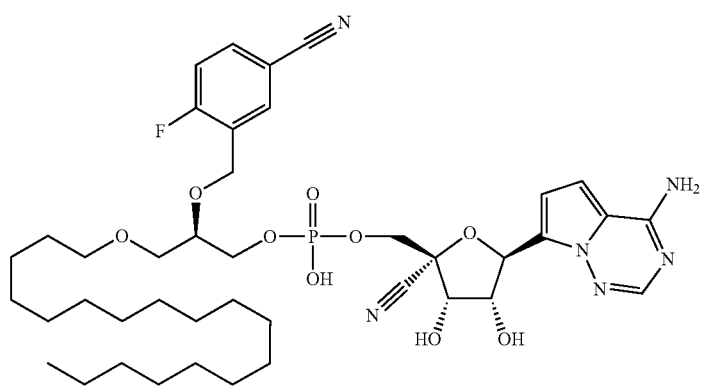 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(C#N)ccc1F]

TABLE 20-continued
Some Compounds of Formula VIIa
Structure
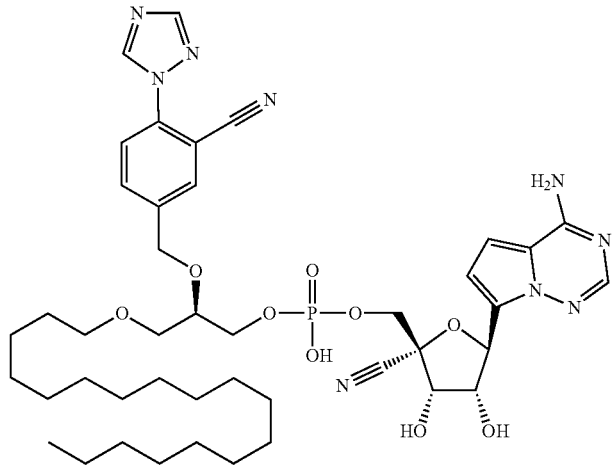 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
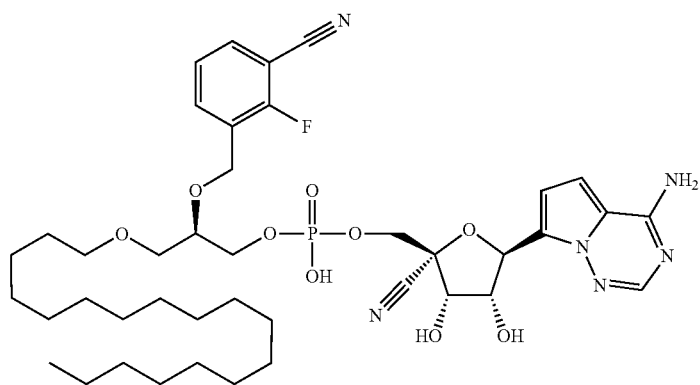 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
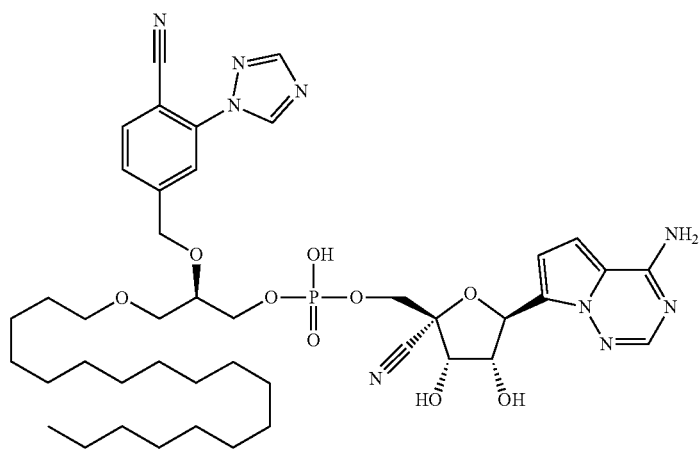 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]

TABLE 20-continued
Some Compounds of Formula VIIa
Structure
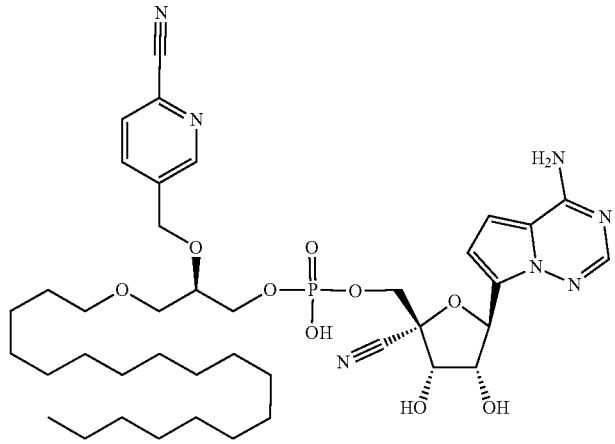 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)nc1]
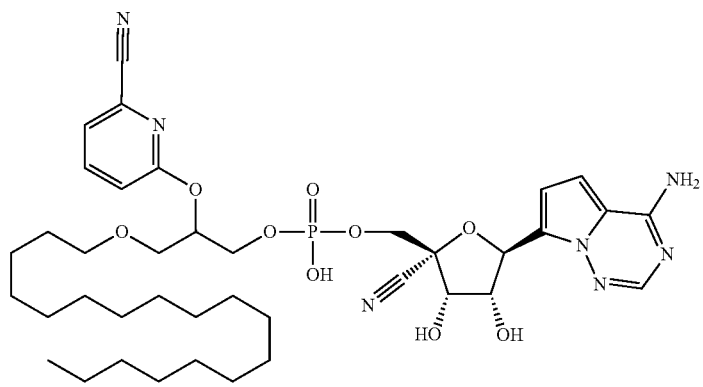 [SMILES: CCCCCCCCCCCCCCCCCCOCC(COP(=O)(O)OC[C@@]1(C#N)O[C@@H](c2ccc3c(N)ncnn23)[C@H](O)[C@@H]1O)Oc1cccc(C#N)n1]
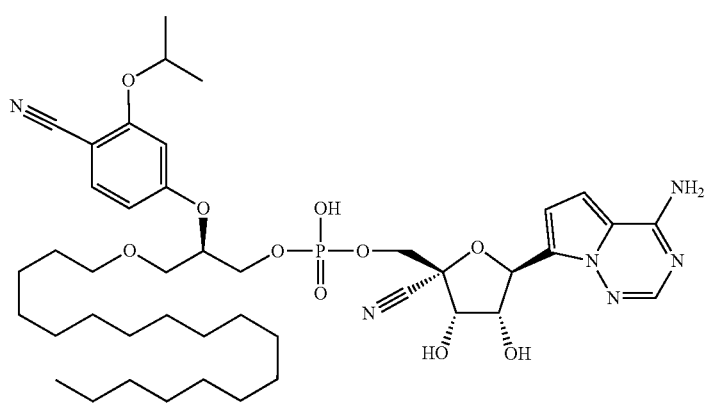 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(OC(C)C)c1]
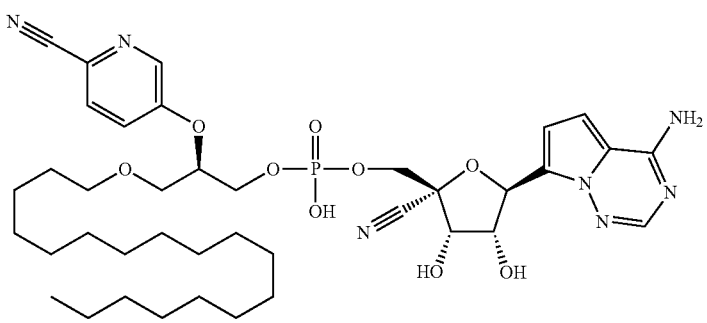 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)nc1]

TABLE 20-continued
Some Compounds of Formula VIIa
Structure
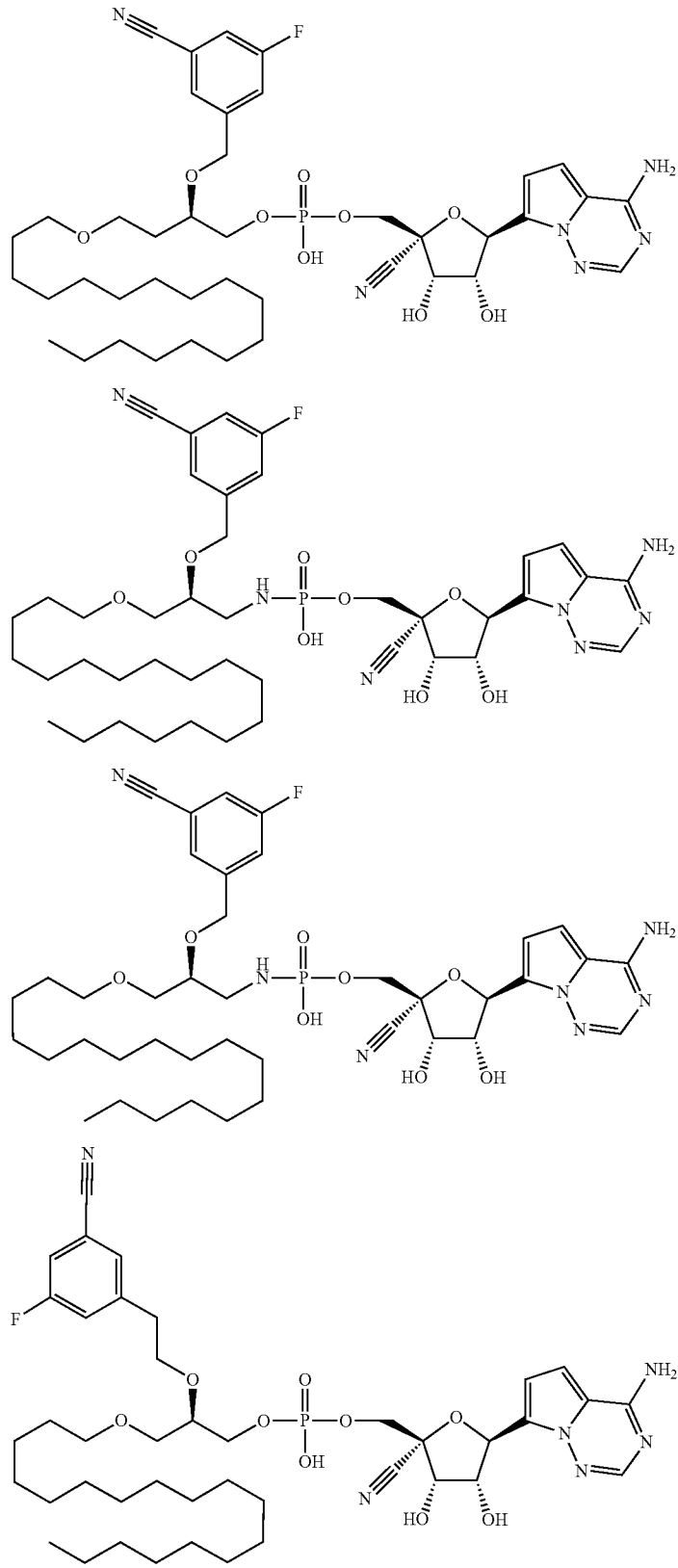

TABLE 20-continued
Some Compounds of Formula VIIa
Structure
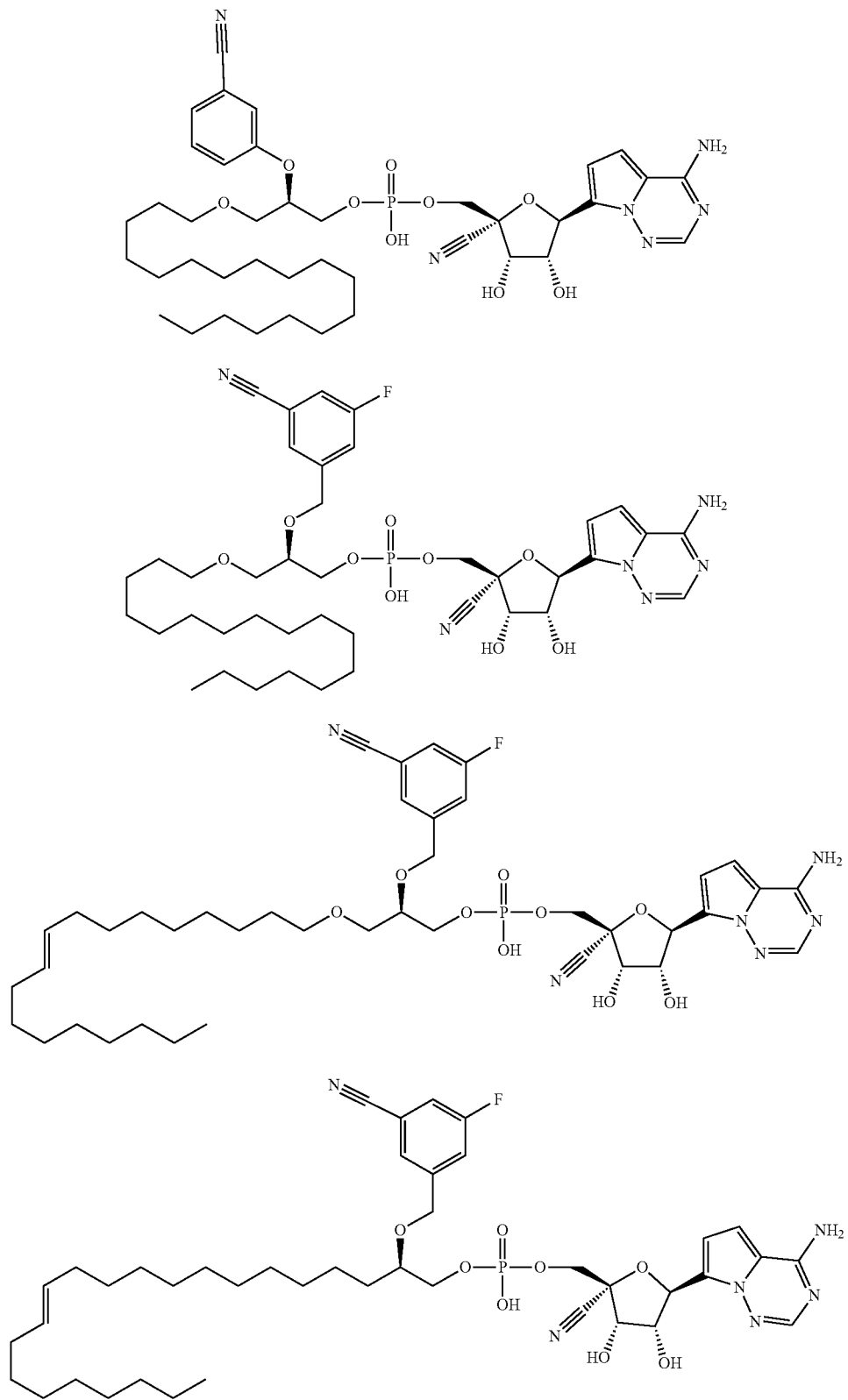

TABLE 20-continued
Some Compounds of Formula VIIa
Structure
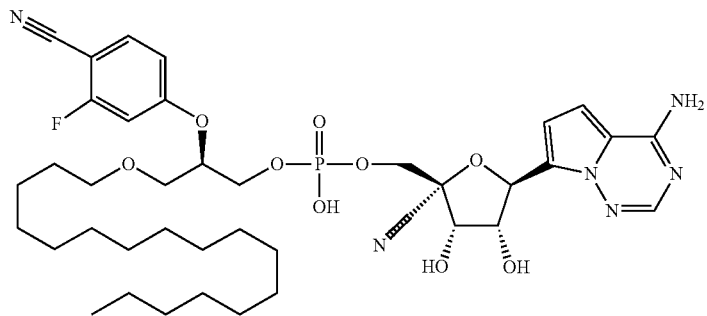 [SMILES: C=N[C@]1(COP(=O)(O)OC[C@@H](COCCCCCCCCCCCCCCCCC)Oc2ccc(C#N)c(F)c2)O[C@@H](c2ccc3c(N)ncnn23)[C@H](O)[C@@H]1O]
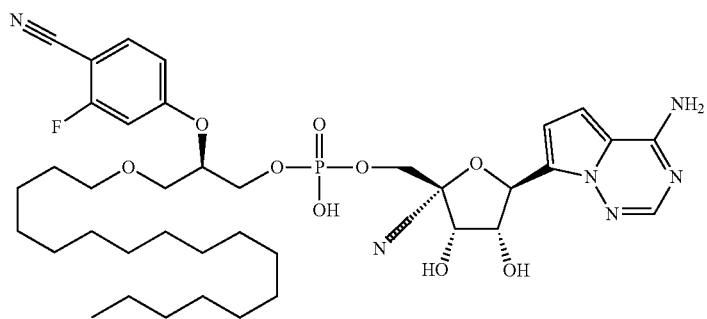 [SMILES: C=N[C@]1(COP(=O)(O)OC[C@@H](COCCCCCCCCCCCCCCCCC)Oc2ccc(C#N)c(F)c2)O[C@@H](c2ccc3c(N)ncnn23)[C@H](O)[C@@H]1O]
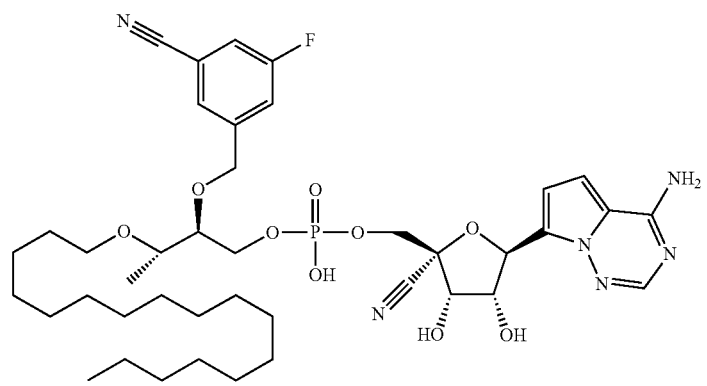 [SMILES: CCCCCCCCCCCCCCCCCO[C@@H](C)[C@H](COP(=O)(O)OC[C@@]1(C#N)O[C@@H](c2ccc3c(N)ncnn23)[C@H](O)[C@@H]1O)OCc1cc(F)cc(C#N)c1]
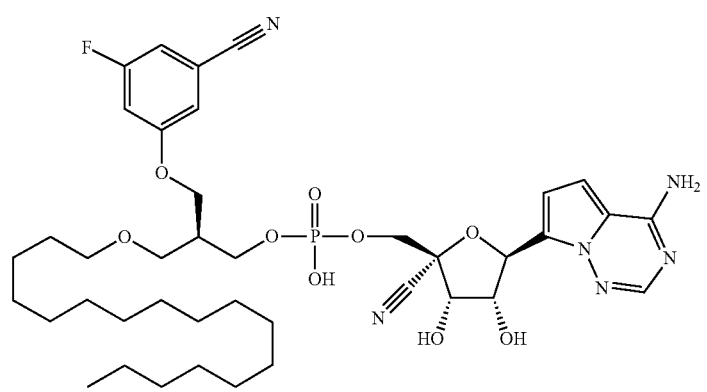 [SMILES: CCCCCCCCCCCCCCCCCOC[C@@H](COc1cc(F)cc(C#N)c1)COP(=O)(O)OC[C@@]1(C#N)O[C@@H](c2ccc3c(N)ncnn23)[C@H](O)[C@@H]1O]

TABLE 20-continued
Some Compounds of Formula VIIa
Structure
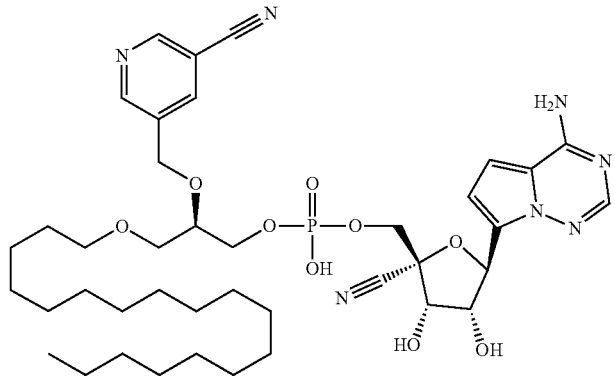 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cncc(C#N)c1]
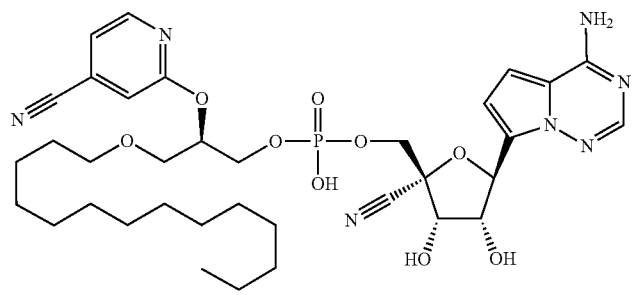 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1cc(C#N)ccn1]
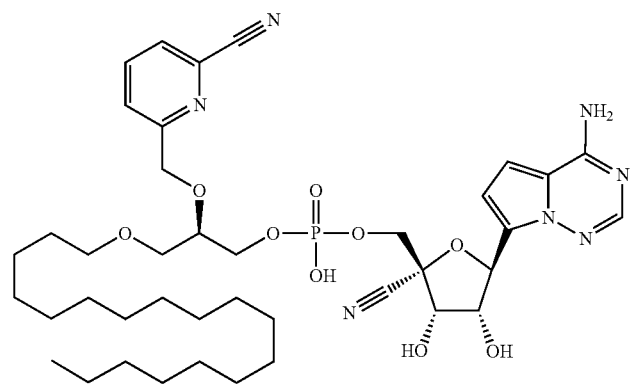 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)n1]
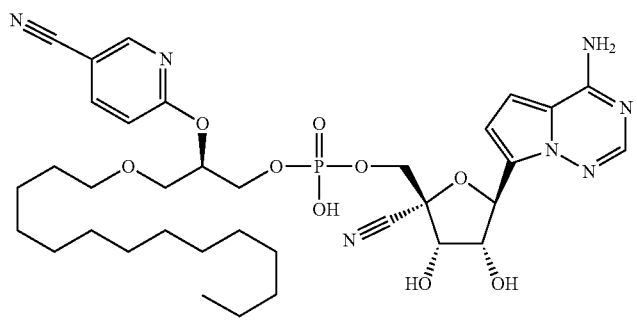 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)cn1]

TABLE 20-continued
Some Compounds of Formula VIIa
Structure
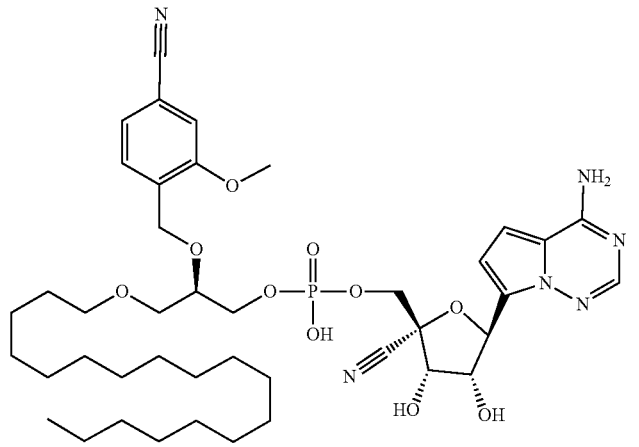 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1OC]
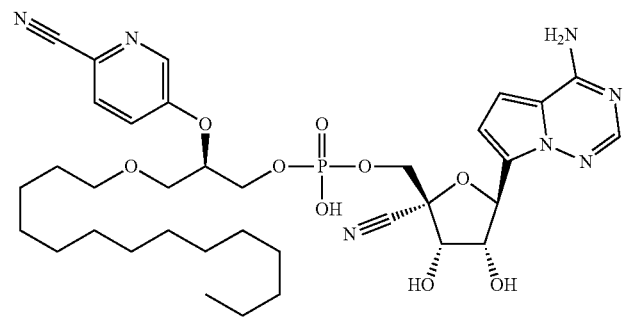 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)nc1]
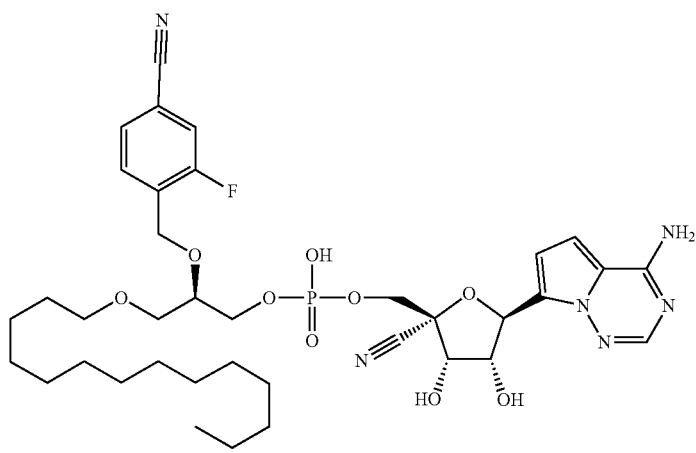 [SMILES: CCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]
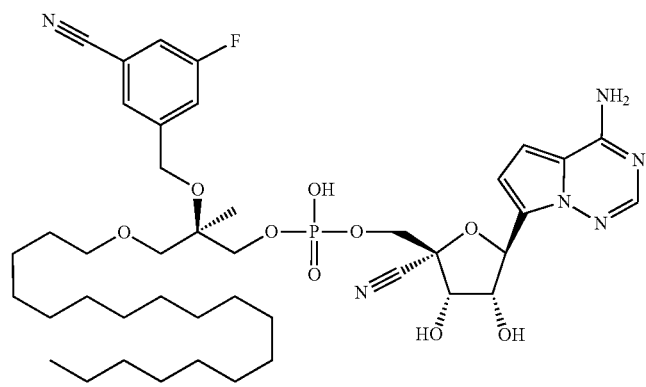 [SMILES: CCCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]

TABLE 20-continued

Some Compounds of Formula VIIa
Structure

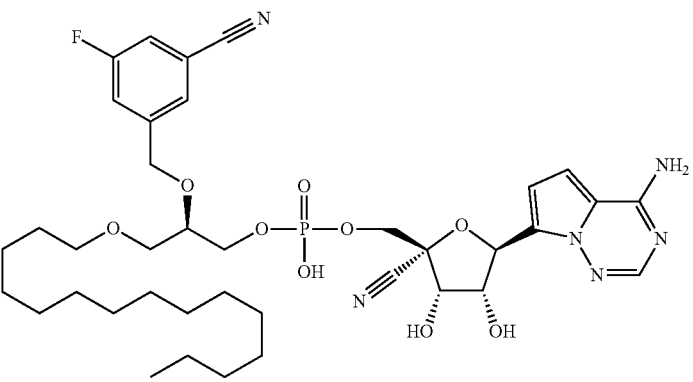 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

In some embodiments, the compound of Formula I has a Formula VIIb:

Formula VIIb

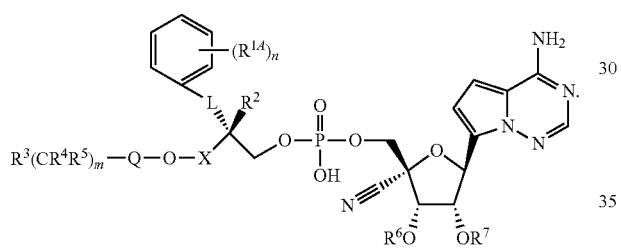

The description of substituents of Formula I (e.g., $R^{1A}$, $R^2$, $R^3$, $R^4$, $R^5$, $R^6$, $R^7$, Q, X, L, m and n) applies to Formula VIIb. In some embodiments, the compounds and pharmaceutically acceptable salts of Formula VIIb include the compounds in Table 21 and the pharmaceutically acceptable salts thereof.

TABLE 21

Some Compounds of Formula VIIb
Structure

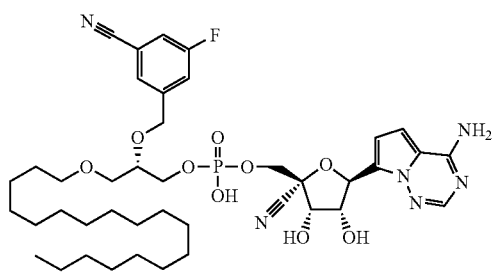 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 21-continued

Some Compounds of Formula VIIb
Structure

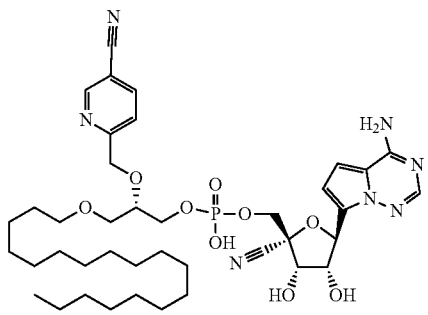 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1]

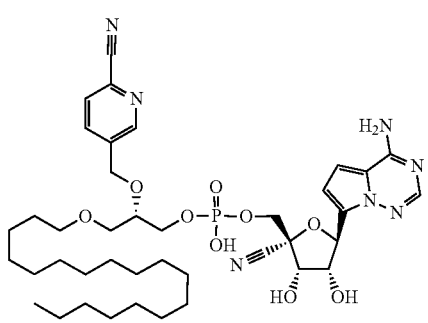 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)nc1]

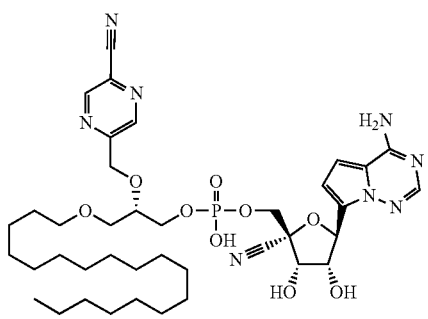 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cnc(C#N)cn1]

TABLE 21-continued

Some Compounds of Formula VIIb
Structure

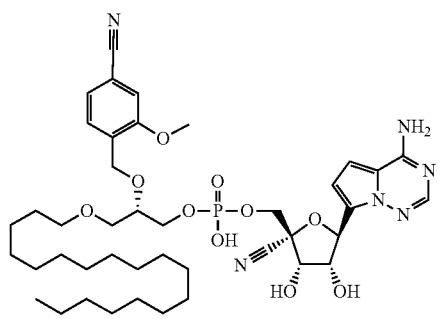 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cc1OC]

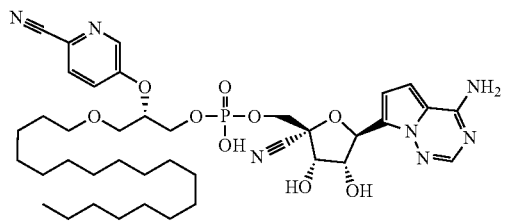 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)Oc1ccc(C#N)nc1]

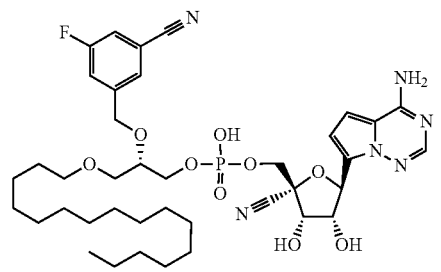 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]

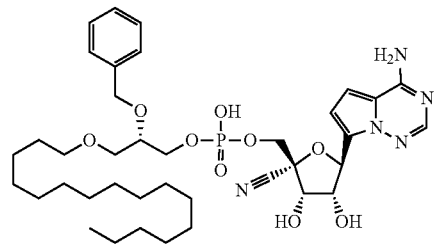 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccccc1]

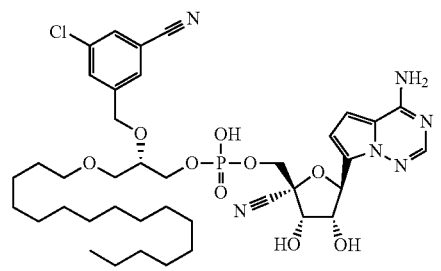 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(Cl)cc(C#N)c1]

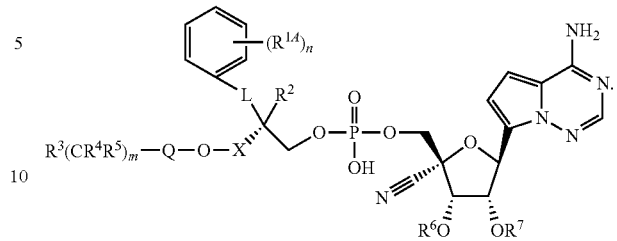

Formula VIIc

The description of substituents of Formula I (e.g., $R^{14}$, $R^2$, $R^3$, $R^4$, $R^5$, $R^6$, $R^7$, Q, X, L, m and n) applies to Formula VIIc. In some embodiments, the compounds and pharmaceutically acceptable salts of Formula VIIc include the compounds in Table 22 and the pharmaceutically acceptable salts thereof.

TABLE 22

Some Compounds of Formula VIIc
Structure

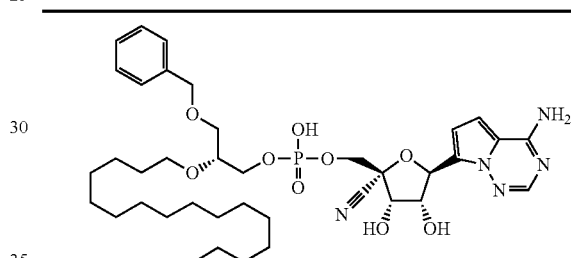

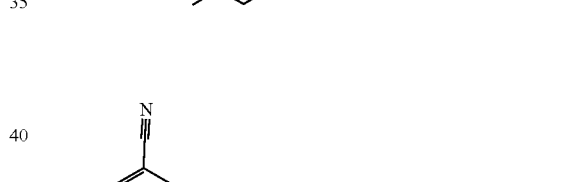

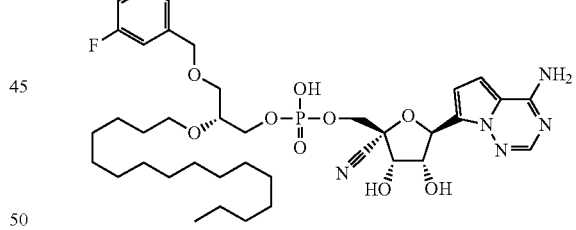

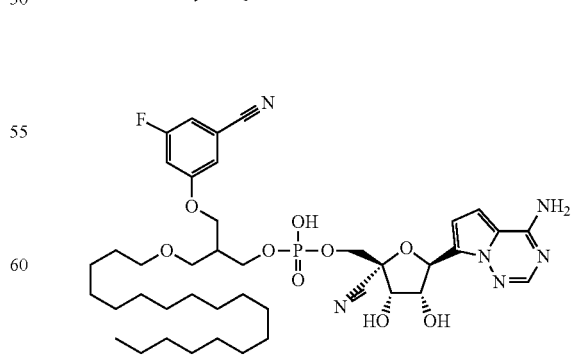

In some embodiments, the compound of Formula I has a Formula VIIc:

In some embodiments, the compound of Formula I has a Formula VIII:

Formula VIII
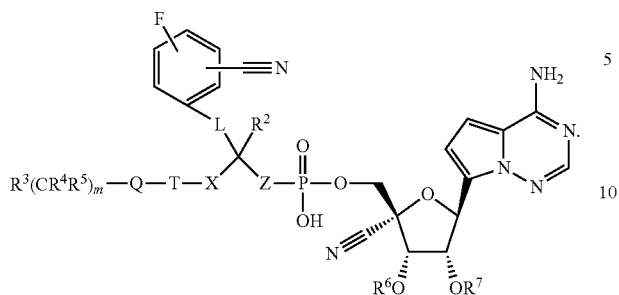
The description of substituents of Formula I (e.g., $R^2$, $R^3$, $R^4$, $R^5$, $R^6$, $R^7$, Q, T, X, Z, L, and m) applies to Formula VIII.
In some embodiments, the compounds and pharmaceutically acceptable salts of Formula VIII include the compounds in Table 23 and the pharmaceutically acceptable salts thereof.
TABLE 23
Some Compounds of Formula VIII
Structure
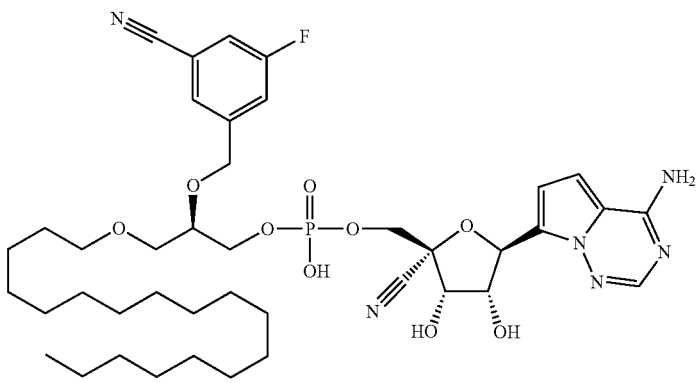 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
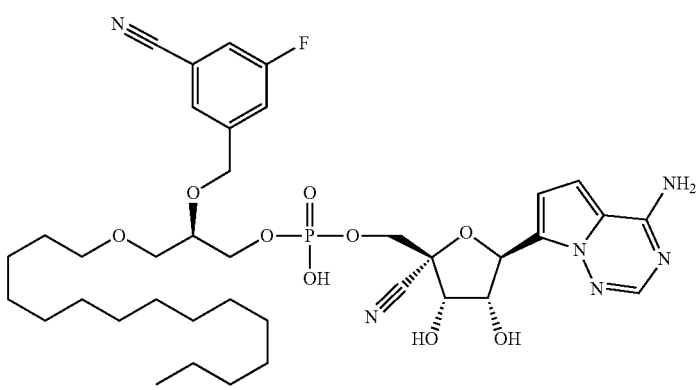 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 23-continued
Some Compounds of Formula VIII
Structure
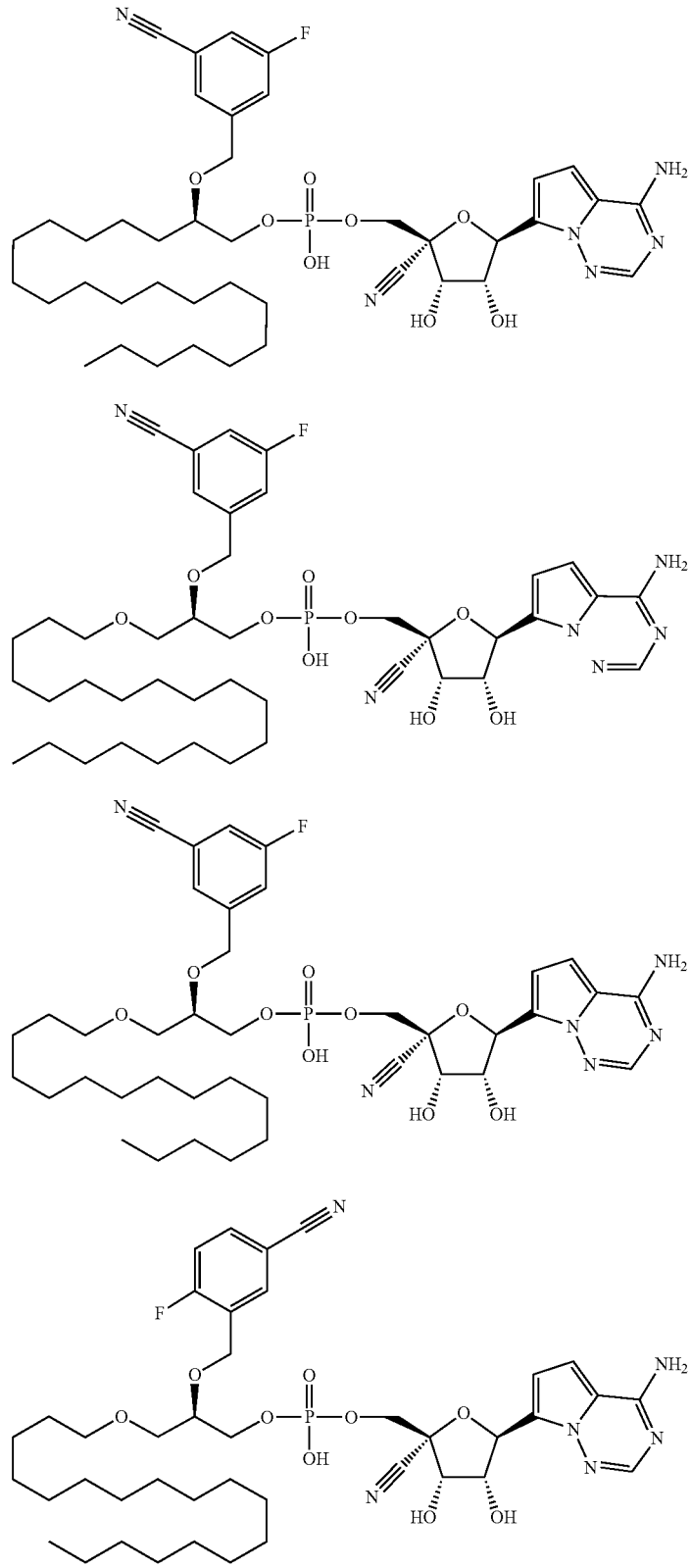

TABLE 23-continued
Some Compounds of Formula VIII
Structure
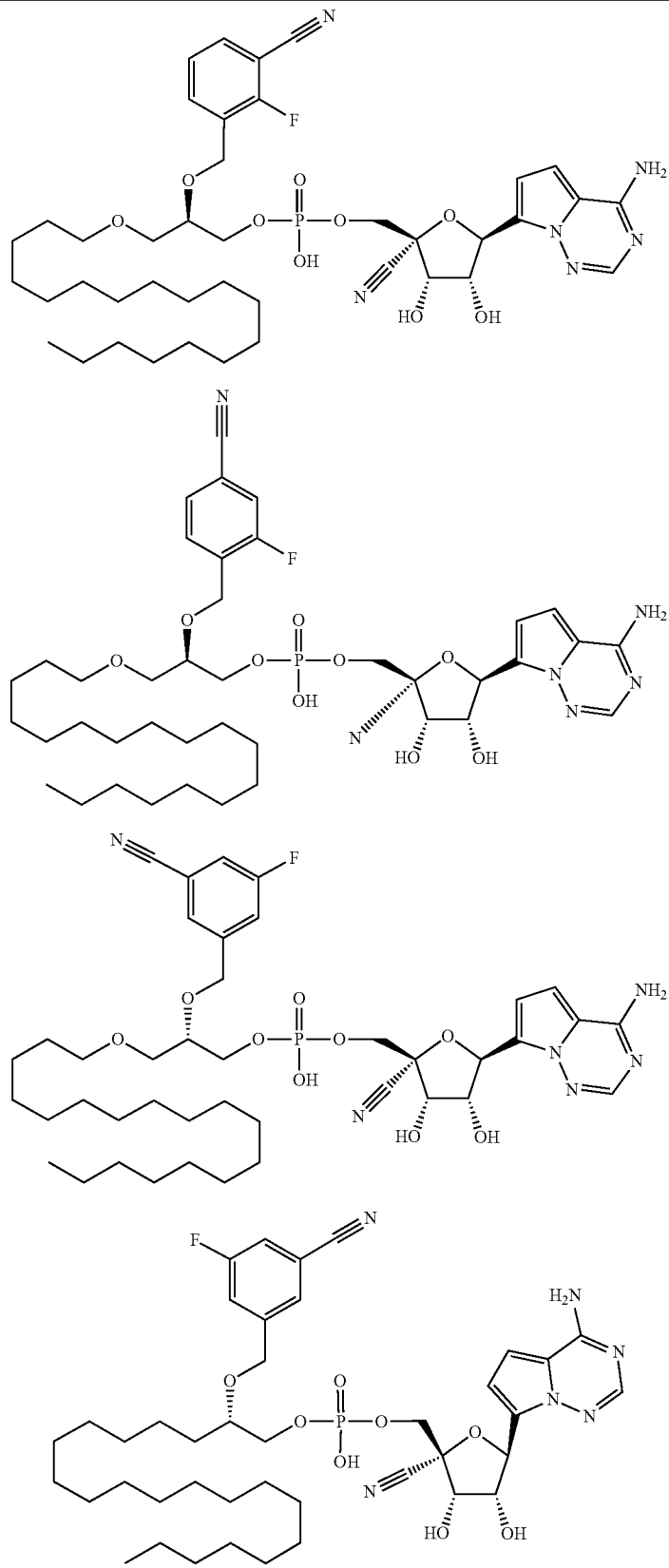

TABLE 23-continued
Some Compounds of Formula VIII
Structure
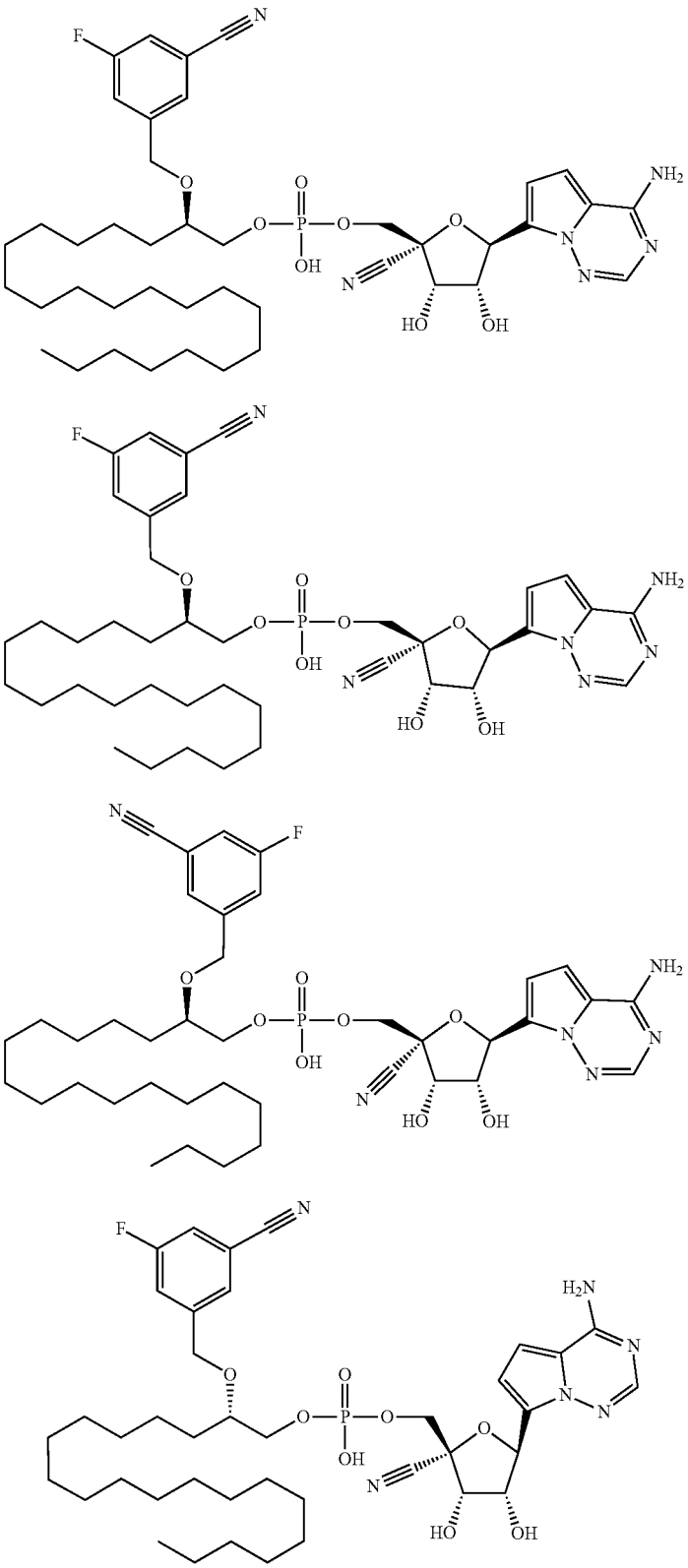

TABLE 23-continued
Some Compounds of Formula VIII
Structure
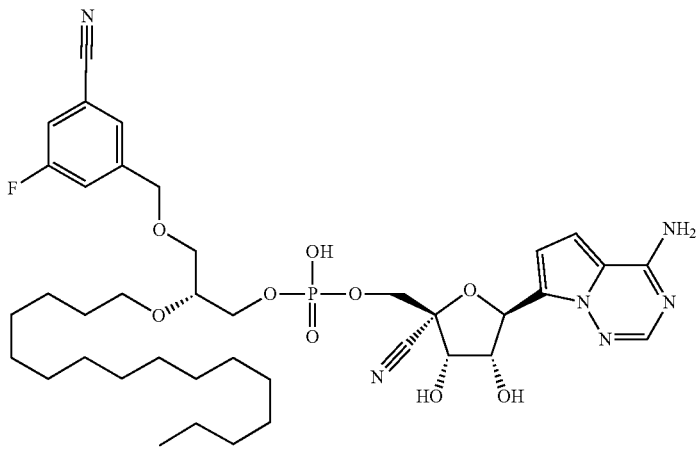 [SMILES: CCCCCCCCCCCCCCCCO[C@H](COCc1cc(F)cc(C#N)c1)COP(=O)(O)OC[C@@]1(C#N)O[C@@H](c2ccc3c(N)ncnn23)[C@H](O)[C@@H]1O]
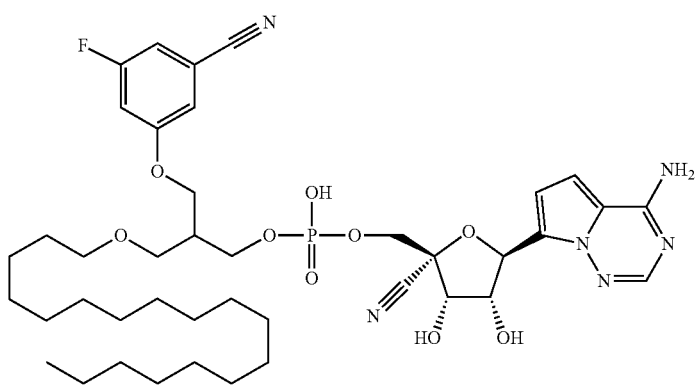 [SMILES: CCCCCCCCCCCCCCCCCCOCC(COc1cc(F)cc(C#N)c1)COP(=O)(O)OC[C@@]1(C#N)O[C@@H](c2ccc3c(N)ncnn23)[C@H](O)[C@@H]1O]
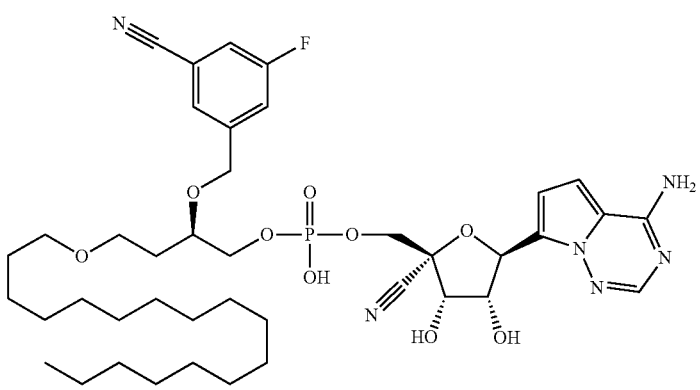 [SMILES: CCCCCCCCCCCCCCCCCOCC[C@H](COP(=O)(O)OC[C@@]1(C#N)O[C@@H](c2ccc3c(N)ncnn23)[C@H](O)[C@@H]1O)OCc1cc(F)cc(C#N)c1]
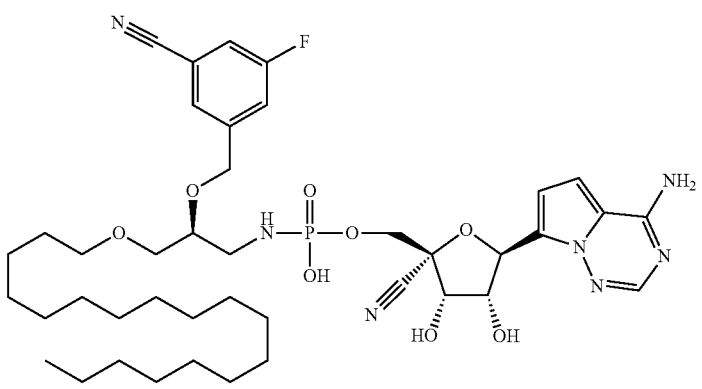 [SMILES: CCCCCCCCCCCCCCCCCCOC[C@H](CNP(=O)(O)OC[C@@]1(C#N)O[C@@H](c2ccc3c(N)ncnn23)[C@H](O)[C@@H]1O)OCc1cc(F)cc(C#N)c1]

TABLE 23-continued
Some Compounds of Formula VIII
Structure
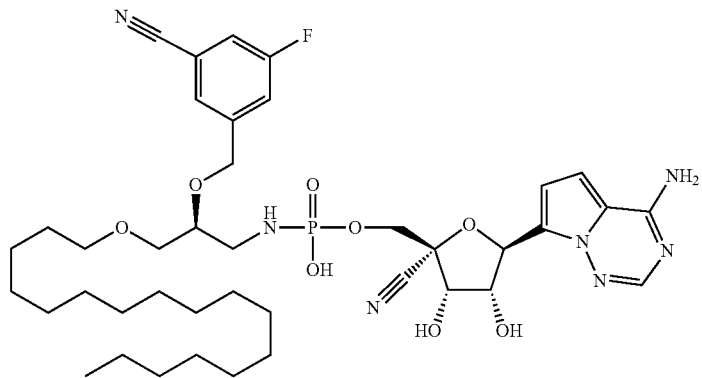 [SMILES: CCCCCCCCCCCCCCCCCOC[C@H](CNP(=O)(O)OC[C@@]1(C#N)O[C@@H](c2ccc3c(N)ncnn23)[C@H](O)[C@@H]1O)OCc1cc(F)cc(C#N)c1]
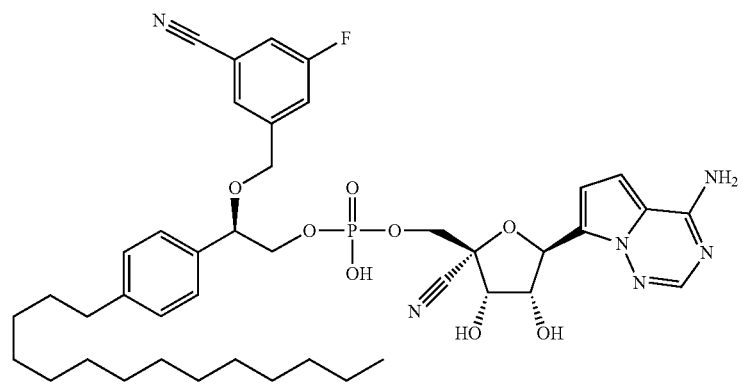 [SMILES: CCCCCCCCCCCCCCc1ccc([C@H](COP(=O)(O)OC[C@@]2(C#N)O[C@@H](c3ccc4c(N)ncnn34)[C@H](O)[C@@H]2O)OCc2cc(F)cc(C#N)c2)cc1]
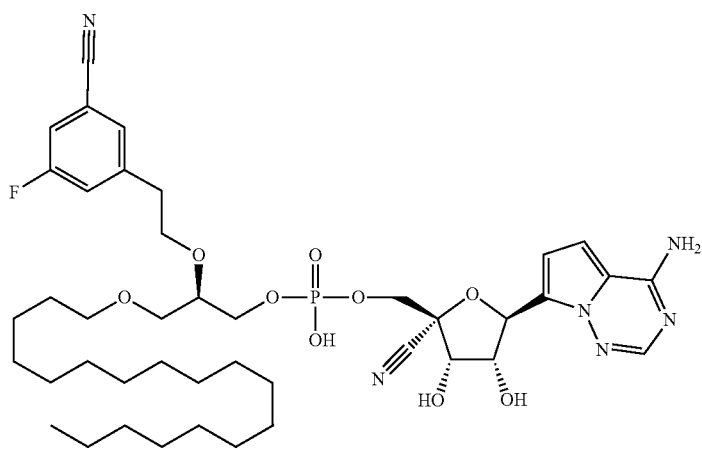 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCCc1cc(F)cc(C#N)c1]

TABLE 23-continued
Some Compounds of Formula VIII
Structure
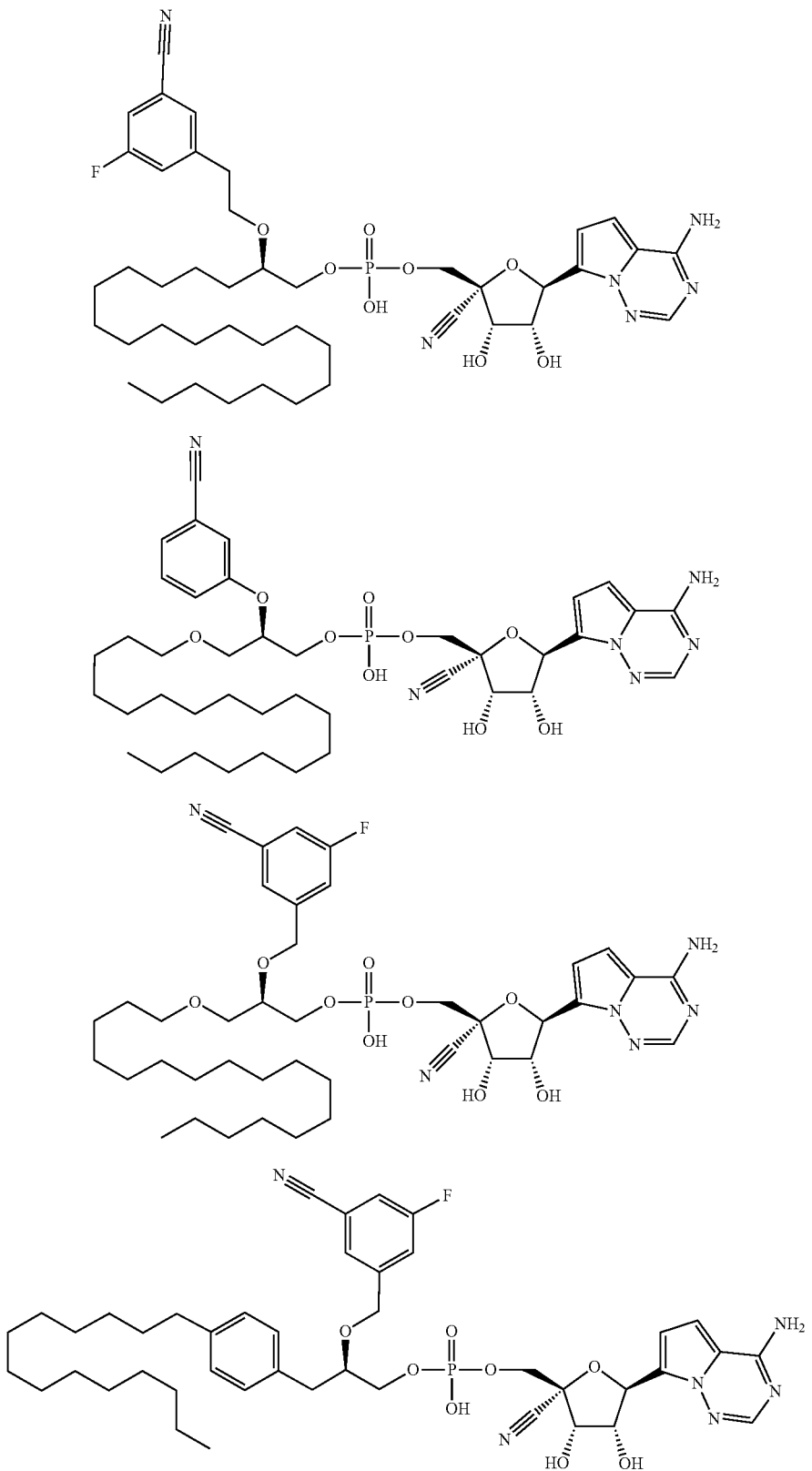

TABLE 23-continued
Some Compounds of Formula VIII
Structure
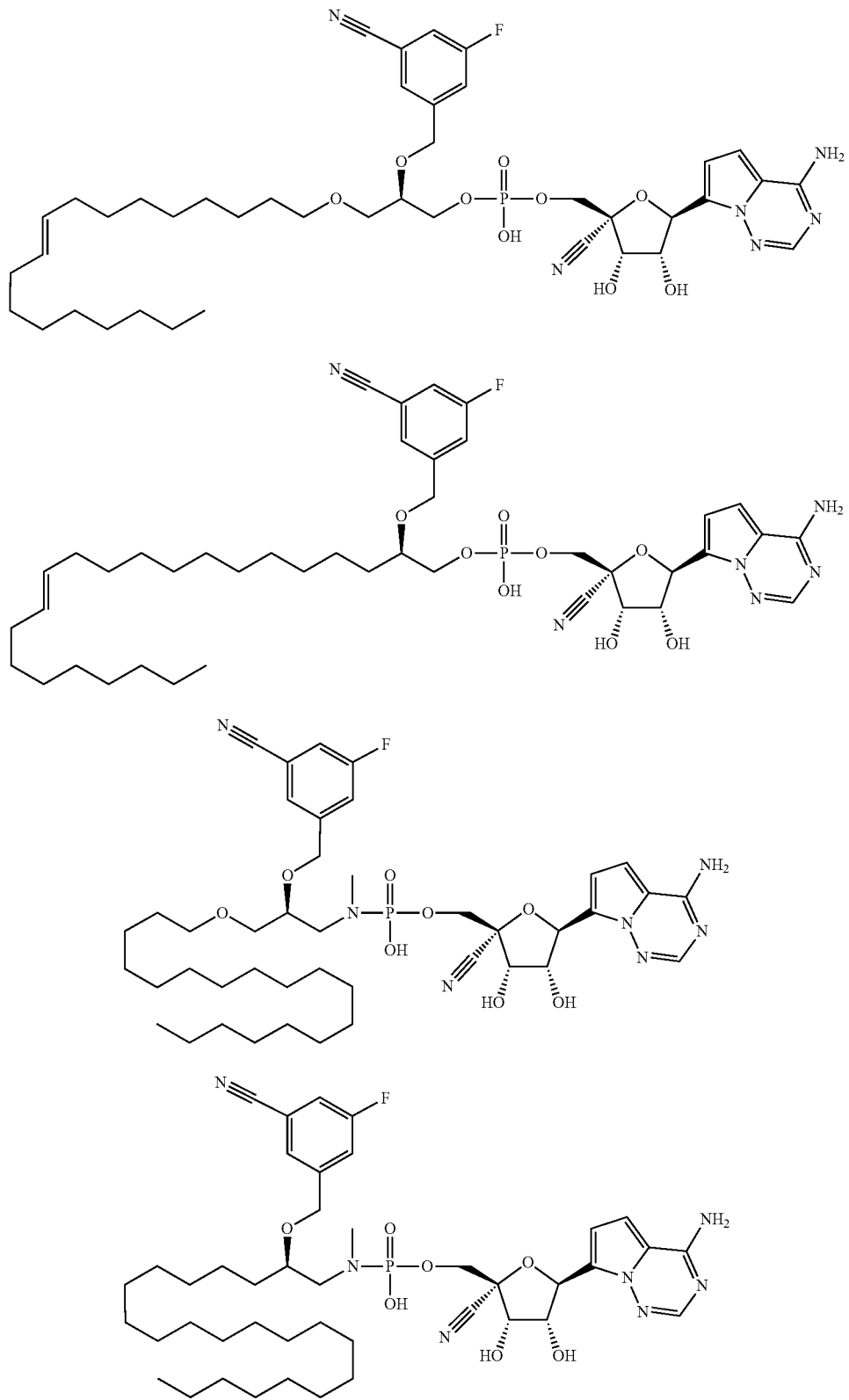

TABLE 23-continued
Some Compounds of Formula VIII
Structure
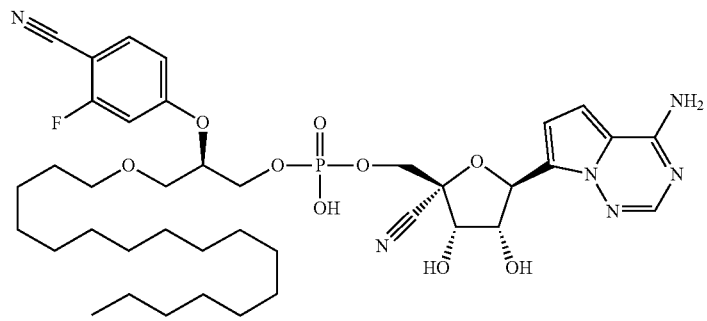 [SMILES: CCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(F)c1]
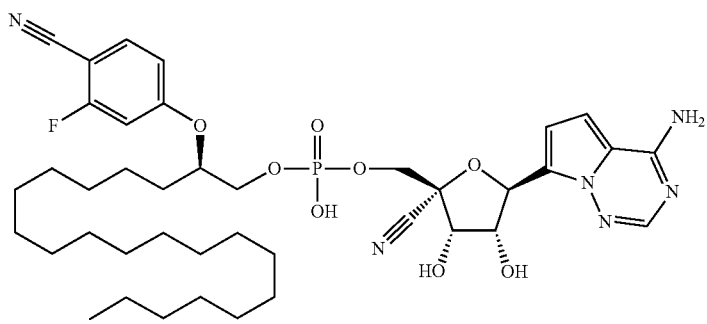 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1]
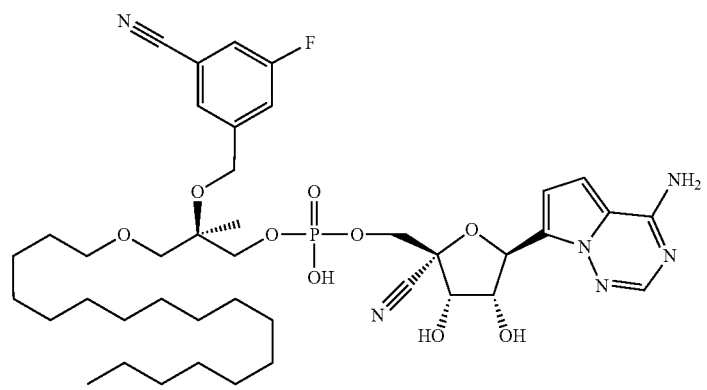 [SMILES: CCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]
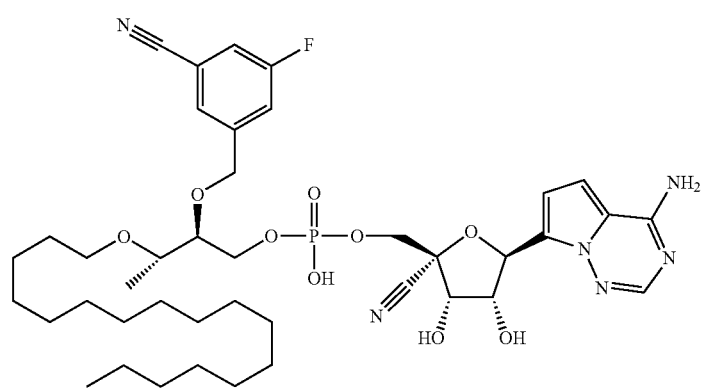 [SMILES: CCCCCCCCCCCCCCCCCO[C@@H](C)[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 23-continued
Some Compounds of Formula VIII
Structure
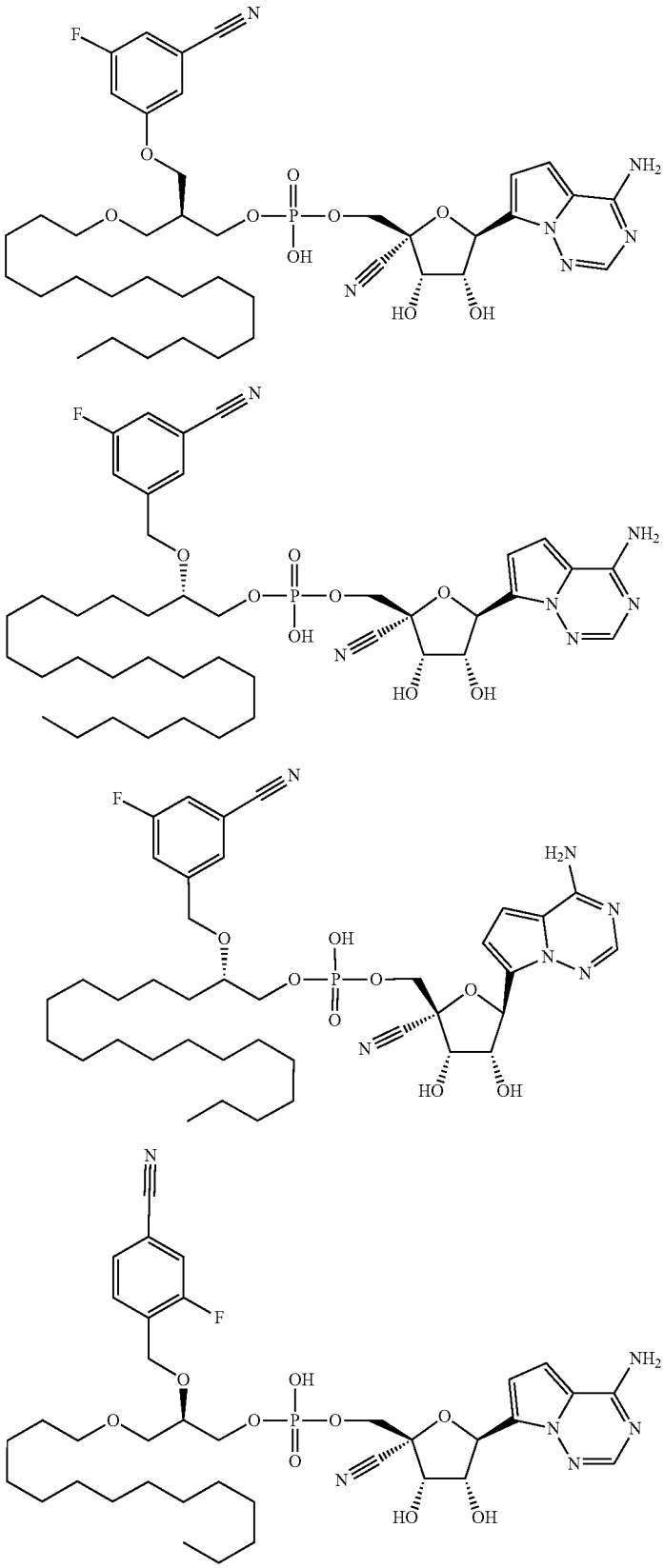

TABLE 23-continued
Some Compounds of Formula VIII
Structure
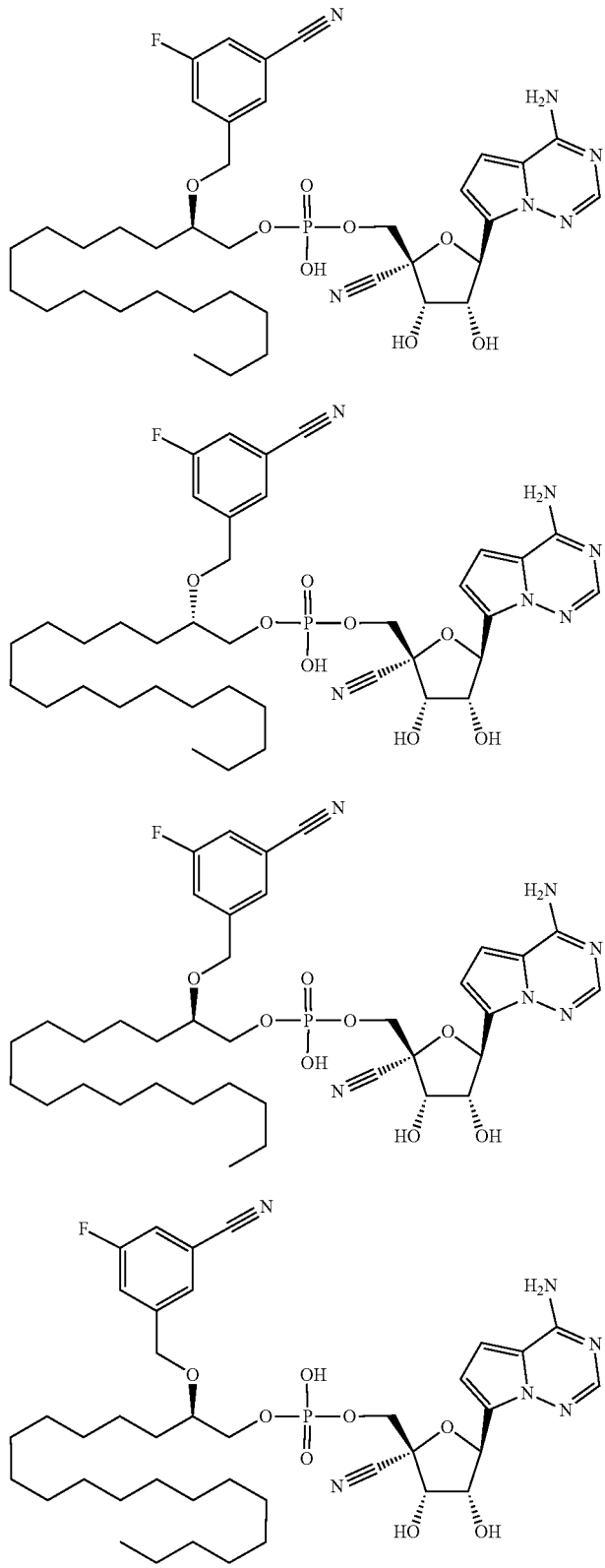

TABLE 23-continued
Some Compounds of Formula VIII
Structure
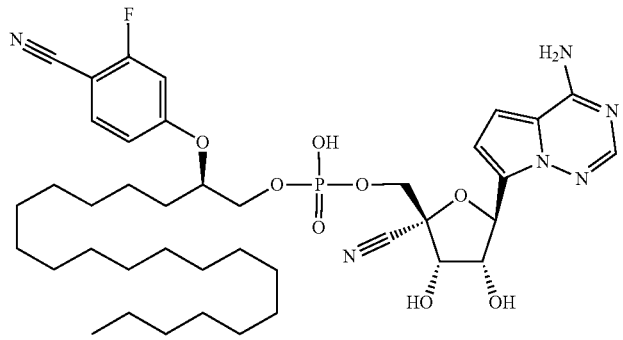 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1]
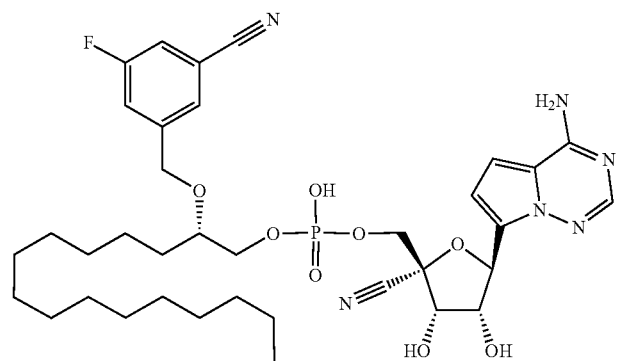 [SMILES: CCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
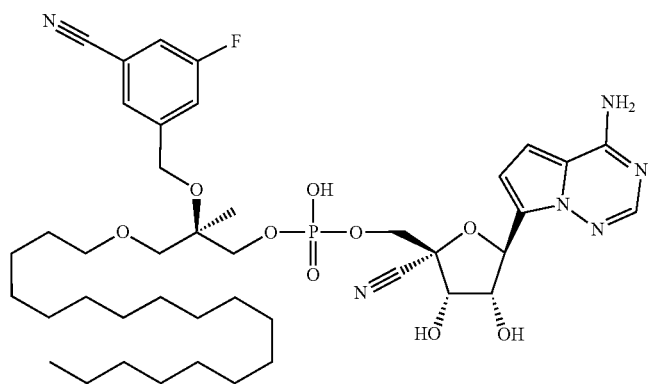 [SMILES: CCCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]
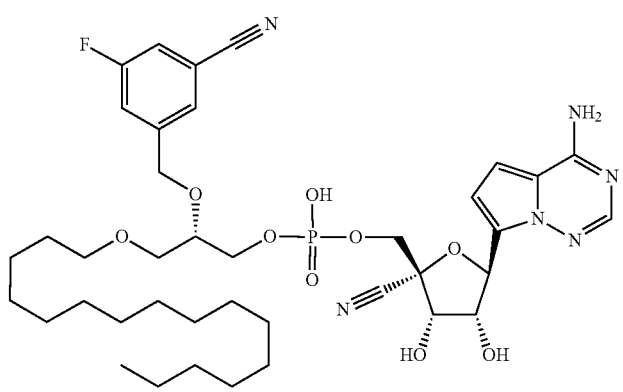 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 23-continued
Some Compounds of Formula VIII
Structure
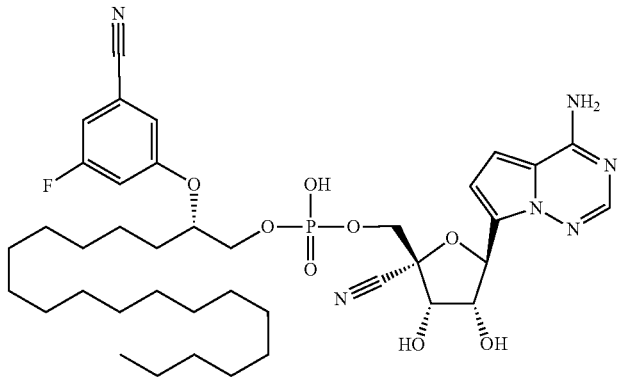 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)Oc1cc(F)cc(C#N)c1]
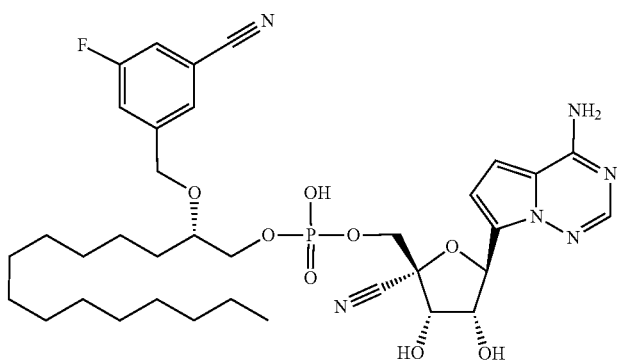 [SMILES: CCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
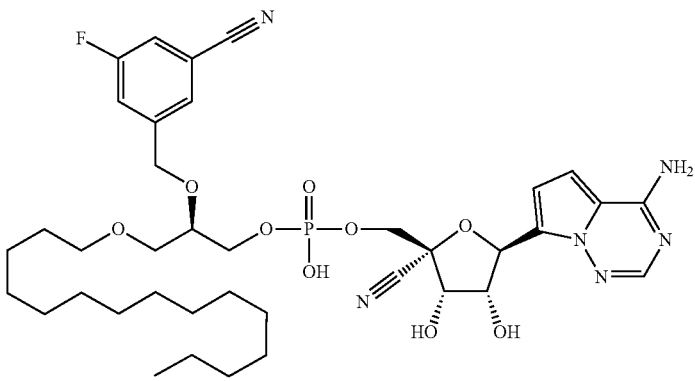 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
In some embodiments, the compound of Formula I has a Formula VIIIa:
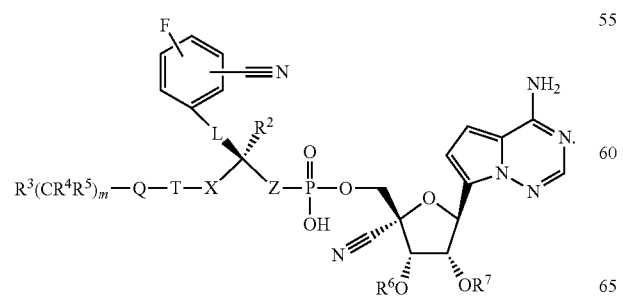
Formula VIIIa The description of substituents of Formula I (e.g., $R^2$, $R^3$, $R^4$, $R^5$, $R^6$, $R^7$, Q, T, X, Z, L, and m) applies to Formula VIIIa.
In some embodiments, the compounds and pharmaceutically acceptable salts of Formula VIIIa include the compounds in Table 24 and the pharmaceutically acceptable salts thereof.
TABLE 24
Some Compounds of Formula VIIIa
Structure
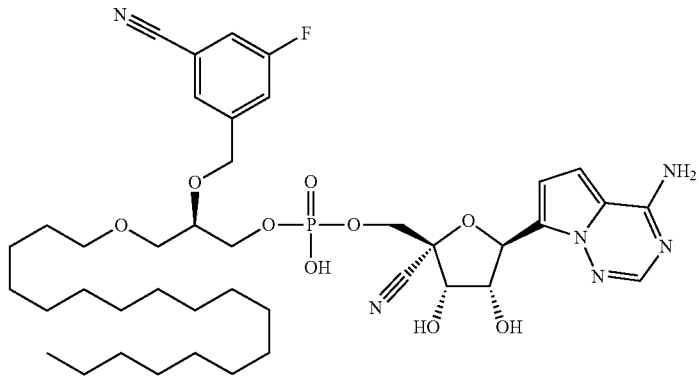 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
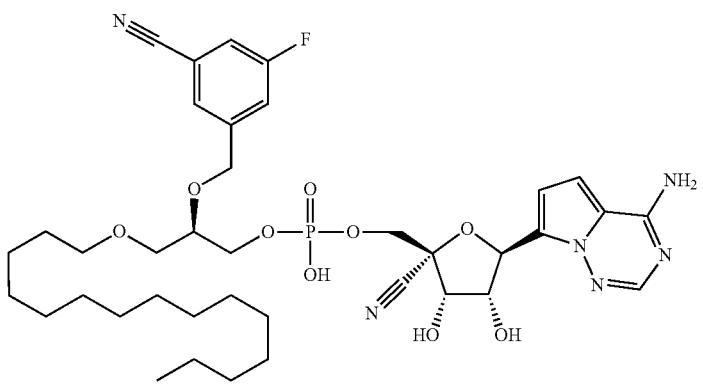 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
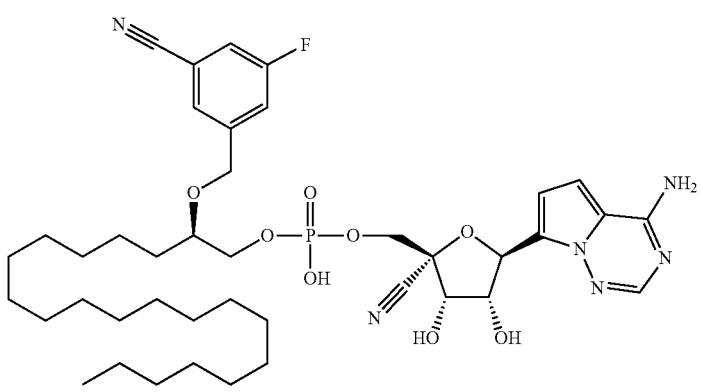

TABLE 24-continued
Some Compounds of Formula VIIIa
Structure
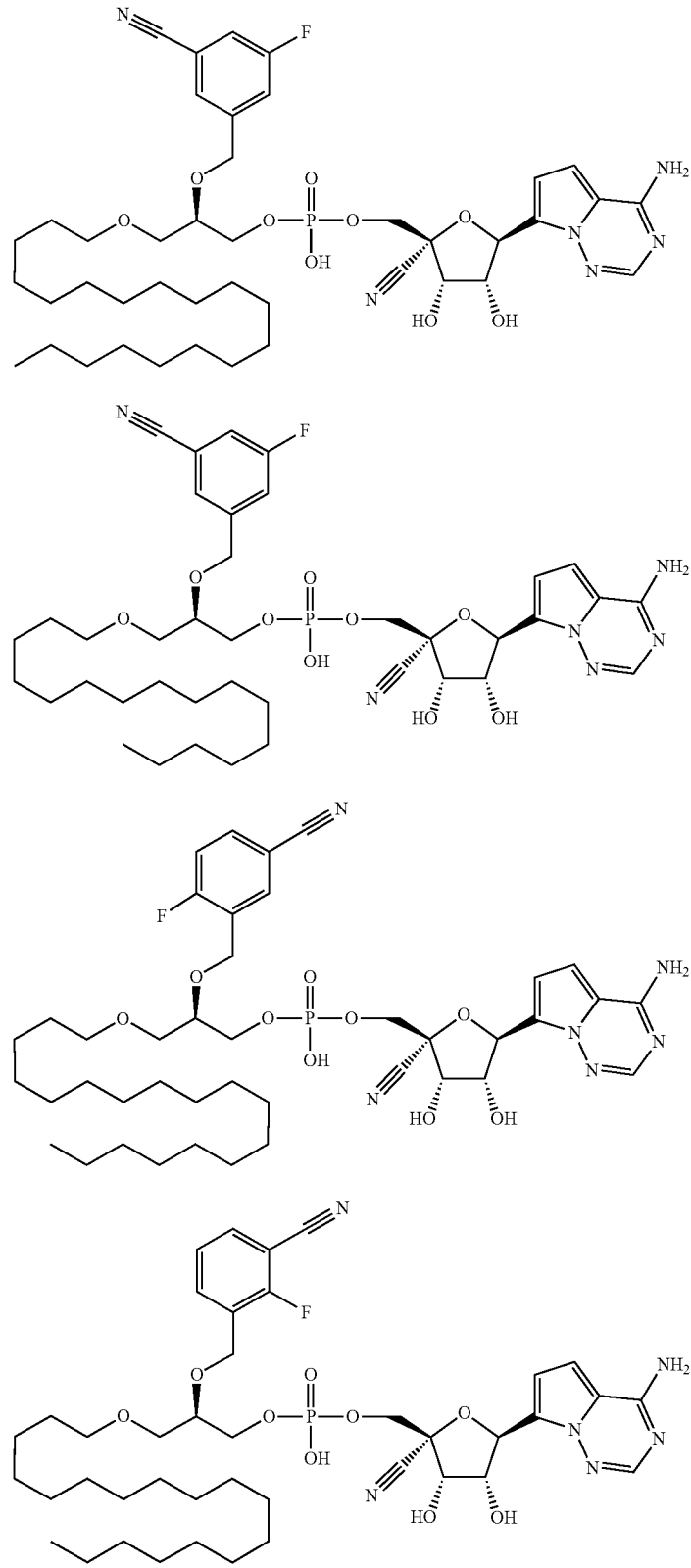

TABLE 24-continued
Some Compounds of Formula VIIIa
Structure
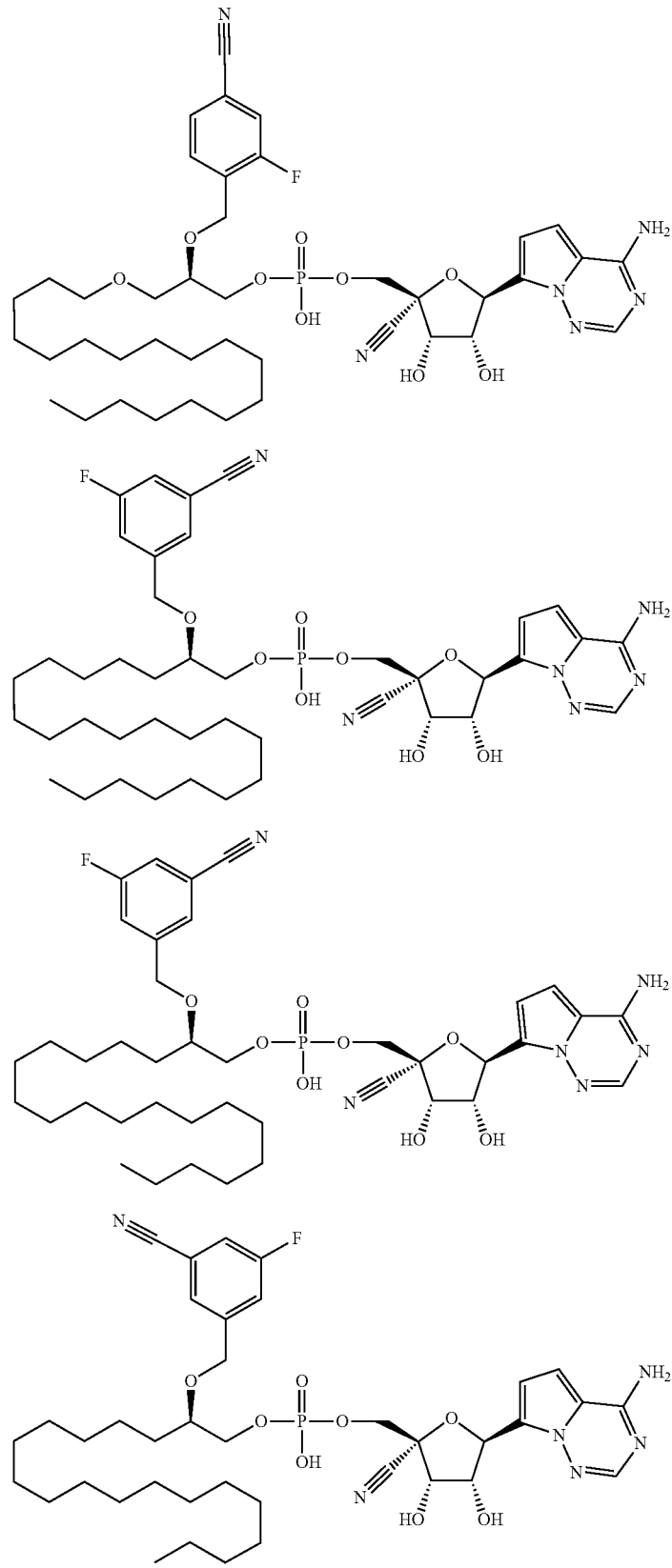

TABLE 24-continued
Some Compounds of Formula VIIIa
Structure
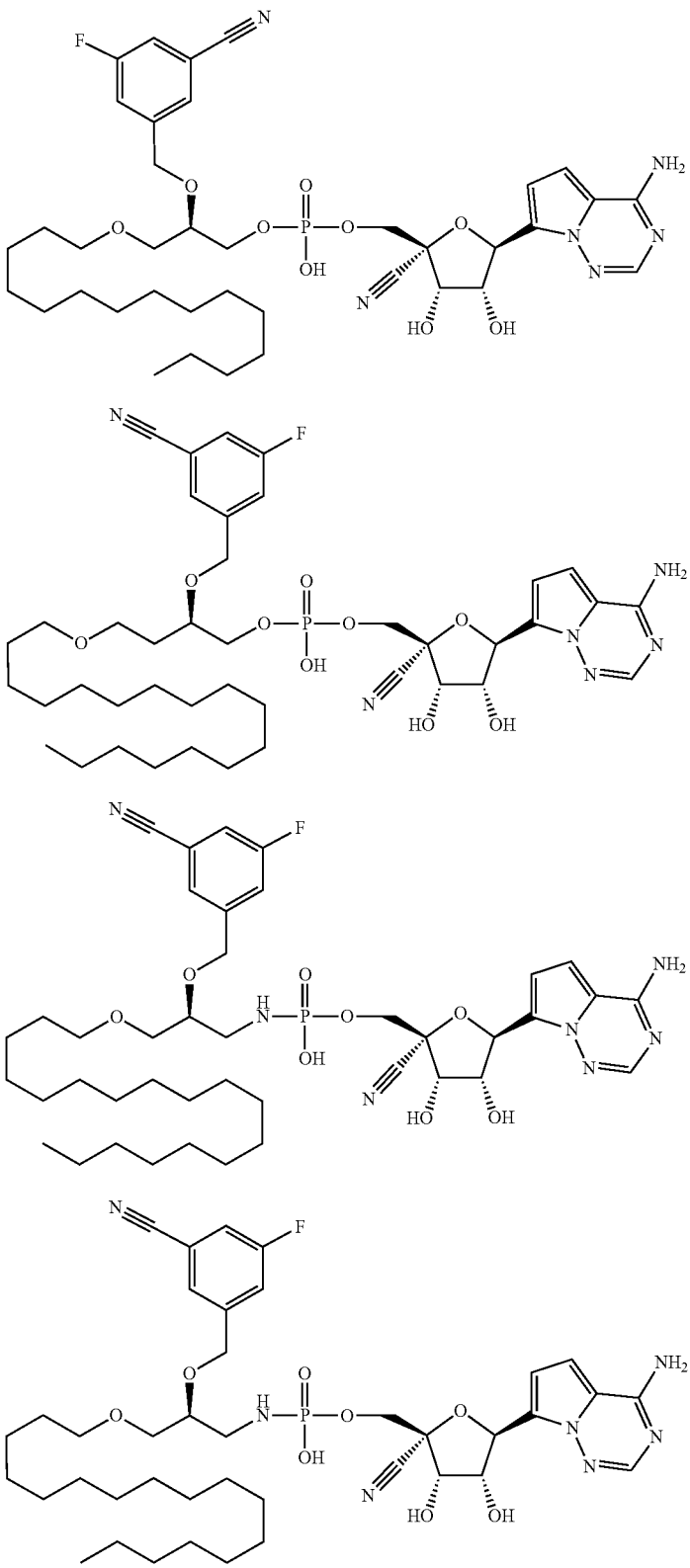

TABLE 24-continued
Some Compounds of Formula VIIIa
Structure
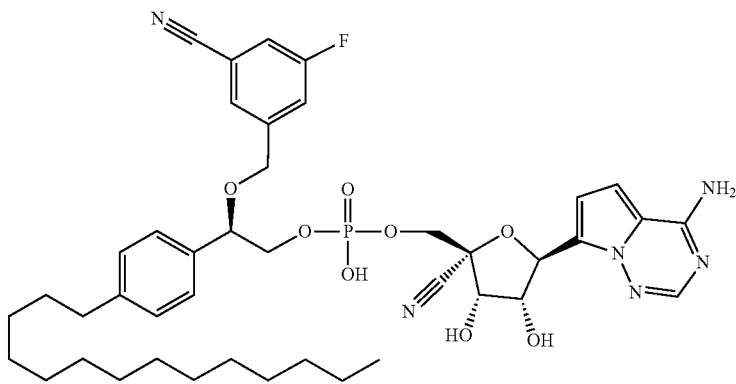 [SMILES: CCCCCCCCCCCCCCc1ccc([C@H](COP(=O)(O)OC[C@@]2(C#N)O[C@@H](c3ccc4c(N)ncnn34)[C@H](O)[C@@H]2O)OCc2cc(F)cc(C#N)c2)cc1]
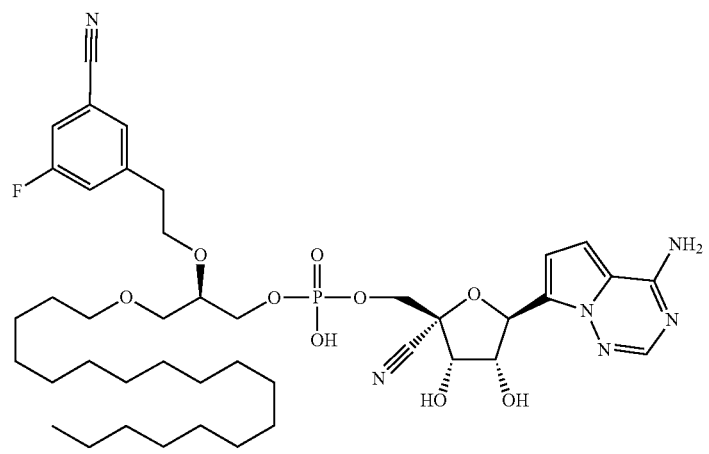 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCCc1cc(F)cc(C#N)c1]
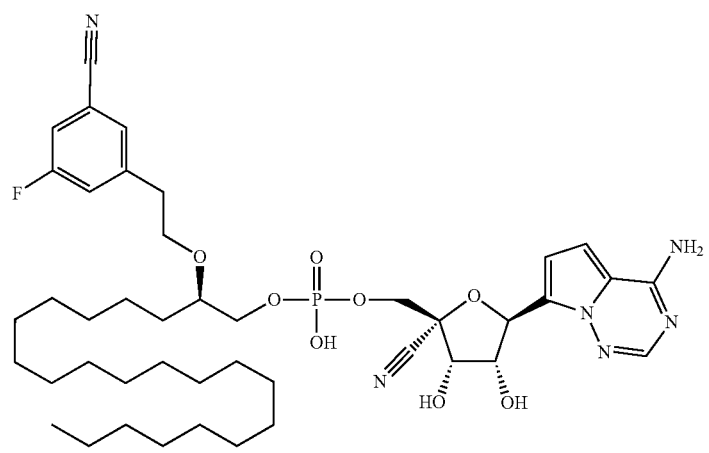 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCCc1cc(F)cc(C#N)c1]

TABLE 24-continued
Some Compounds of Formula VIIIa
Structure
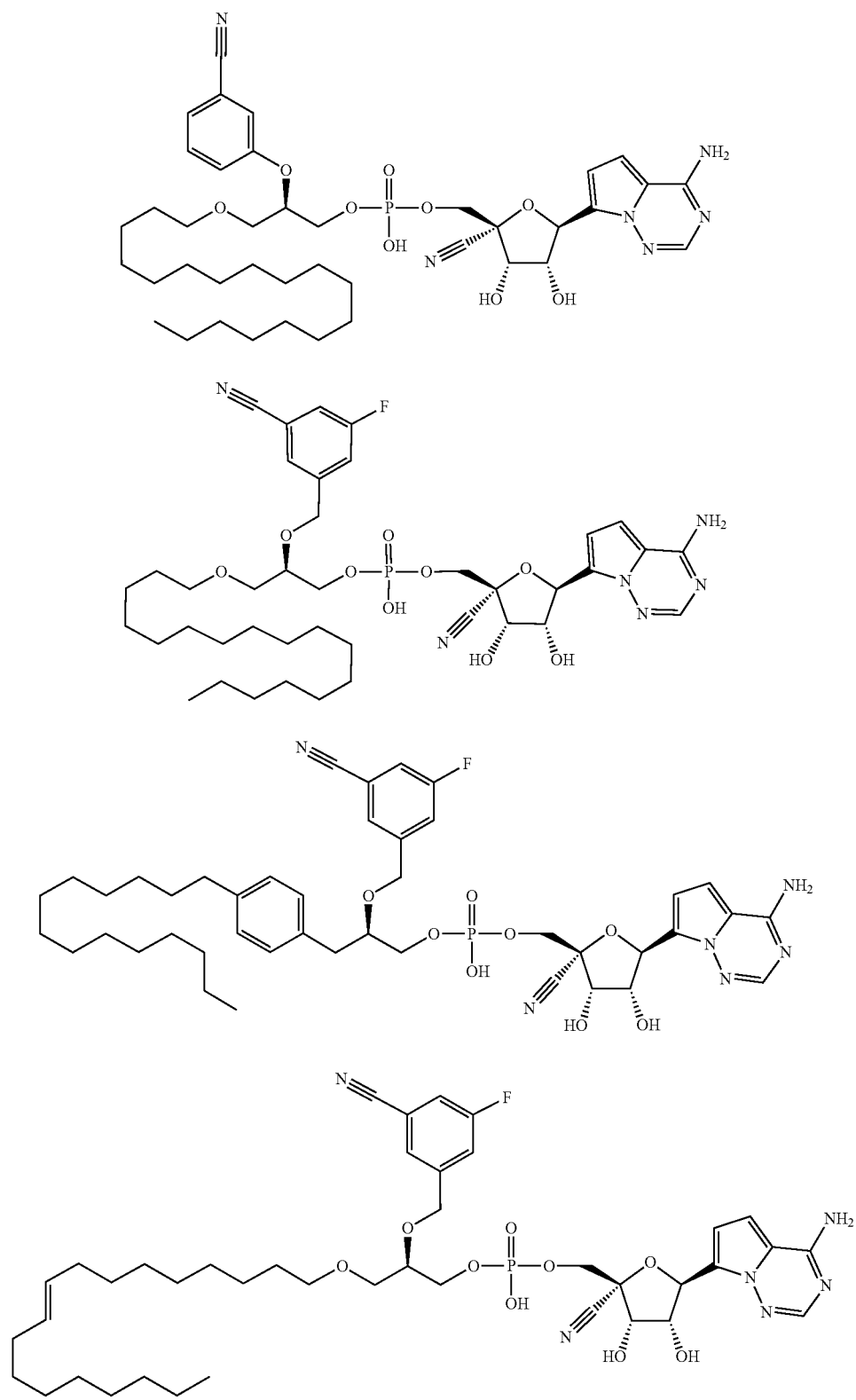

TABLE 24-continued
Some Compounds of Formula VIIIa
Structure
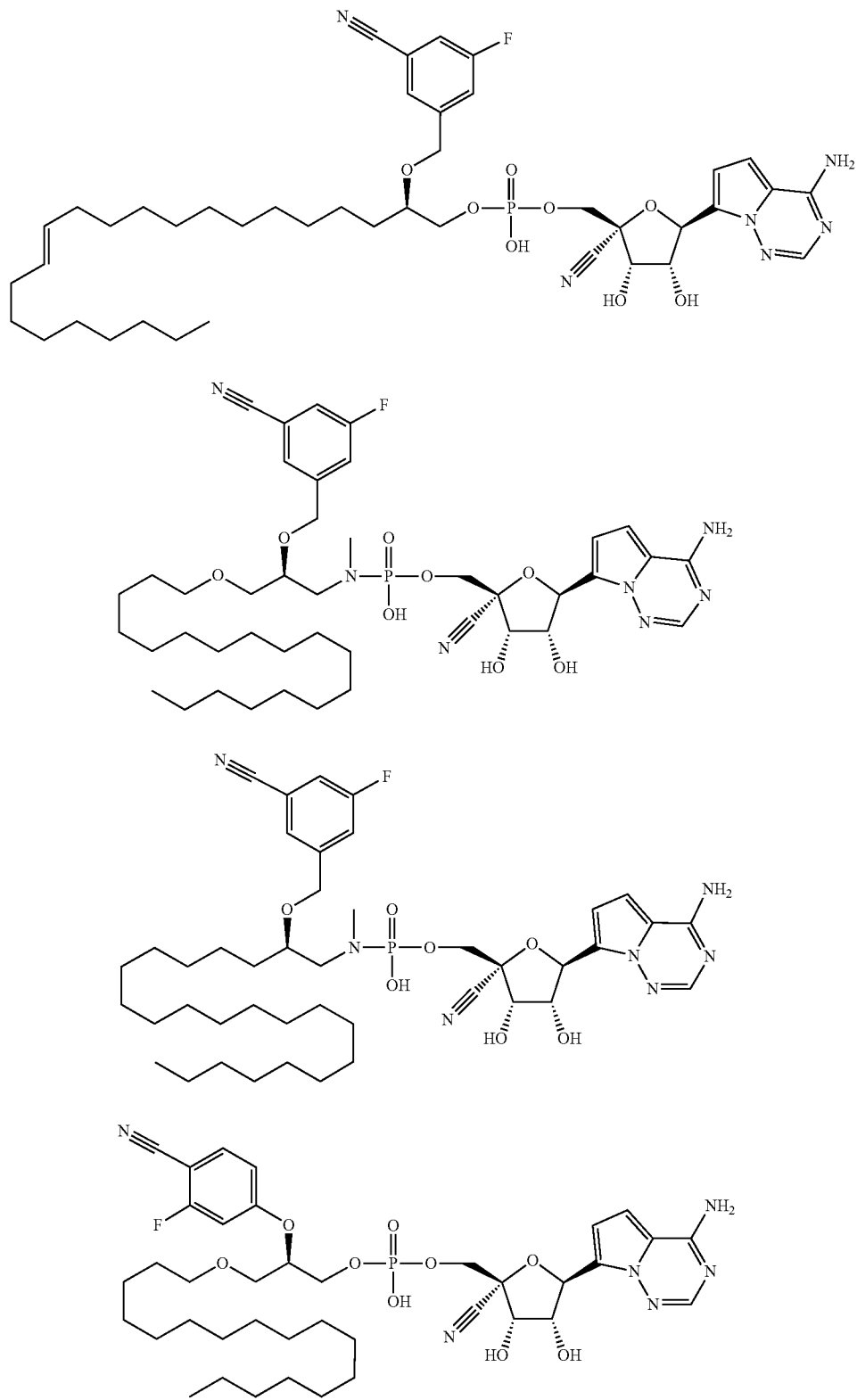

TABLE 24-continued
Some Compounds of Formula VIIIa
Structure
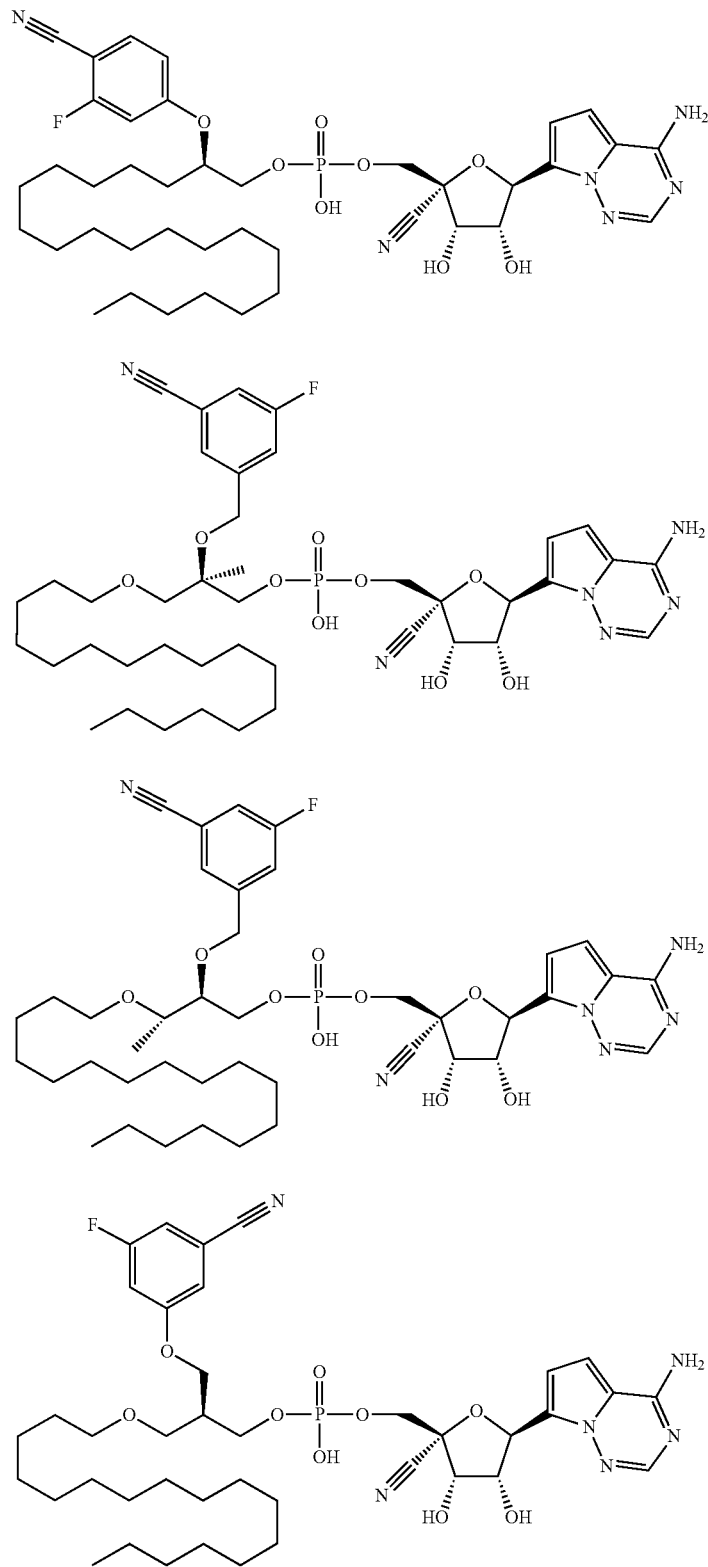

TABLE 24-continued
Some Compounds of Formula VIIIa
Structure
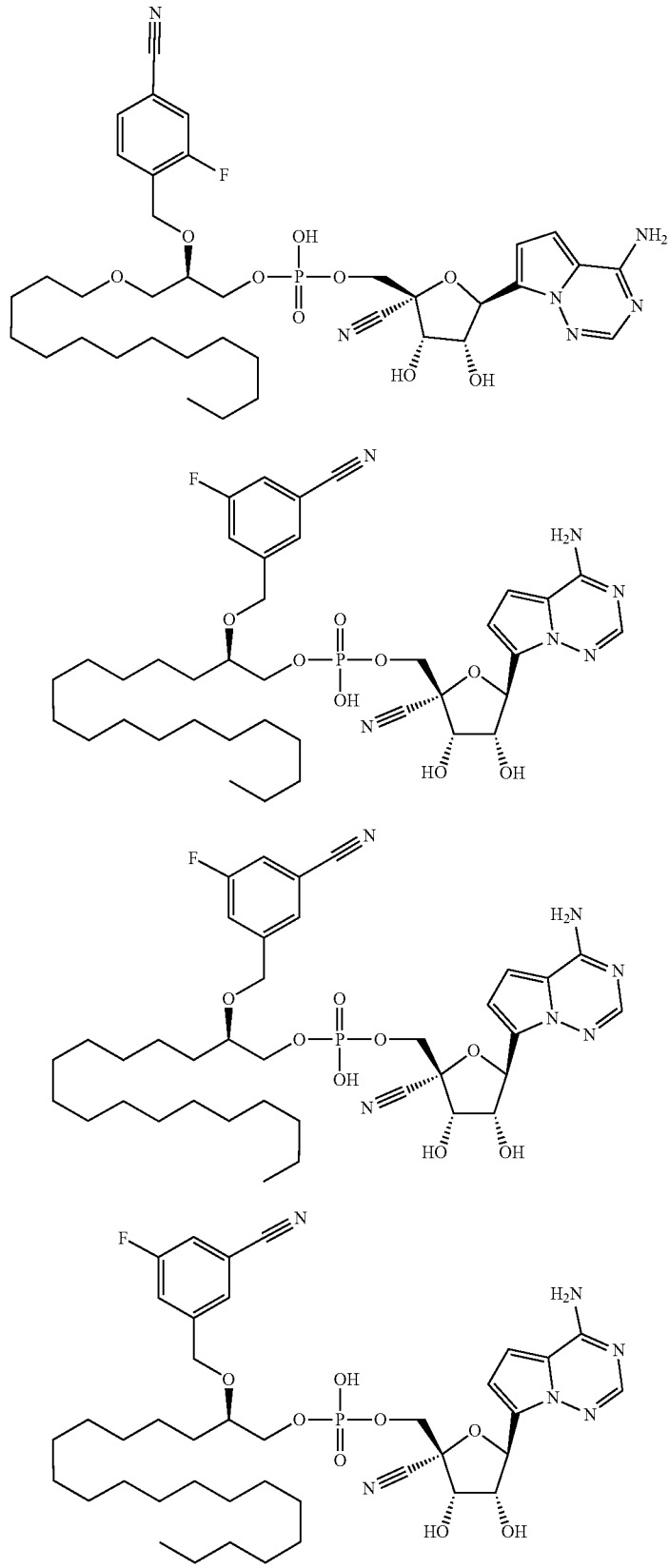

TABLE 24-continued

Some Compounds of Formula VIIIa
Structure

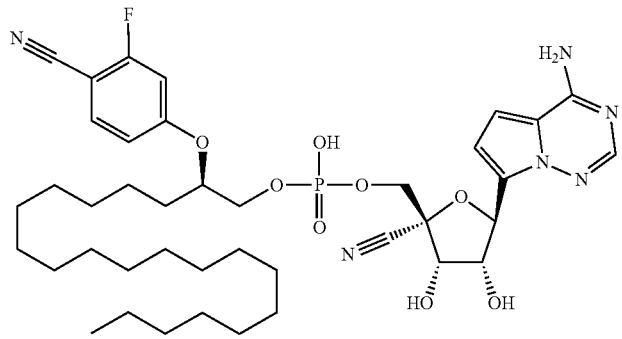 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1]

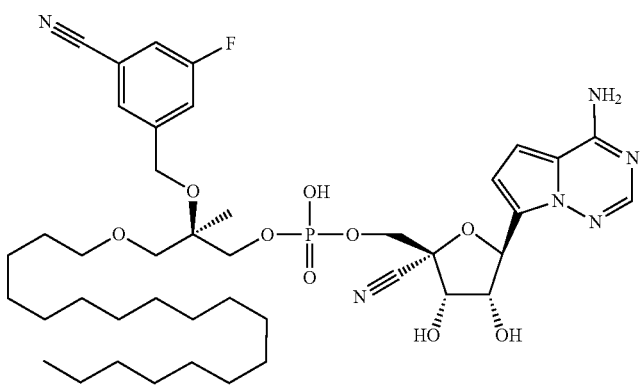 [SMILES: CCCCCCCCCCCCCCCCCCOC[C@](C)(COP(=O)(O)OC[C@@]1(C#N)O[C@@H](c2ccc3c(N)ncnn23)[C@H](O)[C@@H]1O)OCc1cc(F)cc(C#N)c1]

In some embodiments, the compound of Formula I has a Formula VIIIb:

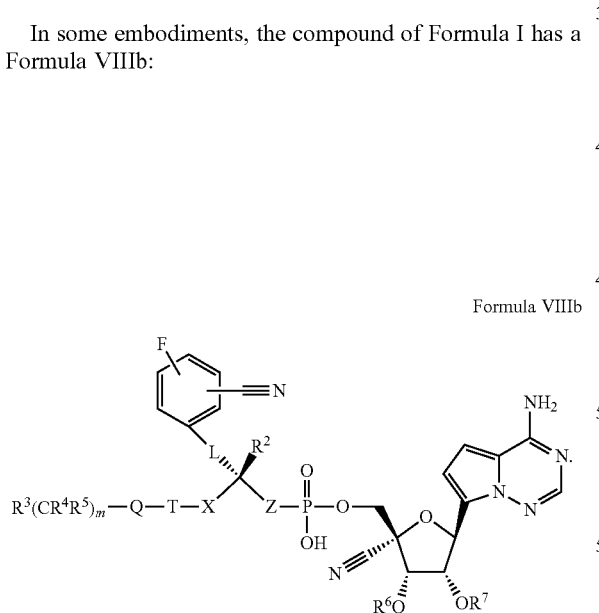

Formula VIIIb

The description of substituents of Formula I (e.g., $R^2$, $R^3$, $R^4$, $R^5$, $R^6$, $R^7$, Q, T, X, Z, L, and m) applies to Formula VIIIb.

In some embodiments, the compounds and pharmaceutically acceptable salts of Formula VIIIb include the compounds in Table 25 and the pharmaceutically acceptable salts thereof.

TABLE 25

Some Compounds of Formula VIIIb
Structure

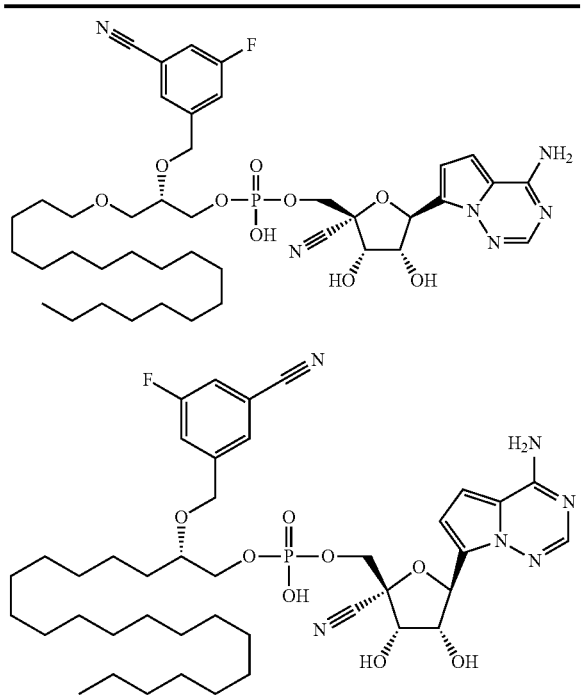

TABLE 25-continued
Some Compounds of Formula VIIIb
Structure
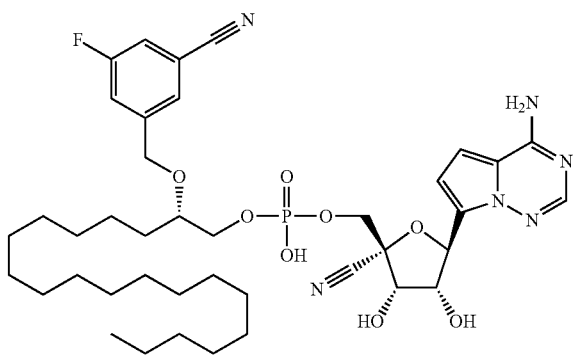 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
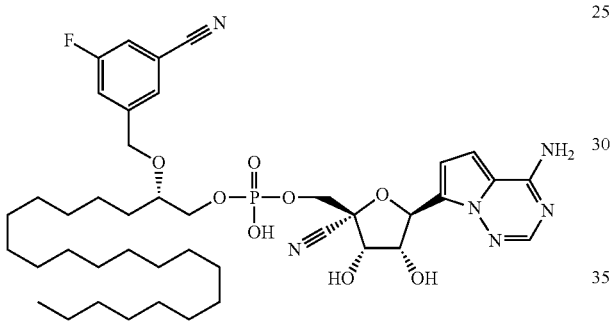
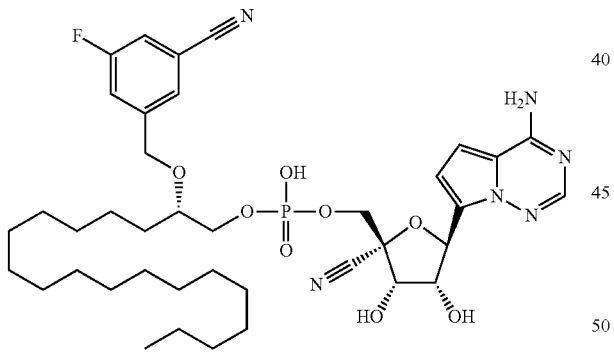
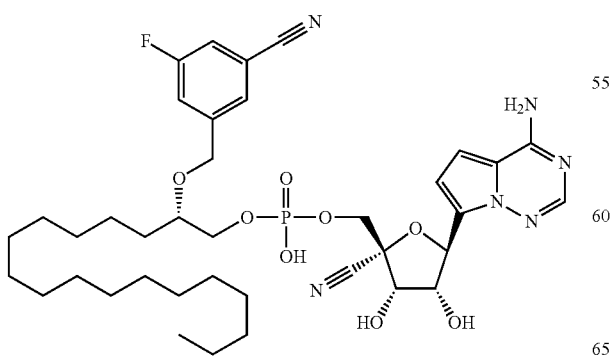
TABLE 25-continued
Some Compounds of Formula VIIIb
Structure
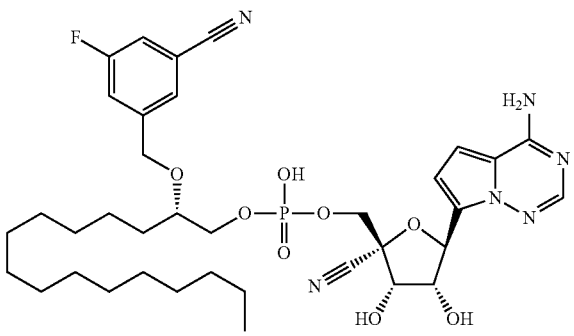 [SMILES: CCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 25-continued

Some Compounds of Formula VIIIb
Structure

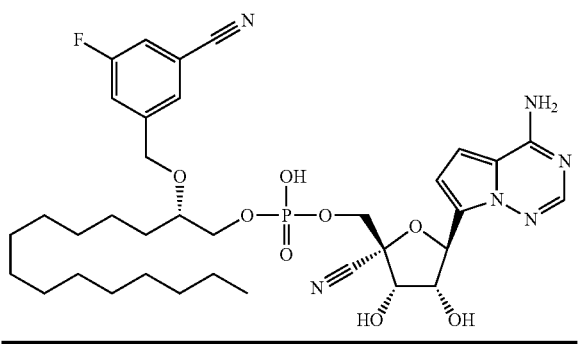

In some embodiments, the compound of Formula I has a Formula VIIIc:

Formula VIIIc

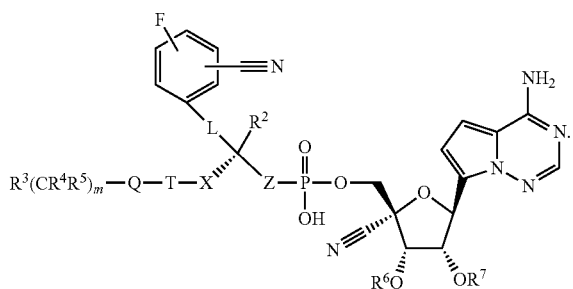

The description of substituents of Formula I (e.g., $R^2$, $R^3$, $R^4$, $R^5$, $R^6$, $R^7$, Q, T, X, Z, L, and m) applies to Formula VIIIc.

In some embodiments, the compounds and pharmaceutically acceptable salts of Formula VIIIc include the compounds in Table 26 and the pharmaceutically acceptable salts thereof.

TABLE 26

A Compound of Formula VIIIc
Structure

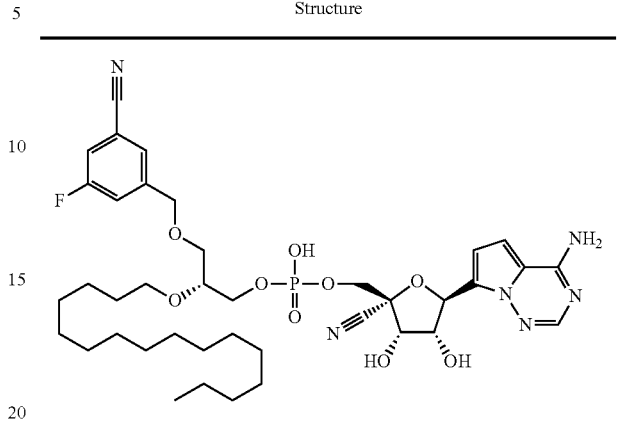

In some embodiments, the compound of Formula I has a Formula IX:

Formula IX

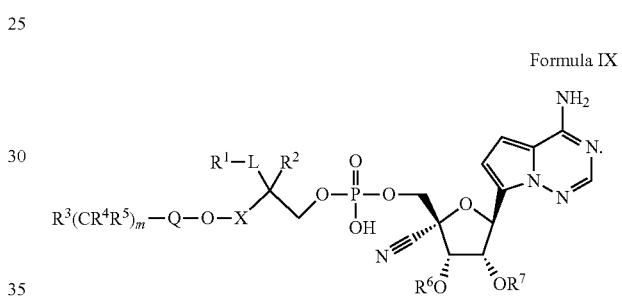

The description of substituents of Formula I (e.g., $R^1$, $R^2$, $R^3$, $R^4$, $R^5$, $R^6$, $R^7$, Q, X, L, and m) applies to Formula IX.

In some embodiments, the compounds and pharmaceutically acceptable salts of Formula IX include the compounds in Table 27 and the pharmaceutically acceptable salts thereof.

TABLE 27

Some Compounds of Formula IX
Structure

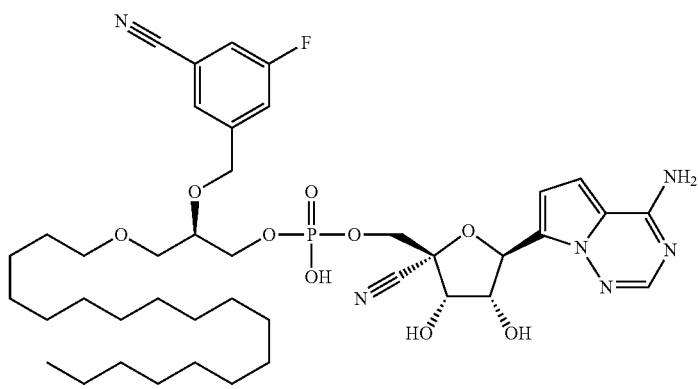 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 27-continued
Some Compounds of Formula IX
Structure
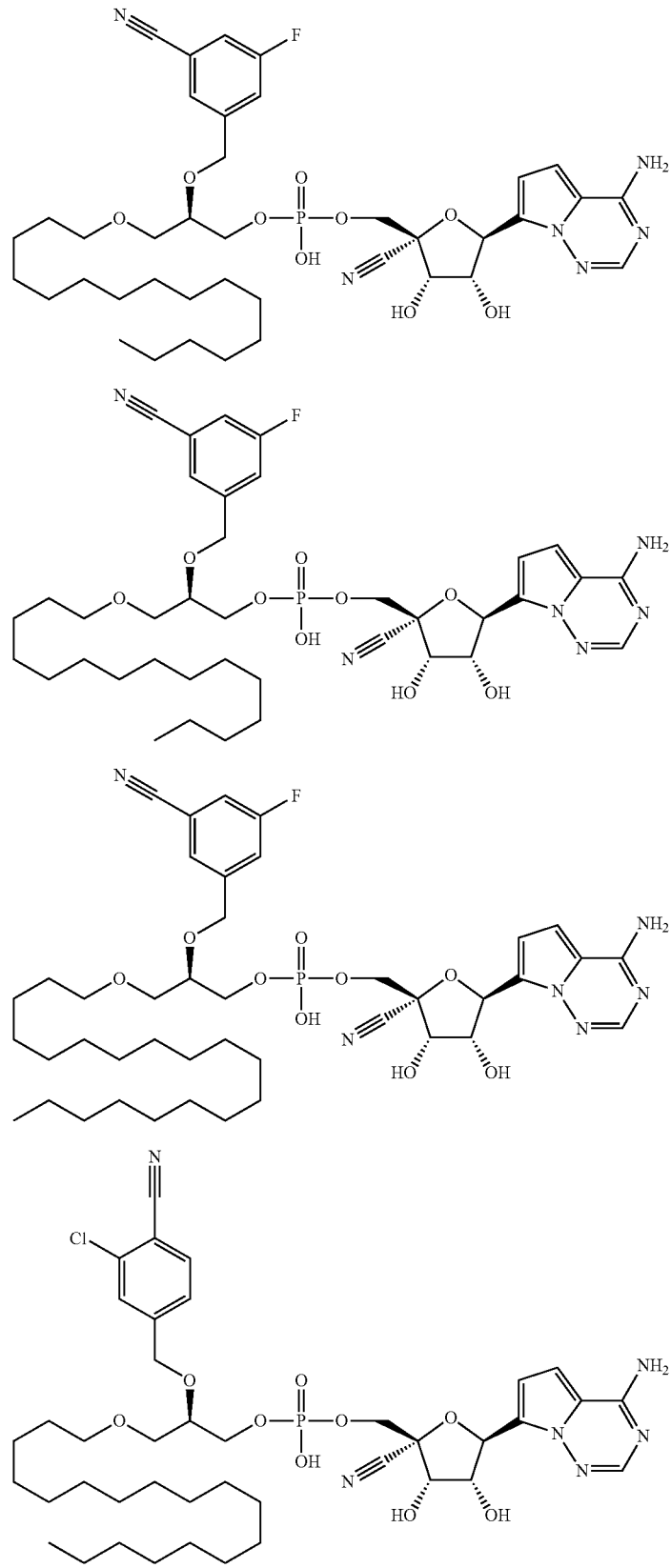

TABLE 27-continued
Some Compounds of Formula IX
Structure
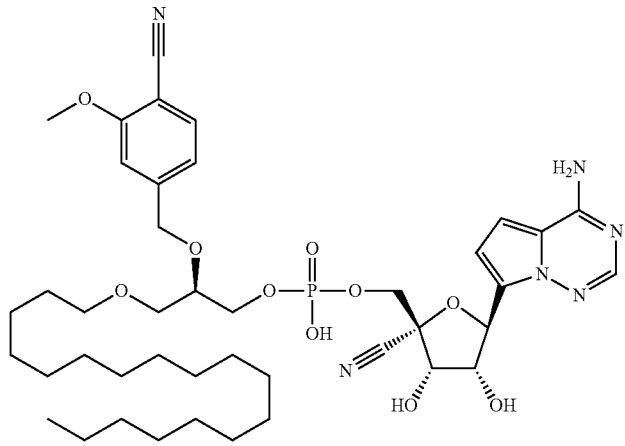 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]
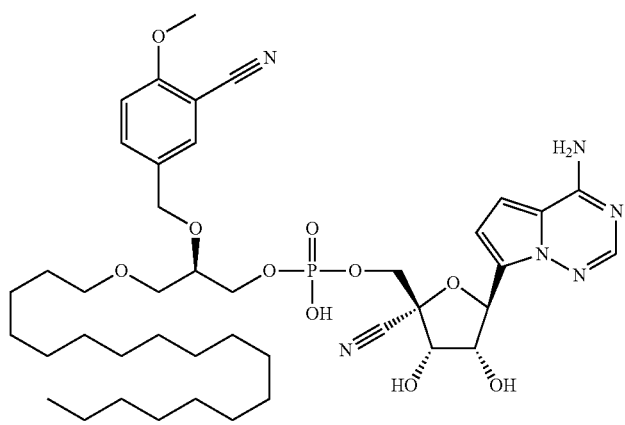 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]
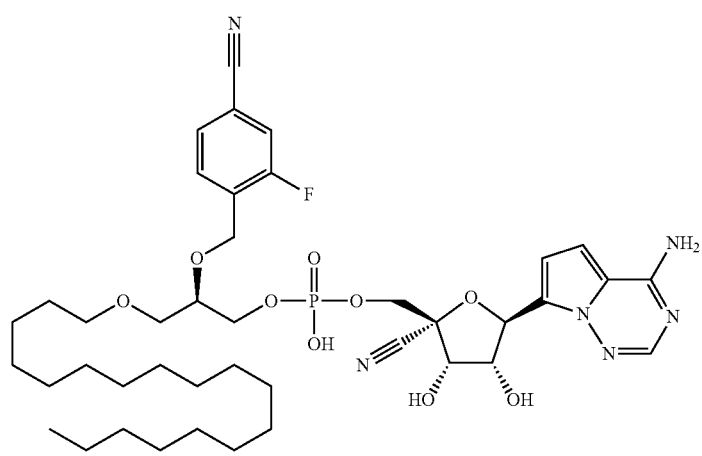 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]

TABLE 27-continued
Some Compounds of Formula IX
Structure
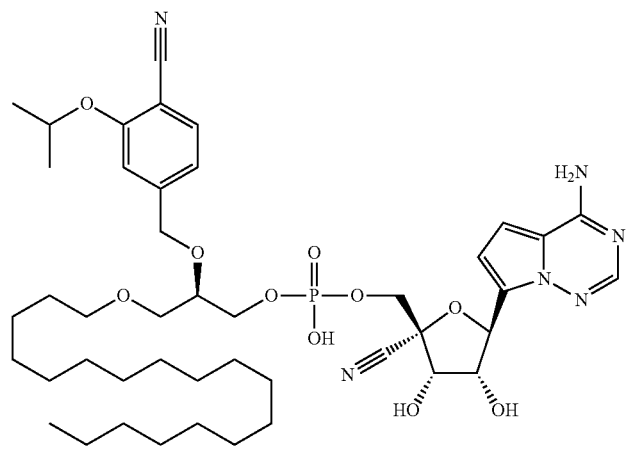 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]
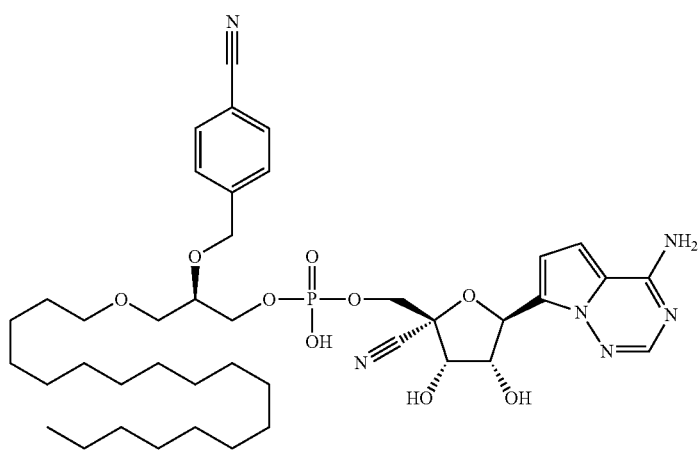 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]
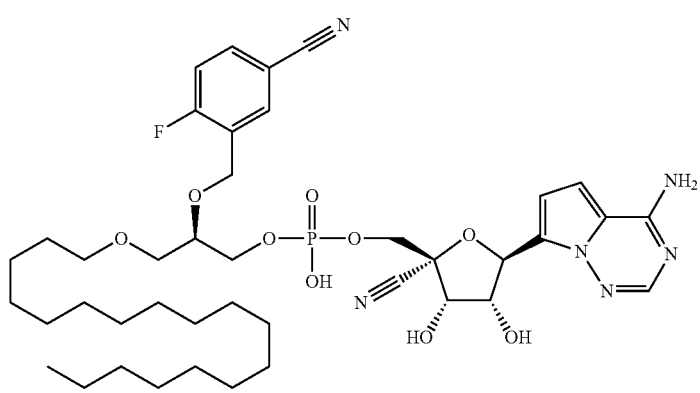 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(C#N)ccc1F]

TABLE 27-continued
Some Compounds of Formula IX
Structure
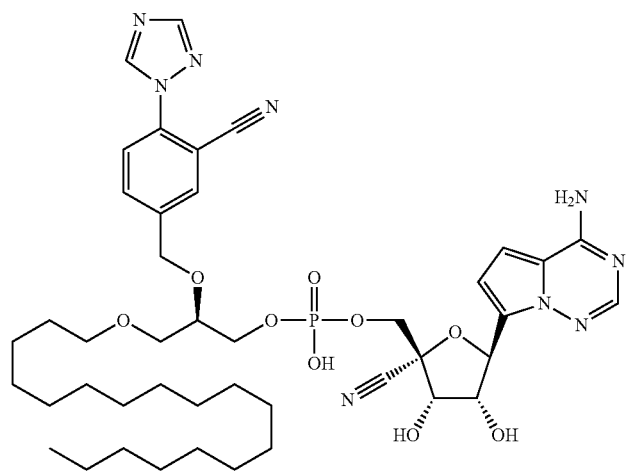 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
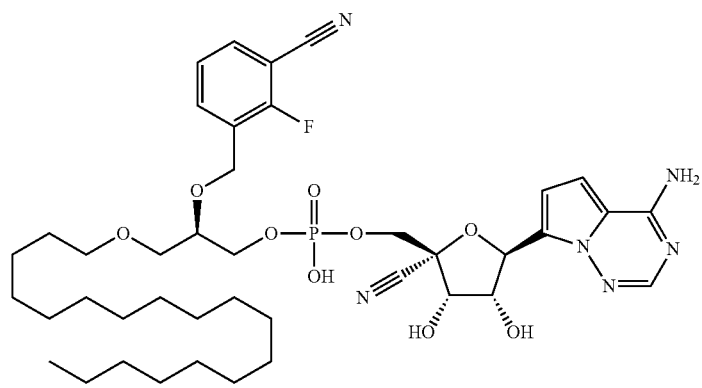 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
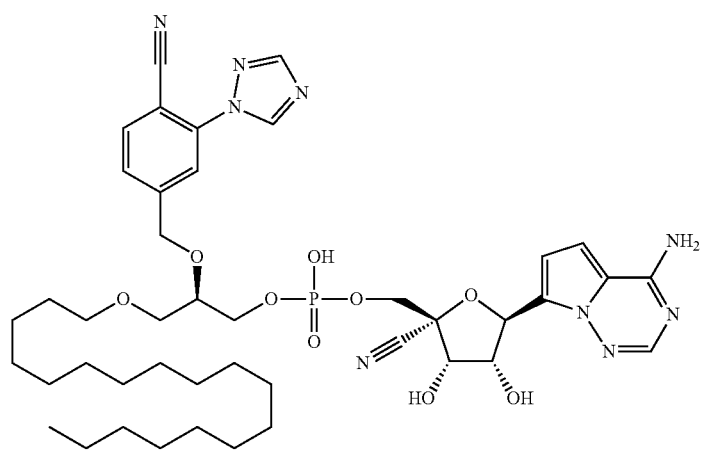 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]

TABLE 27-continued
Some Compounds of Formula IX
Structure
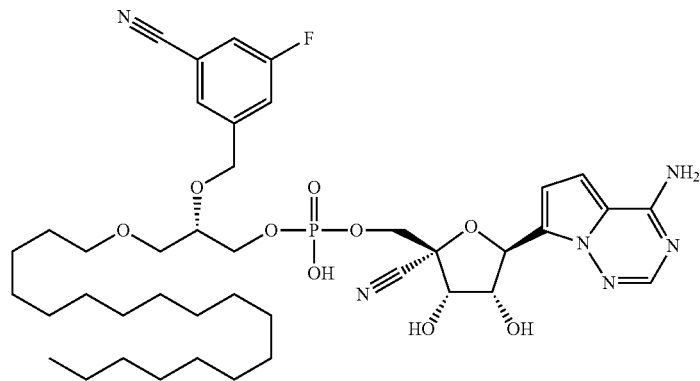 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]
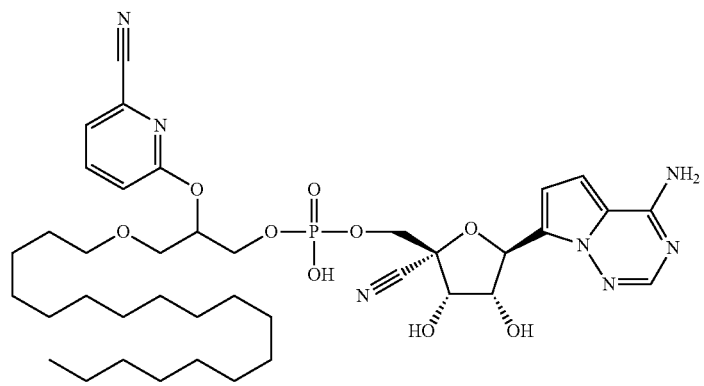 [SMILES: CCCCCCCCCCCCCCCCCCOCC(COP(=O)(O)OC[C@@]1(C#N)O[C@@H](c2ccc3c(N)ncnn23)[C@H](O)[C@@H]1O)Oc1cccc(C#N)n1]
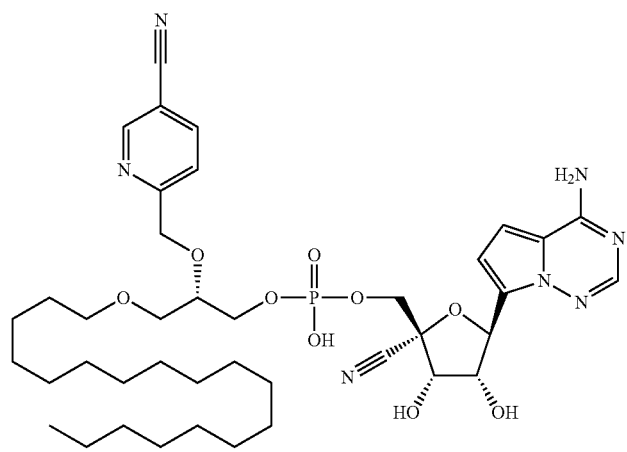 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1]

TABLE 27-continued
Some Compounds of Formula IX
Structure
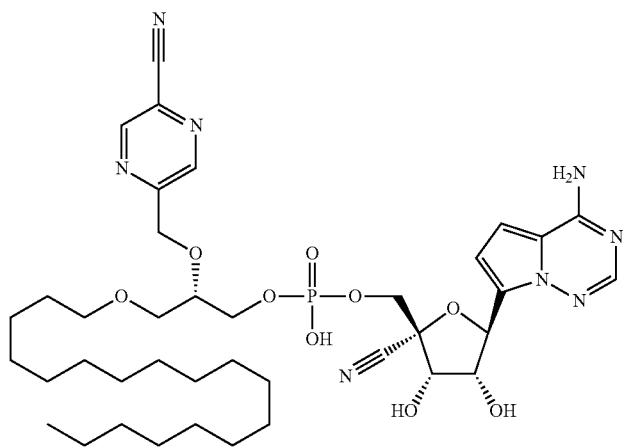 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cnc(C#N)cn1]
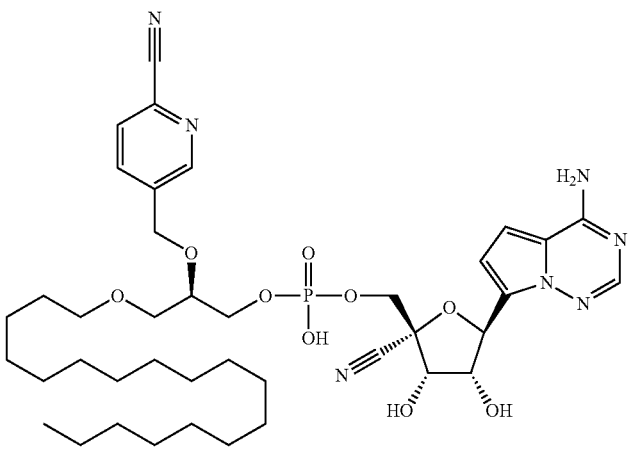 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)nc1]
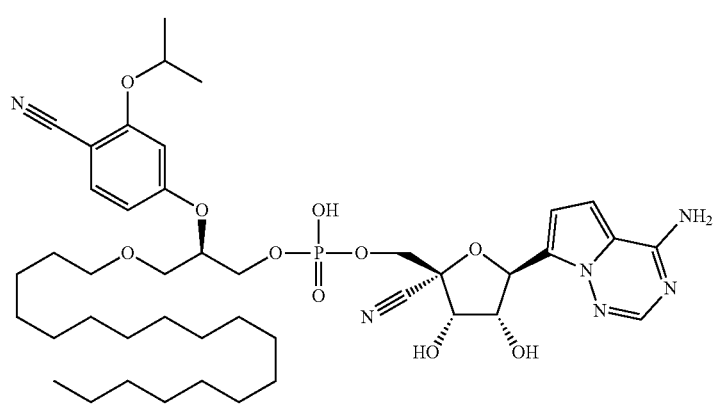 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)c(OC(C)C)c1]

TABLE 27-continued
Some Compounds of Formula IX
Structure
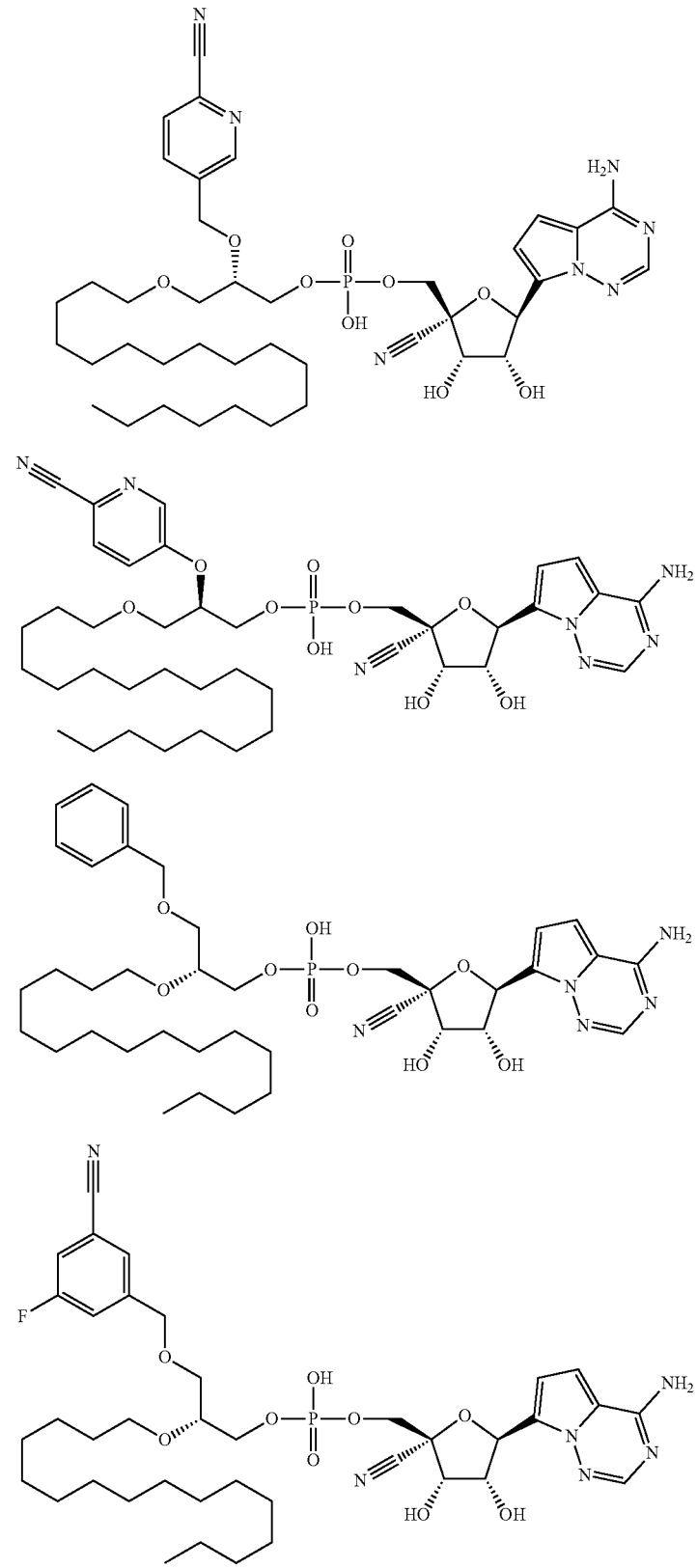

TABLE 27-continued
Some Compounds of Formula IX
Structure
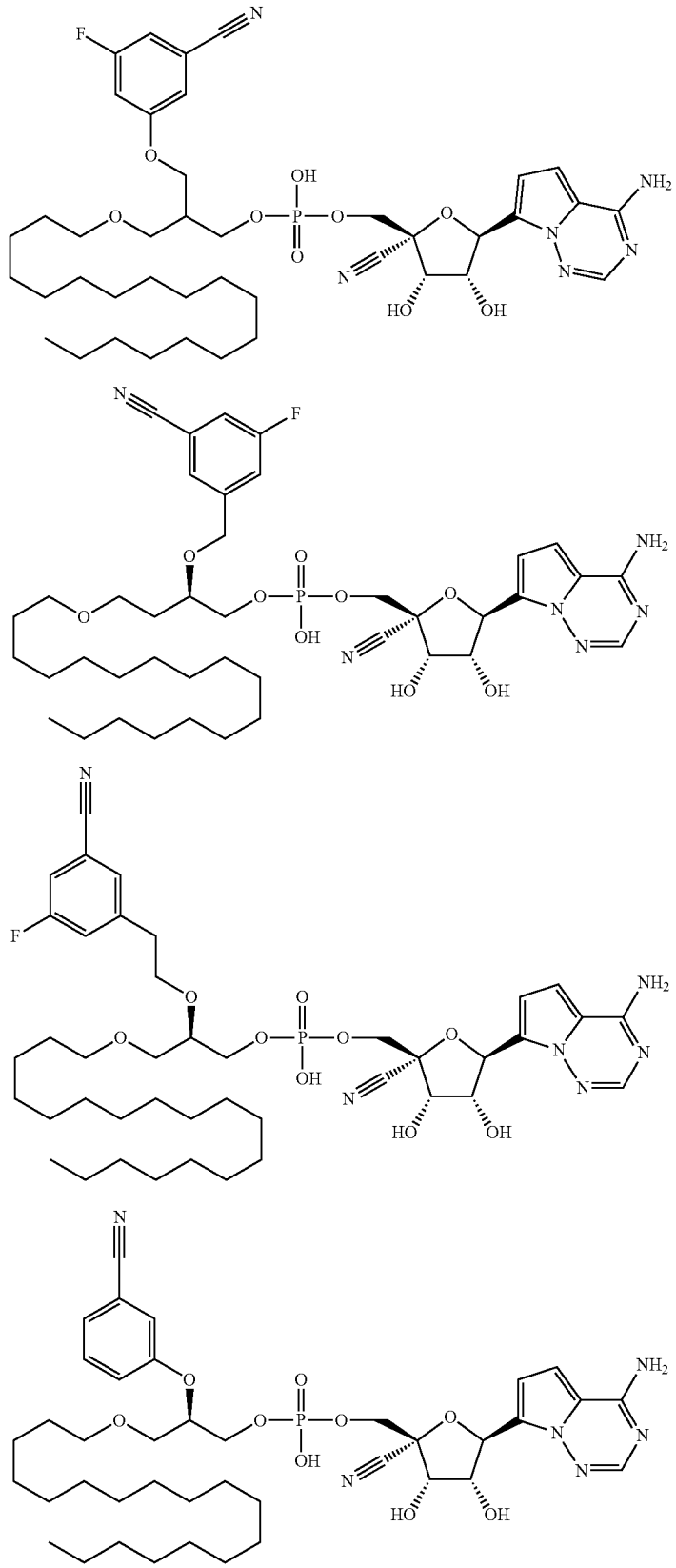

TABLE 27-continued
Some Compounds of Formula IX
Structure
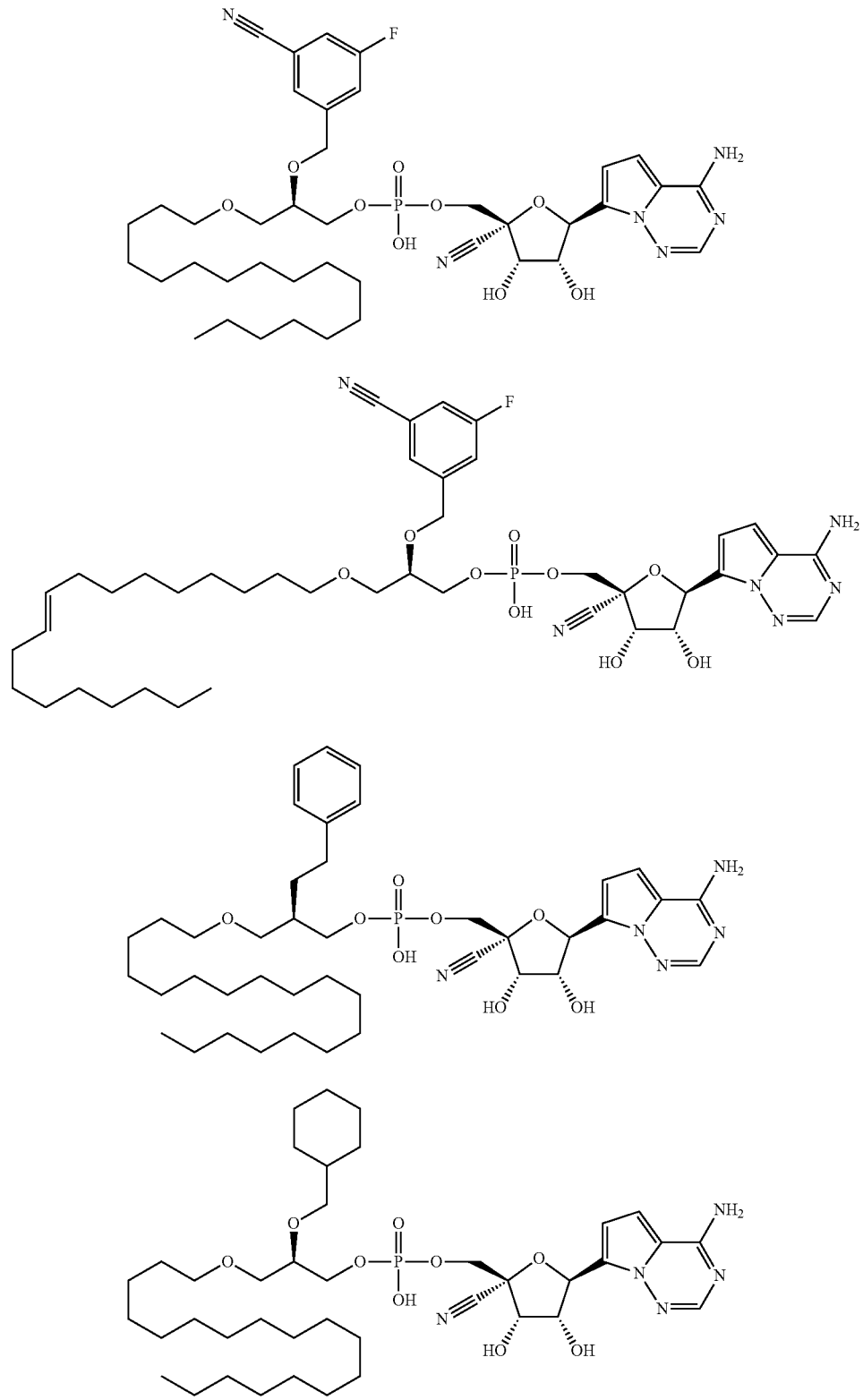

TABLE 27-continued
Some Compounds of Formula IX
Structure
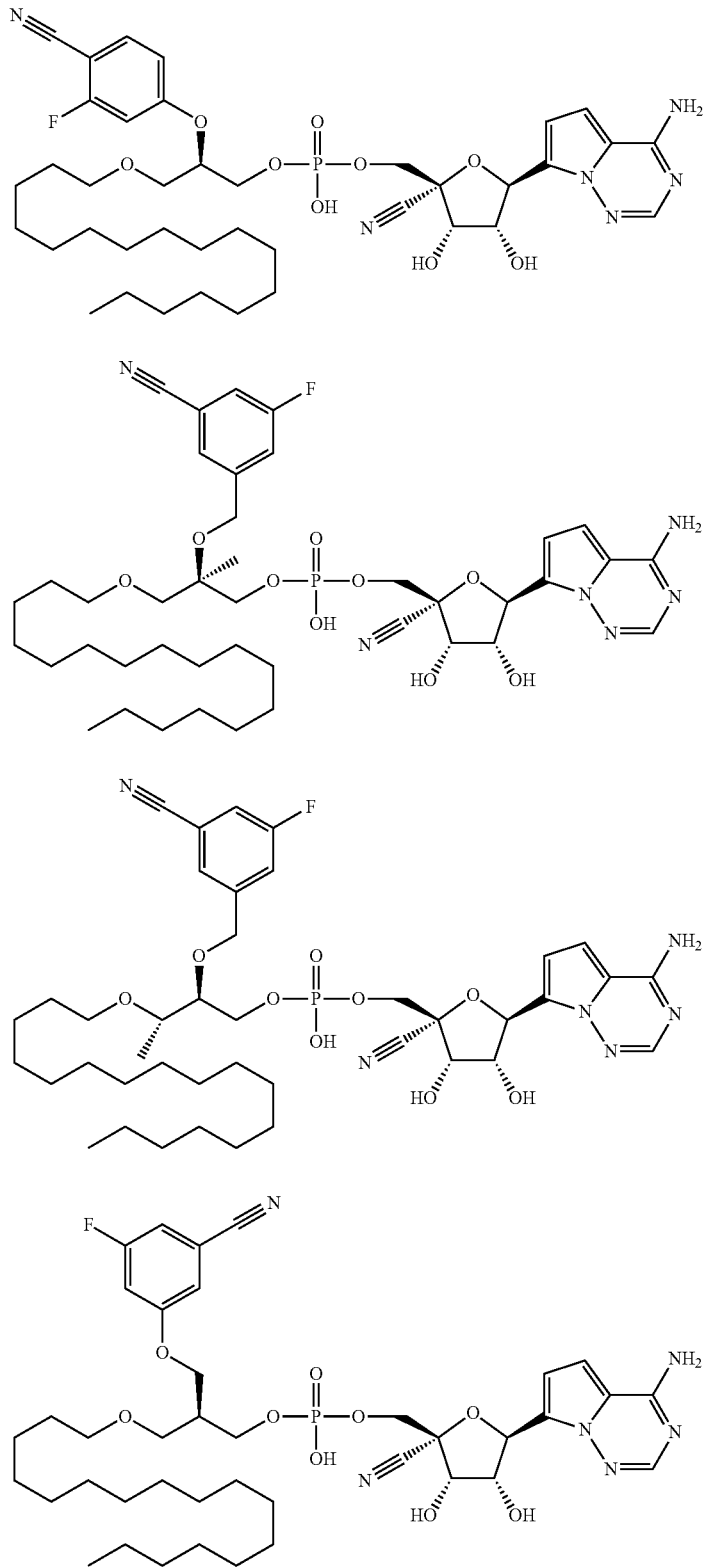

TABLE 27-continued
Some Compounds of Formula IX
Structure
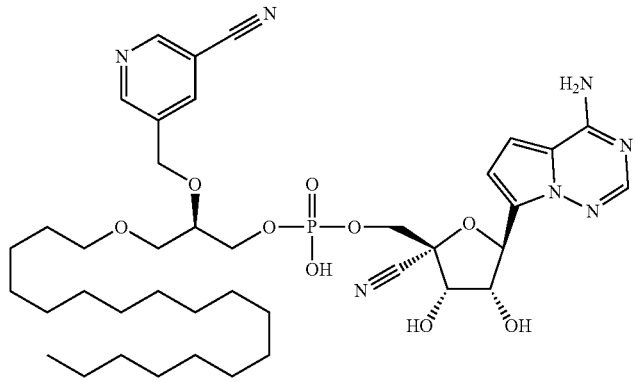 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cncc(C#N)c1]
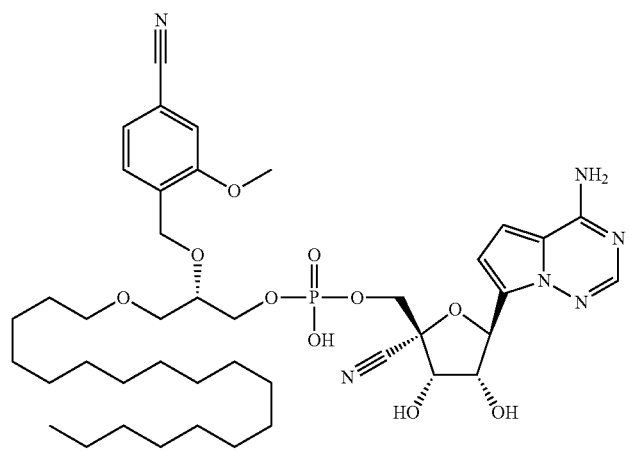 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cc1OC]
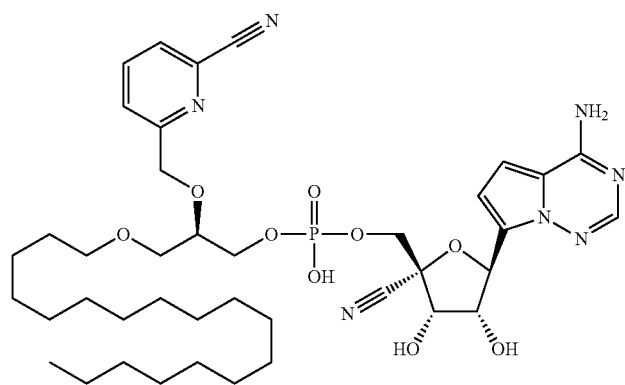 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)n1]
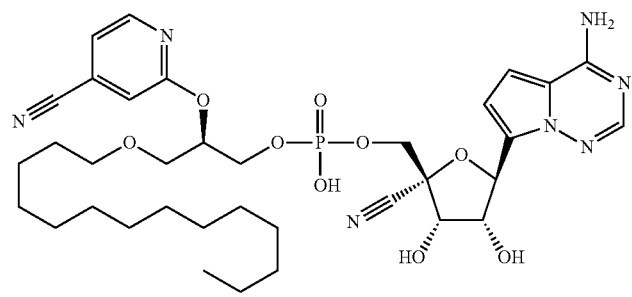 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1cc(C#N)ccn1]

TABLE 27-continued
Some Compounds of Formula IX
Structure
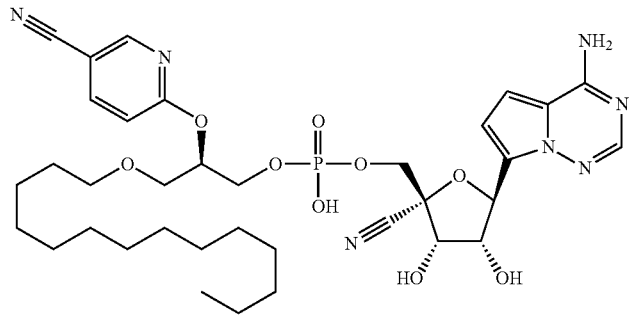 [SMILES: CCCCCCCCCCCCCCOC[C@H](COP(=O)(O)OC[C@@]1(C#N)O[C@@H](c2ccc3c(N)ncnn23)[C@H](O)[C@@H]1O)Oc1ccc(C#N)cn1]
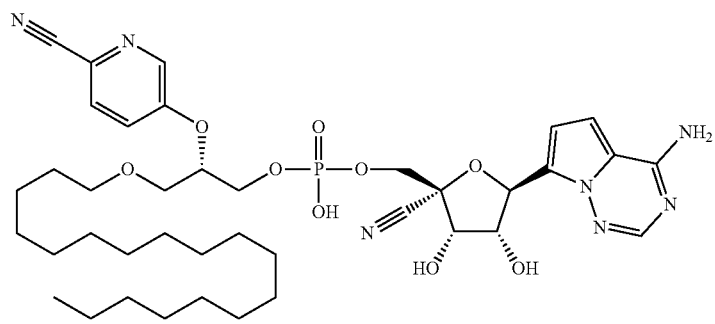 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)Oc1ccc(C#N)nc1]
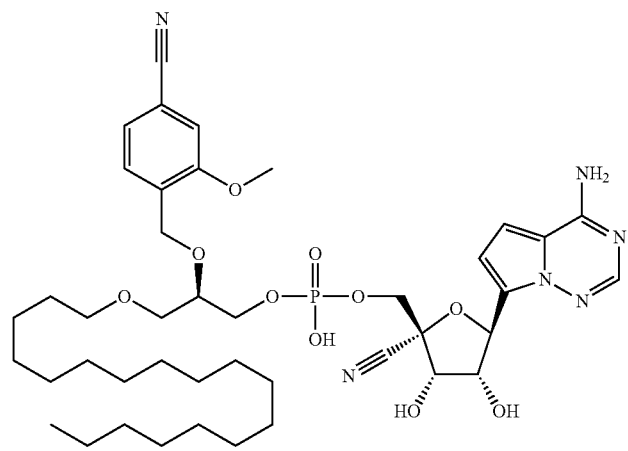 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1OC]
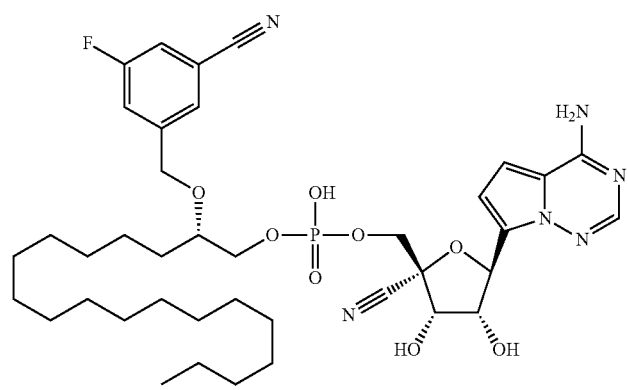 [SMILES: CCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 27-continued
Some Compounds of Formula IX
Structure
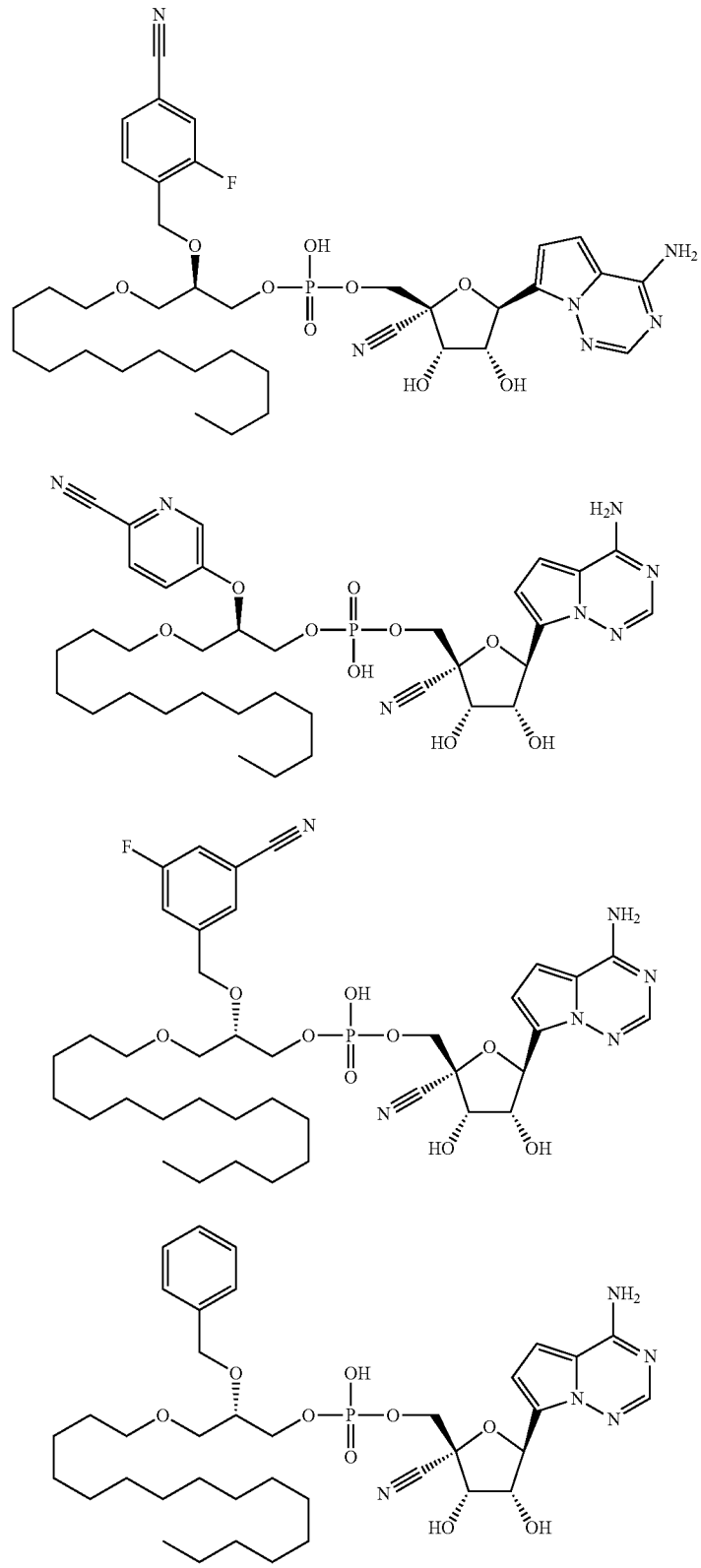

TABLE 27-continued
Some Compounds of Formula IX
Structure
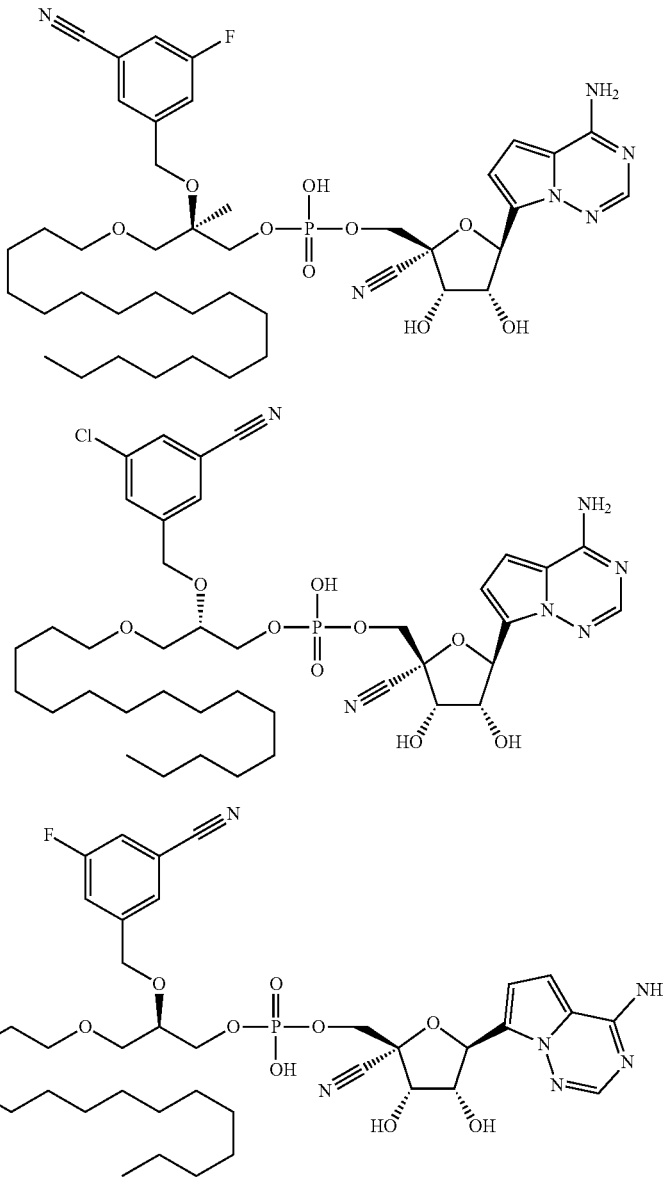
In some embodiments, the compound of Formula I has a Formula IXa:
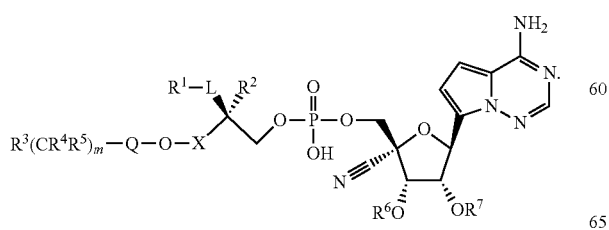
Formula IXa The description of substituents of Formula I (e.g., $R^1$, $R^2$, $R^3$, $R^4$, $R^5$, $R^6$, $R^7$, Q, X, L, and m) applies to Formula IXa.

In some embodiments, the compounds and pharmaceutically acceptable salts of Formula IXa include the compounds in Table 28 and the pharmaceutically acceptable salts thereof.

TABLE 28

Some Compounds of Formula IXa
Structure

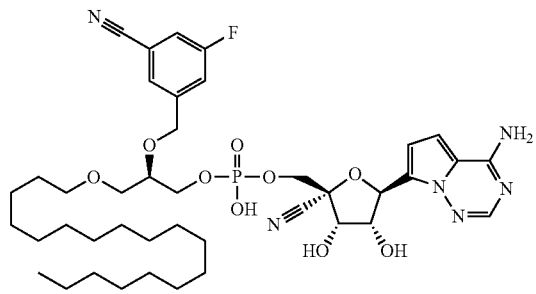 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

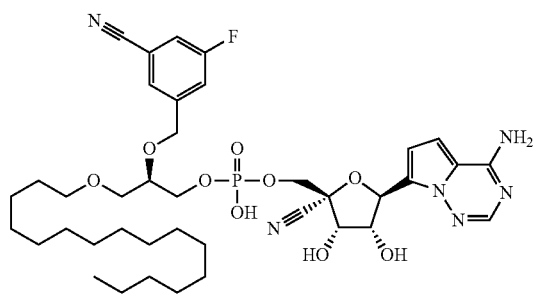 [SMILES: CCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

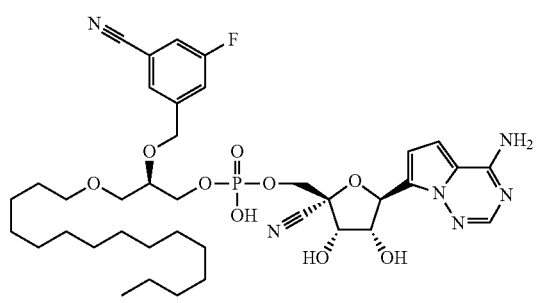 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

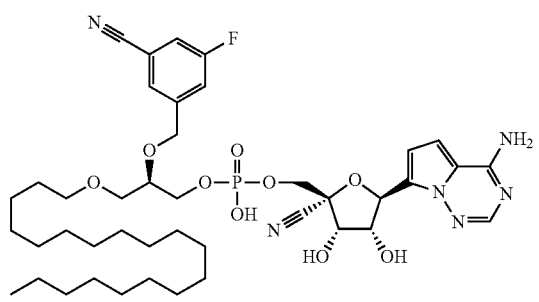 [SMILES: CCCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 28-continued

Some Compounds of Formula IXa
Structure

TABLE 28-continued

Some Compounds of Formula IXa
Structure

TABLE 28-continued
Some Compounds of Formula IXa
Structure
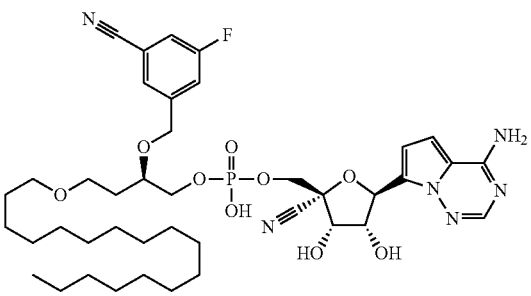 [SMILES: CCCCCCCCCCCCCCCCCOCC[C@H](COP(=O)(O)OC[C@@]1(C#N)O[C@@H](c2ccc3c(N)ncnn23)[C@H](O)[C@@H]1O)OCc1cc(F)cc(C#N)c1]
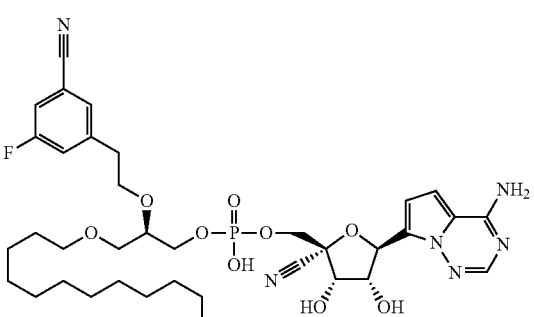
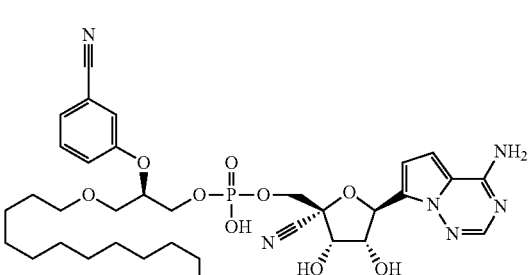
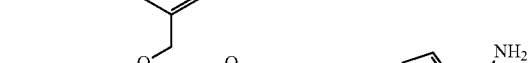
TABLE 28-continued
Some Compounds of Formula IXa
Structure
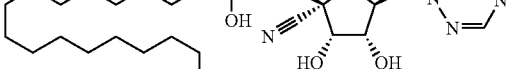
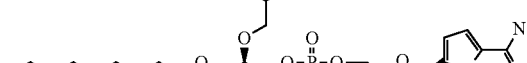

TABLE 28-continued
Some Compounds of Formula IXa
Structure
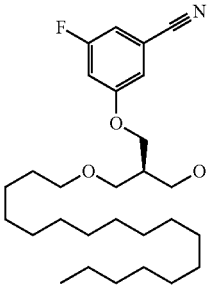
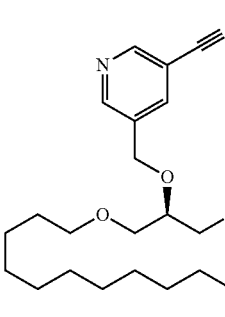
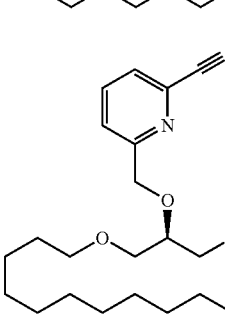
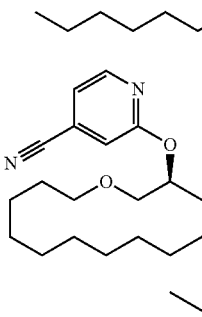
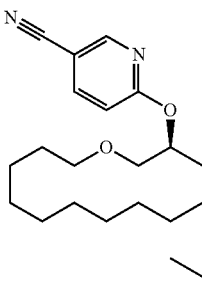
TABLE 28-continued
Some Compounds of Formula IXa
Structure
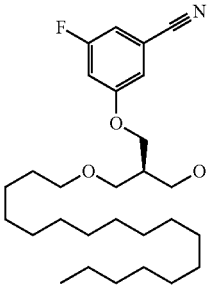
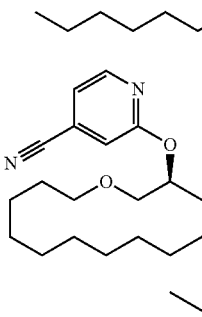
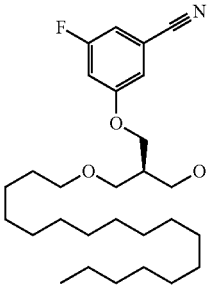
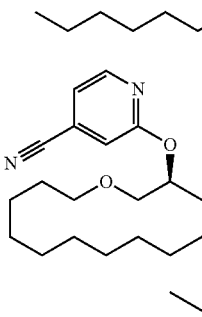

TABLE 28-continued

Some Compounds of Formula IXa
Structure

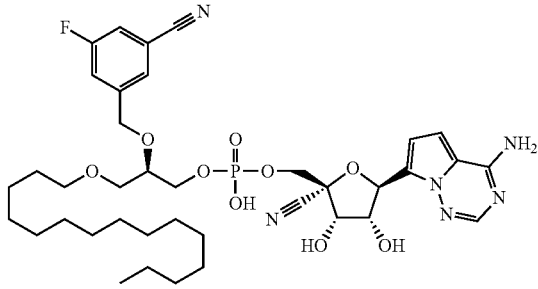 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

In some embodiments, the compound of Formula I has a Formula IXb:

Formula IXb

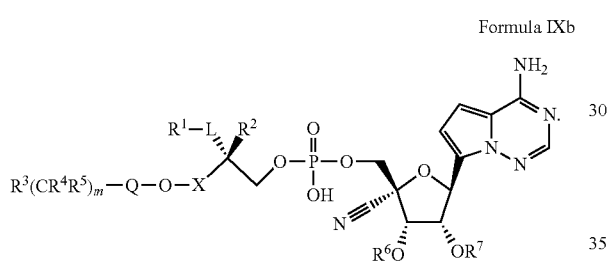

The description of substituents of Formula I (e.g., $R^1$, $R^2$, $R^3$, $R^4$, $R^5$, $R^6$, $R^7$, Q, X, L, and m) applies to Formula IXb.

In some embodiments, the compounds and pharmaceutically acceptable salts of Formula IXb include the compounds in Table 29 and the pharmaceutically acceptable salts thereof.

TABLE 29

Some Compounds of Formula IXb
Structure

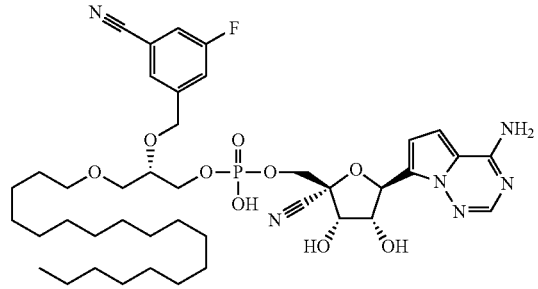 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 29-continued

Some Compounds of Formula IXb
Structure

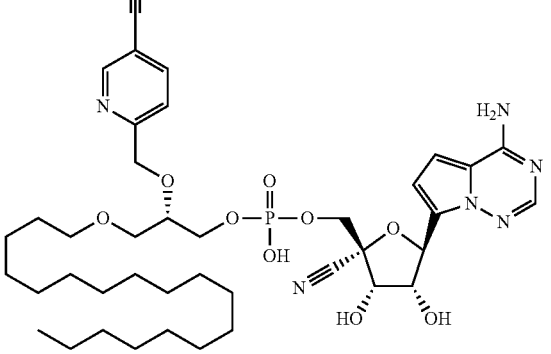

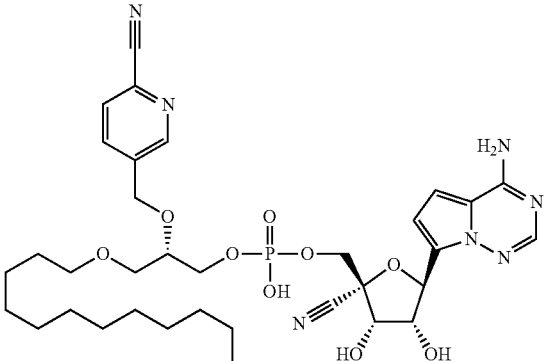

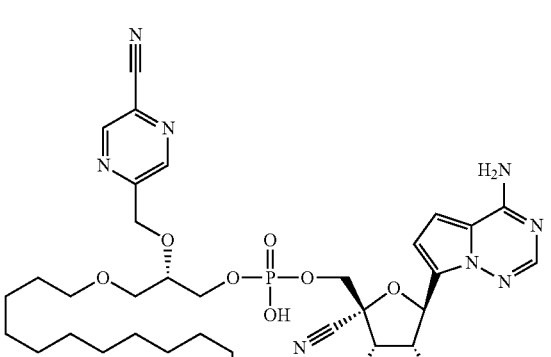

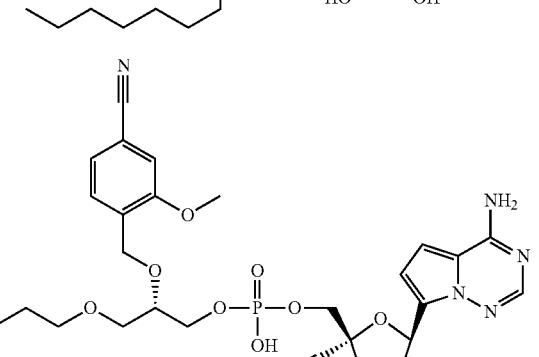

TABLE 29-continued

Some Compounds of Formula IXb
Structure

[Chemical structures of compounds]

In some embodiments, the compound of Formula I has a Formula IXc:


Formula IXc

The description of substituents of Formula I (e.g., $R^1$, $R^2$, $R^3$, $R^4$, $R^5$, $R^6$, $R^7$, Q, X, L, and m) applies to Formula IXc.

In some embodiments, the compounds and pharmaceutically acceptable salts of Formula IXc include the compounds in Table 30 and the pharmaceutically acceptable salts thereof.

TABLE 30

Some Compounds of Formula IXc
Structure

[Chemical structures of compounds]

In some embodiments, the compound of Formula I has a Formula X:

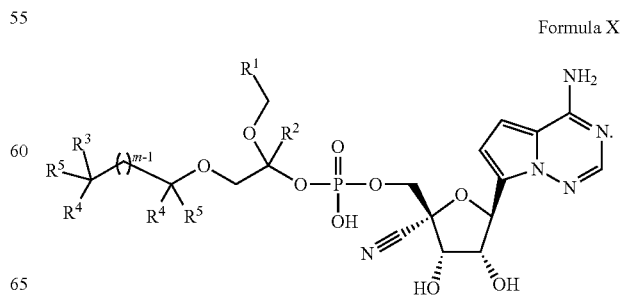

Formula X

The description of substituents of Formula I (e.g., $R^1$, $R^2$, $R^3$, $R^4$, $R^5$, and m) applies to Formula X. In some embodiments, the compounds and pharmaceutically acceptable salts of Formula X include the compounds in Table 31 and the pharmaceutically acceptable salts thereof.
TABLE 31
Compounds of Formula X
Structure
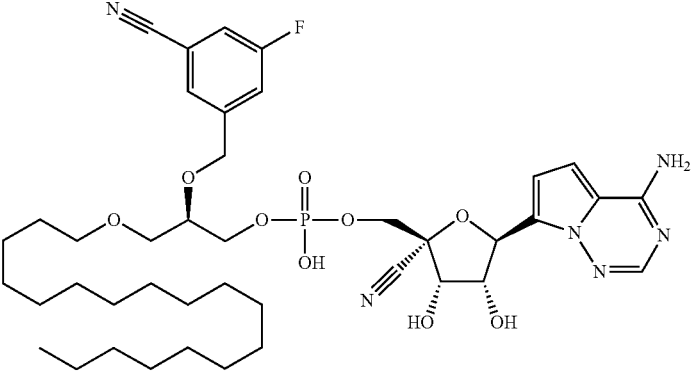 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
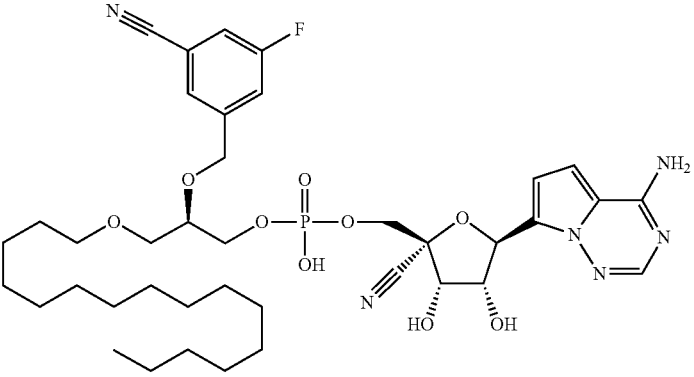 [SMILES: CCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
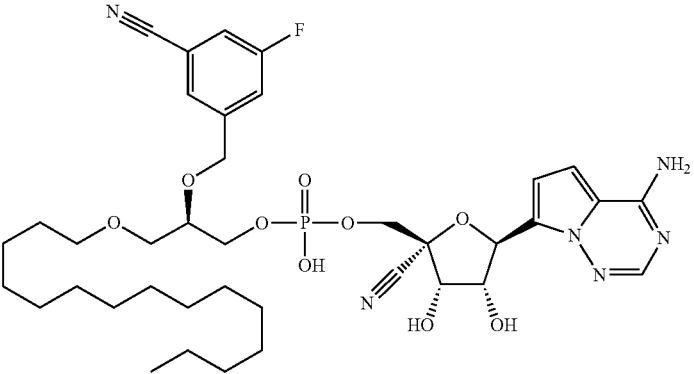 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 31-continued
Compounds of Formula X
Structure
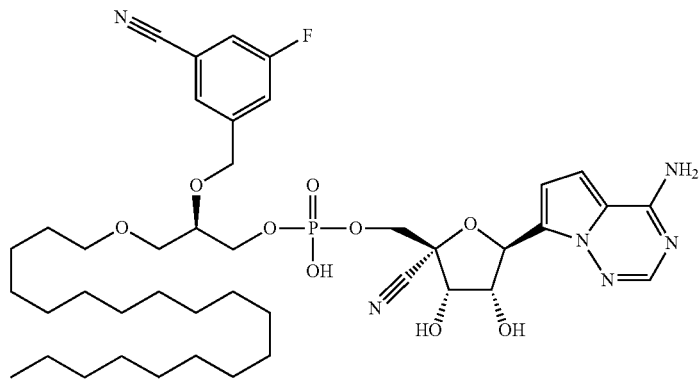 [SMILES: CCCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
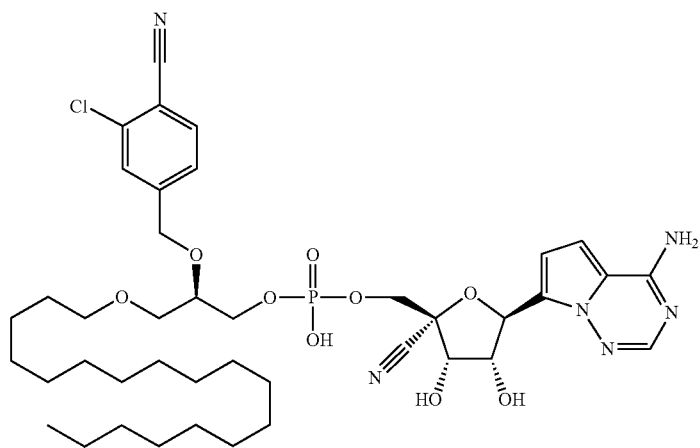 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(Cl)c1]
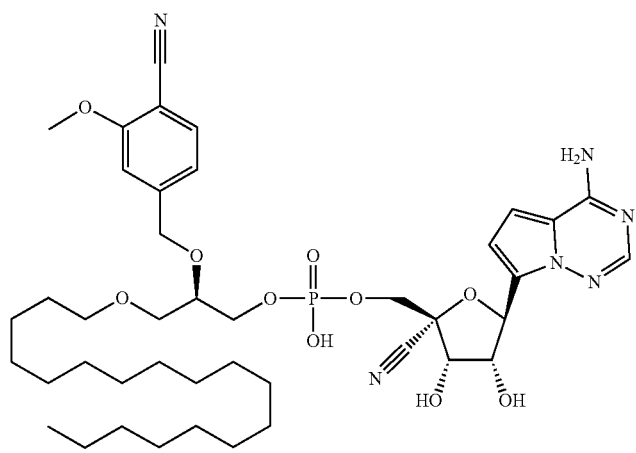 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]

TABLE 31-continued
Compounds of Formula X
Structure
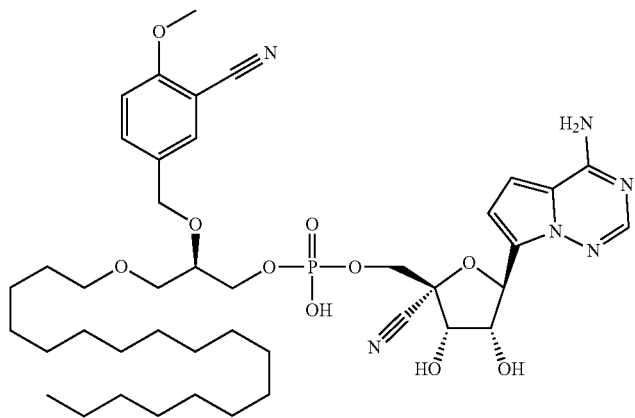 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]
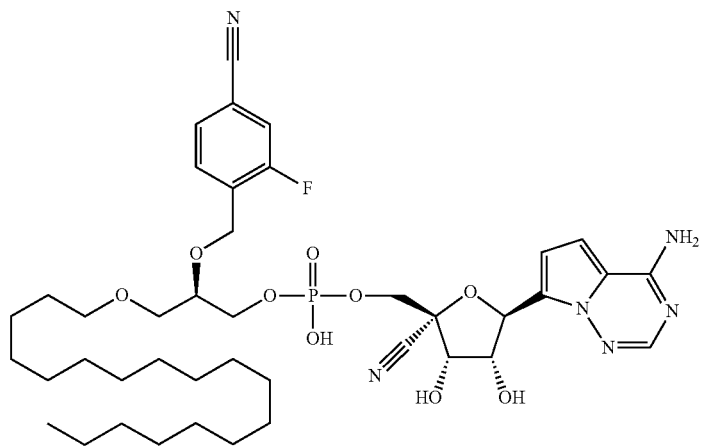 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]
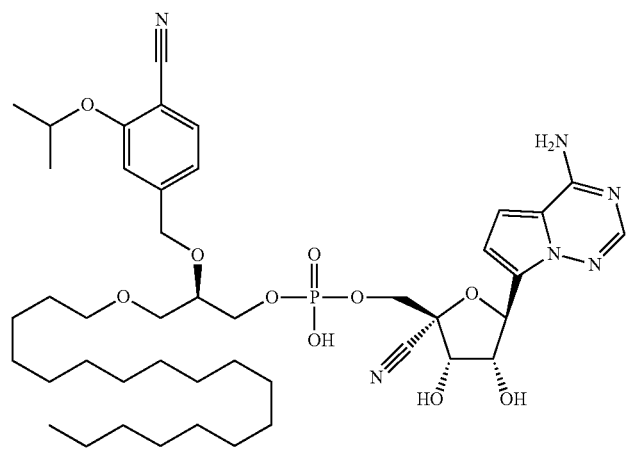 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]

TABLE 31-continued
Compounds of Formula X
Structure
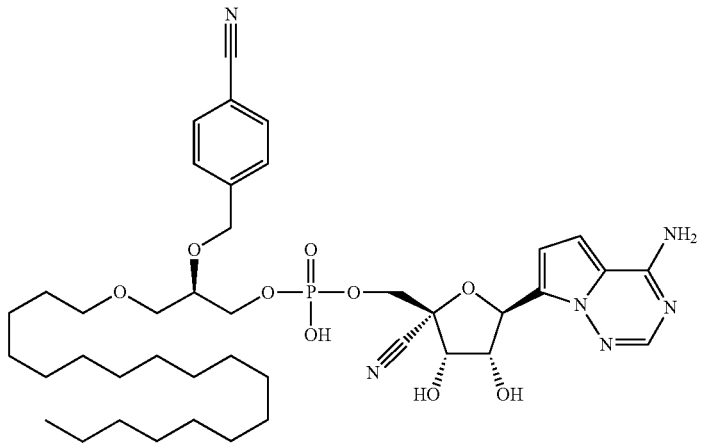 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]
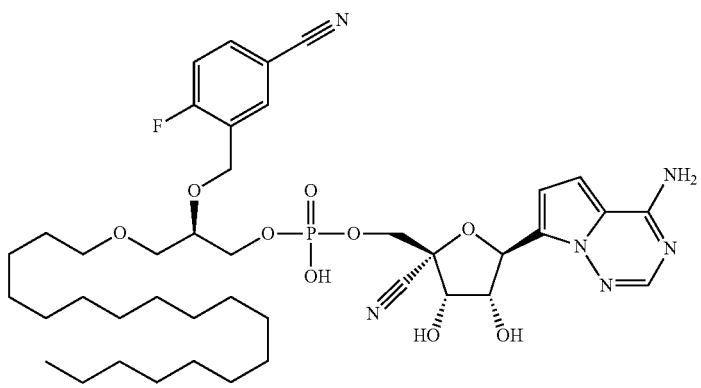 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(C#N)ccc1F]
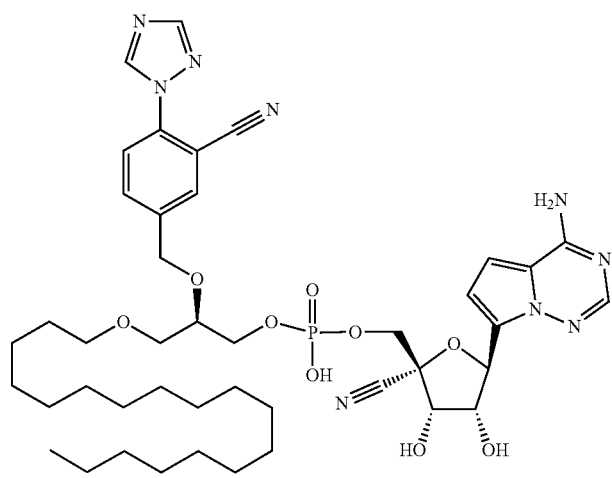 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]

TABLE 31-continued
Compounds of Formula X
Structure
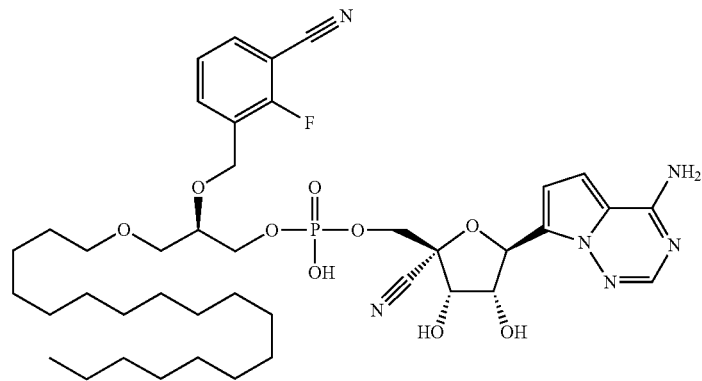 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
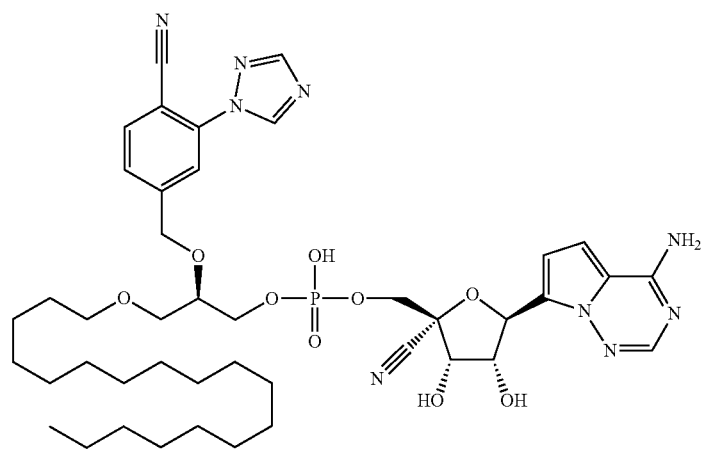 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]
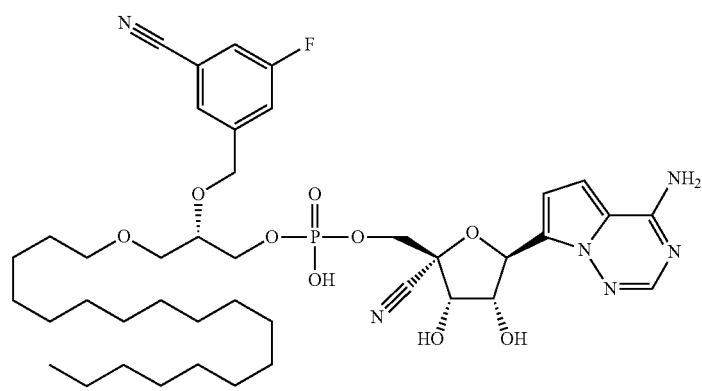 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 31-continued
Compounds of Formula X
Structure
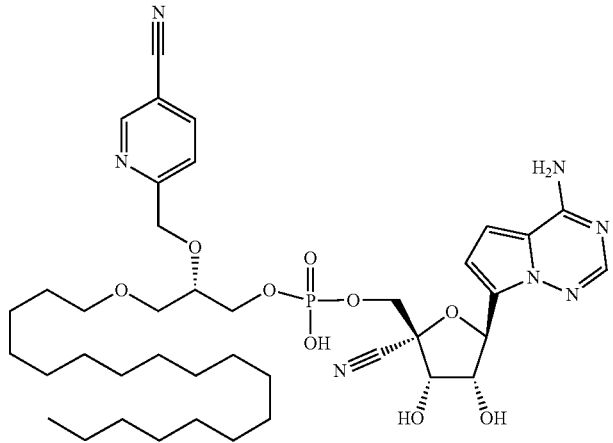 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cn1]
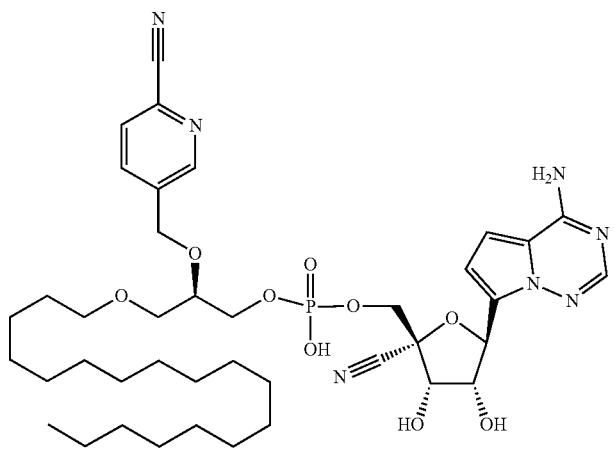 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)nc1]
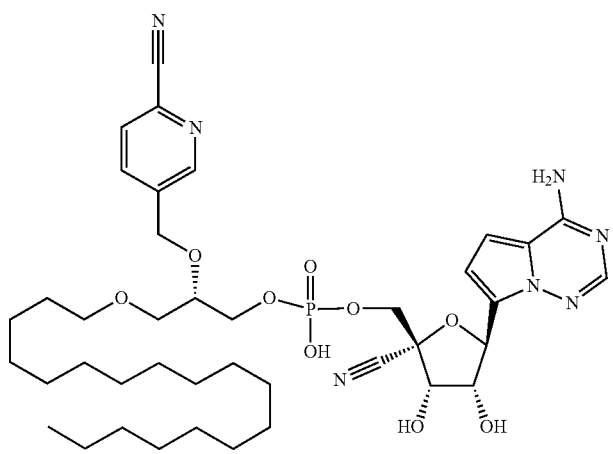 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)nc1]

TABLE 31-continued
Compounds of Formula X
Structure
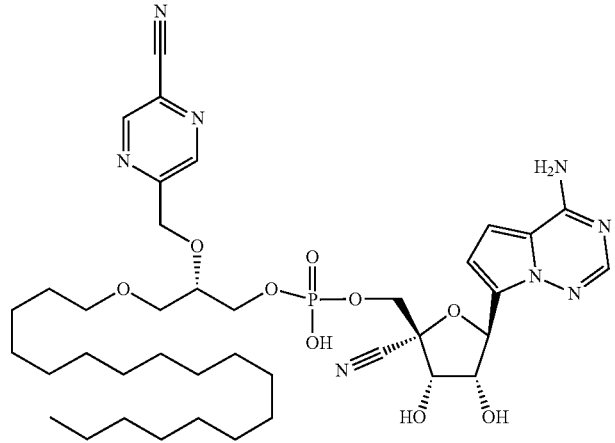
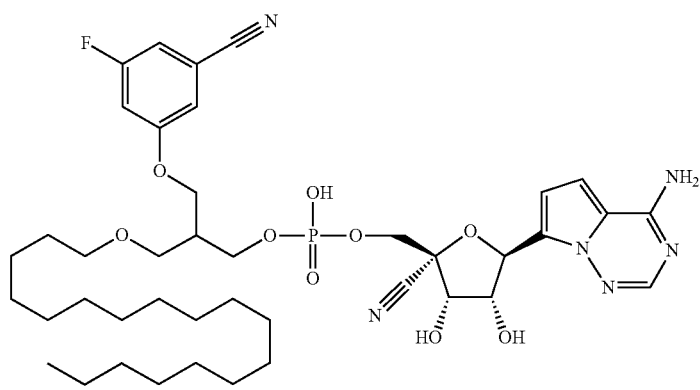 [SMILES: CCCCCCCCCCCCCCCCCCOCC(COc1cc(F)cc(C#N)c1)COP(=O)(O)OC[C@@]1(C#N)O[C@@H](c2ccc3c(N)ncnn23)[C@H](O)[C@@H]1O]
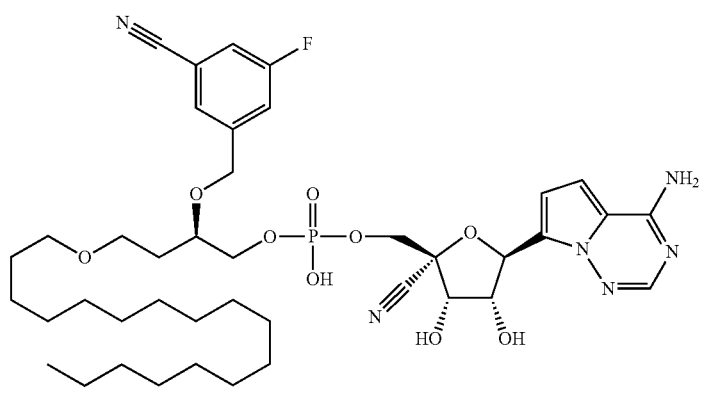 [SMILES: CCCCCCCCCCCCCCCCCOCC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 31-continued
Compounds of Formula X
Structure
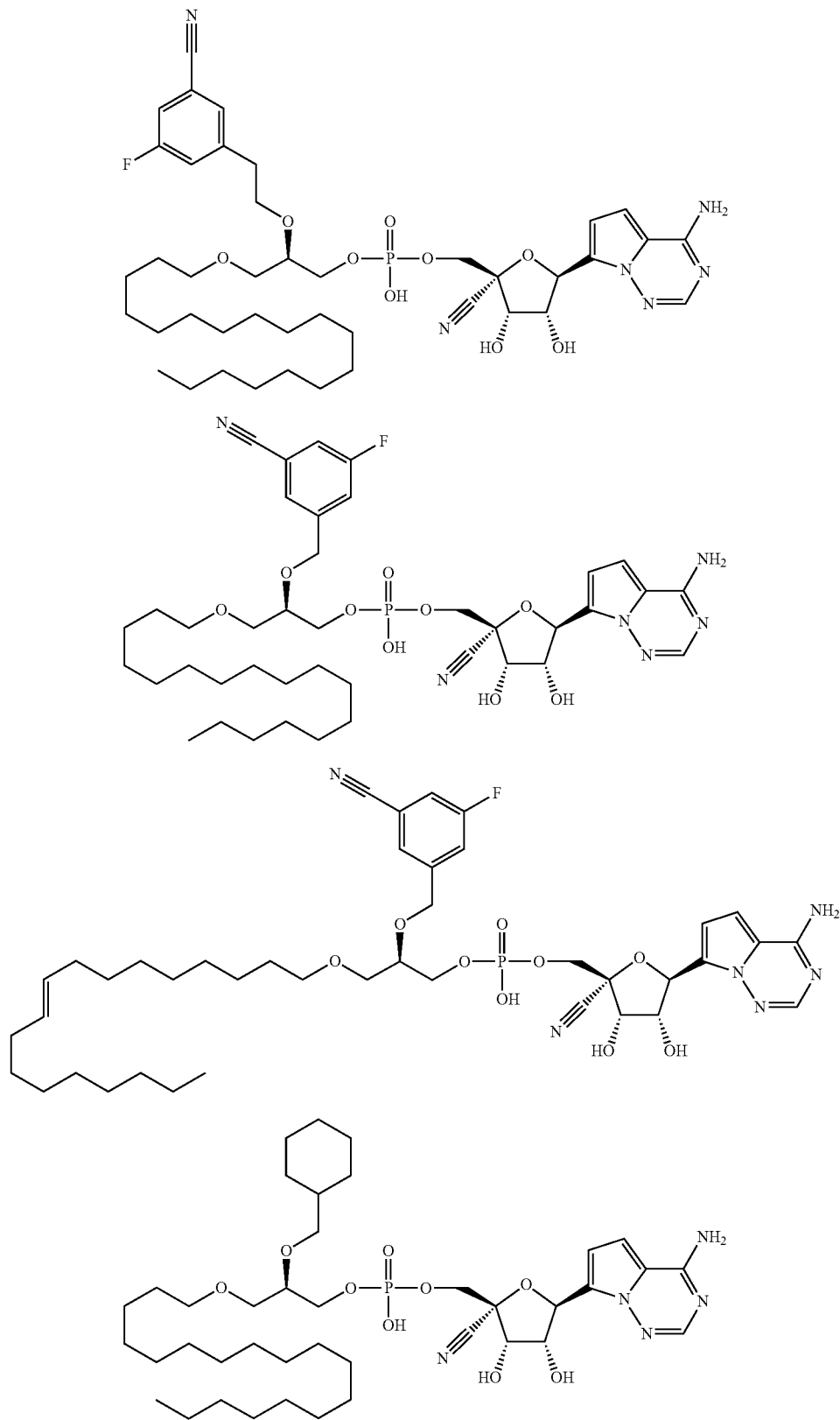

TABLE 31-continued
Compounds of Formula X
Structure
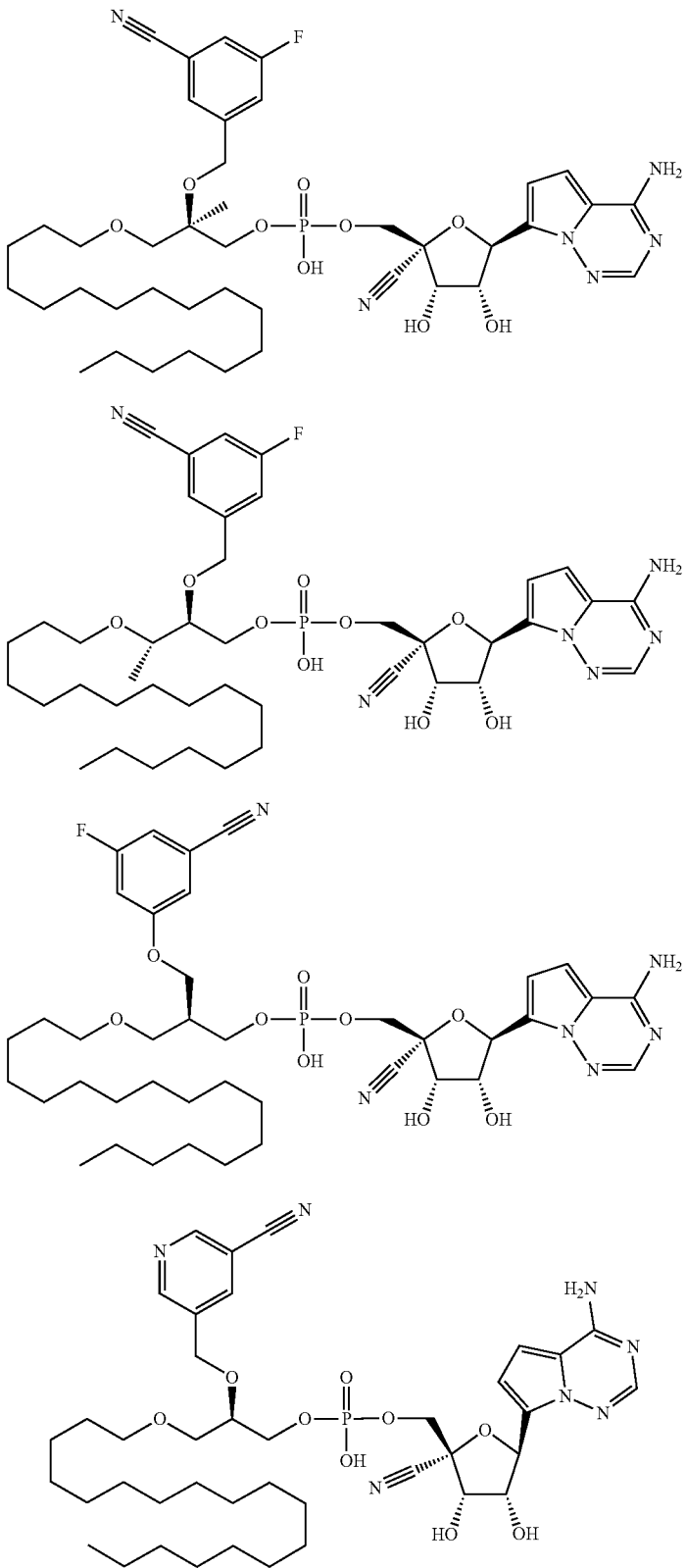

TABLE 31-continued
Compounds of Formula X
Structure
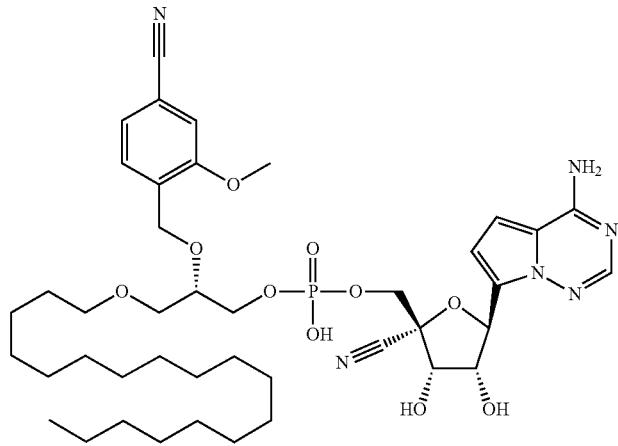 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)cc1OC]
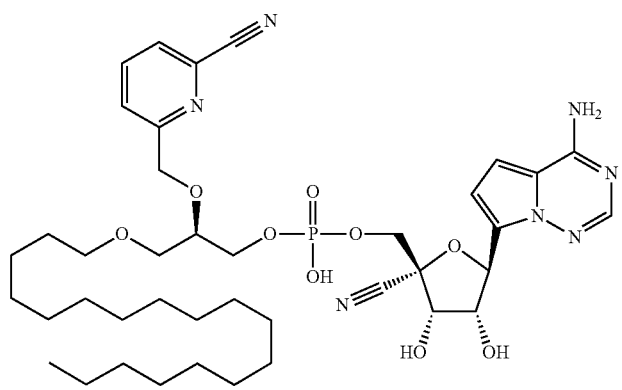 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)n1]
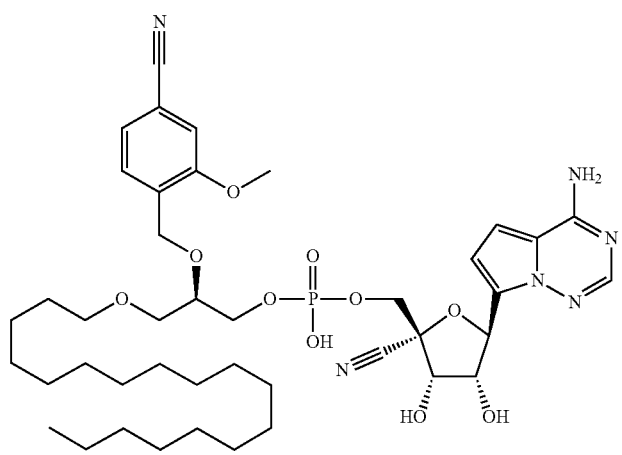 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1OC]

TABLE 31-continued
Compounds of Formula X
Structure
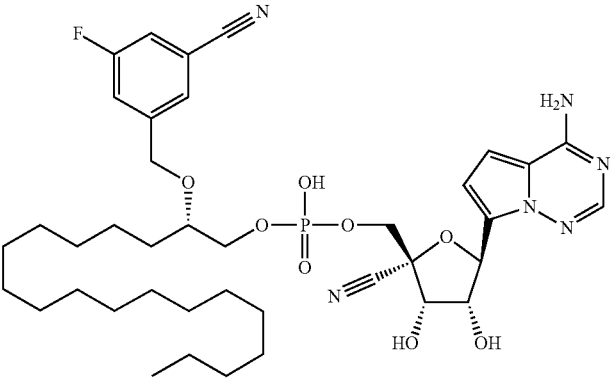 [SMILES: CCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
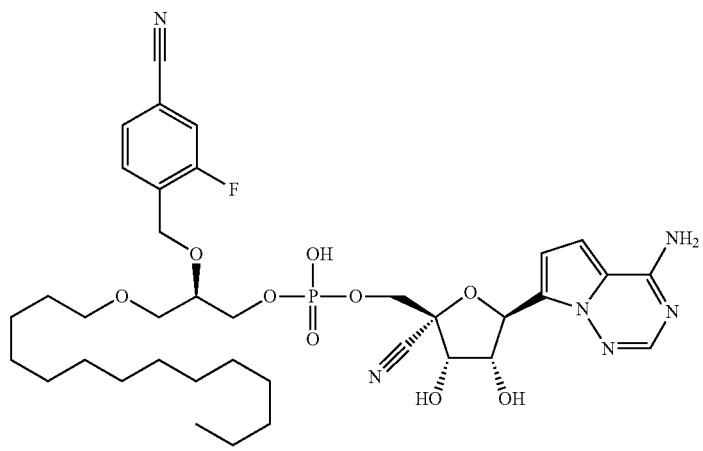 [SMILES: CCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]
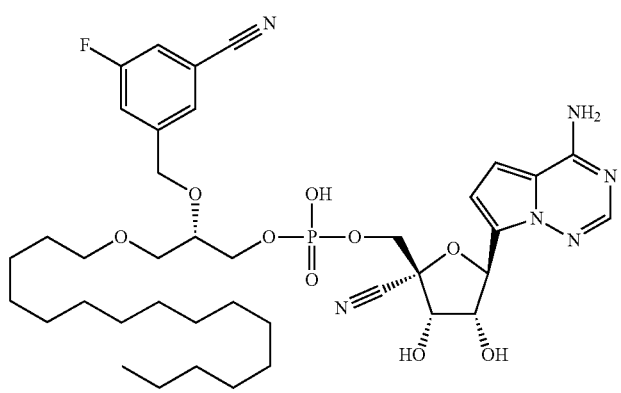 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1cc(F)cc(C#N)c1]
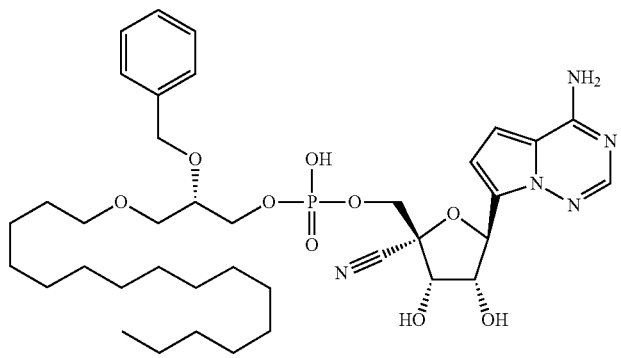 [SMILES: CCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccccc1]

TABLE 31-continued
Compounds of Formula X
Structure
In some embodiments, the compound of Formula I has a Formula Xa:
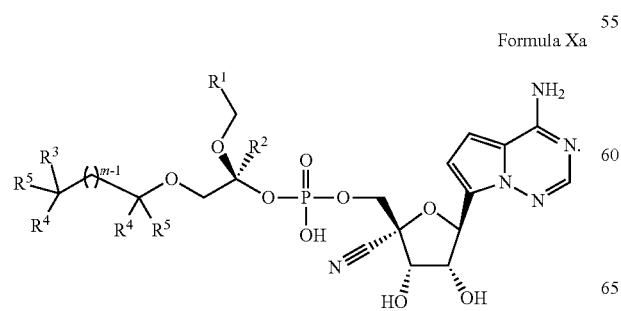
Formula Xa The description of substituents of Formula I (e.g., $R^1$, $R^2$, $R^3$, $R^4$, $R^5$, and m) applies to Formula Xa.
In some embodiments, the compounds and pharmaceutically acceptable salts of Formula Xa include the compounds in Table 32 and the pharmaceutically acceptable salts thereof.
TABLE 32
Compounds of Formula Xa
Structure
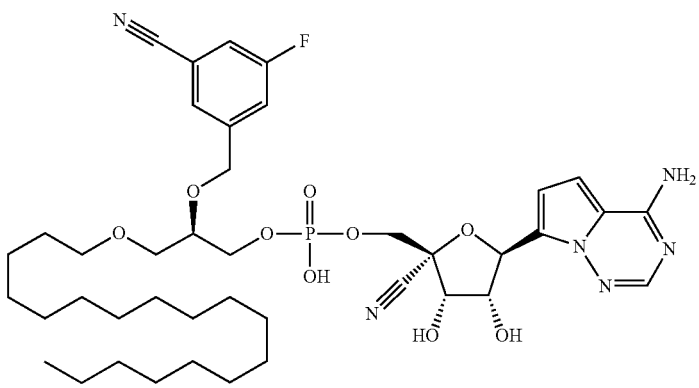 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
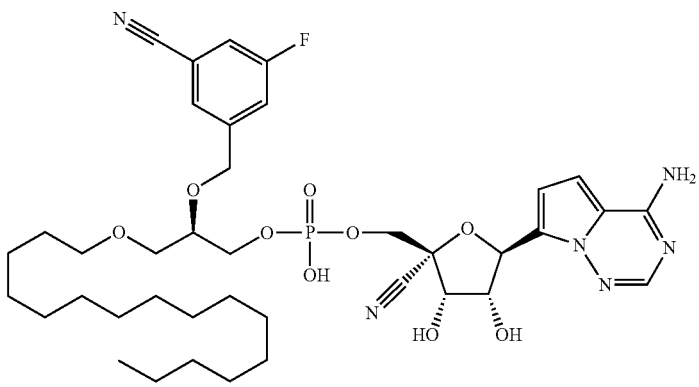 [SMILES: CCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
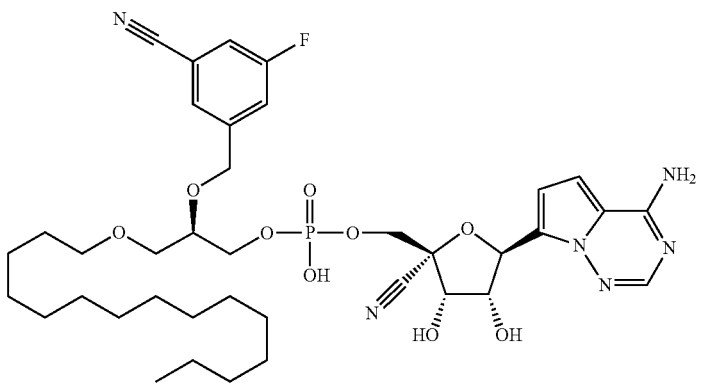 [SMILES: CCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 32-continued
Compounds of Formula Xa
Structure
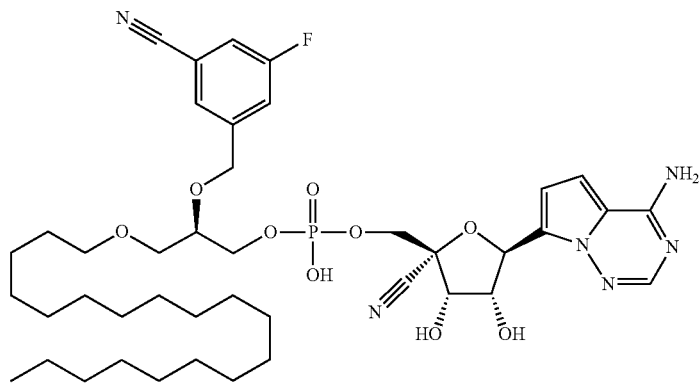 [SMILES: CCCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(F)cc(C#N)c1]
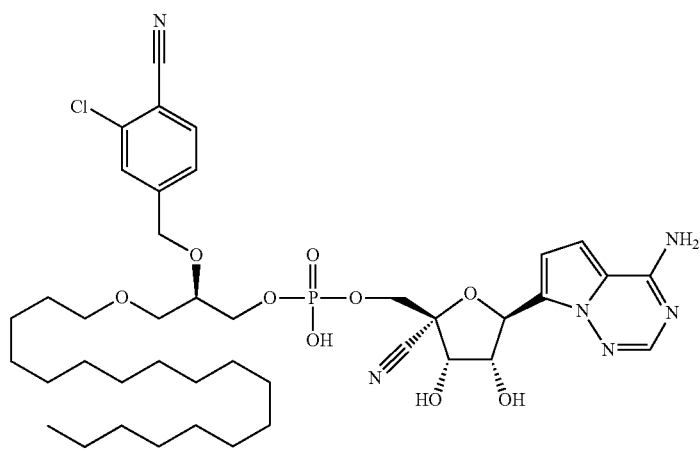 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(Cl)c1]
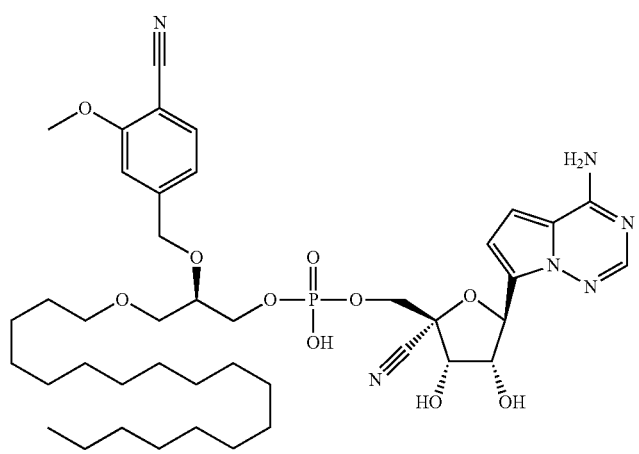 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC)c1]

TABLE 32-continued
Compounds of Formula Xa
Structure
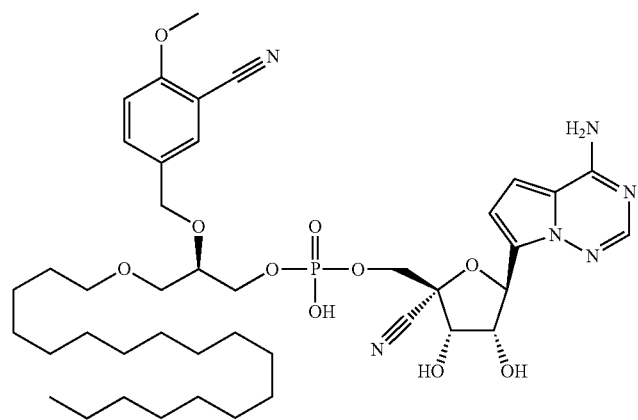 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(OC)c(C#N)c1]
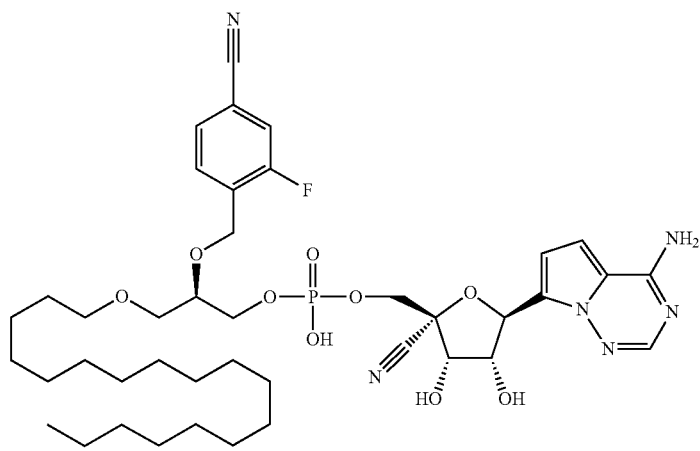 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1F]
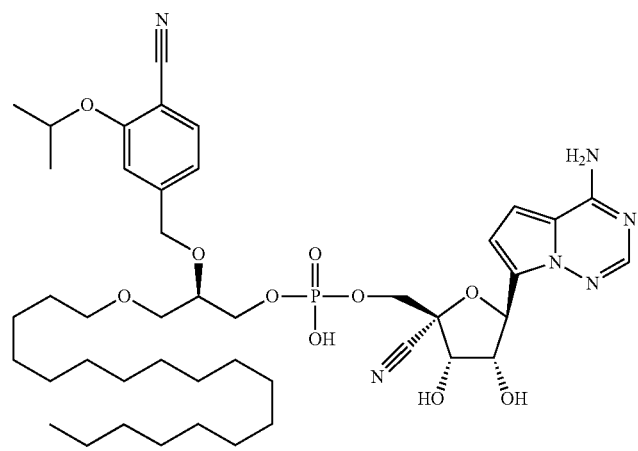 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]

TABLE 32-continued
Compounds of Formula Xa
Structure
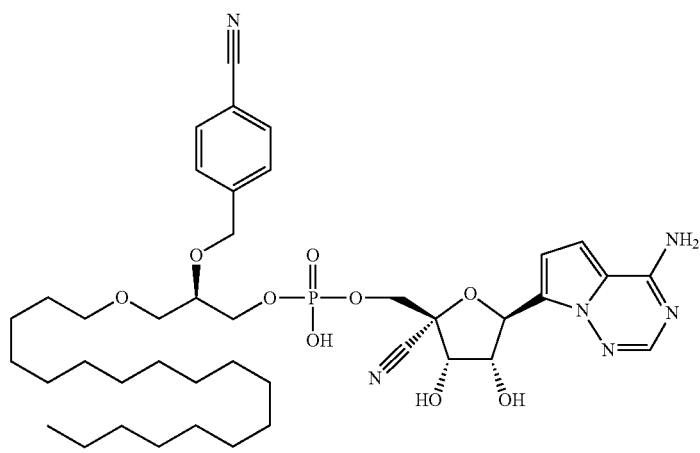 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1]
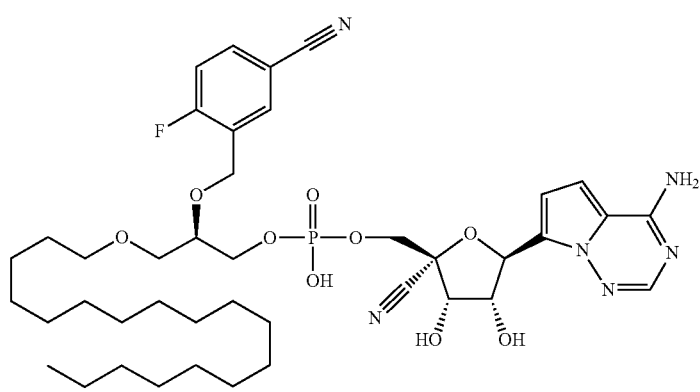 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cc(C#N)ccc1F]
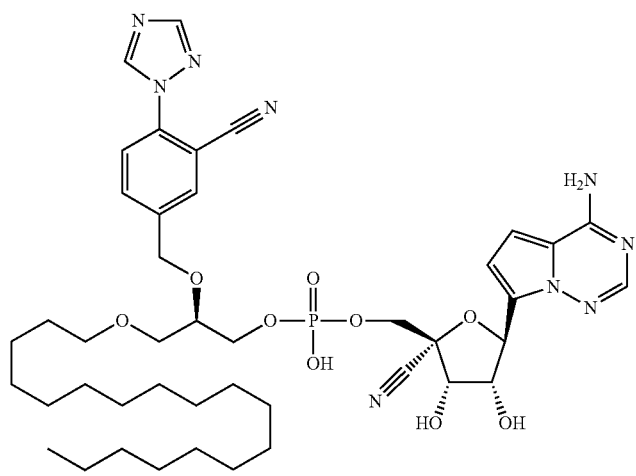 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]

TABLE 32-continued
Compounds of Formula Xa
Structure
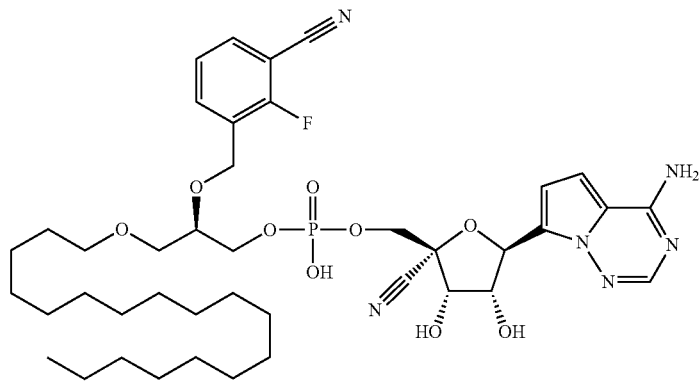 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)c1F]
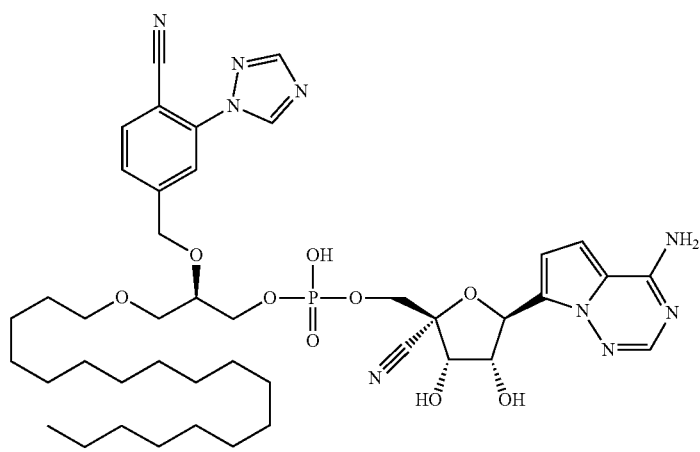 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)c(-n2cncn2)c1]
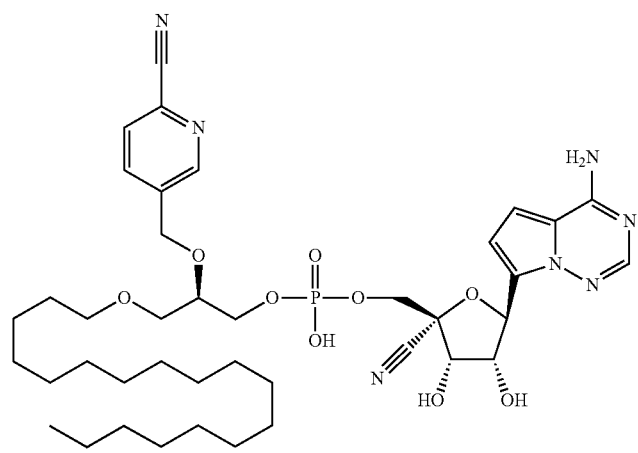 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)nc1]

TABLE 32-continued
Compounds of Formula Xa
Structure
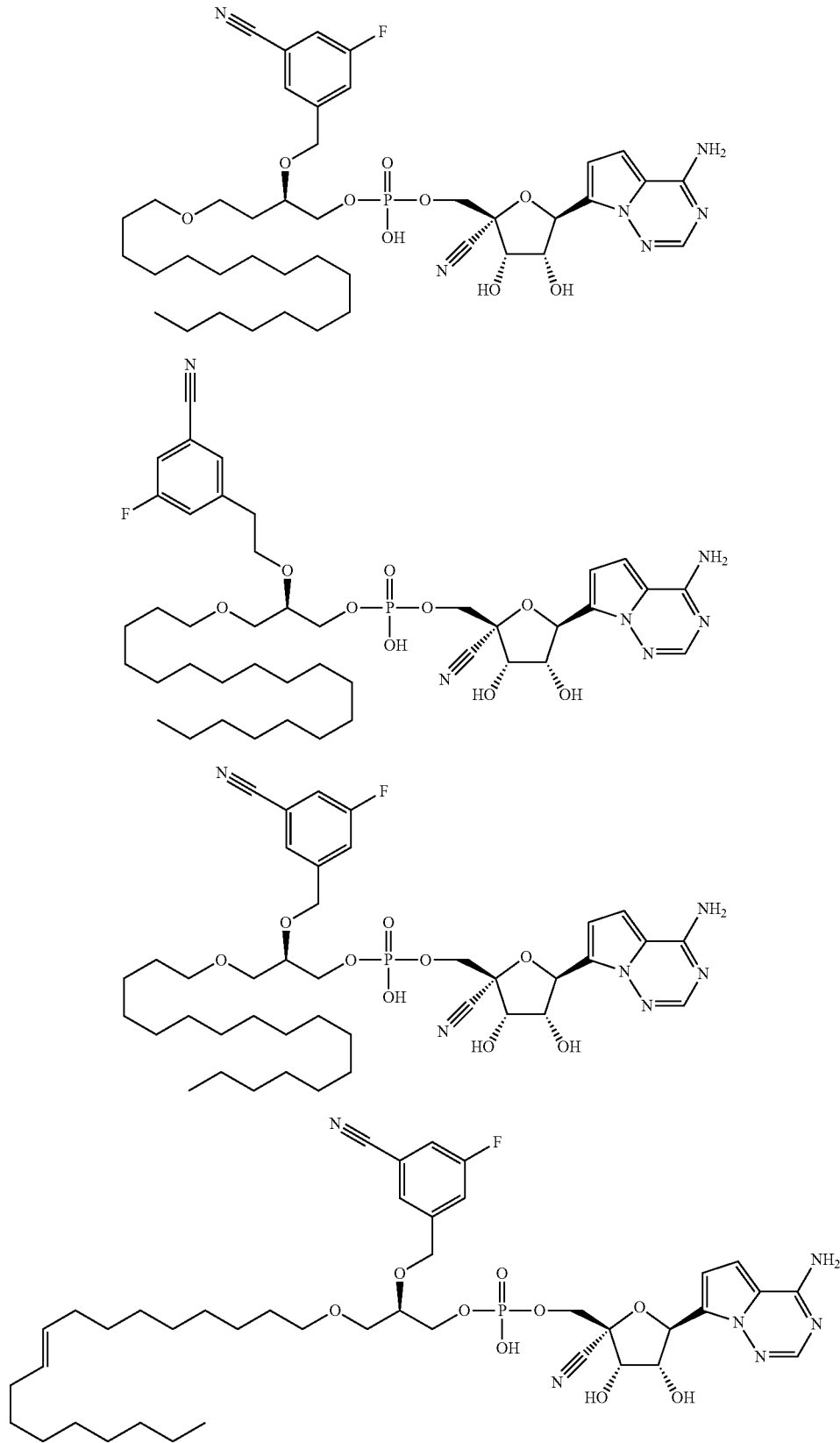

TABLE 32-continued
Compounds of Formula Xa
Structure
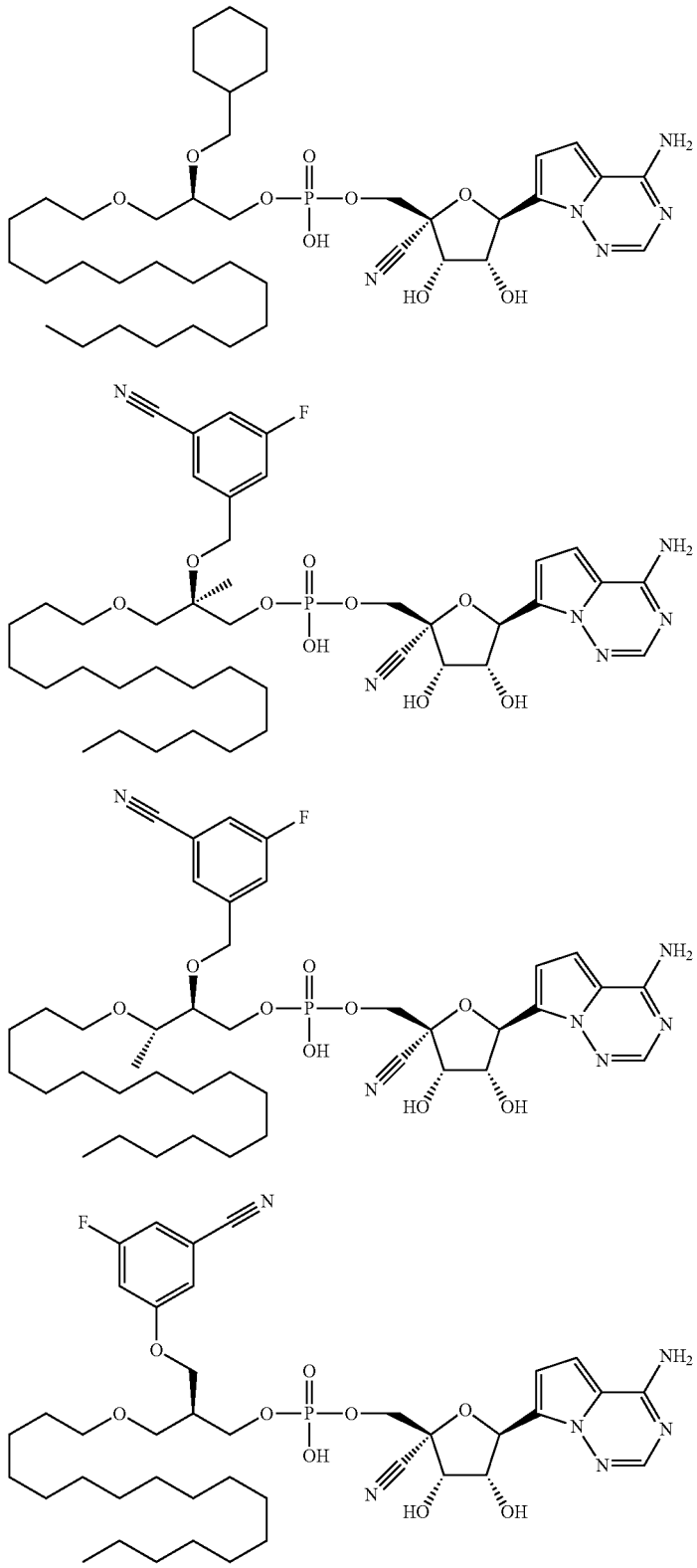

TABLE 32-continued
Compounds of Formula Xa
Structure
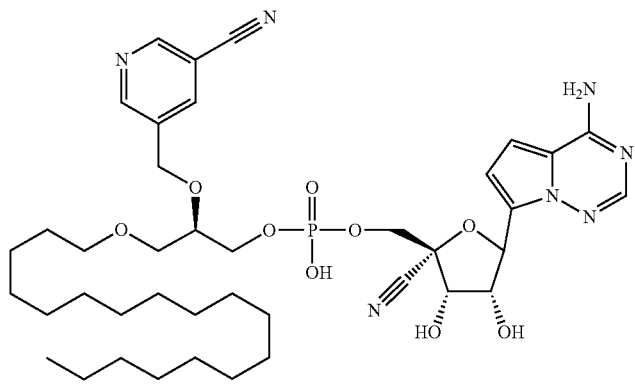 [SMILES: CCCCCCCCCCCCCCCCCCOC[C@H](COP(=O)(O)OC[C@@]1(C#N)OC(c2ccc3c(N)ncnn23)[C@H](O)[C@@H]1O)OCc1cncc(C#N)c1]
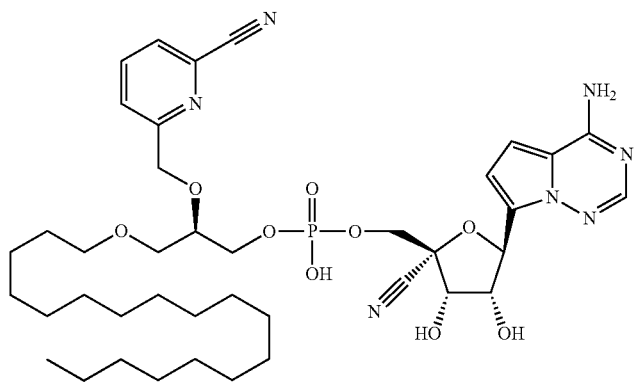 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1cccc(C#N)n1]
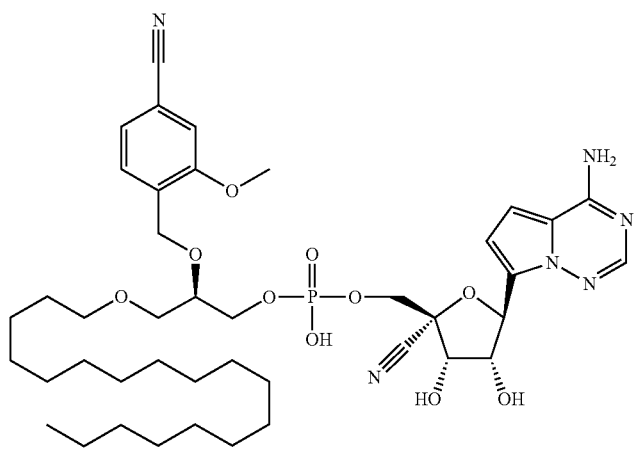 [SMILES: CCCCCCCCCCCCCCCCCCOC[C@H](COP(=O)(O)OC[C@@]1(C#N)O[C@@H](c2ccc3c(N)ncnn23)[C@H](O)[C@@H]1O)OCc1ccc(C#N)cc1OC]

TABLE 32-continued
Compounds of Formula Xa
Structure
[Three chemical structures shown]
In some embodiments, the compound of Formula I has a Formula Xb:
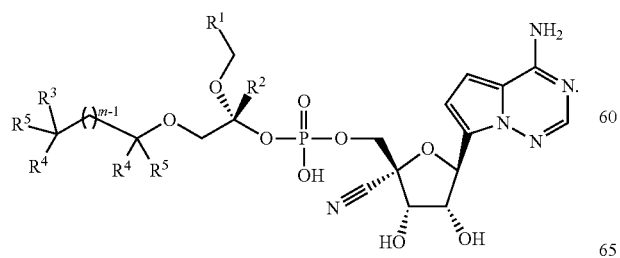
Formula Xb The description of substituents of Formula I (e.g., $R^1$, $R^2$, $R^3$, $R^4$, $R^5$, and m) applies to Formula Xb.

In some embodiments, the compounds and pharmaceutically acceptable salts of Formula Xb include the compounds in Table 33 and the pharmaceutically acceptable salts thereof.

TABLE 33

Compounds of Formula Xb
Structure

TABLE 33-continued

Compounds of Formula Xb
Structure

In some embodiments, the compound of Formula I has a Formula XI:

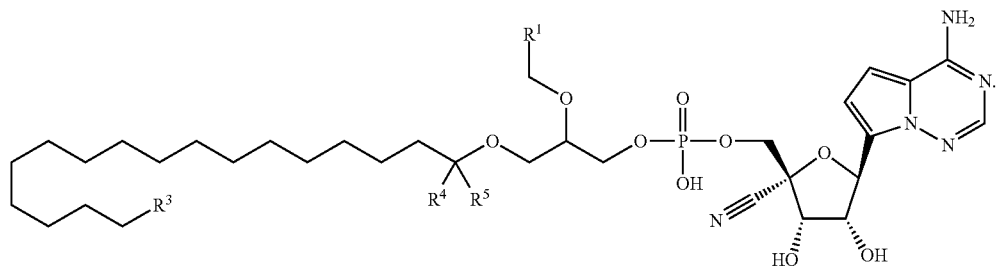

Formula XI

The description of substituents of Formula I (e.g., $R^1$, $R^3$, $R^4$, and $R^5$) applies to Formula XI. In some embodiments, the compounds and pharmaceutically acceptable salts of Formula XI include the compounds in Table 34 and the pharmaceutically acceptable salts thereof.

TABLE 34

Some Compounds of Formula XI
Structure

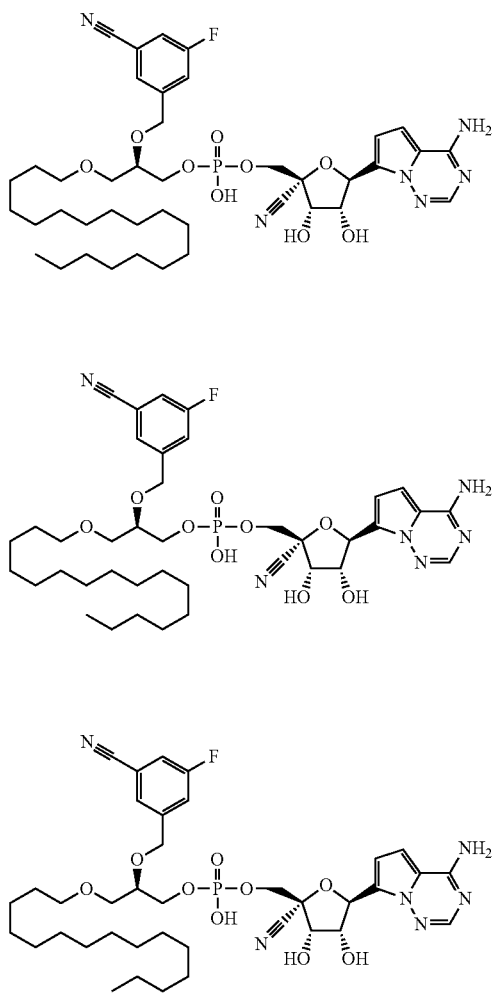

TABLE 34-continued

Some Compounds of Formula XI
Structure

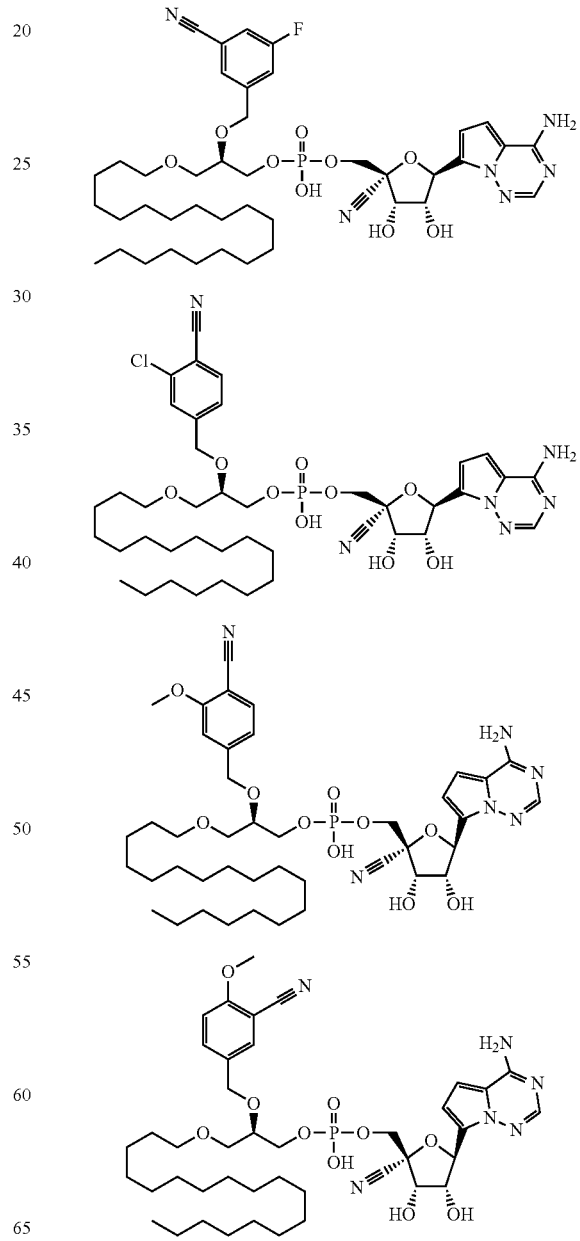

TABLE 34-continued
Some Compounds of Formula XI
Structure
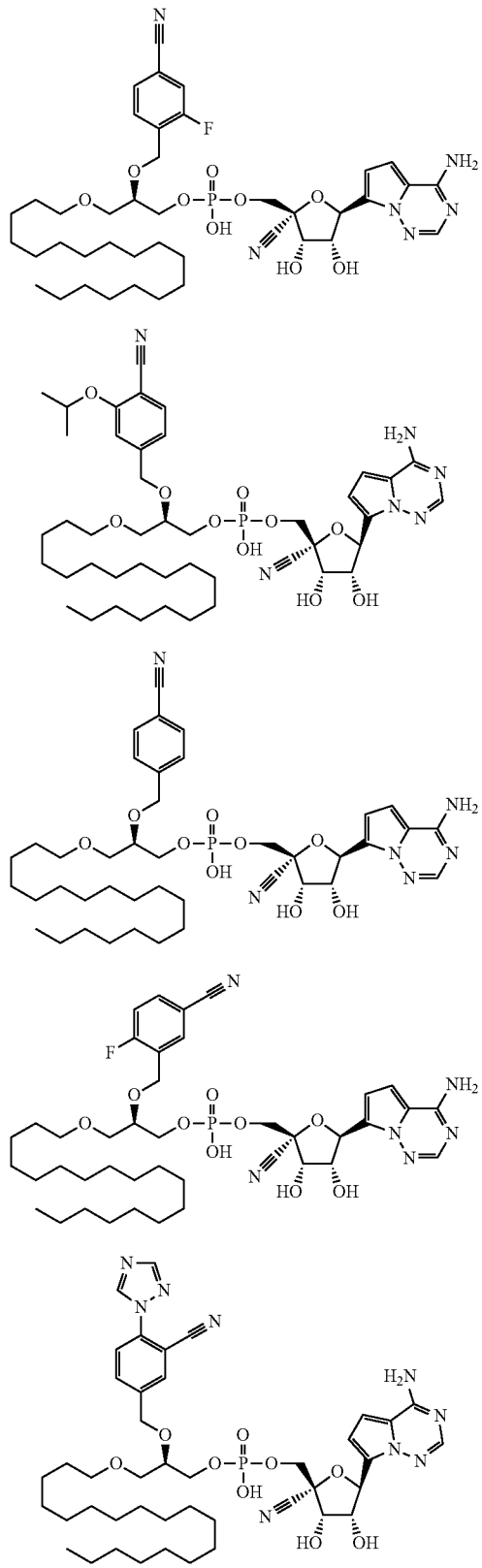
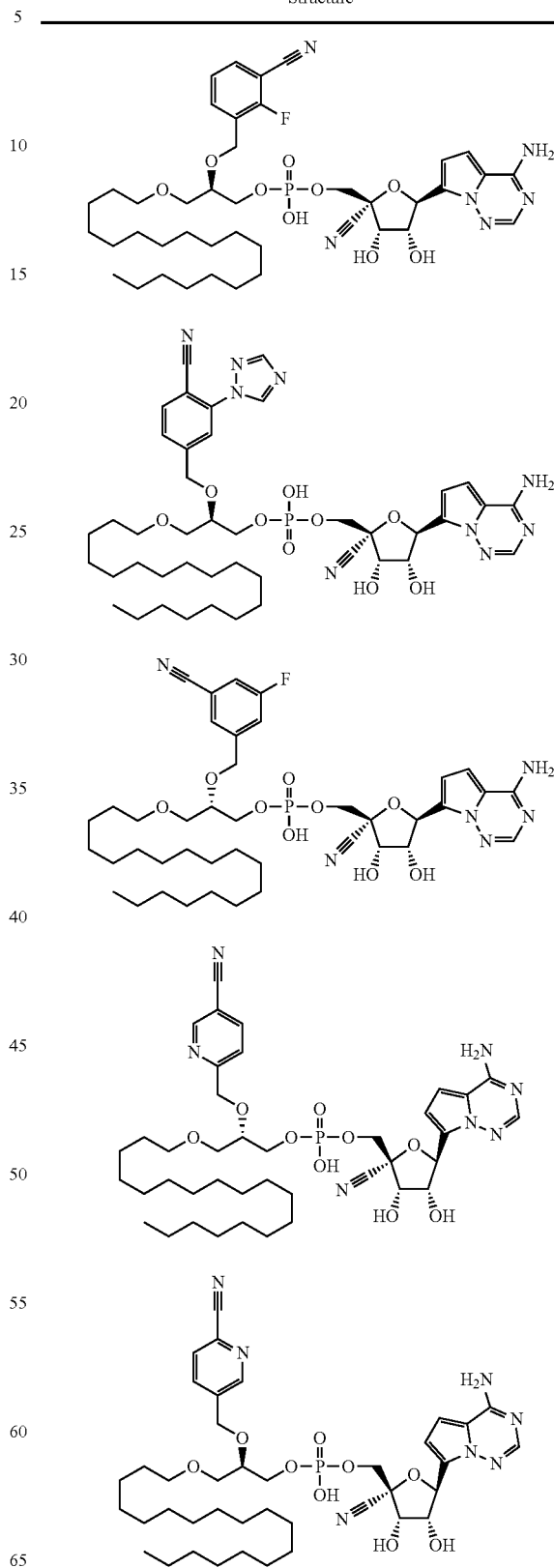

TABLE 34-continued
Some Compounds of Formula XI
Structure
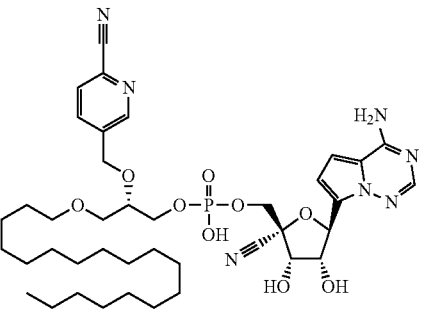 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1ccc(C#N)nc1]
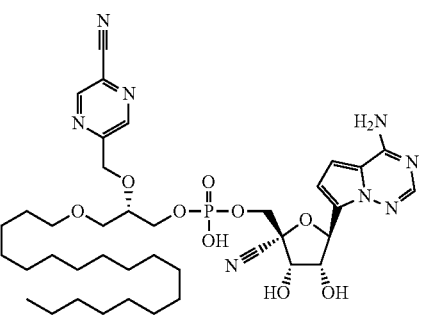 [SMILES: CCCCCCCCCCCCCCCCCCOC[C@@H](COP(=O)(O)OC[C@@]1(C#N)O[C@@H](c2ccc3c(N)ncnn23)[C@H](O)[C@@H]1O)OCc1cnc(C#N)cn1]
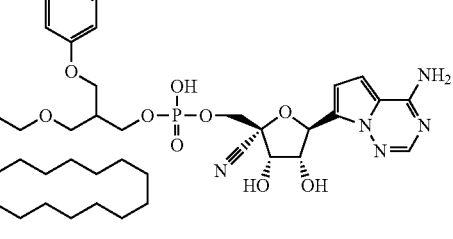
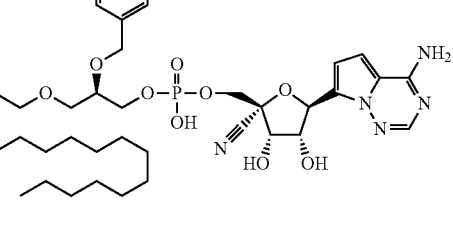
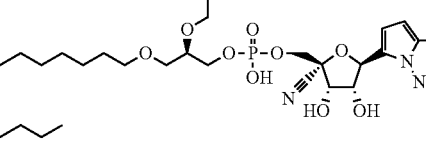
TABLE 34-continued
Some Compounds of Formula XI
Structure
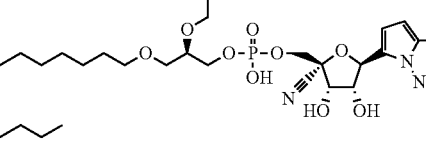
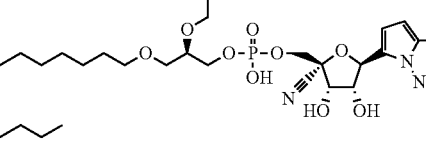
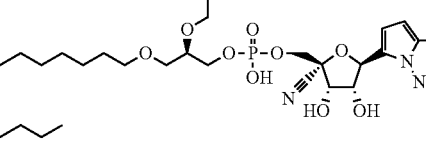
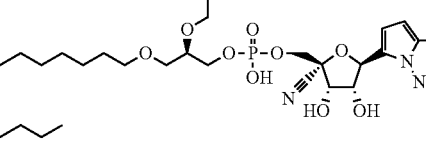
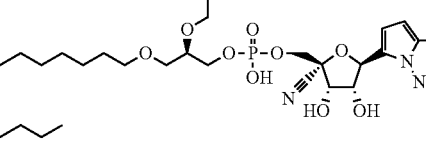

TABLE 34-continued
Some Compounds of Formula XI
Structure
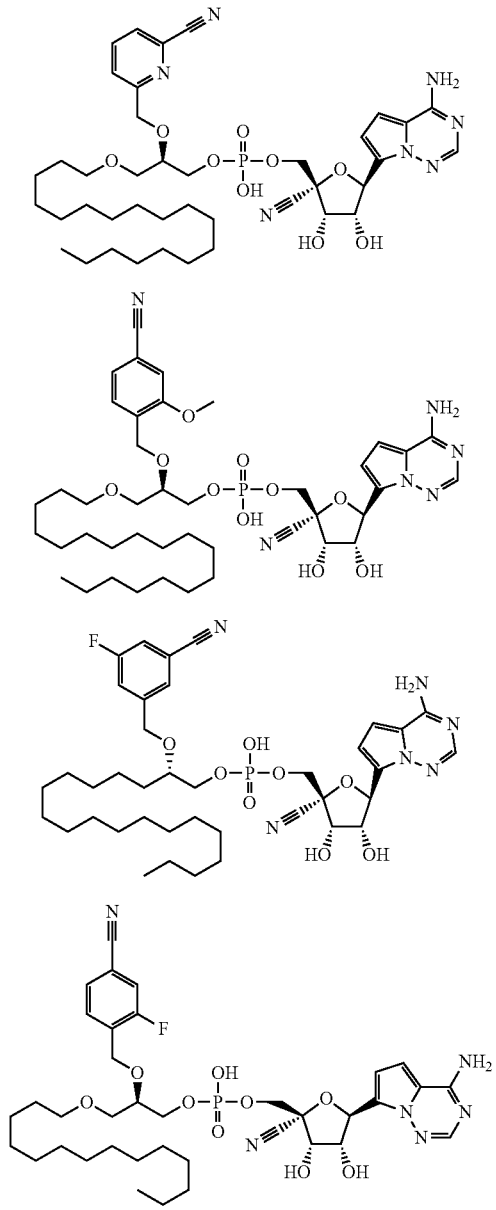
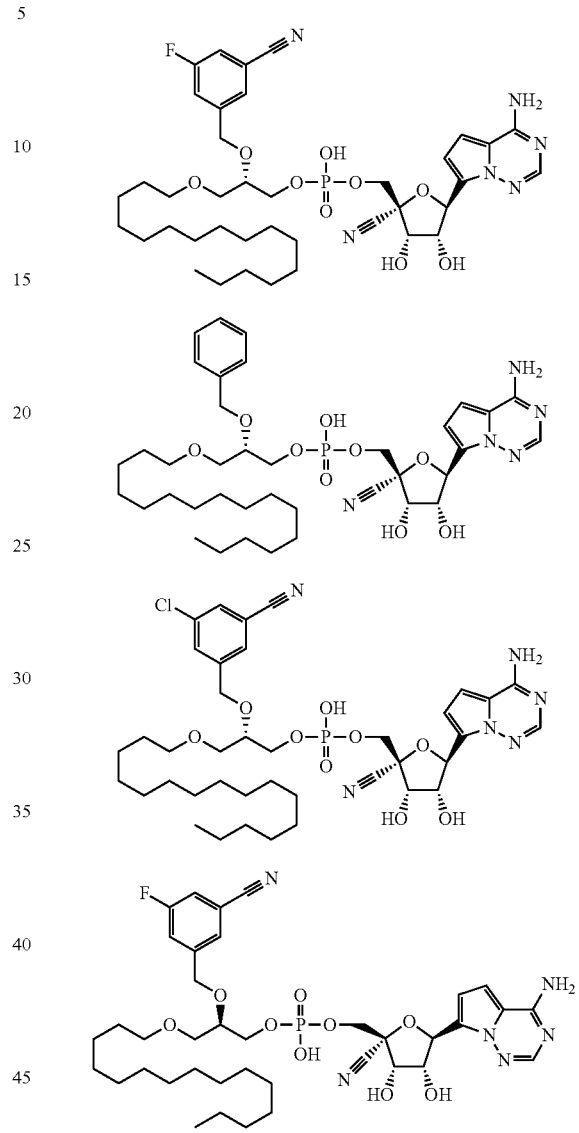
In some embodiments, the compound of Formula I has a Formula XIa:
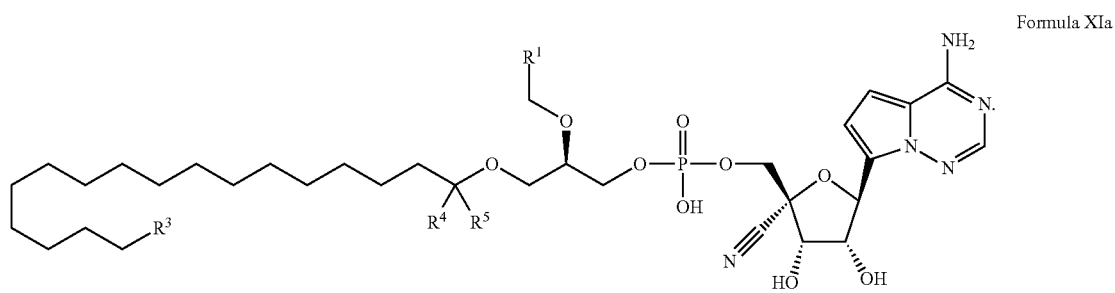
Formula XIa

525

The description of substituents of Formula I (e.g., $R^1$, $R^3$, $R^4$, and $R^5$) applies to Formula XIa.

In some embodiments, the compounds and pharmaceutically acceptable salts of Formula XIa include the compounds in Table 35 and the pharmaceutically acceptable salts thereof.

TABLE 35

Some Compounds of Formula XIa
Structure

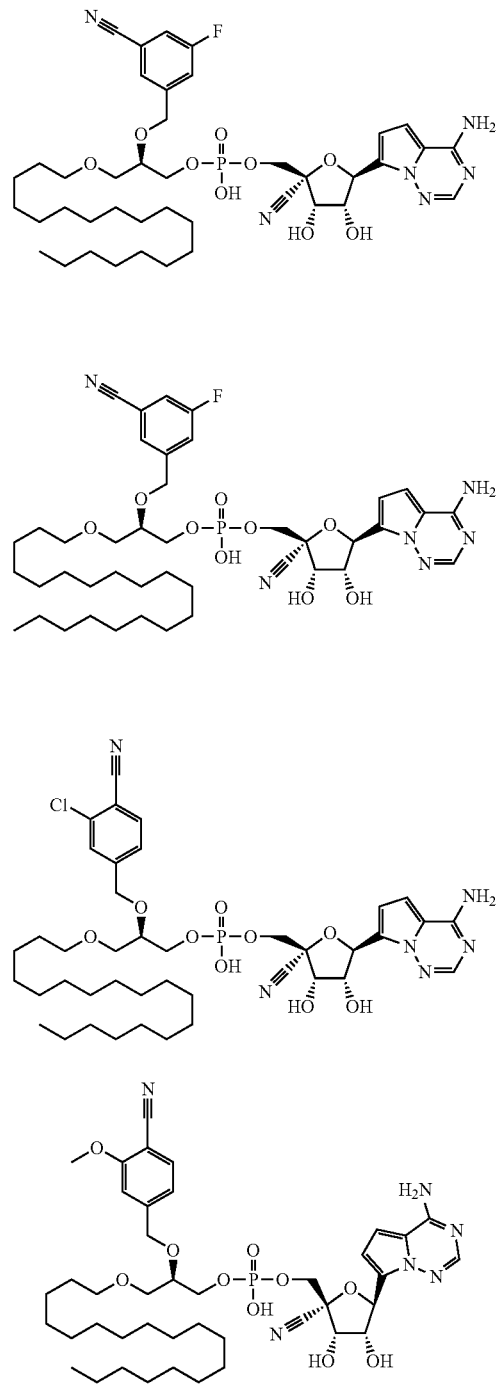

526

TABLE 35-continued

Some Compounds of Formula XIa
Structure

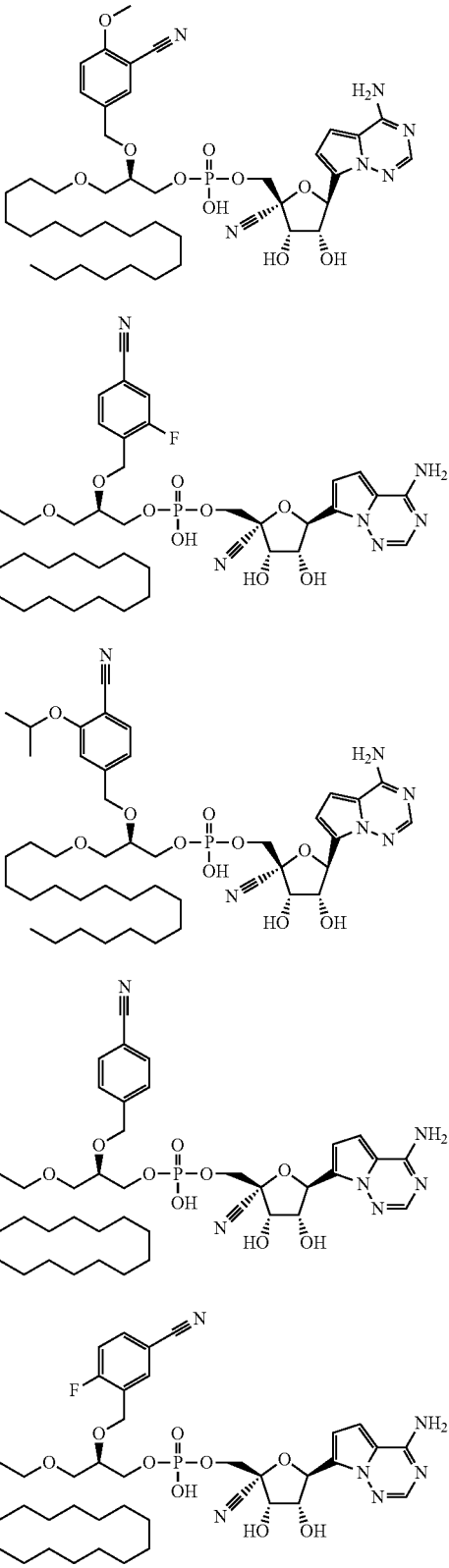

TABLE 35-continued
Some Compounds of Formula XIa
Structure
In some embodiments, the compound of Formula I has a Formula XIb:
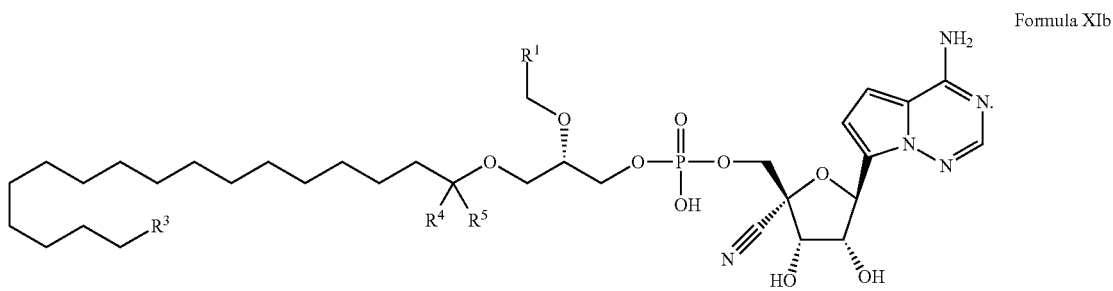
Formula XIb The description of substituents of Formula I (e.g., $R^1$, $R^3$, $R^4$, and $R^5$) applies to Formula XIb.

In some embodiments, the compounds and pharmaceutically acceptable salts of Formula XIb include the compounds in Table 36 and the pharmaceutically acceptable salts thereof.

TABLE 36

Compounds of Formula XIb
Structure

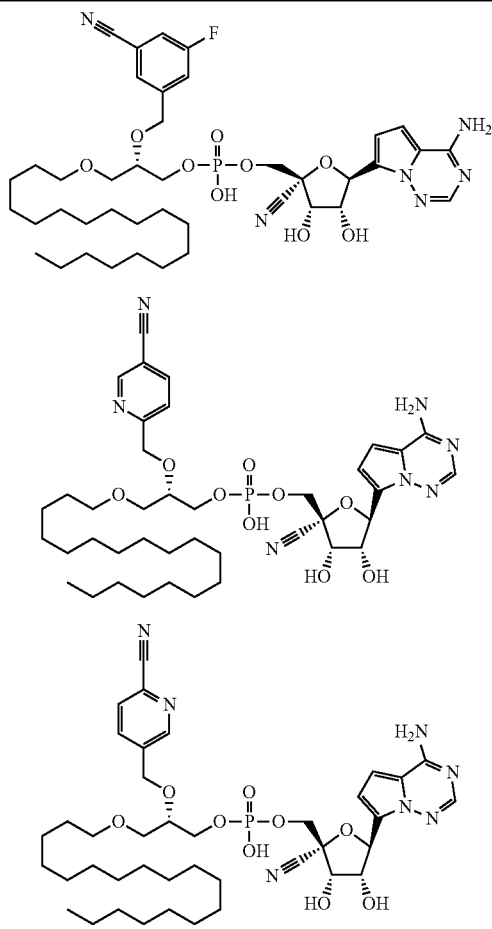

TABLE 36-continued

Compounds of Formula XIb
Structure

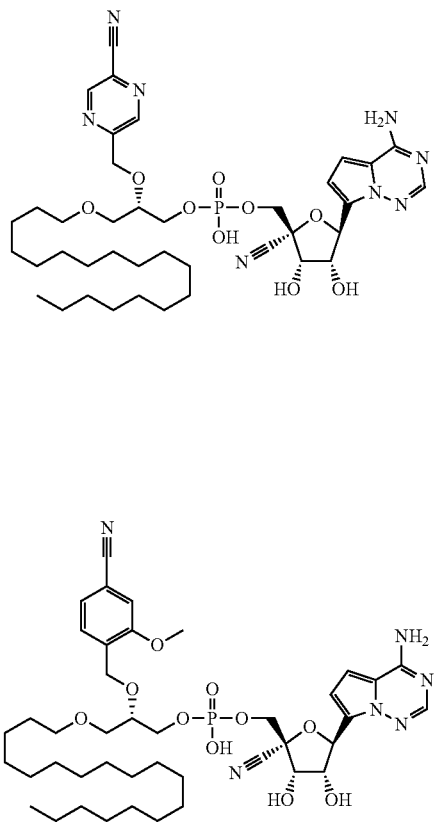

In some embodiments, the compound of Formula I has a Formula XII:

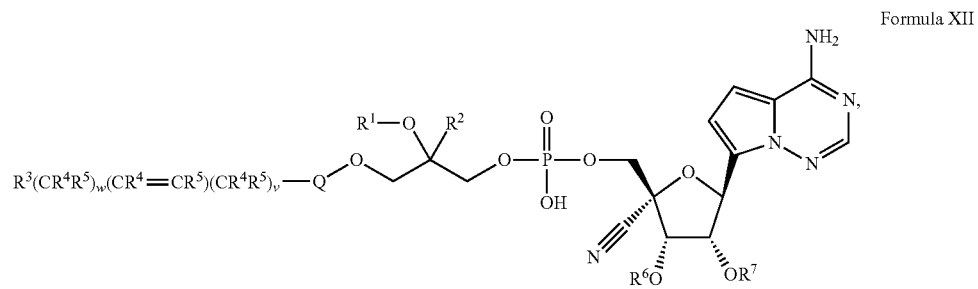

Formula XII wherein w+v is 9, 10, 11, 12, 13, 14, 15, 16, 17, 18, or 19.

The description of substituents of Formula I (e.g., $R^1$, $R^2$, $R^3$, $R^4$, $R^5$, $R^6$, $R^7$, Q, and L) applies to Formula XII.

In some embodiments, the compounds and pharmaceutically acceptable salts of Formula XII include the compounds in Table 37 and the pharmaceutically acceptable salts thereof.

TABLE 37

Some Compounds of Formula XII
Structure

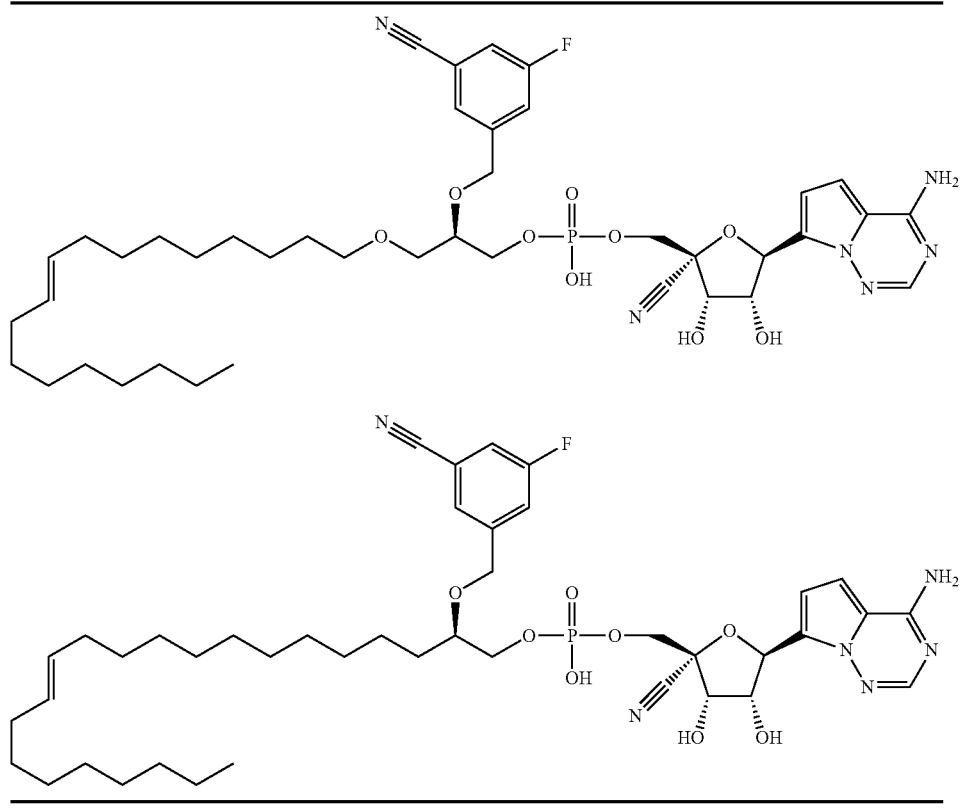

In some embodiments, the compound of Formula I has a Formula XIIa:

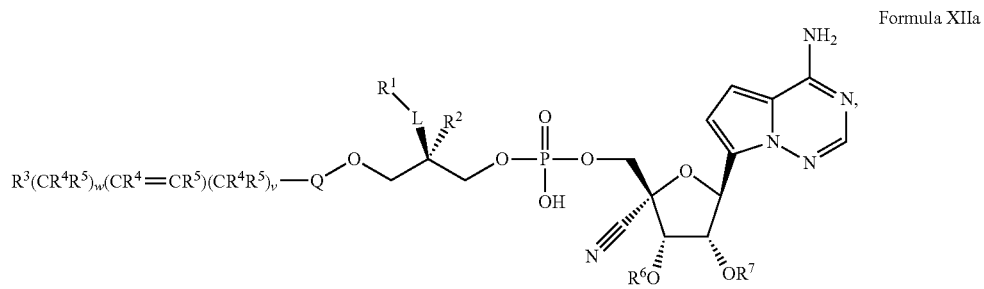

Formula XIIa wherein w+v is 9, 10, 11, 12, 13, 14, 15, 16, 17, 18, or 19.

The description of substituents of Formula I (e.g., $R^1$, $R^2$, $R^3$, $R^4$, $R^5$, $R^6$, $R^7$, Q, and L) applies to Formula XIIa.

In some embodiments, the compounds and pharmaceutically acceptable salts of Formula XIIa include the compounds in Table 37, above, and the pharmaceutically acceptable salts thereof.

In some embodiments, the compound of Formula I has a Formula XIIb:

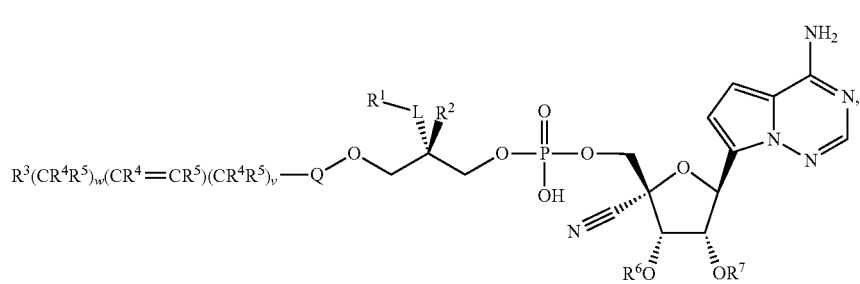

Formula XIIb wherein w+v is 9, 10, 11, 12, 13, 14, 15, 16, 17, 18, or 19.

The description of substituents of Formula I (e.g., $R^1$, $R^2$, $R^3$, $R^4$, $R^5$, $R^6$, $R^7$, Q, and L) applies to Formula XIIb.

In some embodiments, the compound of Formula I has a Formula XIII.

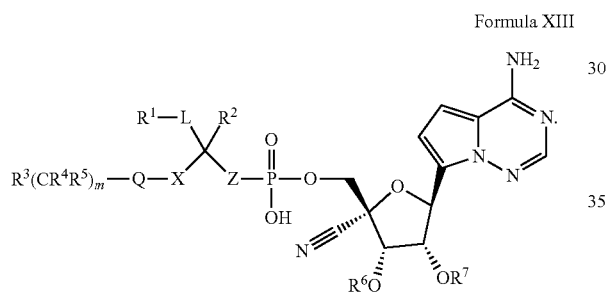

Formula XIII

The description of substituents of Formula I (e.g., $R^1$, $R^2$, $R^3$, $R^4$, $R^5$, $R^6$, $R^7$, Q, X, Z, L, and m) applies to Formula XIII In some embodiments, the compounds and pharmaceutically acceptable salts of Formula XIII include the compounds in Table 38 and the pharmaceutically acceptable salts thereof.

TABLE 38

Some Compounds of Formula XIII
Structure

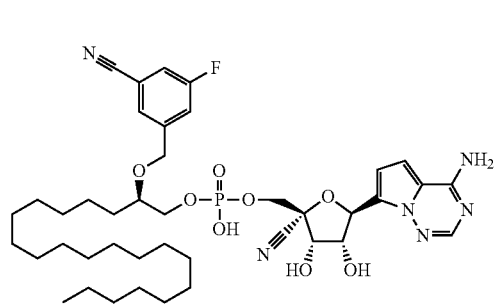

TABLE 38-continued

Some Compounds of Formula XIII
Structure

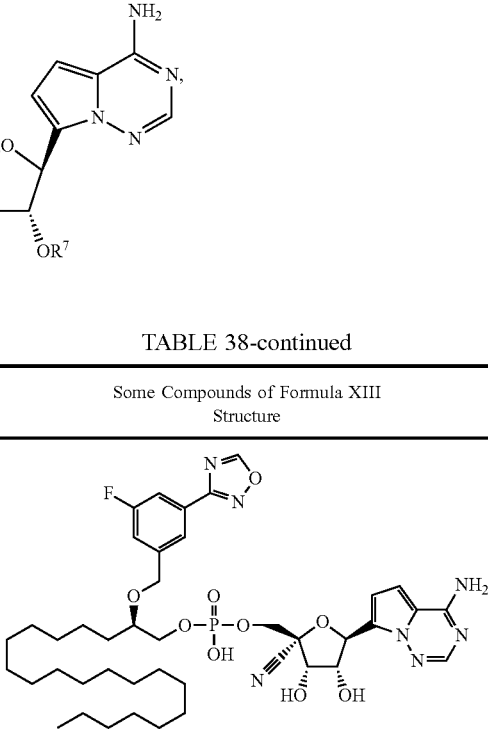

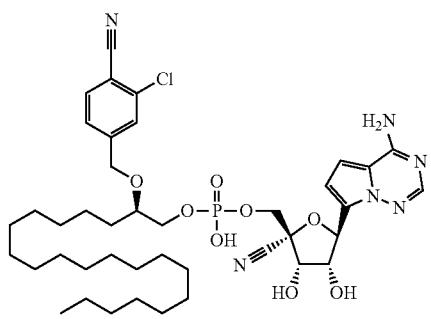

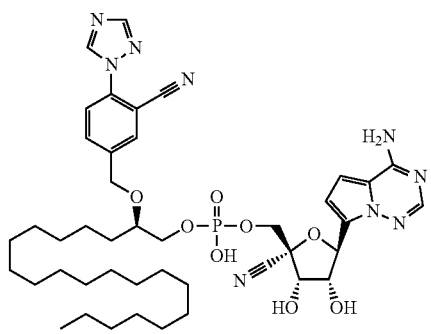

TABLE 38-continued
Some Compounds of Formula XIII
Structure
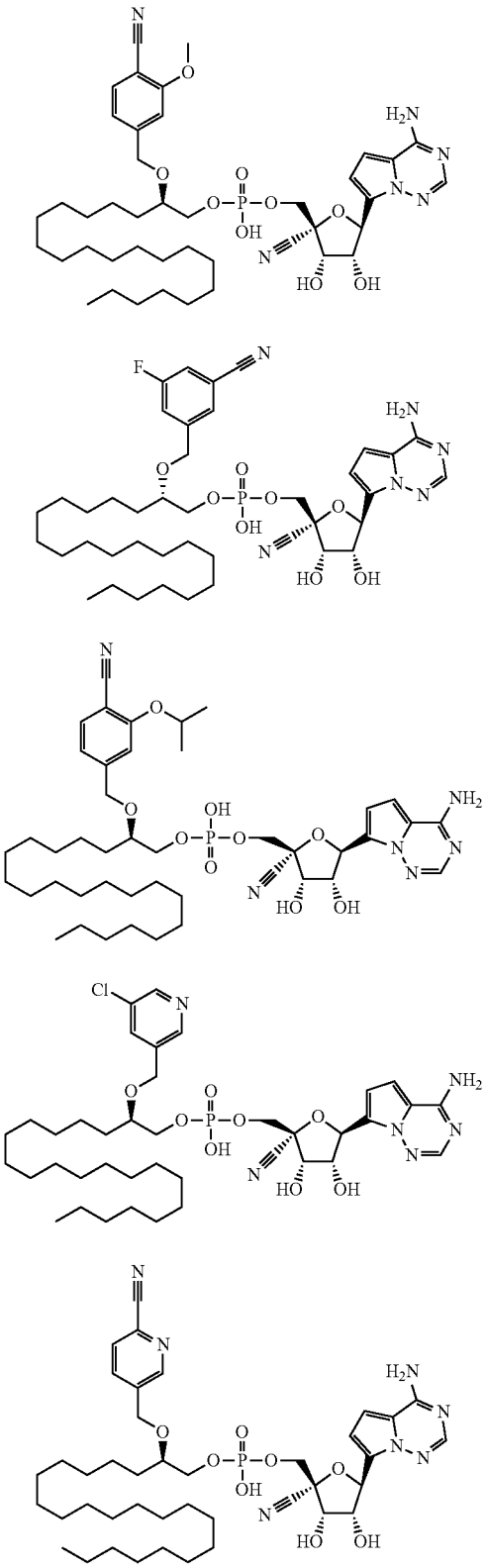
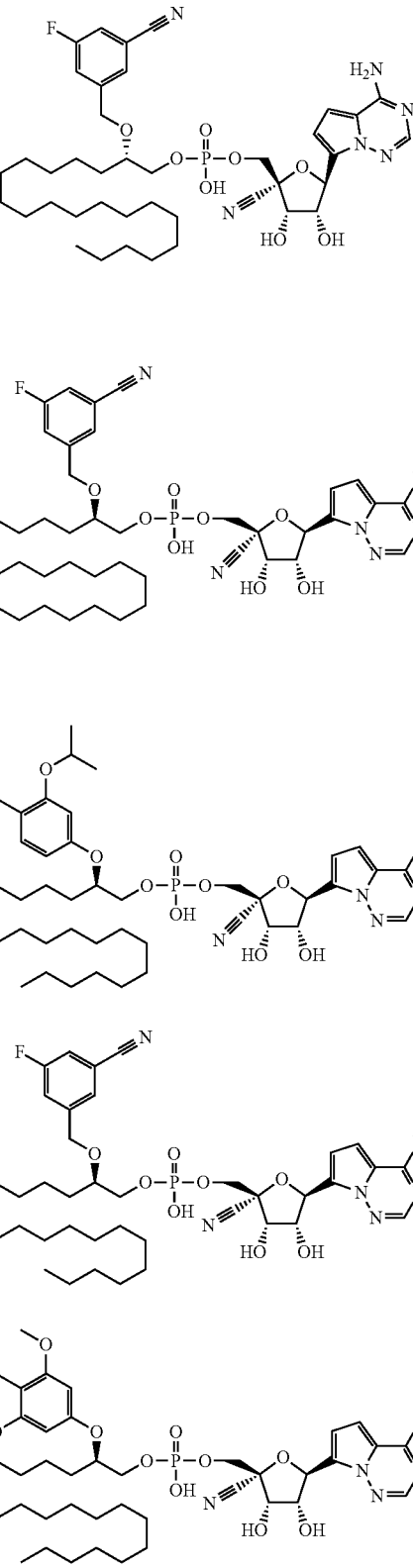

TABLE 38-continued

Some Compounds of Formula XIII

Structure

TABLE 38-continued
Some Compounds of Formula XIII
Structure
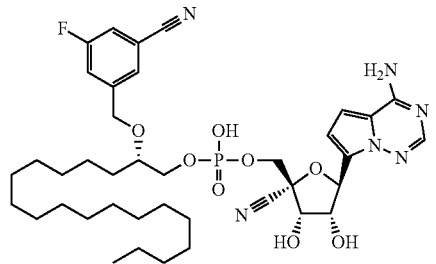 [SMILES: CCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
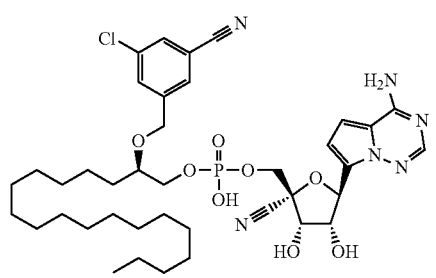 [SMILES: CCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
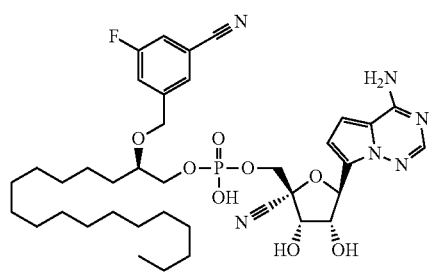 [SMILES: CCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
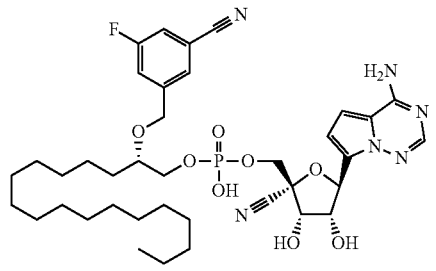 [SMILES: CCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]
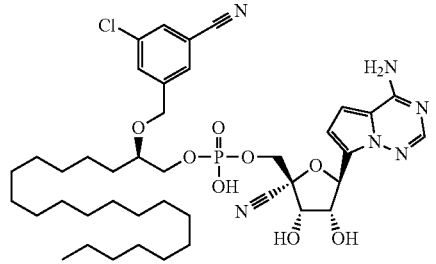 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
TABLE 38-continued
Some Compounds of Formula XIII
Structure
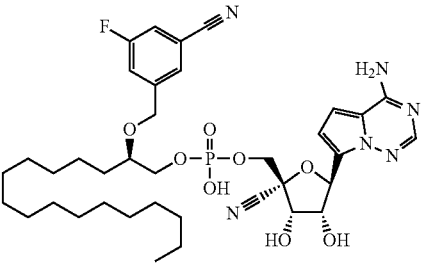
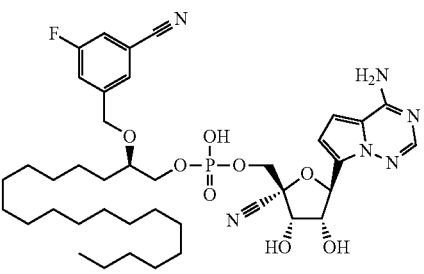 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
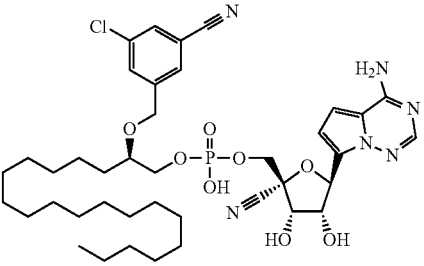 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]
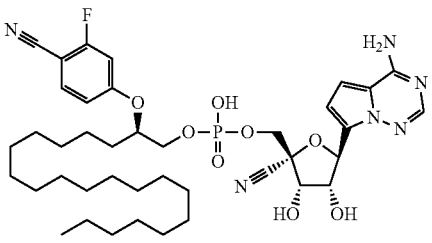 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(F)c1]
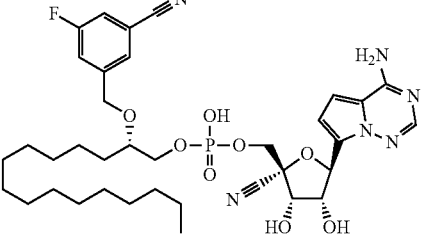
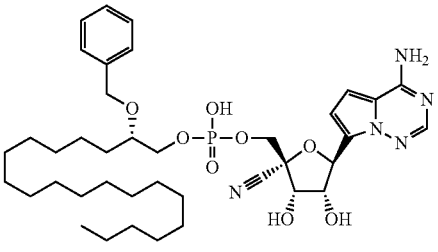

TABLE 38-continued

Some Compounds of Formula XIII
Structure

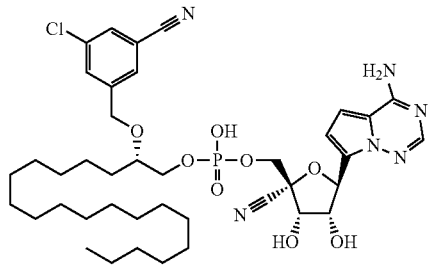 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(Cl)cc(C#N)c1]

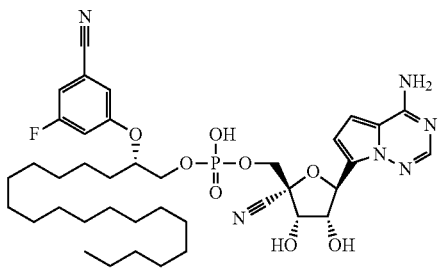 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)Oc1cc(F)cc(C#N)c1]

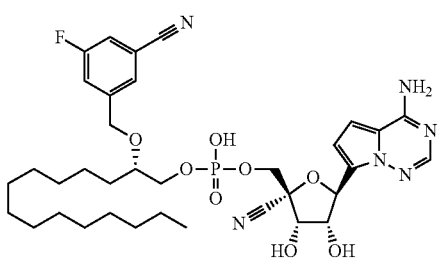 [SMILES: CCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

In some embodiments, the compound of Formula I has a Formula XIIIa:

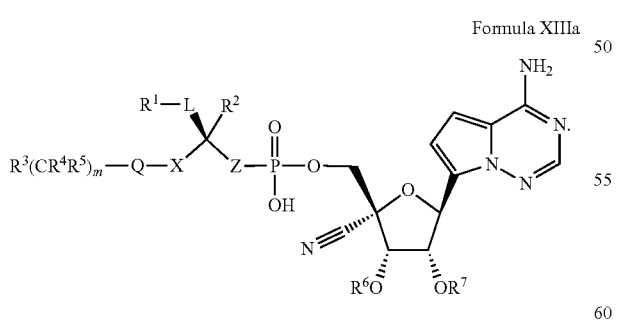

Formula XIIIa

The description of substituents of Formula I (e.g., $R^1$, $R^2$, $R^3$, $R^4$, $R^5$, $R^6$, $R^7$, Q, X, Z, L, and m) applies to Formula XIIIa. In some embodiments, the compounds and pharmaceutically acceptable salts of Formula XIIIa include the compounds in Table 39 and the pharmaceutically acceptable salts thereof.

TABLE 39

Some Compound of Formula XIIIa
Structure

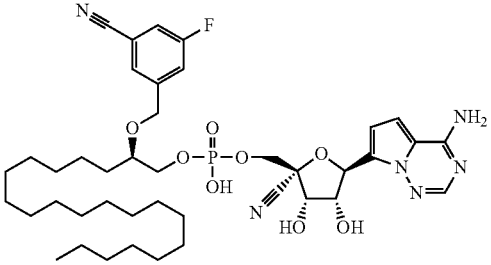 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]

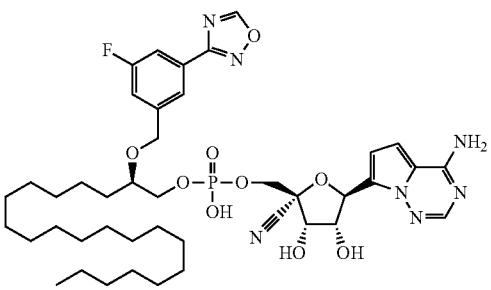 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(-c2ncon2)c1]

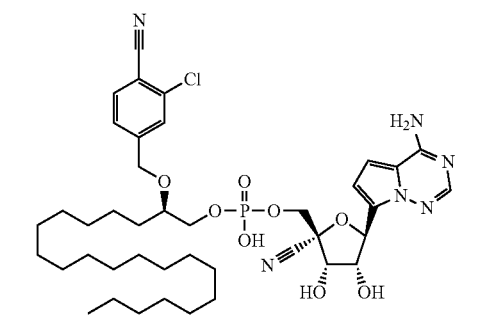

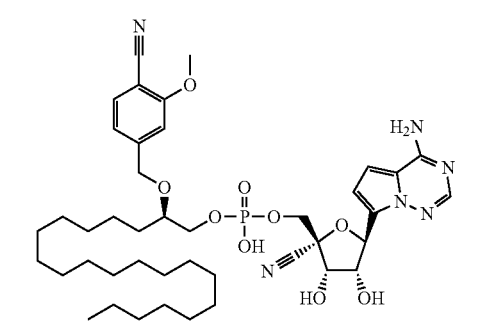 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC)c1]

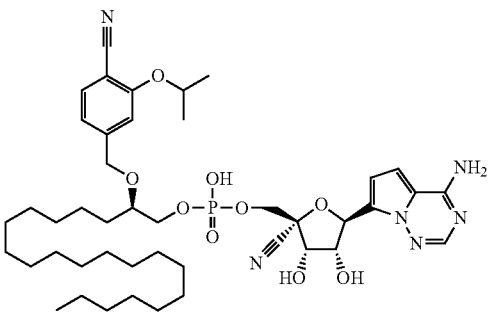 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)c(OC(C)C)c1]

TABLE 39-continued
Some Compound of Formula XIIIa
Structure
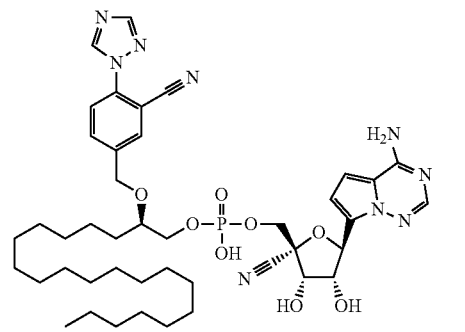 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(-n2cncn2)c(C#N)c1]
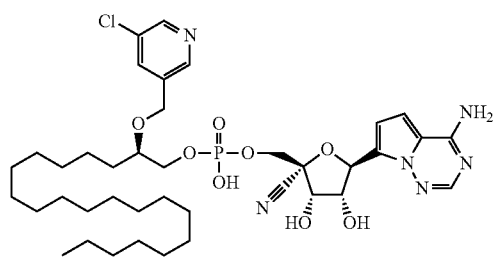 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cncc(Cl)c1]
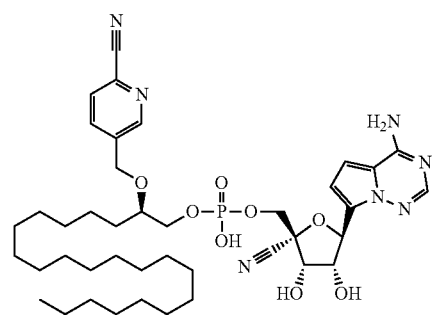 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1ccc(C#N)nc1]
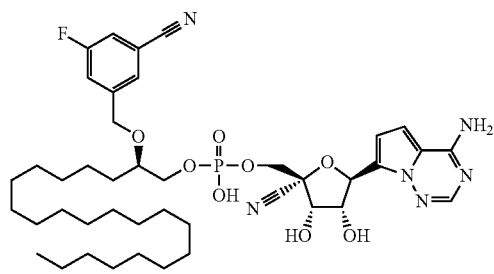 [SMILES: CCCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
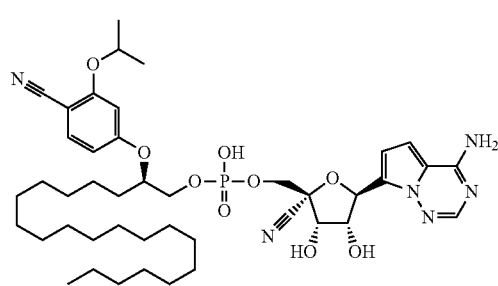 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1ccc(C#N)c(OC(C)C)c1]
TABLE 39-continued
Some Compound of Formula XIIIa
Structure
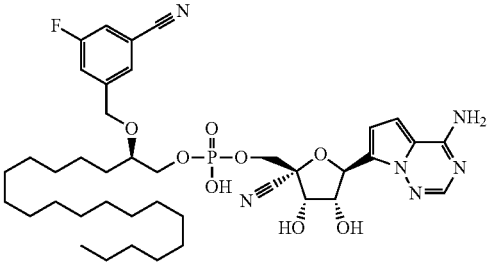
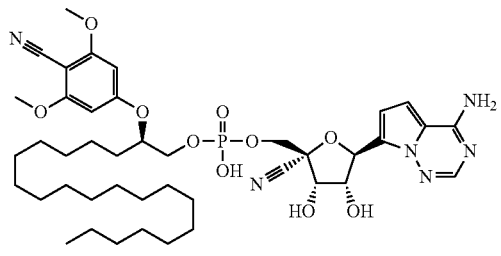 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)Oc1cc(OC)c(C#N)c(OC)c1]

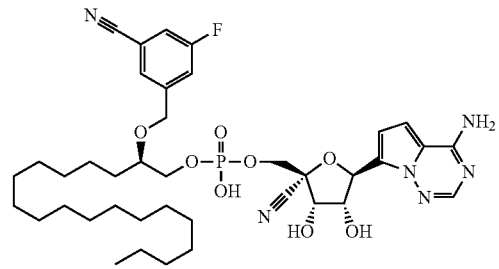 [SMILES: CCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]
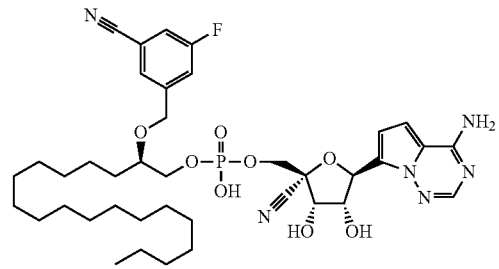 [SMILES: CCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]

TABLE 39-continued
Some Compound of Formula XIIIa
Structure
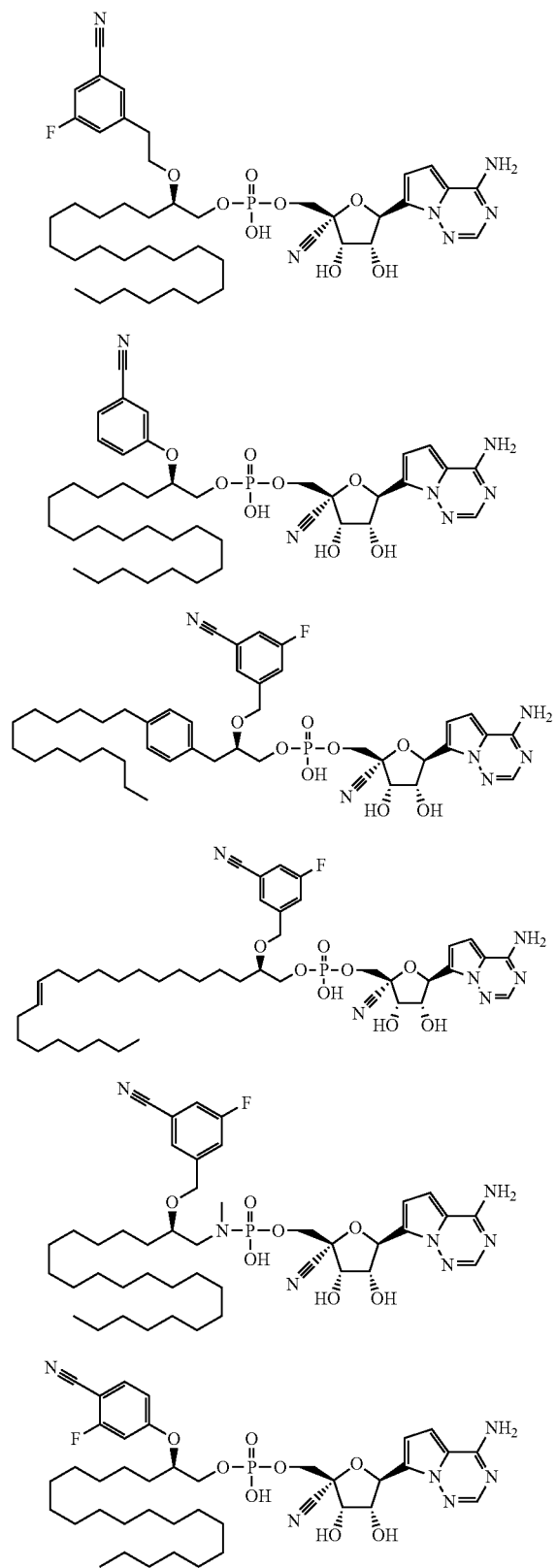
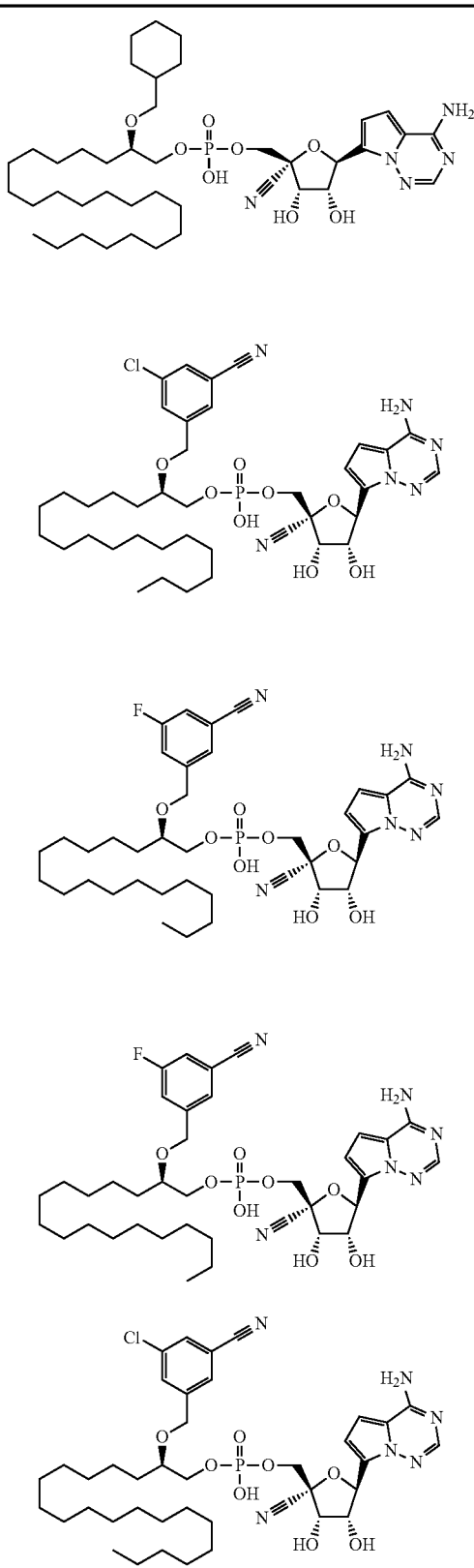

TABLE 39-continued

Some Compound of Formula XIIIa
Structure

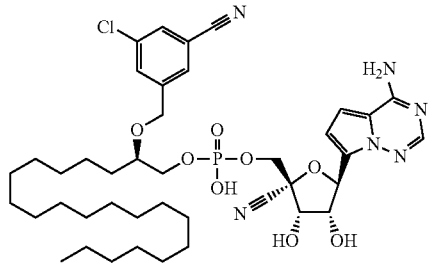 [SMILES: CCCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(Cl)cc(C#N)c1]

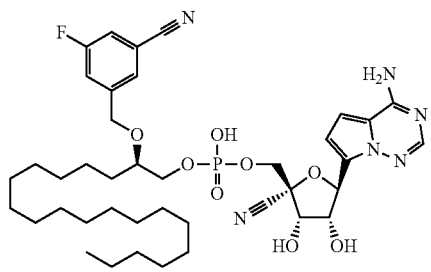 [SMILES: CCCCCCCCCCCCCCCCCC[C@H](COP(=O)(O)OC[C@@]1(C#N)O[C@@H](c2ccc3c(N)ncnn23)[C@H](O)[C@@H]1O)OCc1cc(F)cc(C#N)c1]

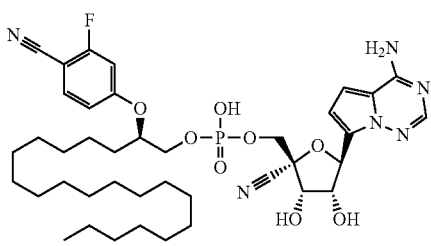

In some embodiments, the compound of Formula I has a Formula XIIIb

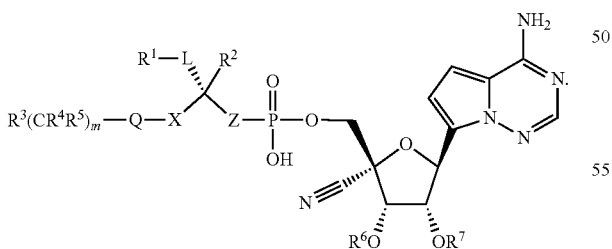

Formula XIIIb

The description of substituents of Formula I (e.g., $R^1$, $R^2$, $R^3$, $R^4$, $R^5$, $R^6$, $R^7$, Q, X, Z, L, and m) applies to Formula XIIIb.

In some embodiments, the compounds and pharmaceutically acceptable salts of Formula XIIIb include the compounds in Table 40 and the pharmaceutically acceptable salts thereof.

TABLE 40

Compound of Formula XIIIb
Structure

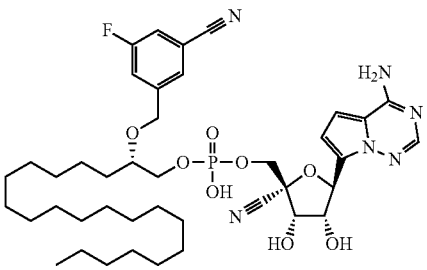 [SMILES: CCCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

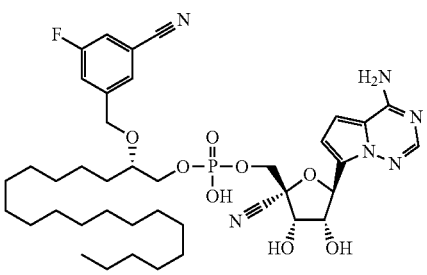 [SMILES: CCCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

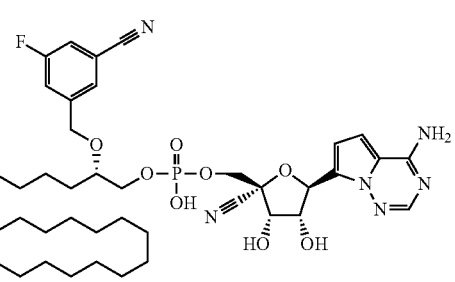

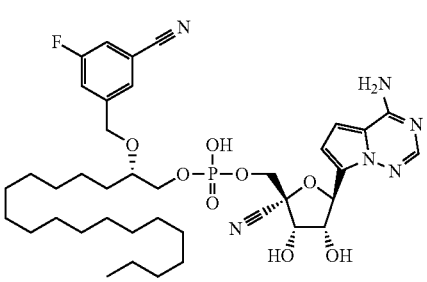 [SMILES: CCCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

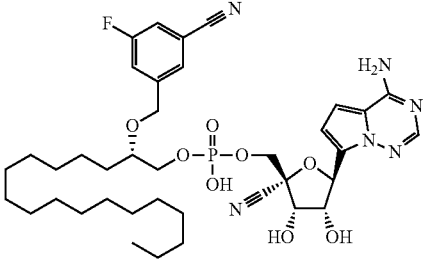 [SMILES: CCCCCCCCCCCCCCCC[C@@H](COP(=O)(O)OC[C@@]1(C#N)O[C@@H](c2ccc3c(N)ncnn23)[C@H](O)[C@@H]1O)OCc1cc(F)cc(C#N)c1]

TABLE 40-continued

Compound of Formula XIIIb
Structure

[Chemical structure diagrams]

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g., $^{14}$C or $^{3}$H) compound, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies. The conversion products, so long as they are not otherwise found in vivo, are useful in diagnostic assays for therapeutic dosing of the compounds even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

IV. Pharmaceutical Formulations

Also disclosed herein are pharmaceutical formulations comprising a pharmaceutically effective amount of a compound of the present disclosure (e.g., a compound of Formula I, Ia, Ib, II, III, IV, V, VI, VII, VIII, IX, X, XI, XIa, XIb, XII, XIII, XIIIa, or XIIIb), or a pharmaceutically acceptable salt thereof, and a pharmaceutically acceptable carrier or excipient. Also provided herein is a pharmaceutical formulation comprising a pharmaceutically effective amount of a compound of the present disclosure, or a pharmaceutically acceptable salt thereof, and a pharmaceutically acceptable carrier or excipient.

The compounds disclosed herein can be formulated with conventional carriers and excipients. Tablets can contain, for instance, excipients, glidants, fillers, binders, or a combination thereof. Aqueous formulations are prepared in sterile form, and when intended for delivery by other than oral administration generally will be isotonic. Exemplary excipients include, but are not limited to, those set forth in the "HANDBOOK OF PHARMACEUTICAL EXCIPIENTS" (1986). Excipients can include, for example, ascorbic acid and other antioxidants, chelating agents such as EDTA, carbohydrates such as dextran, hydroxyalkylcellulose, hydroxyalkylmethylcellulose, stearic acid, and combinations thereof. In some embodiments, the formulation is basic. In some embodiments, the formulation is acidic. In some embodiments, the formulation has a neutral pH. In some embodiments, the pH of the formulations is from 2 to 11 (e.g., 2, 3, 4, 5, 6, 7, 8, 9, 10, 11, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 7-8, 7-9, 7-10, 7-11, 8-9, 8-10, 8-11, 9-10, or 9-11).

In some embodiments, the compounds disclosed herein have pharmacokinetic properties (e.g., oral bioavailability)

suitable for oral administration of the compounds. Formulations suitable for oral administration can, for instance, be presented as discrete units such as capsules, cachets or tablets, each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient can also be administered, for instance, as a bolus, electuary, or paste.

A tablet can be made by compression or molding, optionally with one or more accessory ingredients. Compressed tablets can be prepared by compressing in a suitable machine the active ingredient in a free-flowing form such as, for instance, a powder or granules, optionally mixed with a binder, lubricant, inert diluent, preservative, surface active, dispersing agent, or a combination thereof. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

For infections of the eye or other external tissues (e.g., mouth and skin), the formulations can be applied as a topical ointment or cream containing the active ingredient(s) in an amount of, for example, 0.075 to 20% w/w (including active ingredient(s) in a range from 0.1% to 20% in increments of 0.1% w/w such as 0.6% w/w, 0.7% w/w, etc.), from 0.2% to 15% w/w, or from 0.5% to 10% w/w. When formulated in an ointment, the active ingredients can be employed in some embodiments with either a paraffinic or a water-miscible ointment base. Alternatively, the active ingredients can be formulated in a cream with an oil-in-water cream base.

In some embodiments, the aqueous phase of the cream base can include, for example, from 30% to 90% (e.g., 35%, 40%, 45%, 50%, 55%, 60%, 65%, 70%, 75%, 80%, 85%) w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. In some embodiments, the cream base can include, for instance, a compound that enhances absorption or penetration of the active ingredient through the skin or other affected areas. Examples of such dermal penetration enhancers include, but are not limited to, dimethyl sulfoxide and related analogs. In some embodiments, the cream or emulsion does not include water.

The oily phase of the emulsions can be constituted from known ingredients in a known manner. In some embodiments, the phase comprises merely an emulsifier (otherwise known as an emulgent). In some embodiments, the phase comprises a mixture of at least one emulsifier with a fat, an oil, or a combination thereof. In some embodiments, a hydrophilic emulsifier is included together with a lipophilic emulsifier that acts as a stabilizer. Together, the emulsifier(s) with or without stabilizer(s) can make up the so-called emulsifying wax, and the wax together with the oil and fat make up the so-called emulsifying ointment base that can form the oily dispersed phase of the cream formulations.

Emulgents and emulsion stabilizers suitable for use in the formulation can include, but are not limited to, TWEEN® 60, TWEEN® 80, SPAN® 80, cetostearyl alcohol, benzyl alcohol, myristyl alcohol, glyceryl mono-stearate, sodium lauryl sulfate, and combinations thereof.

The choice of suitable oils or fats for the formulation can be based on achieving the desired cosmetic properties. In some embodiments, the cream can be a non-greasy, non-staining, and washable product with suitable consistency to avoid leakage from tubes or other containers. In some embodiments, esters can be included, such as, for example, straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate, a blend of branched chain esters known as CRODAMOL® CAP, or a combination thereof. In some embodiments, high melting point lipids such as white soft paraffin and/or liquid paraffin or other mineral oils can be included.

In some embodiments, the compounds disclosed herein are administered alone. In some embodiments, the compounds disclosed herein are administered in pharmaceutical formulations. In some embodiments, the pharmaceutical formulations are for veterinary use. In some embodiments, the pharmaceutical formulations are for human use. In some embodiments, the pharmaceutical formulations disclosed herein include at least one additional therapeutic agent.

Pharmaceutical formulations disclosed herein can be in any form suitable for the intended method of administration. The pharmaceutical formulations disclosed herein can be presented in unit dosage form and can be prepared by any of the methods well known in the art of pharmacy. Exemplary techniques and formulations can be found, for instance, in REMINGTON'S PHARMACEUTICAL SCIENCES (Mack Publishing Co., Easton, PA). Such methods can include the step of bringing into association a compound disclosed herein with the carrier that constitutes one or more accessory ingredients. In general, the formulations can be prepared by uniformly and intimately bringing into association the active ingredient with liquid carriers or finely divided solid carriers or both, and then, if necessary, shaping the product.

When used for oral use for example, tablets, troches, lozenges, aqueous or oil suspensions, dispersible powders or granules, emulsions, hard or soft capsules, solutions, syrups or elixirs can be prepared. Formulations intended for oral use can be prepared according to any method known to the art for the manufacture of pharmaceutical formulations and such formulations can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl mono stearate or glyceryl distearate alone or with a wax can be employed.

Formulations for oral use can be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin, or olive oil.

Aqueous suspensions can contain the active materials in admixture with excipients suitable for the manufacture of aqueous suspensions. Such excipients can include, for instance, a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain, for example, one or more preservatives such as ethyl or n-propyl p-hydroxy-benzoate, one or more coloring agents, one or more flavoring agents, one or more sweetening agents (such as sucrose or saccharin), or combinations thereof. Further non-limiting examples of suspending agents include cyclodextrin. In some embodiments, the suspending agent is sulfobutyl ether beta-cyclodextrin (SEB-beta-CD), for example CAPTISOL®.

Oil suspensions can be formulated by suspending the active ingredient in a vegetable oil (e.g., arachis oil, olive oil, sesame oil, coconut oil, or a combination thereof), a mineral oil such as liquid paraffin, or a combination thereof. The oral suspensions can contain, for instance, a thickening agent, such as beeswax, hard paraffin, cetyl alcohol, or a combination thereof. In some embodiments, sweetening agents, such as those set forth above, and/or flavoring agents, are added to provide a palatable oral preparation. In some embodiments, the formulations disclosed herein are preserved by the addition of an antioxidant such as ascorbic acid.

Dispersible powders and granules suitable for preparation of an aqueous suspension by the addition of water can provide the active ingredient in admixture with a dispersing or wetting agent, a suspending agent, a preservative, and combinations thereof. Suitable dispersing or wetting agents and suspending agents are exemplified by those disclosed above. Additional excipients, for example sweetening, flavoring and coloring agents, can also be present.

The pharmaceutical formulations can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion can also contain sweetening and flavoring agents. Syrups and elixirs can be formulated with sweetening agents, such as for instance, glycerol, sorbitol or sucrose. Such formulations can also contain, for instance, a demulcent, a preservative, a flavoring, a coloring agent, or a combination thereof.

The pharmaceutical formulations can be in the form of a sterile injectable or intravenous preparation, such as a sterile injectable aqueous or oleaginous suspension. This suspension can be formulated according to the known art using those suitable dispersing or wetting agents and suspending agents which have been mentioned above. The sterile injectable or intravenous preparation can also be a sterile injectable solution or suspension in a non-toxic parenterally acceptable diluent or solvent, such as a solution in 1,3-butane-diol or prepared as a lyophilized powder. Among the acceptable vehicles and solvents that can be employed are water, Ringer's solution and isotonic sodium chloride solution. In addition, sterile fixed oils can be employed as a solvent or suspending medium. For this purpose, any bland fixed oil can be employed including synthetic mono- or diglycerides. In addition, fatty acids such as oleic acid can likewise be used in the preparation of injectables. Among the acceptable vehicles and solvents that can be employed include, but are not limited to, water, Ringer's solution isotonic sodium chloride solution, and hypertonic sodium chloride solution.

The amount of active ingredient that can be combined with the carrier material to produce a single dosage form will vary depending upon the host treated and the particular mode of administration. For example, a time-release formulation intended for oral administration to humans can contain approximately 1 mg to 1000 mg of active material compounded with an appropriate and convenient amount of carrier material, which can vary from 5% to 95% of the total formulations (weight:weight). The pharmaceutical formulation can be prepared to provide easily measurable amounts for administration. For example, an aqueous solution intended for intravenous infusion can contain from 3 µg to 500 µg of the active ingredient per milliliter of solution in order that infusion of a suitable volume at a rate of 30 mL/hr can occur.

Formulations suitable for topical administration to the eye also include eye drops wherein the active ingredient is dissolved or suspended in a suitable carrier, especially an aqueous solvent for the active ingredient. In some embodiments, the compounds disclosed herein are included in the pharmaceutical formulations disclosed herein in a concentration of 0.5% to 20% (e.g., 0.5% to 10%, 1.5% w/w).

Formulations suitable for topical administration in the mouth include lozenges can comprise an active ingredient (i.e., a compound disclosed herein and/or additional therapeutic agents) in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for vaginal administration can be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions that can contain anti-oxidants, buffers, bacteriostats and solutes that render the formulation isotonic with the blood of the intended recipient; and aqueous and non-aqueous sterile suspensions that can include suspending agents and thickening agents.

The formulations can be presented in unit-dose or multi-dose containers, for example, sealed ampoules and vials, and can be stored in a freeze-dried (lyophilized) condition requiring only the addition of the sterile liquid carrier, for example water for injection, immediately before use. Extemporaneous injection solutions and suspensions are prepared from sterile powders, granules and tablets of the kind previously described. Preferred unit-dosage formulations are those containing a daily dose or unit daily sub-dose, as herein above recited, or an appropriate fraction thereof, of the active ingredient.

It should be understood that in addition to the ingredients particularly mentioned above the formulations can include other agents conventional in the art having regard to the type of formulation in question, for example those suitable for oral administration can include flavoring agents.

Further provided are veterinary formulations comprising a compound disclosed herein together with a veterinary carrier therefor.

Veterinary carriers are materials useful for the purpose of administering the formulation and can be solid, liquid or gaseous materials which are otherwise inert or acceptable in the veterinary art and are compatible with the active ingredient. These veterinary formulations can be administered orally, parenterally, or by any other desired route.

Compounds herein are used to provide controlled release pharmaceutical formulations containing as active ingredient one or more of the compounds ("controlled release formulations") in which the release of the active ingredient can be controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. In some embodiments, the from 0.0001 to 100 mg/kg body weight per day; for instance, from 0.01 to 10 mg/kg body weight per day; from 0.01 to 5 mg/kg body weight per day; from 0.05 to 0.5 mg/kg body weight per day. For example, the daily candidate dose for an adult human of approximately 70 kg body weight can range from 1 mg to 1000 mg (e.g., from 5 mg to 500 mg), and can take the form of single or multiple doses.

V. Kits

Also provided herein are kits that includes a compound disclosed herein or a pharmaceutically acceptable salt thereof. In some embodiments the kits described herein can comprise a label and/or instructions for use of the compound in the treatment of a disease or condition in a subject (e.g., human) in need thereof. In some embodiments, the disease or condition is viral infection.

In some embodiments, the kit can also comprise one or more additional therapeutic agents and/or instructions for use of additional therapeutic agents in combination with the compound disclosed herein in the treatment of the disease or condition in a subject (e.g., human) in need thereof.

In some embodiments, the kits provided herein comprise individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units can include pills, tablets, capsules, prefilled syringes or syringe cartridges, IV bags, inhalers, nebulizers etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit can contain a single dosage unit and in others multiple dosage units are present, such as the number of dosage units required for a specified regimen or period.

Also provided are articles of manufacture that include a compound disclosed herein, or a pharmaceutically acceptable salt, stereoisomer, mixture of stereoisomers or tautomer thereof; and a container. In some embodiments, the container of the article of manufacture is a vial, jar, ampoule, preloaded syringe, blister package, tin, can, bottle, box, an intravenous bag, an inhaler, or a nebulizer.

VI. Administration

One or more compounds of the disclosure are administered by any route appropriate to the condition to be treated. Suitable routes include oral, rectal, inhalation, pulmonary, topical (including buccal and sublingual), vaginal and parenteral (including subcutaneous, intramuscular, intravenous, intradermal, intrathecal and epidural), and the like. In some embodiments, the compounds disclosed herein are administered by inhalation or intravenously. It will be appreciated that the route can vary with for example the condition of the recipient.

In the methods of the present disclosure for the treatment of a viral infection, the compounds of the present disclosure can be administered at any time to a subject who can come into contact with the virus or is already suffering from the viral infection. In some embodiments, the compounds of the present disclosure can be administered prophylactically to subjects coming into contact with subjects suffering from the viral infection or at risk of coming into contact with humans suffering from the viral infection, e.g., healthcare providers. In some embodiments, administration of the compounds of the present disclosure can be to subjects testing positive for the viral infection but not yet showing symptoms of the viral infection. In the methods of the present disclosure for the treatment of a viral infection, the compounds of the present disclosure can be administered at any time to a human who can come into contact with the virus or is already suffering from the viral infection. In some embodiments, the compounds of the present disclosure can be administered prophylactically to humans coming into contact with humans suffering from the viral infection or at risk of coming into contact with humans suffering from the viral infection, e.g., healthcare providers. In some embodiments, administration of the compounds of the present disclosure can be to humans testing positive for the viral infection but not yet showing symptoms of the viral infection. In some embodiments, administration of the compounds of the present disclosure can be to humans upon commencement of symptoms of the viral infection.

In some embodiments, the methods disclosed herein comprise event driven administration of the compound disclosed herein, or a pharmaceutically acceptable salt thereof, to the subject.

As used herein, the terms "event driven" or "event driven administration" refer to administration of the compound of any one of Formulas I-XIIIb, or a pharmaceutically acceptable salt thereof, (1) before an event (e.g., 2 hours, 1 day, 2 days, 5 day, or 7 or more days before the event) that would expose the subject to the virus (or that would otherwise increase the subject's risk of acquiring the viral infection); and/or (2) during an event (or more than one recurring event) that would expose the subject to the virus (or that would otherwise increase the subject's risk of acquiring the viral infection); and/or (3) after an event (or after the final event in a series of recurring events) that would expose the subject to the virus (or that would otherwise increase the subject's risk of acquiring the viral infection). In some embodiments, the event driven administration is performed pre-exposure of the subject to the virus. In some embodiments, the event driven administration is performed post-exposure of the subject to the virus. In some embodiments, the event driven administration is performed pre-exposure of the subject to the virus and post-exposure of the subject to the virus.

In certain embodiments, the methods disclosed herein involve administration prior to and/or after an event that would expose the subject (e.g., human) to the virus or that would otherwise increase the subject's (e.g., human's) risk of acquiring the viral infection, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP).

In some embodiments, a compound disclosed herein, or a pharmaceutically acceptable salt thereof, is administered before exposure of the subject to the virus.

In some embodiments, a compound disclosed herein, or a pharmaceutically acceptable salt thereof, is administered before and after exposure of the subject to the virus.

In some embodiments, a compound disclosed herein, or a pharmaceutically acceptable salt thereof, is administered after exposure of the subject to the virus.

An example of event driven dosing regimen includes administration of a compound disclosed herein, or a pharmaceutically acceptable salt thereof, within 24 to 2 hours before the virus, followed by administration of a compound disclosed herein, or a pharmaceutically acceptable salt, every 24 hours during the period of exposure, followed by a further administration of a compound disclosed herein, or a pharmaceutically acceptable salt thereof, after the last exposure, and one last administration of a compound disclosed herein, or a pharmaceutically acceptable salt thereof, 24 hours later.

A further example of an event driven dosing regimen includes administration of the compound of any one of Formulas I-XIIIb, or a pharmaceutically acceptable salt thereof, within 24 hours before the viral exposure, then daily administration during the period of exposure, followed by a last administration approximately 24 hours later after the last exposure (which can be an increased dose, such as a double dose).

Effective dose of active ingredient depends at least on the nature of the condition being treated, toxicity, whether the compound is being used prophylactically or against an active viral infection, the method of delivery, and the pharmaceutical formulation, and will be determined by the clinician using conventional dose escalation studies. It can be expected to be from 0.0001 mg/kg to 100 mg/kg body weight per day (e.g., from 0.01 mg/kg to 10 mg/kg body weight per day; from 0.01 mg/kg to 5 mg/kg body weight per day; from 0.05 mg/kg to 0.5 mg/kg body weight per day). In some embodiments, the daily candidate dose for an adult human of approximately 70 kg body weight is from 1 mg to 2000 mg (e.g., 5 mg to 500 mg, 500 mg to 1000 mg, 1000 mg to 1500 mg, 1500 mg to 2000 mg) and can take the form of single or multiple doses (e.g., 2 doses per day, 3 doses per day). For example, the daily candidate dose for an adult human of approximately 70 kg body weight can range from 1 mg to 1000 mg (e.g., from 5 mg to 500 mg) and can take the form of single or multiple doses.

Any suitable period of time for administration of the compounds of the present disclosure is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 1, 2, 3, 4, 5, 6, 7, 8, 9, 10, 11, 12, 13, 14, or 15 weeks. Longer periods of administration are also contemplated.

In some embodiments, the compounds disclosed herein are administered once daily. In some embodiments, the compounds disclosed herein are administered twice daily. In some embodiments, the compounds disclosed herein are administered once every alternate day. In some embodiments, the compounds disclosed herein are administered once a week. In some embodiments, the compounds disclosed herein are administered twice a week.

In some embodiments, one or more compounds disclosed herein are administered once daily. The once daily dose can be administered for as long as required, for example for up to 5 days, up to 7 days, up to 10 days, up to 15 days, up to 20 days, up to 25 days, up to a month or longer. In some embodiments, the once daily dose is administered for up to 20 days, up to 15 days, up to 14 days, up to 13 days, up to 12 days, up to 10 days, up to 8 days, up to 6 days, up to 4 days, up to 3 days, up to 2 days, or for one day.

In some embodiments, the one or more compounds disclosed herein are dosed once daily, for 6 to 12 days, for example for 8-10 days. In some embodiments, the one or more compounds are administered once daily for 9 days. In some embodiments, the one or more compounds are administered once daily for 10 days. In some embodiments 50-150 mg of one or more compounds disclosed herein is administered once daily for 5 to 12 days, for e.g., for 5 days, 6 days, 7 days, 8 days, 9 days, 10 days, 11 days, or 12 days. In some embodiments 100 mg of one or more compounds disclosed herein is administered once daily for 5 to 12 days, for e.g., for 5 days, 6 days, 7 days, 8 days, 9 days, 10 days, 11 days, or 12 days. In some embodiments 500-2000 mg (e.g., 500-1000 mg, 1000-1500 mg) of one or more compounds disclosed herein is administered once daily for 5 to 12 days, for e.g., for 5 days, 6 days, 7 days, 8 days, 9 days, 10 days, 11 days, or 12 days.

In some embodiments, one or more compounds disclosed herein are administered twice daily. The twice daily dose can be administered for as long as required, for example for up to 5 days, up to 7 days, up to 10 days, up to 15 days, up to 20 days, up to 25 days, up to a month or longer. In some embodiments, the twice daily dose is administered for up to 20 days, up to 15 days, up to 14 days, up to 13 days, up to 12 days, up to 10 days, up to 8 days, up to 6 days, up to 4 days, up to 3 days, up to 2 days, or for one day.

In some embodiments, the one or more compounds disclosed herein are dosed twice daily, for 6 to 12 days, for example for 8-10 days. In some embodiments, the one or more compounds are administered twice daily for 9 days. In some embodiments, the one or more compounds are administered twice daily for 10 days. In some embodiments 1-1000 mg of one or more compounds disclosed herein is administered twice daily for 5 to 12 days, for e.g., for 5 days, 6 days, 7 days, 8 days, 9 days, 10 days, 11 days, or 12 days. In some embodiments 500-1500 mg (e.g., 500-1000 mg, 1000-1500 mg) of one or more compounds disclosed herein is administered twice daily for 5 to 12 days, for e.g., for 5 days, 6 days, 7 days, 8 days, 9 days, 10 days, 11 days, or 12 days.

VII. Methods of Use

The present disclosure also provides a method of treating or preventing a viral infection in a subject (e.g., human) in need thereof, the method comprising administering to the subject a compound described herein.

In some embodiments, the present disclosure provides a method of treating a viral infection in a subject (e.g., human)

in need thereof, the method comprising administering to a subject in need thereof a compound described herein.

In some embodiments, the present disclosure provides for methods of treating or preventing a viral infection in a subject (e.g., human) in need thereof, the method comprising administering to the subject a compound disclosed herein and at least one additional active therapeutic or prophylactic agent.

In some embodiments, the present disclosure provides for methods of treating a viral infection in a subject (e.g., human) in need thereof, the method comprising administering to the subject a compound disclosed herein, and at least one additional active therapeutic agent.

In some embodiments, the present disclosure provides for methods of inhibiting a viral polymerase in a cell, the methods comprising contacting the cell infected a virus with a compound disclosed herein, whereby the viral polymerase is inhibited.

In some embodiments, the present disclosure provides for methods of inhibiting a viral polymerase in a cell, the methods comprising contacting the cell infected a virus with a compound disclosed herein, and at least one additional active therapeutic agent, whereby the viral polymerase is inhibited.

Also provided here are the uses of the compounds disclosed herein for use in treating or preventing a viral infection in a subject in need thereof. For example, provided herein are uses of the compounds disclosed herein for use in treating a viral infection in a subject in need thereof.

A. Paramyxoviridae

In some embodiments, the viral infection is a Paramyxoviridae virus infection. As such, in some embodiments, the present disclosure provides methods for treating a Paramyxoviridae infection in a subject (e.g., a human) in need thereof, the method comprising administering to the subject a compound disclosed herein. In some embodiments, the Paramyxoviridae virus includes a BSL4 pathogen. Paramyxoviridae viruses include, but are not limited to, Nipah virus, Hendra virus, measles, mumps, and parainfluenza virus.

In some embodiments, the present disclosure provides a method for manufacturing a medicament for treating a Paramyxoviridae virus infection in a subject (e.g., human) in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a subject (e.g., human) of Paramyxoviridae virus infection.

In some embodiments, the present disclosure provides a compound of the present disclosure, or a pharmaceutically acceptable salt thereof, for use in the treatment of a Paramyxoviridae virus infection in a subject (e.g., human) in need thereof.

B. Pneumoviridae

In some embodiments, the viral infection is a Pneumoviridae virus infection. In some embodiments, the present disclosure provides a method of treating a Pneumoviridae virus infection in a subject (e.g., human) in need thereof, the method comprising administering to the human a therapeutically effective amount of a compound of the present disclosure, or a pharmaceutically acceptable salt thereof. Pneumoviridae viruses include, but are not limited to, respiratory syncytial virus (RSV) and human metapneumovirus. In some embodiments, the Pneumoviridae virus infection is a respiratory syncytial virus (RSV) infection. In some embodiments, the Pneumoviridae virus infection is human metapneumovirus infection.

In some embodiments, the present disclosure provides a method for manufacturing a medicament for treating a Pneumoviridae virus infection in a subject (e.g., human) in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a subject (e.g., human) of a Pneumoviridae virus infection. In some embodiments, the Pneumoviridae virus infection is a respiratory syncytial virus infection. In some embodiments, the Pneumoviridae virus infection is human metapneumovirus infection.

In some embodiments, the present disclosure provides a method for manufacturing a medicament for treating a Pneumoviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Pneumoviridae virus infection. In some embodiments, the Pneumoviridae virus infection is a respiratory syncytial virus infection. In some embodiments, the Pneumoviridae virus infection is human metapneumovirus infection.

In some embodiments, the present disclosure provides a compound of the present disclosure, or a pharmaceutically acceptable salt thereof, for use in the treatment of a Pneumoviridae virus infection in a human in need thereof. In some embodiments, the Pneumoviridae virus infection is a respiratory syncytial virus (RSV) infection. In some embodiments, the Pneumoviridae virus infection is human metapneumovirus infection.

In certain embodiments, the present disclosure provides methods for treating an RSV infection, comprising administering to a subject (e.g., a human) infected with respiratory syncytial virus a therapeutically effective amount a compound of the present disclosure or a pharmaceutically acceptable salt thereof. In some embodiments, the human is suffering from a chronic respiratory syncytial viral infection. In some embodiments, the human is acutely infected with RSV.

In certain embodiments, a method of inhibiting RSV replication is provided, comprising administering a compound of the present disclosure, or a pharmaceutically acceptable salt thereof, to a subject (e.g., a human).

In certain embodiments, the present disclosure provides a method for reducing the viral load associated with RSV infection, wherein the method comprises administering to a subject (e.g., a human) infected with RSV a therapeutically effective amount of a compound of the present disclosure, or a pharmaceutically acceptable salt thereof, wherein the therapeutically effective amount is sufficient to reduce the RSV viral load in the subject.

As described more fully herein, compounds of the present disclosure can be administered with one or more additional therapeutic agent(s) to a subject (e.g., a human) infected with RSV. The additional therapeutic agent(s) can be administered to the infected subject (e.g., a human) at the same time as a compound of the present disclosure or before or after administration of a compound of the present disclosure.

In certain embodiments, a compound of the present disclosure, or a pharmaceutically acceptable salt thereof, for use in treating or preventing an RSV infection is provided. In certain embodiments, a compound of the present disclosure (e.g., a compound of Formula I through Formula XIIIb), or a pharmaceutically acceptable salt thereof, for the manufacture of a medicament for treating or preventing an RSV infection is provided.

In some embodiments, a method of inhibiting RSV replication is provided, wherein the method comprises administering to a subject (e.g., human) in need thereof, a compound disclosed herein, wherein the administration is by inhalation.

In some embodiments, the present disclosure provides a method for reducing the viral load associated with RSV infection, wherein the method comprises administering to a human infected with RSV a compound disclosed herein.

C. Picornaviridae

In some embodiments, the viral infection is a Picornaviridae virus infection. In some embodiments, the present disclosure provides a method of treating a Picornaviridae virus infection in a human in need thereof, the method comprising administering to the subject (e.g., human) a therapeutically effective amount of a compound of the present disclosure, or a pharmaceutically acceptable salt thereof. Picornaviridae viruses are enteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection. In some embodiments, the Picornaviridae virus infection is enterovirus infection. In some embodiments, the Picornaviridae virus infection is selected from the group consisting of Coxsackie A virus infection, Coxsackie A virus infection, enterovirus D68 infection, enterovirus B69 infection, enterovirus D70 infection, enterovirus A71 infection, and poliovirus infection. In some embodiments, the Picornaviridae virus is foot and mouth disease virus (FMDV).

In some embodiments, the present disclosure provides a method for manufacturing a medicament for treating a Picornaviridae virus infection in a subject (e.g., human) in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a subject (e.g., human) of a Picornaviridae virus infection. In some embodiments, the Picornaviridae virus infection is human rhinovirus infection.

In some embodiments, the present disclosure provides a compound of the present disclosure, or a pharmaceutically acceptable salt thereof, for use in the treatment of a Picornaviridae virus infection in a subject (e.g., human) in need thereof. In some embodiments, the Picornaviridae virus infection is human rhinovirus infection.

D. Flaviviridae

In some embodiments, the viral infection is a Flaviviridae virus infection. In some embodiments, the present disclosure provides a method of treating a Flaviviridae virus infection in a subject (e.g., human) in need thereof, the method comprising administering to the subject (e.g., human) a therapeutically effective amount of a compound of the present disclosure, or a pharmaceutically acceptable salt thereof. Representative Flaviviridae viruses include, but are not limited to, dengue, Yellow fever, West Nile, Zika, Japanese encephalitis virus, tick-borne encephalitis virus (TBEV), and Hepatitis C (HCV). In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Japanese encephalitis virus infection. In some embodiments, the Flaviviridae virus infection is a tick-borne encephalitis virus (TBEV) infection. In some embodiments, the Flaviviridae virus infection is a Hepatitis C virus infection. In some embodiments, the Flaviviridae virus infection is bovine viral diarrhea virus (BVDV). In some embodiments, the Flaviviridae virus infection is swine fever virus (SFV).

In some embodiments, the present disclosure provides a method for manufacturing a medicament for treating a Flaviviridae virus infection in a subject (e.g., human) in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a subject (e.g., human) of a Flaviviridae virus infection. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection.

In some embodiments, the present disclosure provides a compound of the present disclosure, or a pharmaceutically acceptable salt thereof, for use in the treatment of a Flaviviridae virus infection in a human in need thereof. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection.

E. Filoviridae

In some embodiments, the viral infection is a Filoviridae virus infection. In some embodiments, the present disclosure provides a method of treating a Filoviridae virus infection in a subject (e.g., human) in need thereof, the method comprising administering to the subject (e.g., human) a therapeutically effective amount of a compound of the present disclosure, or a pharmaceutically acceptable salt thereof. Representative Filoviridae viruses include, but are not limited to, ebola (variants Zaire, Bundibugio, Sudan, Tai forest, or Reston) and marburg. In some embodiments, the Filoviridae virus infection is an ebola virus infection. In some embodiments, the Filoviridae virus infection is a marburg virus infection.

In some embodiments, the present disclosure provides a method for manufacturing a medicament for treating a Filoviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Filoviridae virus infection. In some embodiments, the Filoviridae virus infection is an ebola virus infection.

In some embodiments, the present disclosure provides a compound of the present disclosure, or a pharmaceutically acceptable salt thereof, for use in the treatment of a Filoviridae virus infection in a subject (e.g., human) in need thereof. In some embodiments, the Filoviridae virus infection is an ebola virus infection. In some embodiments, the Filoviridae virus infection is a marburg virus infection.

VIII. Combination Therapy

The compounds described herein can also be used in combination with one or more additional therapeutic agents or prophylactic agents. As such, also provided herein are methods for treatment of viral infections in a subject in need thereof, wherein the methods comprise administering to the subject a compound disclosed herein and a therapeutically effective amount of one or more additional therapeutic or prophylactic agents. In some embodiments, the methods comprise administering to the subject a compound disclosed herein and a therapeutically effective amount of one or more additional therapeutic agents. In some embodiments, the compounds disclosed herein are combined with at least one other active therapeutic agent, wherein the combination is used for treating a viral infection in a subject in need thereof. In some embodiments, the combination can be used to treat multiple separate viral infections (e.g., RSV and HIV) in one subject. In some embodiments, the compounds disclosed herein are combined with at least one other active therapeutic agent to cover a broader spectrum of respiratory viruses in one treatment without need for a diagnostic.

In some embodiments, the combination can be used to treat the same virus (e.g., RSV) in one subject. Active therapeutic agents include, but are not limited to, approved drugs, therapeutic agents currently in clinical trials, therapeutic agents that have shown efficacy in an animal model, therapeutic agents that have shown potency in in vitro assays, or any of the above.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, β-D-N4-hydroxycytidine or a combination thereof.

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is an HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogues. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiments, the additional therapeutic agent is selected from the group consisting of cidofovir, adefovir, adefovir dipivoxil, tenofovir, TDF, and combinations thereof. In some embodiments, the additional therapeutic agent is selected from the group consisting of cidofovir, adefovir dipivoxil, TDF, and combinations thereof.

In some embodiments, the additional therapeutic agent is an HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, and combinations thereof. In some embodiments, the additional therapeutic agent is selected from the group consisting of daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agent is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

In some embodiments, the additional therapeutic agent is an agent for treatment of malaria. In some embodiments, the additional therapeutic agent is chloroquine.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is an agent for treatment of COVID-19 (coronavirus disease 2019, a disease caused by a virus named SARS-CoV-2). In some embodiments, the additional therapeutic agent is selected from a group consisting of IFX-1, FM-201, CYNK-001, DPP4-Fc, ranpirnase, nafamostat, LB-2, AM-1, anti-viroporins, remdesivir, VV116, GS-441524, GS-5245, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo [3,2-d] pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino [8,7-h]quinolone-1,7-diamine), JK-$C_5$, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NSSA inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IB PB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007 sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is an HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies).

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is a HIV combination drug. Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV capsid inhibitor (e.g., lenacapavir).

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some embodiments, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiments, the additional therapeutic agent is selected from the group consisting of raltegravir, elvitegravir, dolutegravir, abacavir, lamivudine, bictegravir and combinations thereof. In some embodiments, the additional therapeutic agent is bictegravir. In some embodiments, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some embodiments, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is an inhibitor of Bruton tyrosine kinase (BTK, AGMX1, AT, ATK, BPK, IGHD3, IMD1, PSCTK1, XLA; NCBI Gene ID: 695). For example, in some embodiments, the additional therapeutic agent is selected from the group consisting of (S)-6-amino-9-(1-(but-2-yno yl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is tyrphostin A9 (A9).

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), room temperature11, MRTX-849 (G12C) and KRAS(G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, and combinations thereof. in some embodiments, the additional therapeutic agent is carfilzomib.

In some embodiments, the additional therapeutic agent is a vaccine. For example, in some embodiments, the additional therapeutic agent is a DNA vaccine, RNA vaccine, live-attenuated vaccine, therapeutic vaccine, prophylactic vaccine, protein-based vaccine, or a combination thereof. In some embodiments, the additional therapeutic agent is mRNA-1273. In some embodiments, the additional therapeutic agent is INO-4800 or INO-4700. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g., influenza A [H5N1] virus monovalent vaccine and influenza A [H1N1] 2009 virus monovalent vaccines), (ii) trivalent vaccine for influenza A and B viruses (e.g., Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g., Adenovirus Type 4 and Type 7 Vaccine, Live, Oral). In some embodiments, the additional therapeutic agent is a rotavirus vaccine (e.g., Rotarix for rotavirus serotype G1, G3, G4, or G9 and RotaTeq for rotavirus serotype Gl, G2, G3, or G4). In some embodiments, the additional therapeutic agent is a hepatitis A virus vaccine (e.g., Havrix and Vaqta). In some embodiments, the additional therapeutic agent is poliovirus vaccines (e.g., Kinrix, Quadracel, and Ipol). In some embodiments, the additional therapeutic agent is a yellow fever virus vaccine (e.g., YF-Vax). In some embodiments, the additional therapeutic agent is a Japanese encephalitis virus vaccine (e.g., Ixiaro and JE-Vax). In some embodiments, the additional therapeutic agent is a measles vaccine (e.g., M-M-R II and ProQuad). In some embodiments, the additional therapeutic agent is a mumps vaccine (e.g., M-M-R II and ProQuad). In some embodiments, the additional therapeutic agent is a rubella vaccine (e.g., M-M-R II and ProQuad). In some embodiments, the additional therapeutic agent is a varicella vaccine (e.g., ProQuad). In some embodiments, the additional therapeutic agent is a rabies vaccine (e.g., Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g., HEV239). In some embodiments, the additional therapeutic agent is a SARS-COV-2 vaccine.

In some embodiments, the additional therapeutic agent is an antibody, for example a monoclonal antibody. For example, the additional therapeutic agent is an antibody against SARS-COV-2 selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS CoV antibody CR-3022. In some embodiments, the additional therapeutic agent is aPD-1 antibody.

In some embodiments, the additional therapeutic agent is recombinant cytokine gene-derived protein injection.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of ribavirin, favipiravir, lamivudine, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is selected from the group consisting of 6'-fluorinated aristeromycin analogues, acyclovir fleximer analogues, disulfiram, thiopurine analogues, ASC09F, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro [4.5] decan-3-one derivatives, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an antibody. In some embodiments, the additional therapeutic agent is an antibody that binds to a coronavirus, for example an antibody that binds to SARS or MERS. In some embodiments, the additional therapeutic agent is a of SARS-COV-2 virus antibody.

Formulations of the disclosure are also used in combination with other active ingredients. For the treatment of SARS-COV-2 virus infections, in some embodiments, the other active therapeutic agent is active against coronavirus infections, for example SARS-COV-2 virus infections. The compounds and formulations of the present disclosure are also intended for use with general care provided subjects with SARS-COV-2 viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen or steroids), corticosteroids such as methylprednisolone, immonumodulatory medications (e.g., interferon), other small molecule or biologics antiviral agents targeting SARS-COV-2 (such as but not limited to lopinavir/ritonavir, EIDD-1931, favipiravir, ribavirine, neutralizing antibodies, etc.), vaccines, pain medications, and medications for other common diseases in the subject population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine.

In some embodiments, the additional therapeutic agent is an immunomodulator. Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide.

In some embodiments, the additional therapeutic agent is an IL-6 inhibitor, for example tocilizumab, sarilumab, or a combination thereof.

In some embodiments, the additional therapeutic agent is an anti-TNF inhibitor. For example, the additional therapeutic agent is adalimumab, etanercept, golimumab, infliximab, or a combination thereof.

In some embodiments, the additional therapeutic agent is a JAK inhibitor, for example the additional therapeutic agent is baricitinib, filgotinib, olumiant, or a combination thereof.

In some embodiments, the additional therapeutic agent is an inflammation inhibitor, for example pirfenidone.

In some embodiments, the additional therapeutic agent is an antibiotic for secondary bacterial pneumonia. For example, the additional therapeutic agent is macrolide antibiotics (e.g., azithromycin, clarithromycin, and *Mycoplasma pneumoniae*), fluoroquinolones (e.g., ciprofloxacin and levofloxacin), tetracyclines (e.g., doxycycline and tetracycline), or a combination thereof.

In some embodiments, the compounds disclosed herein are used in combination with pneumonia standard of care (see e.g., Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the subjects. The options include: (i) antibiotics, (ii) cough medicine, and (iii) fever reducers/pain relievers (for e.g., aspirin, ibuprofen (Advil, Motrin IB, others) and acetaminophen (Tylenol, others)). In some embodiments, the additional therapeutic agent is bromhexine anti-cough.

In some embodiments, the compounds disclosed herein are used in combination with immunoglobulin from cured COVID-19 subjects. In some embodiments, the compounds disclosed herein are used in combination with plasma transfusion. In some embodiments, the compounds disclosed herein are used in combination with stem cells.

In some embodiments, the additional therapeutic agent is an TLR agonist. Examples of TLR agonists include, but are not limited to, vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

In some embodiments, the additional therapeutic agent is selected from the group consisting of bortezomid, flurazepam, ponatinib, sorafenib, paramethasone, clocortolone, flucloxacillin, sertindole, clevidipine, atorvastatin, cinolazepam, clofazimine, fosaprepitant, and combinations thereof.

In some embodiments, the additional therapeutic agent is carrimycin, suramin, triazavirin, dipyridamole, bevacizumab, meplazumab, GD31 (rhizobium), NLRP inflammasome inhibitor, or a-ketoamine. In some embodiments, the additional therapeutic agent is recombinant human angiotensin-converting enzyme 2 (rhACE2). In some embodiments, the additional therapeutic agent is viral macrophage inflammatory protein (vMIP).

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

It is also possible to combine any compound of the disclosure with one or more additional active therapeutic agents in a unitary dosage form for simultaneous or sequential administration to a subject. The combination therapy can be administered as a simultaneous or sequential regimen. When administered sequentially, the combination can be administered in two or more administrations.

Co-administration of a compound of the disclosure with one or more other active therapeutic agents generally refers to simultaneous or sequential administration of a compound of the disclosure and one or more other active therapeutic agents, such that therapeutically effective amounts of the compound of the disclosure and one or more other active therapeutic agents are both present in the body of the subject.

Co-administration includes administration of unit dosages of the compounds of the disclosure before or after administration of unit dosages of one or more other active therapeutic agents, for example, administration of the compounds of the disclosure within seconds, minutes, or hours of the administration of one or more other active therapeutic agents. For example, a unit dose of a compound of the disclosure can be administered first, followed within seconds or minutes by administration of a unit dose of one or more other active therapeutic agents. Alternatively, a unit dose of one or more other therapeutic agents can be administered first, followed by administration of a unit dose of a compound of the disclosure within seconds or minutes. In some cases, it can be desirable to administer a unit dose of a compound of the disclosure first, followed, after a period of hours (e.g., 1-12 hours), by administration of a unit dose of one or more other active therapeutic agents. In other cases, it can be desirable to administer a unit dose of one or more other active therapeutic agents first, followed, after a period of hours (e.g., 1-12 hours), by administration of a unit dose of a compound of the disclosure.

The combination therapy can provide "synergy" and "synergistic," i.e., the effect achieved when the active ingredients used together is greater than the sum of the effects that results from using the compounds separately. A synergistic effect can be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect can be attained when the compounds are administered or delivered sequentially, e.g., in separate tablets, pills or capsules, or by different injections in separate syringes. In general, during alternation therapy, an effective dosage of each active ingredient is administered sequentially, i.e., serially, whereas in combination therapy, effective dosages of two or more active ingredients are administered together. A synergistic anti-viral effect denotes an antiviral effect which is greater than the predicted purely additive effects of the individual compounds of the combination.

A. Combination Therapy for the Treatment of Pneumoviridae Virus Infections

The compounds and pharmaceutically acceptable salts thereof disclosed herein can be used in combination with any of the active therapeutic agents discussed in Section VIII herein and/or with other active therapeutic agents for the treatment of Pneumoviridae virus infections discussed specifically here in Section VIII.A. In some embodiments, the other active therapeutic agent is active against Pneumoviridae virus infections, particularly respiratory syncytial virus infections and/or metapneumovirus infections. As described more fully herein, compounds of the present disclosure can be administered with one or more additional therapeutic agent(s) to an subject (e.g., a human) infected with RSV.

Further, in certain embodiments, when used to treat or prevent RSV, a compound of the present disclosure may be administered with one or more (e.g., one, two, three, four or more) additional therapeutic agent(s) selected from the group consisting of RSV combination drugs, RSV vaccines, RSV RNA polymerase inhibitors, immunomodulators toll-like receptor (TLR) modulators, interferon alpha receptor ligands, hyaluronidase inhibitors, respiratory syncytial surface antigen inhibitors, cytotoxic T-lymphocyte-associated protein 4 (ipi4) inhibitors, cyclophilin inhibitors, RSV viral entry inhibitors, antisense oligonucleotide targeting viral mRNA, short interfering RNAs (siRNA) and ddRNAi endonuclease modulators, ribonucelotide reductase inhibitors, farnesoid X receptor agonists, RSV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, RSV replication inhibitors, arginase inhibitors, and other RSV drugs.

Non-limiting examples of these other active therapeutic agents active against RSV include active monoclonal antibody and nanobody therapeutic agents, agents active against RSV infections, respiratory syncytial virus protein F inhibitors, viral replication inhibitors, RNA polymerase inhibitors, siRNA-based therapies, and combinations thereof. Non-limiting examples of active monoclonal antibody and nanobody therapeutic agents include palivizumab, RSV-IGIV (RESPIGAM®), MEDI-557 (motavizumab), MEDI8897 (nirsevimab), MK-1654, ALX-0171, A-60444 (also known as RSV604), anti-RSV G protein antibodies, and mixtures thereof. Other non-limiting examples of other active therapeutic agents active against respiratory syncytial virus infections include respiratory syncytial virus protein F inhibitors, such as MDT-637, BMS-433771, AK-0529, RV-521 (sisunatovir), JNJ-53718678 (rilematovir), BTA-585, and presatovir; RNA polymerase inhibitors, such as ribavirin, A-60444 (also known as RSV604), JNJ-64417184, ALS-8112 (JNJ-64041575; lumicitabine), and ALS-8112 (the parent nuc of lumicitabine); and viral replication inhibitors, such as EDP-938 and nitazoxanide; siRNA-based therapies, such as ALN-RSV01; and combinations thereof.

In some embodiments, the other active therapeutic agent can be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-00VP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent can be a vaccine for the treatment or prevention of metapneumovirus infections, including but not limited to mRNA-1653 and rHMPV-Pa vaccine.

B. Combination Therapy for the Treatment of Picornaviridae Virus Infections

The compounds and pharmaceutically acceptable salts thereof disclosed herein can be used in combination with any of the active therapeutic agents discussed in Section VIII herein and/or with other active therapeutic agents for the treatment of Picornaviridae virus infections discussed specifically here in Section VIII.B. In some embodiments, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent can be a vaccine for the treatment or prevention of Picornaviridae virus infections, including but not limited to EV71 vaccines, TAK-021, and EV-D68 adenovector-based vaccine.

C. Combination Therapy for the Treatment of Respiratory Infections

The compounds and pharmaceutically acceptable salts thereof disclosed herein can be used in combination with any of the active therapeutic agents discussed in Section VIII herein and/or with other active therapeutic agents discussed specifically here in Section VIII.C. Many of the infections of the Pneumoviridae and Picornaviridae viruses are respiratory infections. Therefore, additional active therapeutics used to treat respiratory symptoms and sequelae of infection can be used in combination with the compounds provided herein. The additional agents can be administered orally or by direct inhalation. For example, other additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. ALLERGY CLIN. IMMUNOL., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that can be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AISTM), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluorophenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-adrenoreceptor agonist bronchodilators

Combinations comprising inhaled β2-adrenoreceptor agonist bronchodilators such as formoterol, albuterol or salmeterol with the compounds provided herein are also suitable, but non-limiting, combinations useful for the treatment of respiratory viral infections.

Combinations of inhaled β2-adrenoreceptor agonist bronchodilators such as formoterol or salmeterol with ICS's can be used to treat both the bronchoconstriction and the inflammation (SYMBICORT® and ADVAIR®, respectively). The combinations comprising these ICS and β2-adrenoreceptor agonist combinations along with the compounds provided herein are also suitable, but non-limiting, combinations useful for the treatment of respiratory viral infections.

Other examples of Beta 2 adrenoceptor agonists include, but are not limited to, bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype), which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)- amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Rev atropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, and bencycloquidium bromide.

Mucolytic Agents

The compounds provided herein can also be combined with mucolytic agents to treat both the infection and symptoms of respiratory infections. A non-limiting example of a mucolytic agent is ambroxol. Similarly, the compounds can be combined with expectorants to treat both the infection and symptoms of respiratory infections. A non-limiting example of an expectorant is guaifenesin.

Nebulized hypertonic saline is used to improve immediate and long-term clearance of small airways in subjects with lung diseases (Kuzik, J. *Pediatrics* 2007, 266). Thus, the compounds provided herein can also be combined with nebulized hypertonic saline particularly when the virus infection is complicated with bronchiolitis. The combination of the compound provided herein with hypertonic saline can also comprise any of the additional agents discussed above. In some embodiments, 3% hypertonic saline is used.

D. Combination Therapy for the Treatment of COPD

The compounds and pharmaceutically acceptable salts thereof disclosed herein can be used in combination with any of the active therapeutic agents discussed in Section VIII herein and/or with other active therapeutic agents for the treatment of respiratory exacerbations of COPD discussed specifically here in Section VIII.D. In some embodiments, the other active therapeutic agents include other active agents against COPD. Non-limiting examples of these other active therapeutic agents include anti-IL5 antibodies, such as benralizumab, mepolizumab; dipeptidyl peptidase I (DPP1) inhibitors, such as AZD-7986 (INS-1007); DNA gyrase inhibitor/topoisomerase IV inhibitors, such as ciprofloxacin hydrochloride; MDR associated protein 4/phosphodiesterase (PDE) 3 and 4 inhibitors, such as RPL-554; CFTR stimulators, such as ivacaftor, QBW-251; MMP-9/MMP-12 inhibitors, such as RBx-10017609; Adenosine A1 receptor antagonists, such as PBF-680; GATA 3 transcription factor inhibitors, such as SB-010; muscarinic receptor modulator/nicotinic acetylcholine receptor agonists, such as ASM-024; MARCKS protein inhibitors, such as BIO-11006; kit tyrosine kinase/PDGF inhibitors such as masitinib; phosphodiesterase (PDE) 4 inhibitors, such as roflumilast, CHF-6001; phosphoinositide-3 kinase delta inhibitors, such as nemiralisib; 5-Lipoxygenase inhibitors, such as TA-270; muscarinic receptor antagonist/beta 2 adrenoceptor agonist, such as batefenterol succinate, AZD-887, ipratropium bromide; TRN-157; elastase inhibitors, such as erdosteine; metalloprotease-12 inhibitors such as FP-025; interleukin 18 ligand inhibitors, such as tadekinig alfa; skeletal muscle troponin activators, such as CK-2127107; p38 MAP kinase inhibitors, such as acumapimod; IL-17 receptor modulators, such as CNTO-6785; CXCR2 chemokine antagonists, such as danirixin; leukocyte elastase inhibitors, such as POL-6014; epoxide hydrolase inhibitors, such as GSK-2256294; HNE inhibitors, such as CHF-6333; VIP agonists, such as aviptadil; phosphoinositide-3 kinase delta/gamma inhibitors, such as RV-1729; complement C3 inhibitors, such as APL-1; and G-protein coupled receptor-44 antagonists, such as AM-211.

Other non-limiting examples of active therapeutic agents also include, but are not limited to, budesonide, adipocell, nitric oxide, PUR-1800, YLP-001, LT-4001, azithromycin, gamunex, QBKPN, sodium pyruvate, MUL-1867, mannitol, MV-130, MEDI-3506, BI-443651, VR-096, OPK-0018, TEV-48107, doxofylline, TEV-46017, OligoG-COPD-5/20, STEMPEUCEL®, ZP-051, and lysine acetylsalicylate.

In some embodiments, the other active therapeutic agent may be a vaccine that is active against COPD, including but not limited to MV-130 and GSK-2838497A.

E. Combination Therapy for the Treatment of Flaviviridae Virus Infections

The compounds and pharmaceutically acceptable salts thereof disclosed herein can be used in combination with any of the active therapeutic agents discussed in Section VIII herein and/or with other active therapeutic agents for the treatment of Flaviviridae virus infections discussed specifically here in Section VIII.E. In some embodiments, the other active therapeutic agent is active against Flaviviridae virus infections.

For treatment of the Flaviviridae virus infections, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent can be a vaccine for the treatment or prevention of dengue, including but not limited to TETRAVAX-DV, DENGVAXIA®, DPIV-001, TAK-003, live attenuated dengue vaccine, tetravalent dengue fever vaccine, tetravalent DNA vaccine, rDEN2delta30-7169; and DENY-1 PIV.

F. Combination Therapy for the Treatment of Filoviridae Virus Infections

The compounds and pharmaceutically acceptable salts thereof disclosed herein can be used in combination with any of the active therapeutic agents discussed in Section VIII herein and/or with other active therapeutic agents for the treatment of Filoviridae virus infections discussed specifically here in Section VIII.F. In some embodiments, the other active therapeutic agent is active against Filoviridae virus infections (e.g., marburg virus, ebola virus, Sudan virus, and cueva virus infections). Non-limiting examples of these other active therapeutic agents include: MR186-YTE, remdesivir, ribavirin, palivizumab, motavizumab, RSV-IGIV (RESPIGAM®), MEDI-557, A-60444, MDT-637, BMS-433771, amiodarone, dronedarone, verapamil, Ebola Convalescent Plasma (ECP), TKM-100201, BCX4430 ((2S, 3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as INMA-ZEB (atoltivimab, maftivimab, and odesivimab), ZMapp, and mAb114 (EBANGA).

Other non-limiting active therapeutic agents active against Ebola include, but are not limited to, an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent can be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The compounds provided herein can also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compounds provided herein are also intended for use with general care provided to subjects with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the subject population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

G. Combination Therapy for the Treatment of Influenza

The compounds and pharmaceutically acceptable salts thereof disclosed herein can be used in combination with any of the active therapeutic agents discussed in Section VIII herein and/or with other active therapeutic agents for the treatment of influenza virus infections discussed specifically here in Section VIII.G. In some embodiments, the compounds provided herein are also used in combination with other active therapeutic agents for the treatment of influenza virus infections. The compounds and compositions provided herein are also used in combination with other active therapeutic agents. In some embodiments, the compounds provided herein can also be combined with influenza treatments. In some embodiments, the compounds provided herein are used with influenza treatments when treating influenza viruses. In some embodiments, the compounds provided herein are used with influenza treatments to treat a broader spectrum of respiratory viruses, such as those disclosed herein. In some embodiments, the influenza treatment is a neuraminidase (NA) inhibitor. In some embodiments, the influenza treatment is an M2 inhibitor. Examples of influenza treatments include, but are not limited to, AB-5080, ALS-1, amantadine (GOCOVRI®), AV-001, AV-5124, AVM-0703, baloxavir marboxil (XOFLUZA®), CB-012, CC-42344, CD-388, CT-P27, Codivir, DAS-181, DNK-651, ENOB-FL-01, ENOB-FL-11, favipiravir, GP-584, GP-681, H-015, HC-imAb, HEC-116094HCl·3$H_2O$, HNC-042, histamine glutarimide, IFV-PA, Ingavirin, INI-2004, INNA-051, KYAH01-2019-121, laninamivir, molnupiravir, niclosamide, nitazoxanide, norketotifen, NX-2016, oseltamivir phosphate (TAMIFLU®), peramivir (RAPIVAB®), REVTx-99, rimantadine, S-416, SAB-176, STP-702, T-705IV, TG-1000, TJ-27, TSR-066, 7HP-349, VIR-2482, VIS-410, VIS-FLX, XC-221, zanamivir (RELENZA®), zanamivir-dinitrophenyl conjugate, ZSP-1273, and ZX-7101A.

IX. Compound Preparation

In some embodiments, the present disclosure provides processes and intermediates useful for preparing the compounds disclosed herein or pharmaceutically acceptable salts thereof.

Compounds disclosed herein can be purified by any of the means known in the art, including chromatographic means, including but not limited to high-performance liquid chromatography (HPLC), preparative thin layer chromatography, flash column chromatography, and ion exchange chromatography. Any suitable stationary phase can be used, including but not limited to, normal and reversed phases as well as ionic resins. In some embodiments, the disclosed compounds are purified via silica gel and/or alumina chromatography.

During any of the processes for preparation of the compounds provided herein, it can be necessary and/or desirable to protect sensitive or reactive groups on any of the molecules concerned. This can be achieved by means of conventional protecting groups as described in standard works, such as T. W. Greene and P. G. M. Wuts, Protective Groups in Organic Synthesis, 4$^{th}$ ed., Wiley, New York 2006. The protecting groups can be removed at a convenient subsequent stage using methods known from the art.

Exemplary chemical entities useful in methods of the embodiments will now be described by reference to illustrative synthetic schemes for their general preparation herein and the specific examples that follow. Skilled artisans will recognize that, to obtain the various compounds herein, starting materials can be suitably selected so that the ultimately desired substituents will be carried through the reaction scheme with or without protection as appropriate to yield the desired product. Alternatively, it can be necessary or desirable to employ, in the place of the ultimately desired substituent, a suitable group that can be carried through the reaction scheme and replaced as appropriate with the desired substituent. Furthermore, one of skill in the art will recognize that the transformations shown in the schemes below can be performed in any order that is compatible with the functionality of the particular pendant groups.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in the schemes below, and the particular examples that follow.

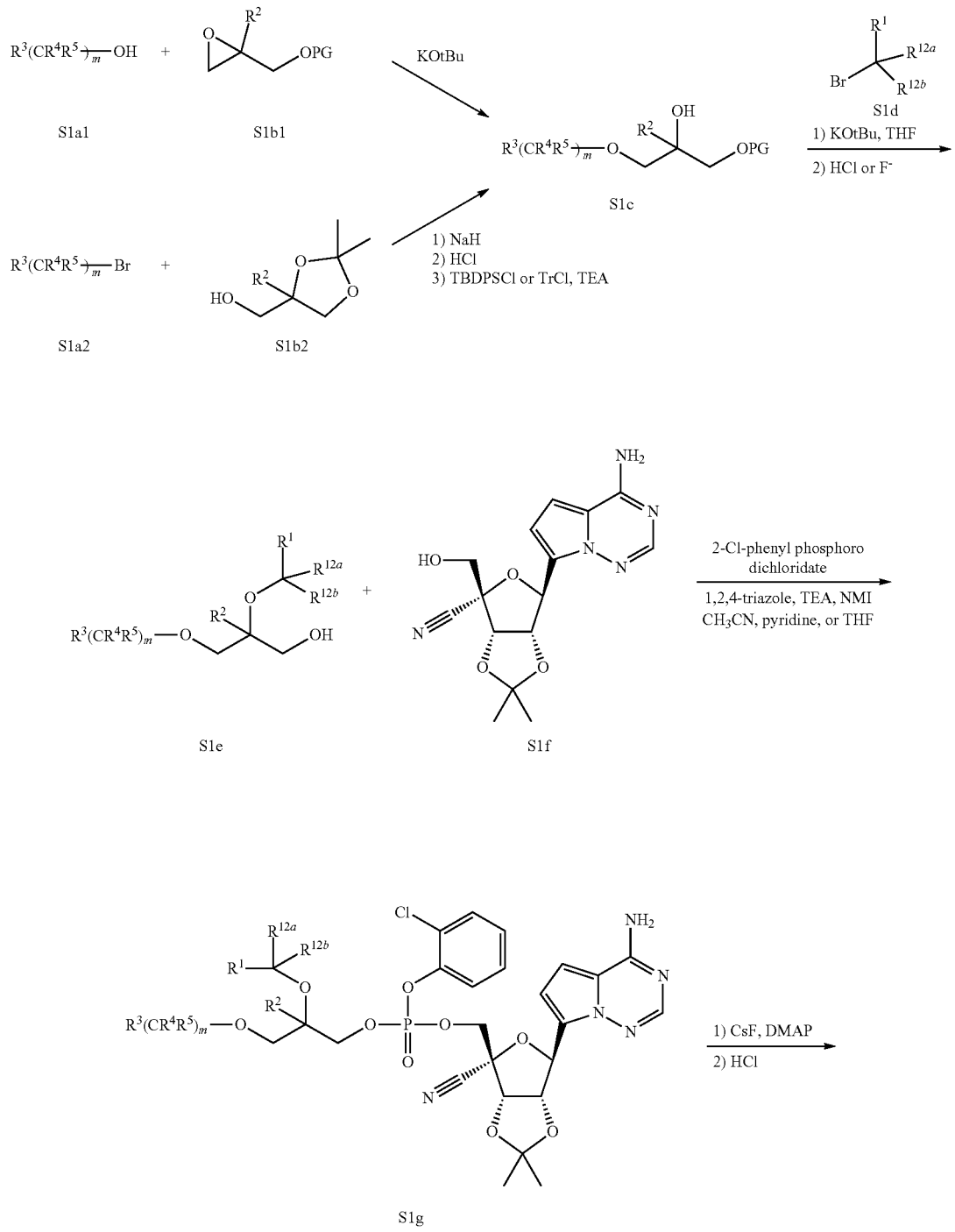

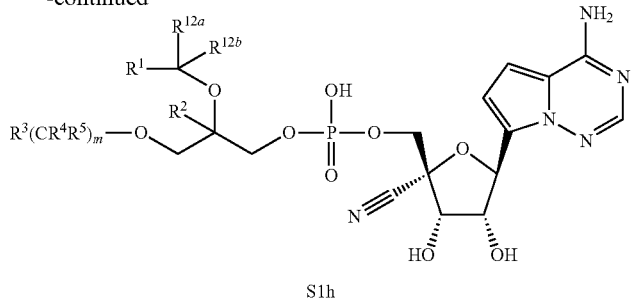

S1h

Scheme 1 shows a general synthesis of compounds beginning with addition of an alcohol S1a1 to an epoxide S1b1 with PG (e.g., Tr, TBDPS) under basic conditions (e.g., KOtBu or NaH) to afford alcohol S1c. Alternatively, addition of alcohol S1b2 to alkyl halide S1a2 (e.g., Br) under basic conditions (e.g., NaH) followed by acetonide removal under acidic conditions (e.g. HCl) and protection of the primary alcohol under basic conditions (e.g., TBDPSCl, TEA) affords S1c. A substitution reaction with the halide S1d (e.g., Br) under basic conditions (e.g., KOtBu or NaH) and removal of PG (e.g., HCl or TBAF) affords alcohol S1e. The alcohol S1e and nucleoside S1f are coupled with 2-Cl-phenyl phosphorodichloridate under basic conditions (e.g., 1,2,4-triazole, TEA, NMI, $CH_3CN$, pyridine, or THF) to afford S1g. Removal of the 2-Cl-phenol (e.g., CsF, DMAP) and acetonide (e.g., HCl) affords final compounds (e.g., Compounds 1, 3-10, 12-20, 22, 53, 55, 61, 63, 66, 67, 68, 73, and 75 of Table 1) of the type S1h.

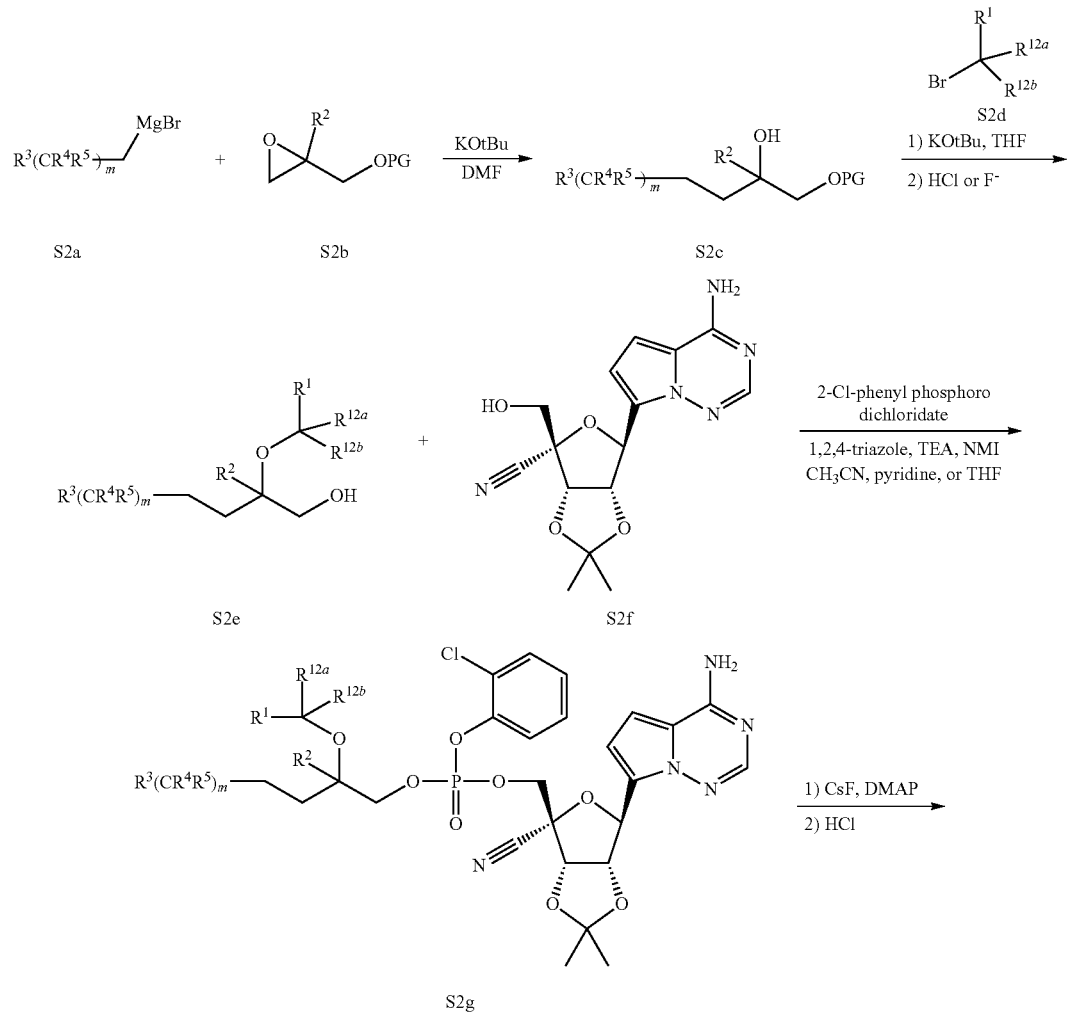

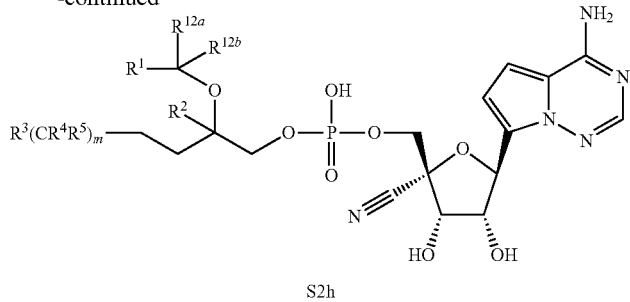

S2h

Scheme 2 shows a general synthesis of compounds beginning with addition of an alkyl Grignard S2a to an epoxide S2b with PG (e.g., Tr, TBDPS) to afford alcohol S2c. A substitution reaction with the halide S2d (e.g., Br) under basic conditions (e.g., KOtBu) and removal of PG (e.g., HCl or TBAF) affords alcohol S2e. The alcohol S2e and nucleoside S2f are coupled with 2-Cl-phenyl phosphorodichloridate under basic conditions (e.g., 1,2,4-triazole, TEA, NMI, $CH_3CN$, pyridine, or THF) to afford S2g. Removal of the 2-Cl-phenol (e.g., CsF DMAP) and acetonide (e.g., HCl) affords final compounds (e.g., Compounds 2, 11, 25-37, 56, 62, 70, 74, and 76 of Table 1) of the type S2h.

Scheme 3

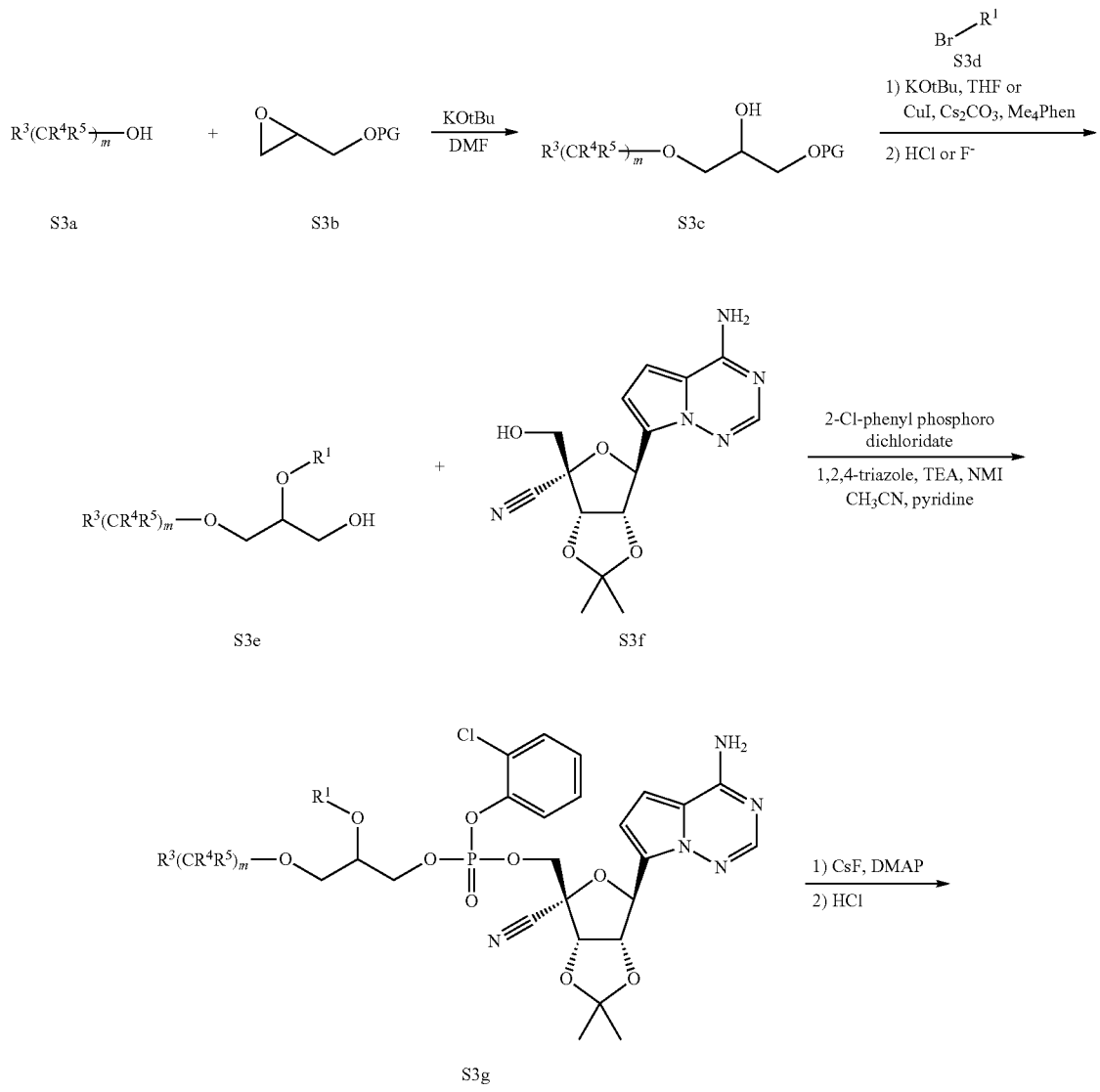

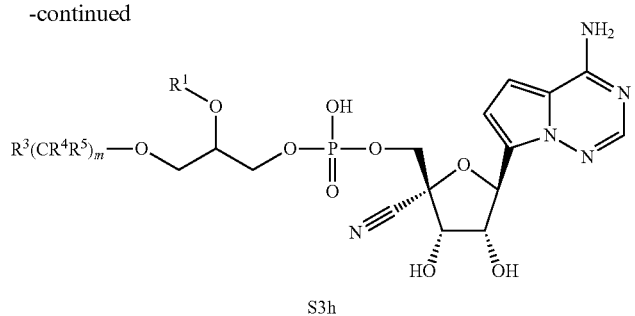

S3h

Scheme 3 shows a general synthesis of compounds beginning with addition of an alcohol S3a to an epoxide S3b with PG (e.g., Tr, TBDPS) under basic conditions (e.g., KOtBu) to afford alcohol S3c. A substitution reaction under basic conditions (e.g., KOtBu) or an Ullmann C—O coupling (e.g., CuI, $Cs_2CO_3$, $Me_4Phen$) with the halide S3d (e.g., Br) followed by removal of PG (e.g., HCl or TBAF) affords alcohol S3e. The alcohol S3e and nucleoside S3f are coupled with 2-Cl-phenyl phosphorodichloridate under basic conditions (e.g., 1,2,4-triazole, TEA, NMI, $CH_3CN$, pyridine) to afford S3g. Removal of the 2-Cl-phenol (e.g., CsF DMAP) and acetonide (e.g., HCl) affords final compounds (e.g., Compounds 21, 23, 24, 50, 59, 69, 71, 72, and 77 of Table 1) of the type S3g.

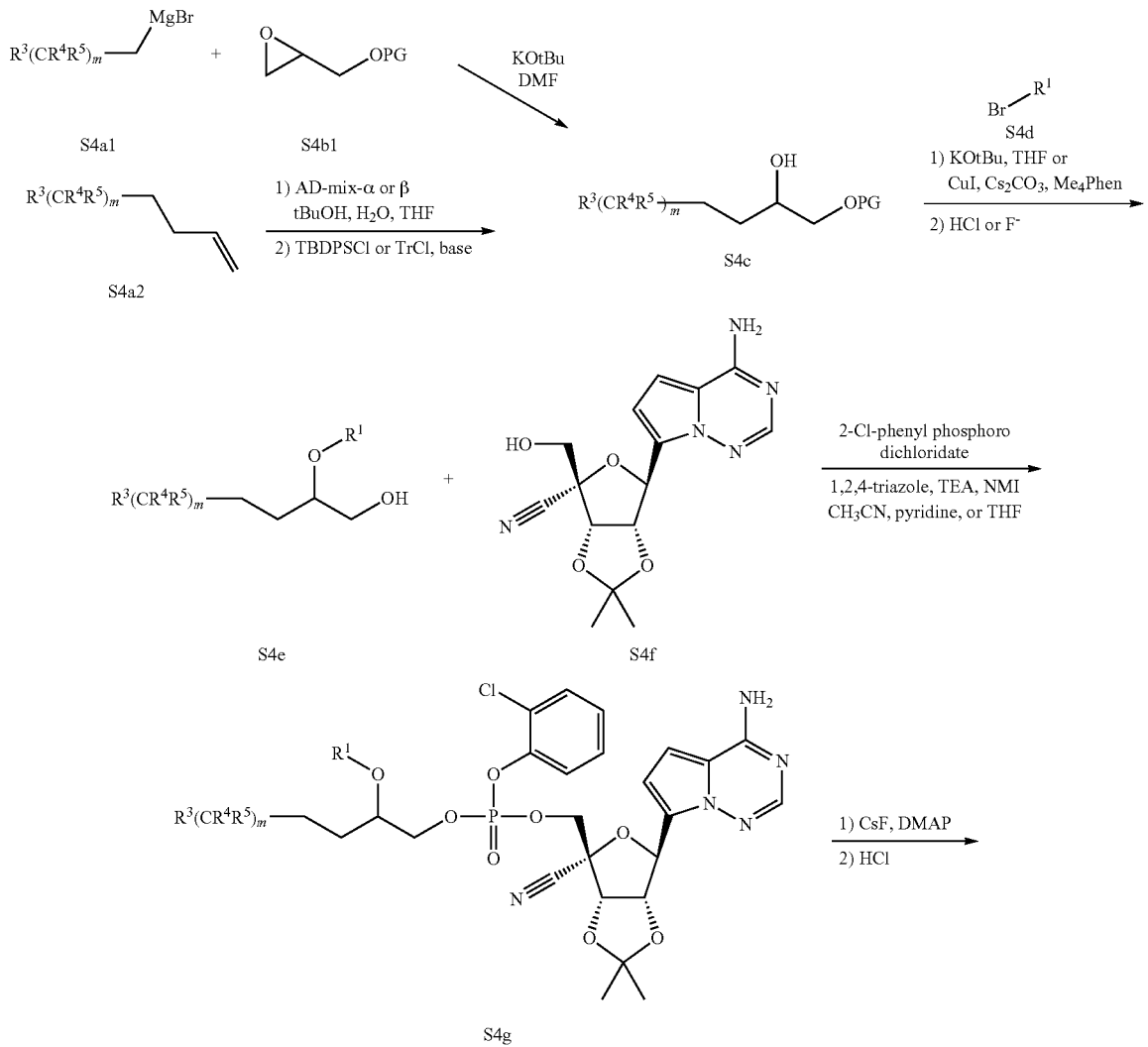

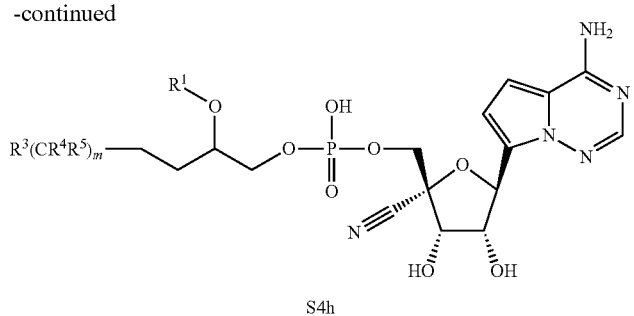

S4h

Scheme 4 shows a general synthesis of compounds beginning with addition of an alkyl grignard S4a1 to an epoxide S4b with PG (e.g., Tr, TBDPS) under basic conditions (e.g., KOtBu) to afford alcohol S4c. Alternatively, dihydroxylation of a terminal alkene S4a2 (where $CR^4R^5$ groups are not connected through a double bond) followed by protection (e.g., TrCl or TBDPSCl) of the primary alcohol affords alcohol S4c. A substitution reaction under basic conditions (e.g., KOtBu) or an Ullmann C—O coupling (e.g., CuI, $Cs_2CO_3$, $Me_4Phen$) with the halide S4d (e.g., Br) followed by removal of PG (e.g., HCl or TBAF) affords alcohol S4e. The alcohol S4e and nucleoside S4f are coupled with 2-Cl-phenyl phosphorodichloridate under basic conditions (e.g., 1,2,4-triazole, TEA, NMI, $CH_3CN$, pyridine, or THF) to afford S4g. Removal of the 2-Cl-phenol (e.g., CsF DMAP) and acetonide (e.g., HCl) affords final compounds (e.g., Compounds 38-40, 51, and 60 of Table 1) of the type S4g.

Scheme 5

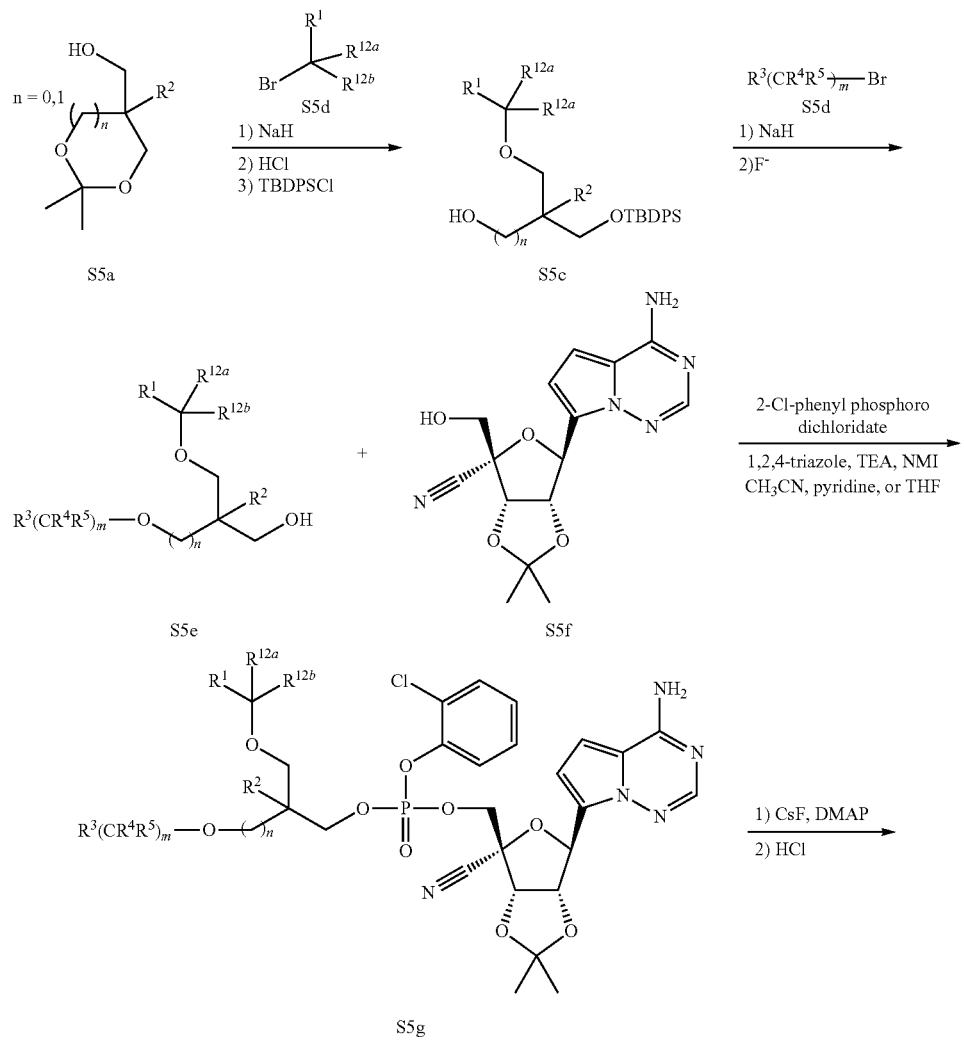

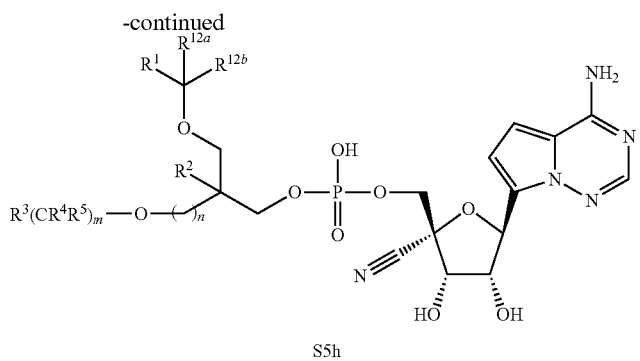

S5h

Scheme 5 shows a general synthesis of compounds beginning with substitution reaction of an alcohol S5a to halide S5b under basic conditions (e.g., NaH) followed by acetonide cleavage under acidic conditions (e.g., HCl) and protection of the alcohol (e.g., TBDPSCl) to afford alcohol S5c. A substitution reaction under basic conditions (e.g., NaH) with the alkyl halide S5d (e.g., Br) followed by removal of protecting group (e.g., TBAF) affords alcohol S5e. The alcohol S4e and nucleoside S4f are coupled with 2-Cl-phenyl phosphorodichloridate under basic conditions (e.g., 1,2,4-triazole, TEA, NMI, $CH_3CN$, pyridine, or THF) to afford S5g. Removal of the 2-Cl-phenol (e.g., CsF DMAP) and acetonide (e.g., HCl) affords final compounds (e.g., Compounds 41 and 42 of Table 1) of the type S5 h.

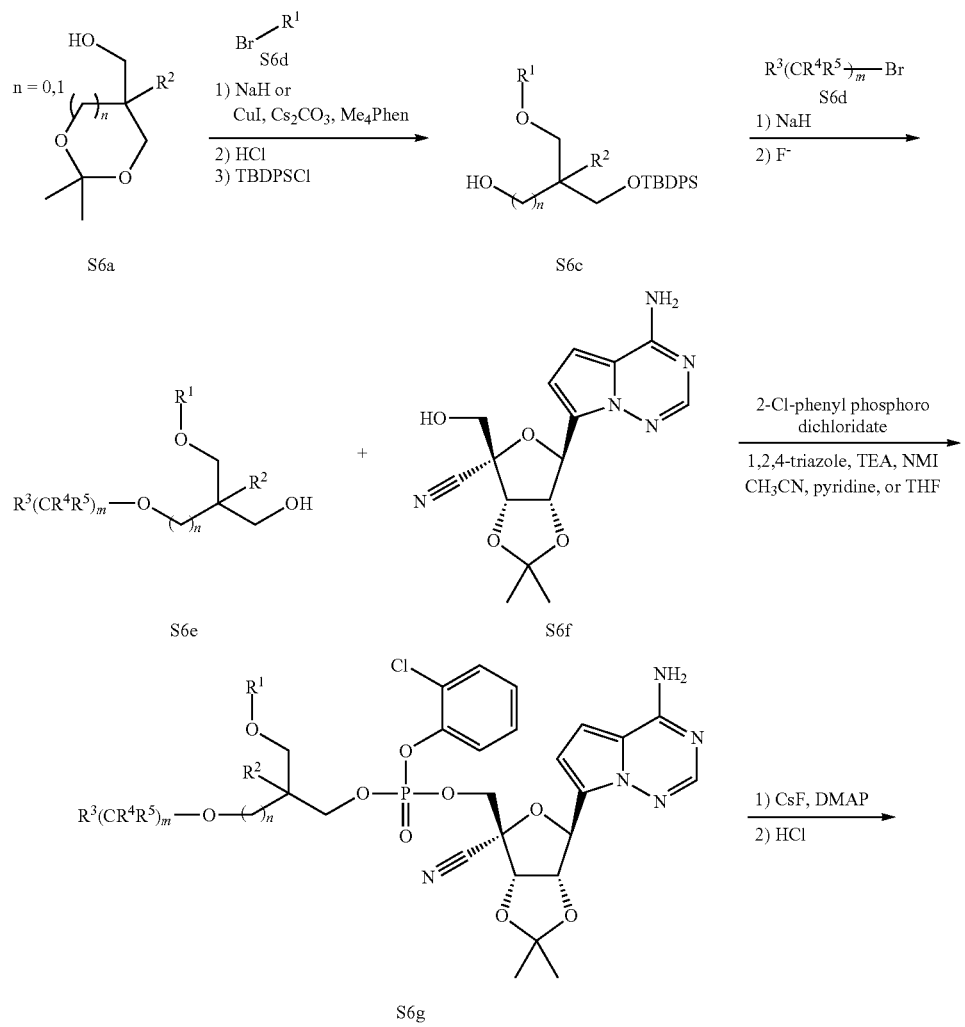

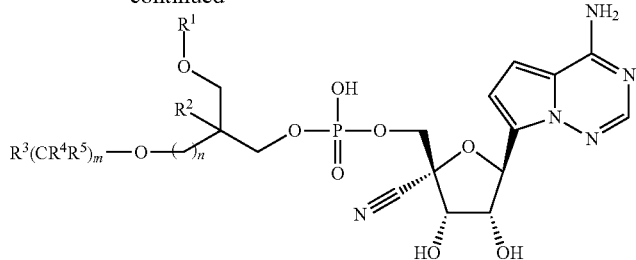

S6h

Scheme 6 shows a general synthesis of compounds beginning with substitution reaction under basic conditions (e.g., NaH) or Ullmann C—O coupling (e.g., CuI, Cs$_2$CO$_3$, Me$_4$Phen) of alcohol S6a to halide S6b (e.g., Br) followed by acetonide cleavage under acidic conditions (e.g., HCl) and protection of the alcohol (e.g., TBDPSCl) to afford alcohol S6c. A substitution reaction under basic conditions (e.g., NaH) with alkyl halide S6d (e.g., Br) followed by removal of protecting group (e.g., TBAF) affords alcohol S6e. The alcohol S6e and nucleoside S6f are coupled with 2-Cl-phenyl phosphorodichloridate under basic conditions (e.g., 1,2,4-triazole, TEA, NMI, CH$_3$CN, pyridine, or THF) to afford S6g. Removal of the 2-Cl-phenol (e.g., CsF DMAP) and acetonide (e.g., HCl) affords final compounds (e.g., Compounds 43 and 65 of Table 1) of the type S6 h.

Scheme 7

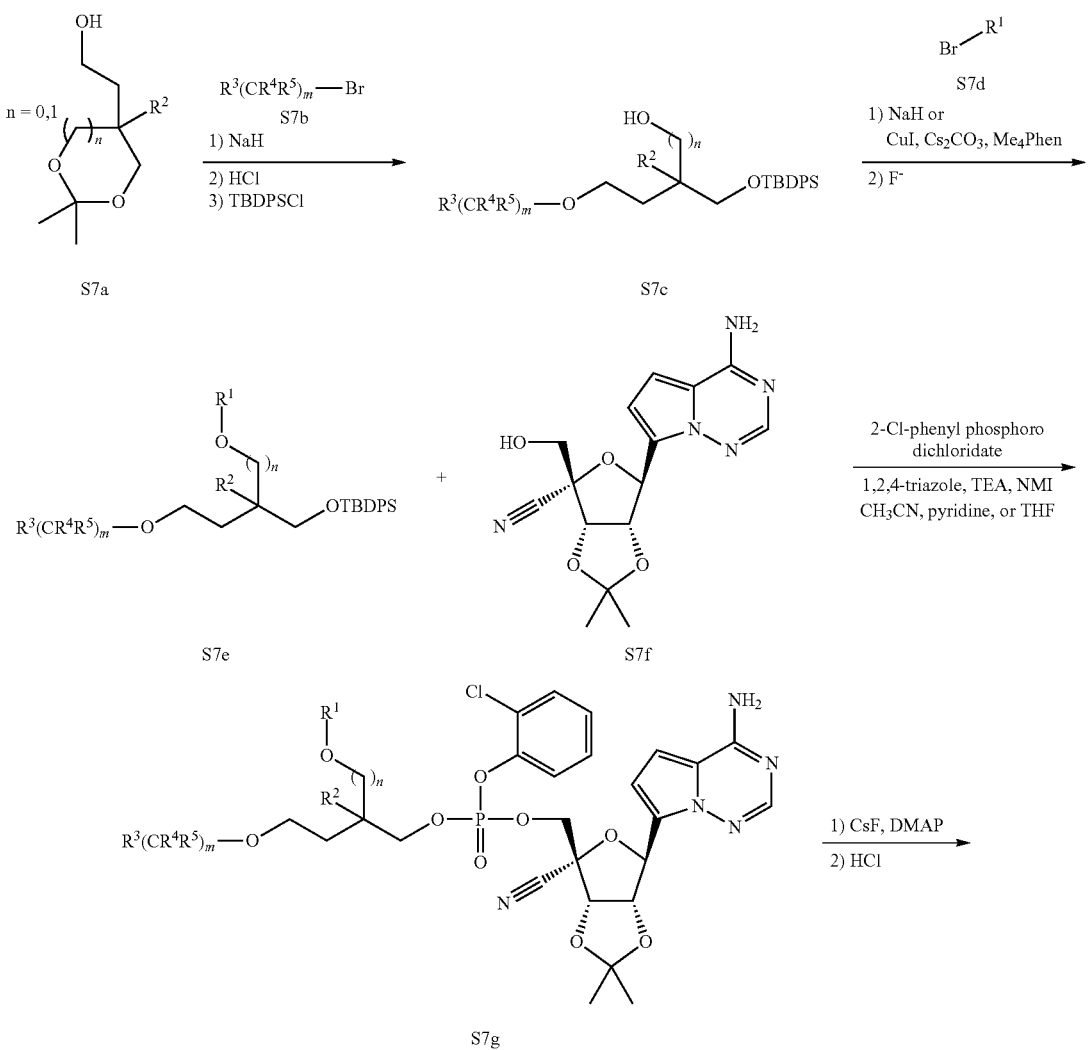

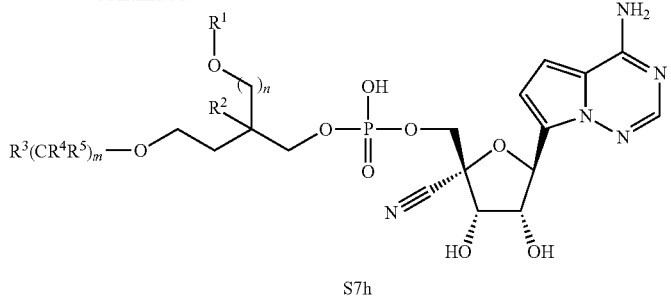

S7h

Scheme 7 shows a general synthesis of compounds beginning with substitution reaction under basic conditions (e.g., NaH) of alkyl halide S7b followed by acetonide cleavage under acidic conditions (e.g., HCl) and protection of the alcohol (e.g., TBDPSCl) to afford alcohol S7c. A substitution reaction under basic conditions (e.g., NaH) or Ullmann C—O coupling (e.g., CuI, Cs$_2$CO$_3$, Me$_4$Phen) with halide S7d (e.g., Br) followed by removal of protecting group (e.g., TBAF) affords alcohol S7e. The alcohol S7e and nucleoside S7f are coupled with 2-Cl-phenyl phosphorodichloridate under basic conditions (e.g., 1,2,4-triazole, TEA, NMI, CH$_3$CN, pyridine, or THF) to afford S7g. Removal of the 2-Cl-phenol (e.g., CsF DMAP) and acetonide (e.g., HCl) affords final compounds (e.g., Compound 44 of Table 1) of the type S7 h.

Scheme 8

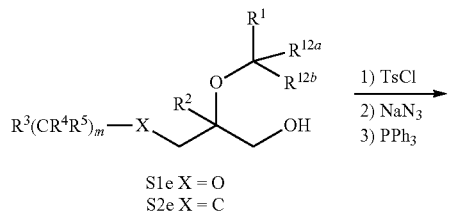

S1e X = O
S2e X = C

1) TsCl
2) NaN$_3$
3) PPh$_3$

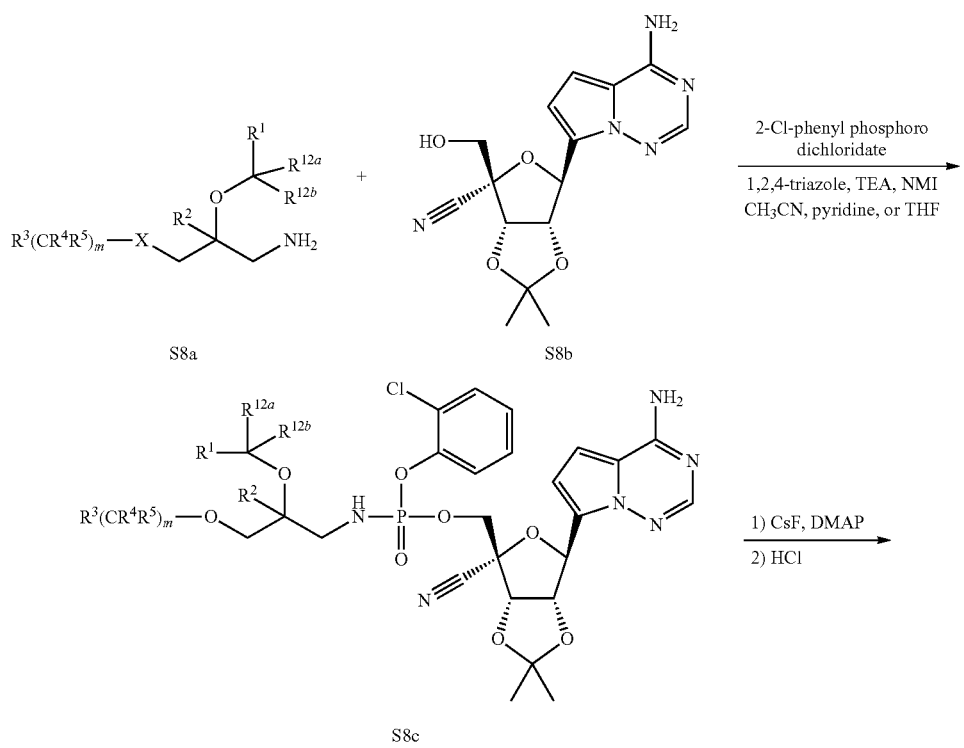

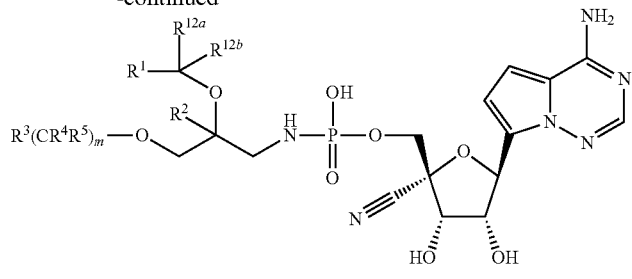

S8d

Scheme 8 shows a general synthesis of compounds beginning with tosylations of the alcohol (e.g., S1e or S2e) followed by substitution with sodium azide and treatment with triphenyl phosphine to afford the amine S8a. The amine S8a and nucleoside S8b are coupled with 2-Cl-phenyl phosphorodichloridate under basic conditions (e.g., 1,2,4-triazole, TEA, NMI, $CH_3CN$, pyridine, or THF) to afford S8c. Removal of the 2-Cl-phenol (e.g., CsF DMAP) and acetonide (e.g., HCl) affords final compounds (e.g., Compounds 45 and 46 of Table 1) of the type S8d.

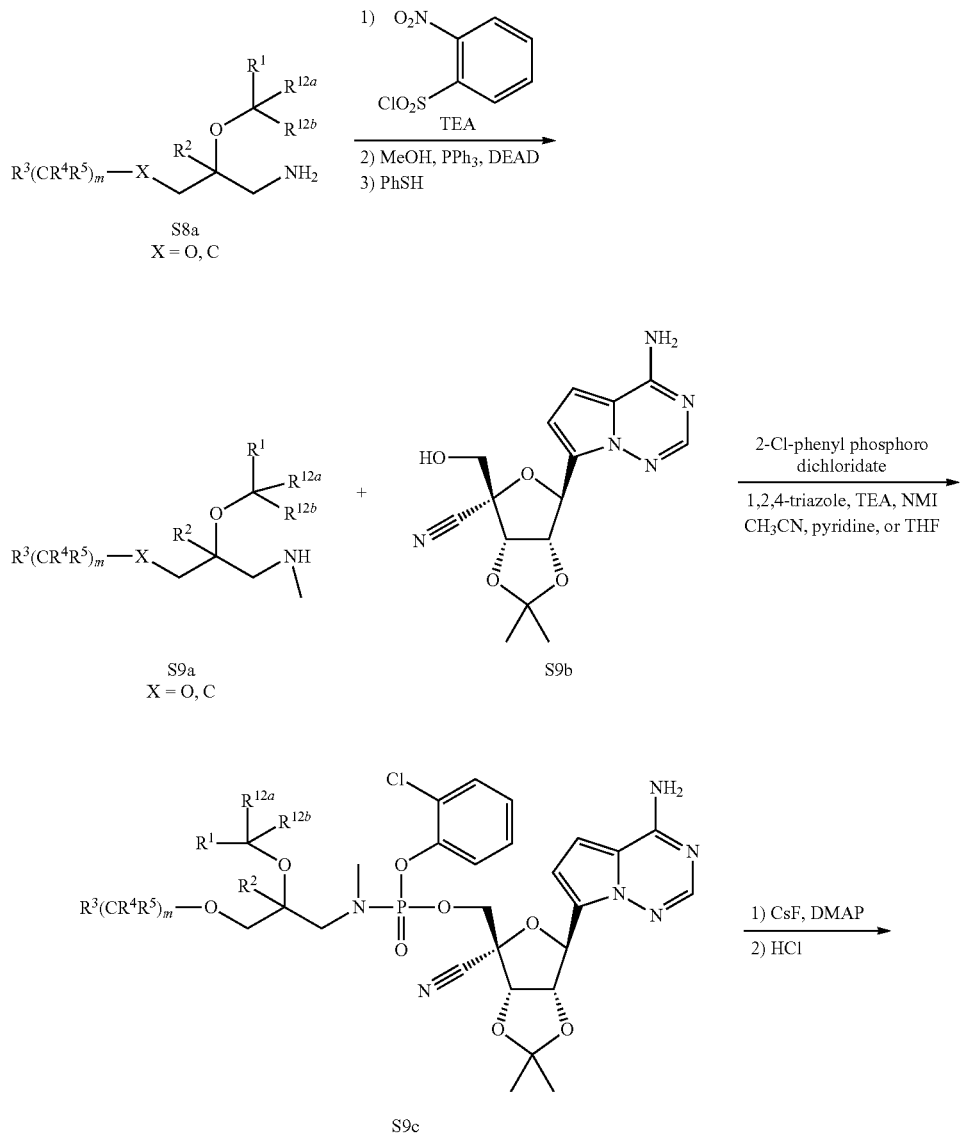

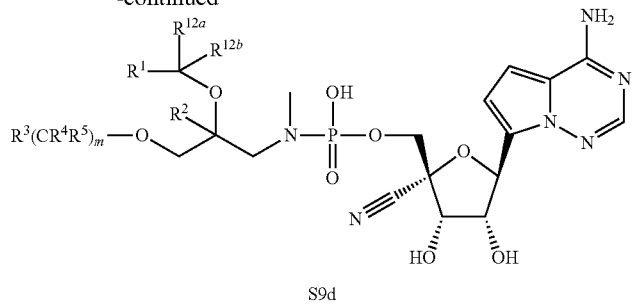

S9d

Scheme 9 shows a general synthesis of compounds beginning with sulphonylation (e.g., 2-nitrobenzenesulfonyl chloride) of amine S8a (e.g., X=O or CH$_2$) followed by a Mitsunobu reaction (e.g., MeOH, PPh3, DEAD) and desulphonylation (e.g., PhSH) to afford amine S9a. The amine S9a and nucleoside S9b are coupled with 2-Cl-phenyl phosphorodichloridate under basic conditions (e.g., 1,2,4-triazole, TEA, NMI, CH$_3$CN, pyridine, or THF) to afford S9c. Removal of the 2-Cl-phenol (e.g., CsF DMAP) and acetonide (e.g., HCl) affords final compounds (e.g., Compounds 57 and 58 of Table 1) of the type S9d.

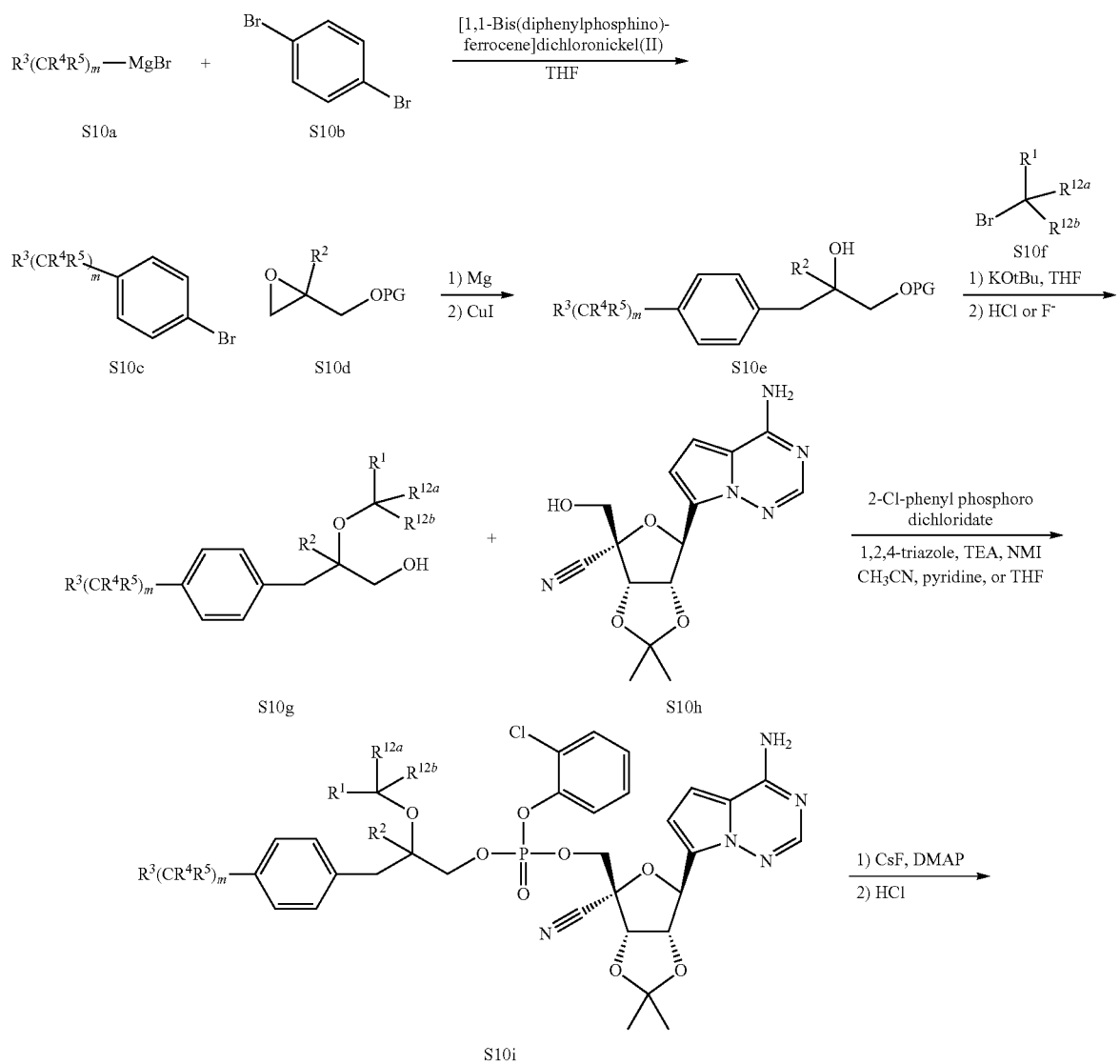

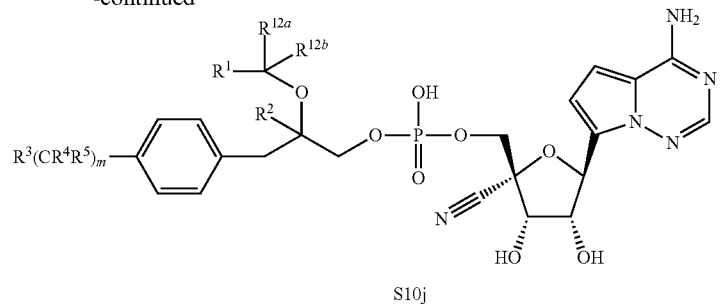

S10j

Scheme 10 shows a general synthesis of compounds beginning with the coupling of the Grignard S10a with S10b (e.g., [1,1-Bis(diphenylphosphino)ferrocene]dichloronickel (II)) to afford S10c. Metallation of the aryl halide S10c (e.g., Mg; CuI) and addition to epoxide S10d with PG (e.g., Tr, TBDPS) affords alcohol S10e. A substitution reaction with the halide S10f (e.g., Br) under basic conditions (e.g., KOtBu) and removal of PG (e.g., HCl or TBAF) affords alcohol S10g. The alcohol S10g and nucleoside S10h are coupled with 2-Cl-phenyl phosphorodichloridate under basic conditions (e.g., 1,2,4-triazole, TEA, NMI, CH$_3$CN, pyridine, or THF) to afford S10i. Removal of the 2-Cl-phenol (e.g., CsF, DMAP) and acetonide (e.g., HCl) affords final compounds (e.g., Compound 54 of Table 1) of the type S10j.

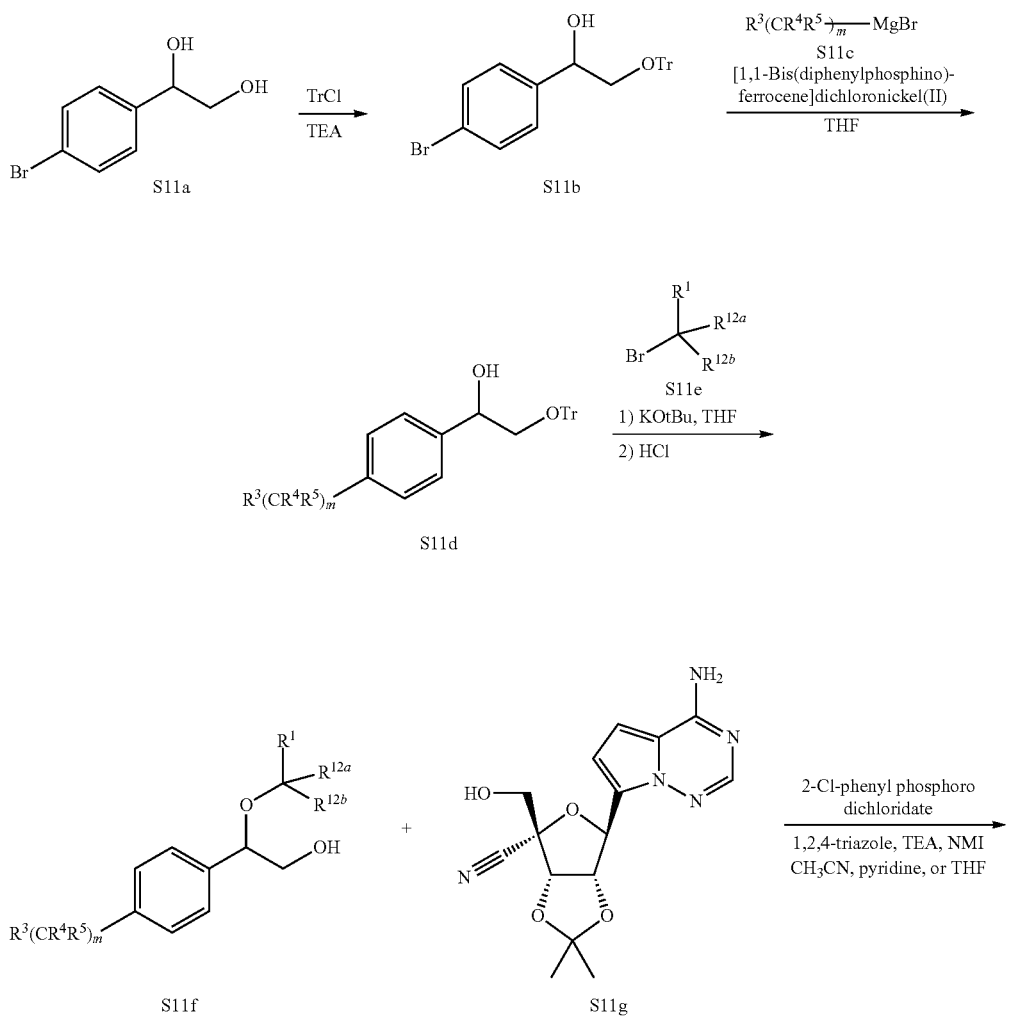

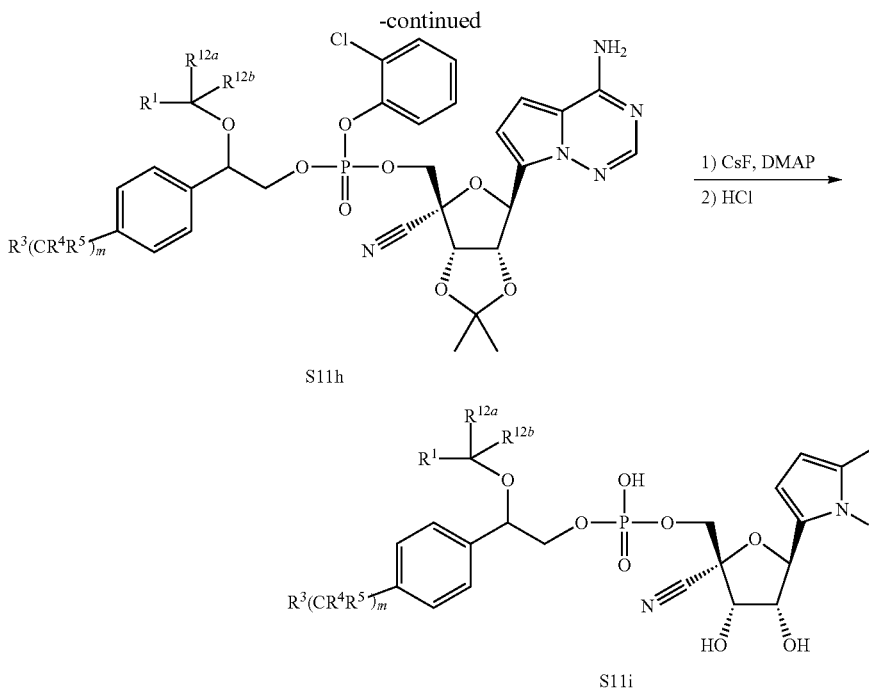

S11h

S11i

Scheme 11 shows a general synthesis of compounds beginning with protection of the primary alcohol S11a (e.g., TrCl) to afford S11b. S11b is then cross-coupled to the Grignard S11c with metal catalyst (e.g., [1,1-Bis(diphenylphosphino)ferrocene]-dichloronickel(II)) to afford S11d. A substitution reaction with the halide S11e (e.g., Br) under basic conditions (e.g., KOtBu) and removal of the protecting group under acidic conditions (e.g., HCl) affords alcohol S11f. The alcohol S11f and nucleoside S11g are coupled with 2-Cl-phenyl phosphorodichloridate under basic conditions (e.g., 1,2,4-triazole, TEA, NMI, CH$_3$CN, pyridine, or THF) to afford S11 h. Removal of the 2-Cl-phenol (e.g., CsF, DMAP) and acetonide (e.g., HCl) affords final compounds (e.g., Compound 47 of Table 1) of the type S11i.

Scheme 12

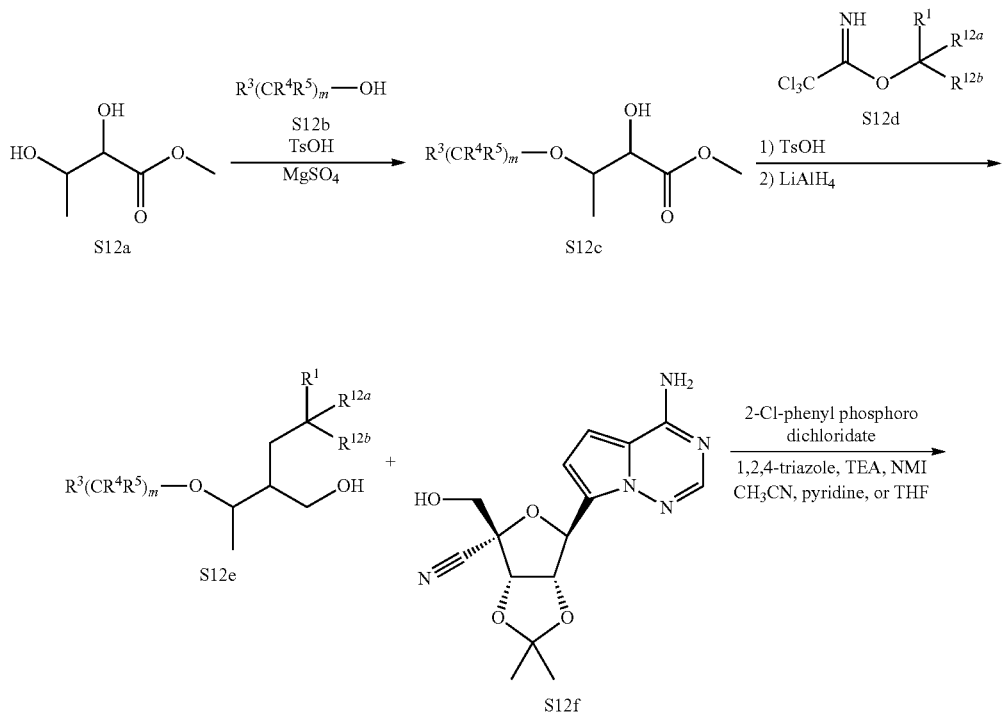

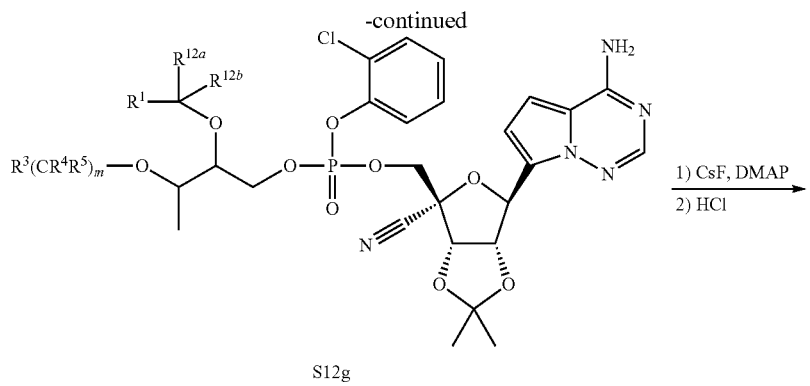

S12g

S12h

Scheme 12 shows a general synthesis of compounds beginning with addition of an alcohol S12b to S12a under acidic conditions (e.g., TsOH, MgSO$_4$, Servi, S. *J. Org. Chem.* 1985, 50, 5865) to afford alcohol S12c. A substitution reaction with S12d under acidic conditions (e.g., TsOH) and reduction of the ester (e.g., LiAlH$_4$) affords alcohol S12e. The alcohol S12e and nucleoside S1f are coupled with 2-Cl-phenyl phosphorodichloridate under basic conditions (e.g., 1,2,4-triazole, TEA, NMI, CH$_3$CN, pyridine, or THF) to afford S12g. Removal of the 2-Cl-phenol (e.g., CsF, DMAP) and acetonide (e.g., HCl) affords final compounds (e.g., Compound 64 of Table 1) of the type S12 h.

Scheme 13

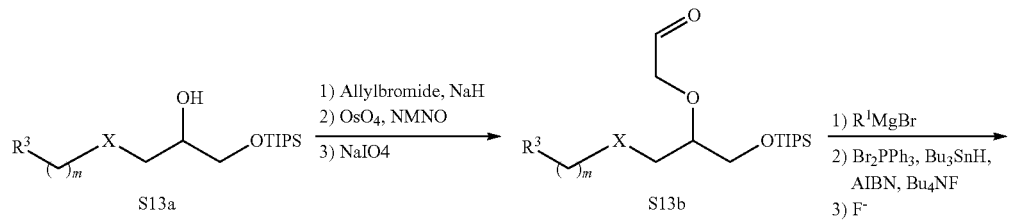

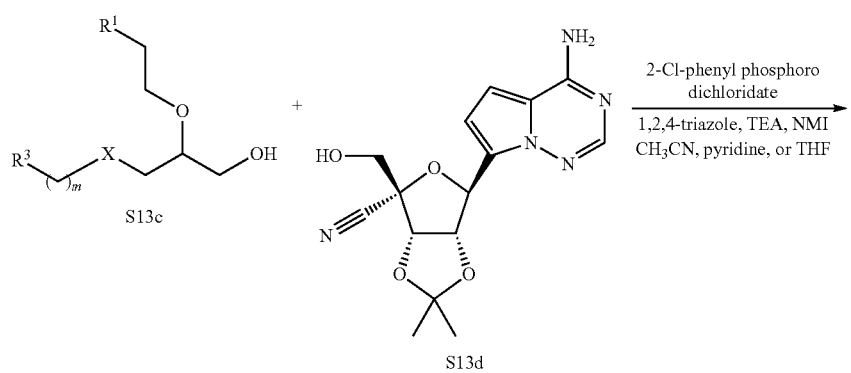

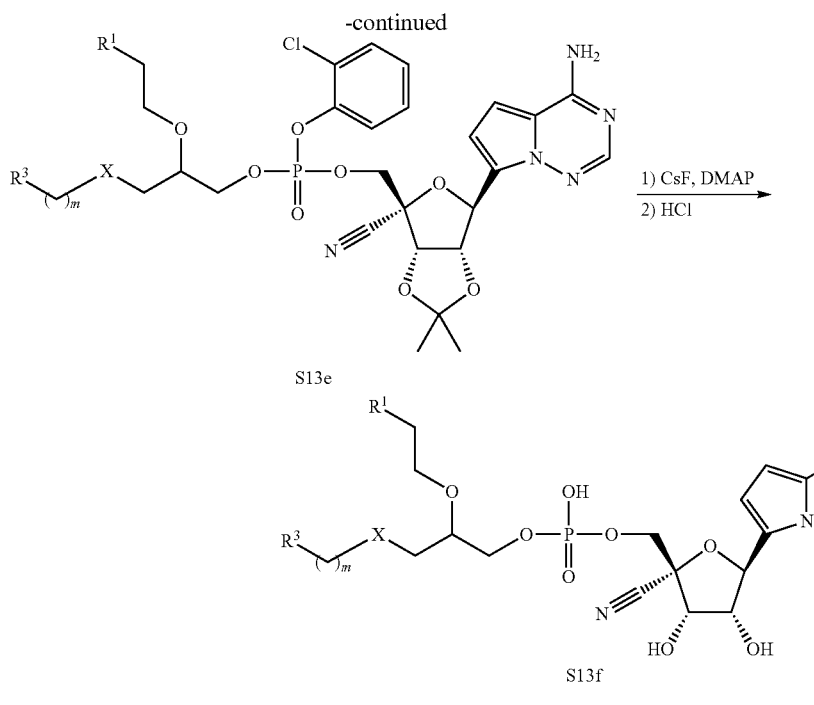

S13e

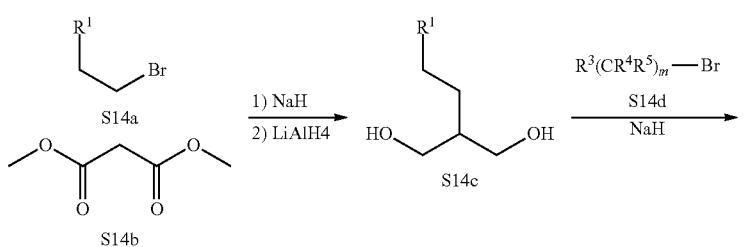

S13f

X = O, CH$_2$

Scheme 13 shows a general synthesis of compounds beginning with allylation of alcohol S13a followed by dihydroxylation (e.g., OsO4, NMNO) and cleavage of the vincinal diols (e.g., NaIO$_4$) to afford aldehyde S13b. Addition of a Grignard reagent to the aldehyde affords the secondary alcohol that is deoxygenated (e.g., Br$_2$PPh$_3$, Bu$_3$SnH, AIBN, Bu$_4$NF) followed by removal of the protecting group (e.g., TBAF) to afford S13c. The alcohol S13c and nucleoside S13d are coupled with 2-Cl-phenyl phosphorodichloridate under basic conditions (e.g., 1,2,4-trizole, TEA, NMI, CH$_3$CN, pyridine, or THF) to afford S13e. Removal of the 2-Cl-phenol (e.g., CsF, DMAP) and acetonide (e.g., HCl) affords final compounds (e.g., Compound 48 or Compound 49 of Table 1) of the type S13f.

Scheme 14

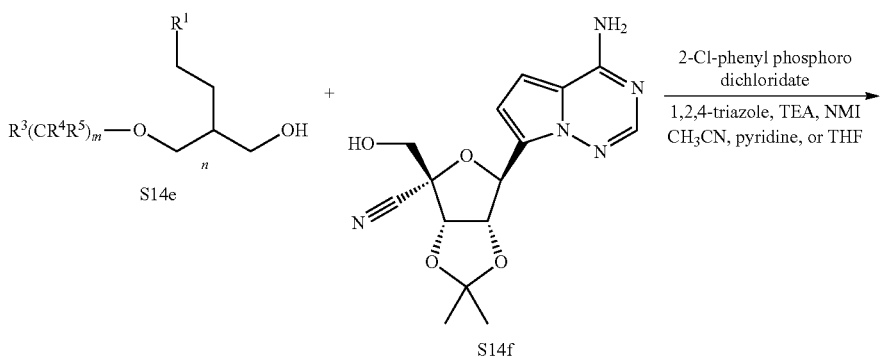

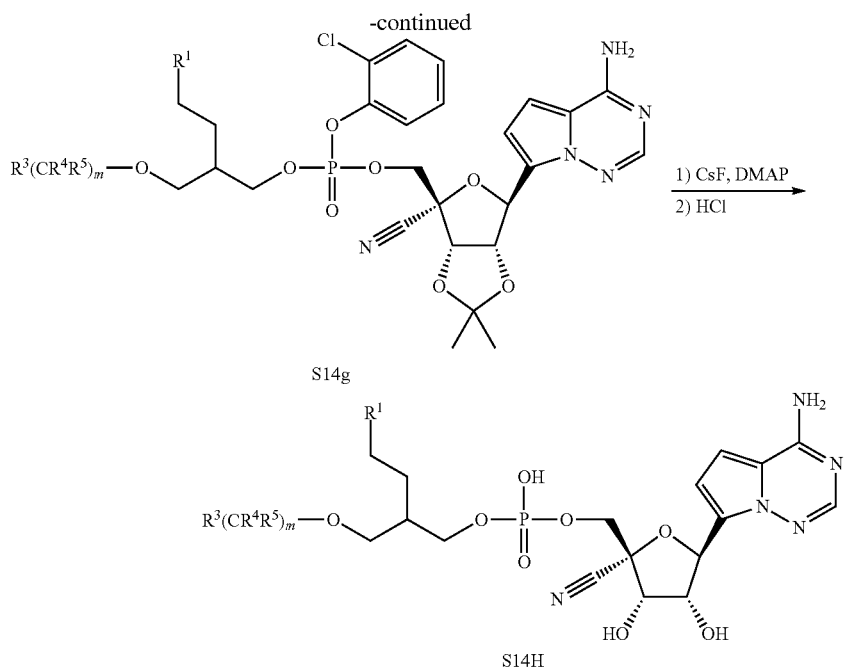

S14g

S14H

Scheme 14 shows a general synthesis of compounds beginning with a substitution reaction of malonate S14b to the alkyl halide S14a under basic conditions (e.g., NaH) followed by reduction (e.g., LiAlH₄) of the esters to afford S14c. A substitution reaction of alcohol S14c with the alkyl halide (e.g., Br) S14d under basic conditions (e.g., NaH) affords S14e (Subba Reddy et al., EUR. J. ORG. CHEM 2013, 10, 1993-1999). The alcohol S14e and nucleoside S14f are coupled with 2-Cl-phenyl phosphorodichloridate under basic conditions (e.g., 1,2,4-triazole, TEA, NMI, CH₃CN, pyridine, or THF) to afford S14e. Removal of the 2-Cl-phenol (e.g., CsF, DMAP) and acetonide (e.g., HCl) affords final compounds (e.g., Compound 52 of Table 1) of the type S14f.

Scheme 15

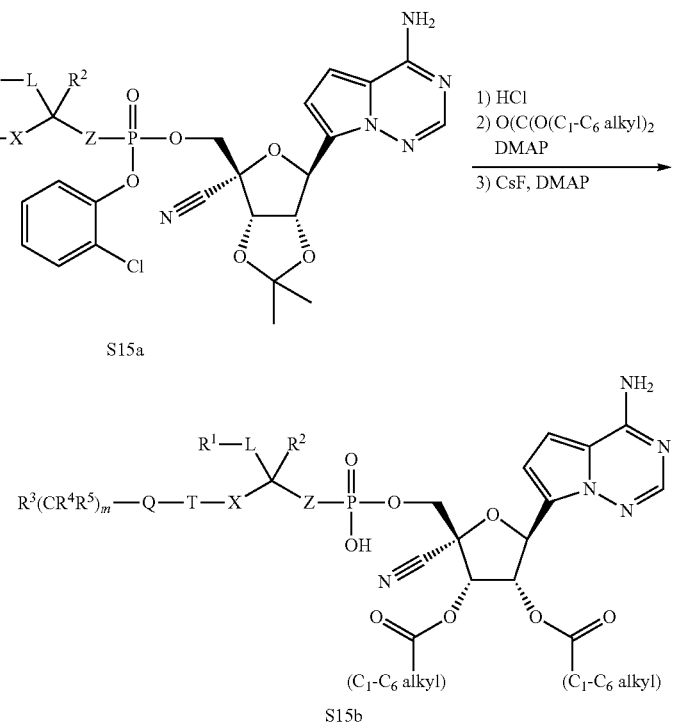

S15a

S15b

Scheme 15 shows a general synthesis of compounds beginning with acetonide cleavage under acid conditions (e.g., HCl), followed by esterification of the 2'- and 3'-ribose alcohols with an anhydride reagent under basic conditions (e.g., DMAP). Removal of the 2-Cl-phenol (e.g., CsF, DMAP) affords final compounds of the type S15b.

EXAMPLES

A. Abbreviations

Certain abbreviations and acronyms are used in describing the experimental details. Although most of these would be understood by one skilled in the art, Table 41 contains a list of many of these abbreviations and acronyms.

TABLE 41

| List of abbreviations and acronyms. | |
| --- | --- |
| Abbreviation | Meaning |
| Ac | acetate |
| ACN | acetonitrile |
| AIBN | azobisisobutyronitrile |
| Bn | benzyl |
| Bu | butyl |
| Bz | benzoyl |
| BzCl | benzoyl chloride |
| CDI | 1,1'-carbonyldiimidazole |
| DAST | diethylaminosulfur trifluoride |
| DCE | 1,2-dichloroethane |
| DCM | dichloromethane |
| DIPEA | N,N-diisopropylethylamine |
| DMAP | 4-dimethylamiopyridine |
| DMDO | dimethydioxirane |
| DMSO | dimethylsulfoxide |
| DMF | dimethylformamide |
| DMTrCl | 4,4'-dimethoxytritylchloride |
| DMTr | 4,4'-dimethoxytrityl |
| EDCI | N-(3-dimethylaminopropyl)-N'-ethylcarbodiimide hydrochloride |
| Et | ethyl |
| Imid | imidazole |
| KOtBu | potassium tert-butoxide |
| LC | liquid chromatography |
| MCPBA | meta-chloroperbenzoic acid |
| Me | methyl |
| m/z | mass to charge ratio |
| MS or ms | mass spectrum |
| NIS | N-iodosuccinimide |
| NMI | N-Methylimidazole |
| NMP | N-methyl-2-pyrrolidone |
| Ph | phenyl |
| Ph$_3$P | triphenylphosphine |
| PMB | para-methoxybenzyl |
| PMBCl | para-methoxybenzyl chloride |
| PhOC(S)Cl | phenylchlorothionoformate |
| (PhO)$_3$PMeI | methyltriphenoxyphosphonium iodide |
| Pyr | pyridine |
| RT | room temperature |
| SFC | supercritical fluid chromatography |
| TBAF | tetrabutylammonium fluoride |
| TBS | tert-butyldimethylsilyl |
| TBSCl | tert-Butyldimethylsilyl chloride |
| TMSN$_3$ | trimethylsilyl azide |
| TEA | triethylamine |
| TES | triethylsilane |
| TFA | trifluoroacetic acid |
| THF | tetrahydrofuran |
| TMS | trimethylsilyl |
| TMSCl | trimethylsilyl chloride |
| Ts | 4-toluenesulfonyl |
| TsOH | tosylic acid |
| δ | parts per million referenced to residual non-deuterated solvent peak |

B. Intermediates

Intermediate I-1: (S)-1-O-trityl-3-(heptadecyloxy) propane-1,2-diol

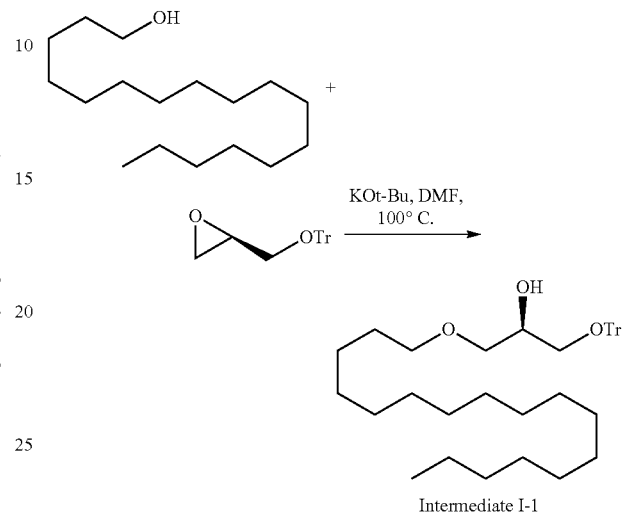

Potassium tert-butoxide (18.7 mmol) and hexadecanol (8.42 mmol) were added to a solution of (S)—O-trityloxiran-2-ylmethanol (4.68 mmol) in DMF (40 mL). The resulting mixture was stirred at 100° C. for 2 h, cooled to room temperature, diluted with ether (300 mL), washed with brine (100 mL×2), dried with sodium sulfate, and purified by silica gel column chromatography (0% to 20% EtOAc in hexanes) to give Intermediate I-1. $^1$H NMR (400 MHz, DMSO-d6) δ 7.50-7.10 (m, 15H), 4.86 (d, J=5.4 Hz, 1H), 3.76 (q, J=5.4 Hz, 1H), 3.38 (m, 2H), 3.33 (s, 2H), 2.95 (m, 2H), 1.41 (m, 2H), 1.22 (d, J=11.2 Hz, 28H), 0.89-0.79 (m, 3H).

Intermediate I-2: (R)-3-fluoro-5-(((1-(heptadecyloxy)-3-(trityloxy)propan-2-yl)oxy)methyl) benzonitrile

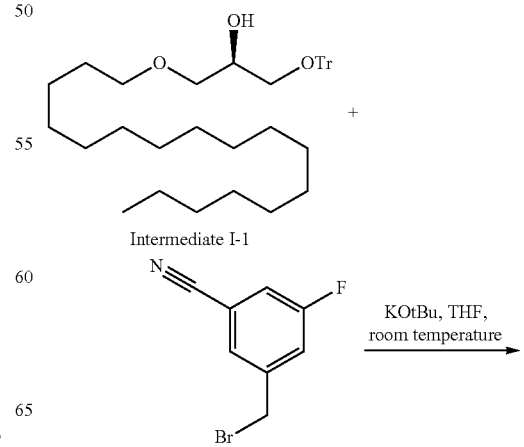

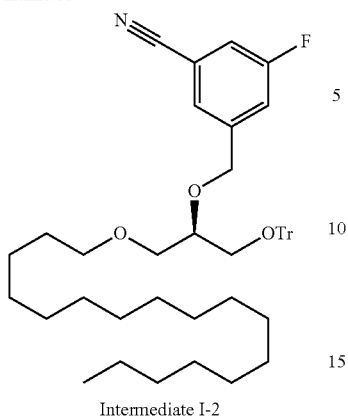

Intermediate I-2

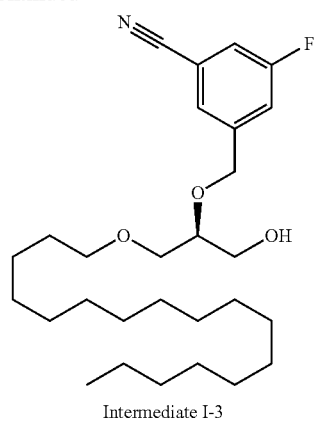

Intermediate I-3

To a solution of Intermediate I-1 (1.52 mmol) in THF (8 mL) was added potassium tert-butoxide (3.04 mL, 1.0 M, 3.04 mmol). The mixture was stirred for 20 min and 3-(bromomethyl)-5-fluoro-benzonitrile (3.04 mmol) added. The resulting mixture was stirred for 4 h at room temperature, diluted with water (50 mL) and extracted with EtOAc (3×50 mL). The organic fractions were combined, washed with brine (50 mL), dried over Na$_2$SO$_4$, filtered, concentrated in vacuo, and purified by silica gel chromatography (0% to 10% EtOAc in hexanes) to give Intermediate I-2. $^1$H NMR (400 MHz, DMSO-d6) δ 7.77 (d, J=8.9 Hz, 1H), 7.66 (s, 1H), 7.58 (d, J=9.6 Hz, 1H), 7.43-7.16 (m, 15H), 4.68 (s, 2H), 3.77-3.66 (m, 1H), 3.50 (m, 2H), 3.32 (m, 2H, buried by solvent peak), 3.15 (dd, J=10.1, 3.8 Hz, 1H), 3.07 (dd, J=10.1, 5.7 Hz, 1H), 1.42 (s, 2H), 1.34-1.00 (m, 28H), 0.85 (t, J=6.6 Hz, 3H).

Intermediate I-3: (S)-3-fluoro-5-(((1-(heptadecyloxy)-3-hydroxypropan-2-yl)oxy)methyl) benzonitrile To a solution of Intermediate I-2 (1.42 mmol) in THF-iPrOH-MeOH (1.4:1.4:1.4 mL) was added 25% HCl (0.7 mL). The resulting mixture was heated at 65° C. for 45 min, cooled, and sat NaHCO$_3$ (10 mL) added. After stirring for 5 min, the mixture was extracted with EtOAc (100 mL×2). The aqueous layer was extracted with EtOAc (50 mL×2). The combined organic layer was dried with sodium sulfate, concentrated in vacuo, and purified by silica gel column chromatography (0% to 40% EtOAc in hexanes) to give Intermediate I-3. $^1$H NMR (400 MHz, Acetonitrile-d3) δ 7.61 (s, 1H), 7.50 (dd, J=9.6, 2.4 Hz, 1H), 7.44 (dt, J=8.5, 1.8 Hz, 1H), 4.73 (s, 2H), 3.68-3.50 (m, 5H), 3.43 (m, 2H), 2.84 (t, J=5.7 Hz, 1H), 1.55 (m, 2H), 1.39-1.21 (m, 28H), 0.91 (t, J=6.7 Hz, 3H).

Intermediate I-3a1: (3aS,4R,6S,6aS)-6-(4-aminopyrrolo[2,1-f][1,2,4]triazin-7-yl)-4-(((tert-butyldimethylsily)oxy)methyl)-2,2-dimethyltetrahydrofuro[3,4-d][1,3]dioxole-4-carbonitrile

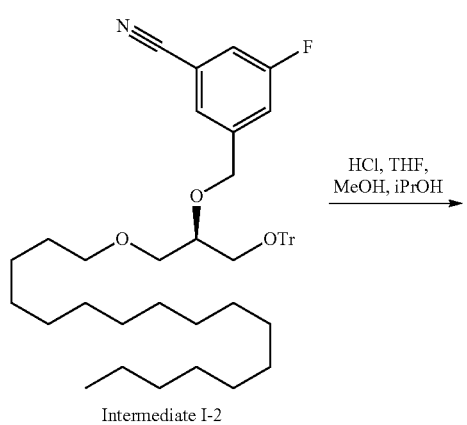

Intermediate I-2

HCl, THF, MeOH, iPrOH →

Intermediate I-3a1

Intermediate I-3a1 was prepared according to WO2015/069939. For example, pages 127-138 of WO2015/069939 provide a process for preparing this compound (identified as compound 14k in WO2015/069939).

Intermediate I-3a: (3aS,4R,6S,6aS)-6-(4-aminopyr-rolo[2,1-f][1,2,4]triazin-7-yl)-4-(hydroxymethyl)-2,2-dimethyltetrahydrofuro[3,4-d][1,3]dioxole-4-carbonitrile

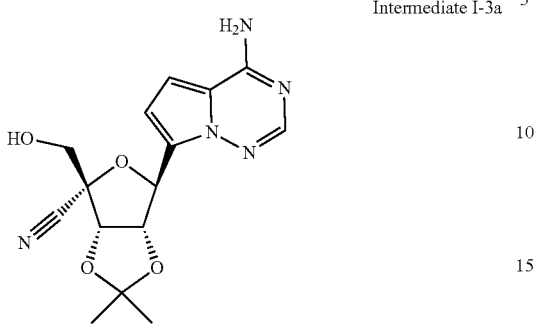

Intermediate I-3a

Took up Intermediate I-3a1 (18.87 mmol) in THF (100 mL). Added TBAF 1.0 M in THF (28.31 mmol) in one portion at ambient temperature. Allowed to stir at ambient temperature for 10 min. The reaction was determined to be complete by LCMS. The reaction mixture was quenched with water and the organics were removed under reduced pressure. The crude was partitioned between EtOAc and Water. The layers were separated and the aqueous was washed with EtOAc. The organics were combined and dried over sodium sulfate. The solids were filtered off and the solvent removed under reduced pressure. The crude was purified by silica gel chromatography 120 g column 0% to 10% $CH_3OH$ in $CH_2Cl_2$ to afford Intermediate I-3a. LC/MS: $t_R$=0.76 min, MS m/z=332.14 [M+1]; LC system: Thermo Accela 1250 UHPLC. MS system: Thermo LCQ Fleet; Column: Kinetex 2.6μ XB-C18 100A, 50×3.00 mm. Solvents: Acetonitrile with 0.1% formic acid, Water with 0.1% formic acid. Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min. $^1$H NMR (400 MHz, DMSO-$d_6$) δ 7.87-7.80 (m, 3H), 6.85 (d, J=4.5 Hz, 1H), 6.82 (d, J=4.5 Hz, 1H), 5.74 (t, J=5.8 Hz, 1H), 5.52 (d, J=4.2 Hz, 1H), 5.24 (dd, J=6.8, 4.2 Hz, 1H), 4.92 (d, J=6.8 Hz, 1H), 3.65 (dd, J=6.1, 1.7 Hz, 2H), 1.61 (s, 3H), 1.33 (s, 3H).

Intermediate I-4: ((3aS,4R,6S,6aS)-6-(4-aminopyr-rolo[2,1-f][1,2,4]triazin-7-yl)-4-cyano-2,2-dimethyl-tetrahydrofuro[3,4-d][1,3]dioxol-4-yl)methyl (2-chlorophenyl) ((R)-2-((3-cyano-5-fluorobenzyl)oxy)-3-(heptadecyloxy)propyl) phosphate

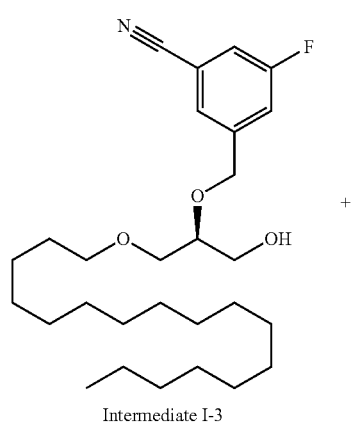

Intermediate I-3

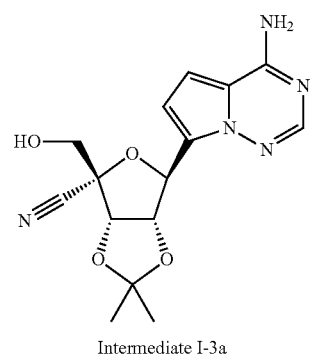

Intermediate I-3a

| 2-Cl-phenyl phosphoro dichloridate, 1,2,4-triazole, TEA, NMI ↓

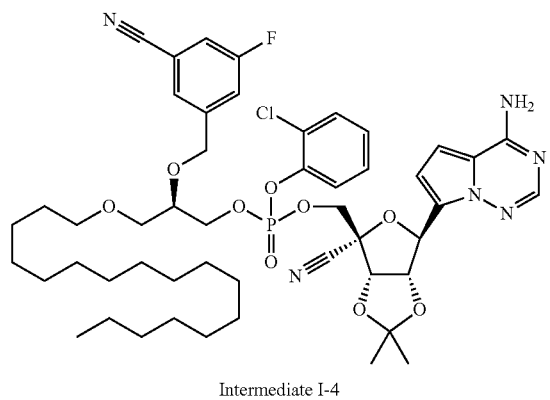

Intermediate I-4

To a solution of 1H-1,2,4-triazole (0.844 mmol) and TEA (0.118 mL, 0.844 mmol) in ACN (0.5 mL)-pyridine (0.2 mL) was added 2-chlorophenyl phosphorodichloridate (0.065 mL, 0.392 mmol) at room temperature. The reaction mixture was stirred at room temperature for 30 min, Intermediate I-3a (0.392 mmol) and then 1-methylimidazole (0.0631 mL, 0.792 mmol) added. The resulting mixture was stirred for 1 h at room temperature and Intermediate I-3 (0.430 mmol) added. The reaction resulting reaction mixture was stirred for 2 h and 30 min and concentrated in vacuo and purified by silica gel column chromatography (0% to 100% MeOH in DCM) to give Intermediate I-4. $^1$H NMR (400 MHz, Acetonitrile-d3) δ 7.86 (d, J=3.5 Hz, 1H), 7.54-7.29 (m, 5H), 7.26-7.05 (m, 2H), 6.83-6.63 (m, 2H), 6.26 (s, 2H), 5.67 (m, 1H), 5.34-5.22 (m, 1H), 5.14-5.06 (m, 1H), 4.67-4.42 (m, 4H), 4.41-4.28 (m, 1H), 4.27-4.16 (m, 1H), 3.75 (m, 1H), 3.53-3.42 (m, 2H), 3.42-3.28 (m, 2H), 1.72 (s, 3H), 1.58-1.44 (m, 2H), 1.38 (s, 3H), 1.35-1.17 (m, 28H), 0.90 (m, 3H). $^{19}$F NMR (376 MHz, Acetonitrile-d3) δ−112.78, −112.79. $^{31}$P NMR (162 MHz, Acetonitrile-d3) δ−7.31, −7.36. MS m/z [M+1]=967.

Intermediate I-5: (R)-3-((1-(octadecyloxy)-3-(trityloxy)propan-2-yl)oxy)benzonitrile

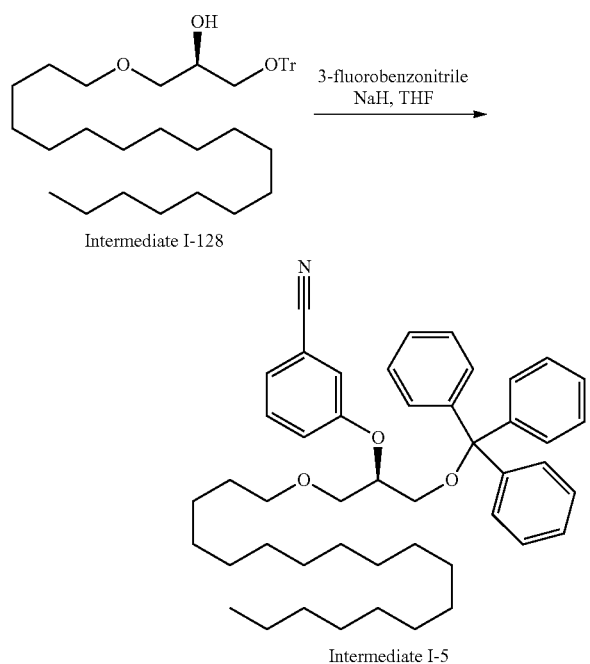

Intermediate I-128

Intermediate I-5

To a solution of Intermediate I-128 (1.14 mmol) in DMF (10 mL) was added NaH (60% in mineral oil) at room temperature. The mixture was stirred at room temperature for 1 h and 3-fluorobenzonitrile (115 mg, 0.950 mmol) added. The resulting mixture was then heated at 60° C. for 30 min, diluted with EtOAc (100 mL) and the reaction quenched by adding water (10 mL). The organic phase was dried with sodium sulfate, concentrated in vacuo, and purified by silica gel column chromatography (0% to 10% EtOAc in hexanes) to give Intermediate I-5. 1H NMR (400 MHz, DMSO-d6) δ 7.77 (d, J=8.9 Hz, 1H), 7.66 (s, 1H), 7.58 (d, J=9.6 Hz, 1H), 7.43-7.16 (m, 16H), 4.68 (s, 2H), 3.77-3.66 (m, 1H), 3.56-3.43, (m, 2H), 3.15 (dd, J=10.1, 3.8 Hz, 1H), 3.07 (dd, J=10.1, 5.7 Hz, 1H), 1.42 (s, 2H), 1.34-1.00 (m, 30H), 0.85 (t, J=6.6 Hz, 3H).

Intermediate I-6: (S)-3-((1-hydroxy-3-(octadecyloxy)propan-2-yl)oxy)benzonitrile

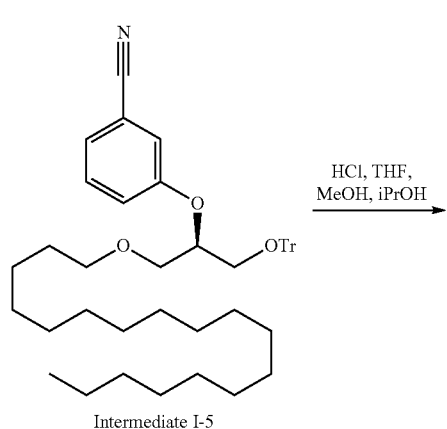

Intermediate I-5

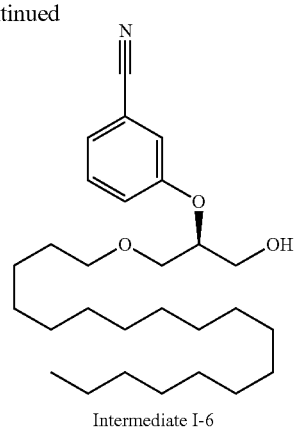

Intermediate I-6

To a solution of Intermediate I-5 (0.469 mmol) as prepared, for instance, as described above, in THF-iPrOH-MeOH (1.5:1.5:1.5 mL) was added 25% HCl (0.3 mL). The resulting mixture was heated at 65° C. for 45 min, cooled, and sat NaHCO₃ (10 mL) added. After stirring for 5 min, it was extracted with EtOAc (50 mL×2). The aqueous layer was extracted with EtOAc (20 mL×2). The combined organic layer was dried with sodium sulfate, concentrated in vacuo, and purified by silica gel column chromatography (0% to 40% EtOAc in hexanes) to give Intermediate I-6. ¹H NMR (400 MHz, Acetonitrile-d3) δ 7.48-7.42 (m, 1H), 7.37 (m, 1H), 7.34-7.27 (m, 2H), 4.51 (ddd, J=10.1, 5.7, 4.3 Hz, 1H), 3.78-3.54 (m, 4H), 3.44 (m, 2H), 2.98 (t, J=6.1 Hz, 1H), 1.51 (m, 2H), 1.38-1.19 (m, 30H), 0.91 (m, 3H).

Intermediate I-7: ((3aS,4R,6S,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl (2-chlorophenol) ((R)-2-(3-cyanophenoxy)-3-(octadecyloxy)propyl) phosphate

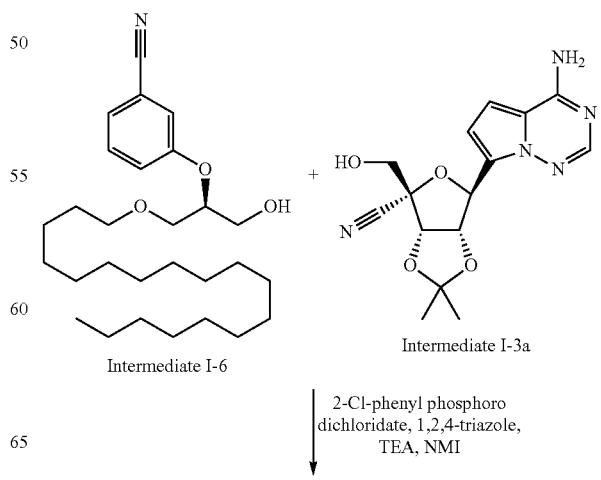

Intermediate I-6

Intermediate I-3a

| 2-Cl-phenyl phosphoro dichloridate, 1,2,4-triazole, TEA, NMI

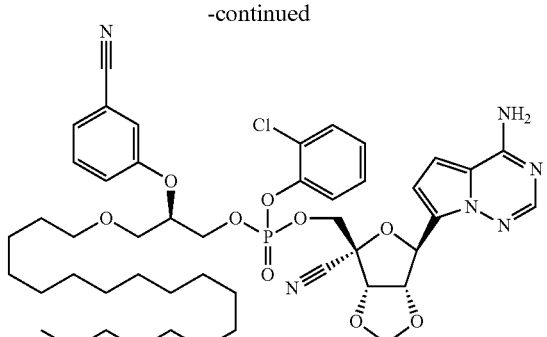

Intermediate I-7

To a solution of 1H-1,2,4-Triazole (1.00 mmol) in THF (2 mL) were added TEA (0.139 mL, 1.00 mmol) and 2-chlorophenyl phosphorodichloridate (0.0807 mL, 0.49 mmol) added at room temperature and stirred for 30 min. To this mixture was added Intermediate I-3a (0.38 mmol) in one portion followed by 1-methylimidazole (0.0391 mL, 0.49 mmol). The resulting mixture was stirred for 30 min and then Intermediate I-6 (0.38 mmol) in THF (2 mL) added dropwise. After 15 h stirring at room temperature, the mixture was concentrated in vacuo and purified by silica gel column chromatography (0% to 10% MeOH in DCM) to give Intermediate I-7. $^1$H NMR (400 MHz, Methanol-d4) δ 7.83 (m, 1H), 7.55-7.05 (m, 8H), 6.83-6.72 (m, 2H), 5.68 (m, 1H), 5.33-5.29 (m, 1H), 5.16 (d, J=6.6 Hz, 0.5H), 5.11 (d, J=6.6 Hz, 0.5H), 4.71-4.64 (m, 1H), 4.60-4.37 (m, 4H), 3.63-3.51 (m, 2H), 3.46-3.34 (m, 2H), 1.73 (s, 3H), 1.53-1.42 (m, 2H), 1.38 (s, 3H), 1.34-1.17 (m, 30H), 0.89 (t, J=6.7 Hz, 3H). $^{31}$P NMR (162 MHz, Methanol-d4) δ −6.46, −6.48. MS m/z [M+1]=949.

Intermediate I-8: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-(3-cyanophenoxy)-3-(octadecyloxy)propyl) hydrogen phosphate

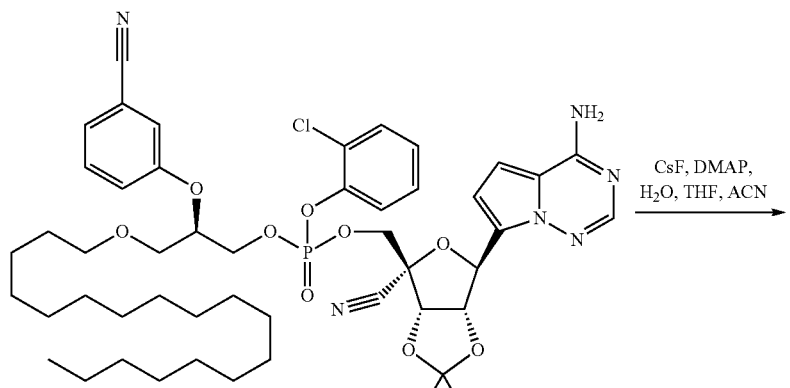

Intermediate I-7

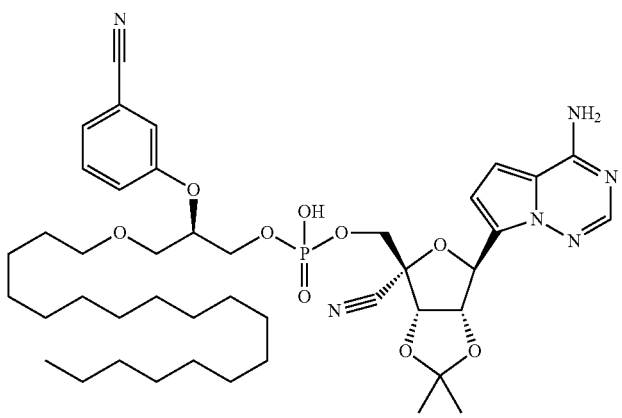

Intermediate I-8

Intermediate I-7 (0.179 mmol) was dissolved in THF-ACN (2:1 mL) and CsF (1.55 mmol) in water (0.2 mL) and then DMAP (0.66 mmol) added. The resulting mixture was heated at 80° C. for 3.5 h. After dilution with PBS buffer pH 7 (10 mL), the mixture was partitioned between brine (20 mL) and EtOAc (40 mL). Aqueous layer was extracted with EtOAc (20 mL×3). The combined organic layer was dried under sodium sulfate, concentrated in vacuo, and purified by silica gel column chromatography (0%-50% MeOH in DCM) to give Intermediate I-8. MS m/z [M+1]=839.

Intermediate I-9: (R)-2-chloro-4-(((1-(octadecyloxy)-3-(trityloxy)propan-2-yl)oxy)methyl) benzonitrile

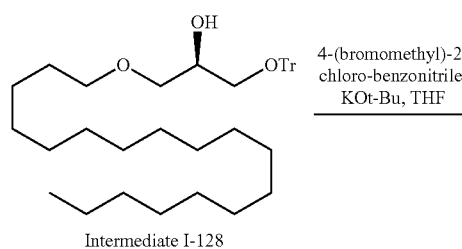

Intermediate I-128

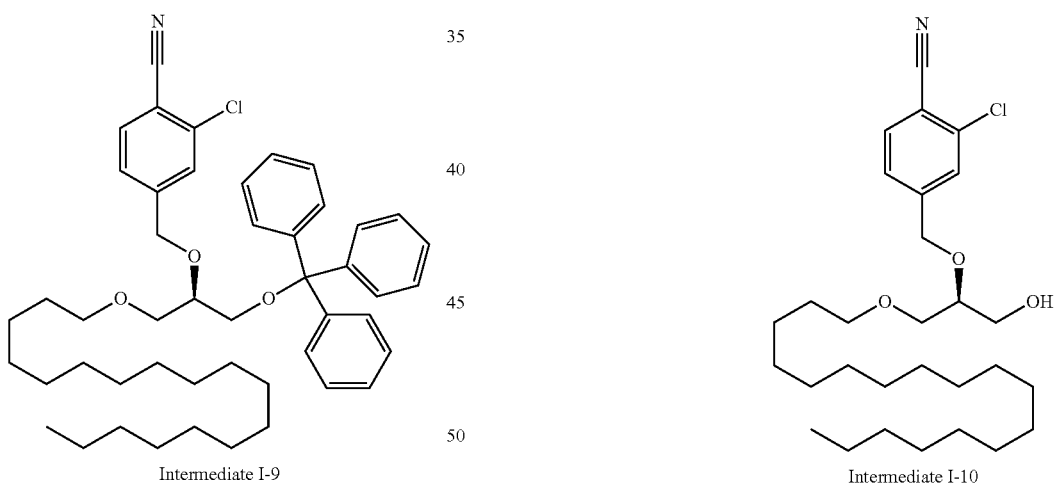

Intermediate I-9

Intermediate I-9

Intermediate I-10

To a solution of Intermediate I-128 (2.56 mmol) in THF (20 mL) was added sodium tert-butoxide powder (5.11 mmol). The solution was stirred for 40 min at room temperature. 4-(bromomethyl)-2-chloro-benzonitrile (5.11 mmol) in THF (5 mL) was added drop wise and the mixture stirred for 7 h at room temperature. The reaction mixture was diluted with water (50 mL) and extracted with EtOAc (3×50 mL). The organic fractions were combined, washed with brine (50 mL), dried over $Na_2SO_4$, filtered, concentrated in vacuo, and purified by silica gel chromatography (0% to 10% EtOAc in hexanes) to give Intermediate I-9. $^1$H NMR (400 MHz, Chloroform-d) δ 7.62 (d, J=8.0 Hz, 1H), 7.58 (d, J=1.4 Hz, 1H), 7.49-7.42 (m, 6H), 7.37-7.24 (m, 10H), 4.73 (s, 2H), 3.74 (m, 1H), 3.60 (d, J=5.2 Hz, 2H), 3.44 (t, J=6.6 Hz, 2H), 3.26 (m, 2H), 1.64-1.52 (m, 2H), 1.43-1.06 (s, 30H), 0.91 (t, J=6.7 Hz, 3H).

Intermediate I-10: (S)-2-chloro-4-(((1-hydroxy-3-(octadecyloxy)propan-2-yl)oxy)methyl) benzonitrile To a solution of Intermediate I-9 (0.815 mmol) in THF-iPrOH-MeOH (3:3:3 mL) was added 25% HCl (0.5 mL). The resulting mixture was heated at 65° C. for 45 min, cooled, and 10 mL sat $NaHCO_3$ added. After stirring for 5 min, it was extracted with EtOAc (40 mL×3). The combined organic layer was dried with sodium sulfate, concentrated in vacuo, and purified by silica gel chromatography (0% to 40% EtOAc in hexanes) to give Intermediate I-10. 1H NMR (400 MHz, Acetonitrile-d3) δ 7.77 (d, J=8.0 Hz, 1H), 7.69 (d, J=1.4 Hz, 1H), 7.47 (dd, J=8.0, 1.4 Hz, 1H), 4.75 (s, 2H), 3.67-3.48 (m, 5H), 3.42 (m, 2H), 2.83 (t, J=5.7 Hz, 1H), 1.54 (m, 2H), 1.40-1.22 (m, 30H), 0.96-0.86 (m, 3H).

Intermediate I-11: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-chloro-4-cyanobenzyl) oxy)-3-(octadecyloxy)propyl) (2-chlorophenyl) phosphate

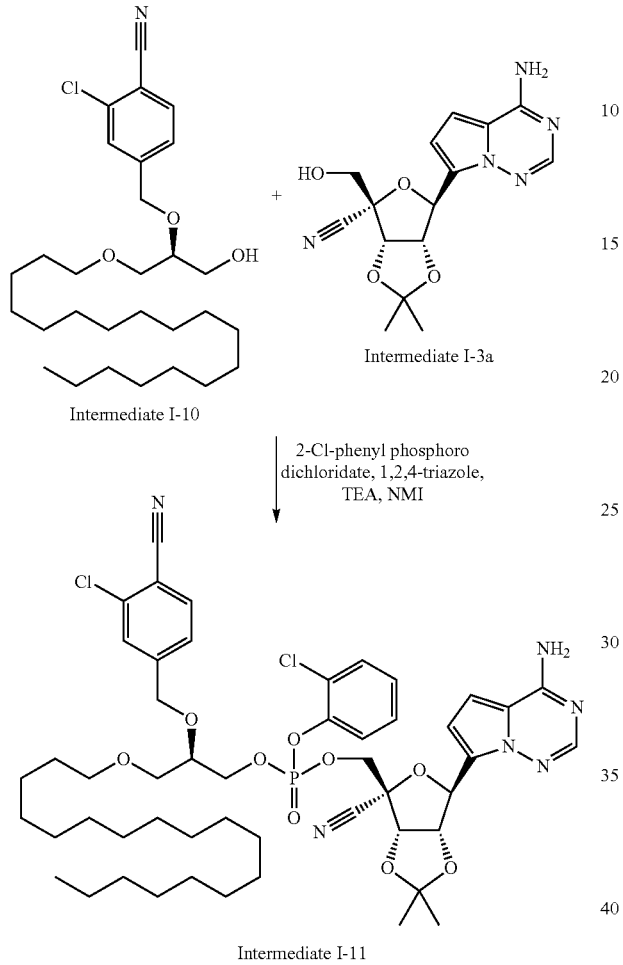

1H-1,2,4-triazole (0.664 mmol) was dissolved in THF (2 mL) AND TEA (0.09 mL, 0.664 mmol) added at room temperature. To the mixture was added 2-chlorophenyl phosphorodichloridate (0.081 mL, 0.501 mmol) dropwise. The reaction mixture was stirred at room temperature for 30 min. Intermediate I-3a (0.251 mmol) was added in one portion and the mixture stirred at room temperature for 15 min. To the mixture were added Intermediate I-10 (0.275 mmol) in THF (2 mL) and 1-methylimidazole (0.04 mL, 0.506 mmol) were added at room temperature. The resulting mixture was stirred for 1h, concentrated in vacuo, and purified by silica gel (0% to 10% MeOH in DCM) to give Intermediate I-11. $^1$H NMR (400 MHz, Acetonitrile-d3) δ 7.86 (s, 1H), 7.66 (d, J=7.9 Hz, 1H), 7.54 (d, J=6.1 Hz, 1H), 7.48-7.40 (m, 1H), 7.39-7.29 (m, 2H), 7.24-7.12 (m, 2H), 6.80-6.67 (m, 2H), 6.38 (s, 2H), 5.69-5.65 (m, 1H), 5.32-5.24 (m, 1H), 5.13-5.01 (m, 1H), 4.65 (s, 1H), 4.60 (s, 1H), 4.58-4.44 (m, 2H), 4.40-4.30 (m, 1H), 4.29-4.17 (m, 1H), 3.76 (m, 1H), 3.51-3.41 (m, 2H), 3.42-3.30 (m, 2H), 1.72 (s, 3H), 1.49 (m, 2H), 1.37 (s, 3H), 1.34-1.06 (m, 30H), 0.89 (t, J=6.7 Hz, 3H). $^{31}$P NMR (162 MHz, Acetonitrile-d3) δ−7.32, −7.38. MS m/z [M+1]=997.

Intermediate I-12: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-chloro-4-cyanobenzyl) oxy)-3-(octadecyloxy) propyl) hydrogen phosphate

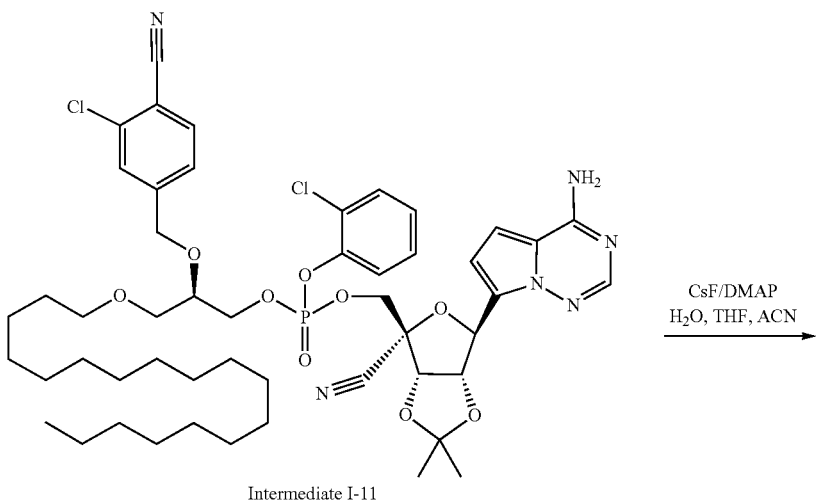

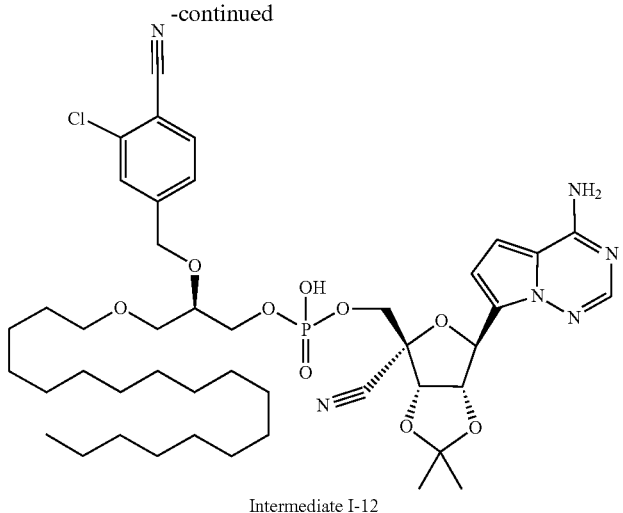

Intermediate I-12

Intermediate I-11 (0.179 mmol) was dissolved in THF-ACN (2:1 mL) and CsF (1.46 mmol) in water (0.2 mL) and then DMAP (0.621 mmol) added. The resulting mixture was heated at 80° C. for 4 h. After dilution with citric acid NaOH buffer (pH 4, 10 mL), the mixture was partitioned between brine (20 mL) and EtOAc (40 mL). Aqueous layer was extracted with EtOAc (20 mL×3). The combined organic layer was dried under sodium sulfate, concentrated in vacuo, and purified by silica gel column chromatography (0% to 50% MeOH in DCM) to give Intermediate I-12. MS m/z [M+1]=887.

Intermediate I-14: (R)-docosane-1,2-diol

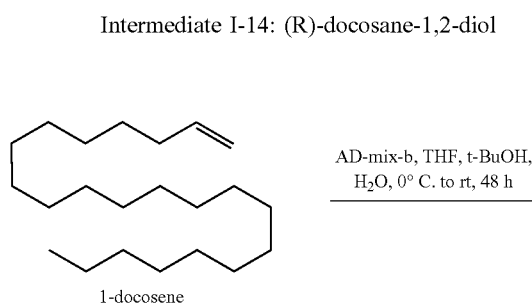

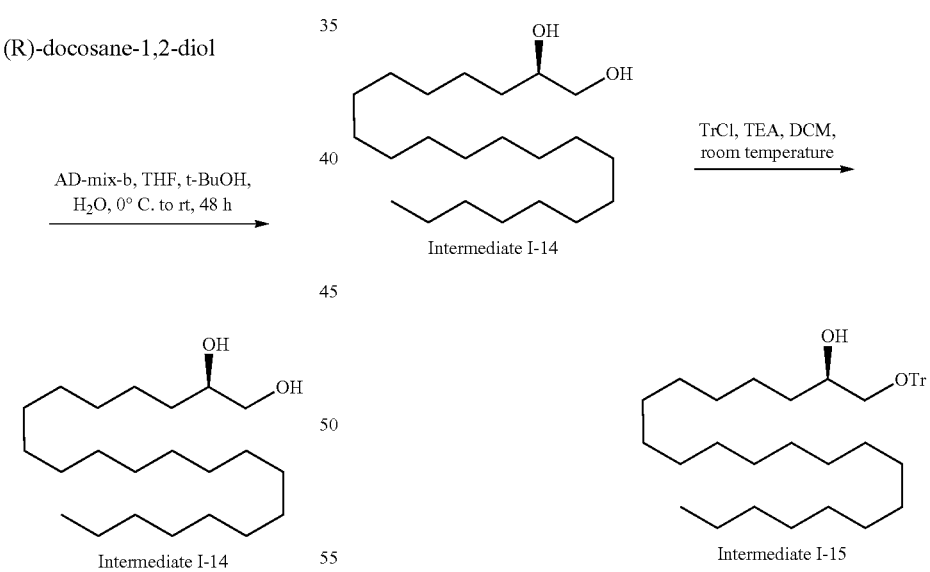

AD-mix-β (28 g) was dissolved in t-butanol (100 mL)-water (100 mL) and cooled to 0° C. Then 1-docosene (6.2 g, 20.1 mmol) in THF (100 mL) was added dropwise at 0° C. The resulting mixture was stirred at room temperature for 48 h and Na$_2$SO$_3$ (30 g) added. The mixture was extracted with EtOAc (150 mL×3), and the extract washed with brine (100 mL) and dried with sodium sulfate concentrated in vacuo. The obtained residue was purified by silica gel column chromatography (0% to 50% EtOAc in hexanes) to give Intermediate I-14. $^1$H NMR (400 MHz, DMSO-d6) δ 4.39 (t, J=5.7 Hz, 1H), 4.31 (d, J=4.9 Hz, 1H), 3.41-3.33 (m, 1H), 3.23 (m, 2H), 1.39 (m, 2H), 1.24 (s, 36H), 0.92-0.79 (m, 3H).

Intermediate I-15: (R)-1-(trityloxy)docosan-2-ol

Intermediate I-14 (60% purity, 4.3 mmol) was dissolved in DCM (20 mL) and TEA (1.5 mL, 10.8 mmol) added. The resulting mixture was stirred for 5 min and TrCl (4.30 mmol) in DCM (10 mL) added dropwise at room temperature. The resulting mixture was stirred for 20 h and hexanes (20 mL) added. The solid was filtered off, the filtrate concentrated in vacuo, and purified by silica gel column chromatography (0% to 20% EtOAc in hexanes) to give Intermediate I-15. $^1$H NMR (400 MHz, Chloroform-d) δ 7.46 (dd, J=7.7, 1.8 Hz, 6H), 7.33 (dd, J=8.4, 6.6 Hz, 6H), 7.29-7.23 (m, 2H), 3.78

(m, 1H), 3.20 (dd, J=9.4, 3.2 Hz, 1H), 3.04 (dd, J=9.3, 7.6 Hz, 1H), 1.56 (s, 1H), 1.48-1.19 (m, 36H), 0.90 (t, J=6.7 Hz, 3H).

Intermediate I-16: (R)-3-((1-(triphenyl-14-ox-idaneyl)docosan-2-yl)oxy)benzonitrile

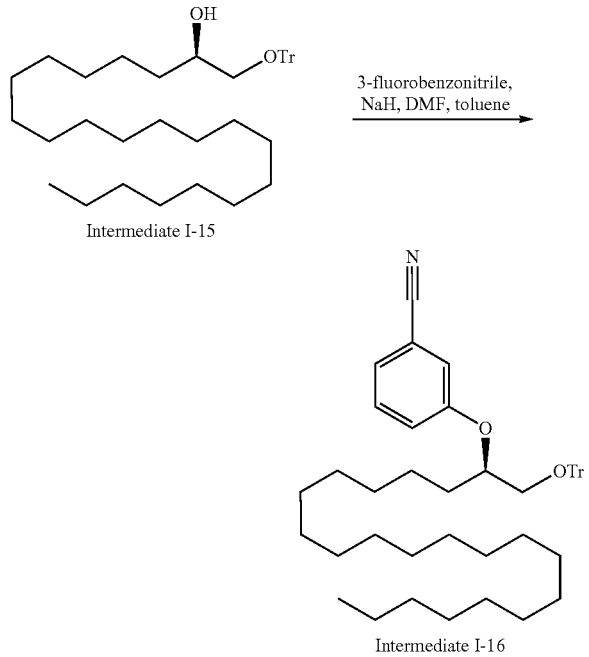

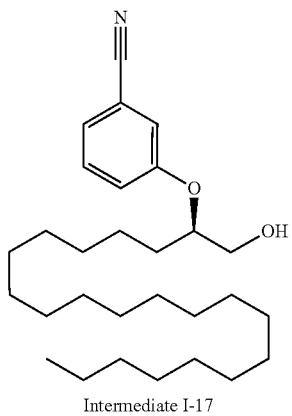

Intermediate I-17

To a solution of Intermediate I-16 (1.71 mmol) in toluene-MeOH (10:6 mL) was added 25% HCl (1.0 mL). The resulting mixture was heated at 65° C. for 90 min, cooled, and sat NaHCO₃ (50 mL) added. After stirring for 5 min, it was extracted with EtOAc (150 mL×2). The aqueous layer was extracted with EtOAc (100 mL). The combined organic layer was dried with sodium sulfate, concentrated in vacuo, and purified by silica gel column chromatography (0% to 40% EtOAc in hexanes) to give Intermediate I-17. ¹H NMR (400 MHz, Chloroform-d) δ 7.39 (t, J=7.9 Hz, 1H), 7.29-7.25 (m, 1H), 7.24-7.17 (m, 2H), 4.39 (m, 1H), 3.92-3.72 (m, 2H), 1.75-1.61 (m, 2H), 1.56 (s, 1H), 1.49-1.21 (m, 36H), 0.98-0.83 (m, 3H).

To a solution of Intermediate I-15 (75% purity, 1.71 mmol) in DMF (15 mL)-toluene (10 mL) was added NaH (60% in mineral oil, 2.85 mmol) at rt. The mixture was stirred at room temperature for 1 h and 3-fluorobenzonitrile (0.238 mL, 2.22 mmol) added. The resulting mixture was then heated at 60° C. for 18 h, cooled to room temperature, quenched with NH₄Cl solution (20 mL), diluted with EtOAc (200 mL), washed with water (100 mL), dried with sodium sulfate, concentrated in vacuo, and purified by silica gel column chromatography (0% to 10% EtOAc in hexanes) to give Intermediate I-16. ¹H NMR (400 MHz, Chloroform-d) δ 7.42 (d, J=7.4 Hz, 6H), 7.38-7.14 (m, 13H), 4.46-4.27 (m, 1H), 3.36 (dd, J=10.2, 6.0 Hz, 1H), 3.26 (dd, J=10.1, 4.1 Hz, 1H), 1.70 (q, J=6.9 Hz, 2H), 1.47-1.04 (m, 36H), 0.91 (t, J=6.7 Hz, 3H).

Intermediate I-17: (R)-3-((1-hydroxydocosan-2-yl)oxy)benzonitrile

Intermediate I-18: ((3aS,4R,6S,6aS)-6-(4-aminopyr-rolo[2,1-f][1,2,4]triazin-7-yl)-4-cyano-2,2-dimethyl-tetrahydrofuro[3,4-d][1,3]dioxol-4-yl)methyl (2-chlorophenyl) ((R)-2-(3-cyanophenoxy)docosyl) phosphate

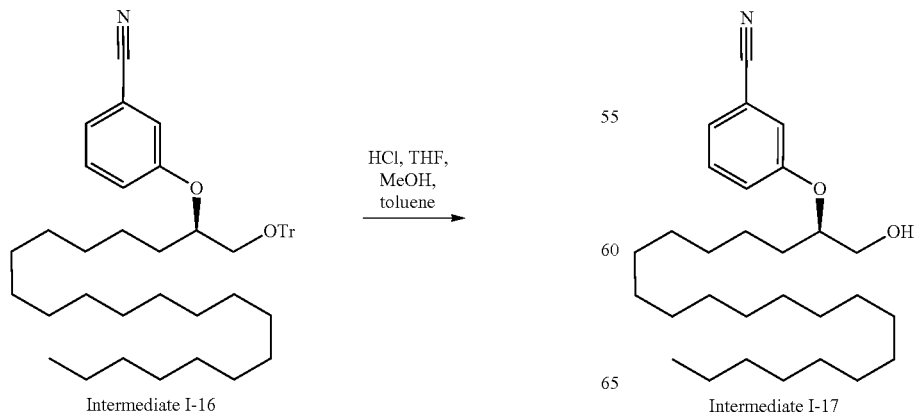

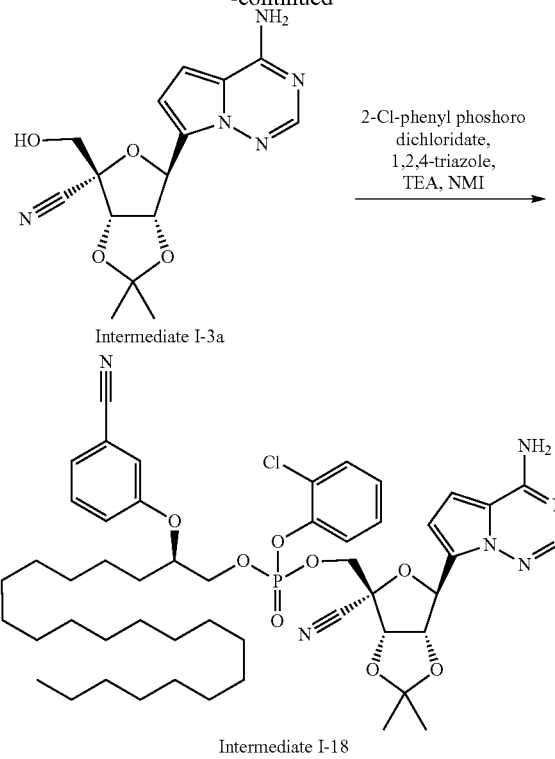

Intermediate I-3a

2-Cl-phenyl phoshoro dichloridate, 1,2,4-triazole, TEA, NMI →

1H-1,2,4-triazole (0.664 mmol) was dissolved in THF (2 mL) and TEA (0.09 mL, 0.664 mmol) added at room temperature. To the mixture was added 2-chlorophenyl phosphorodichloridate (0.081 mL, 0.501 mmol) dropwise. The reaction mixture was stirred at room temperature for 30 min at room temperature. Intermediate I-3a (0.251 mmol) was added in one portion and the mixture stirred at room temperature for 15 min. To the mixture were added Intermediate I-17 (0.275 mmol) in THF (2 mL) and 1-methylimidazole (0.04 mL, 0.506 mmol) were added at room temperature. The resulting mixture was stirred for 1 h, concentrated in vacuo, and purified by silica gel (0% to 10% MeOH in DCM) to give Intermediate I-18. $^1$H NMR (400 MHz, Acetonitrile-d3) δ 7.87 (m, 1H), 7.52-7.09 (m, 8H), 6.79 (m, 1H), 6.77-6.68 (m, 1H), 6.31 (s, 2H), 5.68 (m, 1H), 5.34-5.26 (m, 1H), 5.15-5.06 (m, 1H), 4.59-4.42 (m, 3H), 4.40-4.17 (m, 2H), 1.72 (m, 3H), 1.59 (m, 2H), 1.40-1.18 (m, 39H), 0.96-0.84 (m, 3H). $^{31}$P NMR (162 MHz, Acetonitrile-d3) δ −7.54, −7.60. MS m/z [M+1]=948.

Intermediate I-19: ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-(3-cyanophenoxy)docosyl) hydrogen phosphate

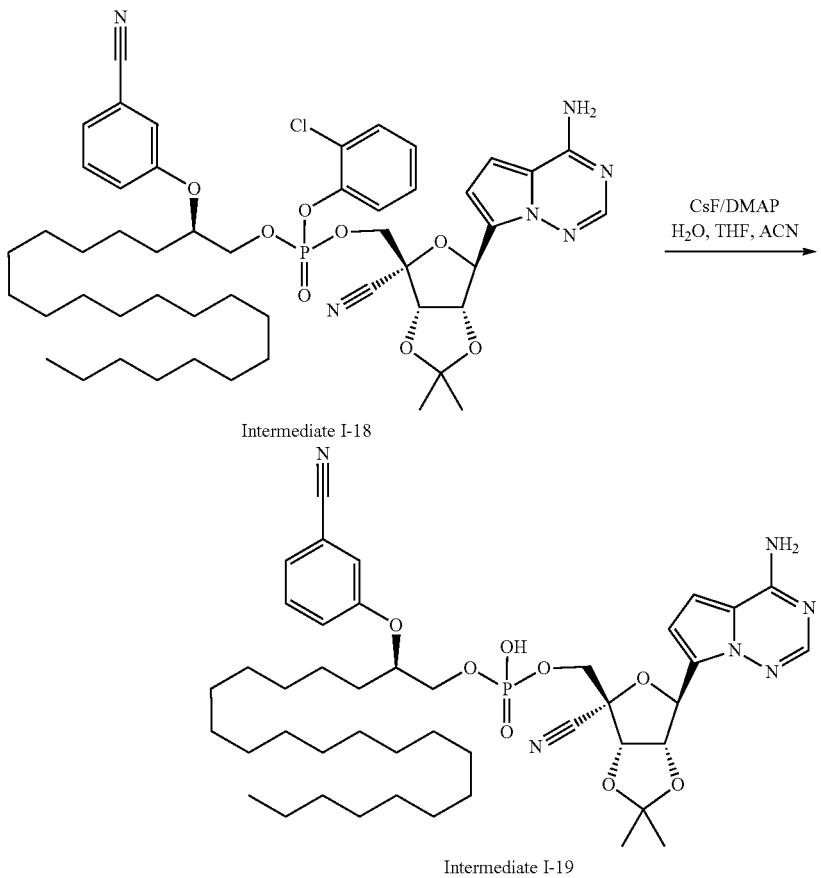

Intermediate I-18

CsF/DMAP
H₂O, THF, ACN →

Intermediate I-19

Intermediate I-18 (0.179 mmol) was dissolved in THF-ACN (2:1 mL), CsF (1.46 mmol) in water (0.2 mL) and then DMAP (0.621 mmol) added. The resulting mixture was heated at 80° C. for 4 h. After dilution with citric acid NaOH buffer (pH 4, 10 mL), the mixture was partitioned between brine (20 mL) and EtOAc (40 mL). Aqueous layer was extracted with EtOAc (20 mL×3). The combined organic layer was dried under sodium sulfate, concentrated in vacuo, and purified by silica gel column chromatography (0% to 50% MeOH in DCM) to give Intermediate I-19. MS m/z [M+1]=837.

Intermediate I-21: (2R)-1-[tert-butyl(dimethyl)silyl]oxy-3-octadecoxy-propan-2-ol

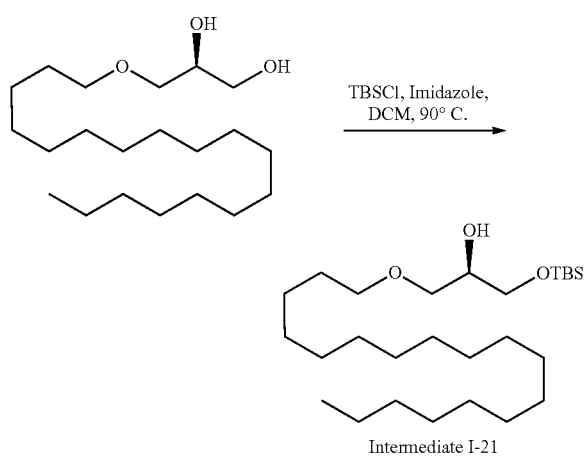

Intermediate I-21

A solution of t-butyldimethylsilyl chloride (2.32 mmol) in dichloromethane (2 mL) was added to a solution of (2S)-3-octadecoxypropane-1,2-diol (1.45 mmol) and imidazole (2.90 mmol) in dichloromethane (5 mL) at 0° C. over a period of 1 min. After 2 h the ice bath was removed. After 3 h, the reaction was washed with water (5 mL). The aqueous phase was extracted with dichloromethane (10 mL). The combined organic phases were dried over sodium sulfate and the solvent was removed under reduced pressure. The residue was subjected to flash chromatography (0% to 30% ethyl acetate/hexanes). The fractions containing product were combined and the solvent was removed under reduced pressure, providing Intermediate I-21. $^1$H NMR (400 MHz, Chloroform-d) δ 3.83 (p, J=5.4 Hz, 1H), 3.74-3.62 (m, 2H), 3.50-3.42 (m, 4H), 1.58 (q, J=7.0 Hz, 2H), 1.27 (m, 30H), 0.91 (m, 12H), 0.09 (s, 6H).

Intermediate I-22: 3-[[(1R)-1-[[tert-butyl(dimethyl)silyl]oxymethyl]-2-octadecoxy-ethoxy]methyl]-5-fluoro-benzonitrile

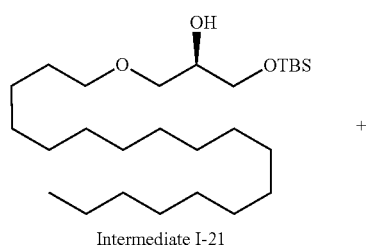

Intermediate I-21

+

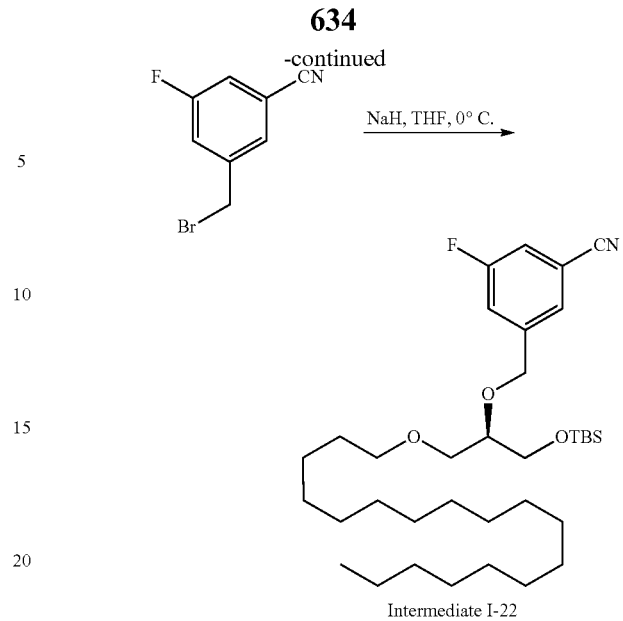

Intermediate I-22

Sodium hydride 60% dispersion in mineral oil (1.31 mmol) was suspended in tetrahydrofuran (5 mL) and cooled to 0° C. A solution of Intermediate I-21 (0.654 mmol) in tetrahydrofuran (2 mL) was added over 30 seconds. After 30 minutes a solution of 3-(bromomethyl)-5-fluoro-benzonitrile (1.44 mmol) in tetrahydrofuran (2 mL) was added. The ice bath was removed. After 16 hours the reaction was quenched with water (10 mL) at 0° C. Gas evolution was observed. The mixture was extracted with ethyl acetate (3×10 mL). The combined organic phases were dried over sodium sulfate and the solvent was removed under reduced pressure. The residue was subjected to flash chromatography (0% to 20% ethyl acetate/hexanes, using ELSD detection). The fractions containing product were combined and the solvent was removed under reduced pressure, providing Intermediate I-22. $^1$H NMR (400 MHz, Chloroform-d) δ 7.48 (s, 1H), 7.41 (m, 1H), 7.28-7.23 (m, 1H), 4.77 (s, 2H), 3.73 (d, J=4.9 Hz, 2H), 3.66 (qd, J=5.7, 4.1 Hz, 1H), 3.55 (qd, J=10.3, 5.0 Hz, 2H), 3.46 (td, J=6.7, 1.2 Hz, 2H), 1.65-1.52 (m, 2H), 1.28 (s, 30H), 0.91 (d, J=7.1 Hz, 13H), 0.09 (s, 6H). $^{19}$F NMR (376 MHz, Chloroform-d) δ −110.67−−110.85 (m).

Intermediate I-23: 3-fluoro-5-[[(1S)-1-(hydroxymethyl)-2-octadecoxy-ethoxy]methyl] benzonitrile

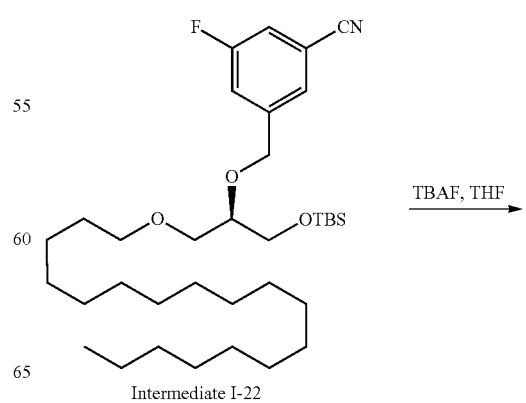

Intermediate I-22

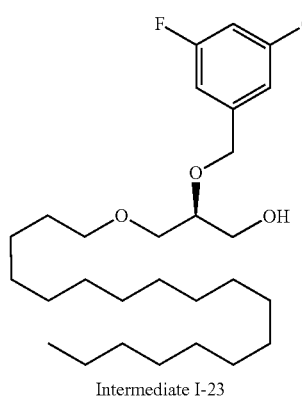

Intermediate I-23

A solution of tetrabutylammonium fluoride in tetrahydrofuran (1.71 mL, 1.71 mmol) was added to a solution of Intermediate I-22 (0.569 mmol) in tetrahydrofuran (5 mL). After 45 minutes the reaction was diluted with ethyl acetate (20 mL). The organic phase was washed with water (3×5 mL) and brine (5 ml). The organic phase was dried over sodium sulfate and the solvent was removed under reduced pressure. The residue was subjected to flash chromatography (0% to 20% ethyl acetate/hexanes, using ELSD). The fractions containing product were combined and the solvent was removed under reduced pressure, providing Intermediate I-23. 1H NMR (400 MHz, Chloroform-d) δ 7.48 (s, 1H), 7.41-7.35 (m, 1H), 7.33-7.29 (m, 1H), 4.83-4.68 (m, 2H), 3.86-3.78 (m, 1H), 3.78-3.68 (m, 2H), 3.68-3.56 (m, 2H), 3.47 (td, J=6.6, 2.2 Hz, 2H), 1.66-1.50 (m, 2H), 1.40-1.23 (m, 30H), 0.90 (t, J=6.8 Hz, 3H). 19F NMR (376 MHz, Chloroform-d) δ−110.36 (t, J=8.4 Hz).

Intermediate I-24: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)-3-(octadecyloxy)propyl) phosphate

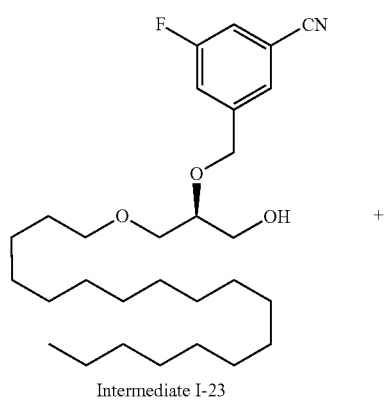

Intermediate I-23

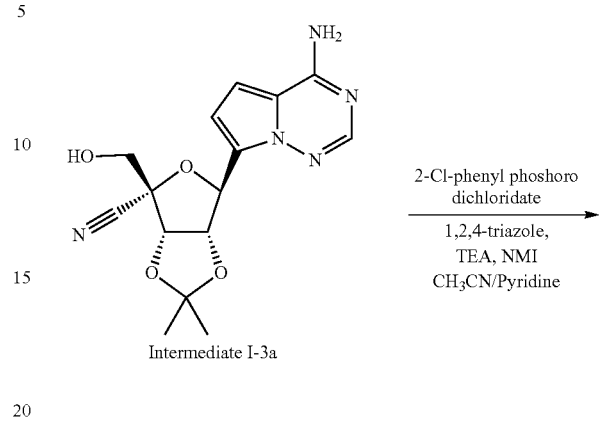

Intermediate I-3a

Intermediate I-24

To a solution of 1H-1,2,4-triazole (1.62 mmol) and TEA (0.226 mL, 1.62 mmol) in CH$_3$CN (2.5 mL), pyridine (2.5 mL) was added 2-chlorophenyl phosphorodichloridate (0.124 mL, 0.755 mmol) dropwise at room temperature. The reaction mixture was stirred at room temperature for 30 min. A solution of Intermediate I-23 (0.755 mmol) in MeCN (2.5 mL), pyridine (/2.5 mL) under Ar atmosphere was added to above reaction mixture at once, and stirred vigorously for 90 min. To this mixture was added Intermediate I-3a (0.755 mmol) followed by 1-methylimidazole (0.1 mL, 1.26 mmol) and stirred overnight. The mixture was concentrated to remove pyridine, co evaporated with Toluene (30 mL) once. To this mixture was added 10% Citric acid (43 mL), followed by 1 N NaOH (7 mL), and water (20 mL) to complete transfer. The aqueous layer was extracted with EtOAc (3×100 mL). The organic fractions were combined, washed with brine, dried over Na$_2$SO$_4$, filtered and concentrated in vacuo prior to purification by silica gel chromatography (0-20% MeOH in DCM) to afford Intermediate I-24. MS m/z [M+1]=981.2.

Intermediate I-25: ((3aS,4R,6S,6aS)-6-(4-aminopyr-rolo[2,1-f][1,2,4]triazin-7-yl)-4-cyano-2,2-dimethyl-tetrahydrofuro[3,4-d][1,3]dioxol-4-yl)methyl ((R)-2-((3-cyano-5-fluorobenzyl) oxy)-3-(octadecyloxy) propyl) hydrogen phosphate

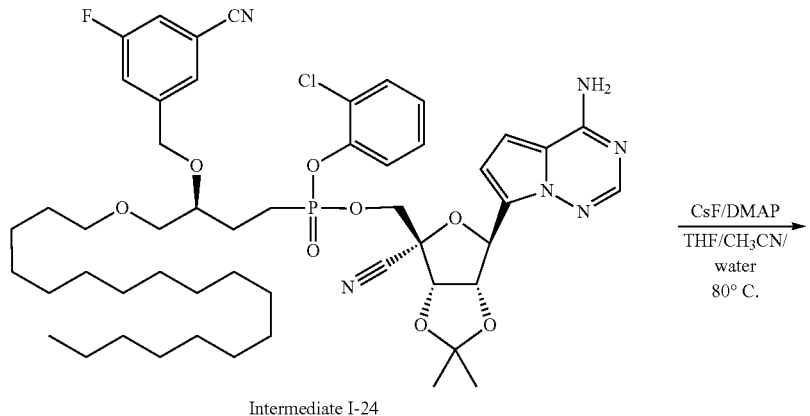

Intermediate I-24

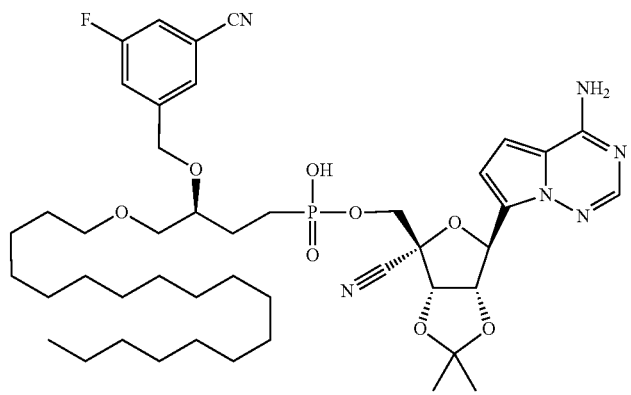

Intermediate I-25

Intermediate I-24 (0.458 mmol) was dissolved in 2:1 THF: ACN (6:3 mL). Solution of Cesium fluoride (1.83 mmol) in water (0.578 mL) was added to the solution followed by 4-(dimethylamino)pyridine (1.6 mmol). The reaction mixture was heated to 80° C. and stirred for 3 h. The reaction was cooled to rt, added 10% citric acid in water (20 mL) followed by 2 M NaOH to adjust pH 3-4. Extracted with EtOAc (50 mL×2) and conformed, no desired product in the aqueous layer by LCMS. Combined organic layers washed with brine once and dried over $Na_2SO_4$, filtered and concentrated in vacuo prior to purification by silica gel chromatography (0% to 50% MeOH in DCM) to afford Intermediate I-25. MS m/z [M+1]=871.3.

Intermediate I-26: (S)-5-(((1-hydroxy-3-(octadecyloxy)propan-2-yl)oxy)methyl)-2-methoxy benzonitrile

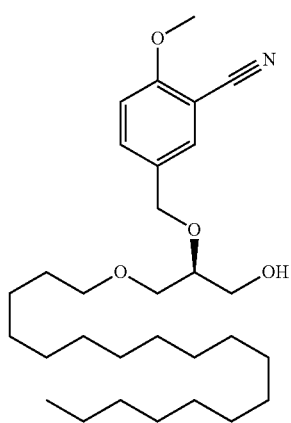

Intermediate I-26

Intermediate I-26 was synthesized in a manner similar to Intermediate I-23 using 5-(bromomethyl)-2-methoxybenzonitrile instead of 3-(bromomethyl)-5-fluorobenzonitrile. MS m/z [M+1]=490.

Intermediate I-27: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl)hydrogen phosphate

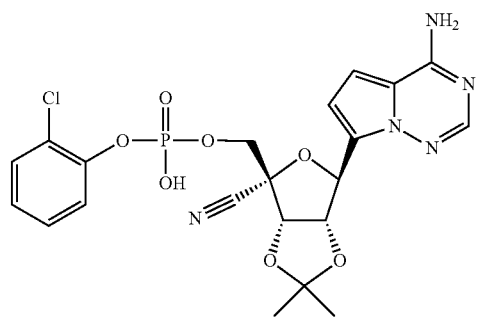

Intermediate I-27

Charge a 200 mL round bottom flask with stir bar, add 1,2,4-Triazole (26.2 mmol), THF (60 mL, 15 V), TEA (3.65 mL, 26.2 mmol). Cool to 0° C., and add 2-chlorophenyl phosphorodichloridate (1.96 mL, 12.1 mmol) drop wise about 20 min (white precipitation forms). The reaction mixture was warm to room temp and stir for 1 h. To this mixture was added dry Intermediate I-3a (12.1 mmol) in one portion, used THF (30 mL) to bring sticking solid around flask to reaction mixture and stir for 1 h. Filter the slurry, rinse the filter cake of Et₃N—HCl with THF (~3-5 Vol, 160 mL), and filtrate concentrated under reduced pressure (~25 mL, 3 Volume). To this mixture was added EtOAc (10 V, 250 mL), water (10 V, 250 mL) and transfer to separatory funnel (used EtOAc/Water ~1 V, 100 mL) to complete transfer. Make pH of solution 8-9 by adding sat-Na₂CO₃ solution (adding Na₂CO₄ is not necessary if the pH of the solution is already ~8). The aqueous layer contains product and the organic layer consist organic impurity with trace desired product. Collect aqueous layer in to 500 mL RB-Flask, charge stir bar and add 5% HCl in water drop wish over 30-40 min, to reach pH ~3 (keep adding until no more precipitation forming) and allow the slurry to form solid. Solid formation takes place and disappears, let it to stand for 1 h, greasy yellowish droplet forms (pure product). Transfer to Separatory flask, and extract with EtOAc (200 mL×3) and once with DCM/IPA (4:1, 100 mL). Combined organic layer dried over Na₂SO₄, solvent concentrated and dried to give Intermediate I-27. ¹H NMR (400 MHz, DMSO-d₆) δ 8.77 (d, J=91.2 Hz, 2H), 8.40 (s, 1H), 8.07 (s, 1H), 7.50 (dd, J=19.3, 8.1 Hz, 2H), 7.29-7.20 (m, 1H), 7.15 (d, J=4.5 Hz, 1H), 7.10 (t, J=7.7 Hz, 1H), 6.98 (d, J=4.5 Hz, 1H), 5.66 (d, J=3.6 Hz, 1H), 5.32 (dd, J=6.6, 3.8 Hz, 1H), 5.12 (d, J=6.6 Hz, 1H), 4.31-4.13 (m, 2H), 1.69 (s, 3H), 1.39 (s, 3H). MS m/z [M+1]=522.0.

Intermediate I-28: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-4-methoxybenzyl)oxy)-3-(octadecyloxy)propyl) phosphate

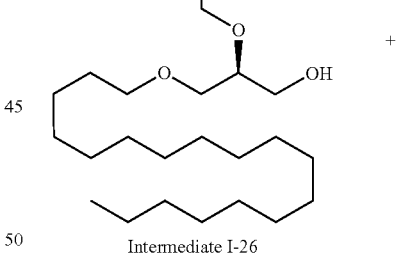

Intermediate I-26

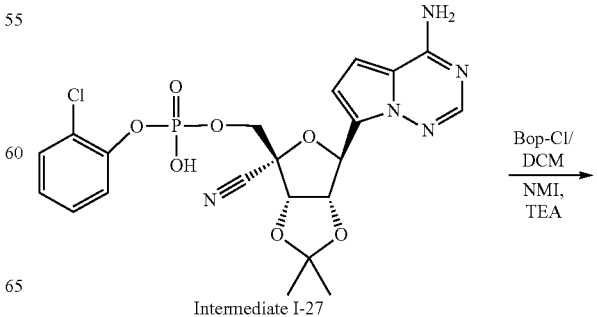

Intermediate I-27

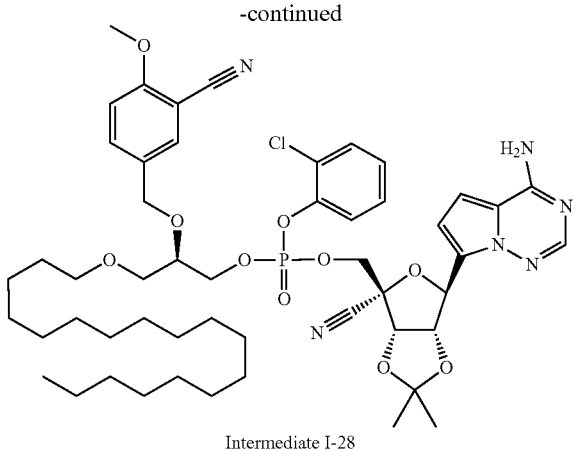

Intermediate I-28

Intermediate I-26 (0.041 mmol), Intermediate I-27 (0.061 mmol) were taken in a 20 mL vial, dried under vacuum (1 h), add DCM (2 mL), add NMI (13.4 uL, 0.163 mmol), TEA (11.5 uL, 0.081 mmol) followed by Bop-Cl (10.4 mg, 0.04 mmol). The reaction stirred at room temperature for 2 h. Solvent concentrated under reduced pressure. The crude product was dissolved in DCM, loaded on 24 g column, eluted with 100% Hex, 4 min, 0%-100% EtOAc 6 min, and 100% EtOAc 6 min. The product eluted at 100% EtOAc, fractions containing pure product were combined, concentered to afford Intermediate I-28. $^1$H NMR (400 MHz, Chloroform-d) δ 7.93 (d, J=6.5 Hz, 1H), 7.58-7.32 (m, 4H), 7.23-7.02 (m, 2H), 6.90 (dd, J=8.6, 5.0 Hz, 1H), 6.72 (d, J=4.5 Hz, 1H), 6.60 (dd, J=6.8, 4.5 Hz, 1H), 5.77-5.61 (m, 2H), 5.28 (td, J=6.5, 3.1 Hz, 1H), 5.13 (dd, J=15.1, 6.6 Hz, 1H), 4.68-4.41 (m, 5H), 4.40-4.22 (m, 1H), 3.91 (s, 3H), 3.79 (dp, J=22.7, 5.1 Hz, 1H), 3.51 (dd, J=16.0, 5.3 Hz, 2H), 3.41 (q, J=6.4 Hz, 2H), 1.79 (d, J=2.4 Hz, 3H), 1.60-1.46 (m, 2H), 1.39 (s, 3H), 1.27 (d, J=2.5 Hz, 30H), 0.90 (t, J=6.7 Hz, 3H). MS m/z [M+1]=993.3.

Intermediate I-29: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-cyano-4-methoxy benzyl)oxy)-3-(octadecyloxy) propyl) hydrogen phosphate

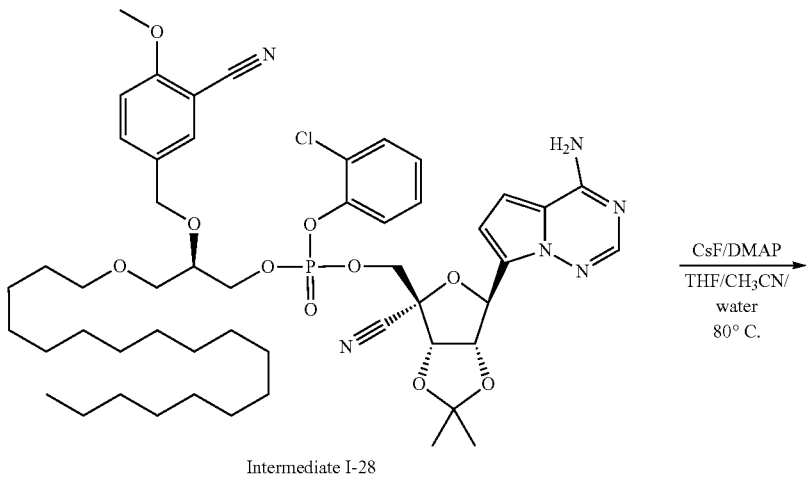

Intermediate I-28

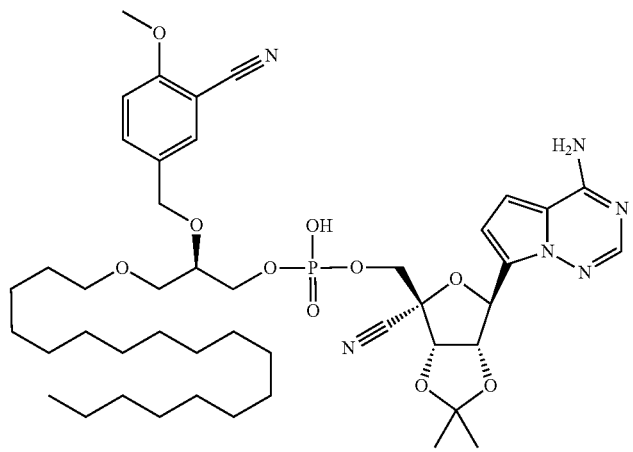

Intermediate I-29

Intermediate I-28 (0.02 mmol) was dissolved in 2:1 THF:ACN (1:0.5 mL). Solution of cesium fluoride (0.101 mmol) in water (0.026 mL) was added to the solution followed by 4-(dimethylamino)pyridine (0.08 mmol). The reaction mixture was stirred at 80° C. for 3 h. The reaction was cooled to room temperature, added 10% citric acid in water (20 mL) followed by 2 M NaOH to adjust pH 3-4. Extracted with EtOAc (50 mL×2), conformed no desired product in the aqueous layer by LCMS. Combined organic layers washed with a brine once and dried over $Na_2SO_4$, filtered and concentrated in vacuo prior to purification by silica gel chromatography (0% to 50% MeOH in DCM) to afford Intermediate I-29. $^1$H NMR (400 MHz, Methanol-$d_4$) δ 7.85 (s, 1H), 7.62-7.53 (m, 2H), 7.11-7.00 (m, 1H), 6.87 (d, J=4.5 Hz, 1H), 6.81 (d, J=4.5 Hz, 1H), 5.65 (d, J=3.6 Hz, 1H), 5.26 (dd, J=6.6, 3.7 Hz, 1H), 5.15 (d, J=6.6 Hz, 1H), 4.66-4.49 (m, 2H), 4.20-4.08 (m, 2H), 3.95 (t, J=5.4 Hz, 2H), 3.92 (s, 3H), 3.72 (dt, J=9.1, 4.7 Hz, 1H), 3.56-3.36 (m, 4H), 2.91-2.72 (m, 6H, 1.5eq Citrate), 1.71 (s, 3H), 1.54 (m, 2H), 1.40 (s, 3H), 1.29 (d, J=7.3 Hz, 30H), 0.92 (t, J=6.7 Hz, 3H). MS m/z [M+1]=883.2.

Intermediate I-30: (S)-6-((1-hydroxy-3-(octadecyloxy)propan-2-yl)oxy)picolinonitrile

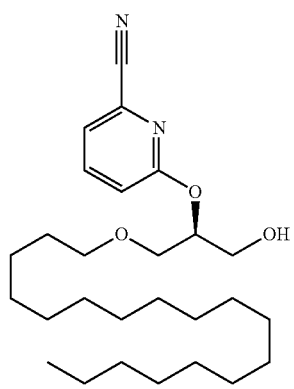

Intermediate I-30

Intermediate I-30 was synthesized in a manner similar to Intermediate I-16 using 6-fluoropicolinonitrile instead of 3-fluorobenzonitrile. MS m/z [M+1]=447.2.

Intermediate I-31: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((6-cyanopyridin-2-yl)oxy)-3-(octadecyloxy)propyl) phosphate

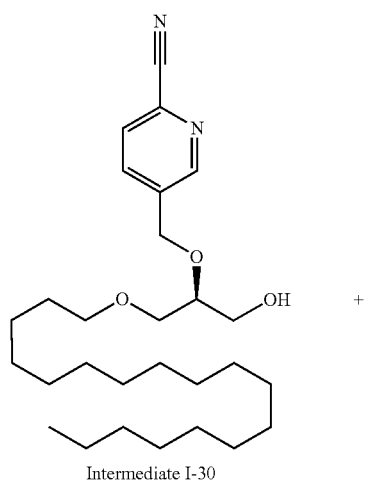

Intermediate I-30

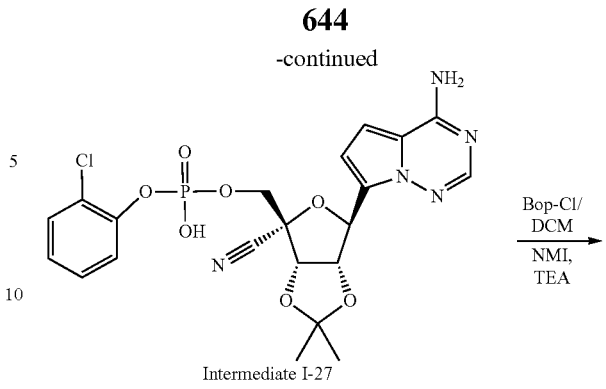

Intermediate I-27

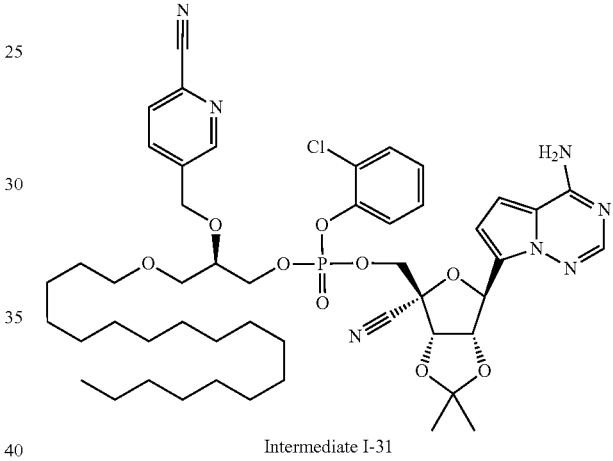

Intermediate I-31

Intermediate I-30 (0.119 mmol), Intermediate I-27 (0.178 mmol) were taken in a 20 mL vial, dried under vacuum (1 h), add DCM (3 mL), NMI (38 uL, 0.476 mmol), TEA (33 uL, 0.238 mmol) followed by Bop-Cl (0.143 mmol). The reaction stirred at room temperature for 2 h. After 2 h add excess of NMI (38 uL, 4eq), TEA (35 uL, 2eq solution turns clear) followed by Bop-Cl (36 mg, 4eq) stir at room temperature overnight. Solvent concentrated under reduced pressure. The crude product was dissolved in DCM, loaded on 24 g column, eluted with 100% Hex, 3 min, 0% to 100% EtOAc 6 min, and 100% EtOAc 6 min. The product eluted at 100% EtOAc, fractions containing pure product were combined, concentered to afford Intermediate I-31. $^1$H NMR (400 MHz, Chloroform-d) δ 7.98-7.86 (m, 1H), 7.61 (dt, J=21.6, 8.0 Hz, 1H), 7.44-7.22 (m, 3H), 7.20-7.00 (m, 2H), 6.98-6.88 (m, 1H), 6.72 (dd, J=4.5, 2.5 Hz, 1H), 6.64-6.57 (m, 1H), 5.78 (s, 2H), 5.68 (dt, J=8.0, 3.2 Hz, 1H), 5.48 (dt, J=28.2, 4.8 Hz, 1H), 5.27 (ddd, J=12.0, 6.8, 3.1 Hz, 1H), 5.14 (ddd, J=19.1, 11.5, 6.6 Hz, 1H), 4.72-4.36 (m, 4H), 3.79-3.61 (m, 2H), 3.55-3.33 (m, 2H), 1.78 (d, J=5.4 Hz, 3H), 1.54 (dt, J=11.0, 7.2 Hz, 2H), 1.41-1.36 (m, 3H), 1.26 (d, J=6.0 Hz, 30H), 0.90 (t, J=6.7 Hz, 3H). MS m/z [M+1]=950.1.

Intermediate I-32: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((6-cyanopyridin-2-yl)oxy)-3-(octadecyloxy)propyl) hydrogen phosphate

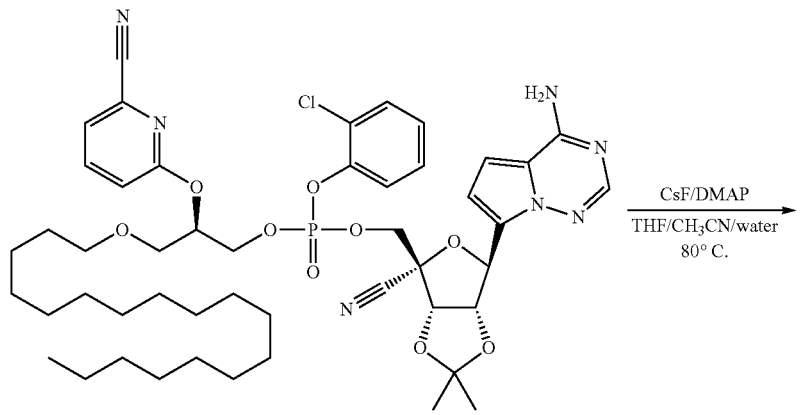

Intermediate I-31 (0.062 mmol) was dissolved in 2:1 THF:ACN (2:1 mL). Solution of cesium fluoride (0.311 mmol) in water (0.078 mL) was added to the solution followed by 4-(dimethylamino) pyridine (0.249 mmol). The reaction mixture was stirred at 80° C. for 3 h. The reaction was cooled to room temperature, added 10% citric acid in water (20 mL) followed by 2 M NaOH to adjust pH 3-4. Extracted with MeTHF/EtOAc (3:2, 50 mL×2), conformed no desired product in the aqueous layer by LCMS. Combined organic layers washed with brine once and dried over $Na_2SO_4$, filtered and concentrated in vacuo prior to purification by silica gel chromatography (0% to 50% MeOH in DCM) to afford Intermediate I-32. $^1$H NMR (400 MHz, Chloroform-d) δ 7.85 (d, J=6.6 Hz, 1H), 7.73 (q, J=8.0 Hz, 1H), 7.38 (t, J=7.6 Hz, 1H), 7.04 (dd, J=14.6, 8.6 Hz, 1H), 6.83 (dt, J=12.9, 5.0 Hz, 2H), 5.69-5.58 (m, 1H), 5.44 (t, J=5.1 Hz, 1H), 5.27 (td, J=8.1, 7.5, 3.8 Hz, 1H), 5.16 (t, J=5.4 Hz, 1H), 4.66-4.32 (m, 1H), 4.22-4.03 (m, 3H), 3.70-3.57 (m, 2H), 3.51-3.34 (m, 2H), 1.69 (s, 3H), 1.52-1.42 (m, 2H), 1.38 (d, J=2.9 Hz, 3H), 1.26 (d, J=17.7 Hz, 30H), 0.90 (t, J=6.6 Hz, 3H). MS m/z [M+1]=840.1.

Intermediate I-33: (S)-5-(((1-hydroxy-3-(octadecyloxy)propan-2-yl)oxy)methyl) picolino nitrile

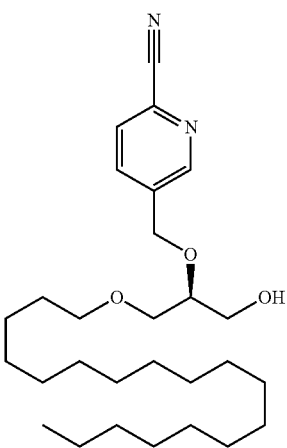

Intermediate I-33 was synthesized in a manner similar to Intermediate I-23 using 5-(bromomethyl)picolinonitrile instead of 3-(bromomethyl)-5-fluorobenzonitrile. MS m/z [M+1]=461.4.

Intermediate I-34: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((6-cyanopyridin-3-yl)methoxy)-3-(octadecyloxy)propyl) phosphate

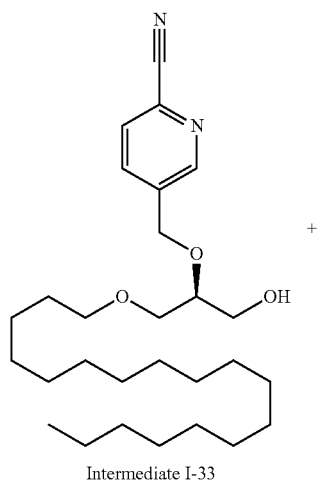

Intermediate I-33

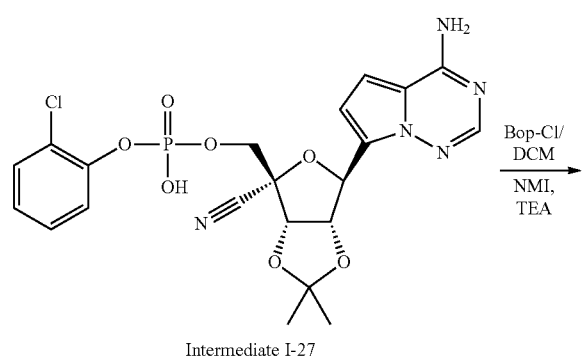

Intermediate I-27

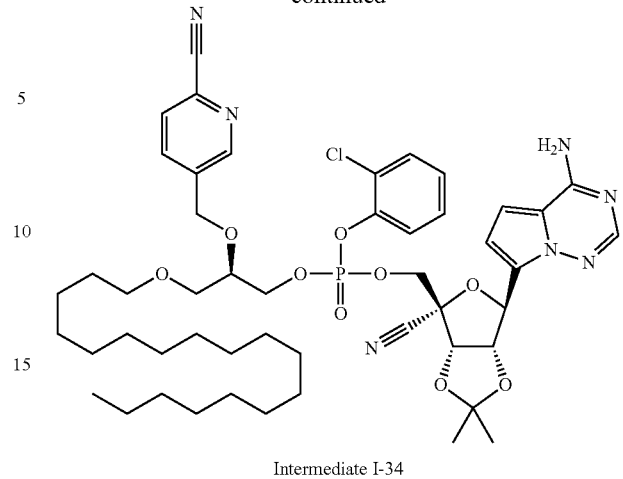

Intermediate I-34

Intermediate I-33 (0.119 mmol), Intermediate I-27 (0.178 mmol) were taken in a 20 mL vial, dried under vacuum (1 h), add DCM (3 mL), NMI (38 uL, 0.476 mmol), TEA (33 uL, 0.238 mmol) followed by Bop-Cl (0.143 mmol). The reaction stirred at room temperature for 2 h. after 2 h add excess of NMI (38 uL, 4eq), TEA (35 uL, 2eq solution turns clear) followed by Bop-Cl (36 mg, 4eq) stir at room temperature overnight. Solvent concentrated under reduced pressure. The crude product was dissolved in DCM, loaded on 24 g column, eluted with 100% Hex, 3 min, 0% to 100% EtOAc 6 min, and 100% EtOAc 6 min. The product elutes at 100% EtOAc, fractions containing pure product were combined, concentered to afford Intermediate I-34. $^1$H NMR (400 MHz, Chloroform-d) δ 8.60 (dd, J=19.4, 2.0 Hz, 1H), 7.91 (d, J=7.6 Hz, 1H), 7.83 (ddd, J=14.0, 8.0, 2.1 Hz, 1H), 7.58 (t, J=8.4 Hz, 1H), 7.47-7.31 (m, 2H), 7.22-7.00 (m, 2H), 6.71 (d, J=4.5, 3.2 Hz, 1H), 6.60 (dd, J=11.2, 4.5 Hz, 1H), 5.80 (s, 2H), 5.66 (t, J=2.3 Hz, 1H), 5.34-5.24 (m, 1H), 5.12 (dd, J=20.0, 6.6 Hz, 1H), 4.86-4.65 (m, 2H), 4.62-4.18 (m, 4H), 3.94-3.77 (m, 1H), 3.53 (dd, J=16.2, 5.2 Hz, 2H), 3.41 (qd, J=6.8, 2.0 Hz, 2H), 1.79 (d, J=3.5 Hz, 3H), 1.61-1.48 (m, 2H), 1.39 (s, 3H), 1.27 (d, J=2.1 Hz, 32H), 0.90 (t, J=6.7 Hz, 3H). MS m/z [M+1]=964.8.

Intermediate I-35: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((6-cyanopyridin-3-yl) methoxy)-3-(octadecyloxy) propyl) hydrogen phosphate

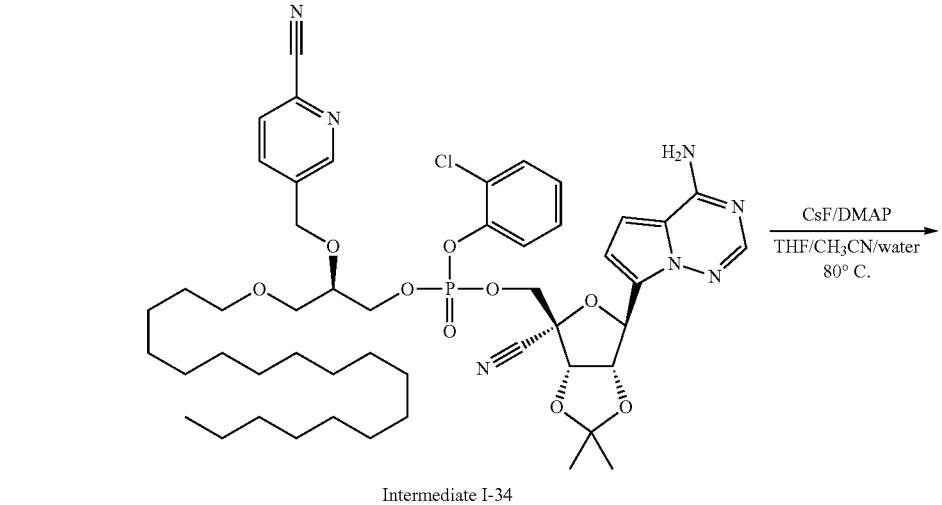

Intermediate I-34

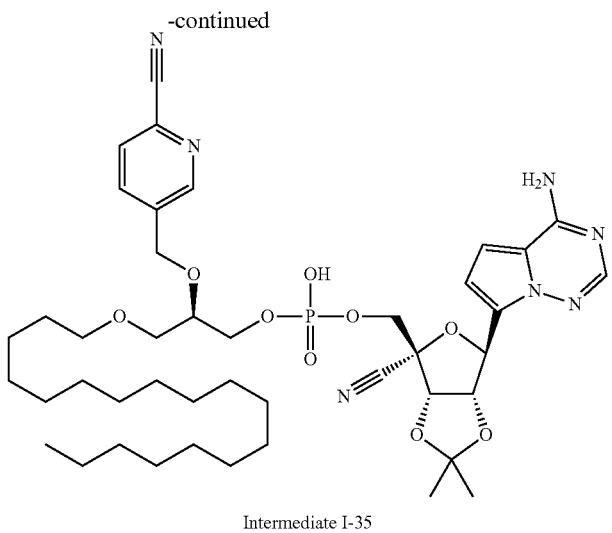

Intermediate I-35

Intermediate I-34 (0.068 mmol) was dissolved in 2:1 THF:ACN (2:1 mL). Solution of cesium fluoride (0.342 mmol) in water (0.092 mL) was added to the solution followed by 4-(dimethylamino)pyridine (0.342 mmol). The reaction mixture was stirred at 80° C. for 3 h. The reaction was cooled to room temperature, added 10% citric acid in water (8.5 mL) followed by 2 M NaOH to adjust pH 3-4. Extracted with MeTHF/EtOAc (3:2, 50 mL×2), conformed no desired product in the aqueous layer by LCMS. Combined organic layers washed with brine once and dried over $Na_2SO_4$, filtered and concentrated in vacuo prior to purification by silica gel chromatography (0-50% MeOH in DCM) to afford Intermediate I-35. $^1$H NMR (400 MHz, Chloroform-d) δ 7.85 (d, J=6.6 Hz, 1H), 7.73 (q, J=8.0 Hz, 1H), 7.38 (t, J=7.6 Hz, 1H), 7.04 (dd, J=14.6, 8.6 Hz, 1H), 6.83 (dt, J=12.9, 5.0 Hz, 2H), 5.67-5.55 (m, 1H), 5.44 (t, J=5.1 Hz, 1H), 5.27 (td, J=8.1, 7.5, 3.8 Hz, 1H), 5.16 (t, J=5.4 Hz, 1H), 4.67-4.32 (m, 2H), 4.24-3.99 (m, 3H), 3.76-3.53 (m, 2H), 3.50-3.35 (m, 3H), 1.69 (s, 3H), 1.52-1.42 (m, 2H), 1.38 (d, J=2.9 Hz, 3H), 1.26 (d, J=17.7 Hz, 30H), 0.90 (t, J=6.6 Hz, 3H). MS m/z [M+1]=854.3.

Intermediate I-36: (R)-1-(trityloxy)nonadecan-2-ol

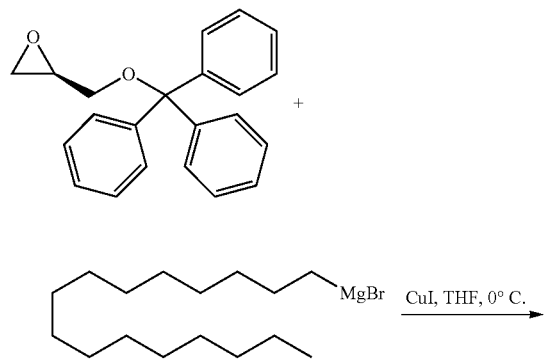

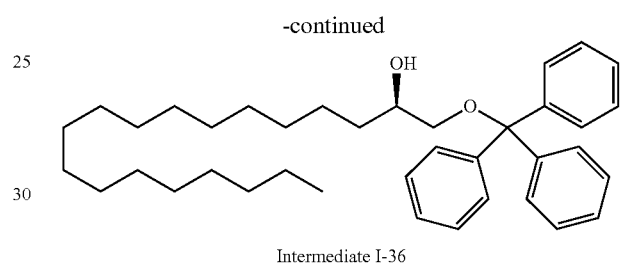

Intermediate I-36

A solution of (R)-2-((trityloxy)methyl)oxirane (6.32 mmol, 1 equiv.) and copper (I) iodide (1.81 mmol, 0.286 equiv.) in THF (20 mL) was cooled in an ice bath. Hexadecylmagnesium bromide (24 mL, 0.4 M, 1.52 equiv.) was added gradually over a period of 35 min. The solution was stirred for 4 h while gradually coming to room temperature in the ice bath. The reaction mixture was quenched with saturated ammonium chloride (50 mL) and water (50 mL). The aqueous layer was extracted with EtOAc (3×100 mL). The organic fractions were dried over $Na_2SO_4$, filtered and concentrated in vacuo prior to purification twice by silica gel chromatography (0% to 15% EtOAc in hexanes) to afford Intermediate I-36. $^1$H NMR (400 MHz, Chloroform-d) δ 7.50-7.20 (m, 15H), 3.80-3.71 (m, 1H), 3.21-3.13 (m, 1H), 3.06-2.98 (m, 1H), 2.29 (d, J=3.4 Hz, 1H), 1.46-1.16 (m, 32H), 0.92-0.84 (m, 3H).

Intermediate I-37: (R)-3-fluoro-5-(((1-(trityloxy)nonadecan-2-yl)oxy)methyl)benzonitrile

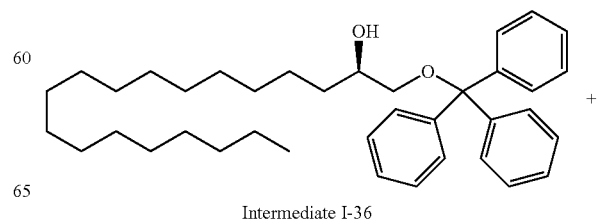

Intermediate I-36

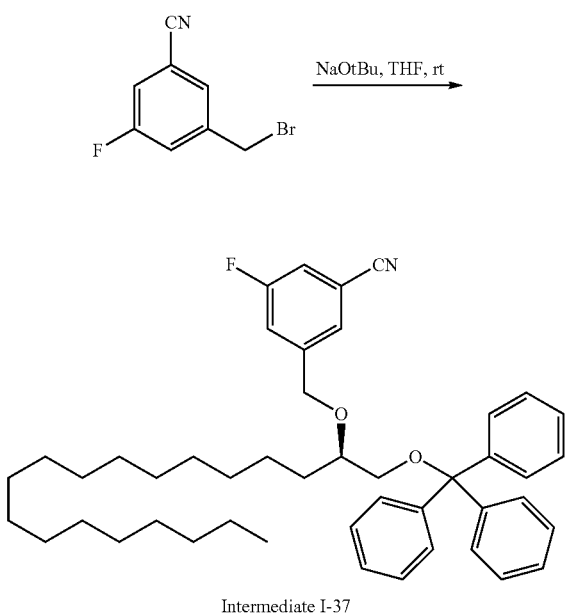

Intermediate I-37

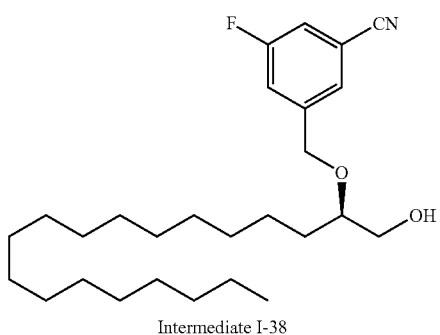

Intermediate I-38

To a solution of Intermediate I-36 (2.08 mmol, 1 equiv.) in THF (10 mL) was added sodium tert-butoxide (2.08 mL, 2.0 M in THF, 2 equiv.). The solution was stirred for 20 min at room temperature prior to the addition of 3-(bromomethyl)-5-fluorobenzonitrile (4.05 mmol, 1.94 equiv.). The solution was stirred for 7 h at room temperature. The reaction mixture was diluted with water (50 mL) and extracted with EtOAc (3×50 mL). The organic fractions were combined, washed with brine (50 mL), dried over $Na_2SO_4$, filtered and concentrated in vacuo prior to purification by silica gel chromatography (0% to 10% EtOAc in hexanes) to afford Intermediate I-37. $^1$H NMR (400 MHz, Chloroform-d) δ 7.48-7.20 (m, 18H), 4.71 (d, J=12.8 Hz, 1H), 4.55 (d, J=12.8 Hz, 1H), 3.56-3.47 (m, 1H), 3.23-3.17 (m, 2H), 1.57-1.47 (m, 2H), 1.34-1.18 (m, 30H), 0.92-0.83 (m, 3H). $^{19}$F NMR (376 MHz, Chloroform-d) δ −110.57-−110.69 (m).

Intermediate I-38: (R)-3-fluoro-5-(((1-hydroxynonadecan-2-yl)oxy)methyl)benzonitrile To a solution of Intermediate I-37 (1.66 mmol, 1 equiv.) in 1:1:1 THF:iPrOH:MeOH (21 mL total) was added concentrated HCl (0.53 mL, 6.37 mmol, 3.85 equiv.). The reaction mixture was heated to 65° C. and stirred for 1 h and 30 min. The solution was quenched with saturated sodium bicarbonate (50 mL) and water (50 mL). The aqueous layer was extracted with EtOAc (3×50 mL). The organic extracts were combined, washed with brine, dried over $Na_2SO_4$, filtered and concentrated in vacuo prior to purification by silica gel chromatography (0% to 100% EtOAc in hexanes) to afford Intermediate I-38. $^1$H NMR (400 MHz, Chloroform-d) δ 7.46-7.43 (m, 1H), 7.36-7.31 (m, 1H), 7.30-7.24 (m, 1H), 4.64-4.62 (m, 2H), 3.80-3.70 (m, 1H), 3.66-3.48 (m, 2H), 1.79-1.71 (m, 1H), 1.68-1.45 (m, 2H), 1.40-1.16 (m, 30H), 0.91-0.84 (m, 3H). $^{19}$F NMR (376 MHz, Chloroform-d) δ −110.27-−110.40 (m).

Intermediate I-39: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)nonadecyl) phosphate

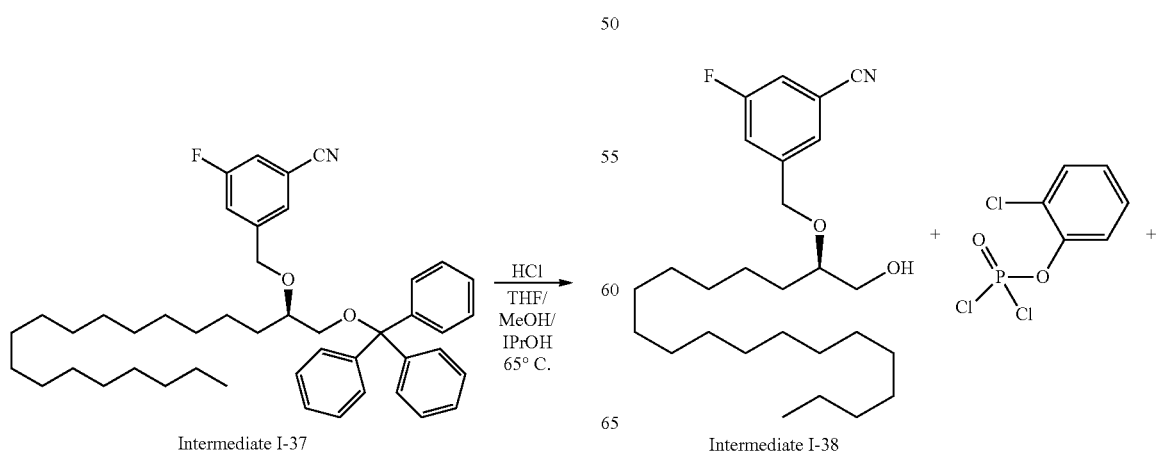

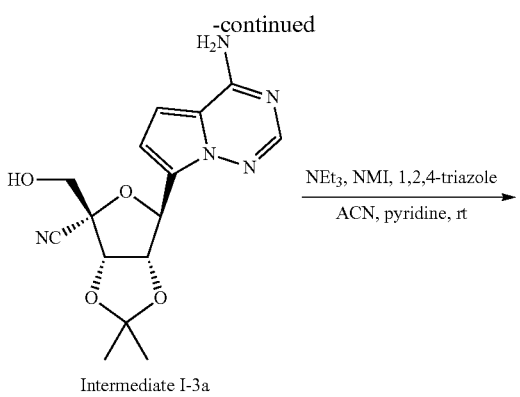

Intermediate I-40: ((3aS,4R,6S,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl ((R)-2-((3-cyano-5-fluorobenzyl) oxy)nonadecyl) hydrogen phosphate An oven-dried round bottom flask was charged with 1H-1,2,4-triazole (0.744 mmol, 2.15 equiv.). The triazole was dissolved in ACN (5.0 mL) and pyridine (5.0 mL). Triethylamine (0.104 mL, 0.744 mmol, 2.15 equiv.) was added to the solution followed by 2-chlorophenyl phosphorodichloridate (0.06 mL, 0.346 mmol, 1 equiv.). The reaction mixture was stirred at room temperature for 24 min prior to the addition of Intermediate I-3a (0.346 mmol, 1 equiv.) in one portion followed by 1-methylimidazole (0.06 mL, 0.698 mmol, 2.02 equiv.). The solution was stirred for one hour. Intermediate I-38 (0.380 mmol, 1.1 equiv.) was added and the reaction mixture was stirred for an additional 2 h and 30 min. The reaction was quenched with a buffered solution of 4:1 citric acid (20% in water): 1M NaOH (19 mL). The aqueous layer was extracted with EtOAc (3×50 mL). The organic fractions were combined, washed with brine, dried over $Na_2SO_4$, filtered and concentrated in vacuo prior to purification by silica gel chromatography (0% to 20% MeOH in DCM) to afford Intermediate I-39. MS m/z [M+1]=937.27.

Intermediate I-39 (0.244 mmol, 1 equiv.) was dissolved in 2:1 THF:ACN (4.5 mL total). Cesium fluoride (2.12 mmol, 8.68 equiv.) dissolved in water (0.30 mL) was added to the solution followed by 4-(dimethylamino)pyridine (0.900 mmol, 3.69 equiv.). The reaction mixture was heated to 80° C. and stirred for 5 h and 30 min. The reaction was quenched with a buffered solution containing citric acid (2.86 mmol, 11.7 equiv.) in 20 mL of water and NaOH (0.29 mL, 2 M, 2.34 equiv.). The aqueous layer was extracted with EtOAc (2×50 mL). The organic fractions were combined, washed with brine, dried over $Na_2SO_4$, filtered and concentrated in vacuo prior to purification by silica gel chromatography (0% to 50% MeOH in DCM) to afford Intermediate I-40. $^1$H NMR (400 MHz, Methanol-d4) δ 7.82 (s, 1H), 7.51-7.47 (m, 1H), 7.43-7.34 (m, 2H), 6.86-6.77 (m, 2H), 5.63 (d, J=3.6 Hz, 1H), 5.29-5.23 (m, 1H), 5.13 (d, J=6.6 Hz, 1H), 4.73 (d, J=13.1 Hz, 1H), 4.54-4.46 (m, 1H), 4.16-4.07 (m, 2H), 3.94-3.82 (m, 2H), 3.60-3.49 (m, 1H), 1.69 (s, 3H), 1.47-1.20 (m, 35H), 0.93-0.86 (m, 3H). $^{19}$F NMR (376 MHz, Methanol-d4) δ –112.67--113.35 (m). $^{31}$P NMR (162 MHz, Methanol-d4) δ –0.12--0.64 (m). MS m/z [M+1]=827.24.

Intermediate I-41: (R)-2-methoxy-4-(((1-(trityloxy)henicosan-2-yl)oxy)methyl)benzonitrile Intermediate I-42: (R)-4-(((1-hydroxyhenicosan-2-yl)oxy)methyl)-2-methoxybenzonitrile

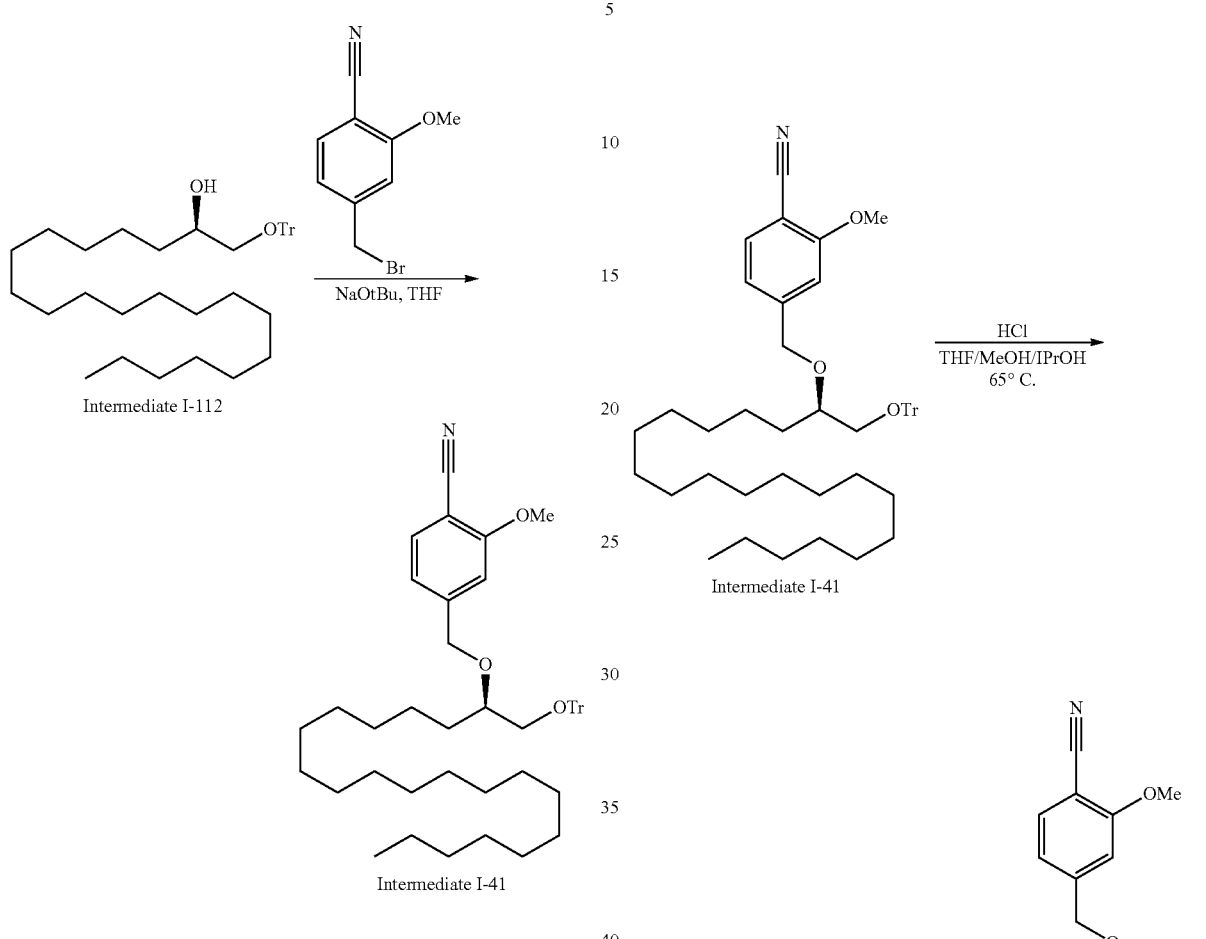

To a solution of Intermediate I-112 (1.88 mmol, 1.0 equiv.) in THF (6.0 mL) cooled in an ice bath was added sodium tert-butoxide (2.0 mL, 2.0 M in THF, 2.12 equiv.). 4-(bromomethyl)-2-methoxybenzonitrile (2.57 mmol, 1.36 equiv.) was added in one portion. The solution was stirred overnight at room temperature. The reaction mixture was heated to 60° C. and stirred for 5 h and 30 min then at room temperature overnight. The solution was cooled in an ice bath and sodium tert-butoxide (1.00 mL, 2.0 M in THF, 1.06 equiv.) was added followed by additional 4-(bromomethyl)-2-methoxybenzonitrile (0.792 mmol, 0.420 equiv.). After stirring for 7 h and 30 min, additional 4-(bromomethyl)-2-methoxybenzonitrile (1.08 mmol, 0.575 equiv.) was added and the solution was again stirred overnight at room temperature. The reaction mixture was quenched with water (100 mL) and extracted with EtOAc (3×100 mL). The organic fractions were combined, washed with brine, dried over $Na_2SO_4$, filtered and concentrated in vacuo prior to purification twice by silica gel chromatography (0-75% EtOAc in hexanes, then 0% to 15% EtOAc in hexanes to afford Intermediate I-41. $^1$H NMR (400 MHz, Chloroform-d) δ 7.49 (d, 1H), 7.47-7.41 (m, 6H), 7.35-7.20 (m, 9H), 7.02-6.99 (m, 1H), 6.96-6.92 (m, 1H), 4.72 (d, J=13.0 Hz, 1H), 4.59 (d, J=13.0 Hz, 1H), 3.84 (s, 3H), 3.57-3.48 (m, 1H), 3.24-3.14 (m, 2H), 1.58-1.48 (m, 2H), 1.37-1.15 (m, 34H), 0.91-0.84 (m, 3H).

To a solution of Intermediate I-41 (1.02 mmol, 1 equiv.) in 1:1:1 THF:iPrOH:MeOH (18.0 mL total) was added concentrated HCl (0.33 mL, 3.91 mmol, 3.85 equiv.). The reaction mixture was heated to 65° C. and stirred for 4 h and 30 min. The solution was quenched with saturated sodium bicarbonate (50 mL) and water (50 mL). The aqueous layer was extracted with EtOAc (3×50 mL). The organic extracts were combined, washed with brine, dried over $Na_2SO_4$, filtered and concentrated in vacuo prior to purification by silica gel chromatography (0% to 20% EtOAc in hexanes then 0% to 100% EtOAc in hexanes to afford Intermediate I-42. $^1$H NMR (400 MHz, Chloroform-d) δ 7.55-7.50 (m, 1H), 7.02-6.99 (m, 1H), 6.99-6.94 (m, 1H), 4.69-4.59 (m, 2H), 3.96-3.93 (m, 3H), 3.78-3.70 (m, 1H), 3.64-3.47 (m, 2H), 1.85-1.74 (m, 1H), 1.69-1.17 (m, 36H), 0.92-0.84 (m, 3H).

Intermediate I-43: a3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((4-cyano-3-methoxybenzyl)oxy)henicosyl) phosphate

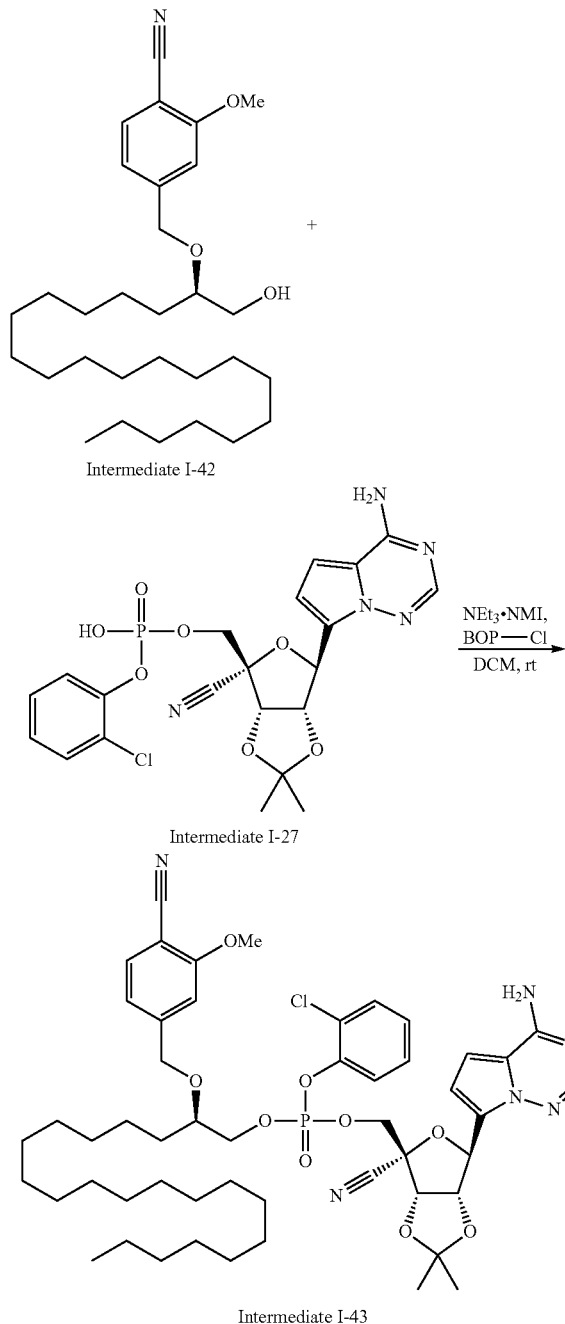

To a solution of Intermediate I-42 (0.192 mmol, 1 equiv.), Intermediate I-27 (0.192 mmol, 1 equiv.), triethylamine (0.04 mL, 0.287 mmol, 1.5 equiv.) and 1-methylimidazole (0.04 mL, 0.502 mmol, 2.62 equiv.) in DCM (2.0 mL) was added BOP—Cl (0.617 mmol, 3.22 equiv.). The solution was stirred at room temperature for 4 h. An additional 5 mg of ((3aS,4R,6aS)-6-(4-aminopyrrolo[2,1-f][1,2,4]triazin-7-yl)-4-cyano-2,2-dimethyltetrahydro furo [3,4-d][1,3]dioxol-4-yl)methyl (2-chlorophenyl) hydrogen phosphate (0.00958 mmol, 0.05 equiv.) was added and the solution was stirred at room temperature for 6 days. The reaction mixture was diluted with 2:1 Et$_2$O: EtOAc (60 mL) and quenched with 4:1 water:saturated NaHCO$_3$ (50 mL). The layers were separated and the aqueous layer was extracted with 2:1 Et$_2$O: EtOAc (60 mL) and once more with EtOAc (50 mL). The organic extracts were combined, dried over Na$_2$SO$_4$, filtered and concentrated in vacuo prior to purification by silica gel (0%-10% MeOH in DCM) to afford Intermediate I-43. MS m/z [M+1]=977.4.

Intermediate I-44: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((4-cyano-3-methoxybenzyl) oxy)henicosyl) hydrogen phosphate

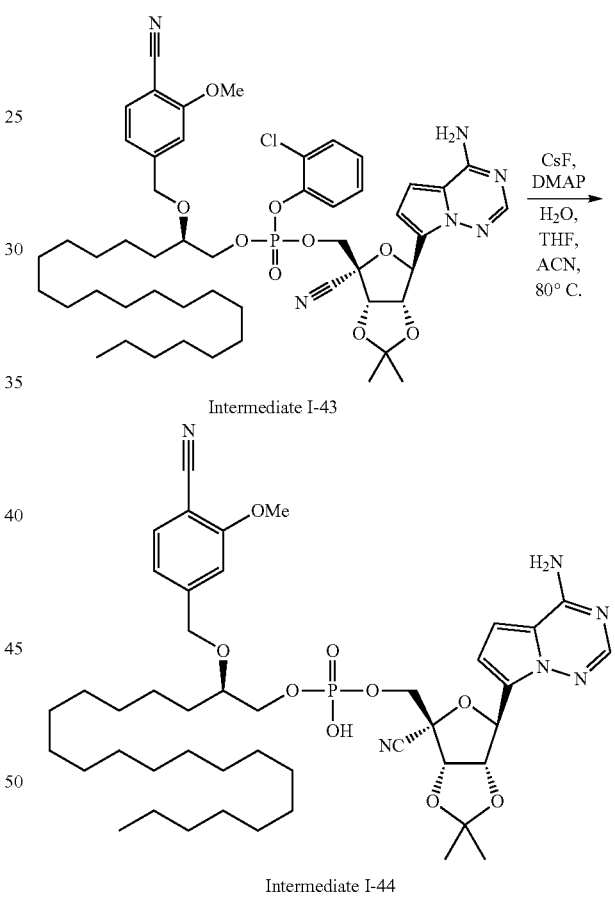

Intermediate I-43 (0.102 mmol, 1.0 equiv.) was dissolved in 2:1 THF:ACN (4.5 mL total). Cesium fluoride (1.45 mmol, 14.2 equiv.) dissolved in water (0.70 mL) was added to the solution followed by 4-(dimethylamino)pyridine (0.409 mmol, 4 equiv.). The reaction mixture was heated to 80° C. and stirred for 5 h 30 min. The reaction was quenched with a buffered solution containing citric acid (4.65 mL, 0.22 M, 10 equiv.) and NaOH (0.10 mL, 2 M, 2 equiv.). The aqueous layer was extracted with EtOAc (2×). The organic fractions were combined, washed with brine, dried over Na$_2$SO$_4$, filtered and concentrated in vacuo prior to purification by silica gel chromatography (0%-50% MeOH in DCM) to afford Intermediate I-44. MS m/z [M+1]=867.4.

Intermediate I-45: (S)-icosane-1,2-diol

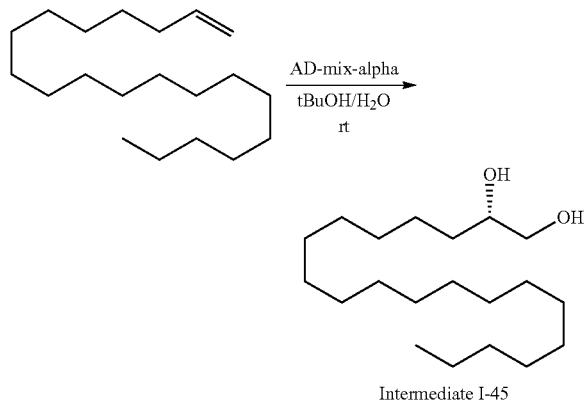

Intermediate I-45

To a solution of tBuOH (50 mL) and water (50 mL) was added AD-mix-α (1.32 g per mmol of olefin). The mixture was stirred vigorously for 5 min prior to cooling in an ice bath over 10 min. Eicosene (8.77 mol, 1 equiv.) was added in one portion and the reaction mixture was stirred at room temperature overnight. Sodium sulfite (15.0 g, 0.119 mol, 13.6 equiv.) was added and the solution was stirred at room temperature for 1 h. The mixture was filtered through Celite and the filtrate was concentrated in vacuo to remove tBuOH. The concentrated filtrate was diluted with water (25 mL) and extracted with EtOAc (3×75 mL). The organic extracts were washed with brine, dried over Na₂SO₄, filtered and concentrated in vacuo prior to purification by silica gel (0% to 100% EtOAc in hexanes) followed by further elution of the product using 0%-40% MeOH in DCM to afford Intermediate I-45. ¹H NMR (400 MHz, Chloroform-d) δ 3.78-3.62 (m, 2H), 3.50-3.40 (m, 1H), 2.04-1.19 (m, 36H), 0.92-0.85 (m, 3H).

Intermediate I-46: (S)-1-(trityloxy)icosan-2-ol

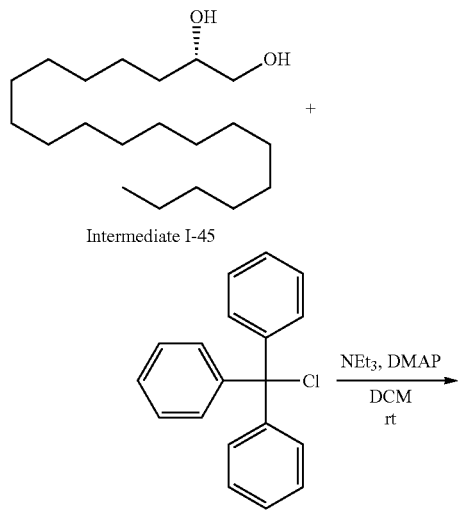

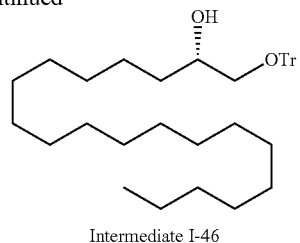

Intermediate I-46

To a solution of Intermediate I-45 (1.08 mmol, 1 equiv.) and 4-(dimethylamino)pyridine (0.426 mmol, 0.394 equiv.) in DCM (10 mL) was added triethylamine (0.17 mL, 1.24 mmol, 1.15 equiv.). This was followed by the addition of trityl chloride (1.10 mmol, 1.02 equiv). The reaction mixture was stirred at room temperature overnight. An additional 25 mg of trityl chloride (0.090 mmol, 0.083 equiv.) was added and the solution was stirred at room temperature for an additional 6 h. The reaction mixture was diluted with DCM (50 mL) and poured into ice water (50 mL). The layers were separated, and the aqueous layer was extracted with an additional 50 mL of DCM. The organic extracts were combined, washed with brine (50 mL), dried over Na₂SO₄, filtered and concentrated in vacuo prior to purification by silica gel (0%-90% DCM in hexanes) to afford Intermediate I-46. H NMR (400 MHz, Chloroform-d) δ 7.46-7.20 (m, 15H), 3.80-3.71 (m, 1H), 3.18 (dd, J=9.3, 3.3 Hz, 1H), 3.02 (dd, J=9.4, 7.6 Hz, 1H), 2.29 (s, 1H), 1.47-1.15 (m, 34H), 0.91-0.84 (m, 3H).

Intermediate I-47: (S)-3-fluoro-5-(((1-(trityloxy)icosan-2-yl)oxy)methyl)benzonitrile

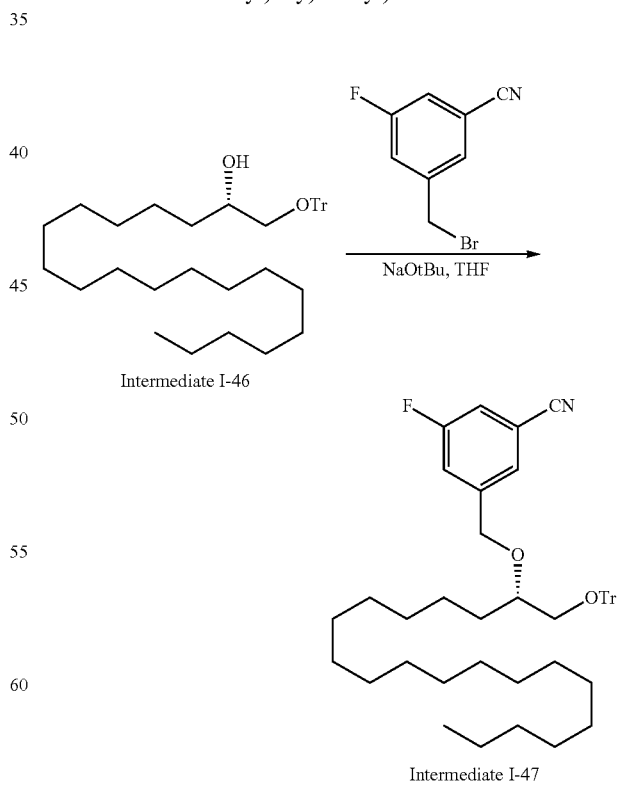

Intermediate I-47

To a solution of Intermediate I-46 (0.294 mmol, 1 equiv.) in THF (3.0 mL) was added sodium tert-butoxide (0.29 mL, 2.0 M in THF, 2 equiv.). The solution was stirred for 5 min at room temperature prior to the addition of 3-(bromomethyl)-5-fluorobenzonitrile (0.784 mmol, 2.67 equiv.). The solution was stirred at room temperature overnight. The reaction mixture was diluted with water (25 mL) and extracted with EtOAc (3×25 mL). The organic fractions were combined, washed with brine, dried over $Na_2SO_4$, filtered and concentrated in vacuo prior to purification by silica gel chromatography (0% to 10% EtOAc in hexanes) to afford Intermediate I-47. $^1$H NMR (400 MHz, Chloroform-d) δ 7.52-7.21 (m, 18H), 4.71 (d, J=12.8 Hz, 1H), 4.55 (d, J=12.8 Hz, 1H), 3.55-3.48 (m, 1H), 3.23-3.18 (m, 2H), 1.64-1.44 (m, 2H), 1.34-1.20 (m, 32H), 0.91-0.85 (m, 3H). $^{19}$F NMR (376 MHz, Chloroform-d) δ −110.57-−110.72 (m).

Intermediate I-48: (S)-3-fluoro-5-(((1-hydroxyicosan-2-yl)oxy)methyl)benzonitrile

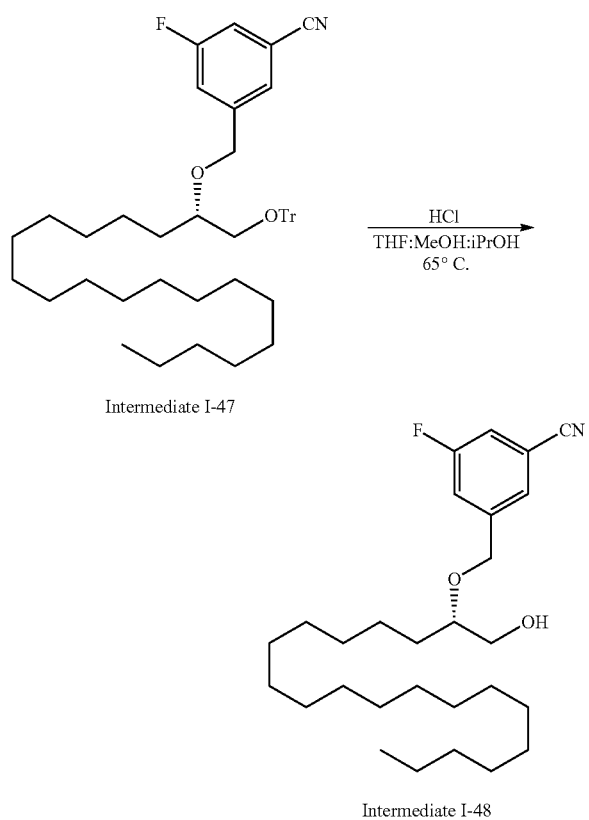

To a solution of Intermediate I-47 (0.286 mmol, 1 equiv.) in 1:1:1 THF:iPrOH:MeOH (6 mL total) was added concentrated HCl (0.10 mL, 1.20 mmol, 4.19 equiv.). The reaction mixture was heated to 65° C. and stirred for 1 h and 30 min. The solution was quenched with saturated sodium bicarbonate (50 mL) and water (50 mL). The aqueous layer was extracted with EtOAc (2×50 mL). The organic extracts were combined, dried over $Na_2SO_4$, filtered and concentrated in vacuo prior to purification by silica gel chromatography (0% to 100% EtOAc in hexanes) to afford Intermediate I-48. $^1$H NMR (400 MHz, Chloroform-d) δ 7.45 (s, 1H), 7.37-7.31 (m, 1H), 7.29-7.24 (m, 1H), 4.65-4.61 (m, 2H), 3.78-3.70 (m, 1H), 3.65-3.56 (m, 1H), 3.56-3.48 (m, 1H), 1.88-1.45 (m, 3H), 1.41-1.19 (m, 32H), 0.88 (t, J=6.7 Hz, 3H). $^{19}$F NMR (376 MHz, Chloroform-d) δ −110.26-−110.38 (m).

Intermediate I-49: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((S)-2-(3-cyano-5-fluorobenzyl)oxy)icosyl) phosphate

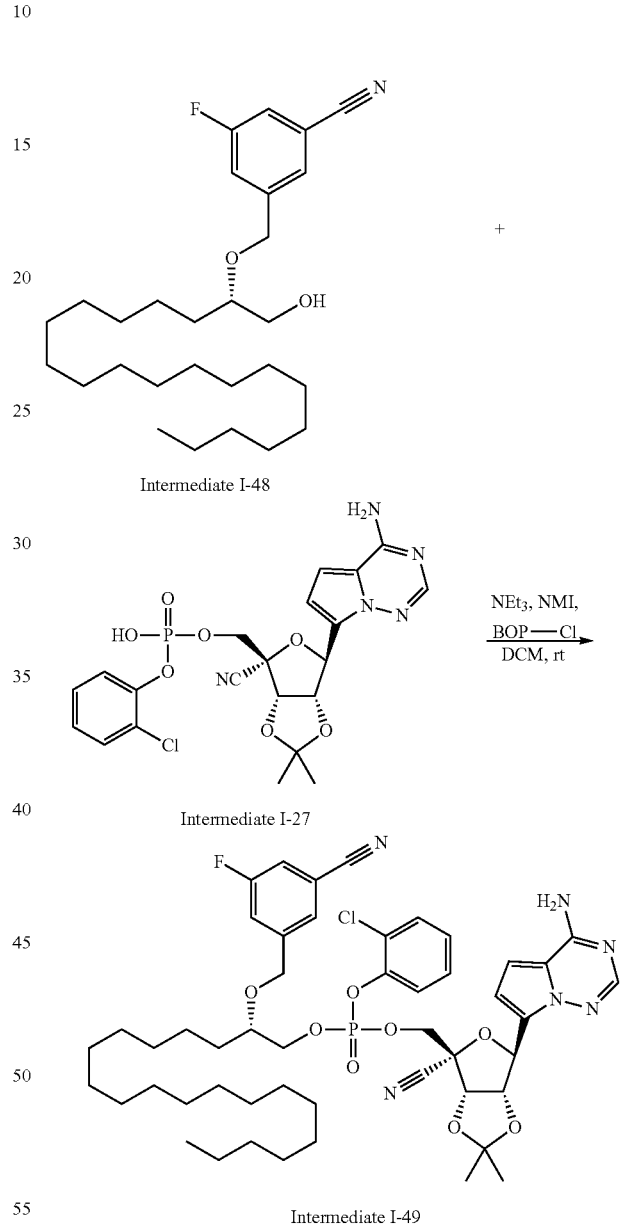

To a solution of Intermediate I-48 (0.148 mmol, 1 equiv.), Intermediate I-27 (0.134 mmol, 1 equiv.), triethylamine (0.07 mL, 0.537 mmol, 4 equiv.) and 1-methylimidazole (0.02 mL, 0.268 mmol, 2 equiv.) in DCM (5.0 mL) was added BOPCl (0.537 mmol, 4 equiv.). The solution was stirred at room temperature overnight. An additional 140 mg of BOP—Cl (0.550 mmol, 4.1 equiv.) and 0.05 mL of 1-methylimidazole (0.627 mmol. 4.68 equiv.) was added and the solution was stirred at room temperature for 3 h. An additional 54 mg of BOP—Cl (0.212 mmol, 1.58 equiv.)

was added and the reaction mixture was stirred for 1 h. The solution was diluted with EtOAc (20 mL) and quenched with 4:1 water:saturated NaHCO₃ (20 mL). The layers were separated and the aqueous layer was extracted with EtOAc (2×20 mL). The organic extracts were combined, washed with brine, dried over Na₂SO₄, filtered and concentrated in vacuo prior to purification by silica gel (0% to 10% MeOH in DCM) to afford Intermediate-49. MS m/z [M+1]=951.33.

Intermediate I-50: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-(3-cyano-5-fluorobenzyl)oxy) icosyl) hydrogen phosphate

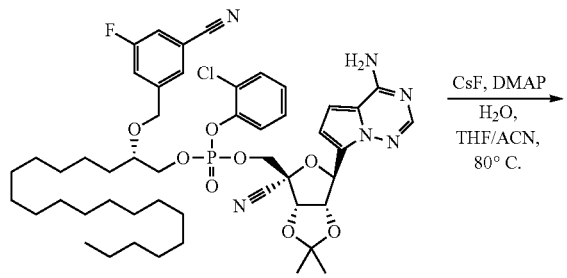

Intermediate I-49

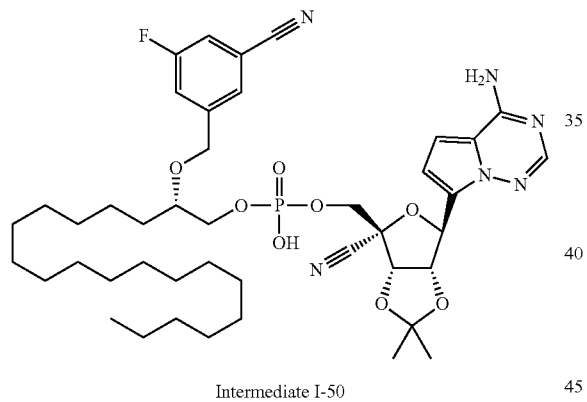

Intermediate I-50

Intermediate I-49 (0.0851 mmol, 1.0 equiv.) was dissolved in 2:1 THF:ACN (4.5 mL total). Cesium fluoride (0.829 mmol, 9.74 equiv.) dissolved in water (0.50 mL) was added to the solution followed by 4-dimethylaminopyridine (0.341 mmol, 4.0 equiv.). The reaction mixture was heated to 80° C. and stirred for 2 h then for an additional 40 min. The reaction was quenched with a buffered solution of citric acid (20 mL, 0.22 M, 51.7 equiv.) and NaOH (0.44 mL, 2 M, 10.3 equiv.). The aqueous layer was extracted with EtOAc (3×30 mL). The organic fractions were combined, washed with brine, dried over Na₂SO₄, filtered and concentrated in vacuo prior to purification by silica gel chromatography (0%-40% MeOH in DCM) to afford Intermediate I-50. ¹H NMR (400 MHz, Methanol-d₄) δ 7.87-7.80 (m, 1H), 7.52-7.31 (m, 3H), 6.89-6.76 (m, 2H), 5.67-5.59 (m, 1H), 5.30-5.22 (m, 1H), 5.17-5.08 (m, 1H), 4.77-4.69 (m, 1H), 4.54-4.45 (m, 1H), 4.16-4.06 (m, 2H), 3.95-3.80 (m, 2H), 3.62-3.51 (m, 1H), 1.73-1.65 (m, 3H), 1.52-1.16 (m, 37H), 0.93-0.86 (m, 3H). MS m/z [M+1]=841.34.

Intermediate I-51a: (S)-2-(5-bromopyridin-3-yl)methoxy)-3-(octadecyloxy)propan-1-ol

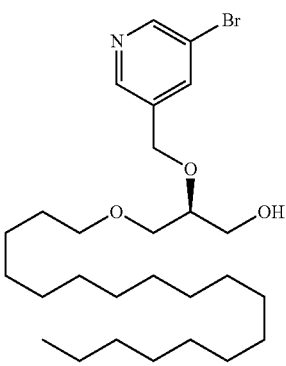

Intermediate I-51a

Intermediate I-51a was prepared in a manner similar to Intermediate I-23 using 3-bromo-5-(bromomethyl)pyridine instead of intermediate 3-(bromomethyl)-5-fluorobenzonitrile. ¹H NMR (400 MHz, Chloroform-d) δ 8.66 (d, J=2.1 Hz, 1H), 8.62-8.50 (m, 1H), 8.13-7.97 (m, 1H), 4.88-4.70 (m, 2H), 3.84-3.77 (m, 1H), 3.77-3.69 (m, 2H), 3.64-3.55 (m, 2H), 3.47 (td, J=6.7, 1.6 Hz, 2H), 1.66-1.52 (m, 2H), 1.40-1.20 (m, 30H), 0.98-0.84 (m, 3H). MS m/z [M+1]=514.3.

Intermediate I-51: (S)-5-(((1-hydroxy-3-(octadecyloxy)propan-2-yl)oxy)methyl) nicotino nitrile

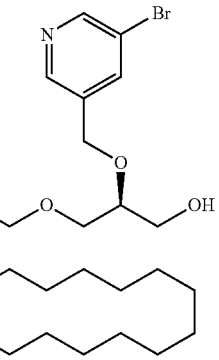

Intermediate I-51a

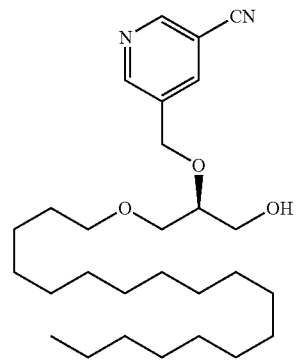

Intermediate I-51

Tetrakis(triphenylphosphine)palladium(0) (15.3 µmol) was added to a vigorously stirred mixture of Intermediate I-51a (146 µmol), zinc(II) cyanide (35.9 mg, 309 µmol), and N,N-dimethylformamide (2.0 mL) at room temperature, and the resulting mixture was heated to 100° C. After 3 h, the resulting mixture was cooled to room temperature, and diethyl ether (40 mL), ethyl acetate (20 mL), saturated sodium bicarbonate solution (10 mL), and saturated aqueous sodium carbonate solution (5 mL) were added sequentially. The organic layer was washed with water (2×80 mL), was dried over anhydrous magnesium sulfate, was filtered, and was concentrated under reduced pressure. The residue was purified by flash column chromatography on silica gel (0 to 50% ethyl acetate in hexanes) to give Intermediate I-51. MS m/z [M+1]=461.4

Intermediate I-52: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((5-cyano pyridin-3-yl)methoxy)-3-(octadecyloxy)propyl) phosphate

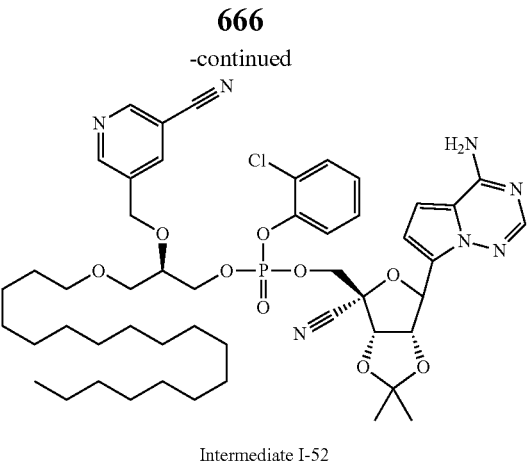

Intermediate I-52

To a solution of Intermediate I-51 (0.0918 mmol, 1 equiv.), Intermediate I-27 (0.0918 mmol, 1 equiv.), triethylamine (0.02 mL, 0.143 mmol, 1.56 equiv.) and 1-methylimidazole (0.02 mL, 0.251 mmol, 2.73 equiv.) in DCM (2.0 mL) was added BOP—Cl (0.255 mmol, 2.78 equiv.). The solution was stirred at room temperature overnight. The solution was allowed to stand at room temperature for 2 days. An additional 70 mg of BOP—Cl (0.275 mmol, 2.99 equiv.) and 0.03 mL of 1-methylimidazole (0.376 mmol. 4.1 equiv.) was added and the solution was stirred at room temperature overnight. The solution was diluted with EtOAc (20 mL) and quenched with 4:1 water:saturated NaHCO$_3$ (20 mL). The layers were separated and the aqueous layer was extracted with EtOAc (2×20 mL). The organic extracts were combined, washed with brine, dried over Na$_2$SO$_4$, filtered and concentrated in vacuo prior to purification by silica gel (0% to 10% MeOH in DCM) to afford Intermediate I-52. MS m/z [M+1]=964.33.

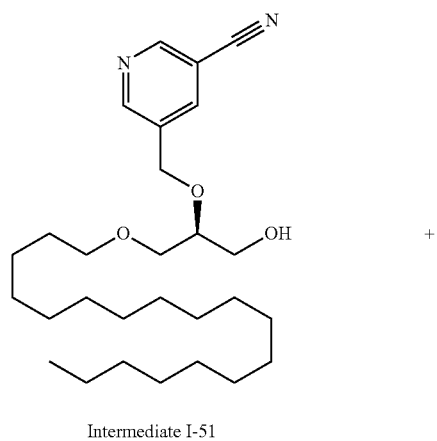

Intermediate I-51

Intermediate I-53: ((3aS,4R,6aS)-6-(4-aminopyrrolo[2,1-f][1,2,4]triazin-7-yl)-4-cyano-2,2-dimethyltetrahydrofurol[3,4-d][1,3]dioxol-4-yl)methyl ((R)-2-((5-cyanopyridin-3-yl) methoxy)-3-(octadecyloxy) propyl) hydrogen phosphate

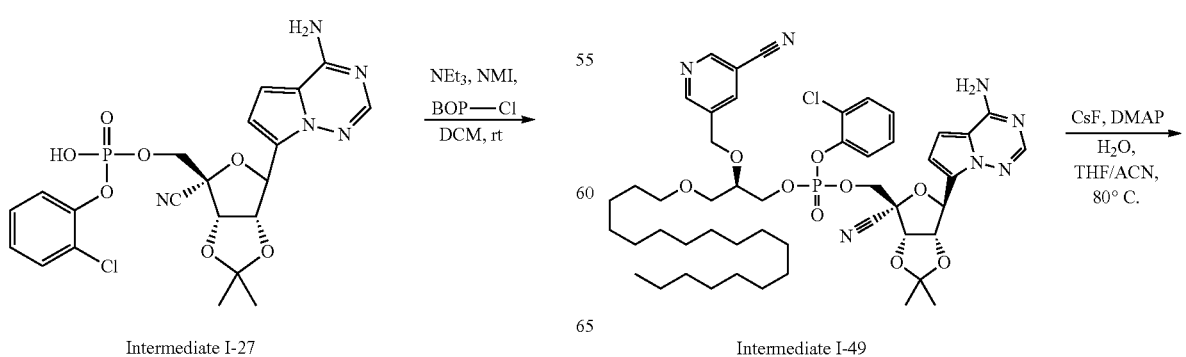

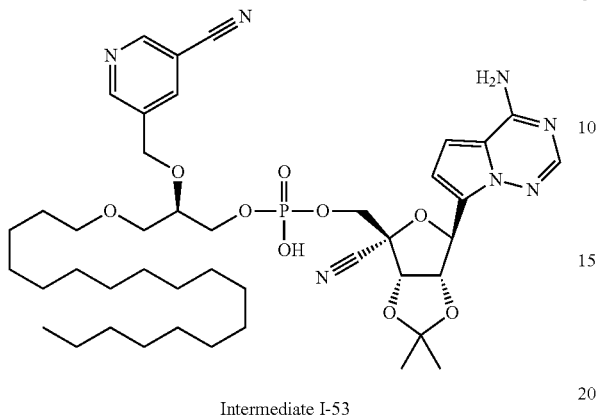

Intermediate I-53

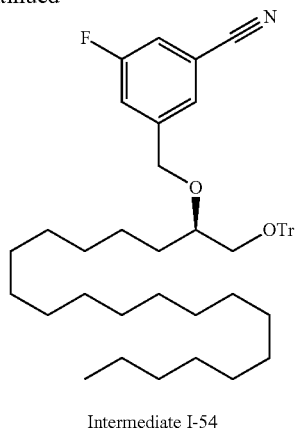

Intermediate I-54

Intermediate I-52 (0.0649 mmol, 1 equiv.) was dissolved in 2:1 THF:ACN (4.5 mL total). Cesium fluoride (0.876 mmol, 13.5 equiv.) dissolved in water (0.50 mL) was added to the solution followed by 4-(dimethylamino)pyridine (0.260 mmol, 4 equiv.). The reaction mixture was heated to 80° C. and stirred for 2 h and 30 min. The reaction was quenched with a buffered solution of citric acid (20 mL, 0.22 M, 67.8 equiv.) and NaOH (0.44 mL, 2 M, 13.6 equiv.). The aqueous layer was extracted with EtOAc (3×30 mL). The organic fractions were combined, washed with brine, dried over Na$_2$SO$_4$, filtered and concentrated in vacuo prior to purification by silica gel chromatography (0%-40% MeOH in DCM) to afford Intermediate I-53. $^1$H NMR (400 MHz, Methanol-d4) δ 8.75-8.71 (m, 2H), 8.19-8.16 (m, 1H), 7.84 (s, 1H), 6.84-6.78 (m, 2H), 5.63 (d, J=3.6 Hz, 1H), 5.26 (dd, J=6.6, 3.6 Hz, 1H), 5.14 (d, J=6.6 Hz, 1H), 4.81-4.64 (m, 2H), 4.16-4.08 (m, 2H), 3.99-3.90 (m, 2H), 3.79-3.71 (m, 1H), 3.53-3.36 (m, 4H), 1.69 (s, 3H), 1.59-1.48 (m, 2H), 1.41-1.21 (m, 33H), 0.92-0.87 (m, 3H). MS m/z [M+1] =854.28.

Intermediate I-54: (R)-3-fluoro-5-(((1-(trityloxy)henicosan-2-yl)oxy)methyl)benzonitrile

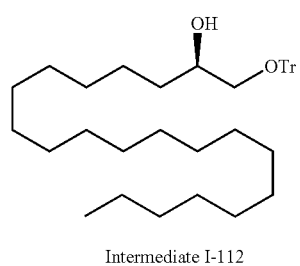

Intermediate I-112

To a solution of Intermediate I-112 (2.24 mmol, 1.0 equiv.) in THF (10.0 mL) cooled in an ice bath was gradually added NaH (60% dispersion in mineral oil) (9.79 mmol, 4.37 equiv.). The solution was stirred vigorously for 5 min. 3-(bromomethyl)-5-fluorobenzonitrile (3.00 mmol, 1.34 equiv.) was added in one portion. The reaction mixture was heated to 80° C. and stirred under nitrogen for 2 h and then for an additional 15 min. The solution was stirred at 60° C. overnight. The reaction mixture was quenched with saturated ammonium chloride until gas evolution ceased. The solution was diluted with water (100 mL) and the aqueous layer extracted with EtOAc (3×100 mL). The organic fractions were combined, washed with brine (100 mL), dried over Na$_2$SO$_4$, filtered and concentrated in vacuo prior to purification by silica gel chromatography (0%-10% EtOAc in hexanes) to afford Intermediate I-54. $^1$H NMR (400 MHz, Chloroform-d) δ 7.47-7.21 (m, 18H), 4.71 (d, J=12.9 Hz, 1H), 4.55 (d, J=12.8 Hz, 1H), 3.55-3.47 (m, 1H), 3.23-3.17 (m, 2H), 1.58-1.46 (m, 2H), 1.35-1.18 (m, 34H), 0.92-0.84 (m, 3H). $^{19}$F NMR (376 MHz, Chloroform-d) δ −110.60-−110.67 (m).

Intermediate I-55: (R)-3-fluoro-5-(((1-hydroxyhenicosan-2-yl)oxy)methyl)benzonitrile

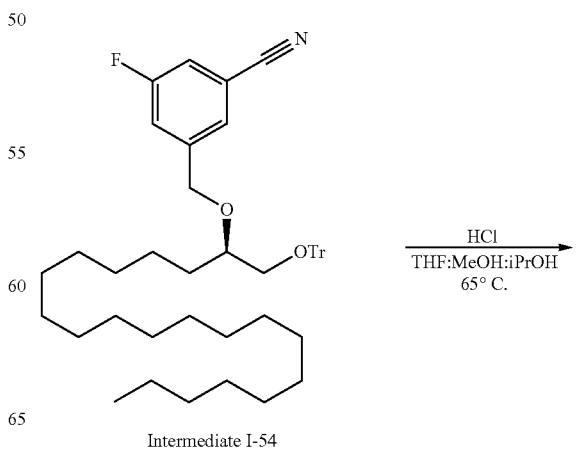

Intermediate I-54

-continued

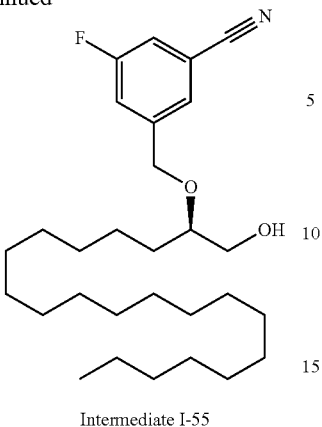

Intermediate I-55

-continued

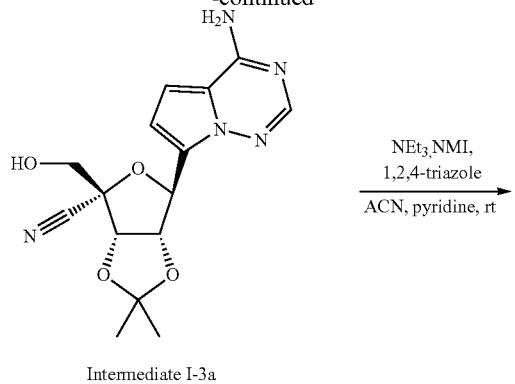

Intermediate I-3a

To a solution of Intermediate I-54 (1.27 mmol, 1 equiv.) in 1:1:1 THF:iPrOH:MeOH (21 mL total) was added concentrated HCl (0.41 mL, 12.0 M, 3.85 equiv.). The reaction mixture was heated to 65° C. and stirred for 2 h. The solution was quenched with saturated sodium bicarbonate until gas evolution ceased and water (50 mL). The pH of the aqueous layer was adjusted to 7 using saturated sodium bicarbonate. The aqueous layer was extracted with EtOAc (2×75 mL). The organic extracts were combined, washed with brine (50 mL), dried over $Na_2SO_4$, filtered and concentrated in vacuo prior to purification by silica gel chromatography (0%-100% EtOAc in hexanes) to afford Intermediate I-55. $^1$H NMR (400 MHz, Chloroform-d) δ 7.46-7.43 (m, 1H), 7.37-7.31 (m, 1H), 7.30-7.24 (m, 1H), 4.65-4.61 (m, 2H), 3.79-3.70 (m, 1H), 3.65-3.48 (m, 2H), 1.76 (s, 1H), 1.68-1.47 (m, 2H), 1.45-1.17 (m, 34H), 0.93-0.83 (m, 3H). $^{19}$F NMR (376 MHz, Chloroform-d) δ −110.27−−110.37 (m).

Intermediate I-56: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)henicosyl) phosphate

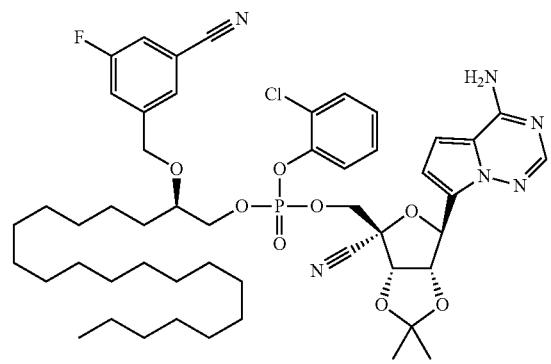

Intermediate I-56

An oven-dried round bottom flask was charged with 1H-1,2,4-triazole (2.60 mmol, 2.15 equiv.). The triazole was dissolved in ACN (10.0 mL) and pyridine (10.0 mL). Triethylamine (0.36 mL, 2.60 mmol, 2.15 equiv.) was added to the solution under argon followed by 2-chlorophenyl phosphorodichloridate (0.20 mL, 1.21 mmol, 1 equiv.). The reaction mixture was stirred at room temperature for 27 min prior to the addition of Intermediate I-3a (1.21 mmol, 1 equiv.) in one portion followed by 1-methylimidazole (0.16 mL, 2.02 mmol, 1.67 equiv.). The solution was stirred for around 1 h. Intermediate I-55 (1.33 mmol, 1.1 equiv.) was added and the reaction mixture was stirred for an additional 2 h under argon. The reaction was quenched with a buffered solution of 4:1 citric acid (20% in water): 1M NaOH (50 mL). The aqueous layer was extracted with EtOAc (4×50 mL). The organic fractions were combined, washed with brine (50 mL), dried over $Na_2SO_4$, filtered and concentrated in vacuo prior to purification by silica gel chromatography (0-20% MeOH in DCM) to afford Intermediate I-56. MS m/z [M+1]=965.24.

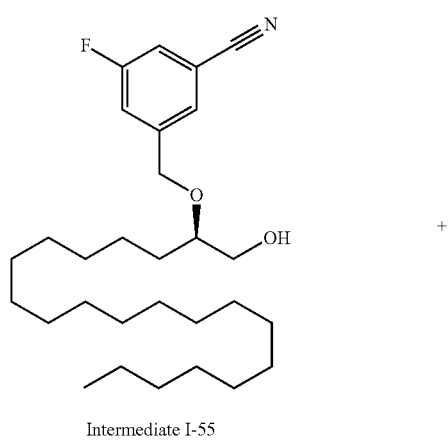

Intermediate I-55

+

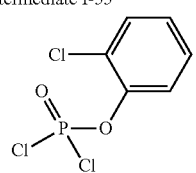

+

Intermediate I-57: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-cyano-5-fluorobenzyl) oxy)henicosyl) hydrogen phosphate Intermediate I-58: ((2R,3S,4R,5S)-5-(4-aminopyrrolo[2,1-f][1,2,4]triazin-7-yl)-2-cyano-3,4-dihydroxytetrahydrofuran-2-yl)methyl (2-chlorophenyl) ((R)-2-((3-cyano-5-fluorobenzyl) oxy)-3-(heptadecyloxy)propyl) phosphate

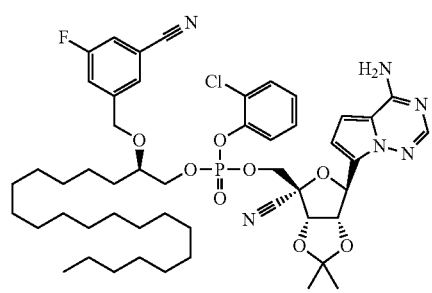

Intermediate I-56

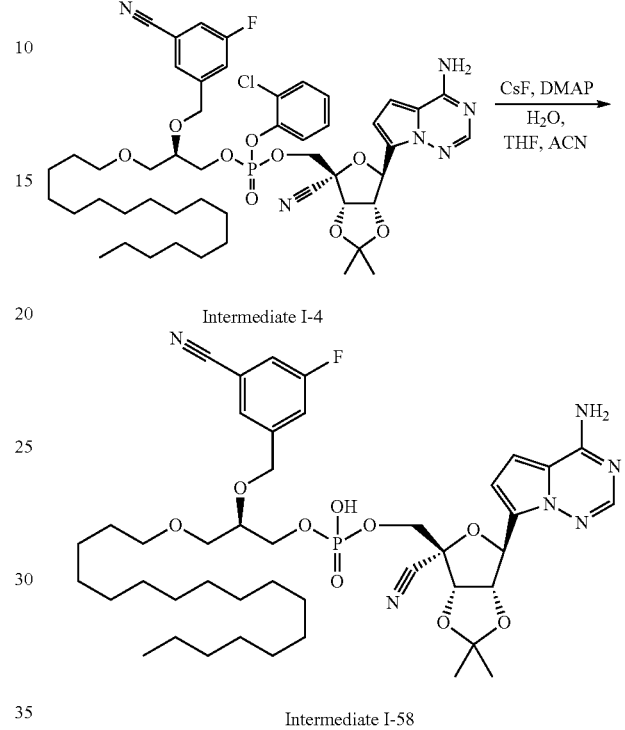

Intermediate I-4

Intermediate I-58

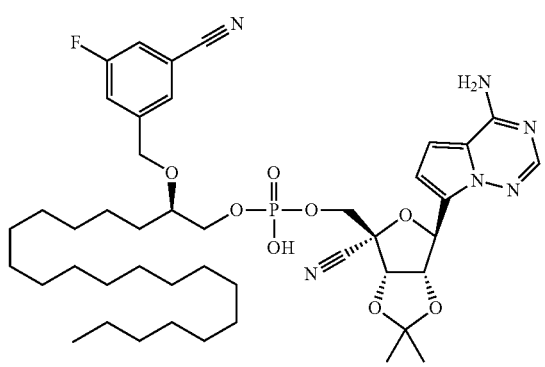

Intermediate I-57

Intermediate I-56 (1.22 mmol, 1.0 equiv.) was dissolved in 2:1 THF:ACN (13.5 mL total). Cesium fluoride (3.65 mmol, 3 equiv.) dissolved in water (1.5 mL) was added to the solution followed by 4-dimethylaminopyridine (4.09 mmol, 3.37 equiv.). The reaction mixture was heated to 80° C. and stirred for 1 h and 30 min then for an additional 30 min. The reaction was quenched with a buffered solution of citric acid (12.2 mmol, 10 equiv.) dissolved in water (60 mL) and NaOH (1.22 mL, 2 M, 2 equiv.). The aqueous layer was extracted with EtOAc (3×100 mL). The organic fractions were combined, washed with 3:2 water:brine (50 mL), dried over $Na_2SO_4$, filtered and concentrated in vacuo prior to purification by silica gel chromatography (0%-50% MeOH in DCM) to afford Intermediate I-57. MS m/z [M+1]=855.25.

Intermediate I-4 (0.0724 mmol) was dissolved in THF-ACN (1:0.5 mL) and CsF (95.4 mg, 0.628 mmol) in water (0.1 mL) and then DMAP (0.267 mmol) added. The resulting mixture was heated at 80° C. for 3.5 h. After dilution with PBS buffer pH 7 (5 mL), the mixture was partitioned between brine (10 mL) and EtOAc (20 mL). Aqueous layer was extracted with EtOAc (10 mL×3). The combined organic layer was dried under sodium sulfate, concentrated in vacuo, and purified by silica gel column chromatography (0% to 50% MeOH in DCM) to give Intermediate I-58. MS m/z [M+1]=857.

Intermediate I-59: (S)-1-(trityloxy)henicosan-2-ol

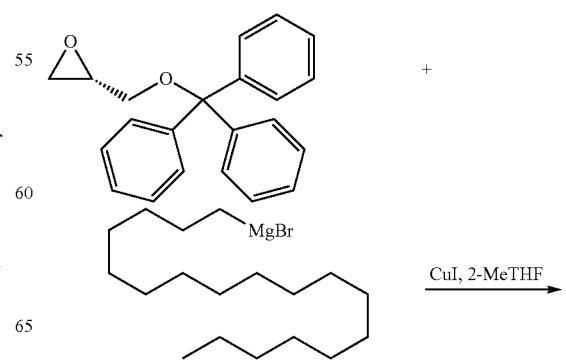

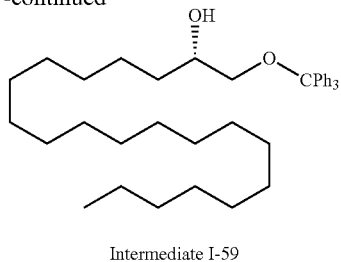

Intermediate I-59

(S)-2-((trityloxy)methyl)oxirane (7.11 mmol) was dissolved in 2-MeTHF (7.0 mL). To this was added copper (I) iodide (0.777 mmol). The white slurry was cooled in an ice bath. Octadecylmagnesium bromide (42 mL, 0.213 M) was added gradually over a period of 45 min while maintaining the internal temperature no higher than 11.4° C. The solution was stirred for 3 h and 15 min while gradually coming to room temperature in the ice bath. The reaction mixture was quenched with saturated ammonium chloride (50 mL) and water (50 mL). The organic layer was separated. The aqueous layer was extracted with EtOAc (2×75 mL). The organic fractions were washed with 1:1 brine:water, dried over $Na_2SO_4$, filtered and concentrated in vacuo. The crude material was dry loaded onto silica and purified twice by silica gel chromatography (0-100% EtOAc in hexanes then 0-20% EtOAc in hexanes) to afford Intermediate I-59. $^1$H NMR (400 MHz, Chloroform-d) δ 7.47-7.41 (m, 6H), 7.34-7.22 (m, 9H), 3.81-3.72 (m, 1H), 3.18 (dd, J=9.4, 3.3 Hz, 1H), 3.03 (dd, J=9.3, 7.5 Hz, 1H), 2.31 (s, 1H), 1.50-1.16 (m, 36H), 0.89 (t, J=6.7 Hz, 3H).

Intermediate I-60: (S)-3-fluoro-5-(((1-(trityloxy) henicosan-2-yl)oxy)methyl)benzonitrile

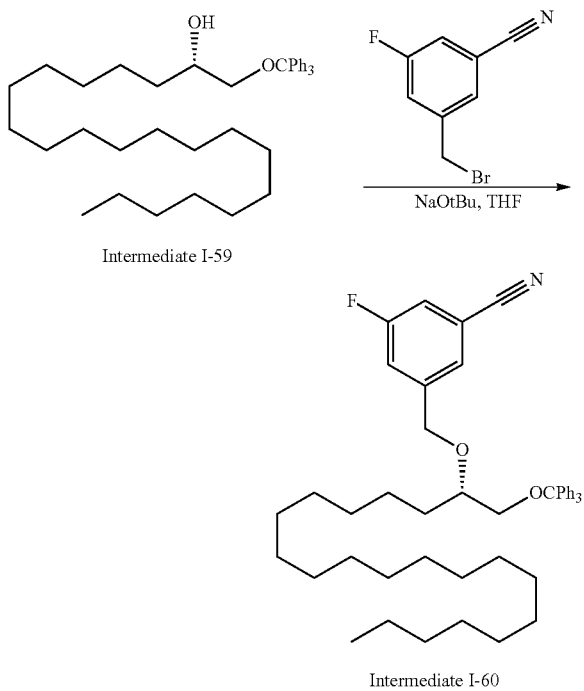

To a solution of Intermediate I-59 (2.72 mmol) in THF (15 mL) was added sodium tert-butoxide (2.7 mL, 2.0 M in THF). The solution was stirred for 5 min at room temperature prior to the addition of 3-(bromomethyl)-5-fluorobenzonitrile (5.05 mmol). The solution was stirred at room temperature overnight. The reaction mixture was diluted with water (75 mL) and extracted with EtOAc (3×50 mL). The organic fractions were combined, washed with brine, dried over $Na_2SO_4$, filtered and concentrated in vacuo prior to purification by silica gel chromatography (0-10% EtOAc in hexanes) to afford Intermediate I-60. $^1$H NMR (400 MHz, Chloroform-d) δ 7.48-7.19 (m, 18H), 4.71 (d, J=12.8 Hz, 1H), 4.55 (d, J=12.9 Hz, 1H), 3.55-3.47 (m, 1H), 3.23-3.18 (m, 2H), 1.58-1.47 (m, 2H), 1.34-1.18 (m, 34H), 0.91-0.85 (m, 3H). $^{19}$F NMR (376 MHz, Chloroform-d) δ −110.59-- −110.68 (m).

Intermediate I-61: (S)-3-fluoro-5-(((1-hydroxyhenicosan-2-yl)oxy)methyl)benzonitrile

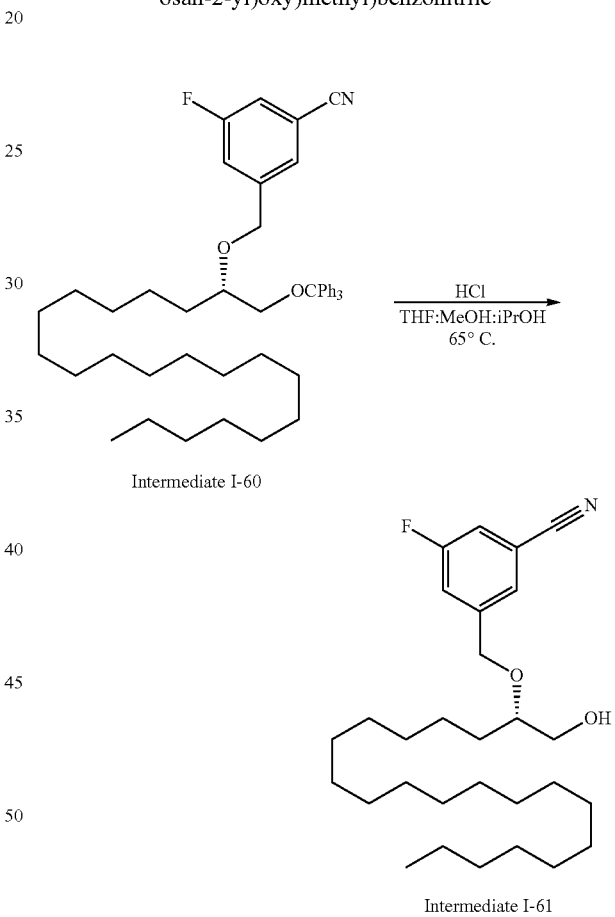

To a solution of Intermediate I-60 (2.03 mmol) in 1:1:1 THF:MeOH:iPrOH (21.0 mL total) was added concentrated HCl (0.65 mL). The reaction mixture was gradually heated to 65° C. and stirred for 3 h and 45 min. The solution was allowed to stand at room temperature overnight prior to quenching with saturated $NaHCO_3$ (50 mL) and water (50 mL). The aqueous layer was extracted with EtOAc (3×100 mL). The organic extracts were combined, dried over $Na_2SO_4$, filtered and purified by silica gel chromatography (0-60% EtOAc in hexanes) to afford Intermediate I-61. $^1$H NMR (400 MHz, Chloroform-d) δ 7.46-7.43 (m, 1H), 7.36-7.31 (m, 1H), 7.30-7.25 (m, 1H), 4.65-4.61 (m, 2H), 3.79-

3.69 (m, 1H), 3.66-3.56 (m, 1H), 3.56-3.48 (m, 1H), 1.83-1.73 (m, 1H), 1.68-1.46 (m, 2H), 1.44-1.18 (m, 34H), 0.88 (t, J=6.7 Hz, 3H). $^{19}$F NMR (376 MHz, Chloroform-d) δ –110.27 – –110.38 (m).

Intermediate I-62: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((S)-2-((3-cyano-5-fluorobenzyl)oxy) henicosyl) phosphate

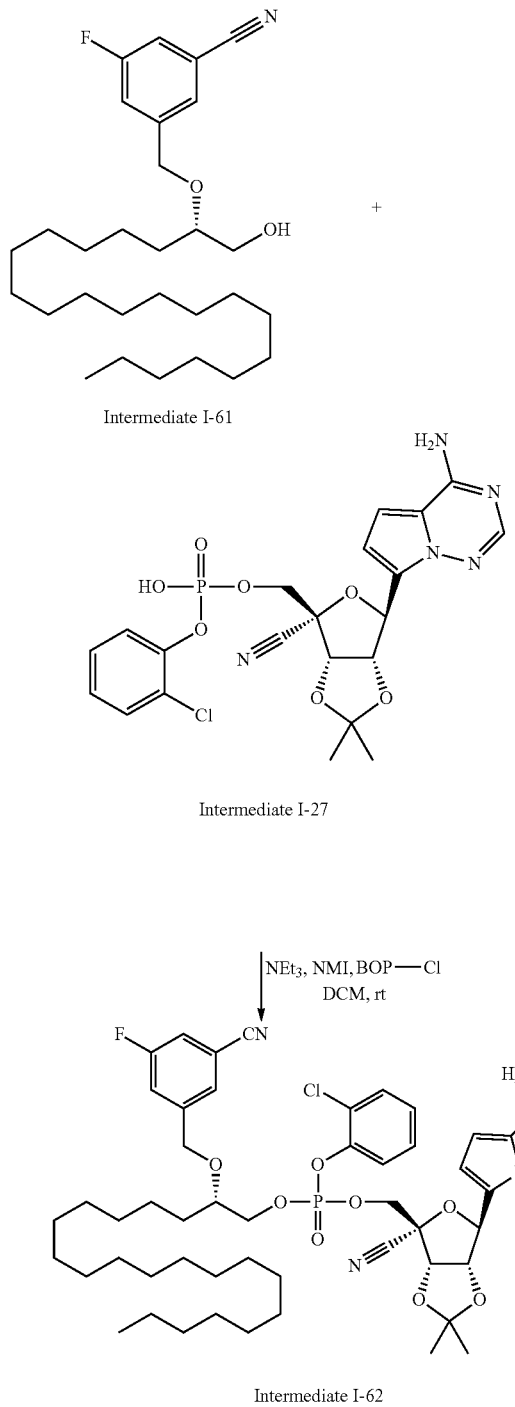

To a solution of Intermediate I-61 (0.369 mmol), Intermediate I-27 (0.369 mmol), triethylamine (0.10 mL, 0.738 mmol) and 1-methylimidazole (0.09 mL, 1.11 mmol) in DCM (5.0 mL) was added BOP—Cl (1.03 mmol). The solution was stirred at room temperature overnight. The solution was diluted with EtOAc (50 mL) and quenched with 4:1 water:saturated NaHCO$_3$ (50 mL). The layers were separated and the aqueous layer was extracted with EtOAc (2×50 mL). The organic extracts were combined, washed with 1:1 water:brine (40 mL), dried over Na$_2$SO$_4$, filtered and concentrated in vacuo prior to purification by silica gel (0-10% MeOH in DCM) to afford Intermediate I-62. MS m/z [M+1]=965.3.

Intermediate I-63: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl)oxy) henicosyl) hydrogen phosphate

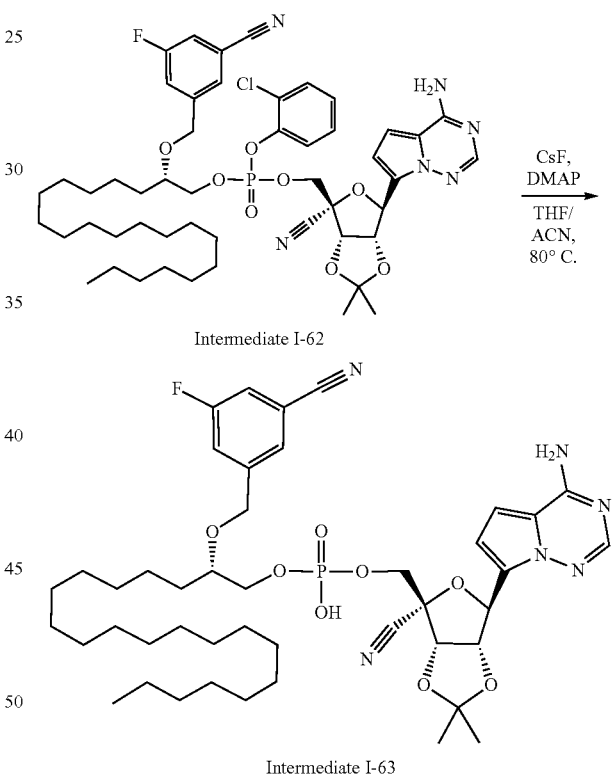

Intermediate I-62 (0.303 mmol) was dissolved in 2:1 THF:ACN (4.5 mL total). Cesium fluoride (1.24 mmol) dissolved in water (0.50 mL) was added to the solution followed by 4-dimethylaminopyridine (0.910 mmol). The reaction mixture was heated to 80° C. and stirred for 5 h. The reaction was quenched with a buffered solution of citric acid (20 mL, 0.22 M) and NaOH (0.44 mL, 2 M). The aqueous layer was extracted with EtOAc (3×30 mL). The organic fractions were combined, washed with brine (20 mL), dried over Na$_2$SO$_4$, filtered and concentrated in vacuo prior to purification by silica gel chromatography (0-40% MeOH in DCM) to afford Intermediate I-63. MS m/z [M+1]=855.3.

Intermediate I-64: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-4-(1H-1,2,4-triazol-1-yl)benzyl)oxy)henicosyl) phosphate

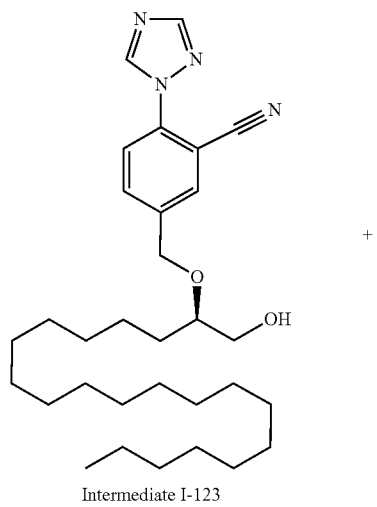

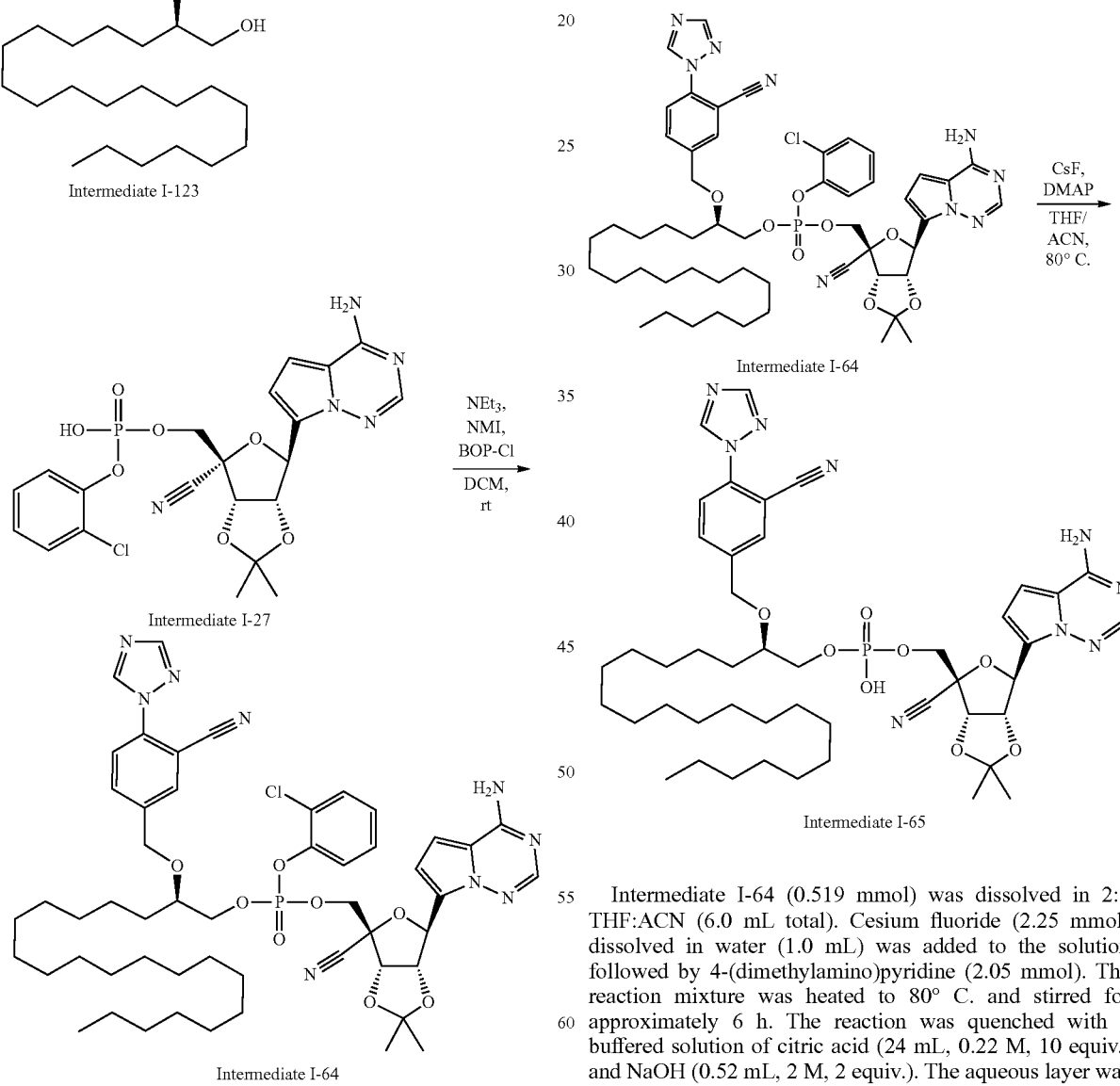

To a solution of Intermediate I-123 (0.575 mmol), Intermediate I-27 (0.575 mmol), triethylamine (0.16 mL, 1.15 mmol) and 1-methylimidazole (0.14 mL, 1.72 mmol) in DCM (5.0 mL) was added BOP—Cl (1.96 mmol). The solution was stirred at room temperature for 2 h prior to diluting with EtOAc (50 mL) and quenching with 4:1 water:saturated NaHCO$_3$ (50 mL). The layers were separated and the aqueous layer was extracted with EtOAc (2×50 mL). The organic extracts were combined, washed with brine, dried over Na$_2$SO$_4$, filtered and concentrated in vacuo prior to purification by silica gel (0-10% MeOH in DCM) to afford Intermediate I-64. MS m/z [M+1]=1014.3.

Intermediate I-65: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-cyano-4-(1H-1,2,4-triazol-1-yl)benzyl)oxy)henicosyl) hydrogen phosphate Intermediate I-64 (0.519 mmol) was dissolved in 2:1 THF:ACN (6.0 mL total). Cesium fluoride (2.25 mmol) dissolved in water (1.0 mL) was added to the solution followed by 4-(dimethylamino)pyridine (2.05 mmol). The reaction mixture was heated to 80° C. and stirred for approximately 6 h. The reaction was quenched with a buffered solution of citric acid (24 mL, 0.22 M, 10 equiv.) and NaOH (0.52 mL, 2 M, 2 equiv.). The aqueous layer was extracted with EtOAc (3×30 mL). The organic fractions were combined, washed with brine, dried over Na$_2$SO$_4$, filtered and concentrated in vacuo prior to purification by silica gel chromatography (0-40% MeOH in DCM) to afford Intermediate I-65. MS m/z [M+1]=904.2

Intermediate I-66: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) icosyl phosphate

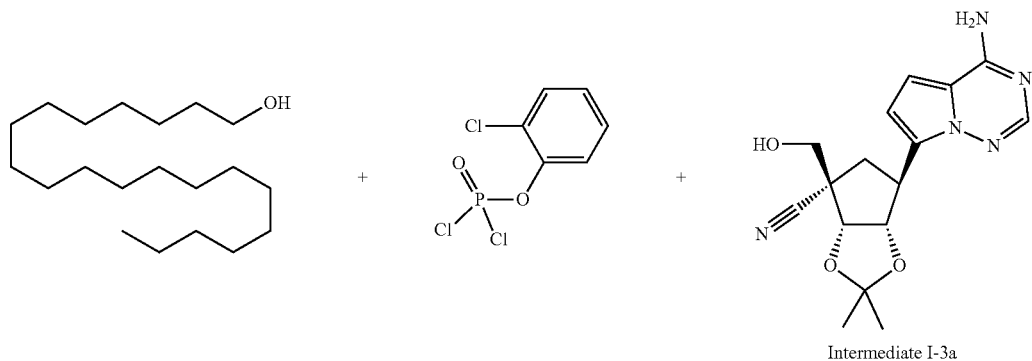

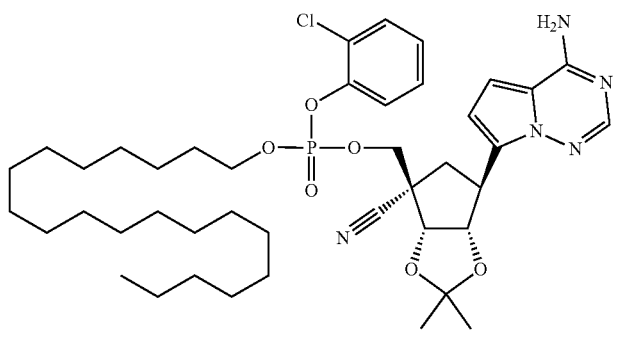

Intermediate I-66

1H-1,2,4-triazole (2.40 mmol) was dissolved in THF (4 mL). TEA (0.33 mL, 2.40 mmol) was added to the solution followed by 2-chlorophenyl phosphorodichloridate (0.16 mL, 0.996 mmol). The reaction mixture was stirred at rt for 17 min. Intermediate I-3a (0.905 mmol) was added in one portion followed by 1-methylimidazole (0.09 mL, 1.18 mmol). The solution was stirred for 18 min, and then 1-eicosanol (0.905 mmol) was added followed by an additional 4 mL of THF. The reaction mixture was stirred for 1 h and 30 min prior to dilution with 4:1 water:saturated NaHCO$_3$ (50 mL). The aqueous layer was extracted with EtOAc (3×50 mL). The organic fractions were combined, washed with 1:1 brine:water (50 mL), dried over Na$_2$SO$_4$, filtered and purified by silica gel chromatography (0-100% EtOAc in hexanes) to afford Intermediate I-66 as a diastereomeric mixture. $^1$H NMR (400 MHz, Methanol-d4) δ 7.82-7.79 (m, 1H), 7.48-7.40 (m, 1H), 7.37-7.29 (m, 1H), 7.21-7.12 (m, 2H), 6.86-6.82 (m, 1H), 6.78-6.76 (m, 1H), 5.67-5.63 (m, 1H), 5.35-5.29 (m, 1H), 5.20-5.13 (m, 1H), 4.59-4.46 (m, 2H), 4.24-4.12 (m, 2H), 1.74-1.71 (m, 3H), 1.68-1.57 (m, 2H), 1.41-1.37 (m, 3H), 1.34-1.24 (m, 34H), 0.93-0.86 (m, 3H). $^{31}$P NMR (162 MHz, Methanol-d$_4$) δ −7.61--8.02 (m). MS m/z [M−1]=800.2.

Intermediate I-67: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl icosyl hydrogen phosphate

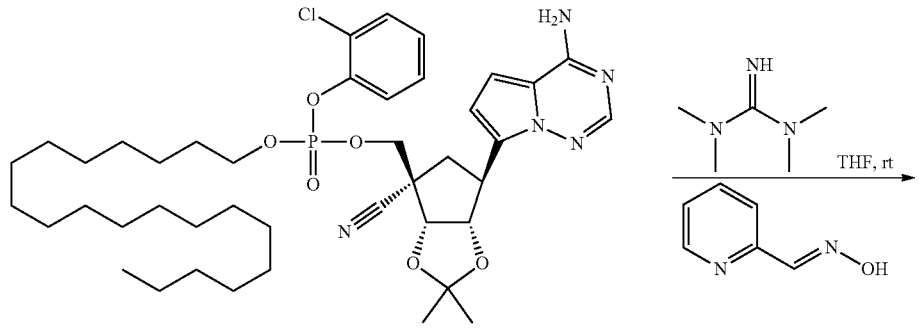

Intermediate I-66

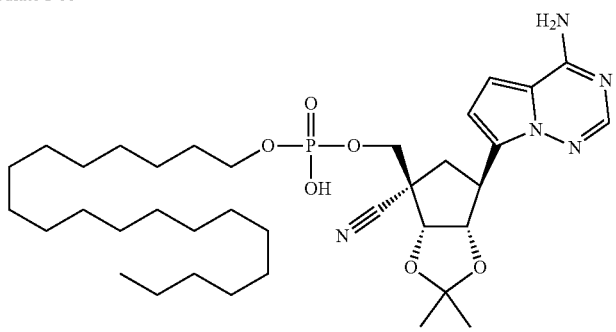

Intermediate I-67

To a solution of Intermediate I-66 (0.428 mmol) in THF (5.0 mL) was added 1,1,3,3-tetramethylguanidine (0.32 mL, 2.57 mmol) and syn-2-pyridinealdoxime (4.28 mmol). The reaction mixture was stirred at rt overnight. The solution was concentrated in vacuo and purified by silica gel (0-40% MeOH in DCM) to afford Intermediate I-67. $^1$H NMR (400 MHz, Methanol-d4) δ 7.84 (s, 1H), 6.86 (d, J=4.5 Hz, 1H), 6.80 (d, J=4.5 Hz, 1H), 5.64 (d, J=3.6 Hz, 1H), 5.28 (dd, J=6.6, 3.6 Hz, 1H), 5.14 (d, J=6.6 Hz, 1H), 4.14-4.03 (m, 2H), 3.80 (q, J=6.5 Hz, 2H), 1.70 (s, 3H), 1.57-1.46 (m, 2H), 1.39 (s, 3H), 1.36-1.20 (m, 34H), 0.92-0.87 (m, 3H). $^{31}$P NMR (162 MHz, Methanol-d4) δ 0.08--0.68 (m). MS m/z [M-1]=692.2.

Intermediate I-68: (R)-3-chloro-5-(((1-(trityloxy)nonadecan-2-yl)oxy)methyl)benzonitrile

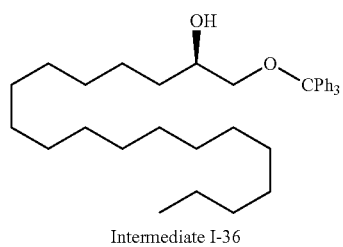

Intermediate I-36

+

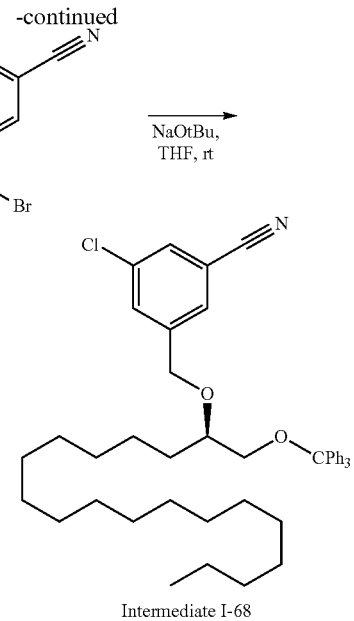

Intermediate I-68

To a solution of Intermediate I-36 (3.68 mmol) in THF (15 mL) was added sodium tert-butoxide (3.8 mL, 2.0 M in THF). The solution was stirred for 5 min at room temperature prior to the addition of 3-(bromomethyl)-5-chlorobenzonitrile (4.25 mmol). The solution was stirred at room temperature overnight. The reaction mixture was diluted with water (100 mL) and extracted with EtOAc (3×75 mL). The organic fractions were combined, washed with 1:1 brine:water (100 mL), dried over Na$_2$SO$_4$, filtered and concentrated in vacuo prior to purification by silica gel chromatography (0-10% EtOAc in hexanes) to afford Intermediate I-68. $^1$H NMR (400 MHz, Chloroform-d) δ 7.59-7.41 (m, 9H), 7.34-7.21 (m, 9H), 4.70 (d, J=12.8 Hz, 1H), 4.54 (d, J=12.7 Hz, 1H), 3.55-3.47 (m, 1H), 3.24-3.18 (m, 2H), 1.57-1.48 (m, 2H), 1.36-1.18 (m, 30H), 0.88 (t, J=6.8 Hz, 3H).

Intermediate I-69: (R)-3-chloro-5-(((1-hydroxynonadecan-2-yl)oxy)methyl)benzonitrile

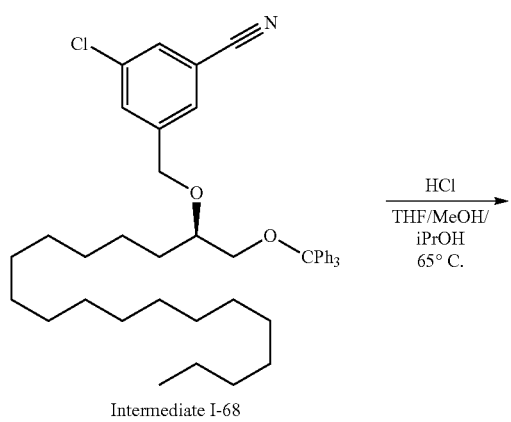

Intermediate I-68

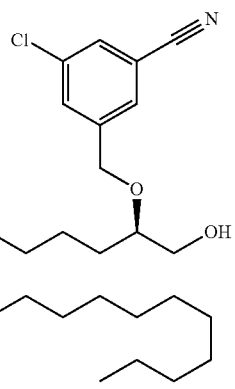

Intermediate I-69

To a solution of Intermediate I-68 (2.01 mmol) in 1:1:1 THF:MeOH:iPrOH (15.0 mL total) was added concentrated HCl (0.65 mL, 12 M). The reaction mixture was gradually heated to 65° C. and stirred for 4 h. The solution was quenched with a solution of saturated NaHCO$_3$ (50 mL) and water (50 mL). The aqueous layer was extracted with EtOAc (3×60 mL). The organic extracts were combined, dried over Na$_2$SO$_4$, filtered and purified by silica gel chromatography (0-50% EtOAc in hexanes) to afford Intermediate I-69. $^1$H NMR (400 MHz, Chloroform-d) δ 7.60-7.57 (m, 1H), 7.57-7.52 (m, 2H), 4.63-4.60 (m, 2H), 3.79-3.69 (m, 1H), 3.66-3.56 (m, 1H), 3.56-3.47 (m, 1H), 1.82-1.73 (m, 1H), 1.67-1.46 (m, 2H), 1.43-1.16 (m, 30H), 0.88 (t, J=6.7 Hz, 3H).

Intermediate I-70: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-chloro-5-cyanobenzyl) oxy)nonadecyl) (2-chlorophenyl) phosphate

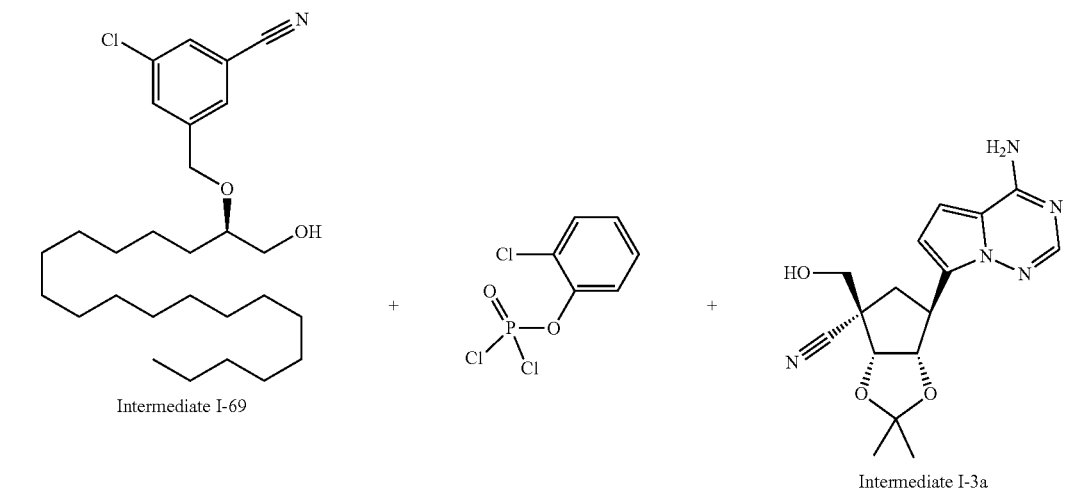

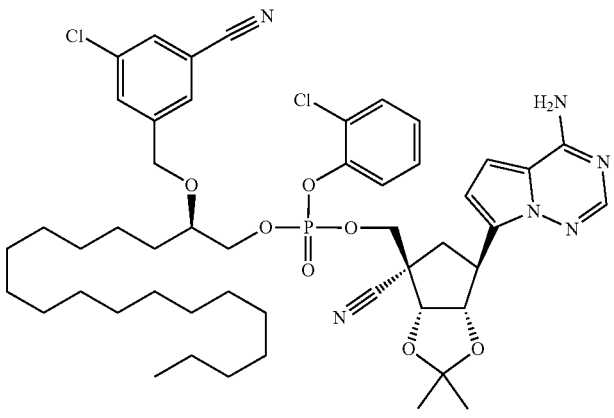

Intermediate I-70

1H-1,2,4-triazole (1.40 mmol, 3.16 equiv.) was dissolved in THF (3.0 mL). TEA (0.16 mL, 1.18 mmol) was added to the solution followed by 2-chlorophenyl phosphorodichloridate (0.08 mL, 0.49 mmol). The reaction mixture was stirred at rt for 7 min prior to the addition of Intermediate I-3a (0.49 mmol) in one portion followed by 1-methylimidazole (0.05 mL, 0.58 mmol). The solution was stirred for an additional 15 min before adding Intermediate I-69 (0.44 mmol) dissolved in THF (3.0 mL). After stirring at room temperature for 5 h and 30 min, the solution was diluted with 4:1 water:saturated NaHCO$_3$ (50 mL). The aqueous layer was extracted with EtOAc (3×50 mL). The organic layers were combined, washed with brine (30 mL), dried over Na$_2$SO$_4$, filtered and concentrated in vacuo prior to purification by silica gel chromatography (0-100% EtOAc in hexanes) to afford Intermediate I-70 as a diastereomeric mixture. $^1$H NMR (400 MHz, Methanol-d$_4$) δ 7.81-7.77 (m, 1H), 7.64-7.50 (m, 3H), 7.47-7.28 (m, 2H), 7.21-7.07 (m, 2H), 6.85-6.80 (m, 1H), 6.78-6.74 (m, 1H), 5.66-5.62 (m, 1H), 5.33-5.27 (m, 1H), 5.18-5.12 (m, 1H), 4.63-4.42 (m, 4H), 4.36-4.24 (m, 1H), 4.24-4.08 (m, 1H), 3.63-3.55 (m, 1H), 1.72 (s, 3H), 1.58-1.16 (m, 35H), 0.93-0.85 (m, 3H). $^{31}$P NMR (162 MHz, Methanol-d$_4$) δ −7.44−−8.04 (m). MS m/z [M−1]=953.2.

Intermediate I-71: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-chloro-5-cyanobenzyl) oxy)nonadecyl) hydrogen phosphate

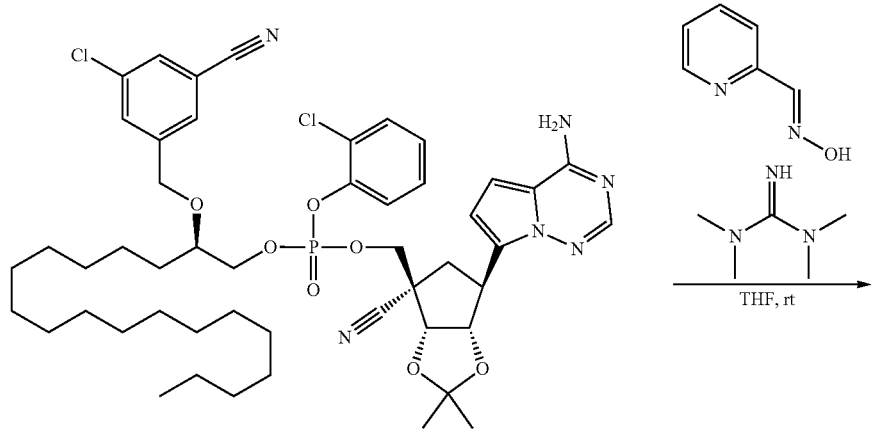

Intermediate I-70

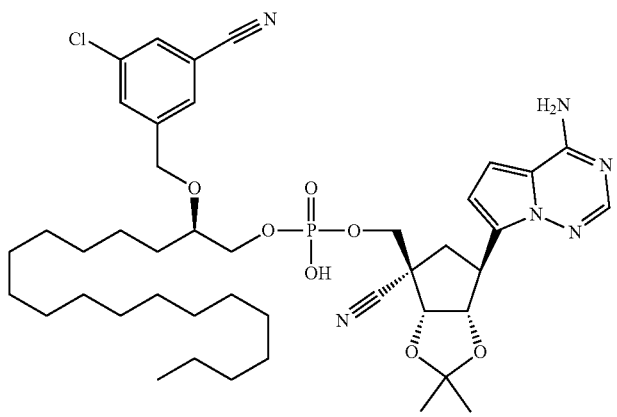

Intermediate I-71

To a solution of Intermediate I-70 (0.147 mmol) in THF (5.0 mL) was added 1,1,3,3-tetramethylguanidine (0.11 mL, 0.881 mmol) and syn-2-pyridinealdoxime (147 mg, 1.20 mmol). The reaction mixture was stirred at room temperature overnight. The solution was concentrated in vacuo and purified by silica gel (0-40% MeOH in DCM) to afford Intermediate I-71. $^1$H NMR (400 MHz, Methanol-d4) δ 7.82 (s, 1H), 7.64-7.57 (m, 3H), 6.83 (d, J=4.5 Hz, 1H), 6.78 (d, J=4.5 Hz, 1H), 5.63 (d, J=3.6 Hz, 1H), 5.25 (dd, J=6.6, 3.6 Hz, 1H), 5.13 (d, J=6.6 Hz, 1H), 4.72 (d, J=13.0 Hz, 1H), 4.49 (d, J=13.0 Hz, 1H), 4.19-4.07 (m, 2H), 3.97-3.79 (m, 2H), 3.58-3.49 (m, 1H), 1.69 (s, 3H), 1.48-1.20 (m, 35H), 0.89 (t, J=6.7 Hz, 3H). $^{31}$P NMR (162 MHz, Methanol-d4) δ −0.36−−1.01 (m). MS m/z [M−1]=843.2

Intermediate I-72: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((6-cyanopyridin-3-yl)oxy)-3-(tetradecyloxy)propyl) phosphate

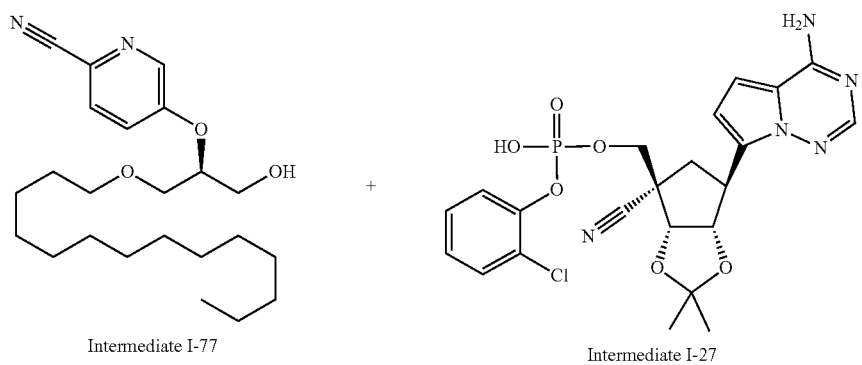

Intermediate I-77 + Intermediate I-27

NEt₃, NMI, BOP-Cl
DCM, rt

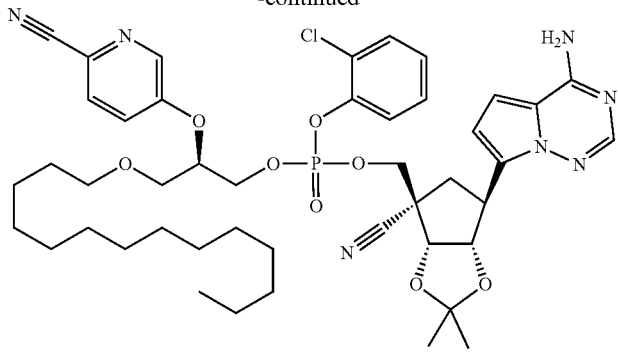

Intermediate I-72

To a solution of Intermediate I-77 (0.0666 mmol, 1 equiv.), Intermediate I-27 (0.0666 mmol), triethylamine (0.02 mL, 0.143 mmol) and 1-methylimidazole (0.02 mL, 0.251 mmol) in DCM (2.0 mL) was added BOP—Cl (0.200 mmol). The solution was stirred at room temperature for 7 h. After 7 h an additional BOP—Cl (0.530 mmol) was added and the reaction mixture was stirred overnight. The reaction mixture was diluted with EtOAc (20 mL) and quenched with 4:1 water:saturated NaHCO₃ (20 mL). The layers were separated and the aqueous layer was extracted twice more with EtOAc (2×20 mL). The organic extracts were combined, washed with brine, dried over Na₂SO₄, filtered and concentrated in vacuo prior to purification by silica gel (0-10% MeOH in DCM) to afford Intermediate I-72. MS m/z [M−1]=894.3.

Intermediate I-73: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((6-cyanopyridin-3-yl)oxy)-3-(tetradecyloxy)propyl) hydrogen phosphate Intermediate I-72 (0.0387 mmol) was dissolved in 2:1 THF:ACN (4.5 mL total). Cesium fluoride (0.790 mmol) dissolved in water (0.50 mL) was added to the solution followed by 4-(dimethylamino)pyridine (0.155 mmol). The reaction mixture was heated to 80° C. and stirred for 3.5 h. The reaction was quenched with a buffered solution of citric acid (20 mL, 0.22 M, 114 equiv.) and NaOH (0.44 mL, 2 M, 22.8 equiv.). The aqueous layer was extracted with EtOAc (3×20 mL). The organic fractions were combined, washed with brine (20 mL), dried over Na₂SO₄, filtered and concentrated in vacuo prior to purification by silica gel chromatography (0-40% MeOH in DCM) to afford Intermediate I-73. $^1$H NMR (400 MHz, Methanol-d4) δ 8.33 (d, J=2.9 Hz, 1H), 7.85 (s, 1H), 7.69 (d, J=8.7 Hz, 1H), 7.55 (dd, J=8.7, 2.9 Hz, 1H), 6.86-6.84 (m, 1H), 6.80 (d, J=4.5 Hz, 1H), 5.64 (d, J=3.6 Hz, 1H), 5.28 (dd, J=6.6, 3.6 Hz, 1H), 5.13 (d, J=6.6 Hz, 1H), 4.80-4.72 (m, 1H), 4.16-3.98 (m, 4H), 3.66-3.32 (m, 4H), 1.70 (s, 3H), 1.53-1.42 (m, 2H), 1.39 (s, 3H), 1.36-1.17 (m, 22H), 0.89 (t, J=6.7 Hz, 3H). $^{31}$P NMR (162 MHz, Methanol-d4) δ −0.48−−0.78 (m). MS m/z [M−1]=784.3.

Intermediate I-74:
(S)-3-(Tetradecyloxy)propane-1,2-diol

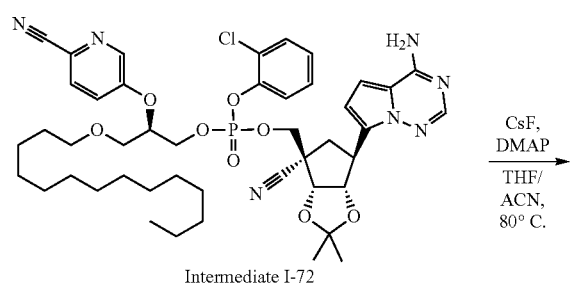

Intermediate I-72

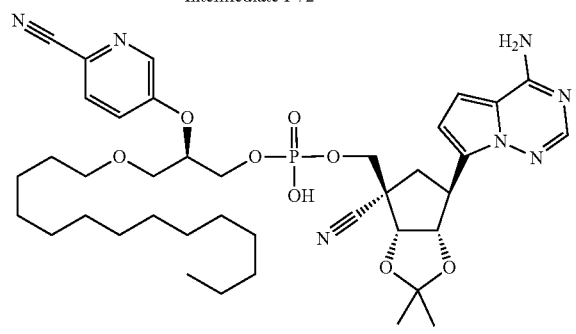

Intermediate I-73

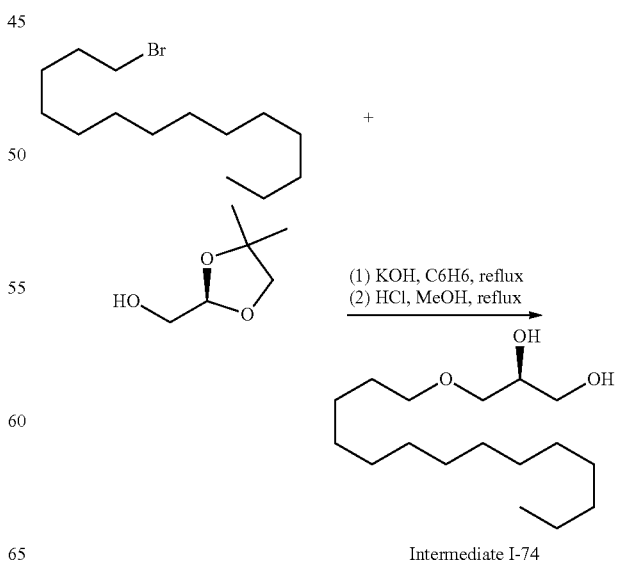

Intermediate I-74

A mixture of (R)-(−)-2,2-dimethyl-1,3-dioxolane-4-methanol (64.9 mmol), powdered potassium hydroxide (229 mmol) and 1-bromotetradecane (64.9 mmol) in benzene (100 mL) were stirred under reflux for 15 hours, while removing the water formed by azeotropic distillation. The reaction mixture was then cooled to rt, filtered, then the volume of the solvent was reduced to half. Water (100 mL) was added and the mixture was then extracted with diethyl ether (3×100 mL), the combined organic phase was combined, dried over $Na_2SO_4$, filtered and the solvent was then removed under reduced pressure to give a crude product. To a solution of above crude intermediate (5 g) in methanol (80 mL), 2M HCl solution (13 mL, 26 mmol) was added and the solution was heated to reflux for 4 h. After cooling to room temperature, the mixture was poured into water, the organic layers were extracted with ether, dried over $Na_2SO_4$ and the solvents were removed under vacuum to give small volume, the product was crystallized from hexanes, yielding Intermediate I-74. $^1$H NMR (400 MHz, Methanol-$d_4$) δ 3.84-3.72 (m, 1H), 3.63-3.56 (m, 1H), 3.56-3.40 (m, 6H), 1.59 (t, J=7.0 Hz, 2H), 1.31 (s, 22H), 0.92 (t, J=6.8 Hz, 3H).

Intermediate I-75: (R)-1-((Tert-butyldimethylsily)oxy)-3-(tetradecyloxy)propan-2-ol

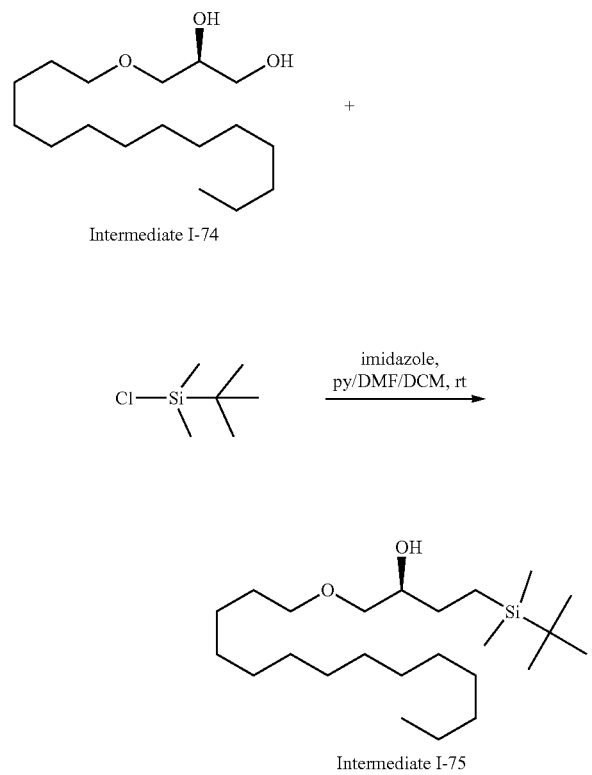

Intermediate I-74 imidazole, py/DMF/DCM, rt

Intermediate I-75

To a solution of Intermediate I-74 (9.78 mmol) and imidazole (2 mmol) in a mixture of pyridine (52 mL), $CH_2Cl_2$ (6 mL) and DMF (6 mL) was added tert-butylchlorodimethylsilane (8.34 mmol) at 0° C. and stirred at room temperature for 5 h. The reaction mixture was diluted with water (10 mL), then extracted with $CH_2Cl_2$, and dried over $Na_2SO_4$. The solvent was evaporated, and the residue was purified by flash chromatography (0-30% EtOAc in hexanes) to yield Intermediate I-75. 1H NMR (400 MHz, Chloroform-d) δ 3.88-3.79 (m, 1H), 3.71-3.61 (m, 2H), 3.53-3.42 (m, 4H), 1.58 (m, 2H), 1.28 (s, 22H), 0.99-0.85 (m, 12H), 0.10 (s, 6H).

Intermediate I-76: (R)-5-((1-((tert-butyldimethylsilyl)oxy)-3-(tetradecyloxy)propan-2-yl) oxy)picolinonitrile

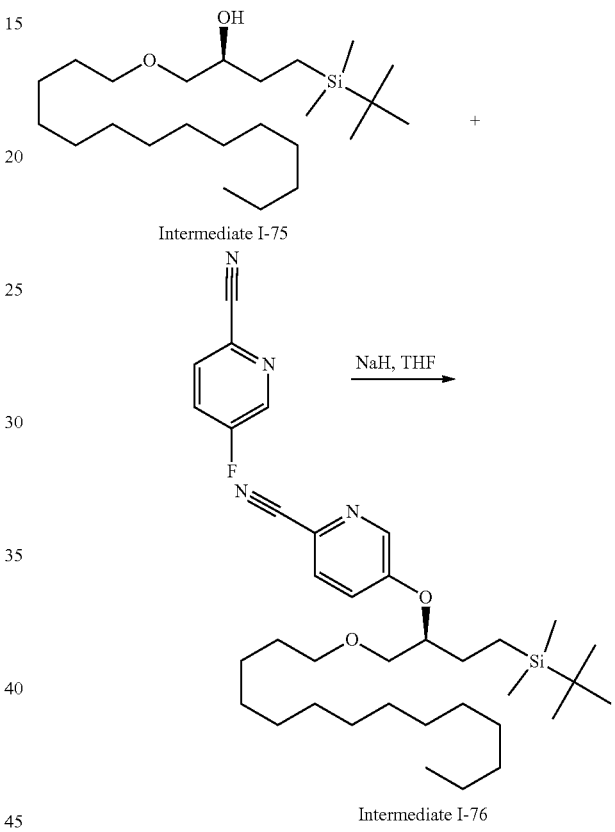

Intermediate I-76

NaH (60% disp. in oil) (3.42 mmol, 4.90 equiv.) was suspended in THF (7.5 mL) and cooled to 0° C. A solution of Intermediate I-75 (0.697 mmol, 1.0 equiv.) in THF (3 mL) was added over 30 sec. After 30 min of stirring at 0° C., a solution of 5-fluoropyridine-2-carbonitrile (2.30 mmol, 3.30 equiv.) in THF (3 ml) was added. The ice bath was removed and the solution was stirred overnight. The reaction was quenched with water (15 mL) at 0° C. The mixture was extracted with EtOAc (3×15 mL). The combined organic phase was dried over sodium sulfate and the solvent was removed under reduced pressure. The residue was subjected to flash chromatography (0-20% EtOAc/hexanes) to afford Intermediate I-76. $^1$H NMR (400 MHz, Chloroform-d) δ 8.42 (d, J=2.9 Hz, 1H), 7.60 (d, J=8.7 Hz, 1H), 7.39 (dd, J=8.7, 2.9 Hz, 1H), 4.62-4.53 (m, 1H), 3.90-3.76 (m, 2H), 3.71-3.56 (m, 2H), 3.52-3.37 (m, 2H), 1.59-1.48 (m, 2H), 1.35-1.20 (m, 22H), 0.91-0.83 (m, 12H), 0.05 (s, 3H), 0.01 (s, 3H).

Intermediate I-77: (S)-5-((1-hydroxy-3-(tetradecyloxy)propan-2-yl)oxy)picolinonitrile

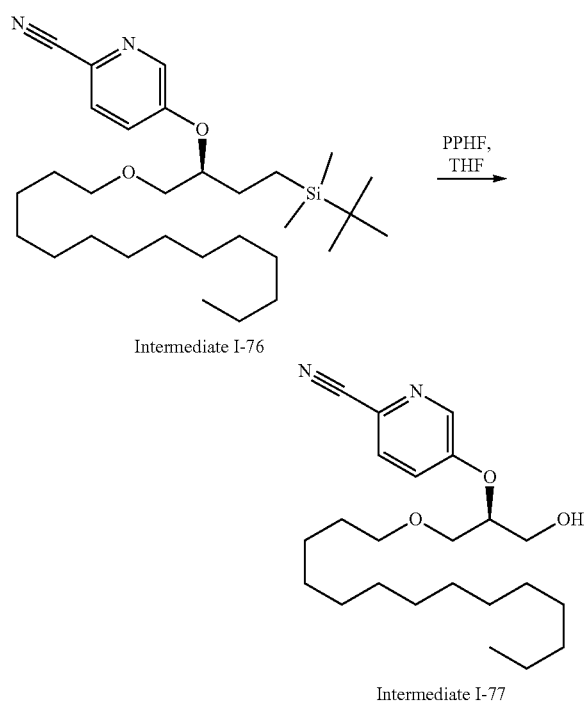

Intermediate I-76

Intermediate I-77

To a solution of Intermediate I-76 (0.664 mmol, 1.0 eq) in dry THF (3.3 mL), in a polyethylene vessel at 0° C., was added HF/pyridine ((HF 70%, pyridine 30%) 1.05 mL, 4.46 mmol, 6.7 eq)). After stirring at rt for 5 h, the mixture was diluted with Et$_2$O and neutralized with aqueous saturated NaHCO$_3$. The combined organic layer was dried, evaporated, and purified by flash chromatography (EtOAc/hexane, 1:1) to give Intermediate I-77. $^1$H NMR (400 MHz, Chloroform-d) δ 8.39 (d, J=2.8 Hz, 1H), 7.60 (d, J=8.6 Hz, 1H), 7.41 (dd, J=8.7, 2.9 Hz, 1H), 4.65-4.54 (m, 1H), 3.98-3.82 (m, 2H), 3.72-3.61 (m, 2H), 3.50-3.36 (m, 2H), 2.65-2.55 (m, 1H), 1.59-1.45 (m, 2H), 1.42-1.14 (m, 22H), 0.91-0.79 (m, 3H).

Intermediate I-78: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-(4-cyano-2-fluorobenzyl) oxy)-3-(tetradecyloxy)propyl) phosphate

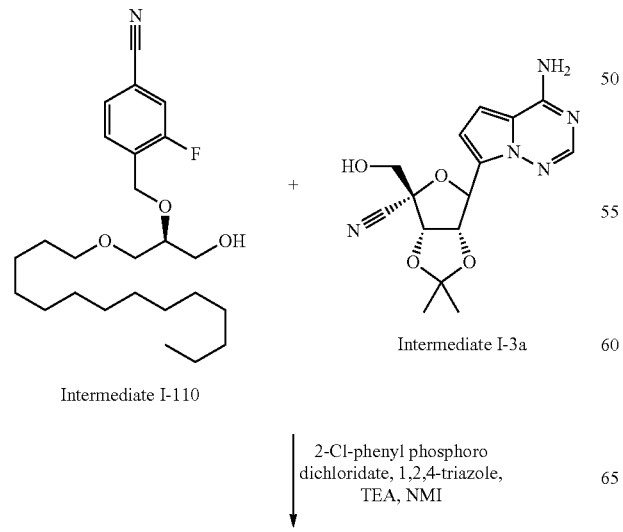

Intermediate I-110

Intermediate I-3a

2-Cl-phenyl phosphoro dichloridate, 1,2,4-triazole, TEA, NMI

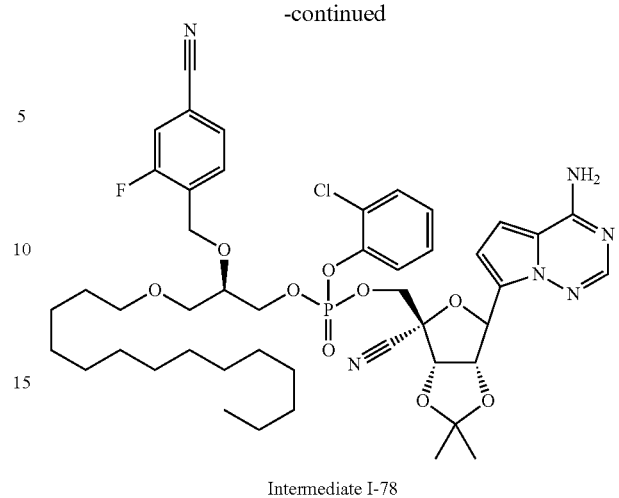

Intermediate I-78

1H-1,2,4-triazole (0.664 mmol) was dissolved in THF (2 mL) and then TEA (0.09 mL, 0.664 mmol) was added to the solution followed by 2-chlorophenyl phosphorodichloridate (0.061 mL, 0.371 mmol). The reaction mixture was stirred at room temperature for 30 min at room temperature. Intermediate I-3a (0.25 mmol) in one portion was added and the mixture stirred at rt for 15 min. To the mixture were Intermediate I-110 (0.275 mmol) in THF (2 mL) and 1-methylimidazole (0.04 mL, 0.506 mmol) at rt. The resulting mixture was stirred for 1 h, concentrated in vacuo, and purified by silica gel (0 to 10% MeOH in DCM) to give Intermediate I-78. $^1$H NMR (400 MHz, Acetonitrile-d3) δ 7.86 (s, 1H), 7.59 (q, J=7.7 Hz, 1H), 7.50-7.40 (m, 3H), 7.39-7.28 (m, 1H), 7.24-7.11 (m, 2H), 6.80-6.68 (m, 2H), 6.38-6.25 (m, 2H), 5.67 (m, 1H), 5.29 (m, 1H), 5.11 (dd, J=6.6, 2.3 Hz, 1H), 4.78-4.62 (m, 2H), 4.57-4.43 (m, 2H), 4.41-4.30 (m, 1H), 4.249-4.17 (m, 1H), 3.79 (m, 1H), 3.52-3.42 (m, 2H), 3.42-3.32 (m, 2H), 1.72 (s, 3H), 1.49 (m, 2H), 1.40-1.06 (m, 22H), 0.95-0.83 (m, 3H). $^{31}$P NMR (162 MHz, Acetonitrile-d3) δ–7.38, –7.42. MS m/z [M+1]=926.

Intermediate I-79: ((3aS,4R,6S,6aS)-6-(4-aminopyrrolo[2,1-f][1,2,4]triazin-7-yl)-4-cyano-2,2-dimethyltetrahydrofurol[3,4-d][1,3]dioxol-4-yl)methyl ((R)-2-((4-cyano-2-fluorobenzyl) oxy)-3-(tetradecyloxy) propyl) hydrogen phosphate

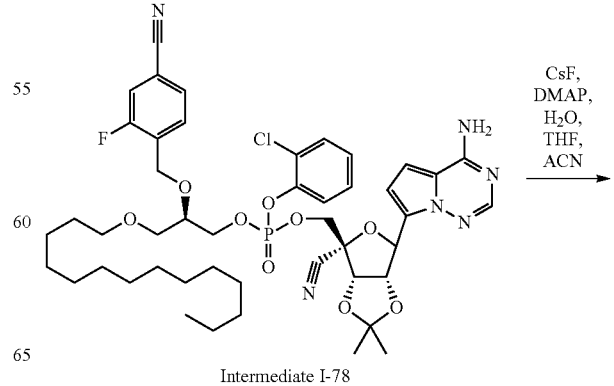

Intermediate I-78

CsF, DMAP, H$_2$O, THF, ACN

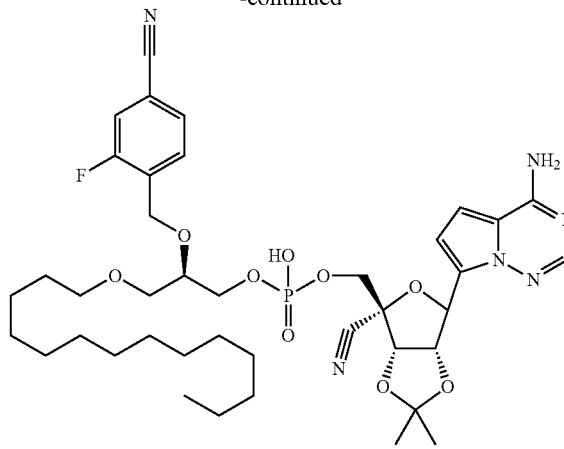

Intermediate I-79

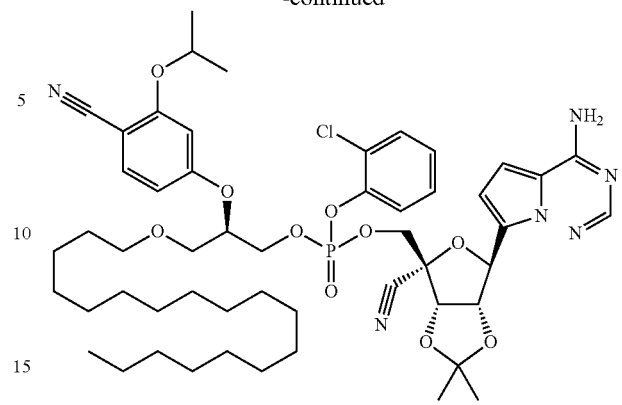

Intermediate I-80

Intermediate I-78 (0.151 mmol) was dissolved in THF and ACN (2:1 mL). Then CsF (1.31 mmol) in water (0.2 mL) and DMAP (0.558 mmol) were added. The resulting mixture was heated at 80° C. for 4 h. After dilution with citric acid-NaOH (4:1) buffer solution (pH 3, 10 mL), the mixture was partitioned between brine (20 mL) and EtOAc (40 mL). Aqueous layer was extracted with EtOAc (20 mL) 3 times. The combined organic layer was dried under sodium sulfate and purified by silica gel column chromatography (0-50% MeOH in DCM) to give Intermediate I-79. $^1$H NMR (400 MHz, Methanol-d4) δ 7.98 (s, 1H), 7.74 (t, J=7.5 Hz, 1H), 7.49-7.40 (m, 2H), 7.21 (d, J=4.7 Hz, 1H), 6.96 (d, J=4.7 Hz, 1H), 5.64 (d, J=3.5 Hz, 1H), 5.22 (dd, J=6.6, 3.6 Hz, 1H), 5.13 (d, J=6.6 Hz, 1H), 4.82 (s, 2H), 4.20 (m, 2H), 4.06 (m, 2H), 3.85 (m, 1H), 3.65-3.53 (m, 2H), 3.50-3.39 (m, 2H), 1.70 (s, 3H), 1.53 (m, 2H), 1.39 (s, 3H), 1.36-1.20 (m, 22H), 0.91 (t, J=6.8 Hz, 3H). $^{19}$F NMR (376 MHz, Methanol-d4) δ−118.17. $^{31}$P NMR (162 MHz, Methanol-d4) δ−0.55. MS m/z [M+1]=815.

Intermediate I-80: ((3aS,4R,6S,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl (2-chlorophenyl) ((R)-2-(4-cyano-3-isopropoxyphenoxy)-3-(octadecyloxy)propyl) phosphate 1H-1,2,4-triazole (0.800 mmol) and TEA (0.11 mL, 0.800 mmol) were dissolved in THF (2.5 mL). To the resulting solution was added 2-chlorophenyl phosphorodichloridate (0.1 mL, 0.604 mmol) dropwise. The reaction mixture was stirred at rt for 30 min and filtered through filter syringe. To the filtrate were added Intermediate I-3a (0.302 mmol) in one portion and then 1-methylimidazole (0.05 mL, 0.609 mmol) dropwise. The resulting mixture was stirred for 20 min and then Intermediate I-111 (0.322 mmol) in THF (2 mL) added. The resulting mixture was stirred at rt for 2 h, concentrated in vacuo, and purified by silica gel column chromatography (0 to 10% MeOH in DCM) to give Intermediate I-80. $^1$H NMR (400 MHz, Acetonitrile-d$_3$) δ 7.88 (d, J=1.1 Hz, 1H), 7.54-7.11 (m, 5H), 6.84-6.68 (m, 2H), 6.65-6.45 (m, 2H), 6.29 (s, 2H), 5.68 (m, 1H), 5.30 (m, 1H), 5.11 (m, 1H), 4.71 (m, 1H), 4.64 (m, 1H), 4.57-4.31 (m, 4H), 3.65-3.53 (m, 2H), 3.41 (m, 2H), 1.72 (s, 3H), 1.49 (m, 2H), 1.38 (s, 3H), 1.35-1.19 (m, 36H), 0.95-0.87 (m, 3H). $^{31}$P NMR (162 MHz, Acetonitrile-d3) δ−7.52, —7.56. MS m/z [M+1]=1007.

Intermediate I-81: ((3aS,4R,6S,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl ((R)-2-(4-cyano-3-isopropoxy phenoxy)-3-(octadecyloxy) propyl) hydrogen phosphate

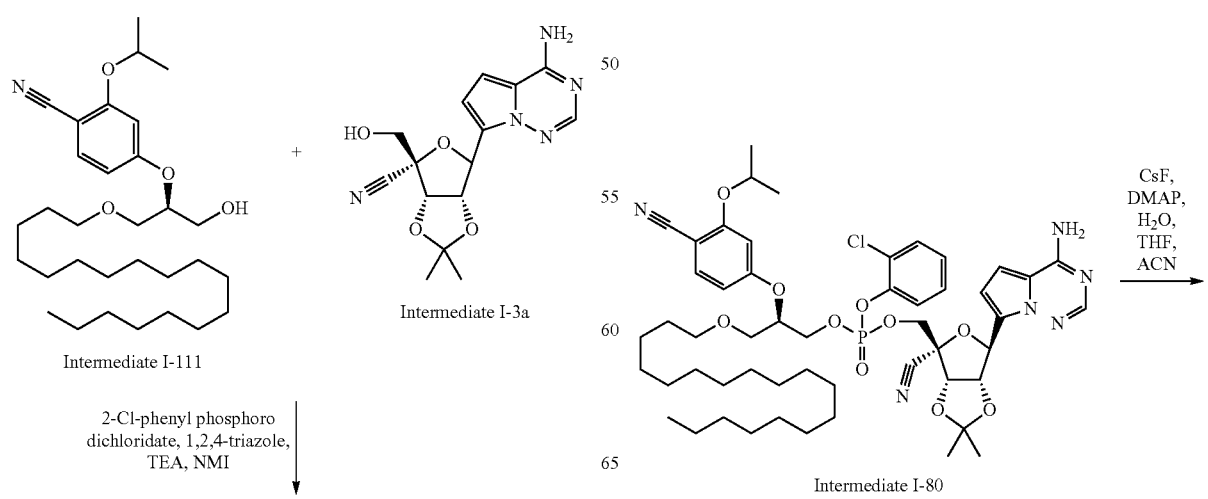

697
-continued

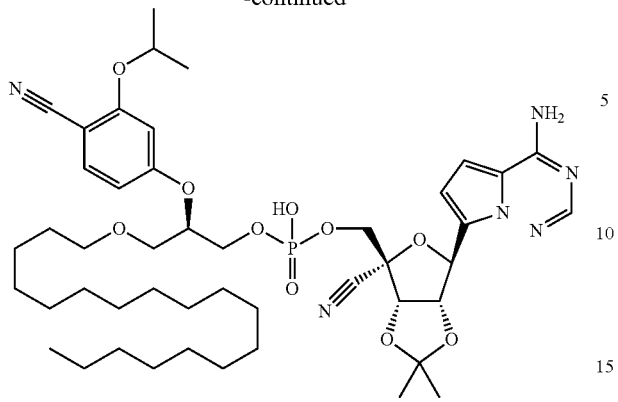

Intermediate I-81

Intermediate I-80 (0.0566 mmol) was dissolved in THF and ACN (2:1 mL) and CsF (0.49 mmol) in water (0.1 mL) and then DMAP (0.209 mmol) added. The resulting mixture was heated at 80° C. for 4 h. After adding citric acid-NaOH (4:1) buffer solution (pH 3, 0.5 mL), the mixture was partitioned between brine and EtOAc. Aqueous layer was extracted with EtOAc 3 times. The combined organic layer was dried under sodium sulfate and purified by silica gel column chromatography (0-50% MeOH in DCM) to yield Intermediate I-81. $^1$H NMR (400 MHz, Methanol-d4) δ 7.86 (s, 1H), 7.41 (d, J=8.6 Hz, 1H), 6.86 (d, J=4.5 Hz, 1H), 6.81 (d, J=4.5 Hz, 1H), 6.69 (d, J=2.2 Hz, 1H), 6.64 (dd, J=8.6, 2.2 Hz, 1H), 5.66 (d, J=3.6 Hz, 1H), 5.29 (dd, J=6.6, 3.6 Hz, 1H), 5.16 (d, J=6.6 Hz, 1H), 4.75-4.59 (m, 2H), 4.28-3.89 (m, 4H), 3.66 (dd, J=10.9, 3.5 Hz, 1H), 3.56 (dd, J=10.9, 6.0 Hz, 1H), 3.52-3.36 (m, 2H), 1.72 (s, 3H), 1.51 (m, 2H), 1.40 (s, 3H), 1.37-1.20 (m, 36H), 0.98-0.83 (m, 3H). $^{31}$P NMR (162 MHz, Methanol-d4) δ−0.61. MS m/z [M+1]=897.

Intermediate I-82: 2-chlorophenyl di(1H-1,2,4-triazol-1-yl)phosphinate 1H-1,2,4-triazole (10.3 mmol) and TEA (1.44 mL, 10.3 mmol) were dissolved in THF (8 mL). To the solution was added 1-chloro-2-dichlorophosphoryloxy-benzene (0.81 mL, 4.92 mmol) dropwise. The reaction mixture was stirred at rt for 30 min and filtered to a graduated plastic tube, the filter cake washed with THF (8 mL), and additional THF added to the filtrate to total volume 20 mL resulting in ca 0.246 M stock solution of Intermediate I-82, which was used in next reactions. 31P NMR (162 MHz, Acetonitrile-d3) δ−16.94.

Intermediate I-83: ((3aS,4R,6S,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl (2-chlorophenyl) ((R)-2-((4-cyano-3-isopropoxybenzyl)oxy)henicosyl) phosphate To a solution of Intermediate I-82 (0.246 M in THF, 1.47 mL, 0.362 mmol) were added Intermediate I-3a (0.302 mmol) in one portion and then 1-methylimidazole (0.05 mL, 0.609 mmol) dropwise. The resulting mixture was stirred for 20 min and then Intermediate I-113 (0.322 mmol) in THF (2 mL) added. The resulting mixture was stirred for 2 h, concentrated in vacuo, and purified by silica gel column chromatography (0 to 10% MeOH in DCM) to give Intermediate I-83. $^1$H NMR (400 MHz, Acetonitrile-d3) δ 7.87 (s, 1H), 7.52-7.42 (m, 2H), 7.41-7.31 (m, 1H), 7.25-7.11 (m, 2H), 7.08 (d, J=5.4 Hz, 1H), 6.93 (m, 1H), 6.78 (m, 1H), 6.73 (m, 1H), 6.26 (s, 2H), 5.67 (m, 1H), 5.29 (m, 1H), 5.10 (m, 1H), 4.71 (m, 1H), 4.64-4.39 (m, 4H), 4.34-4.23 (m, 1H), 4.20-4.08 (m, 1H), 3.63-3.51 (m, 1H), 1.72 (s, 3H), 1.58-1.11 (m, 45H), 0.96-0.83 (m, 3H). $^{31}$P NMR (162 MHz, Acetonitrile-d3) δ −7.28, −7.34. MS m/z [M+1]=1005.

Intermediate I-84: ((3aS,4R,6S,6aS)-6-(4-aminopyr-rolo[2,1-f][1,2,4]triazin-7-yl)-4-cyano-2,2-dimethyl-tetrahydrofuro[3,4-d][1,3]dioxol-4-yl)methyl ((R)-2-((4-cyano-3-isopropoxy benzyl)oxy)henicosyl) hydrogen phosphate

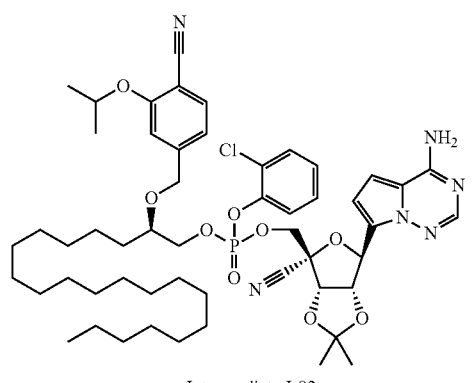

Intermediate I-83

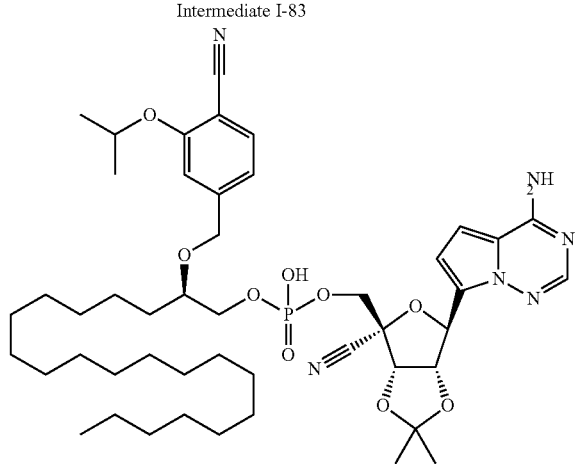

Intermediate I-84

Intermediate I-83 (0.0984 mmol) was dissolved in THF and ACN (3:1.5 mL) and CsF (130 mg, 0.854 mmol) in water (0.2 mL) and then DMAP (0.363 mmol) added. The resulting mixture was heated at 80° C. for 4 h. After adding citric acid-NaOH (4:1) buffer solution (pH 3, 1.0 mL), the mixture was partitioned between brine and EtOAc. Aqueous layer was extracted with EtOAc 3 times. The combined organic layer was dried under sodium sulfate and purified by silica gel column chromatography (0-50% MeOH in DCM) to give Intermediate I-84. $^1$H NMR (400 MHz, Methanol-d4) δ 7.84 (s, 1H), 7.49 (dd, J=7.9, 1.7 Hz, 1H), 7.13 (d, J=1.3 Hz, 1H), 6.98 (dd, J=7.9, 1.3 Hz, 1H), 6.89-6.84 (m, 1H), 6.83-6.76 (m, 1H), 5.65 (d, J=3.6 Hz, 1H), 5.31-5.22 (m, 1H), 5.15 (d, J=6.6 Hz, 1H), 4.80-4.68 (m, 2H), 4.52 (d, J=13.2 Hz, 1H), 4.13 (m, 2H), 3.98-3.79 (m, 2H), 3.56 (m, 1H), 1.71 (s, 3H), 1.51-1.17 (m, 45H), 0.96-0.84 (m, 3H). $^{31}$P NMR (162 MHz, Methanol-d4) δ −0.36. MS m/z [M+1]=895.

Intermediate I-85: ((3aS,4R,6S,6aS)-6-(4-aminopyr-rolo[2,1-f][1,2,4]triazin-7-yl)-4-cyano-2,2-dimethyl-tetrahydrofuro[3,4-d][1,3]dioxol-4-yl)methyl (2-chlorophenol) ((R)-2-(4-cyano-3-isopropoxyphe-noxy)henicosyl) phosphate

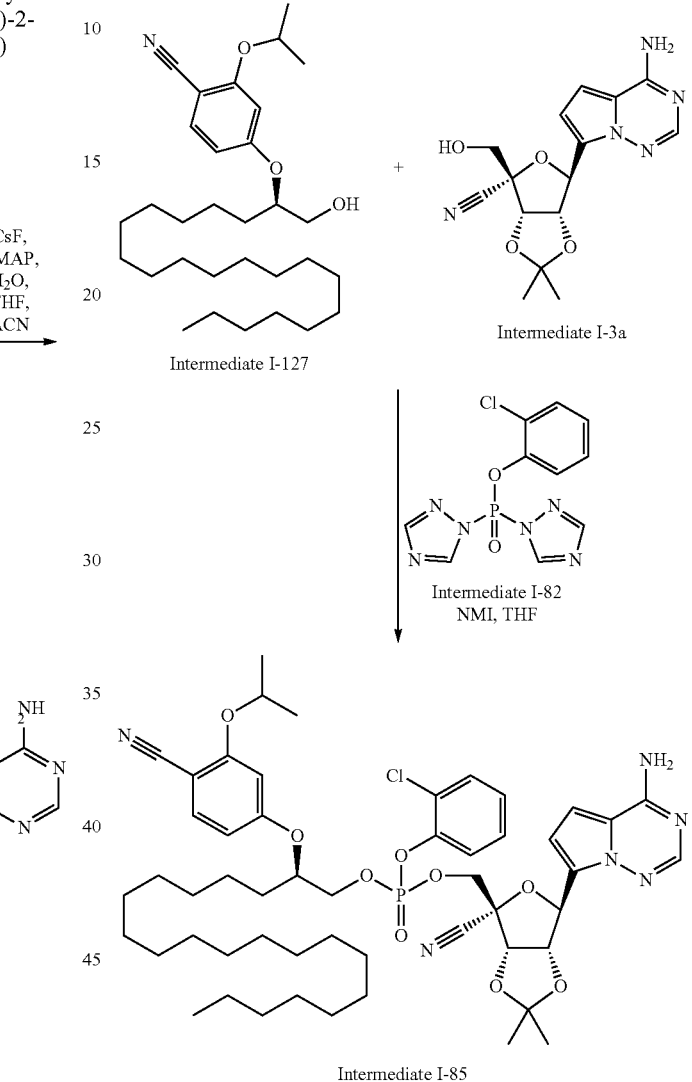

To a solution of Intermediate I-82 (0.246 M in THF, 1.84 mL, 0.453 mmol) were added Intermediate I-3a (0.302 mmol) in one portion at rt and then 1-methylimidazole (0.05 mL, 0.609 mmol) dropwise. The resulting mixture was stirred for 10 min and Intermediate I-127 (0.322 mmol) in THF (2 mL) added. The resulting mixture was stirred for 2 h, concentrated in vacuo, and purified by silica gel column chromatography (0 to 10% MeOH in DCM) to give Intermediate I-85. $^1$H NMR (400 MHz, Acetonitrile-d3) δ 7.88 (m, 1H), 7.49-7.34 (m, 2H), 7.34-7.24 (m, 1H), 7.24-7.01 (m, 2H), 6.82-6.64 (m, 2H), 6.61-6.39 (m, 2H), 6.26 (s, 2H), 5.67 (m, 1H), 5.30 (m, 1H), 5.11 (m, 1H), 4.71-4.37 (m, 4H), 4.36-4.14 (m, 2H), 1.72 (s, 3H), 1.57 (m, 2H), 1.42-1.11 (m, 43H), 0.90 (m, 3H). $^{31}$P NMR (162 MHz, Acetonitrile-d3) δ −7.55, —7.59. MS m/z [M+1]=991.

701

Intermediate I-86: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-(4-cyano-3-isopropoxy phenoxy)henicosyl) hydrogen phosphate

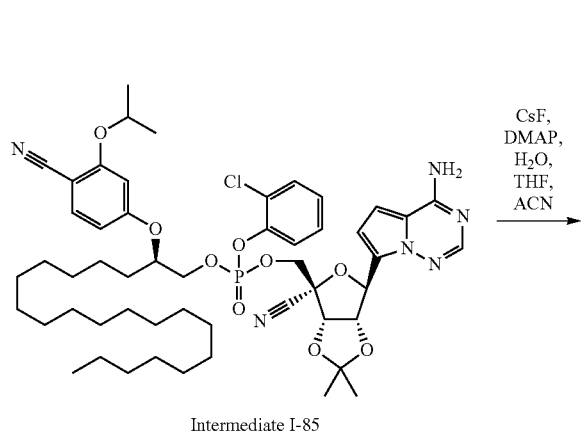

Intermediate I-85

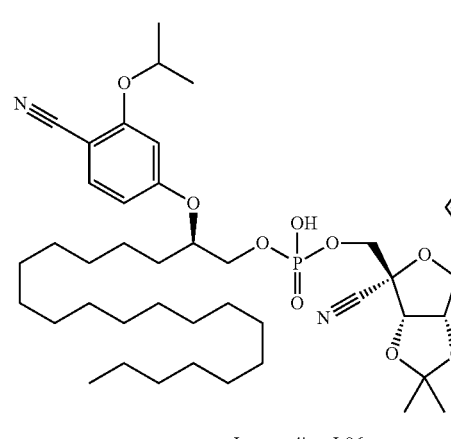

Intermediate I-86

Intermediate I-85 (0.176 mmol) was dissolved in THF and ACN (2:1 mL) and CsF (1.53 mmol) in water (0.2 mL) and then DMAP (0.605 mmol) added. The resulting mixture was heated at 80° C. for 2 h. After adding citric acid-NaOH (4:1, pH 3) buffer solution (1 mL), the mixture was partitioned between brine and EtOAc. Aqueous layer was extracted with EtOAc 3 times. The combined organic layer was dried under sodium sulfate and purified by silica gel column chromatography (0-50% MeOH in DCM) to give Intermediate I-86. $^1$H NMR (400 MHz, Methanol-d4) δ 7.85 (s, 1H), 7.41 (dd, J=8.6, 2.8 Hz, 1H), 6.87 (d, J=4.5 Hz, 1H), 6.81 (d, J=4.5 Hz, 1H), 6.64 (d, J=2.2 Hz, 1H), 6.60 (dd, J=8.7, 2.2 Hz, 1H), 5.66 (d, J=3.7 Hz, 1H), 5.28 (dd, J=6.6, 3.7 Hz, 1H), 5.15 (d, J=6.6 Hz, 1H), 4.66 (m, 1H), 4.58-4.48 (m, 1H), 4.11 (m, 2H), 4.02-3.85 (m, 2H), 1.77-1.51 (m, 5H), 1.45-1.13 (m, 43H), 0.95-0.84 (m, 3H). $^{31}$P NMR (162 MHz, Methanol-d4) δ−0.54. MS m/z [M+1]=882.

702

Intermediate I-87: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-24(4-cyano-3-(1H-1,2,4-triazol-1-yl)benzyl)oxy)-3-(octadecyloxy)propyl) phosphate

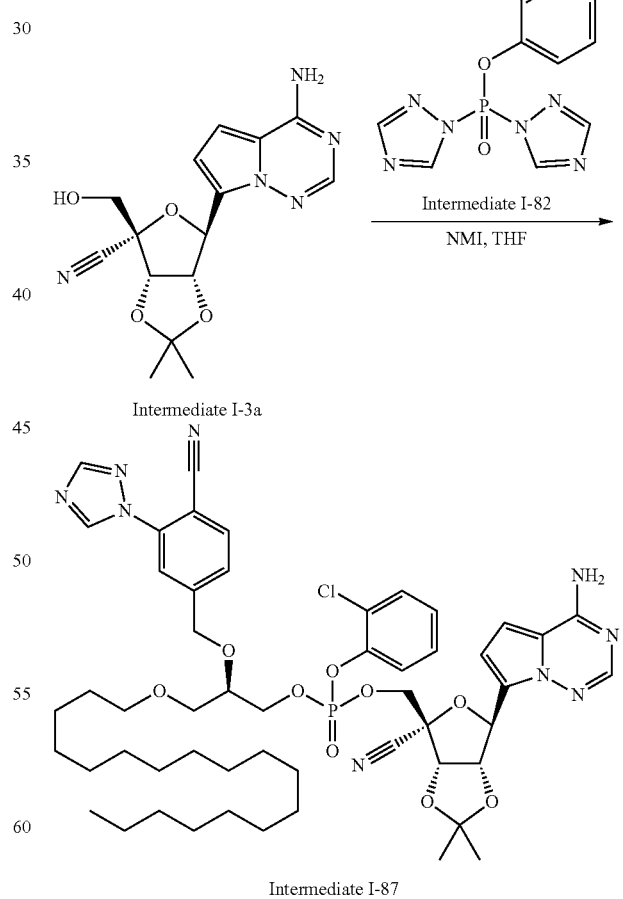

To a solution of Intermediate I-82 (0.246 M in THF, 1.84 mL, 0.453 mmol) were added Intermediate I-3a (0.302 mmol) in one portion and then 1-methylimidazole (0.05 mL, 0.609 mmol) dropwise. The resulting mixture was stirred at rt for 10 min and Intermediate I-119 (0.322 mmol) in THF (2 mL) added. The resulting mixture was stirred for 1 h, concentrated in vacuo, and purified by silica gel (0 to 10% MeOH in DCM) to give Intermediate I-87. $^1$H NMR (400 MHz, Acetonitrile-d3) δ 8.77 (s, 1H), 8.16 (d, J=2.2 Hz, 1H), 7.85 (s, 1H), 7.79 (dd, J=8.0, 2.0 Hz, 1H), 7.71 (dd, J=7.8, 1.4 Hz, 1H), 7.55-7.29 (m, 3H), 7.21-7.04 (m, 2H), 6.77-6.66 (m, 2H), 6.55 (s, 2H), 5.66 (m, 1H), 5.29 (m, 1H), 5.11 (m, 1H), 4.73 (m, 1H), 4.69 (s, 1H), 4.61-4.45 (m, 2H), 4.37 (m, 1H), 4.26 (m, 1H), 3.80 (m, 1H), 3.54-3.48 (m, 2H), 3.44-3.30 (m, 2H), 1.71 (s, 3H), 1.48 (m, 2H), 1.37 (s, 3H), 1.34-1.18 (m, 30H), 0.89 (t, J=6.7 Hz, 3H). $^{31}$P NMR (162 MHz, Acetonitrile-d3) δ−7.28, —7.34. MS m/z [M+1]=1030.

Intermediate I-88: ((3aS,4R,6S,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl ((R)-2(4-cyano-3-(1H-1,2,4-triazol-1-yl)benzyl)oxy)-3-(octadecyloxy)propyl) hydrogen phosphate Intermediate I-87 (0.194 mmol) was dissolved in THF and ACN (3:1.5 mL) and CsF (2.11 mmol) in water (0.3 mL) and then DMAP (0.819 mmol) added. The resulting mixture was heated at 80° C. for 2 h. After adding citric acid-NaOH (4:1) buffer solution (pH 3, 1 mL), the mixture was partitioned between brine and EtOAc. Aqueous layer was extracted with EtOAc 3 times. The combined organic layer was dried under sodium sulfate and purified by silica gel column chromatography (0-50% MeOH in DCM) to give Intermediate I-88. $^1$H NMR (400 MHz, Methanol-d4) δ 9.03 (s, 1H), 8.24 (s, 1H), 7.85-7.80 (m, 3H), 7.63 (dd, J=8.0, 1.5 Hz, 1H), 6.84 (d, J=4.5 Hz, 1H), 6.80 (d, J=4.5 Hz, 1H), 5.62 (d, J=3.6 Hz, 1H), 5.27 (dd, J=6.6, 3.6 Hz, 1H), 5.15 (d, J=6.6 Hz, 1H), 4.83 (d, J=14.0 Hz, 1H, partially buried by solvent peak), 4.77 (d, J=14.0 Hz, 1H), 4.20-4.05 (m, 2H), 4.04-3.91 (m, 2H), 3.78 (m, 1H), 3.58-3.35 (m, 4H), 1.70 (s, 3H), 1.52 (m, 2H), 1.41-1.17 (m, 33H), 0.98-0.73 (m, 3H). $^{31}$P NMR (162 MHz, Methanol-d4) δ−0.46. MS m/z [M+1]=920.

Intermediate I-89: ((3aS,4R,6S,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl (2-chlorophenyl) (3-(3-cyano-5-fluorophenoxy)-2-((octadecyloxy)methyl)propyl) phosphate

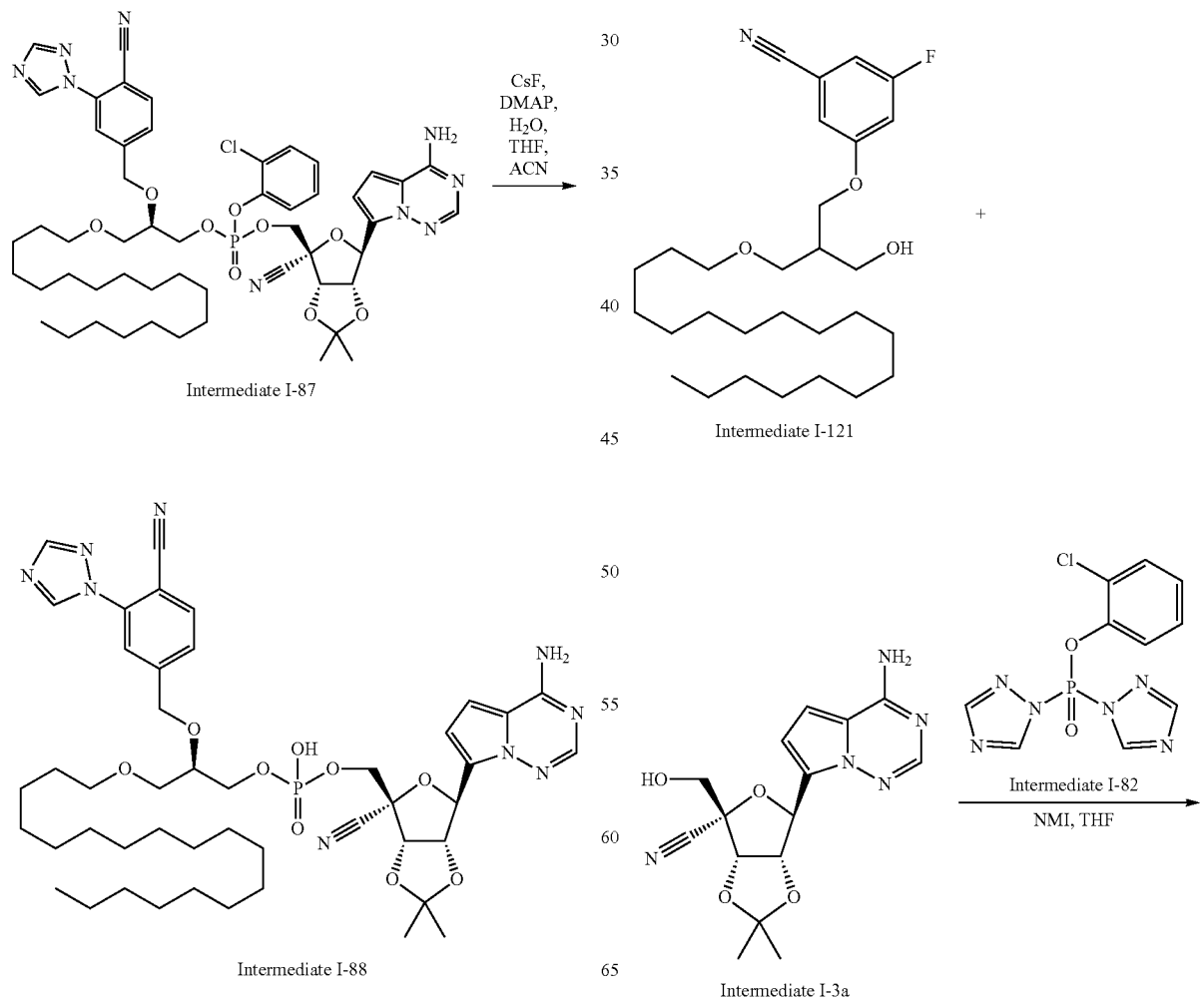

705

-continued

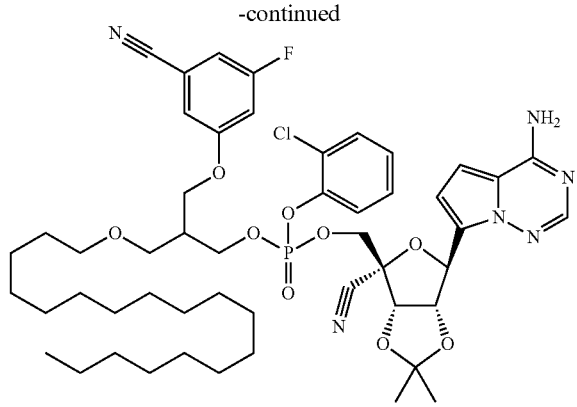

Intermediate I-89

706

-continued

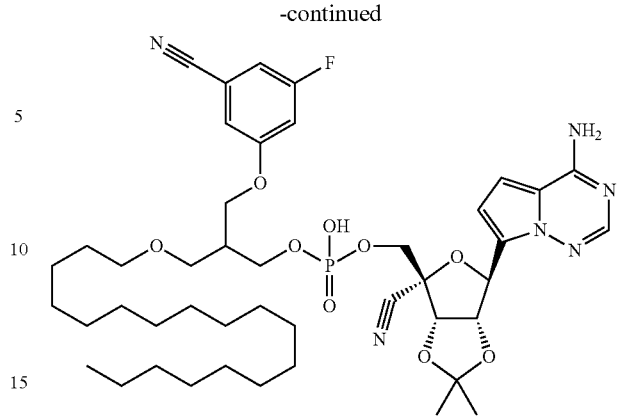

Intermediate I-90

To a solution of Intermediate I-82 (0.246 M in THF, 1.84 mL, 0.453 mmol) were added Intermediate I-3a (0.302 mmol) in one portion and then 1-methylimidazole (0.05 mL, 0.609 mmol) dropwise. The resulting mixture was stirred for 10 min and Intermediate I-121 (0.322 mmol) in THF (2 mL) added. The resulting mixture was stirred for 2 h, concentrated in vacuo, and purified by silica gel (0 to 10% MeOH in DCM) to give Intermediate I-89. $^1$H NMR (400 MHz, Acetonitrile-d3) δ 7.87 (m, 1H), 7.44 (m, 1H), 7.35 (m, 1H), 7.25-7.12 (m, 2H), 7.11-7.02 (m, 2H), 6.97 (m, 1H), 6.82-6.75 (m, 1H), 6.75-6.63 (m, 1H), 6.27 (s, 2H), 5.68 (m, 1H), 5.34-5.21 (m, 1H), 5.16-5.00 (m, 1H), 4.59-4.42 (m, 2H), 4.32 (m, 2H), 4.06-3.88 (m, 2H), 3.44 (m, 2H), 3.36 (m, 2H), 2.39 (m, 1H), 1.72 (s, 3H), 1.49 (m, 2H), 1.40-1.15 (m, 33H), 0.99-0.82 (m, 3H). $^{31}$P NMR (162 MHz, Acetonitrile-d3) δ−7.55, −7.57, −7.64, −7.66. MS m/z [M+1]=982.

Intermediate I-90: ((3aS,4R,6S,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl (3-(3-cyano-5-fluorophenoxy)-2-((octadecyloxy)methyl)propyl) hydrogen phosphate Intermediate I-89 (0.109 mmol) was dissolved in THF and ACN (3:1.5 mL) and CsF (1.12 mmol) in water (0.1 mL) and then DMAP (0.402 mmol) were added. The resulting mixture was heated at 80° C. for 4 h. After adding citric acid-NaOH (4:1) buffer solution (pH 3, 1.0 mL), the mixture was partitioned between brine and EtOAc. Aqueous layer was extracted with EtOAc 3 times. The combined organic layer was dried under sodium sulfate and purified by silica gel column chromatography (0-50% MeOH in DCM) to give Intermediate I-90. $^1$H NMR (400 MHz, Methanol-d4) δ 7.86 (m, 1H), 7.16-6.98 (m, 3H), 6.92-6.86 (m, 1H), 6.84-6.72 (m, 1H), 5.66 (m, 1H), 5.30-5.23 (m, 1H), 5.15 (m, 1H), 4.14-3.94 (m, 6H), 3.54-3.34 (m, 4H), 1.72 (s, 3H), 1.58-1.46 (m, 2H), 1.43-1.11 (m, 33H), 0.99-0.76 (m, 3H). $^{19}$F NMR (376 MHz, Methanol-d4) δ−111.03. $^{31}$P NMR (162 MHz, Methanol-d4) δ−0.42, −0.43. MS m/z [M+1]=872.

Intermediate I-91: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenol) (24(4-cyano-2-methoxybenzyl)oxy)-3-(octadecyloxy)propyl) phosphate

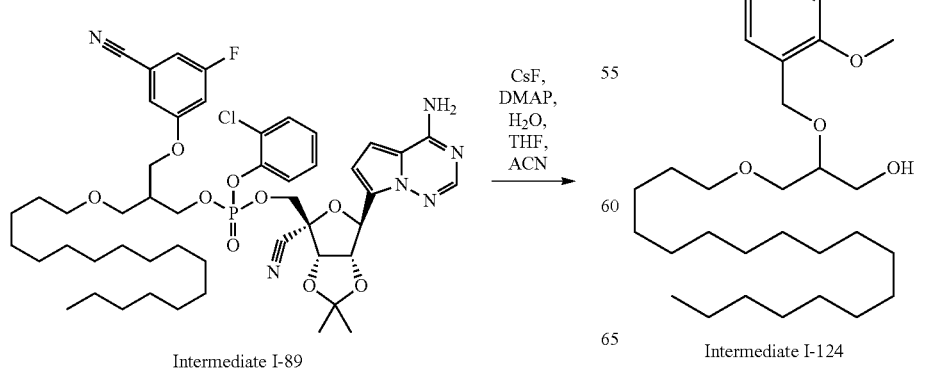

Intermediate I-89

Intermediate I-124

707

-continued

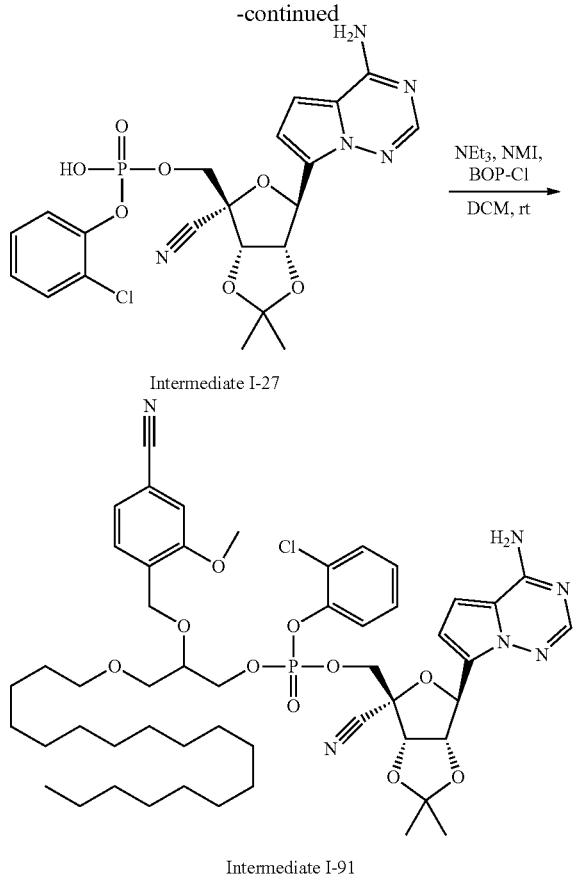

Intermediate I-27

Intermediate I-91

Intermediate I-124 (0.204 mmol) and Intermediate I-27 (0.306 mmol) were taken in a 20 mL vial, dried under vacuum (1 h). To this mixture were added DCM (4 mL), NMI (65 uL, 0.81 mmol), TEA (56 uL, 0.408 mmol) followed by Bop-Cl (0.817 mmol). The reaction stirred at rt for 1 h. Solvent concentrated under reduced pressure. The crude product was dissolved in DCM, loaded on 24 g column, eluted with 100% Hex, 4 min, 0-100% EtOAc 6 min, and 100% EtOAc 6 min. The product elute at 100% EtOAc, fractions containing pure product were combined, concentered to afford Intermediate I-91. MS m/z [M+1]=993.3.

Intermediate I-92: ((3aS,4R,6aS)-6-(4-aminopyrrolo [2,1-f][1,2,4]triazin-7-yl)-4-cyano-2,2-dimethyltetra-hydrofuro[3,4-d][1,3]dioxol-4-yl)methyl (24(4-cyano-2-methoxybenzyl)oxy)-3-(octadecyloxy) propyl) hydrogen phosphate

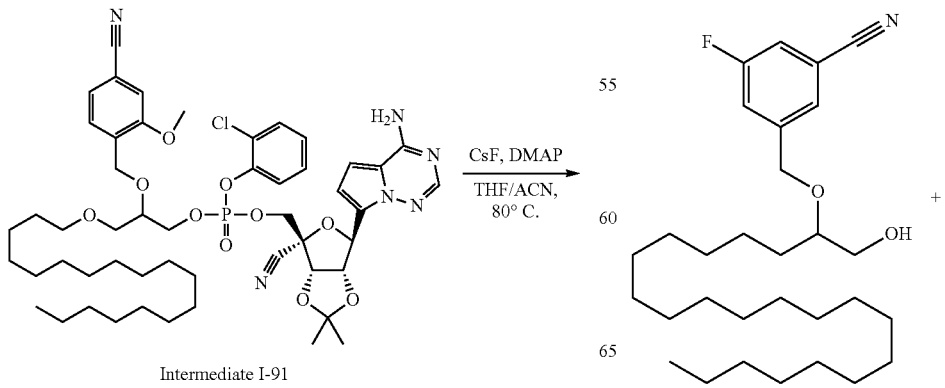

Intermediate I-91

708

-continued

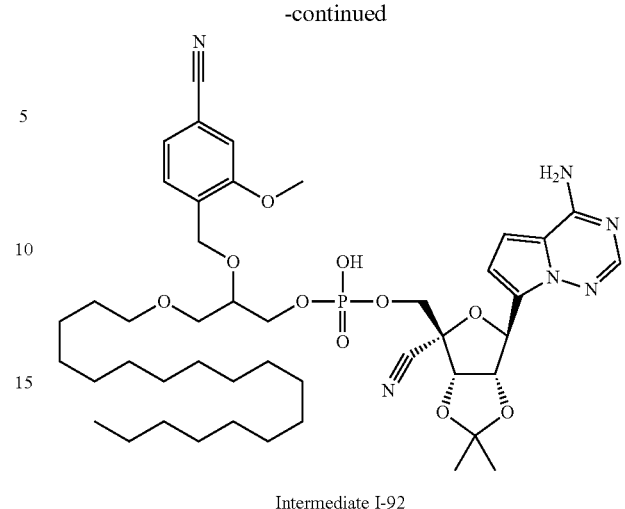

Intermediate I-92

Intermediate I-91 (0.113 mmol) was dissolved in 2:1 THF:ACN (3:1.5 mL). Solution of Cesium fluoride (0.56 mmol) in water (0.09 mL) was added to the solution followed by 4-(dimethylamino)pyridine (0.564 mmol). The reaction mixture was stirred at 80° C. for 3 h. The reaction was cooled to rt, added 10% citric acid in water (15 mL) followed by 1 M NaOH to adjust pH 3-4. Extracted with mixture of 2-MeTHF/EtOAc (3:2, 50 mL×2), conformed no desired product in the aqueous layer by LCMS. Combined organic layers washed with a brine once and dried over $Na_2SO_4$, filtered and concentrated in vacuo prior to purification by silica gel chromatography (0-60% MeOH in DCM) to afford title Intermediate I-92. MS m/z [M+1]=883.3.

Intermediate I-93: ((3aS,4R,6aS)-6-(4-aminopyrrolo [2,1-f][1,2,4]triazin-7-yl)-4-cyano-2,2-dimethyltetra-hydrofuro[3,4-d][1,3]dioxol-4-yl)methyl (2-chloro-phenol) (2-((3-cyano-5-fluorobenzyl)oxy)docosyl) phosphate -continued

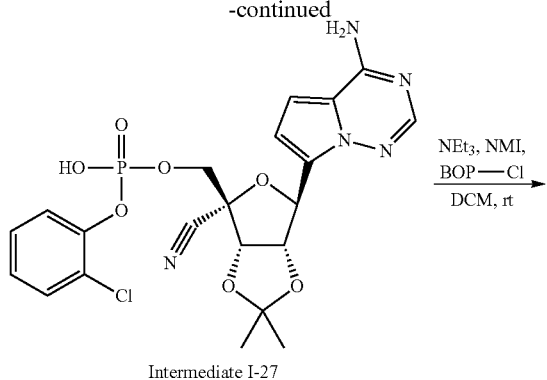

Intermediate I-27

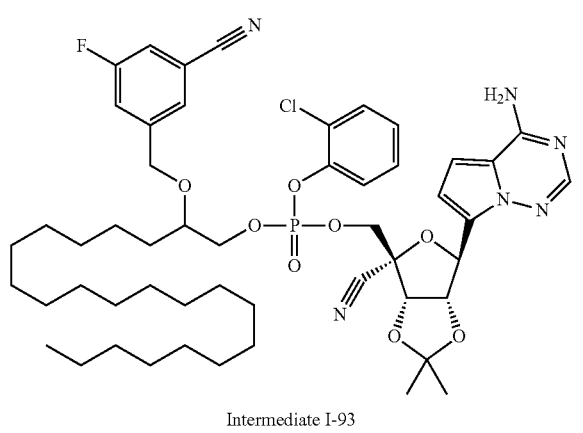

Intermediate I-93

Intermediate I-27 (0.394 mmol) and 3-fluoro-5-(((1-hydroxydocosan-2-yl)oxy) methyl)benzonitrile (0.394) were taken in a 20 mL vial, added DCM (4 mL), NMI (83 uL, 1.05 mmol), TEA (73 uL, 0.526 mmol) followed by Bop-Cl (1.05 mmol) sequentially. The reaction stirred at room temperature for 4 h. Solvent concentrated under reduced pressure. The crude product was dissolved in DCM, loaded on 40 g silica gel column, eluted with 100% Hex 3 min, 0-100% EtOAc 6 min, and 100% EtOAc 6 min. The product elute at 100% EtOAc, fractions containing pure product were combined, concentered to afford Intermediate I-93 as mixture. 1H NMR (400 MHz, Methanol-d4) δ 7.84-7.78 (m, 1H), 7.51-7.44 (m, 2H), 7.43-7.29 (m, 3H), 7.22-7.16 (m, 1H), 7.15-7.08 (m, 1H), 6.84 (dd, J=9.9, 4.4 Hz, 1H), 6.80-6.75 (m, 1H), 5.66 (q, J=3.1 Hz, 1H), 5.32 (m, 1H), 5.22-5.09 (m, 1H), 4.68-4.43 (m, 4H), 4.65-4.47 (m, 1H), 4.25-4.06 (m, 1H), 3.61 (s, 1H), 1.74 (d, J=3.3 Hz, 3H), 1.40 (d, J=4.0 Hz, 3H), 1.29 (d, J=2.8 Hz, 38H), 0.91 (t, J=6.7 Hz, 3H). MS m/z [M+1]=979.3.

Intermediates I-94 & I-95: ((3aS,4R,6aS)-6-(4-aminopyrrolo [2,1-f][1,2,4]triazin-7-yl)-4-cyano-2,2-dimethyltetrahydrofuro[3,4-d][1,3]dioxol-4-yl) methyl ((R)-2-((3-cyano-5-fluoro benzyl)oxy) docosyl) hydrogen phosphate (Intermediate I-94), and ((3aS,4R,6aS)-6-(4-aminopyrrolo[2,1-f][1,2,4]triazin-7-yl)-4-cyano-2,2-dimethyltetrahydrofuro[3,4-d][1,3] dioxol-4-yl)methyl ((S)-2-((3-cyano-5-fluorobenzyl)oxy)docosyl) hydrogen phosphate (Intermediate I-95)

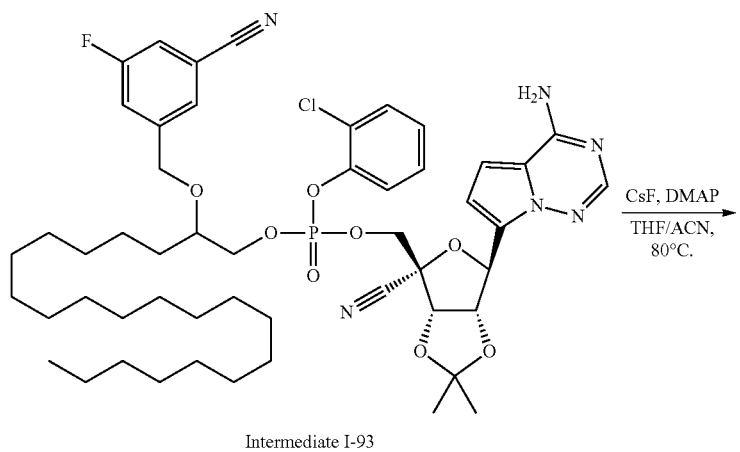

Intermediate I-93

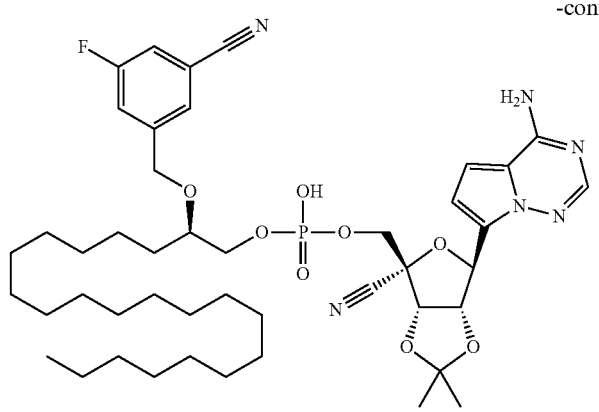

Intermediate I-94

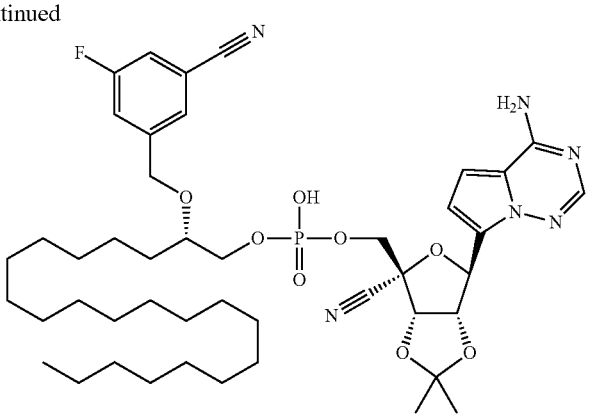

Intermediate I-95

Intermediate I-93 (0.153 mmol) was dissolved in 2:1 THF:ACN (4:2 mL). Solution of Cesium fluoride (0.766 mmol) in water (0.21 mL) was added to the solution followed by 4-(dimethylamino)pyridine (0.766 mmol). The reaction mixture was stirred at 80° C. for 3 h. The reaction was cooled to rt, added 10% citric acid in water (20 mL) followed by 1 M NaOH to adjust pH 3-4. Extracted with 2-MeTHF/EtOAc (3:2, 50 mL×2), conformed no desired product in the aqueous layer by LCMS. Combined organic layers washed with brine solution once and dried over $Na_2SO_4$, filtered and concentrated in vacuo prior to purification by silica gel chromatography (0-50% MeOH in DCM) and isolated compound Intermediate I-94 (MS m/z [M+1]=869.2) and Intermediate I-95 (MS m/z [M+1]=869.2).

Intermediate I-96: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenol) ((R)-2-(4-cyano-3,5-dimethoxyphenoxy)henicosyl) phosphate

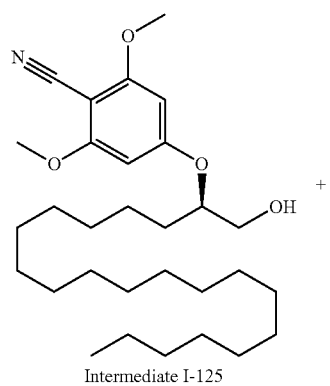

Intermediate I-125

+

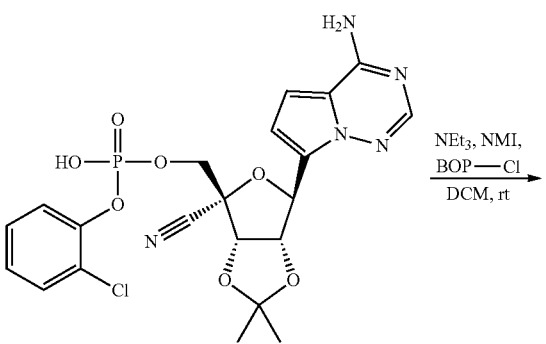

Intermediate I-27

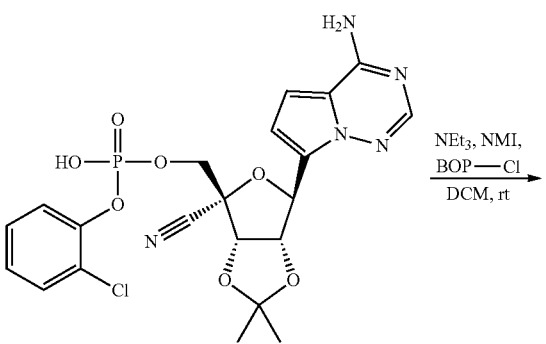

Intermediate I-96

Intermediate I-125 (0.256 mmol), and Intermediate I-27 (0.384 mmol) were taken in a 20 mL vial, added DCM (4 mL), add NMI (81 uL, 1.02 mmol), TEA (71 uL, 0.512 mmol) followed by Bop-Cl (1.02 mmol) sequentially. The reaction stirred at room temperature overnight. Solvent concentrated under reduced pressure. The crude product was dissolved in DCM, loaded on 40 g silica gel column, eluted with 100% Hexane 3 min, 0-100% EtOAc 6 min, and 100% EtOAc 6 min. The product elute at 100% EtOAc, fractions containing pure product were combined, concentered to afford Intermediate I-96. (48%). MS m/z [M+1]=993.2.

Intermediate I-97: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-(4-cyano-3,5-dimethoxy phenoxy)henicosyl) hydrogen phosphate

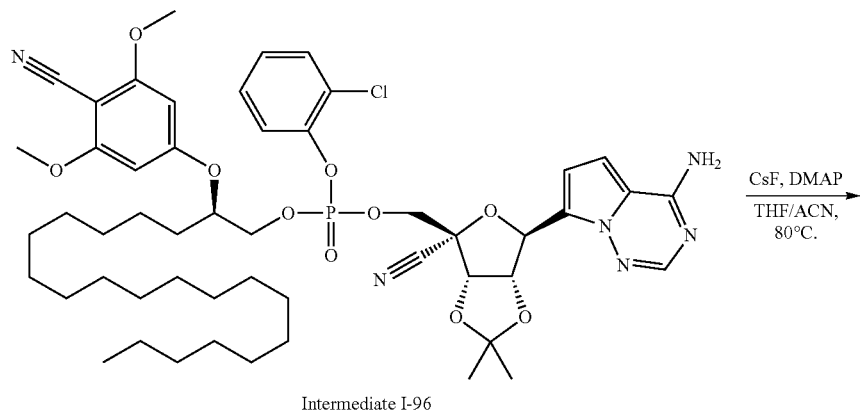

Intermediate I-96

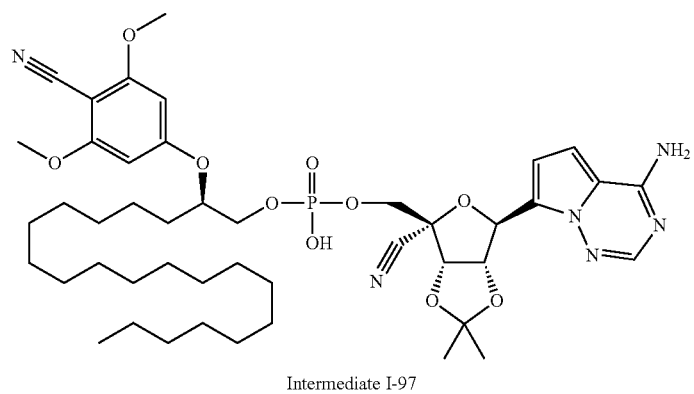

Intermediate I-97

Intermediate I-96 (0.191 mmol) was dissolved in 2:1 THF:ACN (3:6 mL). Solution of Cesium fluoride (0.95 mmol) in water (0.256 mL) was added to the solution followed by 4-(dimethylamino)pyridine (0.956 mmol). The reaction mixture was stirred at 80° C. for 3 h. The reaction was cooled to rt, added 10% citric acid in water (10 mL) followed by 1 M NaOH to adjust pH 3-4. Extracted with 2-MeTHF/EtOAc (3:2, 50 mL×2), conformed no desired product in the aqueous layer by LCMS. Combined organic layers washed with a brine once and dried over $Na_2SO_4$, filtered and concentrated in vacuo prior to purification by silica gel chromatography (0-50% MeOH in DCM) to afford Intermediate I-97. $^1$H NMR (400 MHz, Methanol-d4) δ 7.99 (s, 1H), 7.23 (d, J=4.6 Hz, 1H), 6.96 (d, J=4.7 Hz, 1H), 6.29 (s, 2H), 5.65 (d, J=3.7 Hz, 1H), 5.23 (dd, J=6.5, 3.8 Hz, 1H), 5.12 (d, J=6.4 Hz, 1H), 4.69 (p, J=5.4 Hz, 1H), 4.08 (d, J=4.7 Hz, 2H), 4.02 (t, J=5.9 Hz, 2H), 3.91 (s, 1H), 3.86 (s, 6H), 2.98-2.76 (m, 8H, Citrate salt), 1.72 (d, J=8.8 Hz, 6H), 1.39 (s, 2H), 1.29 (d, J=8.3 Hz, 34H), 0.92 (t, J=6.6 Hz, 3H). MS m/z [M+1]=883.3.

Intermediate I-98: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((5-cyano pyridin-2-yl)oxy)-3-(tetradecyloxy)propyl) phosphate

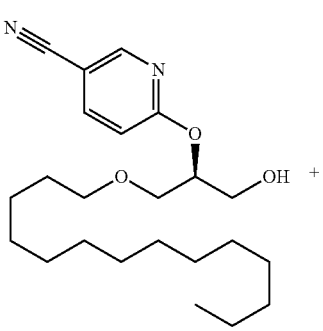

715

-continued

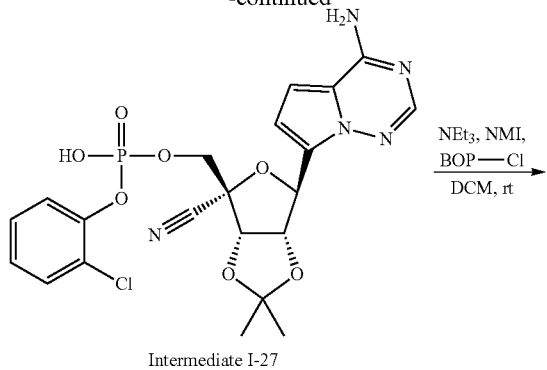

Intermediate I-27

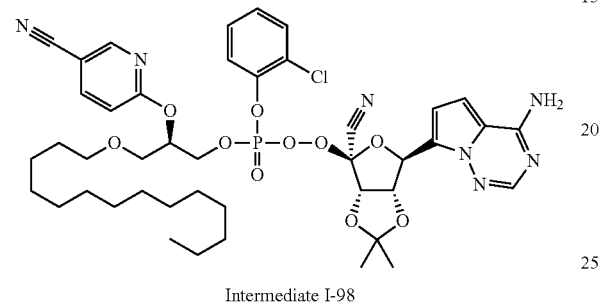

Intermediate I-98

716

(R)-6-((1-hydroxyoctadecan-2-yl)oxy)nicotinonitrile (0.041 mmol), Intermediate I-27 (0.061 mmol) were taken in a 20 mL vial, dried under vacuum (1 h), add DCM (2 mL), add NMI (13.4 uL, 0.163 mmol), TEA (11.5 uL, 0.081 mmol) followed by Bop-Cl (0.04 mmol). The reaction stirred at rt for 2 h. Solvent concentrated under reduced pressure. The crude product was dissolved in DCM, loaded on 24 g column, eluted with 100% Hex, 4 min, 0-100% EtOAc 6 min, and 100% EtOAc 6 min. The product elute at 100% EtOAc, fractions containing pure product were combined, concentered to afford Intermediate I-98. MS m/z [M+1]=894.1

Intermediate I-99: ((3aS,4R,6S,6aS)-6-(4-aminopyrrolo[2,1-f][1,2,4]triazin-7-yl)-4-cyano-2,2-dimethyl-tetrahydrofurol[3,4-d][1,3]dioxol-4-yl)methyl ((R)-2-((5-cyanopyridin-2-yl)oxy) octadecyl) hydrogen phosphate

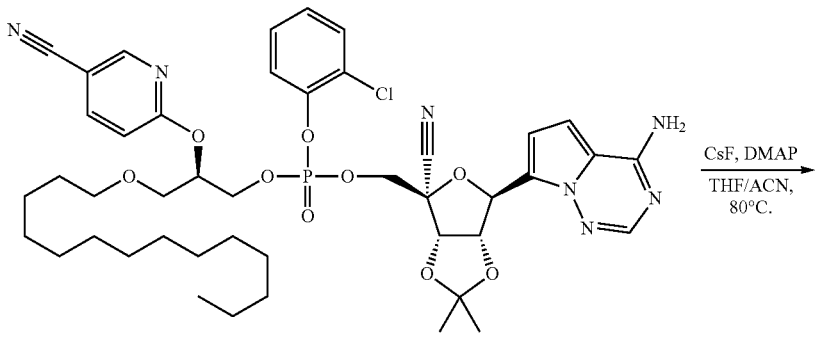

Intermediate I-98

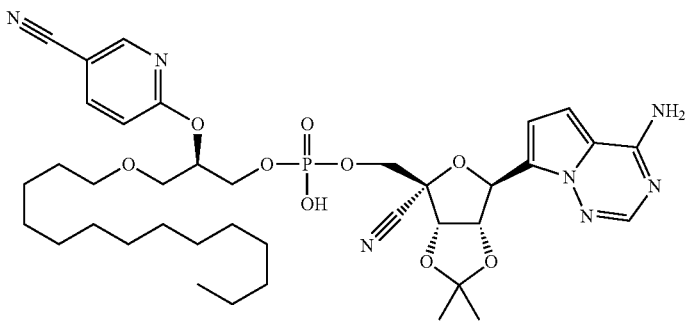

Intermediate I-99

Intermediate I-98 (0.123 mmol) was dissolved in 2:1 THF:ACN (4.5 mL). A solution of Cesium fluoride (0.615 mmol) in water (0.166 mL) was added to the solution followed by 4-(dimethylamino)pyridine (0.615 mmol). The reaction mixture was stirred at 80° C. for 3 h. The reaction was cooled to rt, added 10% citric acid in water (15 mL) followed by 1M NaOH to adjust pH 3-4. Extracted with 2-MeTHF/EtOAc (3:2, 50 mL×2), conformed no desired product in the aqueous layer by LCMS. Combined organic layers washed with a brine once and dried over $Na_2SO_4$, filtered and concentrated in vacuo prior to purification by silica gel chromatography (0-50% MeOH in DCM) to afford Intermediate I-99. $^1$H NMR (400 MHz, Methanol-$d_4$) δ 8.47 (d, J=2.3 Hz, 1H), 8.03-7.96 (m, 1H), 7.94-7.83 (m, 1H), 7.16 (d, J=4.7 Hz, 1H), 7.01-6.92 (m, 2H), 5.65 (dd, J=8.4, 3.7 Hz, 1H), 5.26 (td, J=7.0, 3.7 Hz, 1H), 5.22-5.14 (m, 2H), 4.68-4.37 (m, 3H), 4.21 (d, J=3.9 Hz, 2H), 3.76-3.64 (m, 1H), 3.52 (dd, J=13.0, 6.6 Hz, 1H), 3.44 (t, J=6.5 Hz, 1H), 2.99-2.75 (m, 90H, citrate salt), 1.72 (d, J=7.4 Hz, 3H), 1.54 (dp, J=13.6, 6.3 Hz, 2H), 1.40 (d, J=5.6 Hz, 2H), 1.35-1.19 (m, 22H), 0.91 (t, J=6.6 Hz, 3H). MS m/z [M+1]=784.1.

Intermediate I-100: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) (2-((6-cyanopyridin-3-yl)oxy)-3-(octadecyloxy)propyl) phosphate

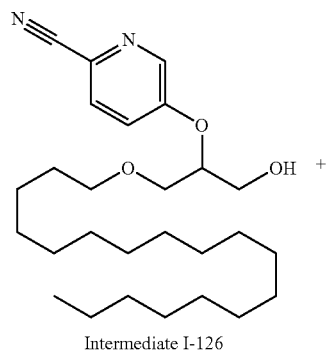

Intermediate I-126

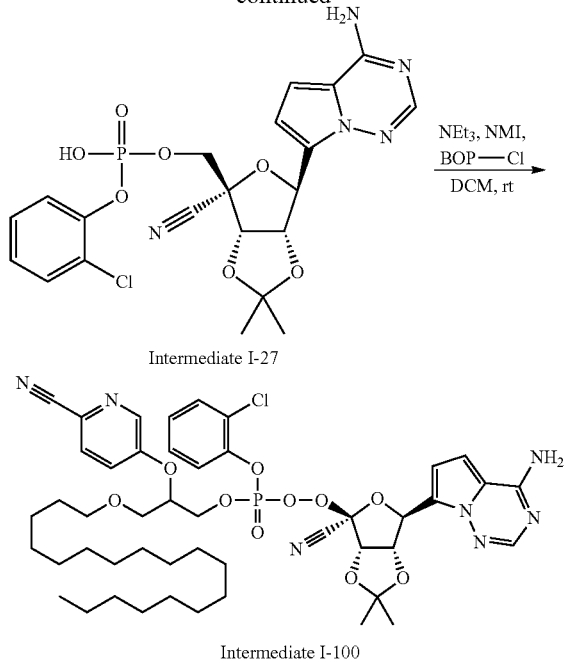

Intermediate I-27

Intermediate I-100

Intermediate I-126 (0.336 mmol, contains minor R-isomer as impurity), Intermediate I-27 (0.061 mmol) were taken in a 20 mL vial, dried under vacuum (1 h), added DCM (2 mL), NMI (0.504 mmol), TEA (93 uL, 0.672 mmol) followed by Bop-Cl (1.34 mmol) sequentially. The reaction stirred at room temperature overnight. Solvent concentrated under reduced pressure, and crude product was dissolved in DCM, loaded on 40 g column, eluted with 100% Hex, 2 min, 0-100% EtOAc 6 min, and 100% EtOAc 6 min. The product elute at 100% EtOAc, fractions containing pure product were combined, concentered to afford Intermediate I-100 as mixture of diastereomers. MS m/z [M+1]=950.3.

Intermediate I-101 and Intermediate I-102: ((3aS, 4R,6S,6aS)-6-(4-aminopyrrolo[2,1-f][1,2,4]triazin-7-yl)-4-cyano-2,2-dimethyltetrahydrofuro[3,4-d][1,3] dioxol-4-yl)methyl ((R)-2-((6-cyanopyridin-3-yl) oxy)docosyl) hydrogen phosphate (Intermediate I-101), and ((3aS,4R,6S,6aS)-6-(4-aminopyrrolo[2, 1-f][1,2,4]triazin-7-yl)-4-cyano-2,2-dimethyltetra hydrofuro[3,4-d][1,3]dioxol-4-yl)methyl ((S)-2-((6-cyanopyridin-3-yl)oxy) docosyl) hydrogen phosphate (Intermediate I-102)

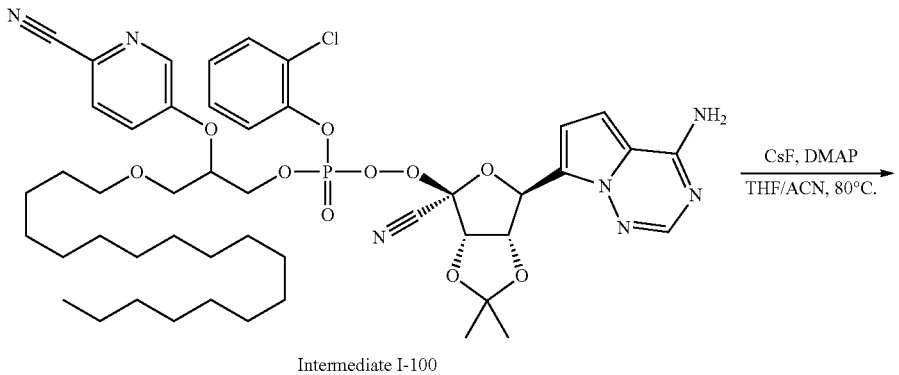

Intermediate I-100

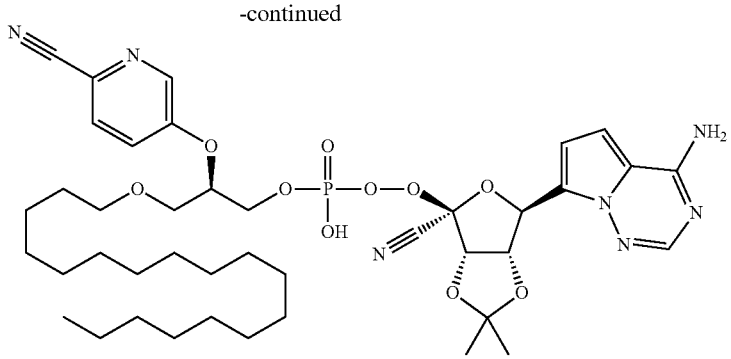

Intermediate I-101

+

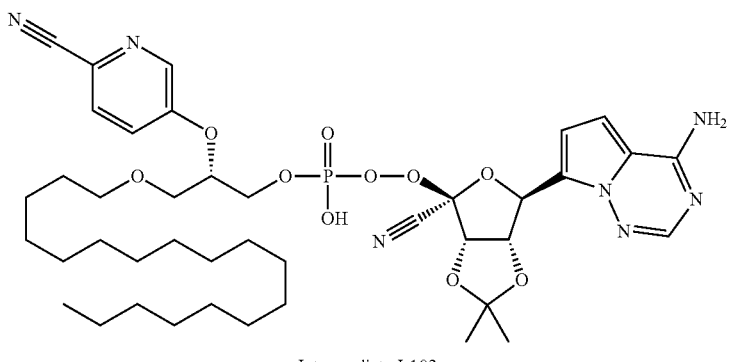

Intermediate I-102

Intermediate I-100 (0.263 mmol) was dissolved in 2:1 THF:ACN (4:2 mL). Solution of Cesium fluoride (1.32 mmol) in water (0.355 mL) was added to the solution followed by 4-(dimethylamino)pyridine (1.32 mmol). The reaction mixture was stirred at 80° C. for 3 h. The reaction was cooled to rt, added 10% citric acid in water (15 mL) followed by 1M NaOH to adjust pH 3-4. Extracted with 2-MeTHF/EtOAc (3:2, 50 mL×2), conformed no desired product in the aqueous layer by LCMS. Combined organic layers washed with a brine once and dried over $Na_2SO_4$, filtered and concentrated in vacuo prior to purification by silica gel chromatography (0-50% MeOH in DCM) to afford Intermediate I-101 and Intermediate I-102.

Intermediate I-101: $^1$H NMR (400 MHz, Methanol-$d_4$) δ 8.35 (d, J=2.9 Hz, 1H), 7.87 (s, 1H), 7.70 (d, J=8.7 Hz, 1H), 7.57 (dd, J=8.7, 2.9 Hz, 1H), 6.86 (d, J=4.5 Hz, 1H), 6.82 (d, J=4.5 Hz, 1H), 5.66 (d, J=3.7 Hz, 1H), 5.30 (dd, J=6.6, 3.7 Hz, 1H), 5.15 (d, J=6.6 Hz, 1H), 4.78 (s, 1H), 4.13 (t, J=4.7 Hz, 2H), 4.04 (t, J=6.1 Hz, 2H), 3.68-3.37 (m, 4H), 2.93-2.72 (m, 3H, Citrate salt), 1.72 (s, 3H), 1.48 (s, 2H), 1.41 (s, 3H), 1.27 (d, J=24.9 Hz, 30H), 0.92 (t, J=6.6 Hz, 3H). MS m/z [M+1]=840.3.

Intermediate I-102: $^1$H NMR (400 MHz, Methanol-$d_4$) δ 8.35 (d, J=2.8 Hz, 1H), 7.87 (s, 1H), 7.71 (d, J=8.7 Hz, 1H), 7.57 (dd, J=8.8, 2.9 Hz, 1H), 6.87 (d, J=4.5 Hz, 1H), 6.82 (d, J=4.5 Hz, 1H), 5.66 (d, J=3.6 Hz, 1H), 5.30 (dd, J=6.6, 3.6 Hz, 1H), 5.15 (d, J=6.6 Hz, 1H), 4.79 (qd, J=5.5, 3.1 Hz, 1H), 4.14 (h, J=6.0, 5.5 Hz, 2H), 4.04 (t, J=6.2 Hz, 2H), 3.64 (dd, J=10.9, 3.2 Hz, 1H), 3.55 (dd, J=11.0, 6.7 Hz, 1H), 3.49-3.36 (m, 2H), 2.96-2.68 (m, 4H, Citrate salt), 1.72 (s, 3H), 1.49 (p, J=6.6 Hz, 2H), 1.41 (s, 3H), 1.27 (d, J=24.5 Hz, 30H), 0.92 (t, J=6.8 Hz, 3H). MS m/z [M+1]=840.3

Intermediate I-103: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) (2-((3-cyano-5-fluorobenzyl)oxy) nonadecyl) phosphate

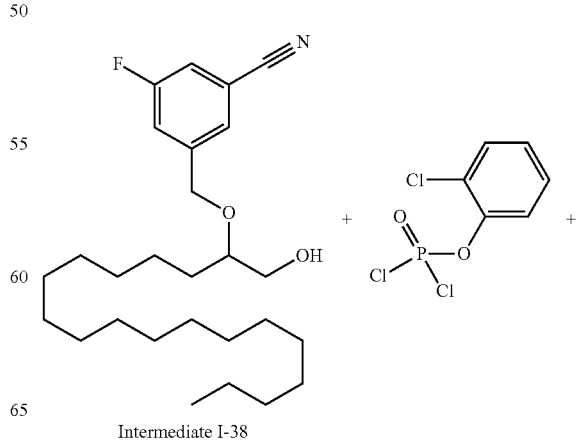

Intermediate I-38

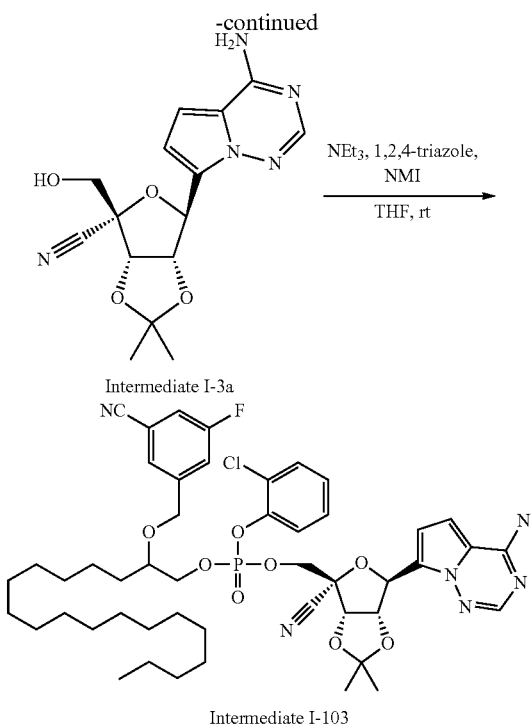

Intermediate I-3a

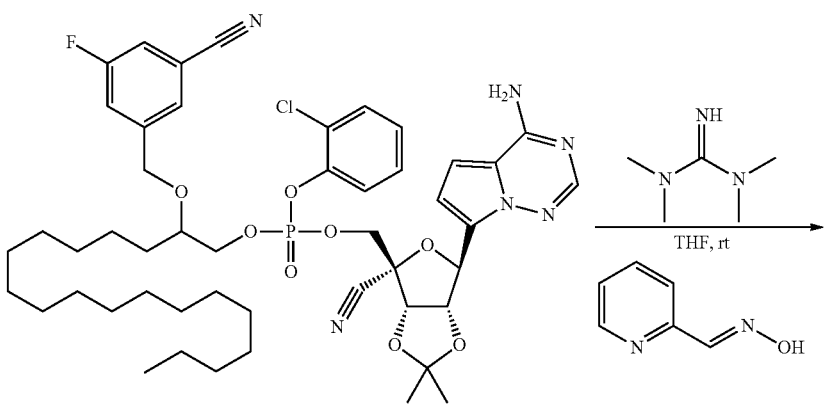

Intermediate I-103

To a solution of 1H-1,2,4-triazole (2.6 mmol) and TEA (0.362 mL, 2.6 mmol) in ACN (8 mL) pyridine (8 mL) was added 2-chlorophenyl phosphorodichloridate (0.199 mL, 1.2 mmol) at rt. The reaction mixture was stirred at rt for 30 min, Intermediate I-3a (1.21 mmol) and then 1-methylimidazole (0.161 mL, 2.02 mmol) added. The resulting mixture was stirred for 1 h at rt and Intermediate I-38 (1.21 mmol) added. The resulting reaction mixture was stirred for 70 min, and concentrated in vacuo, coevaporated with Toluene. The crude purified by silica gel column chromatography (0 to 100% MeOH in DCM) to give Intermediate I-103 as mixture of two isomers. $^1$H NMR (400 MHz, Methanol-d4) δ 7.82 (d, J=6.0 Hz, 1H), 7.50-7.31 (m, 5H), 7.24-7.08 (m, 2H), 6.85 (dd, J=6.3, 4.5 Hz, 1H), 6.79 (d, J=4.5 Hz, 1H), 5.66 (d, J=2.8 Hz, 1H), 5.32 (td, J=6.9, 3.0 Hz, 1H), 5.17 (dd, J=18.8, 6.5 Hz, 1H), 4.68-4.48 (m, 4H), 4.41-4.29 (m, 1H), 4.21-4.12 (m, 1H), 3.63 (h, J=6.1 Hz, 1H), 1.74 (d, J=2.4 Hz, 3H), 1.61-1.43 (m, 2H), 1.39 (d, J=2.7 Hz, 3H), 1.29 (d, J=5.0 Hz, 30H), 0.91 (t, J=6.6 Hz, 3H). $^{31}$P NMR (162 MHz, Methanol-d4) δ −7.75 (d, J=48.9 Hz). MS m/z [M+1]=937.2.

Intermediate I-104: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl) oxy)nonadecyl) hydrogen phosphate

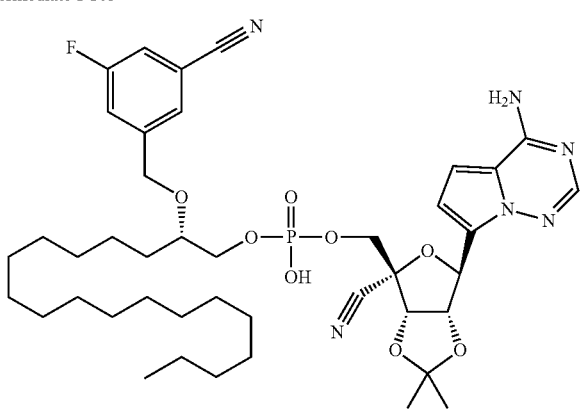

Intermediate I-104

To a solution of Intermediate I-103 (0.587 mmol) in THF (20 mL) was added 1,1,3,3-tetramethylguanidine (0.442 mL, 3.52 mmol) and syn-2-pyridinealdoxime (4.81 mmol). The reaction mixture was stirred at room temperature overnight. The solution was concentrated in vacuo and purified by silica gel (0-40% MeOH in DCM) to afford Intermediate I-104 as major isomer. $^1$H NMR (400 MHz, Methanol-d4) δ 7.85 (s, 1H), 7.51 (s, 1H), 7.40 (dd, J=16.9, 8.9 Hz, 2H), 6.86 (d, J=4.5 Hz, 1H), 6.82 (d, J=4.5 Hz, 1H), 5.65 (d, J=3.7 Hz, 1H), 5.29 (dd, J=6.6, 3.7 Hz, 1H), 5.15 (d, J=6.6 Hz, 1H), 4.75 (d, J=13.0 Hz, 1H), 4.50 (d, J=13.0 Hz, 1H), 4.13 (d, J=4.3 Hz, 2H), 3.90 (m, 2H), 3.59 (s, 1H), 1.71 (s, 3H), 1.44 (d, J=7.1 Hz, 2H), 1.39 (s, 3H), 1.29 (d, J=9.5 Hz, 30H), 0.92 (t, J=6.6 Hz, 3H). $^{31}$P NMR (162 MHz, Methanol-d4) δ−0.48. MS m/z [M−1]=827.2.

Intermediate I-105: ((3aS,4R,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl (2-chlorophenyl) ((R)-2-((6-cyano pyridin-2-yl)methoxy)-3-(octadecyloxy)propyl) phosphate

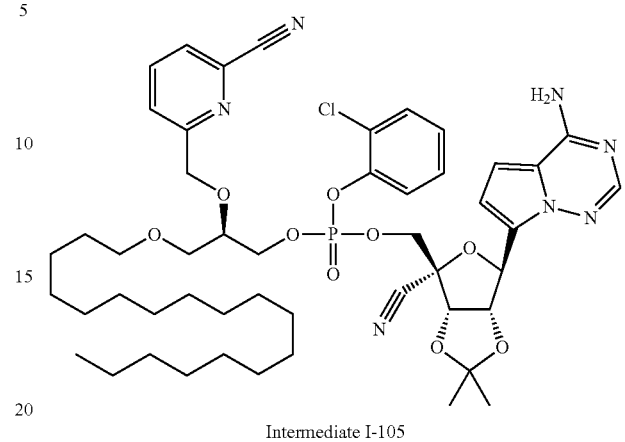

Intermediate I-105

To a solution of 6-[[(1S)-1-(hydroxymethyl)-2-octadecoxy-ethoxy]methyl]pyridine-2-carbonitrile (0.109 mmol), Intermediate I-27 (0.163 mmol), triethylamine (0.03 mL, 0.217 mmol) and 1-Methylimidazole (0.434 mmol) in DCM (4.0 mL) was added Bis(2-oxo-3-oxazolidinyl)phosphinic chloride (0.130 mmol). After 1 h, LCMS showed ~40% conversion to desired product and the rest is the lipid alcohol. One more portion of NMI and BOP—Cl was added and the reaction was stirred at room temperature overnight. The reaction mixture was concentrated in vacuo and the resultant crude was purified by silica gel column chromatography using (0-100% EtOAc/Hexanes) to afford Intermediate I-105. MS m/z [M+1]=964.4.

Intermediate I-106: ((3aS,4R,6aS)-6-(4-aminopyrrolo[2,1-f][1,2,4]triazin-7-yl)-4-cyano-2,2-dimethyl-tetrahydrofuro[3,4-d][1,3]dioxol-4-yl)methyl ((R)-2-((6-cyanopyridin-2-yl) methoxy)-3-(octadecyloxy)propyl) hydrogen phosphate

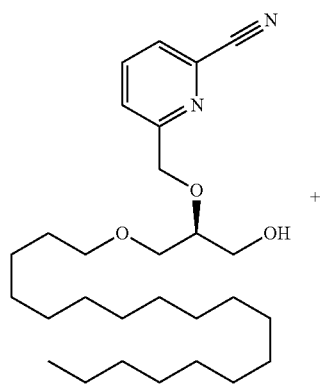

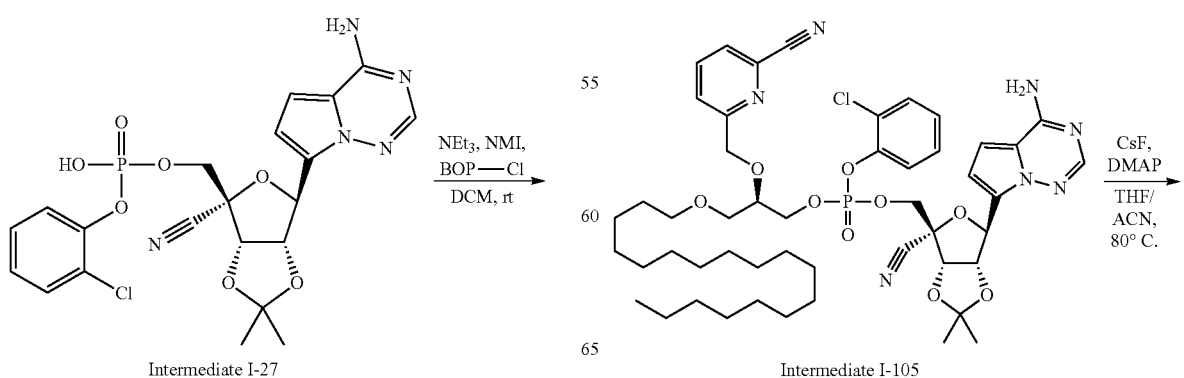

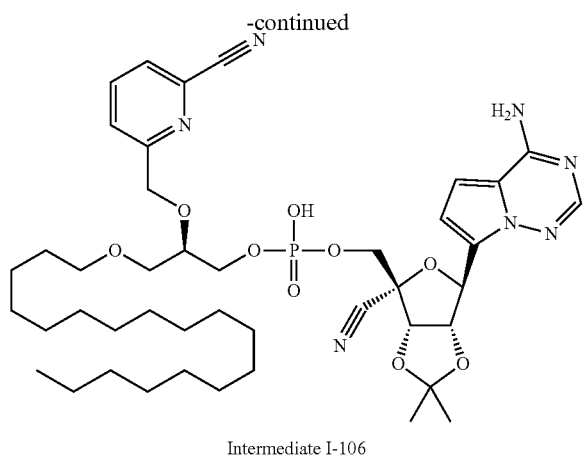

Intermediate I-106

Intermediate I-105 (0.06 mmol) was dissolved in 2:1 THF:ACN (4.5 mL total). Cesium fluoride (0.30 mmol, 5.0 equiv.) dissolved in water (0.50 mL) was added to the solution followed by 4-dimethylaminopyridine (0.241 mmol). The reaction mixture was heated to 80° C. and stirred for 3.5 h. The reaction was quenched with a buffered solution of citric acid (2.73 mL, 0.22 M, 10 equiv.) and NaOH (0.03 mL, 2 M, 1.0 equiv.). The aqueous layer was extracted with EtOAc (3×5 mL). The organic fractions were combined, washed with brine (5 mL), dried over Na$_2$SO$_4$, filtered and concentrated in vacuo prior to purification by silica gel chromatography (0-80% MeOH in DCM) to afford Intermediate I-106. MS m/z [M+1]=854.3.

Intermediate I-107: ((3aS,4R,6aS)-6-(4-aminopyrrolo[2,1-f][1,2,4]triazin-7-yl)-4-cyano-2,2-dimethyltetrahydrofurol[3,4-d][1,3]dioxol-4-yl)methyl (2-chlorophenyl) ((R)-2-((4-cyanopyridin-2-yl)oxy)-3-(tetradecyloxy)propyl) phosphate

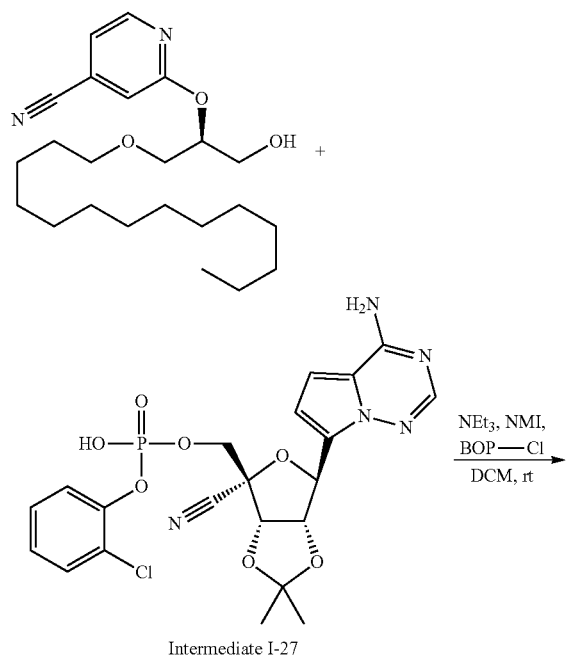

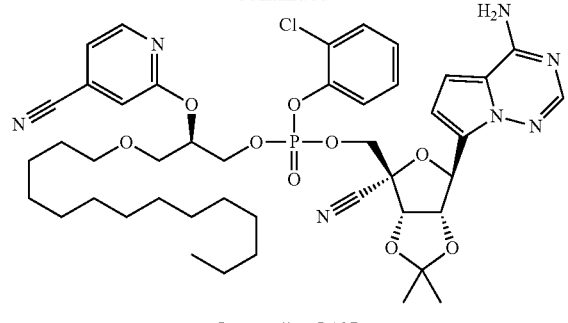

Intermediate I-107

To a solution of Intermediate I-27 (0.199 mmol), 2-[(1S)-1-(hydroxymethyl)-2-tetradecoxy-ethoxy]pyridine-4-carbonitrile (0.133 mmol), triethylamine (0.03 mL, 0.266 mmol) and 1-Methylimidazole (0.531 mmol) in DCM (4.0 mL) was added Bis(2-oxo-3-oxazolidinyl)phosphinic chloride (0.159 mmol). The solution was stirred at room temperature overnight. The reaction mixture was concentrated in vacuo and the resultant crude was purified by silica gel column chromatography using (0-100% EtOAc/Hexanes) to afford Intermediate I-107. MS m/z [M+1]=894.2.

Intermediate I-108: ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((6-cyanopyridin-2-yl) methoxy)-3-(octadecyloxy) propyl) hydrogen phosphate

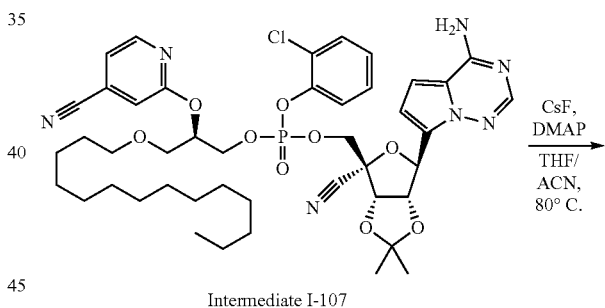

Intermediate I-107

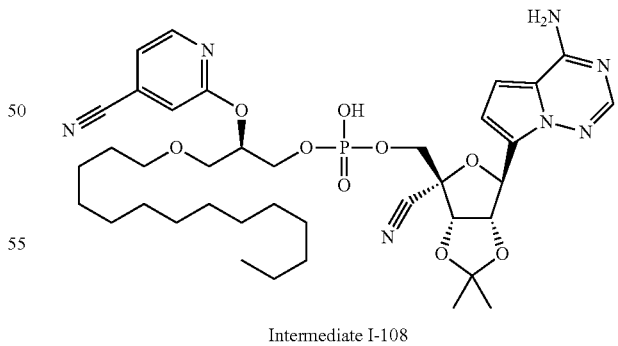

Intermediate I-108

Intermediate I-107 (0.101 mmol) was dissolved in 2:1 THF:ACN (6.0 mL total). Cesium fluoride (0.503 mmol) dissolved in water (0.50 mL) was added to the solution followed by 4-Dimethylaminopyridine (0.403 mmol). The reaction mixture was heated to 80° C. and stirred for 3.5 h. The reaction was quenched with a buffered solution of citric acid (4.57 mL, 0.22 M, 10 equiv.) and NaOH (0.05 mL, 2 M, 1.0 equiv.) and the aqueous layer was extracted with EtOAc (3×5 mL). The organic fractions were combined, washed with brine (5 mL), dried over Na$_2$SO$_4$, filtered and concentrated in vacuo prior to purification by silica gel chromatography (0-80% MeOH in DCM) to afford Intermediate I-108. MS m/z [M+1]=784.1.

Intermediate I-110: (S)-3-fluoro-4-(((1-hydroxy-3-(tetradecyloxy)propan-2-yl)oxy)methyl)benzonitrile

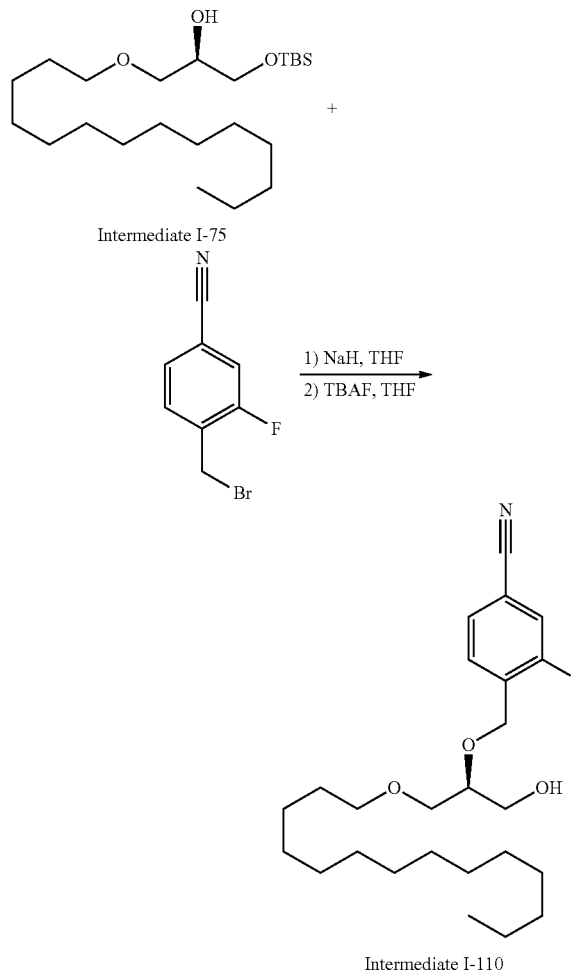

Intermediate I-110

NaH (60% oil dispersion, 2.29 mmol) was suspended in THF (6 mL) and cooled to 0° C. A solution of Intermediate I-75 (0.654 mmol) in THF (2.5 mL) was added over 30 sec. After 30 min at 0° C., a solution of 4-(bromomethyl)-3-fluorobenzonitrile (2.62 mmol, 4 eq) in THF (2.5 mL) was added. The mixture was stirred for 16 h at rt. The reaction was quenched with water (15 mL). The mixture was extracted with EtOAc. The combined organic phase was dried over sodium sulfate and the solvent was removed under reduced pressure. The obtained residue was purified by silica gel column chromatography (0 to 20% EtOAc in hexanes) to give (R)-4-(((1-((tert-butyldimethylsilyl)oxy)-3-(tetradecyloxy)propan-2-yl)oxy)methyl)-3-fluorobenzonitrile as a mixture with impurities. To this mixture (464 mg, 0.866 mmol) in THF (3.3 mL) at 0° C., was added 1M TBAF in THF (2 mL). The mixture was stirred for 1 h, and concentrated to dryness. The residue was purified by silica gel column chromatography (0-60% EtOAc in hexanes) to afford Intermediate I-110. $^1$H NMR (400 MHz, DMSO-d6) δ 7.82 (dd, J=10.0, 1.5 Hz, 1H), 7.80-7.67 (m, 2H), 4.77 (s, 2H), 4.71 (t, J=5.6 Hz, 1H), 3.65-3.34 (m, 6H), 1.52-1.39 (m, 2H), 1.34-1.11 (m, 22H), 0.94-0.78 (m, 3H).

Intermediate I-111: (S)-4-((1-hydroxy-3-(octadecyloxy)propan-2-yl)oxy)-2-isopropoxybenzonitrile

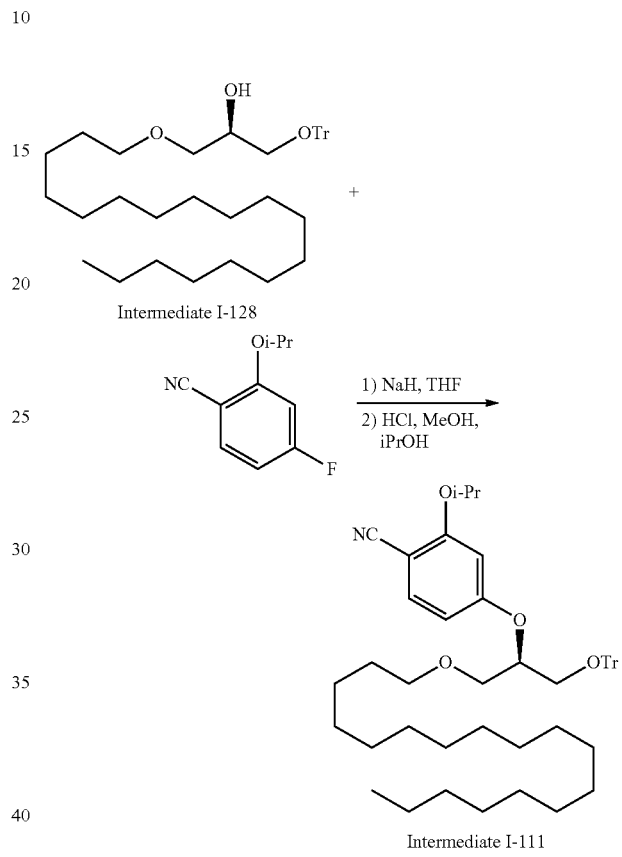

Intermediate I-111

To a solution of Intermediate I-128 (5.11 mmol) in THF (30 mL) was added 60% NaH (12.7 mmol) at 20° C. The resulting mixture was stirred at 20° C. for 30 min and 4-fluoro-2-isopropoxybenzonitrile (10.2 mmol) in DMF (60 mL) was added dropwise. The resulting mixture was warmed to 25° C., stirred for 30 min, and the reaction quenched with aqNH$_4$Cl (2 mL). After diluting with brine (40 mL), the mixture was extracted with EtOAc (30 mL×2), dried with sodium sulfate and concentrated in vacuo to give (R)-2-isopropoxy-4-((1-(octadecyloxy)-3-(trityloxy)propan-2-yl)oxy)benzonitrile as a mixture containing impurities. To a solution of this mixture (4.5 mmol) in MeOH (30 mL) were added i-PrOH (30 mL) and 12 M HCl (30 mL). The reaction mixture was heated to 50° C., stirred for 2 h, water (50 mL) added and extracted with EtOAc (50 mL×3). The organic layer was washed with brine (25 mL×2), concentrated in vacuo, and purified by silica gel column chromatography (petroleum ether/EtOAc=50/1 to 3/1) to give intermediate I-111. $^1$H NMR (CDCl$_3$ 400 MHz): δ 7.45-7.46 (m, 1H), 6.56-6.58 (m, 2H), 4.52-4.60 (m, 2H), 3.88-3.91 (m, 2H), 3.66-3.68 (m, 2H), 3.46-3.47 (m, 2H), 1.54-1.59 (m, 2H), 1.39-1.40 (m, 6H), 1.30 (s, 30H), 0.86-0.90 (t, J=6.4 Hz, 3H).

Intermediate I-112: (R)-1-(trityloxy)henicosan-2-ol

Intermediate I-113: (R)-4-(((1-hydroxyhenicosan-2-yl)oxy)methyl)-2-isopropoxybenzonitrile

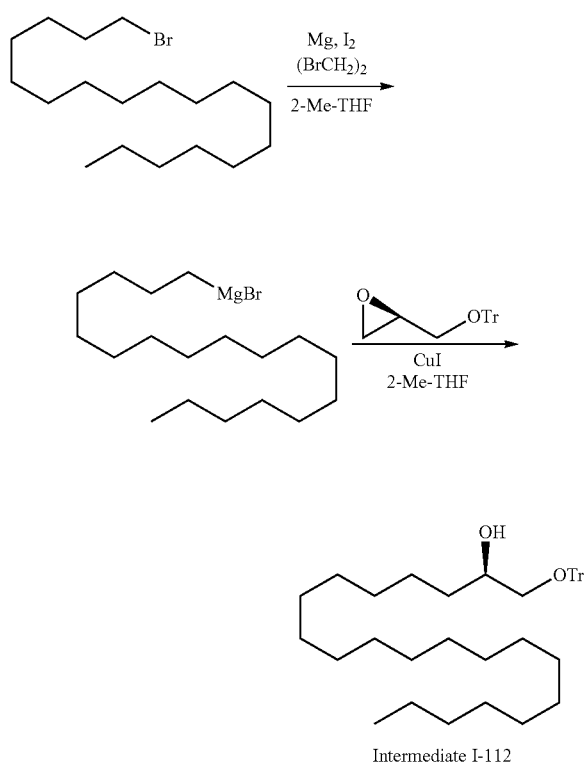

Intermediate I-112

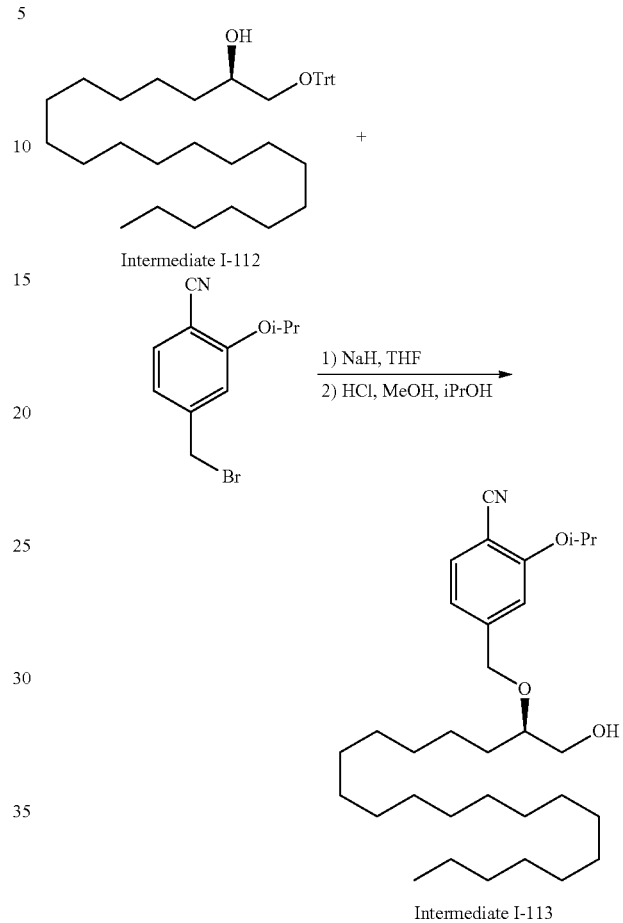

Intermediate I-113

To a mixture of Mg (103.5 mmol, 1.1 eq) in 2-Me-THF (15 mL) were added $I_2$ (899.8 umol, 181.3 uL, 0.01 eq) and $BrCH_2CH_2Br$ (0.1 mL) under $N_2$. Then 1-bromooctadecane (9 mmol) in 2-Me-THF (30 mL) was added dropwise to the mixture. The reaction was stirred until the color of $I_2$ was faded into a colorless solution. Then the remaining 1-bromooctadecane (84.0 mmol) in 2-Me-THF (255 mL) was added and stirred at 25° C. for 4 hr. Compound octadecylmagnesium bromide (0.3M in 300 mL THF) was used to the next step directly. Added octadecylmagnesium bromide (78.3 mmol, 1.3 eq) over 10 min via cannula to mixture of (2R)-2-(trityloxymethyl)oxirane (60.2 mmol, 1 eq) and CuI (3.0 mmol, 0.05 eq) in 2-MeTHF (150 mL) at −20° C. Stirred vigorously 5 min, warmed to 0° C., continue stirring 2 hr. The reaction mixture was quenched by addition of sat. $NH_4Cl$ solution (300 mL), and then the mixture was extracted with Ethyl acetate (150 mL×3). The combined organic layers were washed with $H_2O$ (200 mL×2), dried over $Na_2SO_4$, filtered and concentrated under reduced pressure to give a residue. The residue was purified by flash silica gel chromatography (ISCO®; 120 g SepaFlash® Silica Flash Column, Eluent of 0~3% MTBE/Petroleum ether gradient @ 150 mL/min) to give Intermediate I-112. 1H NMR (400 MHz, CHLOROFORM-d) δ 7.51-7.46 (m, 6H), 7.39-7.28 (m, 9H), 3.81 (br dd, J=3.4, 6.8 Hz, 1H), 3.22 (dd, J=3.2, 9.3 Hz, 1H), 3.07 (dd, J=7.7, 9.2 Hz, 1H), 2.35 (d, J=3.3 Hz, 1H), 1.42 (br s, 2H), 1.37-1.23 (m, 34H), 0.93 (t, J=6.8 Hz, 3H). MS (ESI): m/z=243.0 [M+H]+

To a solution of Intermediate I-112 (5.25 mmol) in THF (30 mL) was added 60% NaH (26.2 mmol) in portions. The resulting mixture was stirred at 70° C. for 30 min and 4-(bromomethyl)-2-isopropoxybenzonitrile (7.88 mmol) in THF (12 mL) was added dropwise. The resulting mixture was stirred at 70° C. for 16 h and the reaction quenched with aqNH4Cl (2 mL). After diluting with brine (40 mL), the mixture was extracted with EtOAc (30 mL×3), dried with sodium sulfate, concentrated in vacuo, and purified by silica gel column chromatography (0 to 20% EtOAc in hexanes) to give (R)-2-isopropoxy-4-(((1-(trityloxy)henicosan-2-yl)oxy)methyl)benzonitrile as a mixture with impurities. To a solution of this mixture (3.9 g, 5.24 mmol) in MeOH (20 mL) were added i-PrOH (20 mL) and 12 M HCl (18 mL). The reaction mixture was heated to 50° C. and stirred for 1 h, water (200 mL) added, extracted with EtOAc (150 mL×2), washed with brine, dried with sodium sulfate, concentrated in vacuo, and purified by silica gel column chromatography (0 to 100% EtOAc in petroleum ether) to afford Intermediate I-113. $^1$H NMR (CDCl$_3$ 400 MHz): δ 7.51 (d, J=8.0 Hz, 1H), 6.99 (s, 1H), 6.91 (d, J=8.0 Hz, 1H), 4.70-4.66 (m, 1H), 4.62 (s, 2H), 3.73-3.72 (m, 1H), 3.60-3.50 (m, 2H), 2.05 (m, 1H), 1.83-1.52 (m, 2H), 1.40 (d, J=6.0 Hz, 6H), 1.37-1.30 (m, 34H), 0.88 (d, J=6.8 Hz, 3H). MS m/z [M+1]=502.3

Intermediate I-114: methyl 4-cyano-3-(1H-1,2,4-triazol-1-yl)benzoate

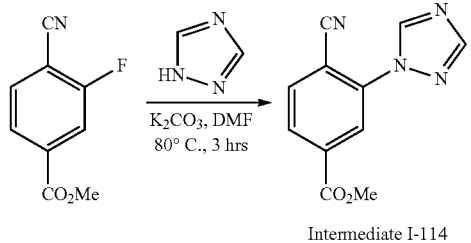

Intermediate I-114

To a solution of methyl 4-cyano-3-fluorobenzoate (106 mmol) in DMF (133 mL) were added 1H-1,2,4-triazole (106 mmol) and K$_2$CO$_3$ (116 mmol) at rt. The resulting mixture was heated at 80° C. for 3 h, cooled to rt, water (100 mL) added, and extracted with EtOAc (50 mL×3). The organic layer was washed with sat NaHCO$_3$ (50 mL), dried with sodium sulfate, concentrated in vacuo, and purified by silica gel column chromatography (petroleum ether/EtOAc=20/1 to 5/1) to give Intermediate I-114. $^1$H NMR (DMSO-d$_6$ 400 MHz): δ 9.29 (s, 1H), 8.39 (s, 1H), 8.32 (d, J=1.6 Hz, 1H), 8.23 (d, J=8.0 Hz, 1H), 8.14 (d, J=8.0 Hz, 1H), 3.93 (s, 3H). MS m/z [M+1]=229.1

Intermediate I-115: 4-(hydroxymethyl)-2-(1H-1,2,4-triazol-1-yl)benzonitrile

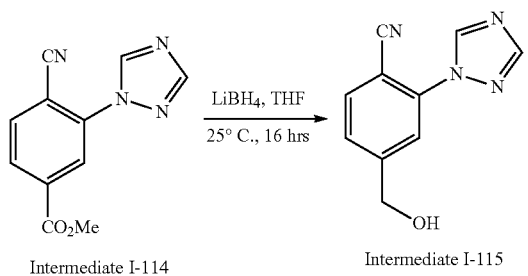 [SMILES: COC(=O)c1ccc(C#N)c(-n2cncn2)c1 ; N#Cc1ccc(CO)cc1-n1cncn1]

To a solution of methyl 4-cyano-3-(1H-1,2,4-triazol-1-yl) benzoate (83.2 mmol) in THF (760 mL) was added LiBH$_4$ (91.5 mmol) in 3 batches. The reaction mixture was stirred at 25° C. for 16 h prior to cooling to 0° C., quenching with water (300 mL), extracting with EtOAc (100 mL×3), collecting the organic layers, washing with brine (100 mL), drying over Na$_2$SO$_4$, filtering and concentrating in vacuo to give Intermediate I-115. MS m/z [M+1]=201.1

Intermediate I-116: (R)-2,2-dimethyl-4-((octadecyloxy)methyl)-1,3-dioxolane

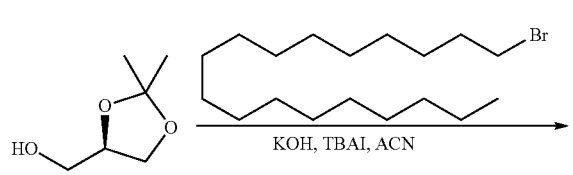

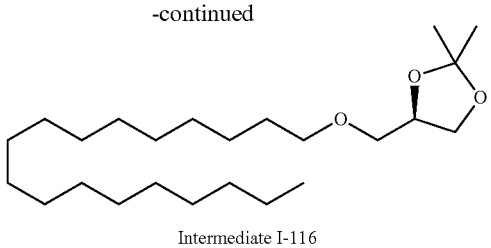

Intermediate I-116

Add (R)-(2,2-dimethyl-1,3-dioxolan-4-yl)methanol (529 mmol, 1.00 eq) into ACN (2850 mL). Add KOH (2.65 mol, 5.00 eq) and TBAI (52.9 mmol, 0.10 eq). Stir at 25° C. for 0.1 h. Add 1-bromooctadecane (635 mmol, 1.20 eq). Stir at 25° C. for 16 hrs. Concentrate in vacuum. The residue was purified by column chromatography (SiO$_2$, Petroleum ether/Ethyl acetate=30/1 to 10/1) to afford Intermediate I-116. TLC R$_f$=0.40 (Eluent: Petroleum ether/Ethyl acetate=10:1).

Intermediate I-117: (S)-3-(octadecyloxy)propane-1,2-diol

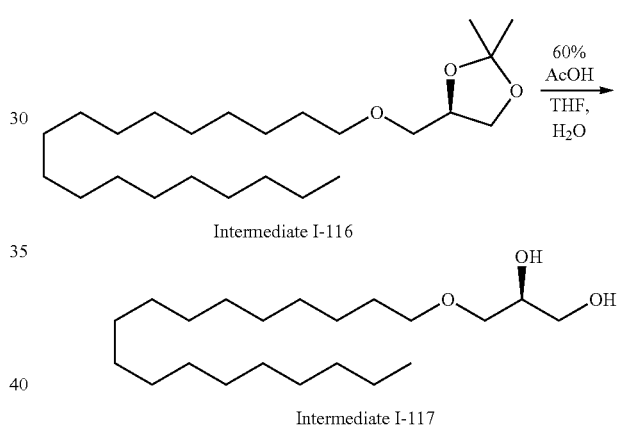

Add Intermediate I-116 (262 mmol, 1.00 eq) into THF (500 mL). Add AcOH (600 mL) and H$_2$O (400 mL) to the solution. Stir at 50° C. for 16 hrs. Concentrate in vacuum. Azeotrope 3 times with toluene. The crude product triturate with Petroleum ether: Ethyl acetate=3:1 at 25° C. for 2 hrs and filtered to afford Intermediate I-117. $^1$H NMR: (CDCl$_3$ 400 MHz): δ 3.86 (s, 1H), 3.54-3.67 (m, 1H), 3.52-3.53 (m, 1H), 3.46-3.51 (m, 4H), 2.67 (s, 1H), 2.25 (s, 1H), 1.58-1.64 (m, 2H), 1.26 (s, 30H), 0.86-0.90 (t, 3H).

Intermediate I-118: (R)-1-(octadecyloxy)-3-((triisopropylsilyl)oxy)propan-2-ol

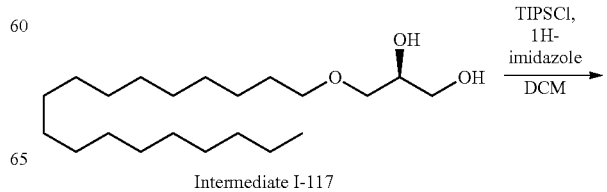

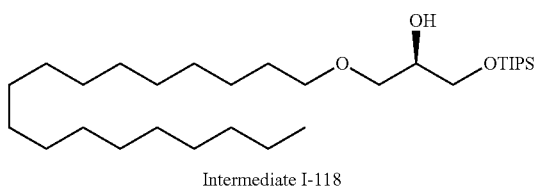

Intermediate I-118

Add Intermediate I-117 (211 mmol, 1.00 eq) and imidazole (423 mmol, 2.00 eq) into DCM (730 mL). Add TIPSCl (338 mmol, 72.5 mL, 1.60 eq) into reaction mixture at 0° C. Stir at 25° C. for 5 hrs. Add water (300 mL) to the reaction mixture. Extract with DCM (200 mL×3). Collect the organic layer. Dry over with $Na_2SO_4$. Concentrate in vacuum. The residue was purified by column chromatography ($SiO_2$, Petroleum ether/Ethyl acetate=20/1 to 1/1) to afford Intermediate I-118. $^1$H NMR: ($CDCl_3$ 400 MHz): δ 3.74-3.83 (m, 1H), 3.72-3.73 (d, J=2.0 Hz, 1H), 3.43-3.49 (m, 4H), 2.27 (brs, 1H), 1.55-1.58 (m, 1H), 1.35-1.20 (m, 30H), 1.05-1.12 (m, 30H), 0.86-0.89 (t, 3H).

Intermediate I-119: (S)-4-(((1-hydroxy-3-(octadecyloxy)propan-2-yl)oxy)methyl)-2-(1H-1,2,4-triazol-1-yl)benzonitrile

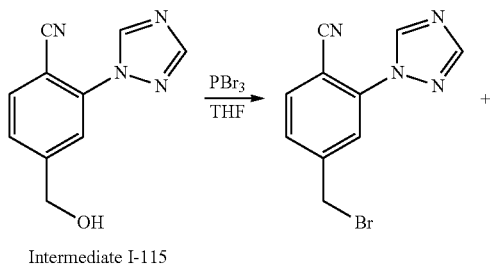

Intermediate I-115

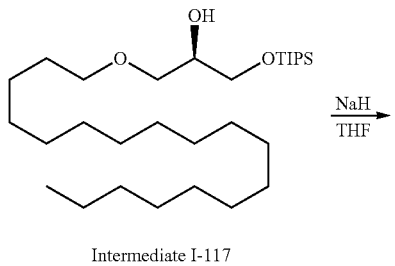

Intermediate I-117

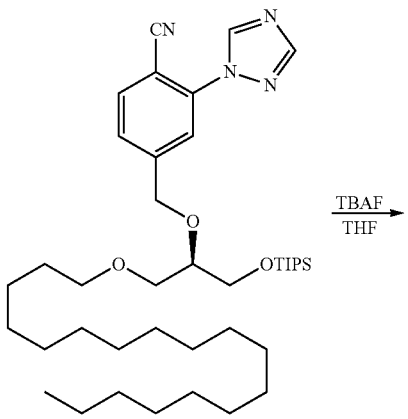

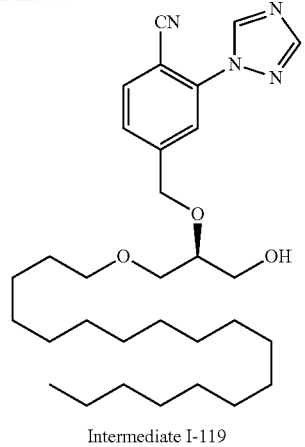

Intermediate I-119

To Intermediate I-115 (14.9 mmol) in DCM (60 mL) was added $PBr_3$ (7.49 mmol) at 25° C. The resulting mixture was stirred at 25° C. for 16 h, concentrated in vacuo, and purified by silica gel column chromatography (petroleum ether/EtOAc=30/1 to 2/1) to give 4-(bromomethyl)-2-(1H-1,2,4-triazol-1-yl)benzonitrile. TLC Rf=0.43 (Eluent: Petroleum ether/Ethyl acetate=1/1).

To 4-(bromomethyl)-2-(1H-1,2,4-triazol-1-yl)benzonitrile (3.17 mmol) in THF (10 mL) was added 60% NaH (15.8 mmol) at 25° C. The resulting mixture was stirred at 25° C. for 30 min and Intermediate I-117 (3.80 mmol) in THF (5 mL) was added dropwise. The mixture was stirred for 2 h and quenched with water (30 mL). The aqueous layer was extracted with EtOAc (30 mL×3), dried with sodium sulfate, concentrated in vacuo, and purified by silica gel column chromatography (petroleum ether/EtOAc=50/1 to 3/1) to give (R)-4-(((1-(octadecyloxy)-3-((triisopropylsilyl)oxy)propan-2-yl)oxy)methyl)-2-(1H-1,2,4-triazol-1-yl)benzonitrile. TLC Rf=0.60 (Eluent: Petroleum ether/Ethyl acetate=5/1).

To (R)-4-(((1-(octadecyloxy)-3-((triisopropylsilyl)oxy)propan-2-yl)oxy)methyl)-2-(1H-1,2,4-triazol-1-yl)benzonitrile (1.90 mmol) in THF (13 mL) was added TBAF (1M in THF, 5.71 mL) at 25° C. The resulting mixture was stirred at 25° C. for 30 min, concentrated in vacuo, and purified by silica gel column chromatography (petroleum ether/EtOAc=50/1 to 2/1) to give Intermediate I-119. $^1$H NMR ($CDCl_3$ 400 MHz): δ 8.78 (s, 1H), 8.19 (s, 1H), 7.80-7.82 (d, J=8.0 Hz, 2H), 7.53-7.55 (d, J=9.2 Hz, 1H), 4.80-4.89 (m, 2H), 3.62-3.74 (m, 3H), 3.59-3.61 (m, 2H), 3.43-3.46 (m, 2H), 2.08-2.14 (m, 1H), 1.54-1.60 (m, 2H), 1.30 (s, 30H), 0.86-0.90 (t, J=6.8 Hz, 3H). MS m/z [M+1]=527.3

Intermediate I-120:
1-(octadecyloxy)-3-(trityloxy)propan-2-one

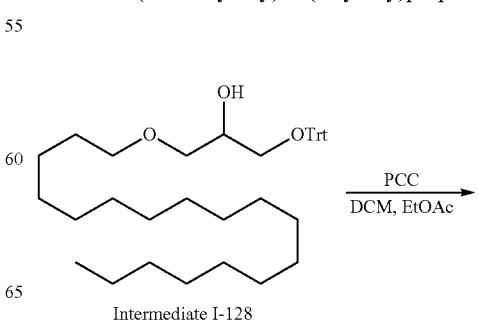

Intermediate I-128

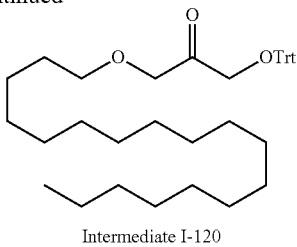

Intermediate I-120

To a solution of PCC (71.0 mmol) and EtOAc (10.3 mmol) in DCM (219 mL) was added dropwise Intermediate I-128 (35.4 mmol) in DCM (109 mL). The resulting mixture was heated at 45° C. for 12 h and filtered. The filtrate was concentrated in vacuo, and purified by silica gel column chromatography (petroleum ether/EtOAc=70/1 to 10/1) to give Intermediate I-120. $^1$H NMR (CDCl$_3$ 400 MHz): δ 7.34-7.36 (m, 6H), 7.18-7.24 (m, 9H), 4.20-4.27 (m, 1H), 4.23 (s, 2H), 3.83 (s, 2H), 1.46-1.48 (m, 3H), 1.18 (m, 30H), 0.80 (t, J=8.0 Hz, 2H).

Intermediate I-121: 3-fluoro-5-(3-hydroxy-2-((octadecyloxy)methyl)propoxy)benzonitrile

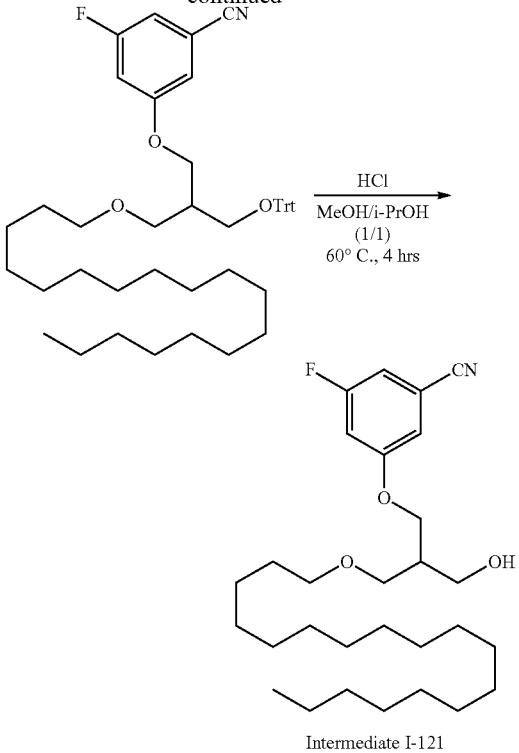

Intermediate I-121

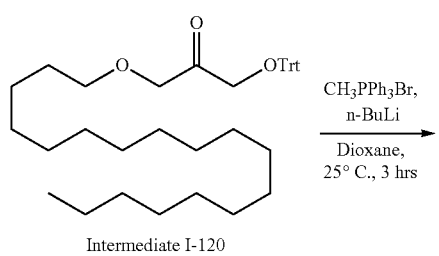

Intermediate I-120

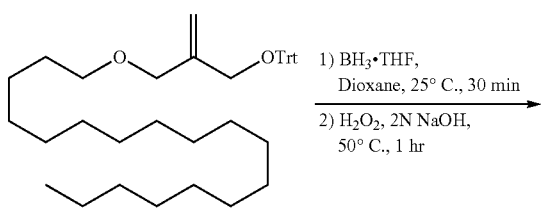

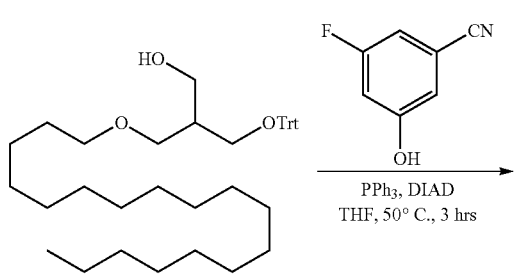

To a solution of CH$_3$PPh$_3$Br (3.19 mmol) in dioxane (2.5 mL) was added n-BuLi (2.5 M, 1.34 mL) at 25° C. The resulting mixture was stirred at 25° C. for 30 min and Intermediate I-120 (1.71 mmol) in dioxane (2.5 mL) was added. The mixture was stirred at 25° C. for 2 h, water (2.0 mL) was added and the resulting mixture was extracted with hexanes (2 mL×3). The combined organic layers were dried with sodium sulfate and concentrated in vacuo to give (((2-((octadecyloxy)methyl)allyl)oxy)methanetriyl)tribenzene. TLC Rf=0.70 (Eluent: Petroleum ether/Ethyl acetate=8/1).

To a solution of (((2-((octadecyloxy)methyl)allyl)oxy)methanetriyl)tribenzene (2.23 mmol) in dioxane (0.8 mL) was added BH$_3$·THF (1.00 M, 2.61 mL) at 25° C. The resulting mixture was stirred at 25° C. for 2 h, and water (0.8 mL), 5 N NaOH (1.60 mL), and H$_2$O$_2$ (20.3 mmol) were added sequentially at 25° C. The resulting mixture was stirred at 50° C. for 2.5 h, cooled to 25° C., water (20 mL) added, and extracted with DCM (20 mL×2). The organic layers were dried with sodium sulfate, filtered, concentrated in vacuo, and purified by silica gel column chromatography (petroleum ether/EtOAc=80/1 to 5/1) to give 3-octadecyloxy-2-((trityloxy)methyl)propan-1-ol. TLC Rf=0.20 (Eluent: Petroleum ether/Ethyl acetate=8/1).

To a solution of 3-(octadecyloxy)-2-((trityloxy)methyl)propan-1-ol (1.66 mmol) in THF (10 mL) were added PPh$_3$ (4.99 mmol) and 3-fluoro-5-hydroxybenzonitrile (2.00 mmol) at 25° C. The mixture was degassed with N$_2$ gas and DEAD (4.99 mmol) was added. The mixture was then stirred at 50° C. for 1 h, cooled to 25° C., concentrated in vacuo, and purified by prep-TLC (SiO$_2$, petroleum ether/EtOAc=8/1) to give 3-fluoro-5-(3-(octadecyloxy)-2-((trityloxy)methyl)propoxy)benzonitrile. TLC Rf=0.70 (Eluent: Petroleum ether/Ethyl acetate=8/1).

To a solution of 3-fluoro-5-(3-(octadecyloxy)-2-((trityloxy)methyl)propoxy)benzonitrile (0.04 mmol) in MeOH (0.12 mL) were added i-PrOH (0.12 mL) and 12 M HCl (81 equiv.). The reaction mixture was heated to 60° C. and stirred for 4 h, cooled to rt, water (20 mL) added, extracted with EtOAc (20 mL×2), dried with sodium sulfate, concentrated in vacuo, and purified by prep-TLC (SiO$_2$, petroleum ether/EtOAc=8/1) to give Intermediate I-121. $^1$H NMR (400 MHz, Chloroform-d) δ 7.04-7.00 (m, 1H), 7.01-6.95 (m, 1H), 6.94-6.85 (m, 1H), 4.13 (d, J=6.3 Hz, 2H), 3.95-3.84 (m, 2H), 3.73-3.64 (m, 2H), 3.52-3.40 (m, 2H), 2.34-2.23 (m, 1H), 1.65-1.52 (m, 2H), 1.38-1.21 (m, 30H), 0.90 (t, J=6.7 Hz, 3H). $^{19}$F NMR (376 MHz, Chloroform-d) δ−108.71. MS m/z [M+1]=478.2

Intermediate I-122: 5-(bromomethyl)-2-(1H-1,2,4-triazol-1-yl)benzonitrile

Added methyl 3-cyano-4-fluorobenzoate (134 mmol, 1.00 eq) into DMF (168 mL). Added 1H-1,2,4-triazole (161 mmol, 1.20 eq) and K$_2$CO$_3$ (161 mmol, 1.20 eq) and heated to 80° C. for 3 hrs. Added water (40 mL) and stirred for 10 min at 25° C. prior to filtering and drying the filter cake under reduced pressure to afford Intermediate I-122a. $^1$H NMR (DMSO-d$_6$ 400 MHz) δ 9.29 (s, 1H), 8.39 (s, 1H), 8.32 (d, J=1.6 Hz, 1H), 8.23 (d, J=8.0 Hz, 1H), 8.14 (d, J=8.0 Hz, 1H), 3.93 (s, 3H). MS m/z [M+1]=229.1.

Added Intermediate I-122a (110 mmol, 1.00 eq) into THF (1.0 L). Cooled the solution to 0° C. Added LiBH$_4$ (132 mmol, 1.21 eq) under N$_2$, and stirred at 25° C. for 16 hrs. Added water (800 mL) at 0° C., and extracted with EtOAc (600 mL*3). The organic layer was washed with brine (2×500 mL), dried over Na$_2$SO$_4$, filtered and concentrated in vacuo to afford Intermediate I-122b. $^1$H NMR (DMSO-d$_6$ 400 MHz) δ 9.17 (s, 1H), 8.35 (s, 1H), 7.84 (s, 3H), 4.63 (m, 2H). MS m/z [M+1]=201.1.

Added Intermediate I-122b (29.9 mmol, 1.00 eq) into THF (42.0 mL). Added PBr$_3$ (14.9 mmol, 0.50 eq) and stirred at 25° C. for 16 hrs. The resulting mixture was poured into H$_2$O (200 mL) and extracted with EtOAc (150 mL×2). The organic layers were washed with sat. NaHCO$_3$ (200 mL) and brine and dried with Na$_2$SO$_4$, filtered and concentrated in vacuo prior to purification by silica gel column chromatography (SiO$_2$, Petroleum ether/Ethyl acetate=1/0 to 0/1) to afford Intermediate I-122. $^1$H NMR (CDCl$_3$ 400 MHz) δ 8.83 (s, 1H), 8.20 (s, 1H), 7.87 (s, 1H), 7.79 (s, 2H), 4.52 (s, 2H).

Intermediate I-123: (R)-5-(((1-hydroxyhenicosan-2-yl)oxy)methyl)-2-(1H-1,2,4-triazol-1-yl)benzonitrile

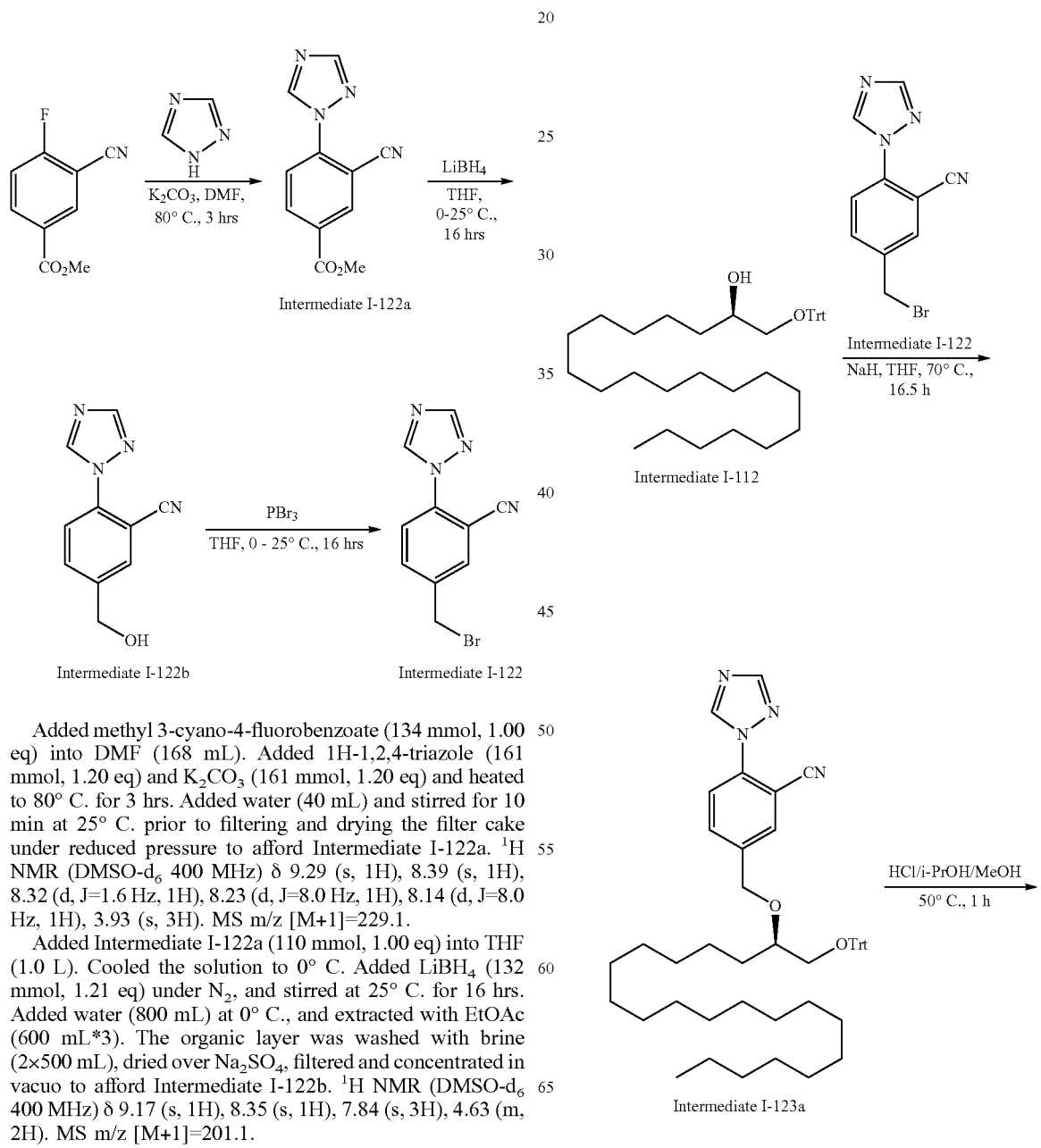

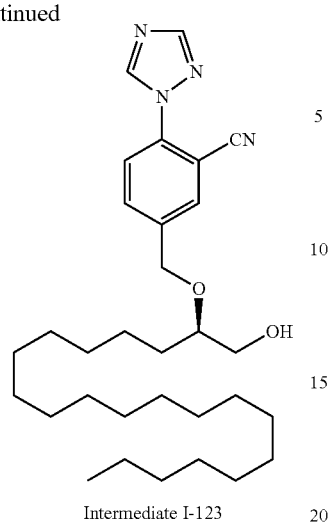

Intermediate I-123

Added Intermediate I-112 (5.25 mmol, 1.00 eq) to a round bottom flask charged with THF (30.0 mL). Added NaH (26.2 mmol, 60% purity, 5.00 eq) in portions. Stirred at 70° C. for 0.5 hr and add Intermediate I-122 (7.88 mmol, 1.50 eq) in THF (12.0 mL). Stir at 70° C. for 16 hrs at which point the resulting mixture was poured into sat.NH₄Cl (200 mL) and extracted with EtOAc (150 mL×2). Washed the organic layer with brine, dried with Na₂SO₄, and concentrated in vacuo. The residue was purified by column chromatography (SiO₂, Petroleum ether/Ethyl acetate=1/0 to 0/1) to afford Intermediate I-123a. TLC Rf=0.2 (Eluent: Petroleum ether/Ethyl acetate=10/1).

Added Intermediate I-123a (2.66 mmol, 1.00 eq) to a round bottom flask charged with MeOH (20.0 mL) and i-PrOH (20.0 mL). Added aq. HCl (12 M, 10.1 mL) and stir at 50° C. for 1 h. Poured the resulting mixture into H₂O (200 mL) and extracted with EtOAc (150 mL×2). Washed the organic layer with brine, dried with Na₂SO₄, and concentrated in vacuo. Purified the crude by column chromatography (SiO₂, Petroleum ether/Ethyl acetate=1/0 to 0/1) to afford Intermediate I-123. CDCl3 400 MHz): δ 8.76 (s, 1H), 8.19 (s, 1H), 7.85 (s, 1H), 7.75 (s, 2H), 4.71 (s, 2H), 3.79-3.75 (m, 1H), 3.66-3.57 (m, 2H), 1.63-1.56 (m, 2H), 1.37-1.25 (m, 34H), 0.88 (t, J=6.4 Hz, 3H). MS m/z [M+1]=511.3.

Intermediate I-124: 4-(((1-hydroxy-3-(octadecyloxy) propan-2-yl)oxy)methyl)-3-methoxybenzonitrile

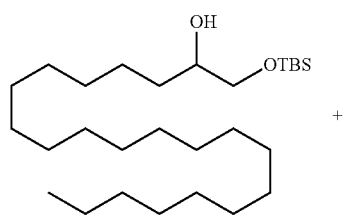

+

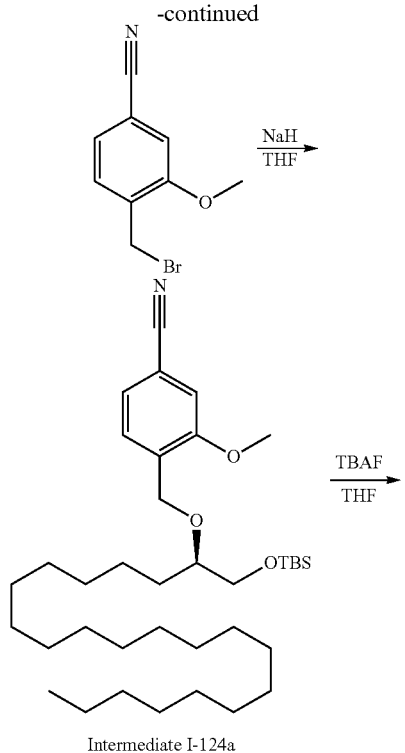

Intermediate I-124a

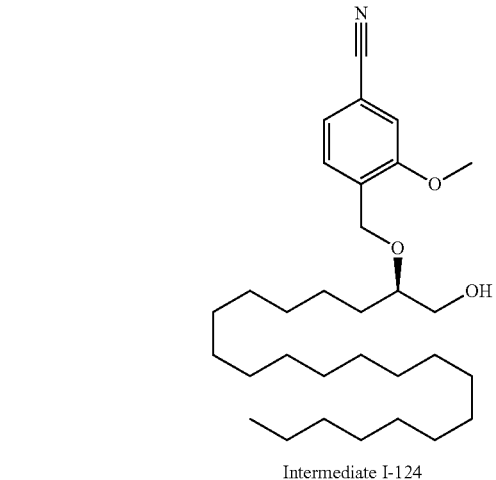

Intermediate I-124

Sodium hydride 60% dispersion in mineral oil (3.42 mmol) was suspended in tetrahydrofuran (7.5 mL) and cooled to 0° C. A solution of the 1-((tert-butyldimethylsilyl) oxy)-3-(octadecyloxy)propan-2-ol (0.697 mmol) in tetrahydrofuran (3 mL) was added over 30 seconds. After 30 minutes a solution of 4-(bromomethyl)-3-methoxybenzonitrile (2.3 mmol) in tetrahydrofuran (3 mL) was added. The ice bath was removed. After 16 hours the reaction was quenched with water (10 mL) at 0° C. The mixture was extracted with ethyl acetate (3×10 mL). The combined organic phases were dried over sodium sulfate and the solvent was removed under reduced pressure. The residue was subjected to flash chromatography (0% to 20% ethyl acetate/hexanes). The fractions containing product were combined and the solvent was removed under reduced pressure, providing Intermediate I-124a.

A solution of tetrabutylammonium fluoride in tetrahydrofuran (2.66 mL, 2.66 mmol) was added to a solution of Intermediate I-124a (0.569 mmol) in tetrahydrofuran (5 mL). After 1 h the resulting mixture was concentrated under reduced pressure. The residue was subjected to flash chromatography (0% to 20% ethyl acetate/hexanes). The fractions containing product were combined and the solvent was removed under reduced pressure, providing Intermediate I-124. $^1$H NMR (400 MHz, Chloroform-d) δ 7.54 (d, J=7.7 Hz, 1H), 7.28 (dd, J=7.7, 1.4 Hz, 1H), 7.08 (d, J=1.4 Hz, 1H), 4.73 (s, 2H), 3.87 (s, 3H), 3.83-3.67 (m, 3H), 3.64-3.52 (m, 2H), 3.45 (td, J=6.6, 2.4 Hz, 2H), 2.34 (s, 1H), 1.66-1.52 (m, 2H), 1.26 (s, 30H), 0.89 (t, J=6.8 Hz, 3H).

Intermediate I-125: (R)-4-((1-hydroxyhenicosan-2-yl)oxy)-2,6-dimethoxybenzonitrile

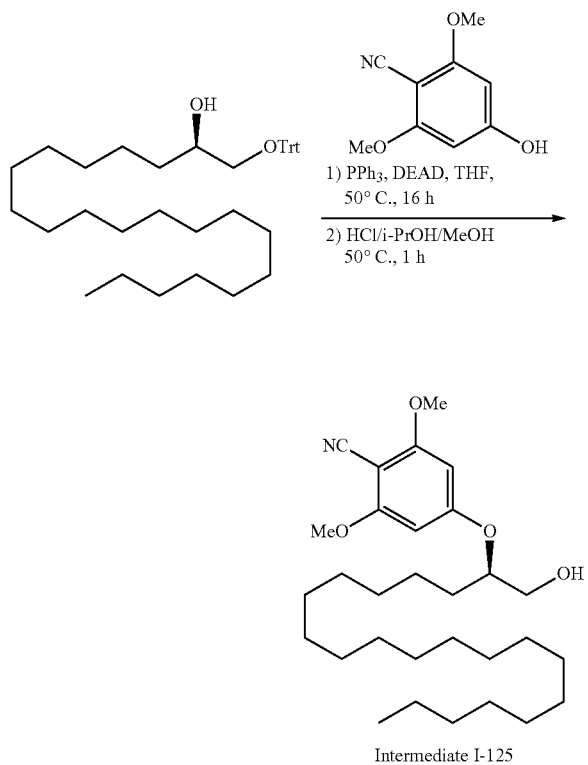

Intermediate I-125

Added Intermediate I-112 (5.25 mmol, 1.00 eq) to a round bottom flask charged with THF (30.0 mL). Added PPh$_3$ (10.5 mmol, 2.00 eq) and 4-hydroxy-2,6-dimethoxybenzonitrile (6.31 mmol, 1.20 eq). Degas with N$_2$ 3×. Added DEAD (10.5 mmol, 2.00 eq) dropwise and stirred at 50° C. for 16 h. Added the resulting solution to a round bottom flask charged with MeOH (21.0 mL) and i-PrOH (21.0 mL). Added HCl (21.0 mL) and stir at 50° C. for 1 h. Poured the solution into H$_2$O (200 mL) and extracted with EtOAc (150 mL×2). Washed the organic layer with brine, dried with Na$_2$SO$_4$, and concentrated under reduced pressure. The crude residue was purified by column chromatography (SiO$_2$, Petroleum ether/Ethyl acetate=1/0 to 0/1) to afford Intermediate I-125. $^1$H NMR (CDCl$_3$ 400 MHz): δ 6.13 (s, 2H), 4.44-4.40 (m, 1H), 3.87 (s, 6H), 3.81-3.77 (m, 2H), 1.80 (br, 1H), 1.70-1.66 (m, 1H), 1.37-1.26 (m, 34H), 0.88 (t, J=6.8 Hz, 3H). MS m/z [M+1]=489.4. MS m/z [M+1]=489.4

Intermediate I-126: 5-((1-hydroxy-3-(octadecyloxy)propan-2-yl)oxy)picolinonitrile

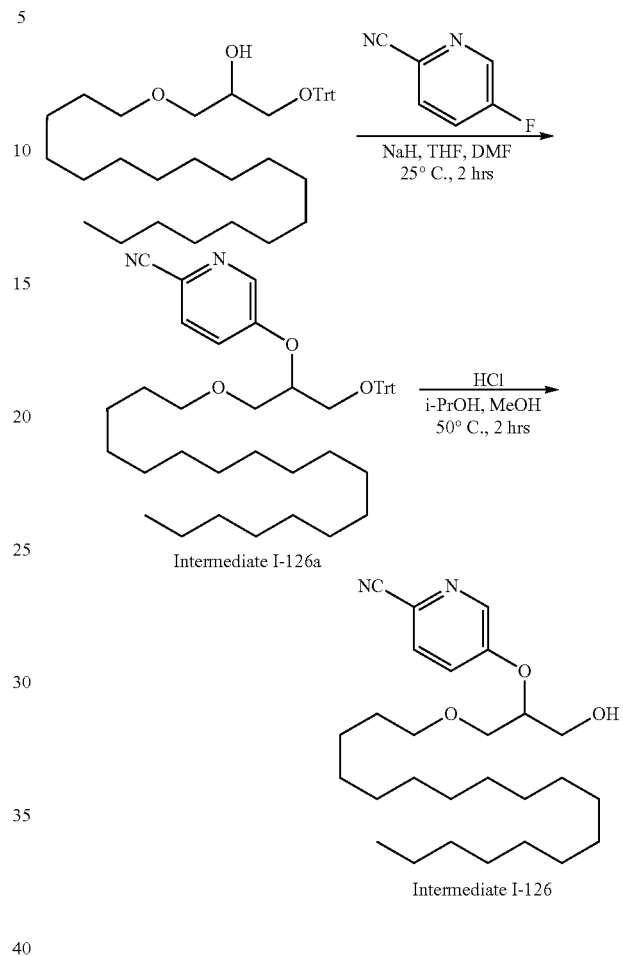

Intermediate I-126

Added 1-(octadecyloxy)-3-(trityloxy)propan-2-ol (0.85 mmol, 1.00 eq) into THF (5.00 mL). Added NaH (2.13 mmol, 60% purity, 2.50 eq) and stirred at 25° C. for 0.5 hr. Added a solution of 5-fluoropicolinonitrile (1.28 mmol, 1.50 eq) in DMF (10.0 mL) and stirred at 25° C. for 1.5 hrs. Cooled to 0° C. and added sat.NH$_4$Cl (20.0 mL). The resulting mixture was extracted with EtOAc (30.0 mL×3), and the organic layer was dried over Na$_2$SO$_4$, and concentrated in vacuum. The residue was purified by column chromatography (SiO$_2$, Petroleum ether/Ethyl acetate=50/1 to 5/1) to afford Intermediate I-126a. TLC R$_f$=0.73 (Eluent: Petroleum ether/Ethyl acetate=5/1).

Added Intermediate I-126a (2.18 mmol, 1.00 eq) into MeOH (15.0 mL). Added i-PrOH (195 mmol, 15.0 mL, 89.9 eq) and HCl (12 M, 15.0 mL, 82.6 eq) and heated to 50° C. for 2 hrs. Added water (50.0 mL) and the resulting mixture was extracted with EtOAc (30.0 mL×3). The organic layer was dried over Na$_2$SO$_4$, and concentrated in vacuum. The residue was purified by column chromatography (SiO$_2$, Petroleum ether/Ethyl acetate=50/1 to 5/1) to afford Intermediate I-126. $^1$H NMR (CDCl$_3$ 400 MHz): δ 8.42-8.43 (d, J=2.8 Hz, 1H), 7.61-7.64 (d, J=8.8 Hz, 1H), 7.39-7.42 (dd, J=3.2 Hz, 1H), 4.61-4.63 (m, 1H), 3.89-3.94 (m, 2H), 3.68-3.69 (m, 2H), 3.42-3.45 (m, 2H), 1.51-1.54 (m, 2H), 1.25 (s, 31H), 0.86-0.89 (t, J=6.4 Hz, 3H). MS m/z [M+1]=447.2.

Intermediate I-127: (R)-4-((1-hydroxyhenicosan-2-yl)oxy)-2-isopropoxybenzonitrile

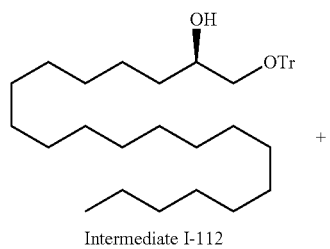

Intermediate I-112

+

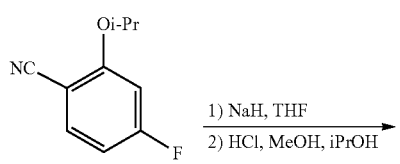

1) NaH, THF
2) HCl, MeOH, iPrOH

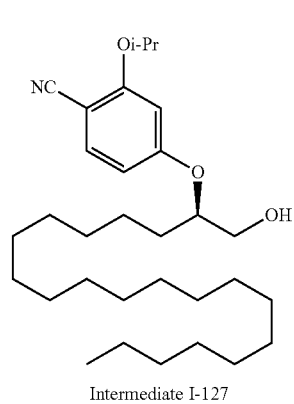

Intermediate I-127

To a solution of Intermediate I-112 (5.25 mmol, 1.00 eq) in THF (15 mL) was added 60% NaH (13.1 mmol) at 25° C. The resulting mixture was stirred at 25° C. for 30 min and cooled to 0° C. and 4-fluoro-2-isopropoxybenzonitrile (7.88 mmol, 1.50 eq) in DMF (30 mL) was added dropwise. The resulting mixture was warmed to 20° C. stirred for 1 h. The mixture was then added to a round bottom flask charged with MeOH (15.0 mL) and i-PrOH (15.0 mL). Added aq. HCl (12.0 M, 10.0 mL) and stir at 50° C. for 1 h. Pour the solution into H$_2$O (200 mL) and extracted with EtOAc (150 mL×2). Wash the organic layer with brine, dried with Na$_2$SO$_4$, and concentrated in vacuo. Purify the crude by column chromatography (SiO$_2$, Petroleum ether/EtOAc=1/0 to 0/1) to afford Intermediate I-127. $^1$H NMR: (CDCl$_3$ 400 MHz): δ 7.44 (d, J=8.4 Hz, 1H), 6.53-6.50 (m, 2H), 4.60-4.57 (m, 1H), 4.41-4.38 (m, 1H), 3.81-3.74 (m, 2H), 1.67 (br, 1H), 1.65-1.63 (m, 2H), 1.40 (d, J=6.0 Hz, 6H), 1.30-1.25 (m, 34H), 0.88 (t, J=6.4 Hz, 3H). MS m/z [M+1]=488.4.

Intermediate I-128: (R)-1-(octadecyloxy)-3-(trityloxy)propan-2-ol

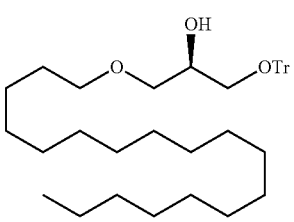

Intermediate I-128

Intermediate I-128 was prepared according to WO2010052718.

Intermediate I-129: (R)-1-(trityloxy)octadecan-2-ol

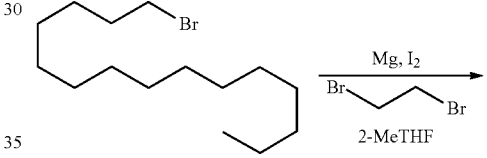

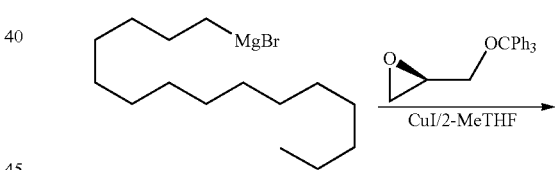

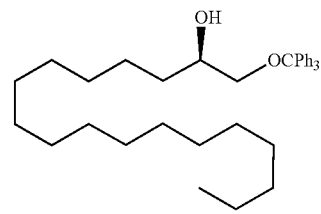

Intermediate I-129

To a solution of Mg (1.9 g, 79.0 mmol, 1.2 eq) in 2-MeTHF (20 mL) was added I$_2$ (174.3 mg, 686.6 umol, 138.3 uL, 0.01 eq) and 1,2-dibromoethane (0.2 mL) under N$_2$. Then 1-bromopentadecane (2.0 g) in 2-MeTHF (20 mL) was added dropwise. The mixture was stirred until the color of I$_2$ was faded to colorless. Then the remaining 1-bromopentadecane (18 g) in 2-MeTHF (180 mL) was added and the mixture was stirred at 25° C. for 4 hr. The crude product pentadecylmagnesium bromide, as brown solution (in 2-MeTHF) was used into the next step without further purification.

Add pentadecylmagnesium bromide (20 g, 63.4 mmol, 1.3 eq) over 10 min via cannula to a mixture of (2R)-2-(trityloxymethyl)oxirane (15.4 g, 48.7 mmol, 1 eq), CuI (464.2 mg, 2.5 mmol, 0.05 eq) in 2-MeTHF (50 mL) at −20° C. The reaction was stirred vigorously for 5 min, warmed to 0° C., and continued stirring for 2 h. The reaction mixture was quenched by addition of sat. NH$_4$Cl solution (350 mL), and then the mixture was extracted with Ethyl acetate (200 mL×3). The combined organic layers were washed with H$_2$O (400 mL×2), dried over Na$_2$SO$_4$, filtered and concentrated under reduced pressure to give a residue. The residue was purified by flash silica gel chromatography (ISCO®; 80 g SepaFlash® Silica Flash Column, Eluent of 0~3% Ethyl acetate/Petroleum ether gradient @ 120 mL/min) to give compound (R)-1-(trityloxy)octadecan-2-ol Intermediate I-129. $^1$H NMR (400 MHz, CHLOROFORM-d) δ 7.39 (d, J=7.6 Hz, 6H), 7.26-7.16 (m, 9H), 3.76-3.67 (m, 1H), 3.13 (dd, J=3.2, 9.3 Hz, 1H), 3.02-2.92 (m, 1H), 2.26 (d, J=3.3 Hz, 1H), 1.34-1.29 (m, 2H), 1.20 (br d, J=9.4 Hz, 27H), 0.83 (t, J=6.8 Hz, 3H).

Intermediate I-130: (R)-3-fluoro-5-(((1-(trityloxy)octadecan-2-yl)oxy)methyl)benzonitrile To a solution of NaH (926.5 mg, 23.2 mmol, 60% purity, 2.5 eq) in THF (80 mL) was added (2R)-1-trityloxyoctadecan-2-ol, Intermediate I-129 (4.9 g, 9.3 mmol, 1 eq) at 0° C. and the mixture was stirred at 0° C. for 30 min. Then 3-(bromomethyl)-5-fluoro-benzonitrile (2.5 g, 11.6 mmol, 1.3 eq) was added and the mixture was stirred at 65° C. for 5 hr. The reaction mixture was quenched by addition of sat. NH$_4$Cl solution (100 mL) at 20° C. and extracted with Ethyl acetate (60 mL×3). The combined organic layers were washed with H$_2$O (120 mL×2), dried over Na$_2$SO$_4$, and concentrated under reduced pressure to give a residue. The residue was purified by flash silica gel chromatography (ISCO®; 20 g SepaFlash® Silica Flash Column, Eluent of 0~3% Ethyl acetate/Petroleum ether gradient @ 45 mL/min) to give compound (R)-3-fluoro-5-(((1-(trityloxy)octadecan-2-yl)oxy)methyl)benzonitrile, Intermediate I-130. $^1$H NMR (400 MHz, CHLOROFORM-d) δ 7.45 (br d, J=7.1 Hz, 6H), 7.36-7.25 (m, 12H), 4.73 (d, J=12.8 Hz, 1H), 4.57 (d, J=12.9 Hz, 1H), 3.53 (td, J=5.2, 10.8 Hz, 1H), 3.22 (d, J=4.6 Hz, 2H), 1.58-1.50 (m, 2H), 1.32-1.22 (m, 28H), 0.89 (br t, J=6.7 Hz, 3H).

Intermediate I-131: (R)-3-fluoro-5-(((1-hydroxyoctadecan-2-yl)oxy)methyl)benzonitrile

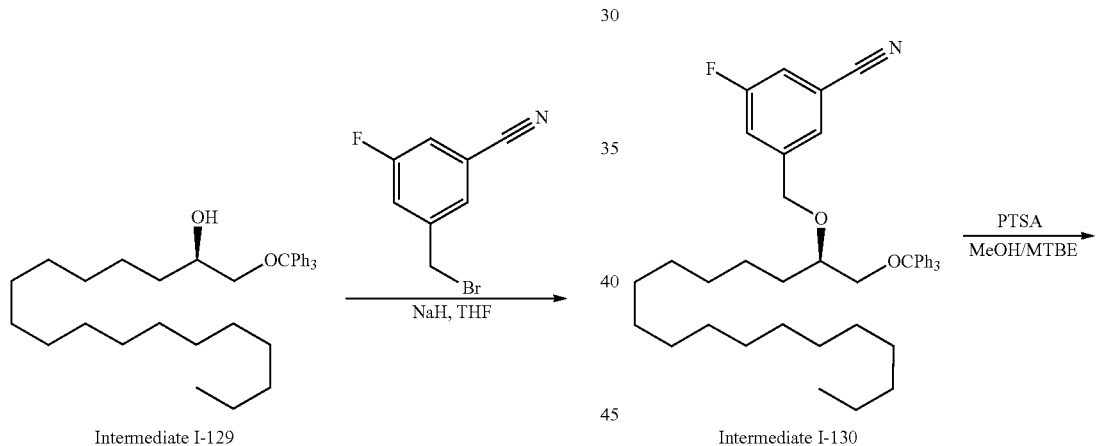

Intermediate I-129 → Intermediate I-130

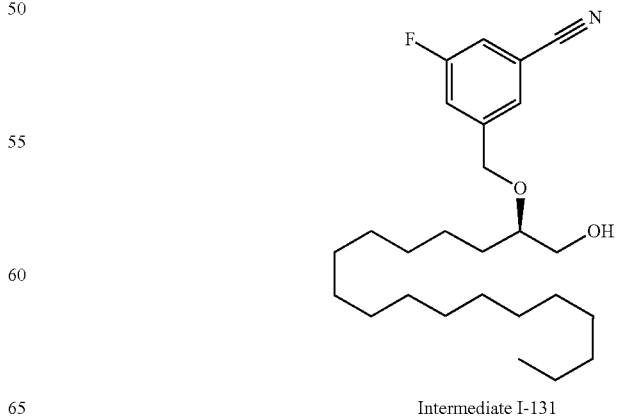

Intermediate I-130 → Intermediate I-131

To a solution of 3-fluoro-5-[[(1R)-1-(trityloxymethyl) heptadecoxy]methyl]benzonitrile, Intermediate I-130 (4.3 g, 6.5 mmol, 1 eq) in MeOH (12 mL) and MTBE (86 mL) was added anisole (351.2 mg, 3.3 mmol, 353.0 uL, 0.5 eq) and PTSA (559.3 mg, 3.3 mmol, 0.5 eq) and the mixture was stirred at 50° C. for 2 hr. The reaction mixture was diluted with sat. NaHCO₃ 100 mL and extracted with Ethyl acetate (60 mL×3). The combined organic layers were washed with H₂O (100 mL×2), dried over Na₂SO₄, filtered and concentrated under reduced pressure to give a residue. The residue was purified by flash silica gel chromatography (ISCO®; 20 g SepaFlash® Silica Flash Column, Eluent of 0~9% Ethyl acetate/Petroleum ether gradient @ 45 mL/min) to give compound (R)-3-fluoro-5-(((1-hydroxyoctadecan-2-yl)oxy) methyl)benzonitrile, Intermediate I-131. ¹H NMR (400 MHz, CHLOROFORM-d) δ 7.46 (s, 1H), 7.35 (br d, J=9.0 Hz, 1H), 7.27 (s, 1H), 4.64 (s, 2H), 3.79-3.72 (m, 1H), 3.67-3.49 (m, 2H), 1.67-1.47 (m, 2H), 1.26 (s, 28H), 0.88 (br t, J=6.6 Hz, 3H). MS (ESI): m/z=442.2 [M+Na]⁺

Intermediate I-132: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)octadecyl) phosphate

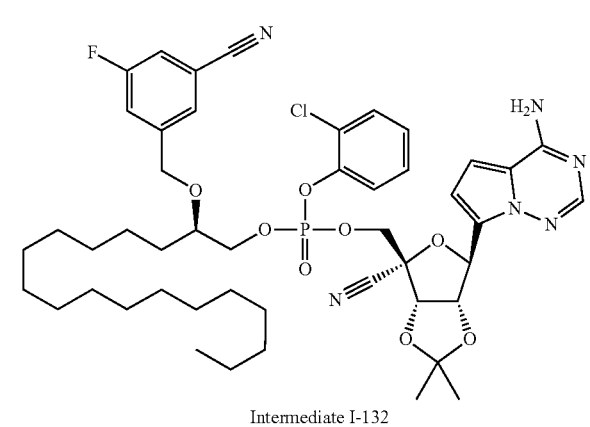

Intermediate I-132

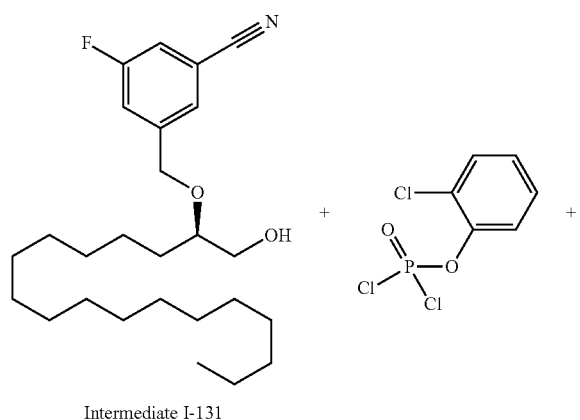

Intermediate I-131

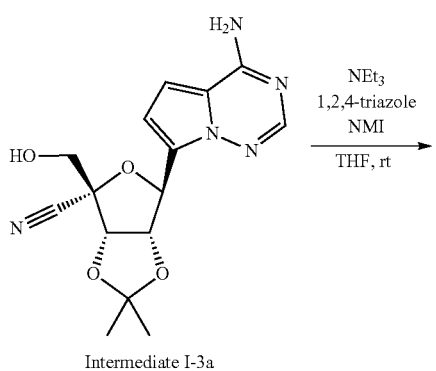

Intermediate I-3a 1H-1,2,4-triazole (187 mg, 2.71 mmol, 5.05 equiv.) was dissolved in THF (6.0 mL). TEA (0.20 mL, 1.42 mmol, 2.65 equiv.) was added to the solution followed by 2-chlorophenyl phosphorodichloridate (0.10 mL, 0.59 mmol, 1.1 equiv.). The reaction mixture was stirred at rt for 6 min prior to the addition of (3aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (192 mg, 0.58 mmol, 1.08 equiv.) in one portion followed by 1-methylimidazole (0.06 mL, 0.70 mmol, 1.3 equiv.). The solution was stirred for an additional 17 min before adding (R)-3-fluoro-5-(((1-hydroxyoctadecan-2-yl)oxy)methyl) benzonitrile, Intermediate I-131 (225 mg, 0.54 mmol, 1 equiv.). After stirring at room temperature for 20 min, the solution was diluted with EtOAc (50 mL) and water (50 mL). The aqueous layer was extracted again with EtOAc (50 mL). The organic layers were combined, washed with brine (50 mL), dried over MgSO₄, filtered and concentrated in vacuo prior to purification by silica gel chromatography (0-100% EtOAc in hexanes) to afford the title compound, Intermediate I-132. ¹H NMR (400 MHz, Methanol-d4) δ 7.80-7.78 (m, 1H), 7.48-7.28 (m, 5H), 7.20-7.08 (m, 2H), 6.85-6.79 (m, 1H), 6.79-6.74 (m, 1H), 5.66-5.62 (m, 1H), 5.32-5.28 (m, 1H), 5.18-5.12 (m, 1H), 4.64-4.44 (m, 4H), 4.36-4.25 (m, 1H), 4.23-4.10 (m, 1H), 3.63-3.55 (m, 1H), 1.72 (s, 3H), 1.61-1.18 (m, 33H), 0.93-0.86 (m, 3H). ¹⁹F NMR (376 MHz, Methanol-d4) δ –112.71--112.81 (m). MS m/z [M+1]=923.1

Intermediate I-133: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-(3-cyano-5-fluorobenzyl)oxy)octadecyl) hydrogen phosphate

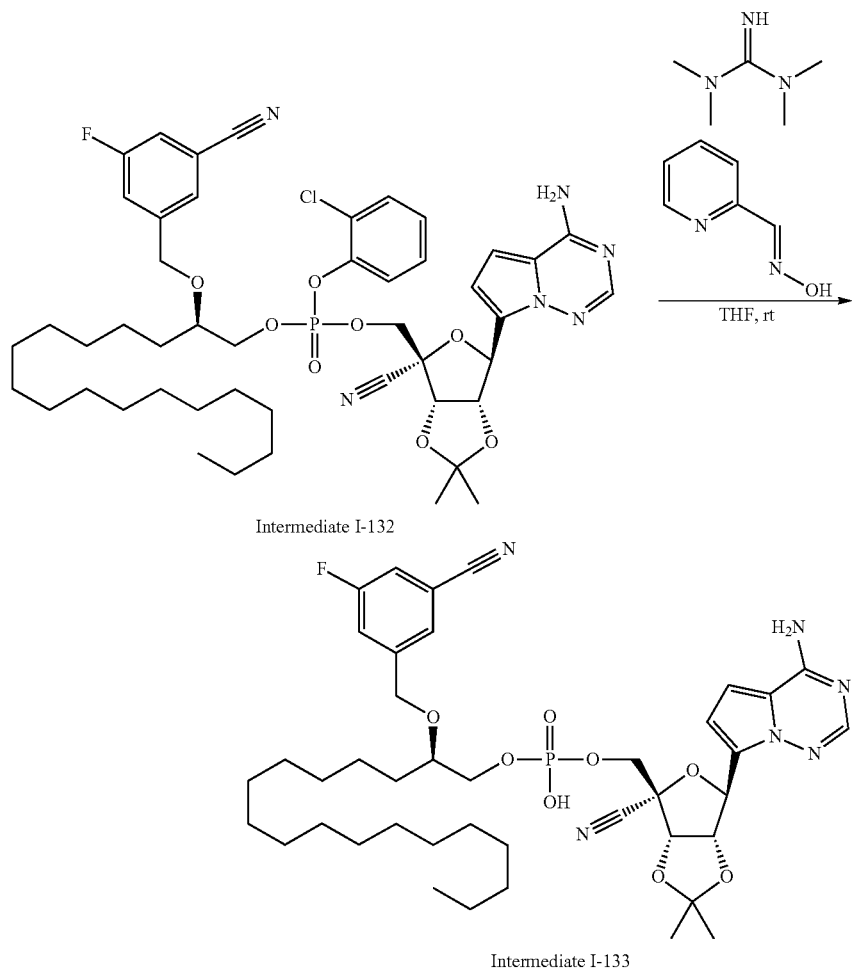

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)octadecyl) phosphate, Intermediate I-132 (110 mg, 0.119 mmol, 1.0 equiv.) in THF (5.0 mL) was added 1,1,3,3-tetramethylguanidine (0.09 mL, 0.715 mmol, 6.0 equiv.) and syn-2-pyridinealdoxime (90 mg, 0.737 mmol, 6.19 equiv.). The reaction mixture was stirred at room temperature overnight. The solution was concentrated in vacuo and purified by silica gel (0-50% MeOH in DCM) to afford the title compound Intermediate I-133. $^1$H NMR (400 MHz, Methanol-d4) δ 7.82 (s, 1H), 7.50-7.47 (m, 1H), 7.43-7.33 (m, 2H), 6.83 (d, J=4.5 Hz, 1H), 6.78 (d, J=4.5 Hz, 1H), 5.63 (d, J=3.6 Hz, 1H), 5.26 (dd, J=6.6, 3.6 Hz, 1H), 5.13 (d, J=6.6 Hz, 1H), 4.73 (d, J=13.0 Hz, 1H), 4.51 (d, J=13.0 Hz, 1H), 4.18-4.07 (m, 2H), 3.96-3.82 (m, 2H), 3.59-3.50 (m, 1H), 1.70 (s, 3H), 1.48-1.21 (m, 33H), 0.90 (t, J=6.7 Hz, 3H). $^{19}$F NMR (376 MHz, Methanol-d4) δ −112.92−−113.07 (m). MS m/z [M+1]=813.2

Intermediate I-134: (S)-1-(trityloxy)octadecan-2-ol

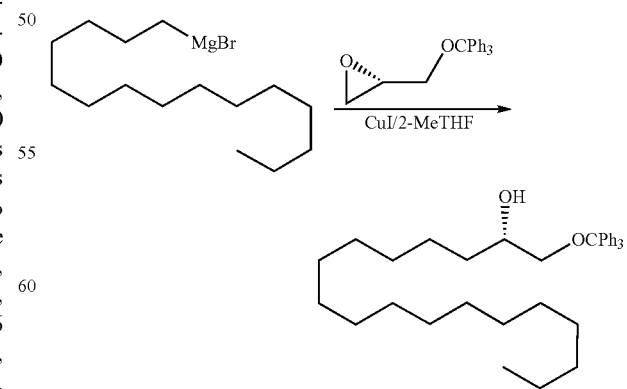

Add bromo(pentadecyl)magnesium (20.8 g, 65.7 mmol, 1.3 eq) over 10 min via cannula to a mixture of (2S)-2-(trityloxymethyl)oxirane (16 g, 50.6 mmol, 1 eq), CuI (481.6 mg, 2.5 mmol, 0.05 eq) in 2-MeTHF (100 mL) at −20° C. The reaction was stirred vigorously for 5 min, warmed to 0° C., and continued stirring for 2 h. The residue was diluted with NH$_4$Cl 300 mL and extracted with EtOAc 300 mL (100 mL×3). The combined organic layers were washed with brine 200 mL (100 mL×2), dried over Na$_2$SO$_4$, filtered and concentrated under reduced pressure to give a residue. The residue was purified by flash silica gel chromatography (ISCO®; 120 g SepaFlash® Silica Flash Column, Eluent of 0~60% Ethyl acetate/Petroleum ether gradient @ 120 mL/min) to give compound (S)-1-(trityloxy)octadecan-2-ol, Intermediate I-134. $^1$H NMR (400 MHz, CHLOROFORM-d) δ 7.38-7.34 (m, 6H), 7.25-7.16 (m, 9H), 3.73-3.64 (m, 1H), 3.12-3.07 (m, 1H), 2.95 (dd, J=7.6, 9.3 Hz, 1H), 2.22 (d, J=3.5 Hz, 1H), 1.34-1.25 (m, 4H), 1.22-1.14 (m, 26H), 0.80 (t, J=6.8 Hz, 3H).

Intermediate I-135: (S)-3-fluoro-5-(((1-(trityloxy)octadecan-2-yl)oxy)methyl)benzonitrile can-2-ol Intermediate I-134 (5 g, 9.5 mmol, 1 eq) at 0° C. and the mixture was stirred at 0° C. for 30 min. Then 3-(bromomethyl)-5-fluoro-benzonitrile (2.4 g, 11.4 mmol, 1.2 eq) was added and the mixture was stirred at 65° C. for 12 hr. The reaction mixture was quenched by addition sat. NH$_4$Cl solution (100 mL) at 20° C. and extracted with Ethyl acetate (50 mL×3). The combined organic layers were washed with H$_2$O (70 mL×2), dried over Na$_2$SO$_4$, and concentrated under reduced pressure to give a residue. The residue was purified by flash silica gel chromatography (ISCO®; 40 g SepaFlash® Silica Flash Column, Eluent of 0~4% Ethyl acetate/Petroleum ether gradient @ 40 mL/min) to give compound (S)-3-fluoro-5-(((1-(trityloxy)octadecan-2-yl)oxy)methyl)benzonitrile Intermediate I-135. $^1$H NMR (400 MHz, CHLOROFORM-d) δ 7.53-7.41 (m, 7H), 7.41-7.23 (m, 11H), 4.81-4.73 (m, 1H), 4.60 (d, J=12.8 Hz, 1H), 3.61-3.52 (m, 1H), 3.29-3.20 (m, 2H), 1.58 (br d, J=6.7 Hz, 2H), 1.30 (br s, 28H), 0.93 (br t, J=6.6 Hz, 3H).

Intermediate I-136: (S)-3-fluoro-5-(((1-hydroxyoctadecan-2-yl)oxy)methyl)benzonitrile

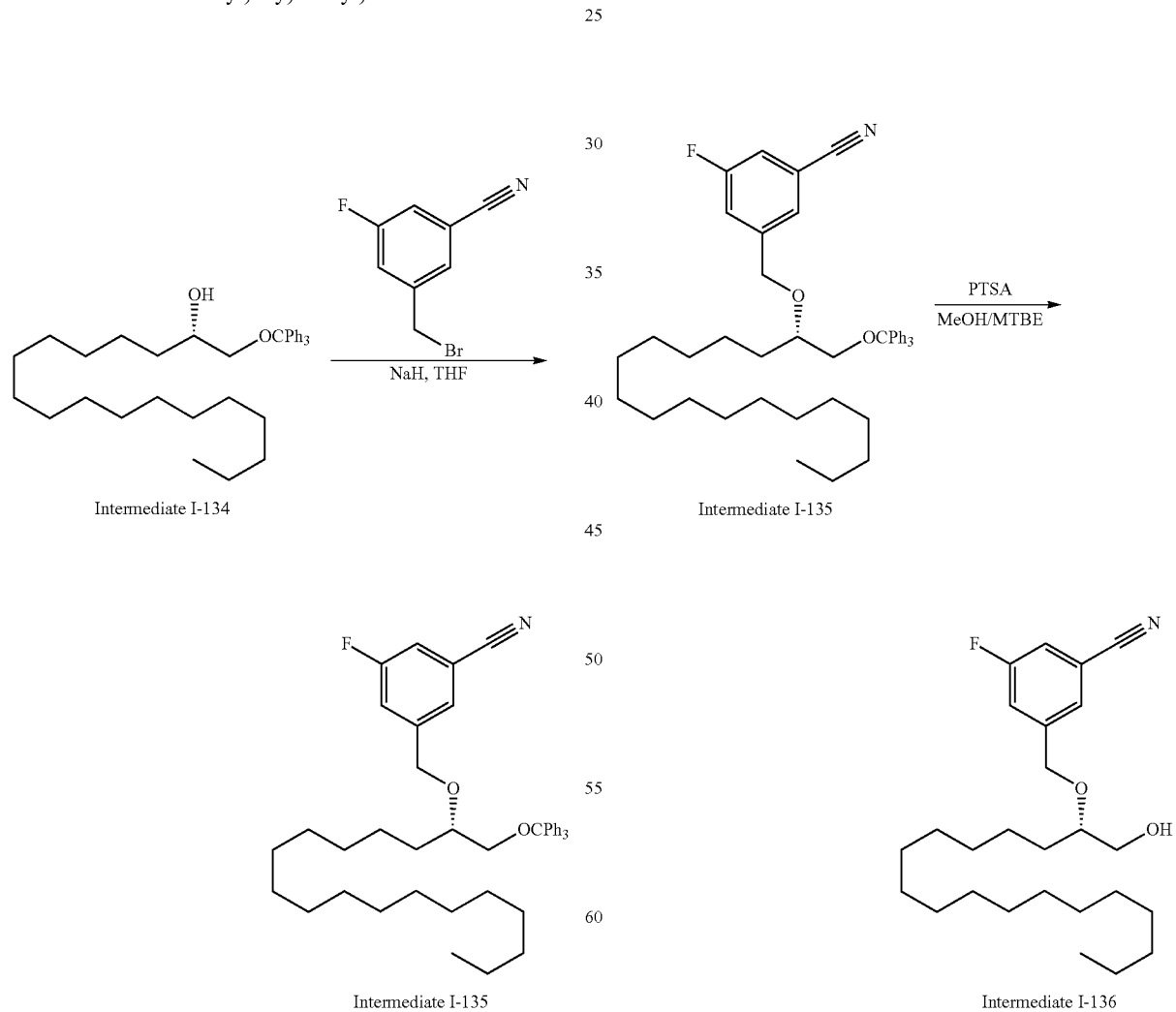

To a solution of NaH (945.5 mg, 23.6 mmol, 60% purity, 2.5 eq) in THF (80 mL) was added (2S)-1-trityloxyoctade- To a solution of 3-fluoro-5-[[(1S)-1-(trityloxymethyl)heptadecoxy]methyl]benzonitrile, Intermediate I-135 (4.4 g, 6.6 mmol, 1 eq) in MTBE (90 mL) and MeOH (13.5 mL) was added anisole (359.4 mg, 3.3 mmol, 361.2 uL, 0.5 eq) and PTSA (572.3 mg, 3.3 mmol, 0.5 eq) and the mixture was stirred at 50° C. for 2 hr. The reaction mixture was diluted with sat. NaHCO$_3$ 100 mL and extracted with Ethyl acetate (60 mL×3). The combined organic layers were washed with H$_2$O (100 mL×2), dried over Na$_2$SO$_4$, filtered and concentrated under reduced pressure to give a residue. The residue was purified by flash silica gel chromatography (ISCO®; 20 g SepaFlash® Silica Flash Column, Eluent of 0~9% Ethyl acetate/Petroleum ether gradient @ 45 mL/min) to give compound (S)-3-fluoro-5-(((1-hydroxyoctadecan-2-yl)oxy)methyl)benzonitrile, Intermediate I-136. $^1$H NMR (400 MHz, CHLOROFORM-d) δ 7.46 (br s, 1H), 7.38-7.32 (m, 1H), 7.28 (br s, 1H), 4.69-4.63 (m, 2H), 3.76 (br d, J=10.3 Hz, 1H), 3.67-3.50 (m, 2H), 1.65-1.52 (m, 2H), 1.36-1.25 (m, 28H), 0.93-0.86 (m, 3H). MS (ESI): m/z=442.2 [M+Na]$^+$ Intermediate I-137: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((S)-2-((3-cyano-5-fluorobenzyl)oxy)octadecyl) phosphate

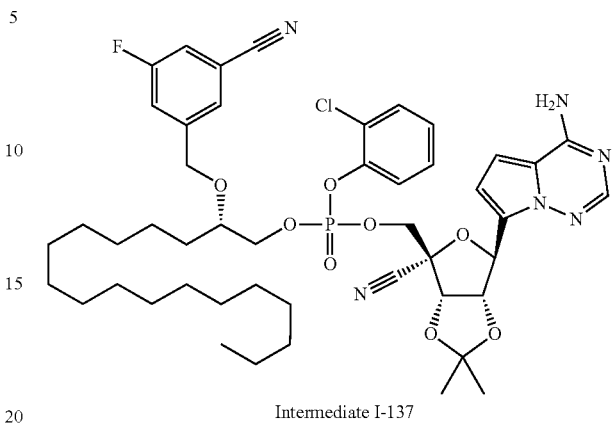

Intermediate I-137

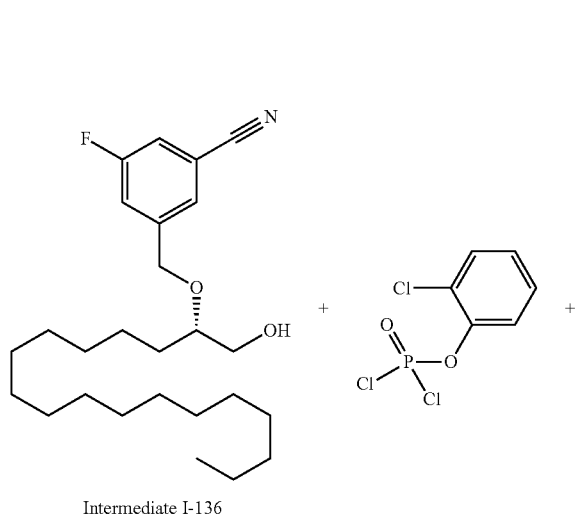

Intermediate I-136

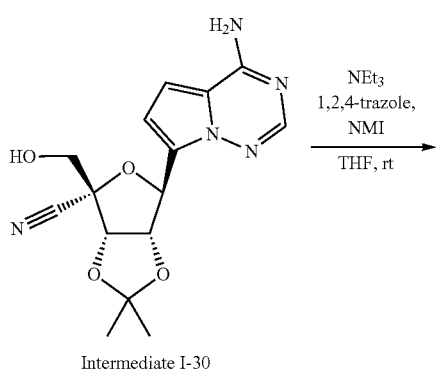

Intermediate I-30

1H-1,2,4-triazole (140 mg, 2.03 mmol, 3.78 equiv.) was dissolved in THF (10.0 mL). TEA (0.20 mL, 1.42 mmol, 2.65 equiv.) was added to the solution followed by 2-chlorophenyl phosphorodichloridate (0.10 mL, 0.59 mmol, 1.1 equiv.). The reaction mixture was stirred at rt for 10 min prior to the addition of (3aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (203 mg, 0.61 mmol, 1.14 equiv.) in one portion followed by 1-methylimidazole (0.06 mL, 0.70 mmol, 1.3 equiv.). The solution was stirred for an additional 15 min before adding (S)-3-fluoro-5-(((1-hydroxyoctadecan-2-yl)oxy)methyl)benzonitrile, Intermediate I-136 (225 mg, 0.54 mmol, 1 equiv.). After stirring at room temperature for 4 h and 15 min, the solution was diluted with EtOAc (50 mL) and water (50 mL). The aqueous layer was extracted again with EtOAc (50 mL). The organic layers were combined, washed with brine (50 mL), dried over MgSO$_4$, filtered and concentrated in vacuo prior to purification by silica gel chromatography (0-100% EtOAc in hexanes) to afford the title compound Intermediate I-137. $^1$H NMR (400 MHz, Methanol-d4) δ 7.82-7.77 (m, 1H), 7.48-7.30 (m, 5H), 7.20-7.08 (m, 2H), 6.86-6.80 (m, 1H), 6.79-6.74 (m, 1H), 5.66-5.62 (m, 1H), 5.34-5.27 (m, 1H), 5.17 (d, J=6.5 Hz, 0.5H), 5.12 (d, J=6.6 Hz, 0.5H), 4.65-4.47 (m, 4H), 4.38-4.28 (m, 1H), 4.20-4.06 (m, 1H), 3.67-3.56 (m, 1H), 1.73-1.70 (m, 3H), 1.58-1.19 (m, 33H), 0.92-0.86 (m, 3H). $^{19}$F NMR (376 MHz, Methanol-d4) δ−112.68−−112.83 (m). MS m/z [M+1]=923.1

Intermediate I-138: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl)oxy)octadecyl) hydrogen phosphate

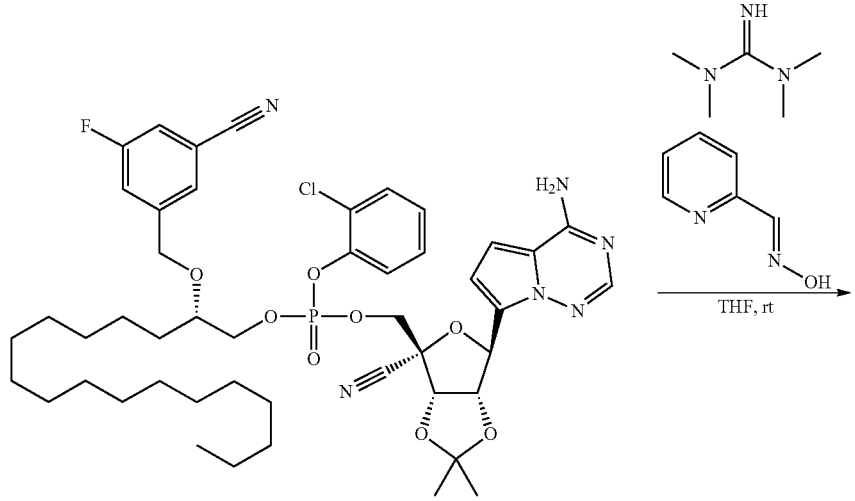

Intermediate I-137

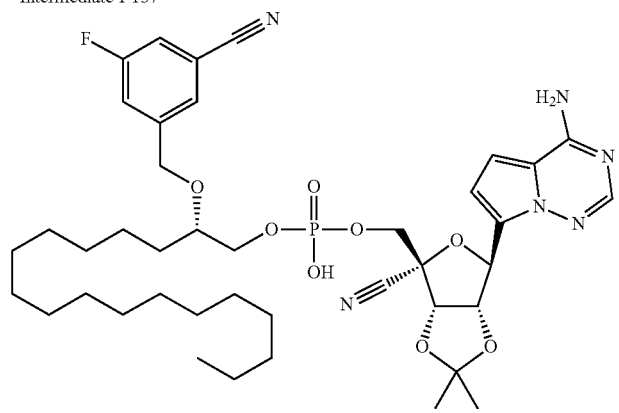

Intermediate I-138

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((S)-2-((3-cyano-5-fluorobenzyl)oxy)octadecyl) phosphate, Intermediate I-137 (130 mg, 0.141 mmol, 1.0 equiv.) in THF (5.0 mL) was added 1,1,3,3-tetramethylguanidine (0.11 mL, 0.845 mmol, 6.0 equiv.) and syn-2-pyridinealdoxime (137 mg, 1.12 mmol, 7.97 equiv.). The reaction mixture was stirred at room temperature overnight. The solution was concentrated in vacuo and purified by silica gel (0-50% MeOH in DCM) to afford the title compound Intermediate I-138. $^1$H NMR (400 MHz, Methanol-d4) δ 7.83 (s, 1H), 7.49 (s, 1H), 7.43-7.33 (m, 2H), 6.85-6.78 (m, 2H), 5.63 (d, J=3.7 Hz, 1H), 5.27 (dd, J=6.6, 3.6 Hz, 1H), 5.12 (d, J=6.6 Hz, 1H), 4.72 (d, J=13.0 Hz, 1H), 4.48 (d, J=13.0 Hz, 1H), 4.17-4.06 (m, 2H), 3.96-3.81 (m, 2H), 3.62-3.52 (m, 1H), 1.69 (s, 3H), 1.49-1.19 (m, 33H), 0.94-0.85 (m, 3H). $^{19}$F NMR (376 MHz, Methanol-d4) δ−112.96−−113.08 (m). MS m/z [M+1]=813.2

Intermediate I-139: Tetradecylmagnesium bromide

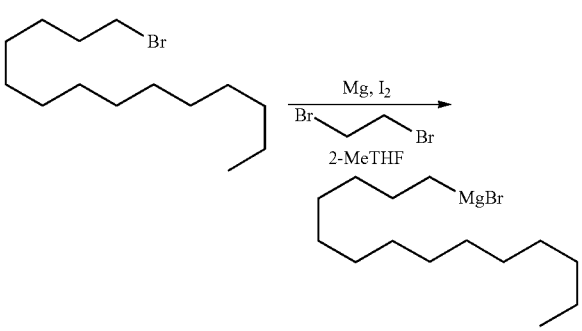

Intermediate I-139

To a solution of Mg (2.5 g, 103.7 mmol, 1.2 eq) in 2-MeTHF (30 mL) was added I$_2$ (228.8 mg, 901.6 umol, 181.6 uL, 0.01 eq) and BrCH₂CH₂Br (0.15 mL) under N₂. Then 1-bromotetradecane (2.0 g, 7.2 mmol) in 2-MeTHF (20 mL) was added dropwise. The mixture was stirred until the color of I₂ was faded to colorless. Then the remaining 1-bromotetradecane (23.0 g, 83.0 mmol) in 2-MeTHF (230 mL) was added and the mixture was stirred at 25° C. for 4 hr. The crude product tetradecylmagnesium bromide, Intermediate I-139 as brown liquid (in 2-MeTHF) was used into the next step without further purification.

Intermediate I-140: (R)-1-(trityloxy)heptadecan-2-ol

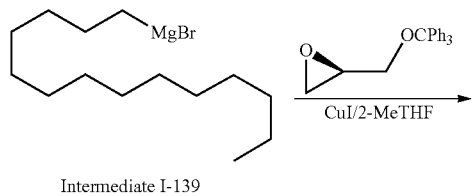

Intermediate I-139

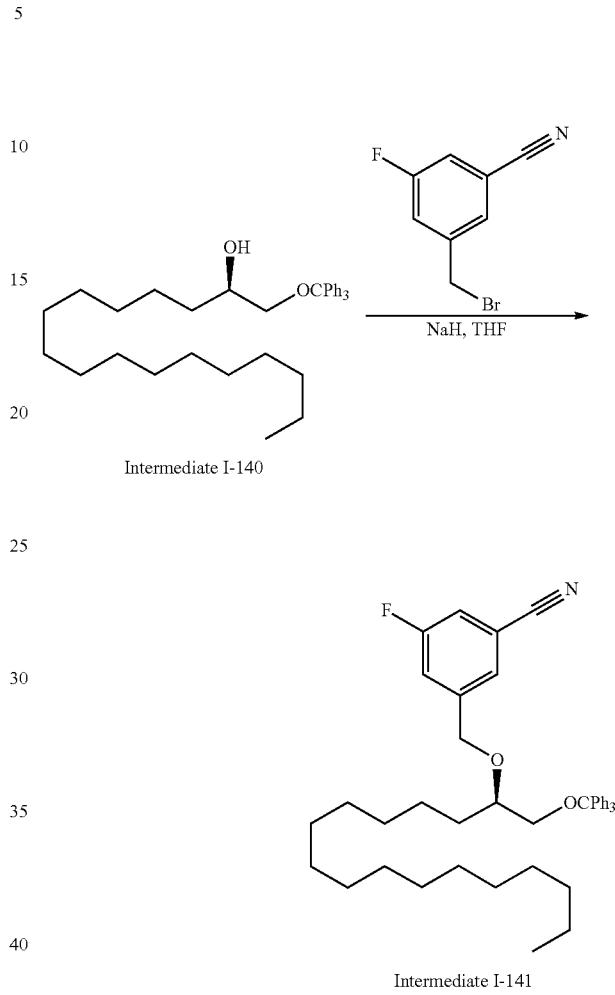

Intermediate I-140

Intermediate I-141: (R)-3-fluoro-5-(((1-(trityloxy)heptadecan-2-yl)oxy)methyl)benzonitrile Add bromo(tetradecyl)magnesium (25 g, 82.9 mmol, 1.3 eq) over 10 min via cannula to mixture of (2R)-2-(trityloxymethyl)oxirane (20.2 g, 63.8 mmol, 1 eq), CuI (607.2 mg, 3.2 mmol, 0.05 eq) in 2-MeTHF (50 mL) at −20° C. The reaction was stirred vigorously for 5 min, warmed to 0° C., and continued stirring for 2 h. The reaction mixture was quenched by addition sat. NH₄Cl solution (350 mL), and then the mixture was extracted with Ethyl acetate (200 mL×3). The combined organic layers were washed with H₂O (400 mL×2), dried over Na₂SO₄, filtered and concentrated under reduced pressure to give a residue. The residue was purified by flash silica gel chromatography (ISCO®; 80 g SepaFlash® Silica Flash Column, Eluent of 0~3% Ethyl acetate/Petroleum ether gradient @ 120 mL/min) to give compound (R)-1-(trityloxy)heptadecan-2-ol, Intermediate I-140. ¹H NMR (400 MHz, CHLOROFORM-d) δ 7.39 (br d, J=7.6 Hz, 5H), 7.26-7.19 (m, 10H), 3.71 (br d, J=2.6 Hz, 1H), 3.12 (dd, J=2.8, 9.3 Hz, 1H), 3.01-2.94 (m, 1H), 2.24 (br d, J=3.0 Hz, 1H), 1.39-1.26 (m, 4H), 1.19 (br d, J=8.9 Hz, 24H), 0.83 (br t, J=6.6 Hz, 3H).

To a solution of NaH (971.2 mg, 24.3 mmol, 60% purity, 2.5 eq) in THF (80 mL) was added (2R)-1-trityloxyheptadecan-2-ol, Intermediate I-140 (5 g, 9.7 mmol, 1 eq) at 0° C. and the mixture was stirred at 0° C. for 30 min. Then 3-(bromomethyl)-5-fluoro-benzonitrile (2.5 g, 11.7 mmol, 1.2 eq) was added and the mixture was stirred at 65° C. for 12 hr. The reaction mixture was quenched by addition sat. NH₄Cl solution (100 mL) at 20° C. and extracted with Ethyl acetate (50 mL×3). The combined organic layers were washed with H₂O (70 mL×2), dried over Na₂SO₄, and concentrated under reduced pressure to give a residue. The residue was purified by flash silica gel chromatography (ISCO®; 20 g SepaFlash® Silica Flash Column, Eluent of 0~3% Ethyl acetate/Petroleum ether gradient @ 45 mL/min) to give compound (R)-3-fluoro-5-(((1-(trityloxy)heptadecan-2-yl)oxy)methyl)benzonitrile, Intermediate I-141. ¹H NMR (400 MHz, CHLOROFORM-d) δ 7.50-7.40 (m, 7H), 7.27 (s, 11H), 4.73 (br d, J=12.9 Hz, 1H), 4.57 (br d, J=12.8 Hz, 1H), 3.60-3.48 (m, 1H), 3.22 (br d, J=4.3 Hz, 2H), 1.55 (br s, 2H), 1.27 (br s, 26H), 0.89 (br t, J=6.4 Hz, 3H).

Intermediate I-142: (R)-3-fluoro-5-(((1-hydroxyheptadecan-2-yl)oxy)methyl)benzonitrile

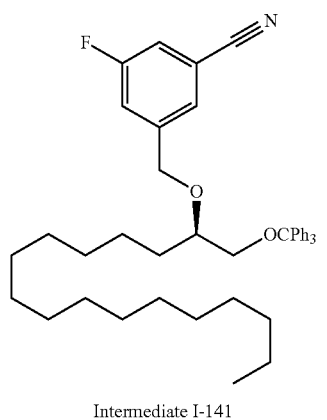

Intermediate I-141

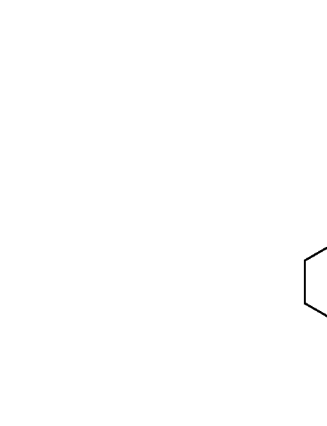

Intermediate I-142

Intermediate I-143: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl) oxy)heptadecyl) phosphate

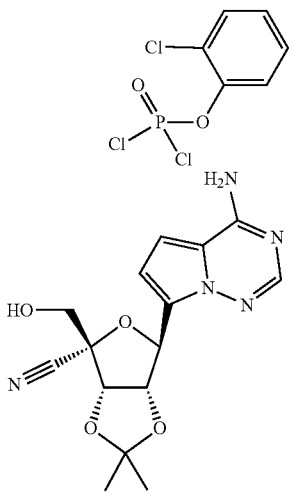

Intermediate I-143

To a solution of (R)-3-fluoro-5-(((1-(trityloxy)heptadecan-2-yl)oxy)methyl)benzonitrile, Intermediate I-141 (2.7 g, 4.2 mmol, 1 eq) in MTBE (54 mL) and MeOH (8.1 mL) was added anisole (225.3 mg, 2.1 mmol, 226.4 uL, 0.5 eq) and PTSA (358.8 mg, 2.1 mmol, 0.5 eq) and the mixture was stirred at 50° C. for 2 hr. The reaction mixture was diluted with sat. NaHCO₃ 80 mL and extracted with Ethyl acetate (40 mL×3). The combined organic layers were washed with H₂O (100 mL×2), dried over Na₂SO₄, filtered and concentrated under reduced pressure to give a residue. The residue was purified by flash silica gel chromatography (ISCO®; 12 g SepaFlash® Silica Flash Column, Eluent of 0~15% Ethyl acetate/Petroleum ether gradient @ 45 mL/min) to give compound (R)-3-fluoro-5-(((1-hydroxyheptadecan-2-yl) oxy)methyl)benzonitrile, Intermediate I-142. ¹H NMR (400 MHz, CHLOROFORM-d) δ 7.46 (br s, 1H), 7.35 (br d, J=8.9 Hz, 1H), 7.29 (br s, 1H), 4.64 (br s, 2H), 3.79-3.70 (m, 1H), 3.66-3.47 (m, 2H), 1.66-1.50 (m, 2H), 1.26 (br s, 26H), 0.89 (br s, 3H). MS (ESI): m/z=428.2 [M+Na]⁺

1H-1,2,4-triazole (236 mg, 3.42 mmol, 3.96 equiv.) was dissolved in THF (10.0 mL). TEA (0.32 mL, 2.29 mmol, 2.65 equiv.) was added to the solution followed by 2-chlorophenyl phosphorodichloridate (0.17 mL, 1.04 mmol, 1.2 equiv.). The reaction mixture was stirred at rt for 5 min prior to the addition of (3aS,4R,6aS)-6-(4-aminopyrrolo[2,1-f][1, 2,4]triazin-7-yl)-4-(hydroxymethyl)-2,2-dimethyltetrahydrofuro[3,4-d][1,3]dioxole-4-carbonitrile, Intermediate I-3a (286 mg, 0.86 mmol, 1.0 equiv.) in one portion followed by 1-methylimidazole (0.09 mL, 1.12 mmol, 1.3 equiv.). The solution was stirred for an additional 10 min before adding (R)-3-fluoro-5-(((1-hydroxyheptadecan-2-yl)oxy)methyl) benzonitrile, Intermediate I-142 (350 mg, 0.86 mmol, 1.0 equiv.). After stirring at room temperature for 4 h and 20 min, the solution was diluted with EtOAc (75 mL) and water (75 mL). The aqueous layer was extracted again with EtOAc (75 mL). The organic layers were combined, washed with brine, dried over MgSO$_4$, filtered and concentrated in vacuo prior to purification by silica gel chromatography (0-100% EtOAc in hexanes) to afford the title compound Intermediate I-143. $^1$H NMR (400 MHz, Methanol-d4) δ 7.81-7.78 (m, 1H), 7.48-7.29 (m, 5H), 7.20-7.07 (m, 2H), 6.86-6.80 (m, 1H), 6.78-6.74 (m, 1H), 5.67-5.62 (m, 1H), 5.33-5.27 (m, 1H), 5.18-5.12 (m, 1H), 4.65-4.44 (m, 4H), 4.36-4.24 (m, 1H), 4.23-4.10 (m, 1H), 3.63-3.55 (m, 1H), 1.72 (s, 3H), 1.59-1.21 (m, 31H), 0.93-0.86 (m, 3H). $^{19}$F NMR (376 MHz, Methanol-d4) δ −112.70−−112.79 (m). MS m/z [M+1]=909.1

Intermediate I-144: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl ((R)-2-((3-cyano-5-fluorobenzyl)oxy)heptadecyl) hydrogen phosphate To a solution of ((3aS,4R,6S,6aS)-6-(4-aminopyrrolo[2,1-f][1,2,4]triazin-7-yl)-4-cyano-2,2-dimethyltetrahydrofuro [3,4-d][1,3]dioxol-4-yl)methyl (2-chlorophenyl) ((R)-2-((3-cyano-5-fluorobenzyl)oxy)heptadecyl) phosphate, Intermediate I-143 (323 mg, 0.355 mmol, 1.0 equiv.) in THF (10.0 mL) was added 1,1,3,3-tetramethylguanidine (0.27 mL, 2.13 mmol, 6.0 equiv.) and syn-2-pyridinealdoxime (258 mg, 2.11 mmol, 5.95 equiv.). The reaction mixture was stirred at room temperature overnight. The solution was concentrated in vacuo and purified by silica gel (0-45% MeOH in DCM) to afford the title compound Intermediate I-144. $^1$H NMR (400 MHz, Methanol-d4) δ 7.82 (s, 1H), 7.51-7.47 (m, 1H), 7.44-7.33 (m, 2H), 6.85-6.76 (m, 2H), 5.63 (d, J=3.6 Hz, 1H), 5.26 (dd, J=6.6, 3.6 Hz, 1H), 5.13 (d, J=6.6 Hz, 1H), 4.73 (d, J=13.0 Hz, 1H), 4.51 (d, J=13.0 Hz, 1H), 4.17-4.07 (m, 2H), 3.95-3.82 (m, 2H), 3.59-3.50 (m, 1H), 1.69 (s, 3H), 1.47-1.20 (m, 31H), 0.90 (t, J=6.8 Hz, 3H). $^{19}$F NMR (376 MHz, Methanol-d4) δ−112.93−−113.12 (m). MS m/z [M+1]=799.2

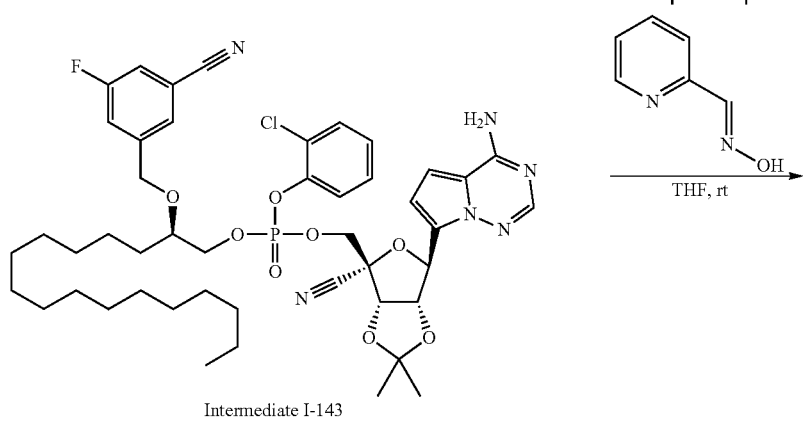

Intermediate I-143

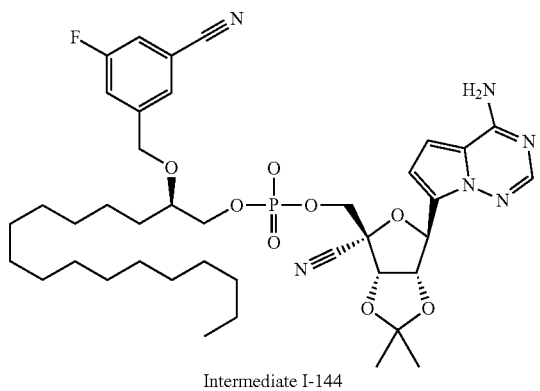

Intermediate I-144

Intermediate I-145: 1-Bromoheptadecane

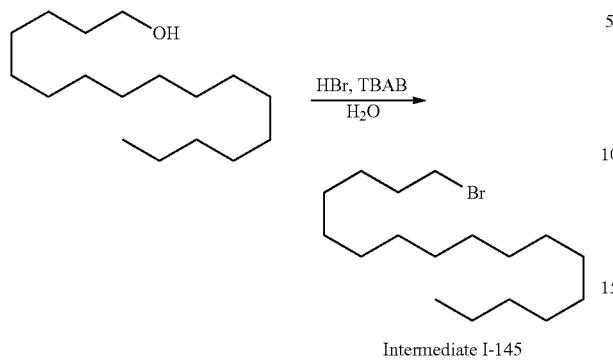

Intermediate I-145

To a solution of heptadecan-1-ol (10 g, 39.0 mmol, 1 eq) in HBr (60 mL, 30% purity) (in H₂O) was added TBAB (502.8 mg, 1.6 mmol, 0.04 eq) at 20° C. Then the mixture was stirred at 100° C. for 12 hr. The reaction mixture was concentrated under reduced pressure to remove solvent. The residue was diluted with H₂O 120 mL and extracted with DCM (80 mL×3). The combined organic layers were washed with H₂O (150 mL×2), dried over Na₂SO₄, filtered and concentrated under reduced pressure to give a residue. The residue was purified by flash silica gel chromatography (ISCO®; 80 g SepaFlash® Silica Flash Column, Eluent of 0% Ethyl acetate/Petroleum ether gradient @ 100 mL/min) to give compound bromoheptadecane, Intermediate I-145 (8.4 g) as a white solid. ¹H NMR (400 MHz, CHLOROFORM-d) δ 3.42 (t, J=6.9 Hz, 2H), 1.86 (quin, J=7.1 Hz, 2H), 1.47-1.39 (m, 2H), 1.27 (s, 26H), 0.89 (t, J=6.8 Hz, 3H).

Intermediate I-146: Heptadecylmagnesium bromide

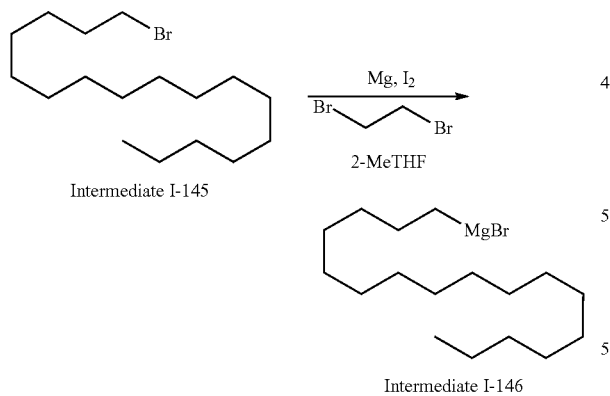

Intermediate I-146

To a solution of Mg (875.2 mg, 36.0 mmol, 1.2 eq) in 2-MeTHF (30 mL) was added I₂ (79.5 mg, 313.1 umol, 63.1 uL, 0.01 eq) and BrCH₂CH₂Br (0.1 mL) under N₂. Then 1-bromoheptadecane, Intermediate I-145 (1 g, 3.1 mmol) in 2-MeTHF (10 mL) was added dropwise. The mixture was stirred until the color of I₂ was faded to colorless. Then the remaining 1-bromoheptadecane (9 g, 28.2 mmol) in 2-MeTHF (90 mL) was added and the mixture was stirred at 25° C. for 4 hr. The crude product heptadecylmagnesium bromide, Intermediate I-146 (in 2-MeTHF) was used into the next step without further purification as a brown solution.

Intermediate I-147: (R)-1-(trityloxy)icosan-2-ol

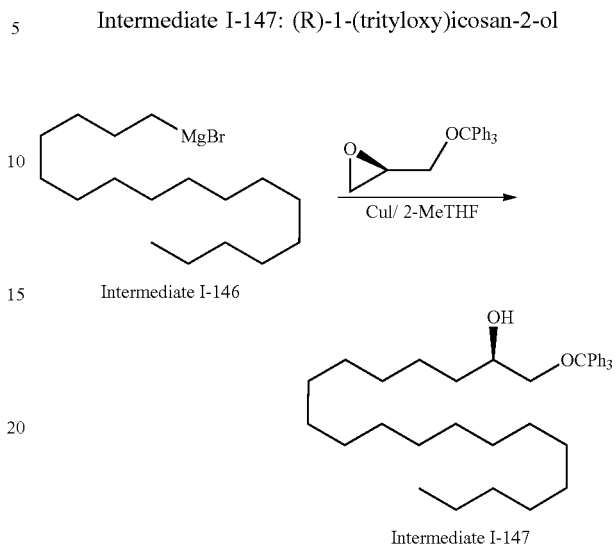

Intermediate I-147

Add bromo(heptadecyl)magnesium, Intermediate I-146 (10 g, 29.1 mmol, 1.3 eq) over 10 min via cannula to a mixture of (2R)-2-(trityloxymethyl)oxirane (7.1 g, 22.4 mmol, 1 eq), CuI (213.1 mg, 1.1 mmol, 0.05 eq) in 2-MeTHF (70 mL) at −20° C. The reaction was stirred vigorously 5 min, warmed to 0° C., then continued stirring 2 hrs. The reaction mixture was quenched by addition of sat. NH₄Cl solution (200 mL), and then the mixture was extracted with Ethyl acetate (120 mL×3). The combined organic layers were washed with H₂O (200 mL×2), dried over Na₂SO₄, filtered and concentrated under reduced pressure to give a residue. The residue was purified by flash silica gel chromatography (ISCO®; 80 g SepaFlash® Silica Flash Column, Eluent of 0~4% Ethyl acetate/Petroleum ether gradient @ 100 mL/min) to give compound (R)-1-(trityloxy)icosan-2-ol, Intermediate I-147. ¹H NMR (400 MHz, CHLOROFORM-d) δ 7.45 (d, J=7.5 Hz, 5H), 7.27 (s, 10H), 3.77 (br dd, J=3.9, 7.4 Hz, 1H), 3.19 (dd, J=3.1, 9.3 Hz, 1H), 3.07-2.98 (m, 1H), 2.32-2.26 (m, 1H), 1.42-1.32 (m, 4H), 1.32-1.22 (m, 30H), 0.89 (t, J=6.7 Hz, 3H).

Intermediate I-148: 3-(bromomethyl)-5-chlorobenzonitrile

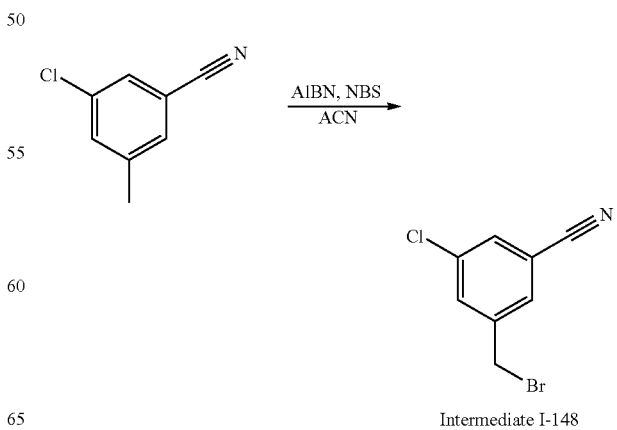

Intermediate I-148

To a solution of 3-chloro-5-methyl-benzonitrile (4.5 g, 29.7 mmol, 1 eq) in ACN (50 mL) was added NBS (5.8 g, 32.6 mmol, 1.1 eq) and AIBN (4.9 g, 29.7 mmol, 1 eq). The mixture was stirred at 80° C. for 12 hr. The reaction mixture was concentrated under reduced pressure to remove solvent. The residue was diluted with $H_2O$ 60 mL and extracted with Ethyl acetate (40 mL×3). The combined organic layers were washed with $H_2O$ (60 mL×2), dried over $Na_2SO_4$, filtered and concentrated under reduced pressure to give a residue. The residue was purified by flash silica gel chromatography (ISCO®; 20 g SepaFlash® Silica Flash Column, Eluent of 0~1% Ethyl acetate/Petroleum ether gradient @ 45 mL/min) to give compound 3-(bromomethyl)-5-chlorobenzonitrile, Intermediate I-148. $^1$H NMR (400 MHz, CHLOROFORM-d) δ 7.65-7.57 (m, 3H), 4.43 (s, 2H).

Intermediate I-149: (R)-3-chloro-5-(((1-(trityloxy) icosan-2-yl)oxy)methyl)benzonitrile momethyl)-5-chloro-benzonitrile, Intermediate I-148 (2.0 g, 8.7 mmol, 1.2 eq) was added and the mixture was stirred at 65° C. for 12 hr. The reaction mixture was quenched by addition of sat. $NH_4Cl$ solution (60 mL) at 20° C. and extracted with Ethyl acetate (40 mL×3). The combined organic layers were washed with $H_2O$ (60 mL×2), dried over $Na_2SO_4$, and concentrated under reduced pressure to give a residue. The residue was purified by flash silica gel chromatography (ISCO®; 20 g SepaFlash® Silica Flash Column, Eluent of 0~3% Ethyl acetate/Petroleum ether gradient @ 45 mL/min) to give compound (R)-3-chloro-5-(((1-(trityloxy)icosan-2-yl)oxy)methyl)benzonitrile, Intermediate I-149. $^1$H NMR (400 MHz, CHLOROFORM-d) δ 7.50 (s, 1H), 7.45 (s, 1H), 7.42 (s, 1H), 7.39-7.35 (m, 5H), 7.25-7.16 (m, 10H), 4.63 (d, J=12.8 Hz, 1H), 4.46 (d, J=12.8 Hz, 1H), 3.48-3.40 (m, 1H), 3.13 (d, J=4.8 Hz, 2H), 1.49-1.41 (m, 2H), 1.23-1.14 (m, 32H), 0.81 (t, J=6.8 Hz, 3H).

Intermediate I-150: (R)-3-chloro-5-(((1-hydroxyicosan-2-yl)oxy)methyl)benzonitrile

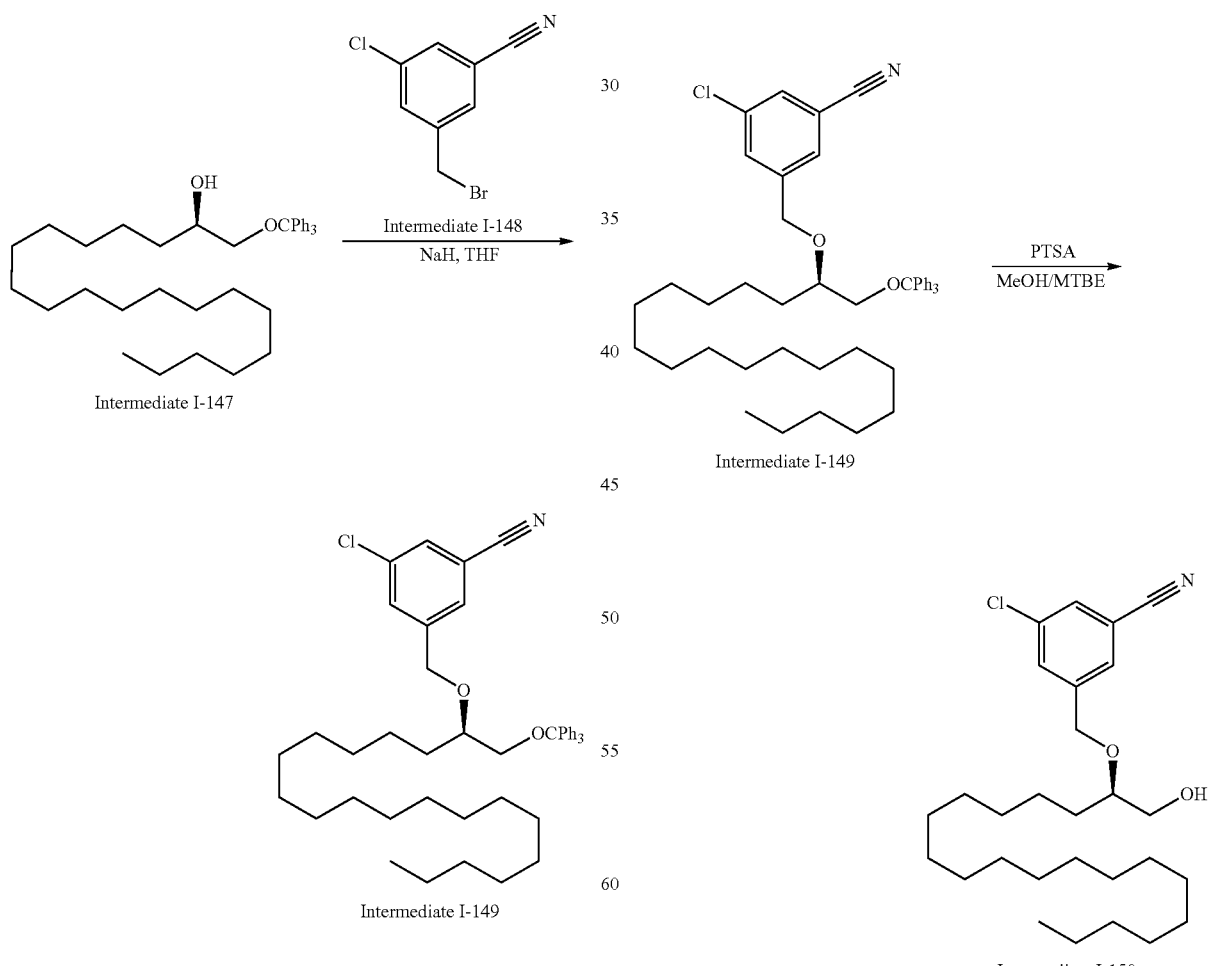

To a solution of (2R)-1-trityloxyicosan-2-ol, Intermediate I-147 (4.0 g, 7.2 mmol, 1 eq) in THF (60 mL) was added NaH (723.0 mg, 18.1 mmol, 60% purity, 2.5 eq) at 0° C. and the mixture was stirred at 0° C. for 30 min. Then 3-(bro- To a solution of 3-chloro-5-[[(1R)-1-(trityloxymethyl) nonadecoxy]methyl]benzonitrile, Intermediate I-149 (3.9 g, 5.5 mmol, 1.0 eq) in MTBE (80 mL) and MeOH (12 mL) was added anisole (298.5 mg, 2.8 mmol, 300.0 uL, 0.5 eq) and PTSA (475.3 mg, 2.8 mmol, 0.5 eq) and the mixture was stirred at 50° C. for 2 hr. The reaction mixture was diluted with sat. NaHCO₃ 120 mL and extracted with Ethyl acetate (80 mL×3). The combined organic layers were washed with H₂O (100 mL×2), dried over Na₂SO₄, filtered and concentrated under reduced pressure to give a residue. The residue was purified by flash silica gel chromatography (ISCO®; 20 g SepaFlash® Silica Flash Column, Eluent of 0~8% Ethyl acetate/Petroleum ether gradient @ 45 mL/min) to give compound (R)-3-chloro-5-(((1-hydroxyicosan-2-yl)oxy) methyl)benzonitrile Intermediate I-150. $^1$H NMR (400 MHz, CHLOROFORM-d) δ 7.61-7.53 (m, 3H), 4.62 (s, 2H), 3.75 (br d, J=10.8 Hz, 1H), 3.66-3.58 (m, 1H), 3.56-3.49 (m, 1H), 1.81 (br s, 1H), 1.67-1.48 (m, 2H), 1.26 (s, 32H), 0.89 (t, J=6.6 Hz, 3H). MS (ESI): ink=486.2 [M+Na]⁺

Intermediate I-151: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-chloro-5-cyanobenzyl)oxy)icosyl) (2-chlorophenyl) phosphate

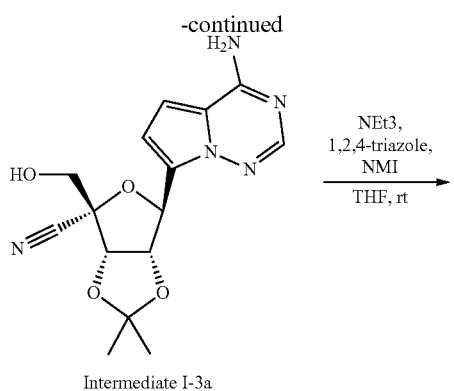

Intermediate I-3a

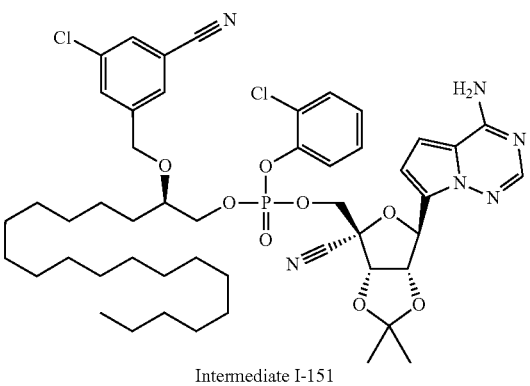

Intermediate I-151

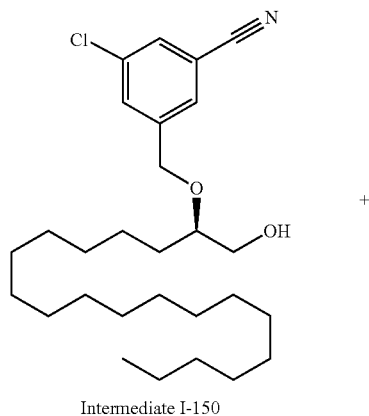

Intermediate I-150

+

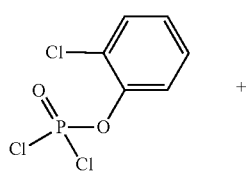

+

1H-1,2,4-triazole (125 mg, 1.81 mmol, 3.46 equiv.) was dissolved in THF (10 mL). TEA (0.19 mL, 1.39 mmol, 2.65 equiv.) was added to the solution followed by 2-chlorophenyl phosphorodichloridate (0.10 mL, 0.575 mmol, 1.1 equiv.). The reaction mixture was stirred at rt for 10 min prior to the addition of (3aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (173 mg, 0.523 mmol, 1.0 equiv.) in one portion followed by 1-methylimidazole (0.10 mL, 1.25 mmol, 2.4 equiv.). The solution was stirred for an additional 9 min before adding (R)-3-chloro-5-(((1-hydroxyicosan-2-yl)oxy) methyl)benzonitrile, Intermediate I-150 (243 mg, 0.523 mmol, 1.0 equiv.). After stirring at room temperature overnight, the solution was diluted with EtOAc (100 mL) and water (100 mL). The aqueous layer was extracted again with EtOAc (100 mL). The organic layers were combined, washed with 1:1 water:brine (100 mL), dried over MgSO₄, filtered and concentrated in vacuo prior to purification by silica gel chromatography (0-100% EtOAc in hexanes) to afford the title compound Intermediate I-151. $^1$H NMR (400 MHz, Methanol-d4) δ 7.81-7.77 (m, 1H), 7.64-7.56 (m, 2H), 7.56-7.51 (m, 1H), 7.48-7.29 (m, 2H), 7.20-7.08 (m, 2H), 6.86-6.80 (m, 1H), 6.78-6.74 (m, 1H), 5.68-5.62 (m, 1H), 5.33-5.26 (m, 1H), 5.19-5.12 (m, 1H), 4.64-4.42 (m, 4H), 4.36-4.25 (m, 1H), 4.24-4.06 (m, 1H), 3.63-3.55 (m, 1H), 1.72 (s, 3H), 1.58-1.20 (m, 37H), 0.93-0.85 (m, 3H). $^{31}$P NMR (162 MHz, Methanol-d4) δ−7.53--8.01 (m). MS m/z [M+1]=967.1

Intermediate I-152: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-24(3-chloro-5-cyanobenzyl)oxy)icosyl) hydrogen phosphate

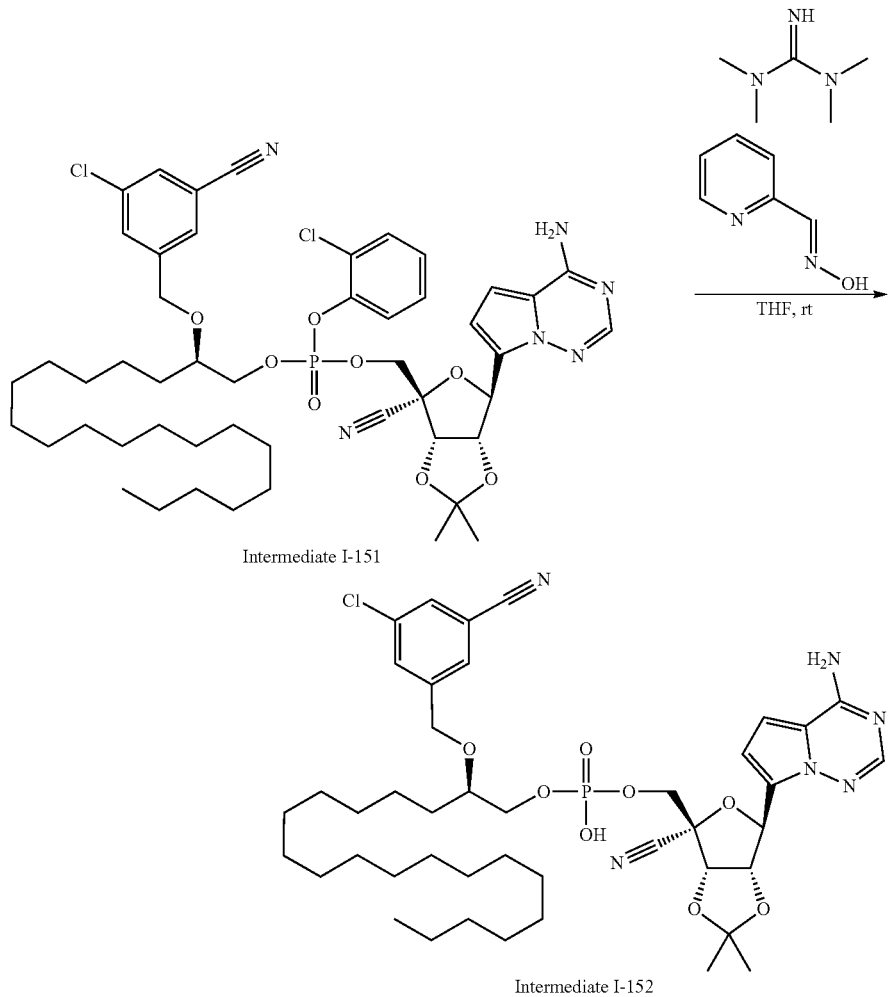

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-chloro-5-cyanobenzyl)oxy)icosyl) (2-chlorophenyl) phosphate, Intermediate I-151 (164 mg, 0.169 mmol, 1.0 equiv.) in THF (5.0 mL) was added 1,1,3,3-tetramethylguanidine (0.13 mL, 1.02 mmol, 6.0 equiv.) and syn-2-pyridinealdoxime (196 mg, 1.60 mmol, 9.47 equiv.). The reaction mixture was stirred at room temperature overnight. The solution was concentrated in vacuo and purified by silica gel (0-40% MeOH in DCM) to afford the title compound Intermediate I-152. $^1$H NMR (400 MHz, Methanol-d4) δ 7.82 (s, 1H), 7.65-7.57 (m, 3H), 6.83 (d, J=4.5 Hz, 1H), 6.78 (d, J=4.5 Hz, 1H), 5.63 (d, J=3.6 Hz, 1H), 5.25 (dd, J=6.6, 3.6 Hz, 1H), 5.13 (d, J=6.6 Hz, 1H), 4.72 (d, J=13.0 Hz, 1H), 4.49 (d, J=12.9 Hz, 1H), 4.17-4.07 (m, 2H), 3.95-3.81 (m, 2H), 3.59-3.50 (m, 1H), 1.69 (s, 3H), 1.47-1.18 (m, 37H), 0.89 (t, J=6.8 Hz, 3H). $^{31}$P NMR (162 MHz, Methanol-d4) δ −0.19—0.73 (m). MS m/z [M+1]=857.2

Intermediate I-153: (R)-3-chloro-5-(((1-(trityloxy)henicosan-2-yl)oxy)methyl)benzonitrile

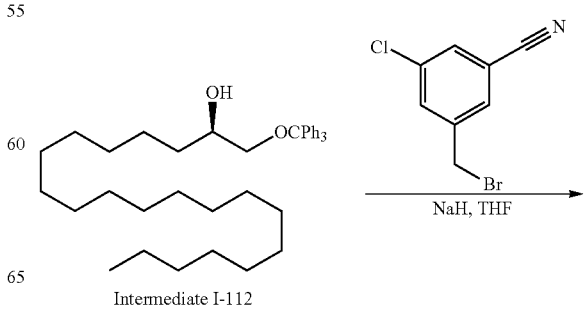

Intermediate I-112

-continued

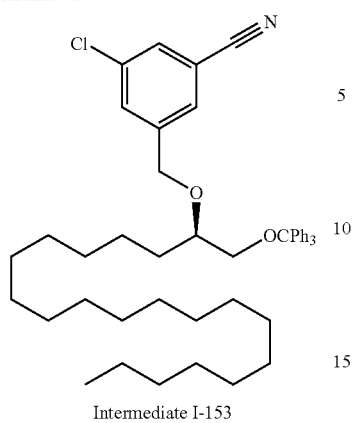

Intermediate I-153

-continued

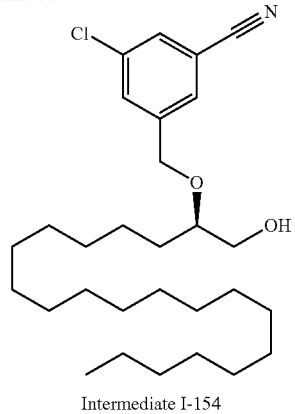

Intermediate I-154

To a solution of (R)-1-(trityloxy)henicosan-2-ol (2.0 g, 3.5 mmol, 1 eq) in THF (80 mL) was added NaH (420.4 mg, 10.5 mmol, 60% purity, 3 eq) at 0° C. The mixture was stirred at 0° C. for 0.5 hr and then 3-(bromomethyl)-5-chloro-benzonitrile (1.2 g, 5.2 mmol, 1.5 eq) was added into the above solution at 0° C. The mixture was stirred at 65° C. for 12 hr. The reaction mixture was quenched by added into sat. NH$_4$Cl 50 mL at 0° C. and extracted with ethyl acetate (20 mL×3). The combined organic layers were washed with NaCl (20 mL×3), dried over Na$_2$SO$_4$, filtered and concentrated under reduced pressure to give a residue. The residue was purified by column chromatography (SiO$_2$, Petroleum ether/MTBE=100/1 to 100/4) to give (R)-3-chloro-5-(((1-(trityloxy)henicosan-2-yl)oxy)methyl)benzonitrile, Intermediate I-153. $^1$H NMR (400 MHz, CHLOROFORM-d) δ 7.64-7.52 (m, 3H), 7.48 (d, J=7.2 Hz, 6H), 7.37-7.26 (m, 11H), 4.78-4.53 (m, 2H), 3.58-3.52 (m, 1H), 3.24 (d, J=4.8 Hz, 2H), 1.29 (s, 36H), 0.92 (t, J=6.7 Hz, 3H).

Intermediate I-154: (R)-3-chloro-5-(((1-hydroxyhenicosan-2-yl)oxy)methyl)benzonitrile To a solution of (R)-3-chloro-5-(((1-(trityloxy)henicosan-2-yl)oxy)methyl)benzonitrile, Intermediate I-153 (1.2 g, 1.6 mmol, 615.7 uL, 1 eq) in MTBE (15 mL) was added anisole (180.1 mg, 1.6 mmol, 181.0 uL, 1 eq), MeOH (2.4 mL) and 4-methylbenzenesulfonic acid (286.8 mg, 1.6 mmol, 1 eq). The mixture was stirred at 50° C. for 6 hr. The reaction mixture was concentrated under reduced pressure to remove solvent. The residue was washed with NaCl (20 mL×3), dried over Na$_2$SO$_4$, filtered and concentrated under reduced pressure to give a residue. The residue was purified by column chromatography (SiO$_2$, Petroleum ether/Ethyl acetate=100/0 to 5/1) to give (R)-3-chloro-5-(((1-hydroxyhenicosan-2-yl)oxy)methyl)benzonitrile, Intermediate I-154. $^1$H NMR (400 MHz, CHLOROFORM-d) δ 7.59 (s, 1H), 7.58-7.53 (m, 2H), 4.62 (s, 2H), 3.80-3.71 (m, 1H), 3.66-3.58 (m, 1H), 3.57-3.49 (m, 1H), 1.76 (br s, 1H), 1.59-1.46 (m, 2H), 1.26 (s, 34H), 0.89 (t, J=6.8 Hz, 3H). MS (ESI): m/z=500.3 [M+Na]$^+$ Intermediate I-155: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl ((R)-2-((3-chloro-5-cyanobenzyl)oxy)henicosyl) (2-chlorophenyl) phosphate

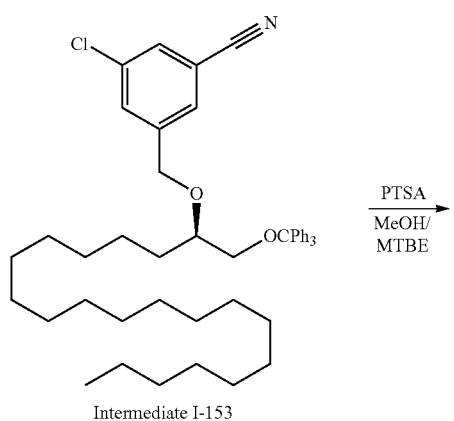

Intermediate I-153

→ PTSA MeOH/ MTBE

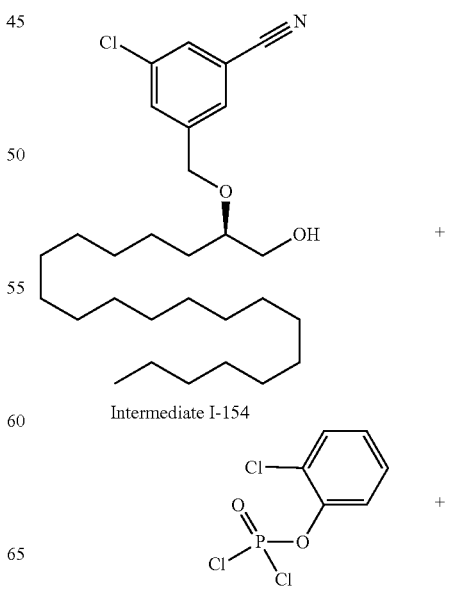

Intermediate I-154

+

+

-continued

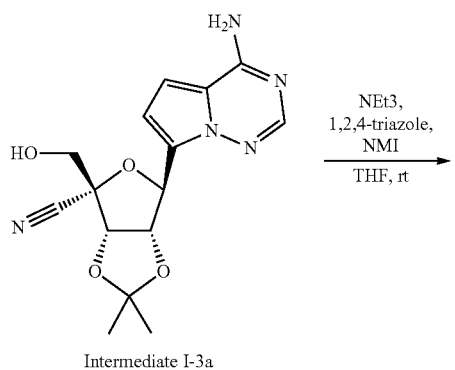

Intermediate I-3a

→ NEt3, 1,2,4-triazole, NMI, THF, rt

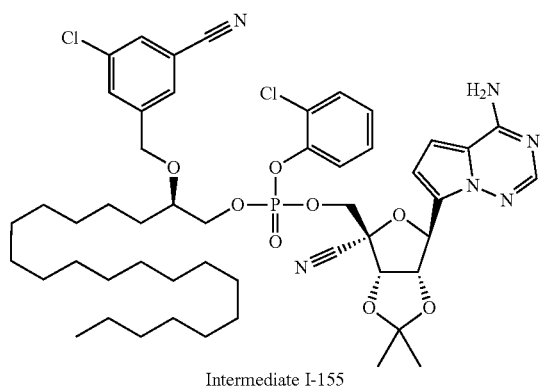

Intermediate I-155

1H-1,2,4-triazole (239 mg, 3.46 mmol, 6.62 equiv.) was dissolved in THF (10 mL). TEA (0.19 mL, 1.39 mmol, 2.65 equiv.) was added to the solution followed by 2-chlorophenyl phosphorodichloridate (0.10 mL, 0.575 mmol, 1.1 equiv.). The reaction mixture was stirred at rt for 6 min prior to the addition of (3aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (173 mg, 0.523 mmol, 1.0 equiv.) in one portion followed by 1-methylimidazole (0.05 mL, 0.680 mmol, 1.3 equiv.). The solution was stirred for an additional 14 min before adding (R)-3-chloro-5-(((1-hydroxyhenicosan-2-yl)oxy)methyl) benzonitrile, Intermediate I-154 (250 mg, 0.523 mmol, 1.0 equiv.). After stirring at room temperature for 4 h, the solution was diluted with EtOAc (100 mL) and water (100 mL). The aqueous layer was extracted again with EtOAc (100 mL). The organic layers were combined, washed with 1:1 water:brine (60 mL), dried over MgSO$_4$, filtered and concentrated in vacuo prior to purification by silica gel chromatography (0-100% EtOAc in hexanes) to afford the title compound Intermediate I-155. $^1$H NMR (400 MHz, Methanol-d$_4$) δ 7.81-7.77 (m, 1H), 7.64-7.56 (m, 2H), 7.55-7.52 (m, 1H), 7.47-7.29 (m, 2H), 7.20-7.08 (m, 2H), 6.86-6.80 (m, 1H), 6.78-6.74 (m, 1H), 5.67-5.62 (m, 1H), 5.32-5.28 (m, 1H), 5.18-5.12 (m, 1H), 4.64-4.42 (m, 4H), 4.36-4.25 (m, 1H), 4.23-4.12 (m, 1H), 3.63-3.55 (m, 1H), 1.72 (s, 3H), 1.59-1.20 (m, 39H), 0.93-0.86 (m, 3H). $^{31}$P NMR (162 MHz, Methanol-d4) δ −7.54−−8.02 (m). MS m/z [M+1]=981.2

Intermediate I-156: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl ((R)-2-((3-chloro-5-cyanobenzyl)oxy)henicosyl) hydrogen phosphate

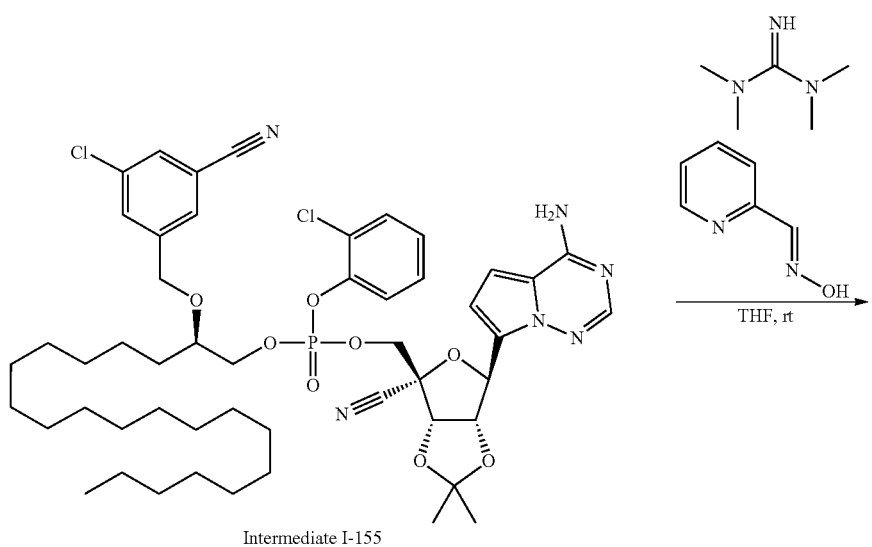

Intermediate I-155

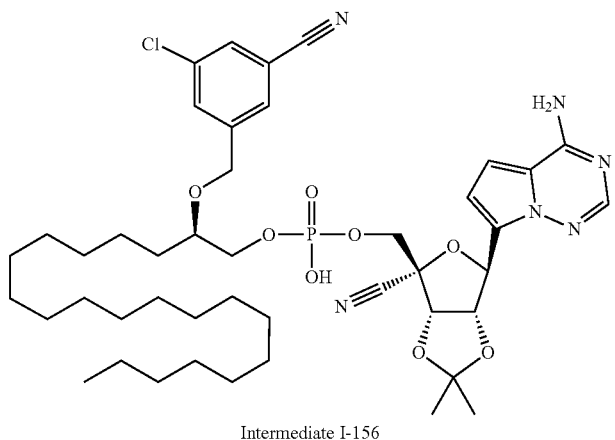

Intermediate I-156

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-chloro-5-cyanobenzyl)oxy)henicosyl) (2-chlorophenyl) phosphate, Intermediate I-155 (178 mg, 0.181 mmol, 1.0 equiv.) in THF (5.0 mL) was added 1,1,3,3-tetramethylguanidine (0.14 mL, 1.09 mmol, 6.0 equiv.) and syn-2-pyridinealdoxime (164 mg, 1.34 mmol, 7.41 equiv.). The reaction mixture was stirred at room temperature overnight. An additional 80 mg of syn-2-pyridinealdoxime (0.655 mmol, 3.61 equiv.) was added and stirred overnight. The solution was concentrated in vacuo and purified by silica gel (0-40% MeOH in DCM) to afford the title compound Intermediate I-156. $^1$H NMR (400 MHz, Methanol-d4) δ 7.82 (s, 1H), 7.65-7.57 (m, 3H), 6.83 (d, J=4.5 Hz, 1H), 6.78 (d, J=4.5 Hz, 1H), 5.63 (d, J=3.6 Hz, 1H), 5.25 (dd, J=6.6, 3.6 Hz, 1H), 5.13 (d, J=6.6 Hz, 1H), 4.72 (d, J=13.0 Hz, 1H), 4.49 (d, J=13.0 Hz, 1H), 4.17-4.07 (m, 2H), 3.96-3.81 (m, 2H), 3.59-3.49 (m, 1H), 1.69 (s, 3H), 1.46-1.21 (m, 39H), 0.90 (t, J=6.8 Hz, 3H). $^{31}$P NMR (162 MHz, Methanol-d4) δ−0.16−−0.78 (m). MS m/z [M+1]=871.1

Intermediate I-161: (R)-3-fluoro-5-(((1-(trityloxy)icosan-2-yl)oxy)methyl)benzonitrile

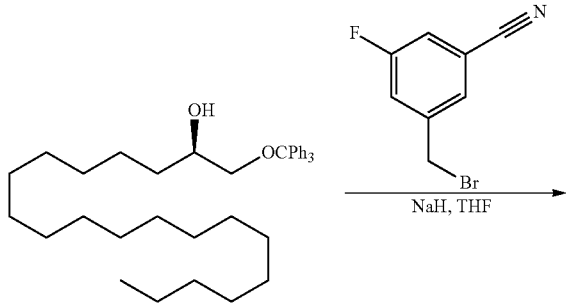

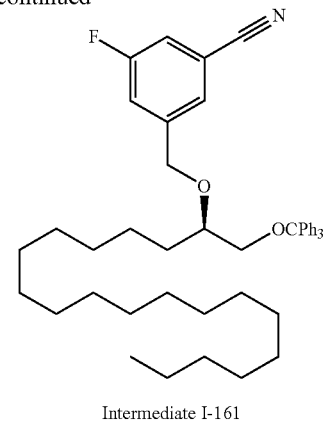

Intermediate I-161

To a solution of (R)-1-(trityloxy)icosan-2-ol (2.5 g, 4.4 mmol, 1 eq) in THF (80 mL) was added NaH (538.7 mg, 13.4 mmol, 60% purity, 3 eq) at 0° C. The mixture was stirred at 0° C. for 0.5 hr and then 3-(bromomethyl)-5-fluoro-benzonitrile (1.9 g, 8.9 mmol, 2 eq) was added into the above solution at 0° C. The mixture was stirred at 65° C. for 12 hr. The reaction mixture was quenched by added into sat. NH$_4$Cl 50 mL at 0° C., and extracted with ethyl acetate (20 mL×3). The combined organic layers were washed with NaCl (20 mL×3), dried over Na$_2$SO$_4$, filtered and concentrated under reduced pressure to give a residue. The residue was purified by column chromatography (SiO$_2$, Petroleum ether/MTBE=100/1 to 100/8) to give (R)-3-fluoro-5-(((1-(trityloxy)icosan-2-yl)oxy)methyl)benzonitrile, Intermediate I-161. $^1$H NMR (400 MHz, CHLOROFORM-d) δ 7.51-7.42 (m, 7H), 7.38-7.24 (m, 12H), 4.82-4.51 (m, 2H), 3.63-3.47 (m, 1H), 3.24 (d, J=4.6 Hz, 2H), 1.43-1.20 (m, 34H), 0.92 (br t, J=6.6 Hz, 3H).

777

Intermediate I-162: (R)-3-fluoro-5-(((1-hydroxyicosan-2-yl)oxy)methyl)benzonitrile

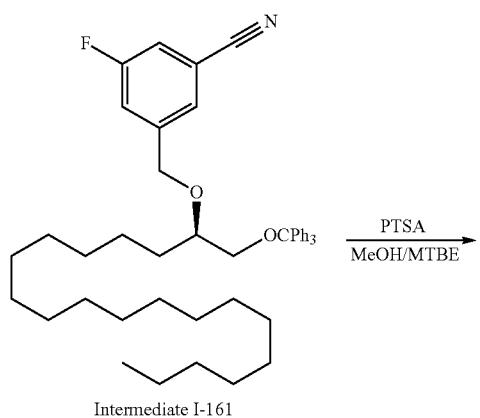

To a solution of (R)-3-fluoro-5-(((1-(trityloxy)icosan-2-yl)oxy)methyl)benzonitrile Intermediate I-161 (1.8 g, 2.6 mmol, 615.7 uL, 1 eq) in MTBE (30 mL) was added anisole (282.1 mg, 2.6 mmol, 283.5 uL, 1 eq), MeOH (4.8 mL) and 4-methylbenzenesulfonic acid (449.2 mg, 2.6 mmol, 1 eq). The mixture was stirred at 50° C. for 6 hr. The reaction mixture was quenched by added into sat NH$_4$Cl 20 mL at 0° C. and extracted with ethyl acetate (30 mL×3). The combined organic layers were washed with NaCl (20 mL×3), dried over Na$_2$SO$_4$, filtered and concentrated under reduced pressure to give a residue. The residue was purified by column chromatography (SiO$_2$, Petroleum ether/Ethyl acetate=100/0 to 5/1) to give (R)-3-fluoro-5-(((1-hydroxyicosan-2-yl)oxy)methyl)benzonitrile, Intermediate I-162. $^1$H NMR (400 MHz, CHLOROFORM-d) δ 7.38 (s, 1H), 7.27 (br d, J=9.0 Hz, 1H), 7.22-7.17 (m, 1H), 4.56 (s, 2H), 3.74-3.63 (m, 1H), 3.58-3.39 (m, 2H), 1.74-1.63 (m, 1H), 1.54-1.39 (m, 3H), 1.18 (s, 32H), 0.81 (t, J=6.6 Hz, 3H). MS (ESI): m/z=470.3 [M+Na]$^+$

778

Intermediate I-163: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)icosyl) phosphate

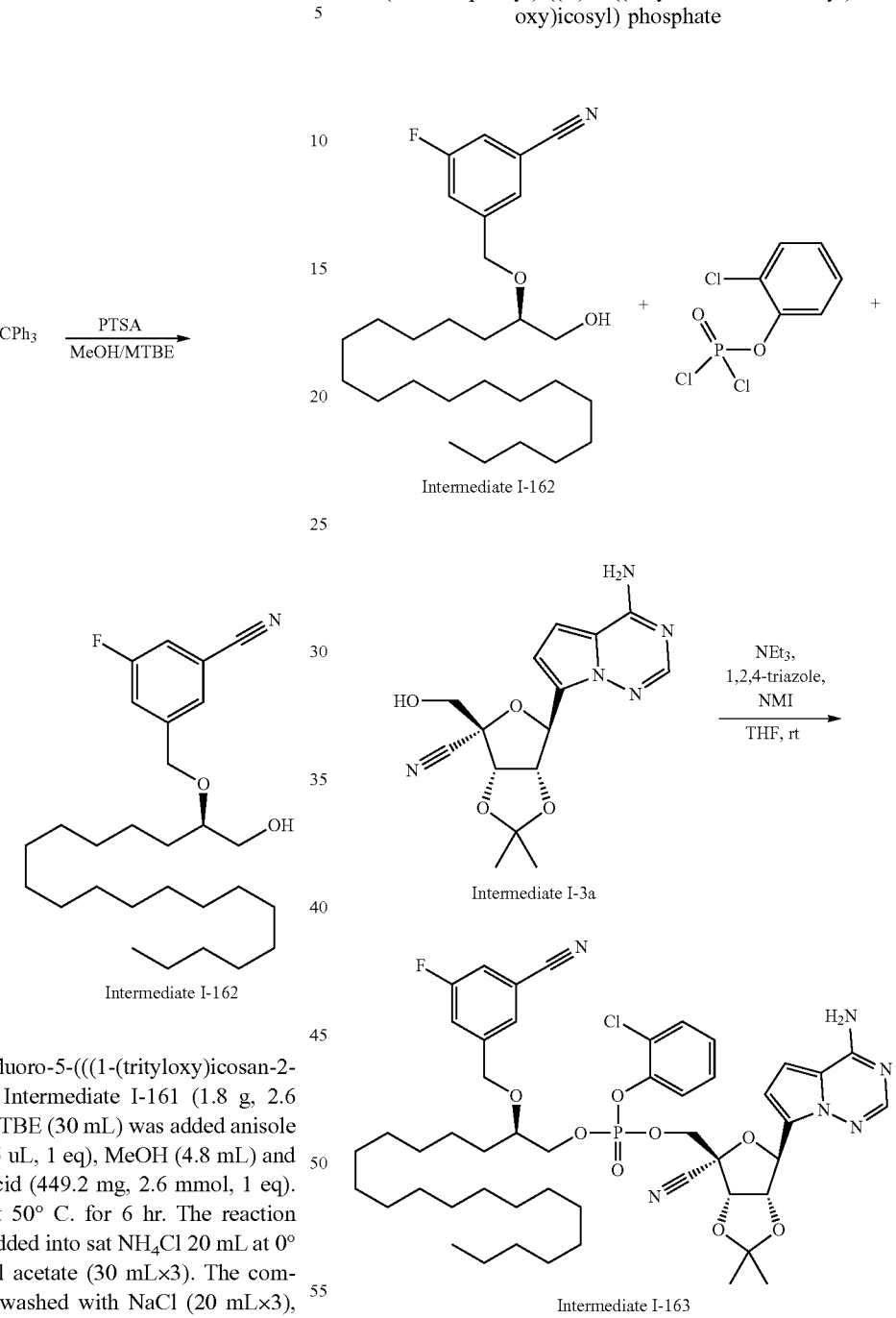

1H-1,2,4-triazole (183 mg, 2.65 mmol, 4.94 equiv.) was dissolved in THF (10.0 mL). TEA (0.20 mL, 1.42 mmol, 2.65 equiv.) was added to the solution followed by 2-chlorophenyl phosphorodichloridate (0.15 mL, 0.912 mmol, 1.7 equiv.). The reaction mixture was stirred at rt for 4 min prior to the addition of (3aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (178 mg, 0.536 mmol, 1.0 equiv.) in one portion followed by 1-methylimidazole (0.06 mL, 0.753 mmol, 1.4 equiv.). The solution was stirred for an additional 10 min before adding (R)-3-fluoro-5-(((1-hydroxyicosan-2-yl)oxy)methyl)benzonitrile, Intermediate I-162 (240 mg, 0.536 mmol, 1.0 equiv.). After stirring at room temperature overnight, the solution was diluted with EtOAc (100 mL) and water (100 mL). The aqueous layer was extracted again with EtOAc (100 mL). The organic layers were combined, washed with brine (50 mL), dried over MgSO$_4$, filtered and concentrated in vacuo prior to purification by silica gel chromatography (0-100% EtOAc in hexanes) to afford the title compound, Intermediate I-163. $^1$H NMR (400 MHz, Methanol-d4) δ 7.81-7.77 (m, 1H), 7.49-7.28 (m, 5H), 7.20-7.07 (m, 2H), 6.86-6.79 (m, 1H), 6.78-6.73 (m, 1H), 5.68-5.60 (m, 1H), 5.33-5.26 (m, 1H), 5.19-5.12 (m, 1H), 4.65-4.43 (m, 4H), 4.37-4.25 (m, 1H), 4.23-4.11 (m, 1H), 3.64-3.55 (m, 1H), 1.72 (s, 3H), 1.58-1.19 (m, 37H), 0.93-0.85 (m, 3H). $^{19}$F NMR (376 MHz, Methanol-d4) δ−112.63--112.76 (m). $^{31}$P NMR (162 MHz, Methanol-d4) δ−7.57-7.94 (m). MS m/z [M+1]=951.2

Intermediate I-164: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-cyano-5-fluorobenzyl)oxy)icosyl) hydrogen phosphate To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)icosyl) phosphate, Intermediate I-163 (267 mg, 0.281 mmol, 1.0 equiv.) in THF (10.0 mL) was added 1,1,3,3-tetramethylguanidine (0.21 mL, 1.68 mmol, 6.0 equiv.) and syn-2-pyridinealdoxime (229 mg, 1.88 mmol, 6.68 equiv.). The reaction mixture was stirred at room temperature overnight. The solution was concentrated in vacuo and purified by silica gel (0-40% MeOH in DCM) to afford the title compound Intermediate I-164. $^1$H NMR (400 MHz, Methanol-d4) δ 7.82 (s, 1H), 7.51-7.47 (m, 1H), 7.43-7.33 (m, 2H), 6.83 (d, J=4.5 Hz, 1H), 6.78 (d, J=4.5 Hz, 1H), 5.63 (d, J=3.6 Hz, 1H), 5.26 (dd, J=6.6, 3.6 Hz, 1H), 5.13 (d, J=6.6 Hz, 1H), 4.73 (d, J=13.0 Hz, 2H), 4.51 (d, J=13.1 Hz, 1H), 4.17-4.07 (m, 2H), 3.95-3.82 (m, 2H), 3.59-3.50 (m, 1H), 1.69 (s, 3H), 1.48-1.19 (m, 37H), 0.89 (t, J=6.7 Hz, 3H). $^{19}$F NMR (376 MHz, Methanol-d4) δ−112.92--113.04 (m). $^{31}$P NMR (162 MHz, Methanol-d4) δ−0.32--0.74 (m). MS m/z [M+1]=841.2

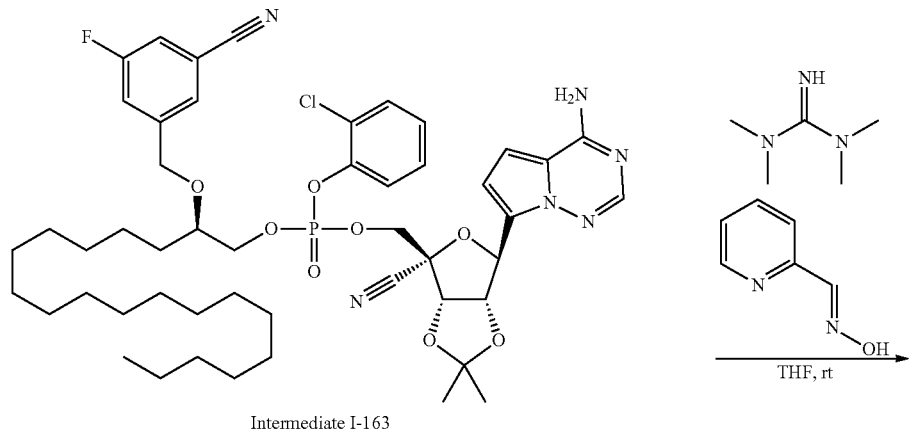

Intermediate I-163

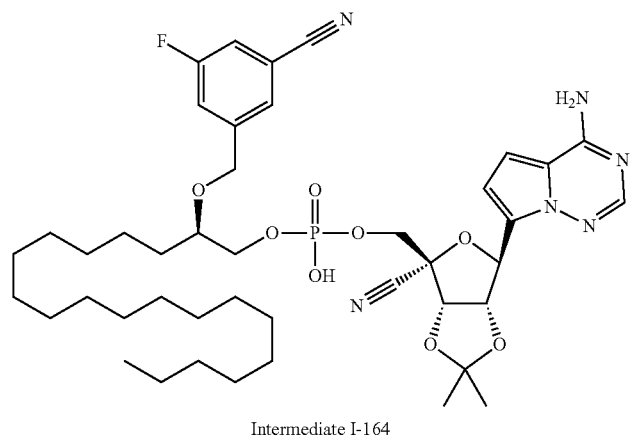

Intermediate I-164

Intermediate I-165: Octadecylmagnesium bromide

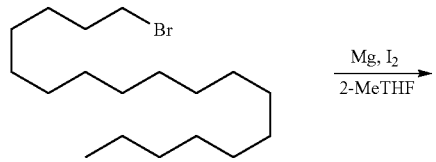

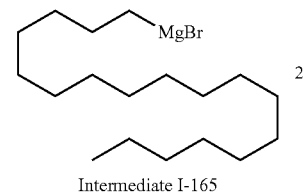

To a solution of Mg (3.4 g, 138.0 mmol, 1.2 eq) in 2-MeTHF (30 mL) was added I₂ (304.5 mg, 1.2 mmol, 241.7 uL, 0.01 eq) and BrCH₂CH₂Br (0.2 mL) under N₂. Then 1-bromooctadecane (4.0 g, 12.0 mmol) in 2-MeTHF (40 mL) was added dropwise. The mixture was stirred until the color of I₂ was faded to colorless. Then the remaining 1-bromooctadecane (36.0 g, 108.0 mmol) in 2-MeTHF (360 mL) was added and the mixture was stirred at 25° C. for 4 hr. The crude product octadecylmagnesium bromide, Intermediate I-165 as brown liquid (in 2-MeTHF) was used into the next step without further purification.

Intermediate I-166: (S)-1-(trityloxy)henicosan-2-ol

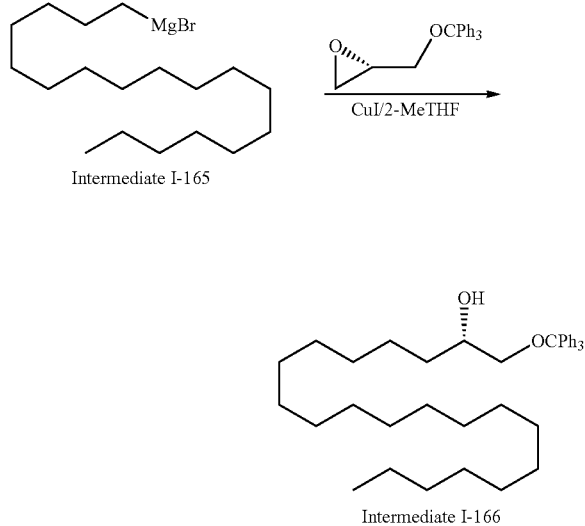

Add bromo(octadecyl)magnesium Intermediate I-165 (40.0 g, 111.8 mmol, 1.3 eq) over 10 min via cannula to mixture of (2S)-2-(trityloxymethyl)oxirane (27.2 g, 86.0 mmol, 1.0 eq), CuI (819.1 mg, 4.3 mmol, 0.05 eq) in 2-MeTHF (100 mL) at −20° C. Stirred vigorously for 5 min, warmed to 0° C., continue stirring 2 h. The reaction mixture was quenched by addition sat. NH₄Cl solution (500 mL), and then the mixture was extracted with Ethyl acetate (250 mL×3). The combined organic layers were washed with H₂O (450 mL×2), dried over Na₂SO₄, filtered and concentrated under reduced pressure to give a residue. The residue was purified by flash silica gel chromatography (Silica Flash Column, Eluent of 0~5% Ethyl acetate/Petroleum ether gradient @ 120 mL/min) to give compound (S)-1-(trityloxy) henicosan-2-ol, Intermediate I-166. ¹H NMR (400 MHz, CHLOROFORM-d) δ 7.41-7.36 (m, 6H), 7.27-7.16 (m, 9H), 3.75-3.66 (m, 1H), 3.16-3.08 (m, 1H), 3.03-2.92 (m, 1H), 2.26-2.20 (m, 1H), 1.36-1.29 (m, 2H), 1.23-1.16 (m, 34H), 0.86-0.80 (m, 3H).

Intermediate I-167: (R)-2-fluoro-4-((1-(trityloxy)henicosan-2-yl)oxy)benzonitrile

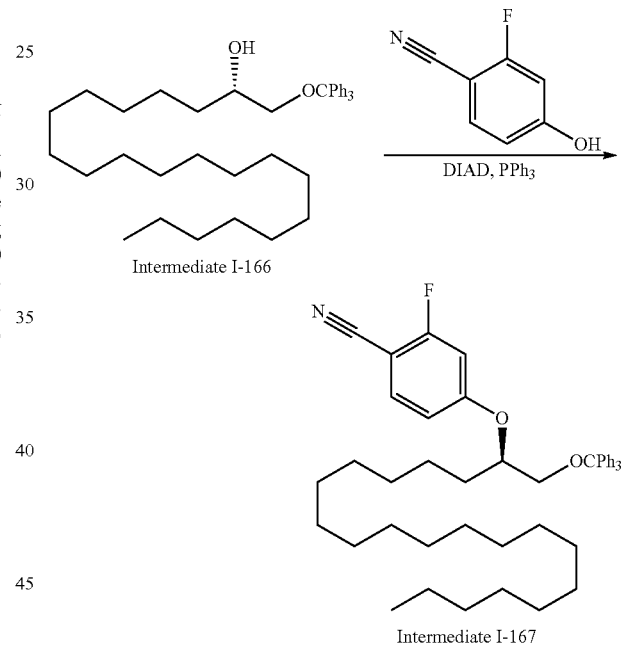

To a solution of (2S)-1-trityloxyhenicosan-2-ol, Intermediate I-166 (3.5 g, 6.1 mmol, 1 eq) in THF (30 mL) was added 2-fluoro-4-hydroxy-benzonitrile (1.0 g, 7.4 mmol, 1.2 eq) and PPh₃ (1.6 g, 6.1 mmol, 1 eq) under N₂. The mixture was cooled to 0° C. and DIAD (1.5 g, 7.4 mmol, 1.4 mL, 1.2 eq) in THF (10 mL) was added to above solution. The mixture was stirred at 20° C. for 12 hr. The reaction mixture was diluted with H₂O 60 mL and extracted with Ethyl acetate (40 mL×2). The combined organic layers were washed with H₂O (80 mL×2), dried over Na₂SO₄, filtered and concentrated under reduced pressure to give a residue. The residue was purified by flash silica gel chromatography (20 g Silica Flash Column, Eluent of 0~3% Ethyl acetate/ Petroleum ether gradient @ 45 mL/min) to give compound (R)-2-fluoro-4-((1-(trityloxy)henicosan-2-yl)oxy)benzonitrile, Intermediate I-167. ¹H NMR (400 MHz, CHLOROFORM-d) δ 7.41-7.36 (m, 1H), 7.29 (br d, J=7.0 Hz, 6H), 7.24-7.12 (m, 9H), 6.69-6.61 (m, 2H), 4.35-4.26 (m, 1H), 3.29-3.14 (m, 2H), 1.63-1.55 (m, 2H), 1.24-1.13 (m, 34H), 0.80 (t, J=6.7 Hz, 3H).

Intermediate I-168: (R)-2-fluoro-4-((1-hydroxyhen-icosan-2-yl)oxy)benzonitrile

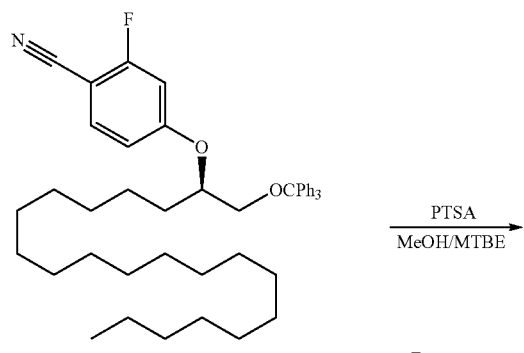

Intermediate I-167

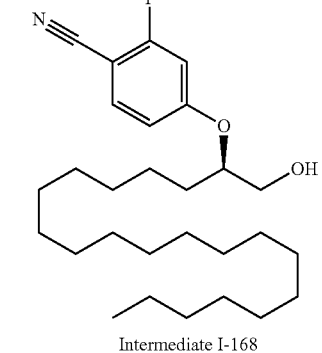

Intermediate I-168

To a solution of 2-fluoro-4-[(1R)-1-(trityloxymethyl) icosoxy]benzonitrile, Intermediate I-167 (2.9 g, 4.2 mmol, 1 eq) in MTBE (58 mL) and MeOH (8.7 mL) was added anisole (227.3 mg, 2.1 mmol, 228.4 uL, 0.5 eq) and PTSA (361.9 mg, 2.1 mmol, 0.5 eq) and the mixture was stirred at 50° C. for 2 hr. The reaction mixture was diluted with sat. NaHCO$_3$ 80 mL and extracted with Ethyl acetate (40 mL×3). The combined organic layers were washed with H$_2$O (50 mL×2), dried over Na$_2$SO$_4$, filtered and concentrated under reduced pressure to give a residue. The residue was purified by flash silica gel chromatography (20 g Silica Flash Column, Eluent of 0~8% Ethyl acetate/Petroleum ether gradient @ 80 mL/min) to give compound (R)-2-fluoro-4-((1-hydroxyhenicosan-2-yl)oxy)benzonitrile, Intermediate I-168. $^1$H NMR (400 MHz, CHLOROFORM-d) δ 7.50-7.36 (m, 1H), 6.80-6.58 (m, 2H), 4.32 (br d, J=4.4 Hz, 1H), 3.86-3.63 (m, 2H), 1.71-1.53 (m, 3H), 1.16 (br d, J=13.9 Hz, 34H), 0.91-0.74 (m, 3H). MS (ESI): m/z=448.3 [M+H]$^+$ Intermediate I-169: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-(4-cyano-3-fluorophenoxy) henicosyl) phosphate

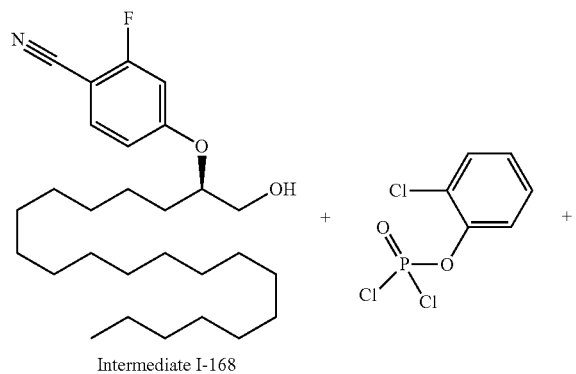

Intermediate I-168

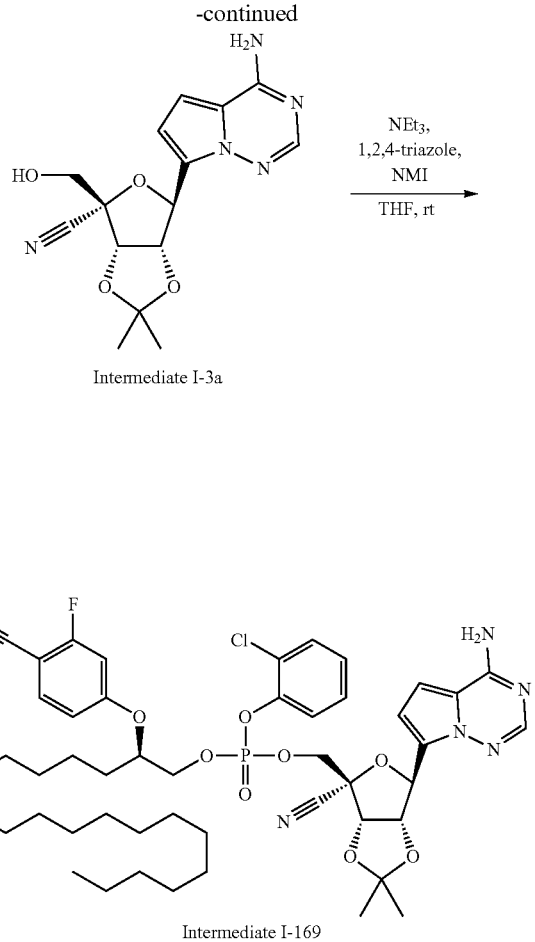

Intermediate I-3a

Intermediate I-169

1H-1,2,4-triazole (176 mg, 2.55 mmol, 4.75 equiv.) was dissolved in THF (10.0 mL). TEA (0.20 mL, 1.42 mmol, 2.65 equiv.) was added to the solution followed by 2-chlorophenyl phosphorodichloridate (0.15 mL, 0.912 mmol, 1.70 equiv.). The reaction mixture was stirred at rt for 4 min prior to the addition of (3aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (178 mg, 0.536 mmol, 1.0 equiv.) in one portion followed by 1-methylimidazole (0.06 mL, 0.753 mmol, 1.40 equiv.). The solution was stirred for an additional 12 min before adding (R)-2-fluoro-4-((1-hydroxyhenicosan-2-yl) oxy)benzonitrile, Intermediate I-168 (240 mg, 0.536 mmol, 1.0 equiv.). After stirring at room temperature for 2 h, the solution was diluted with EtOAc (100 mL) and water (100 mL). The aqueous layer was extracted again with EtOAc (100 mL). The organic layers were combined, washed with brine (50 mL), dried over MgSO$_4$, filtered and concentrated in vacuo prior to purification by silica gel chromatography (0-100% EtOAc in hexanes) to afford the title compound, Intermediate I-169. $^1$H NMR (400 MHz, Methanol-d4) δ 7.82-7.78 (m, 1H), 7.57-7.02 (m, 5H), 6.88-6.75 (m, 4H), 5.67-5.64 (m, 1H), 5.35-5.28 (m, 1H), 5.19 (d, J=6.5 Hz, 0.5H), 5.12 (d, J=6.6 Hz, 0.5H), 4.70-4.44 (m, 3H), 4.38-4.20 (m, 2H), 1.75-1.71 (m, 3H), 1.65-1.56 (m, 2H), 1.45-1.21 (m, 37H), 0.89 (t, J=6.8 Hz, 3H). $^{19}$F NMR (376 MHz, Methanol-d4) δ−107.58−−107.78 (m). $^{31}$P NMR (162 MHz, Methanol-d4) δ−7.68−−8.52 (m). MS m/z [M+1]=951.2

Intermediate I-170: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-(4-cyano-3-fluorophenoxy)henicosyl) hydrogen phosphate

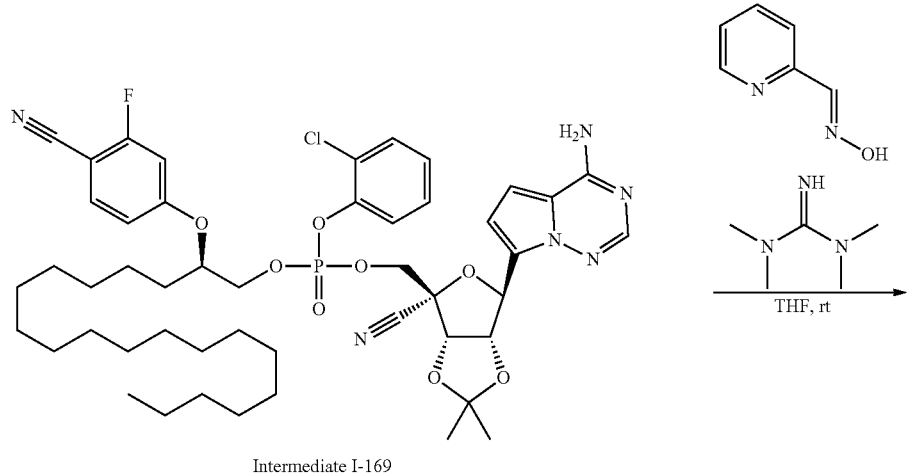

Intermediate I-169

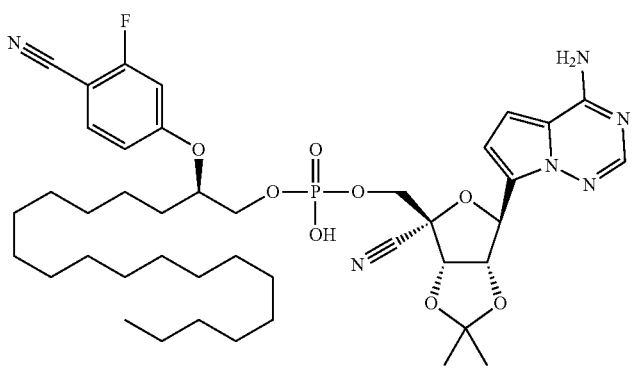

Intermediate I-170

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-(4-cyano-3-fluorophenoxy)henicosyl) phosphate, Intermediate I-169 (234 mg, 0.246 mmol, 1.0 equiv.) in THF (10.0 mL) was added 1,1,3,3-tetramethylguanidine (0.18 mL, 1.48 mmol, 6.0 equiv.) and syn-2-pyridinealdoxime (215 mg, 1.76 mmol, 7.16 equiv.). The reaction mixture was stirred at room temperature overnight. The solution was concentrated in vacuo and purified by silica gel (0-40% MeOH in DCM) to afford the title compound, Intermediate I-170. $^1$H NMR (400 MHz, Methanol-d4) δ 7.83 (s, 1H), 7.56-7.48 (m, 1H), 6.93-6.82 (m, 3H), 6.79 (d, J=4.5 Hz, 1H), 5.64 (d, J=3.6 Hz, 1H), 5.27 (dd, J=6.6, 3.6 Hz, 1H), 5.11 (d, J=6.6 Hz, 1H), 4.59-4.50 (m, 1H), 4.13-4.02 (m, 2H), 4.00-3.89 (m, 2H), 1.70 (s, 3H), 1.67-1.48 (m, 2H), 1.46-1.19 (m, 37H), 0.94-0.86 (m, 3H). $^{19}$F NMR (376 MHz, Methanol-d4) δ −108.02−−108.19 (m). $^{31}$P NMR (162 MHz, Methanol-d4) δ −0.47−−1.27 (m). MS m/z [M+1]=841.2

Intermediate I-171: Tridecylmagnesium bromide

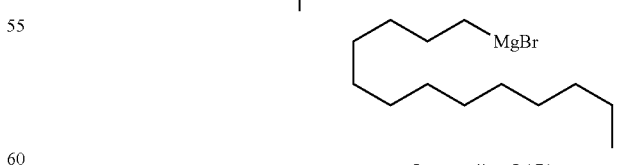

Intermediate I-171

To a solution of Mg (1.5 g, 65.5 mmol, 1.1 eq) in 2-MeTHF (50 mL) was added I$_2$ (144.6 mg, 569.7 umol, 114.7 uL, 0.01 eq) and BrCH$_2$CH$_2$Br (10.9 g, 56.9 mmol, 0.1 mL, 1.0 eq) under N$_2$. Then 1/10 of 1-bromotridecane (1.5 g, 5.7 mmol, 1.5 mL, 0.1 eq) in 2-MeTHF (150 mL) was added dropwise. The mixture was stirred until the color of I₂ was faded to colorless. Then the remaining 1-bromotridecane, Intermediate I-171 (13.5 g, 51.3 mmol, 13.5 mL, 0.9 eq) in 2-MeTHF (150 mL) was added and the mixture was stirred at 25° C. for 4 hr. The crude solution as a gray solution was used into the next step without further purification.

Intermediate I-172: (S)-1-(trityloxy)hexadecan-2-ol

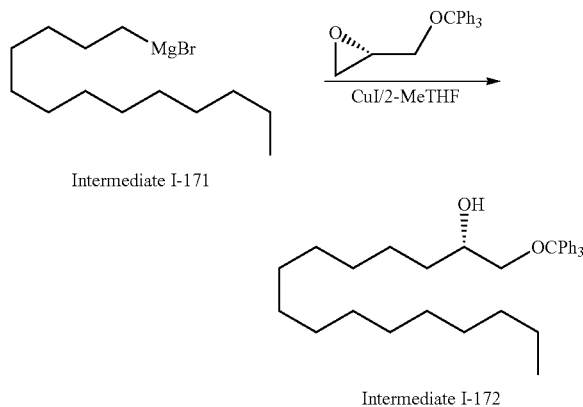

Add tridecylmagnesium bromide, Intermediate I-171 (14.1 g, 49.3 mmol, 1.3 eq) over 30 min via cannula to mixture of (2S)-2-(trityloxymethyl)oxirane (12 g, 37.9 mmol, 1 eq), CuI (361.1 mg, 1.9 mmol, 0.05 eq) in 2-MeTHF (100 mL) at −20° C., warmed to 0° C. The mixture was stirred at 0° C. for 1 hr and stirred at 20° C. for 12 hr. The reaction mixture was quenched by addition sat. NH₄Cl 20 mL at 0° C., and extracted with ethyl acetate (15 mL×3). The combined organic layers were washed with NaCl (10 mL×3), dried over Na₂SO₄, filtered and concentrated under reduced pressure to give a residue. The residue was purified by column chromatography (SiO₂, Petroleum ether/ethyl acetate=100/3 to 100/6) to give (S)-1-(trityloxy)hexadecan-2-ol, Intermediate I-172. ¹H NMR (400 MHz, CHLOROFORM-d) δ 7.48 (br d, J=7.6 Hz, 6H), 7.39-7.25 (m, 11H), 3.88-3.74 (m, 1H), 3.25-3.17 (m, 1H), 3.11-3.01 (m, 1H), 2.35 (d, J=3.4 Hz, 1H), 1.40-1.23 (m, 26H), 0.92 (t, J=6.7 Hz, 3H).

Intermediate I-173: (S)-3-fluoro-5-(((1-(trityloxy)hexadecan-2-yl)oxy)methyl)benzonitrile

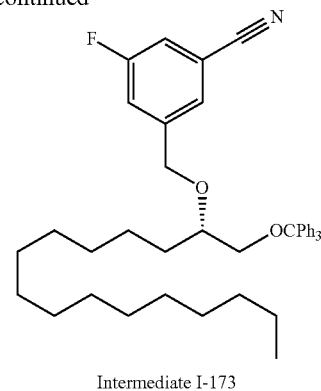

To a solution of (S)-1-(trityloxy)hexadecan-2-ol, Intermediate I-172 (2.5 g, 4.9 mmol, 1 eq) in THF (20 mL) was added NaH (599.1 mg, 14.9 mmol, 60% purity, 3 eq) at 0° C. The mixture was stirred at 0° C. for 0.5 hr and then 3-(bromomethyl)-5-fluoro-benzonitrile (1.6 g, 7.4 mmol, 1.5 eq) was added into the above solution at 0° C. The mixture was stirred at 65° C. for 12 hr. The reaction mixture was quenched by added into sat. NH₄Cl 50 mL at 0° C., and extracted with ethyl acetate (20 mL×3). The combined organic layers were washed with NaCl (20 mL×3), dried over Na₂SO₄, filtered and concentrated under reduced pressure to give a residue. The residue was purified by column chromatography (SiO₂, Petroleum ether/MTBE=100/0 to 10/1) to give (S)-3-fluoro-5-(((1-(trityloxy)hexadecan-2-yl)oxy)methyl)benzonitrile Intermediate I-173. ¹H NMR (400 MHz, CHLOROFORM-d) δ 7.41-7.32 (m, 6H), 7.32-7.09 (m, 12H), 4.74-4.54 (m, 1H), 4.54-4.39 (m, 1H), 3.53-3.35 (m, 1H), 3.13 (d, J=4.8 Hz, 2H), 1.45 (br d, J=4.4 Hz, 2H), 1.26-1.12 (m, 26H), 0.81 (br t, J=6.8 Hz, 3H).

Intermediate I-174: (S)-3-fluoro-5-(((1-hydroxyhexadecan-2-yl)oxy)methyl)benzonitrile

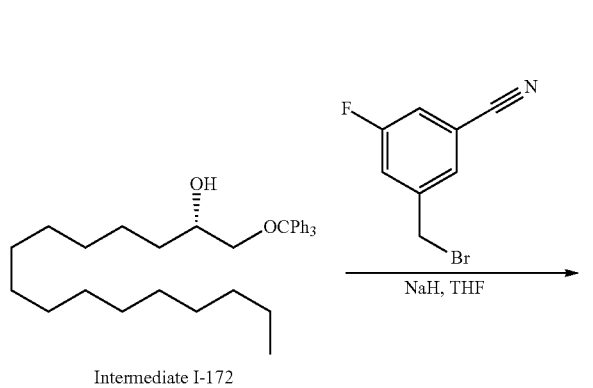

-continued

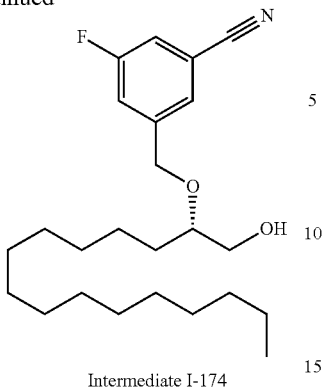

Intermediate I-174

-continued

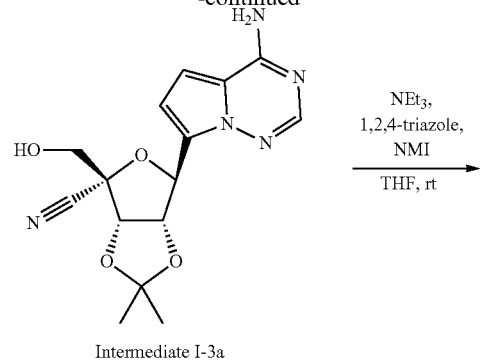

Intermediate I-3a

To a solution of (S)-3-fluoro-5-(((1-(trityloxy)hexadecan-2-yl)oxy)methyl)benzonitrile, Intermediate I-173 (2 g, 3.1 mmol, 1 eq) in MTBE (30 mL) was added anisole (341.2 mg, 3.1 mmol, 342.9 uL, 1 eq), MeOH (4.8 mL) and 4-methylbenzenesulfonic acid (543.3 mg, 3.1 mmol, 1 eq). The mixture was stirred at 50° C. for 3 hr. The reaction mixture was concentrated under reduced pressure to remove solvent. The residue was diluted with 30 mL ethyl acetate, washed with NaCl (20 mL×3), dried over Na$_2$SO$_4$, filtered and concentrated under reduced pressure to give a residue. The residue was purified by column chromatography (SiO$_2$, Petroleum ether/Ethyl acetate=100/0 to 3/1) to give (S)-3-fluoro-5-(((1-hydroxyhexadecan-2-yl)oxy)methyl)benzonitrile, Intermediate I-174. $^1$H NMR (400 MHz, CHLOROFORM-d) δ 7.46 (s, 1H), 7.37-7.27 (m, 2H), 4.64 (s, 2H), 3.78-3.73 (m, 1H), 3.65-3.59 (m, 1H), 3.56-3.50 (m, 1H), 1.79 (br s, 1H), 1.67-1.55 (m, 2H), 1.26 (s, 24H), 0.89 (t, J=6.7 Hz, 3H). MS (ESI): m/z=414.2 [M+Na]$^+$ Intermediate I-175: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl (2-chlorophenyl) ((S)-2-((3-cyano-5-fluorobenzyl)oxy)hexadecyl) phosphate

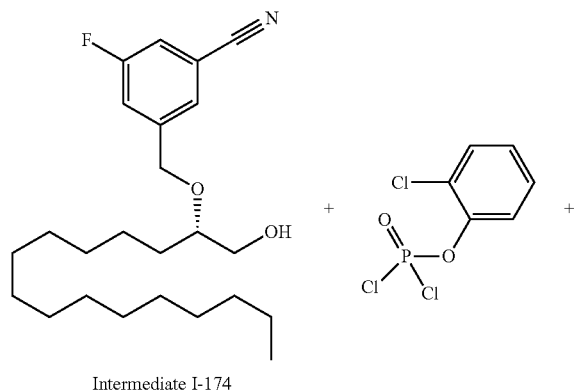

Intermediate I-174

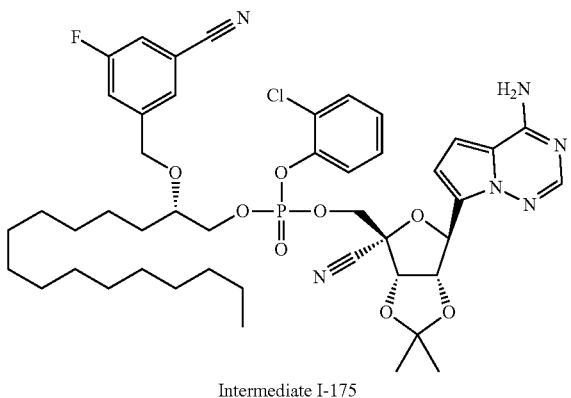

Intermediate I-175

1H-1,2,4-triazole (145 mg, 2.10 mmol, 3.92 equiv.) was dissolved in THF (10.0 mL). TEA (0.30 mL, 2.14 mmol, 4.0 equiv.) was added to the solution followed by 2-chlorophenyl phosphorodichloridate (0.15 mL, 0.912 mmol, 1.70 equiv.). The reaction mixture was stirred at rt for 8 min prior to the addition of (3aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (178 mg, 0.536 mmol, 1.0 equiv.) in one portion followed by 1-methylimidazole (0.10 mL, 1.25 mmol, 2.34 equiv.). The solution was stirred for an additional 8 min before adding (S)-3-fluoro-5-(((1-hydroxyhexadecan-2-yl)oxy)methyl)benzonitrile, Intermediate I-174 (210 mg, 0.536 mmol, 1.0 equiv.). After stirring at room temperature overnight, the solution was diluted with EtOAc (100 mL) and water (100 mL). The aqueous layer was extracted again with EtOAc (100 mL). The organic layers were combined, washed with brine, dried over MgSO$_4$, filtered and concentrated in vacuo prior to purification by silica gel chromatography (0-100% EtOAc in hexanes) to afford the title compound, Intermediate I-175. $^1$H NMR (400 MHz, Methanol-d4) δ 7.81-7.78 (m, 1H), 7.48-7.30 (m, 5H), 7.20-7.07 (m, 2H), 6.85-6.80 (m, 1H), 6.78-6.74 (m, 1H), 5.66-5.62 (m, 1H), 5.34-5.27 (m, 1H), 5.17 (d, J=6.6 Hz, 0.5H), 5.12 (d, J=6.6 Hz, 0.5H), 4.65-4.48 (m, 4H), 4.38-4.27 (m, 1H), 4.20-4.06 (m, 1H), 3.66-3.57 (m, 1H), 1.74-1.69 (m, 3H), 1.58-1.18 (m, 29H), 0.89 (t, J=6.7 Hz, 3H). $^{19}$F NMR (376 MHz, Methanol-d4) δ−112.67---112.83 (m). $^{31}$P NMR (162 MHz, Methanol-d4) δ−7.40--8.14 (m). MS m/z [M+1]=895.0

Intermediate I-176: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl)oxy)hexadecyl) hydrogen phosphate

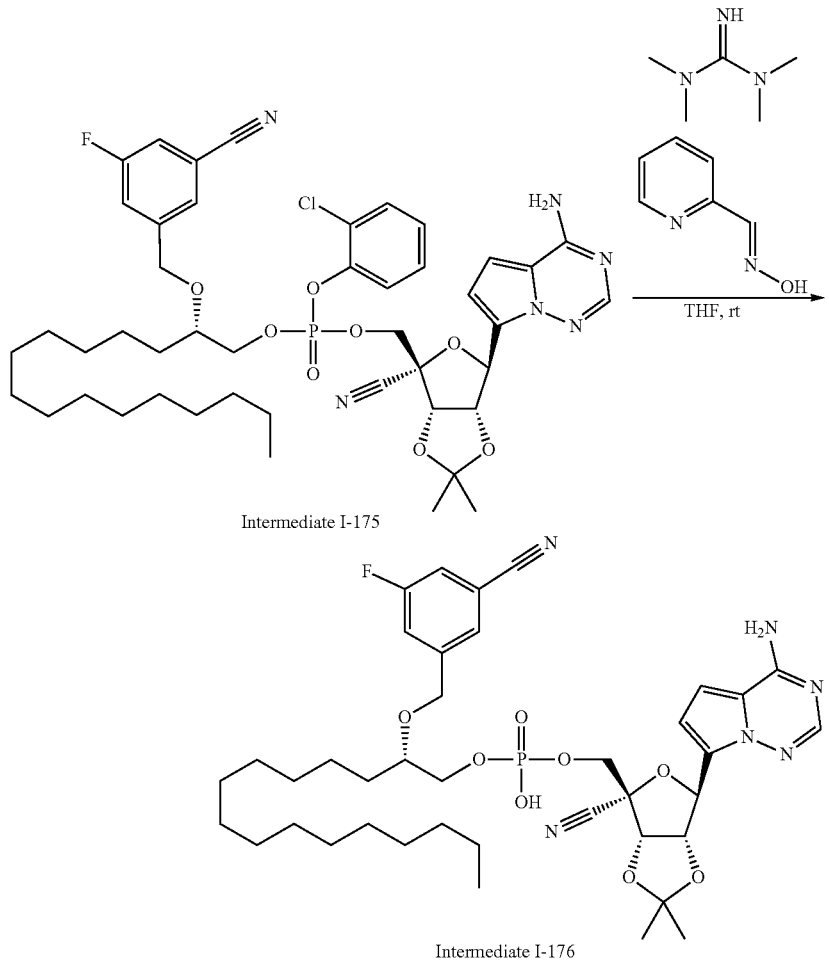

To a solution of ((3aS,4R,6S,6aS)-6-(4-aminopyrrolo[2,1-f][1,2,4]triazin-7-yl)-4-cyano-2,2-dimethyltetrahydrofuro [3,4-d][1,3]dioxol-4-yl)methyl (2-chlorophenyl) ((S)-2-((3-cyano-5-fluorobenzyl)oxy)hexadecyl) phosphate, Intermediate I-175 (306 mg, 0.342 mmol, 1.0 equiv.) in THF (10.0 mL) was added 1,1,3,3-tetramethylguanidine (0.09 mL, 0.683 mmol, 2.0 equiv.) and syn-2-pyridinealdoxime (250 mg, 2.05 mmol, 6.0 equiv.). The reaction mixture was stirred at room temperature overnight. The solution was concentrated in vacuo and purified by silica gel (0-40% MeOH in DCM) to afford the title compound Intermediate I-176. $^1$H NMR (400 MHz, Methanol-d4) δ 7.83 (s, 1H), 7.51-7.48 (m, 1H), 7.43-7.33 (m, 2H), 6.83 (d, J=4.5 Hz, 1H), 6.80 (d, J=4.5 Hz, 1H), 5.63 (d, J=3.6 Hz, 1H), 5.27 (dd, J=6.6, 3.7 Hz, 1H), 5.13 (d, J=6.6 Hz, 1H), 4.73 (d, J=13.0 Hz, 1H), 4.49 (d, J=12.9 Hz, 1H), 4.16-4.06 (m, 2H), 3.97-3.81 (m, 2H), 3.61-3.53 (m, 1H), 1.69 (s, 3H), 1.48-1.19 (m, 29H), 0.92-0.86 (m, 3H). $^{19}$F NMR (376 MHz, Methanol-d4) δ−112.95−−113.06 (m). $^{31}$P NMR (162 MHz, Methanol-d4) δ−0.13−−1.09 (m). MS m/z [M+1]=785.2

Intermediate I-177: Heptadecylmagnesium bromide

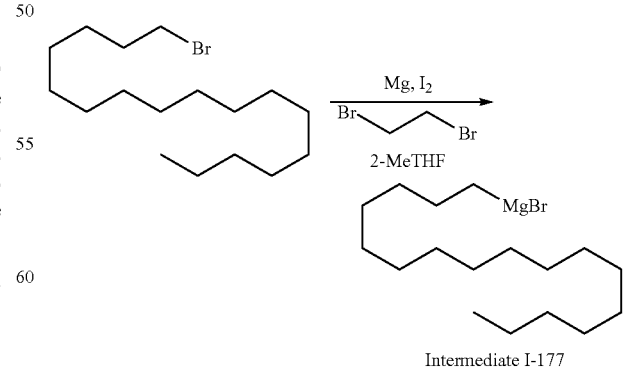

To a solution of Mg (875.2 mg, 36.0 mmol, 1.15 eq) in 2-MeTHF (30 mL) was added I$_2$ (79.5 mg, 313.1 umol, 63.1 uL, 0.01 eq) and BrCH$_2$CH$_2$Br (0.2 mL) under N$_2$. Then 1-bromoheptadecane (1.0 g, 3.1 mmol) in 2-MeTHF (10 mL) was added dropwise. The mixture was stirred until the color of I$_2$ was faded to colorless. Then the remaining 1-bromoheptadecane (9.0 g, 28.2 mmol) in 2-MeTHF (90 mL) was added and the mixture was stirred at 25° C. for 4 hr. The crude product heptadecylmagnesium bromide, Intermediate I-177 as brown liquid (in 2-MeTHF) was used into the next step without further purification.

Intermediate I-178: (S)-1-(trityloxy)icosan-2-ol

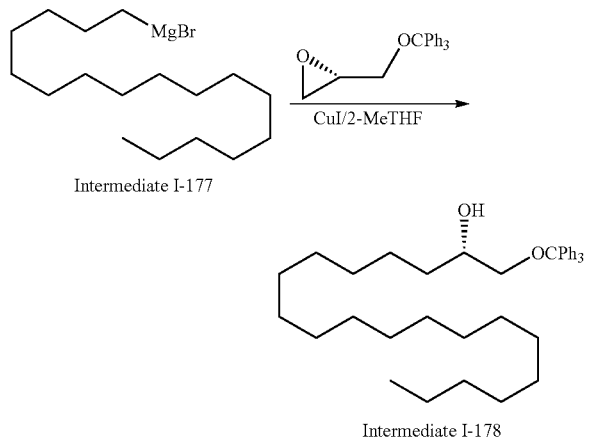

Add bromo(heptadecyl)magnesium (10.0 g, 29.1 mmol, 1.3 eq) over 10 min via cannula to mixture of (2S)-2-(trityloxymethyl)oxirane (7.1 g, 22.4 mmol, 1.0 eq), CuI (213.1 mg, 1.1 mmol, 0.05 eq) in 2-MeTHF (40 mL) at −20° C. Stirred vigorously 5 min, warmed to 0° C., continue stirring 2 h. The reaction mixture was quenched by addition sat. NH$_4$Cl solution (200 mL), and then the mixture was extracted with Ethyl acetate (100 mL×3). The combined organic layers were washed with H$_2$O (150 mL×2), dried over Na$_2$SO$_4$, filtered and concentrated under reduced pressure to give a residue. The residue was purified by flash silica gel chromatography (40 g Silica Flash Column, Eluent of 0~3% Ethyl acetate/Petroleum ether gradient @ 80 mL/min) to give compound (S)-1-(trityloxy)icosan-2-ol, Intermediate I-178. $^1$H NMR (400 MHz, CHLOROFORM-d) δ 7.38 (d, J=7.4 Hz, 6H), 7.26-7.16 (m, 9H), 3.76-3.65 (m, 1H), 3.12 (dd, J=3.2, 9.3 Hz, 1H), 2.96 (dd, J=7.8, 9.1 Hz, 1H), 2.29-2.20 (m, 1H), 1.31 (br s, 2H), 1.25-1.15 (m, 32H), 0.83 (t, J=6.8 Hz, 3H).

Intermediate I-179: (S)-3-chloro-5-(((1-(trityloxy)icosan-2-yl)oxy)methyl)benzonitrile

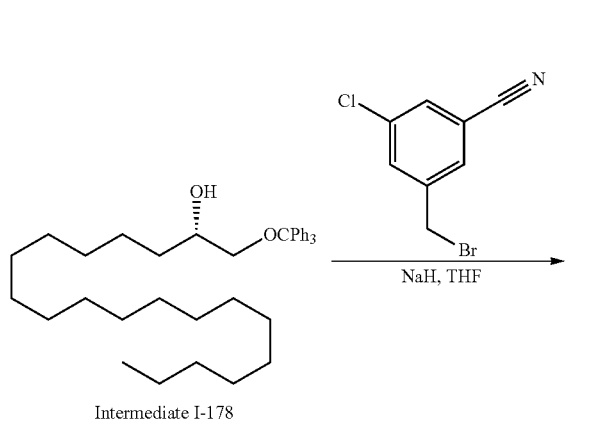

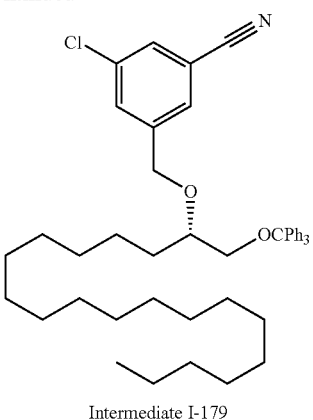

Intermediate I-179

To a solution of (2S)-1-trityloxyicosan-2-ol, Intermediate I-178 (2.5 g, 4.5 mmol, 1.0 eq) in THF (35 mL) was added NaH (448.9 mg, 11.2 mmol, 60% purity, 2.5 eq) at 0° C. and the mixture was stirred at 0° C. for 30 min. Then 3-(bromomethyl)-5-chloro-benzonitrile (1.2 g, 5.4 mmol, 1.2 eq) was added and the mixture was stirred at 65° C. for 12 hr. The reaction mixture was quenched by addition sat. NH$_4$Cl solution (60 ml) at 20° C. and extracted with Ethyl acetate (30 mL×3). The combined organic layers were washed with H$_2$O (60 mL×2), dried over Na$_2$SO$_4$, and concentrated under reduced pressure to give a residue. The residue was purified by flash silica gel chromatography (20 g Silica Flash Column, Eluent of 0~3% Ethyl acetate/Petroleum ether gradient @ 45 mL/min) to give compound (S)-3-chloro-5-(((1-(trityloxy)icosan-2-yl)oxy)methyl)benzonitrile, Intermediate I-179. $^1$H NMR (400 MHz, CHLOROFORM-d) δ 7.53 (s, 1H), 7.48 (s, 1H), 7.45 (s, 1H), 7.43-7.37 (m, 6H), 7.27 (s, 9H), 4.70-4.62 (m, 1H), 4.50 (d, J=12.8 Hz, 1H), 3.53-3.41 (m, 1H), 3.17 (d, J=4.9 Hz, 2H), 1.53-1.44 (m, 2H), 1.26-1.18 (m, 32H), 0.84 (t, J=6.8 Hz, 3H).

Intermediate I-180: (S)-3-chloro-5-(((1-hydroxyicosan-2-yl)oxy)methyl)benzonitrile

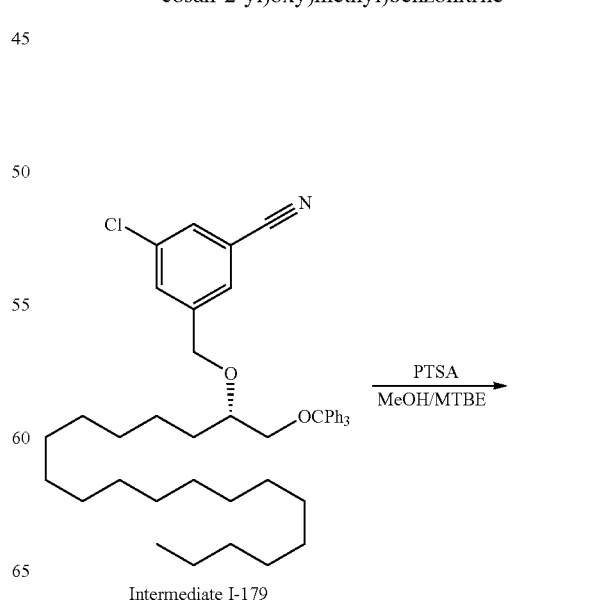

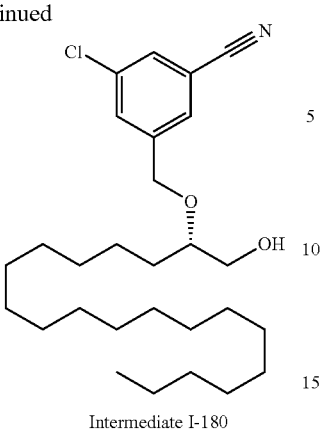

Intermediate I-180

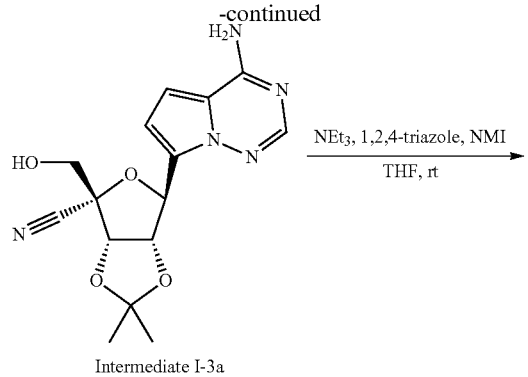

Intermediate I-3a

To a solution of 3-chloro-5-[[(1S)-1-(trityloxymethyl)nonadecoxy]methyl]benzonitrile, Intermediate I-179 (1.9 g, 2.7 mmol, 1.0 eq) in MTBE (40 mL) and MeOH (6 mL) was added anisole (145.4 mg, 1.3 mmol, 146.2 uL, 0.5 eq) and PTSA (231.6 mg, 1.3 mmol, 0.5 eq) and the mixture was stirred at 50° C. for 2 hr. The reaction mixture was diluted with sat. NaHCO$_3$ 80 mL and extracted with Ethyl acetate (40 mL×3). The combined organic layers were washed with H$_2$O (50 mL×2), dried over Na$_2$SO$_4$, filtered and concentrated under reduced pressure to give a residue. The residue was purified by flash silica gel chromatography (12 g Silica Flash Column, Eluent of 0~8% Ethyl acetate/Petroleum ether gradient @ 45 mL/min) to give compound (S)-3-chloro-5-(((1-hydroxyicosan-2-yl)oxy)methyl)benzonitrile, Intermediate I-180. $^1$H NMR (400 MHz, CHLOROFORM-d) δ 7.59 (s, 1H), 7.55 (d, J=2.0 Hz, 2H), 4.62 (s, 2H), 3.75 (dd, J=3.2, 11.6 Hz, 1H), 3.65-3.58 (m, 1H), 3.56-3.48 (m, 1H), 1.82 (br s, 1H), 1.64-1.50 (m, 2H), 1.26 (s, 32H), 0.88 (t, J=6.8 Hz, 3H). MS (ESI): ink=486.2 [M+Na]$^+$ Intermediate I-181: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-((3-chloro-5-cyanobenzyl)oxy)icosyl) (2-chlorophenyl) phosphate

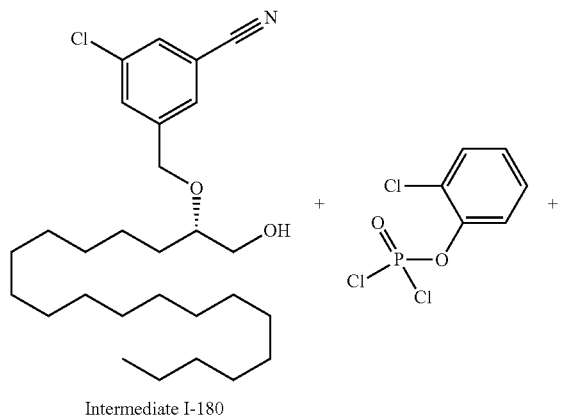

Intermediate I-180

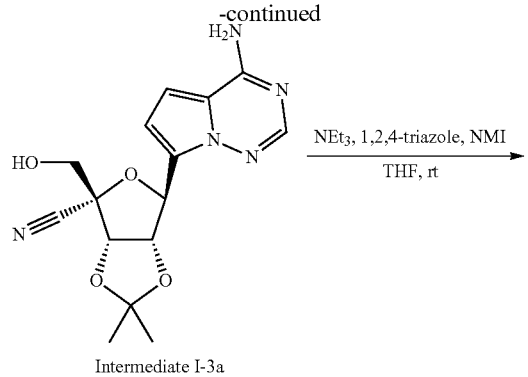

Intermediate I-181

1H-1,2,4-triazole (145 mg, 2.10 mmol, 3.92 equiv.) was dissolved in THF (10.0 mL). TEA (0.30 mL, 2.14 mmol, 4.0 equiv.) was added to the solution followed by 2-chlorophenyl phosphorodichloridate (0.15 mL, 0.912 mmol, 1.70 equiv.). The reaction mixture was stirred at rt for 10 min prior to the addition of (3aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (178 mg, 0.536 mmol, 1.0 equiv.) in one portion followed by 1-methylimidazole (0.10 mL, 1.25 mmol, 2.34 equiv.). The solution was stirred for an additional 12 min before adding (S)-3-chloro-5-(((1-hydroxyicosan-2-yl)oxy)methyl)benzonitrile, Intermediate I-180 (249 mg, 0.536 mmol, 1.0 equiv.). After stirring at room temperature for 2 h and 20 min, the solution was diluted with EtOAc (100 mL) and water (100 mL). The aqueous layer was extracted again with EtOAc (100 mL). The organic layers were combined, washed with brine, dried over MgSO$_4$, filtered and concentrated in vacuo prior to purification by silica gel chromatography (0-100% EtOAc in hexanes) to afford the title compound Intermediate I-181. $^1$H NMR (400 MHz, Methanol-d4) δ 7.81-7.78 (m, 1H), 7.65-7.59 (m, 2H), 7.57-7.54 (m, 1H), 7.46-7.30 (m, 2H), 7.21-7.07 (m, 2H), 6.85-6.80 (m, 1H), 6.79-6.73 (m, 1H), 5.67-5.61 (m, 1H), 5.34-5.26 (m, 1H), 5.17 (d, J=6.6 Hz, 0.5H), 5.12 (d, J=6.6 Hz, 0.5H), 4.64-4.45 (m, 4H), 4.38-4.26 (m, 1H), 4.21-4.06 (m, 1H), 3.66-3.55 (m, 1H), 1.74-1.68 (m, 3H), 1.58-1.17 (m, 37H), 0.93-0.84 (m, 3H). $^{31}$P NMR (162 MHz, Methanol-d4) δ −7.40--8.17 (m). MS m/z [M+1]=967.1

Intermediate I-182: ((3aS,4R,6S,6aS)-6-(4-aminopy-rrolo[2,1-f][1,2,4]triazin-7-yl)-4-cyano-2,2-dimeth-yltetrahydrofuro[3,4-d][1,3]dioxol-4-yl)methyl ((S)-2-((3-chloro-5-cyanobenzyl)oxy)icosyl) hydrogen phosphate

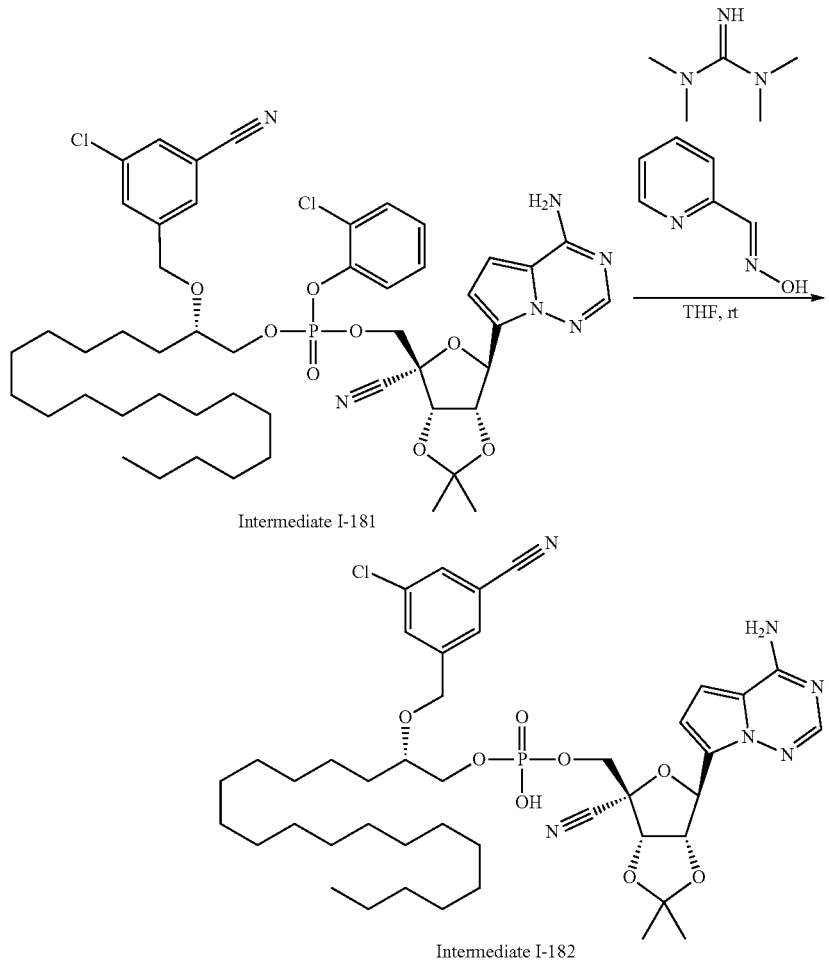

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-((3-chloro-5-cyanobenzyl)oxy)icosyl) (2-chlorophenyl) phosphate, Intermediate I-181 (354 mg, 0.366 mmol, 1.0 equiv.) in THF (10.0 mL) was added syn-2-pyridinealdoxime (268 mg, 2.19 mmol, 6.0 equiv.). The reaction mixture was stirred at room temperature overnight. 1,1,3,3-tetramethylguanidine (0.09 mL, 0.731 mmol, 2.0 equiv.) was added and the solution was stirred again at room temperature overnight. The reaction mixture was concentrated in vacuo and purified by silica gel (0-40% MeOH in DCM) to afford the title compound Intermediate I-182. $^1$H NMR (400 MHz, Methanol-d4) δ 7.83 (s, 1H), 7.66-7.56 (m, 3H), 6.88-6.76 (m, 2H), 5.63 (d, J=3.7 Hz, 1H), 5.26 (dd, J=6.6, 3.7 Hz, 1H), 5.12 (d, J=6.6 Hz, 1H), 4.72 (d, J=12.9 Hz, 1H), 4.47 (d, J=12.9 Hz, 1H), 4.17-4.06 (m, 2H), 3.97-3.81 (m, 2H), 3.61-3.52 (m, 1H), 1.69 (s, 3H), 1.51-1.18 (m, 37H), 0.89 (t, J=6.7 Hz, 3H). $^{31}$P NMR (162 MHz, Methanol-d4) δ–0.28--1.06 (m). MS m/z [M+1]=857.2

Intermediate I-183: (S)-4-((hexadecyloxy)methyl)-2,2-dimethyl-1,3-dioxolane

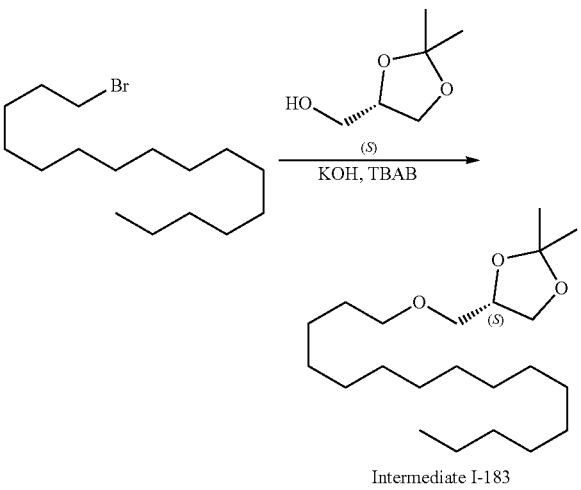

To a solution of 1-bromohexadecane (5 g, 16.3 mmol, 5.0 mL, 1 eq) in [(4S)-2,2-dimethyl-1,3-dioxolan-4-yl]methanol (10 g, 75.6 mmol, 9.3 mL, 4.6 eq) were added KOH (2.3 g, 40.9 mmol, 2.5 eq) and TBAB (1.06 g, 3.2 mmol, 0.2 eq). The mixture was stirred at 40° C. for 12 hr, diluted with H₂O (20 mL), and extracted with ethyl acetate (20 mL×3). The combined organic layers were washed with brine (20 mL), dried over Na₂SO₄, filtered, and concentrated under reduced pressure to give a residue. The residue was purified by column chromatography (SiO₂, Petroleum ether/Ethyl acetate=100/1 to 100/5) to give (S)-4-((hexadecyloxy) methyl)-2,2-dimethyl-1,3-dioxolane, Intermediate I-183. ¹H NMR (400 MHz, CHLOROFORM-d) δ 4.33-4.23 (m, 1H), 4.13-4.02 (m, 1H), 3.80-3.69 (m, 1H), 3.59-3.38 (m, 4H), 1.62-1.51 (m, 2H), 1.46-1.25 (m, 32H), 0.89 (t, J=6.8 Hz, 3H)

Intermediate I-184:
(R)-3-(hexadecyloxy)propane-1,2-diol

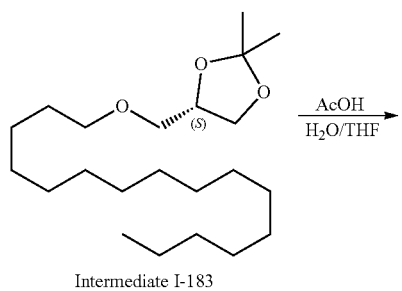

Intermediate I-183

(S)-4-((hexadecyloxy)methyl)-2,2-dimethyl-1,3-dioxolane, Intermediate I-183 (5.3 g, 14.8 mmol, 1 eq) was dissolved in a solution of THF (50 mL), H₂O (40 mL), and AcOH (63.0 g, 1.05 mol, 60 mL, 70.5 eq). The mixture was stirred at 50° C. for 12 hr and concentrated under high vacuum to remove solvent to give crude product (R)-3-(hexadecyloxy)propane-1,2-diol, Intermediate I-184. ¹H NMR (400 MHz, CHLOROFORM-d) δ 3.90-3.85 (m, 1H), 3.76-3.64 (m, 2H), 3.57-3.43 (m, 4H), 1.63-1.54 (m, 2H), 1.35-1.20 (m, 26H), 0.89 (t, J=6.7 Hz, 3H)

Intermediate I-185: (S)-1-(hexadecyloxy)-3-(trityloxy)propan-2-ol

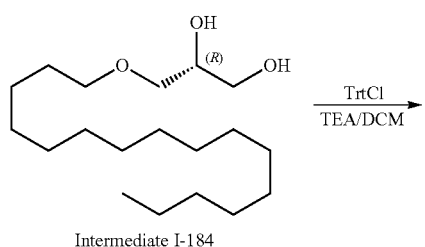

Intermediate I-184

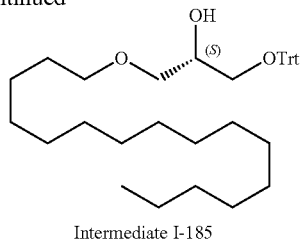

Intermediate I-185

(R)-3-(hexadecyloxy)propane-1,2-diol (5.2 g, 14.7 mmol, 90% purity, 1 eq) was dissolved in a solution of DCM (80 mL), then TEA (2.6 g, 26.6 mmol, 3.7 mL, 1.8 eq) added, and the mixture stirred at 0° C. for 0.5 hr. TrtCl (3.9 g, 14.0 mmol, 0.9 eq) was then added at 0° C. The mixture was stirred at 20° C. for 12 hrs, diluted with DCM (20 mL), washed with H₂O (50 mL×3), dried over Na₂SO₄, filtered, and concentrated under reduced pressure to give a residue. The residue was purified by column chromatography (SiO₂, Petroleum ether/Ethyl acetate=100/1 to 100/6) to give (S)-1-(hexadecyloxy)-3-(trityloxy)propan-2-ol, Intermediate I-185. ¹H NMR (400 MHz, CHLOROFORM-d) δ 7.40-7.30 (m, 6H), 7.28-7.13 (m, 9H), 3.94-3.82 (m, 1H), 3.51-3.30 (m, 4H), 3.19-3.04 (m, 2H), 2.33 (d, J=4.5 Hz, 1H), 1.52-1.41 (m, 2H), 1.30-1.10 (m, 26H), 0.81 (t, J=6.8 Hz, 3H)

Intermediate I-186: (S)-3-fluoro-5-(((1-(hexadecyloxy)-3-(trityloxy)propan-2-yl)oxy)methyl)benzonitrile

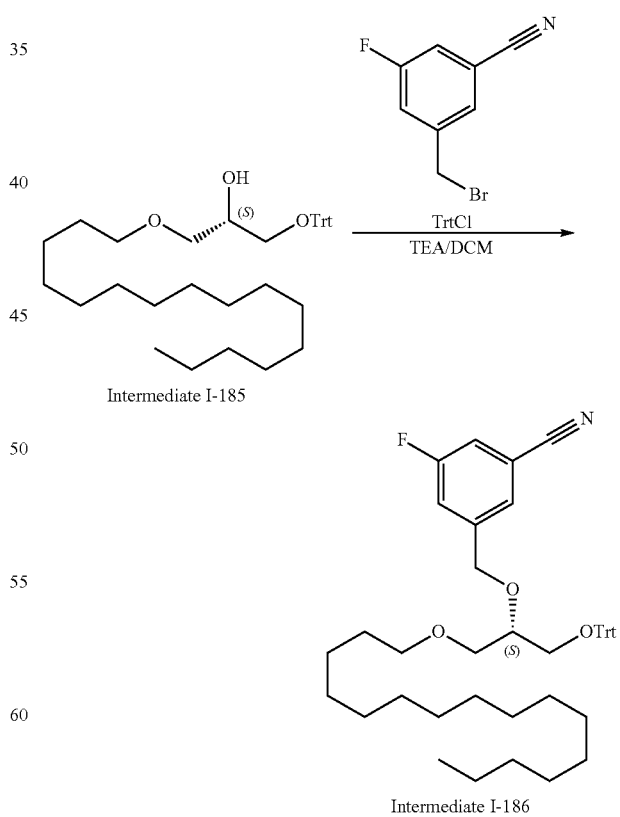

Intermediate I-186

To a solution of (S)-1-(hexadecyloxy)-3-(trityloxy)propan-2-ol, Intermediate I-185 (2 g, 3.5 mmol, 615.7 uL, 1 eq)

in THF (30 mL) was added NaH (429.4 mg, 10.7 mmol, 60% purity, 3 eq) at 0° C. The mixture was stirred at 0° C. for 0.5 hr and then 3-(bromomethyl)-5-fluoro-benzonitrile (1.53 g, 7.16 mmol, 2 eq) was added at 0° C. The mixture was stirred at 65° C. for 12 hr, diluted with sat NH₄Cl solution (20 mL) at 0° C., and extracted with ethyl acetate (30 mL×3). The combined organic layers were washed with brine (20 mL×3), dried over Na₂SO₄, filtered, and concentrated under reduced pressure to give a residue. The residue was purified by column chromatography (SiO₂, Petroleum ether/MTBE=100/1 to 15/1) to give (S)-3-fluoro-5-(((1-(hexadecyloxy)-3-(trityloxy)propan-2-yl)oxy)methyl)benzonitrile, Intermediate I-186. ¹H NMR (400 MHz, CHLOROFORM-d) δ 7.50-7.30 (m, 7H), 7.43-7.23 (m, 11H), 4.72 (s, 2H), 3.79-3.71 (m, 1H), 3.64-3.58 (m, 2H), 3.45 (t, J=6.7 Hz, 2H), 3.35-3.23 (m, 2H), 1.35-1.25 (m, 28H), 0.92 (t, J=6.8 Hz, 3H)

Intermediate I-187: (R)-3-fluoro-5-(((1-(hexadecyloxy)-3-hydroxypropan-2-yl)oxy)methyl)benzonitrile

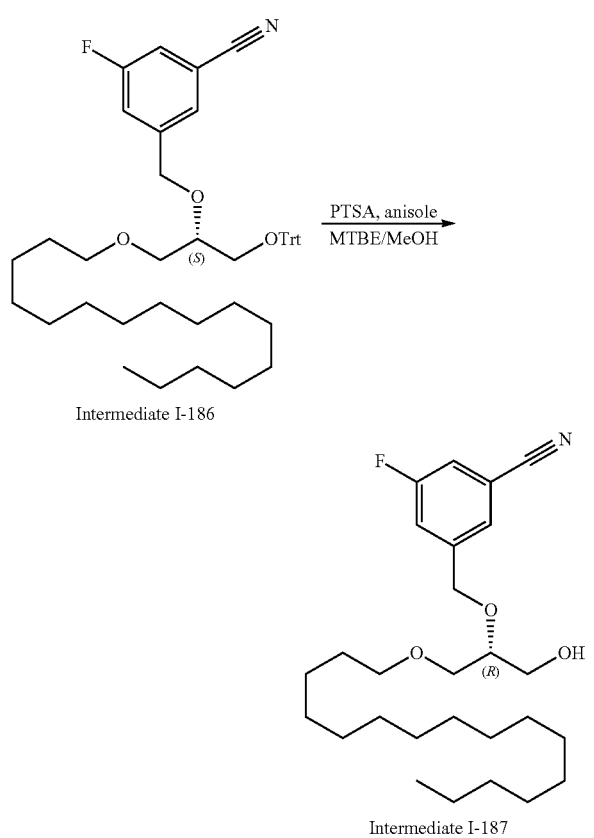

To a solution of (S)-3-fluoro-5-(((1-(hexadecyloxy)-3-(trityloxy)propan-2-yl)oxy)methyl)benzonitrile, Intermediate I-186 (1.8 g, 2.6 mmol, 615.7 uL, 1 eq) in MTBE (30 mL) were added anisole (281.3 mg, 2.6 mmol, 282.7 uL, 1 eq), MeOH (4.8 mL), and 4-methylbenzenesulfonic acid (447.9 mg, 2.6 mmol, 1 eq). The mixture was stirred at 50° C. for 6 hr, the reaction quenched by adding sat NH₄Cl 20 mL at 0° C., and the mixture extracted with ethyl acetate (30 mL×3). The combined organic layer was washed with NaCl (20 mL×3), dried over Na₂SO₄, filtered, and concentrated under reduced pressure to give a residue. The residue was purified by column chromatography (SiO₂, Petroleum ether/Ethyl acetate=100/0 to 3/1) to give Intermediate I-187. ¹H NMR (400 MHz, CHLOROFORM-d) δ 7.47 (s, 1H), 7.37 (d, J=9.0 Hz, 1H), 7.30-7.25 (m, 1H), 4.83-4.64 (m, 2H), 3.85-3.76 (m, 1H), 3.76-3.66 (m, 2H), 3.65-3.55 (m, 2H), 3.50-3.41 (m, 2H), 2.15-2.01 (m, 1H), 1.63-1.50 (m, 2H), 1.40-1.20 (m, 26H), 0.89 (t, J=6.8 Hz, 3H). MS (ESI): ink=450.2 [M+H]⁺

Intermediate I-215: (S)-((2-(benzyloxy)-3-(hexadecyloxy)propoxy)methanetriyl)tribenzene

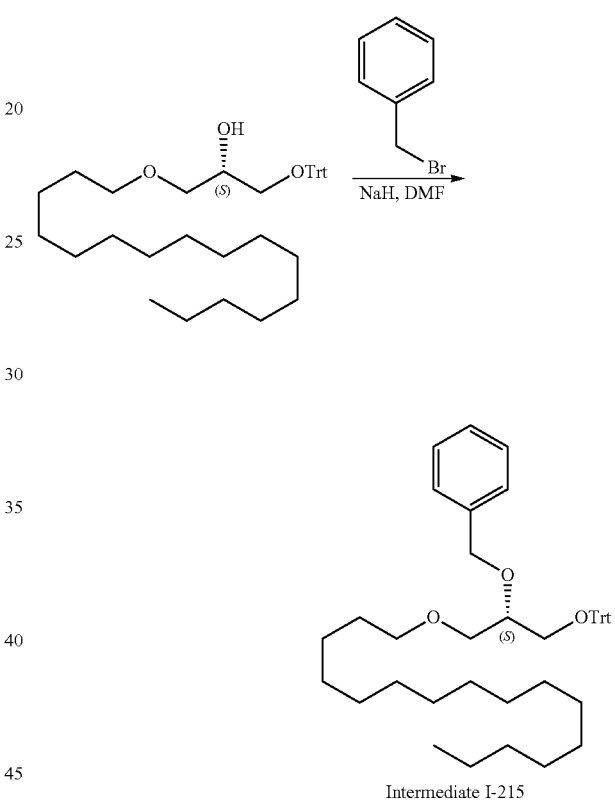

To a solution of (S)-1-(hexadecyloxy)-3-(trityloxy)propan-2-ol, (3 g, 5.3 mmol, 1 eq) in THF (20 mL) was added NaH (644.2 mg, 16.1 mmol, 60% purity, 3 eq) at 0° C. The mixture was stirred at 0° C. for 0.5 hr and then benzyl bromide (1.3 g, 8.0 mmol, 956.7 uL, 1.5 eq) was added into the above solution at 0° C. The mixture was stirred at 65° C. for 12 hr. The reaction was quenched by adding into sat NH₄Cl (50 mL) at 0° C. and the mixture extracted with ethyl acetate (20 mL×3). The combined organic layers were washed with NaCl (20 mL×3), dried over Na₂SO₄, filtered, and concentrated under reduced pressure to give a residue. The residue was purified by column chromatography (SiO₂, Petroleum ether/Ethyl acetate=100/0 to 100/8) to give (S)-((2-(benzyloxy)-3-(hexadecyloxy)propoxy)methanetriyl)tribenzene, Intermediate I-215. ¹H NMR (400 MHz, CHLOROFORM-d) δ 7.55-7.40 (m, 6H), 7.45-7.25 (m, 14H), 4.80-4.66 (m, 2H), 3.85-3.77 (m, 1H), 3.71-3.60 (m, 2H), 3.46 (t, J=6.6 Hz, 2H), 3.30 (d, J=5.0 Hz, 2H), 1.60-1.50 (m, 2H), 1.45-1.28 (m, 26H), 0.95 (t, J=6.7 Hz, 3H)

Intermediate I-216: (R)-2-(benzyloxy)-3-(hexadecyloxy)vropan-1-ol

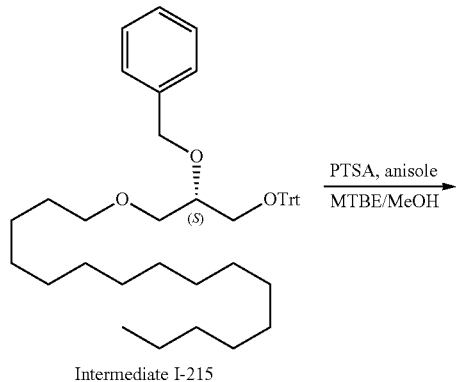

To a solution of (S)-((2-(benzyloxy)-3-(hexadecyloxy)propoxy)methanetriyl)tribenzene, Intermediate I-215 (3.3 g, 5.0 mmol, 1 eq) in MTBE (30 mL) were added anisole (549.9 mg, 5.0 mmol, 552.6 uL, 1 eq, MEOH (4.8 mL), and 4-methylbenzenesulfonic acid (875.6 mg, 5.0 mmol, 1 eq). The mixture was stirred at 50° C. for 3 hr and concentrated under reduced pressure to remove solvent. The residue was diluted with ethyl acetate (30 mL), washed with NaCl (20 mL×3), dried over Na$_2$SO$_4$, filtered, and concentrated under reduced pressure to give a residue. The residue was purified by column chromatography (SiO$_2$, Petroleum ether/Ethyl acetate=100/0 to 100/17) to give Intermediate I-216. $^1$H NMR (400 MHz, CHLOROFORM-d) δ 7.39-7.34 (m, 4H), 7.33-7.28 (m, 1H), 4.79-4.58 (m, 2H), 3.82-3.73 (m, 1H), 3.72-3.65 (m, 2H), 3.64-3.51 (m, 2H), 3.45 (t, J=6.6 Hz, 2H), 2.34-1.93 (m, 1H), 1.63-1.51 (m, 2H), 1.40-1.20 (m, 26H), 0.89 (t, J=6.7 Hz, 3H). MS (ESI): ink=407.3 [M+H]$^+$

Intermediate I-217: Heptadecylmagnesium bromide

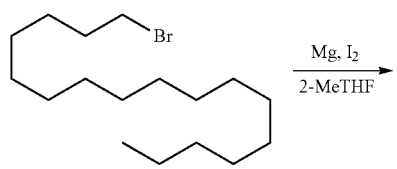

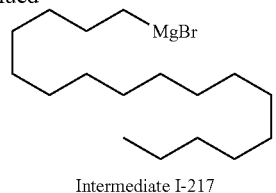

To a solution of Mg (2.2 g, 90.0 mmol, 1.2 eq) in 2-MeTHF (20 ml) were added I$_2$ (198.7 mg, 782.8 umol, 157.7 uL, 0.01 eq) and BrCH$_2$CH$_2$Br (0.15 mL) under N$_2$. Then 1-bromoheptadecane (2.5 g, 7.8 mmol) in 2-MeTHF (25 ml) was added dropwise. The mixture was stirred until the color of I$_2$ was faded to colorless. Then the remaining 1-bromoheptadecane (22.5 g, 70.4 mmol) in 2-MeTHF (225 ml) was added and the mixture was stirred at 25° C. for 4 hr. H NMR of D$_2$O-quenched reaction mixture showed reactant was consumed. The crude product heptadecylmagnesium bromide as brown liquid (in 2-MeTHF) was used into the next step without further purification.

Intermediate I-218: (S)-1-(trityloxy)icosan-2-ol

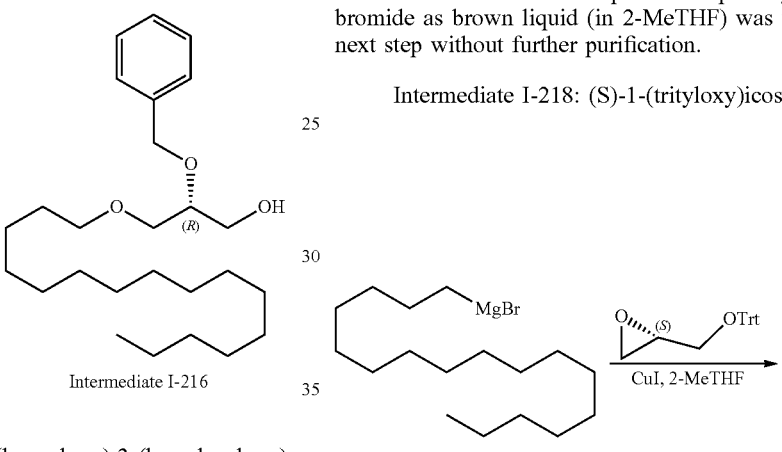

Bromo(heptadecyl)magnesium (25 g, 72.7 mmol, 1.3 eq) was added over 10 min via cannula to mixture of (2S)-2-(trityloxymethyl)oxirane (17.7 g, 56.0 mmol, 1 eq) and CuI (532.9 mg, 2.8 mmol, 0.05 eq) in 2-MeTHF (100 mL) at −20° C. The resulting mixture was stirred vigorously 5 min, warmed to 0° C., and then stirred for 2 h. The reaction was quenched by addition sat. NH$_4$Cl solution (450 ml) and then the mixture was extracted with ethyl acetate (250 mL×3). The combined organic layers were washed with H$_2$O (500 mL×2), dried over Na$_2$SO$_4$, filtered, and concentrated under reduced pressure to give a residue. The residue was purified by flash silica gel chromatography (Silica Flash Column, Eluent of 0~4% Ethyl acetate/Petroleum ether gradient @ 120 mL/min) to give compound (S)-1-(trityloxy)icosan-2-ol, Intermediate I-218. $^1$H NMR (400 MHz, CHLORO- FORM-d) δ 7.47-7.43 (m, 5H), 7.36-7.21 (m, 10H), 3.77 (br s, 1H), 3.19 (dd, J=3.3, 9.4 Hz, 1H), 3.03 (dd, J=7.6, 9.3 Hz, 1H), 2.35-2.25 (m, 1H), 1.45-1.20 (m, 34H), 0.89 (t, J=6.8 Hz, 3H)

Intermediate I-219: (S)-(((42-(benzyloxy)icosyl)oxy)methanetriyl)tribenzene

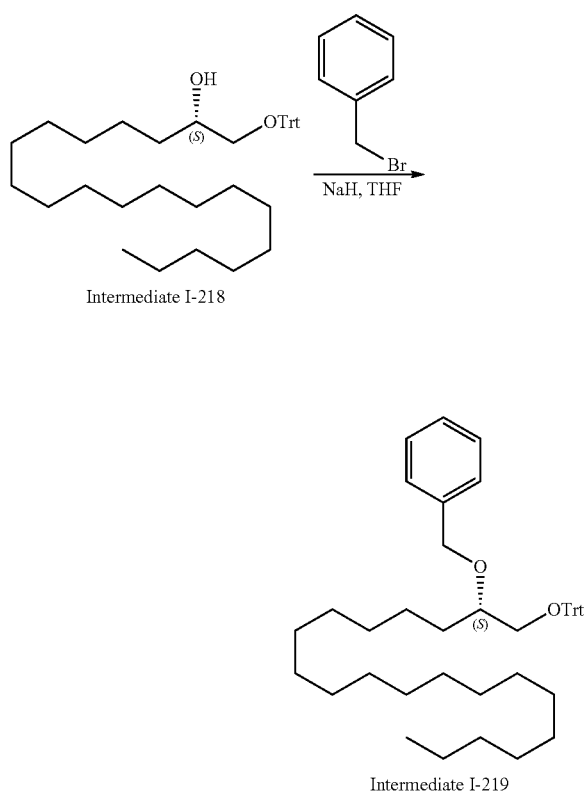

To a solution of (2S)-1-trityloxyicosan-2-ol, Intermediate I-218 (3.0 g, 5.4 mmol, 1 eq) in THF (30 mL) was added NaH (646.4 mg, 16.2 mmol, 60% purity, 3 eq) at 0° C. The mixture was stirred at 0° C. for 0.5 hr and then bromomethylbenzene (1.4 g, 8.1 mmol, 959.8 uL, 1.5 eq) was added into the above solution at 0° C. The mixture was stirred at 65° C. for 12 hr. The reaction was quenched by adding into sat. NH$_4$Cl (60 mL) at 0° C., and the mixture extracted with ethyl acetate (30 mL×3). The combined organic layers were washed with NaCl (30 mL×3), dried over Na$_2$SO$_4$, filtered, and concentrated under reduced pressure to give a residue. The residue was purified by flash silica gel chromatography (Silica Flash Column, Eluent of 0~3% Ethyl acetate/Petroleum ether gradient @ 45 mL/min) to give compound (S)-(((2-(benzyloxy)icosyl)oxy)methanetriyl)tribenzene, Intermediate I-219. $^1$H NMR (400 MHz, CHLOROFORM-d) δ 7.44-7.37 (m, 6H), 7.30-7.13 (m, 14H), 4.66-4.60 (m, 1H), 4.49-4.42 (m, 1H), 3.16-3.10 (m, 1H), 3.10-3.03 (m, 1H), 3.03-2.97 (m, 1H), 1.38-1.34 (m, 2H), 1.28-1.11 (m, 32H), 0.84-0.76 (m, 3H)

Intermediate I-220: (S)-2-(benzyloxy)icosan-1-ol

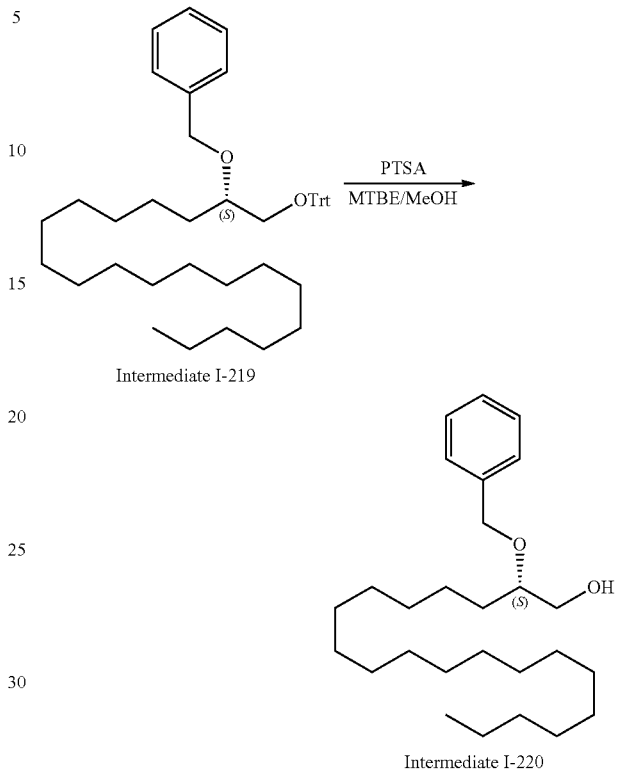

To a solution of [[(2S)-2-benzyloxyicosoxy]-diphenylmethyl]benzene, Intermediate I-219 (2.9 g, 4.5 mmol, 1 eq) in MeOH (9 mL) and MTBE (60 mL) were added anisole (242.4 mg, 2.2 mmol, 243.6 uL, 0.5 eq) and PTSA (385.9 mg, 2.2 mmol, 0.5 eq). The resulting mixture was stirred at 50° C. for 2 hr and the reaction was quenched by adding into sat. NH$_4$Cl (30 mL) at 0° C. and the mixture was extracted with ethyl acetate (15 mL×3). The combined organic layer was washed with NaCl (15 mL×3), dried over Na$_2$SO$_4$, filtered, and concentrated under reduced pressure to give a residue. The residue was purified by flash silica gel chromatography (Silica Flash Column, Eluent of 0~3% Ethyl acetate/Petroleum ether gradient @ 45 mL/min) to Intermediate I-220. $^1$H NMR (400 MHz, CHLOROFORM-d) δ 7.42-7.30 (m, 4H), 7.28-7.23 (m, 1H), 4.70-4.65 (m, 1H), 4.61-4.55 (m, 1H), 3.81-3.71 (m, 1H), 3.61-3.48 (m, 2H), 1.74-1.62 (m, 1H), 1.58-1.45 (m, 1H), 1.44-1.22 (m, 32H), 0.96-0.88 (m, 3H). MS (ESI): m/z=427.3 [M+Na]$^+$ Intermediate I-221: (S)-(2-methyloxiran-2-yl)methanol

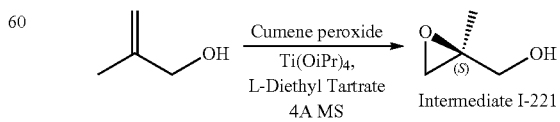

A mixture of 4 A MS (25 g, 300.0 mmol, 1 eq) in DCM (800 mL) was cooled to −35° C., followed by addition of solution of Ti(i-PrO)$_4$ (8.5 g, 30.0 mmol, 8.8 mL, 0.1 eq) in DCM (50 mL) and diisopropyl (2R,3R)-2,3-dihydroxybutanedioate (10.5 g, 45.0 mmol, 9.4 mL, 0.15 eq) using a syringe. Afterward, the mixture was stirred at −35° C. for 30 min and 2-methylprop-2-en-1-ol (21.6 g, 300 mmol, 25.3 mL, 1 eq) in DCM (100 mL) was added to the solution using a syringe, followed by addition of cumene hydroperoxide (82.5 g, 450.0 mmol, 79.3 mL, 83% purity, 1.50 eq). The mixture was stirred at −35° C. for 1 hr and then stirred at −20° C. for 35 hr in a low temperature bath. Trimethylphosphite (60 mL) was added dropwise to the solution at −10° C. to quench excess cumene hydroperoxide. Then the reaction mixture was filtered through a short pad of Celite to give the crude product (S)-(2-methyloxiran-2-yl)methanol, Intermediate I-221 (26.4 g, crude) as a light yellow liquid and was used into the next step without further purification.

Intermediate I-222: (R)-2-methyl-2-((trityloxy)methyl)oxirane

Intermediate I-221      Intermediate I-222

To a solution of (S)-(2-methyloxiran-2-yl)methanol (6.6 g, 74.9 mmol, 2.5 mL, 1 eq) in DCM (800 mL) were added TEA (13.6 g, 134.8 mmol, 18.7 mL, 1.8 eq) and DMAP (1.3 g, 11.2 mmol, 0.15 eq). The mixture was cooled to 0° C. and TrtCl (73.0 g, 262.1 mmol, 3.5 eq) was added at 0° C. The mixture was stirred at 20° C. for 24 hr and washed with 10% citric acid (100 mL×3) and H$_2$O (100 mL×3). The combined organic layers were dried over Na$_2$SO$_4$, filtered, and concentrated under reduced pressure to give a residue. The residue was purified by column chromatography (SiO$_2$, Petroleum ether/MTBE=100/1 to 100/2). The residue was further purified by flash silica gel chromatography (ISCO®; 330 g SepaFlash® Silica Flash Column, Eluent of 0~8% MTBE/Petroleum ether gradient @ 180 mL/min) to give (R)-2-methyl-2-((trityloxy)methyl)oxirane, Intermediate I-222. $^1$H NMR (400 MHz, CHLOROFORM-d) δ 7.53-7.45 (m, 6H), 7.40-7.26 (m, 9H), 3.32-3.07 (m, 2H), 2.87 (s, 1H), 2.50 (s, 1H), 1.29 (s, 3H)

Intermediate I-223 (R)-2-methyl-1-(octadecyloxy)-3-(trityloxy)propan-2-ol

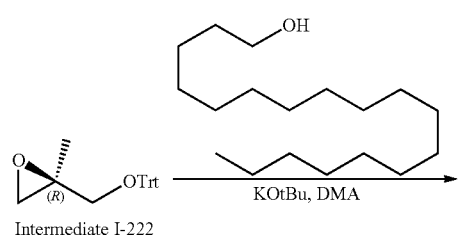

Intermediate I-222

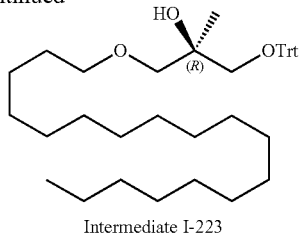

Intermediate I-223

To a solution of (R)-2-methyl-2-((trityloxy)methyl)oxirane, Intermediate I-222 (9.7 g, 29.5 mmol, 1 eq) in DMA (200 mL) were added t-BuOK (6.6 g, 59.1 mmol, 2 eq) and octadecan-1-ol (8 g, 29.5 mmol, 9.8 mL, 1 eq). The mixture was stirred at 80° C. for 12 hr, diluted with H$_2$O (10 mL) and extracted with ethyl acetate (100 mL×3). The combined organic layer was washed with NaCl (50 mL×3), dried over Na$_2$SO$_4$, filtered, and concentrated under reduced pressure to give a residue. The residue was purified by flash silica gel chromatography (ISCO®; 220 g SepaFlash® Silica Flash Column, Eluent of 0~7% Ethyl acetate/Petroleum ether gradient @ 150 mL/min) to give (R)-2-methyl-1-(octadecyloxy)-3-(trityloxy)propan-2-ol, Intermediate I-223 as a colorless oil. $^1$H NMR (400 MHz, CHLOROFORM-d) δ=7.40-7.33 (m, 6H), 7.27-7.12 (m, 9H), 3.43 (d, J=8.9 Hz, 1H), 3.36 (t, J=6.6 Hz, 2H), 3.31 (d, J=8.9 Hz, 1H), 3.03-2.94 (m, 2H), 1.50-1.40 (m, 2H), 1.26-1.15 (m, 30H), 1.13-1.07 (m, 3H), 0.81 (t, J=6.8 Hz, 3H)

Intermediate I-224: (R)-3-fluoro-5-(((2-methyl-1-(octadecyloxy)-3-(trityloxy)propan-2-yl)oxy)methyl)benzonitrile

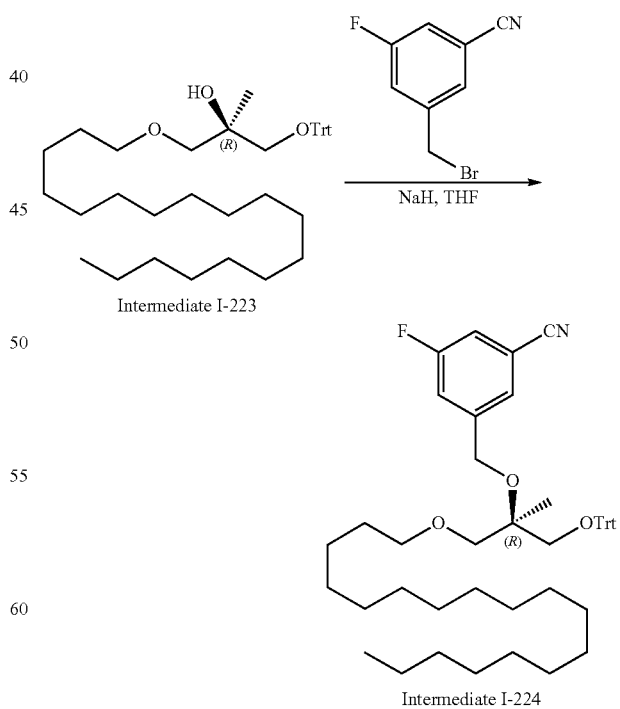

Intermediate I-224

To a solution of (R)-2-methyl-1-(octadecyloxy)-3-(trityloxy)propan-2-ol, Intermediate I-223 (5 g, 8.3 mmol, 615.7 uL, 1 eq) in THF (80 mL) was added NaH (998.3 mg, 24.9 mmol, 60% purity, 3 eq) at 0° C. The mixture was stirred at 0° C. for 0.5 hr and then 3-(bromomethyl)-5-fluoro-benzonitrile (2.6 g, 12.4 mmol, 1.5 eq) was added into the above solution at 0° C. The mixture was stirred at 65° C. for 12 hr. The reaction was quenched by adding into sat NH₄Cl solution (50 mL) at 0° C. and the mixture was extracted with ethyl acetate (80 mL×3). The combined organic layers were washed with NaCl (50 mL×3), dried over Na₂SO₄, filtered, and concentrated under reduced pressure to give a residue. The residue was purified by flash silica gel chromatography (ISCO®; 80 g SepaFlash® Silica Flash Column, Eluent of 0~5% Ethyl acetate/Petroleum ether gradient @ 100 mL/min) to give (R)-3-fluoro-5-(02-methyl-1-(octadecyloxy)-3-(trityloxy)propan-2-yl)oxy)methyl)benzonitrile, Intermediate I-224. ¹H NMR (400 MHz, CHLOROFORM-d) δ=7.42-7.32 (m, 8H), 7.29-7.09 (m, 10H), 4.43-4.27 (m, 2H), 3.60-3.41 (m, 2H), 3.40-3.32 (m, 2H), 3.19-3.07 (m, 2H), 1.54-1.41 (m, 2H), 1.18 (s, 33H), 0.81 (t, J=6.8 Hz, 3H)

Intermediate I-225: (S)-3-fluoro-5-(((1-hydroxy-2-methyl-3-(octadecyloxy)propan-2-yl)oxy)methyl)benzonitrile To a solution of (R)-3-fluoro-5-(((2-methyl-1-(octadecyloxy)-3-(trityloxy)propan-2-yl)oxy)methyl)benzonitrile, Intermediate I-224 (3.3 g, 4.5 mmol, 615.8 uL, 1 eq) in MTBE (30 mL) were added anisole (243.0 mg, 2.2 mmol, 244.3 uL, 0.5 eq), MeOH (4.8 mL), and PTSA (387.0 mg, 2.2 mmol, 0.5 eq). The mixture was stirred at 50° C. for 12 hr, diluted with sat. NaHCO₃ (80 mL), and extracted with ethyl acetate (80 mL×3). The combined organic layers were washed with NaCl (50 mL×3), dried over Na₂SO₄, filtered, and concentrated under reduced pressure to give a residue. The residue was purified by column chromatography (SiO₂, Petroleum ether/Ethyl acetate=100/1 to 20/1) to give (S)-3-fluoro-5-(((1-hydroxy-2-methyl-3-(octadecyloxy)propan-2-yl)oxy)methyl)benzonitrile, Intermediate I-225. ¹H NMR (400 MHz, CHLOROFORM-d) δ=7.49-7.44 (m, 1H), 7.35 (d, J=9.1 Hz, 1H), 7.27-7.23 (m, 1H), 4.69-4.57 (m, 2H), 3.75-3.65 (m, 2H), 3.62-3.49 (m, 2H), 3.48-3.42 (m, 2H), 2.47 (br s, 1H), 1.63-1.53 (m, 2H), 1.45-1.22 (s, 30H), 1.22 (s, 3H), 0.93-0.85 (m, 3H). MS (ESI): m/z=514.2 [M+Na]⁺

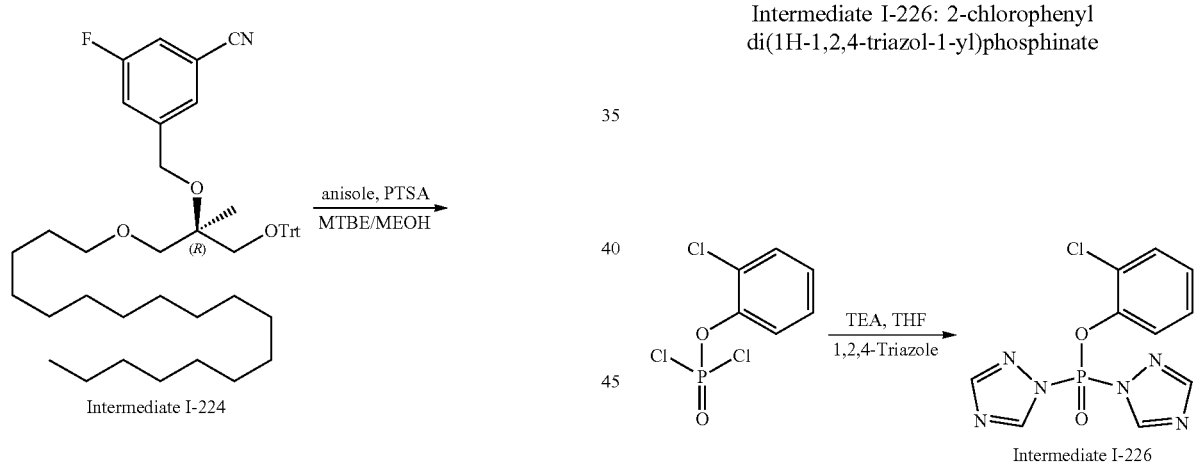

Intermediate I-224

Intermediate I-225

Intermediate I-226: 2-chlorophenyl di(1H-1,2,4-triazol-1-yl)phosphinate

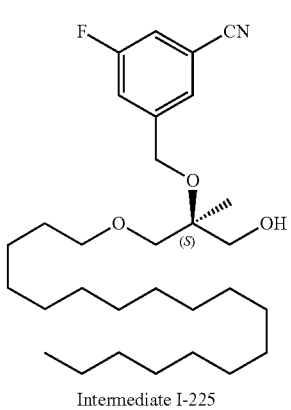

Intermediate I-226

1H-1,2,4-triazole (714 mg, 10.3 mmol) and TEA (1.44 mL, 10.3 mmol) were dissolved in THF (8 mL). To the solution was added 1-chloro-2-dichlorophosphoryloxy-benzene (0.81 mL, 4.92 mmol) dropwise at rt. The reaction mixture was stirred at rt for 30 min and filtered into a graduated tube, the filter cake washed with THF (8 mL), and additional THF added to the filtrate to total volume 20 mL resulting in ca 0.246 M stock solution of Intermediate I-226, which was used in next reactions. ³¹P NMR (162 MHz, Acetonitrile-d₃) δ−16.94.

Intermediate I-227: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl (2-chlorophenyl) ((S)-2-((3-cyano-5-fluorobenzyl)oxy)-3-(hexadecyloxy)propyl) phosphate

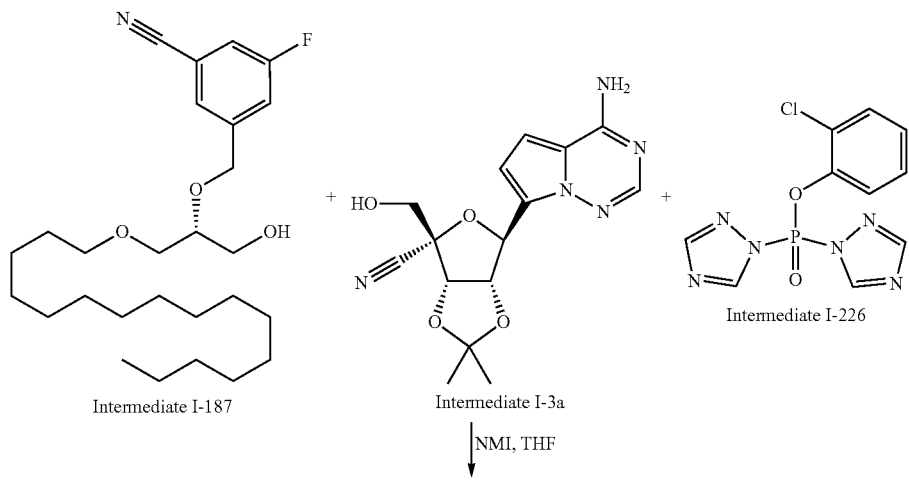

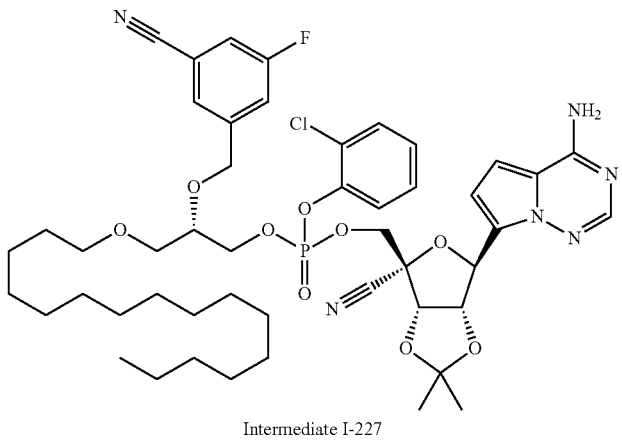

Intermediate I-227

To the solution of Intermediate I-226 (0.246 M in THF, 2.23 mL, 0.549 mmol) were added Intermediate I-3a (171 mg, 0.423 mmol) in one portion and then 1-methylimidazole (0.044 mL, 0.549 mmol). The reaction mixture was stirred at rt for 20 min, Intermediate I-187 (209 mg, 0.464 mmol) in THF (1 mL) added dropwise. The resulting mixture was stirred for 1 h, diluted with EtOAc (50 mL)-water (20 mL)-brine (20 mL) stirred for 10 min, layers separated, and the aqueous layer extracted with EtOAc (20 mL×3). The combined organic layer was dried under sodium sulfate, concentrated in vacuo, and purified by silica gel (0 to 5% MeOH in DCM) to give Intermediate I-227. $^1$H NMR (400 MHz, Acetonitrile-d3) δ 7.89-7.78 (m, 1H), 7.55-7.28 (m, 5H), 7.27-7.05 (m, 2H), 6.80-6.75 (m, 1H), 6.76-6.64 (m, 1H), 6.25 (s, 2H), 5.69-5.56 (m, 1H), 5.32 5.19 (m, 1H), 5.14-5.00 (m, 1H), 4.65-4.61 (m, 2H), 4.58-4.43 (m, 2H), 4.39-4.28 (m, 1H), 4.27-4.12 (m, 1H), 3.85-3.65 (m, 1H), 3.53-3.42 (m, 2H), 3.42-3.30 (m, 2H), 1.73-1.62 (m, 3H), 1.57-1.43 (m, 2H), 1.40-1.06 (m, 29H), 0.94-0.82 (m, 3H). $^{19}$F NMR (376 MHz, Acetonitrile-d$_3$) δ−112.79, −112.83. $^{31}$P NMR (162 MHz, Acetonitrile-d$_3$) δ−7.25, −7.48. MS m/z [M+1]=953.6

Intermediate I-228: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl)oxy)-3-(hexadecyloxy)propyl) hydrogen phosphate

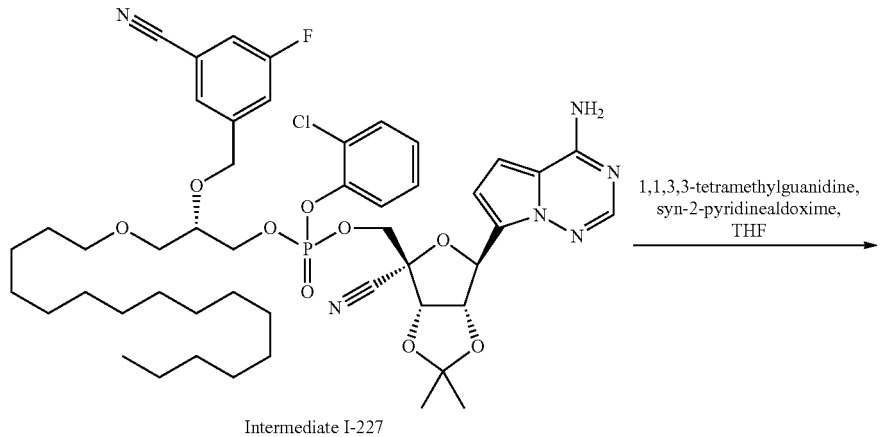

Intermediate I-227

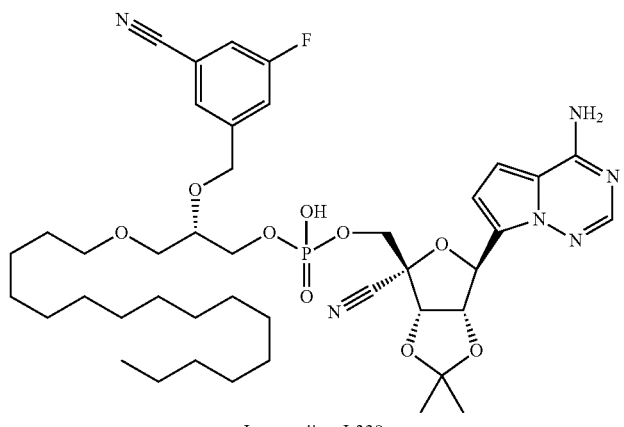

Intermediate I-228

To a solution of Intermediate I-227 (276 mg, 0.3289 mmol) in THF (5 mL) were added 1,1,3,3-tetramethylguanidine (0.218 mL, 1.78 mmol) and syn-2-pyridinealdoxime (143 mg, 1.17 mmol). The reaction mixture was stirred at room temperature for 15 h, diluted with EtOAc (100 mL), washed with sat. aqueous ammonium chloride (25 mL×3), dried with sodium sulfate, concentrated in vacuo, and concentrated in vacuo, and purified by silica gel (0-60% MeOH in DCM) to give Intermediate I-228. $^1$H NMR (400 MHz, Methanol-d4) δ 7.86 (s, 1H), 7.55 (s, 1H), 7.49-7.42 (m, 1H), 7.42-7.29 (m, 1H), 6.87 (d, J=4.6 Hz, 1H), 6.83 (d, J=4.6 Hz, 1H), 5.65 (d, J=3.7 Hz, 1H), 5.28 (dd, J=6.6, 3.7 Hz, 1H), 5.15 (d, J=6.5 Hz, 1H), 4.74 (d, J=13.3 Hz, 1H), 4.62 (d, J=13.2 Hz, 1H), 4.18-4.04 (m, 2H), 4.02-3.87 (m, 2H), 3.80-3.68 (m, 1H), 3.54-3.45 (m, 2H), 3.44-3.36 (m, 2H), 1.71 (s, 3H), 1.59-1.44 (m, 2H), 1.42-1.08 (m, 29H), 0.91 (t, J=6.6 Hz, 3H). $^{19}$F NMR (376 MHz, Methanol-d4) δ−113.04. $^{31}$P NMR (162 MHz, Methanol-d4) δ−0.49. MS m/z [M+1]=842.9

Intermediate I-235: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-(benzyloxy)-3-(hexadecyloxy)propyl) (2-chlorophenyl) phosphate

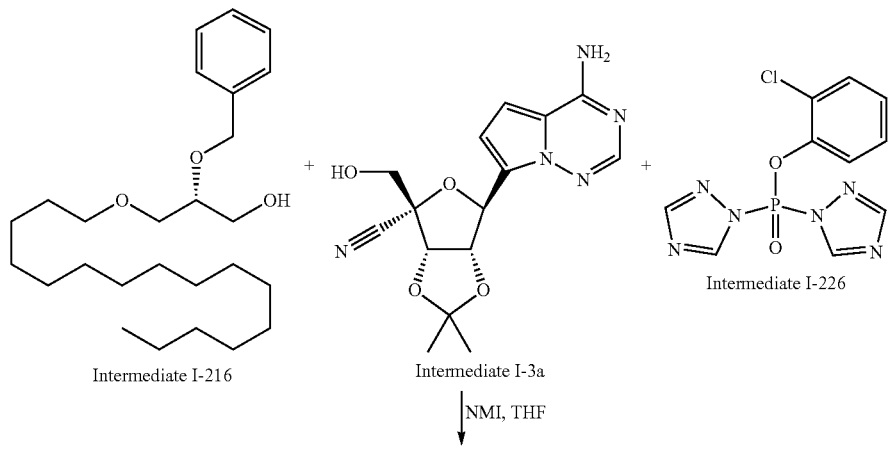

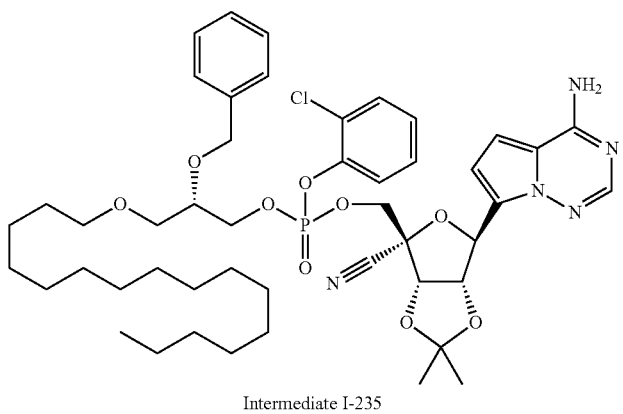

Intermediate I-235

To the solution of Intermediate I-226 (0.246 M in THF, 3.00 mL, 0.738 mmol) were added Intermediate I-3a (200 mg, 0.604 mmol) in one portion and then 1-methylimidazole (0.060 mL, 0.785 mmol). The reaction mixture was stirred at rt for 10 min and then Intermediate I-216 (250 mg, 0.615 mmol) in THF (1 mL) added dropwise. The resulting mixture was stirred for 1 h, diluted with EtOAc (50 mL)-brine (40 m), stirred for 10 min, layers separated, and the aqueous layer extracted with EtOAc (20 mL×3). The combined organic layer was dried with sodium sulfate, concentrated in vacuo, and purified by silica gel (0 to 5% MeOH in DCM) to give Intermediate I-235. $^1$H NMR (400 MHz, Acetonitrile-d3) δ 7.90-7.86 (m, 1H), 7.50-7.43 (m, 1H), 7.42-7.36 (m, 1H), 7.35-7.24 (m, 5H), 7.23-7.14 (m, 2H), 6.81-6.72 (m, 2H), 6.28 (s, 2H), 5.70-5.64 (m, 1H), 5.33-5.25 (m, 1H), 5.12-5.02 (m, 1H), 4.62-4.56 (m, 2H), 4.56-4.44 (m, 2H), 4.39-4.31 (m, 1H), 4.26-4.15 (m, 1H), 3.81-3.70 (m, 1H), 3.50-3.42 (m, 2H), 3.42-3.32 (m, 2H), 1.76-1.66 (m, 3H), 1.57-1.43 (m, 2H), 1.41-1.21 (m, 29H), 0.98-0.81 (m, 3H). $^{31}$P NMR (162 MHz, Acetonitrile-d3) δ −7.31, −7.46. MS m/z [M+1]=910.4

Intermediate I-236: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-(benzyloxy)-3-(hexadecyloxy)propyl) hydrogen phosphate

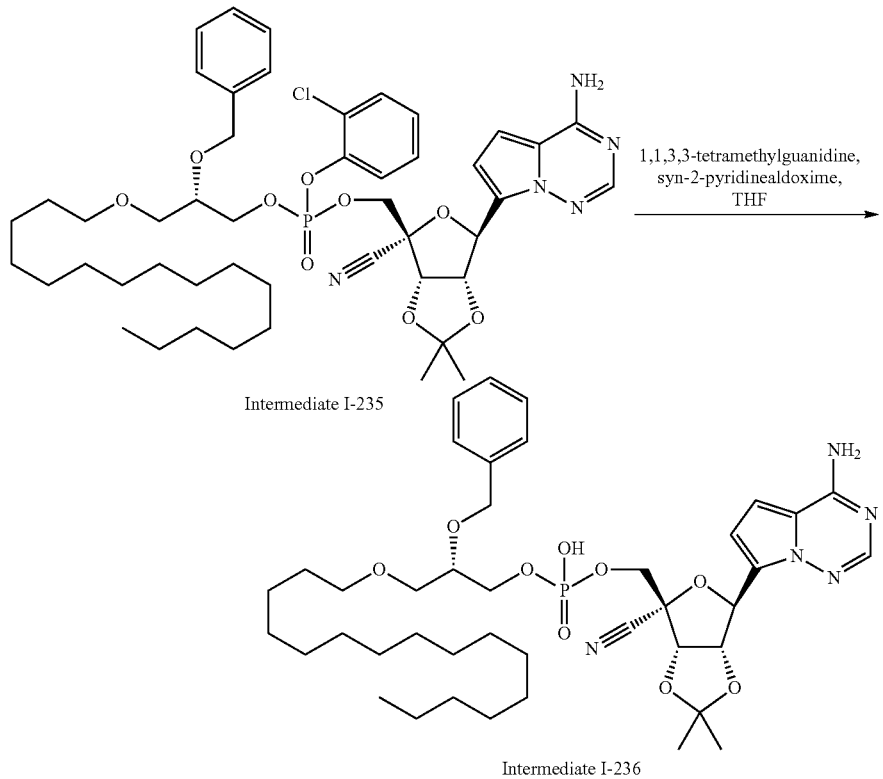

To a solution of Intermediate I-235 (304 mg, 0.334 mmol) in THF (5 mL) were added 1,1,3,3-tetramethylguanidine (0.251 mL, 2.00 mmol) and syn-2-pyridinealdoxime (165 mg, 1.35 mmol). The reaction mixture was stirred at room temperature for 15 h, diluted with EtOAc (100 mL)-2-propanol (4 ml), washed with sat. aqueous ammonium chloride (25 mL×3), dried with sodium sulfate, concentrated in vacuo, concentrated in vacuo, and purified by silica gel (0-60% MeOH in DCM) to give Intermediate I-236. $^1$H NMR (400 MHz, Methanol-d4) δ 7.87 (s, 1H), 7.40-7.19 (m, 5H), 6.92 (d, J=4.6 Hz, 1H), 6.85 (d, J=4.6 Hz, 1H), 5.66 (d, J=3.7 Hz, 1H), 5.25 (dd, J=6.6, 3.7 Hz, 1H), 5.13 (d, J=6.6 Hz, 1H), 4.66 (d, J=11.8 Hz, 1H), 4.58 (d, J=11.8 Hz, 1H), 4.18-4.07 (m, 2H), 4.03-3.89 (m, 2H), 3.80-3.69 (m, 1H), 3.54-3.42 (m, 2H), 3.41-3.37 (m, 2H), 1.71 (s, 3H), 1.58-1.46 (m, 2H), 1.41-1.19 (m, 29H), 0.91 (t, J=6.7 Hz, 3H). $^{31}$P NMR (162 MHz, Methanol-d4) δ −0.47. MS m/z [M+1]=800.4

Intermediate I-237: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-(benzyloxy)icosyl) (2-chlorophenyl) phosphate

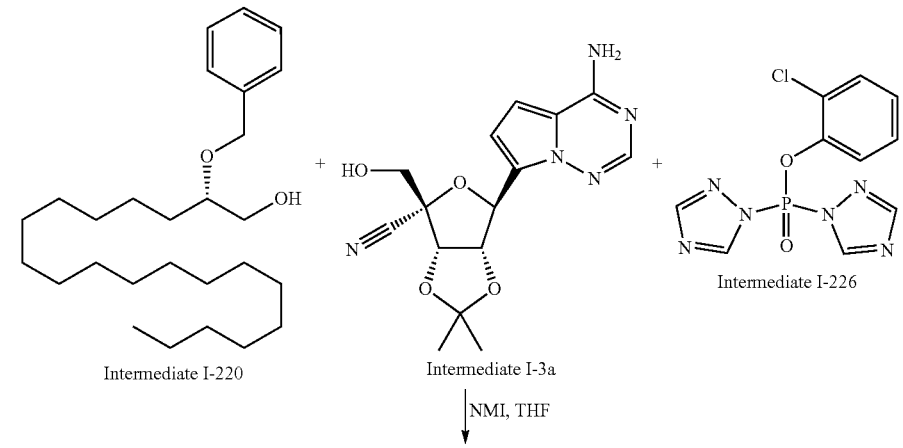

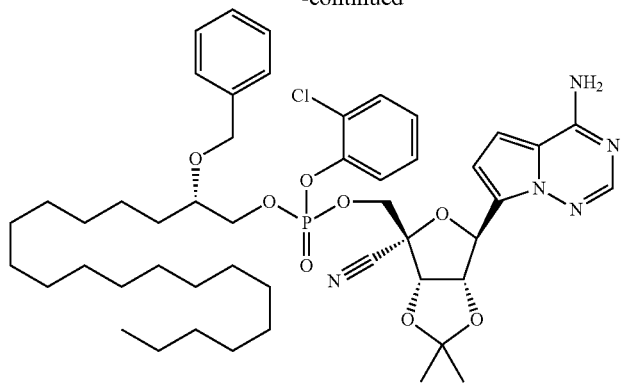

Intermediate I-237

To the solution of Intermediate I-226 (0.246 M in THF, 3.00 mL, 0.738 mmol) were added Intermediate I-3a (215 mg, 0.649 mmol) in one portion and then 1-methylimidazole (0.060 mL, 0.844 mmol). The reaction mixture was stirred at rt for 10 min, then Intermediate I-220 (250 mg, 0.618 mmol) in THF (1 mL) added dropwise. The resulting mixture was stirred for 1 h, diluted with EtOAc (50 mL)-brine (20 m), stirred for 10 min, layers separated, and the aqueous layer extracted with EtOAc (20 mL×3). The combined organic layer dried under sodium sulfate, concentrated in vacuo, and purified by silica gel (0 to 5% MeOH in DCM) to give Intermediate I-237. $^1$H NMR (400 MHz, Acetonitrile-d3) δ 7.96-7.78 (m, 1H), 7.53-7.44 (m, 1H), 7.44-7.35 (m, 1H), 7.32-7.15 (m, 7H), 6.81-6.77 (m, 1H), 6.77-6.70 (m, 1H), 6.26 (s, 2H), 5.70-5.66 (m, 1H), 5.31-5.21 (m, 1H), 5.10 (d, J=6.6 Hz, 0.5H), 5.06 (d, J=6.6 Hz, 0.5H), 4.64-4.38 (m, 4H), 4.35-4.23 (m, 1H), 4.18-4.04 (m, 1H), 3.64-3.50 (m, 1H), 1.75-1.63 (m, 3H), 1.56-1.04 (m, 37H), 0.95-0.79 (m, 3H). $^{31}$P NMR (162 MHz, Acetonitrile-d3) δ-7.23, -7.44. MS m/z [M+1]=908.4

Intermediate I-238: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl ((S)-2-(benzyloxy)icosyl) hydrogen phosphate

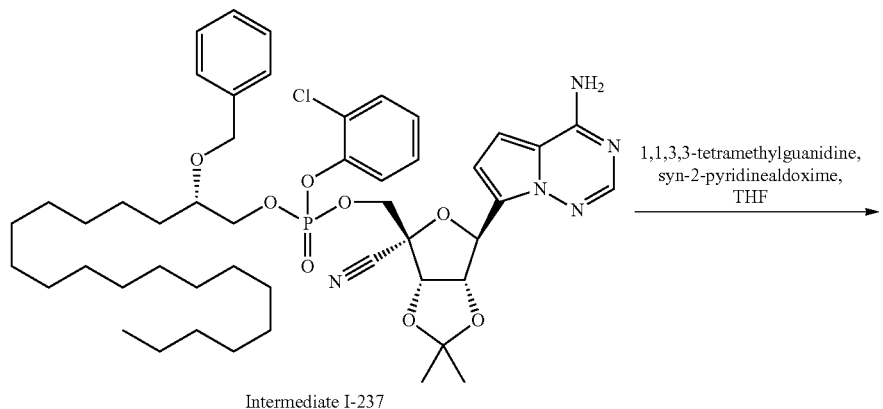

Intermediate I-237

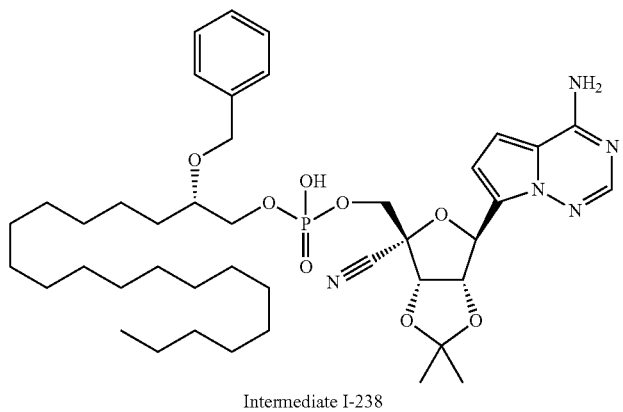

Intermediate I-238

To a solution of Intermediate I-237 (335 mg, 0.369 mmol) in THF (5 mL) were added 1,1,3,3-tetramethylguanidine (0.278 mL, 2.21 mmol) and syn-2-pyridinealdoxime (183 mg, 1.50 mmol). The reaction mixture was stirred at room temperature for 15 h, diluted with EtOAc (100 mL)-2-propanol (4 ml), washed with sat. aqueous ammonium chloride (25 mL×3), dried with sodium sulfate, concentrated in vacuo, and concentrated in vacuo and purified by silica gel (0-60% MeOH in DCM) to give Intermediate I-238 (277 mg, 94%). $^1$H NMR (400 MHz, Methanol-d4) δ 7.87 (s, 1H), 7.36-7.18 (m, 5H), 6.93 (d, J=4.6 Hz, 1H), 6.86 (d, J=4.5 Hz, 1H), 5.67 (d, J=3.6 Hz, 1H), 5.25 (dd, J=6.6, 3.7 Hz, 1H), 5.14 (d, J=6.6 Hz, 1H), 4.67 (d, J=11.6 Hz, 1H), 4.47 (d, J=11.6 Hz, 1H), 4.22-4.09 (m, 2H), 3.90 (t, J=5.5 Hz, 2H), 3.61-3.52 (m, 1H), 1.71 (s, 3H), 1.52-1.13 (m, 37H), 0.97-0.82 (m, 3H). $^{31}$P NMR (162 MHz, Methanol-d4) δ−0.37. MS m/z [M+1]=798.3

Intermediate I-239: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)-2-methyl-3-(octadecyloxy)propyl) phosphate To the solution of Intermediate I-226 (0.246 M in THF, 2.77 mL, 0.683 mmol) were added Intermediate I-3a (185 mg, 0.558 mmol) in one portion and then 1-methylimidazole (0.058 mL, 0.726 mmol). The reaction mixture was stirred at rt for 10 min, then Intermediate I-225 (250 mg, 0.508 mmol) in THF (1 mL) added dropwise. The resulting mixture was stirred for 1 h, diluted with EtOAc (50 mL)-brine (40 m), stirred for 10 min, layers separated, and the aqueous layer extracted with EtOAc (20 mL×3). The combined organic layer dried under sodium sulfate, concentrated in vacuo, and purified by silica gel (0 to 5% MeOH in DCM) to give Intermediate I-239 (288 mg, 52%). $^1$H NMR (400 MHz, Acetonitrile-d3) δ 7.87 (s, 1H), 7.52-7.42 (m, 2H), 7.40-7.32 (m, 3H), 7.25-7.13 (m, 2H), 6.86-6.76 (m, 1H), 6.75-6.69 (m, 1H), 6.26 (s, 2H), 5.69-5.64 (m, 1H), 5.33-5.26 (m, 1H), 5.15-5.05 (m, 1H), 4.61-4.39 (m, 4H), 4.23 (d, J=6.1 Hz, 1H), 4.18 (d, J=5.9 Hz, 1H), 3.51-3.43 (m, 1H), 3.41-3.26 (m, 3H), 1.72 (s, 3H), 1.55-1.45 (m, 2H), 1.38 (s, 3H), 1.35-1.22 (m, 30H), 1.20 (s, 1.5H), 1.17 (s, 1.5H), 0.90 (t, J=6.7 Hz, 3H). $^{31}$P NMR (162 MHz, Acetonitrile-d3) δ−7.48, −7.53. MS m/z [M+1]=995.6.

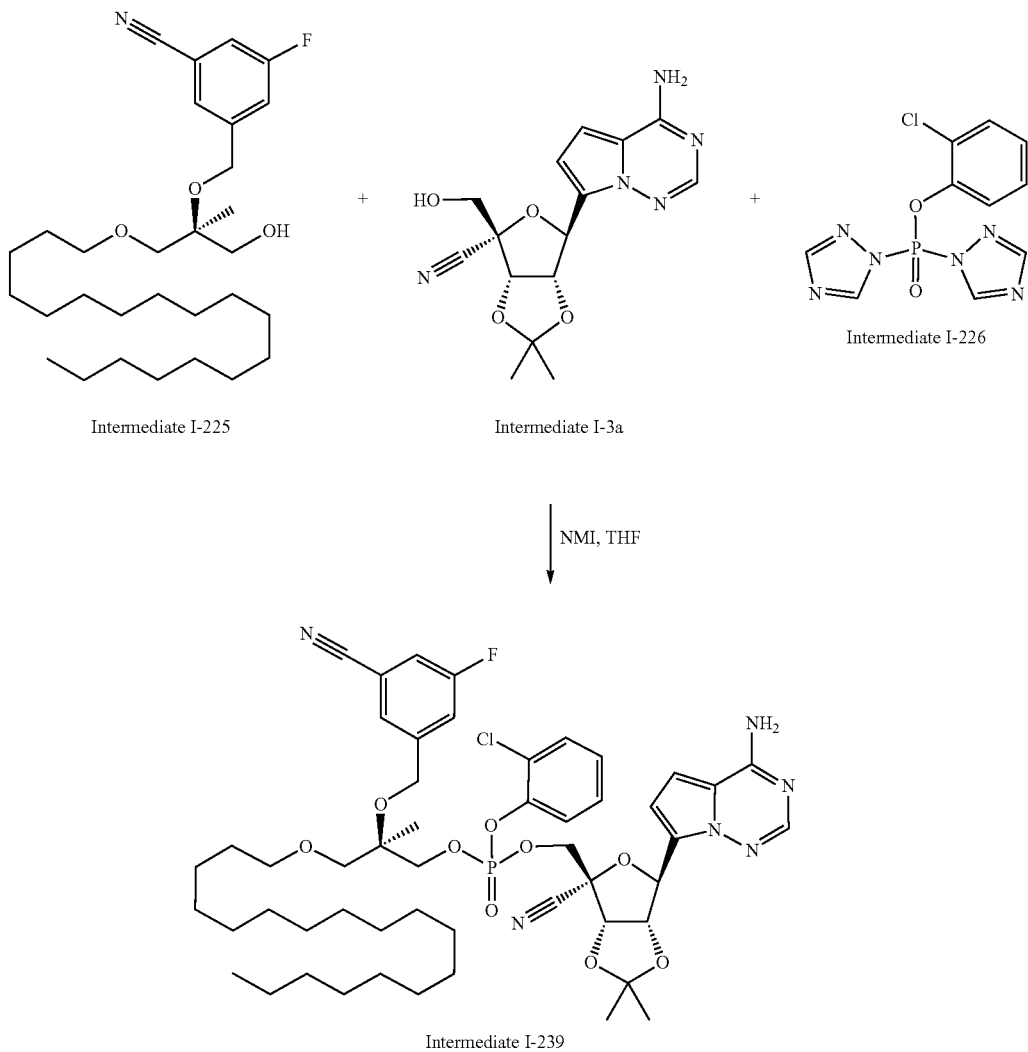

Intermediate I-240: ((3aS,4R,6S,6aS)-6-(4-aminopy-rrolo[2,1-f][1,2,4]triazin-7-yl)-4-cyano-2,2-dimethyltetrahydrofuro[3,4-d][1,3]dioxol-4-yl)methyl ((R)-2-((3-cyano-5-fluorobenzyl)oxy)-2-methyl-3-(octadecyloxy)propyl) hydrogen phosphate

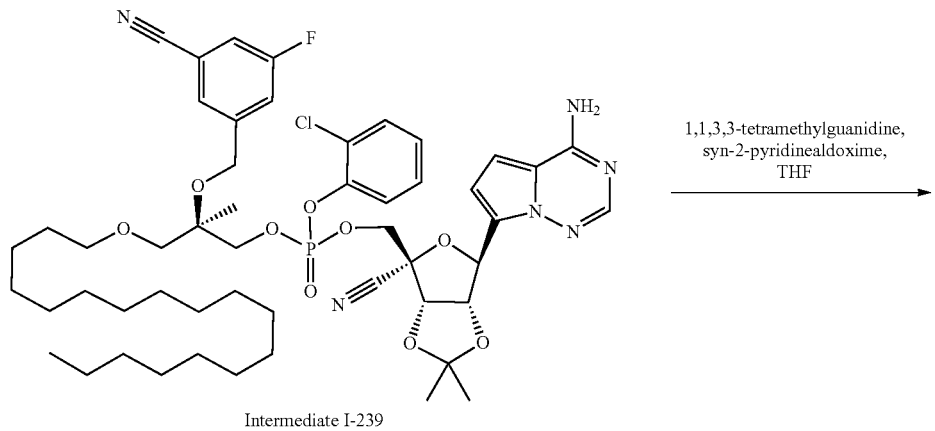

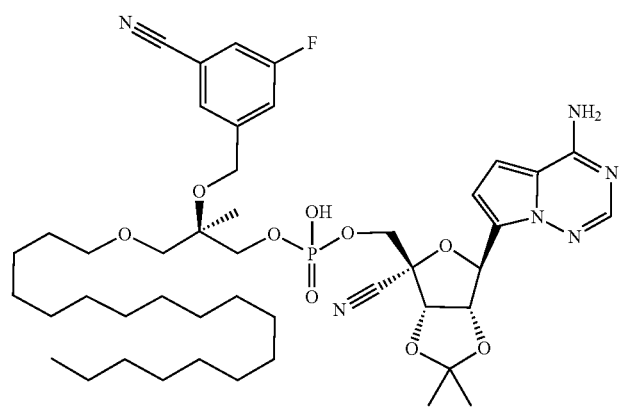

To a solution of Intermediate I-239 (288 mg, 0.289 mmol) in THF (5 mL) were added 1,1,3,3-tetramethylguanidine (0.218 mL, 1.74 mmol) and syn-2-pyridinealdoxime (143 mg, 1.17 mmol). The reaction mixture was stirred at room temperature for 15 h, diluted with EtOAc (100 mL)-2-propanol (10 ml), washed with sat. aqueous ammonium chloride (25 mL×3), dried with sodium sulfate, concentrated in vacuo, and purified by silica gel (0-60% MeOH in DCM) to give Intermediate I-240 (224 mg, 100%). $^{1}$H NMR (400 MHz, Methanol-d4) δ 7.93 (s, 1H), 7.53 (s, 1H), 7.48-7.42 (m, 1H), 7.37-7.30 (m, 1H), 7.03 (d, J=4.6 Hz, 1H), 6.90 (d, J=4.6 Hz, 1H), 5.66 (d, J=3.6 Hz, 1H), 5.26 (dd, J=6.6, 3.7 Hz, 1H), 5.17 (d, J=6.6 Hz, 1H), 4.66 (s, 2H), 4.18-4.06 (m, 2H), 4.04-3.91 (m, 2H), 3.52-3.45 (m, 2H), 3.45-3.38 (m, 2H), 1.71 (s, 3H), 1.60-1.50 (m, 2H), 1.40 (s, 3H), 1.36-1.21 (m, 33H), 0.91 (t, J=6.7 Hz, 3H). $^{31}$P NMR (162 MHz, Methanol-d4) δ −0.67. MS m/z [M+1]=885.3

Intermediate I-245: (S)-3-fluoro-5-((1-(trityloxy)icosan-2-yl)oxy)benzonitrile

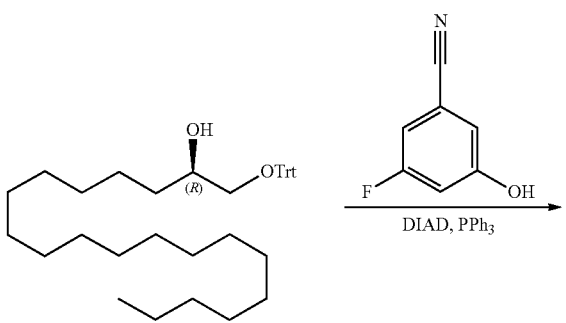

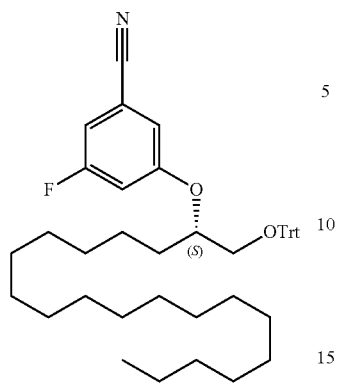

Intermediate I-245

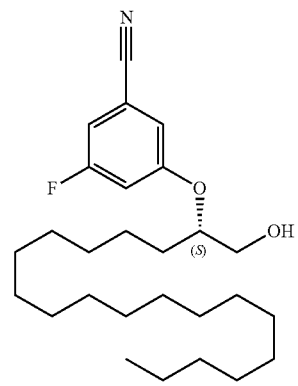

Intermediate I-246

To a solution of (2R)-1-trityloxyicosan-2-ol (3 g, 5.39 mmol, 1 eq) in THF (50 mL) was added 3-fluoro-5-hydroxybenzonitrile (1.11 g, 8.08 mmol, 1.5 eq) and PPh$_3$ (1.70 g, 6.46 mmol, 1.2 eq). The mixture was cooled to 0° C. and DIAD (1.31 g, 6.46 mmol, 1.26 mL, 1.2 eq) was added to above solution. The mixture was stirred at 20° C. for 12 hr. TLC indicated Reactant 1 was consumed and new spot formed. The reaction mixture was concentrated under reduced pressure to remove solvent. The residue was diluted with H$_2$O 30 mL and extracted with ethyl acetate (50 mL×3). The combined organic layers were washed with NaCl (30 mL×3), dried over Na$_2$SO$_4$, filtered and concentrated under reduced pressure to give a residue. The residue was purified by column chromatography (SiO$_2$, Petroleum ether/Ethyl acetate=100/1 to 100/6) to give Intermediate I-245. $^1$H NMR (400 MHz, CHLOROFORM-d) δ 7.42 (d, J=7.2 Hz, 6H), 7.37-7.24 (m, 10H), 7.04 (s, 1H), 7.00-6.89 (m, 2H), 4.48-4.25 (m, 1H), 3.43-3.22 (m, 2H), 1.75-1.65 (m, 2H), 1.33-1.24 (m, 32H), 0.92 (t, J=6.7 Hz, 3H).

Intermediate I-246: (S)-3-fluoro-5-((1-hydroxyicosan-2-yl)oxy)benzonitrile

To a solution of (S)-3-fluoro-5-((1-(trityloxy)icosan-2-yl)oxy)benzonitrile, Intermediate I-245 (2.4 g, 3.6 mmol, 1 eq) in MTBE (30 mL) was added anisole (388.7 mg, 3.6 mmol, 390.7 uL, 1 eq), MeOH (4.8 mL) and 4-methylbenzenesulfonic acid (619.0 mg, 3.6 mmol, 1 eq). The mixture was stirred at 50° C. for 3 hr. TLC indicated the reactant was consumed and new spots formed. The reaction mixture was concentrated under reduced pressure to remove solvent. The residue was diluted with H$_2$O 30 mL and extracted with ethyl acetate (50 mL×3). The combined organic layers were washed with NaCl (30 mL×3), dried over Na$_2$SO$_4$, filtered and concentrated under reduced pressure to give a residue. The residue was purified by column chromatography (SiO$_2$, Petroleum ether/Ethyl acetate=100/0 to 100/9) to give (S)-3-fluoro-5-((1-hydroxyicosan-2-yl)oxy)benzonitrile Intermediate I-246. $^1$H NMR (400 MHz, CHLOROFORM-d) δ 7.03 (s, 1H), 7.00-6.88 (m, 2H), 4.41-4.31 (m, 1H), 3.89-3.72 (m, 2H), 1.76 (br s, 1H), 1.71-1.62 (m, 2H), 1.43-1.21 (m, 32H), 0.89 (t, J=6.8 Hz, 3H). MS (ESI): ink=434.2 [M+H]$^+$ Intermediate I-247: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((S)-2-(3-cyano-5-fluorophenoxy)icosyl) phosphate

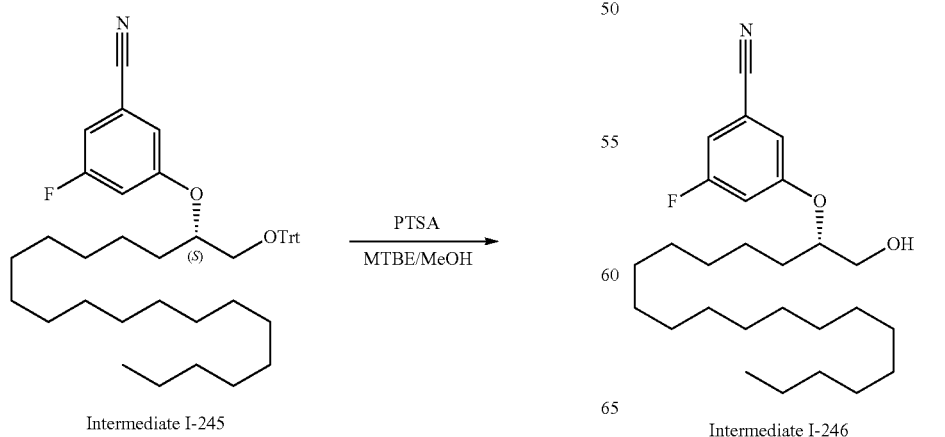

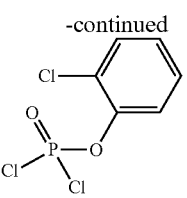

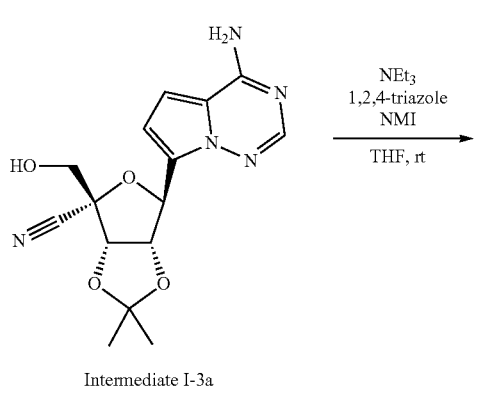

Intermediate I-3a

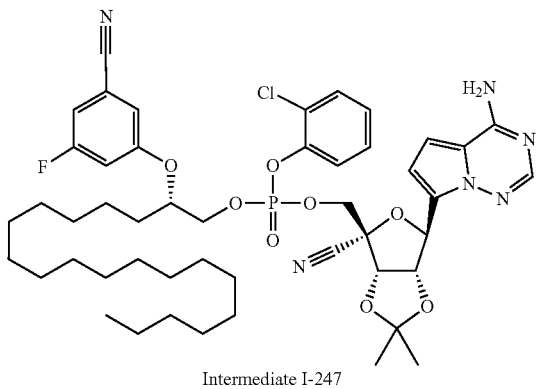

Intermediate I-247

1H-1,2,4-triazole (138 mg, 2 mmol) was dissolved in THF (6.0 mL). TEA (0.21 mL, 1.5 mmol) was added to the solution followed by 2-chlorophenyl phosphorodichloridate (156 mg, 0.63 mmol). The reaction mixture was stirred at rt for 6 min prior to the addition of (3aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (191 mg, 0.58 mmol) in one portion followed by 1-methylimidazole (0.1 mL, 1.38 mmol). The solution was stirred for an additional 17 min before adding (S)-2-(quinolin-2-ylmethoxy)icosan-1-ol, Intermediate I-246 (250 mg, 0.58 mmol, 1 equiv.). After stirring at room temperature for 20 min, the solution was diluted with EtOAc (50 mL) and water (50 mL). The organic layer, separated, washed with brine (5 mL), dried over MgSO$_4$, filtered and concentrated in vacuo prior to purification by silica gel chromatography (0-100% EtOAc in hexanes) to afford the Intermediate I-247. $^1$H NMR (400 MHz, Methanol-d4) δ 7.82 (d, J=3.4 Hz, 1H), 7.41 (ddt, J=7.9, 5.1, 1.2 Hz, 1H), 7.28 (ddt, J=8.5, 7.3, 1.4 Hz, 1H), 7.17-7.01 (m, 5H), 6.86 (dd, J=6.6, 4.5 Hz, 1H), 6.79 (dd, J=4.5, 1.9 Hz, 1H), 5.67 (dd, J=6.3, 3.0 Hz, 1H), 5.33 (dd, J=6.5, 3.0 Hz, 1H), 5.18 (dd, J=6.6, 3.9 Hz, 1H), 4.56 (dddd, J=25.1, 12.5, 10.0, 6.1 Hz, 3H), 4.37 (dddd, J=26.0, 11.4, 6.9, 3.0 Hz, 1H), 4.24 (ddd, J=11.5, 5.5, 2.7 Hz, 1H), 1.74 (s, 3H), 1.40 (s, 3H), 1.31-1.26 (m, 34H), 0.91 (t, J=6.8 Hz, 3H). $^{31}$P NMR (162 MHz, Methanol-d4) δ−7.99 (dt, J=28.7, 7.0 Hz). MS (ESI): m/z=434.2 [M+H]$^+$ Intermediate I-248: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-(3-cyano-5-fluorophenoxy)icosyl) hydrogen phosphate

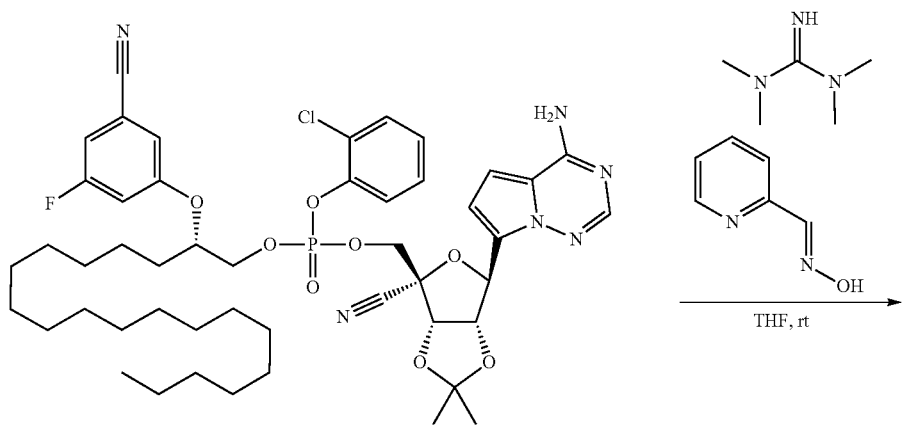

Intermediate I-247

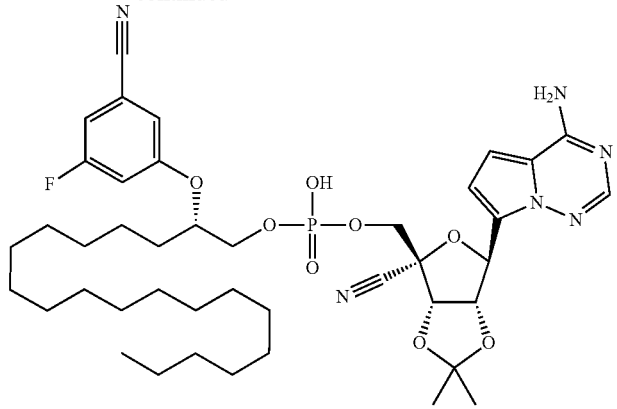

Intermediate I-248

To a solution of Intermediate I-247 (190 mg, 0.2 mmol) in THF (5.0 mL) was added 1,1,3,3-tetramethylguanidine (0.15 mL, 1.22 mmol) and syn-2-pyridinealdoxime (248 mg, 2 mmol). The reaction mixture was stirred at room temperature overnight. The solution was concentrated in vacuo and purified by silica gel (0-50% MeOH in DCM) to afford the Intermediate I-248. MS (ESI): m/z=827.2 [M+H]$^+$ Intermediate I-249: dodecylmagnesium bromide

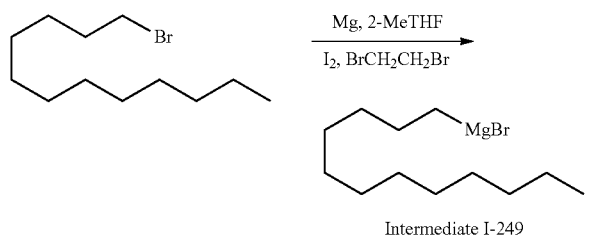

Intermediate I-249

To a solution of Mg (1.7 g, 69.2 mmol, 1.2 eq) in 2-Me THF (30 ml) was added I$_2$ (152.8 mg, 601.9 umol, 121.2 uL, 0.01 eq) and BrCH$_2$CH$_2$Br (0.2 mL) under N$_2$. Then 1-bromododecane (1.5 g, 6.0 mmol) in 2-Me THF (15 ml) was added dropwise. The mixture was stirred until the color of I$_2$ was faded to colorless. Then the remaining 1-bromododecane (13.5 g, 54.2 mmol) in 2-Me THF (135 ml) was added and the mixture was stirred at 25° C. for 4 hr. The crude product dodecylmagnesium bromide, Intermediate I-249 as brown liquid (in 2-Me THF) was used into the next step without further purification.

Intermediate I-250: (S)-1-(trityloxy)pentadecan-2-ol

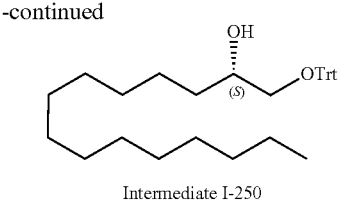

Intermediate I-250

Add bromo(dodecyl)magnesium Intermediate I-249 (15.0 g, 54.8 mmol, 1.3 eq) over 10 min via cannula to mixture of (2S)-2-(trityloxymethyl)oxirane (13.4 g, 42.2 mmol, 1.0 eq), CuI (401.7 mg, 2.1 mmol, 0.05 eq) in 2-Me THF (100 mL) at −20° C. Stirred vigorously for 5 min, warmed to 0° C., continue stirring 2 h. TLC indicated the reactant was consumed completely and two new spots formed. The reaction mixture was quenched by addition sat. NH$_4$Cl solution (300 ml), and then the mixture was extracted with Ethyl acetate (150 mL×3). The combined organic layers were washed with H$_2$O (350 mL×2), dried over Na$_2$SO$_4$, filtered and concentrated under reduced pressure to give a residue. The residue was purified by flash silica gel chromatography (50 g Silica Flash Column, Eluent of 0~4% Ethyl acetate/ Petroleum ether gradient @ 120 mL/min) to give compound (S)-1-(trityloxy)pentadecan-2-ol, Intermediate I-250. $^1$H NMR (400 MHz, CHLOROFORM-d) δ 7.38 (br d, J=7.5 Hz, 6H), 7.27 (br s, 9H), 3.71 (br d, J=3.0 Hz, 1H), 3.12 (dd, J=3.1, 9.3 Hz, 1H), 3.01-2.92 (m, 1H), 2.25 (d, J=2.8 Hz, 1H), 1.32 (br s, 2H), 1.27-1.11 (m, 22H), 0.82 (br t, J=6.7 Hz, 3H).

Intermediate I-251: (S)-3-fluoro-5-(((1-(trityloxy) pentadecan-2-yl)oxy)methyl)benzonitrile

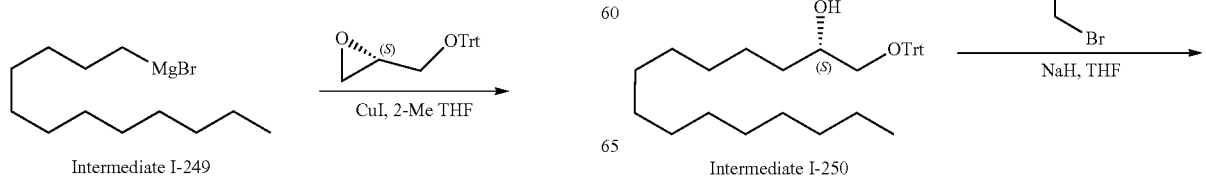

Intermediate I-250

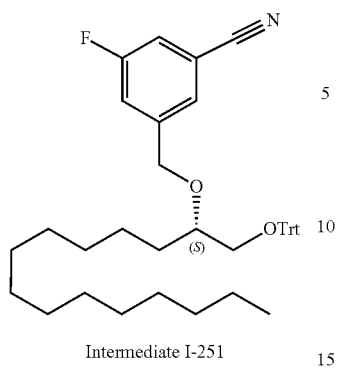

Intermediate I-251

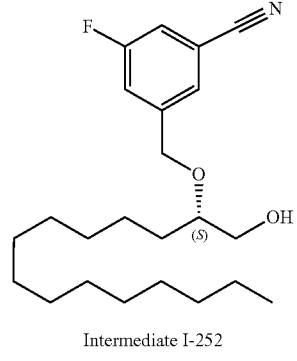

Intermediate I-252

To a solution of (2S)-1-trityloxypentadecan-2-ol, Intermediate I-250 (3.5 g, 7.2 mmol, 1.0 eq) in THF (50 mL) was added NaH (719.0 mg, 18.0 mmol, 60% purity, 2.5 eq) at 0° C. and the mixture was stirred at 0° C. for 30 min. Then 3-(bromomethyl)-5-fluoro-benzonitrile (1.9 g, 9.0 mmol, 1.3 eq) was added and the mixture was stirred at 65° C. for 12 hr. The reaction mixture was quenched by addition sat. NH₄Cl solution (100 ml) at 20° C. and extracted with Ethyl acetate (50 mL×3). The combined organic layers were washed with H₂O (120 mL×2), dried over Na₂SO₄, and concentrated under reduced pressure to give a residue. The residue was purified by flash silica gel chromatography (20 g Silica Flash Column, Eluent of 0~3% Ethyl acetate/Petroleum ether gradient @ 45 mL/min) to give compound (S)-3-fluoro-5-(((1-(trityloxy)pentadecan-2-yl)oxy)methyl) benzonitrile Intermediate I-251. ¹H NMR (400 MHz, CHLOROFORM-d) δ 7.41-7.32 (m, 7H), 7.27-7.13 (m, 11H), 4.64 (d, J=12.9 Hz, 1H), 4.51-4.44 (m, 1H), 3.48-3.40 (m, 1H), 3.14 (d, J=4.8 Hz, 2H), 1.46 (br d, J=4.1 Hz, 2H), 1.25-1.13 (m, 22H), 0.81 (t, J=6.7 Hz, 3H)

Intermediate I-252: (S)-3-fluoro-5-(((1-hydroxypentadecan-2-yl)oxy)methyl)benzonitrile To a solution of 3-fluoro-5-[[(1S)-1-(trityloxymethyl)tetradecoxy]methyl]benzonitrile, Intermediate I-251 (2.7 g, 4.4 mmol, 1.0 eq) in MTBE (54 mL) and MeOH (7.5 mL) was added anisole (235.5 mg, 2.2 mmol, 236.7 uL, 0.5 eq) and PTSA (375.1 mg, 2.2 mmol, 0.5 eq) and the mixture was stirred at 50° C. for 2 hr. TLC indicated Reactant 5 A was consumed completely and many new spots formed. The reaction mixture was diluted with sat. NaHCO₃ 80 mL and extracted with Ethyl acetate (40 mL×3). The combined organic layers were washed with H₂O (50 mL×2), dried over Na₂SO₄, filtered and concentrated under reduced pressure to give a residue. The residue was purified by flash silica gel chromatography (20 g Silica Flash Column, Eluent of 0~8% Ethyl acetate/Petroleum ether gradient @ 45 mL/min) to give compound (S)-3-fluoro-5-(((1-hydroxypentadecan-2-yl)oxy)methyl)benzonitrile, Intermediate I-252. ¹H NMR (400 MHz, CHLOROFORM-d) δ 7.47 (br s, 1H), 7.36 (br d, J=8.9 Hz, 1H), 7.32-7.26 (m, 1H), 4.66 (s, 2H), 3.77 (br dd, J=3.1, 11.5 Hz, 1H), 3.67-3.52 (m, 2H), 1.85 (br s, 1H), 1.67-1.57 (m, 2H), 1.28 (br s, 22H), 1.01-0.85 (m, 3H).

Intermediate I-253: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((S)-2-((3-cyano-5-fluorobenzyl)oxy)pentadecyl) phosphate

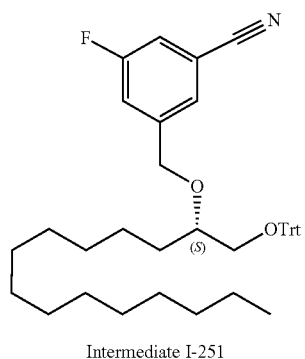

Intermediate I-251

PTSA, MTBE/MeOH →

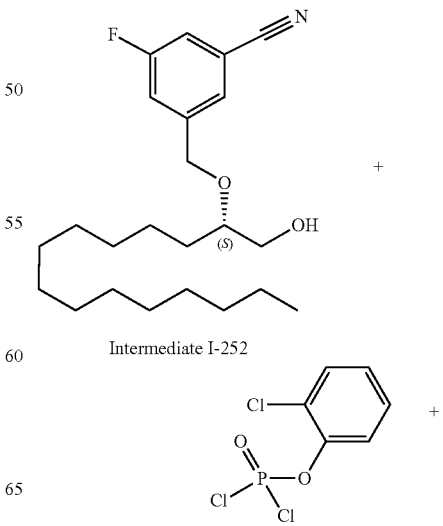

Intermediate I-252

+

+

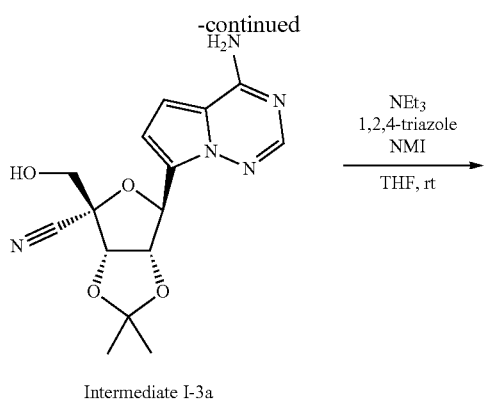

Intermediate I-3a

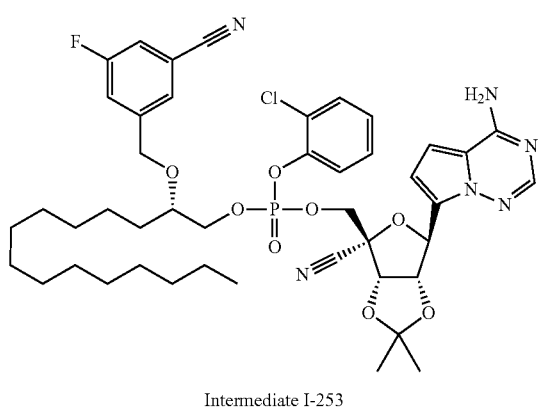

Intermediate I-253

1H-1,2,4-triazole (131 mg, 1.9 mmol) was dissolved in THF (6.0 mL). TEA (0.20 mL, 1.45 mmol, 2.65 equiv.) was added to the solution followed by 2-chlorophenyl phosphorodichloridate (148 mg, 0.60 mmol). The reaction mixture was stirred at rt for 6 min prior to the addition of (3aS,4R,6aS)-6-(4-aminopyrrolo [2,1-f][1,2,4]triazin-7-yl)-4-(hydroxymethyl)-2,2-dimethyltetrahydro furo [3,4-d][1,3]dioxole-4-carbonitrile, Intermediate I-3a (182 mg, 0.55 mmol) in one portion followed by 1-methylimidazole (0.06 mL, 0.70 mmol, 1.3 equiv.). The solution was stirred for an additional 17 min before adding (S)-2-(quinolin-2-yl-methoxy)icosan-1-ol, Intermediate I-252 (250 mg, 0.54 mmol, 1 equiv.). After stirring at room temperature for 20 min, the solution was diluted with EtOAc (50 mL) and water (50 mL). The organic layers were combined, washed with brine (5 mL), dried over MgSO$_4$, filtered and concentrated in vacuo prior to purification by silica gel chromatography (0-100% EtOAc in hexanes) to afford the Intermediate I-253. $^1$H NMR (400 MHz, Methanol-d4) δ 7.83 (d, J=5.8 Hz, 1H), 7.58-7.32 (m, 5H), 7.28-7.06 (m, 2H), 6.94-6.74 (m, 2H), 5.68 (dd, J=3.0, 1.2 Hz, 1H), 5.34 (td, J=6.8, 3.0 Hz, 1H), 5.18 (dd, J=18.5, 6.6 Hz, 1H), 4.63-4.49 (m, 3H), 4.14 (q, J=7.2 Hz, 4H), 2.05 (s, 6H), 1.32-1.26 (m, 24H), 0.93 (t, J=6.8 Hz, 3H). $^{31}$P NMR (162 MHz, Methanol-d4) δ −7.76 (dt, J=48.8, 7.2 Hz). MS (ESI): m/z=881.2 [M+H]+

Intermediate I-254: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl)oxy)pentadecyl) hydrogen phosphate

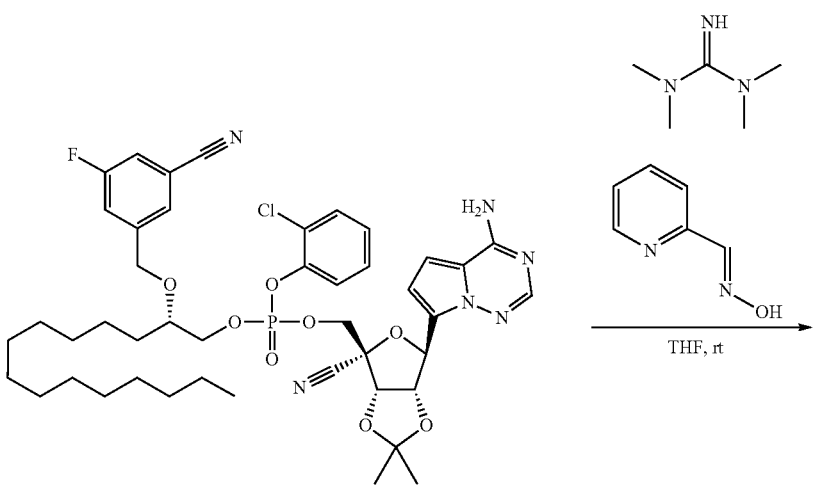

Intermediate I-253

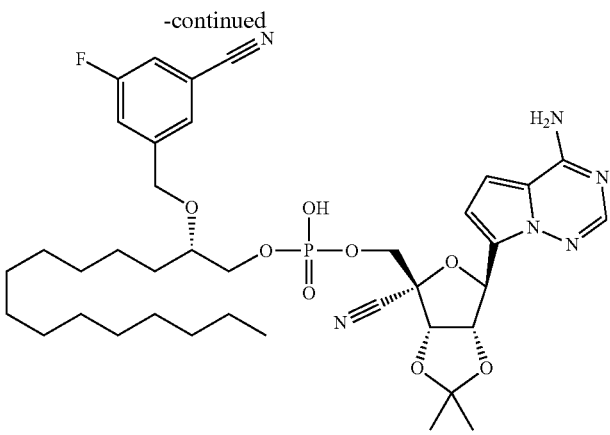

Intermediate I-254

To a solution of Intermediate I-253 (135 mg, 0.14 mmol) in THF (5.0 mL) was added 1,1,3,3-tetramethylguanidine (0.1 mL, 0.84 mmol) and syn-2-pyridinealdoxime (172 mg, 1.4 mmol). The reaction mixture was stirred at room temperature overnight. The solution was concentrated in vacuo and purified by silica gel (0-50% MeOH in DCM) to afford the Intermediate I-254. MS (ESI): m/z=771.3 [M+H]$^+$ Intermediate I-255: (S)-4-((hexadecyloxy)methyl)-2,2-dimethyl-1,3-dioxolane acetate=100/1 to 100/5) to give (S)-4-((hexadecyloxy)methyl)-2,2-dimethyl-1,3-dioxolane, Intermediate I-255 (13.5 g, 3 batches) as a colorless oil. $^1$H NMR (400 MHz, CHLOROFORM-d) δ 4.35-4.16 (m, 1H), 4.09-4.01 (m, 1H), 3.78-3.68 (m, 1H), 3.54-3.38 (m, 4H), 1.61-1.52 (m, 2H), 1.42 (s, 3H), 1.36 (s, 3H), 1.25 (s, 26H), 0.88 (t, J=6.8 Hz, 3H).

Intermediate I-256: (R)-3-(hexadecyloxy)propane-1,2-diol

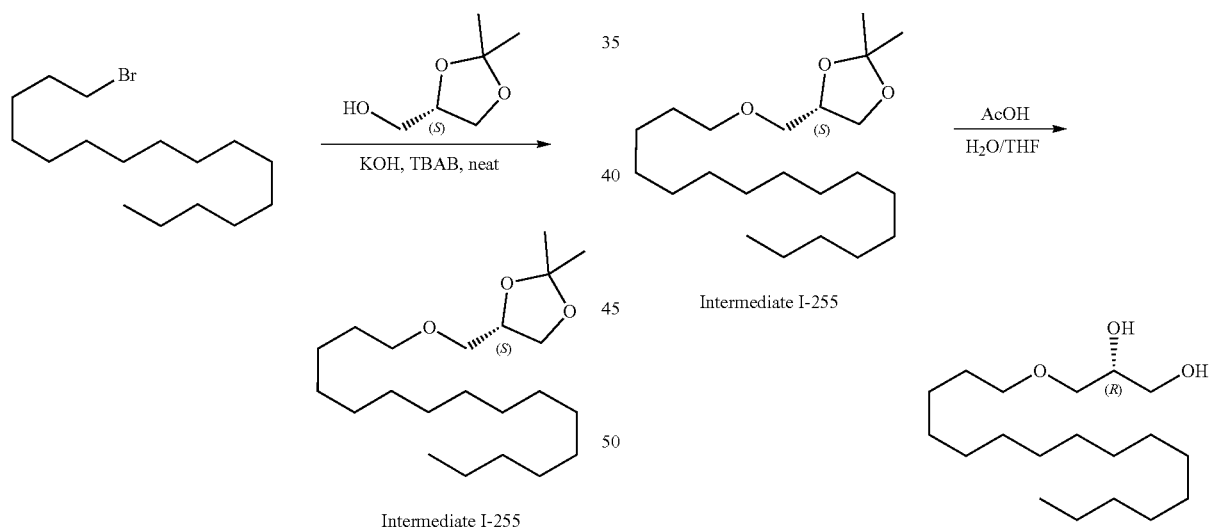

Intermediate I-255

Intermediate I-256

To a solution of 1-bromohexadecane (5 g, 16.3 mmol, 5.0 mL, 1 eq) in [(4S)-2,2-dimethyl-1,3-dioxolan-4-yl]methanol (10.0 g, 75.6 mmol, 9.3 mL, 4.6 eq) was added KOH (2.3 g, 40.9 mmol, 2.5 eq) and TBAB (1.0 g, 3.2 mmol, 0.2 eq). The mixture was stirred at 40° C. for 12 hr. TLC indicated Reactant 1 was consumed and new spots formed. The reaction mixture was diluted with NH$_4$Cl 100 mL and extracted with ethyl acetate (80 mL×3). The combined organic layers were washed with NaCl (50 mL×3), dried over Na$_2$SO$_4$, filtered and concentrated under reduced pressure to give a residue. The residue was purified by column chromatography (SiO$_2$, Petroleum ether/Ethyl To a solution of (S)-4-((hexadecyloxy)methyl)-2,2-dimethyl-1,3-dioxolane, Intermediate I-255 (5 g, 14.0 mmol, 1 eq) in THF (50 mL) was added AcOH (63.0 g, 1.0 mol, 60.0 mL, 74.8 eq) and H$_2$O (40.0 g, 2.2 mol, 40 mL, 158.3 eq). The mixture was stirred at 50° C. for 6 hr. TLC indicated Reactant 2 was consumed completely and one new spot formed. The reaction mixture was concentrated under reduced pressure to remove THF at 50° C. Then 50 mL Tol. was added to the reaction and concentrated under reduced pressure at 50° C. to remove AcOH and H$_2$O to give (R)-3-(hexadecyloxy)propane-1,2-diol, Intermediate I-256

(13 g, 3 batches) was obtained as a white solid. ¹H NMR (400 MHz, CHLOROFORM-d) δ 3.94-3.80 (m, 1H), 3.76-3.61 (m, 2H), 3.56-3.38 (m, 4H), 1.67-1.49 (m, 2H), 1.26 (s, 26H), 0.95-0.83 (m, 3H).

Intermediate I-257: (S)-1-(hexadecyloxy)-3-(trityloxy)propan-2-ol

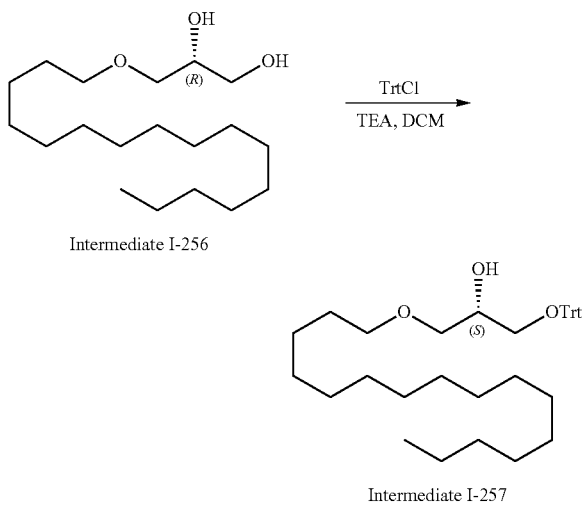

Intermediate I-256

Intermediate I-257

(R)-3-(hexadecyloxy)propane-1,2-diol, Intermediate I-256 (7 g, 19.9 mmol, 90% purity, 1 eq) was dissolved in the solution of DCM (80 mL), TEA (3.6 g, 35.8 mmol, 4.9 mL, 1.8 eq) was added and stirred at 0° C. for 0.5 hr. Trityl chloride (5.2 g, 18.9 mmol, 0.9 eq) was added at 0° C. The mixture was stirred at 20° C. for 12 hr. TLC indicated Reactant 3 was consumed and new spots formed. The reaction mixture was diluted with DCM 50 mL, washed with H₂O (50 mL×3), dried over Na₂SO₄, filtered and concentrated under reduced pressure to give a residue. The residue was purified by column chromatography (SiO₂, Petroleum ether/Ethyl acetate=100/1 to 100/6) to give (S)-1-(hexadecyloxy)-3-(trityloxy)propan-2-ol, Intermediate I-257 (12 g, 2 batches) as a white solid. ¹H NMR (400 MHz, CHLOROFORM-d) δ 7.44-7.38 (m, 6H), 7.27 (s, 13H), 3.96-3.88 (m, 1H), 3.53-3.31 (m, 4H), 3.23-3.12 (m, 2H), 2.02 (s, 1H), 1.29-1.20 (m, 26H), 0.89-0.82 (m, 3H)

Intermediate I-258: (S)-3-chloro-5-(((1-(hexadecyloxy)-3-(trityloxy)propan-2-yl)oxy)methyl)benzonitrile

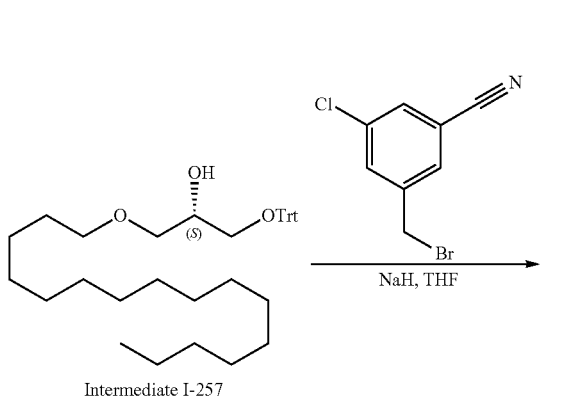

Intermediate I-257

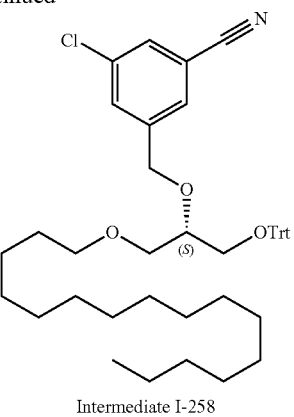

Intermediate I-258

To a solution of (S)-1-(hexadecyloxy)-3-(trityloxy)propan-2-ol, Intermediate I-257 (3 g, 5.3 mmol, 1 eq) in THF (20 mL) was added NaH (644.2 mg, 16.1 mmol, 60% purity, 3 eq) at 0° C. The mixture was stirred at 0° C. for 0.5 hr and then 3-(bromomethyl)-5-chloro-benzonitrile (1.8 g, 8.0 mmol, 1.5 eq) was added into the above solution at 0° C. The mixture was stirred at 65° C. for 12 hr. TLC indicated Reactant 4 was consumed completely and new spots formed. The reaction mixture was quenched by added into sat NH₄Cl 50 mL at 0° C., and extracted with ethyl acetate (30 mL×3). The combined organic layers were washed with NaCl (30 mL×3), dried over Na₂SO₄, filtered and concentrated under reduced pressure to give a residue. The residue was purified by column chromatography (SiO₂, Petroleum ether/MTBE=100/0 to 100/8) to give (S)-3-chloro-5-(((1-(hexadecyloxy)-3-(trityloxy)propan-2-yl)oxy)methyl)benzonitrile, Intermediate I-258. ¹H NMR (400 MHz, CHLOROFORM-d) δ 7.64 (s, 1H), 7.56 (s, 2H), 7.48 (d, J=7.5 Hz, 6H), 7.37-7.25 (m, 11H), 4.70 (s, 2H), 3.80-3.70 (m, 1H), 3.61 (d, J=5.3 Hz, 2H), 3.45 (t, J=6.7 Hz, 2H), 3.36-3.22 (m, 2H), 1.42-1.19 (m, 28H), 0.92 (t, J=6.7 Hz, 3H)

Intermediate I-259: (R)-3-chloro-5-(((1-(hexadecyloxy)-3-hydroxypropan-2-yl)oxy)methyl)benzonitrile

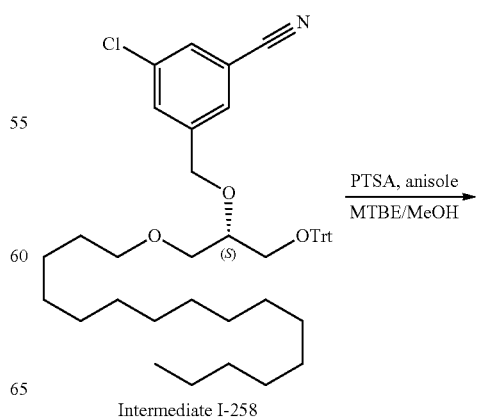

Intermediate I-258

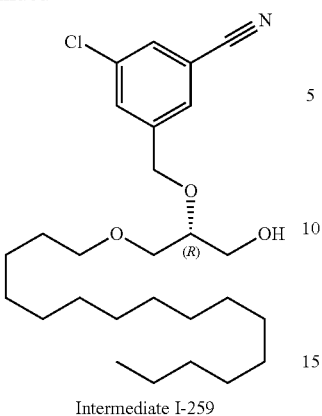

Intermediate I-259

To a solution of (S)-3-chloro-5-(((1-(hexadecyloxy)-3-(trityloxy)propan-2-yl)oxy)methyl)benzonitrile, Intermediate I-258 (3 g, 4.2 mmol, 1 eq) in MTBE (30 mL) was added anisole (457.9 mg, 4.2 mmol, 460.2 uL, 1 eq), MeOH (4.8 mL) and 4-methylbenzenesulfonic acid (729.2 mg, 4.2 mmol, 1 eq). The mixture was stirred at 50° C. for 3 hr. TLC indicated Reactant 5 was consumed completely and new spots formed. The reaction mixture was concentrated under reduced pressure to remove solvent. The residue was diluted with 30 mL ethyl acetate, washed with NaCl (20 mL×3), dried over Na$_2$SO$_4$, filtered and concentrated under reduced pressure to give a residue. The residue was purified by column chromatography (SiO$_2$, Petroleum ether/Ethyl acetate=100/0 to 100/8) to give (R)-3-chloro-5-(((1-(hexadecyloxy)-3-hydroxypropan-2-yl)oxy)methyl)benzonitrile, Intermediate I-259. $^1$H NMR (400 MHz, CHLOROFORM-d) δ 7.61 (s, 1H), 7.59-7.53 (m, 2H), 4.80-4.65 (m, 2H), 3.84-3.76 (m, 1H), 3.75-3.66 (m, 2H), 3.64-3.55 (m, 2H), 3.49-3.42 (m, 2H), 2.20-2.00 (m, 1H), 1.63-1.54 (m, 2H), 1.37-1.22 (m, 26H), 0.93-0.83 (m, 3H). MS (ESI): m/z=466.2 [M+H]$^+$ Intermediate I-260: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((S)-2-((3-cyano-5-fluorobenzyl)oxy)-3-(hexadecyloxy)propyl) phosphate

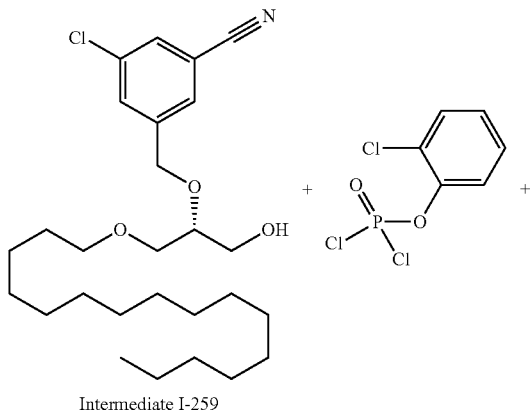

Intermediate I-259

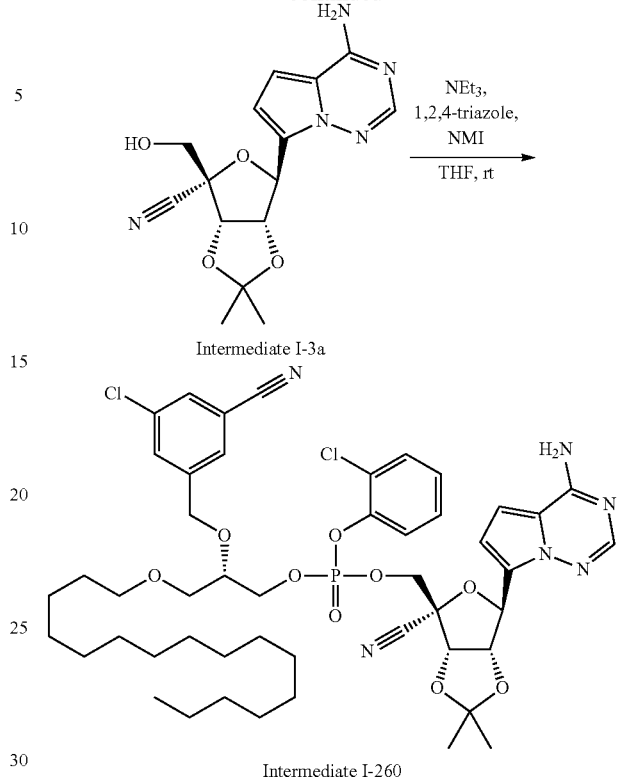

Intermediate I-260

1H-1,2,4-triazole (128 mg, 1.86 mmol) was dissolved in THF (6.0 mL). TEA (0.20 mL, 1.42 mmol) was added to the solution followed by 2-chlorophenyl phosphorodichloridate (0.10 mL, 0.59 mmol). The reaction mixture was stirred at rt for 6 min prior to the addition of (3 aS,4R,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile, Intermediate I-3a (178 mg, 0.54 mmol) in one portion followed by 1-methylimidazole (0.1 mL, 1.3 mmol). The solution was stirred for an additional 17 min before adding (R)-3-chloro-5-(((1-(hexadecyloxy)-3-hydroxypropan-2-yl)oxy)methyl)benzonitrile, Intermediate I-259 (250 mg, 0.54 mmol, 1 equiv.). After stirring at room temperature for 20 min, the solution was diluted with EtOAc (50 mL) and water (50 mL). The aqueous layer was extracted again with EtOAc (50 mL). The organic layers were combined, washed with brine (5 mL), dried over MgSO$_4$, filtered and concentrated in vacuo prior to purification by silica gel chromatography (0-100% EtOAc in hexanes) to afford the Intermediate I-260. $^1$H NMR (400 MHz, Methanol-d4) δ 7.83 (d, J=5.0 Hz, 1H), 7.67-7.61 (m, 3H), 7.49-7.41 (m, 1H), 7.37 (tt, J=8.7, 3.1 Hz, 1H), 7.22-7.11 (m, 2H), 6.86 (dd, J=7.1, 4.5 Hz, 1H), 6.79 (dd, J=4.5, 1.7 Hz, 1H), 5.67 (d, J=3.0 Hz, 1H), 5.33 (ddd, J=7.3, 4.7, 3.0 Hz, 1H), 5.17 (dd, J=17.2, 6.6 Hz, 1H), 4.66 (d, J=2.3 Hz, 2H), 4.57 (ddd, J=13.3, 11.4, 6.5 Hz, 2H), 4.43 (ddt, J=11.1, 7.8, 4.0 Hz, 1H), 4.30 (dtd, J=11.0, 8.4, 5.6 Hz, 1H), 3.88-3.79 (m, 1H), 3.56-3.47 (m, 2H), 3.42 (dt, J=12.0, 6.0 Hz, 2H), 1.77-1.70 (m, 5H), 1.29 (d, J=6.9 Hz, 31H), 0.92 (t, J=6.8 Hz, 4H). $^{31}$P NMR (162 MHz, Methanol-d4) δ−7.78 (dt, J=38.1, 7.2 Hz). MS (ESI): intz=969.1 [M]$^+$ Intermediate I-261: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl)oxy)-3-(hexadecyloxy)propyl) hydrogen phosphate

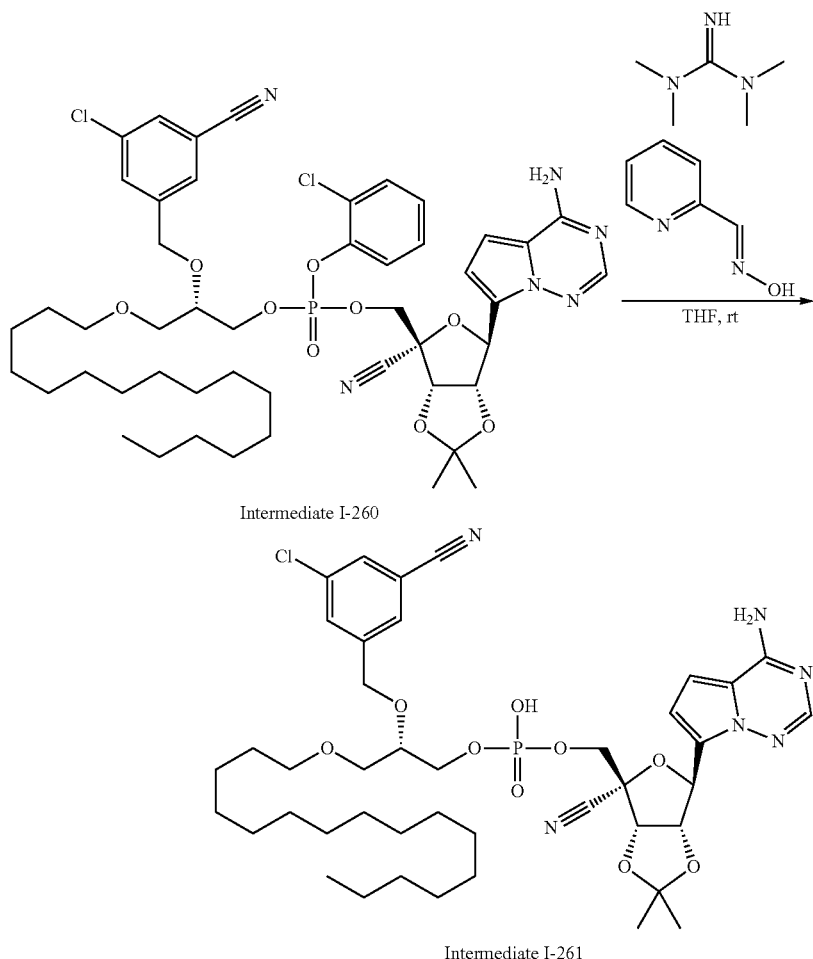

To a solution of Intermediate I-260 (110 mg, 0.119 mmol, 1.0 equiv.) in THF (5.0 mL) was added 1,1,3,3-tetramethylguanidine (0.09 mL, 0.715 mmol, 6.0 equiv.) and syn-2-pyridinealdoxime (90 mg, 0.737 mmol, 6.19 equiv.). The reaction mixture was stirred at room temperature overnight. The solution was concentrated in vacuo and purified by silica gel (0-50% MeOH in DCM) to afford the Intermediate I-261. MS (ESI): m/z=860.2 [M+H]$^+$ Intermediate I-262: (R)-1-(pentadecyloxy)-3-(trityloxy)propan-2-ol)

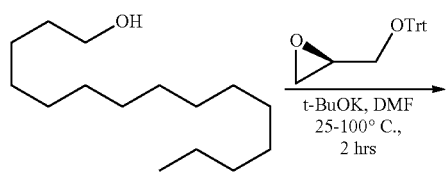

-continued

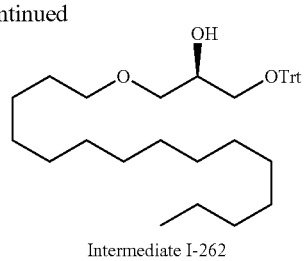

Intermediate I-262

To a solution of pentadecan-1-ol (5.00 g, 21.8 mmol, 1.00 eq) into DMF (100 mL) was added t-BuOK (3.68 g, 32.8 mmol, 1.50 eq) followed by (R)-2-((trityloxy)methyl)oxirane (13.8 g, 43.7 mmol, 2.00 eq) at room temperature. The reaction mixture was stirred at 100° C. for 2 hrs. Water (100 mL) was added at 25° C. and this was extracted with EtOAc (100 mL). The organic layer was dried over Na$_2$SO$_4$, filtered and concentrated in vacuo. The crude residue was purified by silica gel column chromatography (petroleum ether/

EtOAc=50/1 to 20/1) to afford the title compound. TLC Rf=0.70 (Eluent: Petroleum ether/Ethyl acetate=4/1).

Intermediate I-263: (R)-3-fluoro-5-(((1-(pentadecyloxy)-3-(trityloxy)propan-2-yl)oxy)methyl)benzonitrile

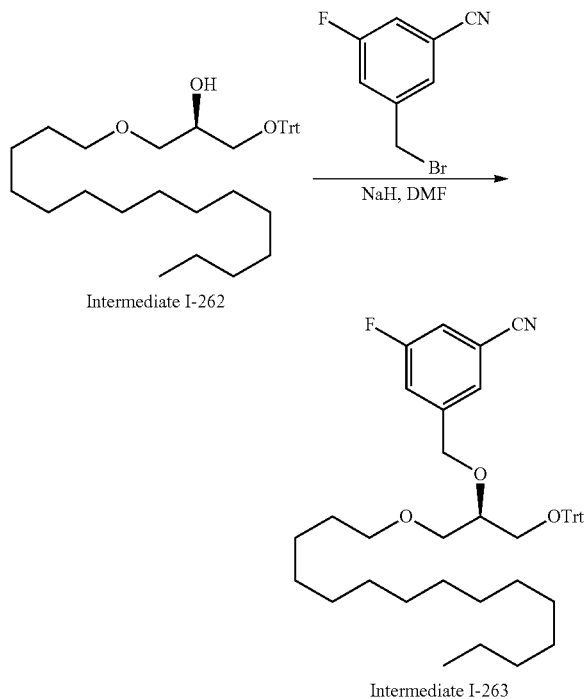

To a solution of (R)-1-(pentadecyloxy)-3-(trityloxy)propan-2-ol (5.00 g, 9.19 mmol, 1.00 eq) in THF(50 mL) at room temperature was added NaH (1.84 g, 45.9 mmol, 60.0% purity, 5.00 eq) in small portions. The solution was stirred for 0.5 h. To the mixture was added a solution of 3-(bromomethyl)-5-fluorobenzonitrile (2.95 g, 13.7 mmol, 1.50 eq) in DMF (100 mL) dropwise and stirring continued for 12 hrs. The reaction was quenched with saturated NH₄Cl (50.0 mL) and extracted with ethyl acetate (50.0 mL×2). The organic layer was dried over Na₂SO₄ and concentrated. The crude product was purified by silica gel chromatography (petroleum ether/EtOAc=1/0 to 0/1) to afford the title compound. TLC Rf=0.80 (Eluent: Petroleum ether/Ethyl acetate=5/1).

Intermediate I-264: Synthesis of (S)-3-fluoro-5-(((1-hydroxy-3-(pentadecyloxy)propan-2-yl)oxy)methyl)benzonitrile

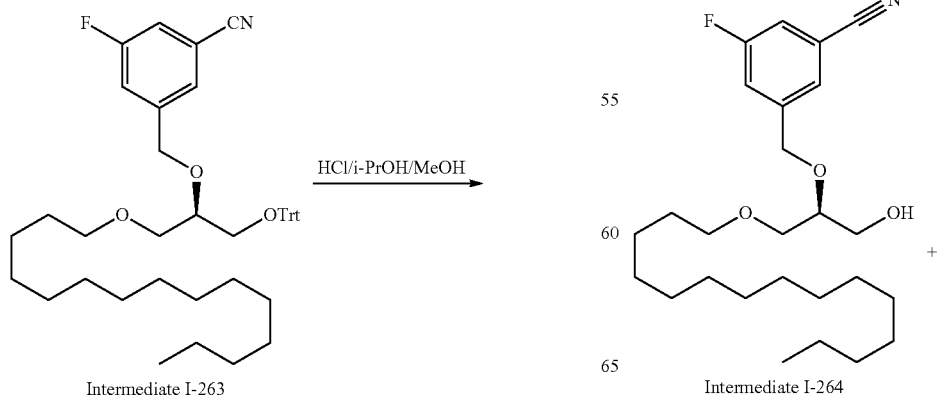

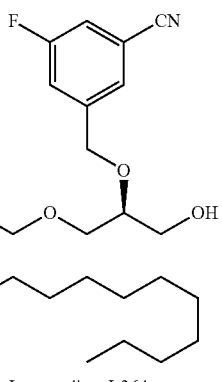

Intermediate I-264

To a mixture of (R)-3-fluoro-5-(((1-(pentadecyloxy)-3-(trityloxy)propan-2-yl)oxy)methyl)benzonitrile (3.60 g, 5.31 mmol, 1.00 eq) in MeOH (14.4 mL) and i-PrOH (14.4 mL) was added HCl (12.0 M, 10.0 mL, 22.8 eq) and stirred at 55° C. for 1 hr. The solution as poured into H₂O (10.0 mL) and extracted with EtOAc (10.0 mL×2). The separated organic layers were washed once with sat. NaHCO₃ (10.0 mL) followed by a wash with brine and drying over Na₂SO₄. The solvent was concentrated in vacuo and the crude residue was purified by silica gel chromatography (petroleum ether/EtOAc=1/0 to 0/1) to afford the title compound. $^1$H NMR (400 MHz, Chloroform-d) δ 7.46 (s, 1H), 7.36 (d, J=8.0 Hz, 1H), 7.27 (t, J=8.0 Hz, 1H), 4.68-4.72 (m, 2H), 3.78-3.80 (m, 1H), 3.70-3.72 (m, 2H), 3.59-3.69 (m, 2H), 3.43-3.58 (m, 2H), 1.59 (s, 1H), 1.54-1.57 (m, 2H), 1.25-1.33 (m, 24H), 0.88 (t, J=8.0 Hz, 3H); MS m/z [M+1]=436.2

Intermediate I-265: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)-3-(pentadecyloxy)propyl) phosphate

845

-continued

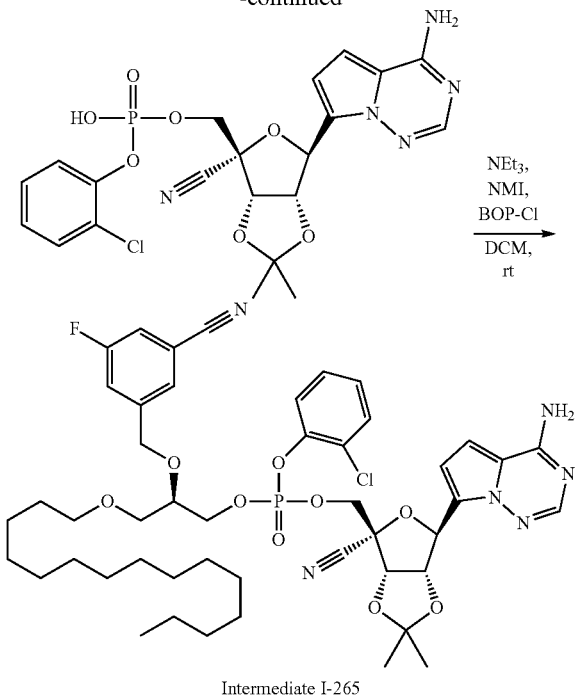

Intermediate I-265

846

(S)-3-fluoro-5-(((1-hydroxy-3-(pentadecyloxy)propan-2-yl)oxy)methyl)benzonitrile (0.12 mg, 0.275 mmol), and ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) hydrogen phosphate (216 mg, 0.413 mmol) were taken in a 20 mL vial, dried under vacuum (1 h). To this mixture were added DCM (4 mL), NMI (0.09 mg, 1.1 mmol), TEA (77 uL, 0.551 mmol) and Bop-Cl (0.281 mg, 1.10 mmol) sequentially. The reaction stirred at room temperature overnight. Solvent concentrated under reduced pressure, and crude product was dissolved in 20% MeOH/DCM, loaded on 40 g column, eluted with 100% Hexane 2 min, 0-100% EtOAc 6 min, and 100% EtOAc 6 min. The product elutes at 100% EtOAc, fractions containing pure product were combined, concentrated to afford the Intermediate I-265. MS m/z [M+1]=939.21.

Intermediate I-266: ((3aS,4R,6S,6aS)-6-(4-aminopyrrolo [2,1-f][1,2,4]triazin-7-yl)-4-cyano-2,2-dimethyltetrahydrofuro[3,4-d][1,3]dioxol-4-yl)methyl ((R)-2-((3-cyano-5-fluorobenzyl)oxy)-3-(pentadecyloxy)propyl) hydrogen phosphate

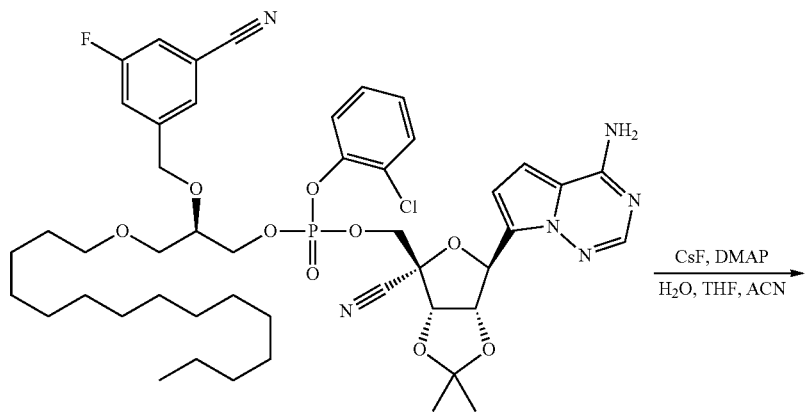

Intermediate I-265

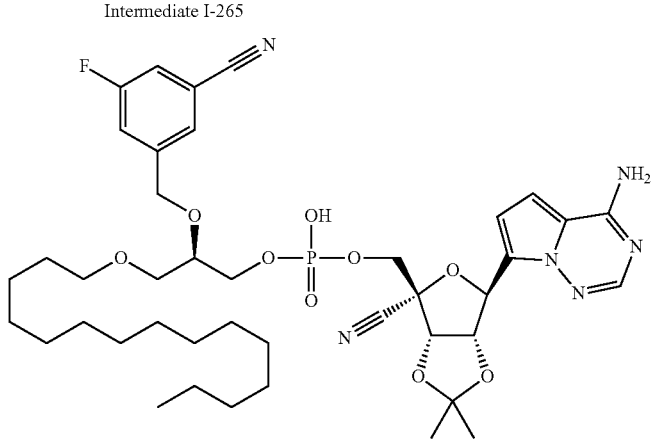

Intermediate I-266

((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (2-chlorophenyl) ((R)-2-((3-cyano-5-fluorobenzyl)oxy)-3-(pentadecyloxy)propyl) phosphate (150 mg, 0.160 mmol) was dissolved in 2:1 THF:ACN (6 mL) and solution of Cesium fluoride (121 mg, 0.798 mmol) in water (0.216 mL) was added followed by 4-(dimethylamino)pyridine (0.097 mg, 0.79 mmol). The reaction mixture was stirred at 80° C. for 3 h. The reaction was cooled to room temperature and added 10% solution of citric acid in water (15 mL) followed by 1M NaOH to adjust pH ~3. Extracted with 2-MeTHF/EtOAc (3:2, 50 mL×2). The combined organic layer washed with brine solution once and dried over $Na_2SO_4$, filtered and concentrated in vacuo prior to purification by silica gel chromatography (0-50% MeOH in DCM) to afford the Intermediate I-266. MS m/z [M+1]=829.12

C. Compounds

Example 1: Compound 1 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl)oxy)-3-(octadecyloxy)propyl) hydrogen phosphate

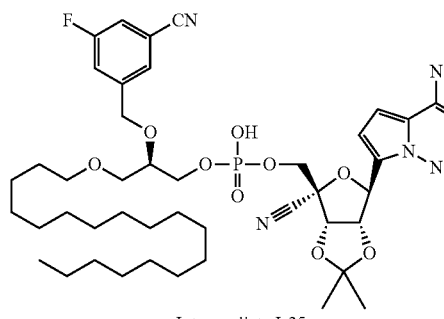

Intermediate I-25

HCl/THF

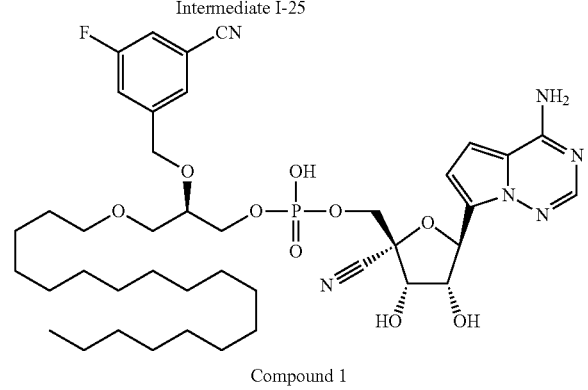

Compound 1

To a solution of Intermediate I-25 (0.321 mmol) in THF (4.0 mL) at 0° C. was added concentrated HCl (0.536 mL, 6.43 mmol) dropwise. The reaction mixture was warmed to room temperature and stirred for 5 h. The solution was cool to 0° C., and added 6 ice pellets, followed by solution of NaOH (2M in water) until reach pH ~8. To this solution was added Phosphoric acid (85% in water) to adjust pH ~3-4. Transferred to separatory funnel, and used water (20 mL), EtOAc/Me-THF (1:1, 50 mL) to complete transfer. Extracted with EtOAc/MeTHF (1:1, 100 mL×2) and combine organic layer washed with brine (70 mL) once. Dried over sodium sulfate, filtered, concentrated under vacuo prior to purification by silica gel chromatography (0-100% MeOH in DCM) to afford Compound 1. $^1$H NMR (400 MHz, Methanol-$d_4$) δ 7.84 (s, 1H), 7.53 (s, 1H), 7.45 (d, J=9.8 Hz, 1H), 7.36 (dt, J=8.3, 1.9 Hz, 1H), 6.95-6.82 (m, 2H), 5.56 (d, J=5.2 Hz, 1H), 4.75-4.61 (m, 2H), 4.59-4.48 (m, 2H), 4.16 (qd, J=10.9, 4.8 Hz, 2H), 3.96 (t, J=6.3 Hz, 2H), 3.76 (dq, J=9.0, 5.2 Hz, 1H), 3.61-3.39 (m, 4H), 1.54 (q, J=6.8 Hz, 2H), 1.29 (d, J=9.8 Hz, 30H), 0.92 (t, J=6.7 Hz, 3H). MS m/z [M+1]=831.3.

Example 7: Compound 7 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-chloro-4-cyanobenzyl)oxy)-3-(octadecyloxy)propyl) hydrogen phosphate

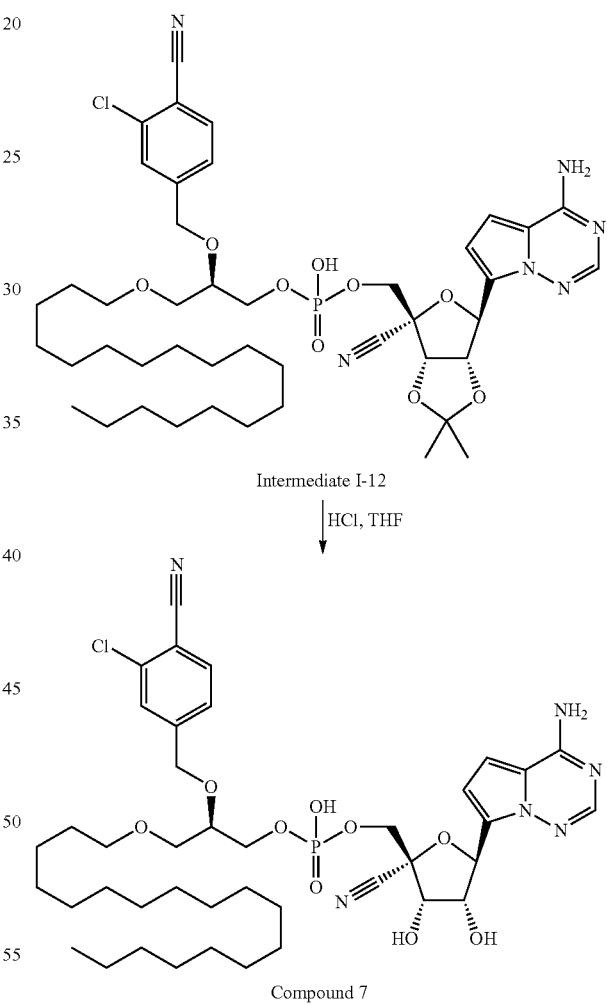

Intermediate I-12 (0.168 mmol) was dissolved in THF (2.0 mL) and then 25% HCl (1.0 ml) added at room temperature. The resulting mixture was stirred at room temperature for 7 h and diluted with DCM-IPA (16 mL:4 mL) and 5N NaOH (0.5 mL) added to the mixture, which was then washed with brine (10 mL×2). The aqueous layer extracted with DCM-IPA (4:1, 20 mL×2) and the combined organic layer was dried with sodium sulfate, concentrated in vacuo, and purified with silica gel column chromatography (0% to 100% MeOH in DCM) to give Compound 7. $^1$H NMR (400 MHz, Methanol-d4) δ 7.83 (s, 1H), 7.67 (d, J=8.0 Hz, 1H), 7.60 (d, J=1.4 Hz, 1H), 7.41 (d, J=8.0 Hz, 1H), 6.88 (d, J=4.6 Hz, 1H), 6.85 (d, J=4.5 Hz, 1H), 5.55 (d, J=5.2 Hz, 1H), 4.73 (d, J=13.9 Hz, 1H), 4.65 (d, J=13.7 Hz, 1H), 4.57 (t, J=5.3 Hz, 1H), 4.53 (d, J=5.5 Hz, 1H), 4.16 (qd, J=10.9, 4.8 Hz, 2H), 3.96 (m, 2H), 3.75 (m, 1H), 3.57-3.37 (m, 4H), 1.52 (m, 2H), 1.39-1.29 (m, 30H), 0.92 (t, J=6.7 Hz, 3H). $^{31}$P NMR (162 MHz, Methanol-d4) δ−0.36. MS m/z [M+1]=847.

Example 9: Compound 9 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-4-methoxybenzyl)oxy)-3-(octadecyloxy)propyl) hydrogen phosphate

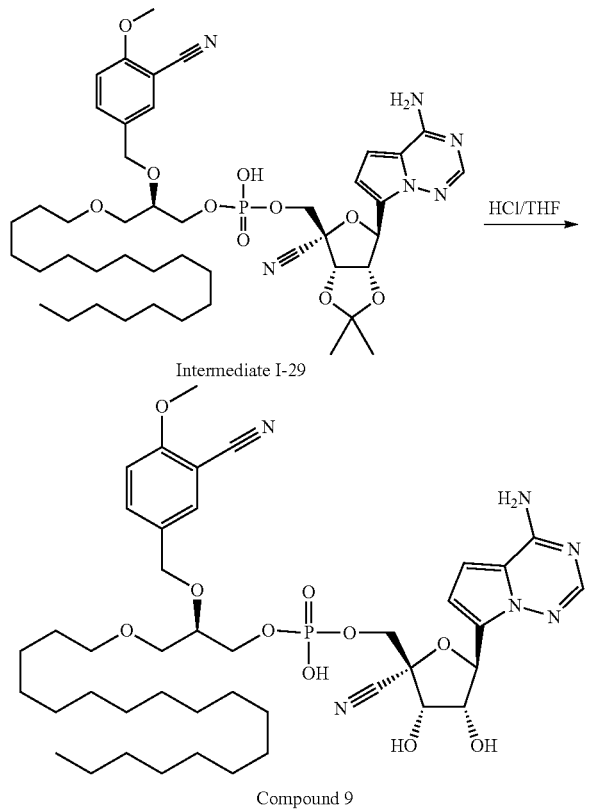

Intermediate I-29

Compound 9

To a solution of Intermediate I-29 (0.011 mmol) in THF (0.5 mL) at 0° C. was added concentrated HCl (0.047 mL, 0.566 mmol) drop wise. The reaction mixture was warmed to room temperature and stirred for 5 h. The solution was cool to 0° C., and added few ice pellets, followed by solution of NaOH (2M in water) until pH ~8. To this solution was added Phosphoric acid (85% in water) to adjust pH ~3-4. Transferred to separatory funnel, use water (20 mL), and EtOAc/Me-THF (1:1, 20 mL) to complete transfer. Extracted with EtOAc/MeTHF (1:1, 50 mL×2) and combine organic layer washed with brine (70 mL) once. Dried over sodium sulfate, filtered, concentrated under vacuo prior to purification by silica gel chromatography (0% to 100% MeOH in DCM) to afford Compound 9. $^1$H NMR (400 MHz, Methanol-d$_4$) δ 7.81 (s, 1H), 7.57 (d, J=7.6 Hz, 2H), 7.13-6.97 (m, 1H), 6.90-6.77 (m, 2H), 5.57 (d, J=5.3 Hz, 1H), 4.68-4.38 (m, 4H), 4.15 (qd, J=10.9, 4.8 Hz, 2H), 3.99-3.86 (m, 5H), 3.81-3.62 (m, 1H), 3.60-3.37 (m, 4H), 1.52 (q, J=6.7 Hz, 2H), 1.29 (d, J=7.9 Hz, 30H), 0.92 (t, J=6.8 Hz, 3H). $^{31}$P NMR (162 MHz, Methanol-d$_4$) δ−0.34. MS m/z [M+1]=843.2.

Example 16: Compound 16 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((4-cyano-3-(1H-1,2,4-triazol-1-yl)benzyl)oxy)-3-(octadecyloxy)propyl) hydrogen phosphate

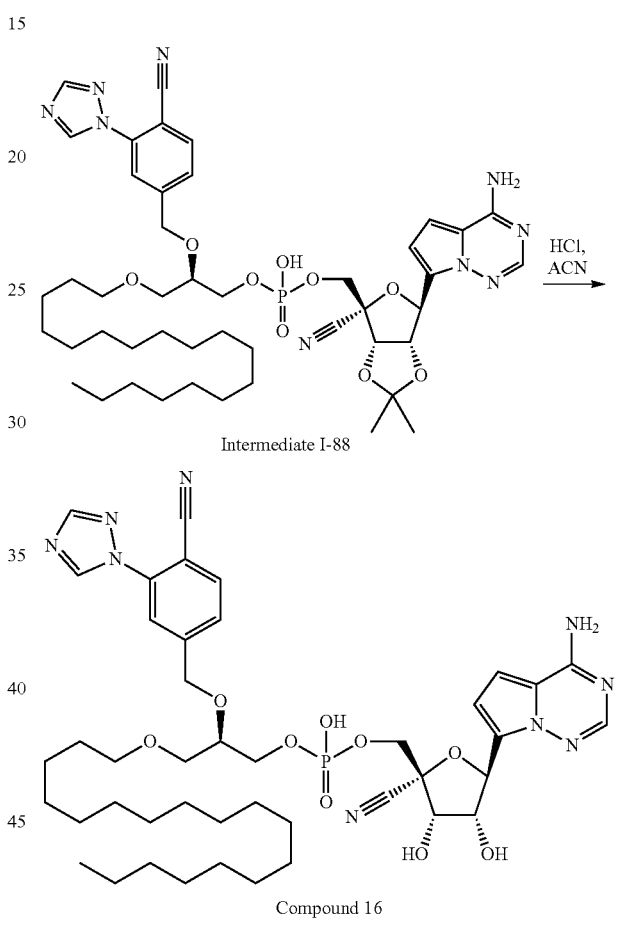

Intermediate I-88

Compound 16

To a solution of Intermediate I-88 (0.159 mmol) in ACN (2 mL)-THF (1 mL) was 25% HCl (1.25 mL) at rt. The solution was stirred at rt for 3 h, diluted with EtOAc (30 mL), washed with water-2-propanol (20 mL:1 mL), and the aqueous layer extracted with EtOAc (15 mL×3). The combined organic layer was dried with sodium sulfate, concentrated in vacuo, and purified by silica gel column chromatography (0 to 100% MeOH in DCM) to give Compound 16 as a white solid. $^1$H NMR (400 MHz, Methanol-d4) δ 9.03 (s, 1H), 8.23 (s, 1H), 8.02 (s, 1H), 7.90-7.81 (m, 2H), 7.68 (d, J=8.0 Hz, 1H), 7.33 (d, J=4.7 Hz, 1H), 7.03 (d, J=4.7 Hz, 1H), 5.51 (d, J=4.8 Hz, 1H), 4.94-4.74 (s, 2H, buried in solvent peak), 4.52-4.39 (m, 2H), 4.28-3.97 (m, 4H), 3.88 (m, 1H), 3.62 (m, 2H), 3.47 (m, 2H), 1.54 (m, 2H), 1.37-1.20 (m, 30H), 0.91 (t, J=6.7 Hz, 3H). $^{31}$P NMR (162 MHz, Methanol-d4) δ−0.46. MS m/z [M+1]=880.

Example 19: Compound 19 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((6-cyanopyridin-3-yl)methoxy)-3-(octadecyloxy)propyl) hydrogen phosphate

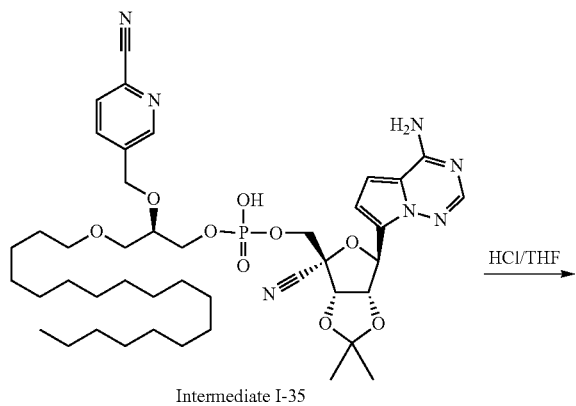

Intermediate I-35

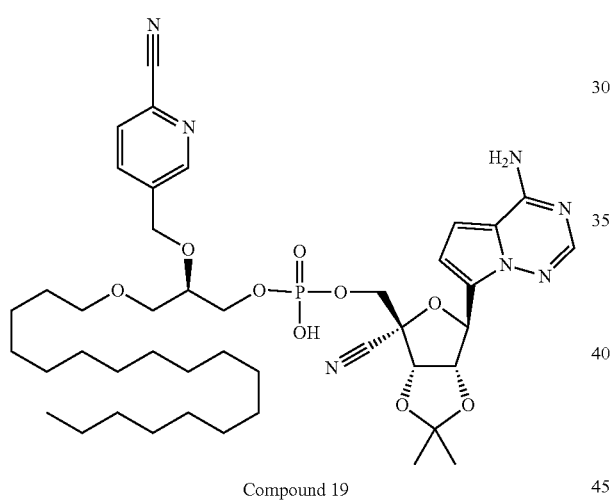

Compound 19

To a solution of Intermediate I-35 (0.038 mmol) in THF (1.5 mL) at 0° C. was added concentrated HCl (0.19 mL, 2.29 mmol) drop wise. The reaction mixture was warmed to room temperature and stirred for 5 h. The solution was cool to 0° C., and added few ice pellets, followed by solution of NaOH (2M in water) until reach pH ~8. To this solution was added Phosphoric acid (85% in water) to adjust pH ~3-4, dilute with DCM-IPA (32/8 mL), transfer to separatory flask, used water (10 mL) to complete transfer. organic layer separated (40 mL×2), washed once with brine/water (3/2, 50 mL), dried over Na$_2$SO$_4$, concentrated, dissolved in 5% MeOH/DCM (use minimum solvent until solid particle dissolute, add additional drop of MeOH if needed), loaded on 24 g gold column, and run 3 min 100% Hex, 2 min 100% DCM, 16 min 0%-100% MeOH. The desired product eluted at ~50% MeOH. Fractions containing product were combined and concentrated to afford Compound 19. $^1$H NMR (400 MHz, Methanol-d4) δ 8.63 (d, J=2.0 Hz, 1H), 7.97 (dd, J=8.0, 2.1 Hz, 1H), 7.81 (s, 1H), 7.76 (d, J=8.0 Hz, 1H), 6.84 (t, J=3.3 Hz, 2H), 5.55 (d, J=5.2 Hz, 1H), 4.83-4.66 (m, 2H), 4.59 (t, J=5.3 Hz, 1H), 4.53 (d, J=5.5 Hz, 1H), 4.16 (qd, J=10.9, 4.8 Hz, 2H), 3.96 (m, 2H), 3.78 (td, J=5.9, 4.0 Hz, 1H), 3.59-3.35 (m, 4H), 1.52 (m, 2H), 1.29 (d, J=7.0 Hz, 32H), 0.92 (t, J=6.7 Hz, 3H). $^{31}$P NMR (162 MHz, Methanol-d$_4$) δ -0.37. MS m/z [M+1]=814.3.

Example 21: Compound 21 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((6-cyanopyridin-2-yl)oxy)-3-(octadecyloxy)propyl) hydrogen phosphate

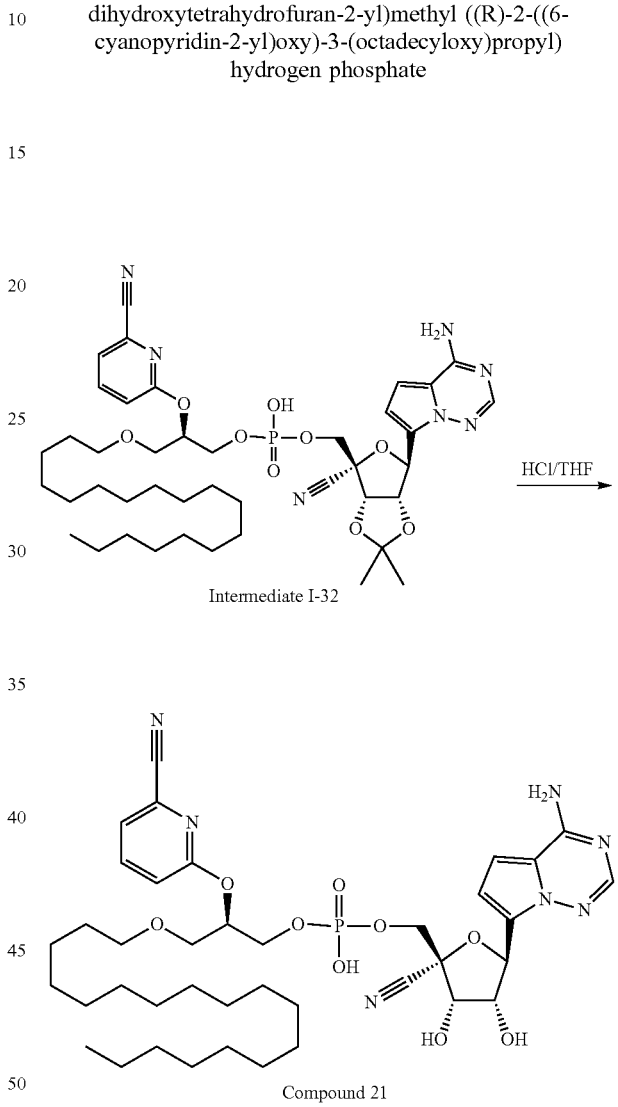

Intermediate I-32

Compound 21

To a solution of Intermediate I-32 (0.029 mmol) in THF (1.5 mL) at 0° C. was added concentrated HCl (0.17 mL, 2.05 mmol) drop wise. The reaction mixture was warmed to room temperature and stirred for 5 h. The solution was cool to 0° C., and added few ice pellets, followed by solution of NaOH (2M in water) until pH ~8. To this solution was added Phosphoric acid (85% in water) to adjust pH ~3-4. Transferred to separatory funnel, and used water (20 mL), EtOAc/Me-THF (1:2, 20 mL) to complete transfer. Extracted with EtOAc/MeTHF (1:2, 50 mL×2) and combine organic layer washed with brine (70 mL) once. Dried over sodium sulfate, filtered, concentrated under vacuo prior to purification by silica gel chromatography (0%-100% MeOH in DCM) to afford Compound 21. $^1$H NMR (400 MHz, Methanol-d$_4$) δ

7.87-7.66 (m, 2H), 7.38 (dd, J=10.3, 7.2 Hz, 1H), 7.06 (dd, J=12.5, 8.5 Hz, 1H), 6.86 (dt, J=7.3, 3.9 Hz, 2H), 5.60-5.39 (m, 2H), 4.67-4.36 (m, 3H), 4.31-4.02 (m, 3H), 3.77-3.58 (m, 2H), 3.53-3.35 (m, 2H), 1.49 (dq, J=12.6, 6.7 Hz, 2H), 1.27 (d, J=21.6 Hz, 30H), 0.92 (t, J=6.8 Hz, 3H). $^{31}$P NMR (162 MHz, Methanol-d$_4$) δ −0.57, −1.25. MS m/z [M+1]=800.1.

Example 23: Compound 23 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-(4-cyano-3-isopropoxyphenoxy)-3-(octadecyloxy) propyl) hydrogen phosphate

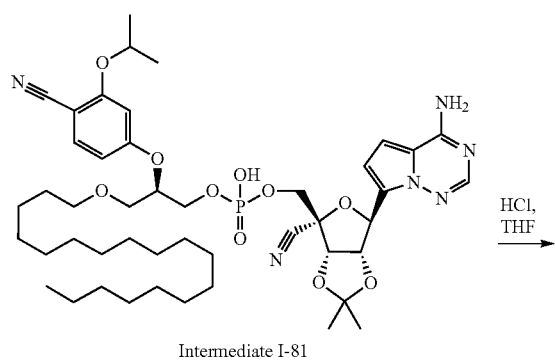

Intermediate I-81

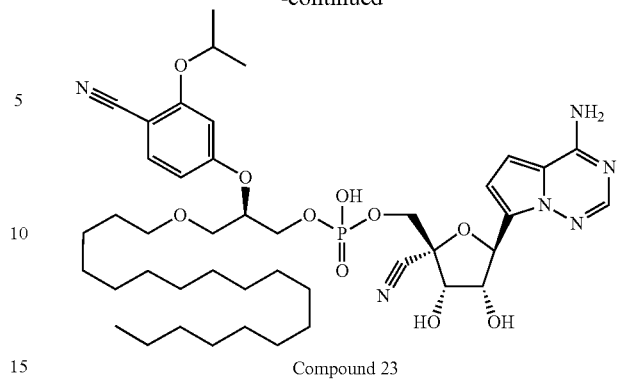

Compound 23

A solution of Intermediate I-81 (0.0446 mmol) in THF (1.0 mL) was 25% HCl (0.8 mL) at rt. The solution was stirred at rt for 3 h, concentrated in vacuo, lyophilized in ACN-water to give Compound 23. $^1$H NMR (400 MHz, Methanol-d4) δ 8.03 (s, 1H), 7.37 (d, J=8.6 Hz, 1H), 7.31 (d, J=4.7 Hz, 1H), 7.07 (d, J=4.7 Hz, 1H), 6.67 (d, J=2.1 Hz, 1H), 6.61 (dd, J=8.8, 2.1 Hz, 1H), 5.57 (d, J=5.5 Hz, 1H), 4.99-4.64 (m, 2H), 4.53-4.43 (m, 2H), 4.27-4.00 (m, 4H), 3.74 (dd, J=10.8, 3.4 Hz, 1H), 3.64 (dd, J=10.9, 5.9 Hz, 1H), 3.52-3.35 (m, 2H), 1.47 (m, 2H), 1.41-1.20 (m, 36H), 0.92 (t, J=6.7 Hz, 3H). $^{31}$P NMR (162 MHz, Methanol-d$_4$) δ −0.67. MS m/z [M+1]=857.

Example 24: Compound 24 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((6-cyanopyridin-3-yl)oxy) docosyl) hydrogen phosphate

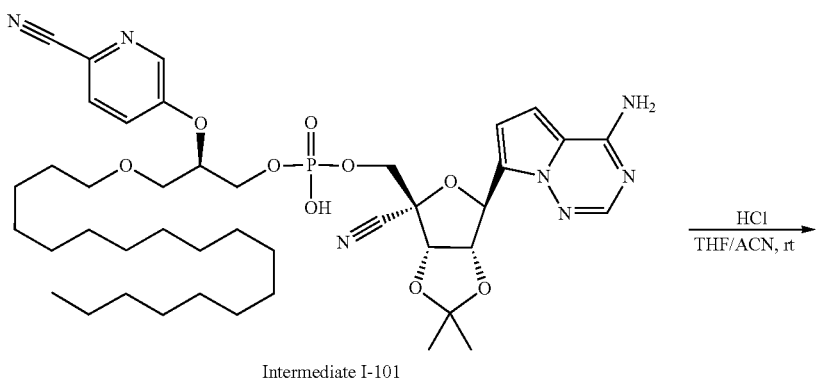

Intermediate I-101

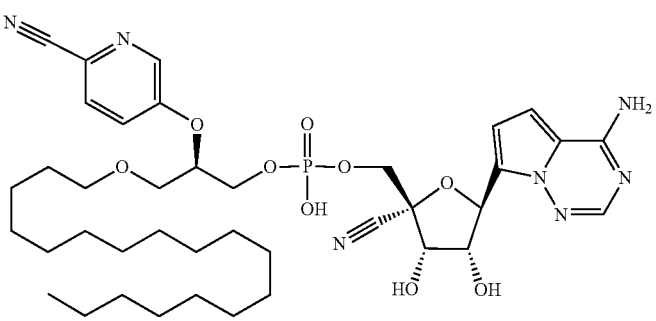

Compound 24

To a solution of Intermediate I-101 (0.153 mmol) in THF (4 mL) was cooled to 0° C., and added concentrated HCl (0.51 mL) dropwise. The reaction mixture was warmed to rt and stirred for 4 h. The solution was cool to 0° C., and added few ice pellets, followed by solution of NaOH (1M in water) until pH ~8. To this solution was added Phosphoric acid (85% in water) to adjust pH ~3-4. Transferred to separatory funnel, use water (20 mL), and EtOAc/Me-THF (1:1, 20 mL) to complete transfer. Extracted with EtOAc/MeTHF ((1:1, 50 mL×2) and combine organic layer washed with brine (70 mL) once. Dried over sodium sulfate, filtered, concentrated under vacuo prior to purification by silica gel chromatography (0-100% MeOH in DCM) to afford Compound 24. $^1$H NMR (400 MHz, Methanol-d$_4$) δ 8.32 (d, J=2.8 Hz, 1H), 7.83 (s, 1H), 7.67 (d, J=8.7 Hz, 1H), 7.53 (dd, J=8.8, 2.9 Hz, 1H), 6.85-6.82 (m, 2H), 5.56 (d, J=5.1 Hz, 1H), 4.80-4.75 (m, 1H), 4.60-4.56 (m, 2H), 4.51 (d, J=5.4 Hz, 1H), 4.19-4.11 (m, 2H), 4.04-4.01 (m, 2H), 3.66-3.62 (m, 1H), 3.58-3.52 (m, 1H), 3.46-3.39 (m, 1H), 1.53-1.41 (m, 2H), 1.27 (d, J=29.6 Hz, 30H), 0.92 (t, J=6.6 Hz, 3H). $^{31}$P NMR (162 MHz, Methanol-d$_4$) δ−0.60. MS m/z [M+1]=800.2.

Example 25: Compound 25 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl) oxy)henicosyl) hydrogen phosphate

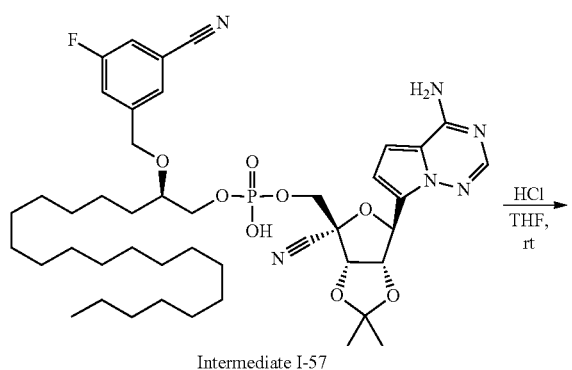

Intermediate I-57

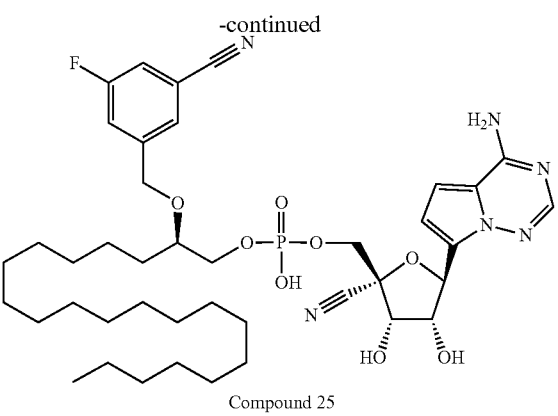

Compound 25

To a solution of Intermediate I-57 (1.06 mmol, 1.0 equiv) in THF (7.0 mL) cooled in an ice bath was added concentrated HCl (1.06 mL, 12.0 M, 12 equiv.). The reaction mixture was warmed to room temperature and stirred for 2 h and 30 min. The solution was diluted with 3:1 DCM:IPA (100 mL) and water (40 mL). The pH of the aqueous layer was adjusted to approximately 3 using 2 M NaOH. The layers were separated. Water (40 mL) was added to the organic and the pH adjusted to 3 using 1 M HCl. The layers were separated once more. The aqueous extracts were combined and extracted with 3:1 DCM:iPrOH (100 mL). The organic extracts were combined, washed with 3:2 brine:water (50 mL), dried over Na$_2$SO$_4$, filtered and concentrated in vacuo prior to purification by silica gel chromatography (0%-60% MeOH in DCM) to afford Compound 25. $^1$H NMR (400 MHz, Methanol-d$_4$) δ 7.78 (s, 1H), 7.48-7.45 (m, 1H), 7.40-7.32 (m, 2H), 6.84-6.80 (m, 2H), 5.54 (d, J=5.1 Hz, 1H), 4.69 (d, J=13.1 Hz, 1H), 4.59-4.44 (m, 3H), 4.20-4.07 (m, 2H), 3.94-3.81 (m, 2H), 3.58-3.50 (m, 1H), 1.48-1.16 (m, 36H), 0.93-0.86 (m, 3H). $^{19}$F NMR (376 MHz, Methanol-d$_4$) δ−112.91−−113.08 (m). $^{31}$P NMR (162 MHz, Methanol-d$_4$) δ−0.12−−0.84 (m). MS m/z [M+1]=815.3.

Example 27: Compound 27 ((2R,3S,4R)-5-(4-aminopyrrolo[2,1-f][1,2,4]triazin-7-yl)-2-cyano-3,4-dihydroxytetrahydrofuran-2-yl)methyl ((R)-2-((4-cyano-3-methoxybenzyl) oxy)henicosyl) hydrogen phosphate

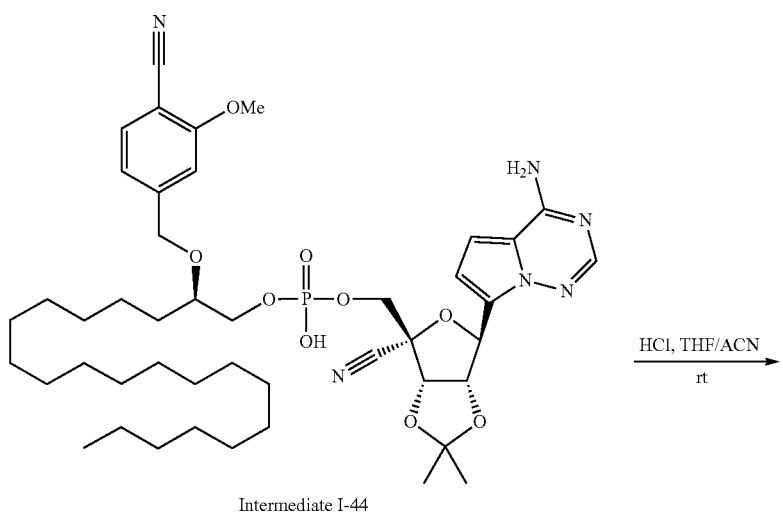

Intermediate I-44

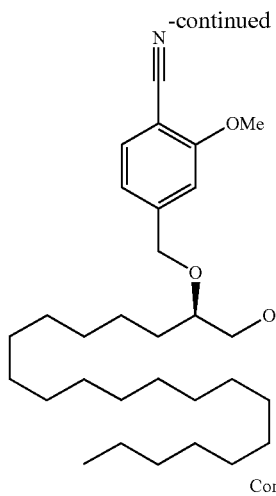

Compound 27

To a solution of Intermediate I-44 (0.0867 mmol, 1 equiv.) in 2:1 THF:ACN (3.0 mL) was added concentrated HCl (0.50 mL, 12.0 M, 69.2 equiv.). The reaction mixture was stirred at room temperature for 3 h. The solution was diluted with 3:1 DCM:iPrOH (40 mL) and water (20 mL). The pH of the aqueous layer was adjusted to 14 using 2 M NaOH then to pH 3 using 1 M HCl. The layers were separated. Water (20 mL) was added to the organic and the pH was adjusted to 3-4 using 1 M HCl. The layers were separated once more. The aqueous extracts were combined and extracted with 3:1 DCM:iPrOH (40 mL). The organic extracts were combined, washed with 2:1 brine:water (30 mL), dried over $Na_2SO_4$, filtered and concentrated in vacuo prior to purification by silica gel chromatography (0%-40% MeOH in DCM). The fractions containing desired product were concentrated, taken up in 1:1 water:ACN and filtered prior to lyophilization to afford Compound 27. $^1$H NMR (400 MHz, Methanol-$d_4$) δ 7.83 (s, 1H), 7.47 (d, J=7.8 Hz, 1H), 7.12 (s, 1H), 7.00-6.92 (m, 2H), 6.87 (d, J=4.6 Hz, 1H), 5.53 (d, J=5.3 Hz, 1H), 4.70 (d, J=13.2 Hz, 1H), 4.57-4.48 (m, 3H), 4.20-4.08 (m, 2H), 4.03-3.83 (m, 5H), 3.60-3.52 (m, 1H), 1.51-1.19 (m, 36H), 0.93-0.86 (m, 3H). $^{31}$P NMR (162 MHz, Methanol-$d_4$) δ −0.17−−0.47 (m). MS m/z [M+1]=827.3.

Example 28: Compound 28 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((4-cyano-3-isopropoxybenzyl) oxy)henicosyl) hydrogen phosphate

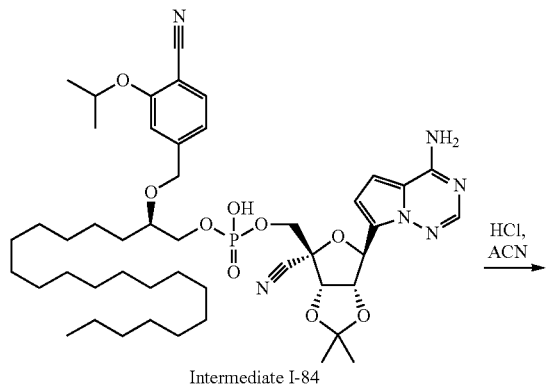

Intermediate I-84

HCl, ACN

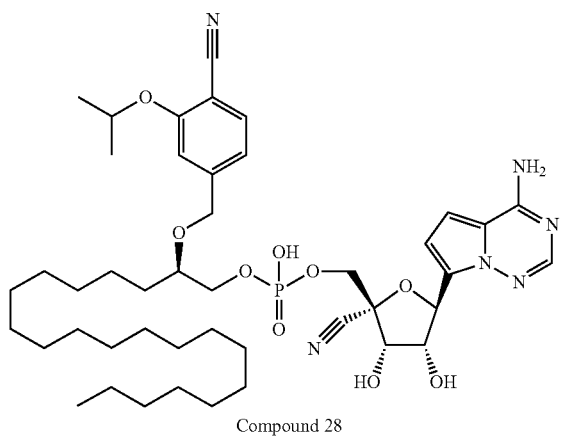

Compound 28

To a solution of Intermediate I-84 (0.0726 mmol) in ACN (2.0 mL)-THF (1 mL) was 25% HCl (0.7 mL) at rt. The solution was stirred at rt for 2 h, diluted with EtOAc (30 mL), washed with water-2-propanol (20 mL:1 mL), and the aqueous layer extracted with EtOAc (15 mL×3). The combined organic layer was dried with sodium sulfate, concentrated in vacuo, and purified by silica gel column chromatography (0 to 100% MeOH in DCM) to give Compound 28. $^1$H NMR (400 MHz, Methanol-$d_4$) δ 8.03 (s, 1H), 7.48 (d, J=7.9 Hz, 1H), 7.37 (d, J=4.7 Hz, 1H), 7.14 (d, J=5.2 Hz, 1H), 7.06 (d, J=4.8 Hz, 1H), 7.00 (d, J=7.9 Hz, 1H), 5.55 (d, J=5.1 Hz, 1H), 4.91-4.72 (s, 2H), 4.59 (d, J=13.2 Hz, 1H), 4.49 (m, 2H), 4.21 (m, 2H), 4.08-3.91 (m, 2H), 3.72-3.58 (m, 1H), 1.56 (m, 2H), 1.50-1.18 (m, 40H), 0.92 (t, J=6.7 Hz, 3H). $^{31}$P NMR (162 MHz, Methanol-$d_4$) δ−0.50. MS m/z [M+1]=855.

Example 30: Compound 30 ((2R,3S,4R)-5-(4-aminopyrrolo[2,1-f][1,2,4]triazin-7-yl)-2-cyano-3,4-dihydroxytetrahydrofuran-2-yl)methyl ((R)-2-((3-cyano-4-(1H-1,2,4-triazol-1-yl)benzyl)oxy)henicosyl) hydrogen phosphate Example 31: Compound 31 ((2R,3S,4R)-5-(4-aminopyrrolo[2,1-f][1,2,4]triazin-7-yl)-2-cyano-3,4-dihydroxytetrahydrofuran-2-yl)methyl ((S)-2-((3-cyano-5-fluorobenzyl) oxy)henicosyl) hydrogen phosphate

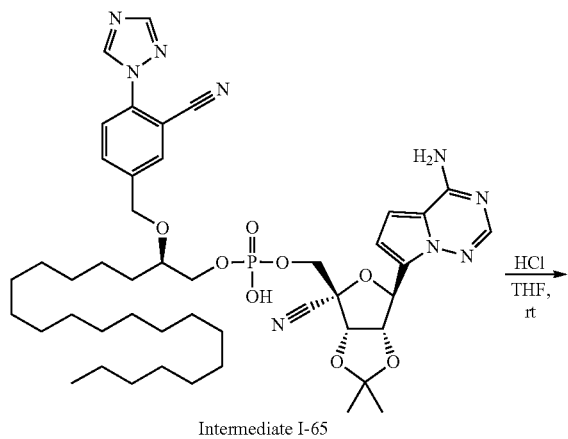

Intermediate I-65

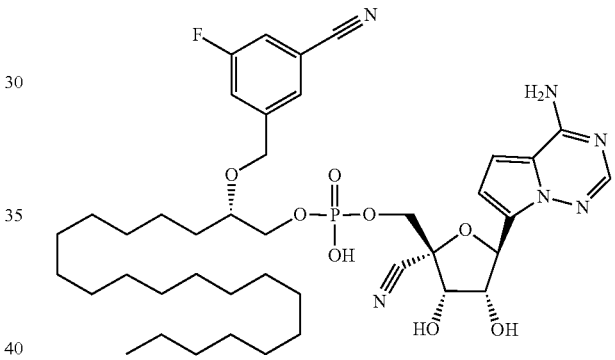

Intermediate I-63

Compound 30

Compound 31

To a solution of Intermediate I-65 (0.392 mmol) in THF (4.0 mL) was added concentrated HCl (1.0 mL, 12.0 M). The reaction mixture was stirred at room temperature for 6 h and 20 min. The solution was diluted with 3:1 DCM:IPA (100 mL) and water (40 mL). The pH of the aqueous layer was adjusted to around 3.5 using a combination of 50% wt KOH and 1 M HCl. The layers were separated. The organic layer was washed with an additional 40 mL of water prior to drying over $Na_2SO_4$, filtering and concentrating in vacuo. The crude residue was loaded onto silica gel and purified by silica gel chromatography (0-40% MeOH in DCM) to afford Compound 30. $^1$H NMR (400 MHz, Methanol-d4) δ 8.99 (s, 1H), 8.23 (s, 1H), 7.87-7.77 (m, 3H), 7.70 (d, J=8.3 Hz, 1H), 6.95 (d, J=4.6 Hz, 1H), 6.88 (d, J=4.6 Hz, 1H), 5.53 (d, J=5.2 Hz, 1H), 4.78 (d, J=12.9 Hz, 1H), 4.60 (d, J=13.1 Hz, 1H), 4.56-4.47 (m, 2H), 4.19-4.06 (m, 2H), 3.99-3.84 (m, 2H), 3.74-3.49 (m, 1H), 1.54-1.19 (m, 36H), 0.90 (t, J=6.7 Hz, 3H). $^{31}$P NMR (162 MHz, Methanol-d4) δ −0.15-−0.48 (m). MS m/z [M+1]=864.2

To a solution of Intermediate I-63 (0.164 mmol) in 2:1 THF:ACN (3.0 mL) was added concentrated HCl (0.12 mL, 12.0 M). The reaction mixture was stirred at room temperature for 1 h and 45 min prior to the addition of more concentrated HCl (0.12 mL, 12.0 M). After stirring for an additional 1.5 h, the reaction mixture was diluted with 3:1 DCM:IPA (40 mL) and water (15 mL). The pH of the aqueous layer was adjusted to between 3.5 and 4 using 50% wt KOH and 1 M HCl. The layers were separated. The organic layer was washed with an additional 15 mL of water prior to drying over $Na_2SO_4$, filtering and concentrating in vacuo. The crude residue was purified by silica gel chromatography four times (0-40% MeOH in DCM) to afford Compound 31. $^1$H NMR (400 MHz, Methanol-d4) δ 7.79 (s, 1H), 7.48-7.46 (m, 1H), 7.41-7.32 (m, 2H), 6.85-6.81 (m, 2H), 5.54 (d, J=5.4 Hz, 1H), 4.73 (d, J=12.9 Hz, 1H), 4.59-4.43 (m, 3H), 4.19-4.06 (m, 2H), 3.94-3.80 (m, 2H), 3.60-3.50 (m, 1H), 1.48-1.16 (m, 36H), 0.93-0.86 (m, 3H). $^{19}$F NMR (376 MHz, Methanol-d4) δ −112.98-−113.11 (m). $^{31}$P NMR (162 MHz, Methanol-d4) δ −0.15-−0.54 (m). MS m/z [M+1]=815.2

Example 34: Compound 34 ((2R,3S,4R)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl)oxy) docosyl) hydrogen phosphate

Example 36: Compound 36 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl)oxy) nonadecyl) hydrogen phosphate

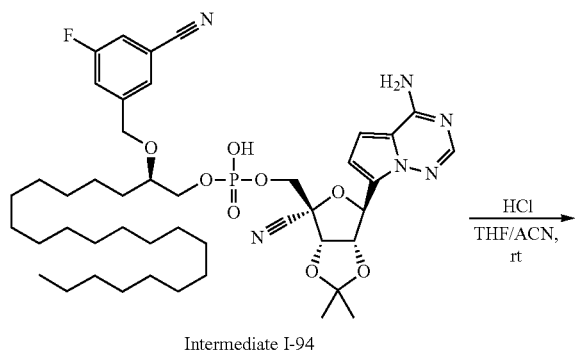

Intermediate I-94

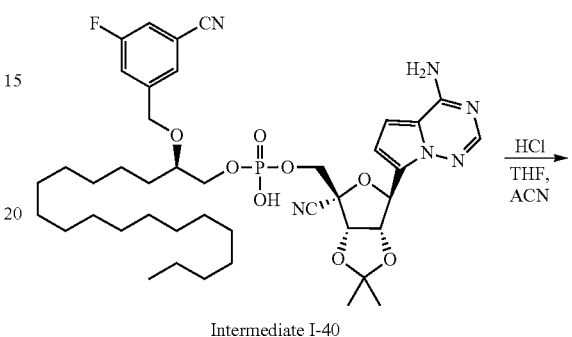

Intermediate I-40

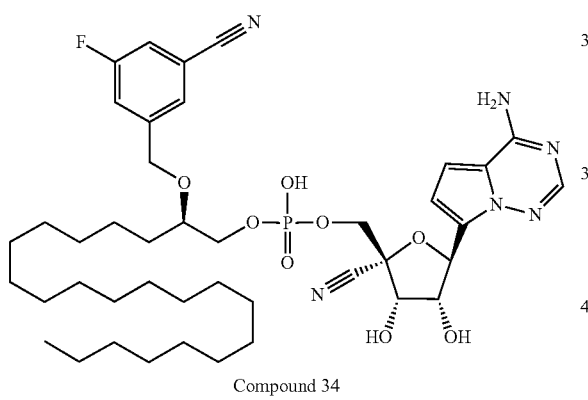

Compound 34

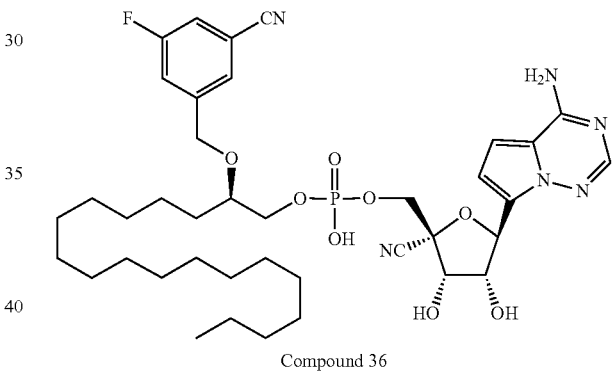

Compound 36

To a solution of Intermediate I-94 (0.082 mmol) in THF (1.5 mL) was cooled to 0° C., and added concentrated HCl (0.414 mL) dropwise. The reaction mixture was warmed to rt and stirred for 3 h. The solution was cool to 0° C., and added few ice pellets, followed by solution of NaOH (2M in water) until pH ~8. To this solution was added Phosphoric acid (85% in water) to adjust pH ~3-4. Transferred to separatory funnel, use water (20 mL), and EtOAc/Me-THF (1:1, 30 mL) to complete transfer. Extracted with EtOAc/MeTHF (1:1, 50 mL×2) and combine organic layer washed with brine (50 mL) once. Dried over sodium sulfate, filtered, concentrated under vacuo prior to purification by silica gel chromatography (0-100% MeOH in DCM) to afford Compound 34. $^1$H NMR (400 MHz, Methanol-d4) δ 7.81 (s, 1H), 7.49 (d, J=2.9 Hz, 1H), 7.41-7.35 (m, 2H), 685-6.83 (m, 2H), 5.56 (d, J=4.9 Hz, 1H), 4.76-4.70 (m, 1H), 4.60-4.56 (m, 1H), 4.55-4.45 (m, 2H), 4.20-4.11 (m, 2H), 3.95-3.85 (m, 2H), 3.63-3.49 (m, 1H), 2.92-2.70 (m, 3H), 1.47-1.43 (m, 2H), 1.35-1.27 (m, 36H), 0.92 (t, J=6.5 Hz, 3H). $^{31}$P NMR (162 MHz, Methanol-d4) δ−0.28. MS m/z [M+1]=829.2.

To a solution of Intermediate I-40 (0.0847 mmol, 1 equiv.) in THF (2.0 mL) was added concentrated HCl (0.50 mL, 12.0 M, 70.9 equiv.). The reaction mixture was stirred at room temperature for 5 h. The solution was diluted with 3:1 DCM:iPrOH (20 mL) and water (10 mL). The pH of the aqueous layer was adjusted to approximately 4 using 2 M NaOH. The layers were separated. Water (10 mL) was added to the organic and the pH adjusted to 3-4 using 1 M HCl. The layers were separated once more. The aqueous extracts were combined and extracted with 3:1 DCM:iPrOH (20 mL). The organic extracts were combined, washed with 3:2 brine: water (30 mL), dried over Na$_2$SO$_4$, filtered and concentrated in vacuo prior to purification by silica gel chromatography (0%-100% MeOH in DCM) to afford Compound 36. $^1$H NMR (400 MHz, Methanol-d4) δ 7.78 (s, 1H), 7.49-7.45 (m, 1H), 7.41-7.32 (m, 2H), 6.85-6.79 (m, 2H), 5.54 (d, J=5.1 Hz, 1H), 4.70 (d, J=13.0 Hz, 1H), 4.60-4.43 (m, 3H), 4.20-4.07 (m, 2H), 3.95-3.81 (m, 2H), 3.59-3.50 (m, 1H), 1.52-1.16 (m, 32H), 0.94-0.84 (m, 3H). $^{19}$F NMR (376 MHz, Methanol-d4) δ−112.89−−113.11 (m). $^{31}$P NMR (162 MHz, Methanol-d4) δ−0.09-0.57 (m). MS m/z [M+1]=787.3.

Example 37: Compound 37 ((2R,3S,4R)-5-(4-aminopyrrolo[2,1-f][1,2,4]triazin-7-yl)-2-cyano-3,4-dihydroxytetrahydrofuran-2-yl)methyl ((S)-2-((3-cyano-5-fluorobenzyl)oxy) icosyl) hydrogen phosphate

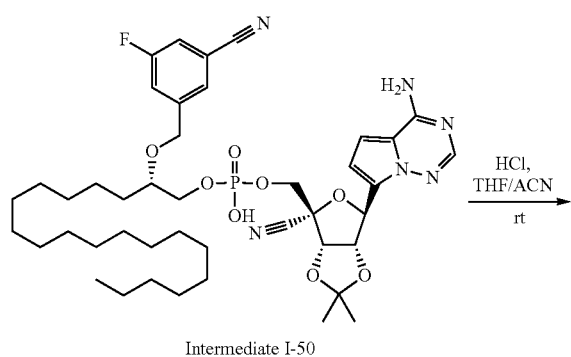

Intermediate I-50

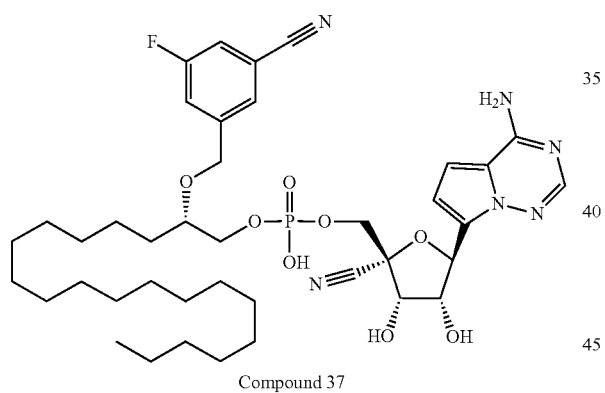

Compound 37

To a solution of Intermediate I-50 (0.0149 mmol, 1.0 equiv) in 2:1 THF:ACN (1.5 mL) was added concentrated HCl (0.25 mL, 12.0 M, 202 equiv.). The reaction mixture was stirred at room temperature for 2 h and 20 min. The solution was diluted with 3:1 DCM:IPA (20 mL) and water (20 mL). The pH of the aqueous layer was adjusted to approximately 3 using 2 M NaOH. The layers were separated. Water (20 mL) was added to the organic and the pH adjusted to 3 using 1 M HCl. The layers were separated once more. The aqueous extracts were combined and extracted with 3:1 DCM:iPrOH (20 mL). The organic extracts were combined, washed with 3:2 brine:water (30 mL), dried over $Na_2SO_4$, filtered and concentrated in vacuo prior to purification by silica gel chromatography (0%-100% MeOH in DCM) to afford Compound 37. $^1$H NMR (400 MHz, Methanol-d4) δ 7.84-7.81 (m, 1H), 7.49-7.45 (m, 1H), 7.42-7.32 (m, 2H), 6.94-6.84 (m, 2H), 5.56-5.51 (m, 1H), 4.77-4.68 (m, 1H), 4.58-4.44 (m, 3H), 4.19-4.06 (m, 2H), 3.96-3.81 (m, 2H), 3.60-3.52 (m, 1H), 1.50-1.17 (m, 34H), 0.93-0.86 (m, 3H). $^{19}$F NMR (376 MHz, Methanol-d4) δ –112.94-–113.09 (m). $^{31}$P NMR (162 MHz, Methanol-d4) δ –0.14-–0.54 (m). MS m/z [M+1]=801.3.

Example 38: Compound 38 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-(4-cyano-3-isopropoxyphenoxy) henicosyl) hydrogen phosphate

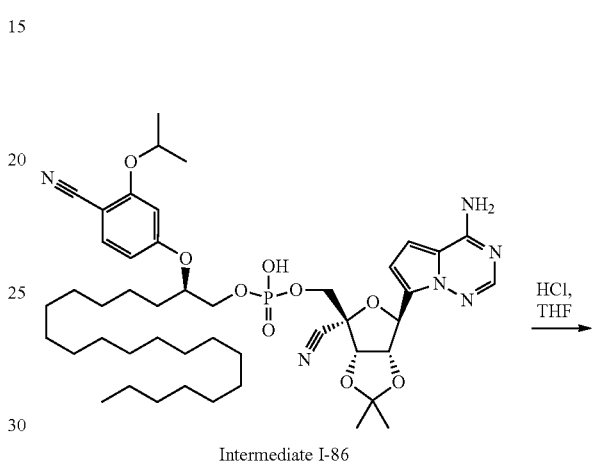

Intermediate I-86

Compound 38

To a solution of Intermediate I-86 (101 mmol) in ACN (2.0 mL)-THF (1.0 mL) was 25% HCl (0.9 mL) at rt. The solution was stirred at rt for 1 h, diluted with EtOAc (30 mL), washed with water-2-propanol (20 mL:1 mL), and the aqueous layer extracted with EtOAc (15 mL×3). The combined organic layer was dried with sodium sulfate, concentrated in vacuo, and purified by silica gel column chromatography (0 to 100% MeOH in DCM) to give Compound 38. $^1$H NMR (400 MHz, Methanol-d4) δ 8.03 (s, 1H), 7.39 (d, J=8.6 Hz, 1H), 7.35 (d, J=4.8 Hz, 1H), 7.03 (d, J=4.7 Hz, 1H), 6.68-6.54 (m, 2H), 5.56 (d, J=5.4 Hz, 1H), 4.75-4.58 (m, 2H), 4.48 (t, J=5.3 Hz, 1H), 4.43 (d, J=5.3 Hz, 1H), 4.24 (dd, J=11.1, 5.8 Hz, 1H), 4.16 (dd, J=11.1, 5.0 Hz, 1H), 4.07 (t, J=5.9 Hz, 2H), 1.71 (m, 2H), 1.50-1.18 (m, 40H), 0.91 (t, J=6.7 Hz, 3H). $^{31}$P NMR (162 MHz, Methanol-d4) δ –0.87. MS m/z [M+1]=841.

Example 39: Compound 39 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-(4-cyano-3,5-dimethoxyphenoxy) henicosyl) hydrogen phosphate

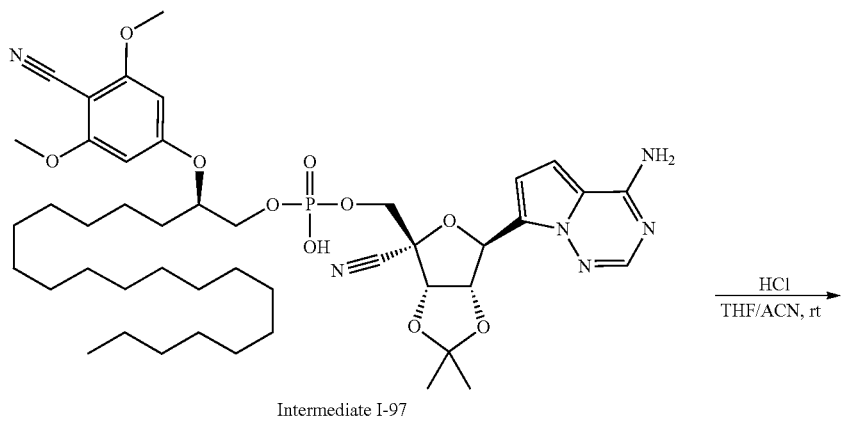

To a solution of Intermediate I-97 (0.036 mmol) in THF (1.5 mL) was cooled to 0° C., and added concentrated HCl (0.15 mL) drop wise. The reaction mixture was warmed to rt and stirred for 3 h. The solution was cool to 0° C., and added few ice pellets, followed by solution of NaOH (2M in water) until pH ~8. To this solution was added Phosphoric acid (85% in water) to adjust pH ~3-4. Transferred to separatory funnel, use water (20 mL), and EtOAc/Me-THF (2:3, 30 mL) to complete transfer. Extracted with EtOAc/MeTHF (2:3, 50 mL×2) and combine organic layer washed with brine (40 mL) once. Dried over sodium sulfate, filtered, concentrated under vacuo prior to purification by silica gel chromatography (0-100% MeOH in DCM) to afford Compound 39. $^1$H NMR (400 MHz, DMSO-d6) δ 8.16 (s, 2H), 7.91 (s, 1H), 6.96 (d, J=4.4 Hz, 1H), 6.78 (d, J=4.5 Hz, 1H), 6.36 (s, 2H), 5.39 (d, J=5.8 Hz, 1H), 4.76-4.70 (m, 1H), 4.45-4.42 (m, 1H), 4.25 (d, J=5.2 Hz, 1H), 4.16-4.12 (m, 1H), 4.05-3.93 (m, 3H), 3.83 (s, 6H), 1.59-1.53 (m, 2H), 1.36-1.19 (m, 34H), 0.85 (t, J=6.5 Hz, 3H). $^{31}$P NMR (162 MHz, DMSO-d6) δ−1.67. MS m/z [M+1]=843.2.

Example 43: Compound 43: ((2R,3S,4R,5S)-5-(4-aminopyrrolo[2,1-f][1,2,4]triazin-7-yl)-2-cyano-3,4-dihydroxytetrahydrofuran-2-yl)methyl (3-(3-cyano-5-fluorophenoxy)-2-((octadecyloxy)methyl)propyl) hydrogen phosphate

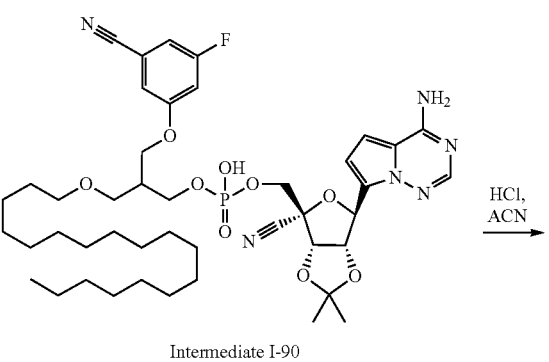

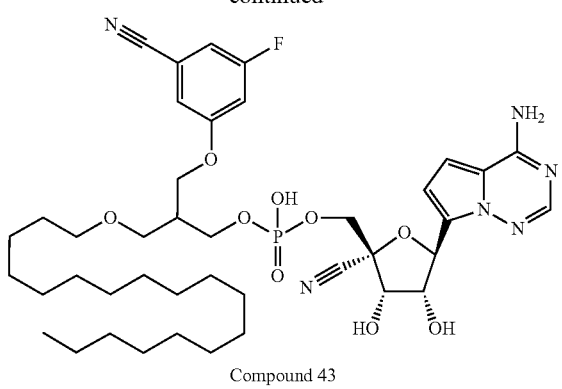

Compound 43

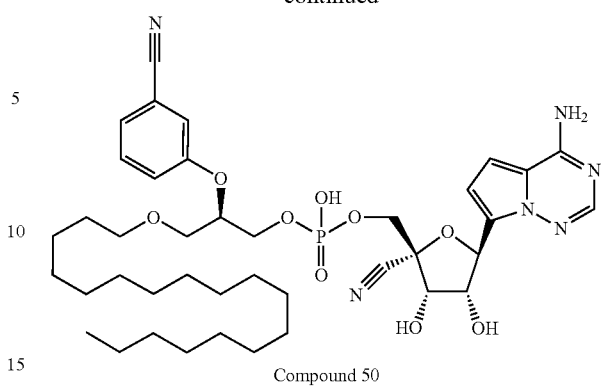

Compound 50

A solution of Intermediate I-90 (0.115 mmol) in ACN (1 mL)-THF (0.5 mL) was 25% HCl (0.6 mL) at rt. The solution was stirred at rt for 3 h, diluted with EtOAc (30 mL), washed with water-2-propanol (20 mL:1 mL), and the aqueous layer extracted with EtOAc (15 mL×3). The combined organic layer was dried with sodium sulfate, concentrated in vacuo, and purified by silica gel column chromatography (0 to 100% MeOH in DCM) to give Compound 43. $^1$H NMR (400 MHz, Methanol-d4) δ 8.03 (s, 1H), 7.35 (d, J=4.7 Hz, 1H), 7.21-7.00 (m, 4H), 5.55 (d, J=4.5 Hz, 1H), 4.51-4.41 (m, 2H), 4.25-3.98 (m, 6H), 3.68-3.50 (m, 2H), 3.45 (m, 2H), 2.51-2.31 (m, 1H), 1.65-1.47 (m, 2H), 1.38-1.18 (m, 30H), 0.92 (m, 3H). $^{19}$F NMR (376 MHz, Methanol-d4) δ−110.96. $^{31}$P NMR (162 MHz, Methanol-d4) δ 0.31, −0.33. MS m/z [M+1]=831.

Example 50: Compound 50 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-(3-cyanophenoxy)-3-(octadecyloxy)propyl) hydrogen phosphate Intermediate I-8 (0.087 mmol) was dissolved in THF (2.0 mL) and then 25% HCl (0.5 mL) added at room temperature. The resulting mixture was stirred at room temperature for 6 h and diluted with DCM-IPA (16 mL:4 mL) and 5N NaOH (0.5 mL) added to the mixture, which was then washed with brine (10 mL×2). The aqueous layer extracted with DCM-IPA (20 mL×2) and the combined organic layer was dried with sodium sulfate, concentrated in vacuo, and purified with silica gel column chromatography (0% to 100% MeOH in DCM) to give Compound 50. $^1$H NMR (400 MHz, Methanol-d4) δ 8.04 (s, 1H), 7.44-7.34 (m, 2H), 7.34-7.27 (m, 2H), 7.25 (dt, J=7.5, 1.2 Hz, 1H), 7.06 (d, J=4.8 Hz, 1H), 5.55 (d, J=5.2 Hz, 1H), 4.72 (m, 1H), 4.52-4.39 (m, 2H), 4.29-4.08 (m, 4H), 3.77-3.59 (m, 2H), 3.53-3.40 (m, 2H), 1.52 (m, 2H), 1.39-1.14 (m, 30H), 0.98-0.60 (m, 3H). $^{31}$P NMR (162 MHz, Methanol-d4) δ−0.80. MS m/z [M+1]=799.

Example 51: Compound 51 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-(3-cyanophenoxy)docosyl) hydrogen phosphate

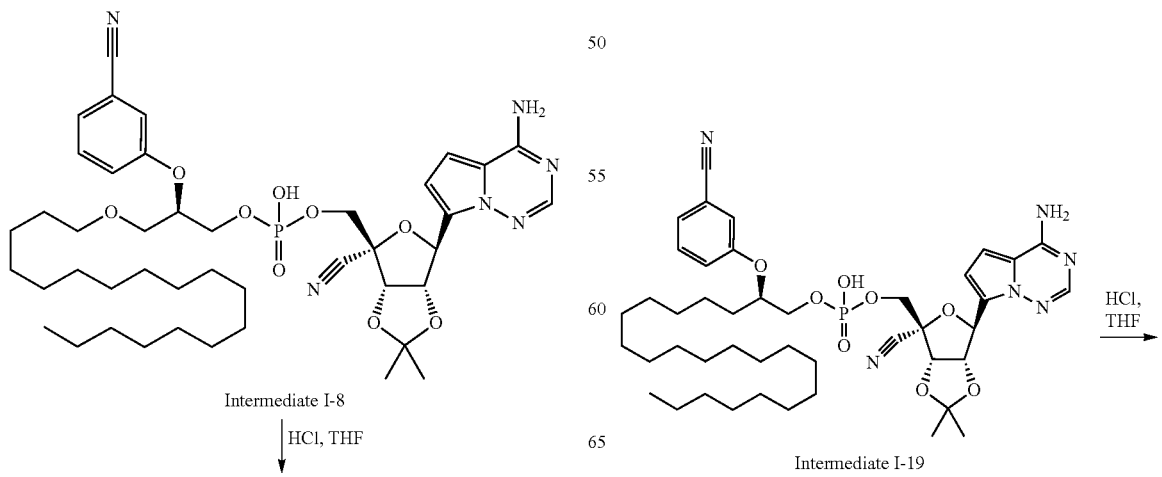

869
-continued

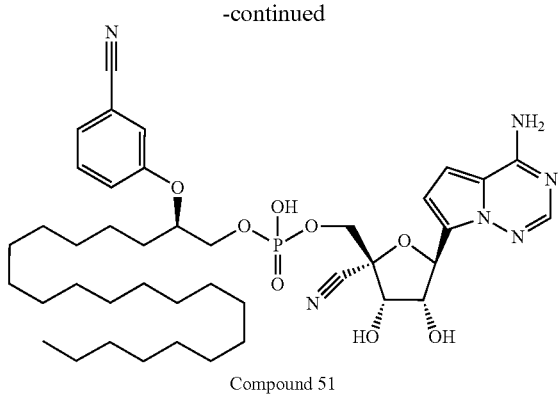

Compound 51

Intermediate I-19 (0.168 mmol) was dissolved in THF (2.0 mL) and then 25% HCl (1.0 mL) added at room temperature. The resulting mixture was stirred at room temperature for 4 h and diluted with DCM-IPA (16 mL:4 mL) and 5N NaOH (0.5 mL) added to the mixture, which was then washed with brine (10 mL×2). The aqueous layer extracted with DCM-IPA (4:1, 20 mL×2) and the combined organic layer was dried with sodium sulfate, concentrated in vacuo, and purified with silica gel column chromatography (0% to 100% MeOH in DCM) to give Compound 51. $^1$H NMR (400 MHz, Methanol-d4) δ 7.84 (s, 1H), 7.43-7.31 (m, 1H), 7.30-7.15 (m, 3H), 6.92 (dd, J=6.3, 4.6 Hz, 1H), 6.85 (d, J=4.5 Hz, 1H), 5.56 (d, J=5.2 Hz, 1H), 4.60-4.41 (m, 3H), 4.19-4.04 (m, 2H), 3.97 (m, 2H), 1.59 (m, 2H), 1.44-1.20 (m, 38H), 0.91 (t, J=6.7 Hz, 3H). $^{31}$P NMR (162 MHz, Methanol-d4) δ −0.44. MS m/z [M+1]=797.

Example 53: Compound 53 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl)oxy)-3-(heptadecyloxy)propyl) hydrogen phosphate

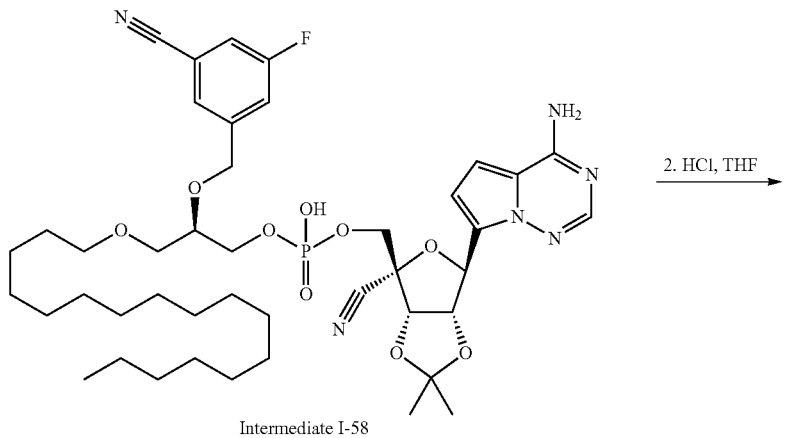

Intermediate I-58

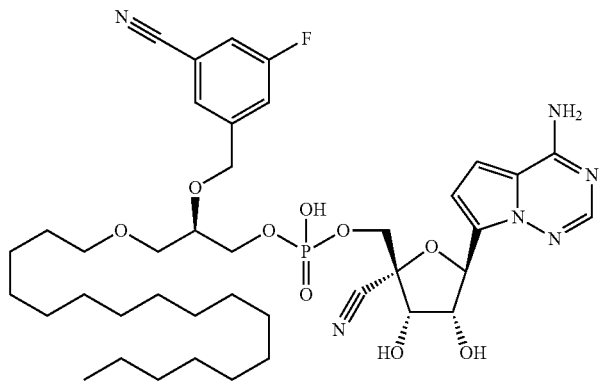

Compound 53

Intermediate I-58 (0.042 mmol) was dissolved in THF (2.0 mL) and then 25% HCl (0.388 mL) added at room temperature. The resulting mixture was stirred at room temperature for 4 h and diluted with DCM-IPA (8 mL:2 mL) and 5N NaOH (0.3 mL) added (pH2) to the mixture, which was then washed with brine (5 mL×2). The aqueous layer extracted with DCM-IPA (10 mL×2) and the combined organic layer was dried with sodium sulfate, concentrated in vacuo, and purified with silica gel column chromatography (0 to 100% MeOH in DCM) to give Compound 53. $^{1}$H NMR (400 MHz, Methanol-d4) δ 7.81 (s, 1H), 7.52 (s, 1H), 7.43 (dt, J=9.5, 1.9 Hz, 1H), 7.36 (dt, J=8.3, 1.9 Hz, 1H), 6.93-6.69 (m, 2H), 5.56 (d, J=5.0 Hz, 1H), 4.71 (d, J=13.3 Hz, 1H), 4.65-4.56 (m, 2H), 4.54 (m, 1H), 4.16 (qd, J=10.9, 4.7 Hz, 2H), 3.96 (m, 2H), 3.75 (m, 1H), 3.58-3.37 (m, 4H), 1.54 (m, 2H), 1.39-1.17 (m, 28H), 0.91 (t, J=6.7 Hz, 3H). $^{19}$F NMR (376 MHz, Methanol-d4) δ−112.90. $^{31}$P NMR (162 MHz, Methanol-d4) δ−0.32. MS m/z [M+1]=817.

Example 66: Compound 66 ((2R,3S,4R)-5-(4-aminopyrrolo[2,1-f][1,2,4]triazin-7-yl)-2-cyano-3,4-dihydroxytetrahydrofuran-2-yl)methyl ((R)-2-((5-cyanopyridin-3-yl)methoxy)-3-(octadecyloxy)propyl) hydrogen phosphate To a solution of Intermediate I-53 (0.0177 mmol, 1.0 equiv) in 2:1 THF:ACN (3.0 mL) was added concentrated HCl (0.30 mL, 12.0 M, 204 equiv.). The reaction mixture was stirred at room temperature for 2 h and 15 min. Additional concentrated HCl (0.15 mL, 12.0 M, 102 equiv.) was added and the solution was stirred for 25 min. The solution was diluted with 3:1 DCM:iPrOH (20 mL) and water (20 mL). The pH of the aqueous layer was adjusted to approximately 10 using 2 M NaOH then to pH 3 using 1 M HCl. The layers were separated. Water (20 mL) was added to the organic and the pH adjusted to 3 using 1 M HCl. The layers were separated once more. The aqueous extracts were combined and extracted with 3:1 DCM:iPrOH (20 mL). The organic extracts were combined, washed with 3:2 brine:water (30 mL), dried over Na$_2$SO$_4$, filtered and concentrated in vacuo prior to purification by silica gel chromatography (0%-100% MeOH in DCM) to afford Compound 66. $^{1}$H NMR (400 MHz, Methanol-d4) δ 8.74-8.70 (m, 2H), 8.17-8.14 (m, 1H), 7.84 (s, 1H), 6.92 (d, J=4.6 Hz, 1H), 6.87 (d, J=4.5 Hz, 1H), 5.53 (d, J=5.3 Hz, 1H), 4.80-4.64 (m, 2H), 4.57-4.48 (m, 2H), 4.19-4.08 (m, 2H), 4.01-3.90 (m, 2H), 3.80-3.74 (m, 1H), 3.56-3.35 (m, 4H), 1.57-1.47 (m, 2H), 1.38-1.21 (m, 30H), 0.93-0.86 (m, 3H). $^{31}$P NMR (162 MHz, Methanol-d4) δ−0.17-−0.57 (m). MS m/z [M+1]=814.4.

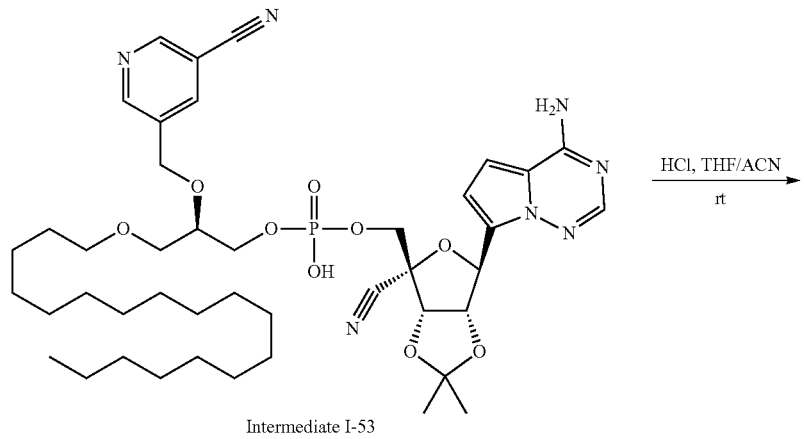

Intermediate I-53

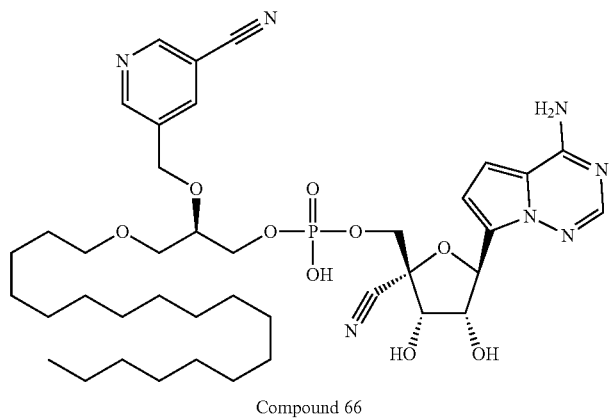

Compound 66

Example 67: Compound 67 ((2R,3S,4R)-5-(4-aminopyrrolo[2,1-f][1,2,4]triazin-7-yl)-2-cyano-3,4-dihydroxytetrahydrofuran-2-yl)methyl ((S)-2-((4-cyano-2-methoxybenzyl)oxy)-3-(octadecyloxy)propyl) hydrogen phosphate, and Compound 73: ((2R,3S,4R)-5-(4-aminopyrrolo[2,1-f][1,2,4]triazin-7-yl)-2-cyano-3,4-dihydroxytetra hydrofuran-2-yl)methyl ((R)-2-((4-cyano-2-methoxybenzyl)oxy)-3-(octadecyloxy)propyl) hydrogen phosphate

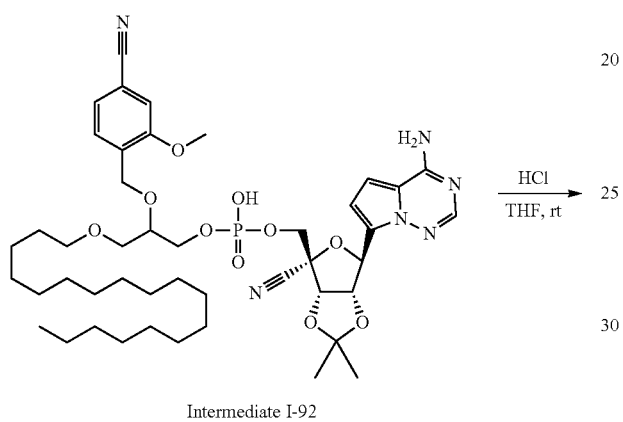

Intermediate I-92

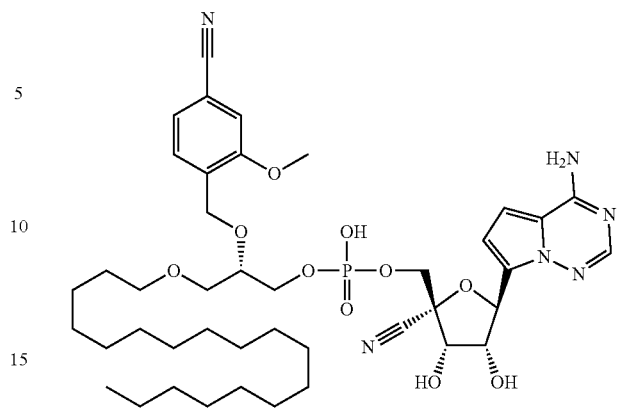

Compound 67

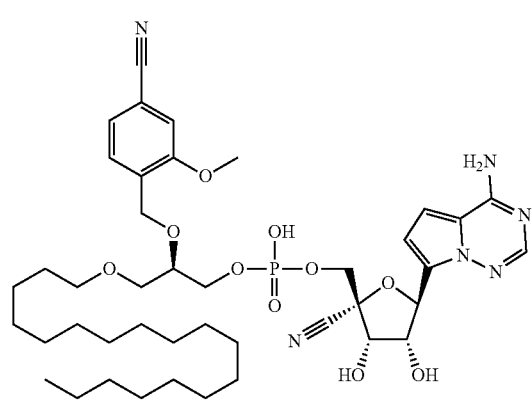

Compound 73

To a solution of Intermediate I-92 (0.062 mmol) in THF (3 mL) at 0° C. was added concentrated HCl (0.26 mL, 3.11 mmol) drop wise. The reaction mixture was warmed to rt and stirred for 5 h. The solution was cool to 0° C., and added few ice pellets, followed by solution of NaOH (2M in water) until pH ~8. To this solution was added Phosphoric acid (85% in water) to adjust pH ~3-4. Transferred to separatory funnel, use water (20 mL), and EtOAc/Me-THF (1:1, 20 mL) to complete transfer. Extracted with EtOAc/MeTHF (1:1, 50 mL×2) and combine organic layer washed with brine (70 mL) once. Dried over sodium sulfate, filtered, concentrated under vacuo prior to purification by silica gel chromatography (0-100% MeOH in DCM) to afford Compound 67 and Compound 73.

Compound 67: $^1$H NMR (400 MHz, Methanol-$d_4$) δ 7.80 (s, 1H), 7.60 (d, J=7.8 Hz, 1H), 7.23 (d, J=7.7, Hz, 1H), 7.20 (d, J=1.4 Hz, 1H), 6.85-6.82 (m, 2H), 5.55 (d, J=5.3 Hz, 1H), 4.68 (s, 2H), 4.60-4.46 (m, 2H), 4.20-4.10 (m, 2H), 3.99-3.96 (m, 2H), 3.86 (s, 3H), 3.81-3.71 (m, 1H), 3.60-3.53 (m, 1H), 3.51-3.45 (m, 1H), 3.44-3.36 (m, 1H), 1.71-1.43 (m, 2H), 1.37-1.21 (m, 30H), 0.92 (t, J=6.7 Hz, 3H). $^{31}$P NMR (162 MHz, Methanol-$d_4$) δ−0.37. MS m/z [M+1]=843.2.

Compound 73: $^1$H NMR (400 MHz, Methanol-$d_4$) δ 7.80 (s, 1H), 7.60 (d, J=7.7 Hz, 1H), 7.23 (d, J=8.0 Hz, 1H), 7.20 (s, 1H), 6.83 (q, J=4.6 Hz, 2H), 5.55 (d, J=5.2 Hz, 1H), 4.69 (s, 2H), 4.62-4.47 (m, 2H), 4.16 (qd, J=10.9, 4.8 Hz, 2H), 3.98 (t, J=5.5 Hz, 2H), 3.86 (s, 3H), 3.76 (p, J=5.0 Hz, 1H), 3.56 (dd, J=10.7, 3.6 Hz, 1H), 3.48 (dd, J=10.8, 6.2 Hz, 1H), 3.41 (q, J=6.7 Hz, 1H), 1.52 (p, J=6.6 Hz, 2H), 1.29 (d, J=11.0 Hz, 30H), 0.92 (t, J=6.6 Hz, 3H). $^{31}$P NMR (162 MHz, Methanol-$d_4$) δ−0.33. MS m/z [M+1]=843.3.

Example 68: Compound 68 ((2R,3S,4R)-5-(4-aminopyrrolo[2,1-f][1,2,4]triazin-7-yl)-2-cyano-3,4-dihydroxytetrahydrofuran-2-yl)methyl ((R)-2-((6-cyanopyridin-2-yl)methoxy)-3-(octadecyloxy)propyl) hydrogen phosphate

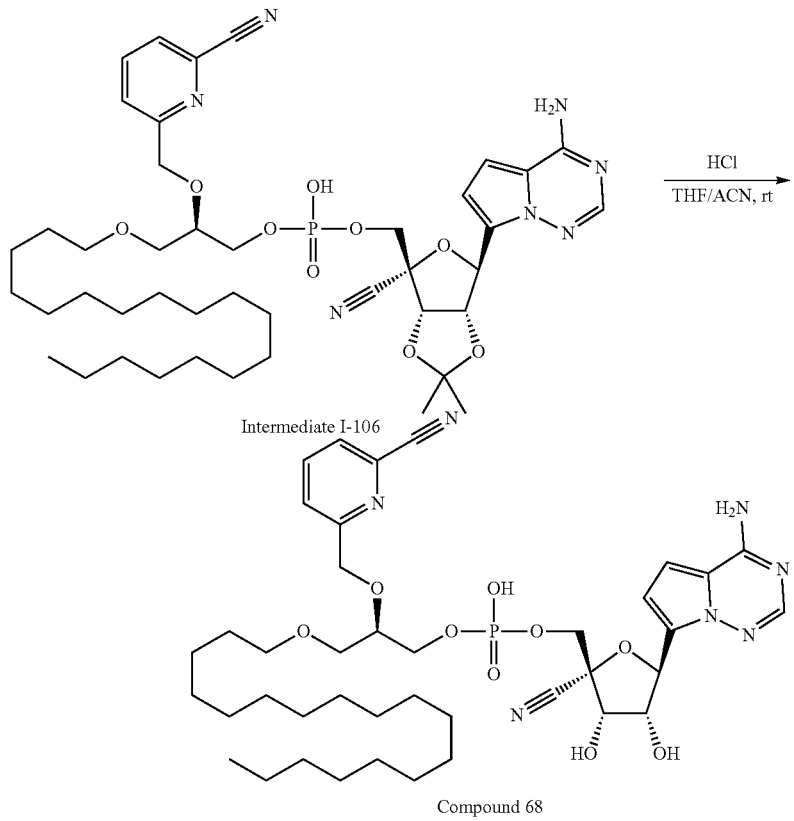

Intermediate I-106

Compound 68

To a solution of Intermediate I-106 (0.0293 mmol) in 2:1 THF:ACN (1.5 mL) was added concentrated HCl (0.036 mL). The reaction mixture was stirred at room temperature for 6 h. The reaction mixture was diluted with 3:1 DCM:IPA (5 mL) and added aqueous solution of $K_2HPO_4 \cdot 3H_2O$ (240 mg in 2.0 mL) until the pH of the aqueous layer is 2-3. The layers were separated. The organic layer was washed with an additional 5 mL of water prior to drying over $Na_2SO_4$, filtering and concentrating in vacuo. The crude residue was purified by silica gel chromatography (0-70% MeOH in DCM) to afford Compound 68. $^1$H NMR (400 MHz, Methanol-d4) δ 7.98-7.85 (m, 2H), 7.81 (s, 1H), 7.73-7.59 (m, 1H), 6.84 (s, 2H), 5.55 (d, J=5.4 Hz, 1H), 4.60-4.56 (m, 1H), 4.52 (d, J=5.5 Hz, 1H), 4.28-4.06 (m, 2H), 4.04-3.91 (m, 2H), 3.85-3.73 (m, 1H), 3.59-3.46 (m, 2H), 3.44-3.36 (m, 2H), 1.58-1.45 (m, 2H), 1.36-1.18 (m, 30H), 0.91 (t, J=6.7 Hz, 3H). $^{31}$P NMR (162 MHz, Methanol-d4) δ −0.38. MS m/z [M+1]=814.2.

Example 69: Compound 69 ((2R,3S,4R)-5-(4-aminopyrrolo[2,1-f][1,2,4]triazin-7-yl)-2-cyano-3,4-dihydroxytetrahydrofuran-2-yl)methyl ((R)-2-((4-cyanopyridin-2-yl)oxy)-3-(tetradecyloxy)propyl) hydrogen phosphate

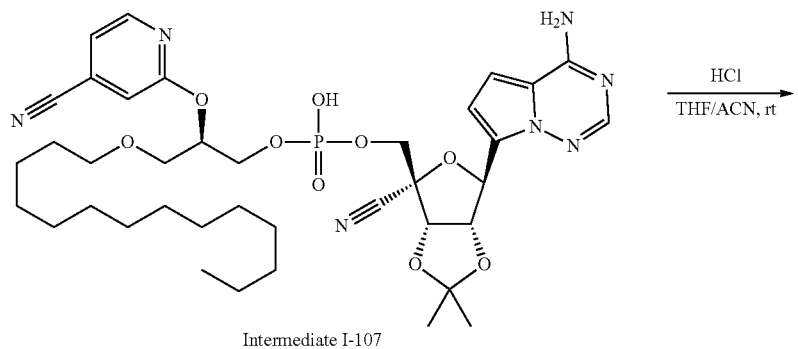

Intermediate I-107

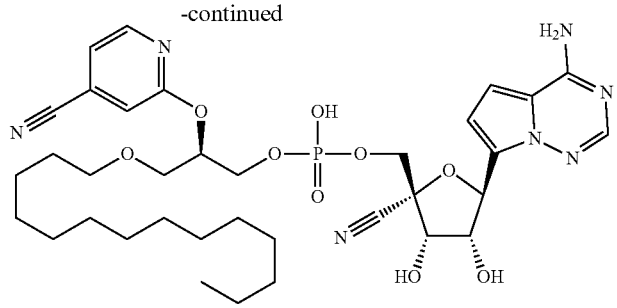

Compound 69

To a solution of Intermediate I-107 (0.0332 mmol) in 2:1 THF:ACN (1.5 mL) was added concentrated HCl (0.041 mL). The reaction mixture was stirred at room temperature for 6 h. The reaction mixture was diluted with 3:1 DCM:IPA (5 mL) and added aqueous solution of $K_2HPO_4 \cdot 3H_2O$ (240 mg in 2.0 mL) until the pH of the aqueous layer is 2-3. The layers were separated. The organic layer was washed with an additional 5 mL of water prior to drying over $Na_2SO_4$, filtering and concentrating in vacuo. The crude residue was purified by silica gel chromatography two times (0-70% MeOH in DCM) to afford Compound 69. $^1$H NMR (400 MHz, Methanol-d4) δ 8.26-8.19 (m, 1H), 7.82 (s, 1H), 7.26-6.99 (m, 2H), 6.85 (s, 2H), 5.55 (d, J=5.4 Hz, 1H), 4.65-4.50 (m, 4H), 4.42 (dd, J=11.0, 5.5 Hz, 1H), 4.64-4.50 (m, 2H), 3.78-3.62 (m, 2H), 3.46-3.39 (m, 2H), 1.60-1.44 (m, 2H), 1.39-1.17 (m, 22H), 0.91 (t, J=6.7 Hz, 3H). $^{31}$P NMR (162 MHz, Methanol-d4) 31P NMR (162 MHz, MeOD) δ−1.17−−1.25. MS m/z [M+1]=744.3.

Example 70: Compound 70 ((2R,3S,4R)-5-(4-aminopyrrolo[2,1-f][1,2,4]triazin-7-yl)-2-cyano-3,4-dihydroxytetrahydrofuran-2-yl)methyl ((S)-2-((3-cyano-5-fluorobenzyl)oxy) docosyl) hydrogen phosphate

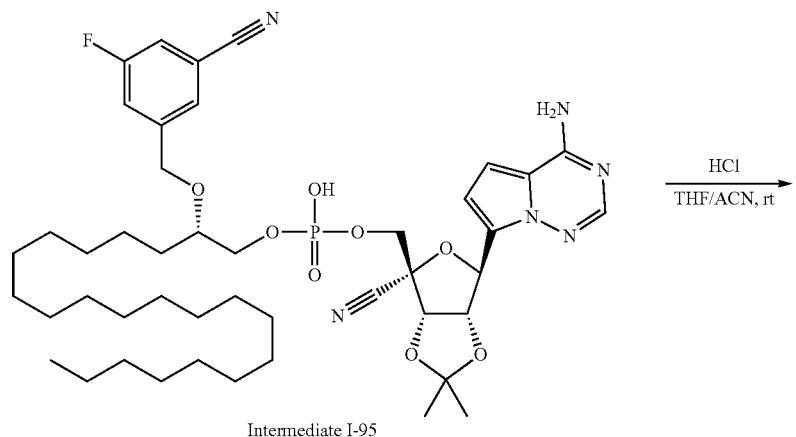

Intermediate I-95

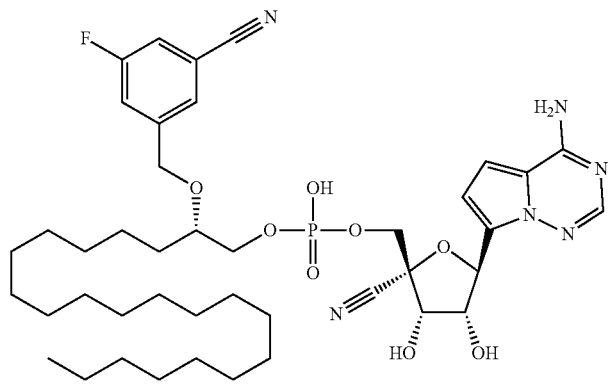

Compound 70

To a solution of Intermediate I-95 (0.02 mmol) in THF (1.5 mL) was cooled to 0° C., and added concentrated HCl (0.1 mL) dropwise. The reaction mixture was warmed to rt and stirred for 3 h. The solution was cool to 0° C., and added few ice pellets, followed by solution of NaOH (2M in water) until pH ~8. To this solution was added Phosphoric acid (85% in water) to adjust pH ~3-4. Transferred to separatory funnel, use water (10 mL), and EtOAc/Me-THF (1:1, 20 mL) to complete transfer. Extracted with EtOAc/MeTHF (1:1, 25 mL×2) and combine organic layer washed with brine (50 mL) once. Dried over sodium sulfate, filtered, concentrated under vacuo prior to purification by silica gel chromatography (0-100% MeOH in DCM) to afford Compound 70. 1H NMR (400 MHz, Methanol-d4) δ 7.80 (s, 1H), 7.48 (s, 1H), 7.41-7.35 (m, 2H), 6.85 (d, J=1.8 Hz, 1H), 6.84 (d, J=1.9 Hz, 1H), 5.56 (d, J=5.1 Hz, 1H), 4.73 (dd, J=13.0, 9.7 Hz, 1H), 4.61-4.45 (m, 3H), 4.23-4.09 (m, 2H), 3.95-3.85 (m, 2H), 3.61-3.51 (m, 1H), 1.48-1.42 (m, 2H), 1.30-1.26 (m, 36H), 0.92 (t, J=6.7 Hz, 3H). 31P NMR (162 MHz, Methanol-d4) δ −0.28. MS m/z [M+1]=829.2.

Example 71: Compound 71 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((5-cyanopyridin-2-yl)oxy) octadecyl) hydrogen phosphate To a solution of Intermediate I-99 (0.153 mmol) in THF (4 mL) was cooled to 0° C., and added concentrated HCl (0.51 mL) drop wise. The reaction mixture was warmed to rt and stirred for 4 h. The solution was cool to 0° C., and added few ice pellets, followed by solution of NaOH (1M in water) until pH ~8. To this solution was added Phosphoric acid (85% in water) to adjust pH ~3-4. Transferred to separatory funnel, use water (20 mL), and EtOAc/Me-THF (1:1, 20 mL) to complete transfer. Extracted with EtOAc/MeTHF ((1:1, 50 mL×2) and combine organic layer washed with brine (70 mL) once. Dried over sodium sulfate, filtered, concentrated under vacuo prior to purification by silica gel chromatography (0-100% MeOH in DCM) to afford Compound 71. $^1$H NMR (400 MHz, Methanol-d$_4$) δ 8.43 (d, J=2.3 Hz, 1H), 7.87 (dd, J=8.7, 2.4 Hz, 1H), 7.84 (s, 1H), 6.93-6.87 (m, 2H), 6.85 (d, J=4.5 Hz, 1H), 5.54 (d, J=5.3 Hz, 1H), 4.64-4.51 (m, 4H), 4.49-4.40 (m, 1H), 4.25-4.16 (m, 2H), 3.72-3.64 (m, 2H), 3.45-3.41 (m, 2H), 3.00-2.64 (m, 10H, Citrate salt), 1.53-1.42 (m, 2H), 1.39-1.15 (m, 22H), 0.91 (t, J=6.7 Hz, 3H). $^{31}$P NMR (162 MHz, Methanol-d$_4$) δ−1.31. MS m/z [M+1]=744.1.

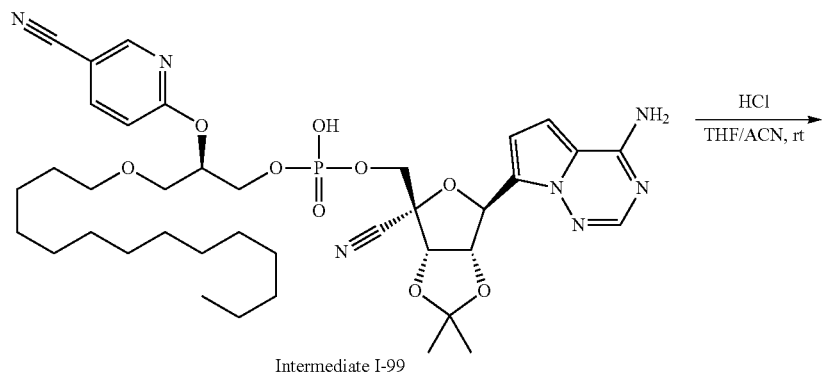

Intermediate I-99

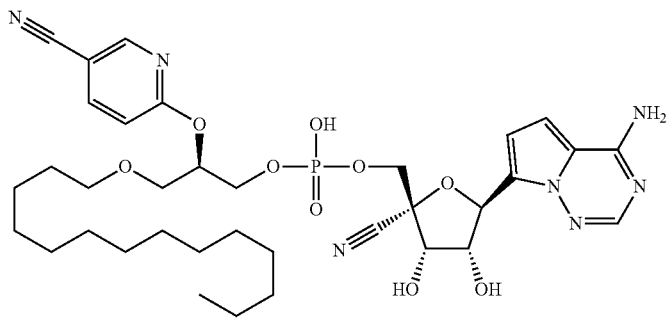

Compound 71

Example 72: Compound 72 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-((6-cyanopyridin-3-yl)oxy)-3-(octadecyloxy)propyl) hydrogen phosphate

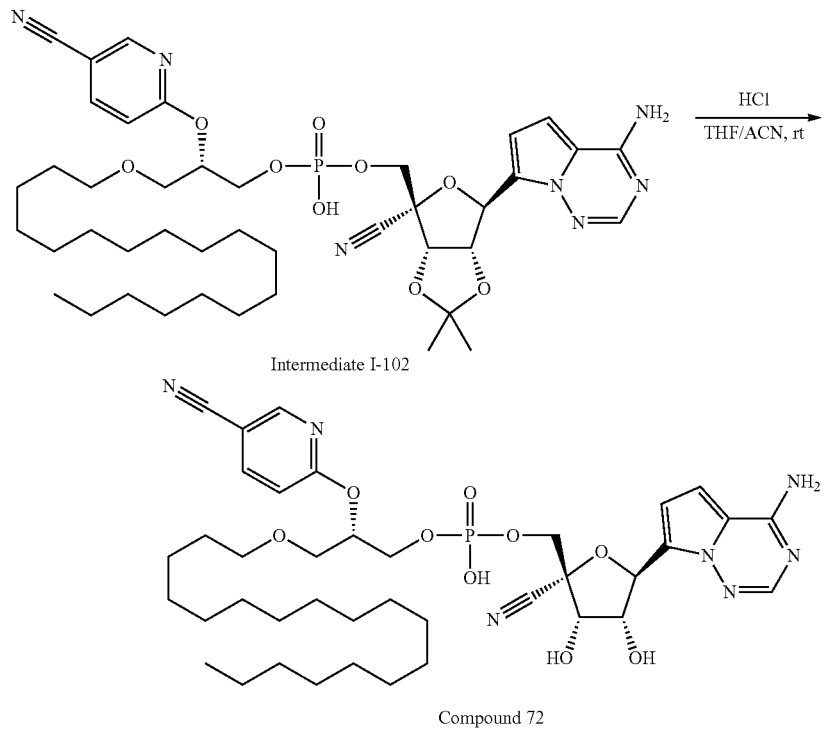

To a solution of Intermediate I-102 (0.095 mmol) in THF (3 mL) was cooled to 0° C., and added concentrated HCl (0.47 mL) dropwise. The reaction mixture was warmed to rt and stirred for 5 h. The solution was cool to 0° C., and added few ice pellets, followed by solution of NaOH (1M in water) until pH ~8. To this solution was added Phosphoric acid (85% in water) to adjust pH ~3-4. Transferred to separatory funnel, use water (20 mL), and EtOAc/Me-THF (1:1, 20 mL) to complete transfer. Extracted with EtOAc/MeTHF ((1:1, 50 mL×2) and combine organic layer washed with brine (70 mL) once. Dried over sodium sulfate, filtered, concentrated under vacuo prior to purification by silica gel chromatography (0-100% MeOH in DCM) to afford Compound 72. $^1$H NMR (400 MHz, Methanol-d4) δ 8.31 (d, J=2.8 Hz, 1H), 8.03 (s, 1H), 7.70 (d, J=8.7 Hz, 1H), 7.59 (dd, J=8.8, 2.9 Hz, 1H), 7.29 (d, J=4.7 Hz, 1H), 7.04 (d, J=4.8 Hz, 1H), 5.55 (d, J=5.1 Hz, 1H), 4.54-4.42 (m, 2H), 4.19 (dd, J=11.0, 5.4 Hz, 1H), 4.14-4.09 (m, 2H), 3.98-3.90 (m, 1H), 3.77-3.72 (m, 2H), 3.66 (dd, J=10.9, 6.6 Hz, 1H), 3.54-3.38 (m, 2H), 1.51 (t, J=6.5 Hz, 2H), 1.38-1.11 (m, 30H), 0.92 (t, J=6.7 Hz, 3H). MS m/z [M+1]=800.2.

Example 73: Compound 73 ((2R,3S,4R)-5-(4-aminopyrrolo[2,1-f][1,2,4]triazin-7-yl)-2-cyano-3,4-dihydroxytetrahydrofuran-2-yl)methyl ((R)-2-((4-cyano-2-methoxybenzyl)oxy)-3-(octadecyloxy)propyl) hydrogen phosphate The method for preparing Compound 73 is described above in Example 67.

Example 74: Compound 74 ((2R,3S,4R)-5-(4-aminopyrrolo[2,1-f][1,2,4]triazin-7-yl)-2-cyano-3,4-dihydroxytetrahydrofuran-2-yl)methyl ((S)-2-((3-cyano-5-fluorobenzyl)oxy) nonadecyl) hydrogen phosphate

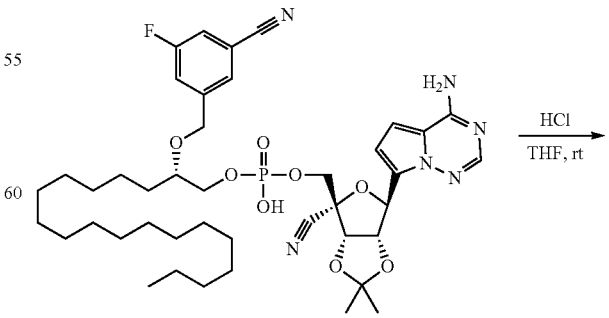

883
-continued

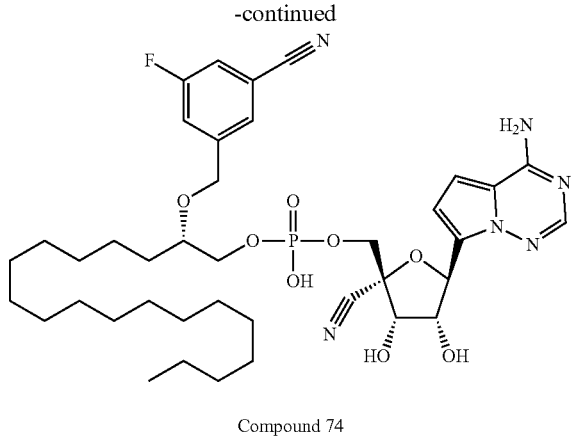

Compound 74

To a solution of Intermediate I-104 (0.242 mmol) in THF (10 mL) cooled in an ice bath was added concentrated HCl (0.504 mL). The reaction mixture was warmed to room temperature and stirred for 5 h. The solution was diluted with 3:1 DCM:IPA (50 mL) and water (20 mL). The pH of the aqueous layer was adjusted to approximately 3 using 2 M NaOH. The layers were separated. Water (20 mL) was added to the organic and the pH adjusted to 3 using 1 M HCl. The layers were separated once more. The aqueous extracts were combined and extracted with 3:1 DCM:iPrOH (60 mL). The organic extracts were combined, washed with 3:2 brine:water (50 mL), dried over $Na_2SO_4$, filtered and concentrated in vacuo prior to purification by silica gel chromatography (0-100% MeOH in DCM) to afford Compound 74. $^1$H NMR (400 MHz, Methanol-d4) δ 7.81 (s, 1H), 7.49 (s, 1H), 7.44-7.32 (m, 2H), 6.87-6.83 (m, 2H), 5.56 (d, J=5.3 Hz, 1H), 4.73 (d, J=13.0 Hz, 1H), 4.60-4.57 (m, 1H), 4.54-4.41 (m, 2H), 4.19-4.11 (m, 2H), 3.94-3.84 (m, 2H), 3.66-3.50 (m, 1H), 1.47-1.42 (m, 2H), 1.34-1.26 (m, 30H), 0.92 (t, J=6.7 Hz, 3H). $^{31}$P NMR (162 MHz, Methanol-d4) δ−0.59. MS m/z [M−1]=787.2.

Example 75: Compound 75 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((4-cyano-2-fluorobenzyl) oxy)-3-(tetradecyloxy)propyl) hydrogen phosphate 884
-continued

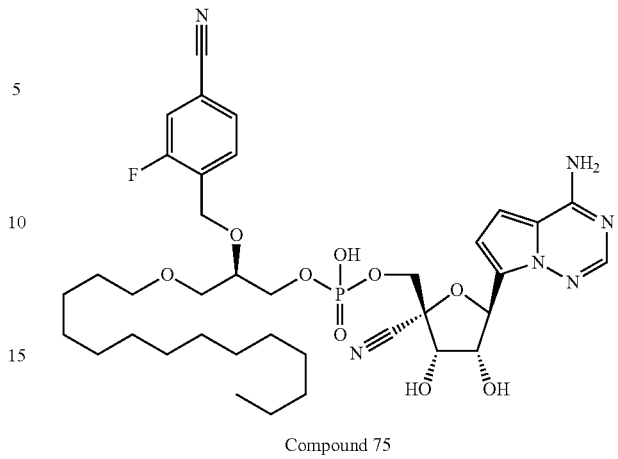

Compound 75

A solution of Intermediate I-79 (0.128 mmol) in THF (2.0 mL) was 25% HCl (0.7 mL) at rt. The solution was stirred at rt for 5 h and diluted with DCM-IPA (16 mL:4 mL). 5N NaOH (0.5 mL) was added (pH2) to the mixture, which was then washed with brine (5 mL×2), the aqueous layer extracted with DCM-IPA (10 mL×2), The combined organic layer was dried with sodium sulfate, concentrated in vacuo, and purified with silica gel column chromatography (0 to 100% MeOH in DCM) to give Compound 75. $^1$H NMR (400 MHz, Methanol-d4) δ 8.07 (s, 1H), 7.75 (t, J=7.5 Hz, 1H), 7.47 (t, J=8.7 Hz, 2H), 7.40 (d, J=4.6 Hz, 1H), 7.07 (d, J=4.7 Hz, 1H), 5.56 (d, J=4.7 Hz, 1H), 4.82 (s, 2H), 4.54-4.43 (m, 2H), 4.18 (m, 2H), 4.04 (m, 2H), 3.85 (m, 1H), 3.59 (m, 2H), 3.46 (m, 2H), 1.54 (m, 2H), 1.47-1.21 (m, 22H), 0.91 (t, J=6.6 Hz, 3H). $^{19}$F NMR (376 MHz, Methanol-d4) δ−118.39. $^{31}$P NMR (162 MHz, Methanol-d4) δ−0.52. MS m/z [M+1]=775.

Example 76: Compound 76 ((2R,3S,4R)-5-(4-aminopyrrolo[2,1-f][1,2,4]triazin-7-yl)-2-cyano-3,4-dihydroxytetrahydrofuran-2-yl)methyl ((R)-2-((3-chloro-5-cyanobenzyl)oxy) nonadecyl) hydrogen phosphate

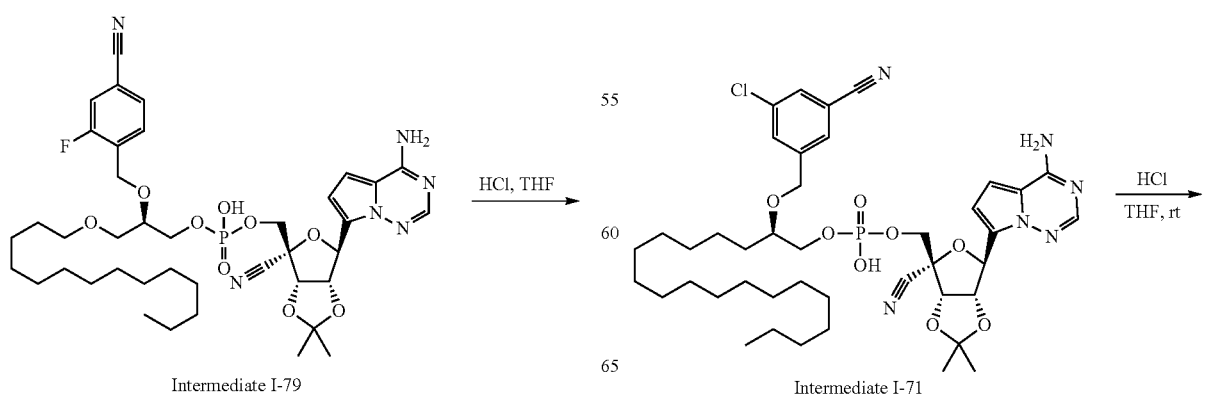

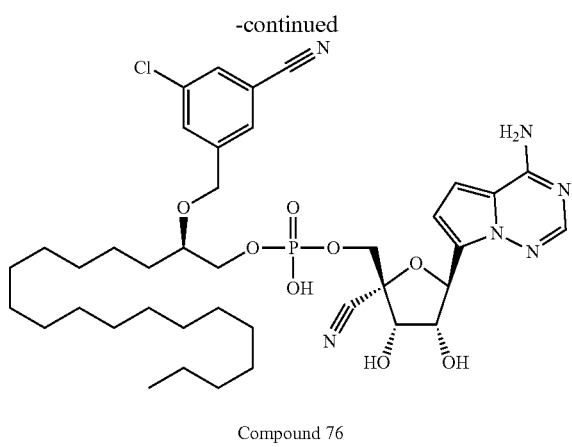

Compound 76

To a solution of Intermediate I-71 (0.145 mmol) in THF (4.0 mL) was added concentrated HCl (0.50 mL). The reaction mixture was stirred at room temperature for 4 h. The solution was diluted with 4:1 DCM:IPA (100 mL) and water (50 mL). The pH of the aqueous layer was adjusted to between 3 to 4 using a combination of 20 wt % KOH and 1 M HCl. The layers were separated. The organic layer was washed with an additional 50 mL of water prior to drying over $Na_2SO_4$, filtering and concentrating in vacuo. The crude residue was loaded onto silica gel and purified by silica gel chromatography (0-40% MeOH in DCM) to afford Compound 76. $^1$H NMR (400 MHz, Methanol-d4) δ 7.85 (s, 1H), 7.63-7.55 (m, 3H), 6.98 (d, J=4.6 Hz, 1H), 6.89 (d, J=4.6 Hz, 1H), 5.53 (d, J=5.1 Hz, 1H), 4.72 (d, J=13.0 Hz, 1H), 4.57-4.45 (m, 3H), 4.21-4.08 (m, 2H), 3.97-3.83 (m, 2H), 3.61-3.53 (m, 1H), 1.54-1.16 (m, 32H), 0.90 (t, J=6.8 Hz, 3H). $^{31}$P NMR (162 MHz, Methanol-d4) δ −0.14−−0.48 (m). MS m/z [M−1]=803.2.

Example 77: Compound 77 ((2R,3S,4R)-5-(4-aminopyrrolo[2,1-f][1,2,4]triazin-7-yl)-2-cyano-3,4-dihydroxytetrahydrofuran-2-yl)methyl ((R)-2-((6-cyanopyridin-3-yl)oxy)-3-(tetradecyloxy)propyl) hydrogen phosphate

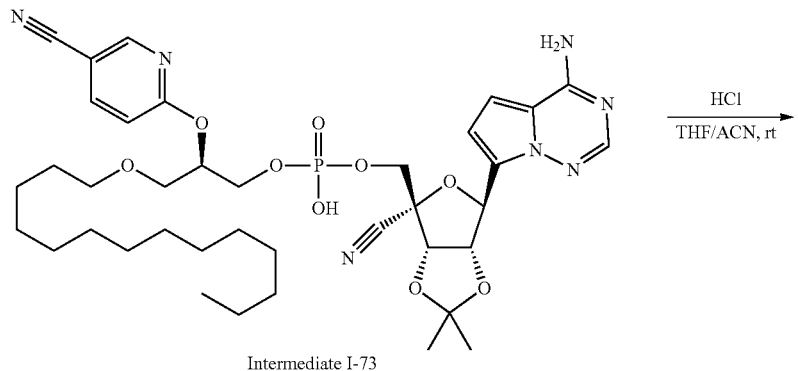

Intermediate I-73

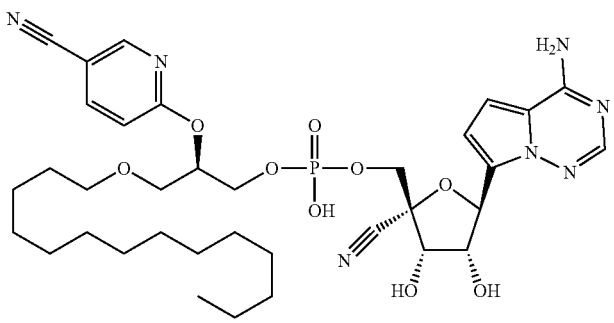

Compound 77

To a solution of Intermediate I-73 (0.0159 mmol) in 2:1 THF:ACN (1.5 mL) was added concentrated HCl (0.25 mL). The reaction mixture was stirred at room temperature for 4 h. The solution was diluted with 3:1 DCM:IPA (20 mL) and water (20 mL). The pH of the aqueous layer was adjusted to approximately 4 using 2 M NaOH. The layers were separated. Water (20 mL) was added to the organic and the pH adjusted to 3 using 1 M HCl. The layers were separated once more. The aqueous extracts were combined and extracted with 3:1 DCM:IPA (20 mL). The organic extracts were combined, washed with 1:1 brine:water (20 mL), dried over Na$_2$SO$_4$, filtered and concentrated in vacuo prior to purification by silica gel chromatography (0-70% MeOH in DCM) to afford the Compound 77. $^1$H NMR (400 MHz, Methanol-d4) δ 8.30 (d, J=2.9 Hz, 1H), 7.83-7.80 (m, 1H), 7.65 (d, J=8.7 Hz, 1H), 7.51 (dd, J=8.8, 2.9 Hz, 1H), 6.86-6.80 (m, 2H), 5.54 (d, J=5.2 Hz, 1H), 4.78-4.71 (m, 1H), 4.57-4.51 (m, 1H), 4.49 (d, J=5.5 Hz, 1H), 4.18-4.07 (m, 2H), 4.04-3.98 (m, 2H), 3.67-3.33 (m, 4H), 1.51-1.41 (m, 2H), 1.37-1.15 (m, 22H), 0.90 (t, J=6.7 Hz, 3H). $^{31}$P NMR (162 MHz, Methanol-d4) δ−0.45−−0.77 (m). MS m/z [M−1]=744.3.

Example 78: Compound 78 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl)oxy)octadecyl) hydrogen phosphate

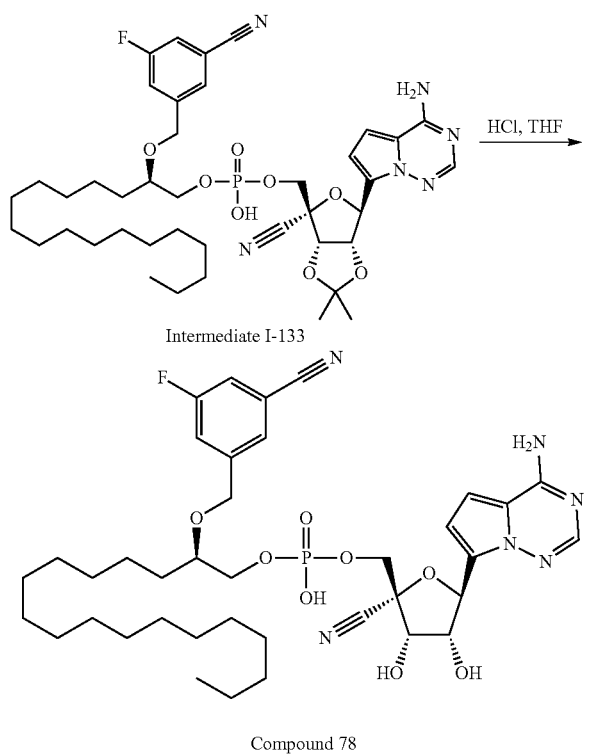

Intermediate I-133

Compound 78

To a solution of ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-cyano-5-fluorobenzyl)oxy)octadecyl) hydrogen phosphate, Intermediate I-133 (84 mg, 0.103 mmol, 1.0 equiv) in THF (4.0 mL) was added concentrated HCl (0.50 mL, 12.0 M, 58.1 equiv.). The reaction mixture was stirred at room temperature for 5 h and 30 min. The solution was diluted with 4:1 DCM:IPA (50 mL) and water (35 mL). The pH of the aqueous layer was adjusted to around 4.5 using a combination of 20 wt % KOH and 1 M HCl. The layers were separated. The organic layer was washed with an additional 35 mL of water prior to drying over Na$_2$SO$_4$, filtering and concentrating in vacuo. The crude residue was loaded onto silica gel and purified by silica gel chromatography (0-30% MeOH in DCM) to afford the title Compound 78. $^1$H NMR (400 MHz, Methanol-d4) δ 7.84 (s, 1H), 7.49-7.45 (m, 1H), 7.42-7.32 (m, 2H), 6.95 (d, J=4.6 Hz, 1H), 6.88 (d, J=4.6 Hz, 1H), 5.53 (d, J=5.1 Hz, 1H), 4.72 (d, J=13.0 Hz, 1H), 4.58-4.46 (m, 3H), 4.21-4.08 (m, 2H), 3.96-3.83 (m, 2H), 3.61-3.52 (m, 1H), 1.54-1.17 (m, 30H), 0.90 (t, J=6.7 Hz, 3H). $^{19}$F NMR (376 MHz, Methanol-d4) δ−112.91−−113.06 (m). $^{31}$P NMR (162 MHz, Methanol-d4) δ−0.02−−0.59 (m). MS m/z [M+1]=773.1

Example 79: Compound 79 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-((3-cyano-5-fluorobenzyl)oxy)octadecyl) hydrogen phosphate

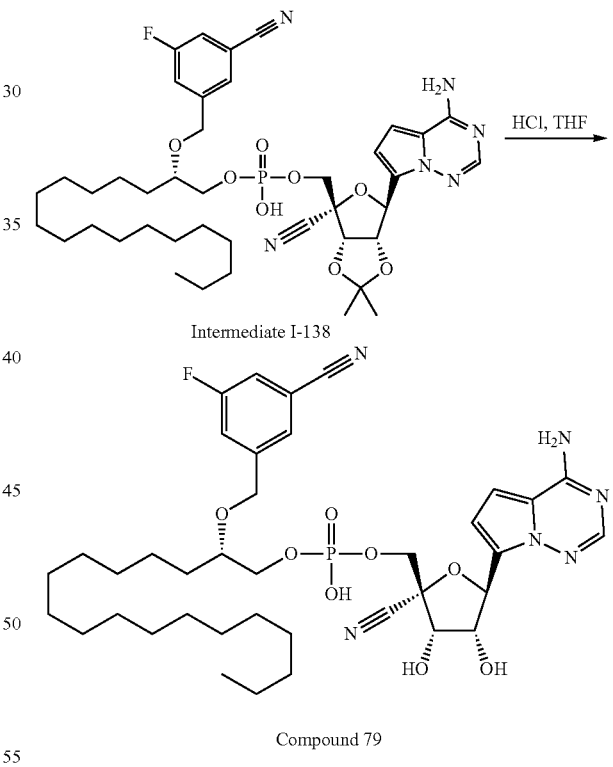

Intermediate I-138

Compound 79

To a solution of ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl)oxy)octadecyl) hydrogen phosphate, Intermediate I-138 (94 mg, 0.116 mmol, 1.0 equiv) in THF (4.0 mL) was added concentrated HCl (0.50 mL, 12.0 M, 51.9 equiv.). The reaction mixture was stirred at room temperature for 6 h. The solution was diluted with 4:1 DCM:IPA (50 mL) and water (35 mL). The pH of the aqueous layer was adjusted to around 3.0 using a combination of 20 wt % KOH and 1 M HCl. The layers were separated. The organic layer was washed with an additional 35 mL of water prior to drying over Na₂SO₄, filtering and concentrating in vacuo. The crude residue was loaded onto silica gel and purified by silica gel chromatography (0-30% MeOH in DCM) to afford the title Compound 79. $^1$H NMR (400 MHz, Methanol-d4) δ 7.85 (s, 1H), 7.51-7.46 (m, 1H), 7.43-7.31 (m, 2H), 7.00 (d, J=4.6 Hz, 1H), 6.90 (d, J=4.6 Hz, 1H), 5.54 (d, J=5.3 Hz, 1H), 4.75 (d, J=13.0 Hz, 1H), 4.58-4.46 (m, 3H), 4.22-4.08 (m, 2H), 3.98-3.84 (m, 2H), 3.62-3.54 (m, 1H), 1.57-1.15 (m, 30H), 0.90 (t, J=6.7 Hz, 3H). $^{19}$F NMR (376 MHz, Methanol-d4) δ−112.84−−113.07 (m). $^{31}$P NMR (162 MHz, Methanol-d4) δ 0.14−−0.76 (m). MS m/z [M+1]=773.1

Example 80: Compound 80 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl)oxy)heptadecyl) hydrogen phosphate

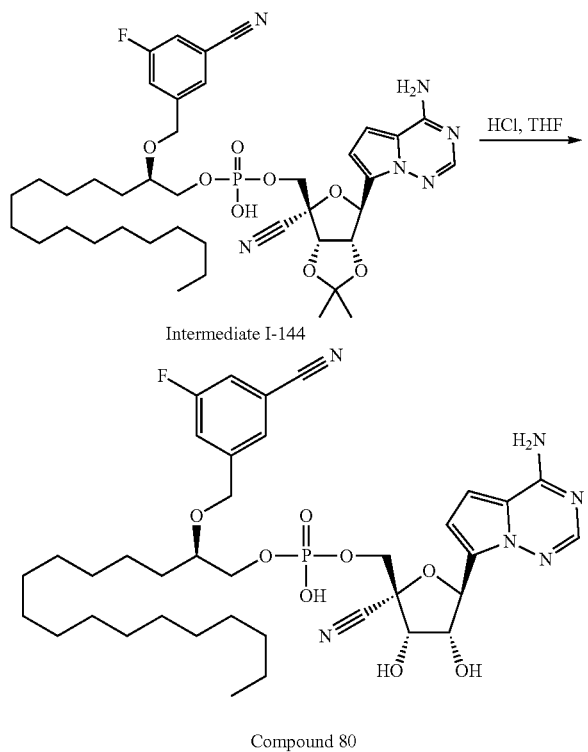

Compound 80

To a solution of ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-cyano-5-fluorobenzyl)oxy)heptadecyl) hydrogen phosphate, Intermediate I-144 (288 mg, 0.361 mmol, 1.0 equiv) in THF (4.0 mL) was added concentrated HCl (0.50 mL, 12.0 M, 16.6 equiv.). The reaction mixture was stirred at room temperature overnight. The solution was diluted with 4:1 DCM:IPA (100 mL) and water (50 mL). The pH of the aqueous layer was adjusted to around 5 using a combination of 20 wt % KOH and 1 M HCl. The layers were separated. The organic layer was washed with an additional 50 mL of water and 30 mL of brine prior to drying over Na₂SO₄, filtering and concentrating in vacuo. The crude residue was loaded onto silica gel and purified by silica gel chromatography (0-35% MeOH in DCM) to afford the title Compound 80. $^1$H NMR (400 MHz, Methanol-d4) δ 7.84 (s, 1H), 7.50-7.45 (m, 1H), 7.43-7.31 (m, 2H), 6.98 (d, J=4.6 Hz, 1H), 6.88 (d, J=4.6 Hz, 1H), 5.53 (d, J=5.0 Hz, 1H), 4.73 (d, J=13.0 Hz, 1H), 4.57-4.46 (m, 3H), 4.24-4.07 (m, 2H), 3.99-3.84 (m, 2H), 3.62-3.53 (m, 1H), 1.53-1.18 (m, 28H), 0.89 (t, J=6.7 Hz, 3H). $^{19}$F NMR (376 MHz, Methanol-d4) δ−112.77−−113.11 (m). $^{31}$P NMR (162 MHz, Methanol-d4) δ−0.08−−0.55 (m). MS m/z [M+1]=759.1

Example 81: Compound 81 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-chloro-5-cyanobenzyl)oxy)icosyl) hydrogen phosphate

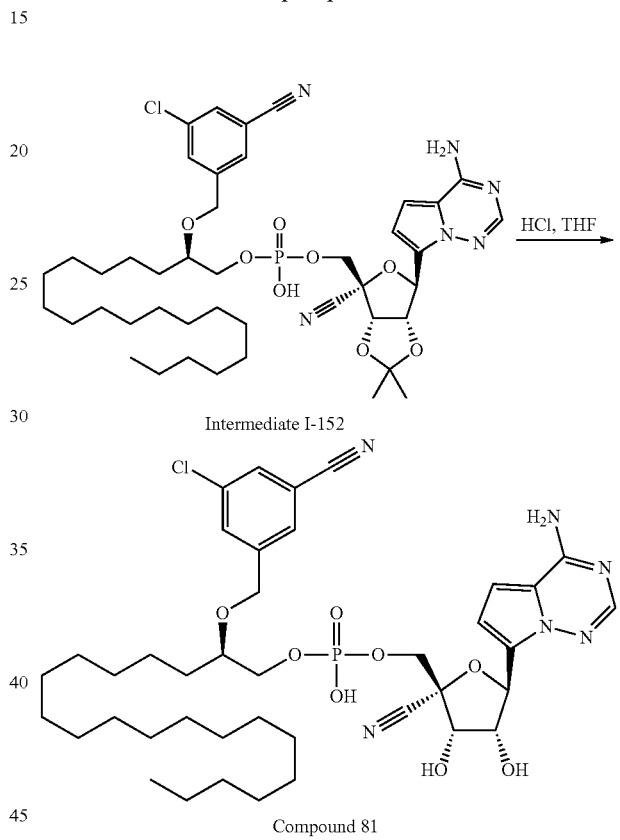

To a solution of ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-chloro-5-cyanobenzyl)oxy)icosyl) hydrogen phosphate, Intermediate I-152 (134 mg, 0.156 mmol, 1.0 equiv) in THF (4.0 mL) was added concentrated HCl (0.50 mL, 12.0 M, 38.4 equiv.). The reaction mixture was stirred at room temperature for 5 h and 15 min. The solution was diluted with 4:1 DCM:IPA (100 mL) and water (50 mL). The pH of the aqueous layer was adjusted to around 3 using a combination of 20 wt % KOH and 1 M HCl. The layers were separated. The organic layer was washed with an additional 50 mL of water and 20 mL of brine prior to drying over Na₂SO₄, filtering and concentrating in vacuo. The crude residue was loaded onto silica gel and purified by silica gel chromatography (0-35% MeOH in DCM) to afford the title Compound 81 as the TFA salt. $^1$H NMR (400 MHz, Methanol-d4) δ 7.80 (s, 1H), 7.62-7.55 (m, 3H), 6.87-6.81 (m, 2H), 5.54 (d, J=5.0 Hz, 1H), 4.69 (d, J=12.9 Hz, 1H), 4.59-4.41 (m, 3H), 4.23-4.07 (m, 2H), 3.97-3.82 (m, 2H), 3.59-3.50 (m, 1H), 1.52-1.16 (m, 34H), 0.89 (t, J=6.7 Hz, 3H). $^{19}$F NMR (376 MHz, Methanol-d4) δ −77.49. $^{31}$P NMR (162 MHz, Methanol-d4) δ −0.10--−0.61 (m). MS m/z [M+1]=817.2

Example 82: Compound 82 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-chloro-5-cyanobenzyl)oxy)henicosyl) hydrogen phosphate

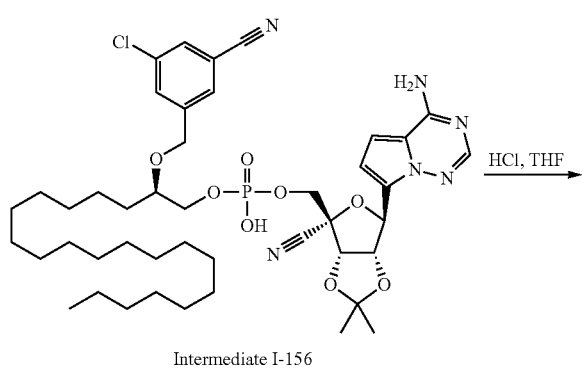

Intermediate I-156

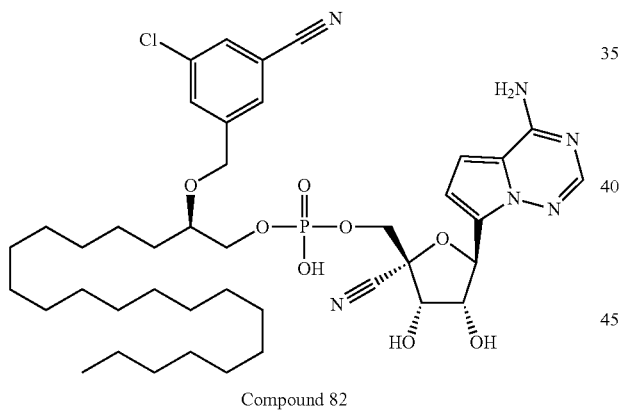

Compound 82

To a solution of ((3aS,4R,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-chloro-5-cyanobenzyl)oxy)henicosyl) hydrogen phosphate, Intermediate I-156 (147 mg, 0.169 mmol, 1.0 equiv) in THF (4.0 mL) was added concentrated HCl (0.50 mL, 12.0 M, 35.6 equiv.). The reaction mixture was stirred at room temperature for 5 h. The solution was diluted with 4:1 DCM:IPA (100 mL) and water (50 mL). The pH of the aqueous layer was adjusted to between 3.5 and 4 using a combination of 20 wt % KOH and 1 M HCl. The layers were separated. The organic layer was washed with an additional 50 mL of water and 20 mL of brine prior to drying over Na$_2$SO$_4$, filtering and concentrating in vacuo. The crude residue was loaded onto silica gel and purified by silica gel chromatography (0-35% MeOH in DCM) to afford the title Compound 82 as the TFA salt after lyophilization. $^1$H NMR (400 MHz, Methanol-d4) δ 7.81 (s, 1H), 7.62-7.54 (m, 3H), 6.89 (d, J=4.6 Hz, 1H), 6.84 (d, J=4.6 Hz, 1H), 5.54 (d, J=5.0 Hz, 1H), 4.70 (d, J=12.9 Hz, 1H), 4.58-4.44 (m, 3H), 4.22-4.08 (m, 2H), 3.96-3.81 (m, 2H), 3.60-3.51 (m, 1H), 1.53-1.16 (m, 36H), 0.94-0.84 (m, 3H). $^{19}$F NMR (376 MHz, Methanol-d4) δ −77.49. $^{31}$P NMR (162 MHz, Methanol-d4) δ 0.09--−0.89 (m). MS m/z [M+1]=831.2

Example 84: Compound 84 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl)oxy)icosyl) hydrogen phosphate

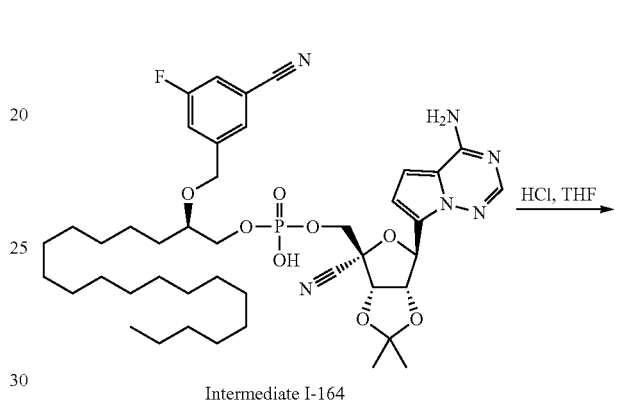

Intermediate I-164

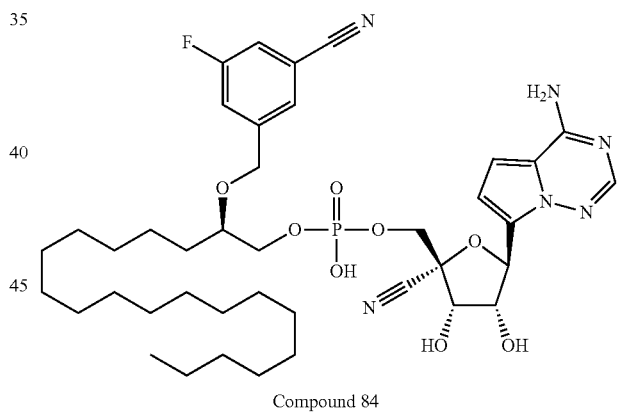

Compound 84

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-((3-cyano-5-fluorobenzyl)oxy)icosyl) hydrogen phosphate, Intermediate I-164 (218 mg, 0.259 mmol, 1.0 equiv) in THF (4.0 mL) was added concentrated HCl (0.50 mL, 12.0 M, 23.1 equiv.). The reaction mixture was stirred at room temperature for 4 h and 30 min prior to concentrating in vacuo and purifying directly by silica gel chromatography (0-40% MeOH in DCM) to afford the title Compound 84 after lyophilization as the HCl salt. $^1$H NMR (400 MHz, Methanol-d4) δ 8.01 (s, 1H), 7.50 (s, 1H), 7.45-7.31 (m, 3H), 7.05 (d, J=4.7 Hz, 1H), 5.53 (d, J=4.9 Hz, 1H), 4.80-4.74 (m, 1H), 4.60 (d, J=13.0 Hz, 1H), 4.51-4.41 (m, 2H), 4.28-4.13 (m, 2H), 4.08-3.89 (m, 2H), 3.69-3.60 (m, 1H), 1.60-1.19 (m, 34H), 0.90 (t, J=6.7 Hz, 3H). ¹⁹F NMR (376 MHz, Methanol-d4) δ −112.83—−112.98 (m). ³¹P NMR (162 MHz, Methanol-d4) δ −0.02—−0.94 (m). MS m/z [M+1]=801.2

Example 85: Compound 85 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-(4-cyano-3-fluorophenoxy)henicosyl) hydrogen phosphate

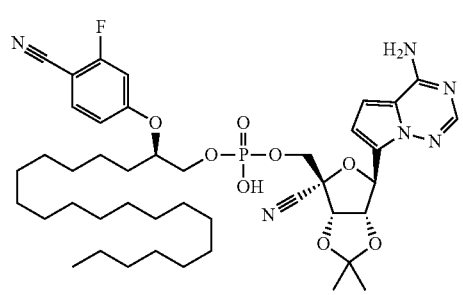

Intermediate I-170

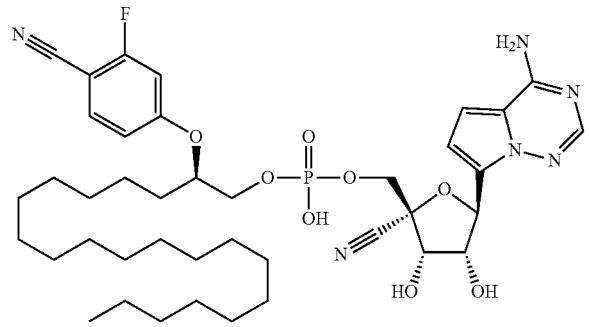

Compound 85

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((R)-2-(4-cyano-3-fluorophenoxy)henicosyl) hydrogen phosphate, Intermediate I-170 (200 mg, 0.238 mmol, 1.0 equiv) in THF (4.0 mL) was added concentrated HCl (0.50 mL, 12.0 M, 25.2 equiv.). The reaction mixture was stirred at room temperature for 5 h and 30 min prior to concentrating in vacuo and purifying directly by silica gel chromatography (0-40% MeOH in DCM) to afford the title Compound 85 after lyophilization as the HCl salt.

¹H NMR (400 MHz, DMSO-d6) δ 8.52-8.10 (m, 2H), 7.93 (s, 1H), 7.77-7.71 (m, 1H), 7.15 (dd, J=12.0, 2.4 Hz, 1H), 7.01 (d, J=4.5 Hz, 1H), 6.95 (dd, J=8.8, 2.4 Hz, 1H), 6.78 (d, J=4.5 Hz, 1H), 5.38 (d, J=5.7 Hz, 1H), 4.73-4.62 (m, 1H), 4.44-4.38 (m, 1H), 4.23 (d, J=5.3 Hz, 1H), 4.16-4.08 (m, 1H), 4.05-3.89 (m, 3H), 1.61-1.48 (m, 2H), 1.39-1.10 (m, 34H), 0.84 (t, J=6.6 Hz, 3H). ¹⁹F NMR (376 MHz, DMSO-d6) δ −106.48—−107.05 (m). ³¹P NMR (162 MHz, DMSO-d6) δ −1.59—−2.32 (m). MS m/z [M+1]=801.3

Example 86: Compound 86 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-((3-cyano-5-fluorobenzyl)oxy)hexadecyl) hydrogen phosphate

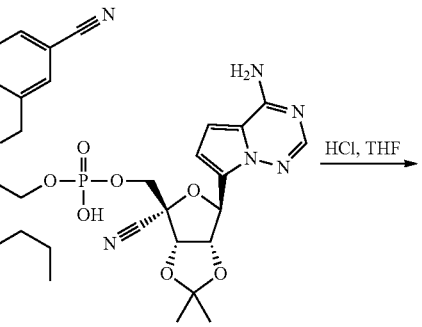

Intermediate I-176

Compound 86

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl)oxy)hexadecyl) hydrogen phosphate, Intermediate I-176 (223 mg, 0.284 mmol, 1.0 equiv) in THF (4.0 mL) was added concentrated HCl (0.50 mL, 12.0 M, 21.1 equiv.). The reaction mixture was stirred at room temperature overnight. The solution was diluted with 4:1 DCM:IPA (100 mL) and water (50 mL). The pH of the aqueous layer was adjusted to around 4 to 4.5 using 20 wt % KOH. The layers were separated. The organic layer was washed with an additional 50 mL of water prior to drying over Na₂SO₄, filtering and concentrating in vacuo. The crude residue was purified by silica gel chromatography (0-40% MeOH in DCM) to afford the title Compound 86. ¹H NMR (400 MHz, Methanol-d4) δ 7.87 (s, 1H), 7.50-7.47 (m, 1H), 7.43-7.37 (m, 1H), 7.37-7.32 (m, 1H), 7.05 (d, J=4.6 Hz, 1H), 6.93 (d, J=4.6 Hz, 1H), 5.53 (d, J=5.2 Hz, 1H), 4.76 (d, J=13.0 Hz, 1H), 4.56-4.45 (m, 3H), 4.23-4.09 (m, 2H), 3.98-3.84 (m, 2H), 3.64-3.55 (m, 1H), 1.56-1.19 (m, 26H), 0.89 (t, J=6.8 Hz, 3H). ¹⁹F NMR (376 MHz, Methanol-d4) δ −112.90—−113.02 (m). ³¹P NMR (162 MHz, Methanol-d4) δ −0.10—−0.58 (m). MS m/z [M+1]=745.2

Example 87: Compound 87 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-((3-chloro-5-cyanobenzyl)oxy)icosyl) hydrogen phosphate

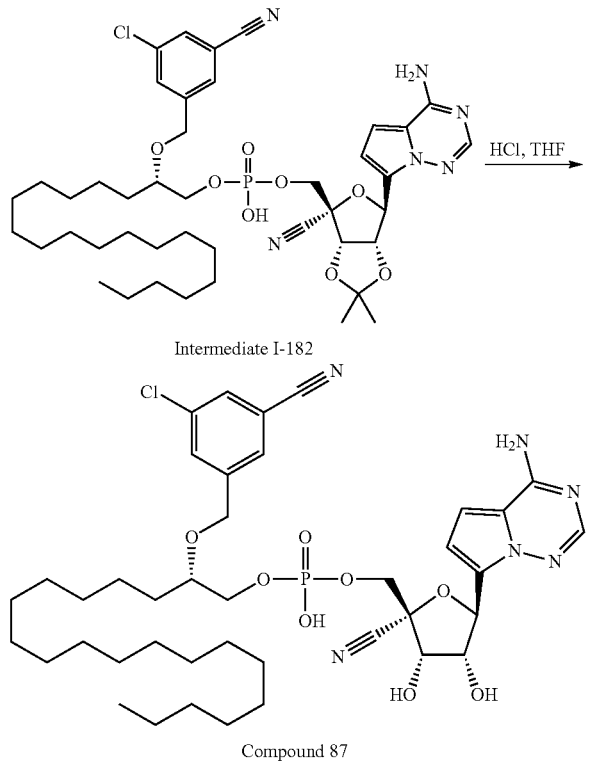

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-((3-chloro-5-cyanobenzyl)oxy)icosyl) hydrogen phosphate, Intermediate I-182 (260 mg, 0.303 mmol, 1.0 equiv) in THF (4.0 mL) was added concentrated HCl (0.50 mL, 12.0 M, 19.8 equiv.). The reaction mixture was stirred at room temperature overnight. The solution was diluted with 4:1 DCM:IPA (100 mL) and water (50 mL). The pH of the aqueous layer was adjusted to around 3 using 20 wt % KOH. The layers were separated. The organic layer was washed with an additional 75 mL of water prior to drying over $Na_2SO_4$, filtering and concentrating in vacuo. The crude residue was purified by silica gel chromatography (0-40% MeOH in DCM) to afford the title Compound 87. $^1$H NMR (400 MHz, Methanol-d4) δ 7.84 (s, 1H), 7.64-7.61 (m, 1H), 7.61-7.57 (m, 2H), 6.97 (d, J=4.6 Hz, 1H), 6.89 (d, J=4.6 Hz, 1H), 5.54 (d, J=5.3 Hz, 1H), 4.73 (d, J=13.0 Hz, 1H), 4.56-4.45 (m, 3H), 4.21-4.07 (m, 2H), 4.00-3.81 (m, 2H), 3.62-3.52 (m, 1H), 1.53-1.17 (m, 34H), 0.94-0.87 (m, 3H). $^{31}$P NMR (162 MHz, Methanol-d4) δ −0.17--0.47 (m). MS m/z [M+1]=817.2

Example 88: Compound 88 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-((3-cyano-5-fluorobenzyl)oxy)-3-(hexadecyloxy)propyl) hydrogen phosphate

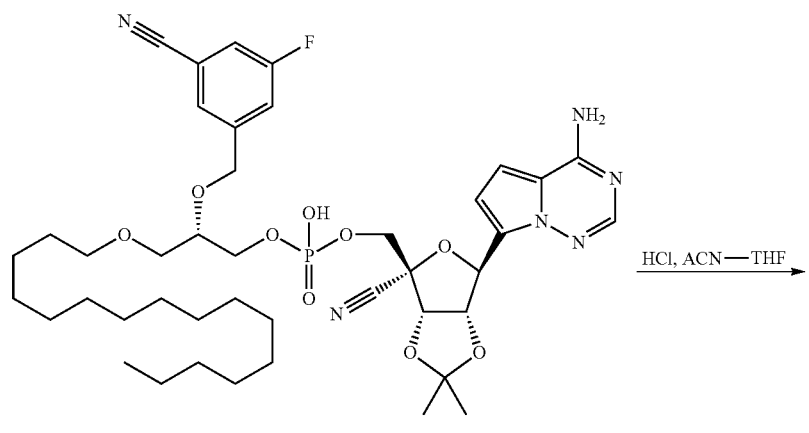

Intermediate I-228

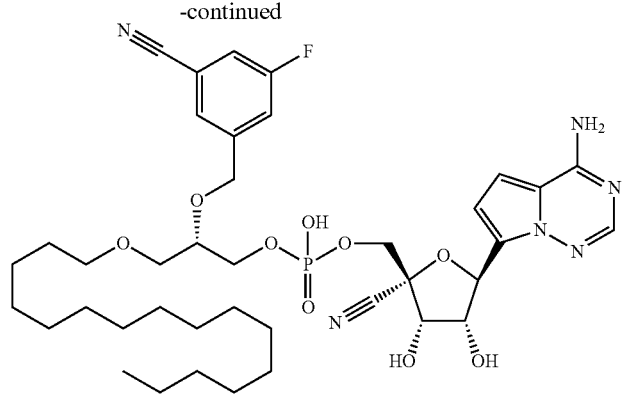

Compound 88

To a solution of Intermediate I-228 (224 mg, 0.266 mmol) in ACN (2 ml)-THF (2 mL) was added 25% HCl (0.4 mL) at rt. The solution was stirred at rt for 15 h, concentrated in vacuo, and purified by silica gel column chromatography (0 to 100% MeOH in DCM) to give Compound 88 (155.4 mg, 70%). $^1$H NMR (400 MHz, Methanol-d4) δ 8.05 (s, 1H), 7.55 (s, 1H), 7.52-7.44 (m, 1H), 7.44-7.31 (m, 2H), 7.06 (d, J=4.7 Hz, 1H), 5.56 (d, J=4.9 Hz, 1H), 4.80 (d, J=13.3 Hz, 1H), 4.73 (d, J=13.2 Hz, 1H), 4.56-4.39 (m, 2H), 4.35-4.18 (m, 2H), 4.19-4.00 (m, 2H), 3.90-3.77 (m, 1H), 3.66 3.53 (m, 2H), 3.53-3.40 (m, 2H), 1.66-1.50 (m, 2H), 1.45-1.20 (m, 26H), 0.91 (t, J=6.7 Hz, 3H). $^{19}$F NMR (376 MHz, Methanol-d4) δ−112.83. $^{31}$P NMR (162 MHz, Methanol-d4) δ−0.90. MS m/z [M+1]=803.4

Example 92: Compound 92 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-(benzyloxy)-3-(hexadecyloxy)propyl) hydrogen phosphate

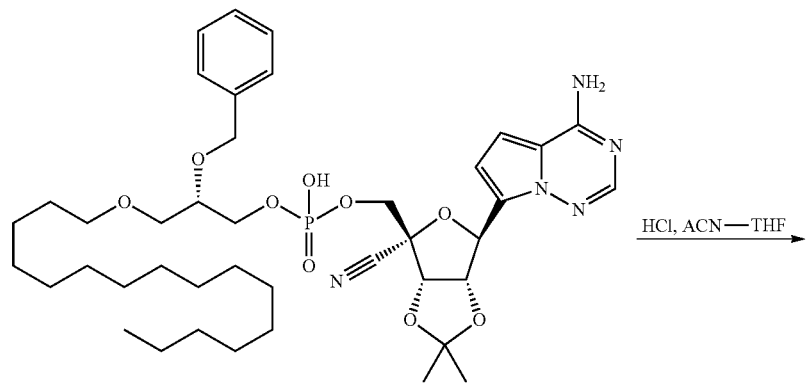

Intermediate I-236

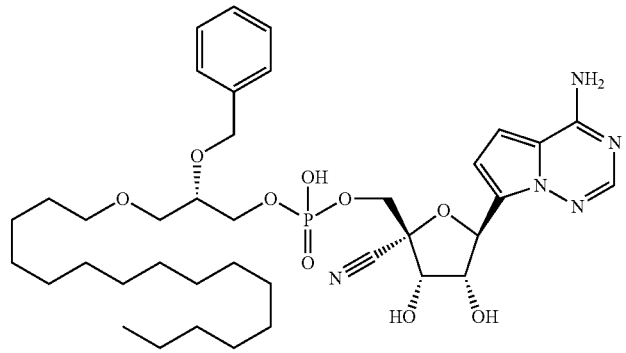

Compound 92

To a solution of Intermediate I-236 (237 mg, 0.296 mmol) in ACN (2 ml)-THF (2 mL) was added 25% HCl (0.4 mL) at rt. The solution was stirred at rt for 6 h, concentrated in vacuo, and purified by silica gel column chromatography (0 to 100% MeOH in DCM) to give Compound 92 (199 mg, 84%). $^1$H NMR (400 MHz, Methanol-d$_4$) δ 7.96 (s, 1H), 7.38-7.20 (m, 6H), 7.07 (d, J=4.8 Hz, 1H), 5.56 (d, J=4.7 Hz, 1H), 4.69 (d, J=11.8 Hz, 1H), 4.62 (d, J=11.8 Hz, 1H), 4.54-4.47 (m, 2H), 4.24 (dd, J=11.1, 5.6 Hz, 1H), 4.17 (dd, J=11.1, 5.2 Hz, 1H), 4.07-3.96 (m, 2H), 3.78 (p, J=5.2 Hz, 1H), 3.58 (dd, J=10.6, 4.2 Hz, 1H), 3.52 (dd, J=10.5, 5.8 Hz, 1H), 3.47-3.38 (m, 2H), 1.60-1.48 (m, 2H), 1.41-1.21 (m, 26H), 0.92 (t, J=6.7 Hz, 3H). $^{31}$P NMR (162 MHz, Methanol-d$_4$) δ −0.36. MS m/z [M+1]=760.3

Example 93: Compound 93 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-(benzyloxy)icosyl) hydrogen phosphate

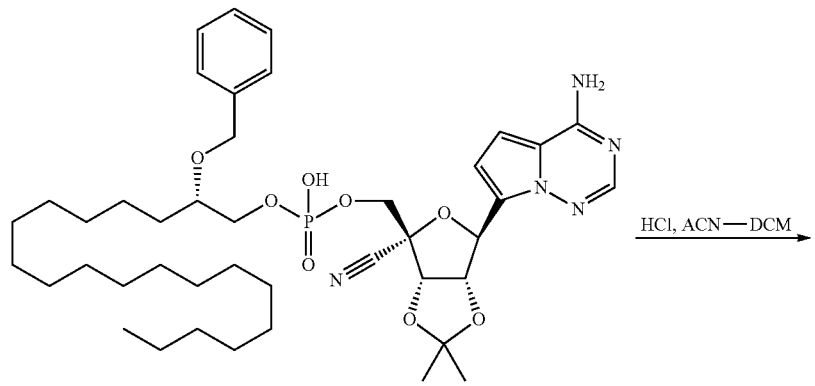

Intermediate I-238

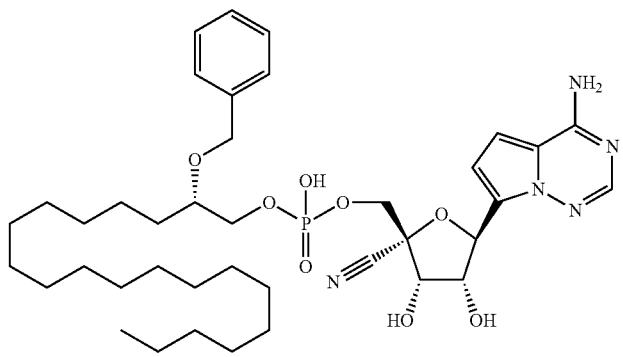

Compound 93

To a solution of Intermediate I-238 (277 mg, 0.347 mmol) in ACN (2 ml)-DCM (2 mL) was added 25% HCl (0.4 mL) at rt. The solution was stirred at rt for 6 h, concentrated in vacuo, and purified by silica gel column chromatography (0 to 100% MeOH in DCM) to give Compound 93 (207.52 mg, 79%). $^1$H NMR (400 MHz, Methanol-d4) δ 8.04 (s, 1H), 7.41 (d, J=4.7 Hz, 1H), 7.38-7.21 (m, 5H), 7.06 (d, J=4.7 Hz, 1H), 5.58 (d, J=5.4 Hz, 1H), 4.66 (d, J=11.6 Hz, 1H), 4.54-4.47 (m, 2H), 4.41 (d, J=5.4 Hz, 1H), 4.36-4.21 (m, 2H), 4.13-4.04 (m, 1H), 4.04-3.93 (m, 1H), 3.69-3.53 (m, 1H), 1.62-1.18 (m, 34H), 0.92 (t, J=6.7 Hz, 3H). $^{31}$P NMR (162 MHz, Methanol-d4) δ −1.25. MS m/z [M+1]=758.3

Example 94: Compound 94 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl)oxy)-2-methyl-3-(octadecyloxy)propyl) hydrogen phosphate

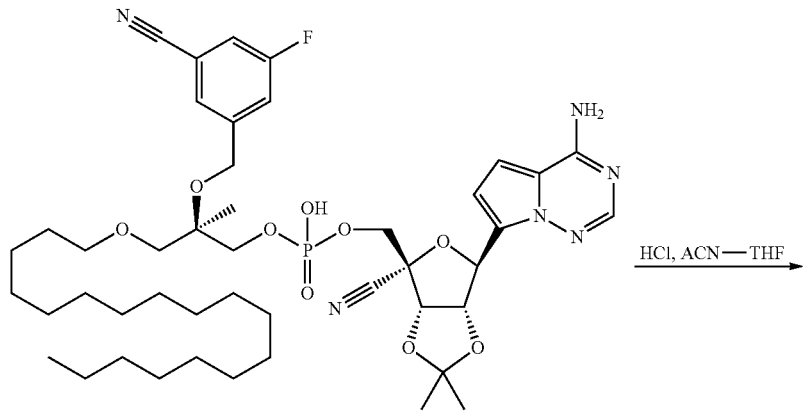

Intermediate I-240

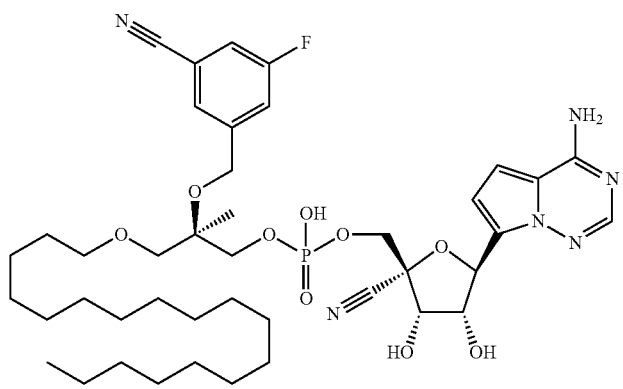

Compound 94

To a solution of Intermediate I-240 (262 mg, 0.296 mmol) in ACN (2 ml)-THF (2 mL) was added 25% HCl (0.4 mL) at rt. The solution was stirred at rt for 15 h, concentrated in vacuo, and purified by silica gel column chromatography (0 to 100% MeOH in DCM) to give Compound 94 (210 mg, 84%). $^{1}$H NMR (400 MHz, Methanol-d4) δ 7.90 (s, 1H), 7.51 (s, 1H), 7.49-7.39 (m, 1H), 7.36-7.29 (m, 1H), 7.07 (d, J=4.6 Hz, 1H), 6.96 (d, J=4.6 Hz, 1H), 5.55 (d, J=5.2 Hz, 1H), 4.65 (s, 2H), 4.58-4.49 (m, 2H), 4.22-4.08 (m, 2H), 4.02-3.86 (m, 2H), 3.53-3.46 (m, 2H), 3.46-3.39 (m, 2H), 1.60-1.47 (m, 2H), 1.40-1.17 (m, 33H), 0.92 (t, J=6.7 Hz, 3H). $^{19}$F NMR (376 MHz, Methanol-d4) δ −113.23. $^{31}$P NMR (162 MHz, Methanol-d4) δ −0.59. MS m/z [M+1]=817.3

Example 96: Compound 96 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-(3-cyano-5-fluorophenoxy)icosyl) hydrogen phosphate

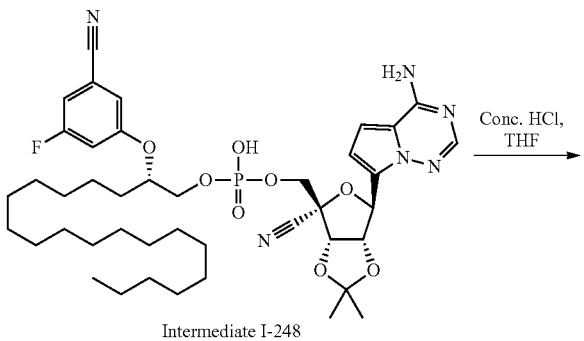

Intermediate I-248

903

-continued

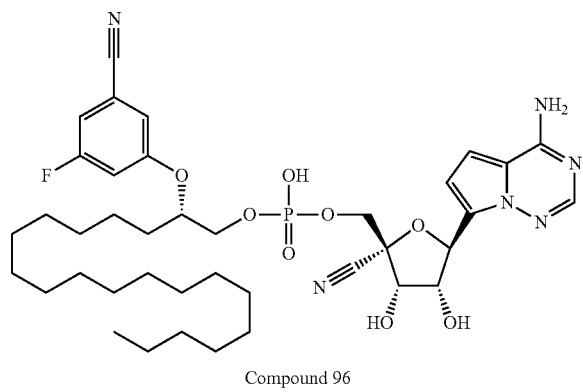

Compound 96

To a solution of Intermediate I-248 (168 mg, 0.203 mmol, 1.0 eq.) in THF (4.0 mL) was added concentrated HCl (0.50 mL, 12.0 M, 58 equiv.). The reaction mixture was stirred at room temperature for 6 h. The solution was diluted with ethyl acetate (50 mL) and neutralized with saturated sodium bicarbonate. The layers were separated. The organic layer was washed with brine, dried over Na$_2$SO$_4$, filtered and concentrated in vacuo. The crude residue was loaded onto silica gel and purified by silica gel chromatography (0-30% MeOH in DCM) to afford the title Compound 96. $^1$H NMR (400 MHz, Methanol-d4) δ 7.83 (s, 1H), 7.16 (d, J=1.6 Hz, 1H), 7.09 (dt, J=10.9, 2.3 Hz, 1H), 7.06-7.00 (m, 1H), 6.88 (d, J=4.5 Hz, 1H), 6.84 (d, J=4.6 Hz, 1H), 5.58 (d, J=5.2 Hz, 1H), 4.63-4.45 (m, 3H), 4.12 (dd, J=6.3, 4.7 Hz, 2H), 3.98 (d, J=6.5 Hz, 2H), 1.67-1.52 (m, 2H), 1.29 (d, J=20.7 Hz, 27H), 0.96-0.89 (m, 4H); $^{31}$P NMR (162 MHz, Methanol-d4) δ−0.73. MS m/z [M+1]=787.3

Example 97: Compound 97 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-((3-cyano-5-fluorobenzyl)oxy)pentadecyl) hydrogen phosphate

904

-continued

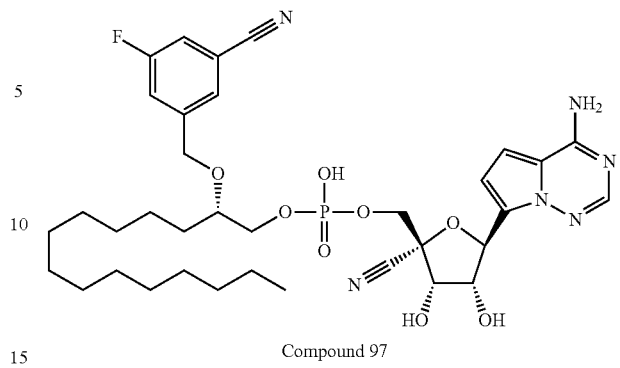

Compound 97

To a solution of Intermediate I-254 (156 mg, 0.203 mmol, 1.0 eq.) in THF (4.0 mL) was added concentrated HCl (0.50 mL, 12.0 M, 58 equiv.). The reaction mixture was stirred at room temperature for 6 h. The solution was diluted with ethyl acetate (50 mL) and neutralized with saturated sodium bicarbonate. The layers were separated. The organic layer was washed with brine, dried over Na$_2$SO$_4$, filtered and concentrated in vacuo. The crude residue was loaded onto silica gel and purified by silica gel chromatography (0-30% MeOH in DCM) to afford the title Compound 97. $^1$H NMR (400 MHz, Methanol-d4) δ 7.98 (s, 1H), 7.52 (d, J=1.4 Hz, 1H), 7.49-7.43 (m, 1H), 7.39 (ddd, J=8.3, 2.6, 1.4 Hz, 1H), 7.24 (d, J=4.7 Hz, 1H), 7.04 (d, J=4.7 Hz, 1H), 5.56 (d, J=5.1 Hz, 1H), 4.81 (d, J=13.1 Hz, 1H), 4.60 (d, J=13.0 Hz, 1H), 4.53-4.43 (m, 2H), 4.32-4.08 (m, 2H), 4.08-3.85 (m, 2H), 3.72-3.59 (m, 1H), 1.54 (dt, J=7.3, 4.7 Hz, 2H), 1.30 (d, J=4.1 Hz, 22H), 0.93 (t, J=6.7 Hz, 3H). $^{31}$P NMR (162 MHz, Methanol-d4) δ−0.45. MS m/z [M+1]=731.3

Example 98: Compound 98 ((2R,3S,4R,5S)-5-(4-aminopyrrolo[2,1-f][1,2,4]triazin-7-yl)-2-cyano-3,4-dihydroxytetrahydrofuran-2-yl)methyl ((S)-2-((3-chloro-5-cyanobenzyl)oxy)-3-(hexadecyloxy)propyl) hydrogen phosphate

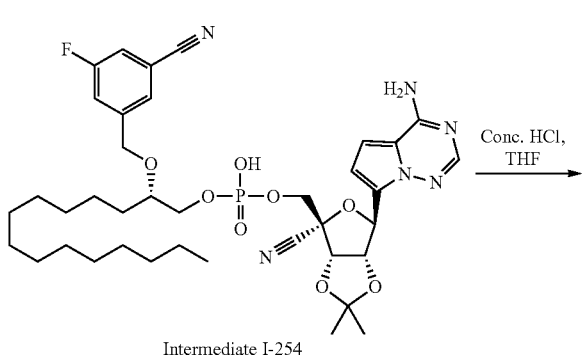

Intermediate I-254

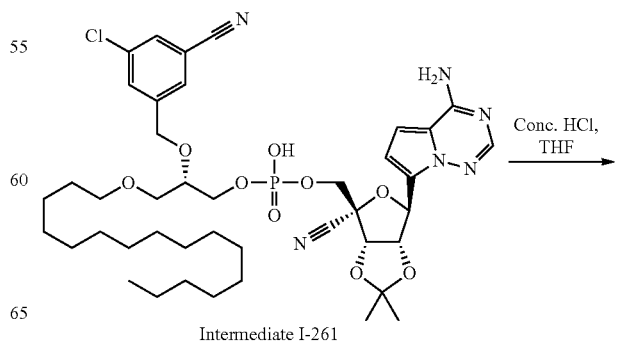

Intermediate I-261

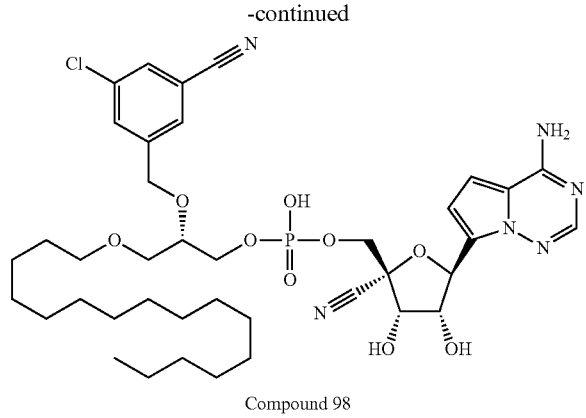

Compound 98

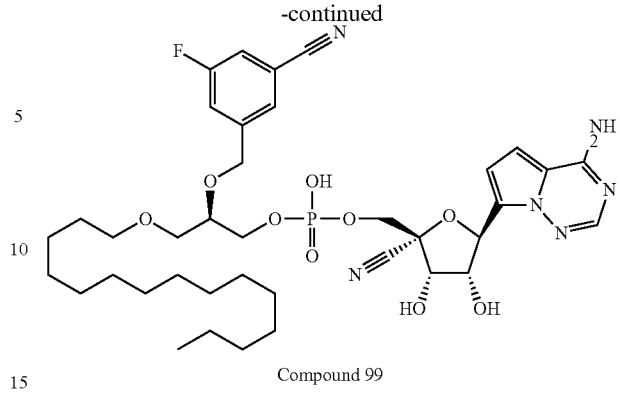

Compound 99

To a solution of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl ((S)-2-((3-cyano-5-fluorobenzyl)oxy)-3-(hexadecyloxy)propyl) hydrogen phosphate Intermediate I-261 (84 mg, 0.103 mmol, 1.0 eq.) in THF (4.0 mL) was added concentrated HCl (0.50 mL, 12.0 M, 58 equiv.). The reaction mixture was stirred at room temperature for 6 h. The solution was diluted with ethyl acetate (50 mL) and neutralized with saturated sodium bicarbonate. The layers were separated. The organic layer was washed with brine dried over $Na_2SO_4$, filtered and concentrated in vacuo. The crude residue was loaded onto silica gel and purified by silica gel chromatography (0-30% MeOH in DCM) to afford the title Compound 98. $^1$H NMR (400 MHz, Methanol-d4) δ 7.91 (s, 1H), 7.71-7.60 (m, 4H), 7.07 (d, J=4.6 Hz, 1H), 6.95 (d, J=4.6 Hz, 1H), 5.56 (d, J=5.2 Hz, 1H), 4.76 (d, J=13.2 Hz, 1H), 4.64 (d, J=13.2 Hz, 1H), 4.56 (t, J=5.3 Hz, 1H), 4.51 (d, J=5.4 Hz, 1H), 4.19 (qd, J=11.0, 5.2 Hz, 2H), 4.00 (hept, J=5.6 Hz, 2H), 3.80 (p, J=5.3 Hz, 1H), 3.53 (q, J=4.2 Hz, 2H), 3.44 (td, J=6.5, 3.0 Hz, 2H), 2.07 (s, 1H), 1.56 (t, J=6.9 Hz, 3H), 1.29 (s, 25H), 0.93 (t, J=6.7 Hz, 3H). $^{31}$P NMR (162 MHz, Methanol-d4) δ −0.65. $^{19}$F NMR (376 MHz, Methanol-d4) δ −77.51. MS m/z [M]=819.3.

Example 99: Compound 99 ((2R,3S,4R,5S)-5-(4-aminopyrrolo[2,1-f][1,2,4]triazin-7-yl)-2-cyano-3,4-dihydroxytetrahydrofuran-2-yl)methyl ((R)-2-((3-cyano-5-fluorobenzyl)oxy)-3-(pentadecyloxy)propyl) hydrogen phosphate

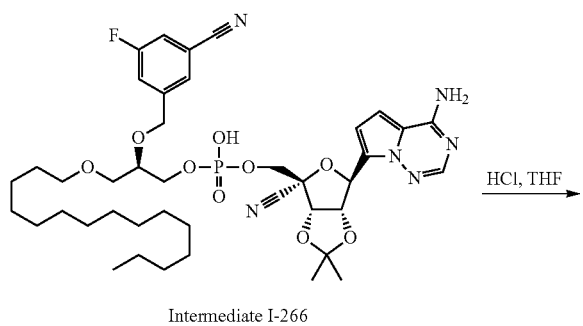

Intermediate I-266 → HCl, THF

To a solution of Intermediate I-266 (200 mg, 0.193 mmol) in THF (5 mL) cooled in an ice bath was added concentrated HCl (0.804 mL). The reaction mixture was warmed to room temperature and stirred for 3 h. The solution was cooled to 0° C., and added few ice pellets, followed by a solution of NaOH (2M in water) drop wise until reach pH ~8. To this solution was added Phosphoric acid (85% in water) to adjust pH ~3. To the solution was added a mixture of Me-THF/EtOAc (3/2, 50 mL). The solution was transferred to a separatory flask, using water (10 mL) to complete transfer. The organic layer was separated and the aqueous layer was extracted once more with a mixture of Me-THF/EtOAc (3/2, 50 mL). The organic fractions were combined and washed once with brine/water (3/2, 50 mL). The organic layer dried over $Na_2SO_4$ and concentrated to afford crude product. The crude product was dissolved in 5% MeOH/DCM, loaded on 24 g gold column and purified by flash column chromatography (3 min 100% Hex, 2 min 100% DCM, 16 min 0-100% MeOH/DCM). The desired product elutes at ~50% MeOH/DCM. Fractions containing pure product were combined and concentrated to afford Compound 99. $^1$H NMR (400 MHz, Methanol-d$_4$) δ 7.81 (s, 1H), 7.53 (s, 1H), 7.45-7.42 (m, 1H), 7.38-7.35 (m, 1H), 6.85 (d, J=4.6 Hz, 1H), 6.83 (d, J=4.6 Hz, 1H), 5.56 (d, J=5.1 Hz, 1H), 4.71 (d, J=13.3 Hz, 1H), 4.62 (d, J=13.4 Hz, 1H), 4.56 (dd, J=17.0, 5.4 Hz, 2H), 4.21-4.11 (m, 2H), 4.01-3.90 (m, 2H), 3.77-3.72 (m, 1H), 3.56-3.45 (m, 2H), 3.45-3.36 (m, 2H), 1.61-1.51 (m, 2H), 1.34-1.27 (m, 24H), 0.92 (t, J=6.8 Hz, 3H). $^{31}$P NMR (162 MHz, Methanol-d$_4$) δ −0.33. MS m/z [M+1]=789.16

D. Biological Examples

Example A. DENV-2 moDC $EC_{50}$

Human monocyte-derived dendritic cells (moDCs) were derived from CD14+ monocytes (AllCells) cultured in Human Mo-DC Differentiation medium containing GM-CSF and IL-4 (Miltenyi Biotec). On day 7, moDCs were harvested by mechanical disruption, washed and suspended in serum-free RPMI. moDCs were infected with Vero-derived Dengue 2, New Guinea strain (NGC) at a MOI=0.1 for two hours in serum-free RPMI with gentle agitation at 37° C. Cells were washed and resuspended in 10% serum-containing RPMI (Gibco, supplemented with sodium pyruvate, NEAA, Penicillin-Streptomycin). 10^5 cells were plated in triplicate in 96-well plates with compounds dispensed at graded doses (Hewlett-Packard D300 Digital Dispenser). All wells were normalized to 0.25% DMSO. At 48 hours, cells were washed with 1×PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example B. moDC $CC_{50}$

Human monocyte-derived dendritic cells (moDCs) were derived from CD14+ monocytes (AllCells) cultured in Human Mo-DC Differentiation medium containing GM-CSF and IL-4 (Miltenyi Biotec). On day 7, moDCs were harvested by mechanical disruption, washed and cultured in triplicate at $1\times10^5$-$5\times10^4$ cells/well in 96-well plates with compounds dispensed at graded doses (Hewlett-Packard D300 Digital Dispenser). All wells were normalized to 0.25% DMSO. After 48 hours, CellTiter Glo (Promega) was added and incubated for 10 minutes at room temp before reading on a luminometer. % viability curves were calculated against no compound and no cell control wells. $CC_{50}$ values were determined using Prism Graphpad software.

Example C. DENV-2 Huh-7 $EC_{50}$

Huh7 (Human hepatocarcinoma 7) cells were maintained in 10% FCS-containing DMEM complete media. On the day of the assay, cells were trypsinized (0.1% Trypsin-EDTA), washed and infected for 2 hours in serum-free DMEM with Dengue serotype 2 New Guinea C (NGC) strain at MOI=0.1 with gentle agitation at 37° C. After 2 hours, cells were washed with serum-free media and suspended in 10% FCS-containing DMEM (Gibco, supplemented with sodium pyruvate, NEAA, Penicillin-Streptomycin). $10^5$ cells were plated in triplicate in 96-well plates with compounds dispensed at graded doses (Hewlett-Packard D300 Digital Dispenser). All wells were normalized to 0.25% DMSO. At 48 hours, cells were washed with 1×PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example D. Huh-7 $CC_{50}$

Human hepatocarcinoma 7 (Huh7) cells were maintained in 10% FCS-containing complete DMEM. On day of assay, cells were trypsinized with 0.1% Trypsin-EDTA, washed and cultured in triplicate at $1$-$2\times10^4$ cells/well in 96-well plates with compounds dispensed at graded doses (Hewlett-Packard D300 Digital Dispenser). All wells were normalized to 0.25% DMSO. After 48 hours, CellTiter Glo (Promega) was added and incubated for 10 minutes at room temp before reading on a luminometer. % viability curves were calculated against no compound and no cell control wells. $CC_{50}$ values were determined using Prism Graphpad software.

Example E. RSV HEp-2 $EC_{50}$

Antiviral activity against RSV is determined using an infectious cytopathic cell protection assay in HEp-2 cells. In this assay, compounds inhibiting viral infection and/or replication produce a cytoprotective effect against the virus-induced cell killing that can be quantified using a cell viability reagent. The techniques used here are novel adaptations of methods described in published literature (Chapman et al., ANTIMICROB AGENTS CHEMOTHER. 2007, 51(9):3346-53).

HEp-2 cells are obtained from ATCC (Manassas, VA) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, MD) is titered before compound testing to determine the appropriate dilution of the virus stock that generates desirable cytopathic effect in HEp-2 cells.

For antiviral tests, HEp-2 cells are grown in large cell culture flasks to near confluency but not fully so. The compounds to be tested are prediluted in DMSO in 384-well compound dilution plates, either in an 8 or 40 sample per plate standardized dose response format. 3-fold serial dilution increments of each test compound are prepared in the plates and test samples are transferred via acoustic transfer apparatus (Echo, Labcyte) at 100 nL per well into cell culture assay 384-well plates. Each compound dilution is transferred in single or quadruplicate samples into dry assay plates, which are stored until assay is ready to go. The positive and negative controls are laid out in opposite on ends of the plate in vertical blocks (1 column).

Subsequently, an infectious mixture is prepared using an appropriate dilution of virus stock previously determined by titration with cells at a density of 50,000/ml and 20 □□L/ well is added to test plates w/compounds via automation (uFlow, Biotek). Each plate includes negative and positive controls (16 replicates each) to create 0% and 100% virus inhibition standards, respectively. Following the infection with RSV, testing plates are incubated for 4 days in a 37° C. cell culture incubator. After the incubation, a cell viability reagent, Cell TiterGlo (Promega, Madison, WI) is added to the assay plates, which are incubated briefly, and a luminescent readout is measured (Envision, Perkin Elmer) in all the assay plates. The RSV-induced cytopathic effect, percentage inhibition, is determined from the levels of remaining cell viability. These numbers are calculated for each tested concentration relative to the 0% and 100% inhibition controls, and the $EC_{50}$ value for each compound is determined by non-linear regression as a concentration inhibiting the RSV-induced cytopathic effect by 50%. Various potent anti-RSV tool compounds are used as positive controls for antiviral activity.

Example F. HEp-2 $CC_{50}$

Cytotoxicity of tested compounds is determined in uninfected HEp-2 cells in parallel with the antiviral activity using the cell viability reagent in a similar fashion as described before for other cell types (Cihlar et al., ANTIMICROB AGENTS CHEMOTHER. 2008, 52(2):655-65). The same protocol as for the determination of antiviral activity is used for the measurement of compound cytotoxicity except that the cells are not infected with RSV. Instead, an uninfected cell mixture at the same density is added at 20 ul/well to plates containing prediluted compounds, also at 100 nL/sample. Assay plates are then incubated for 4 days followed by a cell viability test using the same CellTiter Glo reagent addition and measurement of luminescent readouts. Untreated cell and cells treated at 2 µM puromycin (Sigma, St. Louis, MO) serve as 100% and 0% cell viability control, respectively. The percent of cell viability is calculated for each tested compound concentration relative to the 0% and 100% controls and the $CC_{50}$ value is determined by non-linear regression as a compound concentration reducing the cell viability by 50%.

Example G. HEp-2 and MT4 $CC_{50}$

Cytotoxicity of the compounds was determined in uninfected cells using the cell viability reagent in a similar fashion as described before for other cell types (Cihlar et al., ANTIMICROB AGENTS CHEMOTHER. 2008, 52(2):655-65). HEp-2 (1.5×103 cells/well) and MT-4 (2×103 cells/well) cells were plated in 384-well plates and incubated with the appropriate medium containing 3-fold serially diluted compound ranging from 15 nM to 100,000 nM. Cells were cultured for 4-5 days at 37° C. Following the incubation, the cells were allowed to equilibrate to 25° C., and cell viability was determined by adding Cell-Titer Glo viability reagent. The mixture was incubated for 10 min, and the luminescence signal was quantified using an Envision plate reader. Untreated cell and cells treated at 2 μM puromycin (Sigma, St. Louis, MO) serve as 100% and 0% cell viability control, respectively. The percent of cell viability was calculated for each tested compound concentration relative to the 0% and 100% controls and the $CC_{50}$ value was determined by non-linear regression as a compound concentration reducing the cell viability by 50%.

Example H. RSV NHBE $EC_{50}$

Normal human bronchial epithelial (NHBE) cells were purchased from Lonza (Walkersville, MD, Cat #CC-2540) and cultured in Bronchial Epithelial Growth Media (BEGM) (Lonza, Walkersville, MD, Cat #CC-3170). The cells were passaged 1-2 times per week to maintain <80% confluency. The NHBE cells were discarded after 6 passages in culture.

To conduct the RSV A2 antiviral assay, NHBE cells were plated in 96-well plates at a density of 7,500 cells per well in BEGM and allowed to attach overnight at 37° C. Following attachment, 100 μL of cell culture media was removed and 3-fold serially diluted compound was added using a Hewlett-Packard D300 Digital Dispenser. The final concentration of DMSO was normalized to 0.05%. Following compound addition, the NHBE cells were infected by the addition of 100 μL of RSV A2 at a titer of $1\times10^{4.5}$ tissue culture infectious doses/mL in BEGM and then incubated at 37° C. for 4 days. The NHBE cells were then allowed to equilibrate to 25° C. and cell viability was determined by removing 100 μL of culture medium and adding 100 μL of Cell-Titer Glo viability reagent. The mixtures were incubated for 10 minutes at 25° C., and the luminescence signal was quantified on an Envision luminescence plate reader.

Example I. RSV NHBE FLuc $EC_{50}$

Normal human bronchial epithelial (NHBE) cells are purchased from Lonza (Walkersville, MD Cat #CC-2540) and maintained in Bronchial Epithelial Cell Growth Medium (BEGM) (Lonza, Walkersville, MD, Cat #CC-3170) with all provided supplements in the BulletKit. Cells are passaged 2-3 times per week to maintain sub-confluent densities and are used for experiments at passages 2-4.

Recombinant Respiratory Syncytial virus strain A2 containing the firefly luciferase reporter between the P and M genes (RSV-Fluc, $6.3\times10^6$ $TCID_{50}$/mL) is purchased from Viratree (Durham, NC, Cat #R145).

NHBE cells ($5\times10^3$/well) are seeded in 100 μL white wall/clear bottom 96-well plates (Corning) with culture medium and are incubated for 24 hours at 37° C. with 5% $CO_2$. On the following day, three-fold serial dilutions of compounds prepared in DMSO are added to the wells using the HP D300e digital dispenser with normalization to the highest concentration of DMSO in all wells. The cells are then infected with RSV-Fluc diluted with BEGM media at an MOI of 0.1 for a final volume of 200 μL media/well. Uninfected and untreated wells are included as controls to determine compound efficacy against RSV-Fluc. Following incubation with compound and virus for three days at 37° C. with 5% $CO_2$, 100 μL of culture supernatant is removed from each well and replaced with 100 μL of ONE-Glo luciferase reagent (Promega, Madison, WI, Cat #E6110). The plates are gently mixed by rocking for 10 minutes at 21° C. and luminescence signal is measured using an Envision plate reader (PerkinElmer). Values are normalized to the uninfected and infected DMSO controls (0% and 100% infection, respectively). Non-linear regression analysis is applied to determine the compound concentration at which 50% luminescence signal is reduced ($EC_{50}$) using the XLfit4 add-in for MICROSOFT® EXCEL®. All experiments are performed in duplicate with two technical repeats each.

Example J. RSV NHBE $CC_{50}$

NHBE cells were seeded in black 384-TC-treated plates (Corning) at $2\times10^3$ cells/well in a final volume of 20 μL BEBM+supplements (Lonza). The next day, add 0.1 μL of compound was added to the assay plates using an Echo acoustic dispenser. Plates were incubated for 3 additional days at 37° C. and 5% $CO_2$. On day 3 of treatment, 20 μL of CellTiter Glo (Promega) was added to each well using a Biotek dispenser. After a 10-minute incubation, luminescence signal was measured with 0.1 sec integration time using an EnVision (Perkin-Elmer) plate reader. Values were normalized to the DMSO- and puromycin-treated controls (0% and 100% cell death, respectively). Data was fit using non-linear regression analysis and $CC_{50}$ values were then determined as the concentration reducing the luciferase signal by 50%. The compiled data was generated based on least two independent experimental replicates, each containing technical quadruplicates for each concentration.

Example K. RSV HAE $EC_{50}$

HAE cells are cultured at the air-liquid interface and have an apical side that is exposed to the air and a basal side that is in contact with the medium. Prior to experimentation, HAE were removed from their agar-based shipping packaging and were acclimated to 37° C./5% $CO_2$ overnight in 1 ml of HAE Assay medium (AIR-100-MM, Mattek Corp). HAE were prepared for infection by washing the apical surface twice with 400 μL of PBS (either utilizing direct pipetting methods or by running each transwell through a trough containing PBS) to remove the mucus layer. Apical chambers were drained of PBS and tapped gently onto absorbent material to remove as much PBS as possible. After washing, the cells were transferred to fresh HAE maintenance media containing 4-fold serially diluted compound, delivered to the basal side of the cell monolayer, and apically infected with 100 μL of a 1:600 dilution of RSV A strain A2 1000× stock (ABI, Columbia, MD, cat #10-124-000) in HAE assay medium for 3 hours at 37° C. in 5% $CO_2$. The virus inoculum was removed and the apical surface of the cells was washed 3 times with PBS using either method previously described. The cells were then cultured in the presence of compound for 3 days at 37° C. Following the incubation, total RNA was extracted from the HAE cells using a MagMAX-96 Viral RNA isolation kit (Applied Biosystems, Foster City, CA, Cat #AM1836) and intracellular RSV RNA was quantified by real-time PCR. Approximately 25 ng of purified RNA was added to a PCR reaction mixture that contained 0.9 µM RSV N Forward and RSV N Reverse primers, 0.2 µM RSV N Probe and 1× Taqman RNA-to-Ct 1-Step Kit (Applied Biosystems, Foster City, CA, Cat #4392938). RNA levels were normalized using a Taqman GAPDH control primer set (Applied Biosystems, Foster City, CA, Cat #402869). Real-Time PCR Primers and Probe Used in the RSV A2 HAE Antiviral Assay:

```
RSV N Forward
                                   (SEQ ID NO: 1)
CATCCAGCAAATACACCATCCA, RSV N Reverse
                                   (SEQ ID NO: 2)
TTCTGCACATCATAATTAGGAGTATCAA, RSV N Probe
                                   (SEQ ID NO: 3)
FAM-CGGAGCACAGGAGAT-BHQ.
```

Example L. HRV16 HELA $EC_{50}$

H1-HeLa cells, cultured in complete DMEM medium containing 10% heat-inactivated FBS and 1% Penicillin/Streptomycin, were seeded in 96 well plates at 3000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and the appropriate dilution of virus stock, previously determined by titration and prepared in cell culture media, was added to test plates containing cells and serially diluted compounds. Each plate included 6 wells of infected untreated cells and 6 wells of uninfected cells that served as 0% and 100% virus inhibition control, respectively. Following the infection, test plates were incubated for 96 h in a tissue culture incubator set to 33° C./5% $CO_2$. Following incubation, the H1-HeLa cells were removed from incubation and allowed to equilibrate to 25° C. Cell viability was determined by removing 100 µL of culture medium and adding 100 µL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example M. HRV1A HELA $EC_{50}$

H1-HeLa cells, cultured in complete RPMI 1640 medium containing 10% heat-inactivated FBS and 1% Penicillin/Streptomycin, were seeded in 96 well plates at 5000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and 100 µL of 1/4000 dilution of HRV1a virus stock was added to each well containing cells and serially diluted compounds. Each plate included 6 wells of infected untreated cells and 6 wells of cells containing 5 µM Rupintrivir that served as 0% and 100% virus inhibition control, respectively. Following the infection, test plates were incubated for 96 h in a tissue culture incubator set to 37° C./5% $CO_2$. Following incubation, the H1-HeLa cells were removed from incubation and allowed to equilibrate to 25° C. Cell viability was determined by removing 100 µL of culture medium and adding 100 µL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example N. HRV14 HELA $EC_{50}$

H1-HeLa cells, cultured in complete RPMI 1640 medium containing 10% heat-inactivated FBS and 1% Penicillin/Streptomycin, were seeded in 96 well plates at 5000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and 100 µL of 1/4000 dilution of HRV14 virus stock was added to each well containing cells and serially diluted compounds. Each plate included 6 wells of infected untreated cells and 6 wells of cells containing 5 µM Rupintrivir that served as 0% and 100% virus inhibition control, respectively. Following the infection, test plates were incubated for 96 h in a tissue culture incubator set to 37° C./5% $CO_2$. Following incubation, the H1-HeLa cells were removed from incubation and allowed to equilibrate to 25° C. Cell viability was determined by removing 100 µL of culture medium and adding 100 µL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example O. HRVc15 and HRVc25 $EC_{50}$

First, HRV replicon RNA is prepared. 5 ug of DNA Template (HRVc15 or HRVc25) is linearized with 2 µL of MluI enzyme in NEB buffer-3 in a final volume of 25 µL for 3 hours at 37° C. Following incubation, linearized DNA is purified on a PCR purification column and the following in vitro transcription is performed using the following conditions: 10 µL of RiboMAX Express T7 2× buffer, 1-8 µL of linear DNA template (1 µg), 0-7 µL nuclease free water, 2 µL enzyme mix T7 express. The final volume of 20 µL is mixed and incubated at 37° C. for 30 min. Following incubation, 1 µL of RQ1 RNase free DNase is added and the mixture is incubated at 37° C. for 15 min. The resulting RNA is then purified with the MegaClear Kit (Gibco Life Technologies cat #11835-030) and is eluted two times with 50 µL of elution buffer at 95° C. H1-HeLa cells cultured in complete RPMI 1640 media containing 10% heat-inactivated FBS and 1% Penicillin/Streptomycin are seeded into T-225 flasks at a concentration of 2E6 cells/flask a day prior to transfection and are incubated at 37° C./5% $CO_2$ overnight. On the day of transfection, cells are trypsinized following standard cell culture protocols and are washed two times with PBS. Following washes, cells are resuspended at a concentration of 1E7 cells/mL in PBS and the suspension is stored on wet ice. Electroporation is used to introduce replicon RNA into the H1-HeLa cells. A final volume of 10 µL containing 10 µg of replicon c15 or 1 µg of c25 replicon RNA, respectively, are pipetted into a 4 mm electroporation cuvette. The H1-HeLa cell stock is mixed by gently swirling and 0.5 mL of the cell stock previously prepared is transferred into the cuvette containing the replicon RNA. The combined solution is flicked to mix. Following mixing, cells are immediately electroporated using the following settings: 900V, 25 uF, infinite resistance, 1 pulse. Cuvettes are rested on ice for 10 min. Following the 10 min incubation, add 19 mL of ambient temperature, phenol red-free and antiobiotic-free RPMI 1640 containing 10% heat-inactivated FBS per electroporation. 150 µL (4E4 cells) of the electroporated cell suspension are seeded per well into a 96 well clear-bottom, white cell culture plate, and are incubated at 25° C. for 30 min. Compounds were added directly to the cell cultures in serial 3-fold dilutions using the HP300 digital dispenser (Hewlett Packard, Palo Alto, CA) and were tested in triplicate. Following the addition of compounds, plates are incubated at 33° C. for 48 hrs. Replicon activity is then measured by a Renilla-Glo Luciferase Assay system. Prior to signal quantification, plates are removed from incubators and are allowed to equilibrate to 25° C. after 50 uL is removed from each well. Following manufacturer's protocol, a 1:100 dilution of Renilla-Glo substrate to buffer is prepared and 100 uL of the Renill-Glo luciferase mix is added to each well. Plates are then incubated for 20 min at 25° C. under gentle agitation and luciferase signal are determined with a 0.1 second detection setting using an EnVision luciferase quantification reader. The percentage inhibition of replicon inhibition was calculated for each tested concentration relative to the 0% and 100% inhibition controls included in the experiments and the $EC_{50}$ value for each compound was determined by 4-parametric non-linear regression as the effective concentration of compound that inhibited luciferase signal by 50%.

Example P. DENV-2 Huh-7 Rep $EC_{50}$

In 384 well plates (Greiner, Cat #781091), compounds were acoustically transferred at 200 nl per well in a 8 compound (4 replicates) or 40 compound dose response format (3 replicates). For all plates tested, Balapiravir, GS-5734 and NITD008 were included as positive inhibition controls alongside 0% inhibition, DMSO-only negative control wells. Following compound addition, Huh-7 cells containing the DENV2 replicon construct were harvested following standard cell culture procedures and were adjusted to a concentration of 1.25E5 cells/mL in cell culture media composed of cDMEM without genticin. 40 µL of the cell stock was then added to each well for a final cell density of 5,000 cells/well. Cell and compound mixtures were incubated at 37° C./5% $CO_2$ for 48 hours. Prior to harvesting cells, EnduRen Live Cell Substrate (Promega, Cat #E6481) was prepared by suspending 3.4 mg into 100 uL of DMSO to generate a 60 mM stock solution. The stock solution was then diluted 1:200 in pre-warmed cDMEM and 10 uL of this diluted solution was added to each well of the 384 well plates. Plates were then centrifuged at 500 rpm briefly and were placed on a plate shaker for 2 min. Following mixing, plates were incubated at 7° C./5% $CO_2$ for 1.5 hours prior to measuring luminescence on an Envision luminometer. The percentage inhibition of replicon signal was calculated for each tested concentration relative to the 0% and 100% inhibition controls and the $EC_{50}$ value for each compound was determined by 4-parametric non-linear regression as the effective concentration of compound that inhibited replicon signal by 50%.

Example 0. HCV Rep 1B and 2A $EC_{50}$

Compounds were serially diluted in ten steps of 1:3 dilutions in 384-well plates. All serial dilutions were performed in four replicates per compound within the same 384-well plate. An HCV protease inhibitor ITMN-191 at 100 µM was added as a control of 100% inhibition of HCV replication while puromycin at 10 mM was included as a control of 100% cytotoxicity. To each well of a black polystyrene 384-well plate (Greiner Bio-one, Monroe, NC), 90 µL of cell culture medium (without Geneticin) containing 2000 suspended HCV replicon cells was added with a Biotek µFlow workstation. For compound transfer into cell culture plates, 0.4 µL of compound solution from the compound serial dilution plate was transferred to the cell culture plate on a Biomek FX workstation. The DMSO concentration in the final assay wells was 0.44%. The plates were incubated for 3 days at 37° C. with 5% $CO_2$ and 85% humidity. The HCV replicon assay was a multiplex assay, able to assess both cytotoxicity and antireplicon activity from the same well. The $CC_{50}$ assay was performed first. The media in the 384-well cell culture plate was aspirated, and the wells were washed four times with 100 µL of PBS each, using a Biotek ELX405 plate washer. A volume of 50 µL of a solution containing 400 nM calcein AM (Anaspec, Fremont, CA) in 1×PBS was added to each well of the plate with a Biotek µFlow workstation. The plate was incubated for 30 min at room temperature before the fluorescence signal (excitation 490 nm, emission 520 nm) was measured with a Perkin-Elmer Envision plate reader. The $EC_{50}$ assay was performed in the same wells as the $CC_{50}$ assay. The calcein-PBS solution in the 384-well cell culture plate was aspirated with a Biotek ELX405 plate washer. A volume of 20 µL of Dual-Glo luciferase buffer (Promega, Madison, WI) was added to each well of the plate with a Biotek µFlow Workstation. The plate was incubated for 10 min at room temperature. A volume of 20 µL of a solution containing a 1:100 mixture of Dual-Glo Stop & Glo substrate (Promega, Madison, WI) and Dual-Glo Stop & Glo buffer (Promega, Madison, WI) was added to each well of the plate with a Biotek µFlow Workstation. The plate was then incubated at room temperature for 10 min before the luminescence signal was measured with a Perkin-Elmer Envision Plate Reader.

Example R. HEp-2 RSV-Lucy 384-well Assay
(EC50 RSVFLUC Hep2-384)

HEp-2 cell line was purchased from ATCC (Manassas, VA Cat #CCL-23) and maintained in Dulbecco's Minimum Essential Medium (DMEM) (Corning, New York, NY, Cat

15-018CM) supplemented with 10% fetal bovine serum (FBS) (Hyclone, Logan, UT, Cat #SH30071-03) and 1× Penicillin-Streptomycin-L-Glutamine (Corning, New York, NY, Cat #30-009-CI). Cells were passaged 2 times per week to maintain sub-confluent densities and were used for experiments at passage 5-20. Respiratory syncytial virus recombinant with luciferase (RSV-Luc5) direct pelleted virus ($\geq 1 \times 10^7$ TCID50/ml) was purchased from Microbiologics (Saint Cloud, MN). Viral replication was determined in HEp-2 cells in the following manner.

Compounds are prepared in 384-well polypropylene plates (Greiner, Monroe, NC, Cat #784201) with 8 compounds per plate in grouped replicates of 4 at 10 serially diluted concentrations (1:3).

HEp-2 cells were suspended in DMEM (supplemented with 10% FBS and 1× Penicillin-Streptomycin-L-Glutamine) and 60 uL of 4,000 cells per well were seeded into 384-well plates (Greiner, Monroe, NC, Cat #781080) using Biotek MultiFlo dispenser. After overnight incubation at 37° C. and 5% $CO_2$, 0.4 uL of three-fold serial dilutions of compound was added to each well using a Biomek FX pipette station. RSV-Lucy viruses were diluted in DMEM (supplemented with 10% FBS and 1× Penicillin-Streptomycin-L-Glutaninine) at an MOI=0.5. Virus suspension was added to each 384-well compound plate at 20 uL per well using a Biotek MultiFlo dispenser. The assay plates were incubated for 3 days at 37° C. and 5% $CO_2$. At the end of incubation, One-Glo reagent (Promega, Madison, WI, Cat #E6120) was prepared. The assay plate and the reagent were equilibrated to room temperature for 30 minutes. 50 uL per well of medium was removed from assay plate and 40 uL per well of One-Glo reagent was added to each plate by Biomek FX. The plates were sat at room temp for 15 minutes. Viral replication was then assessed by measuring luminescence signal using and Envision plate reader. Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was then determined as the concentration reducing the viral replication by 50%.

Example S. HEp-2 and MT4 $CC_{50}$

Cytotoxicity of the compounds was determined in uninfected cells using the cell viability reagent in a similar fashion as described before for other cell types (Cihlar et al., ANTIMICROB AGENTS CHEMOTHER. 2008, 52(2):655-65). HEp-2 (1.5×10³ cells/well) and MT-4 (2×10³ cells/well) cells were plated in 384-well plates and incubated with the appropriate medium containing 3-fold serially diluted compound ranging from 15 nM to 100,000 nM. Cells were cultured for 4-5 days at 37° C. Following the incubation, the cells were allowed to equilibrate to 25° C., and cell viability was determined by adding Cell-Titer Glo viability reagent. The mixture was incubated for 10 min, and the luminescence signal was quantified using an Envision plate reader. Untreated cell and cells treated at 2 μM puromycin (Sigma, St. Louis, MO) serve as 100% and 0% cell viability control, respectively. The percent of cell viability was calculated for each tested compound concentration relative to the 0% and 100% controls and the $CC_{50}$ value was determined by non-linear regression as a compound concentration reducing the cell viability by 50%.

Example T. H1-Hela anti-HRV Assay

Both H1-HeLa cells and human rhinovirus 16 (HRV-16) are purchased from ATCC.

H1-HeLa maintenance media is composed of DMEM supplemented with 10% FBS and 1% Penn/Strep. Virus infection medium (VIM) is composed of DMEM+2% FBS.

H1-HeLa cells are seeded into 96-well black/clear bottom plates with 5,000 cells/well in 100 μL/well in H1-HeLa maintenance medium and incubated for 24 hours at 37° C. and 5% $CO_2$. On the following day medium is aspirated and replaced with 100 μL VIM, next three-fold serial dilutions of compounds prepared in DMSO are added to the wells using the HP D300e digital dispenser with normalization to the highest concentration of DMSO in all wells. HRV-16 is diluted with the VIM to an MOI=0.05 and added to the cells in 100 μL/well. On each plate, uninfected and infected DMSO controls are included to determine compound efficacy against HRV. When extensive cytopathic effect is observed in the positive control (usually 3-6 days post infection) following the incubation at 37° C. and 5% $CO_2$, the culture plates are cooled to room temperature. The culture medium is removed and 200 μL of CellTiter Glo (1:2 dilution in PBS) is added to each well. The plates are agitated for 10 minutes on a shaker at room temperature and luminescence signal is measured using an EnVision plate reader (PerkinElmer). Values are normalized to the uninfected and infected DMSO controls (0% and 100% infection, respectively). Non-linear regression analysis is applied to determine the compound concentration at which 50% luminescence signal is reduced ($EC_{50}$) using the XLfit4 add-in for MICROSOFT® EXCEL®. All experiments are performed in duplicate with two technical repeats.

Example U. NHBE RSV-Luc5 384-well Assay (EC50 RSVFLUC NHBE-384)

Normal Human Bronchial Epithelial (NHBE) cells were purchased from Lonza (Walkersville, MD Cat #CC2540) and maintained in BEGM Bronchial Epithelial Cell Growth Medium BulletKit (Lonza CC-3170).

Cells were thawed, expanded, and were used for experiments at passage 2. Respiratory syncytial virus recombinant with luciferase (RSV-Luc5) ($\geq 1 \times 10^7$ Infectious Units/ml (IU/ml) determined by $TCID_{50}$) was purchased from Microbiologics (Saint Cloud, MN). Viral replication was determined in NHBE cells in the following manner.

Compounds are prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner, Monroe, NC, Cat #781091) at 200 nL per well. NHBE cells were harvested and suspended in BEGM Bronchial Epithelial Cell Growth Medium BulletKit and seeded to the pre-spotted assay plates at 5,000 cells per well in 30 μL. RSV-Luc5 virus was diluted in BEGM Bronchial Epithelial Cell Growth Medium BulletKit at 500,000 Infectious Units (IU) per mL and 10 μL per well was added to the assay plates containing cells and compounds, for an MOI of 1. The assay plates were incubated for 3 days at 37° C. and 5% $CO_2$. At the end of incubation, One-Glo reagent (Promega, Madison, WI, Cat #E6120) was prepared. The assay plates and One-Glo reagent were equilibrated to room temperature for at least 15 minutes. 400 μL per well of One-Glo reagent was added and the plates were incubated at room temperature for 15 minutes before reading the luminescence signal on an EnVision multimode plate reader (Perkin Elmer, Waltham, MA). Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was defined as the concentration reducing the viral replication by 50%.

Example V: HEp-2 RSV-Luc5 384-well Assay (EC50 RSVFLUC Hep2-384 v2

HEp-2 cell line was purchased from ATCC (Manassas, VA Cat #CCL-23) and maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03) and 1× Penicillin-Streptomycin-L-Glutamine (Corning, New York, NY, Cat #30-009-CI). Cells were passaged 2 times per week to maintain sub-confluent densities and were used for experiments at passage 5-20. Respiratory syncytial virus recombinant with luciferase (RSV-Luc5) (≥1×107 TCID50/ml) was purchased from Microbiologics (Saint Cloud, MN). Viral replication was determined in HEp-2 cells in the following manner.

Compounds are prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner, Monroe, NC, Cat #781091) at 200 nL per well. HEp-2 cells were harvested and suspended in DMEM (supplemented with 10% FBS and 1× Penicillin-Streptomycin-L-Glittamine) and seeded to the pre-spotted assay plates at 4,000 cells per well in 30 µL. RSV-Luc5 viruses were diluted in DMEM (supplemented with 10% FBS and 1× Penicillin-Streptomycin-L-Glutamine) at 200,000 Infectious Units (IU) per mL and 10 µL per well was added to the assay plates containing cells and compounds, for an MOI=0.5. The assay plates were incubated for 3 days at 37° C. and 5% $CO_2$. At the end of incubation, One-Glo reagent (Promega, Madison, WI, Cat #E6120) was prepared. The assay plates and One-Glo reagent were equilibrated to room temperature for at least 15 minutes. 40 µL per well of One-Glo reagent was added and the plates were incubated at room temp for 15 minutes before reading the luminescence signal on an EnVision multimode plate reader (Perkin Elmer, Waltham, MA). Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was then determined as the concentration reducing the viral replication by 50%.

Example W: Dengue Virus-2 Huh-7 $EC_{50}$

Huh7 hepatoblastoma cells were seeded onto 96-well plates and incubated at 37° C. with 5% $CO_2$ overnight. The plates were seeded at a cell concentration that will yield >70% confluent monolayers in each well after overnight incubation. Eight 3-fold serial dilutions of compounds were diluted in test media (MEM supplemented with 2% FBS and 50 µg/mL gentamicin). The highest test compound concentration was 50 µg/mL. 100 µL of each concentration was added to 5 test wells on the 96-well plate. Of these 5 test wells, 3 wells of each dilution were infected with dengue virus type 2, diluted in test media (approximately 2000 $CCID_{50}$ per well for an MOI of 0.07). Test medium (100 µL) with no virus was added to 2 wells to represent the uninfected cytotoxicity controls. Six additional infected wells received 100 µL media alone as untreated virus controls. Further, 100 µL of media alone was added to 6 uninfected wells to serve as uninfected, untreated controls. Cultures were incubated at 37° C.+5% $CO_2$ until >80% CPE is observed. After cytopathic effect (CPE) is observed microscopically, 0.011% neutral red dye was added for approximately 2 hours. The neutral red dye was removed and wells were rinsed once with PBS to remove residual, unincorporated dye. A 50:50 Sorensen citrate buffer/ethanol solution was added and incubated at room temperature for >30 minutes with agitation, followed by measurement of neutral red dye using a spectrophotometer at 540 nm. The resulting optical density measurement was converted to percent signal of the infected, untreated cell control normalizing to virus controls. $EC_{50}$ and $CC_{50}$ values were determined by linear regression analysis.

Example X: hMPV H1-Hela $EC_{50}$

The human metapneumoavirus (hMPV) anti-viral assay is an anti-nucleoprotein ELISA performed in infected H1-HeLa cells. H1-HeLa cells were maintained in Dulbecco's Modified Eagle's Medium with high glucose (Gibco, Cat #: 11995073) supplemented with 10% FBS (HyClone, Cat #: SH303396.03), 100 units/mL penicillin and 100 µg/mL streptomycin (Gibco, Cat #: 15140122). One day before infection, H1-HeLa cells were seeded into 96-well plates (Corning, Cat. #: 3903) at 0.1 mL/well at $1.5 \times 10^5$ cells/mL in Opti-MEM (Gibco, Cat #: 31985070) supplemented with 2% FBS, and were incubated at 37.0 in a 100% humid atmosphere containing 5% (v/v) $CO_2$ overnight. On the next day, CAN97-83-GFP1 (A2a) hMPV was diluted in Opti-MEM medium containing 200 µg/mL $CaCl_2$ and 2 µg/mL TPCK treated trypsin and distributed to the 96-well plates at 0.1 mL/well for an MOI=0.1. Test compounds were distributed to each well using a HP D300e digital dispenser with a final volume of 200 µL/well. After the plates were centrifuged at 700 g for one hour at room temperature, they were maintained in a humidified chamber at 37.0 with 5% (v/v) $CO_2$ for 96 hours. After the incubation, the medium was removed, and the plates were fixed with 0.1 mL/well 1% formaldehyde for 15 min at room temperature. The fixative was removed, the plates were air dried for 30-60 minutes, and then permeabilized with 0.1 mL/well 0.5% Triton X-100 in PBS for five minutes at room temperature. Following permeabilization, the plates were washed once with 0.1 mL/well blocking buffer consisting of 10% FBS (HyClone, Cat #: SH303396.03), 5% dry milk (AmericanBio, Cat #: AB 10109-01000), and 0.1% Tween 20 (EMD Millipore, Cat #655204) in PBS. The plates were blocked with 0.1 mL/well blocking buffer for 60 minutes at 37° C. afterward. The blocking buffer was removed and 0.05 mL/well human metapneumovirus nucleocapsid antibody (Sigma, Cat #MAB80121) diluted 1:500 in Blocking buffer was added and incubated for two hours at 37° C. The plates were then washed with 0.2 mL/well 0.1% Tween 20/PBS five times, followed by addition of 0.05 mL/well of horseradish peroxidase (HRP) conjugated goat anti-mouse IgG antibody (Fisher Scientific, Cat #501077607) at 1:2000 dilution in the blocking buffer. After one-hour incubation at 37° C., plates were washed five times with 0.2 mL/well 0.1% tween 20 in PBS. The HRP signals were developed by adding 0.1 mL/well of TMB reagent (Thermo Scientific, Cat #: ENN301) and incubating at room until the positive control was apparent. At that point, the reaction was stopped by adding 0.1 mL/well TMB stop solution (SeraCare, Cat #: 5150-0021). The absorbance was measured at 450 nm with an EnVision plate reader. The relative absorbance was calculated by normalizing the absorbance of the compound-treated groups to that of the DMSO-treated groups (set as 100%). $EC_{50}$ values were calculated using a nonlinear four parameter variable slope regression model.

Example Y: hMPV H1-Hela $CC_{50}$

H1-HeLa cell viability was measured using the CellTiter-Glo® Luminescent Cell Viability Assay kit (Promega, Cat #G7573) according to the manufacturer's protocol. H1-HeLa cells were maintained in Dulbecco's Modified Eagle's Medium with high glucose (Gibco, Cat #: 11995073) supplemented with 10% FBS (HyClone, Cat #: SH303396.03), 100 units/mL penicillin and 100 µg/mL streptomycin (Gibco, Cat #: 15140122). One day before compound treatment, H1-HeLa cells were seeded at $1.5 \times 10^5$ cells per well into 96-well plates (Corning, Cat #3904) in Opti-MEM (Gibco, Cat #: 31985070) supplemented with 2% FBS, and were incubated at 37.0 in a 100% humid atmosphere containing 5% (v/v) $CO_2$. After overnight incubation, the cells were treated with three-fold serial dilutions of the compound. At 96 hours post treatment, CellTiter-Glo reagents were added into each well and luminescence signals were recorded by an EnVision plate reader. The relative cell viability was calculated by normalizing the absorbance of the compound-treated groups to that of the DMSO-treated groups (set as 100% viability) and 10 µM puromycin treated groups (set as 0% viability). The $CC_{50}$ (compound concentration for reducing 50% of cell viability) was calculated using a nonlinear regression model (four parameters).

Example Z: H1-HeLa HRV-CTG $EC_{50}$

H1-Hela cell line (ATCC, Manassas, VA, Cat #CRL-1958) was maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03), and 1× Penicillin-Streptomycin-L-Glutamine (Corning, New York, NY, Cat #30-009-CI). Cells were passaged 2 times per week to maintain sub-confluent densities and were used for experiments at passage 5-30. The Human Rhinovirus 1B (HRV1B) (ATCC, Manassas, VA, Cat #VR-1645), Human Rhinovirus 14 (HRV14) (ATCC, Manassas, VA, Cat #VR-284), and Human Rhinovirus 16 (HRV16) (ATCC, Manassas, VA, Cat #BR-283) was obtained through ATCC. Viral infection was monitored by determining viability of H1-HeLa cells as described below.

Test molecules are prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner, Monroe, NC, Cat #781091) at 200 nL per well using an Echo acoustic dispenser (Labcyte, Sunnyvale, CA). H1-HeLa cells were harvested and suspended in DMEM (supplemented with 2% FBS and 1× Penicillin-Streptomycin-L-Glutamine) and seeded to the pre-spotted assay plates at 5,000 cells per well in 30 µL. HRV1B, HRV14, and HRV16 was diluted in DMEM (supplemented with 2% FBS and 1× Penicillin-Streptomycin-L-Glutamine) at 97.1 million Infectious Units (IU) per mL, 151 million IU per mL and 221 million IU per mL respectively. 100 µL of virus per well was added to the assay plates containing cells and compounds, for an MOI of 0.5, 1.0, and 0.25 respectively. The assay plates were incubated for 4 days at 37° C. and 5% $CO_2$. At the end of incubation, Celltiter-Glo (Promega, Madison, WI, Cat #G7573) was prepared. The assay plates and Celltiter-Glo reagent were equilibrated to room temperature for at least 15 minutes. 40 µL per well of Celltiter-Glo reagent was added and the plates were incubated at room temperature for 15 minutes before reading the luminescence signal on an EnVision multimode plate reader (Perkin Elmer, Waltham, MA). Rupintrivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was defined as the concentration reducing viral replication by 50%.

E. Biological Data

Provided below in Table 42 is data related to compounds disclosed herein.

TABLE 42

| | Biological Data for Compounds Disclosed Herein | | | |
| --- | --- | --- | --- | --- |
| Compound # | RSV NHBE FLuc $EC_{50}$ (nM) (per Ex. I) | RSV Hep-2 FLuc $EC_{50}$ (nM) (per Ex. R) | RSV Hep-2 FLuc $EC_{50}$ (v2) (nM) (per Ex. V) | RSV FLuc NHBE 384 $EC_{50}$ (v2) (nM) (per Ex. U) |
| 1 | 104 | 100 | 229 | 54 |
| 7 | 113 | 84 | 284 | 36 |
| 9 | | 53 | 145 | |
| 16 | <6 | | 36 | <3 |
| 19 | 98 | 48 | 60 | |
| 21 | 41 | 136 | 222 | 29 |
| 23 | 16 | | 71 | 4 |
| 24 | | | | 4 |
| 25 | 98 | 291 | 2924 | 169 |
| 27 | 42 | 232 | | |
| 28 | 28 | | 353 | 46 |
| 30 | | | 115 | 14 |
| 31 | 229 | | | 134 |
| 34 | | | 1888 | 272 |
| 36 | 121 | 155 | 353 | 51 |
| 37 | 276 | 304 | 1242 | 82 |
| 38 | 23 | | 212 | 25 |
| 39 | | | 327 | 51 |
| 43 | 129 | | 707 | 98 |
| 50 | 18 | 12 | 91 | |
| 51 | 66 | 421 | 436 | 56 |
| 53 | 69 | 113 | 200 | 22 |
| 66 | 50 | 21 | 56 | |
| 67 | 28 | 229 | | |
| 68 | 36 | 118 | 110 | 9 |
| 69 | 29 | | 674 | 32 |
| 70 | | | 1768 | 165 |
| 71 | 199 | | 2585 | |
| 72 | | | 45 | 4 |
| 73 | 25 | 195 | 104 | 10 |
| 74 | | | 782 | 85 |
| 75 | <10.851 | 385 | 446 | 12 |
| 76 | | | 382 | 113 |
| 77 | 12 | 222 | 90 | |

TABLE 42-continued

Biological Data for Compounds Disclosed Herein

| Compound # | RSV NHBE FLuc EC$_{50}$ (nM) (per Ex. I) | RSV Hep-2 FLuc EC$_{50}$ (nM) (per Ex. R) | RSV Hep-2 FLuc EC$_{50}$ (v2) (nM) (per Ex. V) | RSV FLuc NHBE 384 EC$_{50}$ (v2) (nM) (per Ex. U) |
|---|---|---|---|---|
| 78 | | | 439 | 31 |
| 79 | | | 1088 | 19 |
| 80 | | | 1048 | 36 |
| 81 | | | 445 | 83 |
| 82 | | | 1251 | 147 |
| 84 | | | 325 | 9 |
| 85 | | | 93 | 11 |
| 86 | | | 546 | 25 |
| 87 | | | 443 | 133 |
| 88 | | | 191 | 38 |
| 92 | | | 194 | 47 |
| 93 | | | 3061 | 663 |
| 94 | | | 339 | 59 |
| 96 | | | 368 | 67 |
| 97 | | | 1490 | 45 |
| 98 | | | 34 | 11 |
| 99 | | | 166 | 47 |

TABLE 43

Biological Data for Compounds Disclosed Herein

| Compound # | HRV14 HELA EC$_{50}$ (nM) (per Ex. Z) | HRV 16 HELA EC$_{50}$ (nM) (per Ex. Z) | HRV 1B HELA EC$_{50}$ (nM) (per Ex. Z) |
|---|---|---|---|
| 1 | 8 | 8 | 4 |
| 7 | 50 | 40 | 38 |
| 16 | 11 | 10 | 5 |
| 21 | 60 | 50 | 35 |
| 23 | 9 | 7 | 4 |
| 25 | 103 | 99 | 45 |
| 28 | 47 | 51 | 36 |
| 30 | 12 | 11 | 7 |
| 34 | 276 | 316 | 281 |
| 36 | 113 | 112 | 102 |
| 37 | 183 | 249 | 332 |
| 38 | 28 | 29 | 12 |
| 39 | 34 | 35 | 18 |
| 43 | 75 | 53 | 36 |
| 51 | 49 | 34 | 33 |
| 53 | 35 | 35 | 34 |
| 68 | 35 | 20 | 12 |
| 69 | 106 | 109 | 116 |
| 70 | 162 | 114 | 84 |
| 72 | 3 | 3 | 3 |
| 73 | 26 | 29 | 12 |
| 74 | 67 | 49 | 24 |
| 75 | 37 | 37 | 23 |
| 78 | 38 | 66 | 24 |
| 79 | 38 | 70 | 25 |
| 80 | 88 | 111 | 49 |
| 99 | 37 | 33 | 19 |

TABLE 44

Biological Data for Compounds Disclosed Herein

| Compound # | Dengue Virus-2 Huh-7 EC$_{50}$ (nM) (per Ex. W) | Dengue Virus-2 Huh-7 CC$_{50}$ (nM) (per Ex. W) |
|---|---|---|
| 1 | 9700 | 18000 |
| 7 | 8700 | 19000 |
| 16 | 3900 | 24000 |
| 19 | 6600 | 25000 |
| 23 | 8600 | 26000 |
| 25 | 9200 | 13000 |
| 28 | 9500 | 19000 |
| 30 | 1200 | 5900 |
| 34 | 15000 | 15000 |
| 36 | 10000 | 17000 |
| 37 | 11000 | 16000 |
| 38 | 2900 | 5800 |
| 39 | 9100 | 14000 |
| 43 | 9700 | 14000 |
| 51 | 11000 | 21000 |
| 53 | 9900 | 16000 |
| 70 | 12000 | 12000 |
| 71 | 33000 | >50000 |
| 72 | 2400 | 17000 |
| 73 | 9500 | 19000 |
| 74 | 10000 | 15000 |
| 75 | 23000 | >50000 |

TABLE 45

Biological Data for Compounds Disclosed Herein

| Compound # | HCV Replicon 1B EC50 (nM) (per Ex. Q) | HCV Replicon 2A EC50 (nM) (per Ex. Q) | HCV Replicon 1B CC$_{50}$ (nM) (per Ex. Q) | HCV Replicon 2A CC$_{50}$ (nM) (per Ex. Q) |
|---|---|---|---|---|
| 1 | 13819 | 20621 | >44444.4 | >44444.4 |
| 7 | 16746 | 30620 | >44444.4 | >44444.4 |
| 21 | 13278 | 19218 | >44444.4 | >44444.4 |
| 30 | 3988 | 15813 | >44444.4 | 42438 |
| 36 | 26323 | 21810 | >44444.4 | >44444.4 |
| 37 | 22524 | 26023 | >44444.4 | >44444.4 |
| 51 | 14648 | 19175 | >44444.4 | >44444.4 |
| 53 | 15495 | 15519 | >44444.4 | 36184 |
| 68 | 11487 | 15167 | >44444.4 | >44444.4 |
| 70 | 19613 | 25165 | >44444.4 | 42689 |
| 72 | 465 | >44444.4 | >44444.4 | >44444.4 |
| 73 | 15867 | 20398 | >44444.4 | >44444.4 |
| 74 | 26181 | 22837 | >44444.4 | 35797 |
| 78 | 27650 | 18361 | >44444.4 | 33804 |
| 79 | 24281 | 20027 | >44444.4 | 30157 |
| 80 | 32409 | 21163 | >44444.4 | 36930 |
| 81 | 10671 | 15944 | >44444.4 | 37924 |
| 82 | 11251 | 19159 | >44444.4 | 37635 |

TABLE 46

Biological Data for Compounds Disclosed Herein

| Compound # | hMPV H1-Hela EC$_{50}$ (nM) (per Ex. X) | hMPV H1-Hela CC$_{50}$ (nM) (per Ex. Y) |
|---|---|---|
| 1 | 440 | 3624 |
| 7 | 358 | 3876 |
| 23 | 156 | 10750 |
| 25 | 1282 | 8492 |
| 28 | 625 | 9905 |
| 30 | 188 | 4958 |
| 34 | 646 | 4688 |
| 36 | 1097 | 9558 |
| 38 | 137 | 6191 |
| 43 | 901 | 4003 |
| 68 | 214 | 8713 |
| 72 | 70 | 5100 |
| 76 | 517 | 6389 |
| 79 | 1607 | 6743 |
| 80 | 668 | 7079 |

TABLE 46-continued

Biological Data for Compounds Disclosed Herein

| Compound # | hMPV H1-Hela EC$_{50}$ (nM) (per Ex. X) | hMPV H1-Hela CC$_{50}$ (nM) (per Ex. Y) |
|---|---|---|
| 81 | 453 | 4524 |
| 82 | 1116 | 4026 |
| 84 | 367 | 1822 |
| 88 | 348 | 2210 |

TABLE 47

Biological Data for Compounds Disclosed Herein

| Compound # | RSV NHBE CC$_{50}$ 384 V2 (nM) (per Ex. U) | RSV HEP2-CC$_{50}$- 384-V2 (nM) (per Ex. V) |
|---|---|---|
| 1 | 2398 | >31184.1 |
| 7 | 5961 | >49868.7 |
| 9 |  | >48519.9 |
| 16 | 4607 | >41468.2 |
| 19 |  | 46385 |
| 21 | 3349 | 39660 |
| 23 | 5403 | >42025.7 |
| 24 | 937 |  |
| 25 | 31003 | >50000 |
| 28 | 7560 | 30611 |
| 30 | 1717 | 33084 |
| 31 | 1902 |  |
| 34 | 7248 | >43160.1 |
| 36 | 2744 | >50000 |
| 37 | 3111 | >38137.8 |
| 38 | 7991 | 35337 |
| 39 | 6459 | >41364.2 |
| 43 | 11881 | >30340.5 |
| 50 |  | >50000 |
| 51 | 8327 | >46189.6 |
| 53 | 2818 | 32070 |
| 66 |  | 49089 |
| 68 | 2057 | 42808 |
| 69 | 3286 | >50000 |
| 70 | 3950 | 43528 |
| 71 |  | >50000 |
| 72 | 1611 | >49949.9 |
| 73 | 3819 | >47040.8 |
| 74 | 1535 | 28039 |
| 75 | 4623 | >48458.9 |
| 76 | 3554 | 33682 |
| 77 |  | >50000 |
| 78 | 1204 | 34567 |
| 79 | 2100 | 38111 |
| 80 | 2172 | >50000 |
| 81 | 2483 | 23046 |
| 82 | 6117 | 29010 |
| 84 | 24536 | >50000 |
| 85 | 1443 | >50000 |
| 86 | 2898 | >50000 |
| 87 | 3450 | >34780.7 |
| 88 | 7530 | 36583 |
| 92 | 9555 | >50000 |
| 93 | 8138 | >50000 |
| 94 | 16012 | >50000 |
| 96 | 5240 | >38066.8 |
| 94 | 3911 | >43858.8 |
| 98 | 2902 |  |
| 99 | 1144 | 42315 |

The present disclosure provides reference to various embodiments and techniques. However, it should be understood that many variations and modifications can be made while remaining within the spirit and scope of the present disclosure. The description is made with the understanding that it is to be considered an exemplification of the claimed subject matter, and is not intended to limit the appended claims to the specific embodiments illustrated.

The invention claimed is:

1. A compound of Formula V, or the pharmaceutically acceptable salt thereof,

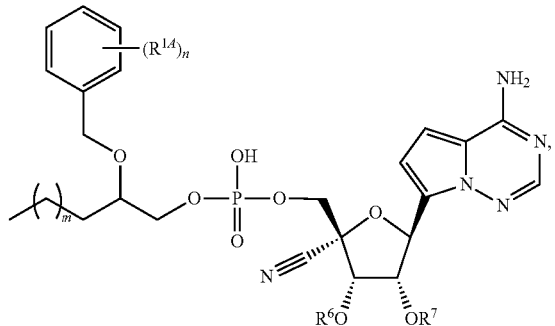

Formula V wherein
n is 1 or 2;
m is 10, 11, 12, 13, 14, 15, 16, 17, 18, 19, 20, or 21;
each $R^{14}$ is independently halo, cyano, $C_1$-$C_3$ alkyl, $C_1$-$C_3$ haloalkyl, $C_1$-$C_3$ alkoxy, $C_1$-$C_3$ haloalkoxy, or 5-10 membered heteroaryl containing one, two, or three heteroatoms selected from N and O;
$R^6$ is H or —C(O)$C_1$-$C_6$ alkyl; and
$R^7$ is H or —C(O)$C_1$-$C_6$ alkyl.

2. A pharmaceutical formulation comprising a pharmaceutically effective amount of a compound of claim 1, or a pharmaceutically acceptable salt thereof, and a pharmaceutically acceptable carrier or excipient.

3. A method of treating or preventing a viral infection in a subject in need thereof, wherein the method comprises administering to the subject a therapeutically effective amount of a pharmaceutical formulation of claim 2, wherein the viral infection is a pneumoviridae virus infection, a picornaviridae virus infection, a flaviviridae virus infection, a filoviridae virus infection, or a paramyxoviridae virus infection.

4. The compound of claim 1, or a pharmaceutically acceptable salt thereof, wherein each $R^{14}$ is independently selected from halo, cyano, $C_1$-$C_3$ alkoxy, $C_1$-$C_3$ haloalkoxy, and 5-10 membered heteroaryl containing one or two heteroatoms selected from N and O.

5. The compound of claim 1, or a pharmaceutically acceptable salt thereof, wherein each $R^{14}$ is independently selected from halo, cyano, methoxy, isopropoxy, triazolyl, and oxadiazolyl.

6. The compound of claim 1, or a pharmaceutically acceptable salt thereof, wherein one $R^{14}$ is cyano and one $R^{14}$ is $C_1$-$C_3$ alkoxy.

7. The compound of claim 1, or a pharmaceutically acceptable salt thereof, wherein one $R^{14}$ is cyano and one $R^{14}$ is methoxy.

8. The compound of claim 1, or a pharmaceutically acceptable salt thereof, wherein one $R^{14}$ is cyano and one $R^{14}$ is halo.

9. The compound of claim 1, or a pharmaceutically acceptable salt thereof, wherein one $R^{14}$ is cyano and one $R^{14}$ is fluoro.

10. The compound of claim 1, or a pharmaceutically acceptable salt thereof, wherein $R^6$ is H; and $R^7$ is H.

11. The compound of claim 1, or a pharmaceutically acceptable salt thereof, wherein $R^6$ is —C(O)$C_1$-$C_6$ alkyl; and $R^7$ is —C(O)$C_1$-$C_6$ alkyl.

12. The compound of claim 1, or a pharmaceutically acceptable salt thereof, wherein n is 1.

13. The compound of claim 1, or a pharmaceutically acceptable salt thereof, wherein n is 2.

14. The compound of claim 1, or a pharmaceutically acceptable salt thereof, wherein m is 14.

15. The compound of claim 1, or a pharmaceutically acceptable salt thereof, wherein m is 15.

16. The compound of claim 1, or a pharmaceutically acceptable salt thereof, wherein m is 16.

17. The compound of claim 1, or a pharmaceutically acceptable salt thereof, wherein m is 17.

18. The compound of claim 1, or a pharmaceutically acceptable salt thereof, wherein m is 18.

* * * * *

SEQUENCE LISTING

```
Sequence total quantity: 3
SEQ ID NO: 1           moltype = DNA  length = 22
FEATURE                Location/Qualifiers
source                 1..22
                       mol_type = other DNA
                       organism = synthetic construct
SEQUENCE: 1
catccagcaa ataccatc ca                                           22

SEQ ID NO: 2           moltype = DNA  length = 28
FEATURE                Location/Qualifiers
source                 1..28
                       mol_type = other DNA
                       organism = synthetic construct
SEQUENCE: 2
ttctgcacat cataattagg agtatcaa                                   28

SEQ ID NO: 3           moltype = DNA  length = 15
FEATURE                Location/Qualifiers
source                 1..15
                       mol_type = other DNA
                       organism = synthetic construct
SEQUENCE: 3
cggagcacag gagat                                                 15
```